US010179782B2

(12) United States Patent
Estrada et al.

(10) Patent No.: US 10,179,782 B2
(45) Date of Patent: Jan. 15, 2019

(54) SUBSTITUTED SULFONAMIDE COMPOUNDS

(71) Applicant: Genentech, Inc., South San Francisco, CA (US)

(72) Inventors: Anthony Estrada, South San Francisco, CA (US); Elisia Villemure, South San Francisco, CA (US); Vishal Verma, San Carlos, CA (US); Daniel Shore, San Francisco, CA (US); Matthew Volgraf, South San Francisco, CA (US); Baihua Hu, Beijing (CN); Aijun Lu, Beijing (CN)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/042,310

(22) Filed: Feb. 12, 2016

(65) Prior Publication Data

US 2016/0264567 A1 Sep. 15, 2016

(51) Int. Cl.

| | |
|---|---|
| ***C07D 417/14*** | (2006.01) |
| ***C07D 403/12*** | (2006.01) |
| ***C07D 401/14*** | (2006.01) |
| ***C07D 405/14*** | (2006.01) |
| ***C07D 401/12*** | (2006.01) |
| ***C07D 403/14*** | (2006.01) |
| ***C07D 409/14*** | (2006.01) |
| ***C07D 417/12*** | (2006.01) |
| ***C07F 9/6512*** | (2006.01) |

(52) U.S. Cl.

CPC ......... *C07D 417/14* (2013.01); *C07D 401/12* (2013.01); *C07D 401/14* (2013.01); *C07D 403/12* (2013.01); *C07D 403/14* (2013.01); *C07D 405/14* (2013.01); *C07D 409/14* (2013.01); *C07D 417/12* (2013.01); *C07F 9/6512* (2013.01)

(58) Field of Classification Search

None

See application file for complete search history.

(56) References Cited

U.S. PATENT DOCUMENTS

| | | | |
|---|---|---|---|
| 2014/0206650 A1 | 7/2014 | Lippa et al. |
| 2014/0329796 A1 | 11/2014 | Suzuki et al. |
| 2015/0284375 A1 | 10/2015 | Kobayashi et al. |
| 2016/0332999 A1 | 11/2016 | Kobayashi et al. |

FOREIGN PATENT DOCUMENTS

| | | |
|---|---|---|
| EP | 2 805 718 A1 | 11/2014 |
| EP | 2 937 335 A1 | 10/2015 |
| WO | 2010/141805 A1 | 12/2010 |
| WO | 2012/152983 A1 | 11/2012 |
| WO | 2014/098098 A1 | 6/2014 |
| WO | 2015/052264 A1 | 4/2015 |
| WO | 2015/115507 A1 | 8/2015 |

OTHER PUBLICATIONS

ISR for PCT/EP2015/052950 (dated Jun. 29, 2016).

Liu Chunjian et al., "Synthesis and evaluation of carbamoylmethylene linked prodrugsof BMS-582949, a clinical p38 alpha inhibitor" Bioorganic &Medicinal Chemistry Letters 23(10):3028-3033 (Mar 15, 2013).

*Primary Examiner* — Sreenivasan Padmanabhan
*Assistant Examiner* — Jody L Karol
(74) *Attorney, Agent, or Firm* — Robert C. Hall

(57) ABSTRACT

The invention is concerned with the compounds of formula I:

I

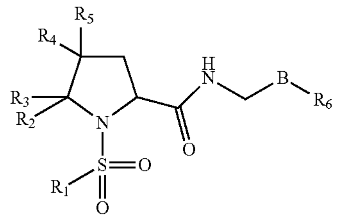

and salts thereof and other compounds of formulas II-IX as disclosed herein. In addition, the present invention relates to methods of manufacturing and methods of using the compounds of formulas I-IX as well as pharmaceutical compositions containing such compounds. The compounds may be useful in treating diseases and conditions mediated by TRPA1, such as pain or asthma.

10 Claims, No Drawings

SUBSTITUTED SULFONAMIDE COMPOUNDS

CROSS-REFERENCE TO RELATED APPLICATION

This application claims the benefit of International Application No. PCT/CN2015/073102, filed Feb. 15, 2015, International Application No. PCT/CN2015/076318, filed Apr. 10, 2015, and International Application No. PCT/CN2016/071061, filed Jan. 15, 2016, all of which are incorporated herein by reference in their entireties.

FIELD OF THE INVENTION

The present invention relates to substituted sulfonamide compounds, their manufacture, pharmaceutical compositions containing them and their use as Transient Receptor Potential (TRP) channel antagonists.

BACKGROUND OF THE INVENTION

TRP channels are a class of ion channels found on the plasma membrane of a variety of human (and other animal) cell types. There are at least 28 known human TRP channels which are broken into a number of families or groups based upon sequence homology and function. TRPA1 is a non-selective cation conducting channel that modulates membrane potential via flux of sodium, potassium and calcium. TRPA1 has been shown to be highly expressed in the human dorsal root ganglion neurons and peripheral sensory nerves. In humans, TRPA1 is activated by a number of reactive compounds such as acrolein, allylisothiocyanate, ozone as well as unreactive compounds such as nicotine and menthol and is thus thought to act as a 'chemosensor.

Many of the known TRPA1 agonists are irritants that cause pain, irritation and neurogenic inflammation in humans and other animals. Therefore, it would be expected that TRPA1 antagonists or agents that block the biological effect of TRPA1 channel activators would be useful in the treatment of diseases such as asthma and its exacerbations, chronic cough and related maladies as well as being useful for the treatment of acute and chronic pain. Recently, it has also been shown that products of tissue damage and oxidative stress, e.g. 4-hydroxynonenal and related compounds, activate the TRPA1 channel. This finding provides additional rationale for the utility of small molecule TRPA1 antagonists in the treatment of diseases related to tissue damage, oxidative stress and bronchial smooth muscle contraction such as asthma, chronic obstructive pulmonary disease (COPD), occupational asthma, and virally-induced lung inflammation. Moreover, recently findings have correlated activation of TRPA1 channels with increased pain perception (Kosugi et al., *J. Neurosci* 27, (2007) 4443-4451; Kremayer et al., *Neuron* 66 (2010) 671-680; Wei et al., *Pain* 152 (2011) 582-591); Wei et al., *Neurosci Lett* 479 (2010) 253-256)) providing additional rationale for the utility of small molecule TRPA1 inhibitors in the treatment of pain disorders.

SUMMARY OF THE INVENTION

The invention provides compounds of the invention, one of which is a compound of formula I:

I

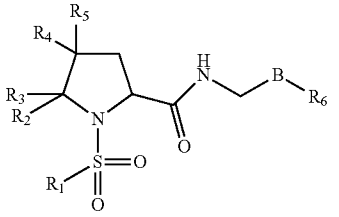

wherein:

B is $B^1$, $B^2$, or $B^3$;

$B^1$ is a 5-membered heteroaryl comprising 2 nitrogen atoms in the ring, wherein each 5-membered heteroaryl is unsubstituted or substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

$B^2$ is phenyl, wherein each phenyl is unsubstituted or substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

$B^3$ is 6-membered heteroaryl, wherein each 6-membered heteroaryl is unsubstituted or substituted with one or more groups independently selected from halogen, CN, $(C_1-C_6)$alkyl, $(C_1-C_6)$haloalkyl, $O(C_1-C_6)$alkyl, $O(C_1-C_6)$haloalkyl, 5 or 6-membered heteroaryl, $(C_3-C_7)$cycloalkyl, and 4, 5, 6, or 7-membered heterocyclyl; and wherein any of the 5 or 6-membered heteroaryl, $(C_3-C_7)$cycloalkyl, or 4, 5, 6, or 7-membered heterocyclyl groups is unsubstituted or substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

$R^1$ is phenyl or heteroaryl, wherein each phenyl or heteroaryl is unsubstituted or substituted with one or more groups independently selected from halogen, CN, $(C_1-C_6)$alkyl, and $(C_1-C_6)$haloalkyl;

$R^2$ is $(C_1-C_6)$alkyl, $(C_1-C_6)$haloalkyl, or $(C_3-C_7)$cycloalkyl; wherein $(C_1-C_6)$alkyl is optionally substituted with $O(C_1-C_6)$alkyl;

$R^3$ is H or $(C_1-C_6)$alkyl; or $R^2$ and $R^3$ together with the atoms to which they are attached form a $(C_3)$cycloalkyl;

$R^4$ is H, F, or CN;

$R^5$ is H or $(C_1-C_6)$alkyl; or one of $R^2$ and $R^3$ and one of $R^4$ and $R^5$ together with the atoms to which they are attached form a $(C_3)$cycloalkyl;

$R^6$ is phenyl, $(C_3-C_7)$cycloalkyl, 5 or 6-membered heteroaryl, or 4, 5, 6 or 7-membered heterocycle, wherein any phenyl, $(C_3-C_7)$cycloalkyl, 5 or 6-membered heteroaryl, or 4, 5, 6 or 7-membered heterocycle of $R^6$ is optionally substituted with one or more groups independently selected from halogen, CN, $SF_5$, $(C_1-C_6)$alkyl, $(C_1-C_6)$haloalkyl, $O(C_1-C_6)$alkyl, or $O(C_1-C_6)$haloalkyl; or $R^6$ is $O-CH_2-R^7$;

$R^7$ is $(C_1-C_6)$alkyl, 4, 5, 6, or 7-membered heterocycle, $(C_3-C_7)$cycloalkyl, or 6-membered heteroaryl, wherein any $(C_1-C_6)$alkyl, 4, 5, 6, or 7-membered heterocycle, $(C_3-C_7)$cycloalkyl, or 6-membered heteroaryl is optionally substituted with one or more groups independently selected from halogen, CN, $(C_1-C_6)$alkyl, $(C_1-C_6)$haloalkyl, $O(C_1-C_6)$alkyl, $(C_3-C_7)$cycloalkyl, and $O(C_1-C_6)$haloalkyl;

or a salt thereof.

The invention further provides a compound of formula II:

II

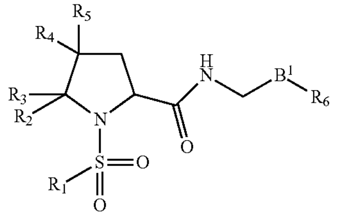

wherein:

$B^1$ is a 5-membered heteroaryl comprising 2 nitrogen atoms in the ring, wherein each 5-membered heteroaryl is unsubstituted or substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

$R^1$ is phenyl or heteroaryl, wherein each phenyl or heteroaryl is unsubstituted or substituted with one or more groups independently selected from halogen, CN, $(C_1-C_6)$alkyl, and $(C_1-C_6)$haloalkyl;

$R^2$ is $(C_1-C_6)$alkyl, $(C_1-C_6)$haloalkyl, or $(C_3-C_7)$cycloalkyl; wherein $(C_1-C_6)$alkyl is optionally substituted with $O(C_1-C_6)$alkyl;

$R^3$ is H or $(C_1-C_6)$alkyl; or $R^2$ and $R^3$ together with the atoms to which they are attached form a $(C_3)$cycloalkyl;

$R^4$ is H, F, or CN;

$R^5$ is H or $(C_1-C_6)$alkyl; or one of $R^2$ and $R^3$ and one of $R^4$ and $R^5$ together with the atoms to which they are attached form a $(C_3)$cycloalkyl;

$R^6$ is phenyl, $(C_3-C_7)$cycloalkyl, 5 or 6-membered heteroaryl, or 4, 5, 6 or 7-membered heterocycle, wherein any phenyl, $(C_3-C_7)$cycloalkyl, 5 or 6-membered heteroaryl, or 4, 5, 6 or 7-membered heterocycle of $R^6$ is optionally substituted with one or more groups independently selected from halogen, CN, $SF_5$, $(C_1-C_6)$alkyl, $(C_1-C_6)$haloalkyl, $O(C_1-C_6)$alkyl, or $O(C_1-C_6)$haloalkyl; or $R^6$ is $O—CH_2—R^7$;

$R^7$ is $(C_1-C_6)$alkyl, 4, 5, 6, or 7-membered heterocycle, $(C_3-C_7)$cycloalkyl, or 6-membered heteroaryl, wherein any $(C_1-C_6)$alkyl, 4, 5, 6, or 7-membered heterocycle, $(C_3-C_7)$cycloalkyl, or 6-membered heteroaryl is optionally substituted with one or more groups independently selected from halogen, CN, $(C_1-C_6)$alkyl, $(C_1-C_6)$haloalkyl, $O(C_1-C_6)$alkyl, $(C_3-C_7)$cycloalkyl, and $O(C_1-C_6)$haloalkyl;

or a salt thereof.

The invention further provides a compound of formula III:

III

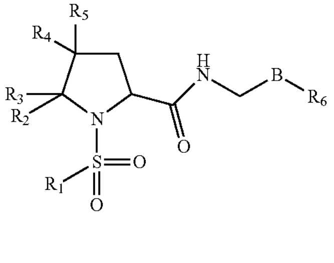

wherein:

B is $B^2$ or $B^3$;

$B^2$ is phenyl, wherein each phenyl is unsubstituted or substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

$B^3$ is 6-membered heteroaryl, wherein each 6-membered heteroaryl is unsubstituted or substituted with one or more groups independently selected from halogen, CN, $(C_1-C_6)$alkyl, $(C_1-C_6)$haloalkyl, $O(C_1-C_6)$alkyl, $O(C_1-C_6)$haloalkyl, 5 or 6-membered heteroaryl, $(C_3-C_7)$cycloalkyl, and 4, 5, 6, or 7-membered heterocyclyl; and wherein any of the 5 or 6-membered heteroaryl, $(C_3-C_7)$cycloalkyl, or 4, 5, 6, or 7-membered heterocyclyl groups is unsubstituted or substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

$R^1$ is phenyl or heteroaryl, wherein each phenyl or heteroaryl is unsubstituted or substituted with one or more groups independently selected from halogen, CN, $(C_1-C_6)$alkyl, and $(C_1-C_6)$haloalkyl;

$R^2$ is $(C_1-C_6)$alkyl, $(C_1-C_6)$haloalkyl, or $(C_3-C_7)$cycloalkyl; wherein $(C_1-C_6)$alkyl is optionally substituted with $O(C_1-C_6)$alkyl;

$R^3$ is H or $(C_1-C_6)$alkyl; or $R^2$ and $R^3$ together with the atoms to which they are attached form a $(C_3)$cycloalkyl;

$R^4$ is H, F, or CN;

$R^5$ is H or $(C_1-C_6)$alkyl; or one of $R^2$ and $R^3$ and one of $R^4$ and $R^5$ together with the atoms to which they are attached form a $(C_3)$cycloalkyl;

$R^6$ is phenyl, $(C_3-C_7)$cycloalkyl, 5 or 6-membered heteroaryl, or 4, 5, 6 or 7-membered heterocycle, wherein any phenyl, $(C_3-C_7)$cycloalkyl, 5 or 6-membered heteroaryl, or 4, 5, 6 or 7-membered heterocycle of $R^6$ is optionally substituted with one or more groups independently selected from halogen, CN, $SF_5$, $(C_1-C_6)$alkyl, $(C_1-C_6)$haloalkyl, $O(C_1-C_6)$alkyl, or $O(C_1-C_6)$haloalkyl; or $R^6$ is $O—CH_2—R^7$;

$R^7$ is $(C_1-C_6)$alkyl, 4, 5, 6, or 7-membered heterocycle, $(C_3-C_7)$cycloalkyl, or 6-membered heteroaryl, wherein any $(C_1-C_6)$alkyl, 4, 5, 6, or 7-membered heterocycle, $(C_3-C_7)$cycloalkyl, or 6-membered heteroaryl is optionally substituted with one or more groups independently selected from halogen, CN, $(C_1-C_6)$alkyl, $(C_1-C_6)$haloalkyl, $O(C_1-C_6)$alkyl, $(C_3-C_7)$cycloalkyl, and $O(C_1-C_6)$haloalkyl;

or a salt thereof.

The invention further provides a compound of formula IV:

IV

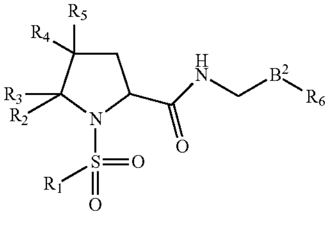

wherein:

$B^2$ is phenyl, wherein each phenyl is unsubstituted or substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

$R^1$ is phenyl or heteroaryl, wherein each phenyl or heteroaryl is unsubstituted or substituted with one or more groups independently selected from halogen, CN, $(C_1-C_6)$alkyl, and $(C_1-C_6)$haloalkyl;

$R^2$ is $(C_1-C_6)$alkyl, $(C_1-C_6)$haloalkyl, or $(C_3-C_7)$cycloalkyl; wherein $(C_1-C_6)$alkyl is optionally substituted with $O(C_1-C_6)$alkyl;

$R^3$ is H or $(C_1-C_6)$alkyl; or $R^2$ and $R^3$ together with the atoms to which they are attached form a $(C_3)$cycloalkyl;

$R^4$ is H, F, or CN;

$R^5$ is H or $(C_1-C_6)$alkyl; or one of $R^2$ and $R^3$ and one of $R^4$ and $R^5$ together with the atoms to which they are attached form a $(C_3)$cycloalkyl;

$R^6$ is phenyl, $(C_3-C_7)$cycloalkyl, 5 or 6-membered heteroaryl, or 4, 5, 6 or 7-membered heterocycle, wherein any phenyl, $(C_3-C_7)$cycloalkyl, 5 or 6-membered heteroaryl, or 4, 5, 6 or 7-membered heterocycle of $R^6$ is optionally substituted with one or more groups independently selected from halogen, CN, $SF_5$, $(C_1-C_6)$alkyl, $(C_1-C_6)$haloalkyl, $O(C_1-C_6)$alkyl, or $O(C_1-C_6)$haloalkyl; or $R^6$ is $O—CH_2—R^7$;

$R^7$ is $(C_1-C_6)$alkyl, 4, 5, 6, or 7-membered heterocycle, $(C_3-C_7)$cycloalkyl, or 6-membered heteroaryl, wherein any $(C_1-C_6)$alkyl, 4, 5, 6, or 7-membered heterocycle, $(C_3-C_7)$ cycloalkyl, or 6-membered heteroaryl is optionally substituted with one or more groups independently selected from halogen, CN, $(C_1-C_6)$alkyl, $(C_1-C_6)$haloalkyl, $O(C_1-C_6)$ alkyl, $(C_3-C_7)$cycloalkyl, and $O(C_1-C_6)$haloalkyl;

or a salt thereof.

The invention further provides a compound of formula V:

V

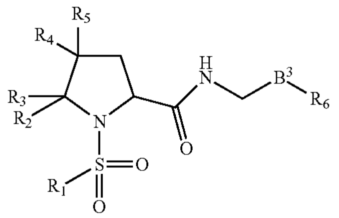

wherein:

$B^3$ is 6-membered heteroaryl, wherein each 6-membered heteroaryl is unsubstituted or substituted with one or more groups independently selected from halogen, CN, $(C_1-C_6)$ alkyl, $(C_1-C_6)$haloalkyl, $O(C_1-C_6)$alkyl, $O(C_1-C_6)$haloalkyl, 5 or 6-membered heteroaryl, $(C_3-C_7)$cycloalkyl, and 4, 5, 6, or 7-membered heterocyclyl; and wherein any of the 5 or 6-membered heteroaryl, $(C_3-C_7)$cycloalkyl, or 4, 5, 6, or 7-membered heterocyclyl groups is unsubstituted or substituted with one or more groups independently selected from halogen, CN, $(C_1-C_6)$alkyl, $(C_1-C_6)$haloalkyl, $O(C_1-C_6)$ alkyl, and $O(C_1-C_6)$haloalkyl;

$R^1$ is phenyl or heteroaryl, wherein each phenyl or heteroaryl is unsubstituted or substituted with one or more groups independently selected from halogen, CN, $(C_1-C_6)$ alkyl, and $(C_1-C_6)$haloalkyl;

$R^2$ is $(C_1-C_6)$alkyl, $(C_1-C_6)$haloalkyl, or $(C_3-C_7)$cycloalkyl; wherein $(C_1-C_6)$alkyl is optionally substituted with $O(C_1-C_6)$alkyl;

$R^3$ is H or $(C_1-C_6)$alkyl; or $R^2$ and $R^3$ together with the atoms to which they are attached form a $(C_3)$cycloalkyl;

$R^4$ is H, F, or CN;

$R^5$ is H or $(C_1-C_6)$alkyl; or one of $R^2$ and $R^3$ and one of $R^4$ and $R^5$ together with the atoms to which they are attached form a $(C_3)$cycloalkyl;

$R^6$ is phenyl, $(C_3-C_7)$cycloalkyl, 5 or 6-membered heteroaryl, or 4, 5, 6 or 7-membered heterocycle, wherein any phenyl, $(C_3-C_7)$cycloalkyl, 5 or 6-membered heteroaryl, or 4, 5, 6 or 7-membered heterocycle of $R^6$ is optionally substituted with one or more groups independently selected from halogen, CN, $SF_5$, $(C_1-C_6)$alkyl, $(C_1-C_6)$haloalkyl, $O(C_1-C_6)$alkyl, or $O(C_1-C_6)$haloalkyl; or $R^6$ is $O—CH_2—R^7$;

$R^7$ is $(C_1-C_6)$alkyl, 4, 5, 6, or 7-membered heterocycle, $(C_3-C_7)$cycloalkyl, or 6-membered heteroaryl, wherein any $(C_1-C_6)$alkyl, 4, 5, 6, or 7-membered heterocycle, $(C_3-C_7)$ cycloalkyl, or 6-membered heteroaryl is optionally substituted with one or more groups independently selected from halogen, CN, $(C_1-C_6)$alkyl, $(C_1-C_6)$haloalkyl, $O(C_1-C_6)$ alkyl, $(C_3-C_7)$cycloalkyl, and $O(C_1-C_6)$haloalkyl;

or a salt thereof.

The invention further provides a compound of formula VI:

VI

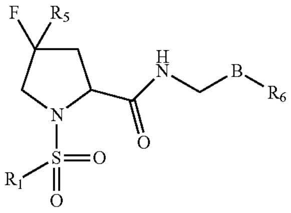

wherein:

B is $B^2$ or $B^3$;

$B^2$ is phenyl, wherein each phenyl is unsubstituted or substituted with one or more groups independently selected from halogen, CN, $(C_1-C_6)$alkyl, and $(C_1-C_6)$haloalkyl;

$B^3$ is a 6-membered heteroaryl, wherein each 6-membered heteroaryl is unsubstituted or substituted with one or more groups independently selected from halogen, $(C_1-C_6)$alkyl, $(C_1-C_6)$haloalkyl, $O(C_1-C_6)$alkyl, $O(C_1-C_6)$haloalkyl, 5 or 6-membered heteroaryl, $(C_3-C_7)$cycloalkyl, and $(C_3-C_7)$heterocyclyl; and wherein any of the 5 or 6-membered heteroaryl, $(C_3-C_7)$cycloalkyl, or $(C_3-C_7)$heterocyclyl groups is unsubstituted or substituted with one or more groups independently selected from halogen, $(C_1-C_6)$alkyl, and $(C_1-C_6)$ haloalkyl;

$R^1$ is phenyl or heteroaryl, wherein each phenyl or heteroaryl is unsubstituted or substituted with one or more groups independently selected from halogen, CN, $(C_1-C_6)$ alkyl, and $(C_1-C_6)$haloalkyl;

$R^5$ is H or $(C_1-C_6)$alkyl;

$R^6$ is a phenyl, $(C_3-C_7)$cycloalkyl, 5- or 6-membered heteroaryl, or 4, 5, 6 or 7-membered heterocycle, wherein any phenyl, $(C_3-C_7)$cycloalkyl, 5- or 6-membered heteroaryl, or 4, 5, 6 or 7-membered heterocycle of $R^6$ is optionally substituted with one or more groups independently selected from halogen, $SF_5$, $(C_1-C_6)$alkyl, $(C_1-C_6)$ haloalkyl, $O(C_1-C_6)$alkyl, and $O(C_1-C_6)$haloalkyl; or $R^6$ is $O—CH_2—R^7$;

$R^7$ is a $(C_1-C_6)$alkyl, 3, 4, 5, 6, or 7-membered heterocycle, 3, 4, 5, 6, or 7-membered cycloalkyl, or 6-membered heteroaryl, wherein any $(C_1-C_6)$alkyl, 3, 4, 5, 6, or 7-membered heterocycle, 3, 4, 5, 6, or 7-membered cycloalkyl, or 6-membered heteroaryl is optionally substituted with one or more groups independently selected from halogen, $(C_1-C_6)$ alkyl, $(C_1-C_6)$haloalkyl, $O(C_1-C_6)$alkyl, $(C_3-C_7)$cycloalkyl, and $O(C_1-C_6)$haloalkyl;

or a salt thereof.

The invention further provides a compound of formula VII:

VII

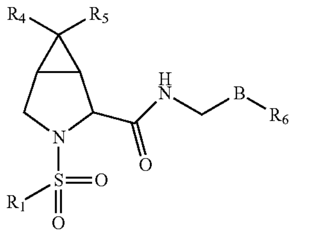

wherein:

B is $B^2$ or $B^3$;

$B^2$ is phenyl, wherein each phenyl is unsubstituted or substituted with one or more groups independently selected from halogen, CN, $(C_1-C_6)$alkyl, and $(C_1-C_6)$haloalkyl;

$B^3$ is a 6-membered heteroaryl, wherein each 6-membered heteroaryl is unsubstituted or substituted with one or more groups independently selected from halogen, $(C_1-C_6)$alkyl, $(C_1-C_6)$haloalkyl, $O(C_1-C_6)$alkyl, $O(C_1-C_6)$haloalkyl, 5 or 6-membered heteroaryl, $(C_3-C_7)$cycloalkyl, and $(C_3-C_7)$heterocyclyl; and wherein any of the 5 or 6-membered heteroaryl, $(C_3-C_7)$cycloalkyl, or $(C_3-C_7)$heterocyclyl groups is unsubstituted or substituted with one or more groups independently selected from halogen, $(C_1-C_6)$alkyl, and $(C_1-C_6)$ haloalkyl;

$R^1$ is phenyl or heteroaryl, wherein each phenyl or heteroaryl is unsubstituted or substituted with one or more groups independently selected from halogen, CN, $(C_1-C_6)$ alkyl, and $(C_1-C_6)$haloalkyl;

$R^4$ and $R^5$ are each independently selected from H, halogen, $(C_1-C_6)$alkyl, $(C_1-C_6)$haloalkyl, $O(C_1-C_6)$alkyl, or $O(C_1-C_6)$haloalkyl;

$R^6$ is a phenyl, $(C_3-C_7)$cycloalkyl, 5- or 6-membered heteroaryl, or 4, 5, 6 or 7-membered heterocycle, wherein any phenyl, $(C_3-C_7)$cycloalkyl, 5- or 6-membered heteroaryl, or 4, 5, 6 or 7-membered heterocycle of $R^6$ is optionally substituted with one or more groups independently selected from halogen, $SF_5$, $(C_1-C_6)$alkyl, $(C_1-C_6)$ haloalkyl, $O(C_1-C_6)$alkyl, and $O(C_1-C_6)$haloalkyl; or $R^6$ is $O—CH_2—R^7$;

$R^7$ is a $(C_1-C_6)$alkyl, 3, 4, 5, 6, or 7-membered heterocycle, 3, 4, 5, 6, or 7-membered cycloalkyl, or 6-membered heteroaryl, wherein any $(C_1-C_6)$alkyl, 3, 4, 5, 6, or 7-membered heterocycle, 3, 4, 5, 6, or 7-membered cycloalkyl, or 6-membered heteroaryl is optionally substituted with one or more groups independently selected from halogen, $(C_1-C_6)$ alkyl, $(C_1-C_6)$haloalkyl, $O(C_1-C_6)$alkyl, $(C_3-C_7)$cycloalkyl, and $O(C_1-C_6)$haloalkyl;

or a salt thereof.

The invention further provides a compound of formula VIII:

VIII

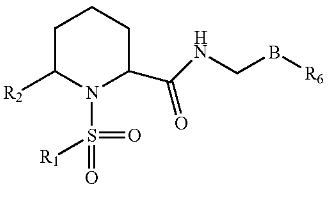

wherein:

B is $B^2$ or $B^3$;

$B^2$ is phenyl, wherein each phenyl is unsubstituted or substituted with one or more groups independently selected from halogen, CN, $(C_1-C_6)$alkyl, and $(C_1-C_6)$haloalkyl;

$B^3$ is a 6-membered heteroaryl, wherein each 6-membered heteroaryl is unsubstituted or substituted with one or more groups independently selected from halogen, $(C_1-C_6)$alkyl, $(C_1-C_6)$haloalkyl, $O(C_1-C_6)$alkyl, $O(C_1-C_6)$haloalkyl, 5 or 6-membered heteroaryl, $(C_3-C_7)$cycloalkyl, and $(C_3-C_7)$heterocyclyl; and wherein any of the 5 or 6-membered heteroaryl, $(C_3-C_7)$cycloalkyl, or $(C_3-C_7)$heterocyclyl groups is unsubstituted or substituted with one or more groups independently selected from halogen, $(C_1-C_6)$alkyl, and $(C_1-C_6)$ haloalkyl;

$R^1$ is phenyl or heteroaryl, wherein each phenyl or heteroaryl is unsubstituted or substituted with one or more groups independently selected from halogen, CN, $(C_1-C_6)$ alkyl, and $(C_1-C_6)$haloalkyl;

$R^2$ is H or $(C_1-C_6)$alkyl;

$R^6$ is a phenyl, $(C_3-C_7)$cycloalkyl, 5- or 6-membered heteroaryl, or 4, 5, 6 or 7-membered heterocycle, wherein any phenyl, $(C_3-C_7)$cycloalkyl, 5- or 6-membered heteroaryl, or 4, 5, 6 or 7-membered heterocycle of $R^6$ is optionally substituted with one or more groups independently selected from halogen, $SF_5$, $(C_1-C_6)$alkyl, $(C_1-C_6)$ haloalkyl, $O(C_1-C_6)$alkyl, and $O(C_1-C_6)$haloalkyl; or $R^6$ is $O—CH_2—R^7$;

$R^7$ is a $(C_1-C_6)$alkyl, 3, 4, 5, 6, or 7-membered heterocycle, 3, 4, 5, 6, or 7-membered cycloalkyl, or 6-membered heteroaryl, wherein any $(C_1-C_6)$alkyl, 3, 4, 5, 6, or 7-membered heterocycle, 3, 4, 5, 6, or 7-membered cycloalkyl, or 6-membered heteroaryl is optionally substituted with one or more groups independently selected from halogen, $(C_1-C_6)$ alkyl, $(C_1-C_6)$haloalkyl, $O(C_1-C_6)$alkyl, $(C_3-C_7)$cycloalkyl, and $O(C_1-C_6)$haloalkyl;

or a salt thereof.

The invention further provides a compound of formula IX:

IX

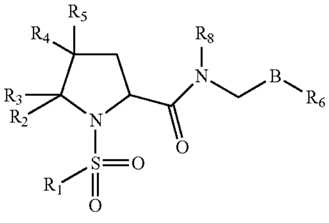

wherein:

B is $B^1$, $B^2$, or $B^3$;

$B^1$ is a 5-membered heteroaryl comprising 2 nitrogen atoms in the ring, wherein each 5-membered heteroaryl is unsubstituted or substituted with one or more groups independently selected from halogen, CN, $(C_1-C_6)$alkyl, $(C_1-C_6)$ haloalkyl, $O(C_1-C_6)$alkyl, and $O(C_1-C_6)$haloalkyl;

$B^2$ is phenyl, wherein each phenyl is unsubstituted or substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

$B^3$ is 6-membered heteroaryl, wherein each 6-membered heteroaryl is unsubstituted or substituted with one or more groups independently selected from halogen, CN, $(C_1-C_6)$ alkyl, $(C_1-C_6)$haloalkyl, $O(C_1-C_6)$alkyl, $O(C_1-C_6)$haloalkyl, 5 or 6-membered heteroaryl, $(C_3-C_7)$cycloalkyl, and 4, 5, 6, or 7-membered heterocyclyl; and wherein any of the 5 or 6-membered heteroaryl, $(C_3-C_7)$cycloalkyl, or 4, 5, 6, or 7-membered heterocyclyl groups is unsubstituted or substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

$R^1$ is phenyl or heteroaryl, wherein each phenyl or heteroaryl is unsubstituted or substituted with one or more groups independently selected from halogen, CN, $(C_1-C_6)$alkyl, and $(C_1-C_6)$haloalkyl;

$R^2$ is $(C_1-C_6)$alkyl, $(C_1-C_6)$haloalkyl, or $(C_3-C_7)$cycloalkyl; wherein $(C_1-C_6)$alkyl is optionally substituted with $O(C_1-C_6)$alkyl;

$R^3$ is H or $(C_1-C_6)$alkyl; or $R^2$ and $R^3$ together with the atoms to which they are attached form a $(C_3)$cycloalkyl;

$R^4$ is H, F, or CN;

$R^5$ is H or $(C_1-C_6)$alkyl; or one of $R^2$ and $R^3$ and one of $R^4$ and $R^5$ together with the atoms to which they are attached form a $(C_3)$cycloalkyl;

$R^6$ is phenyl, $(C_3-C_7)$cycloalkyl, 5 or 6-membered heteroaryl, or 4, 5, 6 or 7-membered heterocycle, wherein any phenyl, $(C_3-C_7)$cycloalkyl, 5 or 6-membered heteroaryl, or 4, 5, 6 or 7-membered heterocycle of $R^6$ is optionally substituted with one or more groups independently selected from halogen, CN, $SF_5$, $(C_1-C_6)$alkyl, $(C_1-C_6)$haloalkyl, $O(C_1-C_6)$alkyl, or $O(C_1-C_6)$haloalkyl; or $R^6$ is $O—CH_2—R^7$;

$R^7$ is $(C_1-C_6)$alkyl, 4, 5, 6, or 7-membered heterocycle, $(C_3-C_7)$cycloalkyl, or 6-membered heteroaryl, wherein any $(C_1-C_6)$alkyl, 4, 5, 6, or 7-membered heterocycle, $(C_3-C_7)$cycloalkyl, or 6-membered heteroaryl is optionally substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

$R^8$ is $CH_2OPO_3Na_2$; $C(=O)OCH_2OPO_3Na_2$; $C(=O)OCH_2OC(=O)CHCHC(=O)OH$; or $C(=O)OCH_2OC(=O)CHCHC(=O)ONa$;

or a salt thereof.

The invention also provides pharmaceutical compositions comprising the compounds, methods of using the compounds, and methods of preparing the compounds.

DETAILED DESCRIPTION OF THE INVENTION

Definitions

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables $R^1$ to $R^5$ of formula I refer to moieties that are attached to the core structure of formula I by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" refers to the fact that one or more hydrogen atoms of a lower alkyl (as defined below) is replaced by one or more halogen atoms (e.g., trifluoromethyl, difluoromethyl, fluoromethyl, chloromethyl, etc.).

The term "alkyl" refers to an aliphatic straight-chain or branched-chain saturated hydrocarbon moiety having 1 to 20 carbon atoms. In particular embodiments the alkyl has 1 to 10 carbon atoms. In particular embodiments the alkyl has 1 to 6 carbon atoms.

The term "alkoxy" denotes a group of the formula —O—R', wherein R' is an alkyl group. Examples of alkoxy moieties include methoxy, ethoxy, isopropoxy, and tert-butoxy.

"Aryl" means a cyclic aromatic hydrocarbon moiety having a mono-, bi- or tricyclic aromatic ring of 6 to 16 carbon ring atoms. The aryl group can be optionally substituted as defined herein. Examples of aryl moieties include, but are not limited to, phenyl, naphthyl, phenanthryl, fluorenyl, indenyl, pentalenyl, azulenyl, and the like, The term "aryl" also includes partially hydrogenated derivatives of the cyclic aromatic hydrocarbon moiety provided that at least one ring of the cyclic aromatic hydrocarbon moiety is aromatic, each being optionally substituted. In one embodiment the aryl has 6 to 14 carbon ring atoms (i.e., $(C_6-C_{14})$aryl). In another embodiment the aryl has 6 to 10 carbon ring atoms (i.e., $(C_6-C_{10})$aryl).

The term "heteroaryl" denotes an aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The terms "halo", "halogen" and "halide", which may be used interchangeably, refer to a substituent fluoro, chloro, bromo, or iodo.

The term "haloalkyl" denotes an alkyl group wherein one or more of the hydrogen atoms of the alkyl group has been replaced by the same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl.

"Cycloalkyl" means a saturated or partially unsaturated carbocyclic moiety having mono- or bicyclic (including bridged bicyclic) rings and 3 to 10 carbon atoms in the ring. The cycloalkyl moiety can optionally be substituted with one or more substituents. In particular embodiments cycloalkyl contains from 3 to 8 carbon atoms (i.e., $(C_3-C_8)$cycloalkyl). In other particular embodiments cycloalkyl contains from 3 to 6 carbon atoms (i.e., $(C_3-C_6)$cycloalkyl). Examples of cycloalkyl moieties include, but are not limited to, cyclopropyl, cyclobutyl, cyclopentyl, cyclohexyl, cycloheptyl, and partially unsaturated (cycloalkenyl) derivatives thereof (e.g. cyclopentenyl, cyclohexenyl, and cycloheptenyl). The cycloalkyl moiety can be attached in a "spirocycloakyl" fashion such as "spirocyclopropyl":

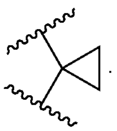

"Heterocycle" or "heterocyclyl" refers to a 4, 5, 6 and 7-membered monocyclic or 7, 8, 9 and 10-membered bicyclic (including bridged bicyclic) heterocyclic moiety that is saturated or partially unsaturated, and has one or more (e.g., 1, 2, 3 or 4 heteroatoms selected from oxygen, nitrogen and sulfur in the ring with the remaining ring atoms being carbon. In particular embodiments heterocycle or heterocyclyl refers to a 4, 5, 6 or 7-membered heterocycle. When used in reference to a ring atom of a heterocycle, a nitrogen or sulfur may also be in an oxidized form, and a nitrogen may be substituted with one or more ($C_1$-$C_6$)alkyl or groups. The heterocycle can be attached to its pendant group at any heteroatom or carbon atom that results in a stable structure and any of the ring atoms can be optionally substituted. Examples of such saturated or partially unsaturated heterocycles include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The term the term heterocycle also includes groups in which a heterocycle is fused to one or more aryl, heteroaryl, or cycloalkyl rings, such as indolinyl, 3H-indolyl, chromanyl, 2-azabicyclo[2.2.1]heptanyl, octahydroindolyl, or tetrahydroquinolinyl.

Unless otherwise indicated, the term "hydrogen" or "hydro" refers to the moiety of a hydrogen atom (—H) and not $H_2$.

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. Another embodiment provides non-pharmaceutically acceptable salts of a compound of formula I, which can be useful as an intermediate for isolating or purifying a compound of formula I. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula I.

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". In certain embodiments the compound is enriched by at least about 90% by weight with a single diastereomer or enantiomer. In other embodiments the compound is enriched by at least about 95%, 98%, or 99% by weight with a single diastereomer or enantiomer.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. In some instances, the stereochemistry has not been determined or has been provisionally assigned. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative, and depicted in Tables 1 and 2 structures for illustrative purposes, while stereochemistry is definitively established, such as from x-ray crystallographic data.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Compounds

In one aspect the present invention provides for compounds of formula I as described herein below as a first embodiment of the invention (embodiment "E1"):

E1: A compound of formula I:

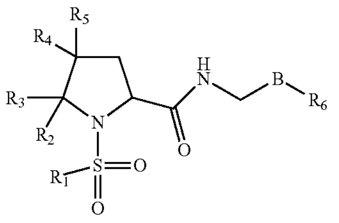

I wherein:

B is $B^1$, $B^2$, or $B^3$;

$B^1$ is a 5-membered heteroaryl comprising 2 nitrogen atoms in the ring, wherein each 5-membered heteroaryl is unsubstituted or substituted with one or more groups independently selected from halogen, $(C_1-C_6)$alkyl, $(C_1-C_6)$haloalkyl, $O(C_1-C_6)$alkyl, and $O(C_1-C_6)$haloalkyl;

$B^2$ is phenyl, wherein each phenyl is unsubstituted or substituted with one or more groups independently selected from halogen, CN, $(C_1-C_6)$alkyl, and $(C_1-C_6)$haloalkyl;

$B^3$ is a 6-membered heteroaryl, wherein each 6-membered heteroaryl is unsubstituted or substituted with one or more groups independently selected from halogen, $(C_1-C_6)$alkyl, $(C_1-C_6)$haloalkyl, $O(C_1-C_6)$alkyl, $O(C_1-C_6)$haloalkyl, 5 or 6-membered heteroaryl, $(C_3-C_7)$cycloalkyl, and $(C_3-C_7)$heterocyclyl; and wherein any of the 5 or 6-membered heteroaryl, $(C_3-C_7)$cycloalkyl, or $(C_3-C_7)$heterocyclyl groups is unsubstituted or substituted with one or more groups independently selected from halogen, $(C_1-C_6)$alkyl, and $(C_1-C_6)$ haloalkyl;

$R^1$ is phenyl or heteroaryl, wherein each phenyl or heteroaryl is unsubstituted or substituted with one or more groups independently selected from halogen, $(C_1-C_6)$alkyl, and $(C_1-C_6)$haloalkyl;

$R^2$ is $(C_1-C_6)$alkyl, $(C_1-C_6)$haloalkyl, or $(C_3-C_7)$cycloalkyl;

$R^3$ is H or $(C_1-C_6)$alkyl; or $R^2$ and $R^3$ together with the atoms to which they are attached form a $(C_3)$cycloalkyl;

$R^4$ is H, F, or CN;

$R^5$ is H or $(C_1-C_6)$alkyl; or one of $R^2$ and $R^3$ and one of $R^4$ and $R^5$ together with the atoms to which they are attached form a $(C_3)$cycloalkyl;

$R^6$ is a 6-membered heteroaryl or 4, 5, 6 or 7-membered heterocycle, wherein any 6-membered heteroaryl or 4, 5, 6 or 7-membered heterocycle of $R^6$ is optionally substituted with one or more groups independently selected from halogen, $(C_1-C_6)$alkyl, $(C_1-C_6)$haloalkyl, and $O(C_1-C_6)$alkyl; or $R^6$ is O—$CH_2$—$R^7$;

$R^7$ is a 6-membered heteroaryl, wherein any 6-membered heteroaryl is optionally substituted with one or more groups independently selected from halogen, $(C_1-C_6)$alkyl, and $(C_1-C_6)$haloalkyl;

or a salt thereof.

Additional embodiments of the invention are set forth below.

E2: The compound of E1, wherein the compound is of formula II:

II

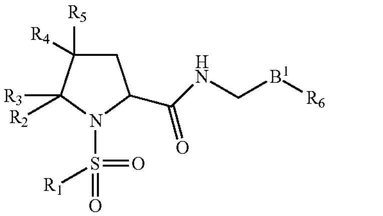

wherein:

$B^1$ is a 5-membered heteroaryl comprising 2 nitrogen atoms in the ring, wherein each 5-membered heteroaryl is unsubstituted or substituted with one or more groups independently selected from halogen, $(C_1-C_6)$alkyl, $(C_1-C_6)$haloalkyl, $O(C_1-C_6)$alkyl, and $O(C_1-C_6)$haloalkyl;

$R^1$ is phenyl or heteroaryl, wherein each phenyl or heteroaryl is unsubstituted or substituted with one or more groups independently selected from halogen, $(C_1-C_6)$alkyl, and $(C_1-C_6)$haloalkyl;

$R^2$ is $(C_1-C_6)$alkyl, $(C_1-C_6)$haloalkyl, or $(C_3-C_7)$cycloalkyl;

$R^3$ is H or $(C_1-C_6)$alkyl; or $R^2$ and $R^3$ together with the atoms to which they are attached form a $(C_3)$cycloalkyl;

$R^4$ is H, F, or CN;

$R^5$ is H or $(C_1-C_6)$alkyl; or one of $R^2$ and $R^3$ and one of $R^4$ and $R^5$ together with the atoms to which they are attached form a $(C_3)$cycloalkyl;

$R^6$ is a 6-membered heteroaryl or 4, 5, 6 or 7-membered heterocycle, wherein any 6-membered heteroaryl or 4, 5, 6 or 7-membered heterocycle of $R^6$ is optionally substituted with one or more groups independently selected from halogen, $(C_1-C_6)$alkyl, $(C_1-C_6)$haloalkyl, and —$O(C_1-C_6)$alkyl;

or a salt thereof.

E3: The compound of any one of E1 or E2, wherein $B^1$ is unsubstituted or substituted pyrazolyl.

E4: The compound of any one of E1-E3, wherein $B^1$ is:

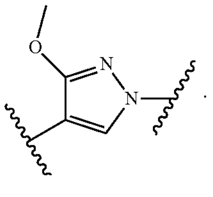 [SMILES: *c1cn(*)nc1OC]

E5: The compound of any one of E1-E3, wherein $B^1$ is:

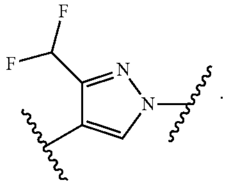 [SMILES: *c1cn(*)nc1C(F)F]

E6: The compound of any one of E1-E3, wherein $B^1$ is:

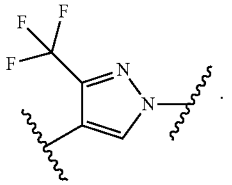 [SMILES: *c1cn(*)nc1C(F)(F)F]

E7: The compound of E1, wherein the compound is of formula III:

III

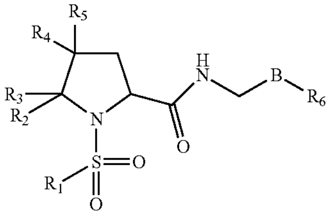

wherein:

B is $B^2$ or $B^3$;

$B^2$ is phenyl, wherein each phenyl is unsubstituted or substituted with one or more groups independently selected from halogen, CN, $(C_1-C_6)$alkyl, and $(C_1-C_6)$haloalkyl;

$B^3$ is a 6-membered heteroaryl, wherein each 6-membered heteroaryl is unsubstituted or substituted with one or more groups independently selected from halogen, $(C_1-C_6)$alkyl, $(C_1-C_6)$haloalkyl, $O(C_1-C_6)$alkyl, $O(C_1-C_6)$haloalkyl, 5 or 6-membered heteroaryl, $(C_3-C_7)$cycloalkyl, and $(C_3-C_7)$heterocyclyl; and wherein any of the 5 or 6-membered heteroaryl, $(C_3-C_7)$cycloalkyl, or $(C_3-C_7)$heterocyclyl groups is unsubstituted or substituted with one or more groups independently selected from halogen, $(C_1-C_6)$alkyl, and $(C_1-C_6)$haloalkyl;

$R^1$ is phenyl or heteroaryl, wherein each phenyl or heteroaryl is unsubstituted or substituted with one or more groups independently selected from halogen, $(C_1-C_6)$alkyl, and $(C_1-C_6)$haloalkyl;

$R^2$ is $(C_1-C_6)$alkyl, $(C_1-C_6)$haloalkyl, or $(C_3-C_7)$cycloalkyl;

$R^3$ is H or $(C_1-C_6)$alkyl; or $R^2$ and $R^3$ together with the atoms to which they are attached form a $(C_3)$cycloalkyl;

$R^4$ is H, F, or CN;

$R^5$ is H or $(C_1-C_6)$alkyl; or one of $R^2$ and $R^3$ and one of $R^4$ and $R^5$ together with the atoms to which they are attached form a $(C_3)$cycloalkyl;

$R^6$ is a 6-membered heteroaryl or 4, 5, 6 or 7-membered heterocycle, wherein any 6-membered heteroaryl or 4, 5, 6 or 7-membered heterocycle of $R^6$ is optionally substituted with one or more groups independently selected from halogen, $(C_1\text{-}C_6)$alkyl, $(C_1\text{-}C_6)$haloalkyl, and —$O(C_1\text{-}C_6)$alkyl; or a salt thereof.

E8: The compound of E7, wherein $B^2$ is unsubstituted or substituted phenyl.

E9: The compound of E7, wherein $B^2$ is:

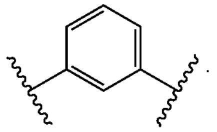 [SMILES: *c1cccc(*)c1]

E10: The compound of E7, wherein $B^2$ is:

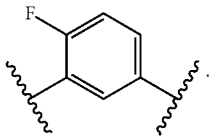 [SMILES: *c1ccc(F)c(*)c1]

E11: The compound of E7, wherein $B^2$ is:

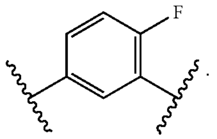 [SMILES: *c1ccc(F)c(*)c1]

E12: The compound of E7, wherein $B^2$ is:

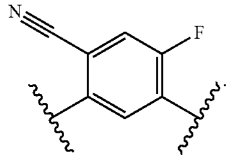

E13: The compound of E7, wherein $B^2$ is:

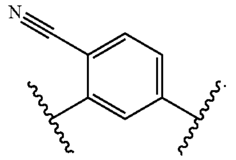

E14: The compound of E7, wherein $B^2$ is:

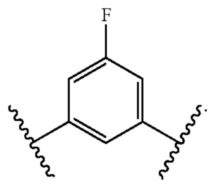 [SMILES: *c1cc(*)cc(F)c1]

E15: The compound of E7, wherein $B^3$ is unsubstituted or substituted 6-membered heteroaryl.

E16: The compound of E15, wherein $B^3$ is:

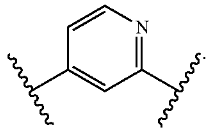 [SMILES: *c1ccnc(*)c1]

E17: The compound of E15, wherein $B^3$ is:

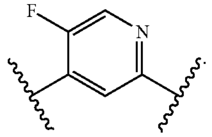 [SMILES: *c1cc(*)c(F)cn1]

E18: The compound of E15, wherein $B^3$ is:

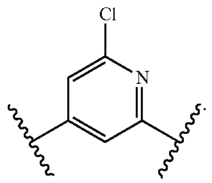 [SMILES: *c1cc(*)nc(Cl)c1]

E19: The compound of E15, wherein $B^3$ is:

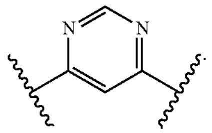 [SMILES: *c1cc(*)ncn1]

E20: The compound of E15, wherein $B^3$ is:

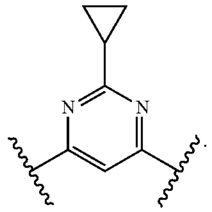

E21: The compound of E15, wherein $B^3$ is:

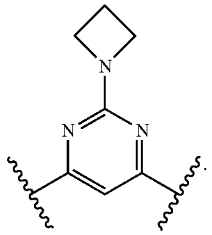 [SMILES: *c1cc(*)nc(N2CCC2)n1]

E22: The compound of E15, wherein $B^3$ is:

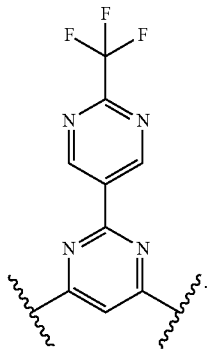 [SMILES: *c1cc(*)nc(-c2cnc(C(F)(F)F)nc2)n1]

E23: The compound of E15, wherein $B^3$ is:

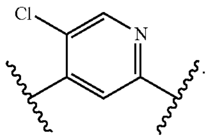

E24: The compound of E15, wherein $B^3$ is:

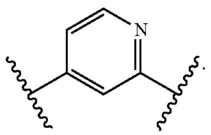 [SMILES: *c1ccnc(*)c1]

E25: The compound of E15, wherein $B^3$ is:

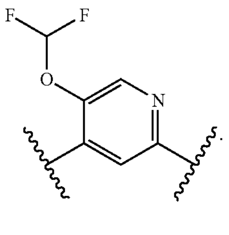 [SMILES: *c1cc(*)c(OC(F)F)cn1]

E26: The compound of E15, wherein $B^3$ is:

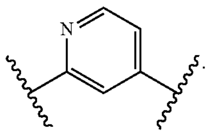 [SMILES: *c1ccnc(*)c1]

E27: The compound of E15, wherein $B^3$ is:

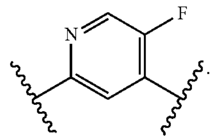 [SMILES: *c1cc(*)c(F)cn1]

E28: The compound of E15, wherein $B^3$ is:

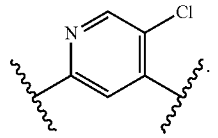 [SMILES: *c1cc(*)c(Cl)cn1]

E29: The compound of E15, wherein $B^3$ is:

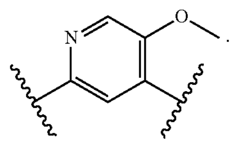 [SMILES: *c1cc(*)c(OC)cn1]

E30: The compound of E1, wherein the compound is of formula IV:

IV

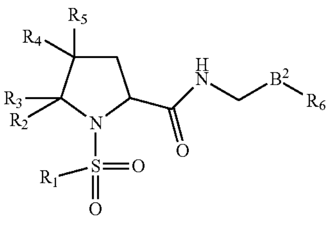

wherein:

$B^2$ is phenyl, wherein each phenyl is unsubstituted or substituted with one or more groups independently selected from halogen, CN, $(C_1-C_6)$alkyl, and $(C_1-C_6)$haloalkyl;

$R^1$ is phenyl or heteroaryl, wherein each phenyl or heteroaryl is unsubstituted or substituted with one or more groups independently selected from halogen, $(C_1-C_6)$alkyl, and $(C_1-C_6)$haloalkyl;

$R^2$ is $(C_1-C_6)$alkyl, $(C_1-C_6)$haloalkyl, or $(C_3-C_7)$cycloalkyl;

$R^3$ is H or $(C_1-C_6)$alkyl; or $R^2$ and $R^3$ together with the atoms to which they are attached form a $(C_3)$cycloalkyl;

$R^4$ is H, F, or CN;

$R^5$ is H or $(C_1-C_6)$alkyl; or one of $R^2$ and $R^3$ and one of $R^4$ and $R^5$ together with the atoms to which they are attached form a $(C_3)$cycloalkyl;

$R^6$ is a 6-membered heteroaryl or 4, 5, 6 or 7-membered heterocycle, wherein any 6-membered heteroaryl or 4, 5, 6 or 7-membered heterocycle of $R^6$ is optionally substituted with one or more groups independently selected from halogen, $(C_1-C_6)$alkyl, $(C_1-C_6)$haloalkyl, and $O(C_1-C_6)$alkyl;

or a salt thereof.

E31: The compound of E30, wherein $B^2$ is:

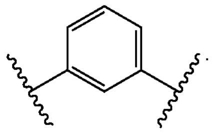 [SMILES: *c1cccc(*)c1]

E32: The compound of E30, wherein $B^2$ is:

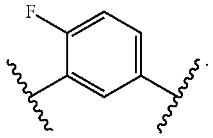

E33: The compound of E30, wherein $B^2$ is:

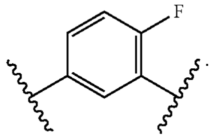

E34: The compound of E30, wherein $B^2$ is:

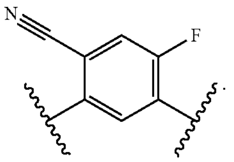 [SMILES: *c1cc(*)c(C#N)cc1F]

E35: The compound of E30, wherein $B^2$ is:

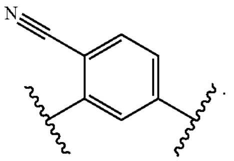 [SMILES: *c1ccc(C#N)c(*)c1]

E36: The compound of E30, wherein $B^2$ is:

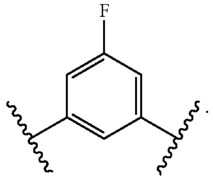 [SMILES: *c1cc(*)cc(F)c1]

E37: The compound of E1, wherein the compound is formula V:

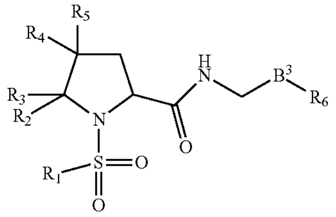

V wherein:

$B^3$ is a 6-membered heteroaryl, wherein each 6-membered heteroaryl is unsubstituted or substituted with one or more groups independently selected from halogen, $(C_1-C_6)$alkyl, $(C_1-C_6)$haloalkyl, $O(C_1-C_6)$alkyl, $O(C_1-C_6)$haloalkyl, 5 or 6-membered heteroaryl, $(C_3-C_7)$cycloalkyl, and $(C_3-C_7)$heterocyclyl; and wherein any of the 5 or 6-membered heteroaryl, $(C_3-C_7)$cycloalkyl, or $(C_3-C_7)$heterocyclyl groups is unsubstituted or substituted with one or more groups independently selected from halogen, $(C_1-C_6)$alkyl, and $(C_1-C_6)$ haloalkyl;

$R^1$ is phenyl or heteroaryl, wherein each phenyl or heteroaryl is unsubstituted or substituted with one or more groups independently selected from halogen, $(C_1-C_6)$alkyl, and $(C_1-C_6)$haloalkyl;

$R^2$ is $(C_1-C_6)$alkyl, $(C_1-C_6)$haloalkyl, or $(C_3-C_7)$cycloalkyl;

$R^3$ is H or $(C_1-C_6)$alkyl; or $R^2$ and $R^3$ together with the atoms to which they are attached form a $(C_3)$cycloalkyl;

$R^4$ is H, F, or CN;

$R^5$ is H or $(C_1-C_6)$alkyl; or one of $R^2$ and $R^3$ and one of $R^4$ and $R^5$ together with the atoms to which they are attached form a $(C_3)$cycloalkyl;

$R^6$ is a 6-membered heteroaryl or 4, 5, 6 or 7-membered heterocycle, wherein any 6-membered heteroaryl or 4, 5, 6 or 7-membered heterocycle of $R^6$ is optionally substituted with one or more groups independently selected from halogen, $(C_1-C_6)$alkyl, $(C_1-C_6)$haloalkyl, and $O(C_1-C_6)$alkyl;

or a salt thereof.

E38: The compound of E37, wherein $B^3$ is:

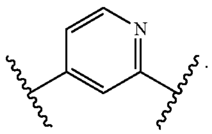

E39: The compound of E37, wherein $B^3$ is:

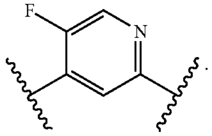 [SMILES: *c1cc(*)c(F)cn1]

E40: The compound of E37, wherein $B^3$ is:

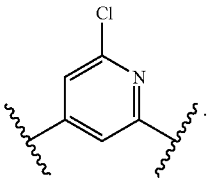 [SMILES: *c1cc(*)nc(Cl)c1]

E41: The compound of E37, wherein $B^3$ is:

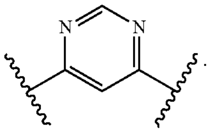 [SMILES: *c1cc(*)ncn1]

E42: The compound of E37, wherein $B^3$ is:

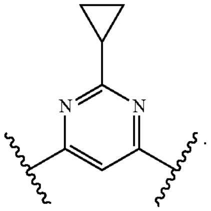 [SMILES: *c1cc(*)nc(C2CC2)n1]

E43: The compound of E37, wherein $B^3$ is:

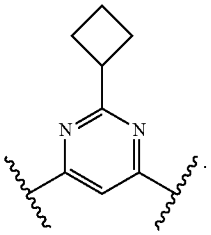 [SMILES: *c1cc(*)nc(C2CCC2)n1]

E44: The compound of E37, wherein $B^3$ is:

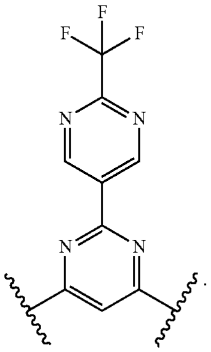 [SMILES: *c1cc(*)nc(-c2cnc(C(F)(F)F)nc2)n1]

E45: The compound of E37, wherein $B^3$ is:

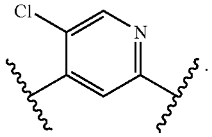 [SMILES: *c1cc(*)c(Cl)cn1]

E46: The compound of E37, wherein $B^3$ is:

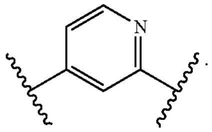 [SMILES: *c1ccnc(*)c1]

E47: The compound of E37, wherein $B^3$ is:

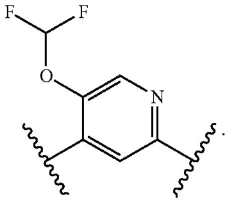 [SMILES: *c1cc(*)c(OC(F)F)cn1]

E48: The compound of E37, wherein $B^3$ is:

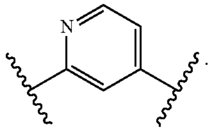 [SMILES: *c1ccnc(*)c1]

E49: The compound of E37, wherein $B^3$ is:

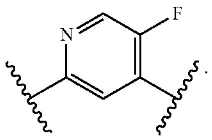 [SMILES: *c1cc(*)c(F)cn1]

E50: The compound of E37, wherein $B^3$ is:

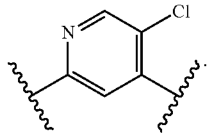

E51: The compound of E37, wherein $B^3$ is:

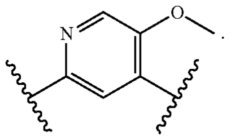 [SMILES: *c1cc(*)c(OC)cn1]

E52: The compound according to any one of E1-51, wherein $R^2$ is $(C_1\text{-}C_6)$alkyl.

E53: The compound according to E52, wherein $R^2$ is $CH_3$.

E54: The compound according to E52, wherein $R^2$ is $CH_2CH_3$.

E55: The compound according to E52, wherein $R^2$ is $C(CH_3)_3$.

E56: The compound according to any one of E1-51, wherein $R^2$ is $(C_1\text{-}C_6)$haloalkyl E57: The compound according to E56, wherein $R^2$ is $C(CF_3)_3$.

E58: The compound according to any one of E1-51, wherein $R^2$ and $R^3$ together with the atoms to which they are attached form a $(C_3)$cycloalkyl.

E59: The compound according to E58, wherein $R^2$ and $R^3$ together with the atoms to which they are attached form spirocyclopropyl.

E60: The compound according to any one of E1-57, wherein $R^3$ is H.

E61: The compound according to any one of E1-57, wherein one of $R^2$ and $R^3$ and one of $R^4$ and $R^5$ together with the atoms to which they are attached form a $(C_3)$cycloalkyl.

E62: The compound according to any one of E1-61, wherein $R^4$ is H.

E63: The compound according to any one of E1-61, wherein $R^4$ is F.

E64: The compound according to any one of E1-61, wherein $R^4$ is CN.

E65: The compound according to any one of E1-61, wherein $R^5$ is H.

E66: The compound according to any one of E1-51, wherein the group

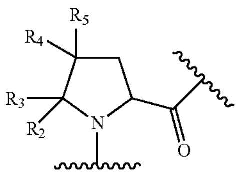

is:

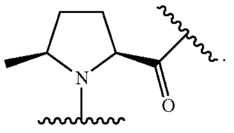 [SMILES: *C(=O)[C@@H]1CC[C@H](C)N1*]

E67: The compound according to any one of E1-51, wherein the group

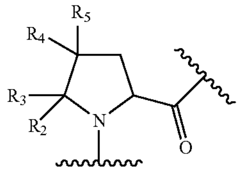

is:

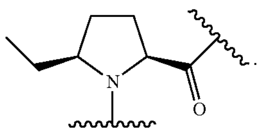 [SMILES: *C(=O)[C@@H]1CC[C@H](CC)N1*]

E68: The compound according to any one of E1-51, wherein the group

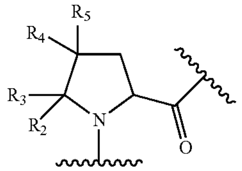

is:

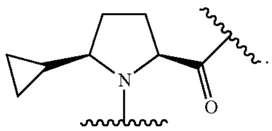 [SMILES: *C(=O)[C@@H]1CC[C@H](C2CC2)N1*]

E69: The compound according to any one of E1-51, wherein the group

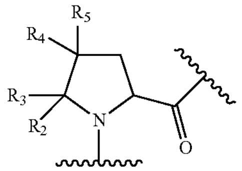

is:

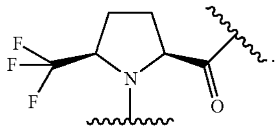 [SMILES: *C(=O)[C@@H]1CC[C@H](C(F)(F)F)N1*]

E70: The compound according to any one of E1-51, wherein the group

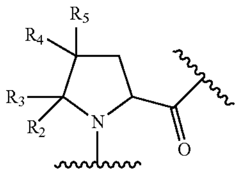

is:

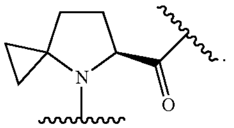 [SMILES: *C(=O)[C@@H]1CCC2(CC2)N1*]

E71: The compound according to any one of E1-51, wherein the group

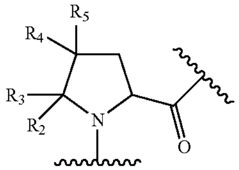

is:

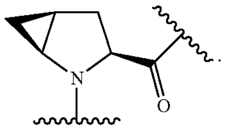 [SMILES: *C(=O)[C@@H]1C[C@@H]2C[C@@H]2N1*]

E72: The compound according to any one of E1-51, wherein the group

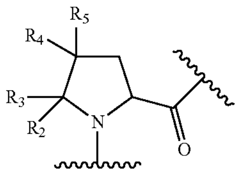

is:

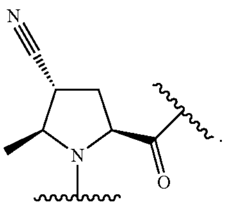

E73: The compound according to any one of E1-51, wherein the group

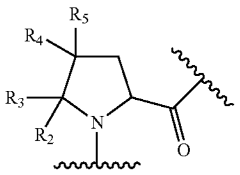

is:

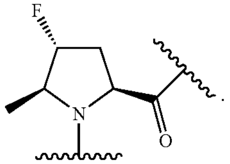

E74: The compound according to any one of E1-73, wherein $R^6$ is 6-membered heteroaryl.

E75: The compound according to E74, wherein $R^6$ ispyridinyl.

E76: The compound according to E75, wherein $R^6$ is:

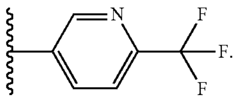

E77: The compound according to E75, wherein $R^6$ is:

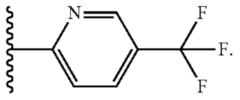 [SMILES: *c1ccc(C(F)(F)F)cn1]

E78: The compound according to E74, wherein $R^6$ is pyrimidinyl.

E79: The compound according to E78, wherein $R^6$ is:

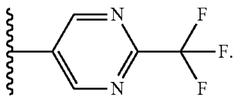

E80: The compound according to any one of E1-79, wherein $R^6$ is 4, 5, 6 or 7-membered heterocycle.

E81: The compound according to any one of E80, wherein $R^6$ is 4-membered heterocycle.

E82: The compound according to any one of E81, wherein $R^6$ is:

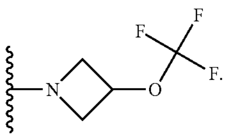 [SMILES: *N1CC(OC(F)(F)F)C1]

E83: The compound according to any one of E80, wherein $R^6$ is 5-membered heterocycle.
E84: The compound according to any one of E80, wherein $R^6$ is 6-membered heterocycle
E85: The compound according to any one of E80, wherein $R^6$ is 7-membered heterocycle.
E86: The compound according to E1, which is:
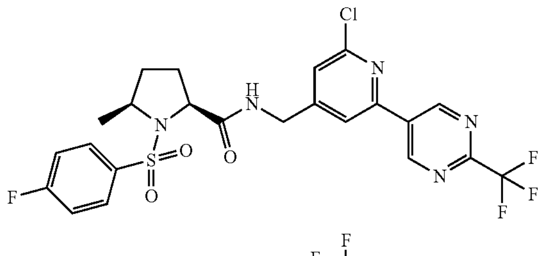
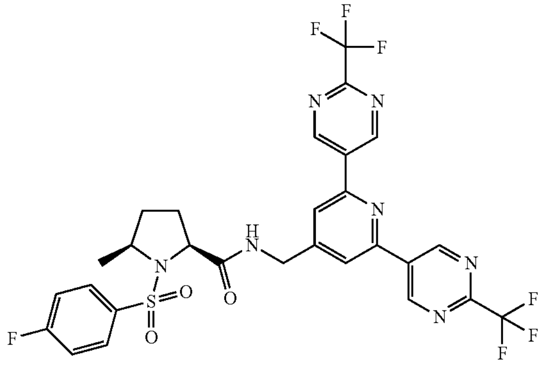
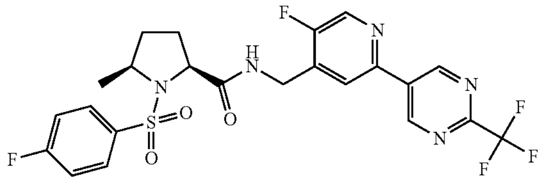
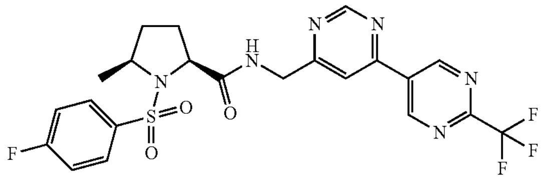
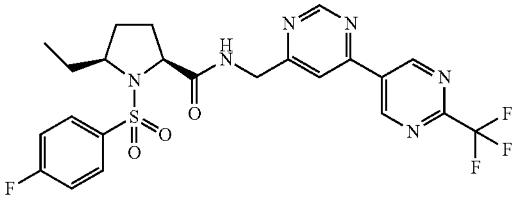
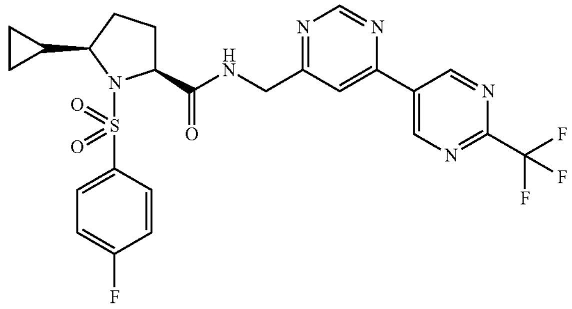
-continued
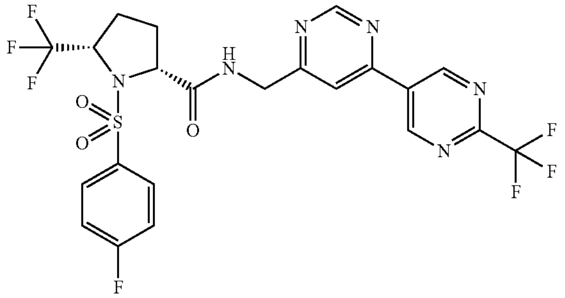
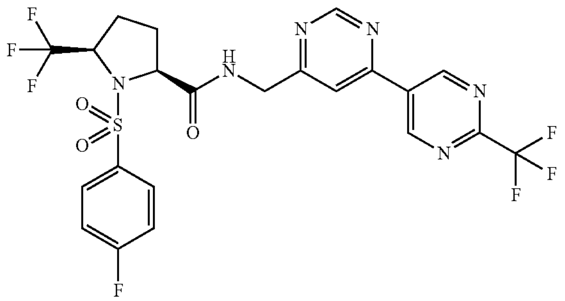
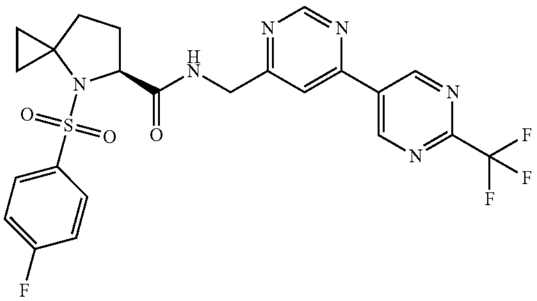
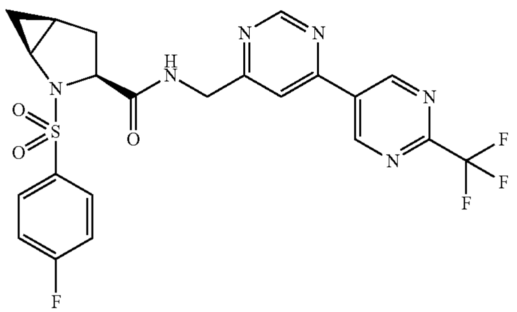
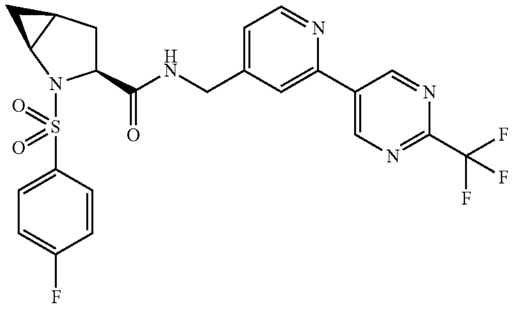

-continued
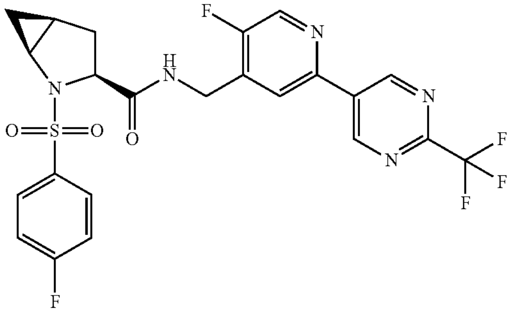
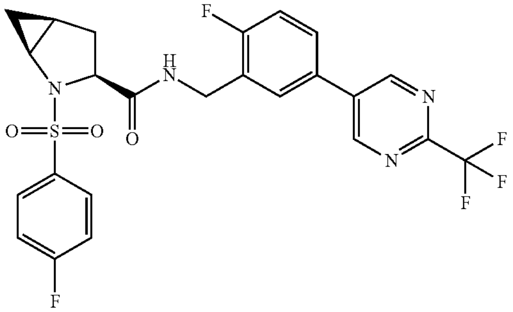
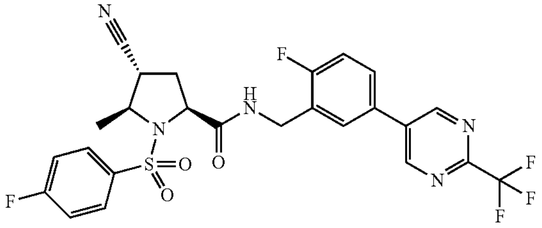
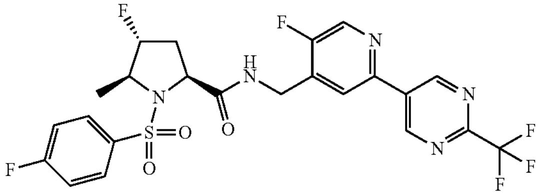
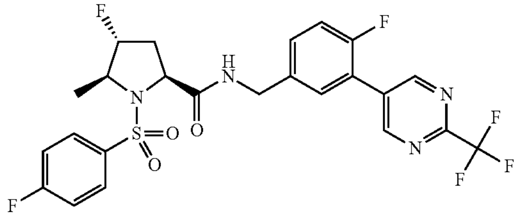
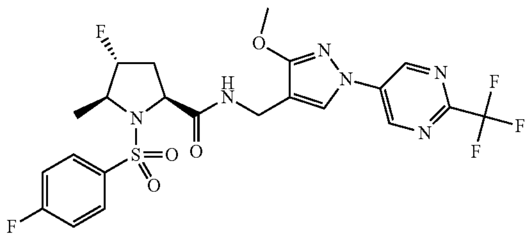
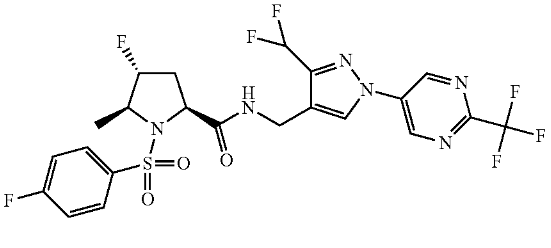
-continued
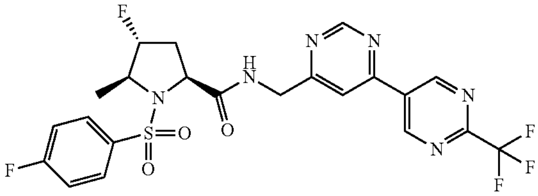
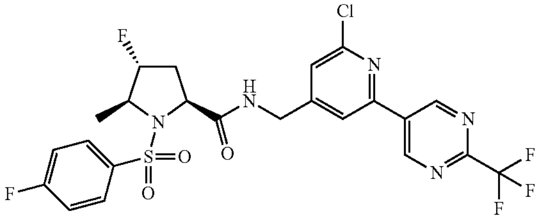
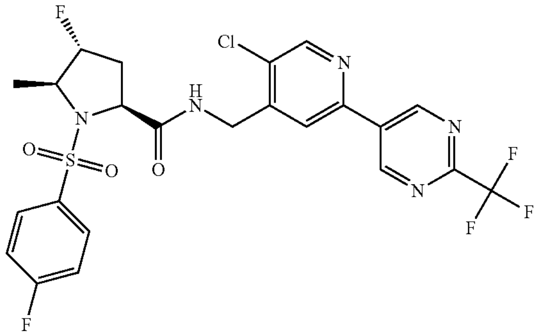
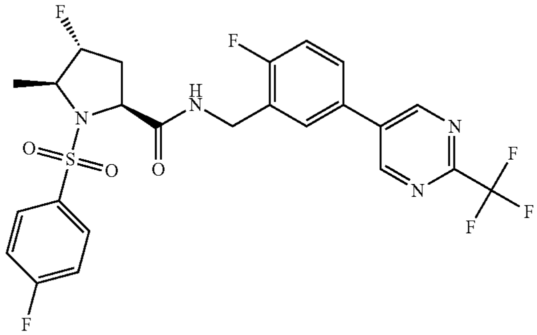
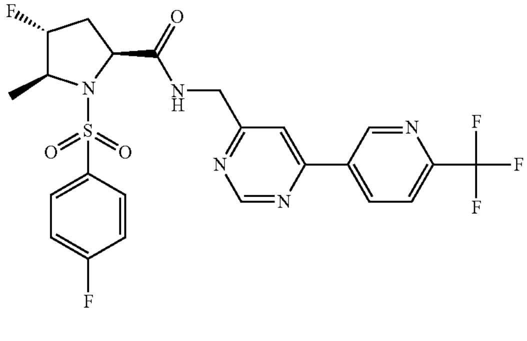

-continued
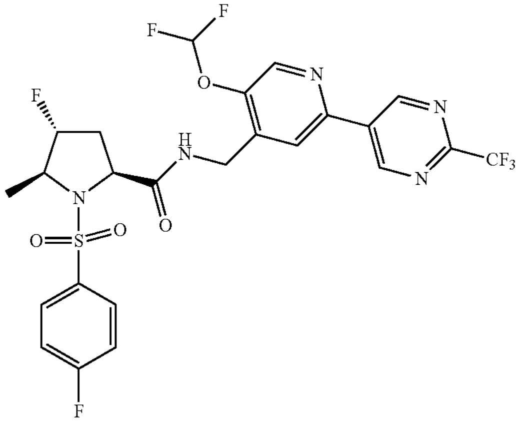
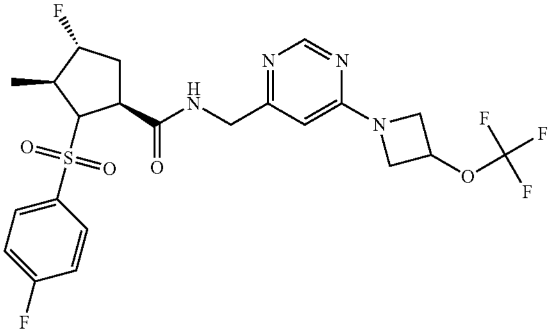
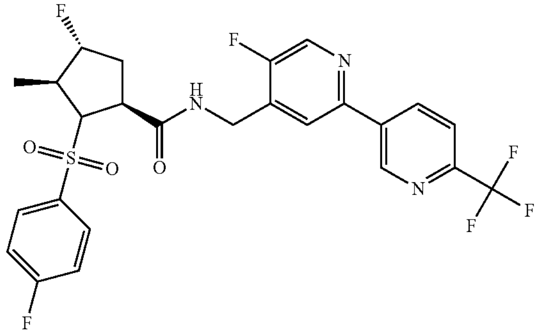
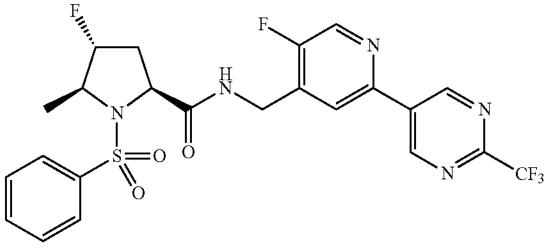
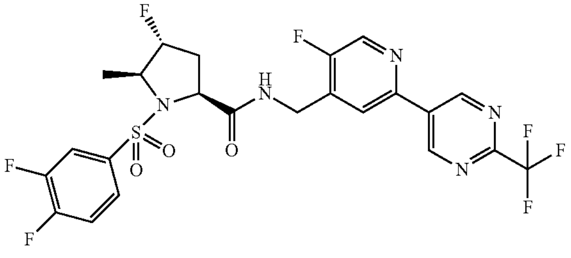
-continued
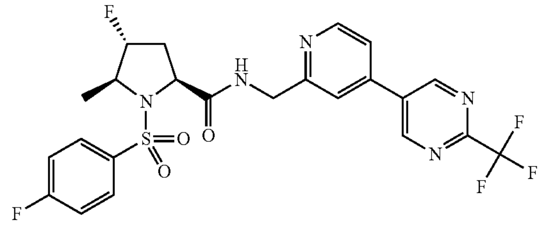
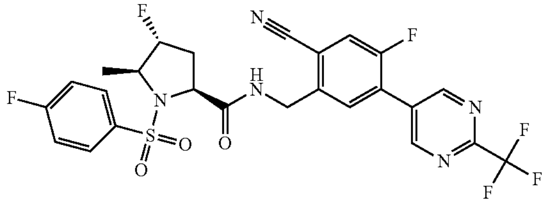
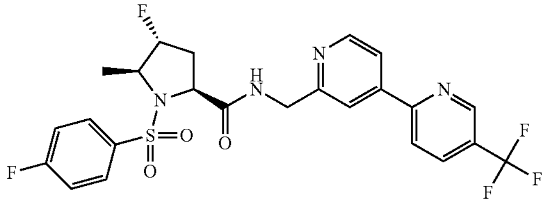
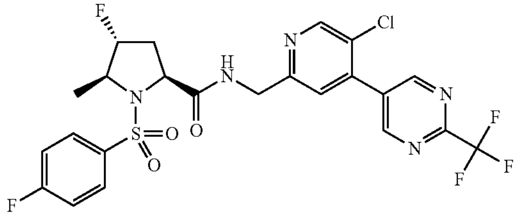
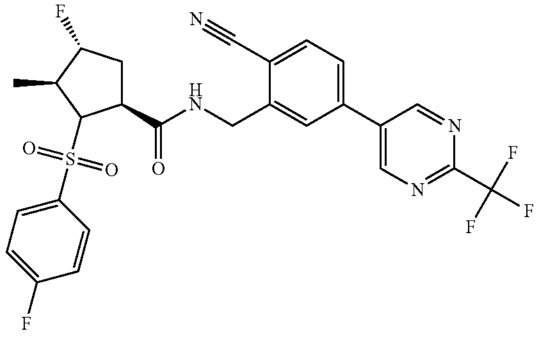
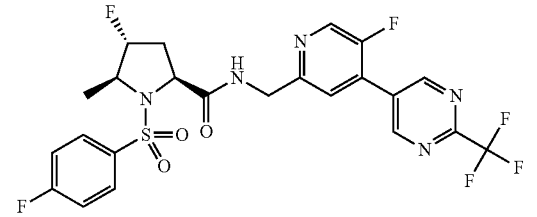
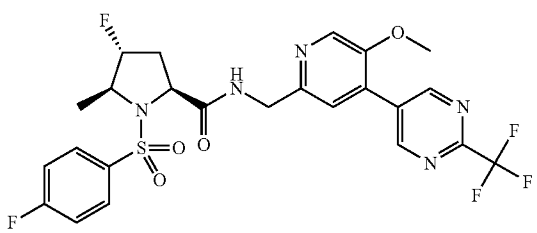

-continued
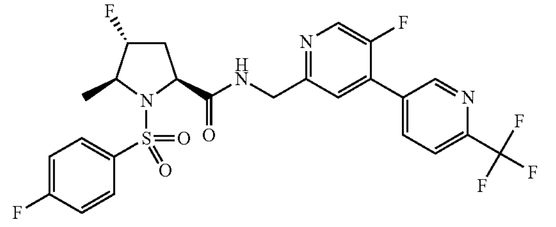
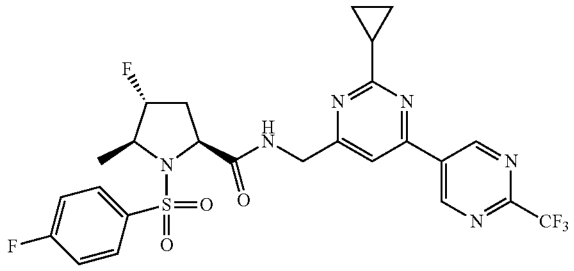
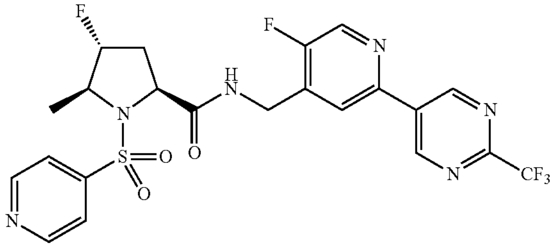
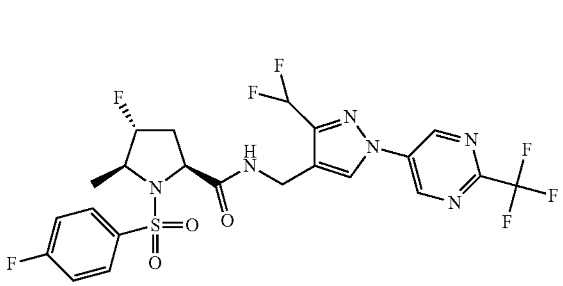
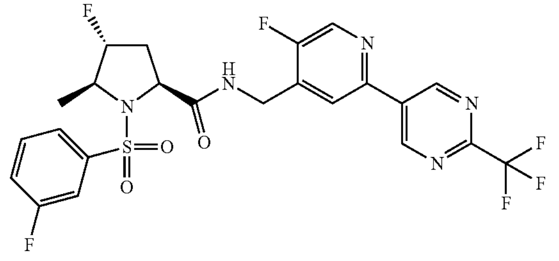
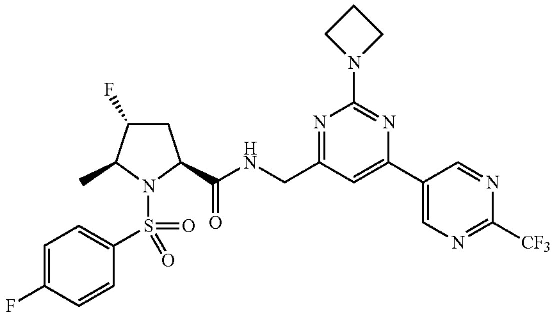
-continued
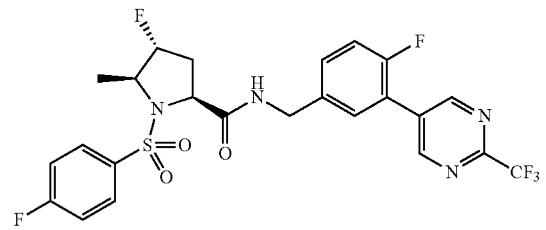
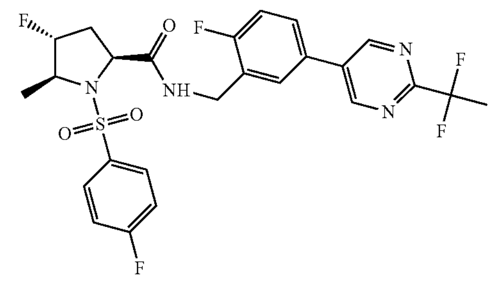
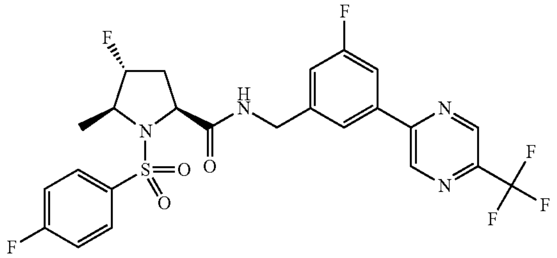
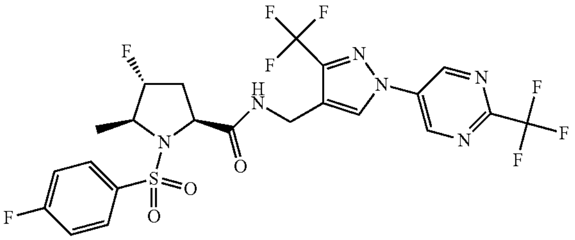
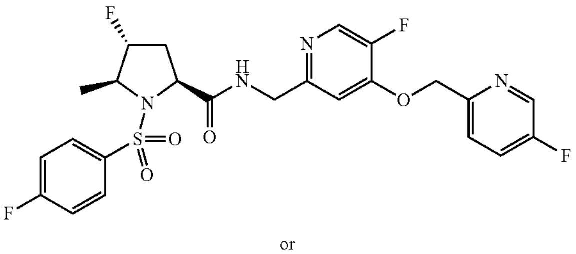
or
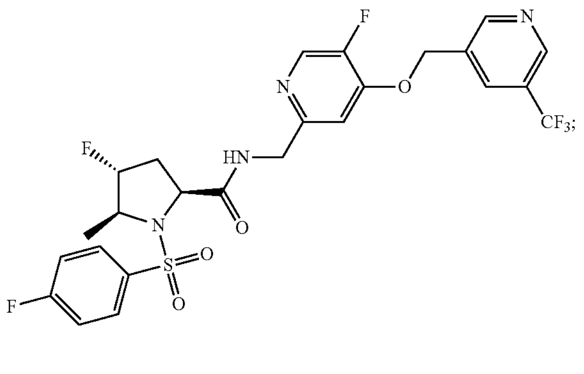
or a salt thereof.

E87: The compound according to E2, which is:
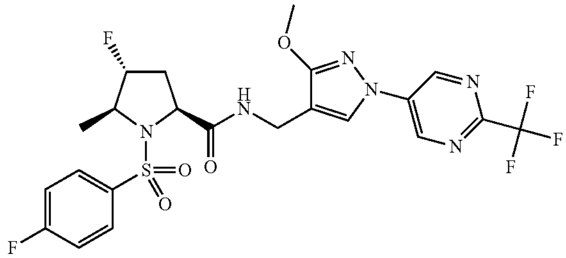
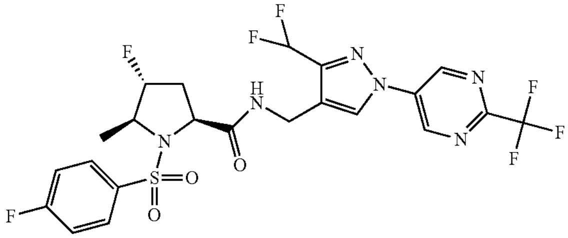
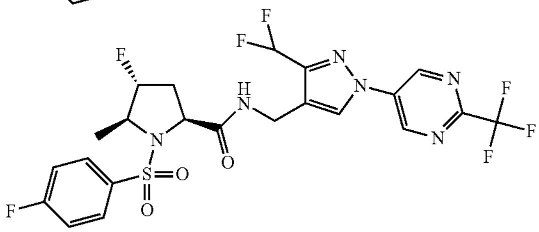
or
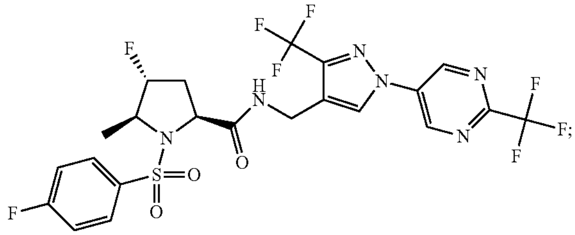
;
or a salt thereof.
E88: The compound according to E7, which is:
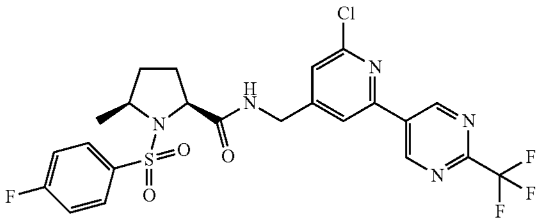
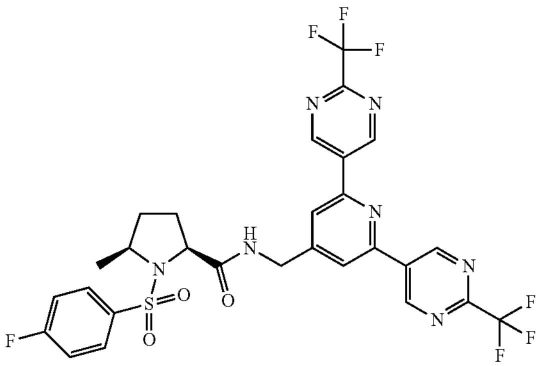
-continued
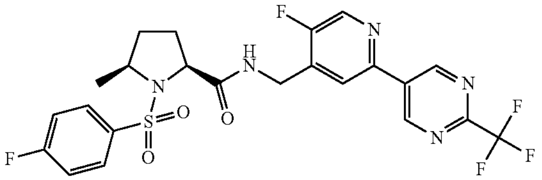
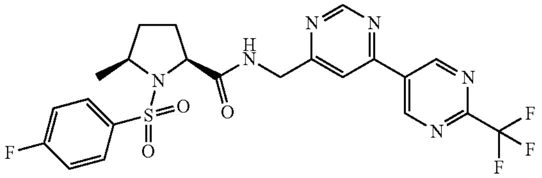
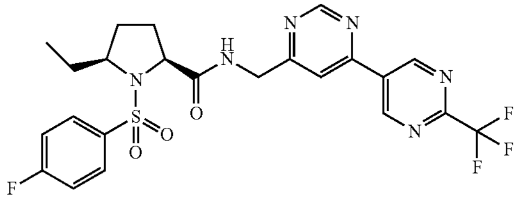
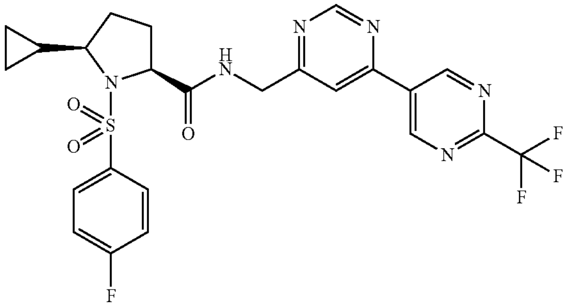
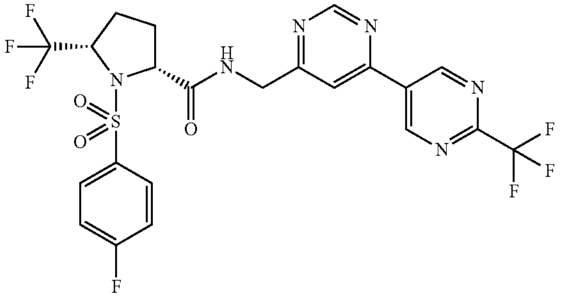
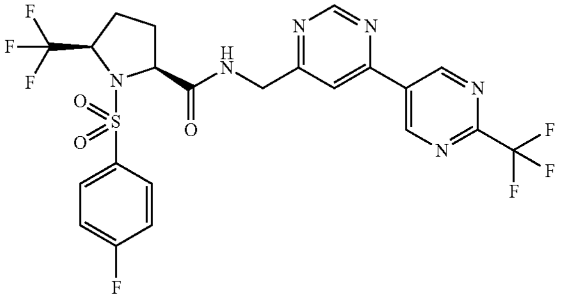

-continued
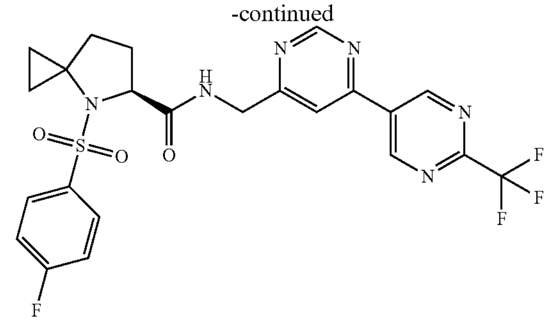
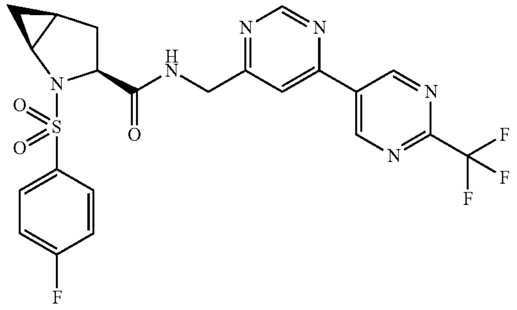
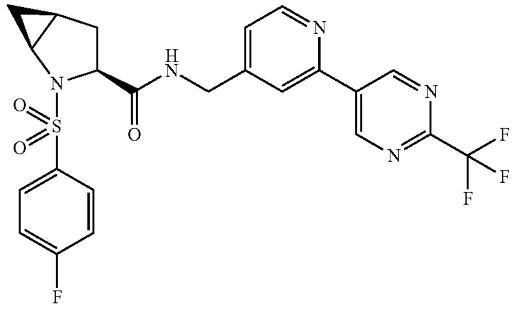
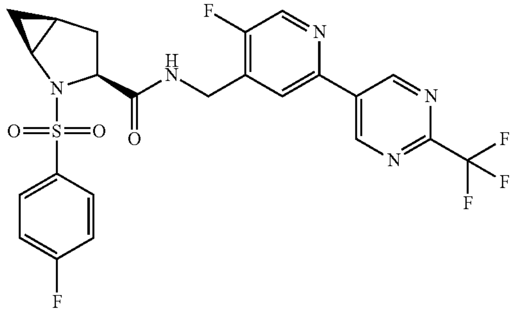
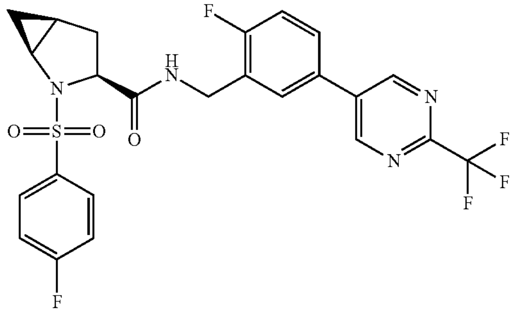
-continued
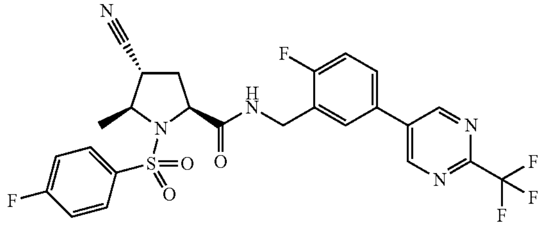
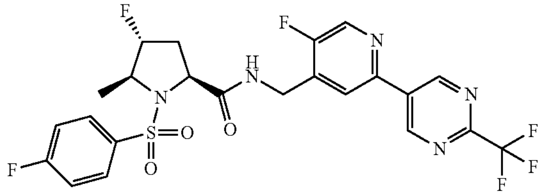
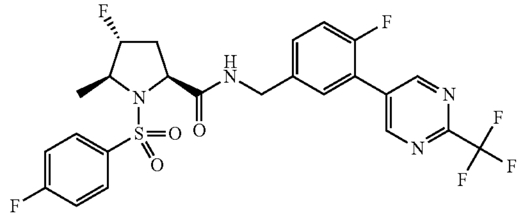
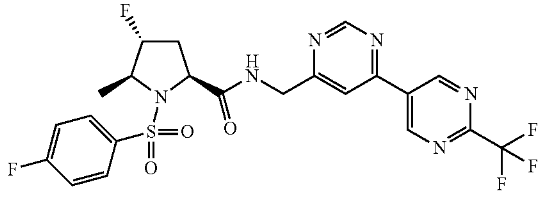
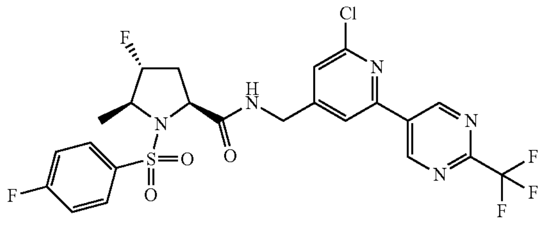
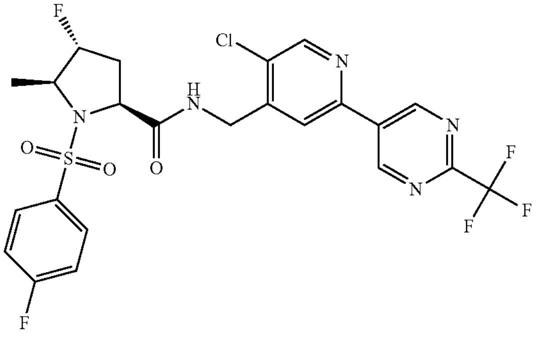
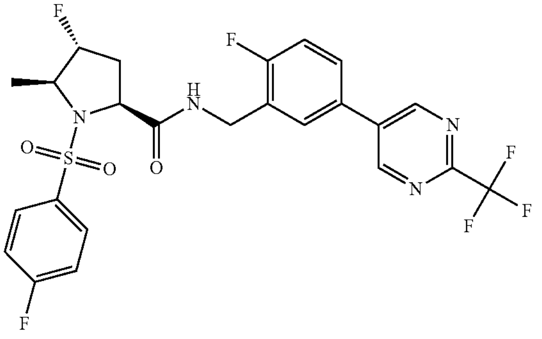

-continued
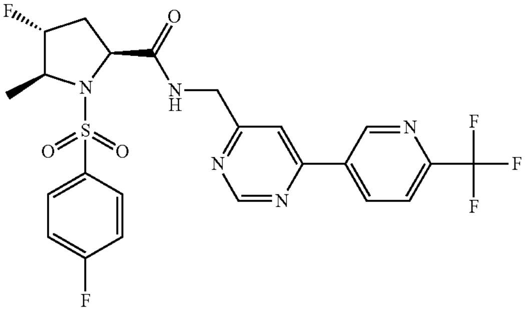
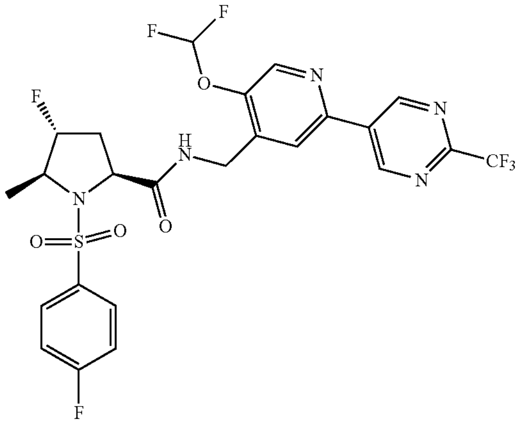
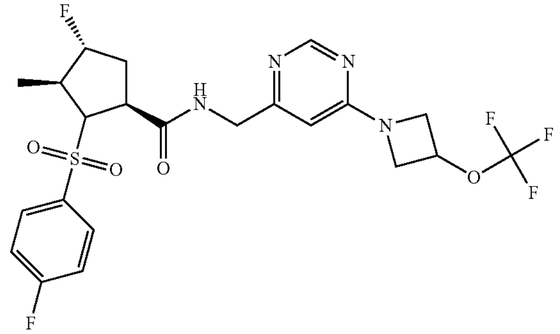
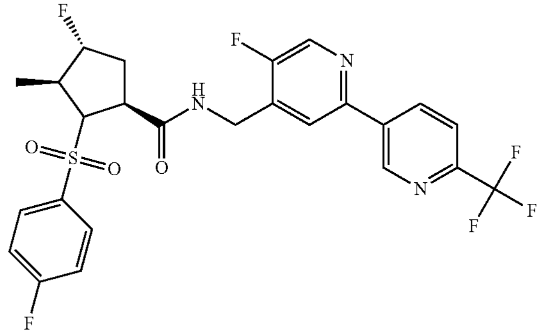
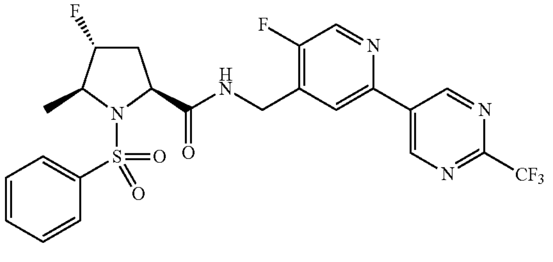
-continued
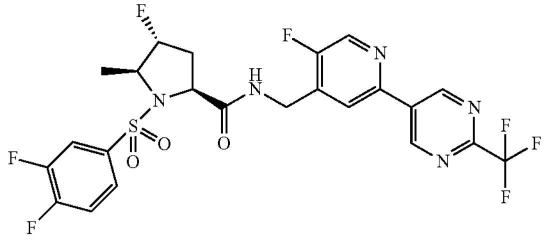
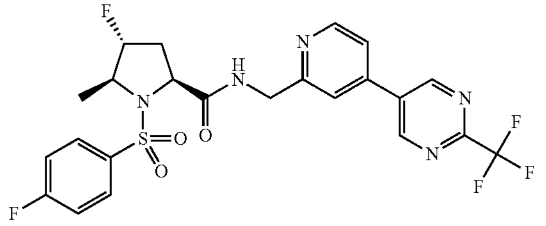
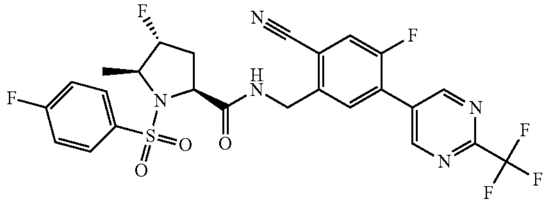
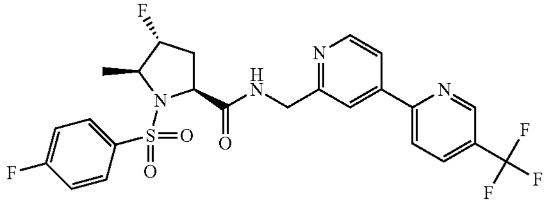
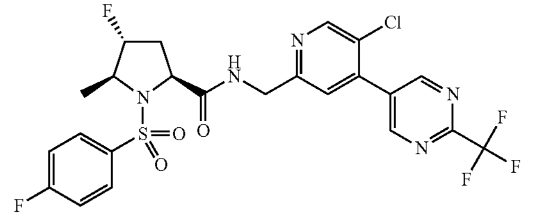
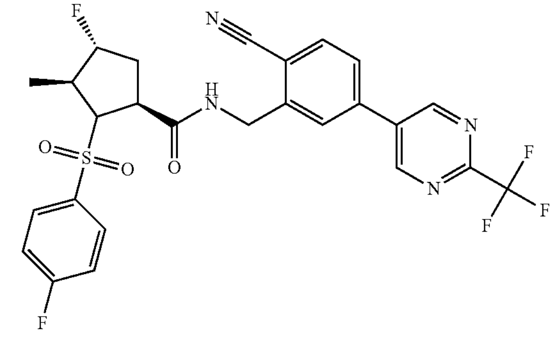
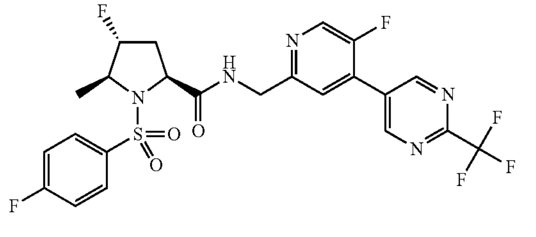

-continued
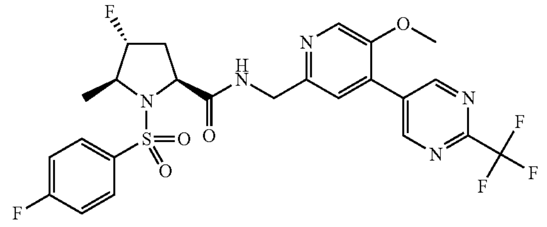
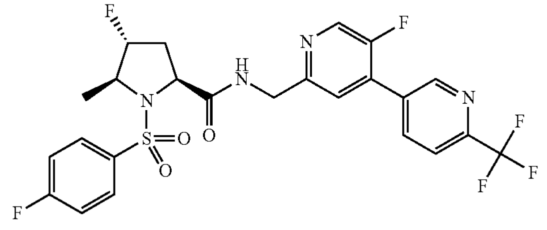
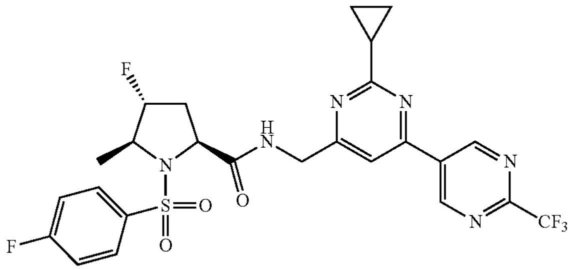
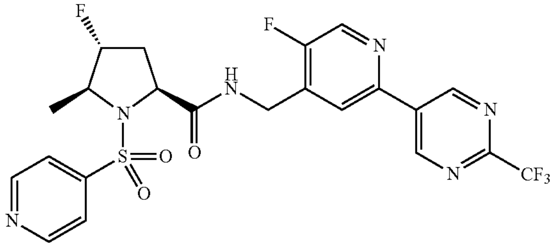
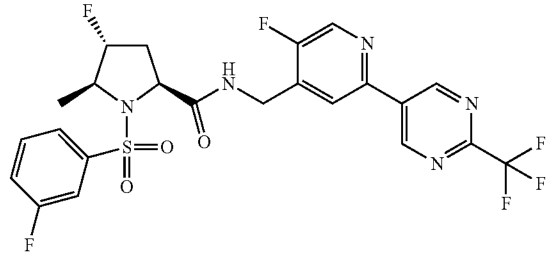
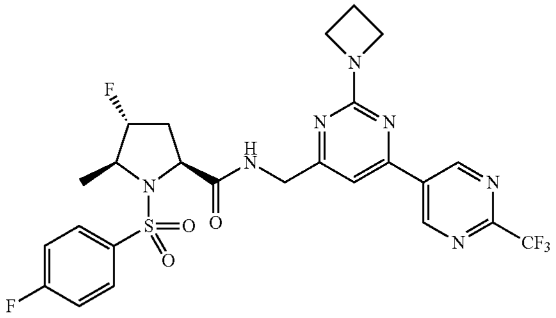
-continued
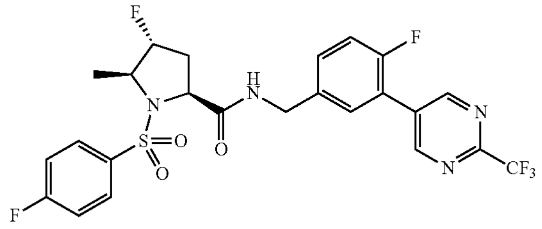
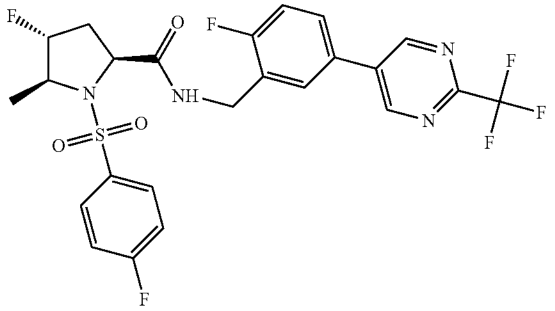
or
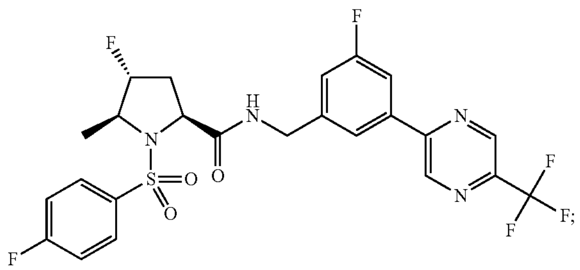
or a salt thereof.
E89: The compound according to E30, which is:
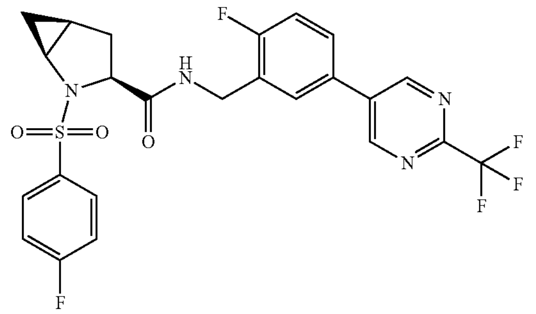
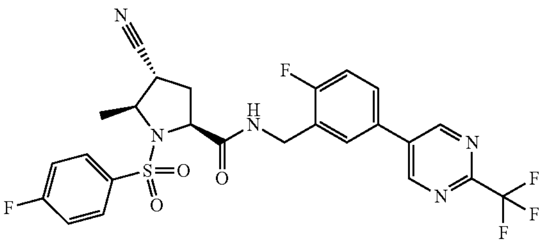

-continued
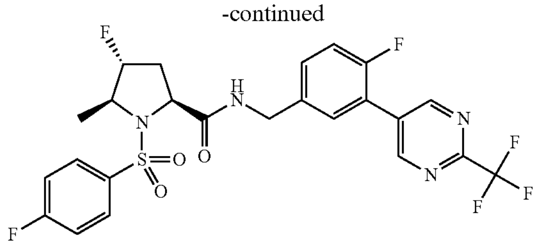
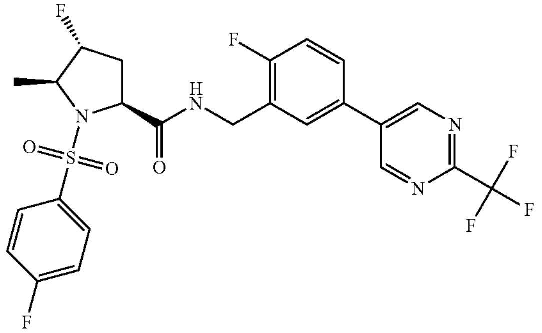
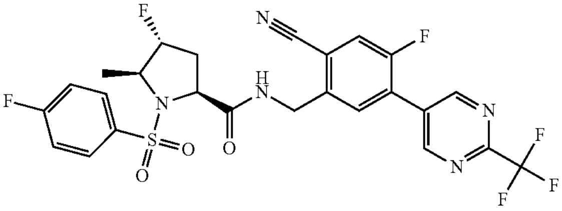
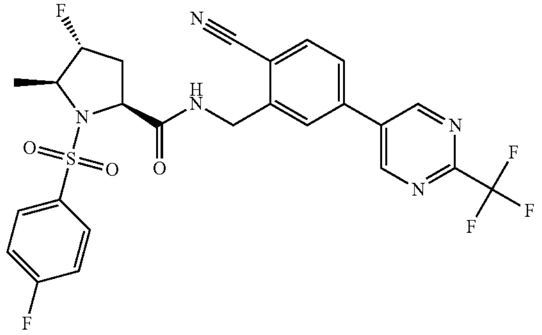
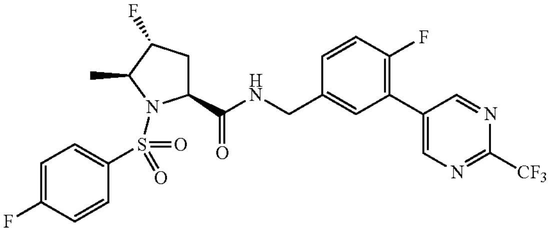
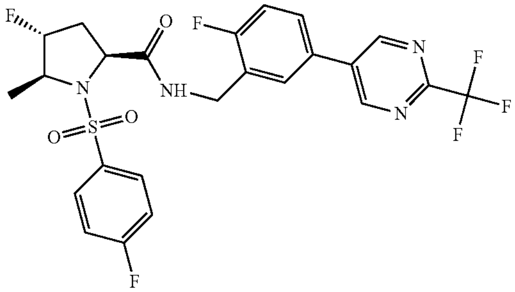
or
-continued
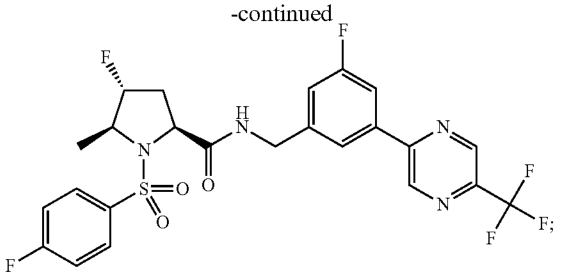
or a salt thereof.
E90: The compound according to E37, which is:
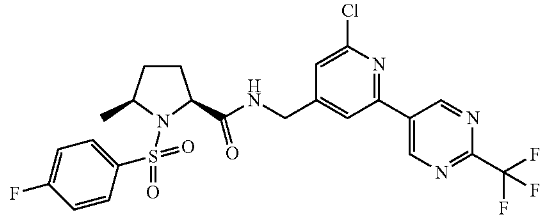
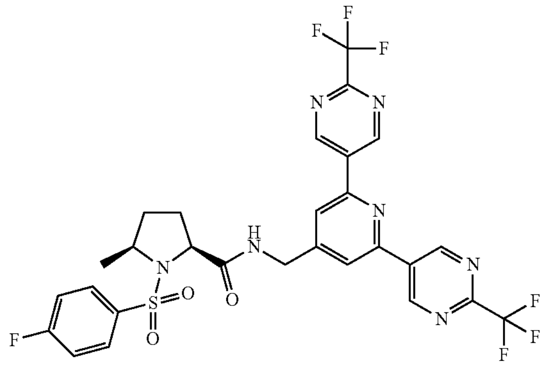
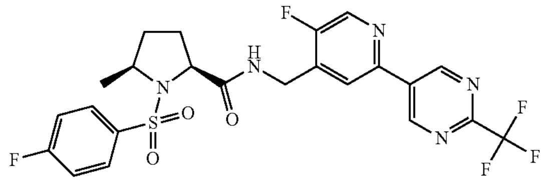
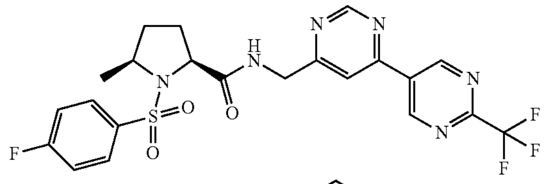
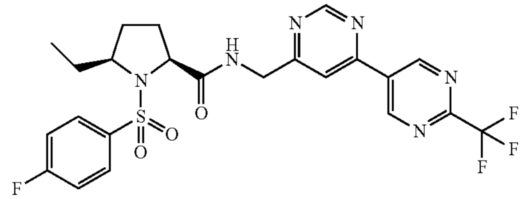

-continued
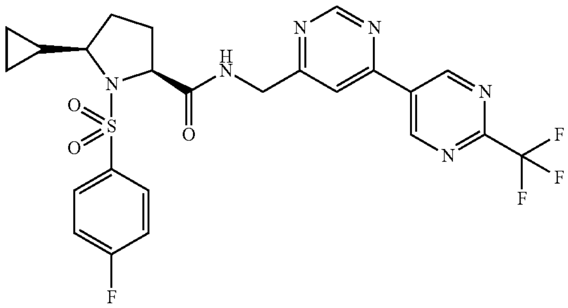
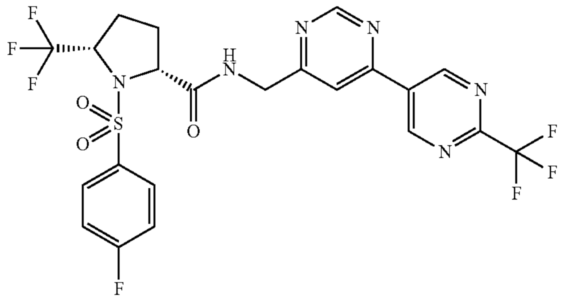
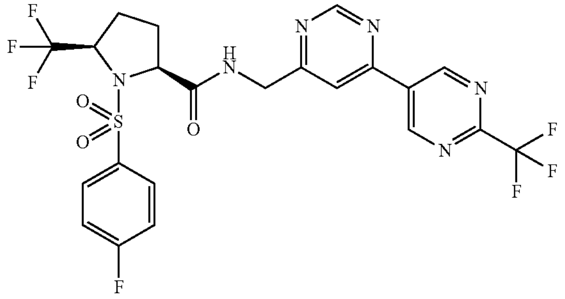
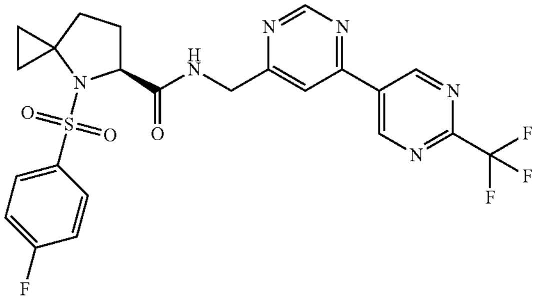
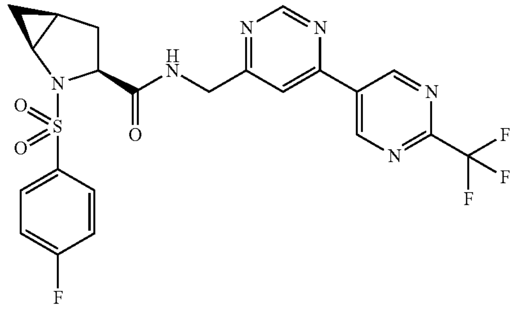
-continued
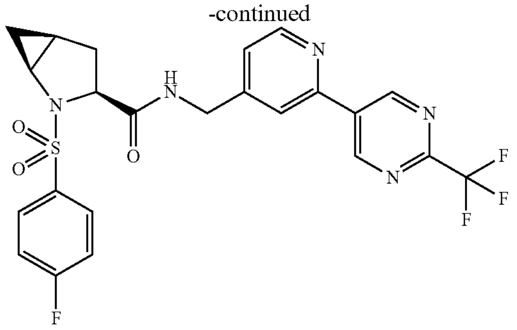
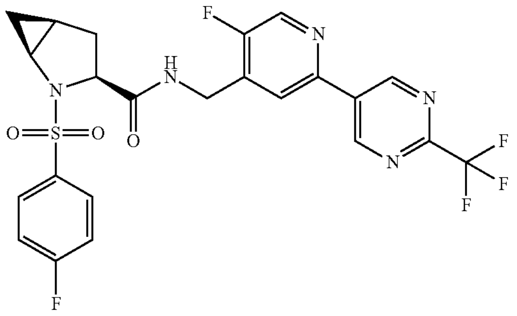
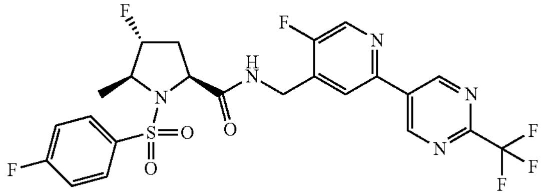
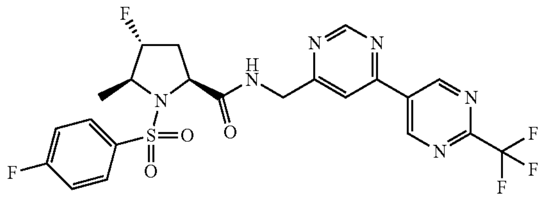
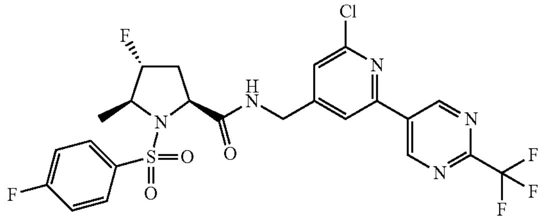
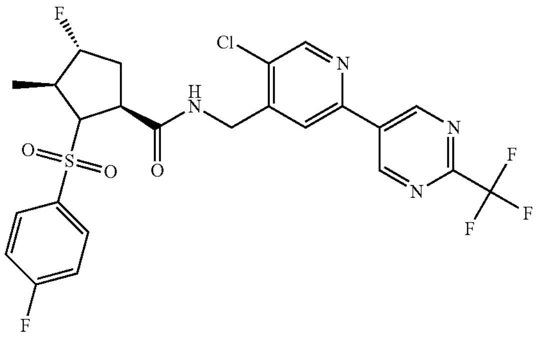

-continued
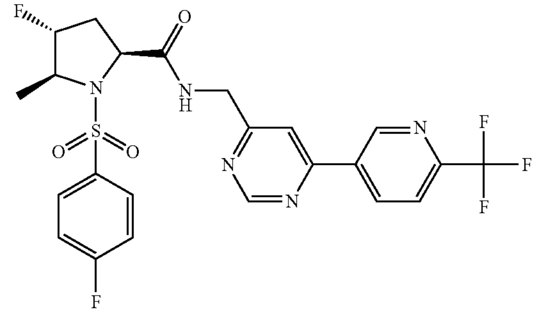
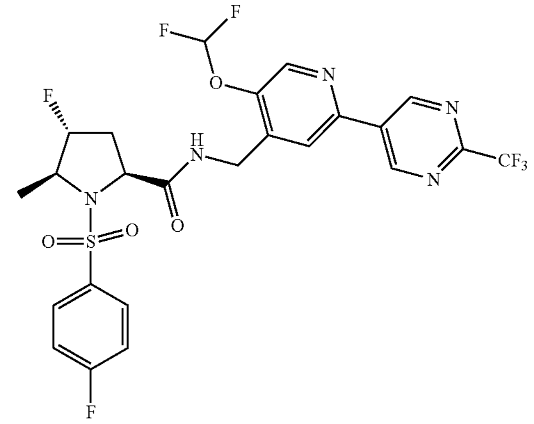
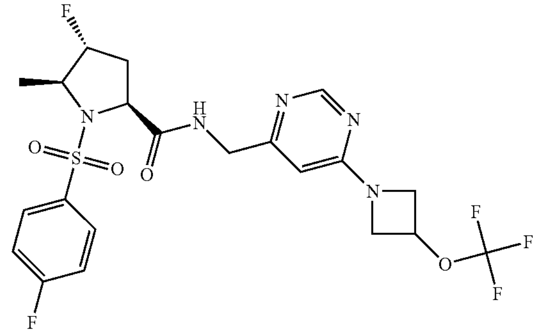
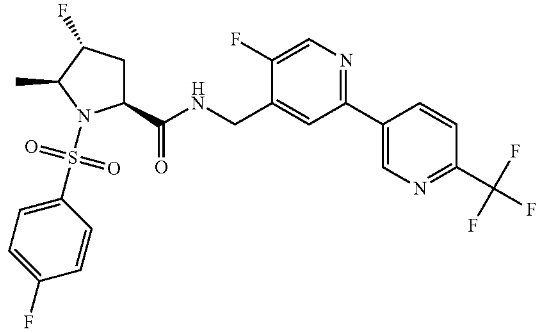
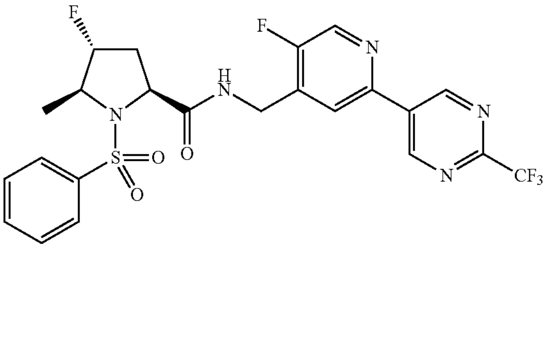
-continued
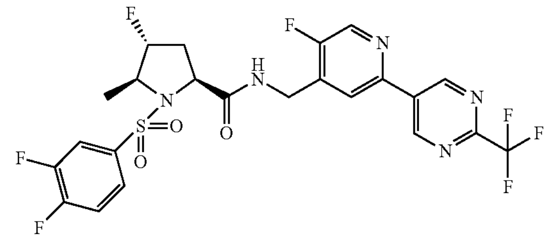
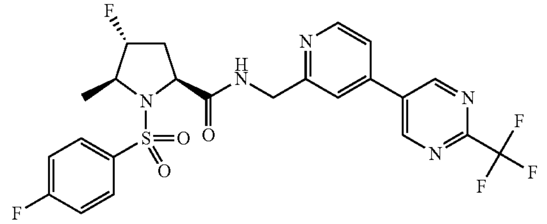
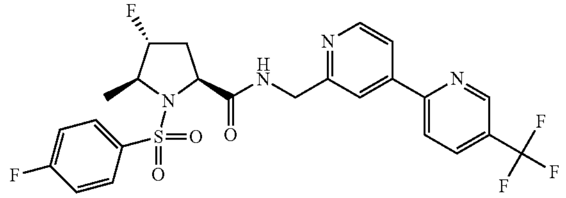
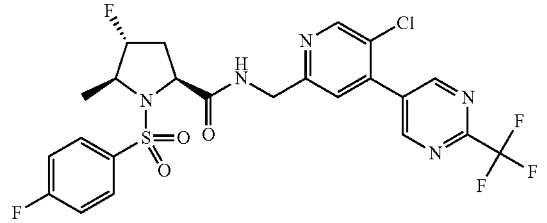
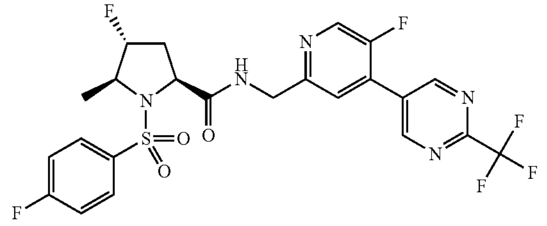
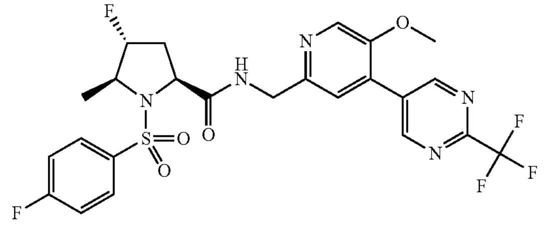
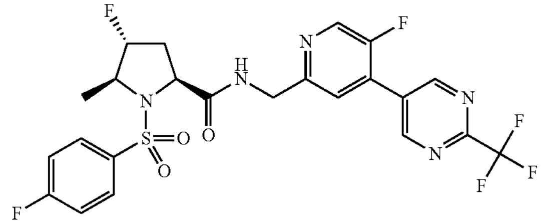

-continued

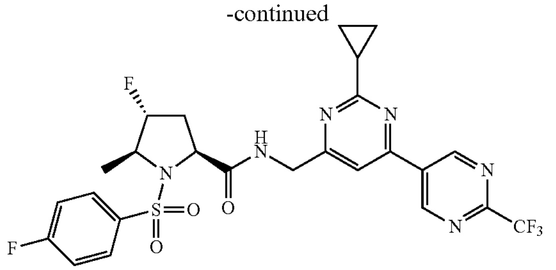

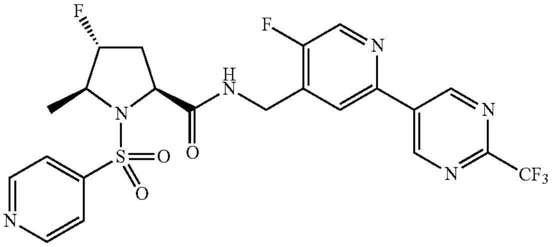

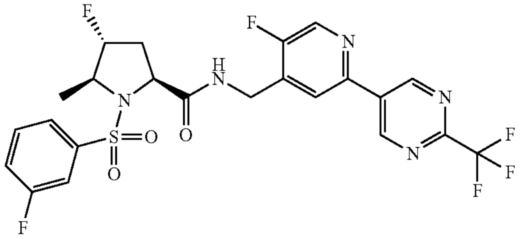

or

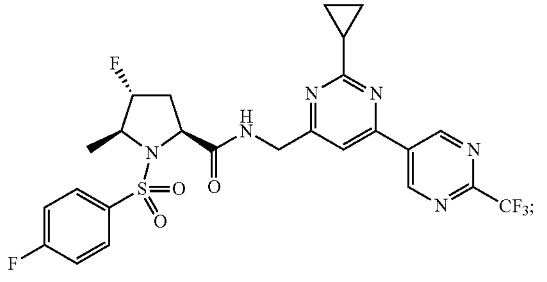

or a salt thereof.

E91: The compound of E1, wherein the compound is:

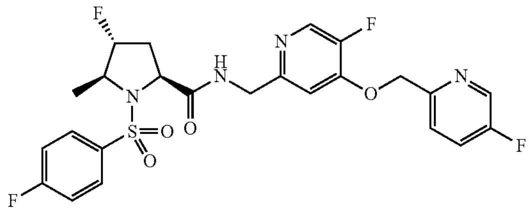

or

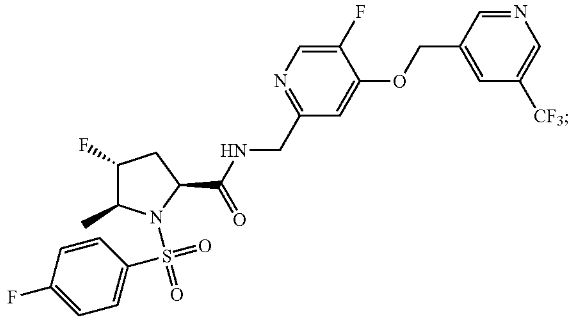

or a salt thereof.

E92: A pharmaceutical composition, comprising a compound as described in any one of E1-91 or a pharmaceutically acceptable salt thereof, and a pharmaceutically acceptable carrier, diluent or excipient.

E93: A compound as described in any one of E1-91 or a pharmaceutically acceptable salt thereof for use in medical therapy.

E94: A compound as described in any one of E1-91 or a pharmaceutically acceptable salt thereof for the treatment or prophylaxis of a respiratory disorder.

E95: A compound as described in any one of E1-91 or a pharmaceutically acceptable salt thereof for the preparation of a medicament for the treatment or prophylaxis of a respiratory disorder.

E96: A method for treating a respiratory disorder in a mammal comprising, administering a compound as described in any one of E1-91 or a pharmaceutically acceptable salt thereof to the mammal.

E97: A compound as described in any one of E1-91 or a pharmaceutically acceptable salt thereof for modulating TRPA1 activity.

E98: A compound as described in any one of E1-91 or a pharmaceutically acceptable salt thereof for the treatment or prophylaxis of a disease or condition mediated by TRPA1 activity.

E99: The compound of E98 wherein the disease or condition is pain, itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia.

E100: The compound of E98 wherein the disease or condition is pain, arthritis, itch, cough, asthma, inflammatory bowel disease, or an inner ear disorder.

E101: The use of a compound as described in any one of E1-91 or a pharmaceutically acceptable salt thereof for the preparation of a medicament for the treatment or prophylaxis of a disease or condition that is mediated by TRPA1 activity.

E102: The use of E101 wherein the disease or condition is pain, itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia.

E103: The use of E101 wherein the disease or condition is pain, arthritis, itch, cough, asthma, inflammatory bowel disease, or an inner ear disorder.

E104: A method for modulating TRPA1 activity, comprising contacting TRPA1 with a compound as described in any one of E1-91 or a salt thereof.

E105: A method for treating a disease or condition mediated by TRPA1 activity in a mammal, comprising administering a compound as described in any one of E1-91 or a pharmaceutically acceptable salt thereof to the mammal.

E106: The method of E105 wherein the disease or condition is pain, itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia.

E107: The method of E105 wherein the disease or condition is pain, arthritis, itch, cough, asthma, inflammatory bowel disease, or an inner ear disorder.

E108: The compound of E1 wherein the salt of the compound of Formula I is a pharmaceutically acceptable salt of the compound of Formula I.

E108: A compound as described in any one of E1-85 or a pharmaceutically acceptable salt thereof, wherein the compound of Formula I does not include the following compounds:

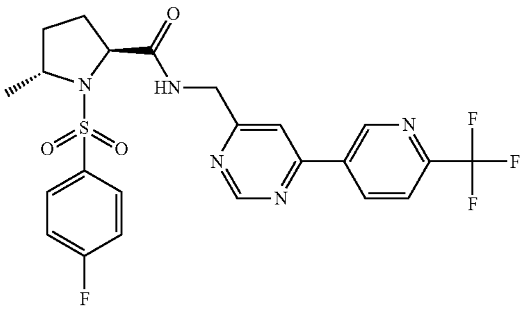

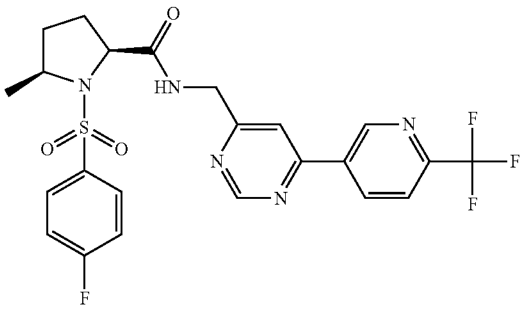

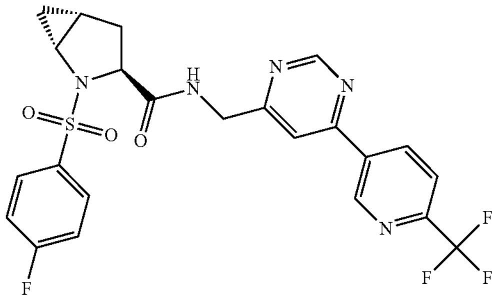

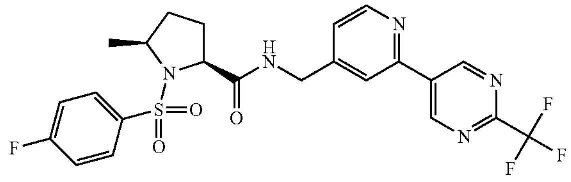

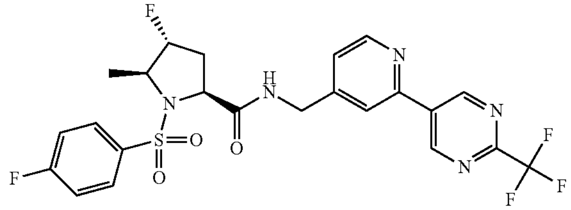

-continued

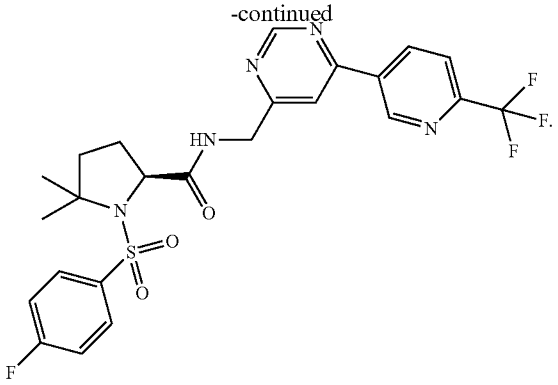

In another aspect the present invention provides for compounds of formula I as described herein below as a second embodiment of the invention (embodiment “EE1”).

EE1: A compound of formula I:

I

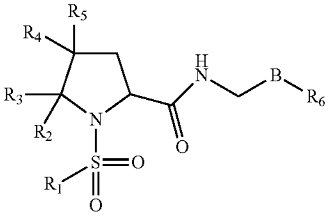

wherein:

B is $B^1$, $B^2$, or $B^3$;

$B^1$ is a 5-membered heteroaryl comprising 2 nitrogen atoms in the ring, wherein each 5-membered heteroaryl is unsubstituted or substituted with one or more groups independently selected from halogen, CN, $(C_1\text{-}C_6)$alkyl, $(C_1\text{-}C_6)$haloalkyl, $O(C_1\text{-}C_6)$alkyl, and $O(C_1\text{-}C_6)$haloalkyl;

$B^2$ is phenyl, wherein each phenyl is unsubstituted or substituted with one or more groups independently selected from halogen, CN, $(C_1\text{-}C_6)$alkyl, $(C_1\text{-}C_6)$haloalkyl, $O(C_1\text{-}C_6)$alkyl, and $O(C_1\text{-}C_6)$haloalkyl;

$B^3$ is 6-membered heteroaryl, wherein each 6-membered heteroaryl is unsubstituted or substituted with one or more groups independently selected from halogen, CN, $(C_1\text{-}C_6)$alkyl, $(C_1\text{-}C_6)$haloalkyl, $O(C_1\text{-}C_6)$alkyl, $O(C_1\text{-}C_6)$haloalkyl, 5 or 6-membered heteroaryl, $(C_3\text{-}C_7)$cycloalkyl, and 4, 5, 6, or 7-membered heterocyclyl; and wherein any of the 5 or 6-membered heteroaryl, $(C_3\text{-}C_7)$cycloalkyl, or 4, 5, 6, or 7-membered heterocyclyl groups is unsubstituted or substituted with one or more groups independently selected from halogen, CN, $(C_1\text{-}C_6)$alkyl, $(C_1\text{-}C_6)$haloalkyl, $O(C_1\text{-}C_6)$alkyl, and $O(C_1\text{-}C_6)$haloalkyl;

$R^1$ is phenyl or heteroaryl, wherein each phenyl or heteroaryl is unsubstituted or substituted with one or more groups independently selected from halogen, $(C_1\text{-}C_6)$alkyl, and $(C_1\text{-}C_6)$haloalkyl;

$R^2$ is $(C_1\text{-}C_6)$alkyl, $(C_1\text{-}C_6)$haloalkyl, or $(C_3\text{-}C_7)$cycloalkyl; wherein $(C_1\text{-}C_6)$alkyl is optionally substituted with $O(C_1\text{-}C_6)$alkyl;

$R^3$ is H or $(C_1\text{-}C_6)$alkyl; or $R^2$ and $R^3$ together with the atoms to which they are attached form a $(C_3)$cycloalkyl;

$R^4$ is H, F, or CN;

$R^5$ is H or $(C_1\text{-}C_6)$alkyl; or one of $R^2$ and $R^3$ and one of $R^4$ and $R^5$ together with the atoms to which they are attached form a $(C_3)$cycloalkyl;

$R^6$ is phenyl, $(C_3\text{-}C_7)$cycloalkyl, 5 or 6-membered heteroaryl, or 4, 5, 6 or 7-membered heterocycle, wherein any phenyl, $(C_3\text{-}C_7)$cycloalkyl, 5 or 6-membered heteroaryl, or 4, 5, 6 or 7-membered heterocycle of $R^6$ is optionally substituted with one or more groups independently selected from halogen, CN, $SF_5$, $(C_1\text{-}C_6)$alkyl, $(C_1\text{-}C_6)$haloalkyl, $O(C_1\text{-}C_6)$alkyl, or $O(C_1\text{-}C_6)$haloalkyl; or $R^6$ is $O—CH_2—R^7$;

$R^7$ is $(C_1\text{-}C_6)$alkyl, 4, 5, 6, or 7-membered heterocycle, $(C_3\text{-}C_7)$cycloalkyl, or 6-membered heteroaryl, wherein any $(C_1\text{-}C_6)$alkyl, 4, 5, 6, or 7-membered heterocycle, $(C_3\text{-}C_7)$cycloalkyl, or 6-membered heteroaryl is optionally substituted with one or more groups independently selected from halogen, CN, $(C_1\text{-}C_6)$alkyl, $(C_1\text{-}C_6)$haloalkyl, $O(C_1\text{-}C_6)$alkyl, and $O(C_1\text{-}C_6)$haloalkyl;

or a salt thereof.

Further additional embodiments of the invention are set forth below.

EE2: The compound of EE1, wherein the compound is of formula II:

II

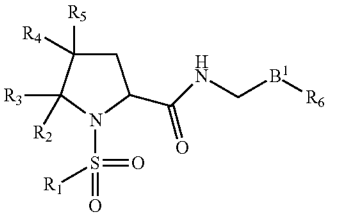

wherein:

$B^1$ is a 5-membered heteroaryl comprising 2 nitrogen atoms in the ring, wherein each 5-membered heteroaryl is unsubstituted or substituted with one or more groups independently selected from halogen, CN, $(C_1\text{-}C_6)$alkyl, $(C_1\text{-}C_6)$haloalkyl, $O(C_1\text{-}C_6)$alkyl, and $O(C_1\text{-}C_6)$haloalkyl;

$R^1$ is phenyl or heteroaryl, wherein each phenyl or heteroaryl is unsubstituted or substituted with one or more groups independently selected from halogen, $(C_1\text{-}C_6)$alkyl, and $(C_1\text{-}C_6)$haloalkyl;

$R^2$ is $(C_1\text{-}C_6)$alkyl, $(C_1\text{-}C_6)$haloalkyl, or $(C_3\text{-}C_7)$cycloalkyl; wherein $(C_1\text{-}C_6)$alkyl is optionally substituted with $O(C_1\text{-}C_6)$alkyl;

$R^3$ is H or $(C_1\text{-}C_6)$alkyl; or $R^2$ and $R^3$ together with the atoms to which they are attached form a $(C_3)$cycloalkyl;

$R^4$ is H, F, or CN;

$R^5$ is H or $(C_1\text{-}C_6)$alkyl; or one of $R^2$ and $R^3$ and one of $R^4$ and $R^5$ together with the atoms to which they are attached form a $(C_3)$cycloalkyl;

$R^6$ is phenyl, $(C_3\text{-}C_7)$cycloalkyl, 5 or 6-membered heteroaryl, or 4, 5, 6 or 7-membered heterocycle, wherein any phenyl, $(C_3\text{-}C_7)$cycloalkyl, 5 or 6-membered heteroaryl, or 4, 5, 6 or 7-membered heterocycle of $R^6$ is optionally substituted with one or more groups independently selected from halogen, CN, $SF_5$, $(C_1\text{-}C_6)$alkyl, $(C_1\text{-}C_6)$haloalkyl, $O(C_1\text{-}C_6)$alkyl, or $O(C_1\text{-}C_6)$haloalkyl; or $R^6$ is $O—CH_2—R^7$;

$R^7$ is $(C_1\text{-}C_6)$alkyl, 4, 5, 6, or 7-membered heterocycle, $(C_3\text{-}C_7)$cycloalkyl, or 6-membered heteroaryl, wherein any $(C_1\text{-}C_6)$alkyl, 4, 5, 6, or 7-membered heterocycle, $(C_3\text{-}C_7)$cycloalkyl, or 6-membered heteroaryl is optionally substituted with one or more groups independently selected from halogen, CN, $(C_1\text{-}C_6)$alkyl, $(C_1\text{-}C_6)$haloalkyl, $O(C_1\text{-}C_6)$alkyl, and $O(C_1\text{-}C_6)$haloalkyl;

or a salt thereof.

EE3. The compound of EE1 or EE2, wherein $B^1$ is unsubstituted or substituted pyrazolyl.

EE4. The compound of any one of EE1-EE3, wherein $B^1$ is:

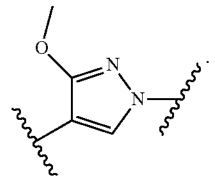 [SMILES: *c1cn(*)nc1OC ; "."]

EE5. The compound of any EE1-EE3, wherein $B^1$ is:

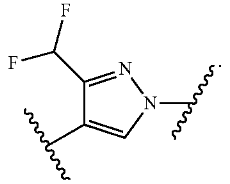 [SMILES: *c1cn(*)nc1C(F)F ; "."]

EE6. The compound of any one of EE1-EE3, wherein $B^1$ is:

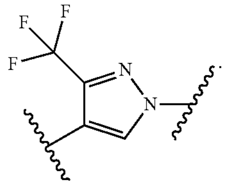 [SMILES: *c1cn(*)nc1C(F)(F)F ; "."]

EE7. The compound of any one of EE1-EE3, wherein $B^1$ is:

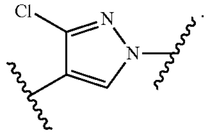

EE8. The compound of EE1, wherein the compound is of formula III:

III

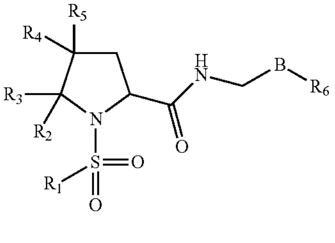

wherein:

B is $B^2$ or $B^3$;

$B^2$ is phenyl, wherein each phenyl is unsubstituted or substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

$B^3$ is 6-membered heteroaryl, wherein each 6-membered heteroaryl is unsubstituted or substituted with one or more groups independently selected from halogen, CN, $(C_1-C_6)$alkyl, $(C_1-C_6)$haloalkyl, $O(C_1-C_6)$alkyl, $O(C_1-C_6)$haloalkyl, 5 or 6-membered heteroaryl, $(C_3-C_7)$cycloalkyl, and 4, 5, 6, or 7-membered heterocyclyl; and wherein any of the 5 or 6-membered heteroaryl, $(C_3-C_7)$cycloalkyl, or 4, 5, 6, or 7-membered heterocyclyl groups is unsubstituted or substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

$R^1$ is phenyl or heteroaryl, wherein each phenyl or heteroaryl is unsubstituted or substituted with one or more groups independently selected from halogen, $(C_1-C_6)$alkyl, and $(C_1-C_6)$haloalkyl;

$R^2$ is $(C_1-C_6)$alkyl, $(C_1-C_6)$haloalkyl, or $(C_3-C_7)$cycloalkyl; wherein $(C_1-C_6)$alkyl is optionally substituted with $O(C_1-C_6)$alkyl;

$R^3$ is H or $(C_1-C_6)$alkyl; or $R^2$ and $R^3$ together with the atoms to which they are attached form a $(C_3)$cycloalkyl;

$R^4$ is H, F, or CN;

$R^5$ is H or $(C_1-C_6)$alkyl; or one of $R^2$ and $R^3$ and one of $R^4$ and $R^5$ together with the atoms to which they are attached form a $(C_3)$cycloalkyl;

$R^6$ is phenyl, $(C_3-C_7)$cycloalkyl, 5 or 6-membered heteroaryl, or 4, 5, 6 or 7-membered heterocycle, wherein any phenyl, $(C_3-C_7)$cycloalkyl, 5 or 6-membered heteroaryl, or 4, 5, 6 or 7-membered heterocycle of $R^6$ is optionally substituted with one or more groups independently selected from halogen, CN, $SF_5$, $(C_1-C_6)$alkyl, $(C_1-C_6)$haloalkyl, $O(C_1-C_6)$alkyl, or $O(C_1-C_6)$haloalkyl; or $R^6$ is $O—CH_2—R^7$;

$R^7$ is $(C_1-C_6)$alkyl, 4, 5, 6, or 7-membered heterocycle, $(C_3-C_7)$cycloalkyl, or 6-membered heteroaryl, wherein any $(C_1-C_6)$alkyl, 4, 5, 6, or 7-membered heterocycle, $(C_3-C_7)$cycloalkyl, or 6-membered heteroaryl is optionally substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

or a salt thereof.

EE9. The compound of EE8, wherein $B^2$ is unsubstituted or substituted phenyl.

EE10. The compound of EE9, wherein $B^2$ is:

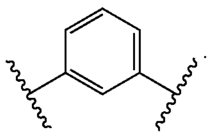 [SMILES: *c1cccc(*)c1 ; "."]

EE11. The compound of EE9, wherein $B^2$ is:

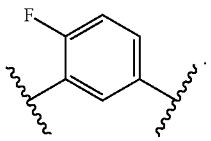

EE12. The compound of EE9, wherein $B^2$ is:

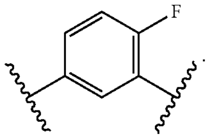

EE13. The compound of EE9, wherein $B^2$ is:

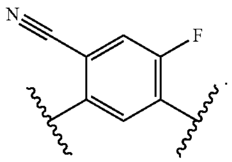 [SMILES: *c1cc(*)c(C#N)cc1F ; "."]

EE14. The compound of EE9, wherein $B^2$ is:

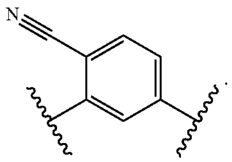

EE15. The compound of EE9, wherein $B^2$ is:

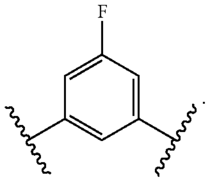

EE16. The compound of EE9, wherein $B^2$ is:

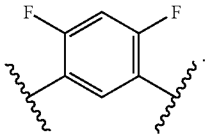 [SMILES: *c1cc(*)c(F)cc1F ; "."]

EE17. The compound of EE9, wherein $B^2$ is:

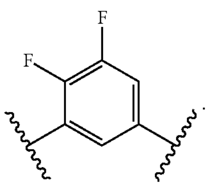 [SMILES: *c1cc(*)c(F)c(F)c1 ; "."]

EE18. The compound of EE8, wherein $B^3$ is unsubstituted or substituted 6-membered heteroaryl.

EE19. The compound of EE18, wherein $B^3$ is:

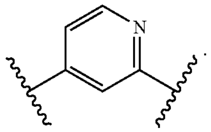

EE20. The compound of EE18, wherein $B^3$ is:

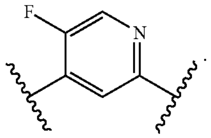

EE21. The compound of EE18, wherein $B^3$ is:

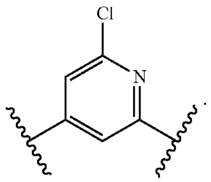

EE22. The compound of EE18, wherein $B^3$ is:

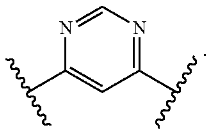 [SMILES: *c1cc(*)ncn1 ; "."]

EE23. The compound of EE18, wherein $B^3$ is:

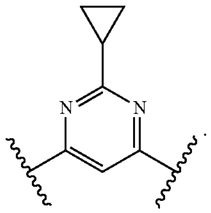

EE24. The compound of EE18, wherein $B^3$ is:

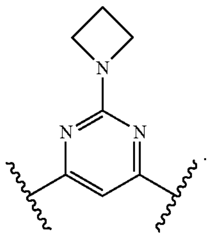

EE25. The compound of EE18, wherein $B^3$ is:

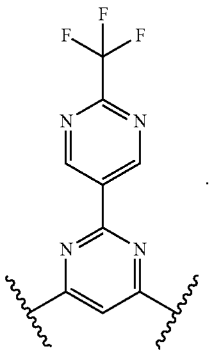 [SMILES: *c1cc(*)nc(-c2cnc(C(F)(F)F)nc2)n1]

EE26. The compound of EE18, wherein $B^3$ is:

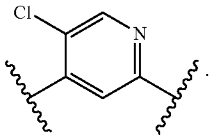 [SMILES: *c1cc(*)c(Cl)cn1]

EE27. The compound of EE18, wherein $B^3$ is:

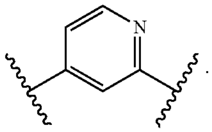 [SMILES: *c1ccnc(*)c1]

EE28. The compound of EE18, wherein $B^3$ is:

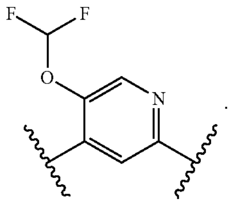 [SMILES: *c1cc(*)c(OC(F)F)cn1]

EE29. The compound of EE18, wherein $B^3$ is:

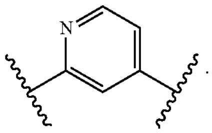 [SMILES: *c1ccnc(*)c1]

EE30. The compound of EE18, wherein $B^3$ is:

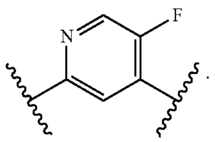 [SMILES: *c1cc(*)c(F)cn1]

EE31. The compound of EE18, wherein $B^3$ is:

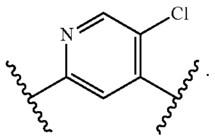

EE32. The compound of EE18, wherein $B^3$ is:

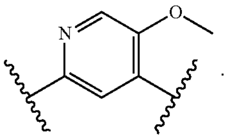 [SMILES: *c1cc(*)c(OC)cn1]

EE33. The compound of EE18, wherein $B^3$ is:

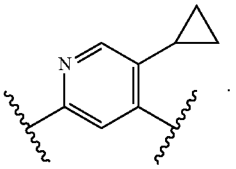 [SMILES: *c1cc(*)c(C2CC2)cn1]

EE34. The compound of EE18, wherein $B^3$ is:

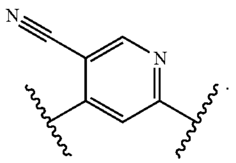 [SMILES: *c1cc(*)c(C#N)cn1]

EE35. The compound of EE18, wherein $B^3$ is:

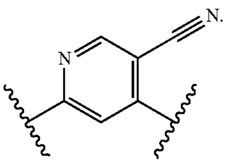 [SMILES: *c1cc(*)c(C#N)cn1]

EE36. The compound of EE18, wherein $B^3$ is:

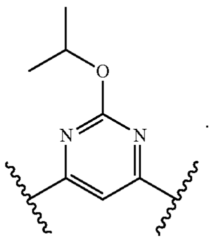 [SMILES: *c1cc(*)nc(OC(C)C)n1]

EE37. The compound of EE18, wherein $B^3$ is:

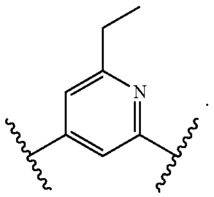 [SMILES: *c1cc(*)nc(CC)c1]

EE38. The compound of EE18, wherein $B^3$ is:

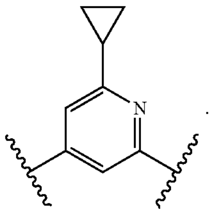 [SMILES: *c1cc(*)nc(C2CC2)c1]

EE39. The compound of EE1, wherein the compound is of formula IV:

IV

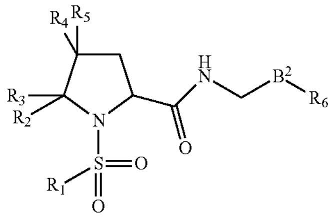

wherein:

$B^2$ is phenyl, wherein each phenyl is unsubstituted or substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

$R^1$ is phenyl or heteroaryl, wherein each phenyl or heteroaryl is unsubstituted or substituted with one or more groups independently selected from halogen, $(C_1-C_6)$alkyl, and $(C_1-C_6)$haloalkyl;

$R^2$ is $(C_1-C_6)$alkyl, $(C_1-C_6)$haloalkyl, or $(C_3-C_7)$cycloalkyl; wherein $(C_1-C_6)$alkyl is optionally substituted with $O(C_1-C_6)$alkyl;

$R^3$ is H or $(C_1-C_6)$alkyl; or $R^2$ and $R^3$ together with the atoms to which they are attached form a $(C_3)$cycloalkyl;

$R^4$ is H, F, or CN;

$R^5$ is H or $(C_1-C_6)$alkyl; or one of $R^2$ and $R^3$ and one of $R^4$ and $R^5$ together with the atoms to which they are attached form a $(C_3)$cycloalkyl;

$R^6$ is phenyl, $(C_3$-$C_7)$cycloalkyl, 5 or 6-membered heteroaryl, or 4, 5, 6 or 7-membered heterocycle, wherein any phenyl, $(C_3$-$C_7)$cycloalkyl, 5 or 6-membered heteroaryl, or 4, 5, 6 or 7-membered heterocycle of $R^6$ is optionally substituted with one or more groups independently selected from halogen, CN, $SF_5$, $(C_1$-$C_6)$alkyl, $(C_1$-$C_6)$haloalkyl, $O(C_1$-$C_6)$alkyl, or $O(C_1$-$C_6)$haloalkyl; or $R^6$ is O—$CH_2$—$R^7$;

$R^7$ is $(C_1$-$C_6)$alkyl, 4, 5, 6, or 7-membered heterocycle, $(C_3$-$C_7)$cycloalkyl, or 6-membered heteroaryl, wherein any $(C_1$-$C_6)$alkyl, 4, 5, 6, or 7-membered heterocycle, $(C_3$-$C_7)$cycloalkyl, or 6-membered heteroaryl is optionally substituted with one or more groups independently selected from halogen, CN, $(C_1$-$C_6)$alkyl, $(C_1$-$C_6)$haloalkyl, $O(C_1$-$C_6)$alkyl, and $O(C_1$-$C_6)$haloalkyl;

or a salt thereof.

EE40. The compound of EE39, wherein $B^2$ is:

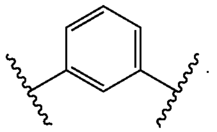 [SMILES: *c1cccc(*)c1]

EE41. The compound of EE39, wherein $B^2$ is:

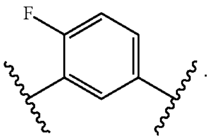 [SMILES: *c1ccc(F)c(*)c1]

EE42. The compound of EE39, wherein $B^2$ is:

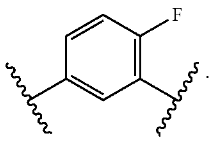 [SMILES: *c1ccc(F)c(*)c1]

EE43. The compound of EE39, wherein $B^2$ is:

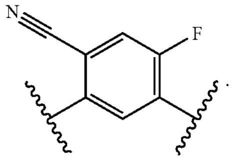 [SMILES: *c1cc(*)c(C#N)cc1F]

EE44. The compound of EE39, wherein $B^2$ is:

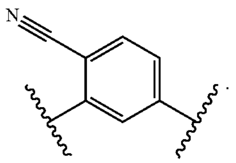

EE45. The compound of EE39, wherein $B^2$ is:

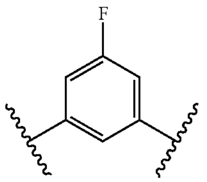 [SMILES: *c1cc(*)cc(F)c1]

EE46. The compound of EE39, wherein $B^2$ is:

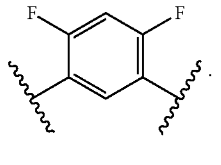 [SMILES: *c1cc(*)c(F)cc1F]

EE47. The compound of EE39, wherein $B^2$ is:

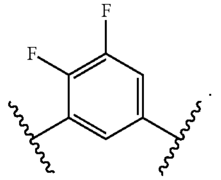 [SMILES: *c1cc(*)c(F)c(F)c1]

EE48. The compound of EE1, wherein the compound is of formula V:

V

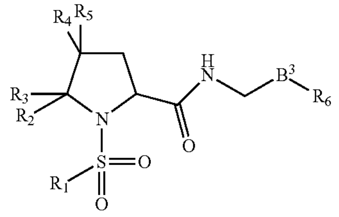

wherein:

$B^3$ is 6-membered heteroaryl, wherein each 6-membered heteroaryl is unsubstituted or substituted with one or more groups independently selected from halogen, CN, $(C_1$-$C_6)$alkyl, $(C_1$-$C_6)$haloalkyl, $O(C_1$-$C_6)$alkyl, $O(C_1$-$C_6)$haloalkyl, 5 or 6-membered heteroaryl, $(C_3$-$C_7)$cycloalkyl, and 4, 5, 6, or 7-membered heterocyclyl; and wherein any of the 5 or 6-membered heteroaryl, $(C_3$-$C_7)$cycloalkyl, or 4, 5, 6, or 7-membered heterocyclyl groups is unsubstituted or substituted with one or more groups independently selected from halogen, CN, $(C_1$-$C_6)$alkyl, $(C_1$-$C_6)$haloalkyl, $O(C_1$-$C_6)$alkyl, and $O(C_1$-$C_6)$haloalkyl;

$R^1$ is phenyl or heteroaryl, wherein each phenyl or heteroaryl is unsubstituted or substituted with one or more groups independently selected from halogen, $(C_1$-$C_6)$alkyl, and $(C_1$-$C_6)$haloalkyl;

$R^2$ is $(C_1$-$C_6)$alkyl, $(C_1$-$C_6)$haloalkyl, or $(C_3$-$C_7)$cycloalkyl; wherein $(C_1$-$C_6)$alkyl is optionally substituted with $O(C_1$-$C_6)$alkyl;

$R^3$ is H or $(C_1$-$C_6)$alkyl; or $R^2$ and $R^3$ together with the atoms to which they are attached form a $(C_3)$cycloalkyl;

$R^4$ is H, F, or CN;

$R^5$ is H or $(C_1-C_6)$alkyl; or one of $R^2$ and $R^3$ and one of $R^4$ and $R^5$ together with the atoms to which they are attached form a $(C_3)$cycloalkyl;

$R^6$ is phenyl, $(C_3-C_7)$cycloalkyl, 5 or 6-membered heteroaryl, or 4, 5, 6 or 7-membered heterocycle, wherein any phenyl, $(C_3-C_7)$cycloalkyl, 5 or 6-membered heteroaryl, or 4, 5, 6 or 7-membered heterocycle of $R^6$ is optionally substituted with one or more groups independently selected from halogen, CN, $SF_5$, $(C_1-C_6)$alkyl, $(C_1-C_6)$haloalkyl, $O(C_1-C_6)$alkyl, or $O(C_1-C_6)$haloalkyl; or $R^6$ is $O—CH_2—R^7$;

$R^7$ is $(C_1-C_6)$alkyl, 4, 5, 6, or 7-membered heterocycle, $(C_3-C_7)$cycloalkyl, or 6-membered heteroaryl, wherein any $(C_1-C_6)$alkyl, 4, 5, 6, or 7-membered heterocycle, $(C_3-C_7)$cycloalkyl, or 6-membered heteroaryl is optionally substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

or a salt thereof.

EE49. The compound of EE48, wherein $B^3$ is:

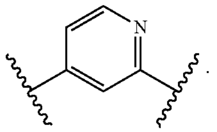 [SMILES: *c1ccnc(*)c1]

EE50. The compound of EE48, wherein $B^3$ is:

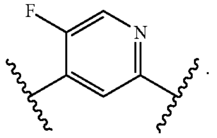 [SMILES: *c1cc(*)c(F)cn1]

EE51. The compound of EE48, wherein $B^3$ is:

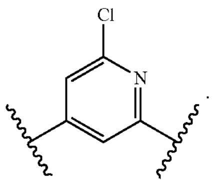 [SMILES: *c1cc(*)nc(Cl)c1]

EE52. The compound of EE48, wherein $B^3$ is:

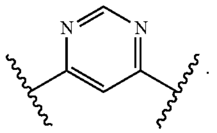 [SMILES: *c1cc(*)ncn1]

EE53. The compound of EE48, wherein $B^3$ is:

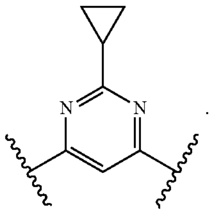 [SMILES: *c1cc(*)nc(C2CC2)n1]

EE54. The compound of EE48, wherein $B^3$ is:

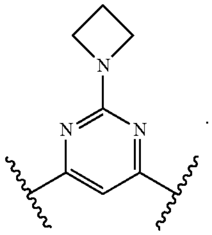 [SMILES: *c1cc(*)nc(N2CCC2)n1]

EE55. The compound of EE48, wherein $B^3$ is:

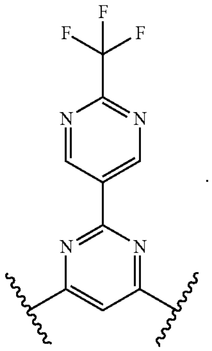 [SMILES: *c1cc(*)nc(-c2cnc(C(F)(F)F)nc2)n1]

EE56. The compound of EE48, wherein $B^3$ is:

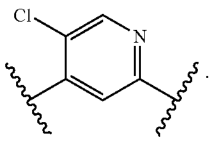 [SMILES: *c1cc(*)c(Cl)cn1]

EE57. The compound of EE48, wherein $B^3$ is:

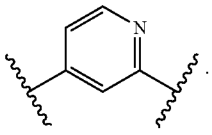 [SMILES: *c1ccnc(*)c1]

EE58. The compound of EE48, wherein $B^3$ is:

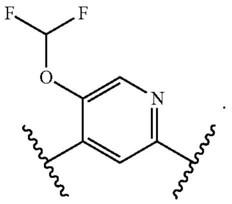 [SMILES: *c1cc(*)c(OC(F)F)cn1]

EE59. The compound of EE48, wherein $B^3$ is:

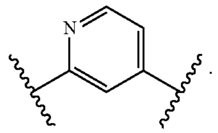

EE60. The compound of EE48, wherein $B^3$ is:

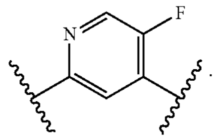 [SMILES: *c1cc(*)c(F)cn1]

EE61. The compound of EE48, wherein $B^3$ is:

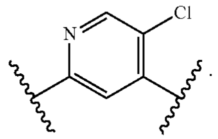

EE62. The compound of EE48, wherein $B^3$ is:

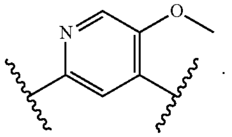 [SMILES: *c1cc(*)c(OC)cn1]

EE63. The compound of EE48, wherein $B^3$ is:

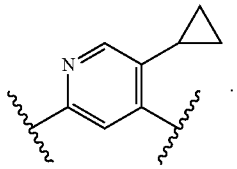 [SMILES: *c1cc(*)c(C2CC2)cn1]

EE64. The compound of EE48, wherein $B^3$ is:

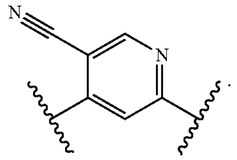 [SMILES: *c1cc(*)c(C#N)cn1]

EE65. The compound of EE48, wherein $B^3$ is:

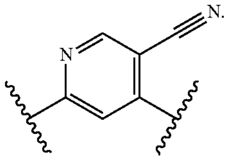 [SMILES: *c1cc(*)c(C#N)cn1]

EE66. The compound of EE48, wherein $B^3$ is:

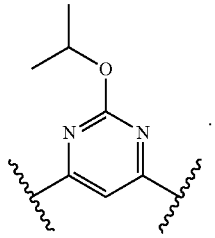 [SMILES: *c1cc(*)nc(OC(C)C)n1]

EE67. The compound of EE48, wherein $B^3$ is:

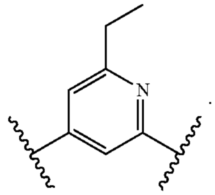 [SMILES: *c1cc(*)nc(CC)c1]

EE68. The compound of EE48, wherein $B^3$ is:

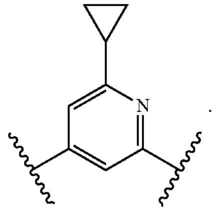 [SMILES: *c1cc(*)nc(C2CC2)c1]

EE69. The compound of any one of EE1-EE68, wherein $R^2$ is $(C_1$-$C_6)$alkyl.

EE70. The compound of EE69, wherein $R^2$ is $CH_3$.

EE71. The compound of EE69, wherein $R^2$ is $CH_2CH_3$.

EE72. The compound of EE69, wherein $R^2$ is $C(CH_3)_3$.

EE73. The compound of any one of EE1-EE68, wherein $R^2$ is $(C_1$-$C_6)$haloalkyl EE74. The compound of EE73, wherein $R^2$ is $C(CF_3)_3$.

EE75. The compound of any one of EE1-EE68, wherein $R^2$ is $—CH_2OCH_3$.

EE76. The compound of any one of EE1-EE68, wherein $R^2$ and $R^3$ together with the atoms to which they are attached form a $(C_3)$cycloalkyl.

EE77. The compound of EE76, wherein $R^2$ and $R^3$ together with the atoms to which they are attached form spirocyclopropyl.

EE78. The compound of any one of EE1-EE75, wherein $R^3$ is H.

EE79. The compound of any one of EE1-EE75, wherein one of $R^2$ and $R^3$ and one of $R^4$ and $R^5$ together with the atoms to which they are attached form a $(C_3)$cycloalkyl.

EE80. The compound of any one of EE1-EE79, wherein $R^4$ is H.

EE81. The compound of any one of EE1-EE79, wherein $R^4$ is F.

EE82. The compound of any one of EE1-EE79, wherein $R^4$ is CN.

EE83. The compound of any one of EE1-EE78, wherein $R^5$ is H.

EE84. The compound of any one of EE1-EE68, wherein the group

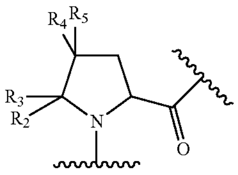

is:

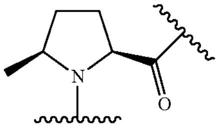

.

EE85. The compound of any one of EE1-EE68, wherein the group

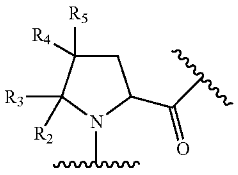

is:

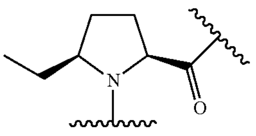

.

EE86. The compound of any one of EE1-EE68, wherein the group

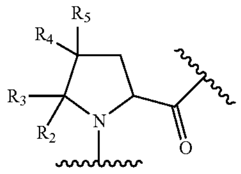

is:

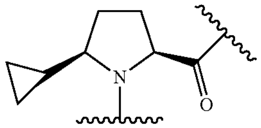

.

EE87. The compound of any one of EE1-EE68, wherein the group

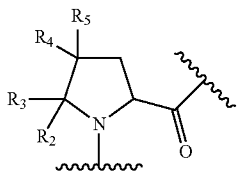

is:

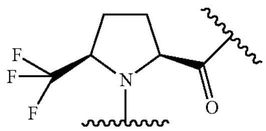

.

EE88. The compound of any one of EE1-EE68, wherein the group

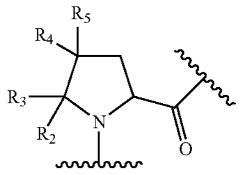

is:

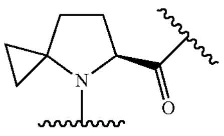

.

EE89. The compound of any one of EE1-EE68, wherein the group

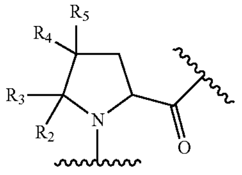

is:

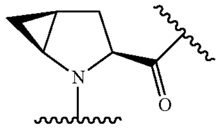

.

EE90. The compound of any one of EE1-EE68, wherein the group

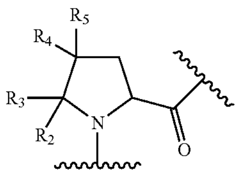

is:

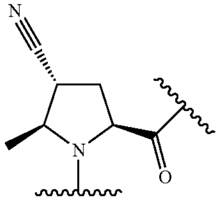

.

EE91. The compound of any one of EE1-EE68, wherein the group

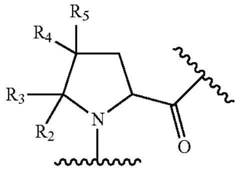

is:

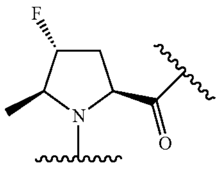

.

EE92. The compound of any one of EE1-EE68, wherein the group

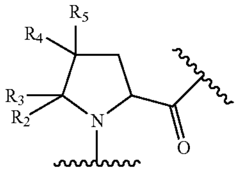

is:

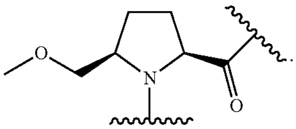 [SMILES: *C(=O)[C@@H]1CC[C@H](COC)N1*]

EE93. The compound of any one of EE1-EE92, wherein $R^6$ is 5-membered heteroaryl.

EE94. The compound of EE93, wherein $R^6$ is:

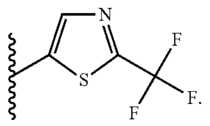 [SMILES: *c1cnc(C(F)(F)F)s1]

EE95. The compound of any one of EE1-EE92, wherein $R^6$ is 6-membered heteroaryl.

EE96. The compound of EE95, wherein $R^6$ is pyridinyl.

EE97. The compound of EE96, wherein $R^6$ is:

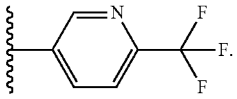

EE98. The compound of EE96, wherein $R^6$ is:

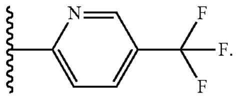

EE99. The compound of EE95, wherein $R^6$ is pyrimidinyl.

EE100. The compound of EE99, wherein $R^6$ is:

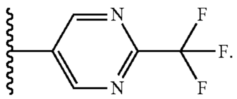

EE101. The compound of EE95, wherein $R^6$ is pyrazinyl.

EE102. The compound of EE101, wherein $R^6$ is:

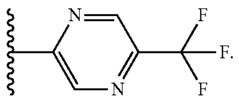 [SMILES: *c1cnc(C(F)(F)F)cn1]

EE103. The compound of any one of EE1-EE92, wherein $R^6$ is 4, 5, 6 or 7-membered heterocycle.

EE104. The compound of EE103, wherein $R^6$ is 4-membered heterocycle.

EE105. The compound of EE104, wherein $R^6$ is:

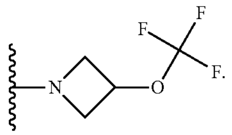 [SMILES: *N1CC(OC(F)(F)F)C1]

EE106. The compound of EE103, wherein $R^6$ is 5-membered heterocycle.

EE107. The compound of EE103, wherein $R^6$ is 6-membered heterocycle.

EE108. The compound of EE107, wherein $R^6$ is:

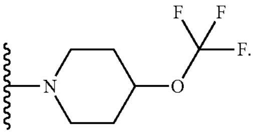 [SMILES: *N1CCC(OC(F)(F)F)CC1]

EE109. The compound of EE107, wherein $R^6$ is:

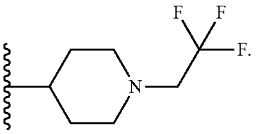 [SMILES: *C1CCN(CC(F)(F)F)CC1]

EE110. The compound of EE103, wherein $R^6$ is 7-membered heterocycle.

EE111. The compound of any one of EE1-EE92, wherein $R^6$ is ($C_3$-$C_7$)cycloalkyl.

EE112. The compound of EE111, wherein $R^6$ is (C6) cycloalkyl.

EE113. The compound of EE112, wherein $R^6$ is:

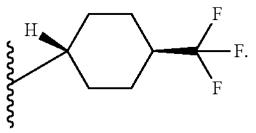 [SMILES: *[C@H]1CC[C@H](C(F)(F)F)CC1]

EE114. The compound of any one of EE1-92, wherein $R^6$ is phenyl.

EE115. The compound of EE114, wherein $R^6$ is:

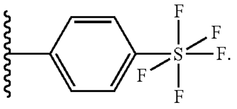 [SMILES: *c1ccc(S(F)(F)(F)(F)F)cc1]

EE116. The compound of any one of EE1-92, wherein $R^6$ is:

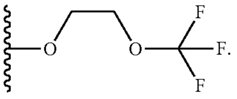 [SMILES: *OCCOC(F)(F)F]

EE117. The compound of any one of EE1-92, wherein $R^6$ is:

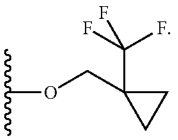 [SMILES: *OCC1(C(F)(F)F)CC1]

EE118. The compound of any one of EE1-92, wherein $R^7$ is ($C_1$-$C_6$)alkyl.

EE119. The compound of any one of EE1-92, wherein $R^7$ is ($C_3$-$C_7$)cycloalkyl.

EE120. The compound of EE119, wherein $R^7$ is ($C_3$) cycloalkyl.

EE121. The compound of any one of EE1-120, wherein $R^1$ is:

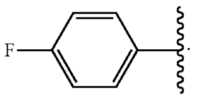 [SMILES: *c1ccc(F)cc1]

EE122. The compound of EE1, which is:

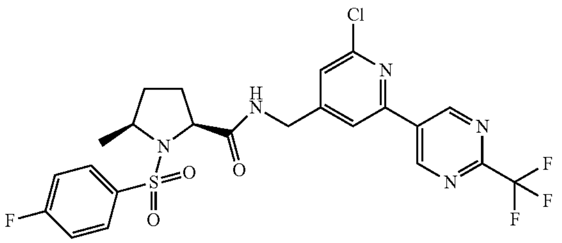

-continued
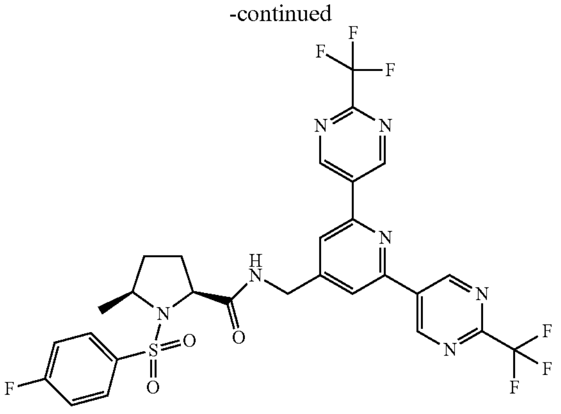
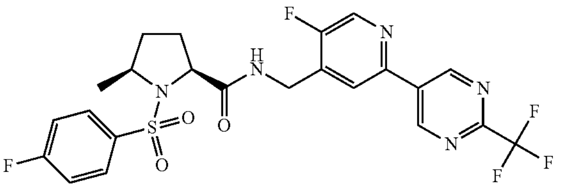
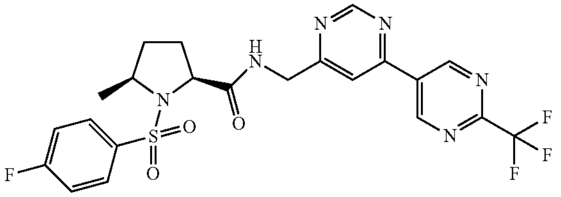
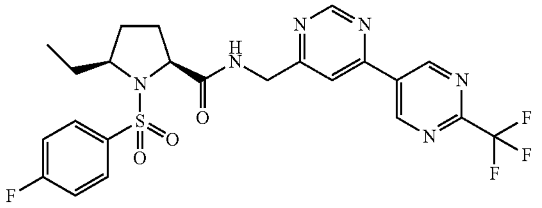
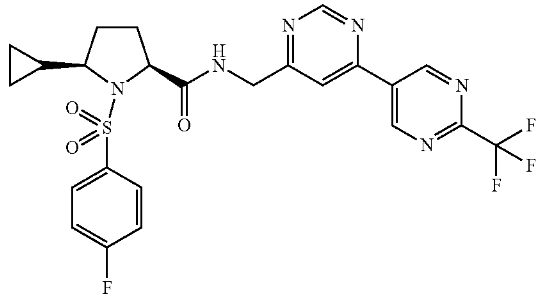
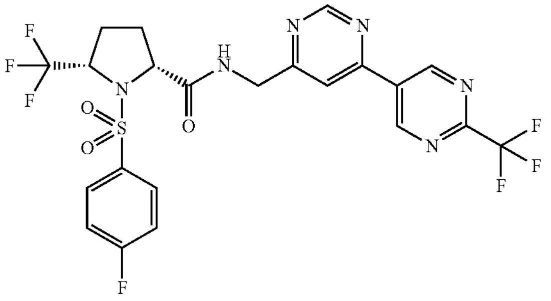
-continued
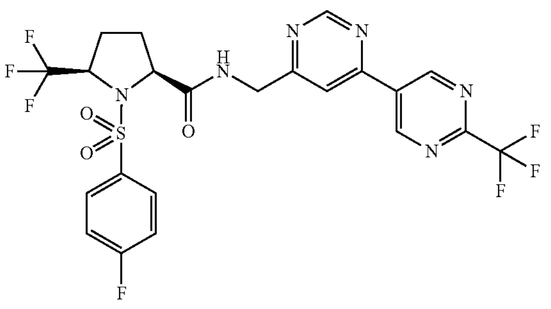
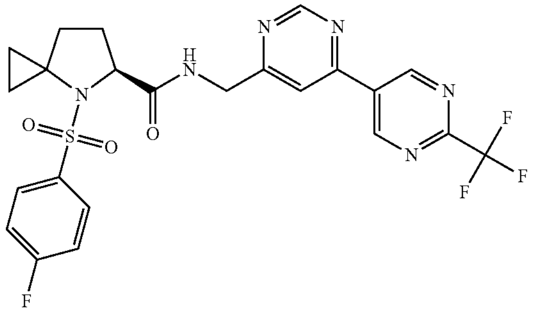
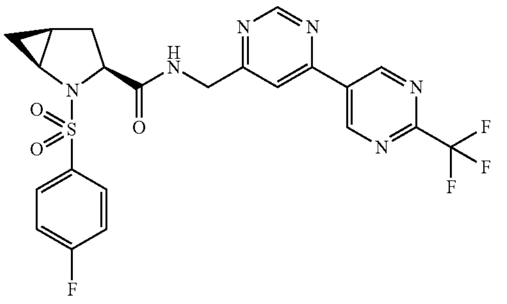
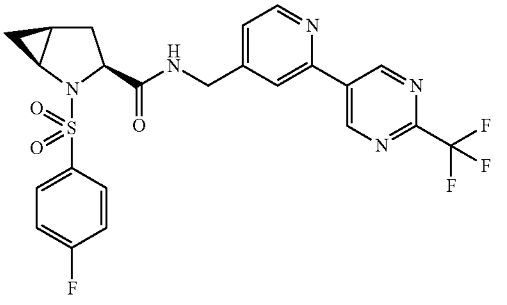
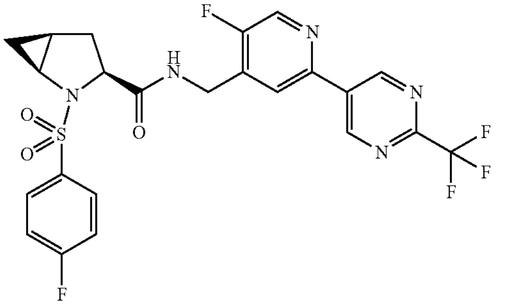

-continued
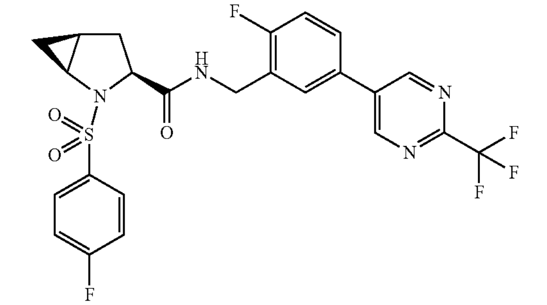
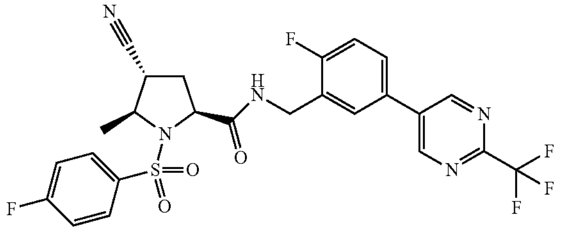
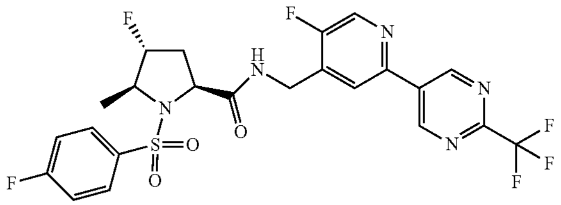
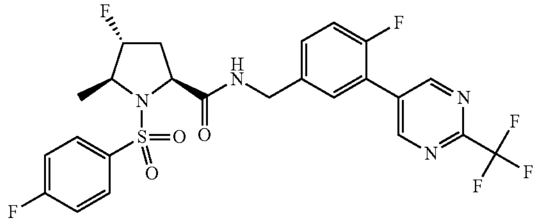
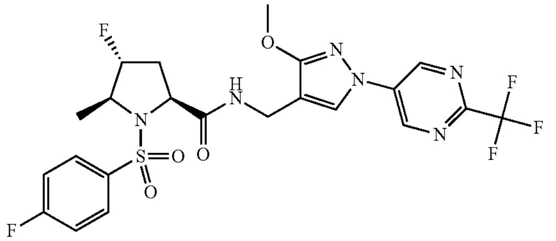
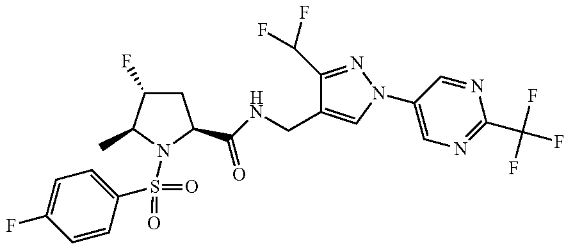
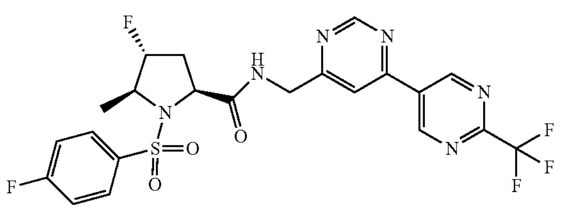
-continued
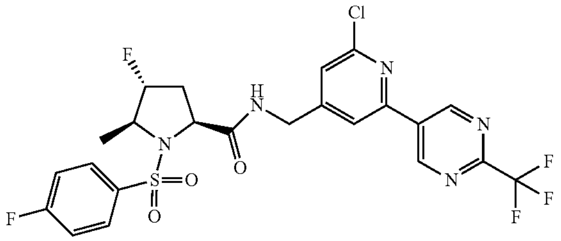
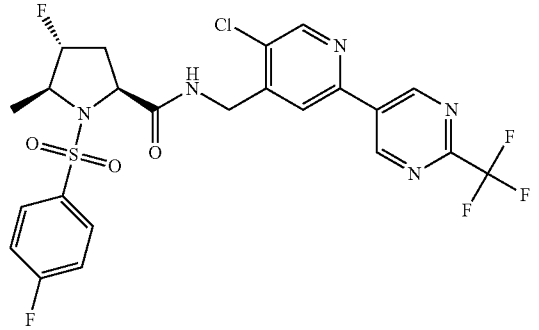
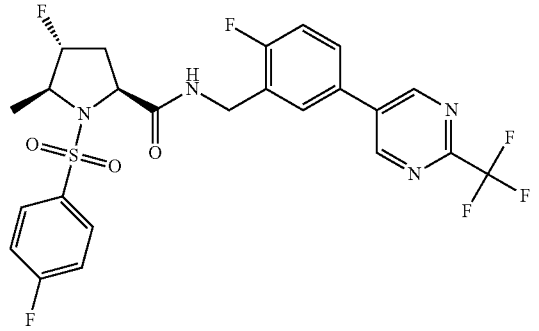
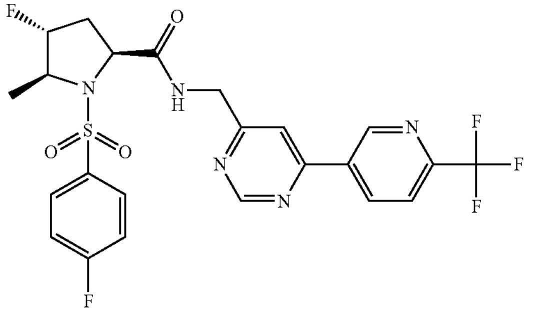
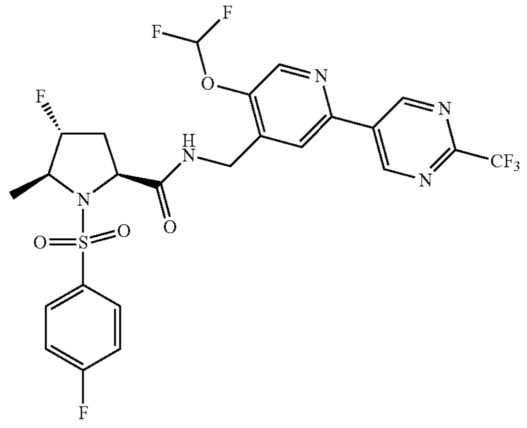

-continued
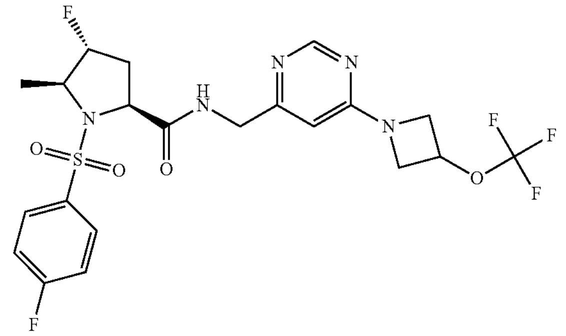
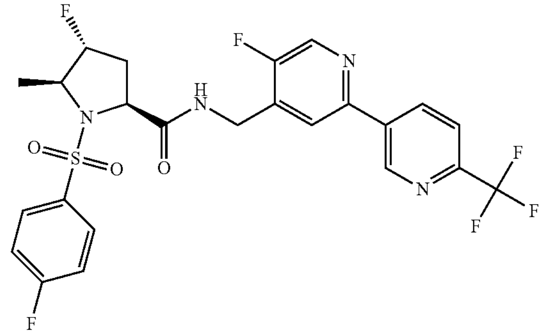
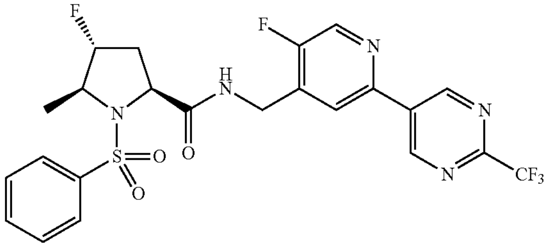
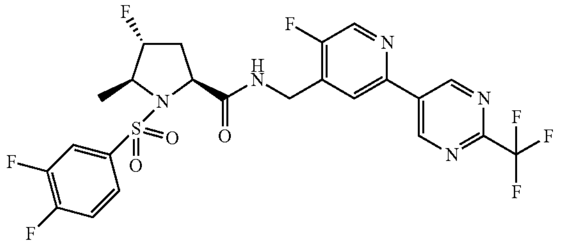
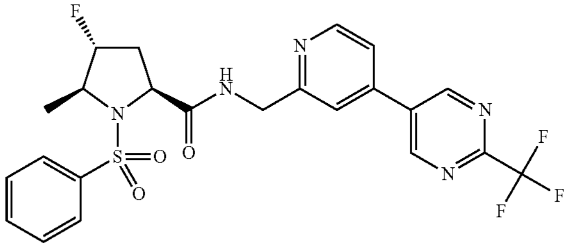
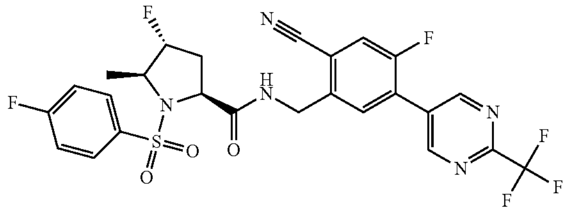
-continued
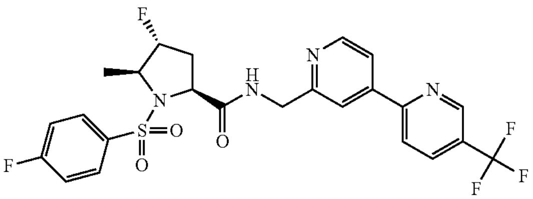
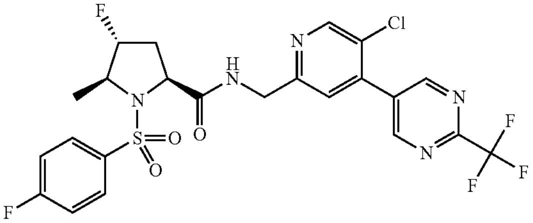
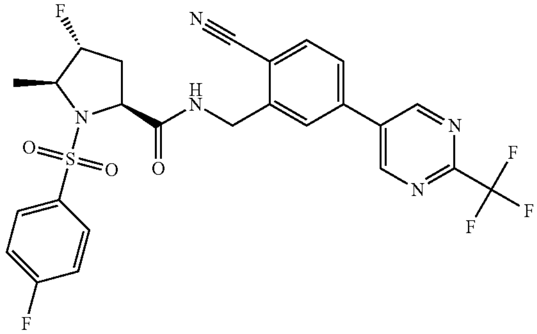
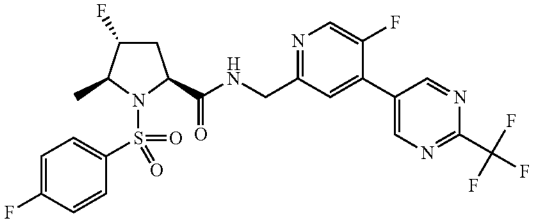
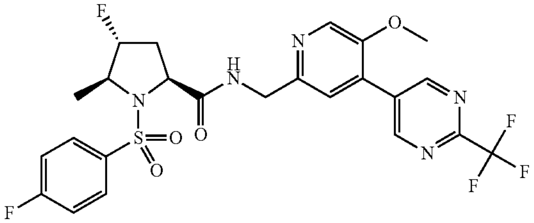
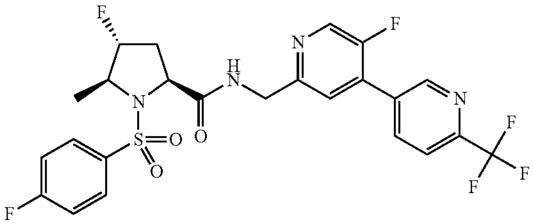
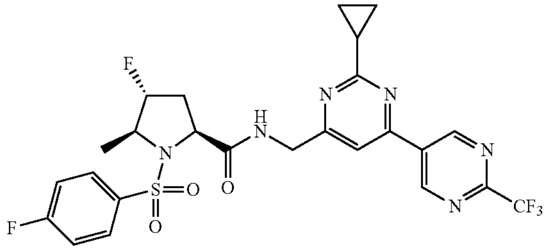

-continued
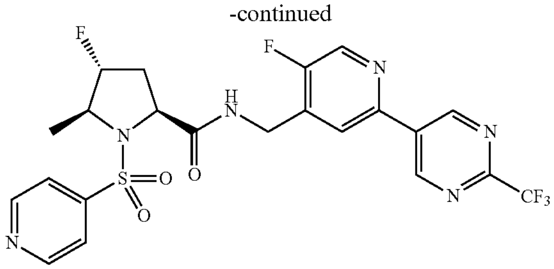
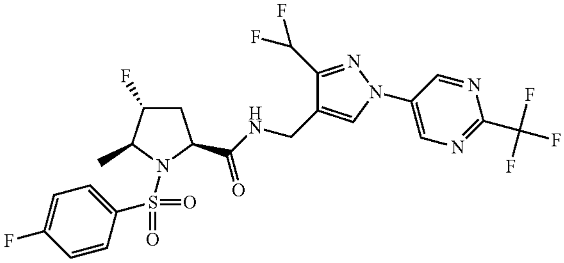
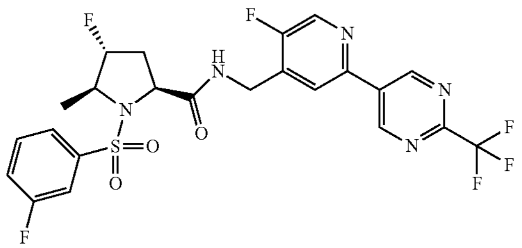
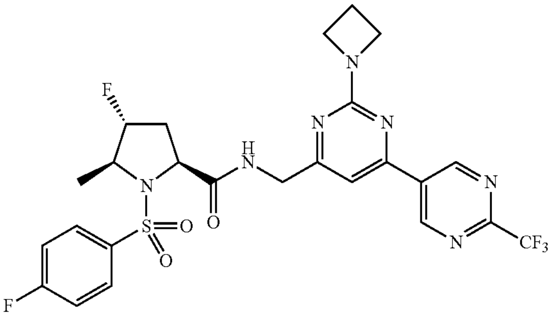
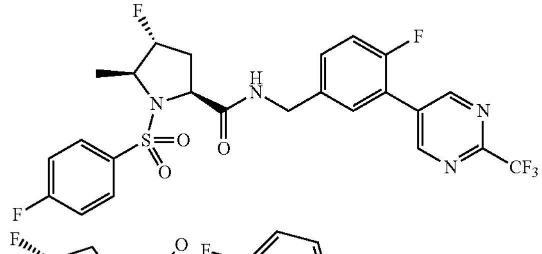
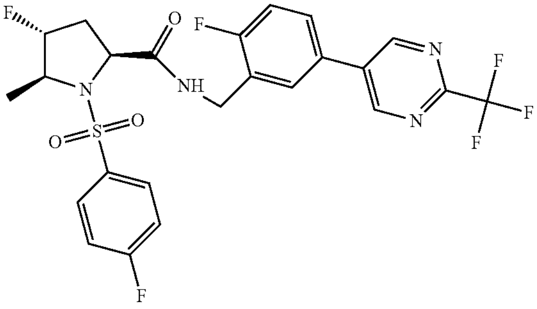
-continued
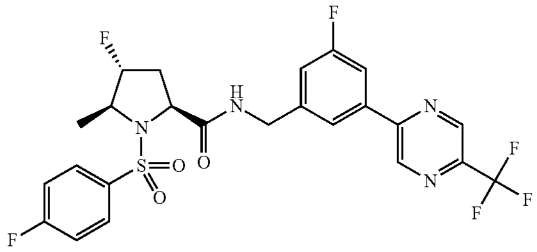
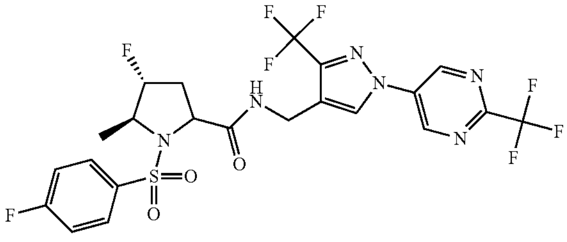
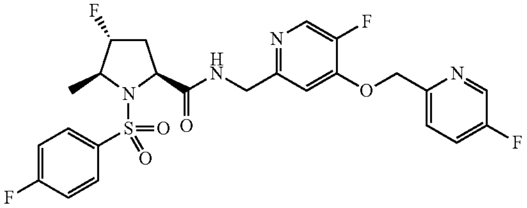
or
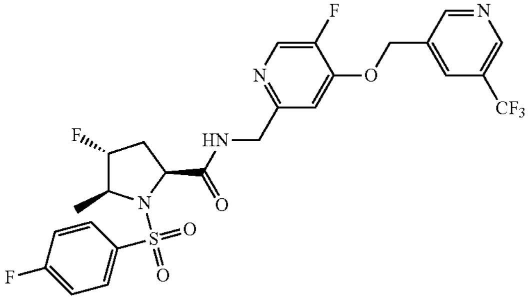
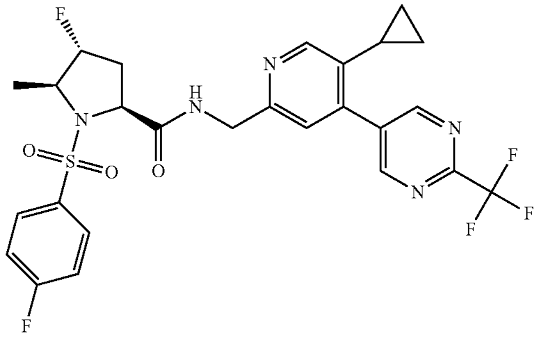
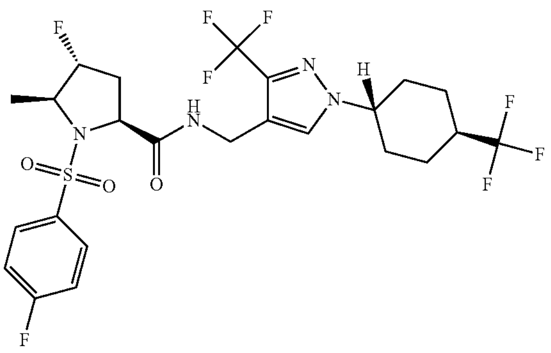

-continued
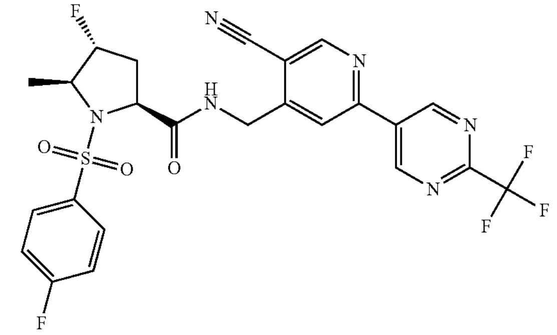
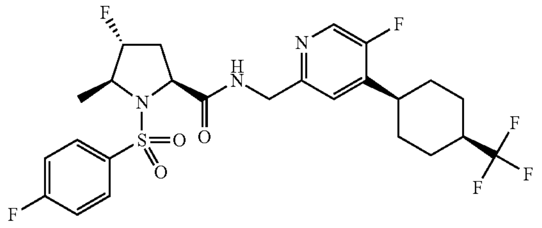
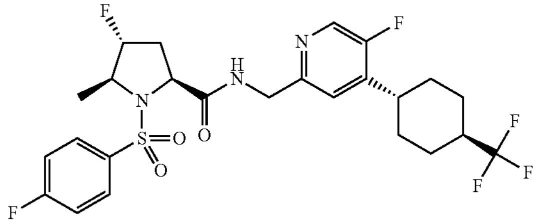
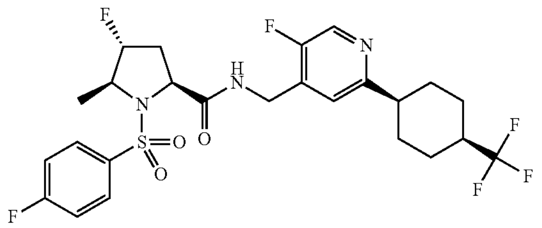
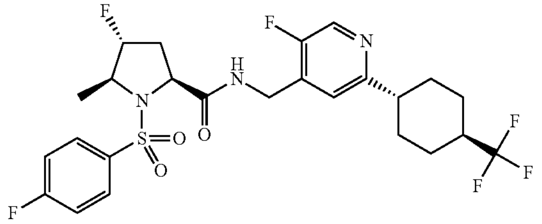
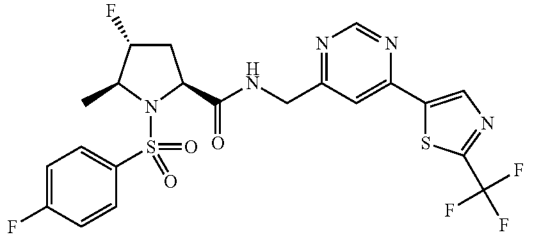
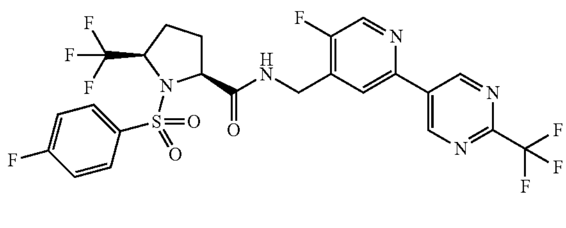
-continued
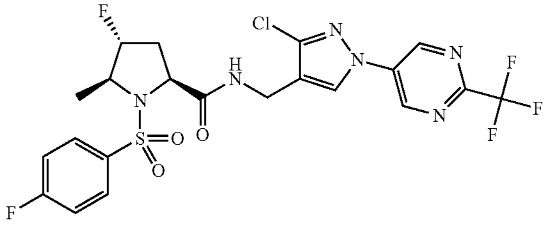
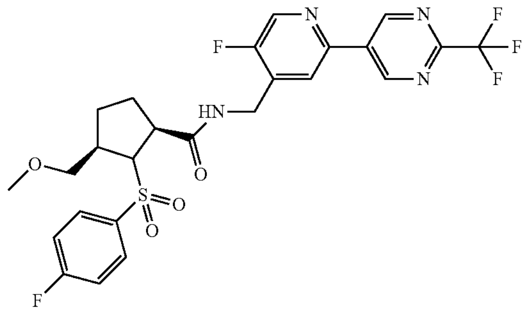
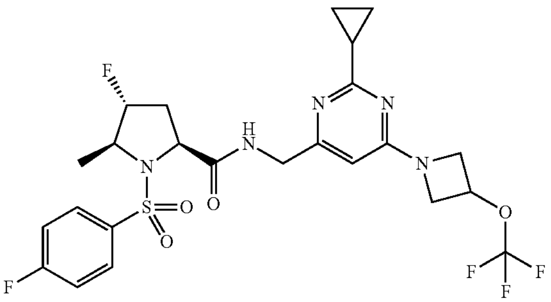
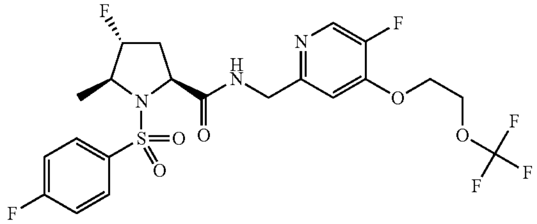
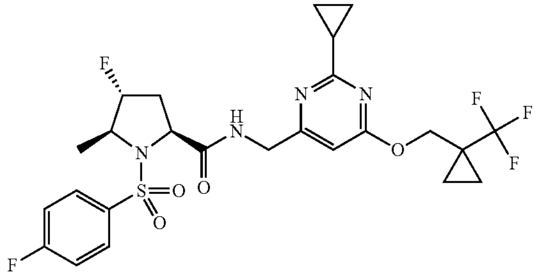
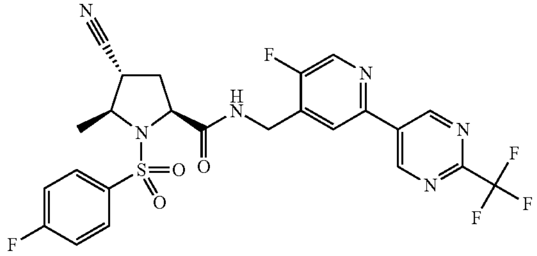

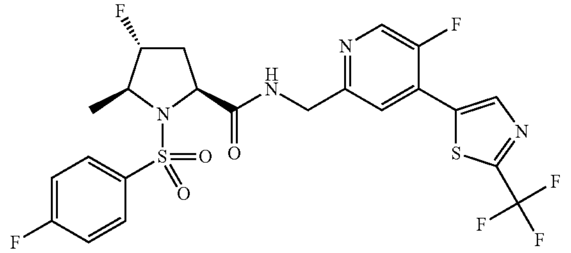
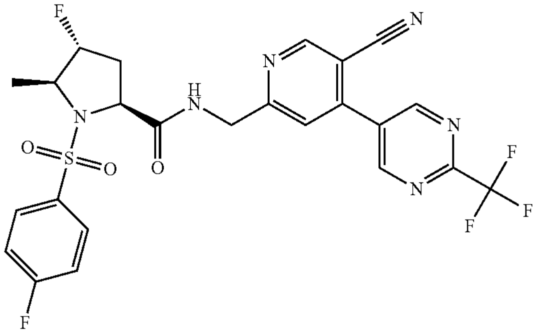
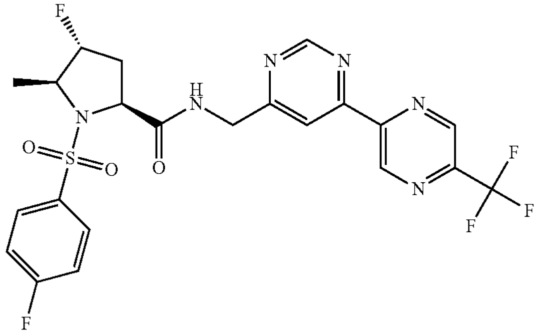
or
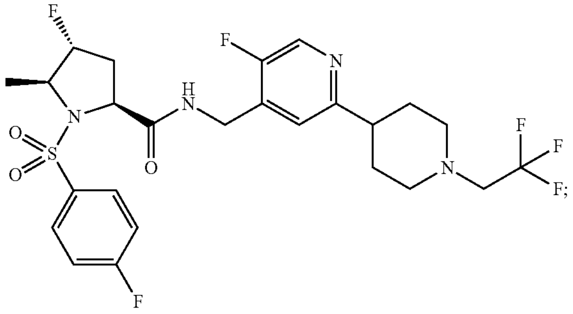
or a salt thereof.
EE123. The compound of EE2, which is:
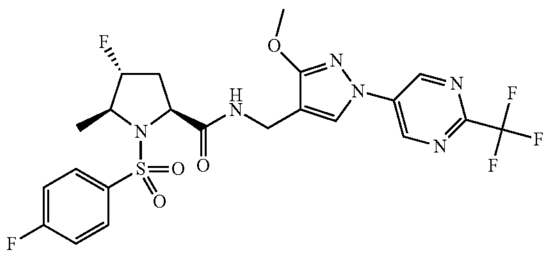
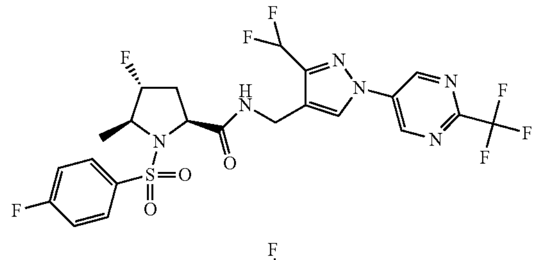
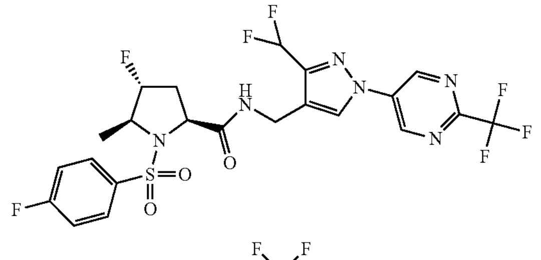
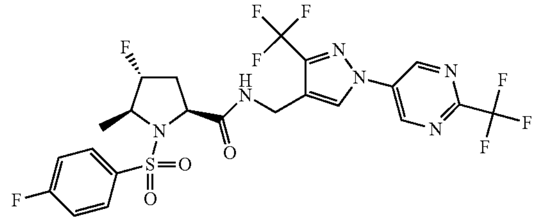
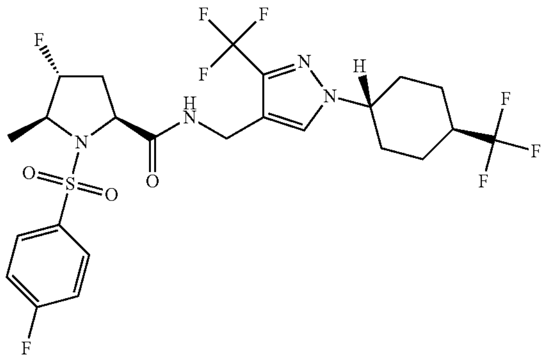
or
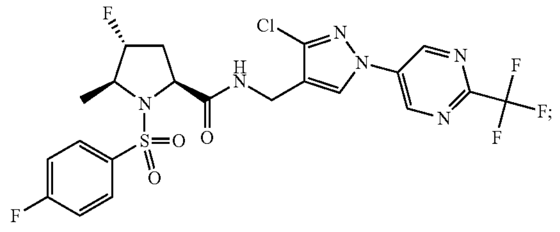 [SMILES: C[C@H]1[C@H](F)C[C@@H](C(=O)NCc2cn(-c3cnc(C(F)(F)F)nc3)nc2Cl)N1S(=O)(=O)c1ccc(F)cc1]
or a salt thereof.
EE124. The compound of EE8, which is:
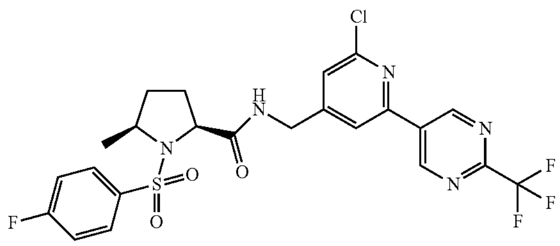

-continued
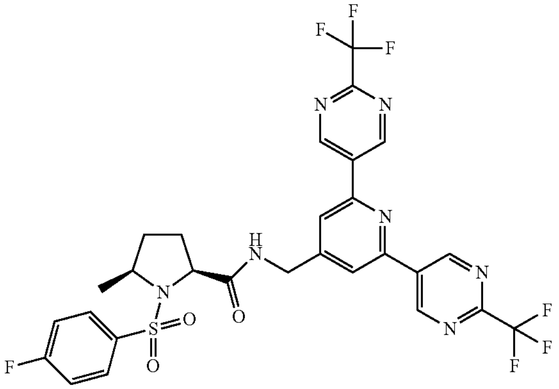
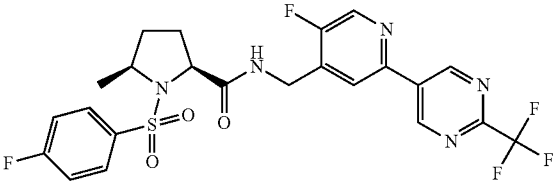
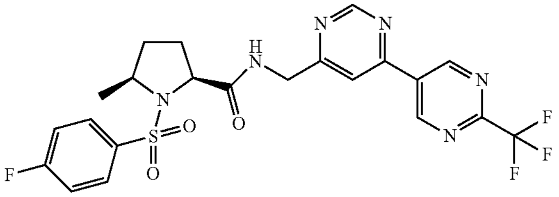
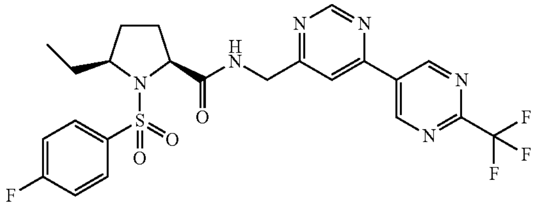
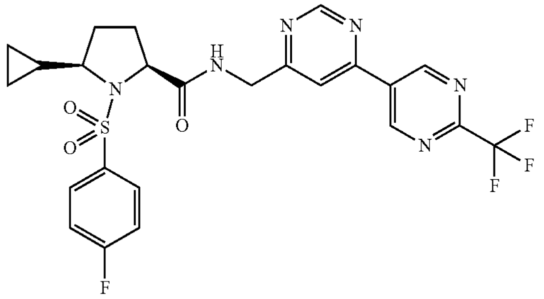
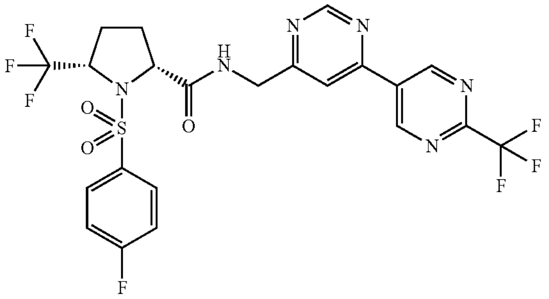
-continued
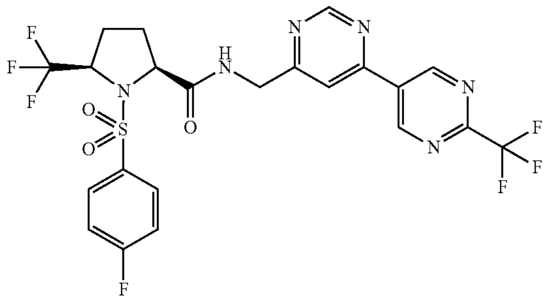
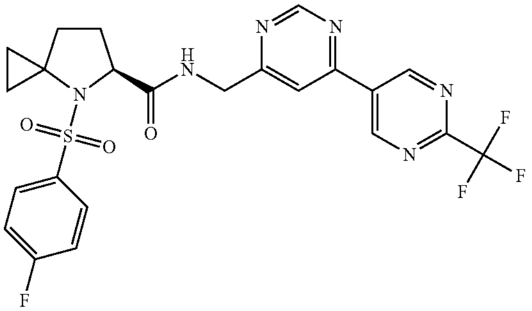
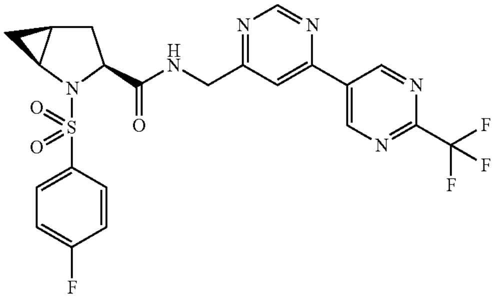
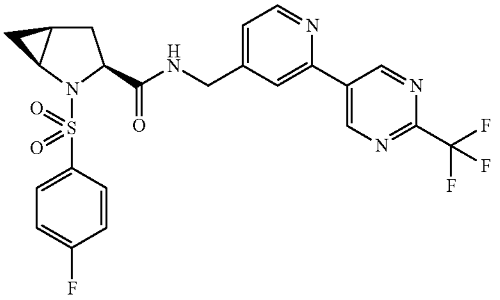
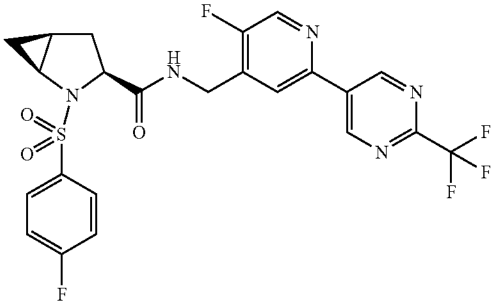

-continued
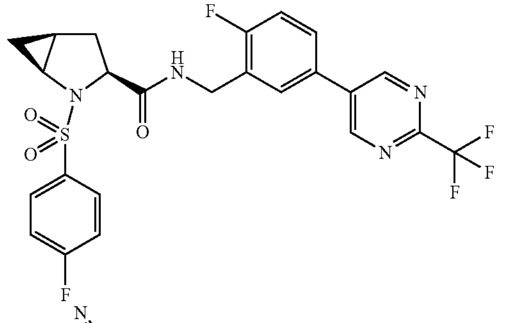
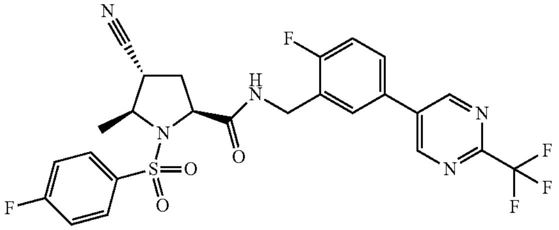
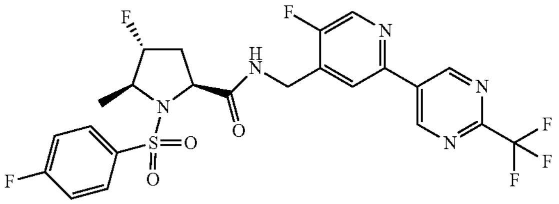
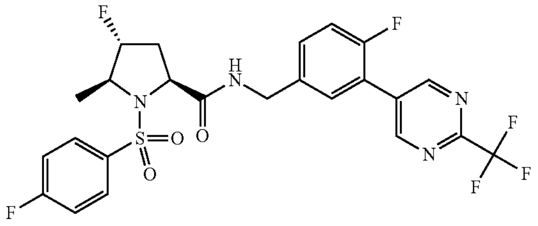
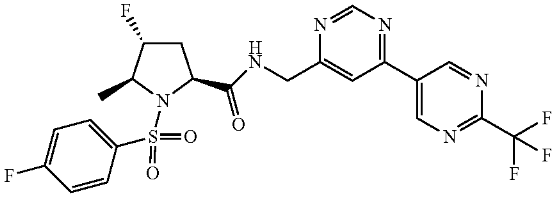
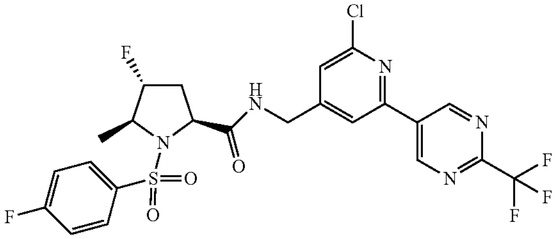
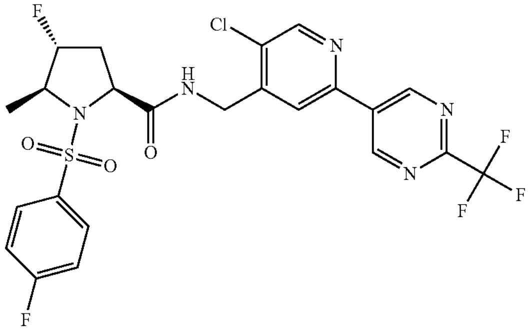
-continued
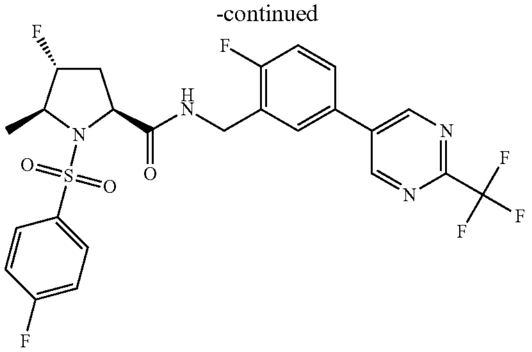
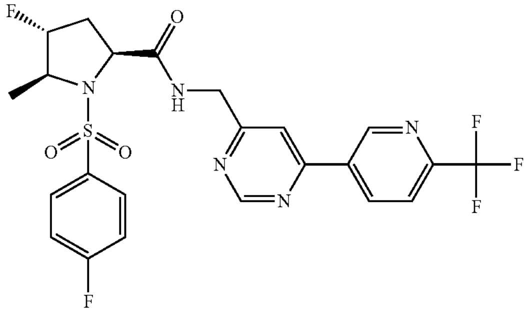
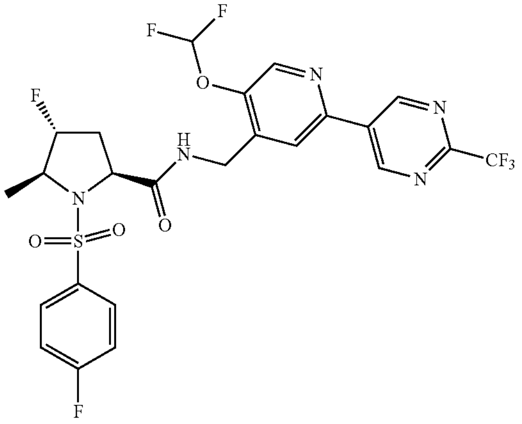
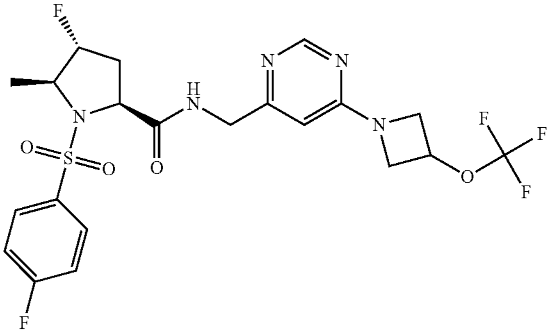
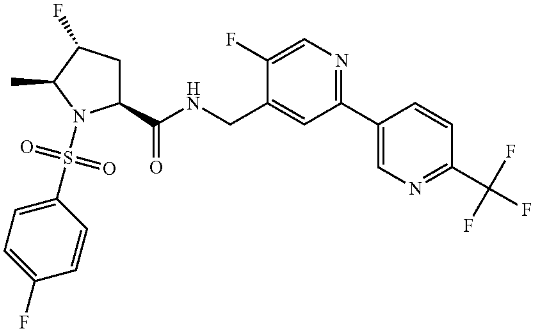

-continued
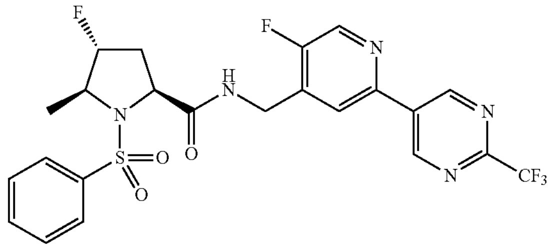
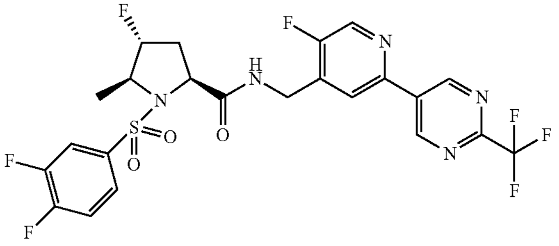
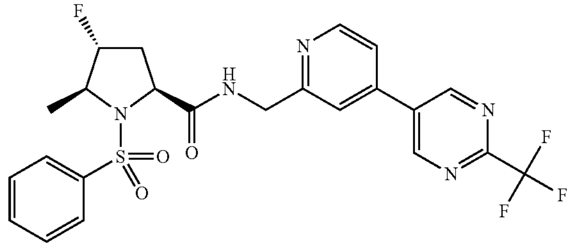
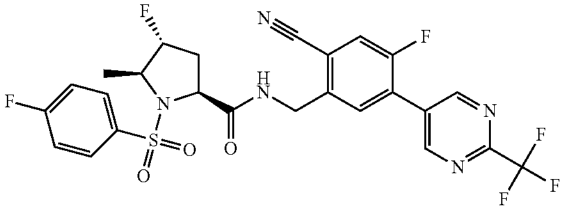
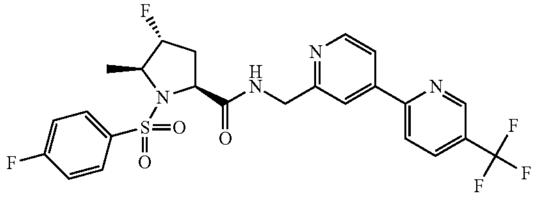
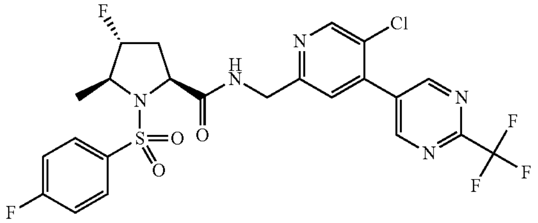
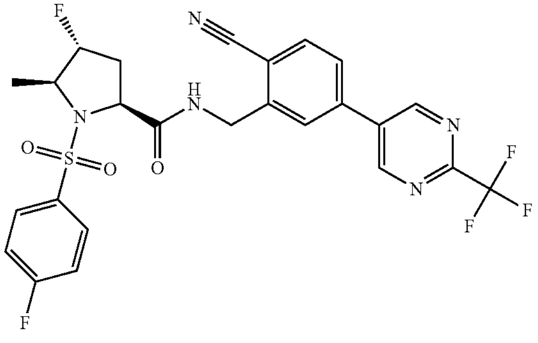
-continued
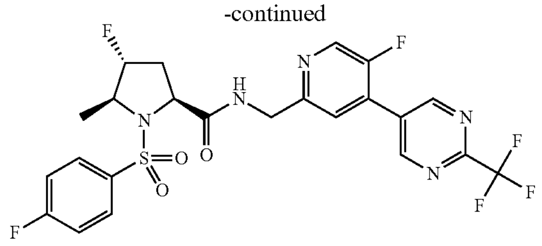
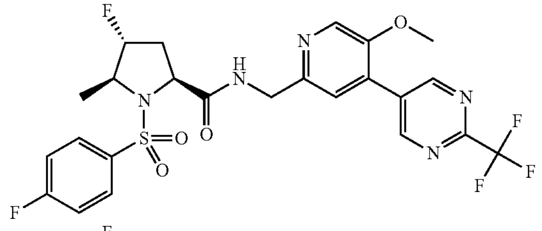
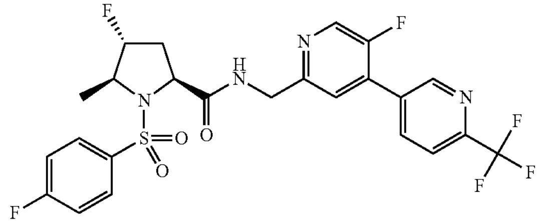
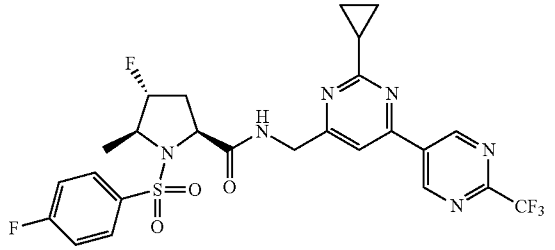
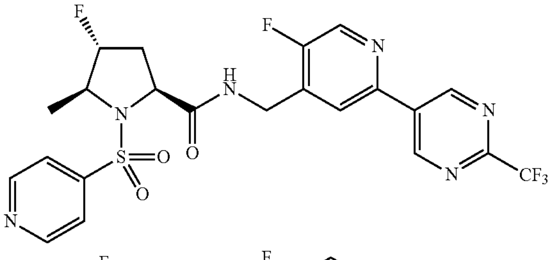
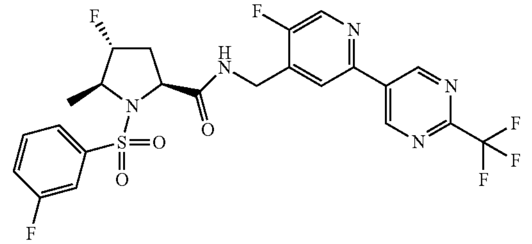
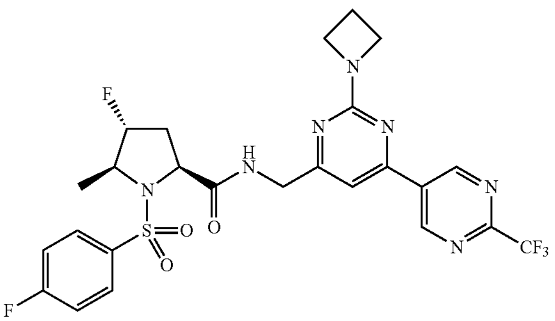

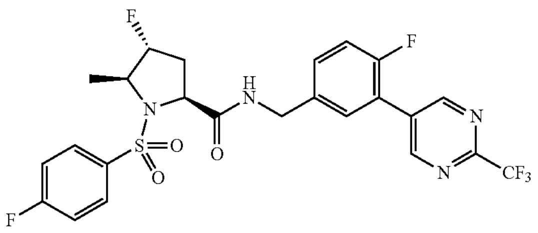
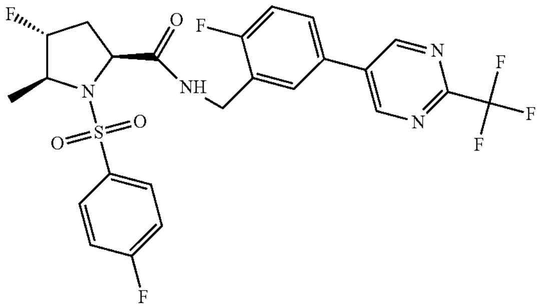
or
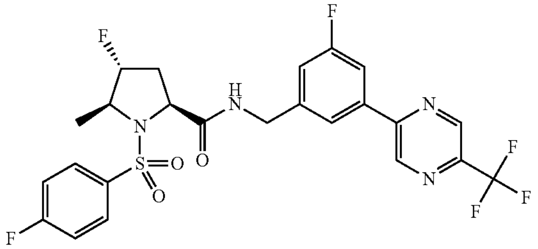
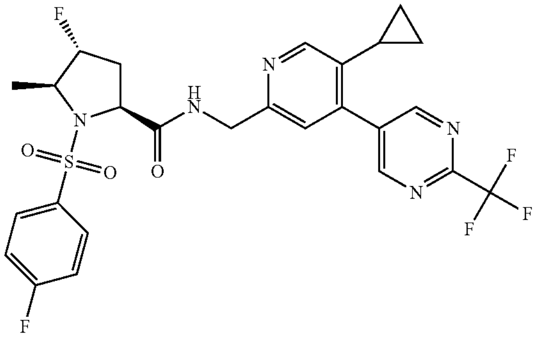
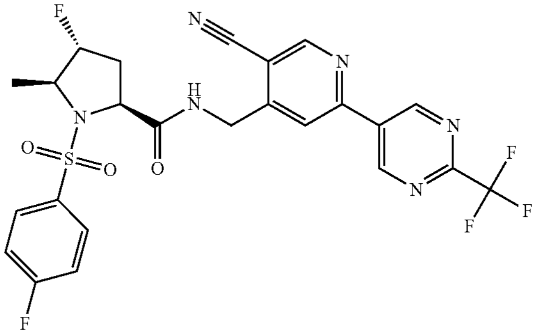
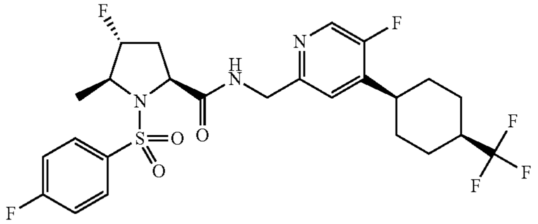
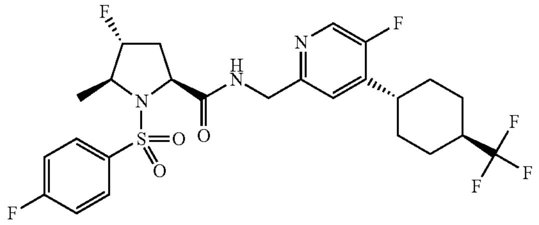
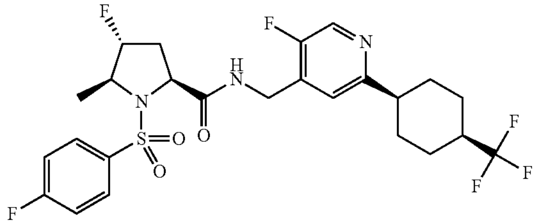
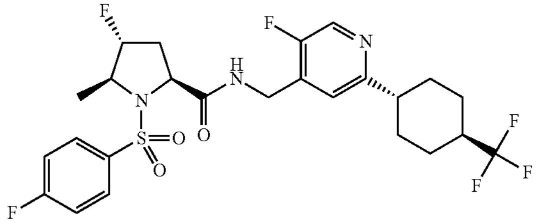
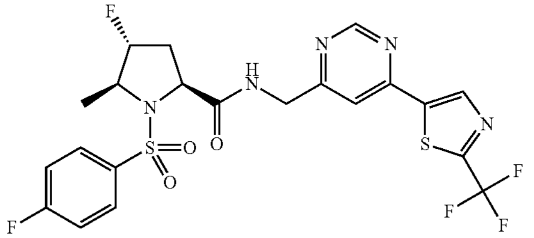
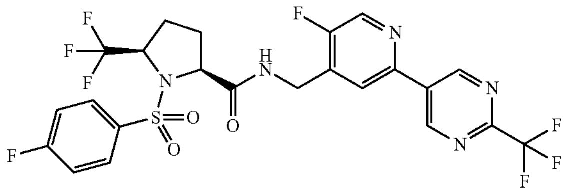
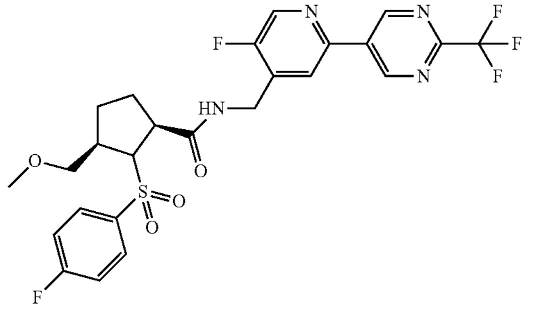
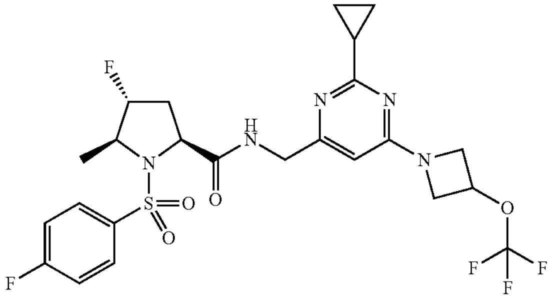

-continued
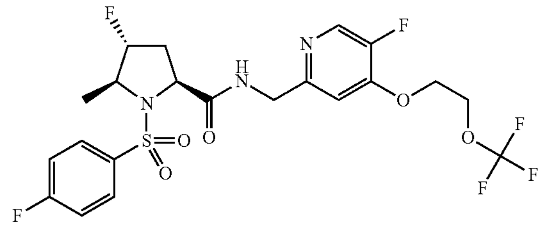
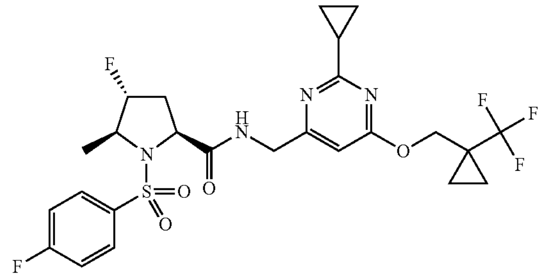
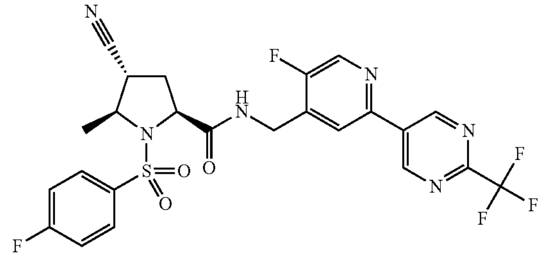
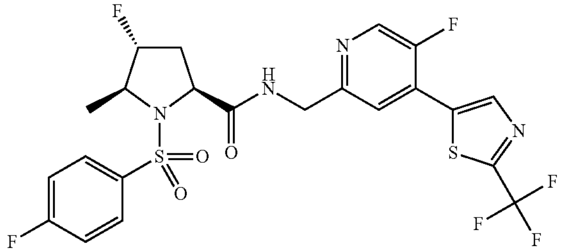
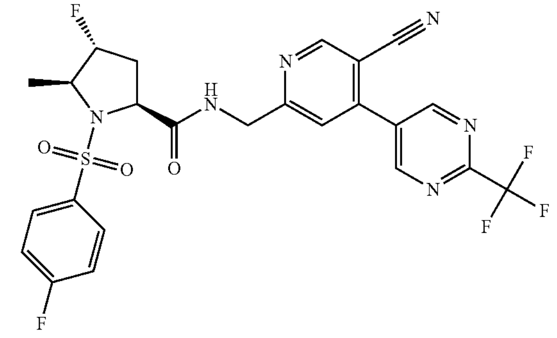
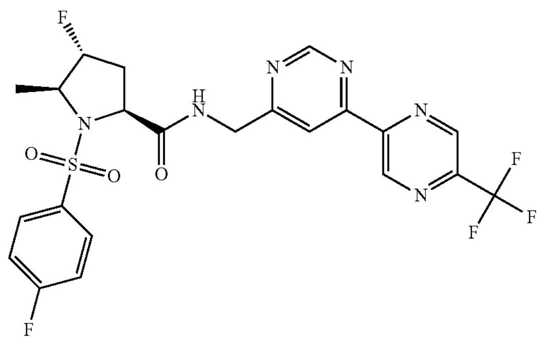
or
-continued
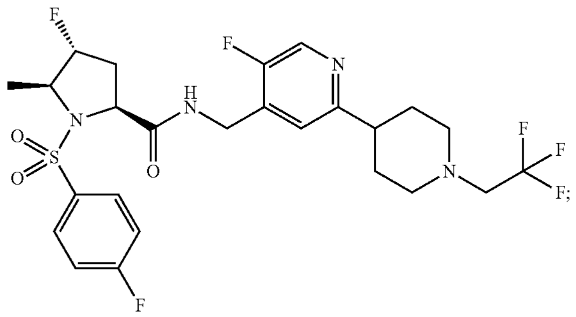
or a salt thereof.
EE125. The compound of EE39, which is:
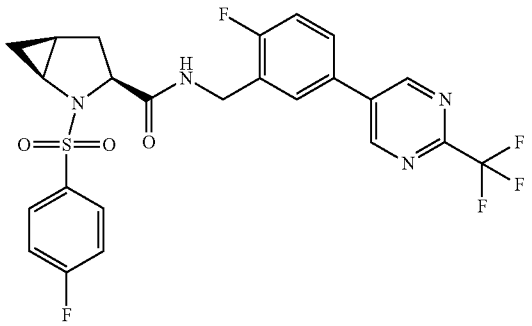
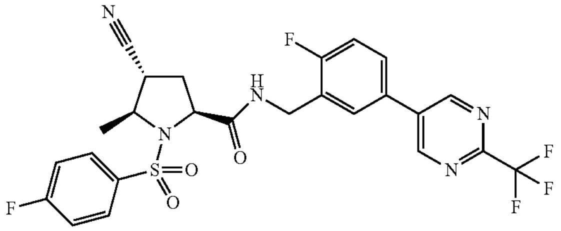
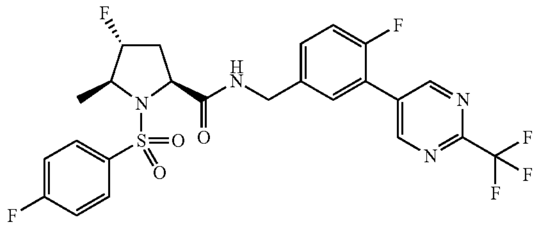
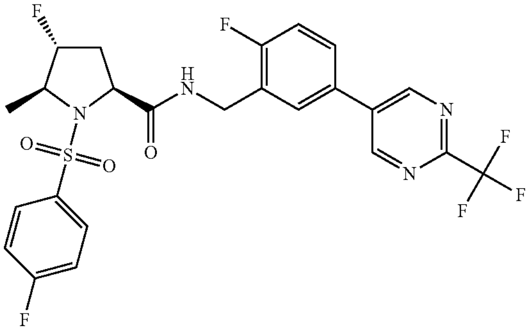

-continued
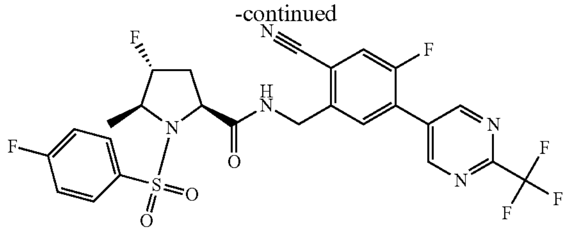
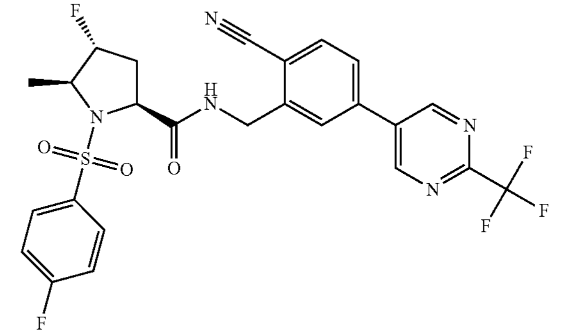
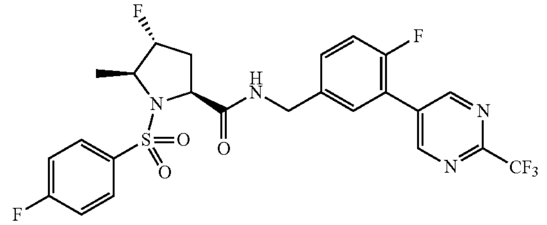
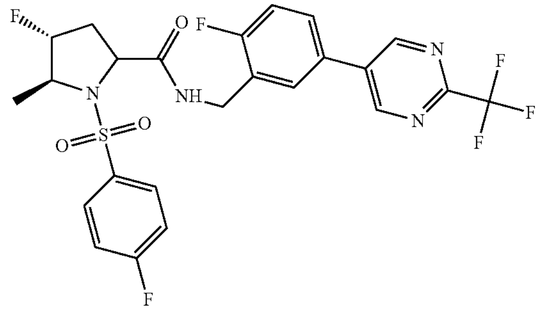
or
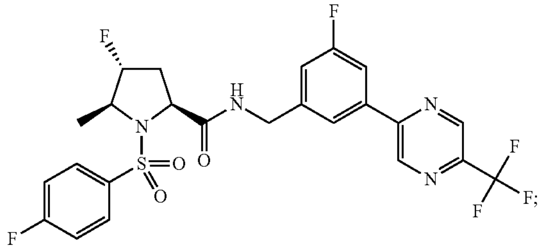
or a salt thereof.
EE126. The compound of EE48, which is:
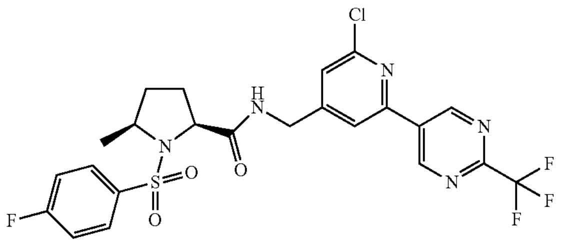
-continued
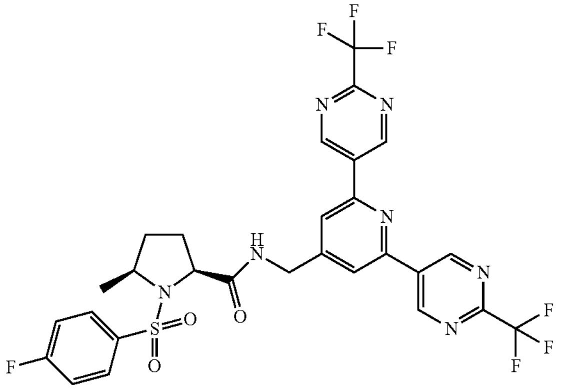
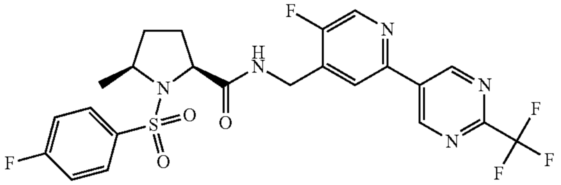
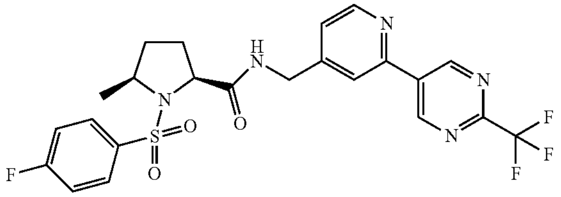
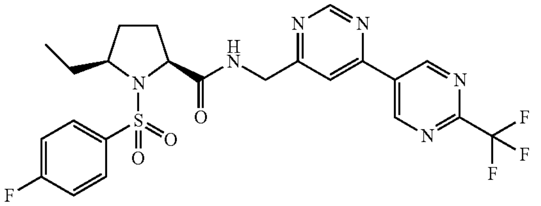
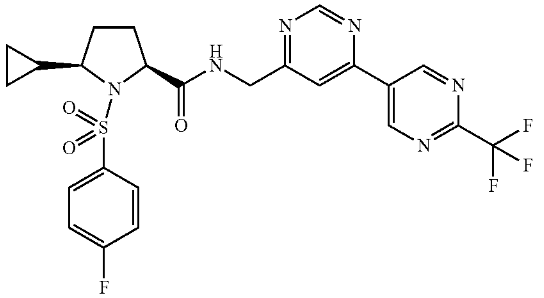
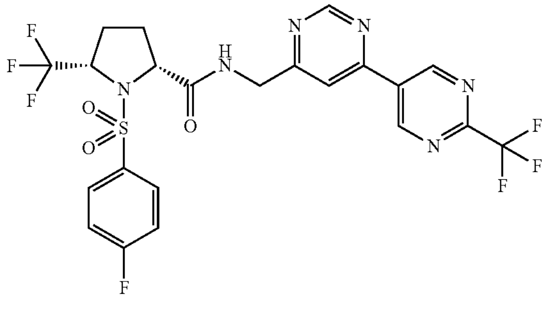

-continued
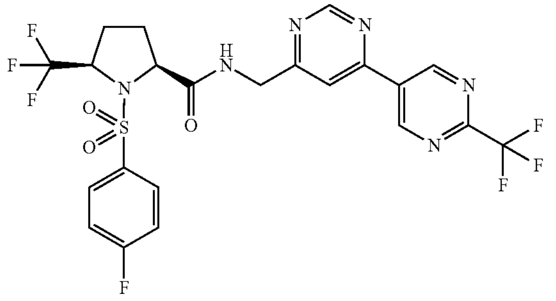
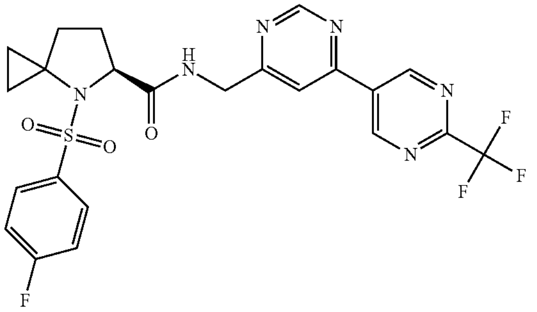
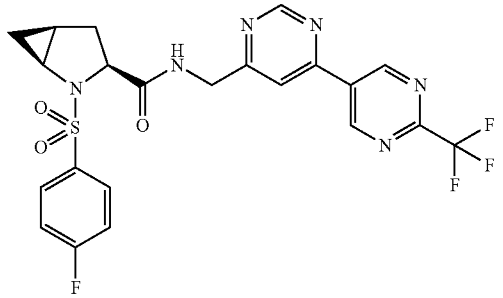
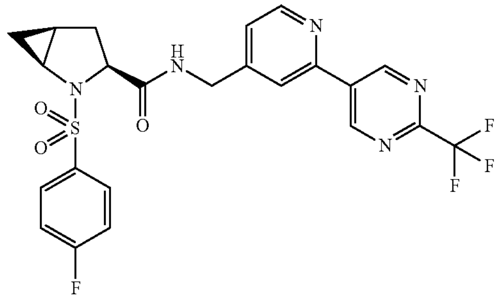
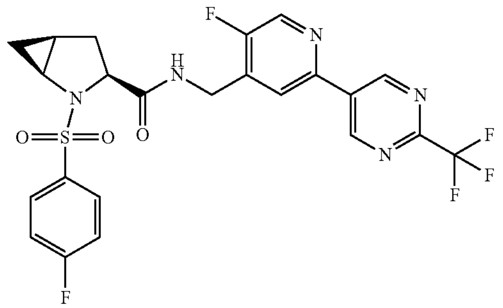
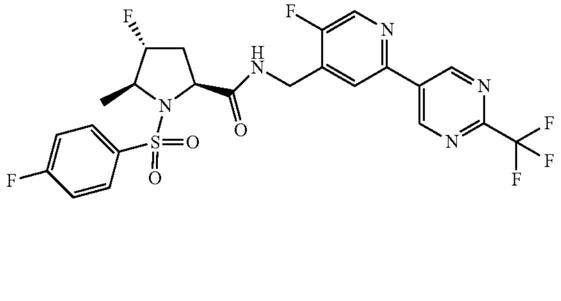
-continued
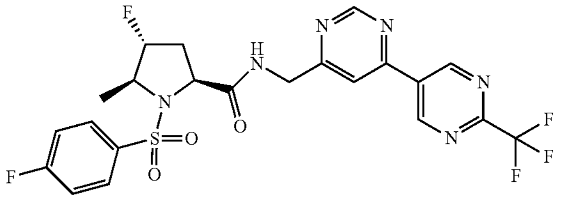
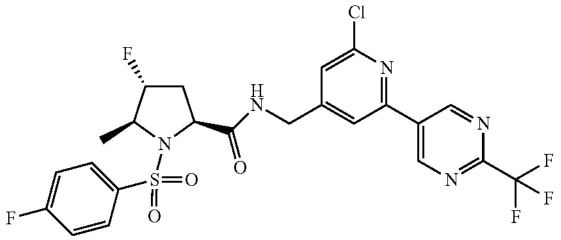
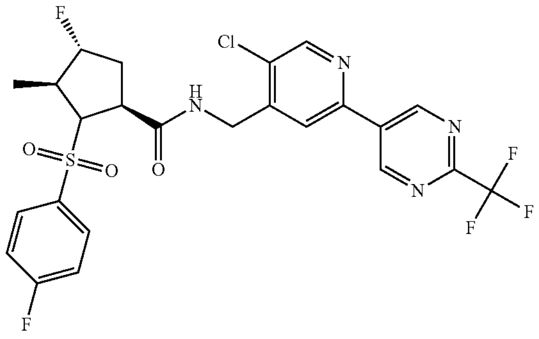
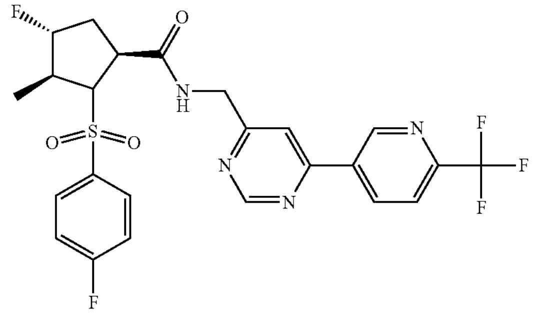
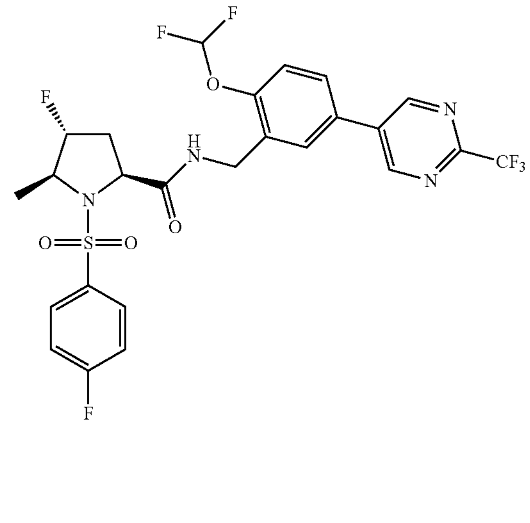

-continued
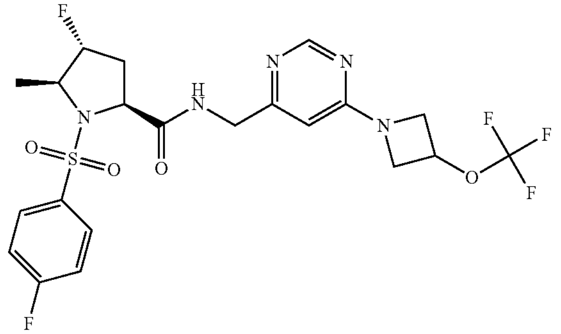
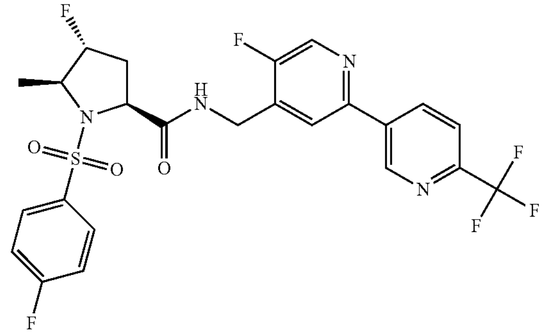
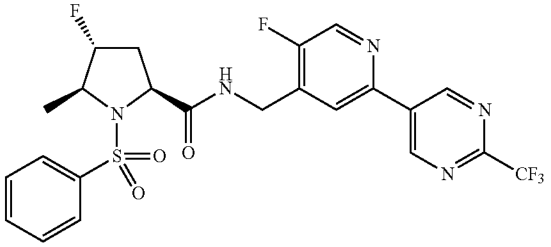
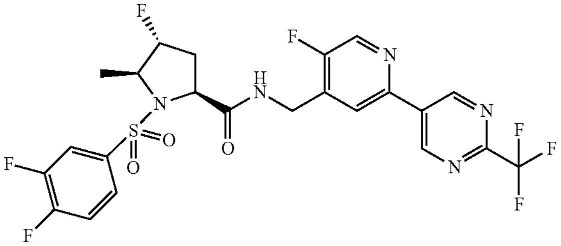
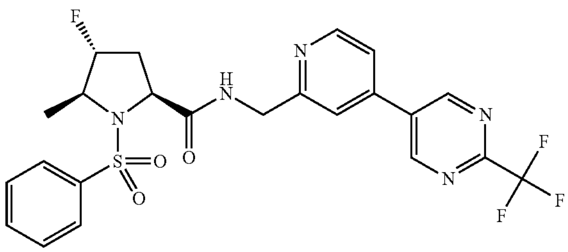
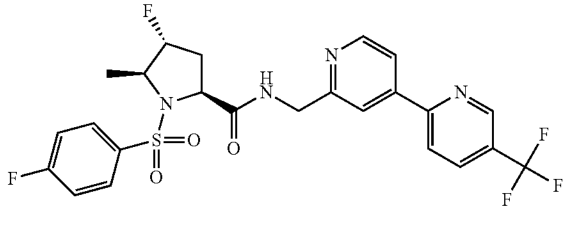
-continued
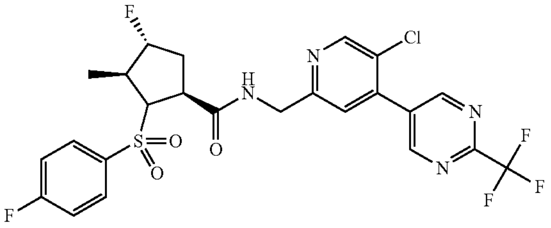
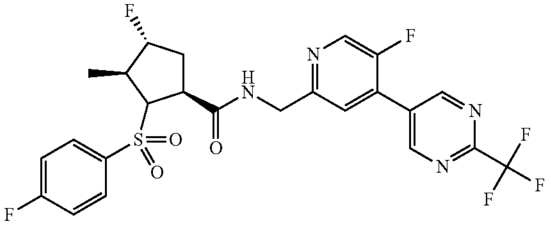
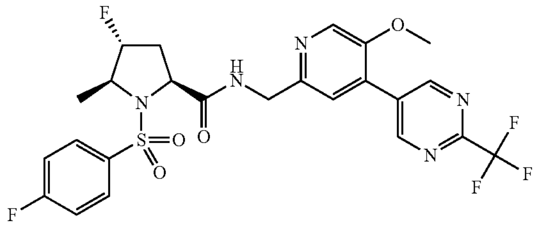
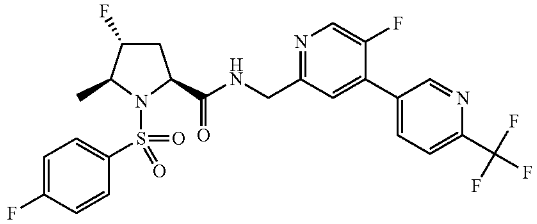
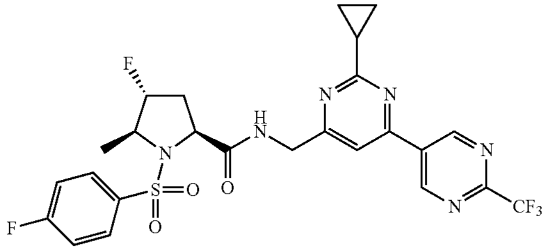
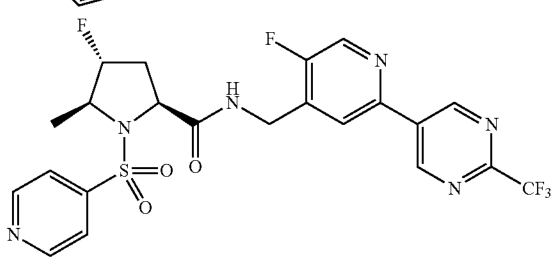
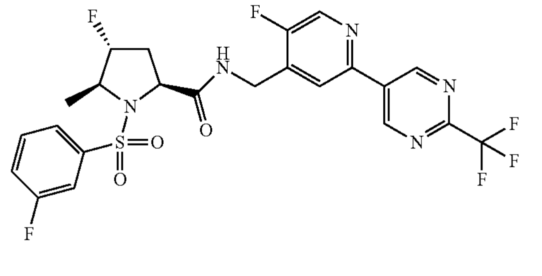

-continued
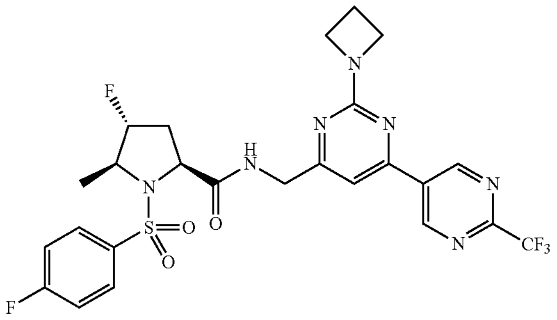
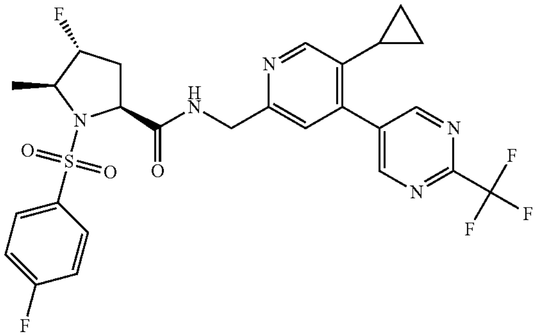
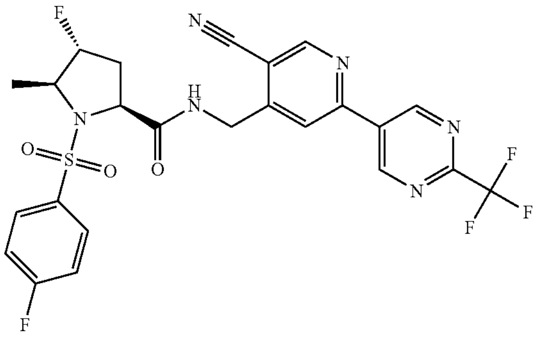
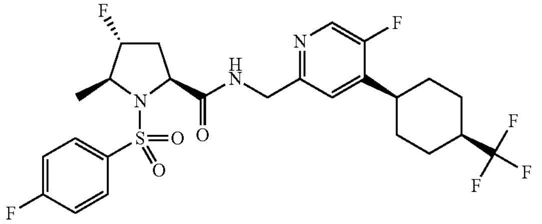
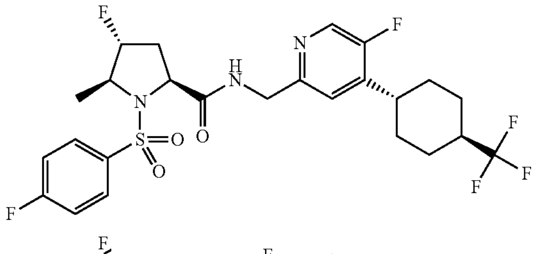
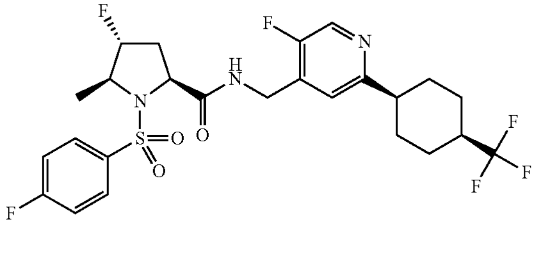
-continued
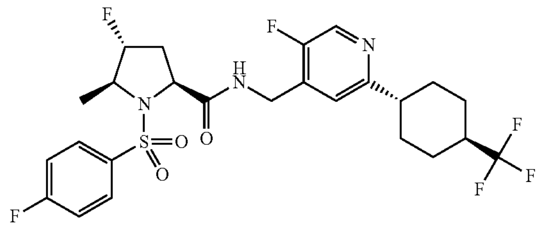
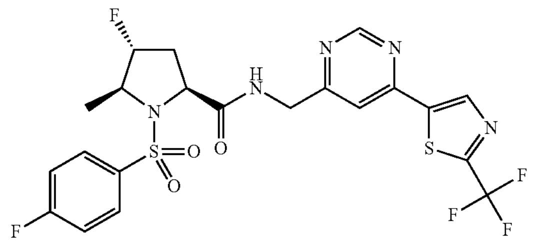
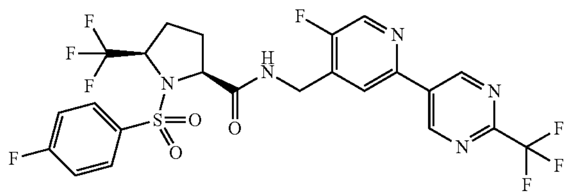
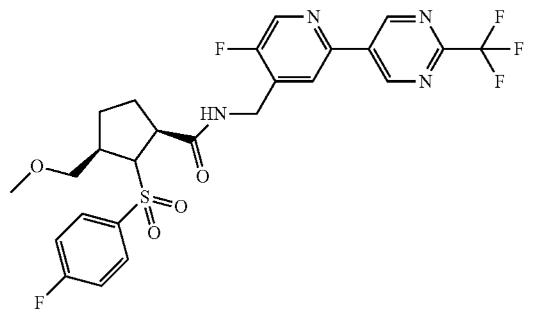
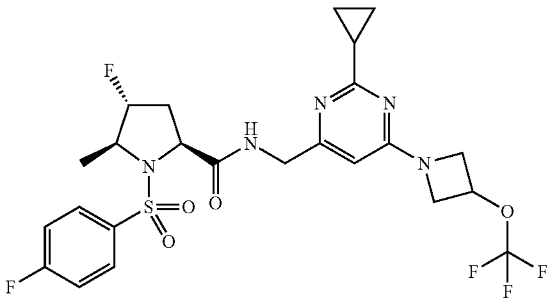
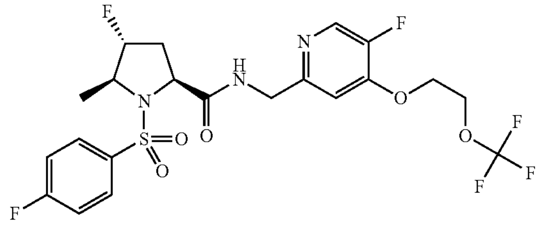

-continued

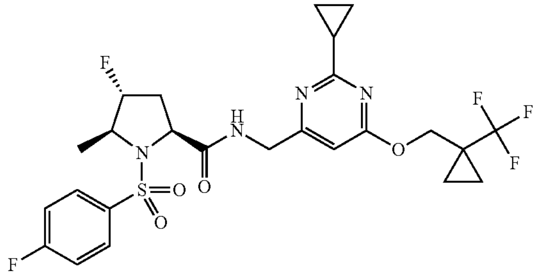

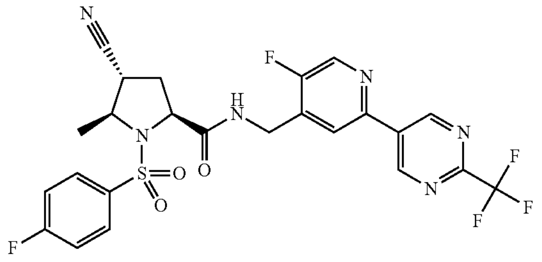

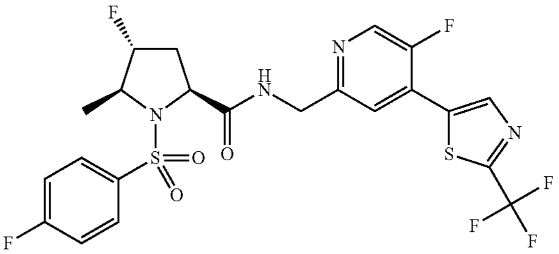

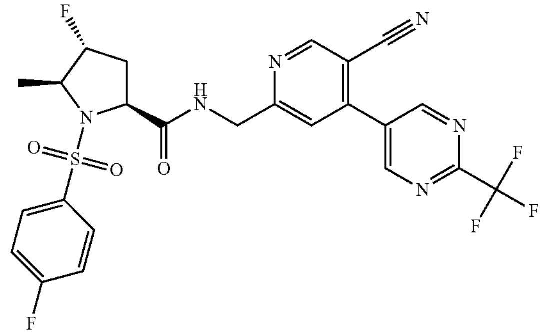

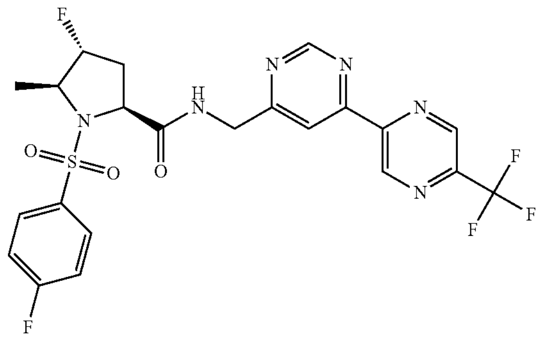

or

-continued

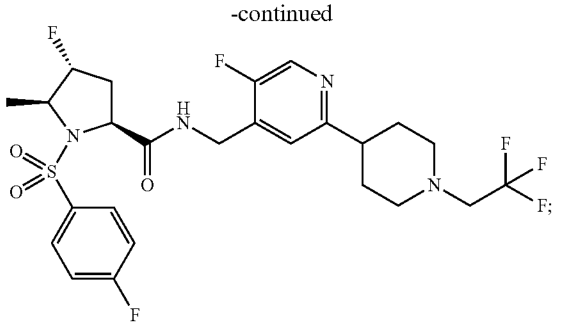

or a salt thereof.

EE127. The compound of EE1, wherein the compound is:

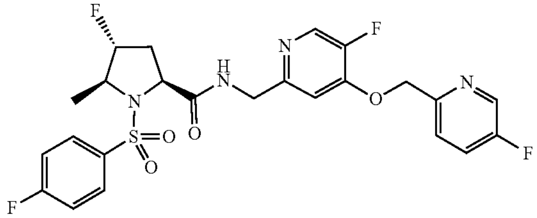

or

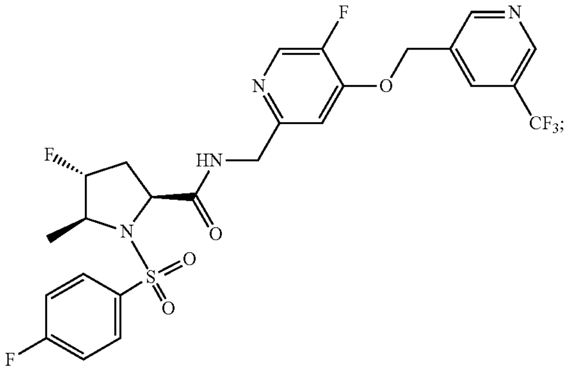

or a salt thereof.

EE128. A compound of formula VI:

VI

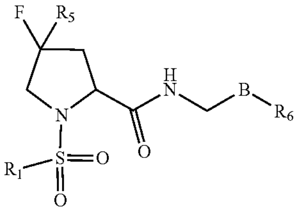

wherein:

B is $B^2$ or $B^3$;

$B^2$ is phenyl, wherein each phenyl is unsubstituted or substituted with one or more groups independently selected from halogen, CN, $(C_1-C_6)$alkyl, and $(C_1-C_6)$haloalkyl;

$B^3$ is a 6-membered heteroaryl, wherein each 6-membered heteroaryl is unsubstituted or substituted with one or more groups independently selected from halogen, $(C_1-C_6)$alkyl, $(C_1-C_6)$haloalkyl, $O(C_1-C_6)$alkyl, $O(C_1-C_6)$haloalkyl, 5 or 6-membered heteroaryl, $(C_3-C_7)$cycloalkyl, and $(C_3-C_7)$heterocyclyl; and wherein any of the 5 or 6-membered heteroaryl, $(C_3-C_7)$cycloalkyl, or $(C_3-C_7)$heterocyclyl groups is unsubstituted or substituted with one or more groups independently selected from halogen, $(C_1-C_6)$alkyl, and $(C_1-C_6)$ haloalkyl;

$R^1$ is phenyl or heteroaryl, wherein each phenyl or heteroaryl is unsubstituted or substituted with one or more groups independently selected from halogen, $(C_1-C_6)$alkyl, and $(C_1-C_6)$haloalkyl;

$R^5$ is H or $(C_1-C_6)$alkyl;

$R^6$ is a phenyl, $(C_3-C_7)$cycloalkyl, 5- or 6-membered heteroaryl, or 4, 5, 6 or 7-membered heterocycle, wherein any phenyl, $(C_3-C_7)$cycloalkyl, 5- or 6-membered heteroaryl, or 4, 5, 6 or 7-membered heterocycle of $R^6$ is optionally substituted with one or more groups independently selected from halogen, $SF_5$, $(C_1-C_6)$alkyl, $(C_1-C_6)$ haloalkyl, $O(C_1-C_6)$alkyl, and $O(C_1-C_6)$haloalkyl; or $R^6$ is $O—CH_2—R^7$;

$R^7$ is a $(C_1-C_6)$alkyl, 3, 4, 5, 6, or 7-membered heterocycle, 3, 4, 5, 6, or 7-membered cycloalkyl, or 6-membered heteroaryl, wherein any $(C_1-C_6)$alkyl, 3, 4, 5, 6, or 7-membered heterocycle, 3, 4, 5, 6, or 7-membered cycloalkyl, or 6-membered heteroaryl is optionally substituted with one or more groups independently selected from halogen, $(C_1-C_6)$ alkyl, $(C_1-C_6)$haloalkyl, $O(C_1-C_6)$alkyl, and $O(C_1-C_6)$haloalkyl;

or a salt thereof.

EE129. The compound of EE128, wherein $B^2$ is:

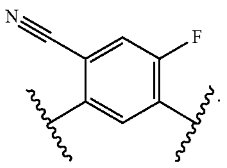 [SMILES: *c1cc(*)c(C#N)cc1F]

EE130. The compound of EE128, wherein $B^2$ is:

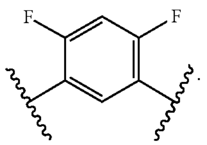 [SMILES: *c1cc(*)c(F)cc1F]

EE131. The compound of EE128, wherein $B^2$ is:

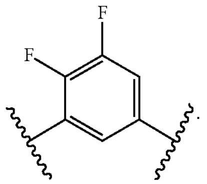 [SMILES: *c1cc(*)c(F)c(F)c1]

EE132. The compound of EE128, wherein $B^2$ is:

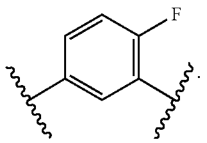 [SMILES: *c1ccc(F)c(*)c1]

EE133. The compound of EE128, wherein $B^3$ is:

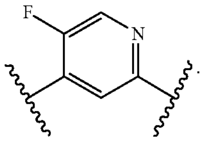 [SMILES: *c1cc(*)c(F)cn1]

EE134. The compound of EE128, wherein $B^3$ is:

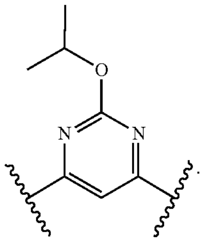 [SMILES: *c1cc(*)nc(OC(C)C)n1]

EE135. The compound of EE128, wherein $B^3$ is:

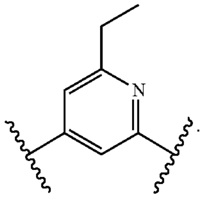 [SMILES: *c1cc(*)nc(CC)c1]

EE136. The compound of EE128, wherein $B^3$ is:

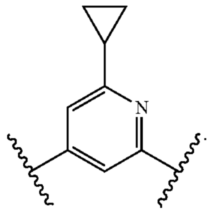 [SMILES: *c1cc(*)nc(C2CC2)c1]

EE137. The compound of EE128, wherein $B^3$ is:

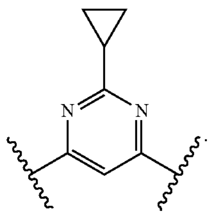

EE138. The compound of EE128, wherein $B^3$ is:

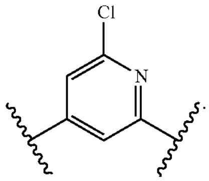 [SMILES: *c1cc(*)nc(Cl)c1]

EE139. The compound of any one of EE128-EE138, wherein $R^5$ is H.

EE140. The compound of any one of EE128-EE138, wherein $R^5$ is $(C_1$-$C_6)$alkyl.

EE141. The compound of EE139, wherein the group

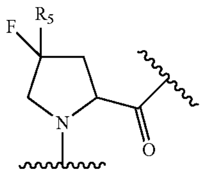

is:

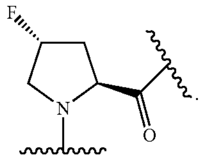

EE142. The compound of EE140, wherein the group

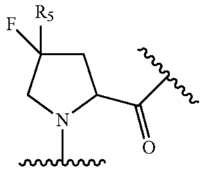

is:

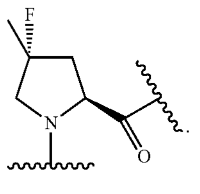 [SMILES: *C(=O)[C@@H]1C[C@@](C)(F)CN1*]

EE143. The compound of any one of EE128-142, wherein $R^6$ is 4, 5, 6 or 7-membered heterocycle.

EE144. The compound of EE143, wherein $R^6$ is 6-membered heterocycle.

EE145. The compound of EE144, wherein $R^6$ is:

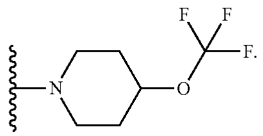 [SMILES: *N1CCC(OC(F)(F)F)CC1]

EE146. The compound of any one of EE128-EE142, wherein $R^6$ is 6-membered heteroaryl.

EE147. The compound of EE146, wherein $R^6$ is:

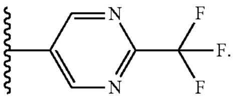

EE148. The compound of any one of EE128-EE142, wherein $R^6$ is:

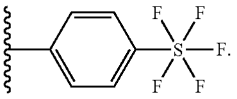 [SMILES: *c1ccc(S(F)(F)(F)(F)F)cc1]

EE149. The compound of any one of EE128-EE142, wherein $R^6$ is:

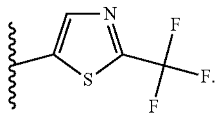 [SMILES: *c1cnc(C(F)(F)F)s1]

EE150. The compound of any one of EE128-EE149, wherein $R^1$ is:

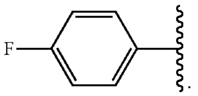

EE151. The compound of EE128, wherein the compound is:

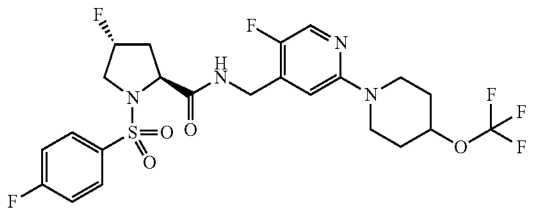

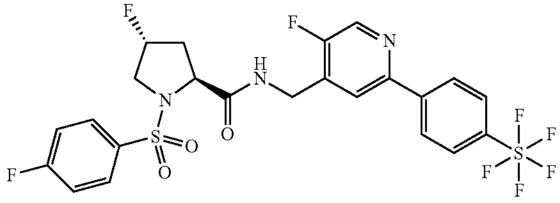

-continued
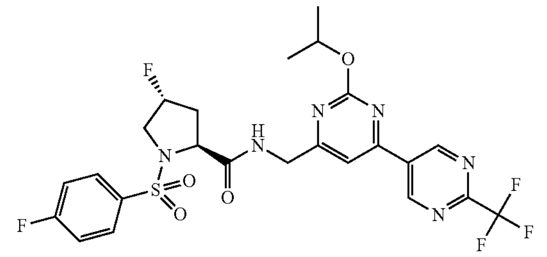
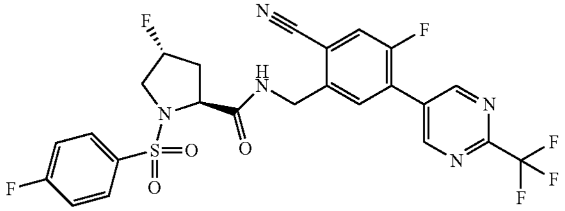
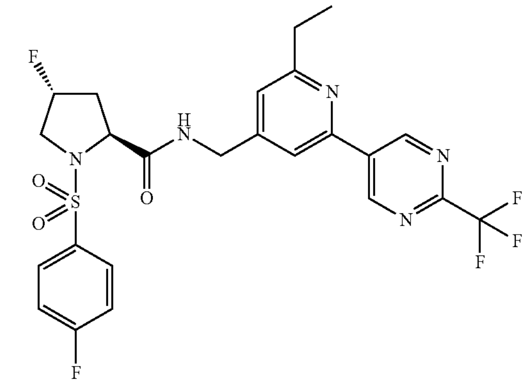
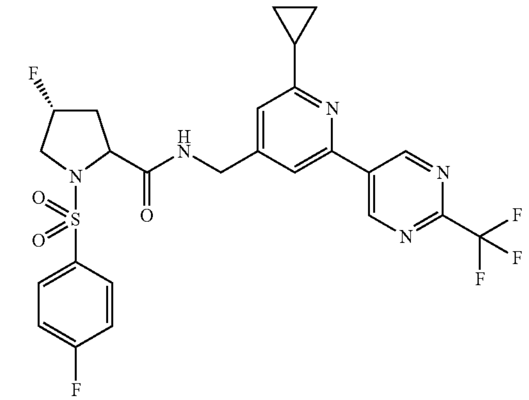
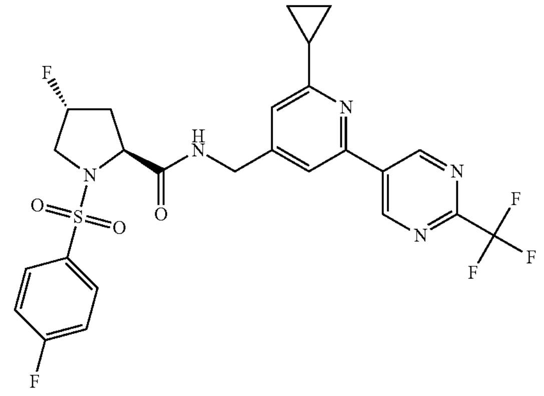
-continued
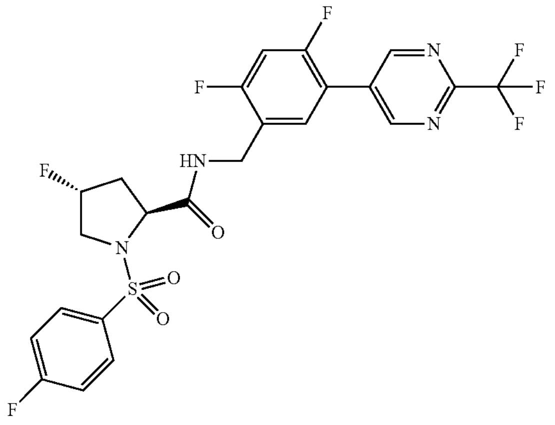
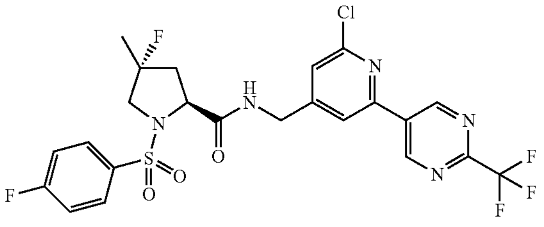
or
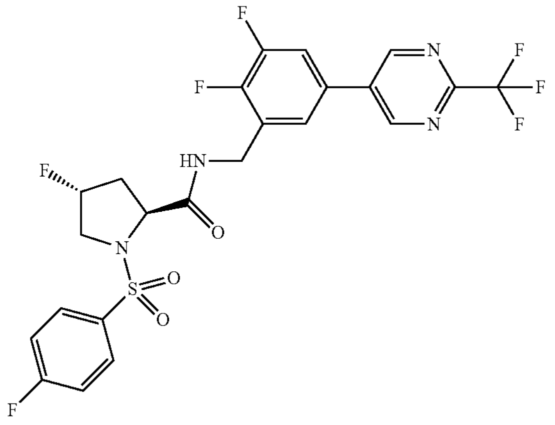
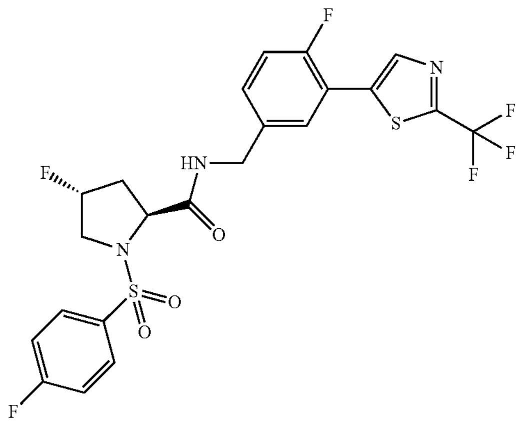
or a salt thereof.

EE152. A compound of formula VII:

VII

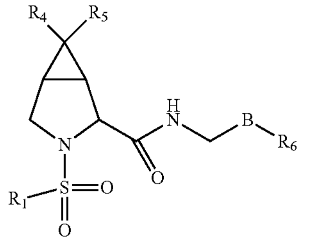

wherein:

B is $B^2$ or $B^3$;

$B^2$ is phenyl, wherein each phenyl is unsubstituted or substituted with one or more groups independently selected from halogen, CN, $(C_1-C_6)$alkyl, and $(C_1-C_6)$haloalkyl;

$B^3$ is a 6-membered heteroaryl, wherein each 6-membered heteroaryl is unsubstituted or substituted with one or more groups independently selected from halogen, $(C_1-C_6)$alkyl, $(C_1-C_6)$haloalkyl, $O(C_1-C_6)$alkyl, $O(C_1-C_6)$haloalkyl, 5 or 6-membered heteroaryl, $(C_3-C_7)$cycloalkyl, and $(C_3-C_7)$heterocyclyl; and wherein any of the 5 or 6-membered heteroaryl, $(C_3-C_7)$cycloalkyl, or $(C_3-C_7)$heterocyclyl groups is unsubstituted or substituted with one or more groups independently selected from halogen, $(C_1-C_6)$alkyl, and $(C_1-C_6)$ haloalkyl;

$R^1$ is phenyl or heteroaryl, wherein each phenyl or heteroaryl is unsubstituted or substituted with one or more groups independently selected from halogen, $(C_1-C_6)$alkyl, and $(C_1-C_6)$haloalkyl;

$R^4$ and $R^5$ are each independently selected from H, halogen, $(C_1-C_6)$alkyl, $(C_1-C_6)$haloalkyl, $O(C_1-C_6)$alkyl, or $O(C_1-C_6)$haloalkyl;

$R^6$ is a phenyl, $(C_3-C_7)$cycloalkyl, 5- or 6-membered heteroaryl, or 4, 5, 6 or 7-membered heterocycle, wherein any phenyl, $(C_3-C_7)$cycloalkyl, 5- or 6-membered heteroaryl, or 4, 5, 6 or 7-membered heterocycle of $R^6$ is optionally substituted with one or more groups independently selected from halogen, $SF_5$, $(C_1-C_6)$alkyl, $(C_1-C_6)$ haloalkyl, $O(C_1-C_6)$alkyl, and $O(C_1-C_6)$haloalkyl; or $R^6$ is $O—CH_2—R^7$;

$R^7$ is a $(C_1-C_6)$alkyl, 3, 4, 5, 6, or 7-membered heterocycle, 3, 4, 5, 6, or 7-membered cycloalkyl, or 6-membered heteroaryl, wherein any $(C_1-C_6)$alkyl, 3, 4, 5, 6, or 7-membered heterocycle, 3, 4, 5, 6, or 7-membered cycloalkyl, or 6-membered heteroaryl is optionally substituted with one or more groups independently selected from halogen, $(C_1-C_6)$ alkyl, $(C_1-C_6)$haloalkyl, $O(C_1-C_6)$alkyl, and $O(C_1-C_6)$haloalkyl;

or a salt thereof.

EE153. The compound of EE152, wherein $B^2$ is:

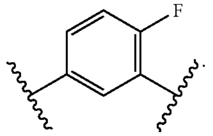 [SMILES: *c1ccc(F)c(*)c1]

EE154. The compound of EE152, wherein $B^3$ is:

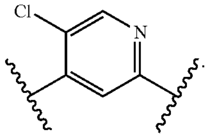

EE155. The compound of EE152, wherein $B^3$ is:

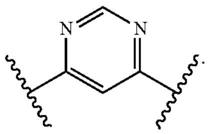 [SMILES: *c1cc(*)ncn1]

EE156. The compound of EE152, wherein $B^3$ is:

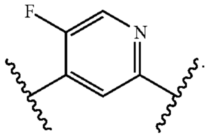

EE157. The compound of any one of EE152-EE156, wherein $R^4$ and $R^5$ are each $CH_3$.

EE158. The compound of any one of EE152-EE156, wherein $R^4$ and $R^5$ are each halogen.

EE159. The compound of EE158, wherein $R^4$ and $R^5$ are each fluorine.

EE160. The compound of any one of EE152-EE156, wherein the group

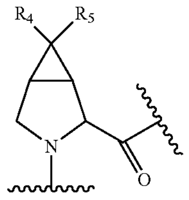

is:

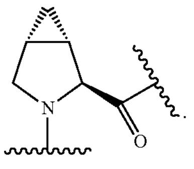 [SMILES: *C(=O)[C@@H]1[C@H]2C[C@H]2CN1*]

EE161. The compound of any one of EE152-156, wherein the group
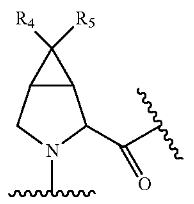
is:
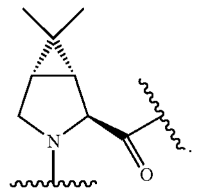 [SMILES: *C(=O)[C@@H]1[C@@H]2[C@H](CN1*)C2(C)C]
EE162. The compound of any one of EE152-EE156, wherein the group
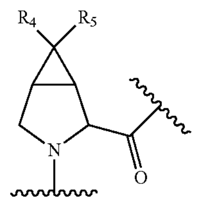
is:
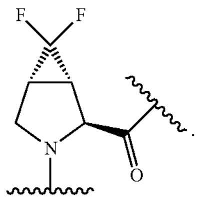 [SMILES: *C(=O)[C@@H]1[C@@H]2[C@H](CN1*)C2(F)F]
EE163. The compound of any one of EE152-EE162, wherein $R^6$ is:
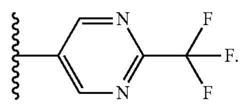
EE164. The compound of EE152, wherein the compound is:
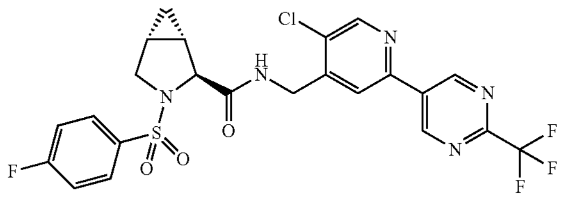
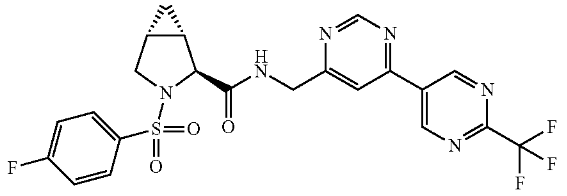
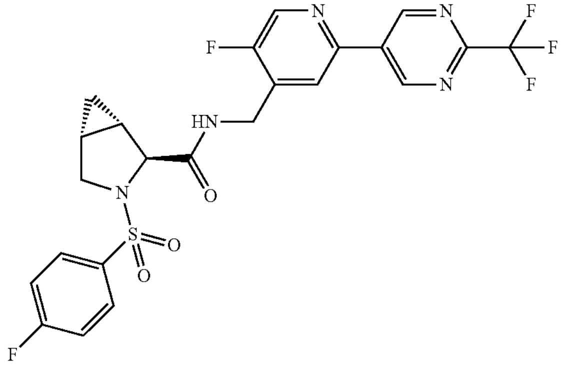
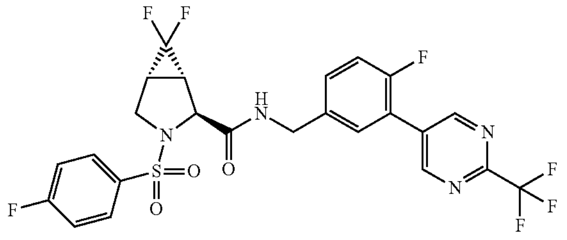
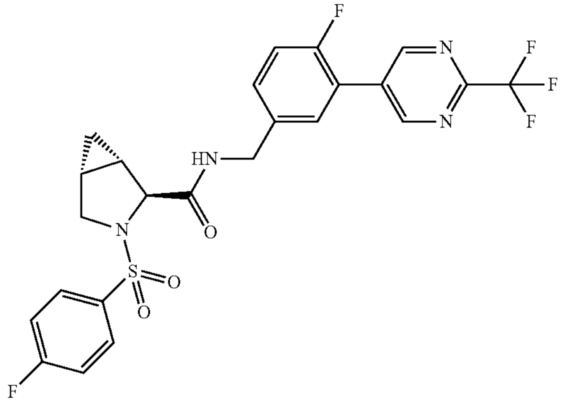
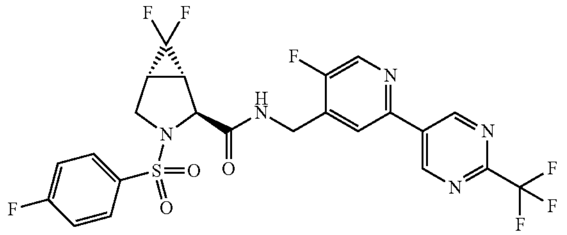

-continued

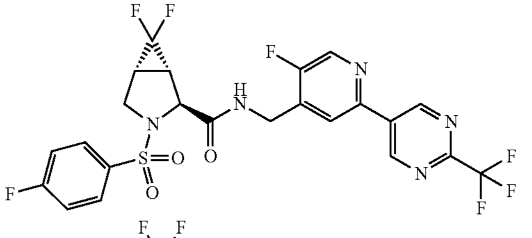

or

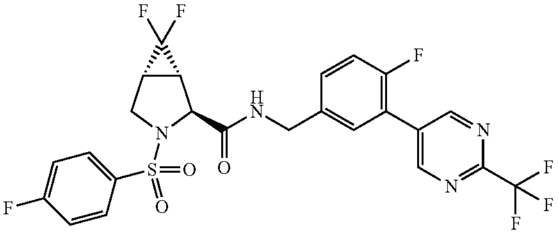

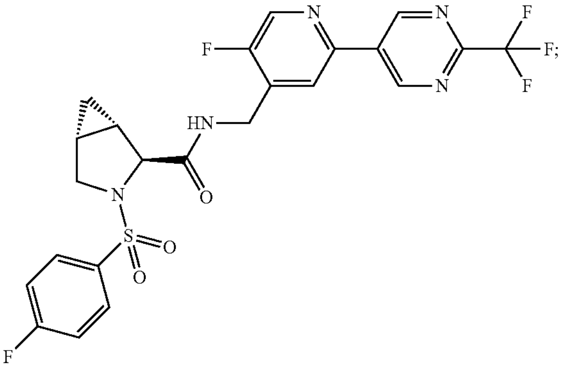

or a salt thereof.

EE165. A compound of formula VIII:

VIII

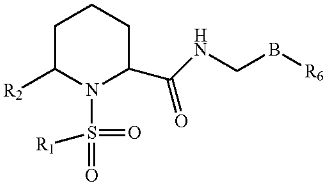

wherein:

B is $B^2$ or $B^3$;

$B^2$ is phenyl, wherein each phenyl is unsubstituted or substituted with one or more groups independently selected from halogen, CN, $(C_1-C_6)$alkyl, and $(C_1-C_6)$haloalkyl;

$B^3$ is a 6-membered heteroaryl, wherein each 6-membered heteroaryl is unsubstituted or substituted with one or more groups independently selected from halogen, $(C_1-C_6)$alkyl, $(C_1-C_6)$haloalkyl, $O(C_1-C_6)$alkyl, $O(C_1-C_6)$haloalkyl, 5 or 6-membered heteroaryl, $(C_3-C_7)$cycloalkyl, and $(C_3-C_7)$heterocyclyl; and wherein any of the 5 or 6-membered heteroaryl, $(C_3-C_7)$cycloalkyl, or $(C_3-C_7)$heterocyclyl groups is unsubstituted or substituted with one or more groups independently selected from halogen, $(C_1-C_6)$alkyl, and $(C_1-C_6)$haloalkyl;

$R^1$ is phenyl or heteroaryl, wherein each phenyl or heteroaryl is unsubstituted or substituted with one or more groups independently selected from halogen, $(C_1-C_6)$alkyl, and $(C_1-C_6)$haloalkyl;

$R^2$ is H or $(C_1-C_6)$alkyl;

$R^6$ is a phenyl, $(C_3-C_7)$cycloalkyl, 5- or 6-membered heteroaryl, or 4, 5, 6 or 7-membered heterocycle, wherein any phenyl, $(C_3-C_7)$cycloalkyl, 5- or 6-membered heteroaryl, or 4, 5, 6 or 7-membered heterocycle of $R^6$ is optionally substituted with one or more groups independently selected from halogen, $SF_5$, $(C_1-C_6)$alkyl, $(C_1-C_6)$haloalkyl, $O(C_1-C_6)$alkyl, and $O(C_1-C_6)$haloalkyl; or $R^6$ is $O—CH_2—R^7$;

$R^7$ is a $(C_1-C_6)$alkyl, 3, 4, 5, 6, or 7-membered heterocycle, 3, 4, 5, 6, or 7-membered cycloalkyl, or 6-membered heteroaryl, wherein any $(C_1-C_6)$alkyl, 3, 4, 5, 6, or 7-membered heterocycle, 3, 4, 5, 6, or 7-membered cycloalkyl, or 6-membered heteroaryl is optionally substituted with one or more groups independently selected from halogen, $(C_1-C_6)$alkyl, $(C_1-C_6)$haloalkyl, $O(C_1-C_6)$alkyl, and $O(C_1-C_6)$haloalkyl;

or a salt thereof.

EE166. The compound of EE165, wherein $B^3$ is:

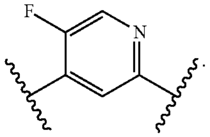

EE167. The compound of any one of EE165-EE166, wherein $R^2$ is $(C_1-C_6)$alkyl.

EE168. The compound of any one of EE165-EE167, wherein the group

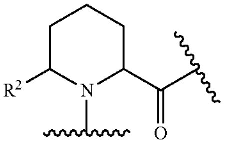

is:

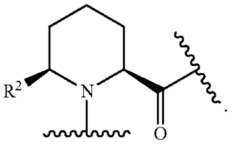

EE169. The compound of any one of EE165-EE168, wherein $R^6$ is:

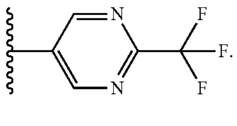 [SMILES: *c1cnc(C(F)(F)F)nc1]

EE170. The compound of EE165, wherein the compound is:

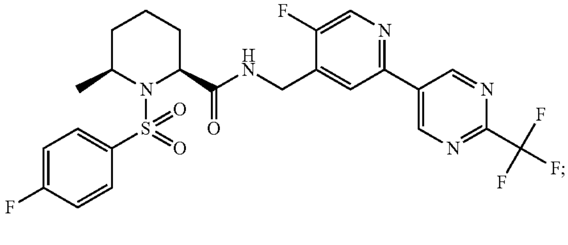 [SMILES: C[C@H]1CCC[C@@H](C(=O)NCc2cc(-c3cnc(C(F)(F)F)nc3)ncc2F)N1S(=O)(=O)c1ccc(F)cc1]

or a salt thereof.

EE171. A pharmaceutical composition, comprising a compound as described in any one of EE1-EE170 or a pharmaceutically acceptable salt thereof, and a pharmaceutically acceptable carrier, diluent or excipient.

EE172. A compound as described in any one of EE1-EE170 or a pharmaceutically acceptable salt thereof for use in medical therapy.

EE173. A compound as described in any one of EE1-EE170 or a pharmaceutically acceptable salt thereof for the treatment or prophylaxis of a respiratory disorder.

EE174. A compound as described in any one of EE1-EE170 or a pharmaceutically acceptable salt thereof for the preparation of a medicament for the treatment or prophylaxis of a respiratory disorder.

EE175. A method for treating a respiratory disorder in a mammal comprising, administering a compound as described in any one of EE1-EE170 or a pharmaceutically acceptable salt thereof to the mammal.

EE176. A compound as described in any one of EE1-EE170 or a pharmaceutically acceptable salt thereof for modulating TRPA1 activity.

EE177. A compound as described in any one of EE1-EE170 or a pharmaceutically acceptable salt thereof for the treatment or prophylaxis of a disease or condition mediated by TRPA1 activity.

EE178. The compound of EE177 wherein the disease or condition is pain, itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia.

EE179. The compound of EE177 wherein the disease or condition is pain, arthritis, itch, cough, asthma, inflammatory bowel disease, or an inner ear disorder.

EE180. The use of a compound as described in any one of EE1-EE170 or a pharmaceutically acceptable salt thereof for the preparation of a medicament for the treatment or prophylaxis of a disease or condition that is mediated by TRPA1 activity.

EE181. The use of EE180 wherein the disease or condition is pain, itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia.

EE182. The use of EE180 wherein the disease or condition is pain, arthritis, itch, cough, asthma, inflammatory bowel disease, or an inner ear disorder.

EE183. A method for modulating TRPA1 activity, comprising contacting TRPA1 with a compound as described in any one of EE1-EE170 or a salt thereof.

EE184. A method for treating a disease or condition mediated by TRPA1 activity in a mammal, comprising administering a compound as described in any one of EE1-EE170 or a pharmaceutically acceptable salt thereof to the mammal.

EE185. The method of EE184 wherein the disease or condition is pain, itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia.

EE186. The method of EE184 wherein the disease or condition is pain, arthritis, itch, cough, asthma, inflammatory bowel disease, or an inner ear disorder.

EE187. The compound of any of the preceding embodiments EE1-EE170, wherein the salt of the compound is a pharmaceutically acceptable salt.

In another aspect the present invention provides for compounds of formula I as described herein below as a third embodiment of the invention (embodiment "EEE1").

EEE1. A compound of formula I:

I

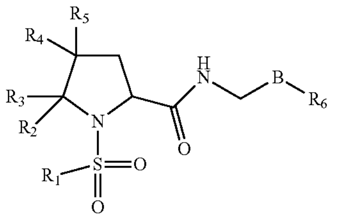

wherein:

B is $B^1$, $B^2$, or $B^3$;

$B^1$ is a 5-membered heteroaryl comprising 2 nitrogen atoms in the ring, wherein each 5-membered heteroaryl is unsubstituted or substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

$B^2$ is phenyl, wherein each phenyl is unsubstituted or substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

$B^3$ is 6-membered heteroaryl, wherein each 6-membered heteroaryl is unsubstituted or substituted with one or more groups independently selected from halogen, CN, $(C_1-C_6)$alkyl, $(C_1-C_6)$haloalkyl, $O(C_1-C_6)$alkyl, $O(C_1-C_6)$haloalkyl, 5 or 6-membered heteroaryl, $(C_3-C_7)$cycloalkyl, and 4, 5, 6, or 7-membered heterocyclyl; and wherein any of the 5 or 6-membered heteroaryl, $(C_3-C_7)$cycloalkyl, or 4, 5, 6, or 7-membered heterocyclyl groups is unsubstituted or substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

$R^1$ is phenyl or heteroaryl, wherein each phenyl or heteroaryl is unsubstituted or substituted with one or more groups independently selected from halogen, CN, $(C_1-C_6)$alkyl, and $(C_1-C_6)$haloalkyl;

$R^2$ is $(C_1-C_6)$alkyl, $(C_1-C_6)$haloalkyl, or $(C_3-C_7)$cycloalkyl; wherein $(C_1-C_6)$alkyl is optionally substituted with $O(C_1-C_6)$alkyl;

$R^3$ is H or $(C_1-C_6)$alkyl; or $R^2$ and $R^3$ together with the atoms to which they are attached form a $(C_3)$cycloalkyl;

$R^4$ is H, F, or CN;

$R^5$ is H or $(C_1-C_6)$alkyl; or one of $R^2$ and $R^3$ and one of $R^4$ and $R^5$ together with the atoms to which they are attached form a $(C_3)$cycloalkyl;

$R^6$ is phenyl, $(C_3-C_7)$cycloalkyl, 5 or 6-membered heteroaryl, or 4, 5, 6 or 7-membered heterocycle, wherein any phenyl, $(C_3-C_7)$cycloalkyl, 5 or 6-membered heteroaryl, or 4, 5, 6 or 7-membered heterocycle of $R^6$ is optionally substituted with one or more groups independently selected from halogen, CN, $SF_5$, $(C_1-C_6)$alkyl, $(C_1-C_6)$haloalkyl, $O(C_1-C_6)$alkyl, or $O(C_1-C_6)$haloalkyl; or $R^6$ is O—$CH_2$—$R^7$;

$R^7$ is $(C_1-C_6)$alkyl, 4, 5, 6, or 7-membered heterocycle, $(C_3-C_7)$cycloalkyl, or 6-membered heteroaryl, wherein any $(C_1-C_6)$alkyl, 4, 5, 6, or 7-membered heterocycle, $(C_3-C_7)$cycloalkyl, or 6-membered heteroaryl is optionally substituted with one or more groups independently selected from halogen, CN, $(C_1-C_6)$alkyl, $(C_1-C_6)$haloalkyl, $O(C_1-C_6)$alkyl, $(C_3-C_7)$cycloalkyl, and $O(C_1-C_6)$haloalkyl;

or a salt thereof.

Further additional embodiments of the invention are set forth below.

EEE2. The compound of EEE1, wherein the compound is of formula II:

II

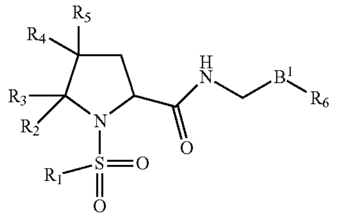

wherein:

$B^1$ is a 5-membered heteroaryl comprising 2 nitrogen atoms in the ring, wherein each 5-membered heteroaryl is unsubstituted or substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

$R^1$ is phenyl or heteroaryl, wherein each phenyl or heteroaryl is unsubstituted or substituted with one or more groups independently selected from halogen, CN, $(C_1-C_6)$alkyl, and $(C_1-C_6)$haloalkyl;

$R^2$ is $(C_1-C_6)$alkyl, $(C_1-C_6)$haloalkyl, or $(C_3-C_7)$cycloalkyl; wherein $(C_1-C_6)$alkyl is optionally substituted with $O(C_1-C_6)$alkyl;

$R^3$ is H or $(C_1-C_6)$alkyl; or $R^2$ and $R^3$ together with the atoms to which they are attached form a $(C_3)$cycloalkyl;

$R^4$ is H, F, or CN;

$R^5$ is H or $(C_1-C_6)$alkyl; or one of $R^2$ and $R^3$ and one of $R^4$ and $R^5$ together with the atoms to which they are attached form a $(C_3)$cycloalkyl;

$R^6$ is phenyl, $(C_3-C_7)$cycloalkyl, 5 or 6-membered heteroaryl, or 4, 5, 6 or 7-membered heterocycle, wherein any phenyl, $(C_3-C_7)$cycloalkyl, 5 or 6-membered heteroaryl, or 4, 5, 6 or 7-membered heterocycle of $R^6$ is optionally substituted with one or more groups independently selected from halogen, CN, $SF_5$, $(C_1-C_6)$alkyl, $(C_1-C_6)$haloalkyl, $O(C_1-C_6)$alkyl, or $O(C_1-C_6)$haloalkyl; or $R^6$ is O—$CH_2$—$R^7$;

$R^7$ is $(C_1-C_6)$alkyl, 4, 5, 6, or 7-membered heterocycle, $(C_3-C_7)$cycloalkyl, or 6-membered heteroaryl, wherein any $(C_1-C_6)$alkyl, 4, 5, 6, or 7-membered heterocycle, $(C_3-C_7)$cycloalkyl, or 6-membered heteroaryl is optionally substituted with one or more groups independently selected from halogen, CN, $(C_1-C_6)$alkyl, $(C_1-C_6)$haloalkyl, $O(C_1-C_6)$alkyl, $(C_3-C_7)$cycloalkyl, and $O(C_1-C_6)$haloalkyl;

or a salt thereof.

EEE3. The compound of any one of EEE1 or EEE2, wherein $B^1$ is unsubstituted or substituted pyrazolyl.

EEE4. The compound of any one of EEE1-3, wherein $B^1$ is:

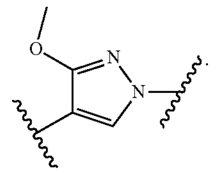 [SMILES: *c1cn(*)nc1OC]

EEE5. The compound of any one of EEE1-3, wherein $B^1$ is:

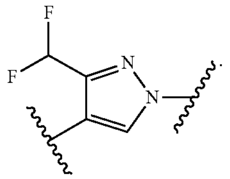 [SMILES: *c1cn(*)nc1C(F)F]

EEE6. The compound of any one of EEE1-3, wherein $B^1$ is:

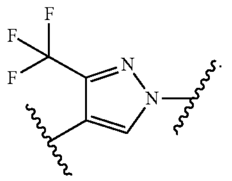 [SMILES: *c1cn(*)nc1C(F)(F)F]

EEE7. The compound of any one of EEE1-3, wherein $B^1$ is:

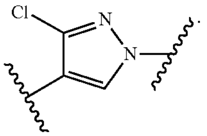 [SMILES: *c1cn(*)nc1Cl]

EEE8. The compound of EEE1, wherein the compound is of formula III:

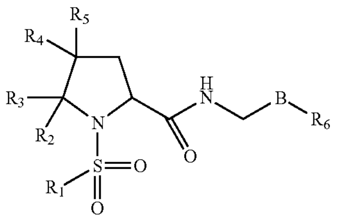

III wherein:

B is $B^2$ or $B^3$;

$B^2$ is phenyl, wherein each phenyl is unsubstituted or substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

$B^3$ is 6-membered heteroaryl, wherein each 6-membered heteroaryl is unsubstituted or substituted with one or more groups independently selected from halogen, CN, $(C_1-C_6)$ alkyl, $(C_1-C_6)$haloalkyl, $O(C_1-C_6)$alkyl, $O(C_1-C_6)$haloalkyl, 5 or 6-membered heteroaryl, $(C_3-C_7)$cycloalkyl, and 4, 5, 6, or 7-membered heterocyclyl; and wherein any of the 5 or 6-membered heteroaryl, $(C_3-C_7)$cycloalkyl, or 4, 5, 6, or 7-membered heterocyclyl groups is unsubstituted or substituted with one or more groups independently selected from halogen, CN, $(C_1-C_6)$alkyl, $(C_1-C_6)$haloalkyl, $O(C_1-C_6)$ alkyl, and $O(C_1-C_6)$haloalkyl;

$R^1$ is phenyl or heteroaryl, wherein each phenyl or heteroaryl is unsubstituted or substituted with one or more groups independently selected from halogen, CN, $(C_1-C_6)$ alkyl, and $(C_1-C_6)$haloalkyl;

$R^2$ is $(C_1-C_6)$alkyl, $(C_1-C_6)$haloalkyl, or $(C_3-C_7)$cycloalkyl; wherein $(C_1-C_6)$alkyl is optionally substituted with $O(C_1-C_6)$alkyl;

$R^3$ is H or $(C_1-C_6)$alkyl; or $R^2$ and $R^3$ together with the atoms to which they are attached form a $(C_3)$cycloalkyl;

$R^4$ is H, F, or CN;

$R^5$ is H or $(C_1-C_6)$alkyl; or one of $R^2$ and $R^3$ and one of $R^4$ and $R^5$ together with the atoms to which they are attached form a $(C_3)$cycloalkyl;

$R^6$ is phenyl, $(C_3-C_7)$cycloalkyl, 5 or 6-membered heteroaryl, or 4, 5, 6 or 7-membered heterocycle, wherein any phenyl, $(C_3-C_7)$cycloalkyl, 5 or 6-membered heteroaryl, or 4, 5, 6 or 7-membered heterocycle of $R^6$ is optionally substituted with one or more groups independently selected from halogen, CN, $SF_5$, $(C_1-C_6)$alkyl, $(C_1-C_6)$haloalkyl, $O(C_1-C_6)$alkyl, or $O(C_1-C_6)$haloalkyl; or $R^6$ is $O—CH_2—R^7$;

$R^7$ is $(C_1-C_6)$alkyl, 4, 5, 6, or 7-membered heterocycle, $(C_3-C_7)$cycloalkyl, or 6-membered heteroaryl, wherein any $(C_1-C_6)$alkyl, 4, 5, 6, or 7-membered heterocycle, $(C_3-C_7)$ cycloalkyl, or 6-membered heteroaryl is optionally substituted with one or more groups independently selected from halogen, CN, $(C_1-C_6)$alkyl, $(C_1-C_6)$haloalkyl, $O(C_1-C_6)$ alkyl, $(C_3-C_7)$cycloalkyl, and $O(C_1-C_6)$haloalkyl;

or a salt thereof.

EEE9. The compound of EEE8, wherein $B^2$ is unsubstituted or substituted phenyl.

EEE10. The compound of EEE9, wherein $B^2$ is:

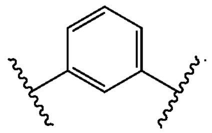 [SMILES: *c1cccc(*)c1]

EEE11. The compound of EEE9, wherein $B^2$ is:

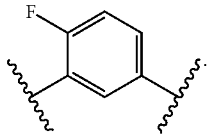 [SMILES: *c1ccc(F)c(*)c1]

EEE12. The compound of EEE9, wherein $B^2$ is:

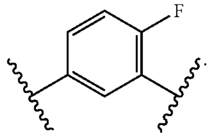 [SMILES: *c1ccc(F)c(*)c1]

EEE13. The compound of EEE9, wherein $B^2$ is:

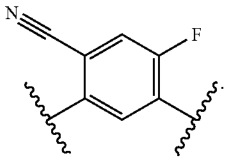 [SMILES: *c1cc(*)c(C#N)cc1F]

EEE14. The compound of EEE9, wherein $B^2$ is:

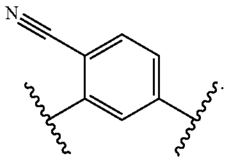

EEE15. The compound of EEE9, wherein $B^2$ is:

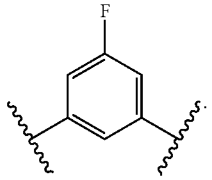 [SMILES: *c1cc(*)cc(F)c1]

EEE16. The compound of EEE9, wherein $B^2$ is:

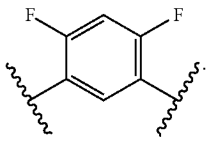 [SMILES: *c1cc(*)c(F)cc1F]

EEE17. The compound of EEE9, wherein $B^2$ is:

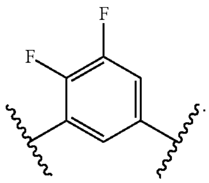 [SMILES: *c1cc(*)c(F)c(F)c1]

EEE18. The compound of EEE9, wherein $B^2$ is:

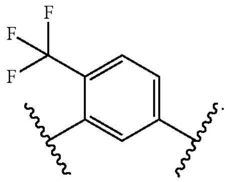 [SMILES: *c1ccc(C(F)(F)F)c(*)c1]

EEE19. The compound of EEE8, wherein $B^3$ is unsubstituted or substituted 6-membered heteroaryl.

EEE20. The compound of EEE19, wherein $B^3$ is:

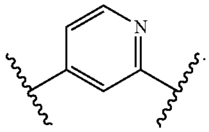 [SMILES: *c1ccnc(*)c1]

EEE21. The compound of EEE19, wherein $B^3$ is:

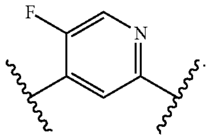 [SMILES: *c1cc(*)c(F)cn1]

EEE22. The compound of EEE19, wherein $B^3$ is:

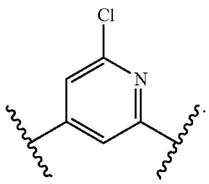 [SMILES: *c1cc(*)nc(Cl)c1]

EEE23. The compound of EEE19, wherein $B^3$ is:

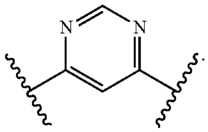 [SMILES: *c1cc(*)ncn1]

EEE24. The compound of EEE19, wherein $B^3$ is:

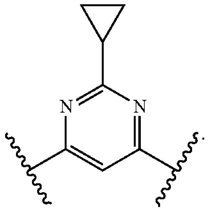 [SMILES: *c1cc(*)nc(C2CC2)n1]

EEE25. The compound of EEE19, wherein $B^3$ is:

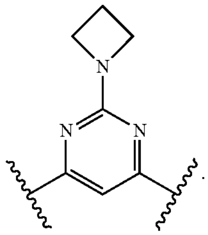 [SMILES: *c1cc(*)nc(N2CCC2)n1]

EEE26. The compound of EEE19, wherein $B^3$ is:

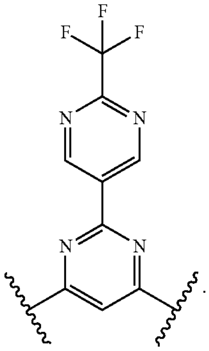 [SMILES: *c1cc(*)nc(-c2cnc(C(F)(F)F)nc2)n1]

EEE27. The compound of EEE19, wherein $B^3$ is:

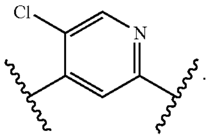

EEE28. The compound of EEE19, wherein $B^3$ is:

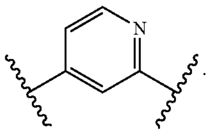 [SMILES: *c1ccnc(*)c1]

EEE29. The compound of EEE19, wherein $B^3$ is:

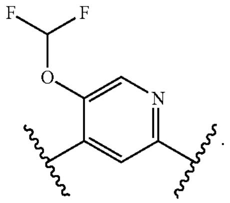 [SMILES: *c1cc(*)c(OC(F)F)cn1]

EEE30. The compound of EEE19, wherein $B^3$ is:

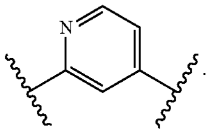 [SMILES: *c1ccnc(*)c1]

EEE31. The compound of EEE19, wherein $B^3$ is:

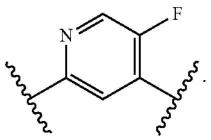

EEE32. The compound of EEE19, wherein $B^3$ is:

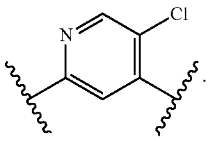 [SMILES: *c1cc(*)c(Cl)cn1]

EEE33. The compound of EEE19, wherein $B^3$ is:

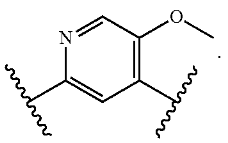 [SMILES: *c1cc(*)c(OC)cn1]

EEE34. The compound of EEE19, wherein B3 is:

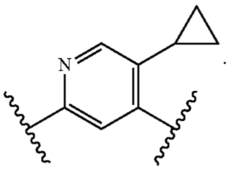 [SMILES: *c1cc(*)c(C2CC2)cn1]

EEE35. The compound of EEE19, wherein $B^3$ is:

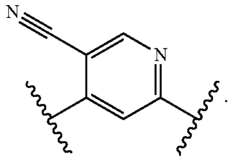

EEE36. The compound of EEE19, wherein $B^3$ is:

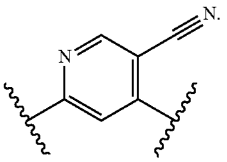 [SMILES: *c1cc(*)c(C#N)cn1]

EEE37. The compound of EEE19, wherein $B^3$ is:

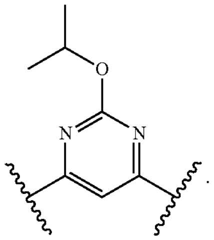 [SMILES: *c1cc(*)nc(OC(C)C)n1]

EEE38. The compound of EEE19, wherein $B^3$ is:

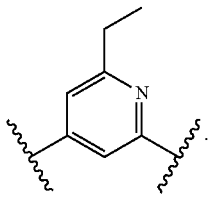 [SMILES: *c1cc(*)nc(CC)c1]

EEE39. The compound of EEE19, wherein $B^3$ is:

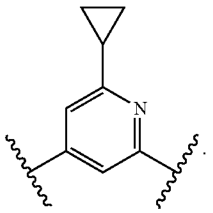 [SMILES: *c1cc(*)nc(C2CC2)c1]

EEE40. The compound of EEE19, wherein $B^3$ is:

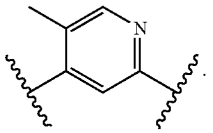 [SMILES: *c1cc(*)c(C)cn1]

EEE41. The compound of EEE19, wherein $B^3$ is:

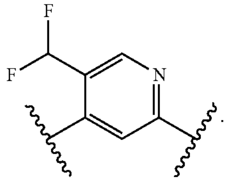

EEE42. The compound of EEE19, wherein $B^3$ is:

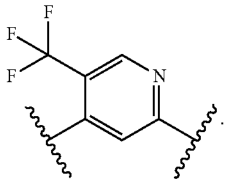

EEE43. The compound of EEE19, wherein $B^3$ is:

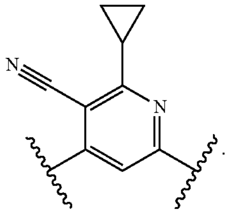 [SMILES: *c1cc(*)c(C#N)c(C2CC2)n1]

EEE44. The compound of EEE19, wherein $B^3$ is:

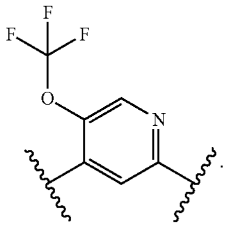 [SMILES: *c1cc(*)c(OC(F)(F)F)cn1]

EEE45. The compound of EEE19, wherein $B^3$ is:

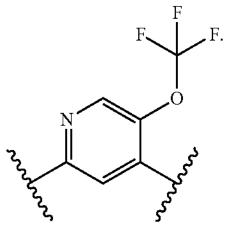 [SMILES: *c1cc(*)c(OC(F)(F)F)cn1]

EEE46. The compound of EEE19, wherein $B^3$ is:

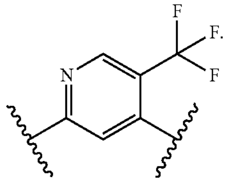 [SMILES: *c1cc(*)c(C(F)(F)F)cn1]

EEE47. The compound of EEE19, wherein $B^3$ is:

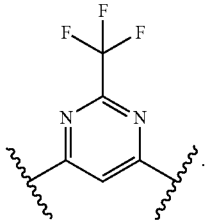 [SMILES: *c1cc(*)nc(C(F)(F)F)n1]

EEE48. The compound of EEE19, wherein $B^3$ is:

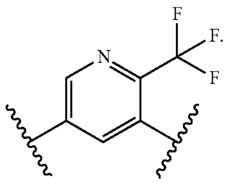 [SMILES: *c1cnc(C(F)(F)F)c(*)c1]

EEE49. The compound of EEE19, wherein $B^3$ is:

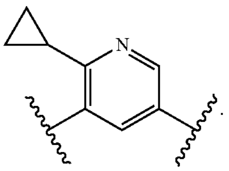 [SMILES: *c1cnc(C2CC2)c(*)c1]

EEE50. The compound of EEE19, wherein $B^3$ is:

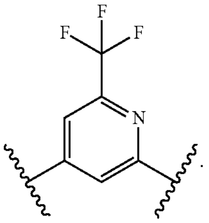 [SMILES: *c1cc(*)nc(C(F)(F)F)c1]

EEE51. The compound of EEE19, wherein $B^3$ is:

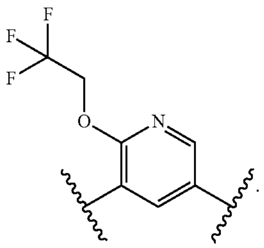 [SMILES: *c1cnc(OCC(F)(F)F)c(*)c1]

EEE52. The compound of EEE19, wherein $B^3$ is:

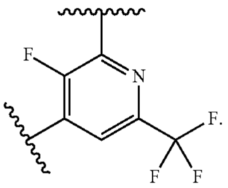 [SMILES: *c1cc(C(F)(F)F)nc(*)c1F]

EEE53. The compound of EEE19, wherein $B^3$ is:

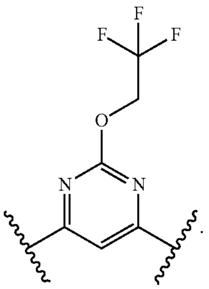 [SMILES: *c1cc(*)nc(OCC(F)(F)F)n1]

EEE54. The compound of EEE19, wherein $B^3$ is:

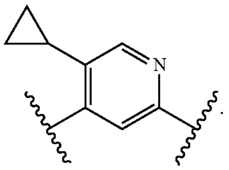 [SMILES: *c1cc(*)c(C2CC2)cn1]

EEE55. The compound of EEE19, wherein $B^3$ is:

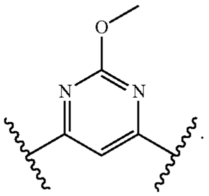 [SMILES: *c1cc(*)nc(OC)n1]

EEE56. The compound of EEE19, wherein $B^3$ is:

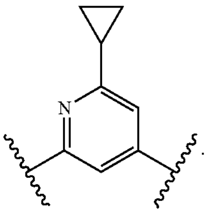 [SMILES: *c1cc(*)nc(C2CC2)c1]

EEE57. The compound of EEE19, wherein $B^3$ is:

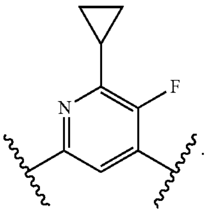 [SMILES: *c1cc(*)c(F)c(C2CC2)n1]

EEE58. The compound of EEE19, wherein $B^3$ is:

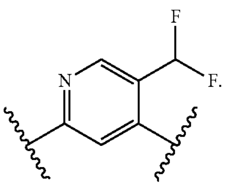 [SMILES: *c1cc(*)c(C(F)F)cn1]

EEE59. The compound of EEE19, wherein $B^3$ is:

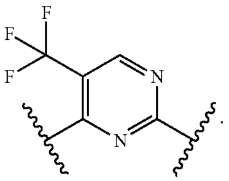

EEE60. The compound of EEE19, wherein $B^3$ is:

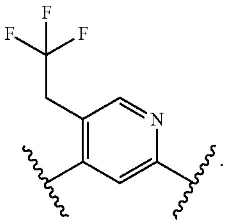 [SMILES: *c1cc(*)c(CC(F)(F)F)cn1]

EEE61. The compound of EEE19, wherein $B^3$ is:

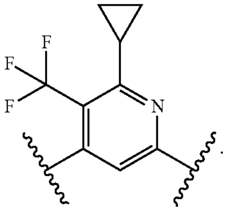

EEE62. The compound of EEE19, wherein $B^3$ is:

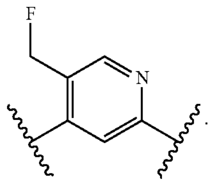 [SMILES: *c1cc(*)c(CF)cn1]

EEE63. The compound of EEE19, wherein $B^3$ is:

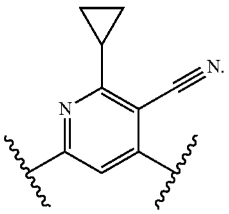 [SMILES: *c1cc(*)c(C#N)c(C2CC2)n1]

EEE64. The compound of EEE19, wherein $B^3$ is:

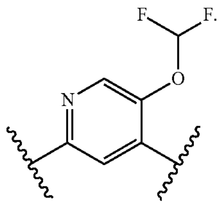 [SMILES: *c1cc(*)c(OC(F)F)cn1]

EEE65. The compound of EEE19, wherein $B^3$ is:

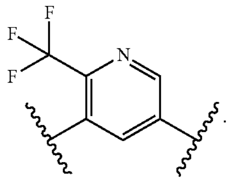 [SMILES: *c1cnc(C(F)(F)F)c(*)c1]

EEE66. The compound of EEE1, wherein the compound is of formula IV:

IV

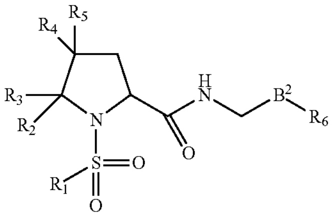

wherein:

$B^2$ is phenyl, wherein each phenyl is unsubstituted or substituted with one or more groups independently selected from halogen, CN, $(C_1-C_6)$alkyl, $(C_1-C_6)$haloalkyl, $O(C_1-C_6)$alkyl, and $O(C_1-C_6)$haloalkyl;

$R^1$ is phenyl or heteroaryl, wherein each phenyl or heteroaryl is unsubstituted or substituted with one or more groups independently selected from halogen, CN, $(C_1-C_6)$alkyl, and $(C_1-C_6)$haloalkyl;

$R^2$ is $(C_1-C_6)$alkyl, $(C_1-C_6)$haloalkyl, or $(C_3-C_7)$cycloalkyl; wherein $(C_1-C_6)$alkyl is optionally substituted with $O(C_1-C_6)$alkyl;

$R^3$ is H or $(C_1-C_6)$alkyl; or $R^2$ and $R^3$ together with the atoms to which they are attached form a $(C_3)$cycloalkyl;

$R^4$ is H, F, or CN;

$R^5$ is H or $(C_1-C_6)$alkyl; or one of $R^2$ and $R^3$ and one of $R^4$ and $R^5$ together with the atoms to which they are attached form a $(C_3)$cycloalkyl;

$R^6$ is phenyl, $(C_3-C_7)$cycloalkyl, 5 or 6-membered heteroaryl, or 4, 5, 6 or 7-membered heterocycle, wherein any phenyl, $(C_3-C_7)$cycloalkyl, 5 or 6-membered heteroaryl, or 4, 5, 6 or 7-membered heterocycle of $R^6$ is optionally substituted with one or more groups independently selected from halogen, CN, $SF_5$, $(C_1-C_6)$alkyl, $(C_1-C_6)$haloalkyl, $O(C_1-C_6)$alkyl, or $O(C_1-C_6)$haloalkyl; or $R^6$ is O—$CH_2$—$R^7$;

$R^7$ is $(C_1-C_6)$alkyl, 4, 5, 6, or 7-membered heterocycle, $(C_3-C_7)$cycloalkyl, or 6-membered heteroaryl, wherein any $(C_1-C_6)$alkyl, 4, 5, 6, or 7-membered heterocycle, $(C_3-C_7)$ cycloalkyl, or 6-membered heteroaryl is optionally substituted with one or more groups independently selected from halogen, CN, $(C_1\text{-}C_6)$alkyl, $(C_1\text{-}C_6)$haloalkyl, $O(C_1\text{-}C_6)$alkyl, $(C_3\text{-}C_7)$cycloalkyl, and $O(C_1\text{-}C_6)$haloalkyl;

or a salt thereof.

EEE67. The compound of EEE66, wherein $B^2$ is:

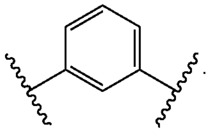 [SMILES: *c1cccc(*)c1]

EEE68. The compound of EEE66, wherein $B^2$ is:

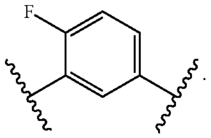 [SMILES: *c1ccc(F)c(*)c1]

EEE69. The compound of EEE66, wherein $B^2$ is:

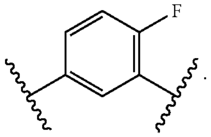 [SMILES: *c1ccc(F)c(*)c1]

EEE70. The compound of EEE66, wherein $B^2$ is:

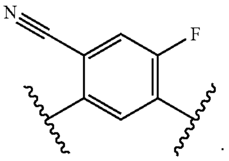

EEE71. The compound of EEE66, wherein $B^2$ is:

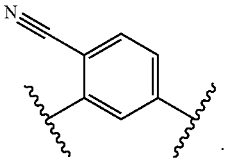 [SMILES: *c1ccc(C#N)c(*)c1]

EEE72. The compound of EEE66, wherein $B^2$ is:

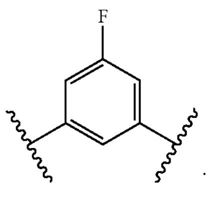 [SMILES: *c1cc(*)cc(F)c1]

EEE73. The compound of EEE66, wherein $B^2$ is:

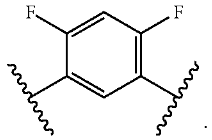 [SMILES: *c1cc(*)c(F)cc1F]

EEE74. The compound of EEE66, wherein $B^2$ is:

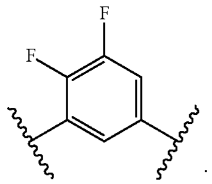

EEE75. The compound of EEE66, wherein $B^2$ is:

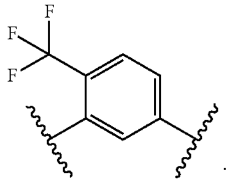 [SMILES: *c1ccc(C(F)(F)F)c(*)c1]

EEE76. The compound of EEE1, wherein the compound is of formula V:

V

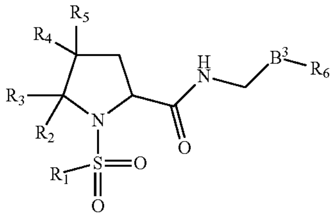

wherein:

$B^3$ is 6-membered heteroaryl, wherein each 6-membered heteroaryl is unsubstituted or substituted with one or more groups independently selected from halogen, CN, $(C_1\text{-}C_6)$alkyl, $(C_1\text{-}C_6)$haloalkyl, $O(C_1\text{-}C_6)$alkyl, $O(C_1\text{-}C_6)$haloalkyl, 5 or 6-membered heteroaryl, $(C_3\text{-}C_7)$cycloalkyl, and 4, 5, 6, or 7-membered heterocyclyl; and wherein any of the 5 or 6-membered heteroaryl, $(C_3\text{-}C_7)$cycloalkyl, or 4, 5, 6, or 7-membered heterocyclyl groups is unsubstituted or substituted with one or more groups independently selected from halogen, CN, $(C_1\text{-}C_6)$alkyl, $(C_1\text{-}C_6)$haloalkyl, $O(C_1\text{-}C_6)$alkyl, and $O(C_1\text{-}C_6)$haloalkyl;

$R^1$ is phenyl or heteroaryl, wherein each phenyl or heteroaryl is unsubstituted or substituted with one or more groups independently selected from halogen, CN, $(C_1\text{-}C_6)$alkyl, and $(C_1\text{-}C_6)$haloalkyl;

$R^2$ is $(C_1\text{-}C_6)$alkyl, $(C_1\text{-}C_6)$haloalkyl, or $(C_3\text{-}C_7)$cycloalkyl; wherein $(C_1\text{-}C_6)$alkyl is optionally substituted with $O(C_1\text{-}C_6)$alkyl;

$R^3$ is H or $(C_1\text{-}C_6)$alkyl; or $R^2$ and $R^3$ together with the atoms to which they are attached form a $(C_3)$cycloalkyl;

$R^4$ is H, F, or CN;

$R^5$ is H or $(C_1-C_6)$alkyl; or one of $R^2$ and $R^3$ and one of $R^4$ and $R^5$ together with the atoms to which they are attached form a $(C_3)$cycloalkyl;

$R^6$ is phenyl, $(C_3-C_7)$cycloalkyl, 5 or 6-membered heteroaryl, or 4, 5, 6 or 7-membered heterocycle, wherein any phenyl, $(C_3-C_7)$cycloalkyl, 5 or 6-membered heteroaryl, or 4, 5, 6 or 7-membered heterocycle of $R^6$ is optionally substituted with one or more groups independently selected from halogen, CN, $SF_5$, $(C_1-C_6)$alkyl, $(C_1-C_6)$haloalkyl, $O(C_1-C_6)$alkyl, or $O(C_1-C_6)$haloalkyl; or $R^6$ is $O—CH_2—R^7$;

$R^7$ is $(C_1-C_6)$alkyl, 4, 5, 6, or 7-membered heterocycle, $(C_3-C_7)$cycloalkyl, or 6-membered heteroaryl, wherein any $(C_1-C_6)$alkyl, 4, 5, 6, or 7-membered heterocycle, $(C_3-C_7)$cycloalkyl, or 6-membered heteroaryl is optionally substituted with one or more groups independently selected from halogen, CN, $(C_1-C_6)$alkyl, $(C_1-C_6)$haloalkyl, $O(C_1-C_6)$alkyl, $(C_3-C_7)$cycloalkyl, and $O(C_1-C_6)$haloalkyl;

or a salt thereof.

EEE77. The compound of EEE76, wherein $B^3$ is:

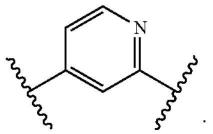 [SMILES: *c1ccnc(*)c1]

EEE78. The compound of EEE76, wherein $B^3$ is:

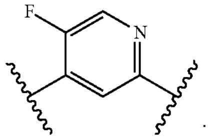

EEE79. The compound of EEE76, wherein $B^3$ is:

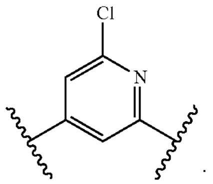 [SMILES: *c1cc(*)nc(Cl)c1]

EEE80. The compound of EEE76, wherein $B^3$ is:

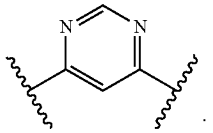 [SMILES: *c1cc(*)ncn1]

EEE81. The compound of EEE76, wherein $B^3$ is:

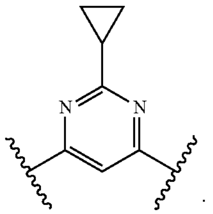

EEE82. The compound of EEE76, wherein $B^3$ is:

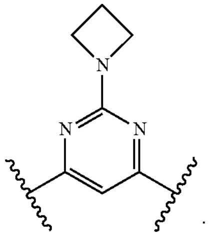 [SMILES: *c1cc(*)nc(N2CCC2)n1]

EEE83. The compound of EEE76, wherein $B^3$ is:

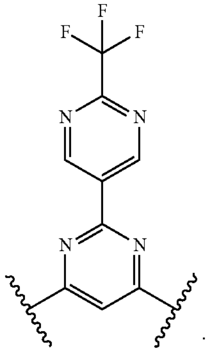 [SMILES: *c1cc(*)nc(-c2cnc(C(F)(F)F)nc2)n1]

EEE84. The compound of EEE76, wherein $B^3$ is:

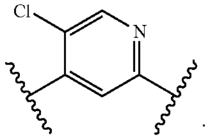

EEE85. The compound of EEE76, wherein $B^3$ is:

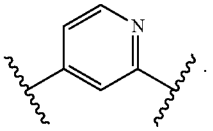 [SMILES: *c1ccnc(*)c1]

EEE86. The compound of EEE76, wherein $B^3$ is:

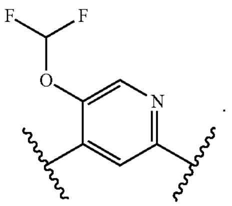 [SMILES: *c1cc(*)c(OC(F)F)cn1]

EEE87. The compound of EEE76, wherein $B^3$ is:

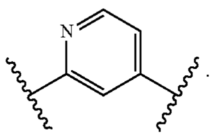 [SMILES: *c1ccnc(*)c1]

EEE88. The compound of EEE76, wherein $B^3$ is:

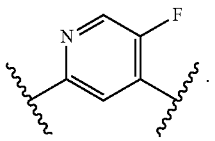 [SMILES: *c1cc(*)c(F)cn1]

EEE89. The compound of EEE76, wherein $B^3$ is:

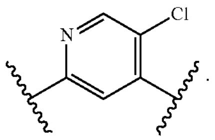 [SMILES: *c1cc(*)c(Cl)cn1]

EEE90. The compound of EEE76, wherein $B^3$ is:

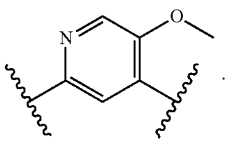 [SMILES: *c1cc(*)c(OC)cn1]

EEE91. The compound of EEE76, wherein $B^3$ is:

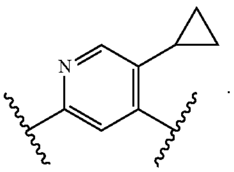 [SMILES: *c1cc(*)c(C2CC2)cn1]

EEE92. The compound of EEE76, wherein $B^3$ is:

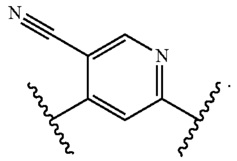 [SMILES: *c1cc(*)c(C#N)cn1]

EEE93. The compound of EEE76, wherein $B^3$ is:

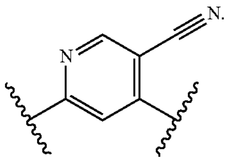 [SMILES: *c1cc(*)c(C#N)cn1]

EEE94. The compound of EEE76, wherein $B^3$ is:

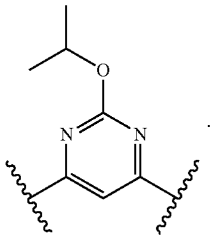 [SMILES: *c1cc(*)nc(OC(C)C)n1]

EEE95. The compound of EEE76, wherein $B^3$ is:

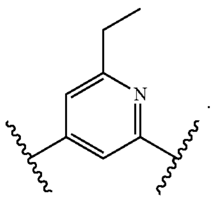 [SMILES: *c1cc(*)nc(CC)c1]

EEE96. The compound of EEE76, wherein $B^3$ is:

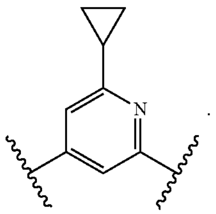 [SMILES: *c1cc(*)nc(C2CC2)c1]

EEE97. The compound of EEE76, wherein $B^3$ is:

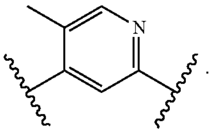 [SMILES: *c1cc(*)c(C)cn1]

EEE98. The compound of EEE76, wherein $B^3$ is:

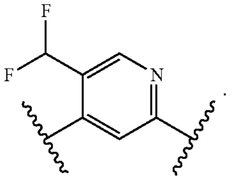 [SMILES: *c1cc(*)c(C(F)F)cn1]

EEE99. The compound of EEE76, wherein $B^3$ is:

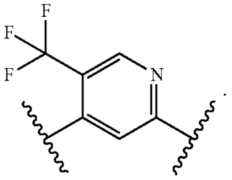 [SMILES: *c1cc(*)c(C(F)(F)F)cn1]

EEE100. The compound of EEE76, wherein $B^3$ is:

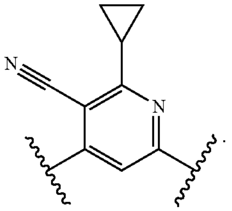 [SMILES: *c1cc(*)c(C#N)c(C2CC2)n1]

EEE101. The compound of EEE76, wherein $B^3$ is:

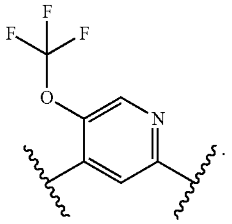 [SMILES: *c1cc(*)c(OC(F)(F)F)cn1]

EEE102. The compound of EEE76, wherein $B^3$ is:

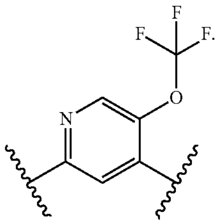 [SMILES: *c1cc(*)c(OC(F)(F)F)cn1]

EEE103. The compound of EEE76, wherein $B^3$ is:

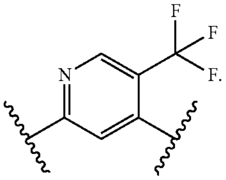 [SMILES: *c1cc(*)c(C(F)(F)F)cn1]

EEE104. The compound of EEE76, wherein $B^3$ is:

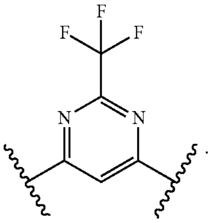 [SMILES: *c1cc(*)nc(C(F)(F)F)n1]

EEE105. The compound of EEE76, wherein $B^3$ is:

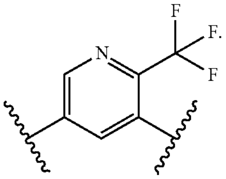 [SMILES: *c1cnc(C(F)(F)F)c(*)c1]

EEE106. The compound of EEE76, wherein $B^3$ is:

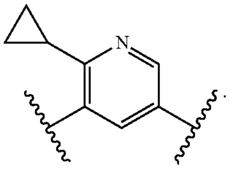 [SMILES: *c1cnc(C2CC2)c(*)c1]

EEE107. The compound of EEE76, wherein $B^3$ is:

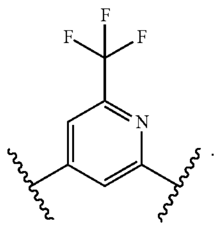 [SMILES: *c1cc(*)nc(C(F)(F)F)c1]

EEE108. The compound of EEE76, wherein $B^3$ is:

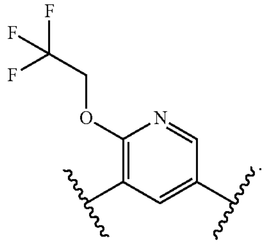 [SMILES: *c1cnc(OCC(F)(F)F)c(*)c1]

EEE109. The compound of EEE76, wherein $B^3$ is:

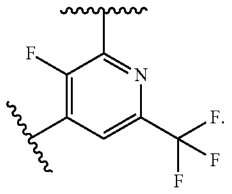 [SMILES: *c1cc(C(F)(F)F)nc(*)c1F]

EEE110. The compound of EEE76, wherein $B^3$ is:

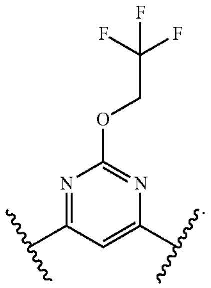 [SMILES: *c1cc(*)nc(OCC(F)(F)F)n1]

EEE111. The compound of EEE76, wherein $B^3$ is:

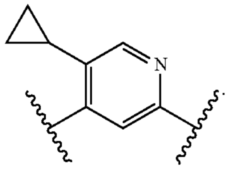 [SMILES: *c1cc(*)c(C2CC2)cn1]

EEE112. The compound of EEE76, wherein $B^3$ is:

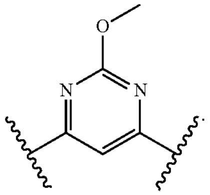 [SMILES: *c1cc(*)nc(OC)n1]

EEE113. The compound of EEE76, wherein $B^3$ is:

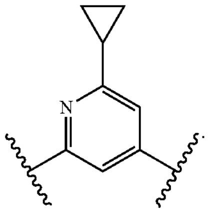 [SMILES: *c1cc(*)nc(C2CC2)c1]

EEE114. The compound of EEE76, wherein $B^3$ is:

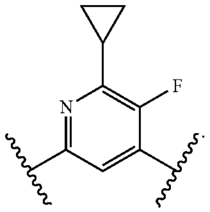 [SMILES: *c1cc(*)c(F)c(C2CC2)n1]

EEE115. The compound of EEE76, wherein $B^3$ is:

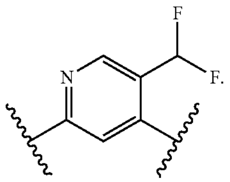 [SMILES: *c1cc(*)c(C(F)F)cn1]

EEE116. The compound of EEE76, wherein $B^3$ is:

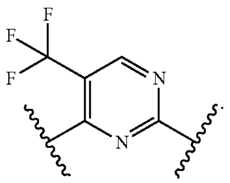 [SMILES: *c1ncc(C(F)(F)F)c(*)n1]

EEE117. The compound of EEE76, wherein $B^3$ is:

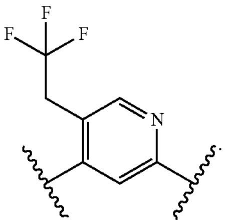 [SMILES: *c1cc(*)c(CC(F)(F)F)cn1]

EEE118. The compound of EEE76, wherein $B^3$ is:

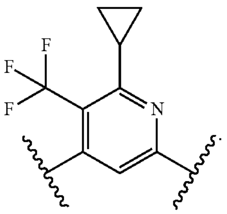 [SMILES: *c1cc(*)c(C(F)(F)F)c(C2CC2)n1]

EEE119. The compound of EEE76, wherein $B^3$ is:

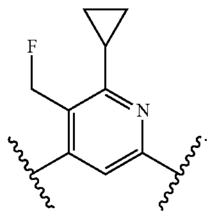 [SMILES: *c1cc(*)c(CF)c(C2CC2)n1]

EEE120. The compound of EEE76, wherein $B^3$ is:

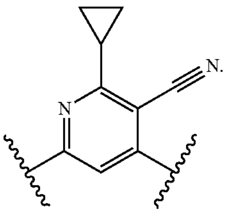 [SMILES: *c1cc(*)c(C#N)c(C2CC2)n1]

EEE121. The compound of EEE76, wherein $B^3$ is:

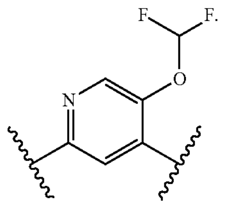 [SMILES: *c1cc(*)c(OC(F)F)cn1]

EEE12. The compound of EEE76, wherein $B^3$ is:

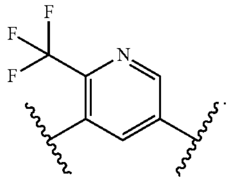 [SMILES: *c1cnc(C(F)(F)F)c(*)c1]

EEE123. The compound of any one of EEE1-122, wherein $R^2$ is $(C_1-C_6)$alkyl.

EEE124. The compound of EEE123, wherein $R^2$ is $CH_3$.

EEE125. The compound of EEE123, wherein $R^2$ is $CH_2CH_3$.

EEE126. The compound of EEE123, wherein $R^2$ is $C(CH_3)_3$.

EEE127. The compound of any one of EEE1-122, wherein $R^2$ is $(C_1-C_6)$haloalkyl EEE128. The compound of EEE127, wherein $R^2$ is $C(CF_3)_3$.

EEE129. The compound of any one of EEE1-122, wherein $R^2$ is $—CH_2OCH_3$.

EEE130. The compound of any one of EEE1-122, wherein $R^2$ and $R^3$ together with the atoms to which they are attached form a $(C_3)$cycloalkyl.

EEE131. The compound of EEE130, wherein $R^2$ and $R^3$ together with the atoms to which they are attached form spirocyclopropyl.

EEE132. The compound of any one of EEE1-129, wherein $R^3$ is H.

EEE133. The compound of any one of EEE1-129, wherein one of $R^2$ and $R^3$ and one of $R^4$ and $R^5$ together with the atoms to which they are attached form a $(C_3)$cycloalkyl.

EEE134. The compound of any one of EEE1-133, wherein $R^4$ is H.

EEE135. The compound of any one of EEE1-133, wherein $R^4$ is F.

EEE136. The compound of any one of EEE1-133, wherein $R^4$ is CN.

EEE137. The compound of any one of EEE1-132, wherein $R^5$ is H.

EEE138. The compound of any one of EEE1-122, wherein the group

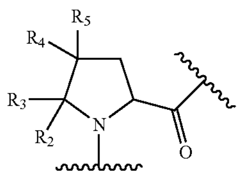

is:

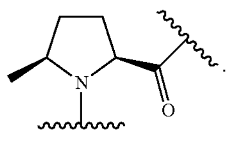

EEE139. The compound of any one of EEE1-122, wherein the group
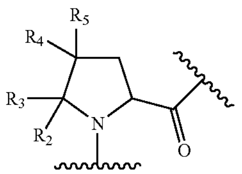
is:
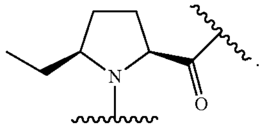 [SMILES: *C(=O)[C@@H]1CC[C@H](CC)N1*]
EEE140. The compound of any one of EEE1-122, wherein the group
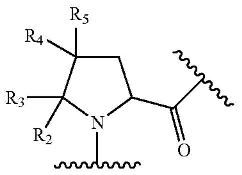
is:
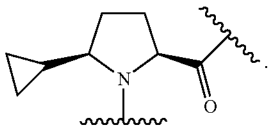 [SMILES: *C(=O)[C@@H]1CC[C@H](C2CC2)N1*]
EEE141. The compound of any one of EEE1-122, wherein the group
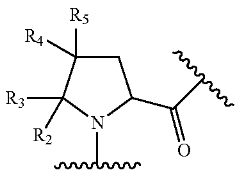
is:
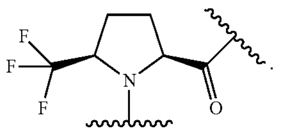 [SMILES: *C(=O)[C@@H]1CC[C@H](C(F)(F)F)N1*]
EEE142. The compound of any one of EEE1-122, wherein the group
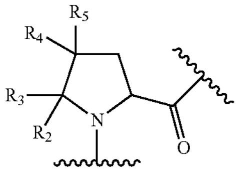
is:
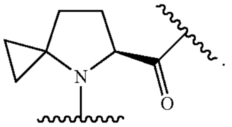 [SMILES: *C(=O)[C@@H]1CCC2(CC2)N1*]
EEE143. The compound of any one of EEE1-122, wherein the group
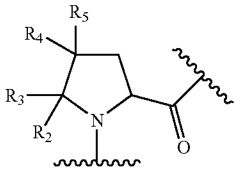
is:
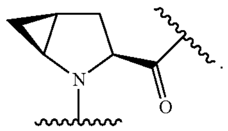 [SMILES: *C(=O)[C@@H]1C[C@@H]2C[C@@H]2N1*]
EEE144. The compound of any one of EEE1-122, wherein the group
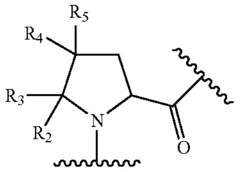
is:
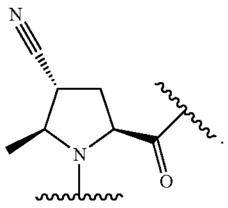

EEE145. The compound of any one of EEE1-122, wherein the group

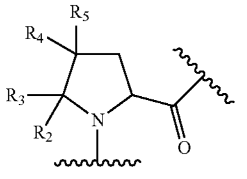

is:

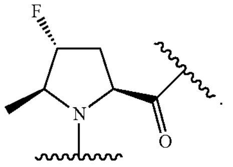

EEE146. The compound of any one of EEE1-122, wherein the group

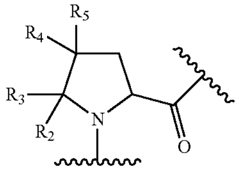

is:

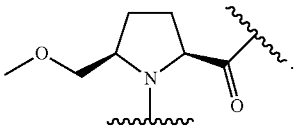 [SMILES: *C(=O)[C@@H]1CC[C@H](COC)N1*]

EEE147. The compound of any one of EEE1-146, wherein $R^6$ is 5-membered heteroaryl.

EEE148. The compound of EEE147, wherein $R^6$ is:

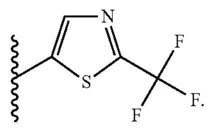 [SMILES: *c1cnc(C(F)(F)F)s1]

EEE149. The compound of any one of EEE1-146, wherein $R^6$ is 6-membered heteroaryl.

EEE150. The compound of EEE149, wherein $R^6$ ispyridinyl.

EEE151. The compound of EEE150, wherein $R^6$ is:

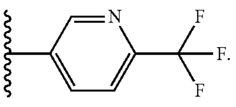 [SMILES: *c1ccc(C(F)(F)F)nc1]

EEE152. The compound of EEE150, wherein $R^6$ is:

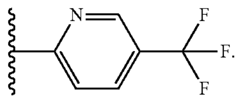 [SMILES: *c1ccc(C(F)(F)F)cn1]

EEE153. The compound of EEE149, wherein $R^6$ is pyrimidinyl.

EEE154. The compound of EEE153, wherein $R^6$ is:

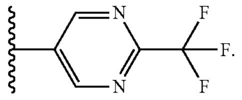

EEE155. The compound of EEE149, wherein $R^6$ is pyrazinyl.

EEE156. The compound of EEE155, wherein $R^6$ is:

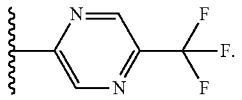 [SMILES: *c1cnc(C(F)(F)F)cn1]

EEE157. The compound of any one of EEE1-146, wherein $R^6$ is 4, 5, 6 or 7-membered heterocycle.

EEE158. The compound of EEE157, wherein $R^6$ is 4-membered heterocycle.

EEE159. The compound of EEE158, wherein $R^6$ is:

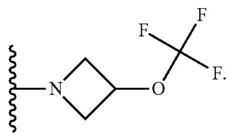 [SMILES: *N1CC(OC(F)(F)F)C1]

EEE160. The compound of EEE157, wherein $R^6$ is 5-membered heterocycle.

EEE161. The compound of EEE157, wherein $R^6$ is 6-membered heterocycle.

EEE162. The compound of EEE161, wherein $R^6$ is:

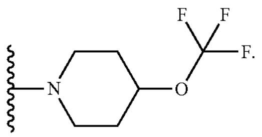 [SMILES: *N1CCC(OC(F)(F)F)CC1]

EEE163. The compound of EEE161, wherein $R^6$ is:

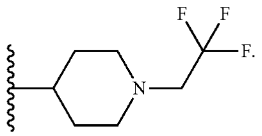 [SMILES: *C1CCN(CC(F)(F)F)CC1]

EEE164. The compound of EEE157, wherein $R^6$ is 7-membered heterocycle.

EEE165. The compound of any one of EEE1-146, wherein $R^6$ is ($C_3$-$C_7$)cycloalkyl.

EEE166. The compound of EEE165, wherein $R^6$ is ($C_6$) cycloalkyl.

EEE167. The compound of EEE166, wherein $R^6$ is:

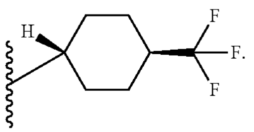 [SMILES: *[C@H]1CC[C@H](C(F)(F)F)CC1]

EEE168. The compound of any one of EEE1-146, wherein $R^6$ is phenyl.

EEE169. The compound of EEE168, wherein $R^6$ is:

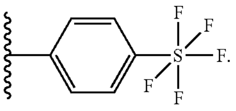 [SMILES: *c1ccc(S(F)(F)(F)(F)F)cc1]

EEE170. The compound of any one of EEE1-146, wherein $R^6$ is:

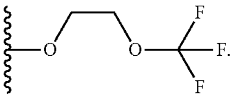 [SMILES: *OCCOC(F)(F)F]

EEE171. The compound of any one of EEE1-146, wherein $R^6$ is:

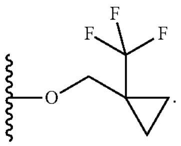 [SMILES: *OCC1(C(F)(F)F)CC1]

EEE172. The compound of any one of EEE1-146, wherein $R^6$ is:

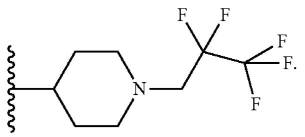 [SMILES: *C1CCN(CC(F)(F)C(F)(F)F)CC1]

EEE173. The compound of any one of EEE1-146, wherein $R^6$ is:

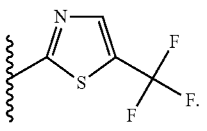 [SMILES: *c1ncc(C(F)(F)F)s1]

EEE174. The compound of any one of EEE1-146, wherein $R^6$ is:

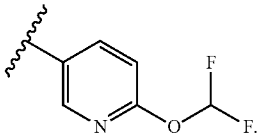 [SMILES: *c1ccc(OC(F)F)nc1]

EEE175. The compound of any one of EEE1-146, wherein $R^6$ is:

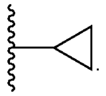 [SMILES: *C1CC1]

EEE176. The compound of any one of EEE1-146, wherein $R^6$ is:

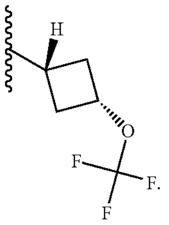 [SMILES: *[C@H]1C[C@@H](OC(F)(F)F)C1]

EEE177. The compound of any one of EEE1-146, wherein $R^6$ is:

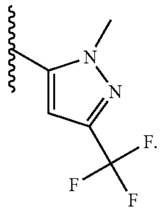 [SMILES: *c1cc(C(F)(F)F)nn1C]

EEE178. The compound of any one of EEE1-146, wherein $R^6$ is:

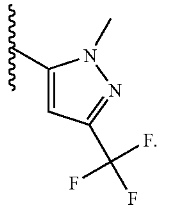 [SMILES: *c1cc(C(F)(F)F)nn1C]

EEE179. The compound of any one of EEE1-146, wherein $R^6$ is:

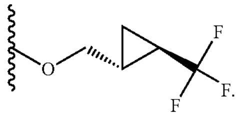 [SMILES: *OC[C@@H]1C[C@H]1C(F)(F)F]

EEE180. The compound of any one of EEE1-146, wherein $R^6$ is:

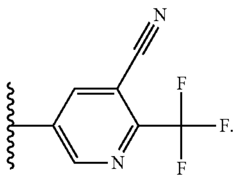 [SMILES: *c1cnc(C(F)(F)F)c(C#N)c1]

EEE181. The compound of any one of EEE1-146, wherein $R^6$ is:

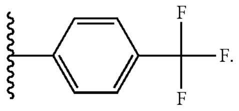 [SMILES: *c1ccc(C(F)(F)F)cc1]

EEE182. The compound of any one of EEE1-146, wherein $R^6$ is:

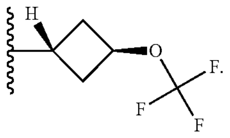 [SMILES: *[C@H]1C[C@H](OC(F)(F)F)C1]

EEE183. The compound of any one of EEE1-146, wherein $R^6$ is:

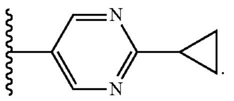 [SMILES: *c1cnc(C2CC2)nc1]

EEE184. The compound of any one of EEE1-146, wherein $R^6$ is:

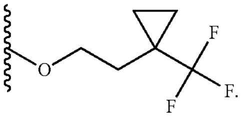 [SMILES: *OCCC1(C(F)(F)F)CC1]

EEE185. The compound of any one of EEE1-146, wherein $R^6$ is:

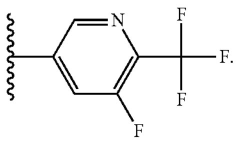 [SMILES: *c1cnc(C(F)(F)F)c(F)c1]

EEE186. The compound of any one of EEE1-146, wherein $R^6$ is:

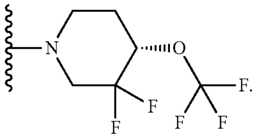 [SMILES: *N1CC[C@H](OC(F)(F)F)C(F)(F)C1]

EEE187. The compound of any one of EEE1-146, wherein $R^7$ is $(C_1-C_6)$alkyl.

EEE188. The compound of any one of EEE1-146, wherein $R^7$ is $(C_3-C_7)$cycloalkyl.

EEE189. The compound of EEE188, wherein $R^7$ is $(C_3)$ cycloalkyl.

EEE190. The compound of any one of EEE1-189, wherein $R^1$ is:

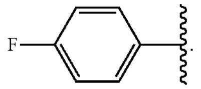

EEE191. The compound of any one of EEE1-189, wherein $R^1$ is:

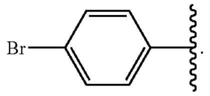

EEE192. The compound of any one of EEE1-189, wherein $R^1$ is:

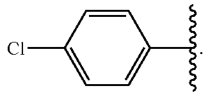

EEE193. The compound of any one of EEE1-189, wherein $R^1$ is:

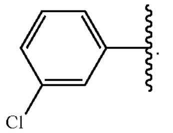 [SMILES: *c1cccc(Cl)c1]

EEE194. The compound of any one of EEE1-189, wherein $R^1$ is:

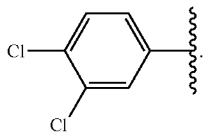 [SMILES: *c1ccc(Cl)c(Cl)c1]

EEE195. The compound of any one of EEE1-189, wherein $R^1$ is:

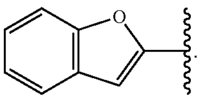 [SMILES: *c1cc2ccccc2o1]
EEE196. The compound of any one of EEE1-189, wherein $R^1$ is:
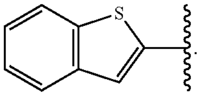 [SMILES: *c1cc2ccccc2s1]
EEE197. The compound of any one of EEE1-189, wherein $R^1$ is:
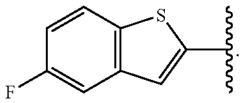
EEE198. The compound of any one of EEE1-189, wherein $R^1$ is:
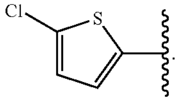 [SMILES: *c1ccc(Cl)s1]
EEE199. The compound of any one of EEE1-189, wherein $R^1$ is:
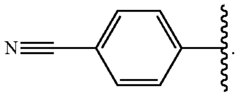
EEE200. The compound of any one of EEE1-189, wherein $R^1$ is:
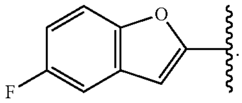 [SMILES: *c1cc2cc(F)ccc2o1]
EEE201. The compound of any one of EEE1-189, wherein $R^1$ is:
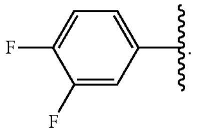
EEE202. The compound of EEE1, which is:
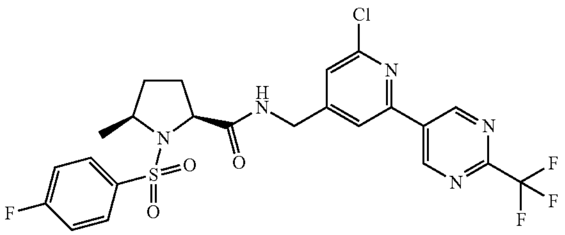
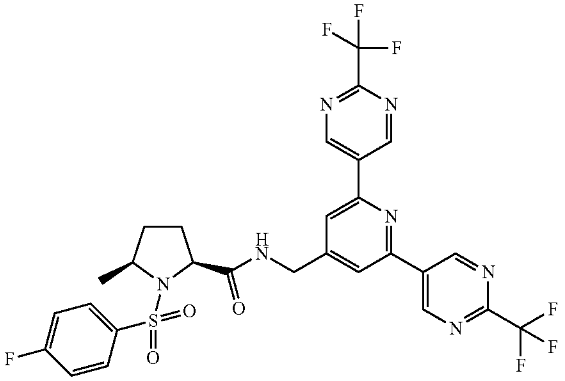
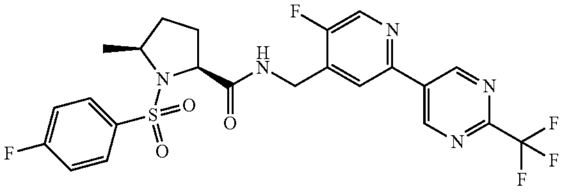
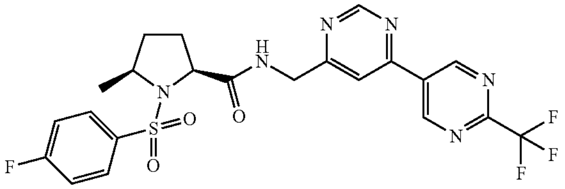
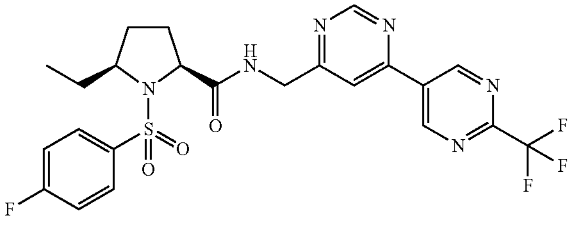
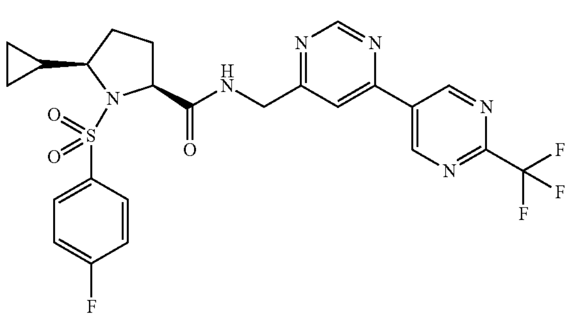

-continued
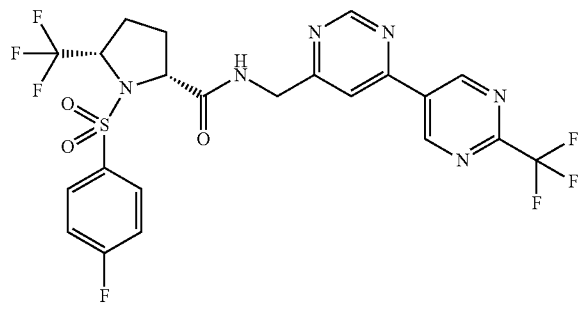
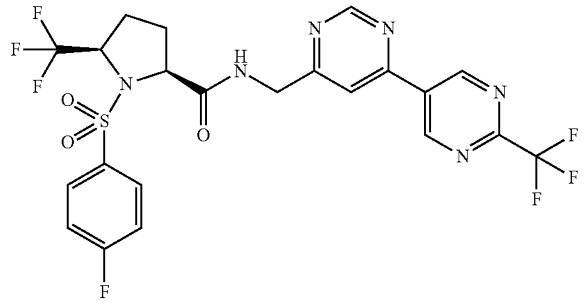
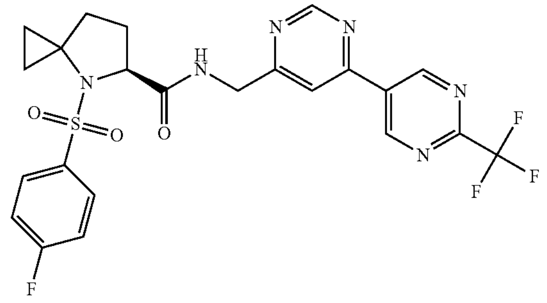
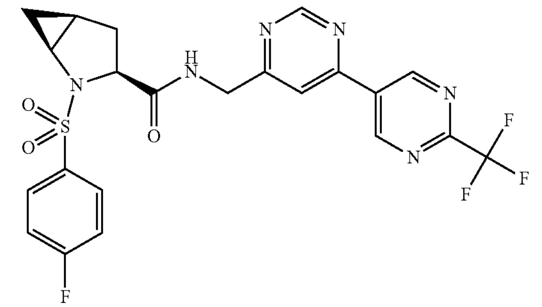
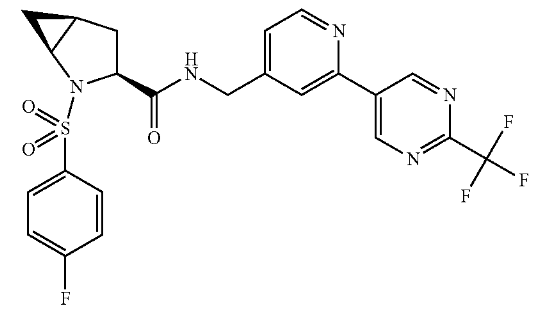
-continued
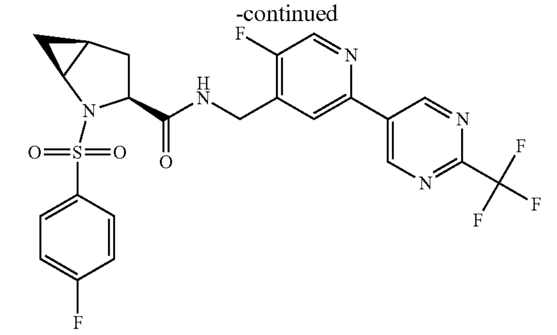
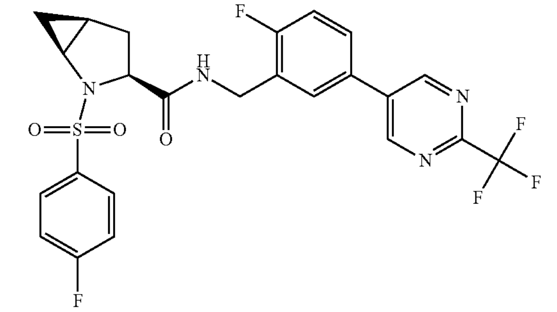
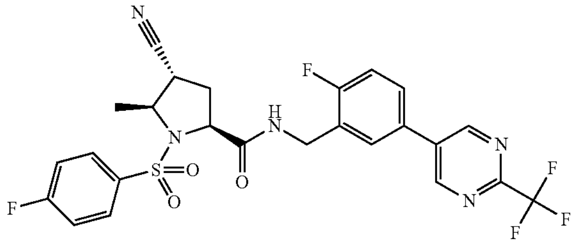
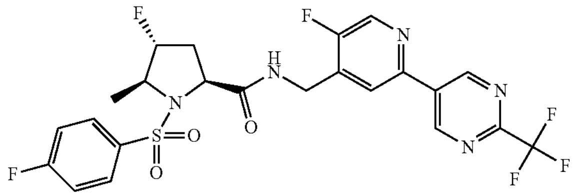
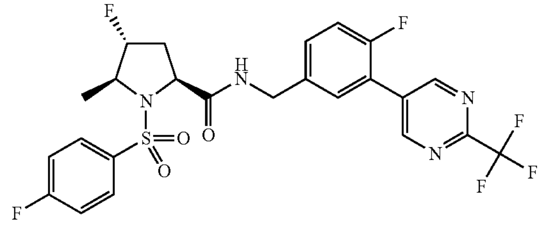
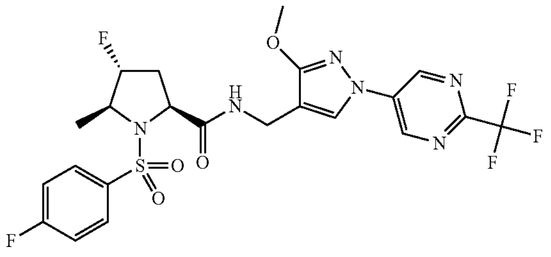

-continued
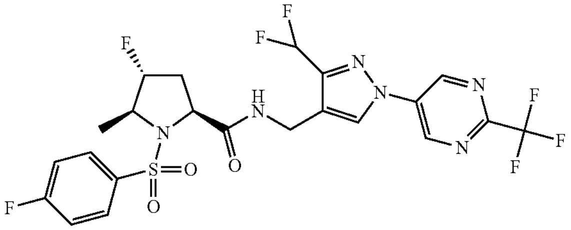
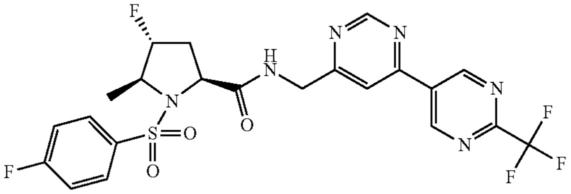
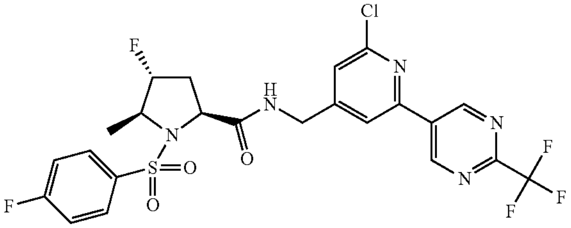
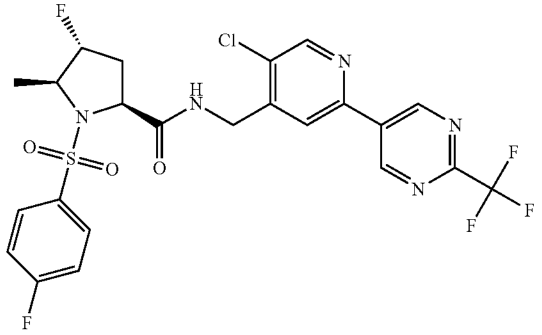
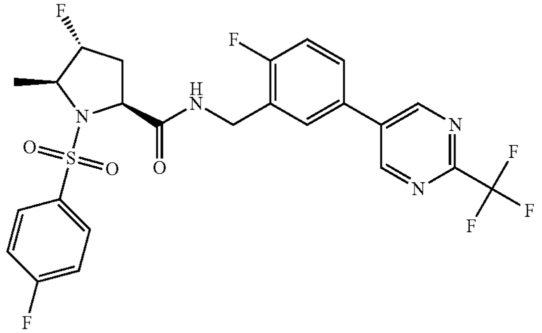
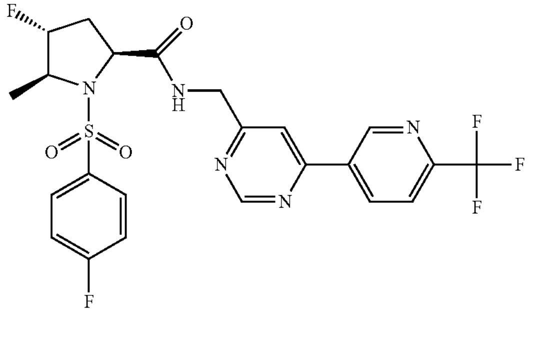
-continued
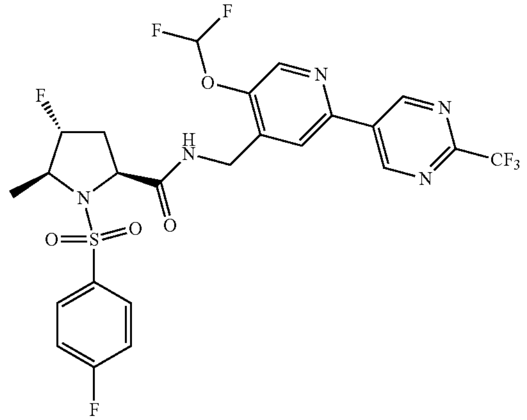
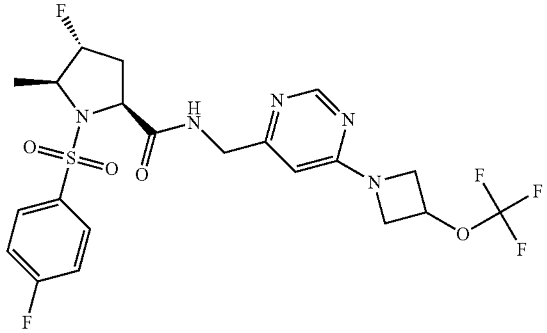
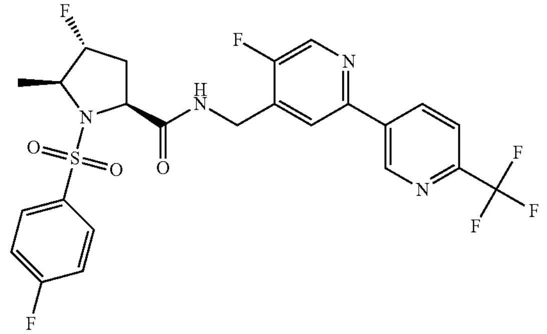
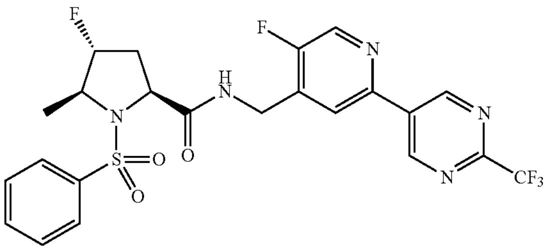
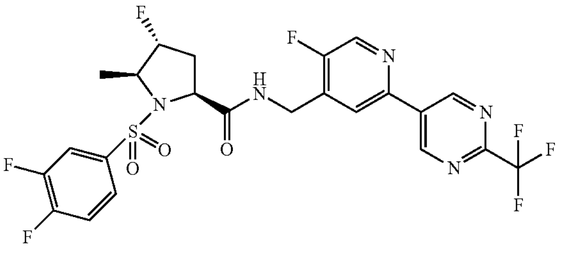

-continued
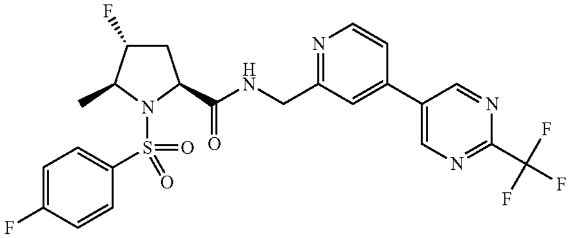
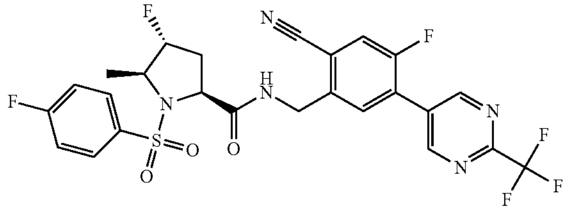
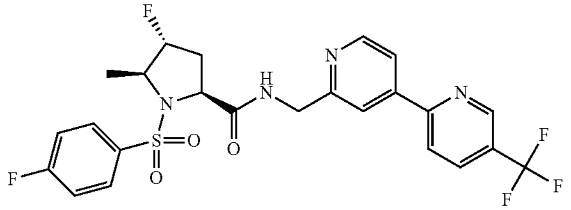
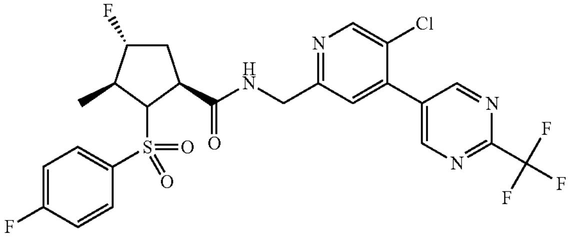
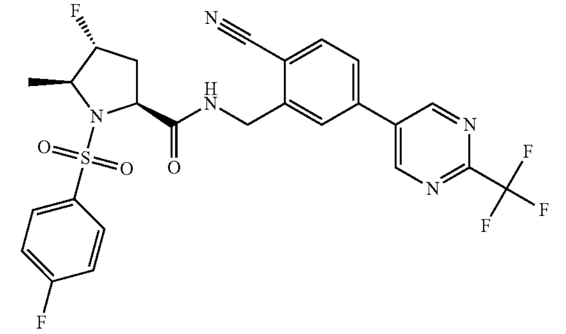
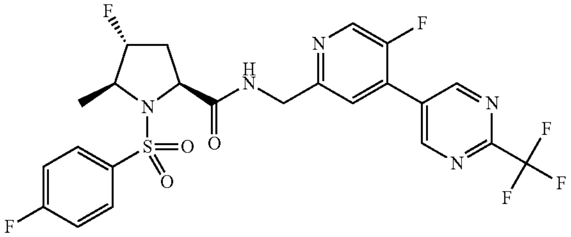
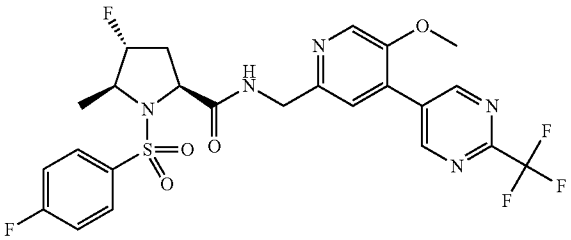
-continued
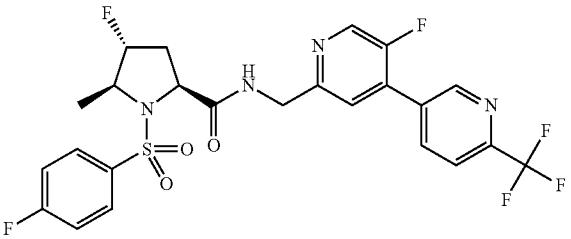
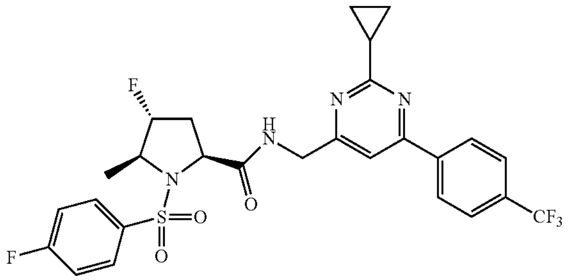
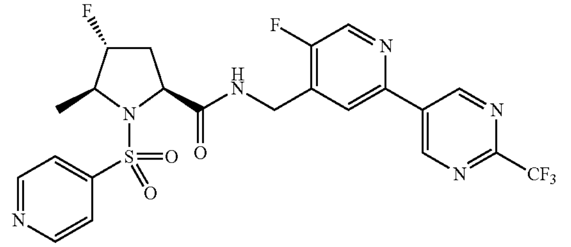
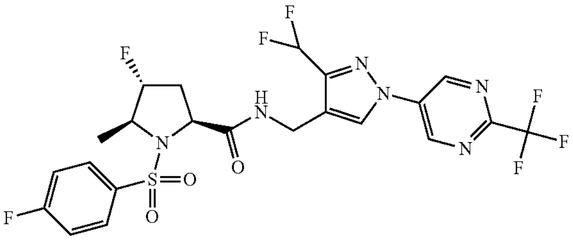
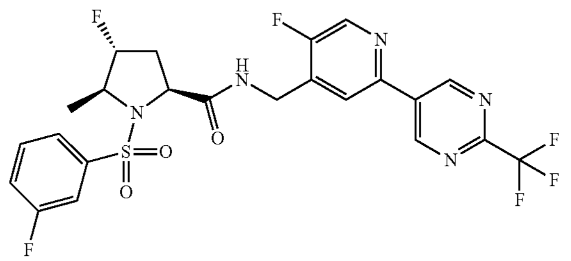
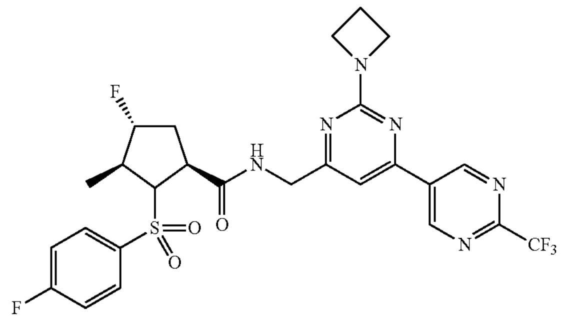

-continued
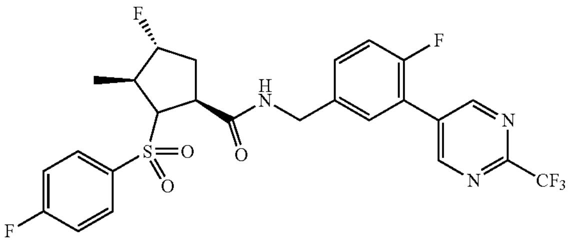
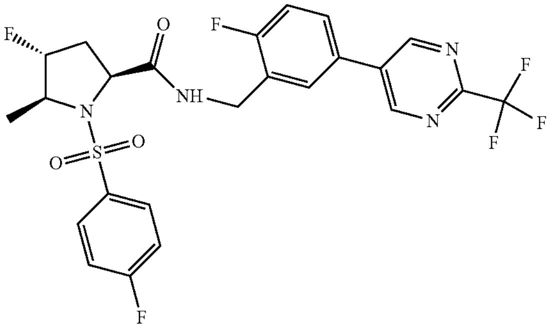
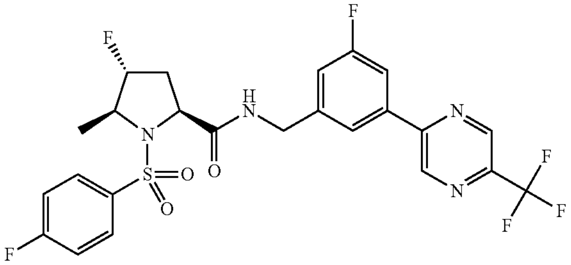
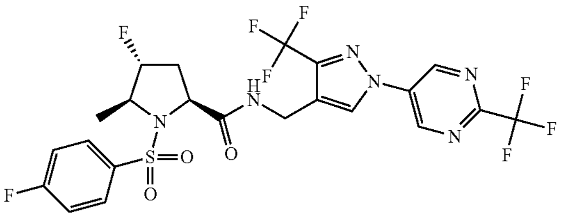
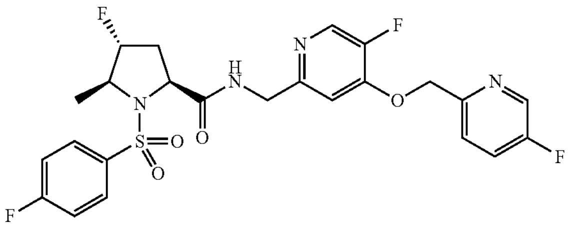
or
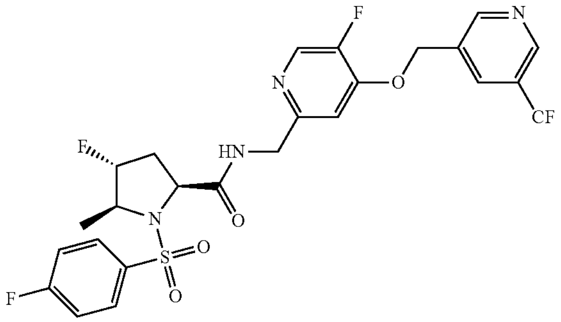
-continued
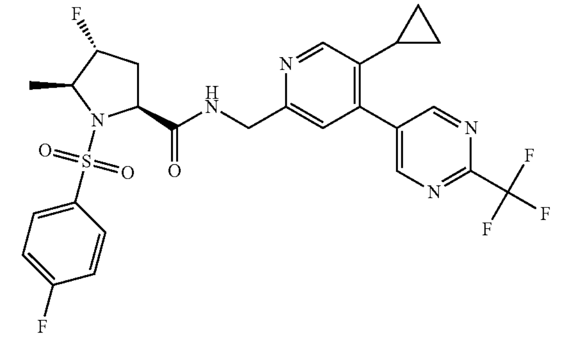
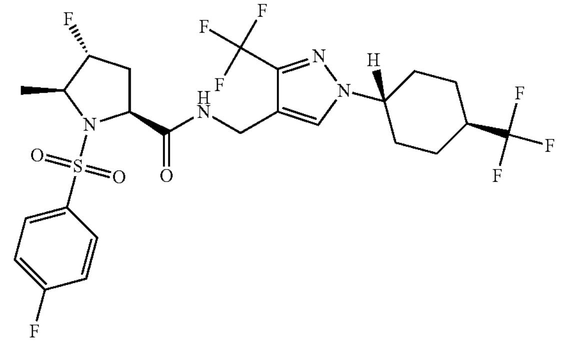
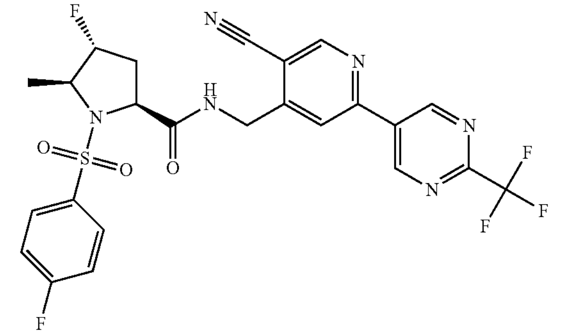
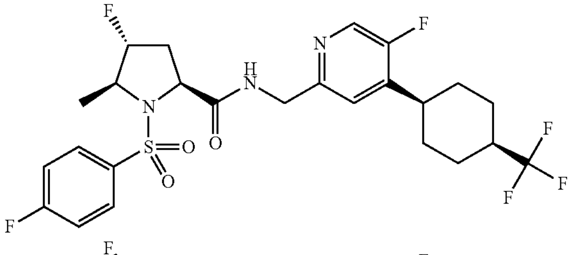
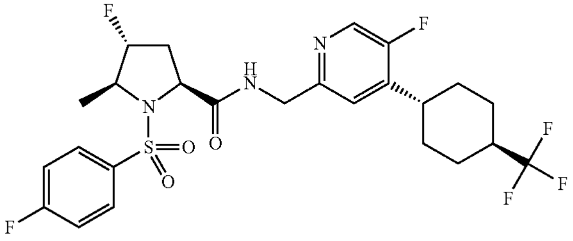
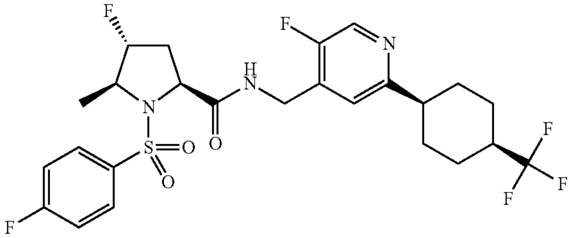

-continued
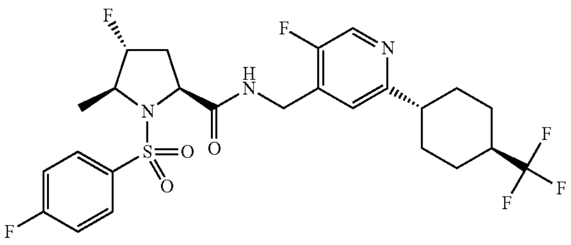
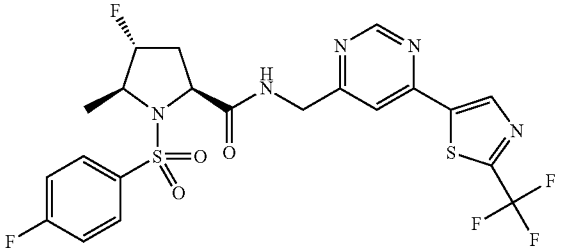
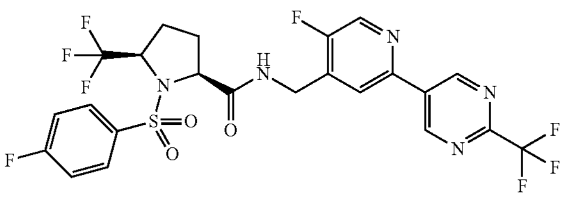
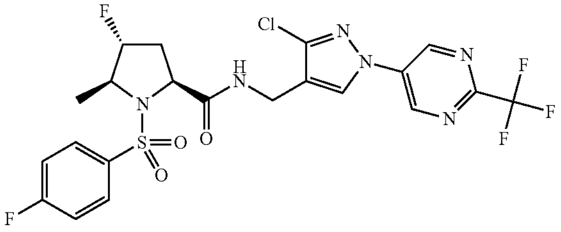
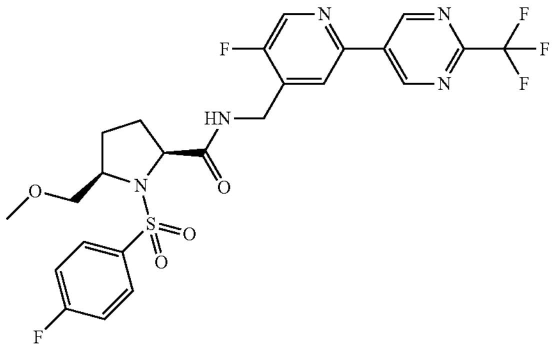
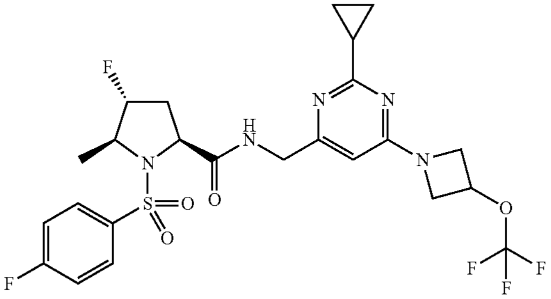
-continued
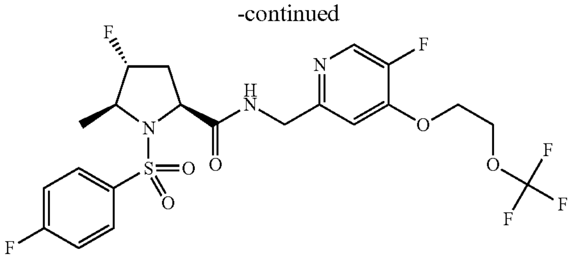
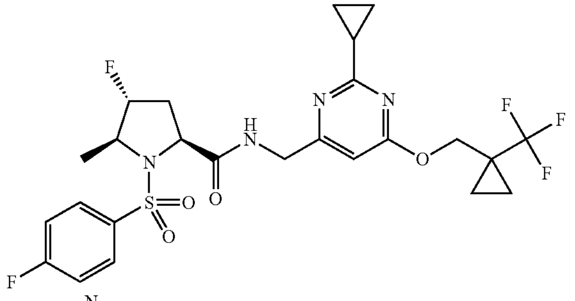
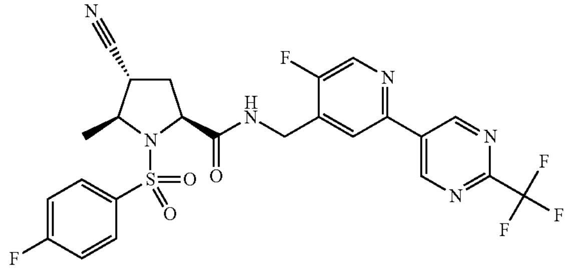
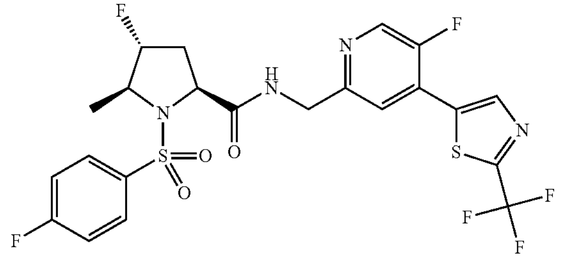
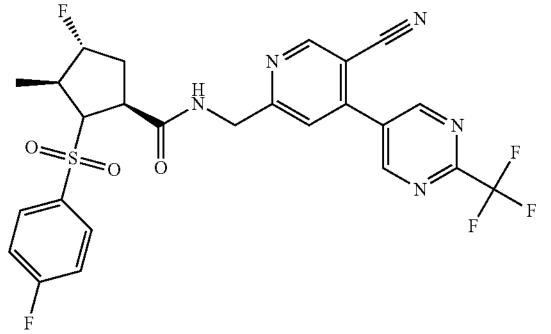
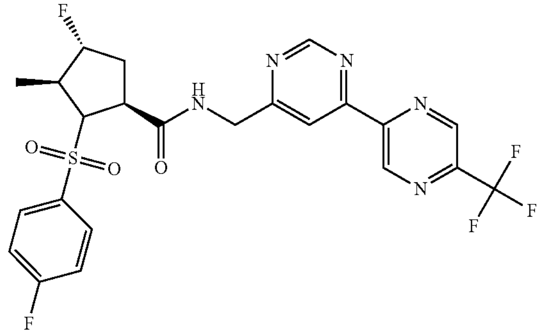

-continued
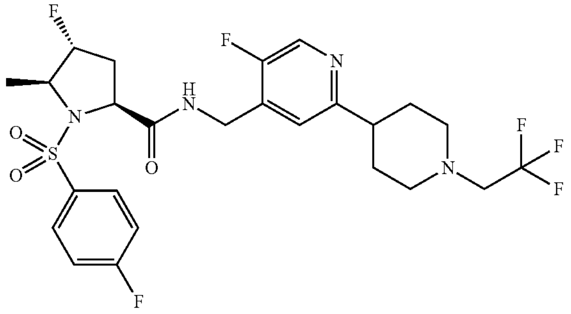
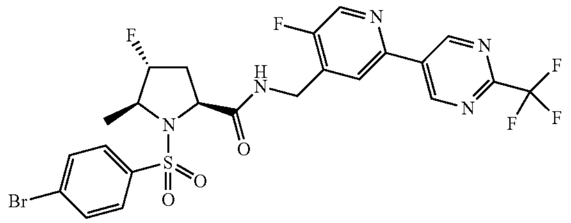
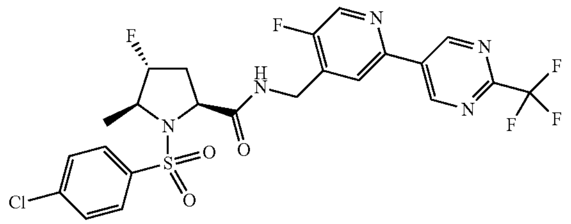
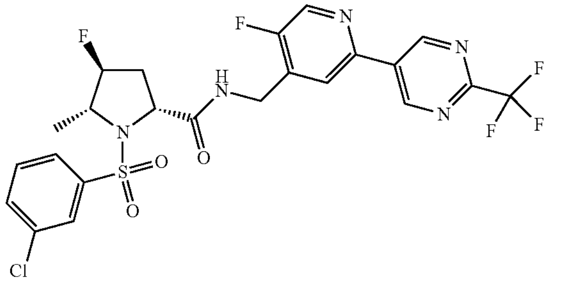
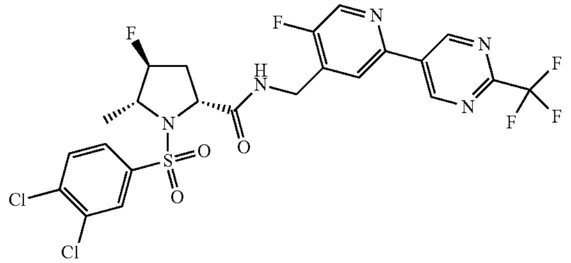
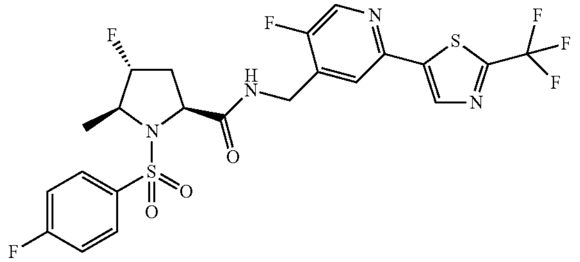
-continued
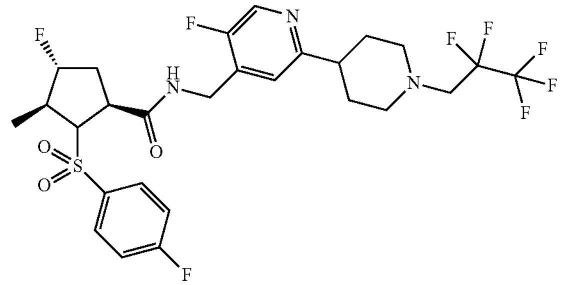
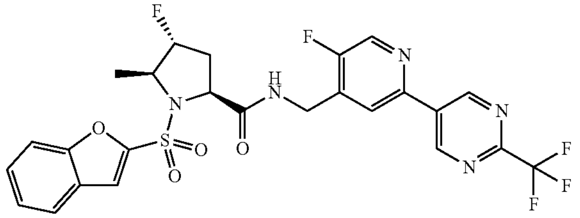
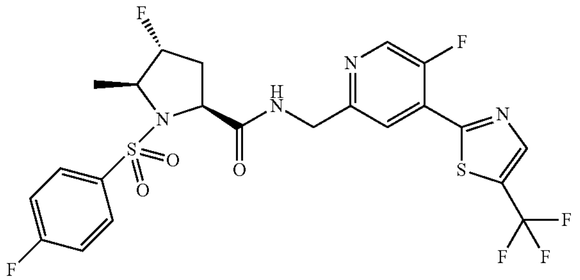
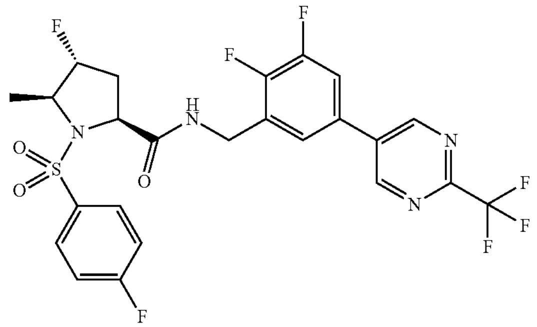
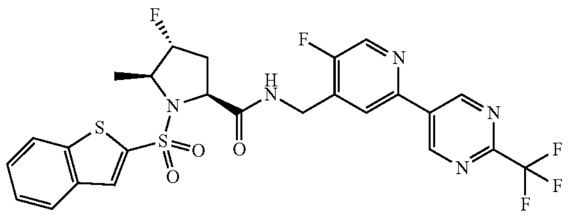
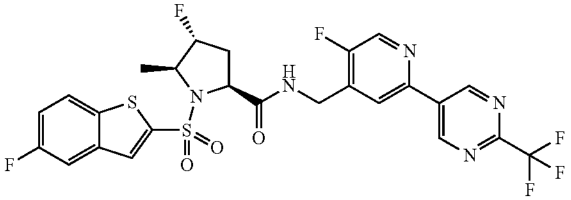

-continued
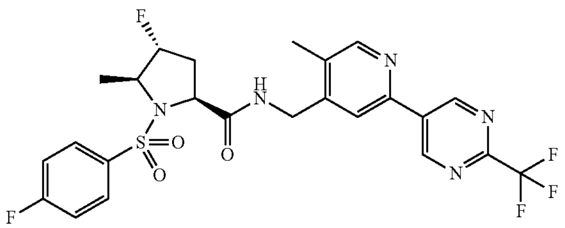
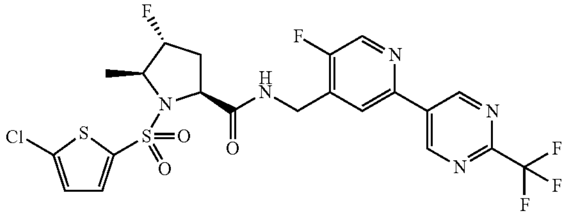
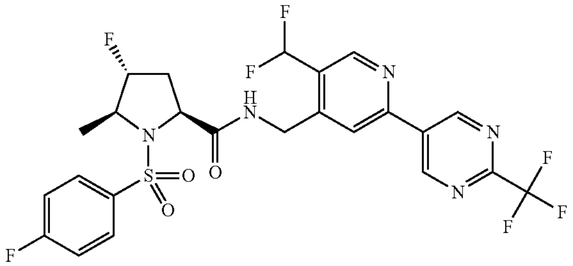
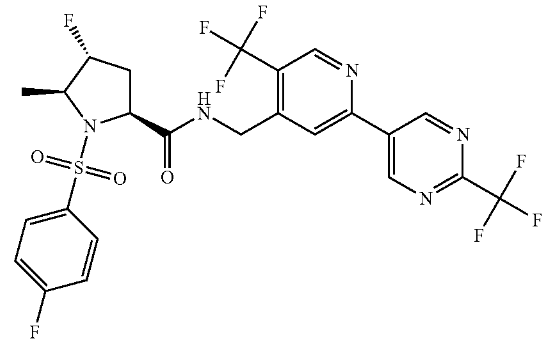
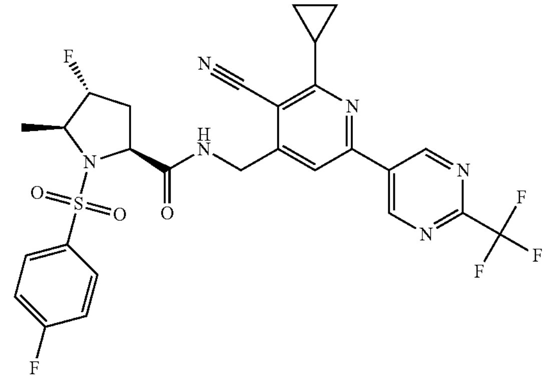
-continued
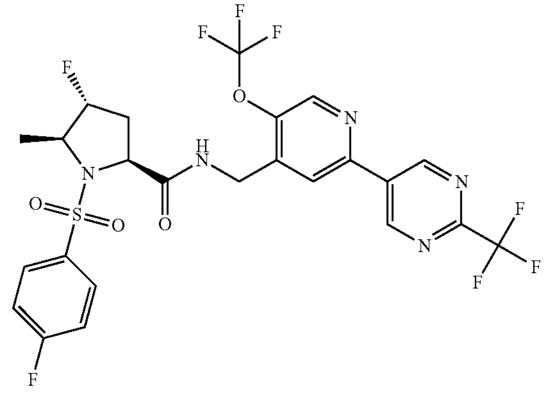
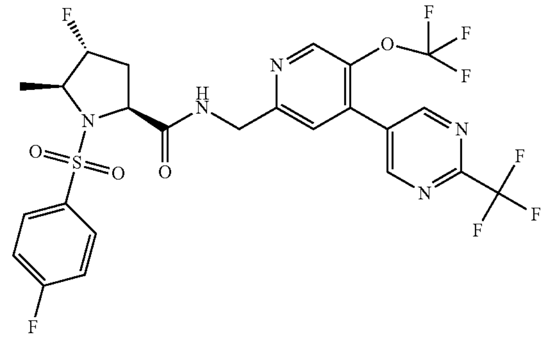
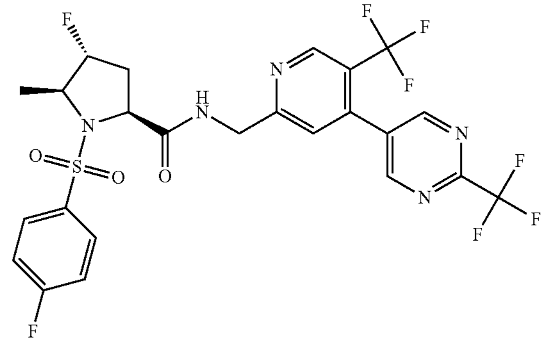
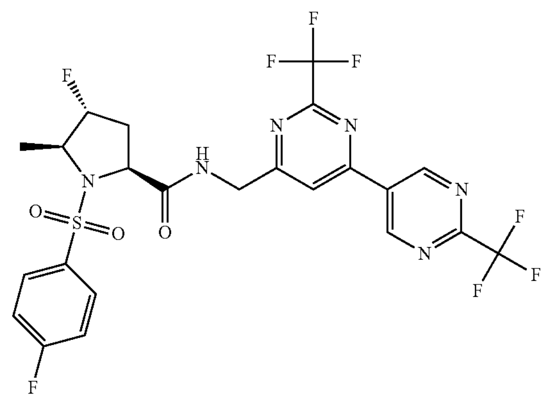

-continued
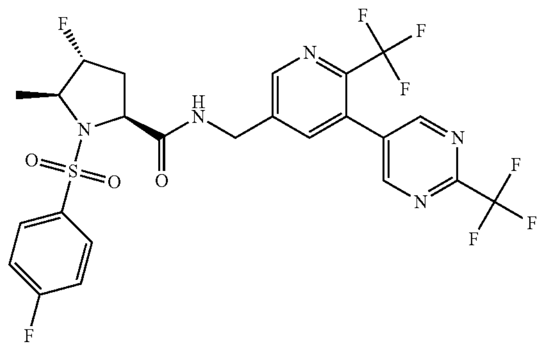
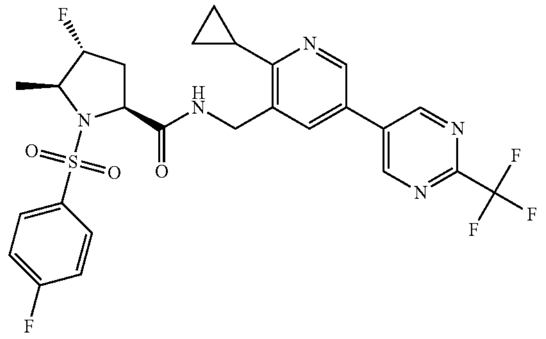
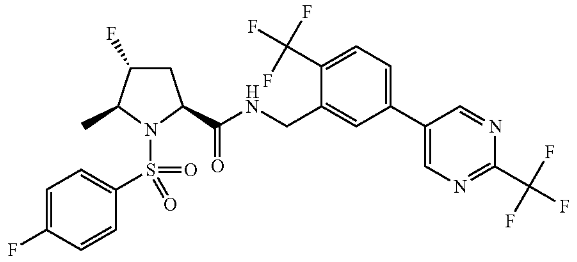
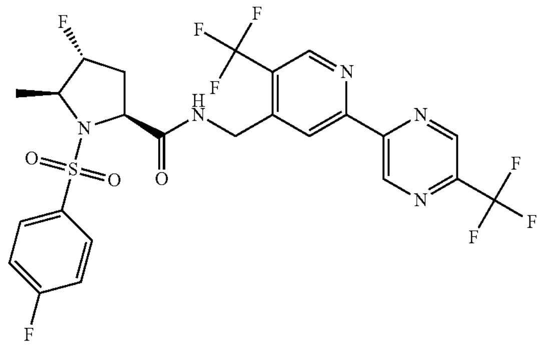
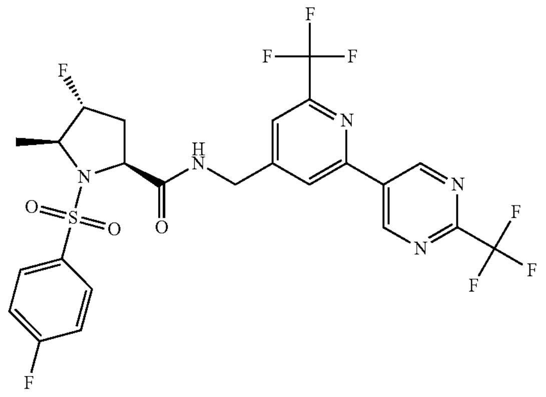
-continued
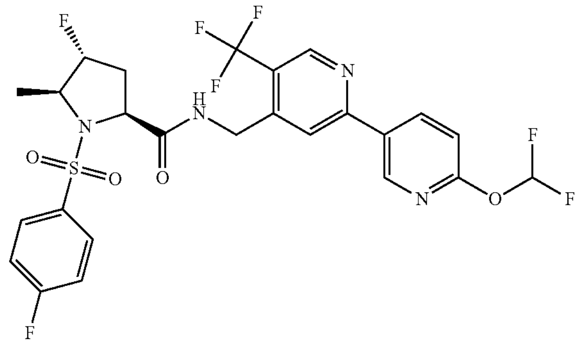
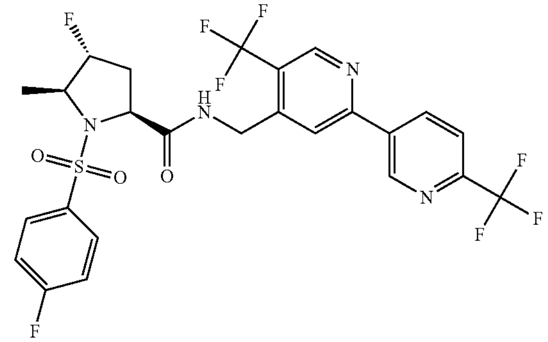
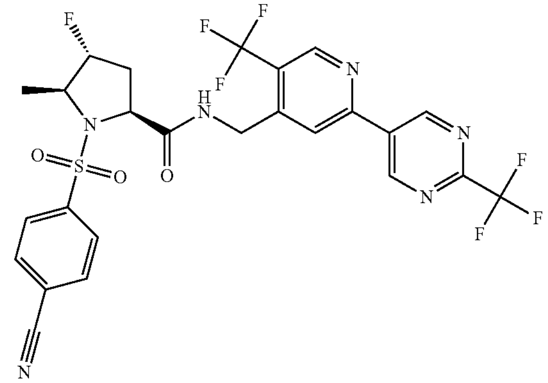
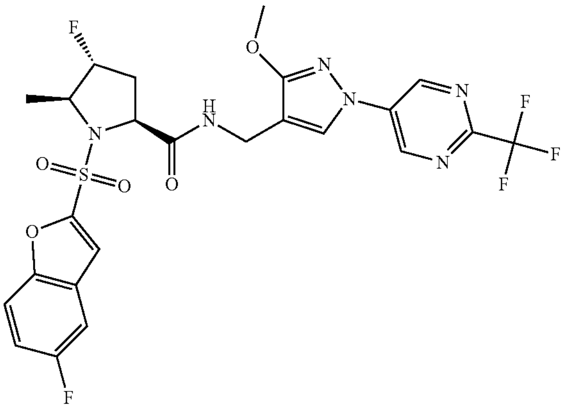

-continued
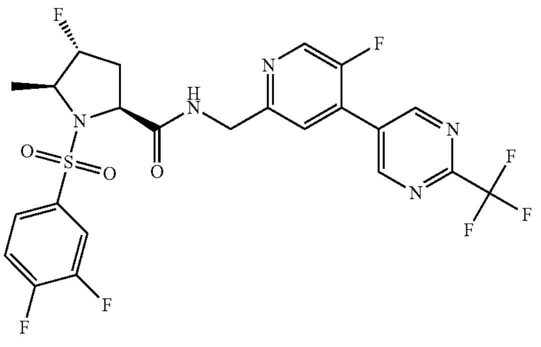
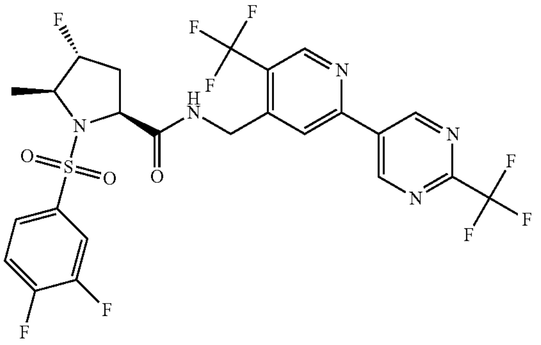
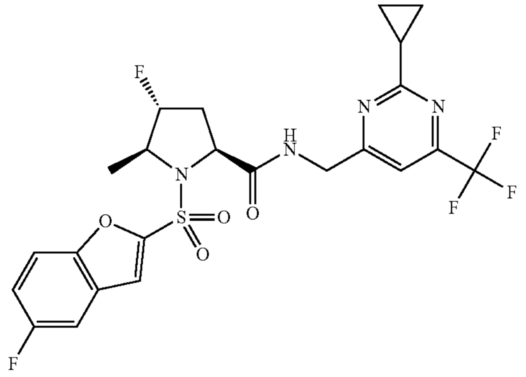
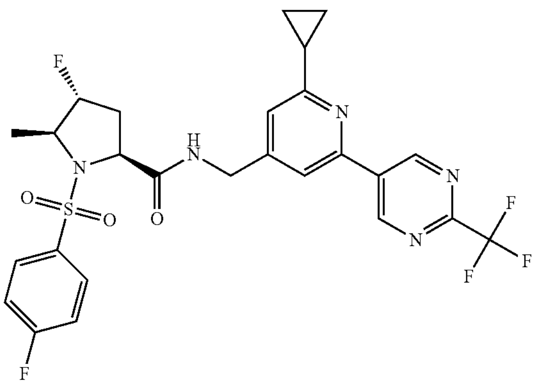
-continued
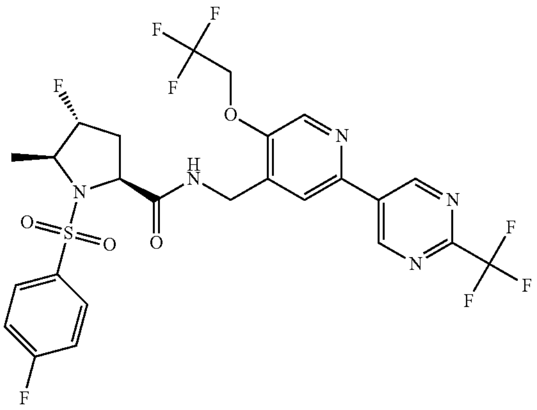
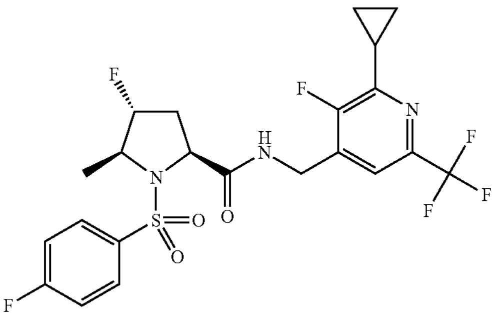
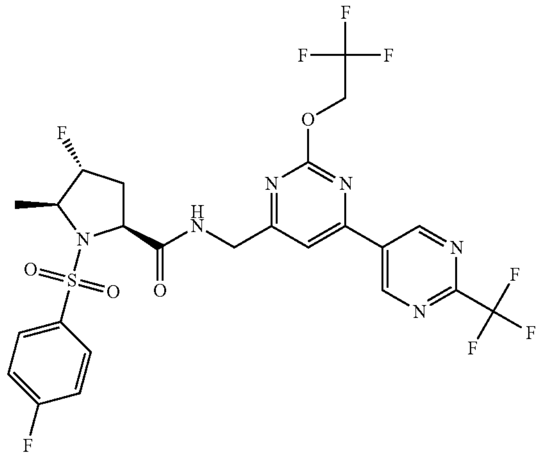
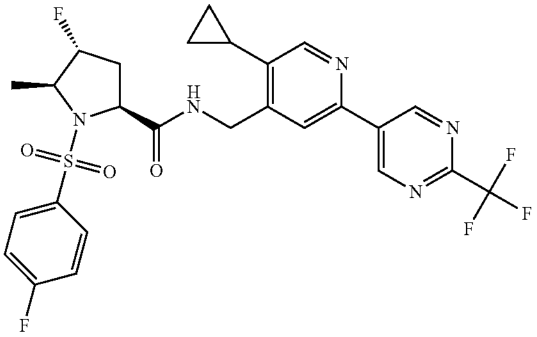

-continued
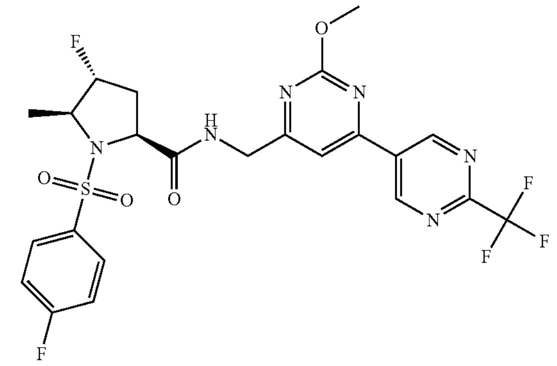
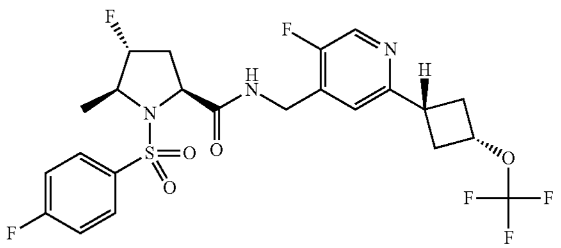
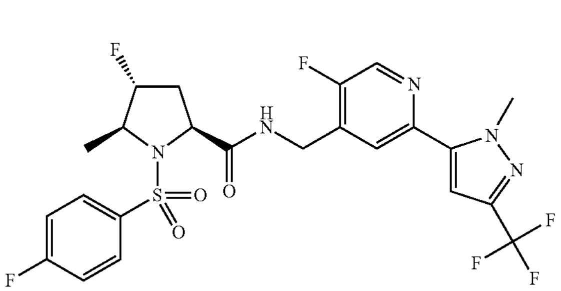
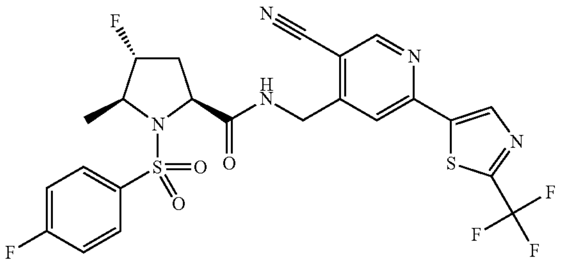
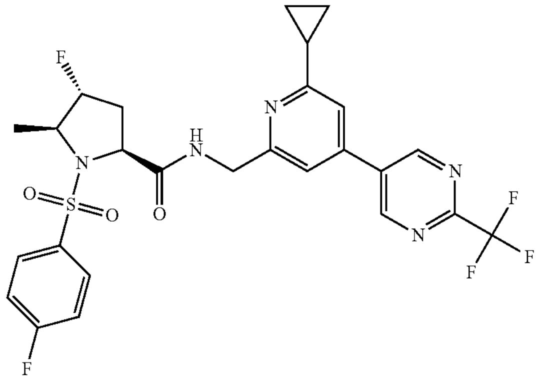
-continued
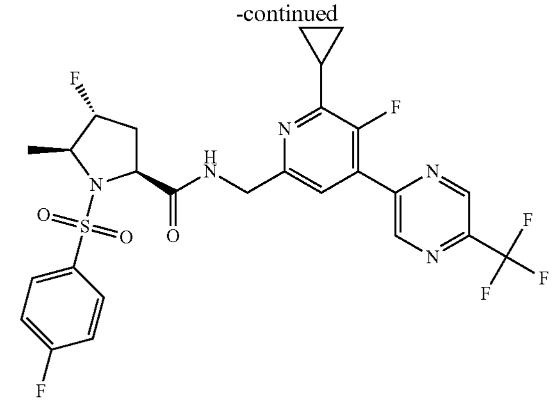
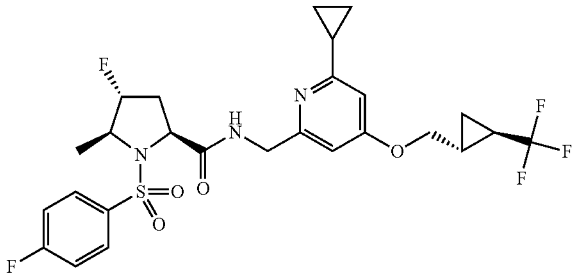
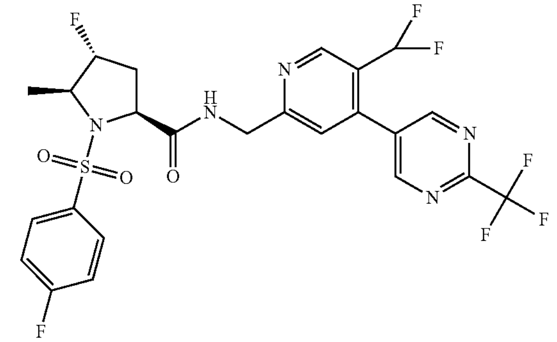
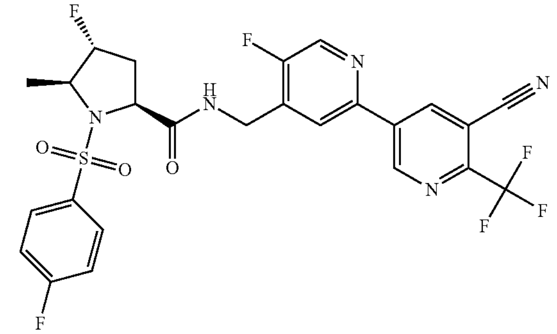
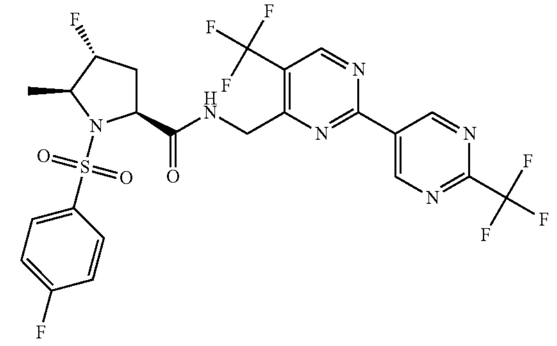

-continued
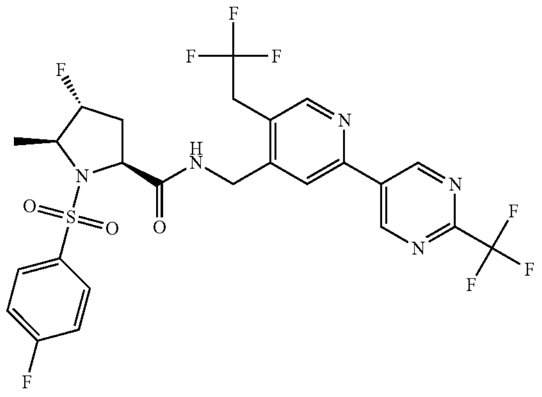
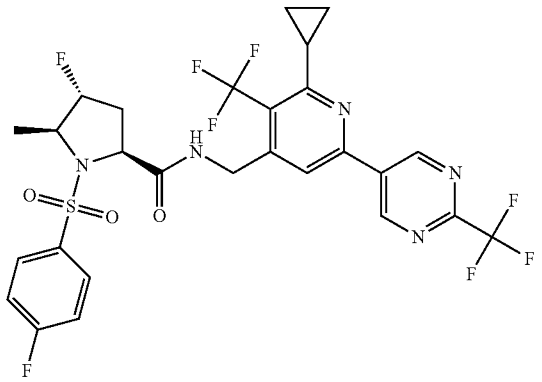
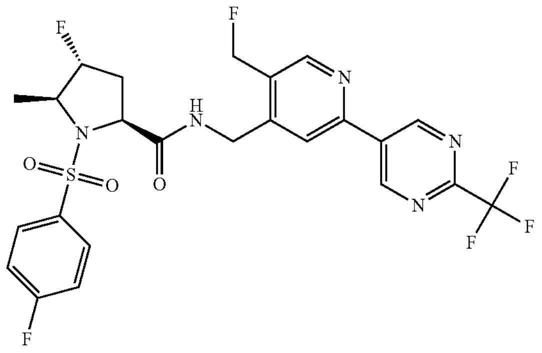
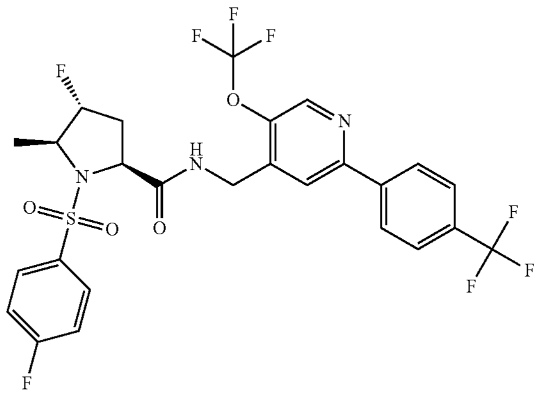
-continued
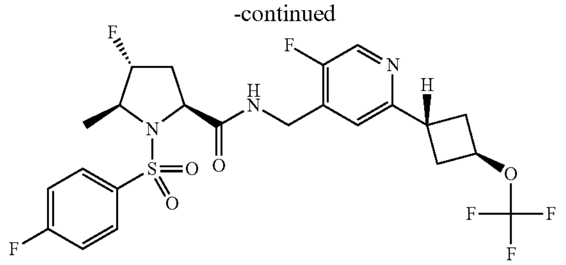
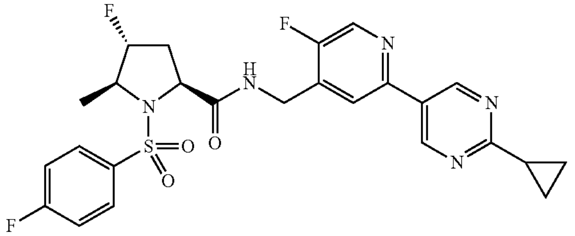
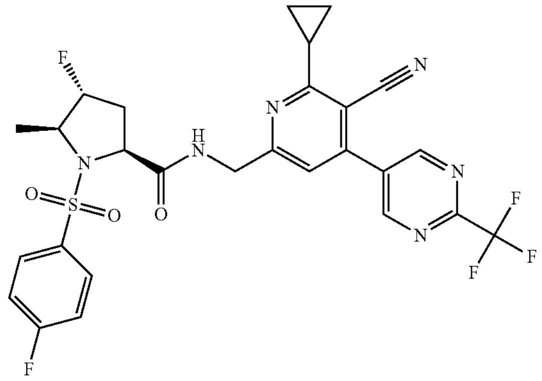
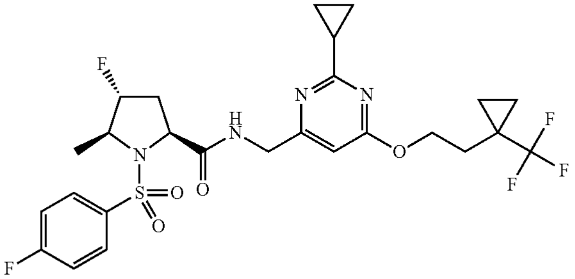
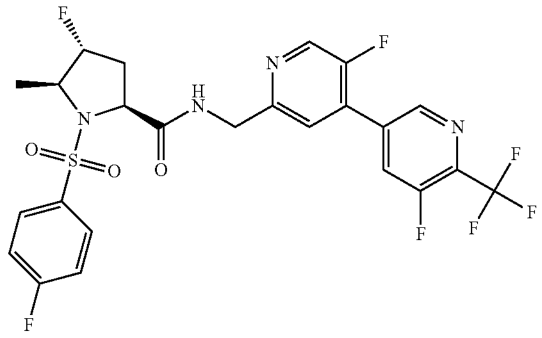
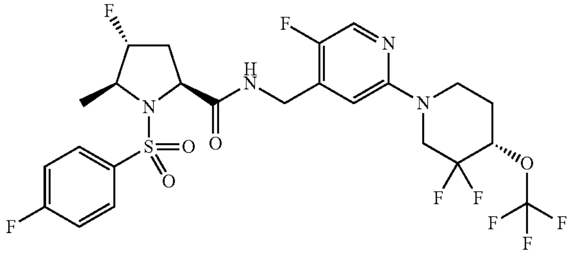

-continued
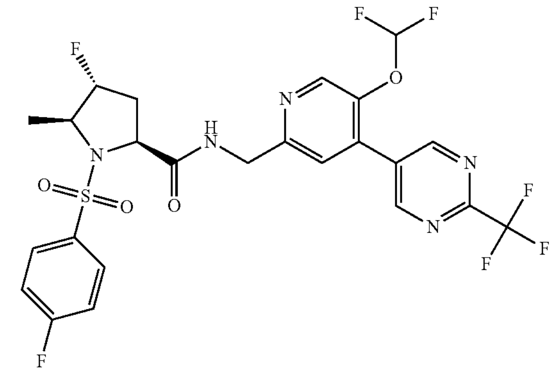
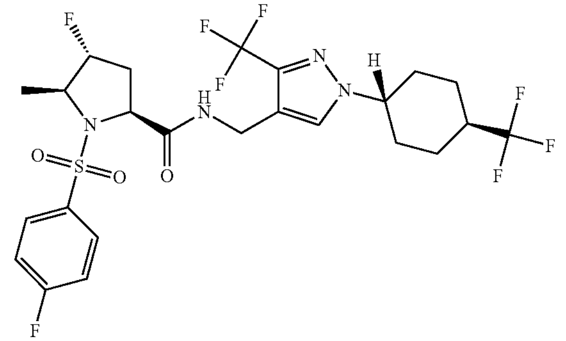
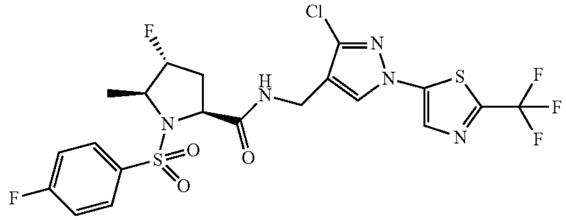
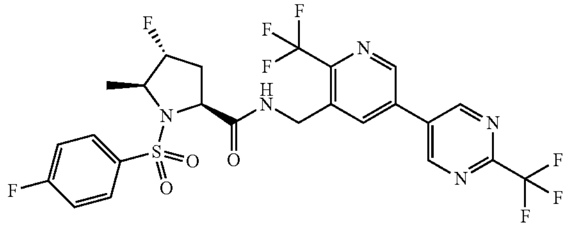
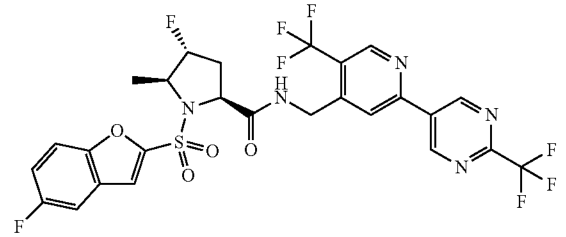
or
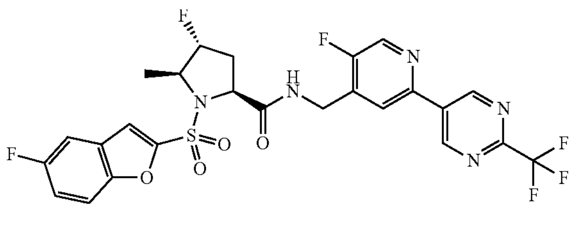
;
or a salt thereof.
EEE203. The compound of EEE2, which is:
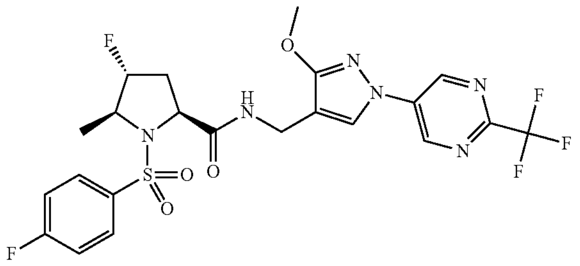
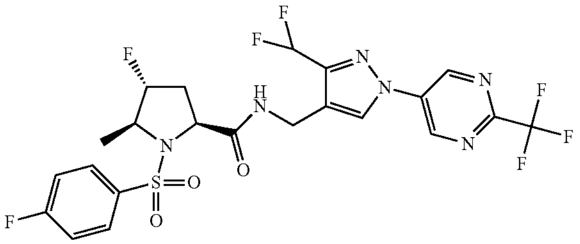
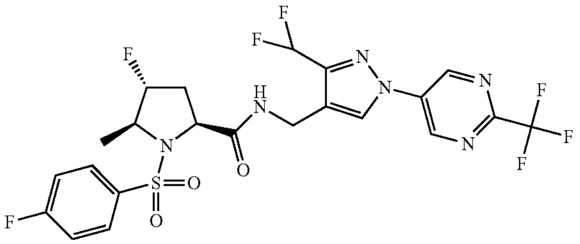
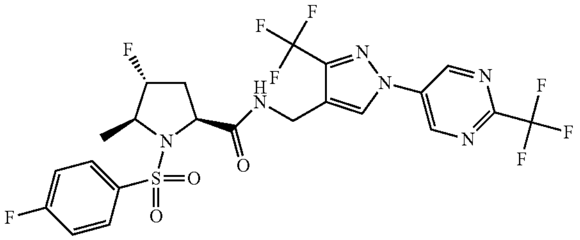
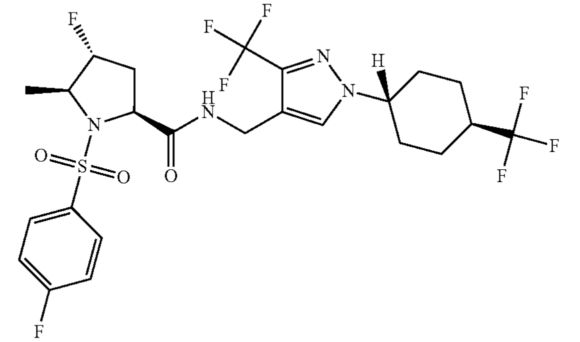
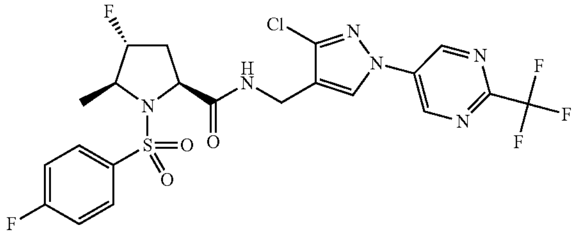

-continued
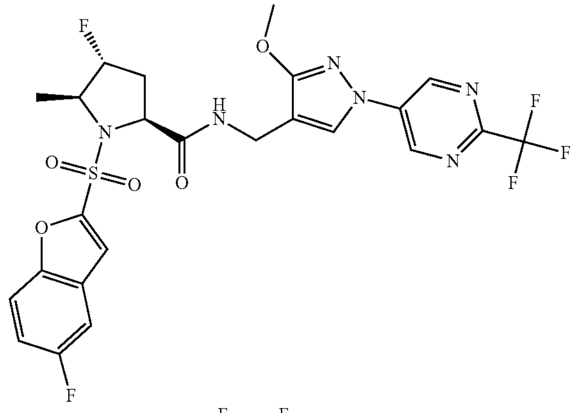
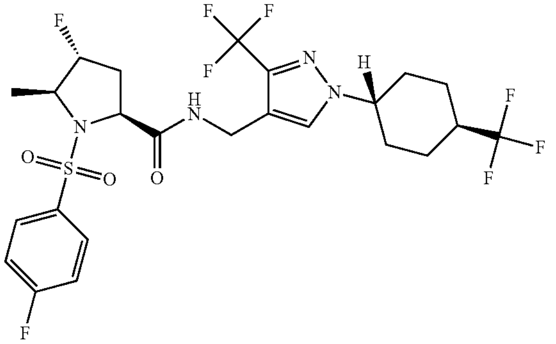
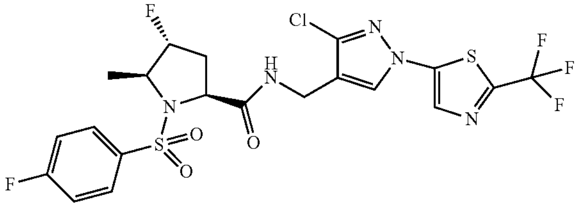
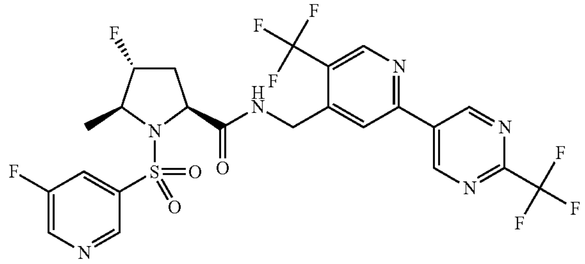
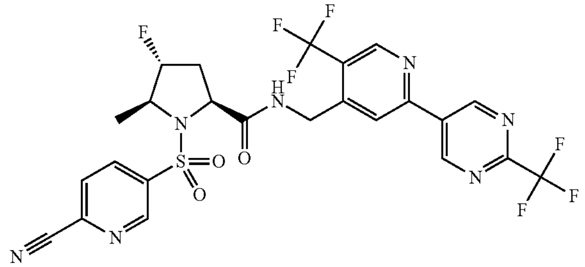
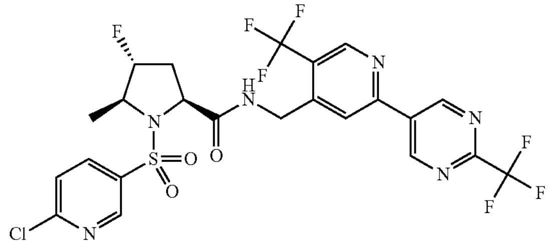
or
-continued
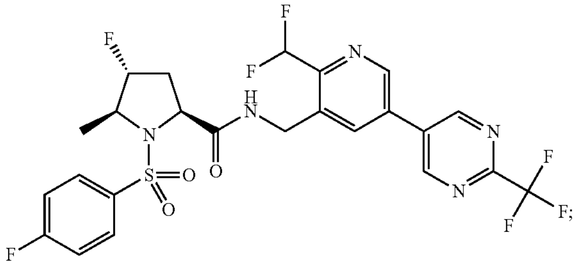
or a salt thereof.
EEE204. The compound of EEE8, which is:
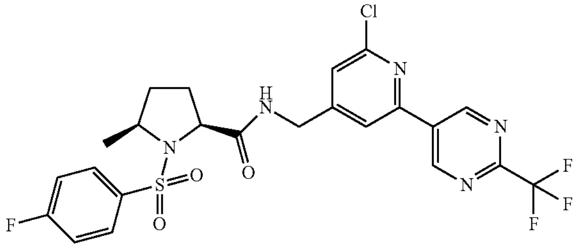
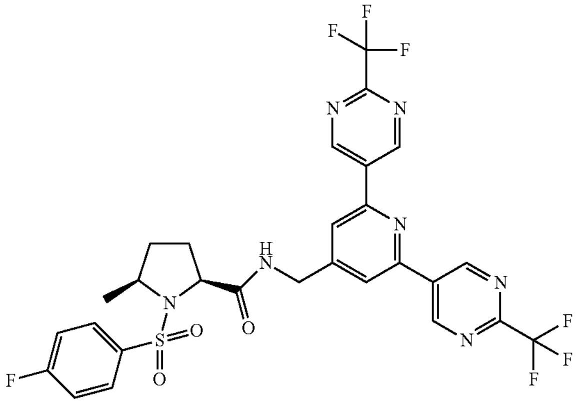
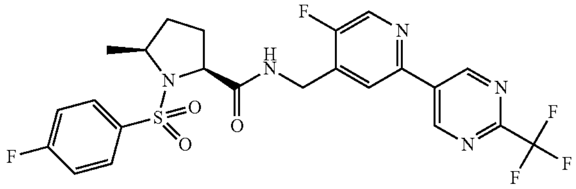
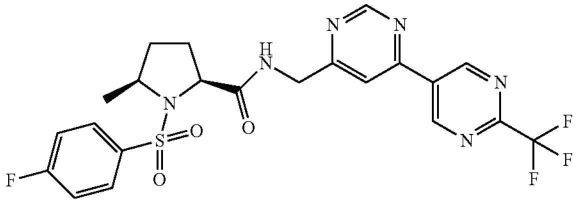
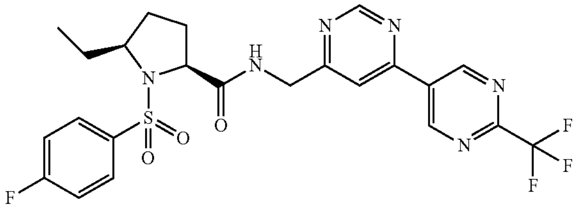

-continued
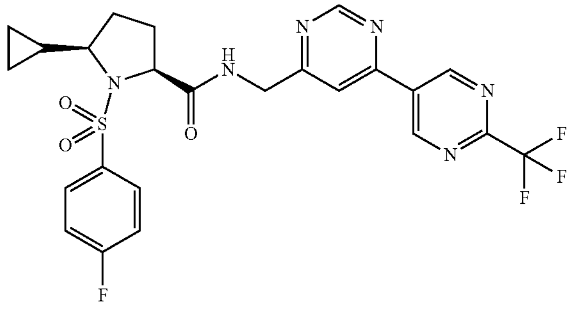
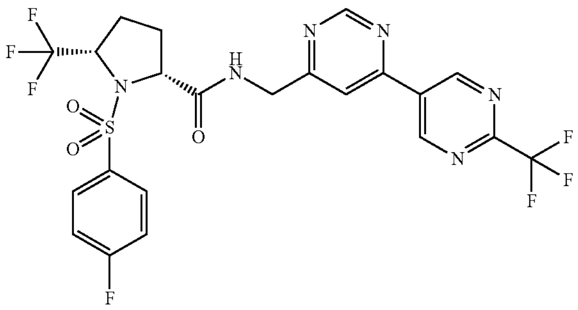
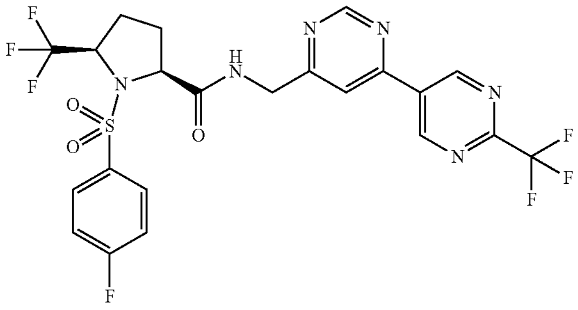
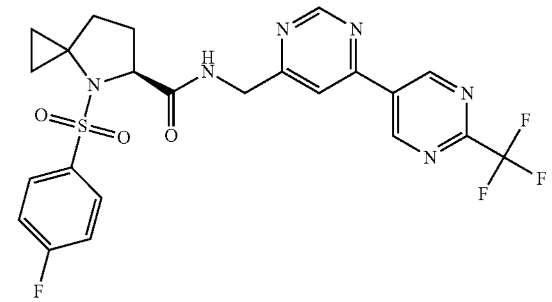
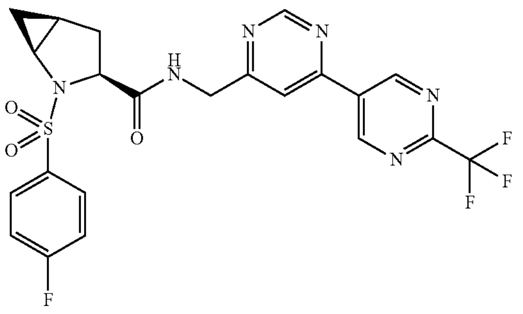
-continued
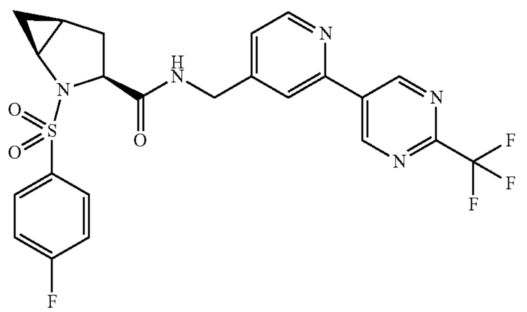
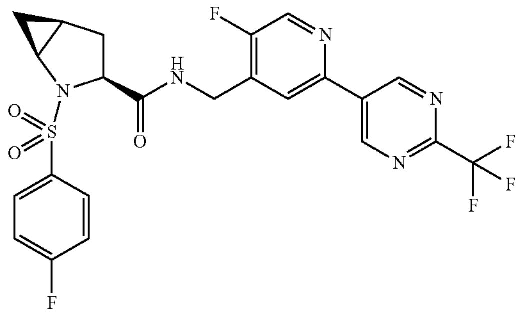
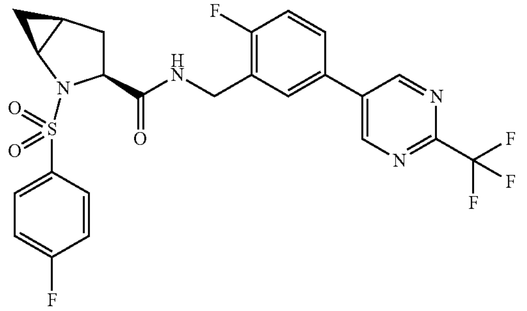
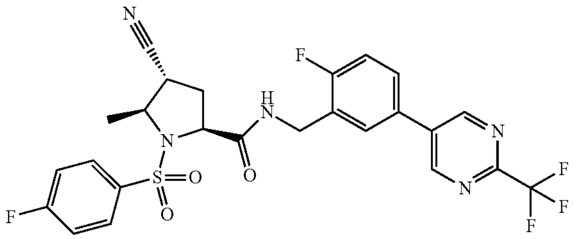
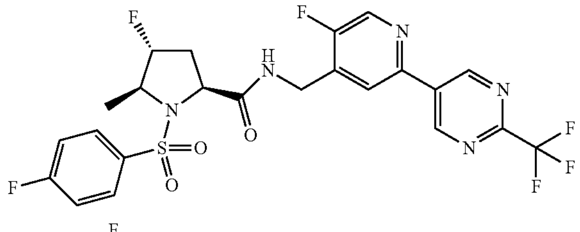
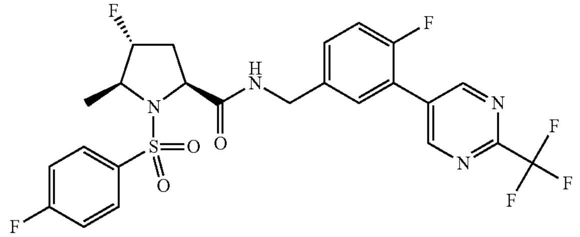

-continued
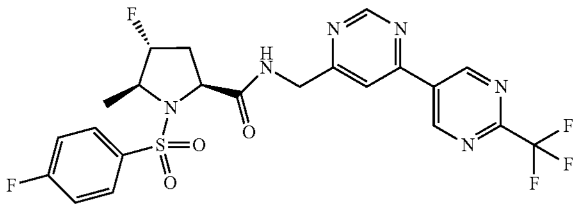
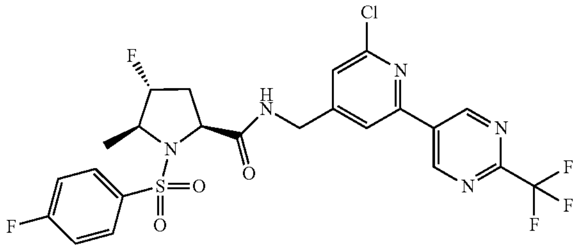
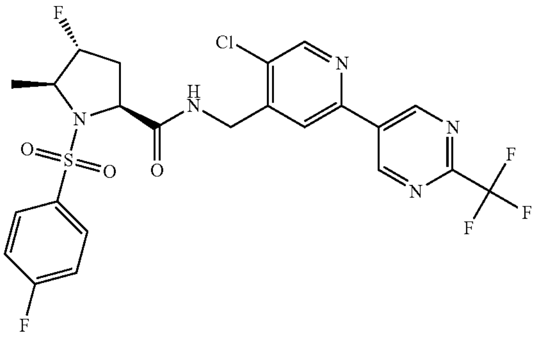
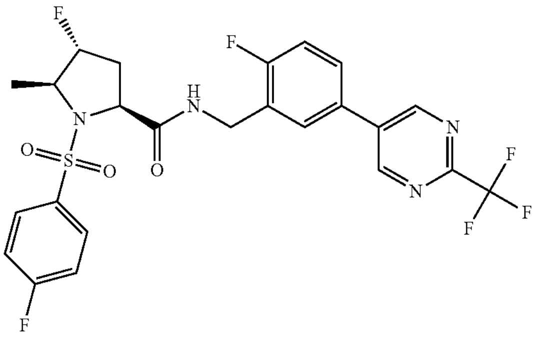
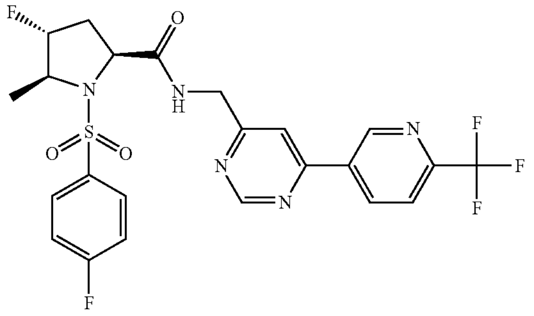
-continued
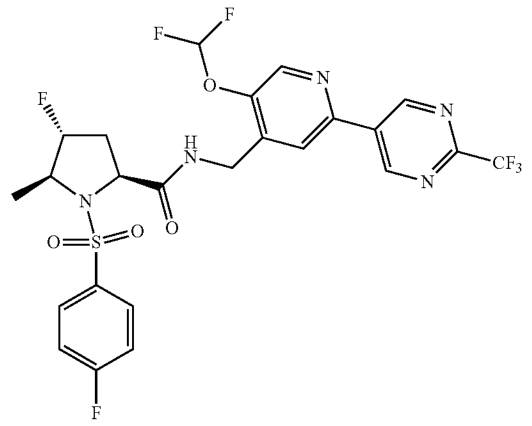
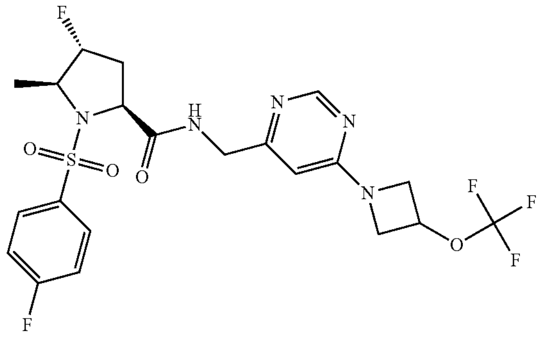
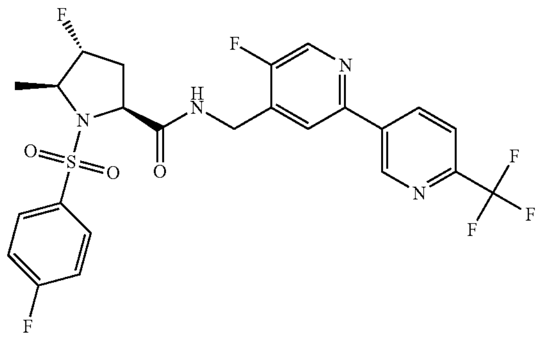
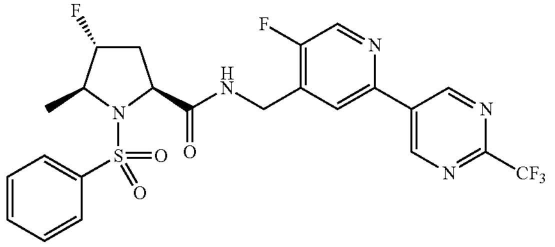
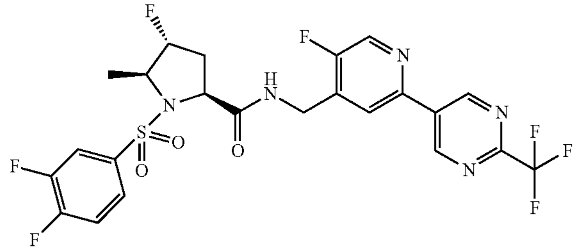

-continued
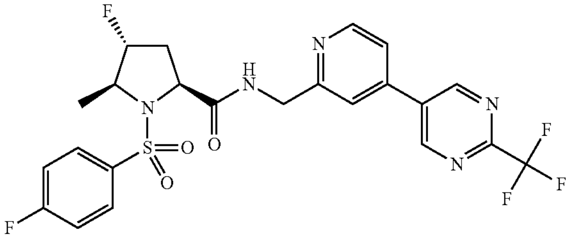
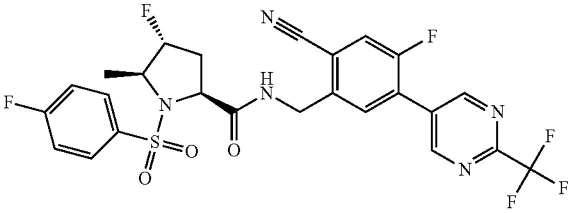
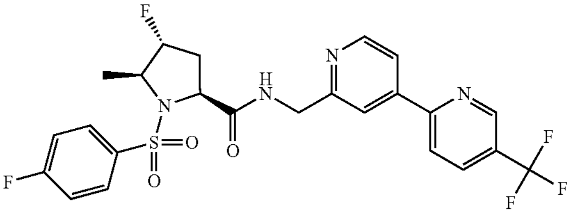
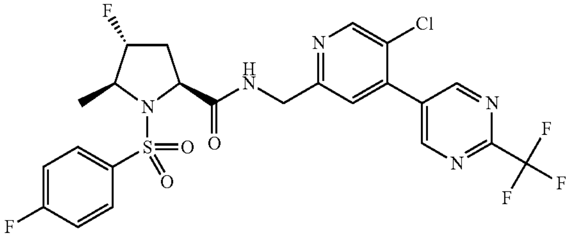
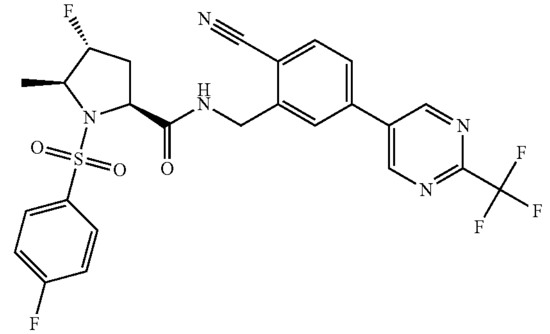
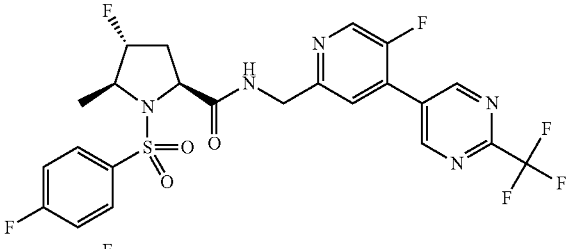
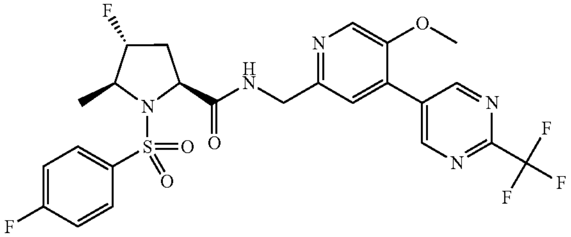
-continued
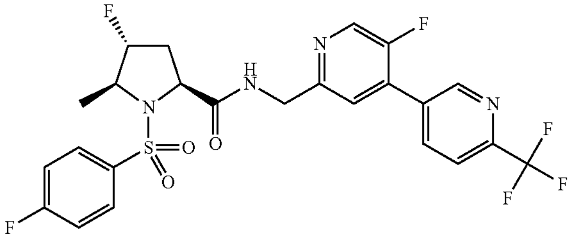
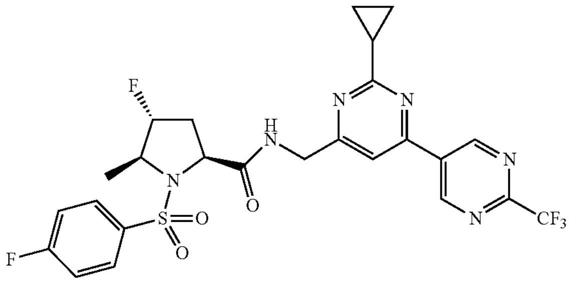
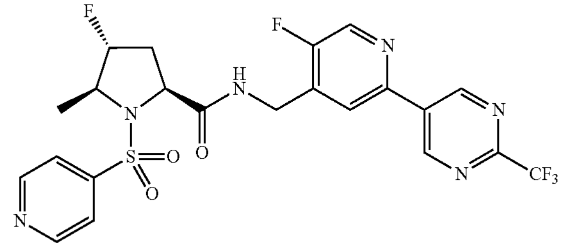
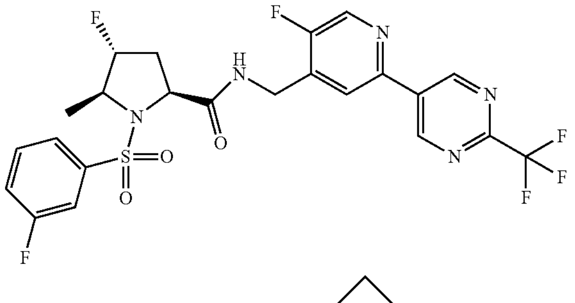
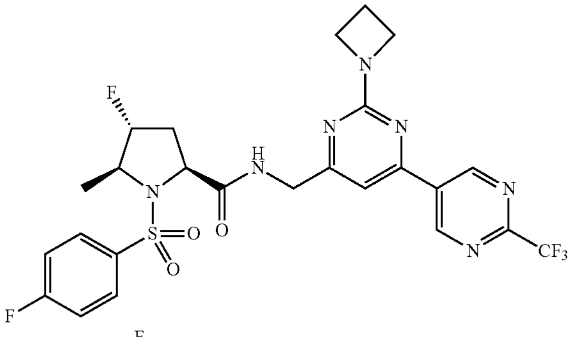
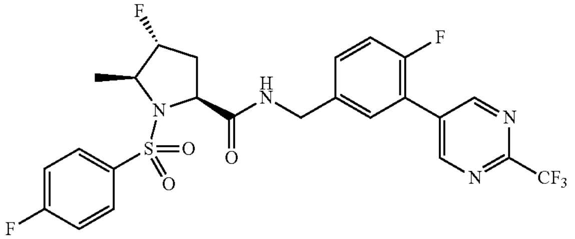

-continued
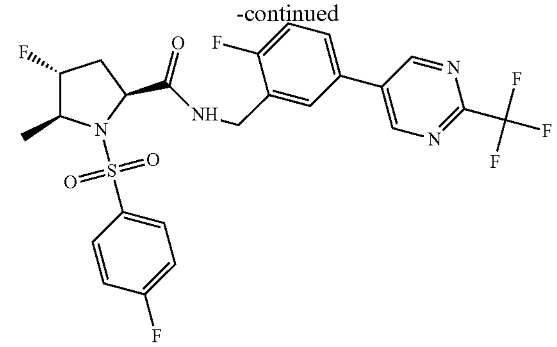
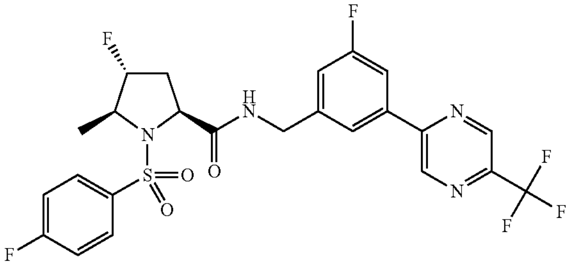
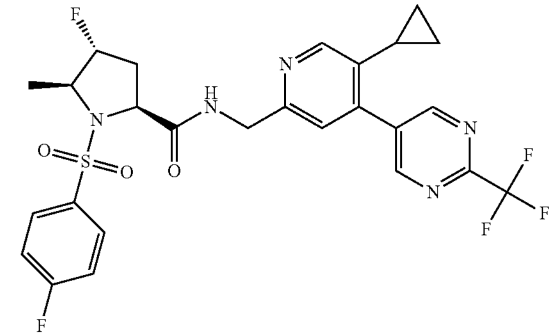
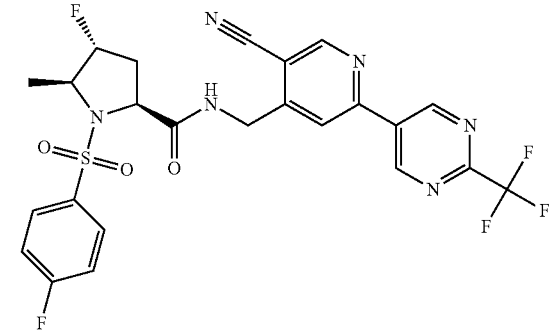
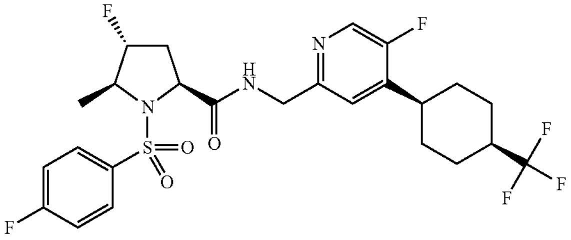
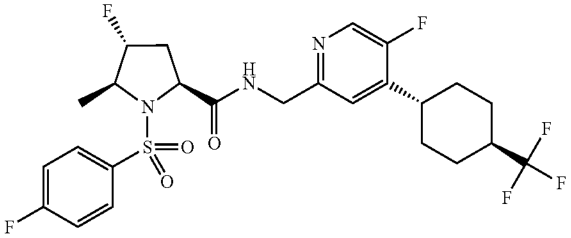
-continued
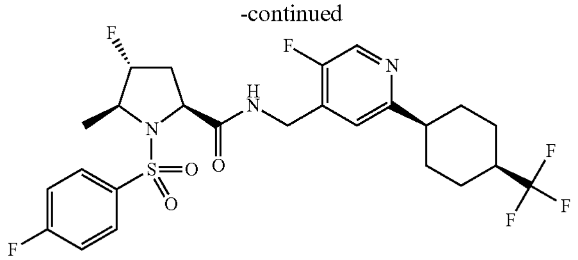
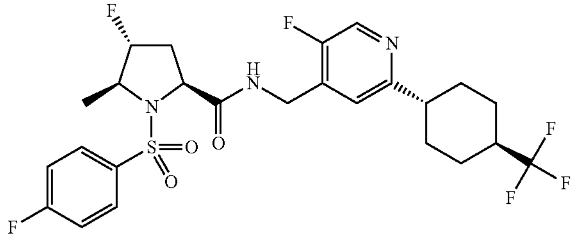
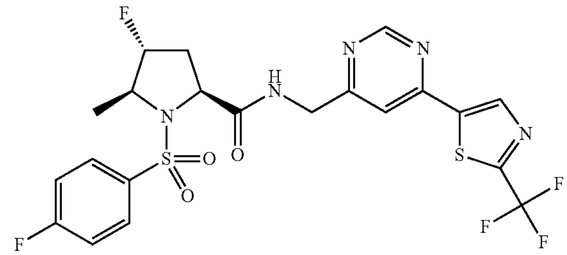
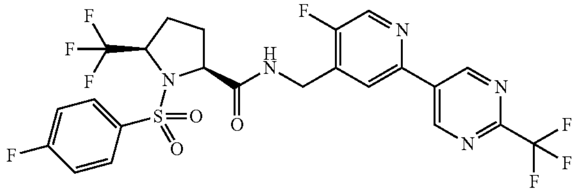
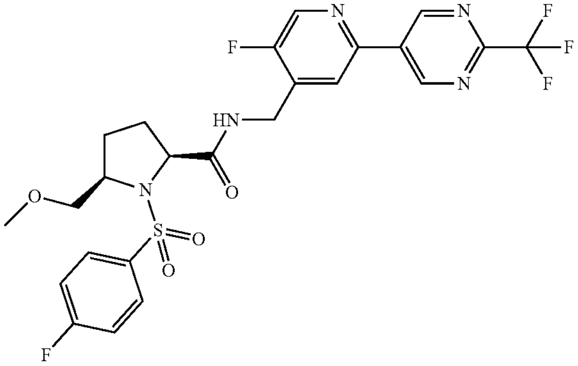
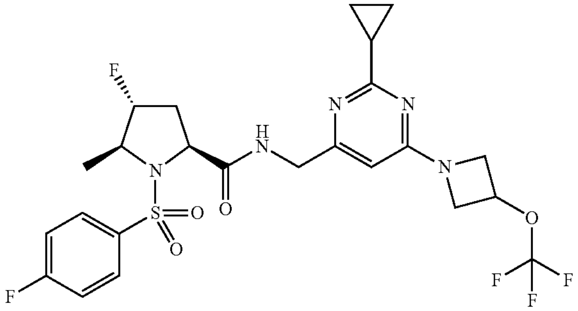

-continued
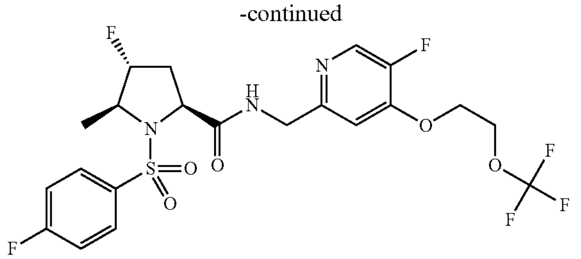
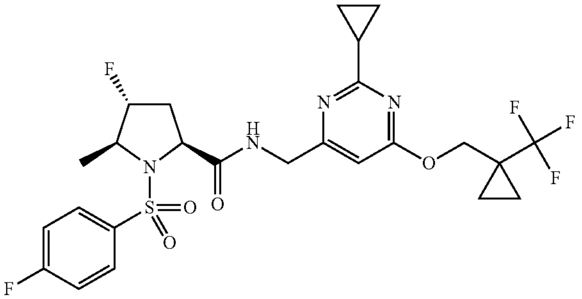
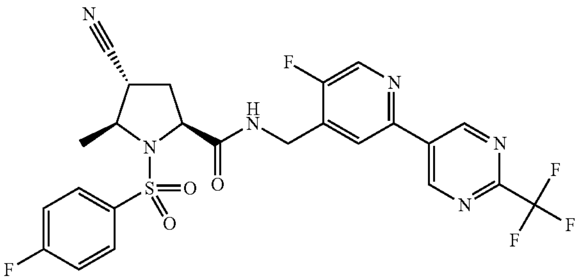
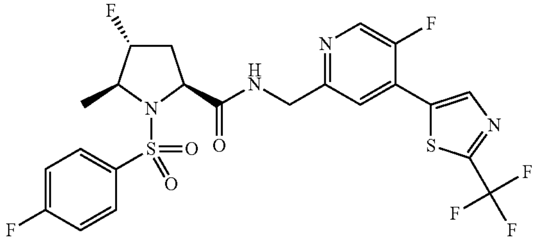
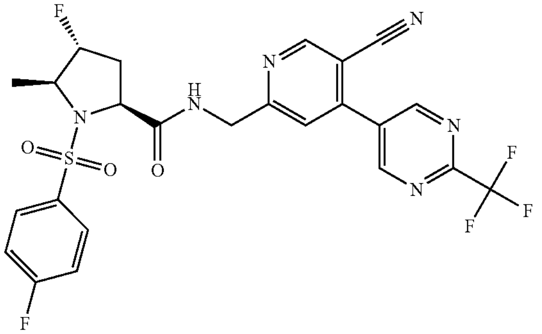
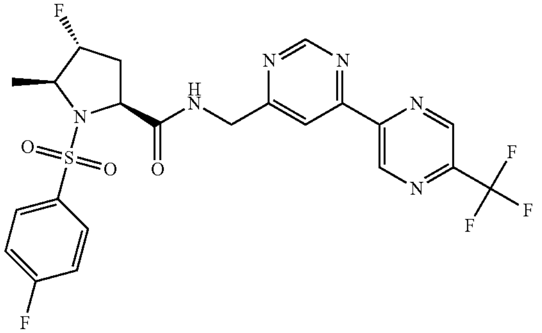
-continued
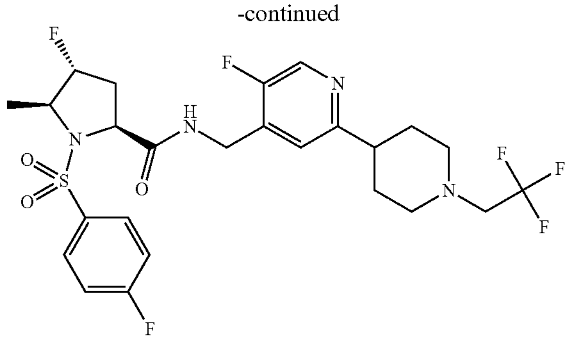
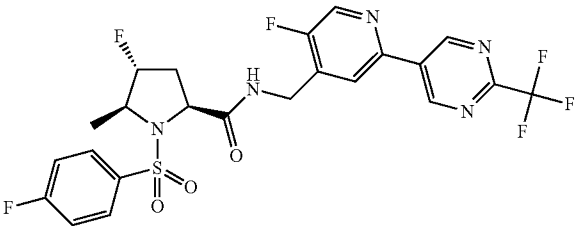
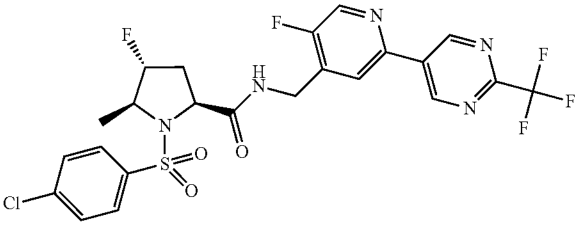
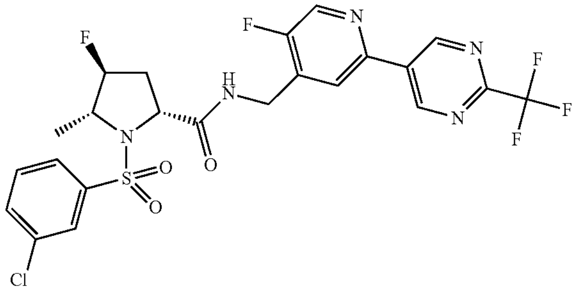
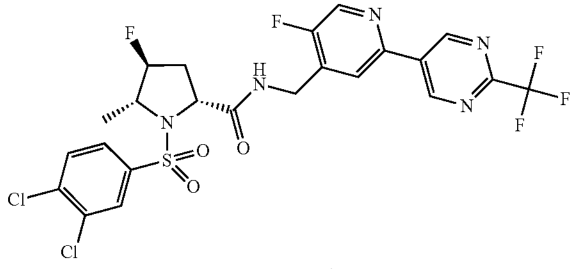
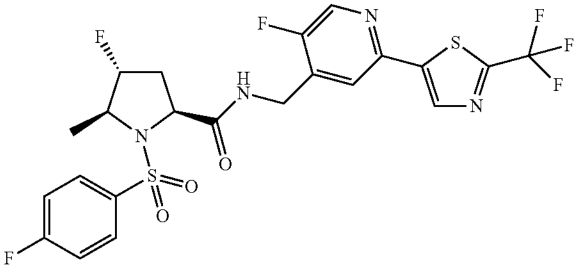

-continued
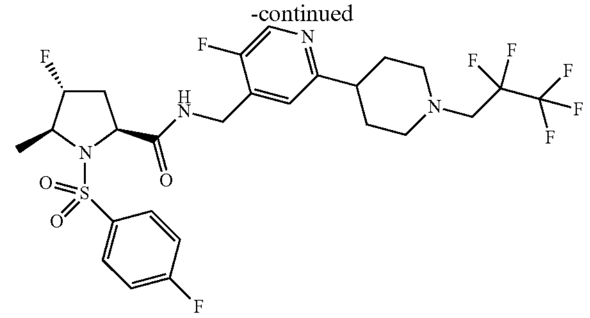
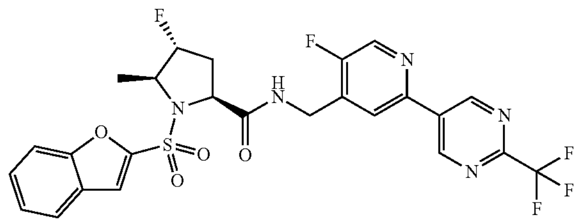
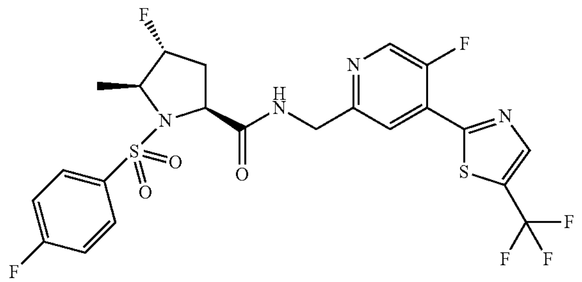
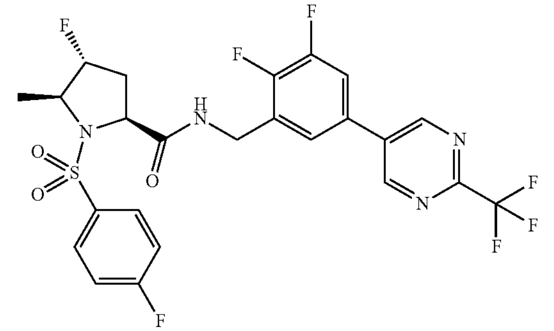
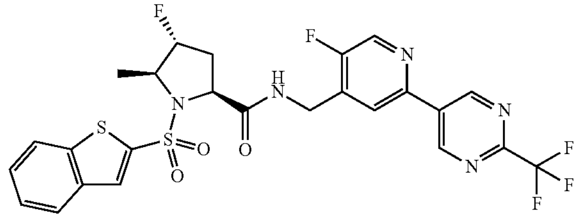
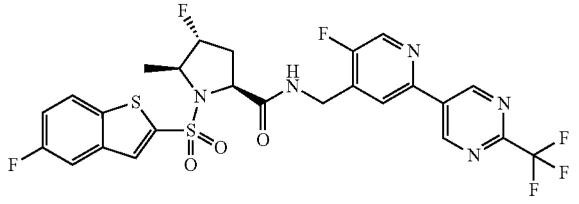
-continued
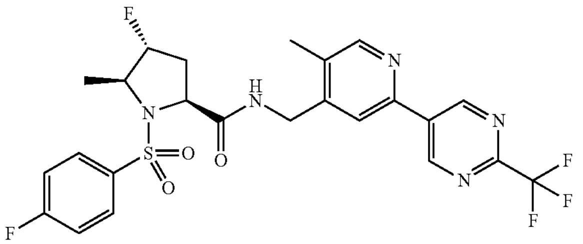
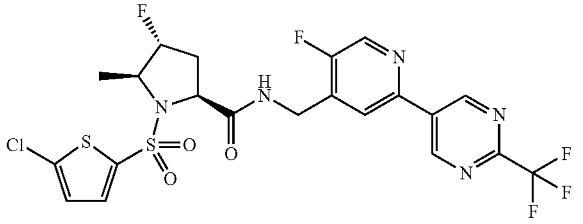
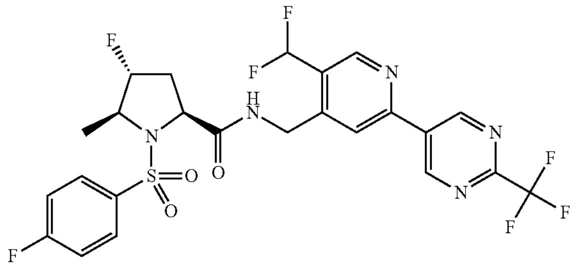
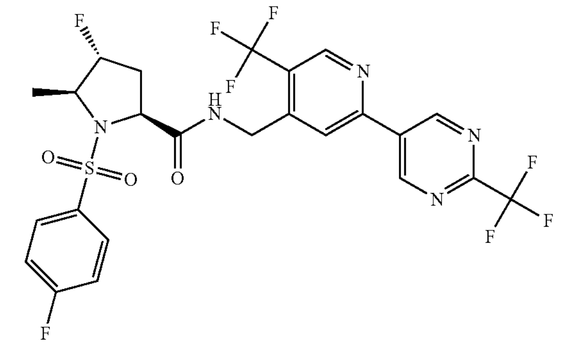
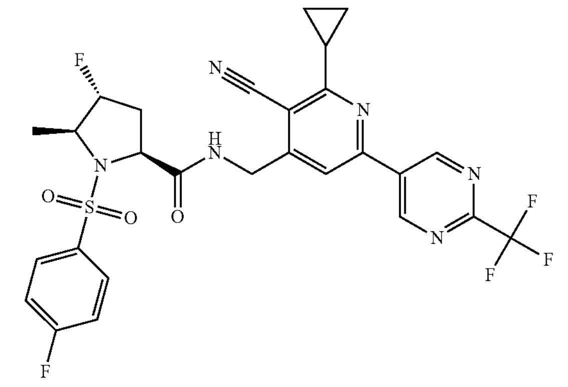

-continued
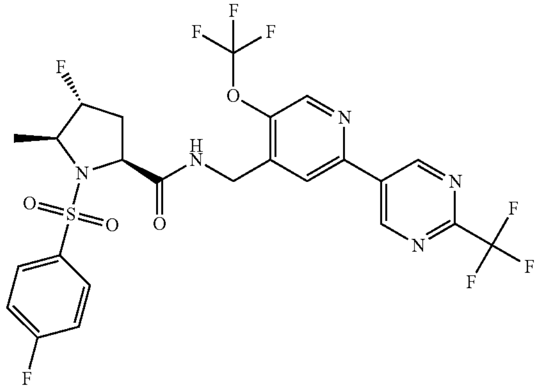
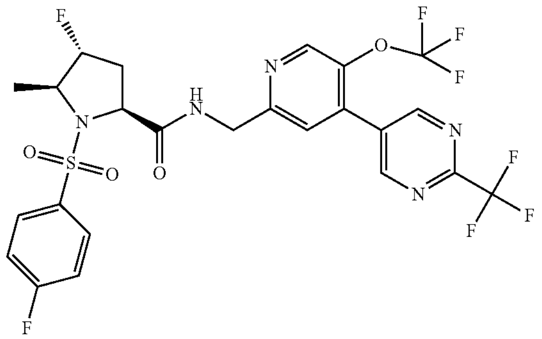
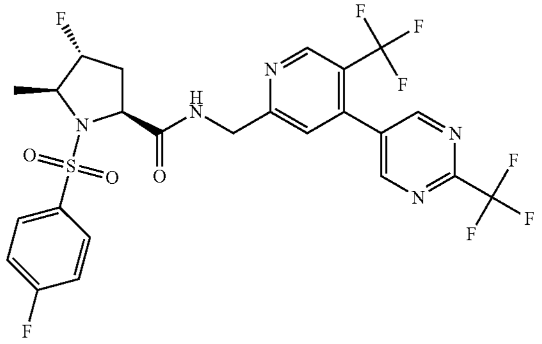
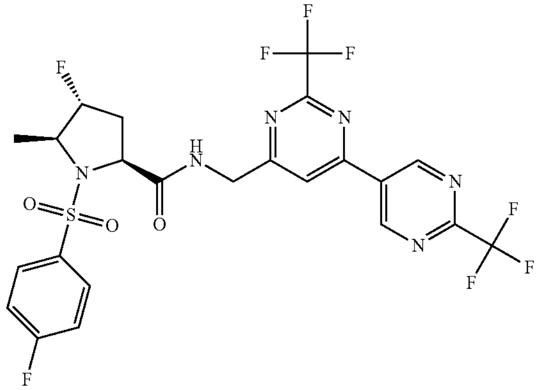
-continued
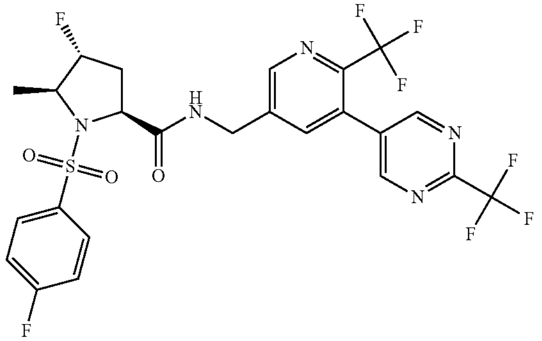
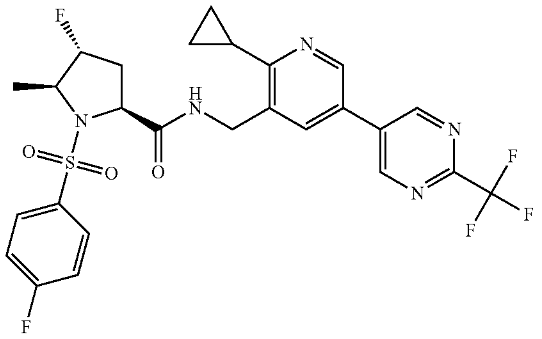
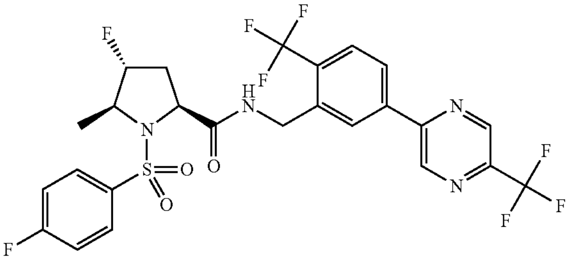
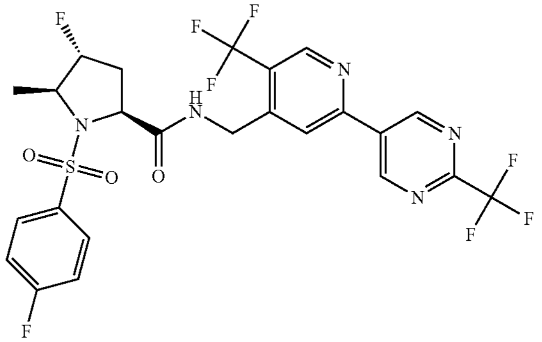
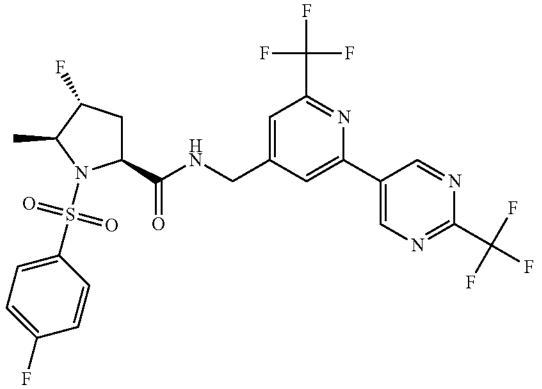

-continued
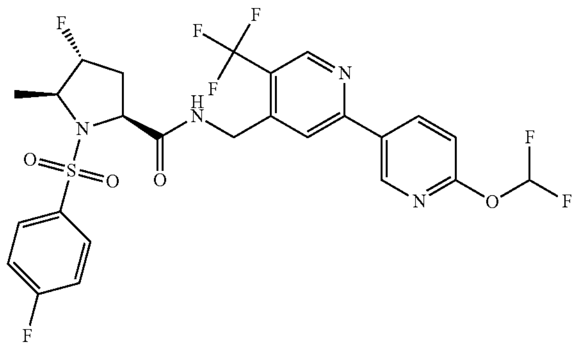
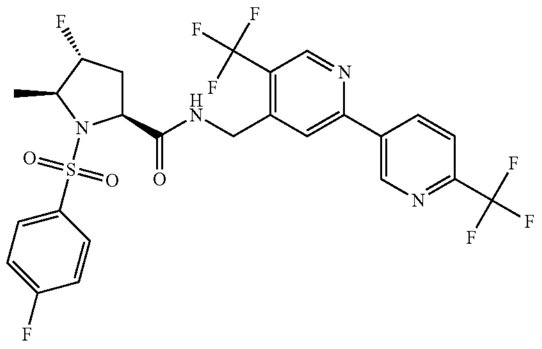
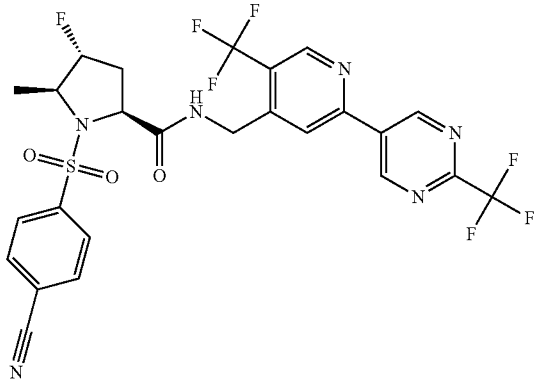
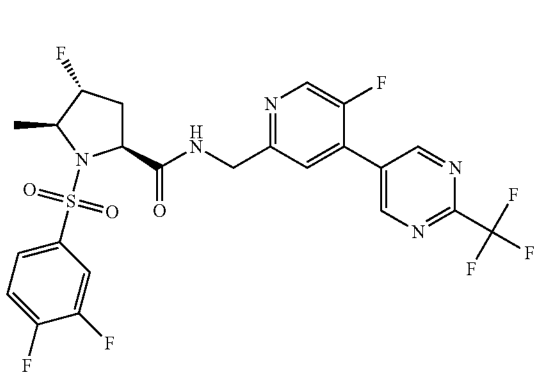
-continued
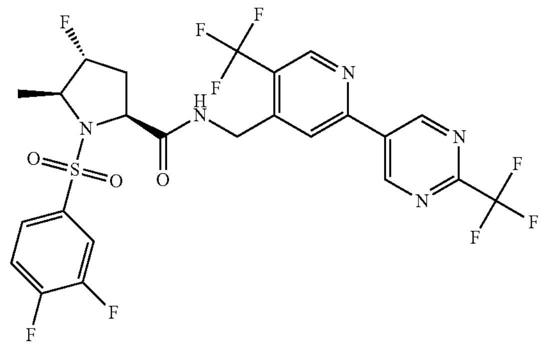
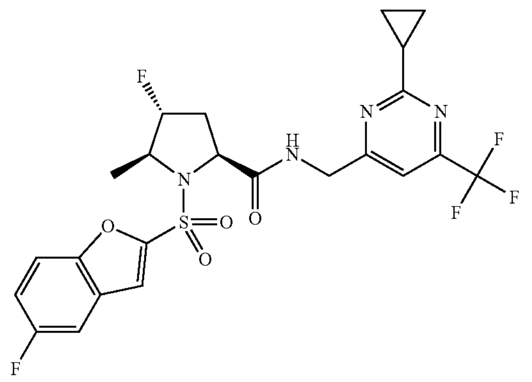
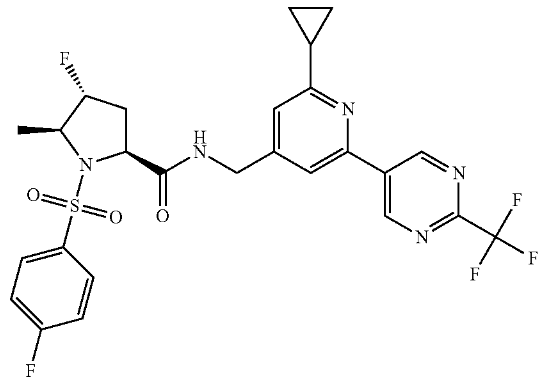
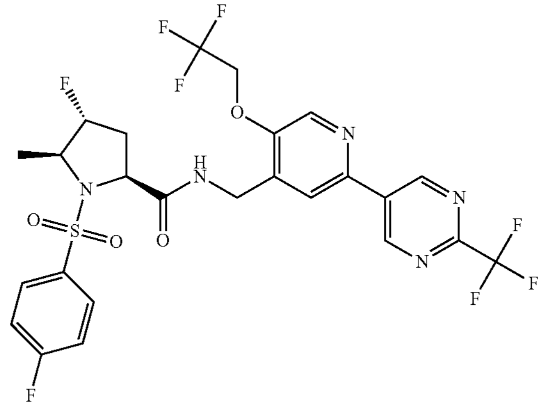

-continued
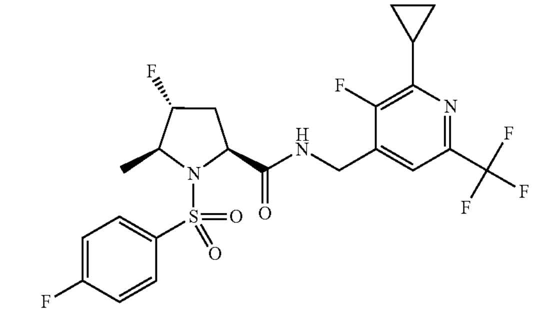
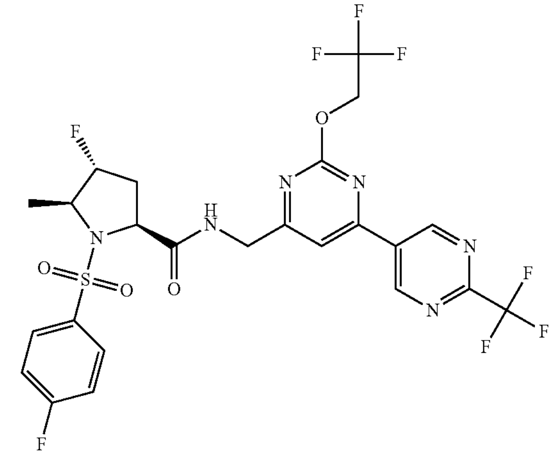
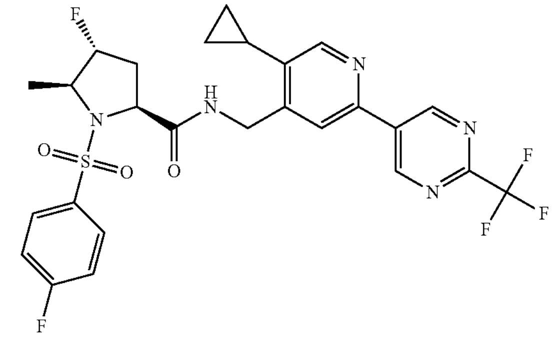
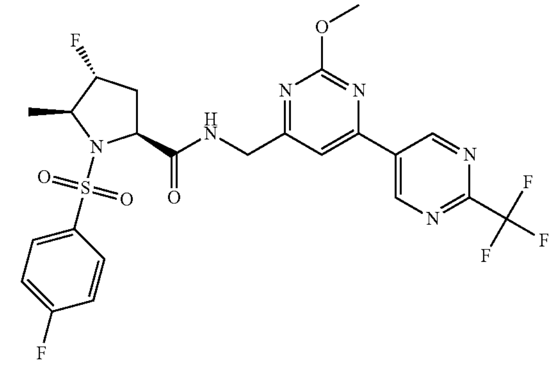
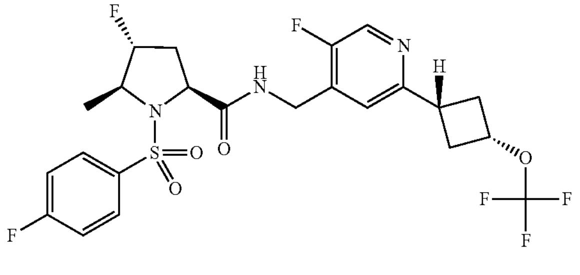
-continued
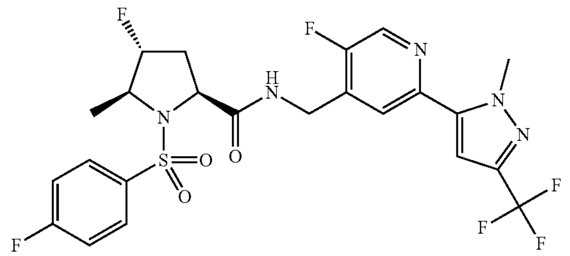
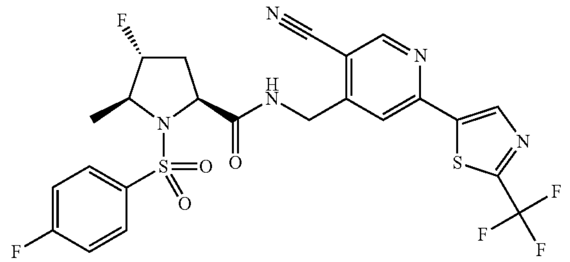
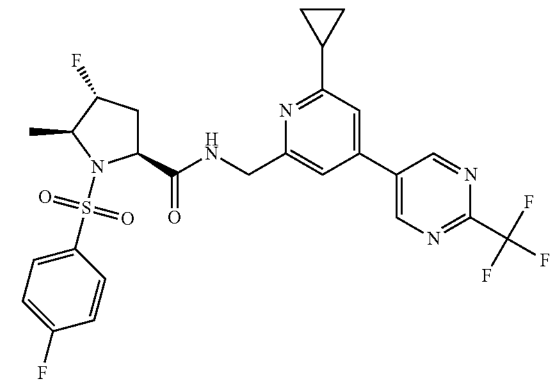
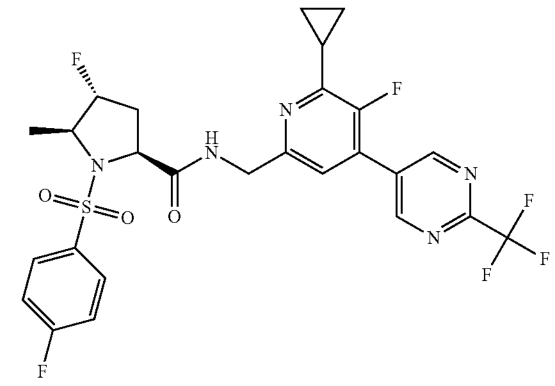
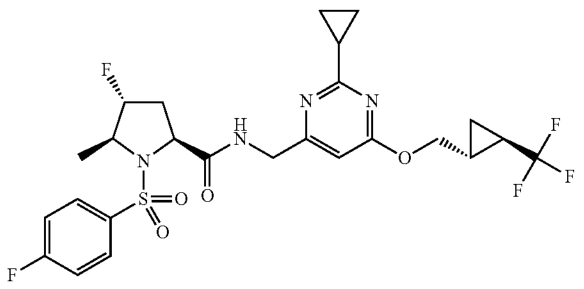

-continued
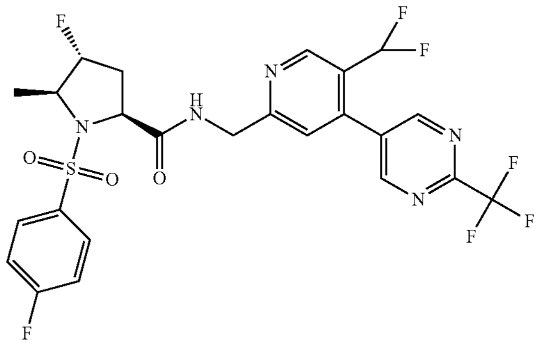
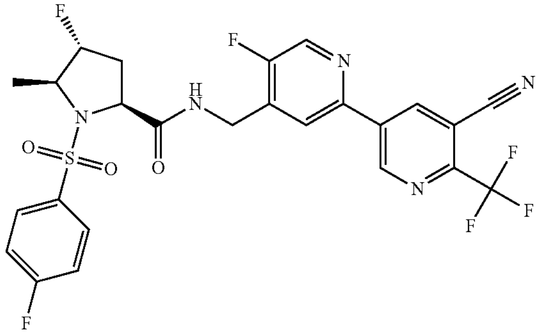
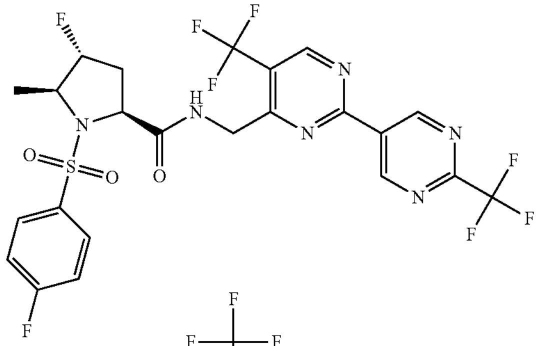
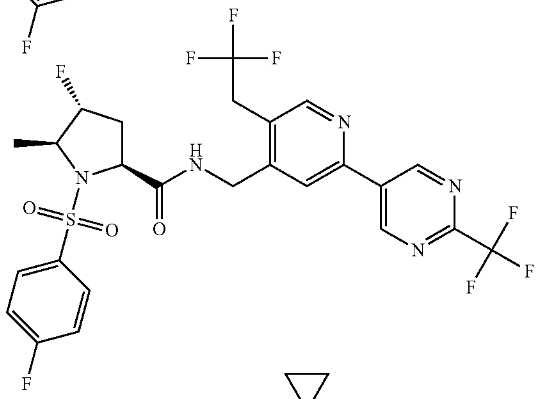
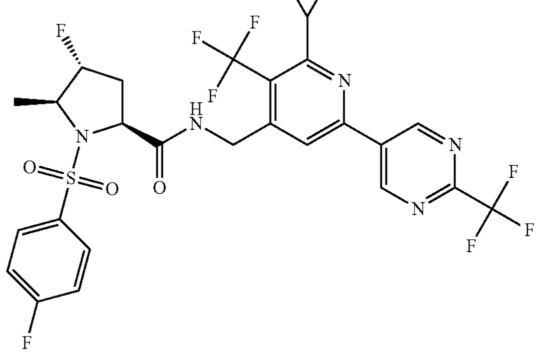
-continued
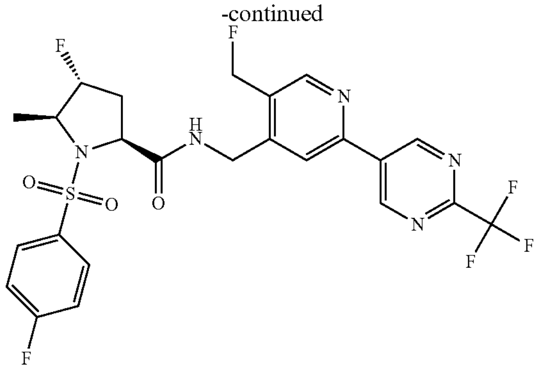
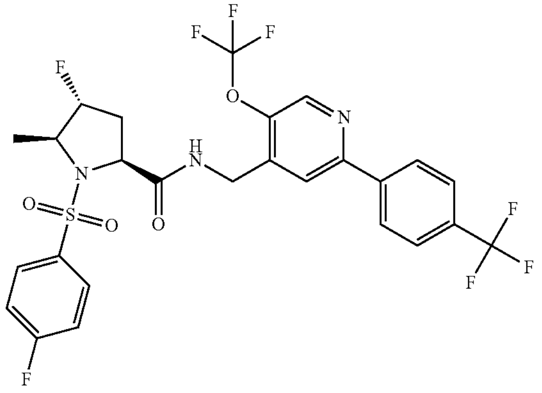
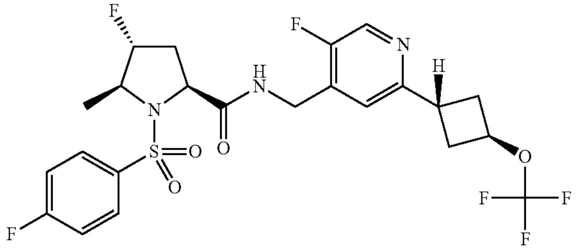
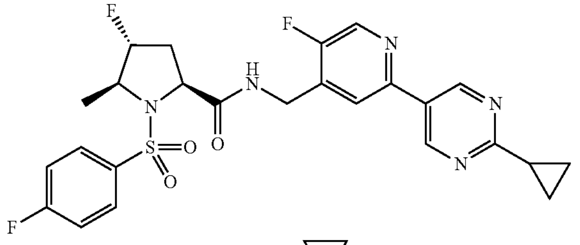
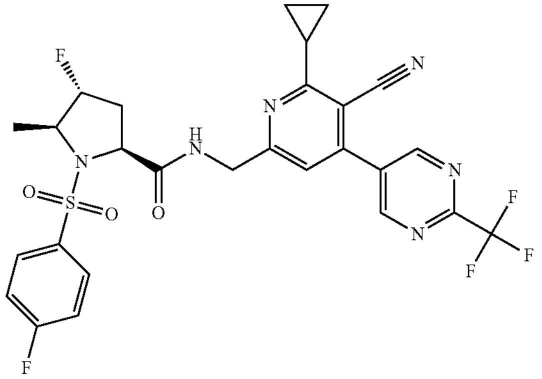

-continued
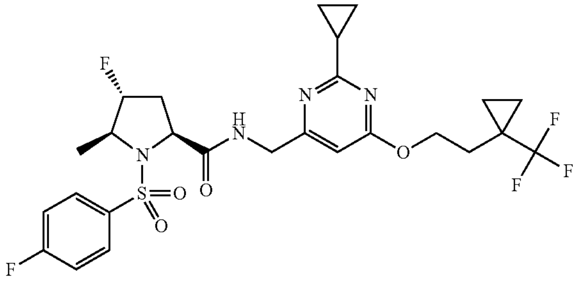
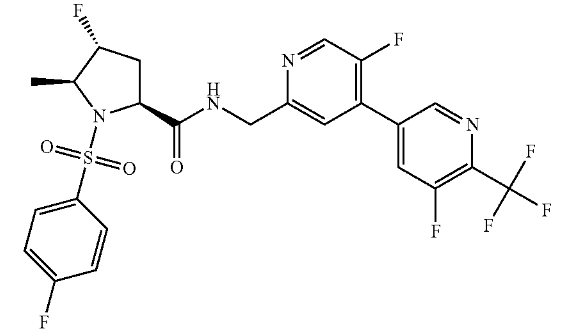
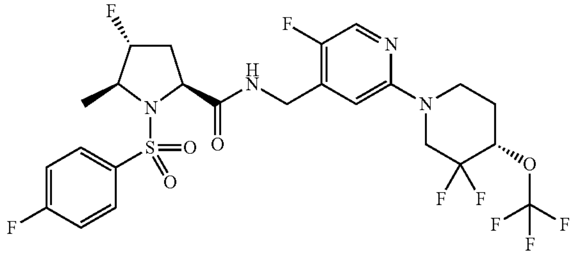
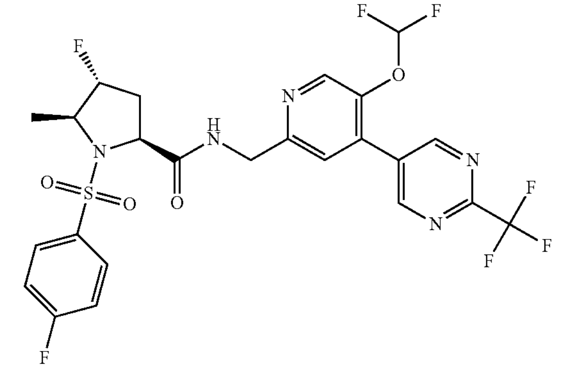
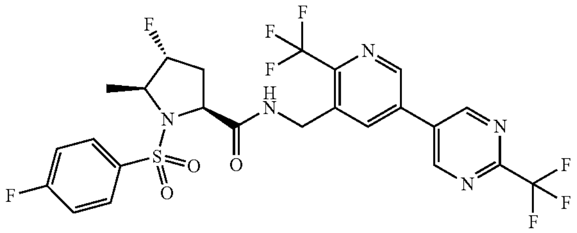
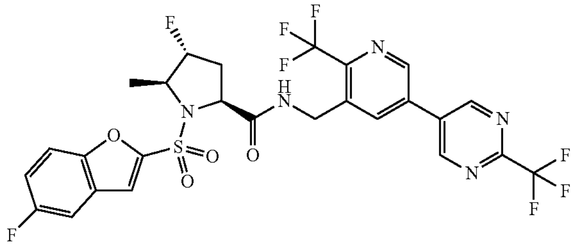
-continued
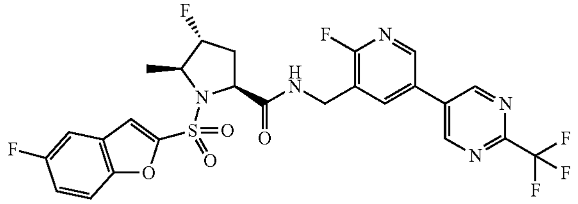
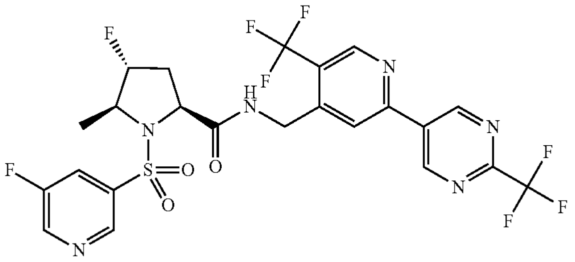
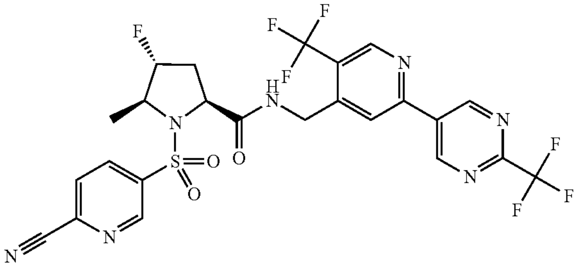
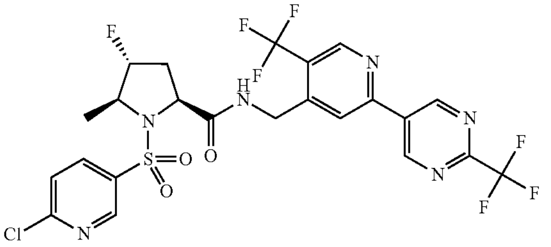
or
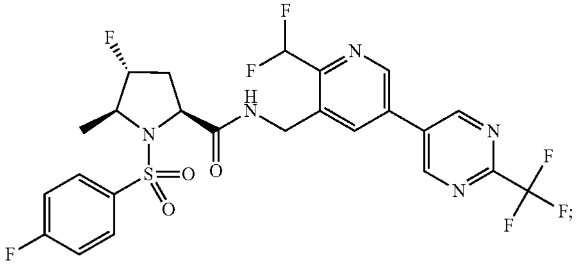 [SMILES: C[C@H]1[C@H](F)C[C@@H](C(=O)NCc2cc(-c3cnc(C(F)(F)F)nc3)cnc2C(F)F)N1S(=O)(=O)c1ccc(F)cc1]
or a salt thereof.
EEE205. The compound of EEE66, which is:
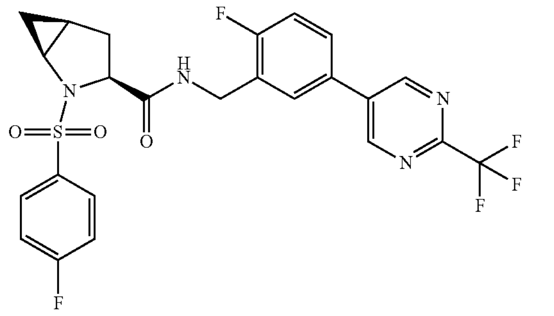

-continued
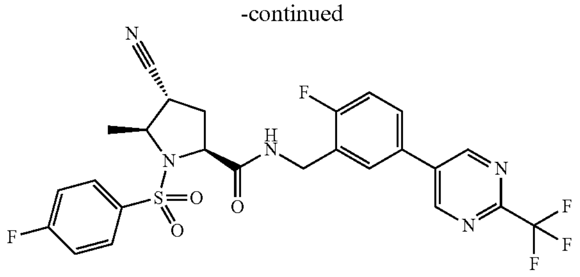
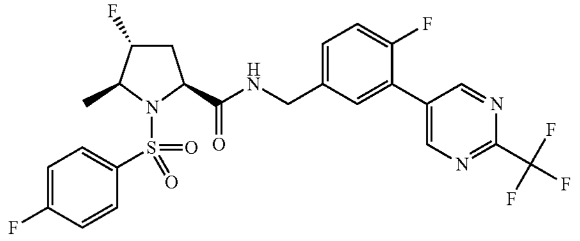
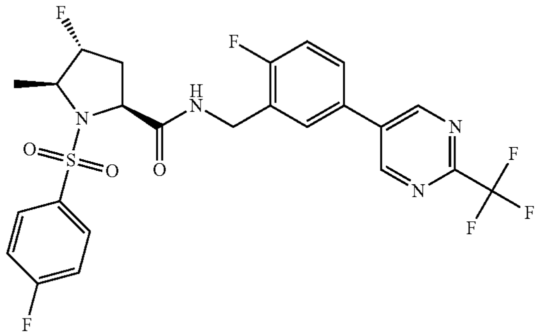
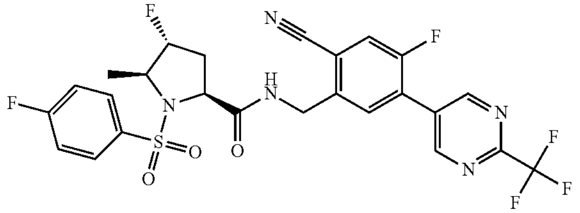
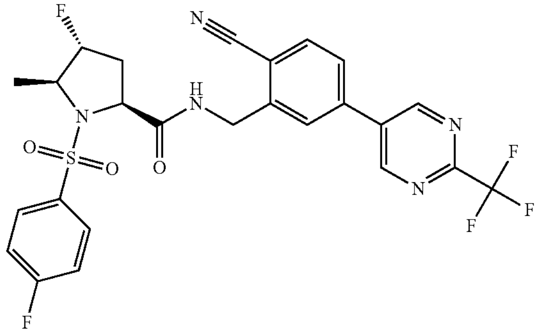
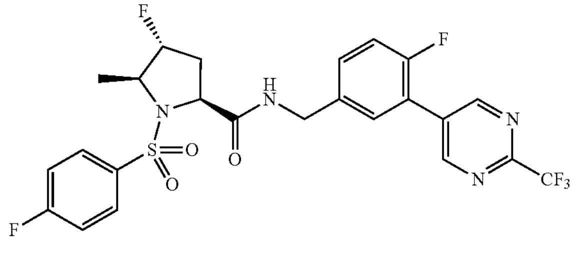
-continued
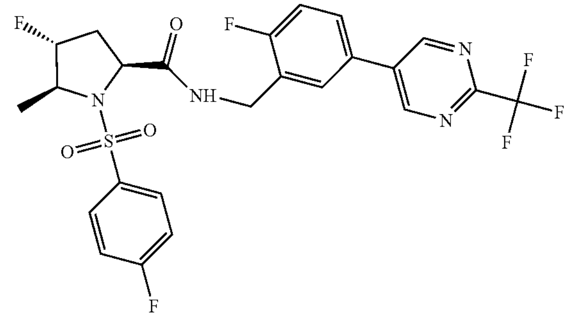
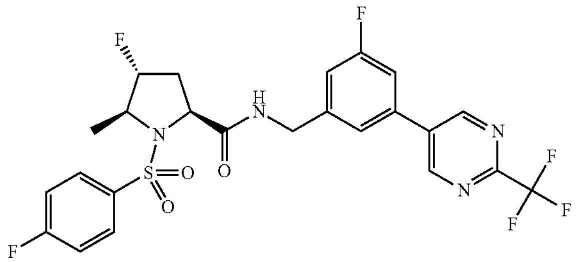
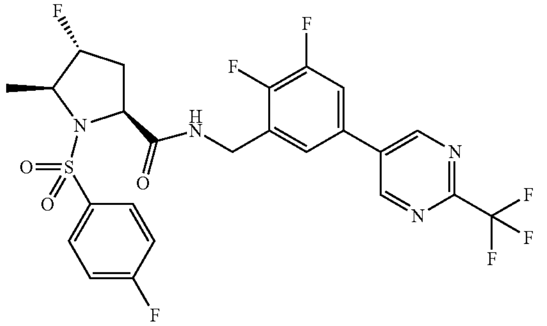
or
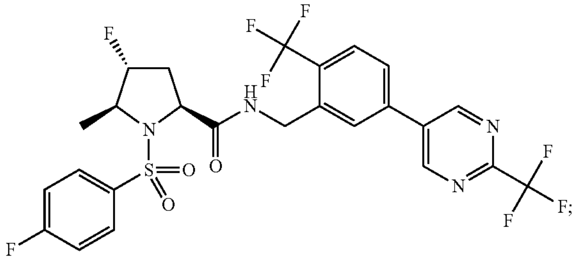
or a salt thereof.
EEE206. The compound of EEE76, which is:
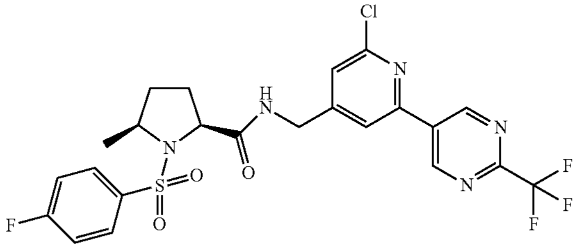

-continued
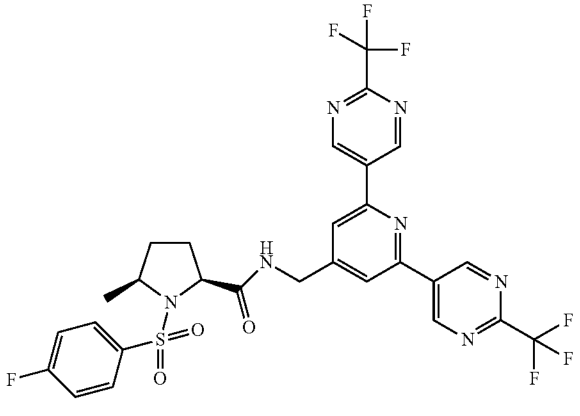
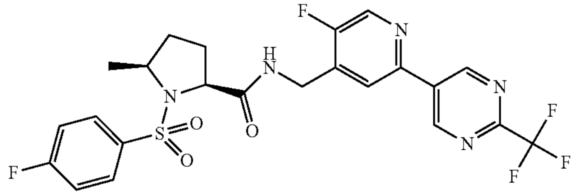
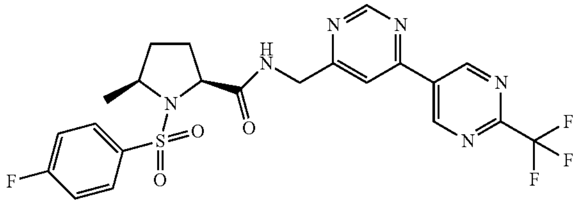
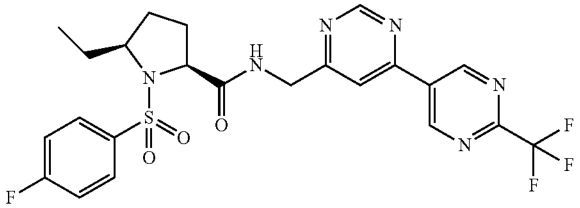
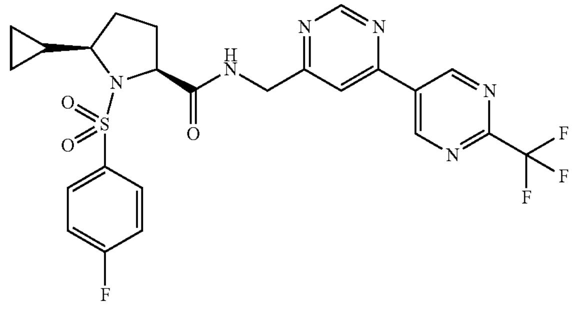
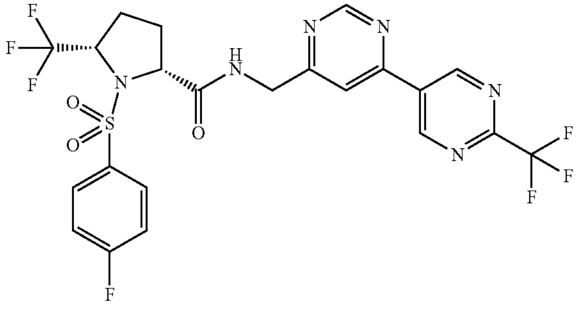
-continued
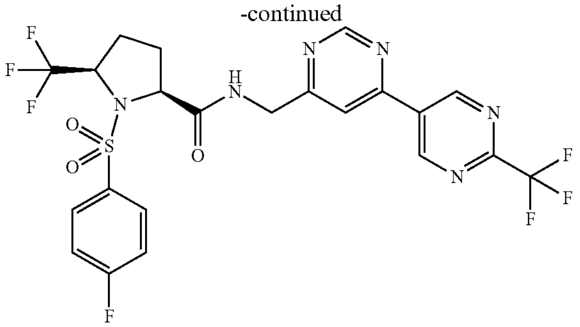
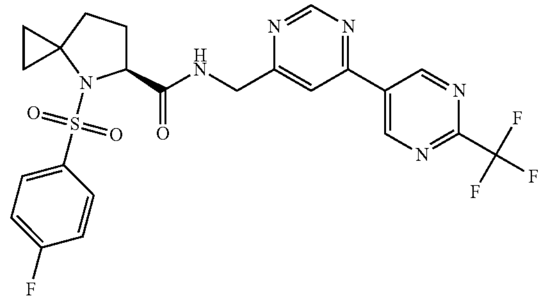
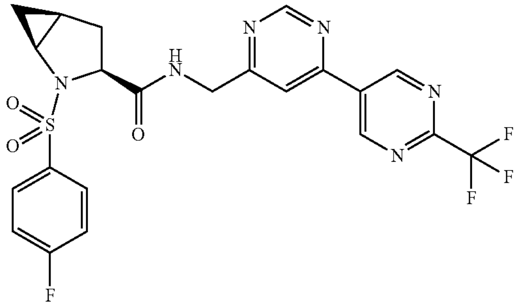
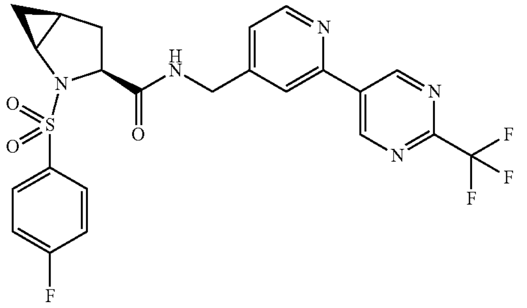
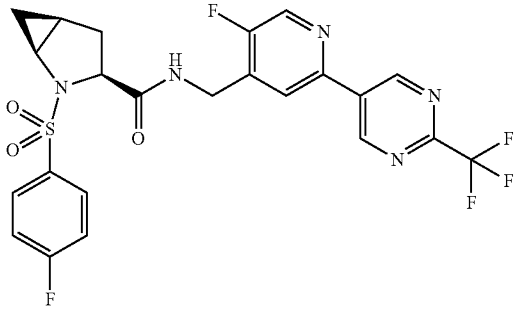
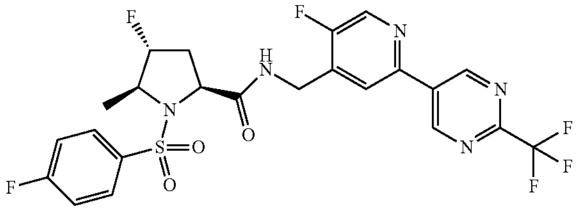

-continued
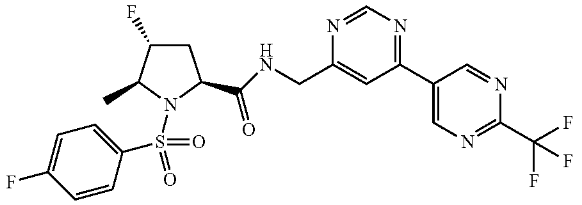
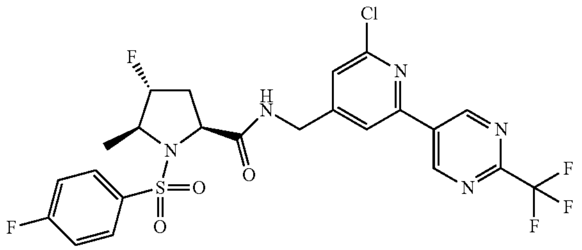
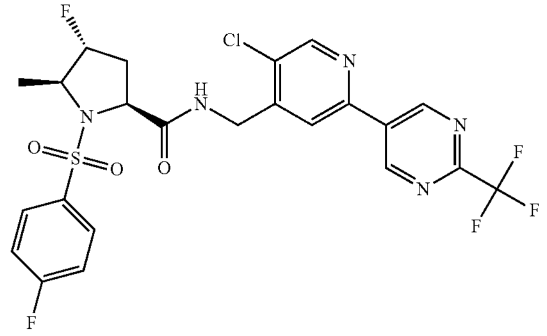
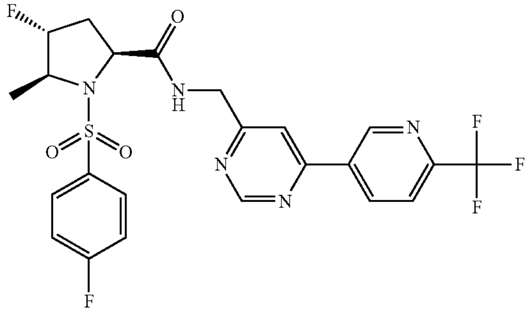
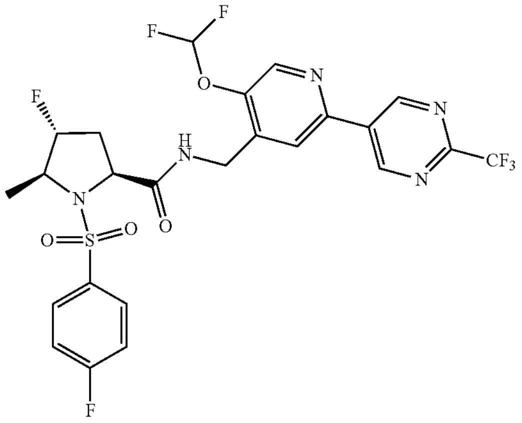
-continued
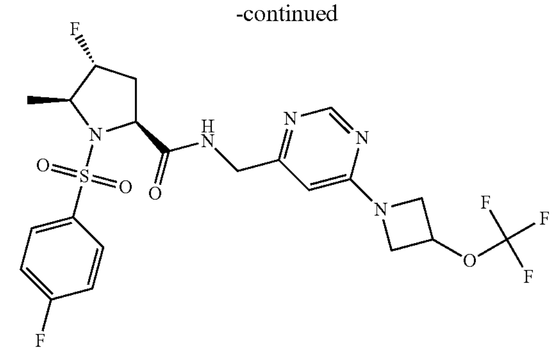
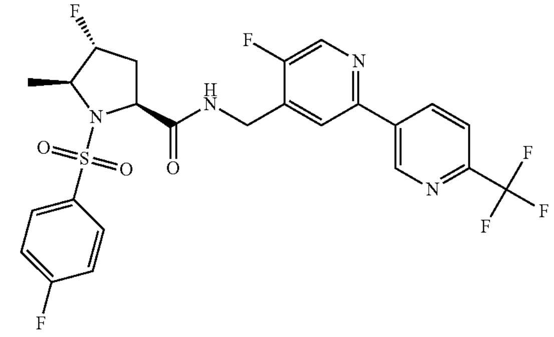
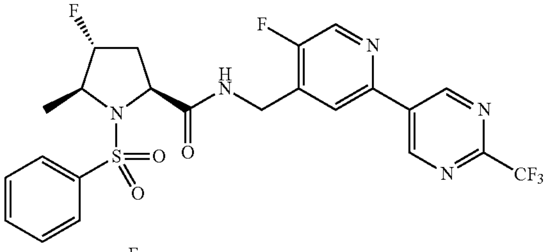
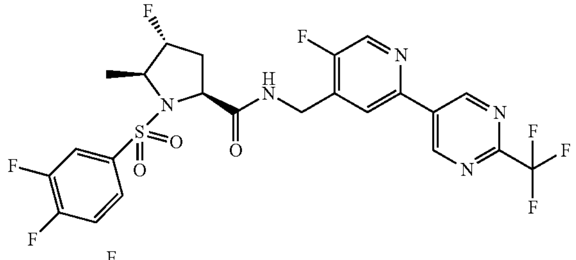
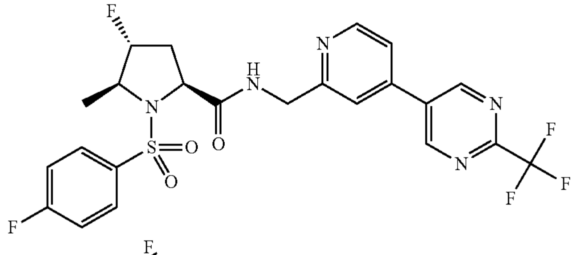
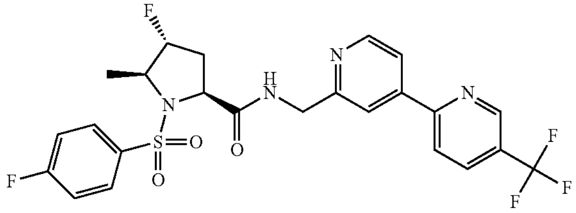

-continued
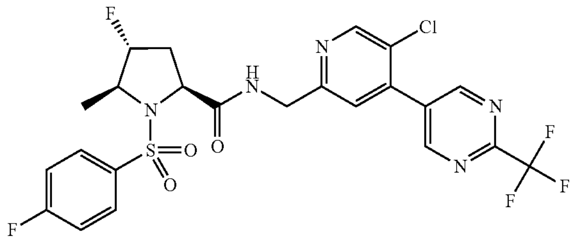
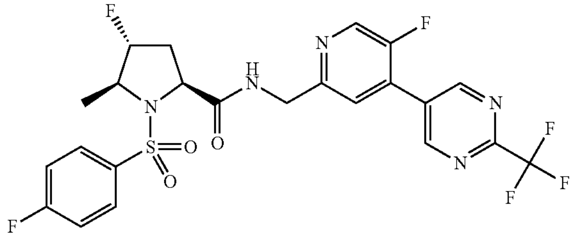
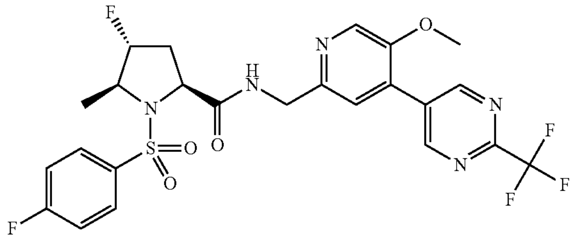
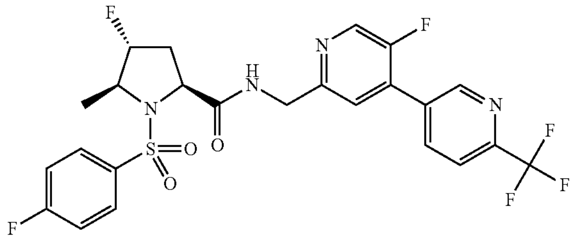
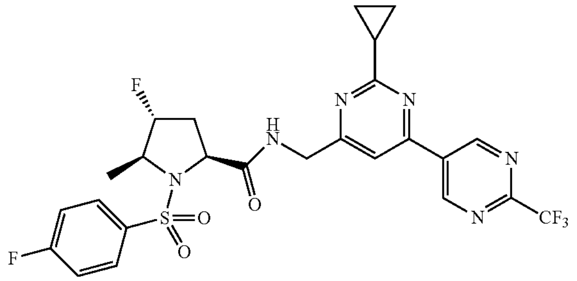
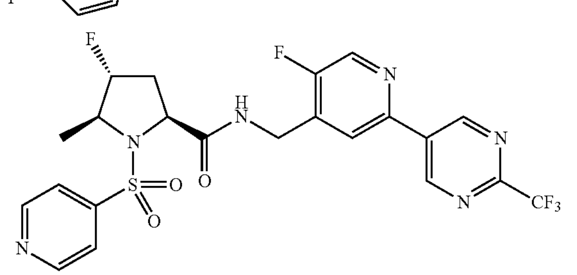
-continued
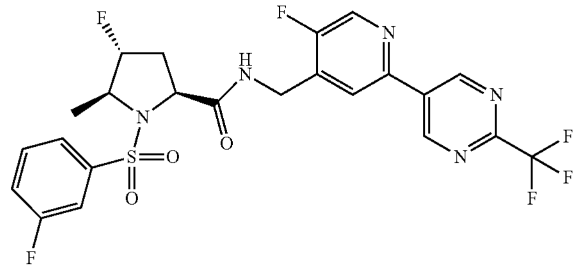
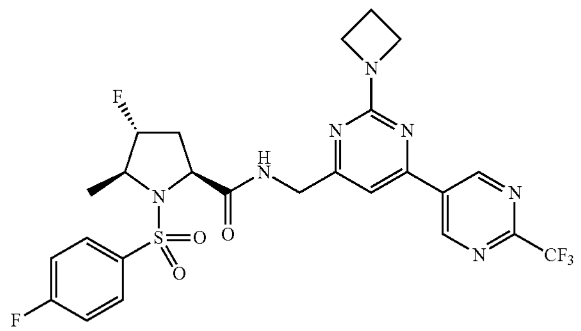
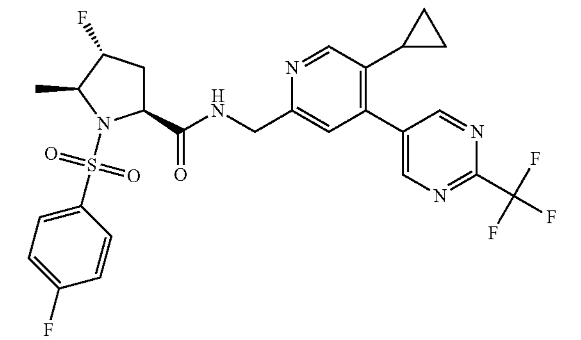
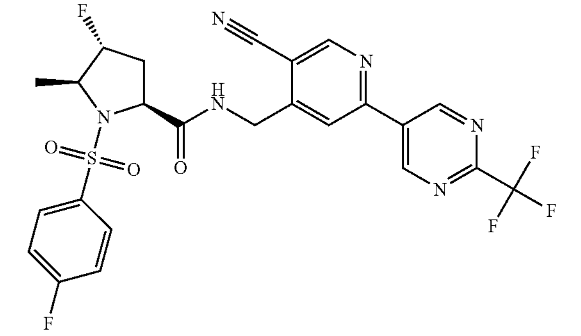
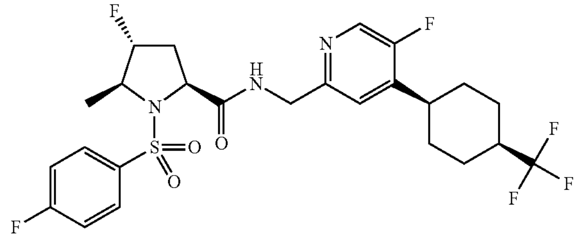

-continued
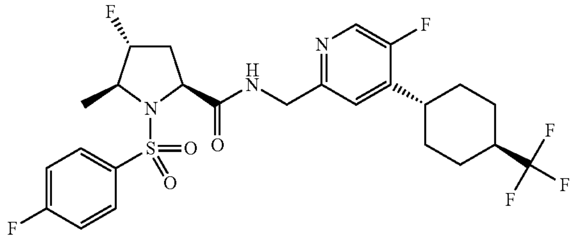
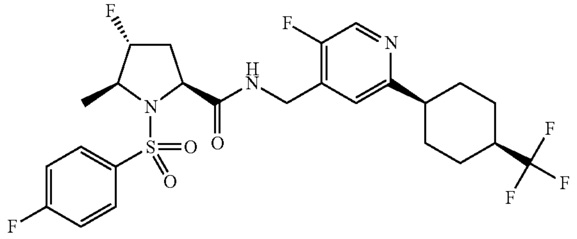
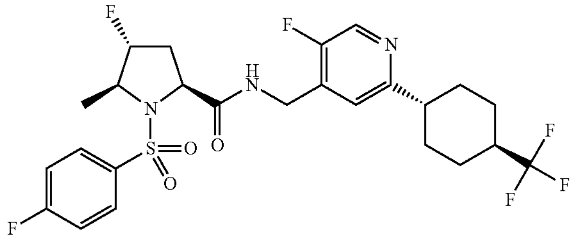
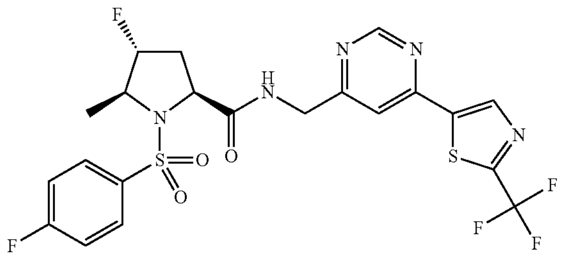
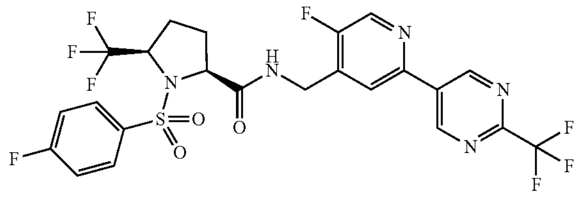
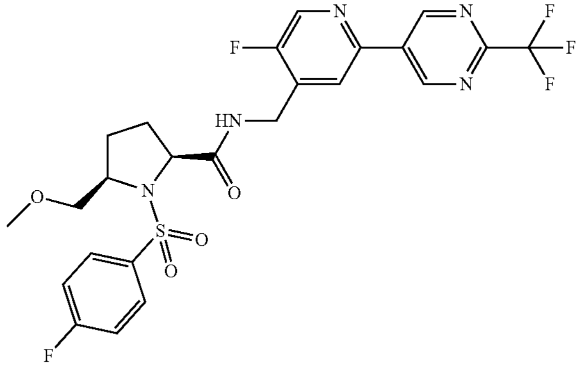
-continued
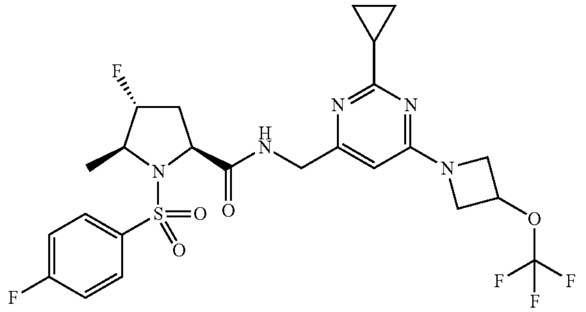
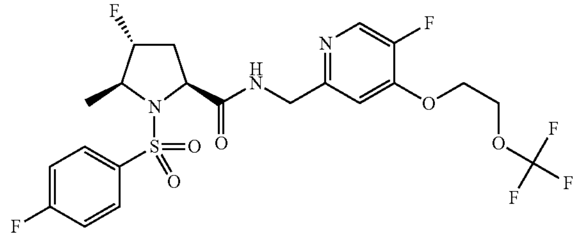
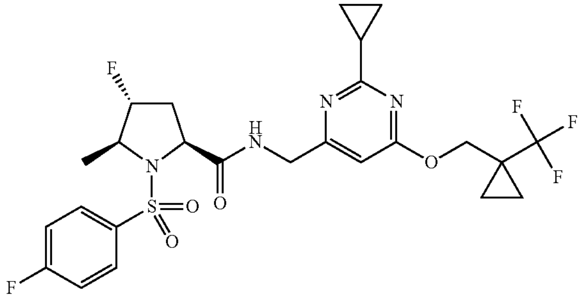
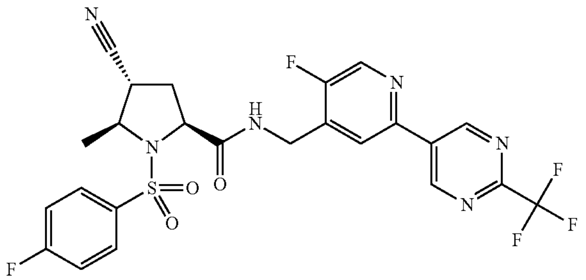
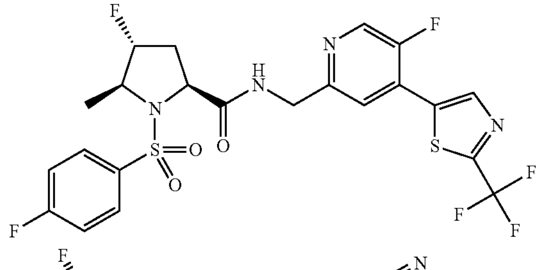
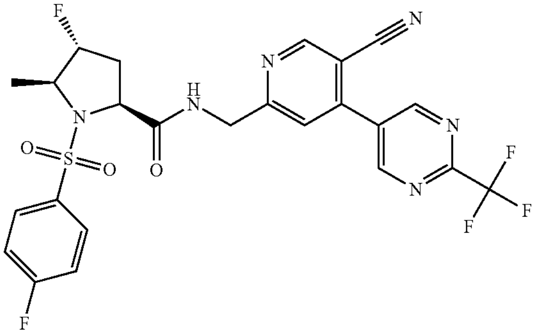

-continued
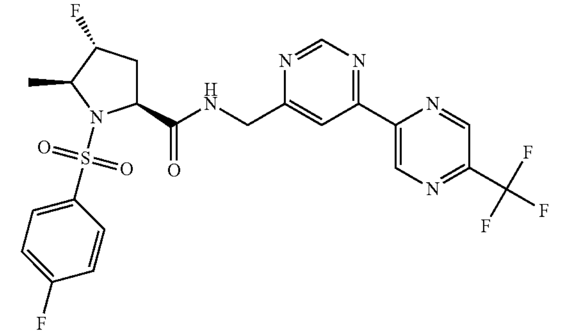
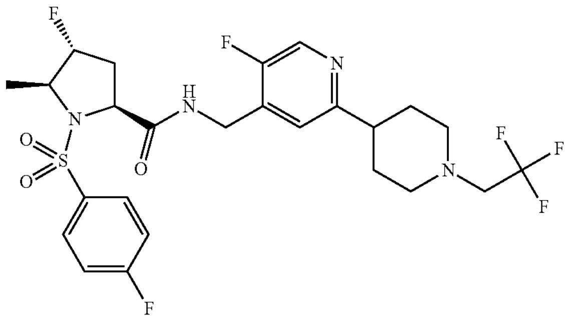
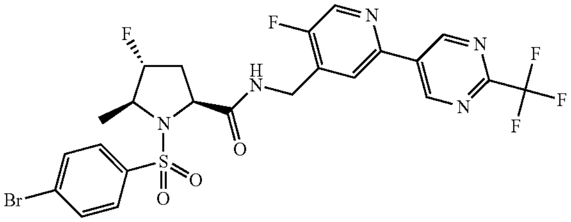
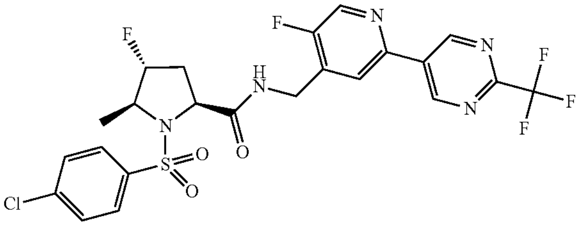
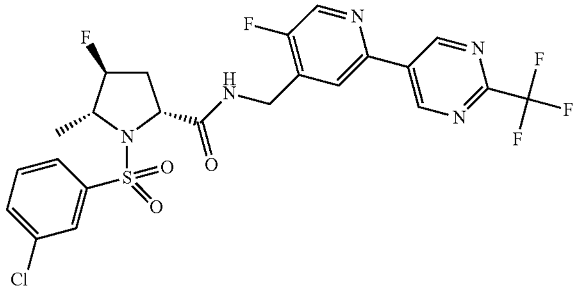
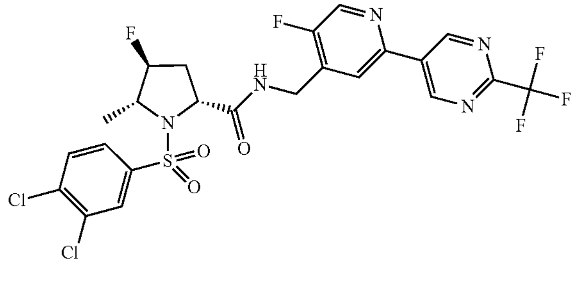
-continued
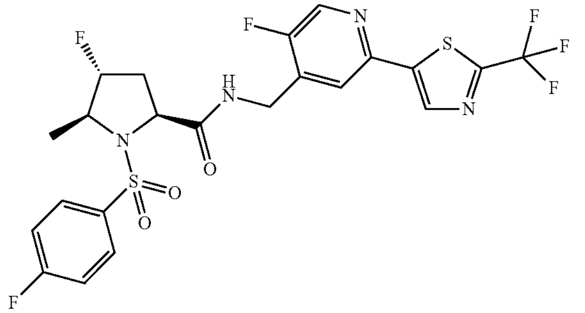
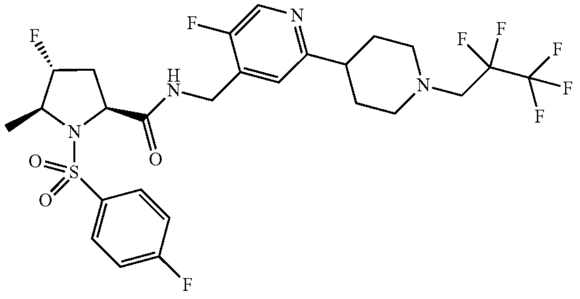
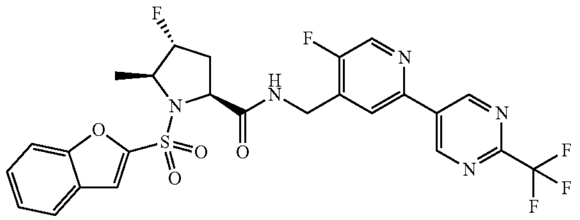
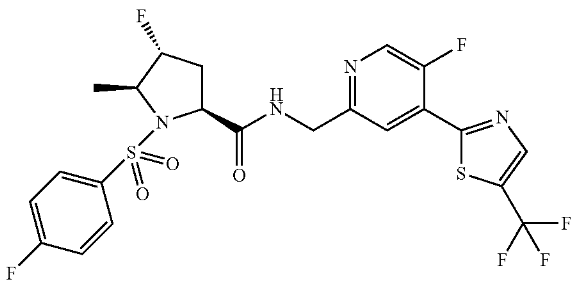
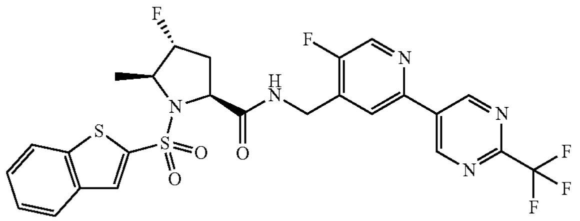
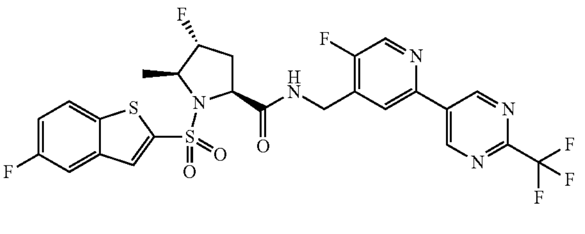

-continued
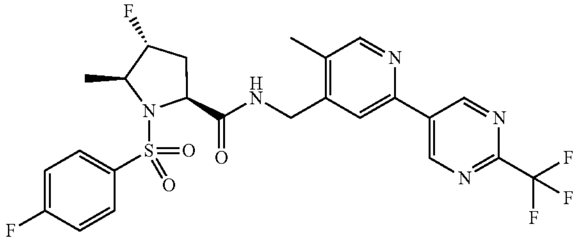
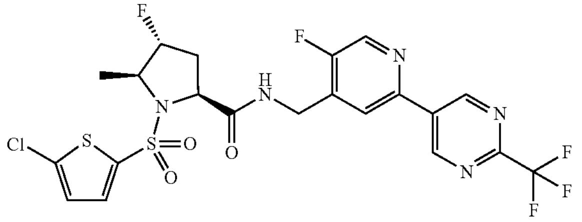
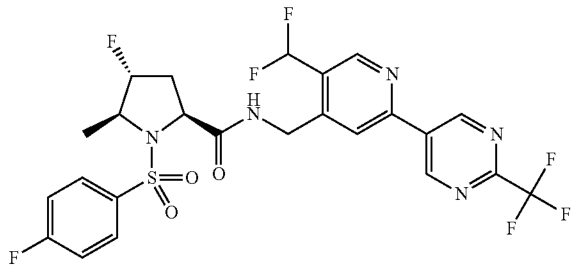
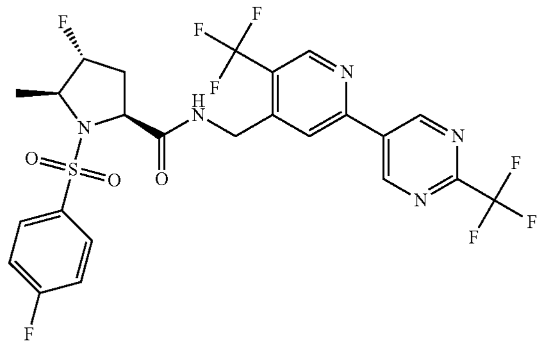
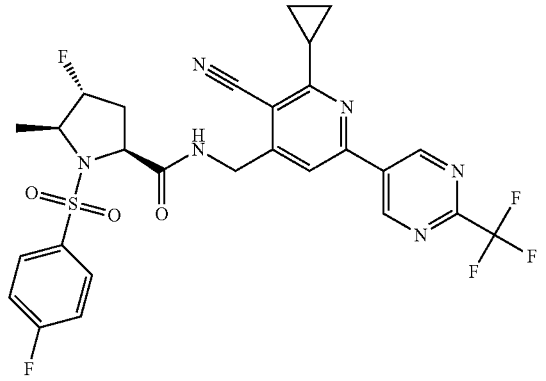
-continued
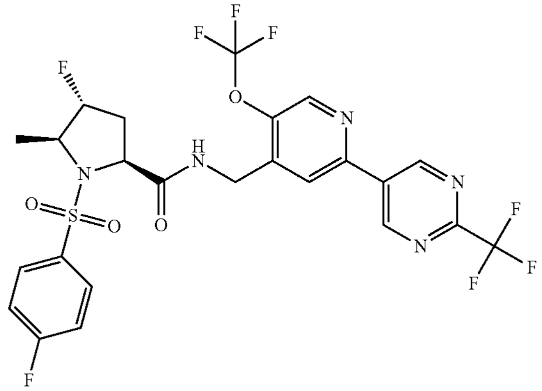
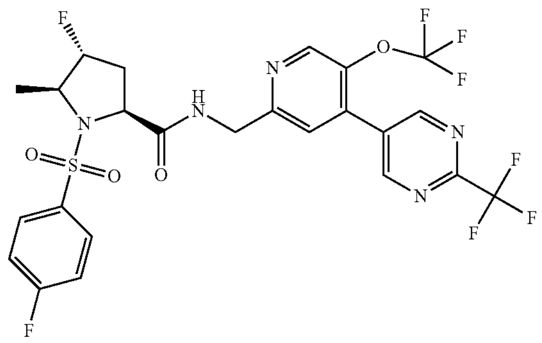
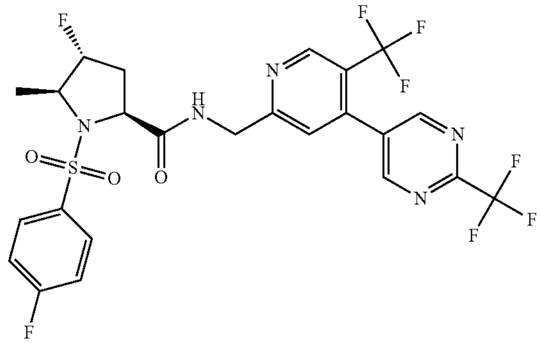
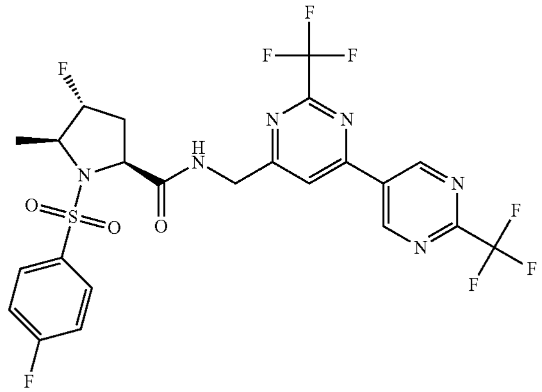

-continued
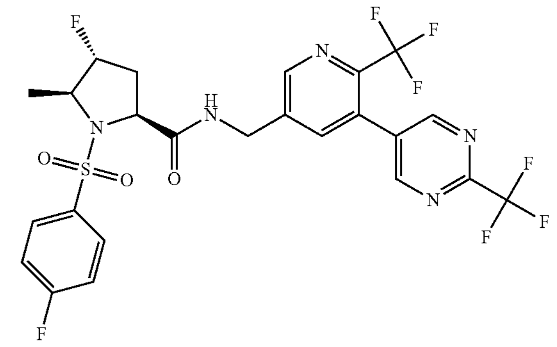
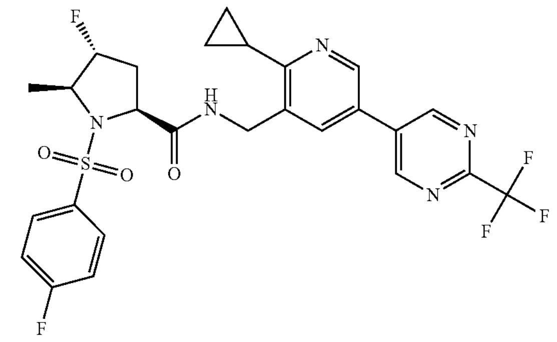
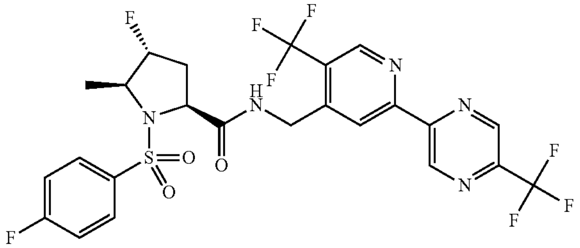
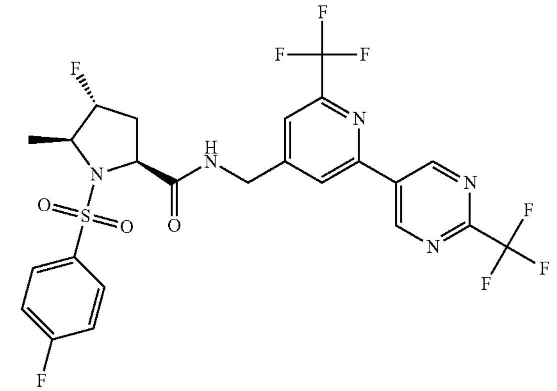
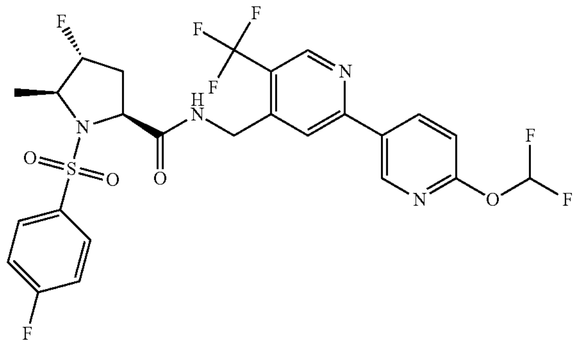
-continued
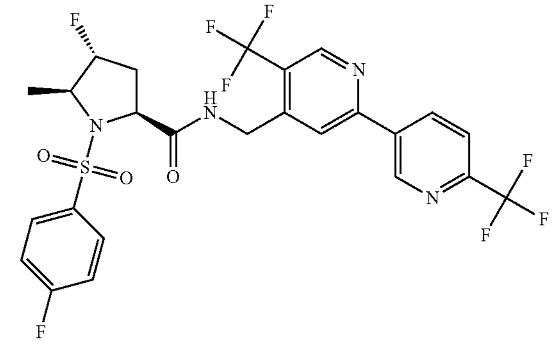
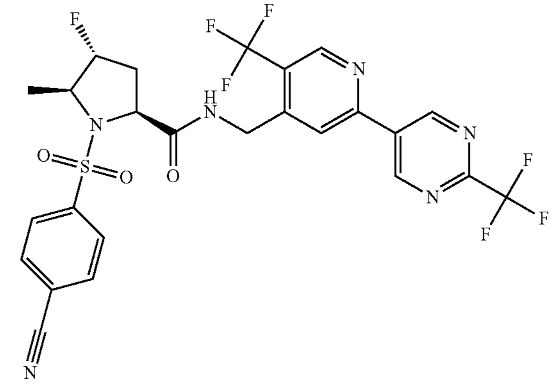
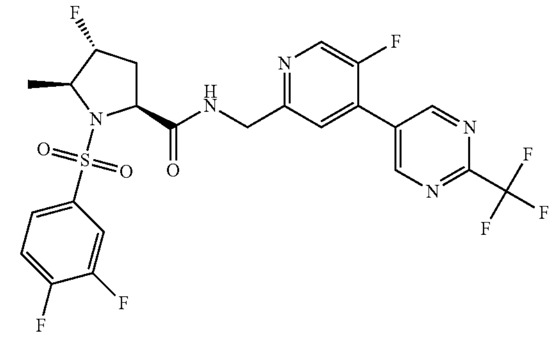
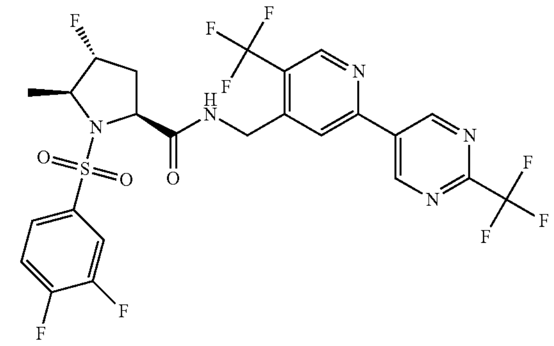

-continued
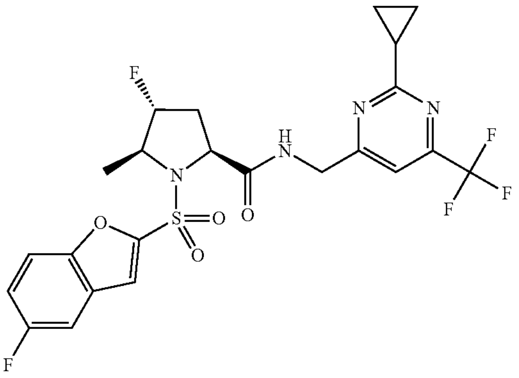
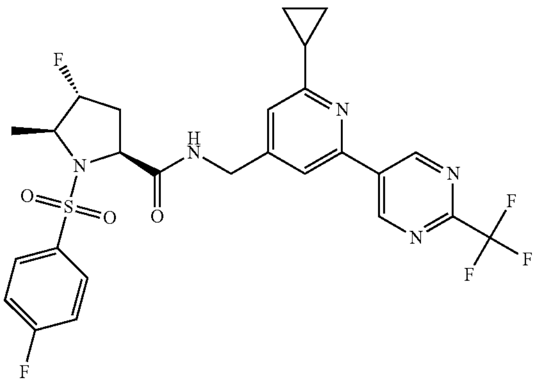
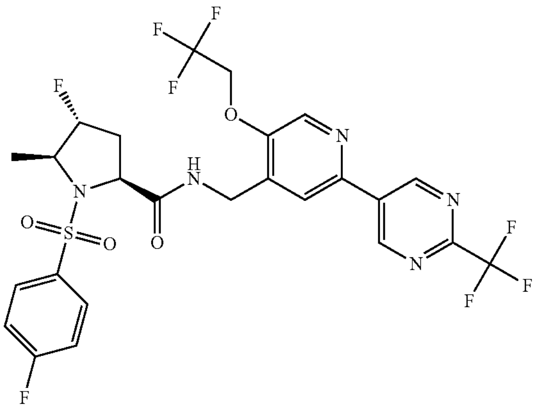
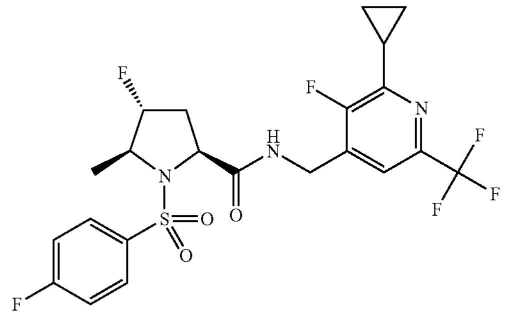
-continued
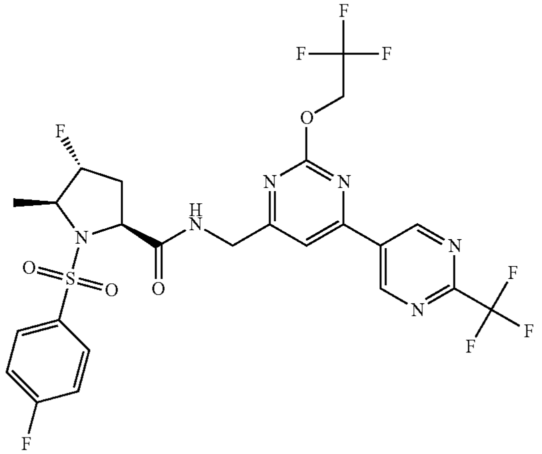
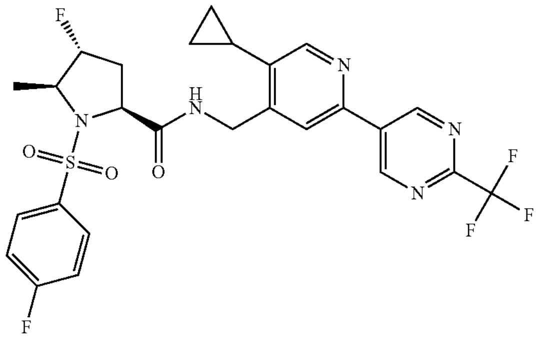
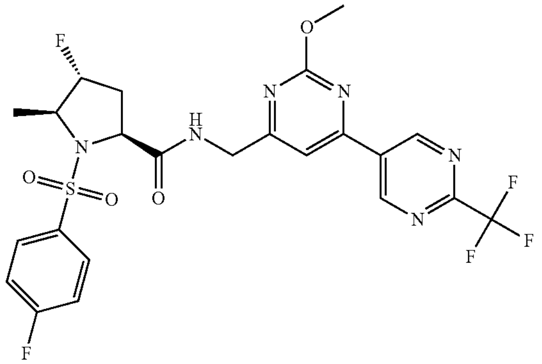
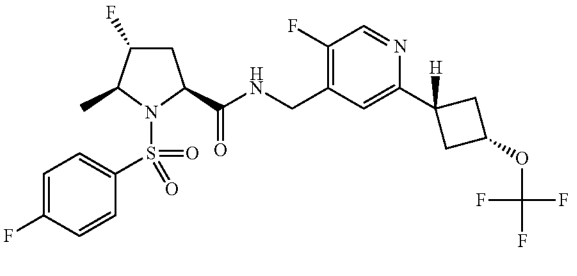
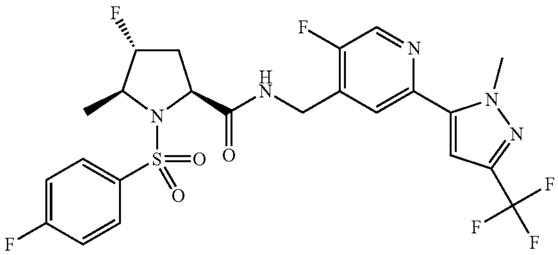

-continued
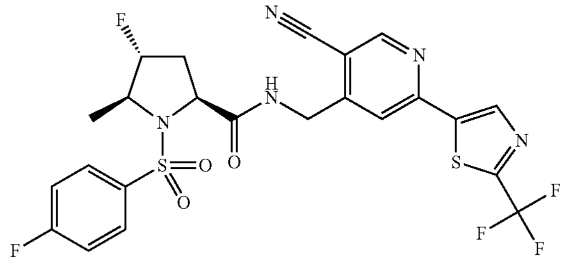
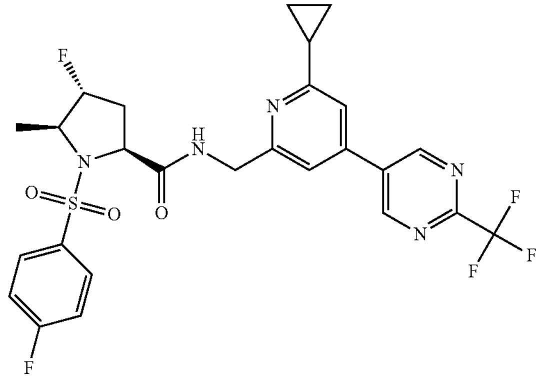
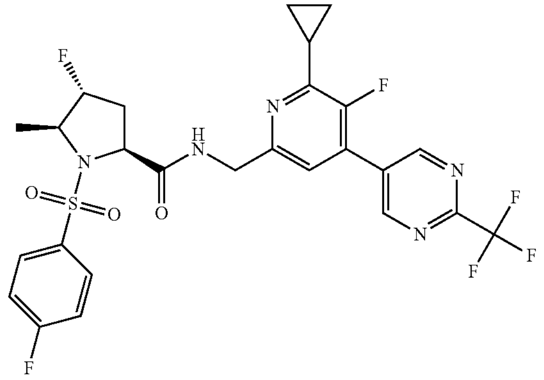
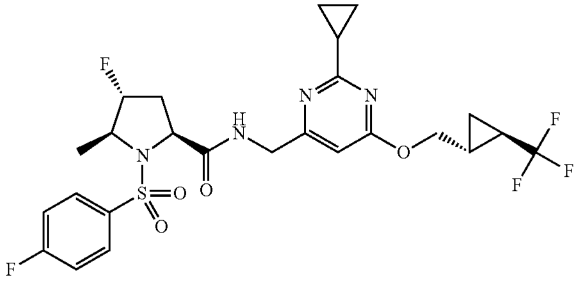
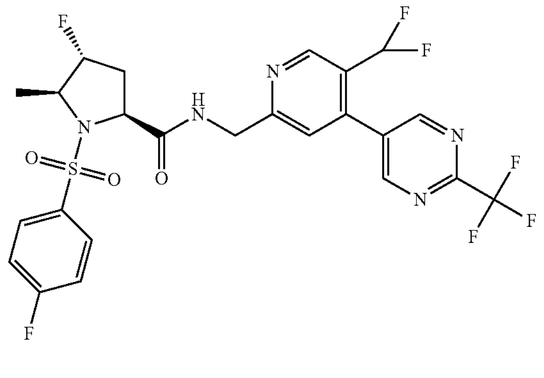
-continued
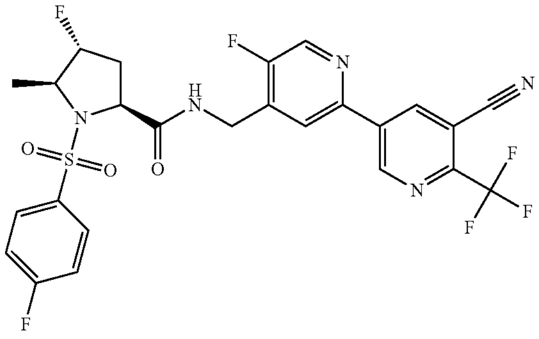
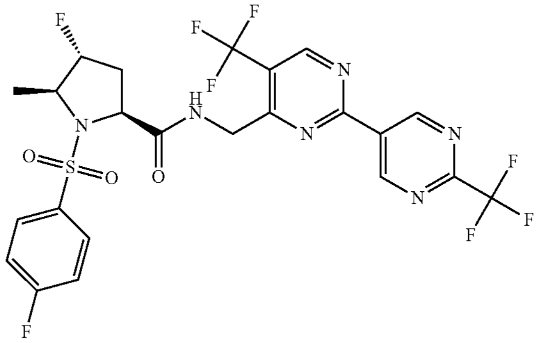
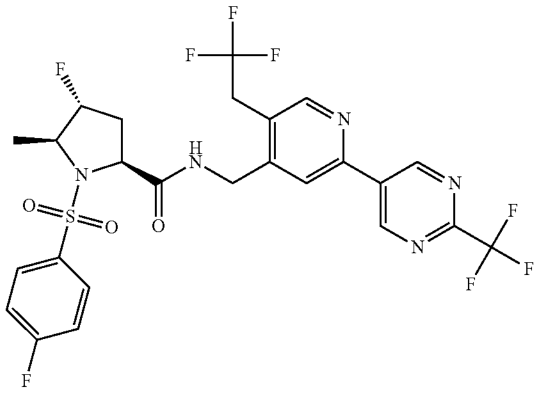
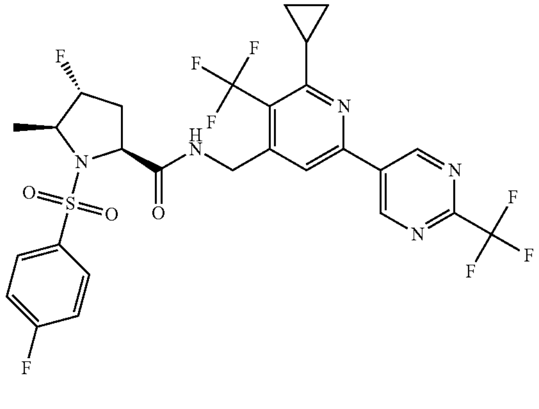

-continued
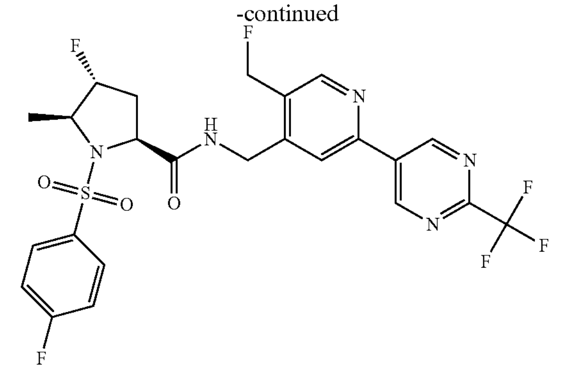
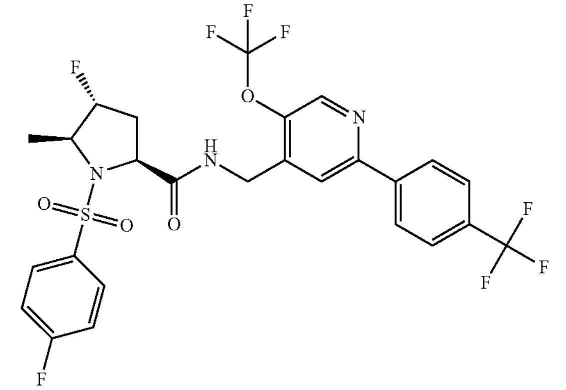
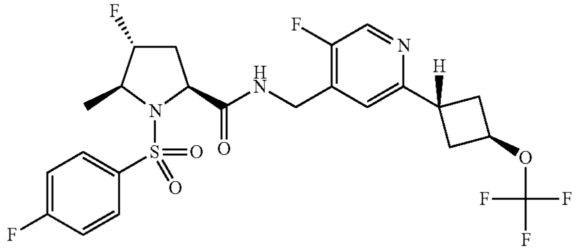
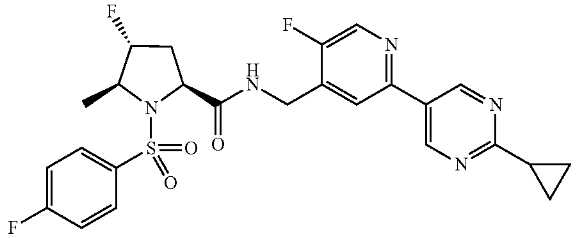
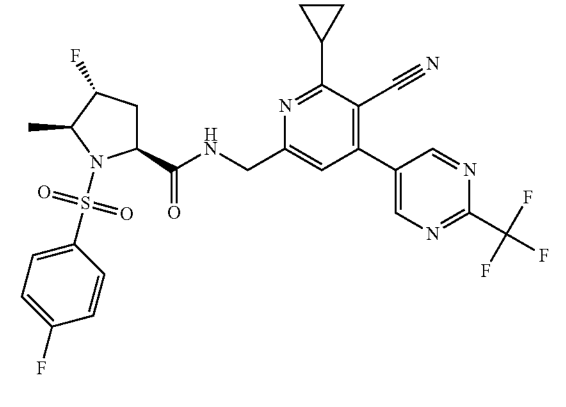
-continued
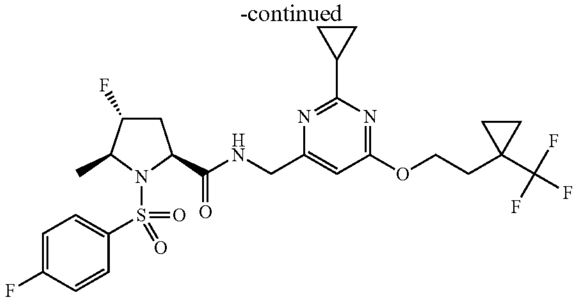
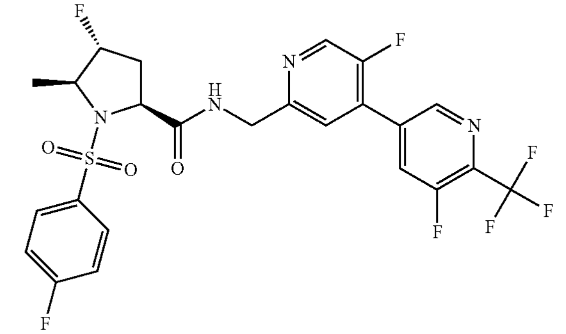
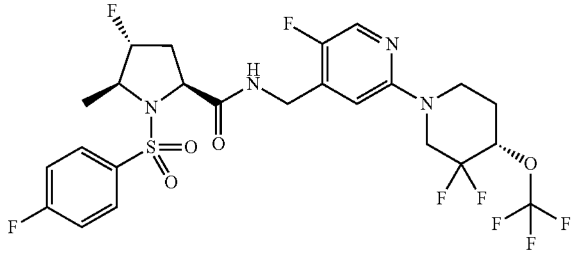
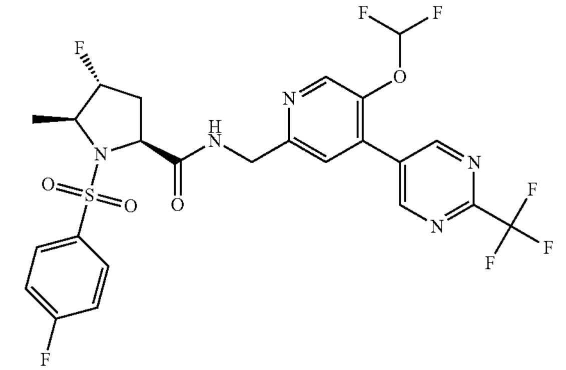
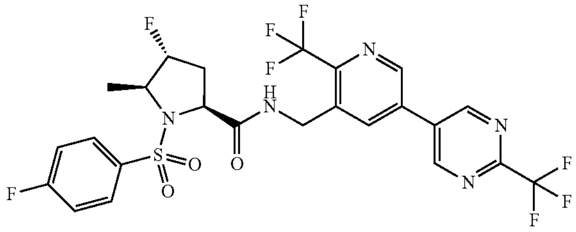
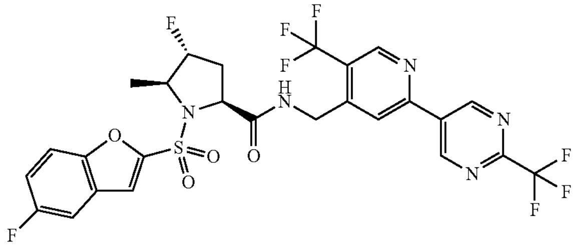

-continued

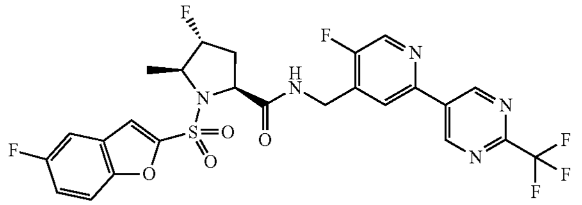

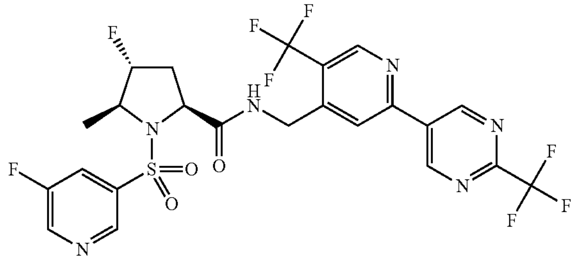

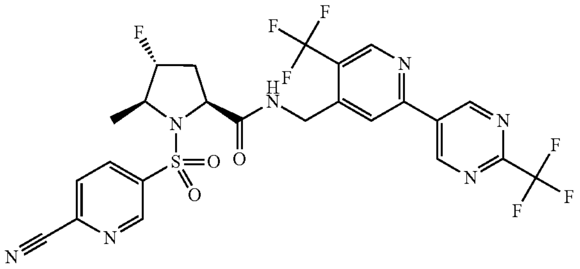

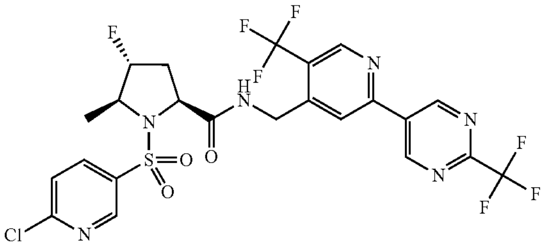

or

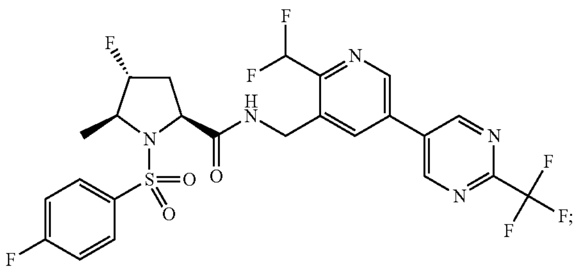

or a salt thereof.

EEE207. The compound of EEE1, wherein the compound is:

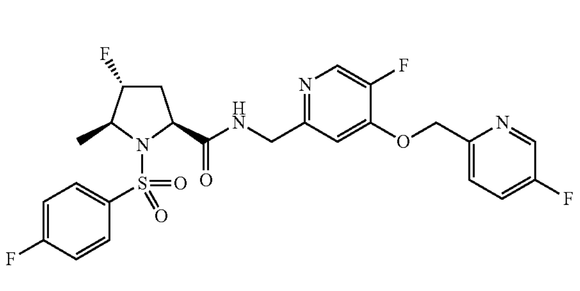

-continued

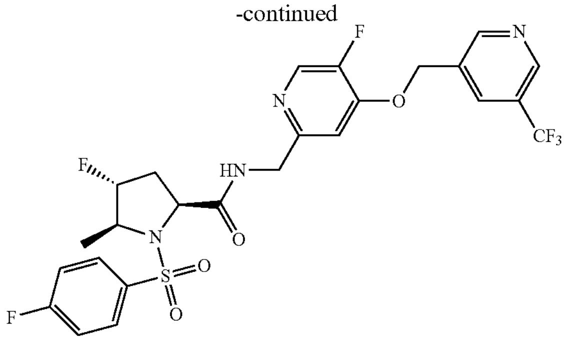

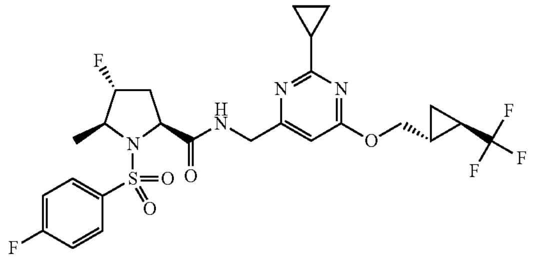

or

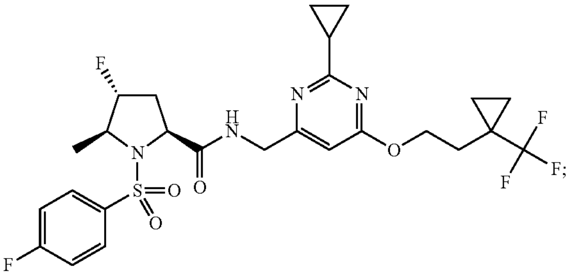

or a salt thereof.

EEE208. A compound of formula VI:

VI

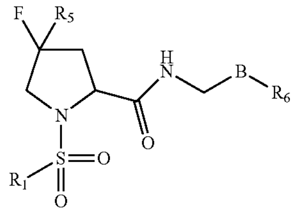

wherein:

B is $B^2$ or $B^3$;

$B^2$ is phenyl, wherein each phenyl is unsubstituted or substituted with one or more groups independently selected from halogen, CN, $(C_1\text{-}C_6)$alkyl, and $(C_1\text{-}C_6)$haloalkyl;

$B^3$ is a 6-membered heteroaryl, wherein each 6-membered heteroaryl is unsubstituted or substituted with one or more groups independently selected from halogen, $(C_1\text{-}C_6)$alkyl, $(C_1\text{-}C_6)$haloalkyl, $O(C_1\text{-}C_6)$alkyl, $O(C_1\text{-}C_6)$haloalkyl, 5 or 6-membered heteroaryl, $(C_3\text{-}C_7)$cycloalkyl, and $(C_3\text{-}C_7)$heterocyclyl; and wherein any of the 5 or 6-membered heteroaryl, $(C_3\text{-}C_7)$cycloalkyl, or $(C_3\text{-}C_7)$heterocyclyl groups is unsubstituted or substituted with one or more groups independently selected from halogen, $(C_1\text{-}C_6)$alkyl, and $(C_1\text{-}C_6)$ haloalkyl;

$R^1$ is phenyl or heteroaryl, wherein each phenyl or heteroaryl is unsubstituted or substituted with one or more groups independently selected from halogen, CN, $(C_1\text{-}C_6)$ alkyl, and $(C_1\text{-}C_6)$haloalkyl;

$R^5$ is H or ($C_1$-$C_6$)alkyl;

$R^6$ is a phenyl, ($C_3$-$C_7$)cycloalkyl, 5- or 6-membered heteroaryl, or 4, 5, 6 or 7-membered heterocycle, wherein any phenyl, ($C_3$-$C_7$)cycloalkyl, 5- or 6-membered heteroaryl, or 4, 5, 6 or 7-membered heterocycle of $R^6$ is optionally substituted with one or more groups independently selected from halogen, $SF_5$, ($C_1$-$C_6$)alkyl, ($C_1$-$C_6$)haloalkyl, O($C_1$-$C_6$)alkyl, and O($C_1$-$C_6$)haloalkyl; or $R^6$ is O—$CH_2$—$R^7$;

$R^7$ is a ($C_1$-$C_6$)alkyl, 3, 4, 5, 6, or 7-membered heterocycle, 3, 4, 5, 6, or 7-membered cycloalkyl, or 6-membered heteroaryl, wherein any ($C_1$-$C_6$)alkyl, 3, 4, 5, 6, or 7-membered heterocycle, 3, 4, 5, 6, or 7-membered cycloalkyl, or 6-membered heteroaryl is optionally substituted with one or more groups independently selected from halogen, ($C_1$-$C_6$)alkyl, ($C_1$-$C_6$)haloalkyl, O($C_1$-$C_6$)alkyl, ($C_3$-$C_7$)cycloalkyl, and O($C_1$-$C_6$)haloalkyl;

or a salt thereof.

EEE209. The compound of EEE208, wherein $B^2$ is:

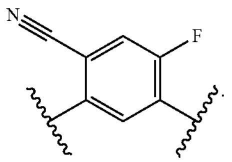

EEE210. The compound of EEE208, wherein $B^2$ is:

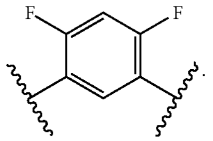 [SMILES: *c1cc(*)c(F)cc1F]

EEE211. The compound of EEE208, wherein $B^2$ is:

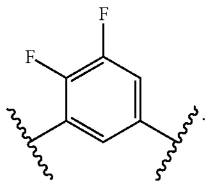 [SMILES: *c1cc(*)c(F)c(F)c1]

EEE212. The compound of EEE208, wherein $B^2$ is:

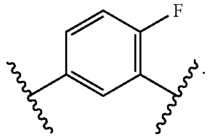 [SMILES: *c1ccc(F)c(*)c1]

EEE213. The compound of EEE208, wherein $B^3$ is:

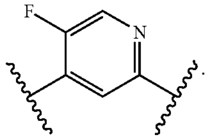

EEE214. The compound of EEE208, wherein $B^3$ is:

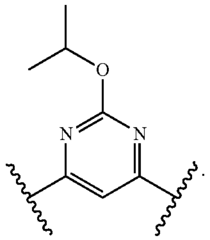 [SMILES: *c1cc(*)nc(OC(C)C)n1]

EEE215. The compound of EEE208, wherein $B^3$ is:

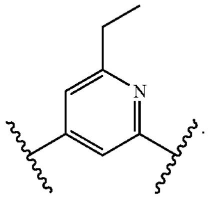 [SMILES: *c1cc(*)nc(CC)c1]

EEE216. The compound of EEE208, wherein $B^3$ is:

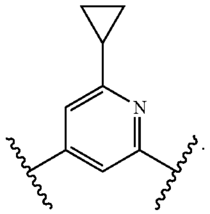 [SMILES: *c1cc(*)nc(C2CC2)c1]

EEE217. The compound of EEE208, wherein $B^3$ is:

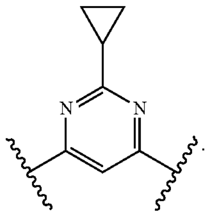 [SMILES: *c1cc(*)nc(C2CC2)n1]

EEE218. The compound of EEE208, wherein $B^3$ is:

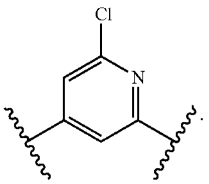 [SMILES: *c1cc(*)nc(Cl)c1]

EEE219. The compound of EEE208, wherein $B^3$ is:

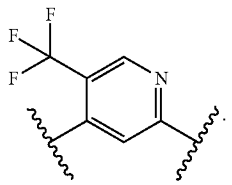

EEE220. The compound of any one of EEE208-219, wherein $R^5$ is H.

EEE221. The compound of any one of EEE208-219, wherein $R^5$ is $(C_1-C_6)$alkyl.

EEE222. The compound of EEE220, wherein the group

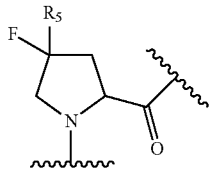

is:

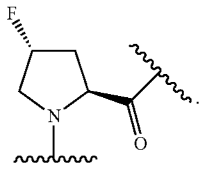 [SMILES: *C(=O)[C@@H]1C[C@@H](F)CN1*]

EEE223. The compound of EEE220, wherein the group

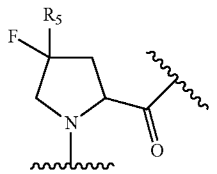

is:

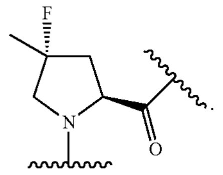 [SMILES: *C(=O)[C@@H]1C[C@@](C)(F)CN1*]

EEE224. The compound of any one of EEE208-223, wherein $R^6$ is 4, 5, 6 or 7-membered heterocycle.

EEE225. The compound of EEE224, wherein $R^6$ is 6-membered heterocycle.

EEE226. The compound of EEE225, wherein $R^6$ is:

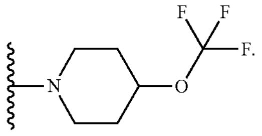

EEE227. The compound of any one of EEE208-223, wherein $R^6$ is 6-membered heteroaryl.

EEE228. The compound of EEE227, wherein $R^6$ is:

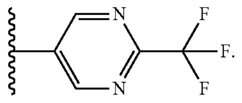 [SMILES: *c1cnc(C(F)(F)F)nc1]

EEE229. The compound of any one of EEE208-223, wherein $R^6$ is:

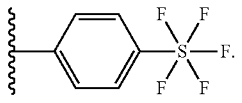 [SMILES: *c1ccc(S(F)(F)(F)(F)F)cc1]

EEE230. The compound of any one of EEE208-223, wherein $R^6$ is:

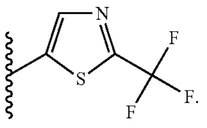 [SMILES: *c1cnc(C(F)(F)F)s1]

EEE231. The compound of any one of EEE1-201 and EEE208-230, wherein $R^1$ is:

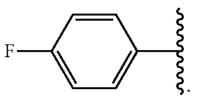

EEE232. The compound of any one of EEE1-201 and EEE208-230, wherein $R^1$ is:

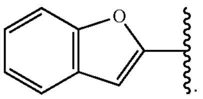
EEE233. The compound of any one of EEE1-201 and EEE208-230, wherein $R^1$ is:
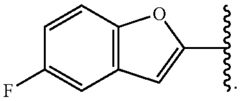 [SMILES: *c1cc2cc(F)ccc2o1]
EEE234. The compound of EEE208, wherein the compound is:
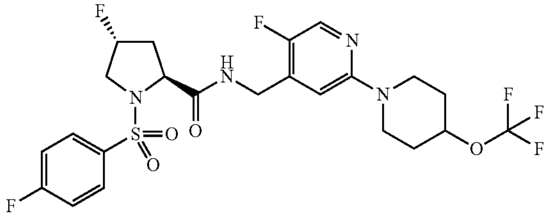
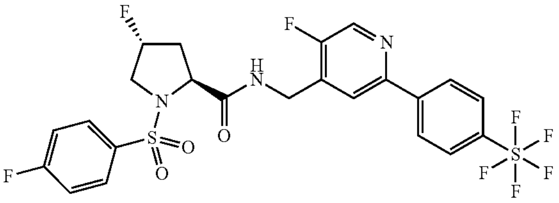
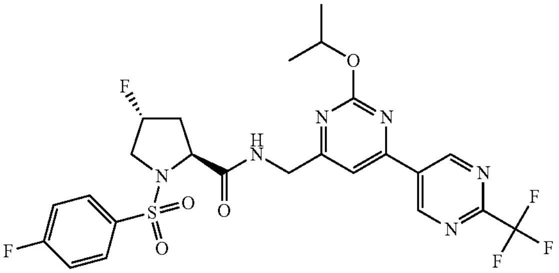
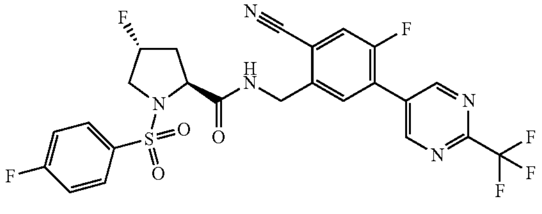
-continued
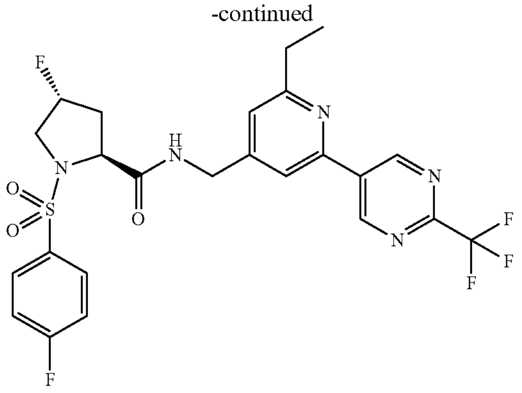
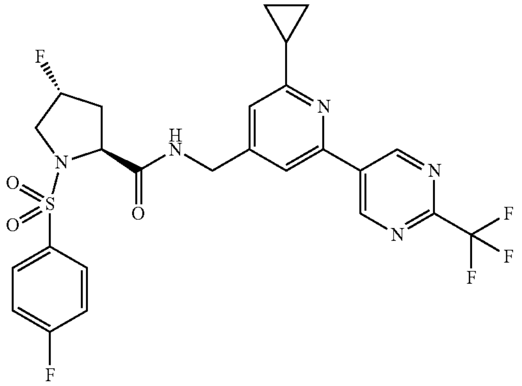
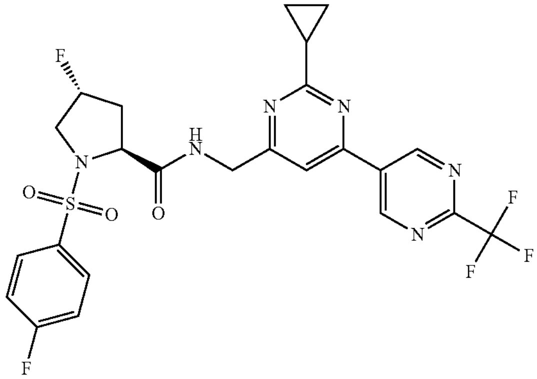
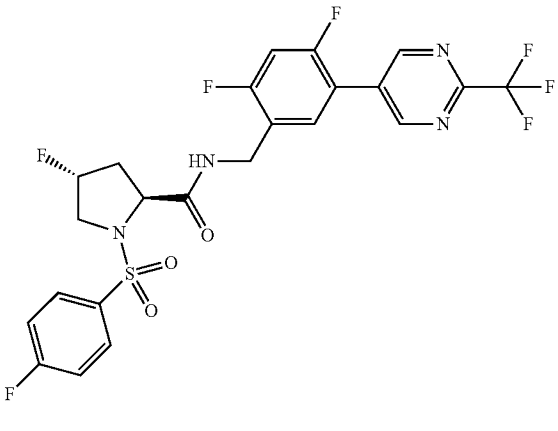

-continued

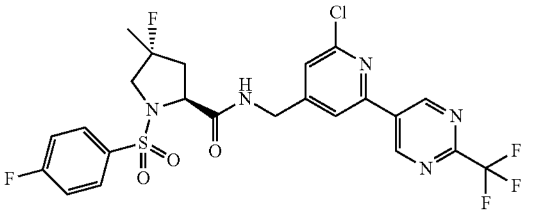

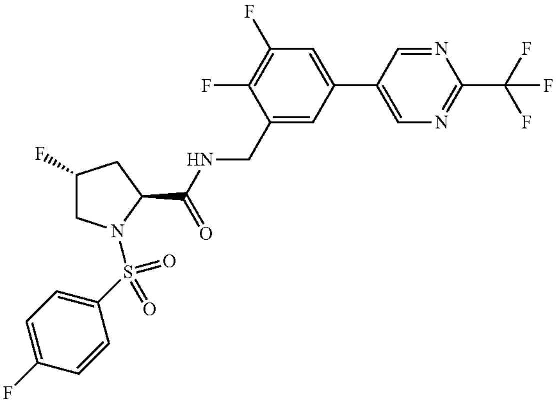

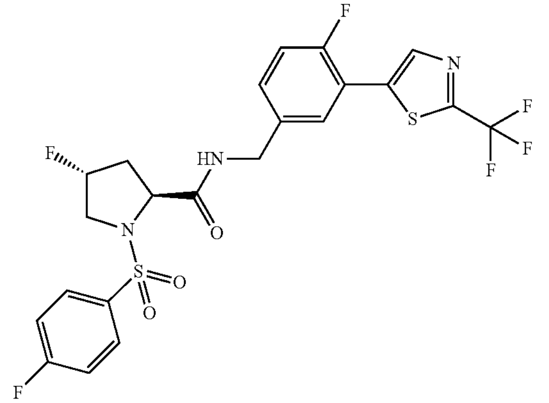

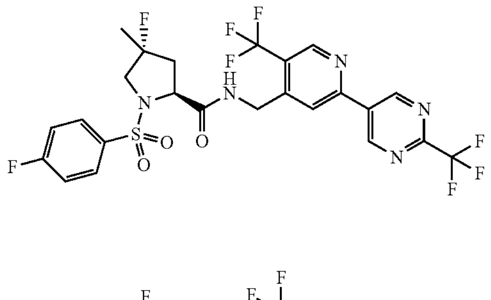

or

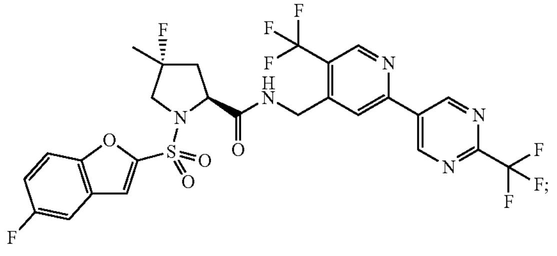

or a salt thereof.

EEE235. A compound of formula VII:

VII

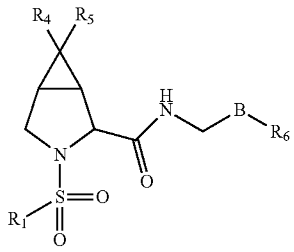

wherein:

B is $B^2$ or $B^3$;

$B^2$ is phenyl, wherein each phenyl is unsubstituted or substituted with one or more groups independently selected from halogen, CN, $(C_1\text{-}C_6)$alkyl, and $(C_1\text{-}C_6)$haloalkyl;

$B^3$ is a 6-membered heteroaryl, wherein each 6-membered heteroaryl is unsubstituted or substituted with one or more groups independently selected from halogen, $(C_1\text{-}C_6)$alkyl, $(C_1\text{-}C_6)$haloalkyl, $O(C_1\text{-}C_6)$alkyl, $O(C_1\text{-}C_6)$haloalkyl, 5 or 6-membered heteroaryl, $(C_3\text{-}C_7)$cycloalkyl, and $(C_3\text{-}C_7)$heterocyclyl; and wherein any of the 5 or 6-membered heteroaryl, $(C_3\text{-}C_7)$cycloalkyl, or $(C_3\text{-}C_7)$heterocyclyl groups is unsubstituted or substituted with one or more groups independently selected from halogen, $(C_1\text{-}C_6)$alkyl, and $(C_1\text{-}C_6)$ haloalkyl;

$R^1$ is phenyl or heteroaryl, wherein each phenyl or heteroaryl is unsubstituted or substituted with one or more groups independently selected from halogen, CN, $(C_1\text{-}C_6)$ alkyl, and $(C_1\text{-}C_6)$haloalkyl;

$R^4$ and $R^5$ are each independently selected from H, halogen, $(C_1\text{-}C_6)$alkyl, $(C_1\text{-}C_6)$haloalkyl, $O(C_1\text{-}C_6)$alkyl, or $O(C_1\text{-}C_6)$haloalkyl;

$R^6$ is a phenyl, $(C_3\text{-}C_7)$cycloalkyl, 5- or 6-membered heteroaryl, or 4, 5, 6 or 7-membered heterocycle, wherein any phenyl, $(C_3\text{-}C_7)$cycloalkyl, 5- or 6-membered heteroaryl, or 4, 5, 6 or 7-membered heterocycle of $R^6$ is optionally substituted with one or more groups independently selected from halogen, $SF_5$, $(C_1\text{-}C_6)$alkyl, $(C_1\text{-}C_6)$ haloalkyl, $O(C_1\text{-}C_6)$alkyl, and $O(C_1\text{-}C_6)$haloalkyl; or $R^6$ is O—$CH_2$—$R^7$;

$R^7$ is a $(C_1\text{-}C_6)$alkyl, 3, 4, 5, 6, or 7-membered heterocycle, 3, 4, 5, 6, or 7-membered cycloalkyl, or 6-membered heteroaryl, wherein any $(C_1\text{-}C_6)$alkyl, 3, 4, 5, 6, or 7-membered heterocycle, 3, 4, 5, 6, or 7-membered cycloalkyl, or 6-membered heteroaryl is optionally substituted with one or more groups independently selected from halogen, $(C_1\text{-}C_6)$ alkyl, $(C_1\text{-}C_6)$haloalkyl, $O(C_1\text{-}C_6)$alkyl, $(C_3\text{-}C_7)$cycloalkyl, and $O(C_1\text{-}C_6)$haloalkyl;

or a salt thereof.

EEE236. The compound of EEE235, wherein $B^2$ is:

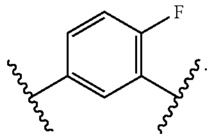

EEE237. The compound of EEE235, wherein $B^3$ is:

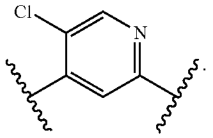

EEE238. The compound of EEE235, wherein $B^3$ is:

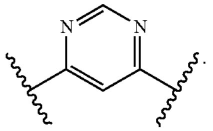

EEE239. The compound of EEE235, wherein $B^3$ is:

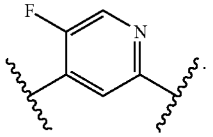

EEE240. The compound of EEE235, wherein $B^3$ is:

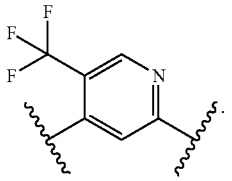

EEE241. The compound of EEE235, wherein $B^3$ is:

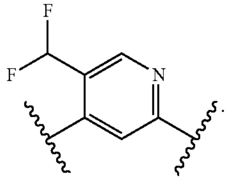

EEE242. The compound of EEE235, wherein $B^3$ is:

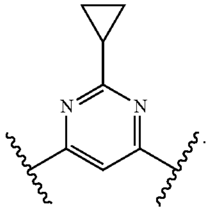

EEE243. The compound of any one of EEE235-242, wherein $R^4$ and $R^5$ are each $CH_3$.

EEE244. The compound of any one of EEE235-242, wherein $R^4$ and $R^5$ are each halogen.

EEE245. The compound of EEE244, wherein $R^4$ and $R^5$ are each fluorine.

EEE246. The compound of any one of EEE235-242, wherein the group

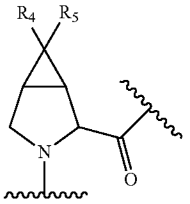

is:

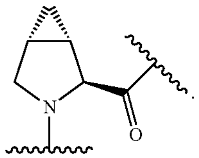 [SMILES: *C(=O)[C@@H]1[C@H]2C[C@H]2CN1*]

EEE247. The compound of any one of EEE235-242, wherein the group

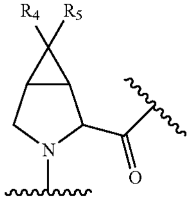

is:

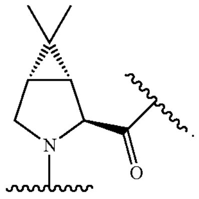 [SMILES: *C(=O)[C@@H]1[C@@H]2[C@H](CN1*)C2(C)C]

EEE248. The compound of any one of EEE235-242, wherein the group

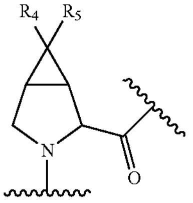

is:
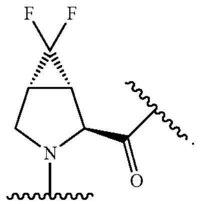 [SMILES: *C(=O)[C@@H]1[C@@H]2[C@H](CN1*)C2(F)F]
EEE249. The compound of any one of EEE235-248, wherein $R^6$ is:
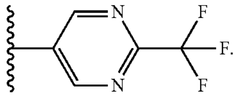 [SMILES: *c1cnc(C(F)(F)F)nc1]
EEE250. The compound of EEE235, wherein the compound is:
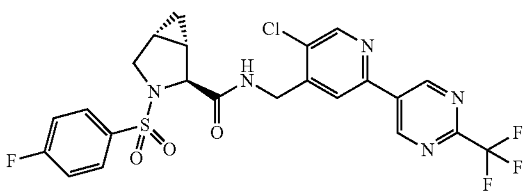
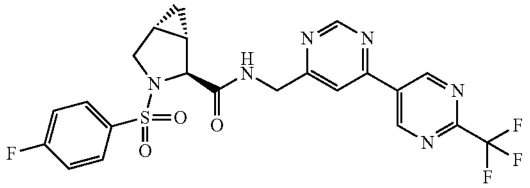
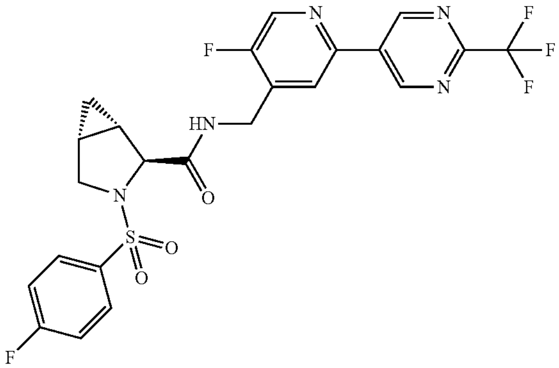
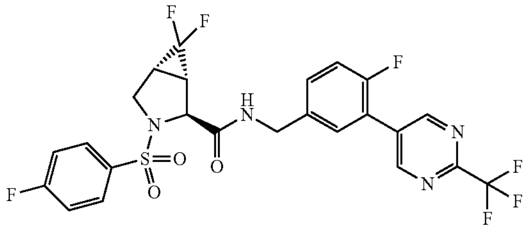
-continued
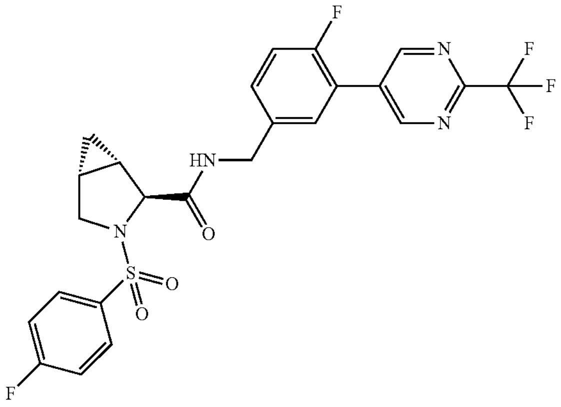
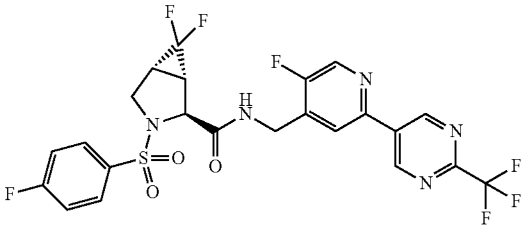
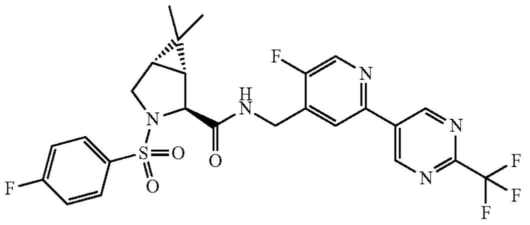
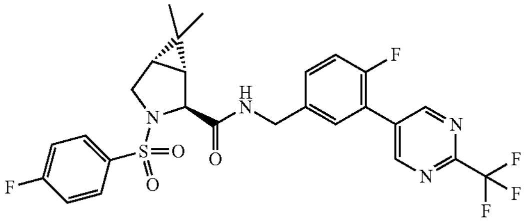
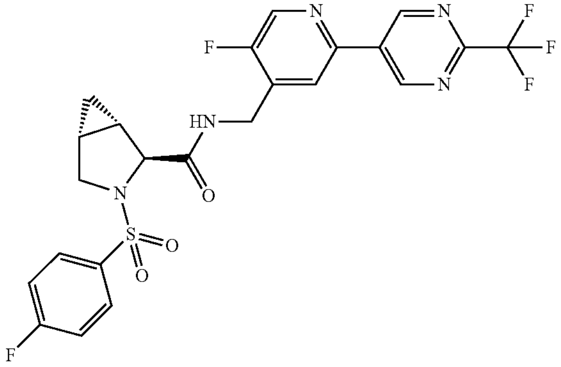
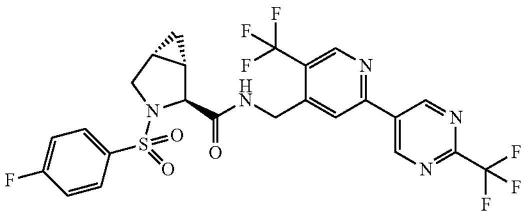

-continued

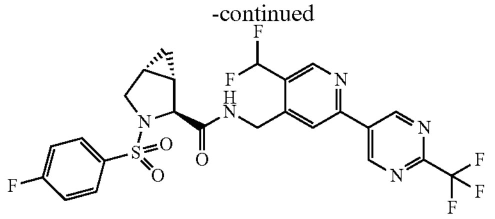

or

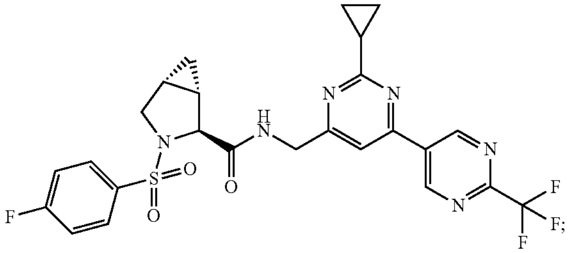

;

or a salt thereof.

EEE251. A compound of formula VIII:

VIII

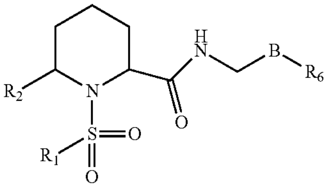

wherein:

B is $B^2$ or $B^3$;

$B^2$ is phenyl, wherein each phenyl is unsubstituted or substituted with one or more groups independently selected from halogen, CN, $(C_1-C_6)$alkyl, and $(C_1-C_6)$haloalkyl;

$B^3$ is a 6-membered heteroaryl, wherein each 6-membered heteroaryl is unsubstituted or substituted with one or more groups independently selected from halogen, $(C_1-C_6)$alkyl, $(C_1-C_6)$haloalkyl, $O(C_1-C_6)$alkyl, $O(C_1-C_6)$haloalkyl, 5 or 6-membered heteroaryl, $(C_3-C_7)$cycloalkyl, and $(C_3-C_7)$heterocyclyl; and wherein any of the 5 or 6-membered heteroaryl, $(C_3-C_7)$cycloalkyl, or $(C_3-C_7)$heterocyclyl groups is unsubstituted or substituted with one or more groups independently selected from halogen, $(C_1-C_6)$alkyl, and $(C_1-C_6)$haloalkyl;

$R^1$ is phenyl or heteroaryl, wherein each phenyl or heteroaryl is unsubstituted or substituted with one or more groups independently selected from halogen, CN, $(C_1-C_6)$alkyl, and $(C_1-C_6)$haloalkyl;

$R^2$ is H or $(C_1-C_6)$alkyl;

$R^6$ is a phenyl, $(C_3-C_7)$cycloalkyl, 5- or 6-membered heteroaryl, or 4, 5, 6 or 7-membered heterocycle, wherein any phenyl, $(C_3-C_7)$cycloalkyl, 5- or 6-membered heteroaryl, or 4, 5, 6 or 7-membered heterocycle of $R^6$ is optionally substituted with one or more groups independently selected from halogen, $SF_5$, $(C_1-C_6)$alkyl, $(C_1-C_6)$haloalkyl, $O(C_1-C_6)$alkyl, and $O(C_1-C_6)$haloalkyl; or $R^6$ is $O—CH_2—R^7$;

$R^7$ is a $(C_1-C_6)$alkyl, 3, 4, 5, 6, or 7-membered heterocycle, 3, 4, 5, 6, or 7-membered cycloalkyl, or 6-membered heteroaryl, wherein any $(C_1-C_6)$alkyl, 3, 4, 5, 6, or 7-membered heterocycle, 3, 4, 5, 6, or 7-membered cycloalkyl, or 6-membered heteroaryl is optionally substituted with one or more groups independently selected from halogen, $(C_1-C_6)$alkyl, $(C_1-C_6)$haloalkyl, $O(C_1-C_6)$alkyl, $(C_3-C_7)$cycloalkyl, and $O(C_1-C_6)$haloalkyl;

or a salt thereof.

EEE252. The compound of EEE251, wherein $B^3$ is:

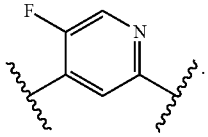

.

EEE253. The compound of any one of EEE251-252, wherein $R^2$ is $(C_1-C_6)$alkyl.

EEE254. The compound of any one of EEE251-253, wherein the group

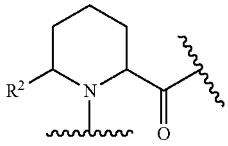

is:

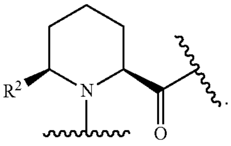

.

EEE255. The compound of any one of EEE251-254, wherein $R^6$ is:

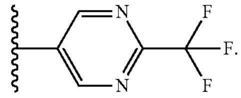 [SMILES: *c1cnc(C(F)(F)F)nc1]

.

EEE256. The compound of EEE251, wherein the compound is:

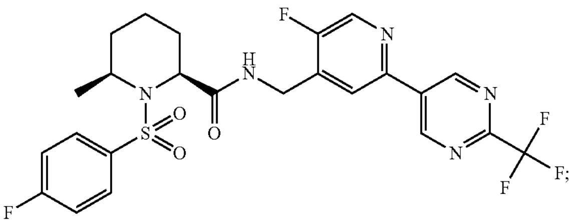 [SMILES: C[C@H]1CCC[C@@H](C(=O)NCc2cc(-c3cnc(C(F)(F)F)nc3)ncc2F)N1S(=O)(=O)c1ccc(F)cc1]

;

or a salt thereof.

EEE257. The compound of any one of EEE1-256, wherein the hydrogen atom of:

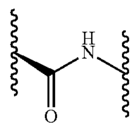

is replaced with a prodrug moiety.

EEE258. The compound of EEE257, wherein the prodrug moiety is:

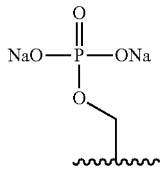

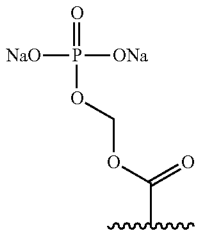

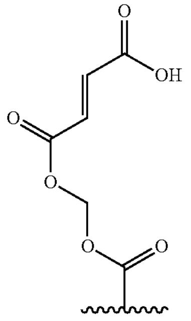

or

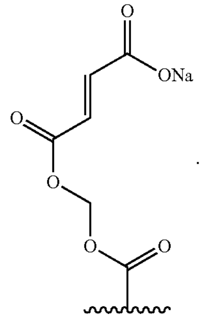

.

EEE259. A compound of formula IX:

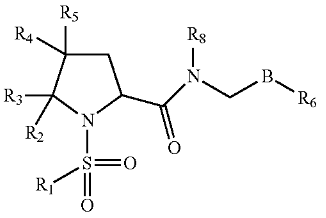

IX wherein:

B is $B^1$, $B^2$, or $B^3$;

$B^1$ is a 5-membered heteroaryl comprising 2 nitrogen atoms in the ring, wherein each 5-membered heteroaryl is unsubstituted or substituted with one or more groups independently selected from halogen, CN, $(C_1\text{-}C_6)$alkyl, $(C_1\text{-}C_6)$haloalkyl, $O(C_1\text{-}C_6)$alkyl, and $O(C_1\text{-}C_6)$haloalkyl;

$B^2$ is phenyl, wherein each phenyl is unsubstituted or substituted with one or more groups independently selected from halogen, CN, $(C_1\text{-}C_6)$alkyl, $(C_1\text{-}C_6)$haloalkyl, $O(C_1\text{-}C_6)$alkyl, and $O(C_1\text{-}C_6)$haloalkyl;

$B^3$ is 6-membered heteroaryl, wherein each 6-membered heteroaryl is unsubstituted or substituted with one or more groups independently selected from halogen, CN, $(C_1\text{-}C_6)$alkyl, $(C_1\text{-}C_6)$haloalkyl, $O(C_1\text{-}C_6)$alkyl, $O(C_1\text{-}C_6)$haloalkyl, 5 or 6-membered heteroaryl, $(C_3\text{-}C_7)$cycloalkyl, and 4, 5, 6, or 7-membered heterocyclyl; and wherein any of the 5 or 6-membered heteroaryl, $(C_3\text{-}C_7)$cycloalkyl, or 4, 5, 6, or 7-membered heterocyclyl groups is unsubstituted or substituted with one or more groups independently selected from halogen, CN, $(C_1\text{-}C_6)$alkyl, $(C_1\text{-}C_6)$haloalkyl, $O(C_1\text{-}C_6)$alkyl, and $O(C_1\text{-}C_6)$haloalkyl;

$R^1$ is phenyl or heteroaryl, wherein each phenyl or heteroaryl is unsubstituted or substituted with one or more groups independently selected from halogen, CN, $(C_1\text{-}C_6)$alkyl, and $(C_1\text{-}C_6)$haloalkyl;

$R^2$ is $(C_1\text{-}C_6)$alkyl, $(C_1\text{-}C_6)$haloalkyl, or $(C_3\text{-}C_7)$cycloalkyl; wherein $(C_1\text{-}C_6)$alkyl is optionally substituted with $O(C_1\text{-}C_6)$alkyl;

$R^3$ is H or $(C_1\text{-}C_6)$alkyl; or $R^2$ and $R^3$ together with the atoms to which they are attached form a $(C_3)$cycloalkyl;

$R^4$ is H, F, or CN;

$R^5$ is H or $(C_1\text{-}C_6)$alkyl; or one of $R^2$ and $R^3$ and one of $R^4$ and $R^5$ together with the atoms to which they are attached form a $(C_3)$cycloalkyl;

$R^6$ is phenyl, $(C_3\text{-}C_7)$cycloalkyl, 5 or 6-membered heteroaryl, or 4, 5, 6 or 7-membered heterocycle, wherein any phenyl, $(C_3\text{-}C_7)$cycloalkyl, 5 or 6-membered heteroaryl, or 4, 5, 6 or 7-membered heterocycle of $R^6$ is optionally substituted with one or more groups independently selected from halogen, CN, $SF_5$, $(C_1\text{-}C_6)$alkyl, $(C_1\text{-}C_6)$haloalkyl, $O(C_1\text{-}C_6)$alkyl, or $O(C_1\text{-}C_6)$haloalkyl; or $R^6$ is $O—CH_2—R^7$;

$R^7$ is $(C_1\text{-}C_6)$alkyl, 4, 5, 6, or 7-membered heterocycle, $(C_3\text{-}C_7)$cycloalkyl, or 6-membered heteroaryl, wherein any $(C_1\text{-}C_6)$alkyl, 4, 5, 6, or 7-membered heterocycle, $(C_3\text{-}C_7)$cycloalkyl, or 6-membered heteroaryl is optionally substituted with one or more groups independently selected from halogen, CN, $(C_1\text{-}C_6)$alkyl, $(C_1\text{-}C_6)$haloalkyl, $O(C_1\text{-}C_6)$alkyl, and $O(C_1\text{-}C_6)$haloalkyl;

$R^8$ is $CH_2OPO_3Na_2$; $C(=O)OCH_2OPO_3Na_2$; $C(=O)OCH_2OC(=O)CHCHC(=O)OH$; or $C(=O)OCH_2OC(=O)CHCHC(=O)ONa$;

or a salt thereof.

EEE260. The compound of EEE259, wherein $R^8$ is:

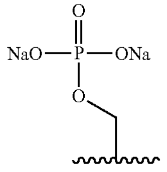

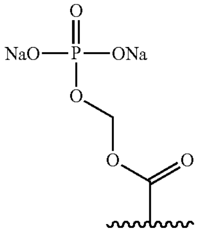

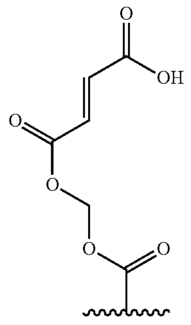

or

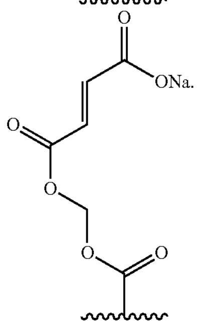

EEE261. The compound of EEE259, wherein the compound is:

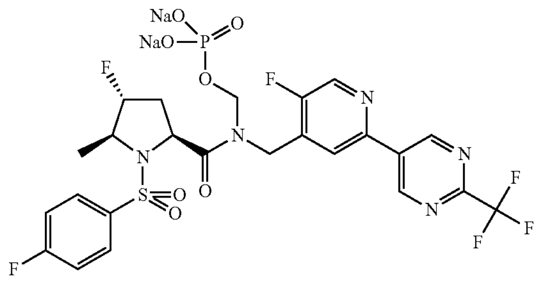

or

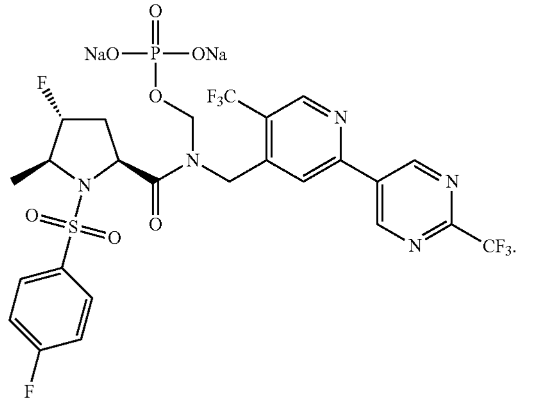

EEE262. The compound of EEE76, wherein $B^3$ is:

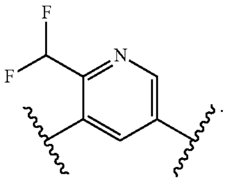 [SMILES: *c1cnc(C(F)F)c(*)c1]

EEE263. The compound of any one of EEE1-189, wherein $R^1$ is:

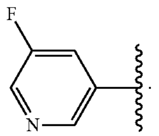

EEE264. The compound of any one of EEE1-189, wherein $R^1$ is:

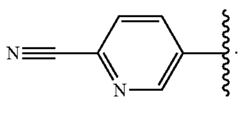 [SMILES: *c1ccc(C#N)nc1]

EEE265. The compound of any one of EEE1-189, wherein $R^1$ is:

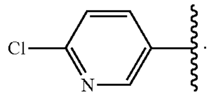 [SMILES: *c1ccc(Cl)nc1]

EEE266. A pharmaceutical composition, comprising a compound as described in any one of EEE1-265 or a pharmaceutically acceptable salt thereof, and a pharmaceutically acceptable carrier, diluent or excipient.

EEE267. A compound as described in any one of EEE1-265 or a pharmaceutically acceptable salt thereof for use in medical therapy.

EEE268. A compound as described in any one of EEE1-265 or a pharmaceutically acceptable salt thereof for the treatment or prophylaxis of a respiratory disorder.

EEE269. A compound as described in any one of EEE1-265 or a pharmaceutically acceptable salt thereof for the preparation of a medicament for the treatment or prophylaxis of a respiratory disorder.

EEE270. A method for treating a respiratory disorder in a mammal comprising, administering a compound as described in any one of EEE1-265 or a pharmaceutically acceptable salt thereof to the mammal.

EEE271. A compound as described in any one of EEE1-265 or a pharmaceutically acceptable salt thereof for modulating TRPA1 activity.

EEE272. A compound as described in any one of EEE1-265 or a pharmaceutically acceptable salt thereof for the treatment or prophylaxis of a disease or condition mediated by TRPA1 activity.

EEE273. The compound of EEE272 wherein the disease or condition is pain, itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia.

EEE274. The compound of EEE272 wherein the disease or condition is pain, arthritis, itch, cough, asthma, inflammatory bowel disease, or an inner ear disorder.

EEE275. The use of a compound as described in any one of EEE1-265 or a pharmaceutically acceptable salt thereof for the preparation of a medicament for the treatment or prophylaxis of a disease or condition that is mediated by TRPA1 activity.

EEE276. The use of EEE275 wherein the disease or condition is pain, itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia.

EEE277. The use of EEE275 wherein the disease or condition is pain, arthritis, itch, cough, asthma, inflammatory bowel disease, or an inner ear disorder.

EEE278. A method for modulating TRPA1 activity, comprising contacting TRPA1 with a compound as described in any one of EEE1-265 or a salt thereof.

EEE279. A method for treating a disease or condition mediated by TRPA1 activity in a mammal, comprising administering a compound as described in any one of EEE1-265 or a pharmaceutically acceptable salt thereof to the mammal.

EEE280. The method of EEE279 wherein the disease or condition is pain, itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia.

EEE281. The method of EEE279 wherein the disease or condition is pain, arthritis, itch, cough, asthma, inflammatory bowel disease, or an inner ear disorder.

EEE282. The method of EEE281 wherein the disease or condition is asthma.

EEE283. The compound of any of the preceding embodiments, wherein the salt of the compound is a pharmaceutically acceptable salt.

In another embodiment of the invention, the compounds of formula I are isotopically-labeled by having one or more atoms therein replaced by an atom having a different atomic mass or mass number. Such isotopically-labeled (i.e., radiolabelled) compounds of formula I are considered to be within the scope of this invention. Examples of isotopes that can be incorporated into the compounds of formula I include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These isotopically-labeled compounds would be useful to help determine or measure the effectiveness of the compounds, by characterizing, for example, the site or mode of action on the ion channels, or binding affinity to pharmacologically important site of action on the ion channels, particularly TRPA1. Certain isotopically-labeled compounds of formula I, for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection. For example, a compound of formula I can be enriched with 1, 2, 5, 10, 25, 50, 75, 90, 95, or 99 percent of a given isotope.

Substitution with heavier isotopes such as deuterium, i.e. $^{2}H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and a $^{13}N$, can be useful in Positron Emission Topography (PET) studies for examining substrate receptor occupancy. Isotopically-labeled compounds of formula I can generally be prepared by conventional techniques known to those skilled in the art or by processes analogous to those described in the Examples as set out below using an appropriate isotopically-labeled reagent in place of the non-labeled reagent previously employed.

In another embodiment, the invention provides for a pharmaceutical composition, comprising a therapeutically effective amount of a compound according to formula I and a pharmaceutically acceptable carrier.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include replacement of the hydrogen atom of the proline (N—H) with a prodrug moiety. The prodrug moiety may include phosphates, phosphate esters, alkyl phosphates, alkyl phosphate esters, acyl ethers, or other prodrug moieties as discussed below. In some embodiments, the prodrug moiety is:

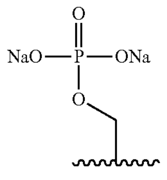

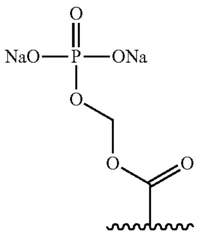

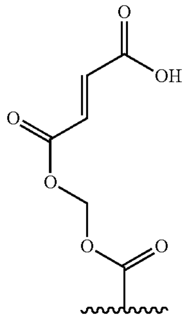

or

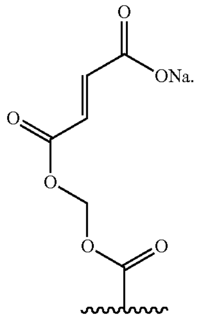

Additional types of prodrugs are also encompassed. For example, where an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methylalanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-$((C_{1-6})$alkanoyloxy)ethyl, 1-methyl-1-$((C_{1-6})$alkanoyloxy)ethyl, $(C_{1-6})$ alkoxycarbonyloxymethyl, N—$(C_{1-6})$alkoxycarbonylaminomethyl, succinoyl, $(C_{1-6})$alkanoyl, alpha-amino$(C_{1-4}$ alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Pharmaceutical Compositions and Administration

In addition to one or more of the compounds provided above (including stereoisomers, geometric isomers, tautomers, solvates, metabolites, isotopes, pharmaceutically acceptable salts, or prodrugs thereof), the invention also provides for compositions and medicaments comprising a compound of formula I or and embodiment thereof and at least one pharmaceutically acceptable carrier. The compositions of the invention can be used to selectively inhibit TRPA1 in patients (e.g., humans).

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In one embodiment, the invention provides for pharmaceutical compositions or medicaments comprising a compound of formula I or an embodiment thereof, and its stereoisomers, geometric isomers, tautomers, solvates, metabolites, isotopes, pharmaceutically acceptable salts, or prodrugs thereof) and a pharmaceutically acceptable carrier, diluent or excipient. In another embodiment, the invention provides for preparing compositions (or medicaments) comprising compounds of the invention. In another embodiment, the invention provides for administering compounds of formula I or its embodiments and compositions comprising compounds of formula I or an embodiment thereof to a patient (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit TRPA1 activity as required to prevent or treat the undesired disease or disorder, such as for example, pain. For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, intracerebral, intraocular, intralesional or subcutaneous administration.

The compositions comprising compounds of formula I or an embodiment thereof are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament). Suitable carriers, diluents and excipients are well known to those skilled in the art and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., a compound of formula I or an embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philidelphia, Pa. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include Sustained-release preparations of a compound of the invention (e.g., compound of formula I or an embodiment thereof) can be prepared. Suitable examples of sustained-release preparations include semipermeable matrices of solid hydrophobic polymers containing a compound of formula I or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

In one example, compounds of formula I or an embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I (or an embodiment thereof) is formulated in an acetate buffer, at pH 5. In another embodiment, the compounds of formula I or an embodiment thereof are sterile. The compound may be stored, for example, as a solid or amorphous composition, as a lyophilized formulation or as an aqueous solution.

Formulations of a compound of the invention (e.g., compound of formula I or an embodiment thereof) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of formula I or an embodiment thereof) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient (s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

For topical formulations, it is desired to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

When the binding target is located in the brain, certain embodiments of the invention provide for a compound of formula I (or an embodiment thereof) to traverse the blood-brain barrier. Certain neurodegenerative diseases are associated with an increase in permeability of the blood-brain barrier, such that a compound of formula I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of formula I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford.

Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I (or an embodiment thereof) across the blood-brain barrier include, but are not limited to, encapsulating the a compound of formula I (or an embodiment thereof) in liposomes that are coupled to antibody binding fragments that bind to receptors on the vascular endothelium of the blood-brain barrier (see, e.g., U.S. Patent Application Publication No. 2002/0025313), and coating a compound of formula I (or an embodiment thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of formula I (or an embodiment thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Indications and Methods of Treatment

Representative compounds of the invention have been shown to modulate TRPA lactivity. Accordingly, the compounds of the invention are useful for treating diseases and conditions mediated by TRPA1 activity. Such diseases and conditions include but are not limited to: pain (acute, chronic, inflammatory, or neuropathic pain); itch or various inflammatory disorders; inner ear disorders; fever or other disorders of thermoregulation; tracheobronchial or diaphragmatic dysfunction; gastrointestinal or urinary tract disorders; chronic obstructive pulmonary disease; incontinence; and disorders associated with reduced blood flow to the CNS or CNS hypoxia.

In a specific embodiment, compounds of the invention can be administered to treat pain, including but not limited to neuropathic and inflammatory pain, among others. Certain types of pain may be considered a disease or disorder, while other types may be considered symptoms of various diseases or disorders, and pain may include various etiologies. Exemplary types of pain treatable with a TRPA1-modulating agent according to the invention include pain associated with, arising from, or caused by: osteoarthritis, rotator cuff disorders, arthritis (e.g., rheumatoid arthritis or inflammatory arthritis; see, Barton et al. *Exp. Mol. Pathol.* 2006, 81(2), 166-170), fibromyalgia, migraine and headache (e.g. cluster headache, sinus headache, or tension headache; see, Goadsby *Curr. Pain Headache Reports* 2004, 8, 393), sinusitis, oral mucositis, toothache, dental trauma, dental extractions, dental infections, burn (Bolcskei et al., *Pain* 2005, 117(3), 368-376), sunburn, dermatitis, psoriasis, eczema, insect sting or bite, musculoskeletal disorders, bony fractures, ligamentous sprains, plantar fasciitis, costochondritis, tendonitis, bursitis, tennis elbow, pitcher's elbow, patellar tendonitis, repetitive strain injury, myofascial syndrome, muscle strain, myositis, temporomandibular joint disorder, amputation, low back pain, spinal cord injury, neck pain, whiplash, bladder spasms, G1 tract disorders, cystitis, interstitial cystitis, cholecystitis, urinary tract infection, urethral colic, renal colic, pharyngitis, cold sores, stomatitis, external otitis, otitis media (Chan et al., *Lancet,* 2003, 361, 385), burning mouth syndrome, mucositis, esophageal pain, esophageal spasms, abdominal disorders, gastroesophageal reflux disease, pancreatitis, enteritis, irritable bowel disorder, inflammatory bowel disease, Crohn's disease, ulcerative colitis, colon distension, abdominal constriction, diverticulosis, diverticulitis, intestinal gas, hemorrhoids, anal fissures, anorectal disorders, prostatitis, epididymitis, testicular pain, proctitis, rectal pain, labor, childbirth, endometriosis, menstrual cramps, pelvic pain, vulvodynia, vaginitis, orolabial and genital infections (e.g. herpes simplex), pleurisy, pericarditis, non-cardiac chest pain, contusions, abrasions, skin incision (Honore, P. et al., *J Pharmacal Exp Ther.,* 2005, 314, 410-21), postoperative pain, peripheral neuropathy, central neuropathy, diabetic neuropathy, acute herpetic neuralgia, post-herpetic neuralgia, trigeminal neuralgia, glossopharyngeal neuralgia, atypical facial pain, gradiculopathy, HIV associated neuropathy, physical nerve damage, causalgia, reflex sympathetic dystrophy, sciatica, cervical, thoracic or lumbar radiculopathy, brachial plexopathy, lumbar plexopathy, neurodegenerative disorders, occipital neuralgia, intercostal neuralgia, supraorbital neuralgia, inguinal neuralgia, meralgia paresthetica, genitofemoral neuralgia, carpal tunnel syndrome, Morton's neuroma, post-mastectomy syndrome, post-thoracotomy syndrome, post-polio syndrome, Guillain-Barre syndrome, Raynaud's syndrome, coronary artery spasm (Printzmetal's or variant angina), visceral hyperalgesia (Pomonis, J. D. et al. *J. Pharmacal. Exp. Ther.* 2003, 306, 387; Walker, K. M. et al., *J. Pharmacal. Exp. Ther.* 2003, 304(1), 56-62), thalamic pain, cancer (e.g. pain caused by cancer, including osteolytic sarcoma, by treatment of cancer by radiation or chemotherapy, or by nerve or bone lesions associated with cancer (see, Menendez, L. et al., *Neurosci. Lett.* 2005, 393 (1), 70-73; Asai, H. et al., *Pain* 2005, 117, 19-29), or bone destruction pain (see, Ghilardi, J. R. et al., *J. Neurosci.* 2005, 25, 3126-31)), infection, or metabolic disease. Additionally, the compounds may be used to treat pain indications such as visceral pain, ocular pain, thermal pain, dental pain, capsaicin-induced pain (as well as other symptomatic conditions induced by capsaicin such as cough, lachrymation, and bronchospasm).

In another specific embodiment, compounds of the invention can be administered to treat itch, which may arise from various sources, such as dermatological or inflammatory disorders.

In another specific embodiment, compounds of the invention can be administered to treat inflammatory disorders, including disorders selected from the group consisting of: renal or hepatobiliary disorders, immunological disorders, medication reactions and unknown/idiopathic conditions. Inflammatory disorders treatable with an inventive agent include, for example, inflammatory bowel disease (IBO), Crohn's disease, and ulcerative colitis (Geppetti, P. et al., *Br. J. Pharmacal.* 2004, 141, 1313-20; Yiangou, Y. et al., *Lancet* 2001, 357, 1338-39; Kimball, E. S. et al., *Neurogastroenterol. Motif.,* 2004, 16, 811), osteoarthritis (Szabo, A. et al., *J. Pharmacal. Exp. Ther.* 2005, 314, 111-119), psoriasis, psoriatic arthritis, rheumatoid arthritis, myasthenia gravis, multiple sclerosis, scleroderma, glomerulonephritis, pancreatitis, inflammatory hepatitis, asthma, chronic obstructive pulmonary disease, allergic rhinitis, uveitis, and cardiovascular manifestations of inflammation including atherosclerosis, myocarditis, pericarditis, and vasculitis.

In another specific embodiment, compounds of the invention can be administered to treat inner ear disorders. Such disorders include, for example, hyperacusis, tinnitus, vestibular hypersensitivity, and episodic vertigo.

For example, compounds of the invention can be administered to treat tracheobronchial and diaphragmatic dysfunctions including, for example, asthma and allergy-related immune responses (Agopyan, N. et al., *Am. J. Physiol. Lung Cell Mol. Physiol.* 2004, 286, L563-72; Agopyan, N. et al., *Toxicol. Appl. Pharmacal.* 2003, 192, 21-35), cough (e.g., acute or chronic cough, or cough caused by irritation from gastroesophageal reflux disease; see, Lalloo, U. G. et al., *J. Appl. Physiol.* 1995, 79(4), 1082-7), bronchospasm, chronic obstructive pulmonary disease, chronic bronchitis, emphysema, and hiccups (hiccoughs, singultus).

In another specific embodiment, compounds of the invention can be administered to treat gastrointestinal and urinary tract disorders such as, bladder overactivity, inflammatory hyperalgesia, visceral hyperreflexia of the urinary bladder, hemorrhagic cystitis (Dinis, P. et al., *J Neurosci.,* 2004, 24, 11253-11263), interstitial cystitis (Sculptoreanu, A. et al., *Neurosci Lett.,* 2005, 381, 42-46), inflammatory prostate disease, prostatitis (Sanchez, M. et al., *Eur J Pharmacal.,* 2005, 515, 20-27), nausea, vomiting, intestinal cramping, intestinal bloating, bladder spasms, urinary urgency, defecation urgency and urge incontinence.

In another specific embodiment, compounds of the invention can be administered to treat disorders associated with reduced blood flow to the CNS or CNS hypoxia. Such disorders include, for example, head trauma, spinal injury, thromboembolic or hemorrhagic stroke, transient ischaemic attacks, cerebral vasospasm, hypoglycaemia, cardiac arrest, status epilepticus, perinatal asphyxia, Alzheimer's disease, and Huntington's Disease.

In other embodiments, compounds of the invention can be administered to treat other diseases, disorders, or conditions mediated through TRPA1 activity, such as anxiety; learning or memory disorders; eye-related disorders (such as glaucoma, vision loss, increased intraocular pressure, and conjunctivitis); baldness (e.g., by stimulating hair growth); diabetes (including insulin-resistant diabetes or diabetic conditions mediated by insulin sensitivity or secretion); obesity (e.g., through appetite suppression); dyspepsia; biliary colic; renal colic; painful bladder syndrome; inflamed esophagus; upper airway disease; urinary incontinence; acute cystitis; and envenomations (such as marine, snake, or insect stings or bites, including jellyfish, spider, or stingray envenomations).

In one specific embodiment, compounds of the invention are administered to treat pain (including but not limited to acute, chronic, neuropathic and inflammatory pain), arthritis, itch, cough, asthma, or inflammatory bowel disease.

In another embodiment, the invention provides for a method for treating neuropathic pain or inflammatory pain, comprising the step of administering a therapeutically effective amount of a compound as described in any one of E1-91 or EE1-170 above to a subject in need thereof.

In another embodiment, the invention provides for a compound as described in any one of E1-91 or EE1-170 above or a pharmaceutically acceptable salt thereof for modulating TRPA1 activity.

In another embodiment, the invention provides for a compound as described in any one of E1-91 or EE1-170 above, or a pharmaceutically acceptable salt thereof for use in medical therapy.

In another embodiment, the invention provides for a method for treating a respiratory disorder selected from chronic obstructive pulmonary disorder (COPD), asthma, allergic rhinitis and bronchospasm, comprising the step of administering a therapeutically effective amount of a compound as described in any one of E1-91 or EE1-170 above to a subject in need thereof.

In another embodiment, the invention provides for a compound as described in any one of E1-91 or EE1-170 above or a pharmaceutically acceptable salt thereof for the treatment or prophylaxis of a respiratory disorder.

In another embodiment, the invention provides for the use of a compound as described in any one of E1-91 or EE1-170 above or a pharmaceutically acceptable salt thereof for the preparation of a medicament for the treatment or prophylaxis of a respiratory disorder.

In another embodiment, the invention provides for a method for treating a respiratory disorder in a mammal (e.g., a human) comprising administering a compound as described in any one of E1-91 or EE1-170 above or a pharmaceutically acceptable salt thereof to the mammal.

In another embodiment, the invention provides for a method for modulating TRPA1 activity, comprising contacting TRPA1 with a compound as described in any one of E1-91 or EE1-170 above or a salt thereof.

In another embodiment, the invention provides for a compound as described in any one of E1-91 or EE1-170 above or a pharmaceutically acceptable salt thereof for the treatment or prophylaxis of a disease or condition mediated by TRPA1 activity. Within aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, wherein the disease or condition is pain (including but not limited to acute, chronic, neuropathic and inflammatory pain), arthritis, itch, cough, asthma, inflammatory bowel disease, or an inner ear disorder.

In another embodiment, the invention provides for the use of a compound as described in any one of E1-91 or EE1-170 above or a pharmaceutically acceptable salt thereof for the preparation of a medicament for the treatment or prophylaxis of a disease or condition that is mediated by TRPA1 activity. Within aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within aspects of this embodiment, the disease or condition is pain (including but not limited to acute, chronic, neuropathic and inflammatory pain), arthritis, itch, cough, asthma, inflammatory bowel disease, or an inner ear disorder.

In another embodiment, the invention provides for a method for treating a disease or condition mediated by TRPA1 activity in a mammal (e.g., a human), comprising administering a compound as described in any one of E1-91 or EE1-170 above or a pharmaceutically acceptable salt thereof to the mammal. Within certain aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, the disease or condition is pain (including but not limited to acute, chronic, neuropathic and inflammatory pain), arthritis, itch, cough, asthma, inflammatory bowel disease, or an inner ear disorder.

In one aspect, compounds of the invention demonstrate surprisingly higher potency as compared to other analogues. For example, the compounds of the invention each contain at least one substituent at the $R^2$ or $R^3$ position. Representative compounds, commensurate in scope of the present invention, and each containing at least one substituent at the $R^2$ or $R^3$ position demonstrate surprisingly enhanced potency, shown below in Table 1:

TABLE 1

| Structure | Name | hTRPA1 CHO Ca2+ AUC EVO (IC50) |
|---|---|---|
| 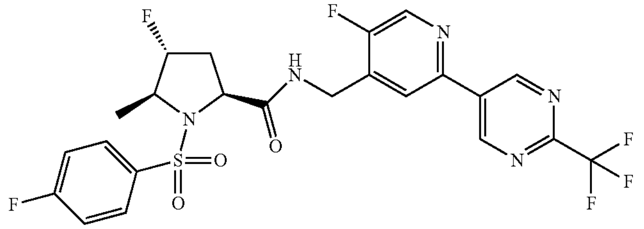 [SMILES: C[C@H]1[C@H](F)C[C@@H](C(=O)NCc2cc(-c3cnc(C(F)(F)F)nc3)ncc2F)N1S(=O)(=O)c1ccc(F)cc1] | (2S,4R,5S)-4-fluoro-1-(4-fluorophenyl)sulfonyl-N-[[5-fluoro-2-[2-(trifluoromethyl)pyrimidin-5-yl]-4-pyridyl]methyl]-5-methyl-pyrrolidine-2-carboxamide | 0.00201 |
| 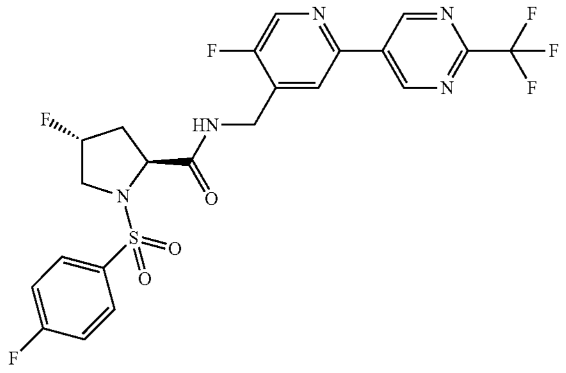 [SMILES: O=C(NCc1cc(-c2cnc(C(F)(F)F)nc2)ncc1F)[C@@H]1C[C@@H](F)CN1S(=O)(=O)c1ccc(F)cc1] | (2S,4R)-4-fluoro-1-(4-fluorophenyl)sulfonyl-N-[[5-fluoro-2-[2-(trifluoromethyl)pyrimidin-5-yl]-4-pyridyl]methyl]pyrrolidine-2-carboxamide | 0.0267 |
| 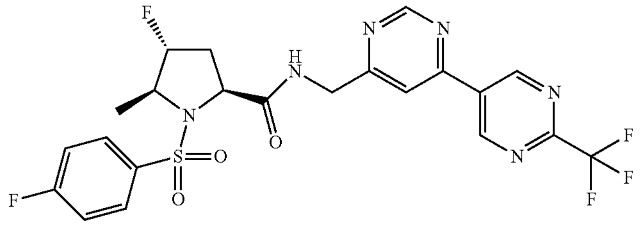 [SMILES: C[C@H]1[C@H](F)C[C@@H](C(=O)NCc2cc(-c3cnc(C(F)(F)F)nc3)ncn2)N1S(=O)(=O)c1ccc(F)cc1] | (2S,4R,5S)-4-fluoro-1-(4-fluorophenyl)sulfonyl-5-methyl-N-[[6-[2-(trifluoromethyl)pyrimidin-5-yl]pyrimidin-4-yl]methyl]pyrrolidine-2-carboxamide | 0.0219 |
| 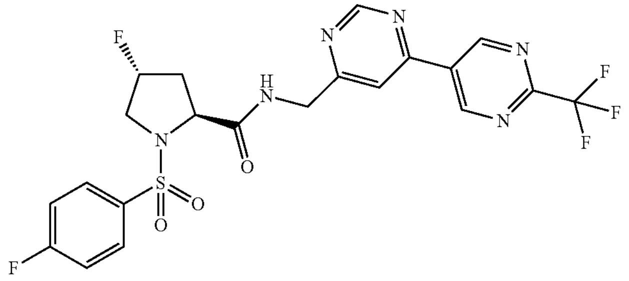 [SMILES: O=C(NCc1cc(-c2cnc(C(F)(F)F)nc2)ncn1)[C@@H]1C[C@@H](F)CN1S(=O)(=O)c1ccc(F)cc1] | (2S,4R)-4-fluoro-1-(4-fluorophenyl)sulfonyl-N-[[6-[2-(trifluoromethyl)pyrimidin-5-yl]pyrimidin-4-yl]methyl]pyrrolidine-2-carboxamide | 0.251 |

TABLE 1-continued

| Structure | Name | hTRPA1 CHO Ca2+ AUC EVO (IC50) |
| --- | --- | --- |
| 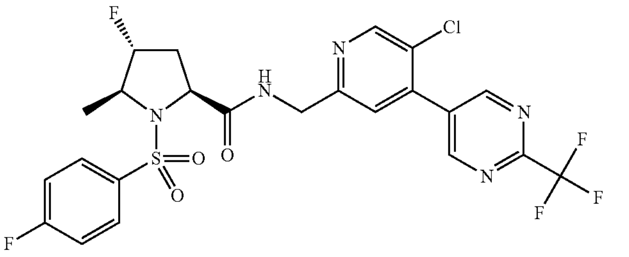 | (2S,4R,5S)-N-[[5-chloro-4-[2-(trifluoromethyl)pyrimidin-5-yl]-2-pyridyl]methyl]-4-fluoro-1-(4-fluorophenyl)sulfonyl-5-methyl-pyrrolidine-2-carboxamide | 0.00431 |
| 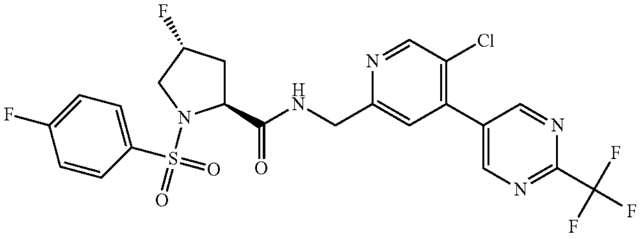 [SMILES: O=C(NCc1cc(-c2cnc(C(F)(F)F)nc2)c(Cl)cn1)[C@@H]1C[C@@H](F)CN1S(=O)(=O)c1ccc(F)cc1] | (2S,4R)-N-[[5-chloro-4-[2-(trifluoromethyl)pyrimidin-5-yl]-2-pyridyl]methyl]-4-fluoro-1-(4-fluorophenyl)sulfonyl-pyrrolidine-2-carboxamide | 0.0422 |
| 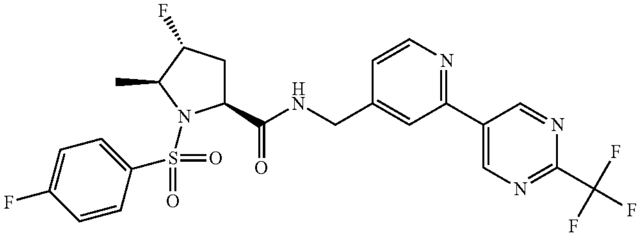 [SMILES: C[C@H]1[C@H](F)C[C@@H](C(=O)NCc2ccnc(-c3cnc(C(F)(F)F)nc3)c2)N1S(=O)(=O)c1ccc(F)cc1] | (2S,4R,5S)-4-fluoro-1-(4-fluorophenyl)sulfonyl-5-methyl-N-[[2-[2-(trifluoromethyl)pyrimidin-5-yl]-4-pyridyl]methyl]pyrrolidine-2-carboxamide | 0.0195 |
| 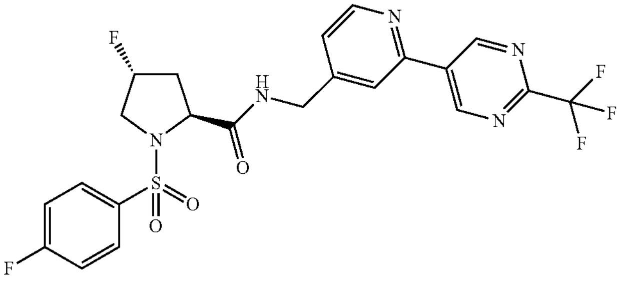 | (2S,4R)-4-fluoro-1-(4-fluorophenyl)sulfonyl-N-[[2-[2-(trifluoromethyl)pyrimidin-5-yl]-4-pyridyl]methyl]pyrrolidine-2-carboxamide | 0.129 |

Combination Therapy

The compounds of the invention may be usefully combined with one or more other compounds of the invention or one or more other therapeutic agent or as any combination thereof, in the treatment of ion channel-mediated diseases and conditions. For example, a compound of the invention may be administered simultaneously, sequentially or separately in combination with other therapeutic agents, including, but not limited to:

opiates analgesics, e.g., morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine;

non-opiate analgesics, e.g., acetomeniphen, salicylates (e.g., aspirin);

nonsteroidal antiinflammatory drugs (NSAIDs), e.g., ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac;

anticonvulsants, e.g., carbamazepine, oxcarbazepine, lamotrigine, valproate, topiramate, gabapentin and pregabalin;

antidepressants such as tricyclic antidepressants, e.g., amitriptyline, clomipramine, despramine, imipramine and nortriptyline;

COX-2 selective inhibitors, e.g., celecoxib, rofecoxib, parecoxib, valdecoxib, deracoxib, etoricoxib, and lumiracoxib;

alpha-adrenergics, e.g., doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline;

barbiturate sedatives, e.g., amobarbital, aprobarbital, butabarbital, butabital, mephobarbital, metharbital, methohexital, pentobarbital, phenobartital, secobarbital, talbutal, theamylal and thiopental;

tachykinin (NK) antagonist, particularly an NK-3, NK-2 or NK-1 antagonist, e.g., (aR,9R)-7-[3,5-bis(trifluoromethyl)benzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy5-(trifluoromethoxy)phenyl]-methylamino]-2-phenylpiperidine (2S,3S);

coal-tar analgesics, in particular paracetamol;

serotonin reuptake inhibitors, e.g., paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine;

noradrenaline (norepinephrine) reuptake inhibitors, e.g., maprotiline, lofepramine, mirtazepine, oxaprotiline, fezolamine, tomoxetine, mianserin, buproprion, buproprion metabolite hydroxybuproprion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics;

dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine;

acetylcholinesterase inhibitors such as donepezil;

5-HT3 antagonists such as ondansetron;

metabotropic glutamate receptor (mGluR) antagonists;

local anaesthetic such as mexiletine and lidocaine;

corticosteroid such as dexamethasone;

antiarrhythimics, e.g., mexiletine and phenytoin;

muscarinic antagonists, e.g., tolterodine, propiverine, tropsium t chloride, darifenacin, solifenacin, temiverine and ipratropium;

cannabinoids;

vanilloid receptor agonists (e.g., resinferatoxin) or antagonists (e.g., capsazepine);

sedatives, e.g., glutethimide, meprobamate, methaqualone, and dichloralphenazone;

anxiolytics such as benzodiazepines, antidepressants such as mirtazapine, topical agents (e.g., lidocaine, capsacin and resiniferotoxin);

muscle relaxants such as benzodiazepines, baclofen, carisoprodol, chlorzoxazone, cyclobenzaprine, methocarbamol and orphrenadine;

anti-histamines or H1 antagonists;

NMDA receptor antagonists;

5-HT receptor agonists/antagonists;

PDEV inhibitors;

Tramadol®;

cholinergic (nicotinc) analgesics;

alpha-2-delta ligands;

prostaglandin E2 subtype antagonists;

leukotriene B4 antagonists;

5-lipoxygenase inhibitors; and

5-HT3 antagonists.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

In another embodiment, provided is an invention as hereinbefore described.

General Preparation of Compounds of Formula I

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15*; Rodd's Chemistry of Carbon Compounds*, Elsevier Science Publishers, 1989, Volumes 1-5 and Supplementals; and *Organic Reactions*, Wiley & Sons: New York, 1991, Volumes 1-40.

The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

EXAMPLES

Although certain exemplary embodiments are depicted and described herein, the compounds of the present invention can be prepared using appropriate starting materials according to the methods described generally herein and/or by methods available to one of ordinary skill in the art.

Intermediates and final compounds were purified by either flash chromatography, and/or by reverse-phase preparative HPLC (high performance liquid chromatography), and/or by supercritical fluid chromatography. Unless otherwise noted, flash chromatography was carried out using pre-packed silica gel cartridges from either ISCO or SiliCycle on an ISCO CombiFlash® chromatography instrument (from Teledyne Isco, Inc.). Reverse-phase preparative HPLC was performed using a (1) Polaris C-18 5 μM column (50×21 mm), or (2) XBridge Prep C-18 OBD 5 μM column (19×150 mm). Supercritical fluid chromatography was carried out using packed columns by Chiral Technologies, Chiralpak AD, Chiralpak AS, Chiralpak IA, Chiralpak IB, Chiralpak IC, Chiralcel OD, or Chiralcel OJ with column dimensions such as (1) 4.6 cm×5 cm, 3 μM, (2) 4.6 cm×5 cm, 5 μM, or (3) 15 cm×21.2 mm, 5 μM.

Mass spectrometry (MS) was performed using a (1) Sciex 15 mass spectrometer in ES+ mode, or (2) Shimadzu LCMS 2020 mass spectrometer in ESI+ mode. Mass spectra data generally only indicates the parent ions unless otherwise stated. MS or HRMS data is provided for a particular intermediate or compound where indicated.

Nuclear magnetic resonance spectroscopy (NMR) was performed using a (1) Bruker AV III 300 NMR spectrometer, (2) Bruker AV III 400 NMR spectrometer, or (3) Bruker AV III 500 NMR spectrometer, and referenced to tetramethylsilane. NMR data is provided for a particular intermediate or compound where indicated.

All reactions involving air-sensitive reagents were performed under an inert atmosphere. Reagents were used as received from commercial suppliers unless otherwise noted.

The synthetic procedures disclosed below for Preparations 1-16 and Examples 1-4, 59, 68, 71, and 78 are applicable to the Examples 1-88 listed in Table 2.

Preparation 1: (2S,4R,5S)-1-[(tert-butoxy)carbonyl]-4-fluoro-5-methylpyrrolidine-2-carboxylic acid

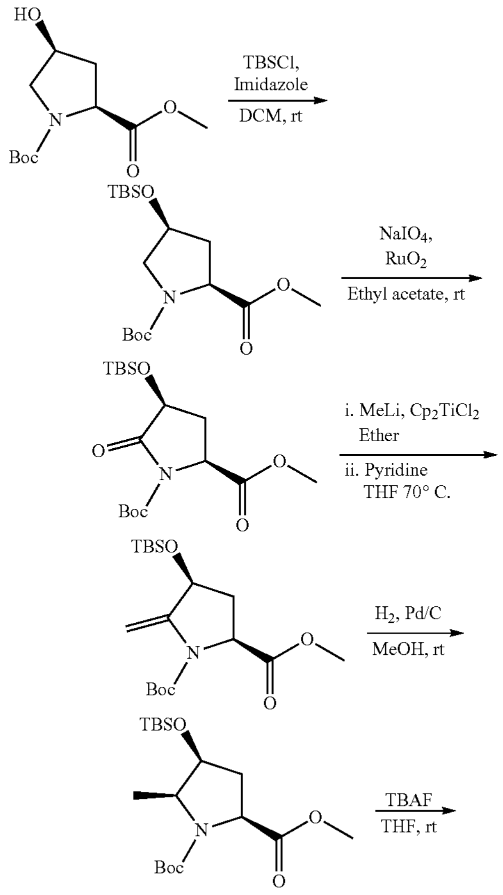

-continued

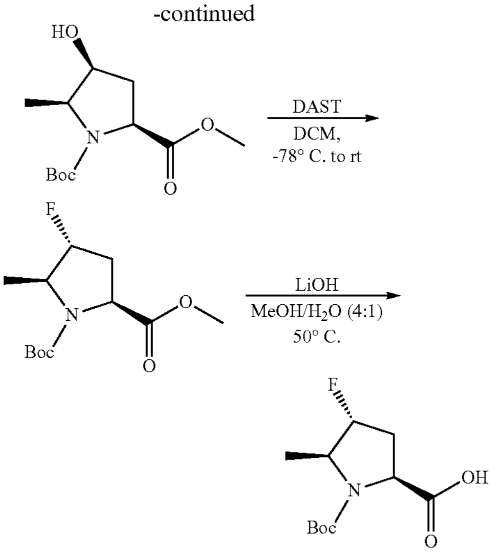

Step 1: Preparation of 1-tert-butyl 2-methyl (2S, 4S)-4-[(tert-butyldimethylsilyl)oxy]-5-oxopyrrolidine-1,2-dicarboxylate

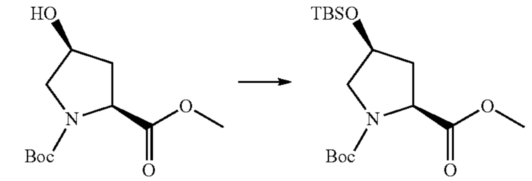 [SMILES: COC(=O)[C@@H]1C[C@H](O)CN1C(=O)OC(C)(C)C ; COC(=O)[C@@H]1C[C@H](O[Si](C)(C)C(C)(C)C)CN1C(=O)OC(C)(C)C]

TBSCl (138 g, 915.59 mmol, 1.50 equiv) in dichloromethane (500 mL) was added dropwise into a solution of 1-tert-butyl 2-methyl (2S,4S)-4-hydroxypyrrolidine-1,2-dicarboxylate (150 g, 611.57 mmol, 1.00 equiv) in dichloromethane (1500 mL) and 1H-imidazole (83 g, 1.22 mol, 2.00 equiv) at room temperature. After being stirred overnight at room temperature the resulting mixture was washed with water, dried over anhydrous sodium sulfate, and concentrated under vacuum. The residue was purified by a silica gel column eluting with ethyl acetate/petroleum ether (1:10). This resulted in the title compound (205 g, 93%) as a colorless oil. LCMS [M+H$^+$] 360; $^1$H NMR (400 MHz, $CDCl_3$) δ 4.48 (t, J=7.4 Hz, 1H), 4.30 (t, J=7.2 Hz, 1H), 3.79 (s, 3H), 2.62-2.55 (m, 1H), 2.04-1.97 (m, 1H), 1.58-1.26 (m, 11H), 0.90 (s, 9H), 0.18 (s, 3H), 0.14 (s, 3H).

Step 2: Preparation of 1-tert-butyl 2-methyl (2S, 4S)-4-[(tert-butyldimethylsilyl)oxy]-5-oxopyrrolidine-1,2-dicarboxylate

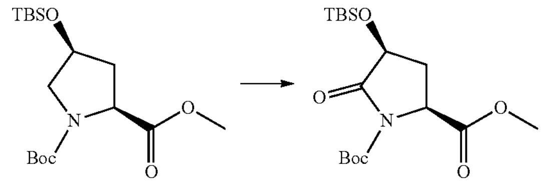 [SMILES: COC(=O)[C@@H]1C[C@H](O[Si](C)(C)C(C)(C)C)CN1C(=O)OC(C)(C)C ; COC(=O)[C@@H]1C[C@H](O[Si](C)(C)C(C)(C)C)C(=O)N1C(=O)OC(C)(C)C]

A mixture of NaIO4 (279 g, 1.30 mol, 4.00 equiv), ruthenium(iv) oxide hydrate (8.7 g, 57.58 mmol, 0.20 equiv), and 1-tert-butyl 2-methyl (2S,4S)-4-[(tert-butyldimethylsilyl)oxy]pyrrolidine-1,2-dicarboxylate (117 g, 325.42 mmol, 1.00 equiv) in ethyl acetate (1.2 L)/water (1.2 L) was stirred overnight at room temperature. The mixture was separated and the organic was washed with saturated $Na_2SO_3$ and brine, dried over anhydrous sodium sulfate and concentrated under vacuum. The residue was purified by a silica gel column eluting with ethyl acetate/petroleum ether (1:10). This resulted in the title compound (73 g, 60%) as a colorless oil. LCMS [$M+H^+$] 374; $^1H$ NMR (400 MHz, $CDCl_3$) δ 4.50-4.46 (t, J=7.4 Hz, 1H), 4.32-4.38 (t, J=7.2 Hz, 1H), 3.78 (s, 3H), 2.62-2.55 (m, 1H), 2.04-1.97 (m, 1H), 1.52 (s, 9H), 0.90 (s, 9H), 0.18 (s, 3H), 0.14 (s, 3H).

Step 3: Preparation of 1-tert-butyl 2-methyl (2S,4S)-4-[(tert-butyldimethylsilyl)oxy]-5-methylidenepyrrolidine-1,2-dicarboxylate

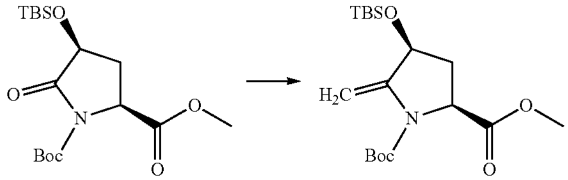

$CH_3Li$ (510 mL, 1.6M in diethyl ether, 11.00 equiv) was added dropwise into a suspension of bis(cyclopenta-1,3-dien-1-yl)titanium dihydrochloride (100 g, 401.67 mmol, 5.00 equiv) in ether (1 L) at −50° C. under nitrogen. The resulting solution was stirred for 80 min at 0° C. and quenched by 1 L of water at −50° C. The mixture was separated and the organic solution was dried over anhydrous sodium sulfate. The resulting solution was diluted with 500 mL of toluene. Most of the diethyl ether was removed under vacuum. A solution of 1-tert-butyl 2-methyl (2S,4S)-4-[(tert-butyldimethylsilyl)oxy]-5-oxopyrrolidine-1,2-dicarboxylate (30 g, 80.32 mmol, 1.00 equiv) and pyridine (25 g, 316.06 mmol, 4.00 equiv) in tetrahydrofuran (100 ml) was added into the above solution at room temperature. After being stirred for 3 h at 70° C. the resulting solution was cooled to room temperature and diluted with 1 L of petroleum ether. The solid was filtered out and the liquid was concentrated under vacuum. The residue was purified by a silica gel column eluting with petroleum ether/ethyl acetate (20:1). This resulted in the title compound (25 g, 84%) as yellow oil; LCMS [$M+H^+$] 372.

Step 4: Preparation of 1-tert-butyl 2-methyl (2S,4S,5S)-4-[(tert-butyldimethylsilyl)oxy]-5-methylpyrrolidine-1,2-dicarboxylate

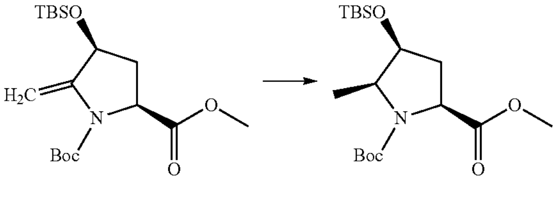

A mixture of 1-tert-butyl 2-methyl (2S,4S)-4-[(tert-butyldimethylsilyl)oxy]-5-methylidenepyrrolidine-1,2-dicarboxylate (25 g, 67.29 mmol, 1.00 equiv), methanol (800 mL) and palladium on carbon (2.5 g) was stirred for 3 h at room temperature under hydrogen. The solid was filtered out and the liquid was concentrated under vacuum. This resulted in the title compound (21 g, 84%) as colorless oil which was used for the next step without further purification. LCMS [$M+H^+$] 374; $^1H$ NMR (300 MHz, $CDCl_3$) δ 4.27-4.11 (m, 2H), 3.97-3.81 (t, 1H), 3.71 (s, 3H), 2.35-2.26 (m, 1H), 2.03-1.91 (m, 1H), 1.45-1.39 (m, 9H), 1.25-1.15 (m, 3H), 0.87 (s, 9H), 0.04 (s, 6H).

Step 5: Preparation of 1-tert-butyl 2-methyl (2S,4S,5S)-4-hydroxy-5-methylpyrrolidine-1,2-dicarboxylate

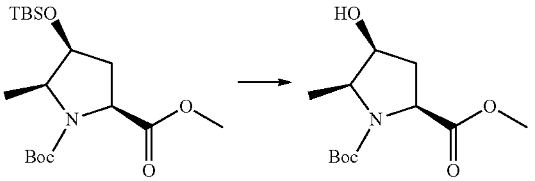

A mixture of 1-tert-butyl 2-methyl (2S,4S,5S)-4-[(tert-butyldimethylsilyl)oxy]-5-methylpyrrolidine-1,2-dicarboxylate (21 g, 56.22 mmol, 1.00 equiv) and TBAF (67 mL, 1M in THF, 1.20 equiv) in tetrahydrofuran (210 mL) was stirred for 2 h at room temperature. The resulting solution was diluted with ethyl acetate, washed with brine/aqueous HCl (0.1%)/water, dried over anhydrous sodium sulfate, and concentrated under vacuum. The residue was purified by a silica gel column eluting with ethyl acetate/petroleum ether (1/10). This resulted in the title compound (14 g, 96%) as colorless oil. LCMS [$M+H^+$] 260.

Step 6: Preparation of 1-tert-butyl 2-methyl (2S,4R,5S)-4-fluoro-5-methylpyrrolidine-1,2-dicarboxylate

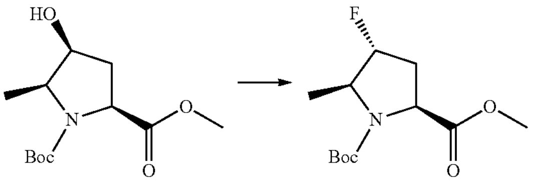

DAST (41 g, 254.36 mmol, 6.00 equiv) was added dropwise into a solution of 1-tert-butyl 2-methyl (2S,4S,5S)-4-hydroxy-5-methylpyrrolidine-1,2-dicarboxylate (11 g, 42.42 mmol, 1.00 equiv) in dichloromethane (250 mL) at −78° C. under nitrogen. The resulting solution was allowed to warm up to room temperature and stirred for 48 h. The mixture was quenched by saturated sodium bicarbonate at 0° C. and the pH value of the mixture was adjusted to 9. The resulting mixture was extracted with ethyl acetate, washed with brine, dried over anhydrous sodium sulfate, and concentrated under vacuum. The residue was purified by a silica gel column eluting with ethyl acetate/petroleum ether (1/10). This resulted in the title compound (4.2 g, 38%) as light yellow oil. LCMS [$M+H^+$] 262; $^1H$ NMR (300 MHz, $CDCl_3$) δ 4.97-4.75 (d, J=51.6 Hz, 1H), 4.48-4.06 (m, 2H), 3.75 (s, 3H), 2.58-2.05 (m, 2H), 1.61-1.42 (m, 9H), 1.28-1.22 (m, 3H).

Step 7: Preparation of (2S,4R,5S)-1-[(tert-butoxy) carbonyl]-4-fluoro-5-methylpyrrolidine-2-carboxylic Acid

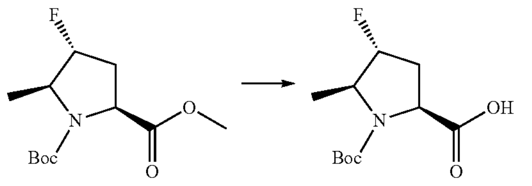

A mixture of 1-tert-butyl 2-methyl (2S,4R,5S)-4-fluoro-5-methylpyrrolidine-1,2-dicarboxylate (2.4 g, 9.19 mmol, 1.00 equiv) and LiOH (441 mg, 18.42 mmol, 2.01 equiv) in methanol (100 mL)/water (25 mL) was stirred for 12 h at 50° C. The resulting mixture was concentrated under vacuum and the mixture was dissolved in water. The pH value of the aqueous solution was adjusted to 3-5 with hydrogen chloride (1N). The resulting solution was extracted with ethyl acetate, dried over anhydrous sodium sulfate, and concentrated under vacuum. This resulted in the title compound (2 g) as a light yellow solid which was used for the next step without further purification. LCMS [M+H$^+$] 148; $^1$H NMR (400 MHz, $CD_3OD$) δ 5.00-4.86 (d, J=51.6 Hz, 1H), 4.36-4.29 (m, 1H), 4.14-4.07 (m, 1H), 2.61-2.51 (m, 1H), 2.32-2.17 (m, 1H), 1.51-1.46 (m, 9H), 1.24-1.22 (d, J=7.2 Hz, 3H).

Preparation 2: (S)-4-(tert-butoxycarbonyl)-4-azaspiro[2.4]heptane-5-carboxylic Acid

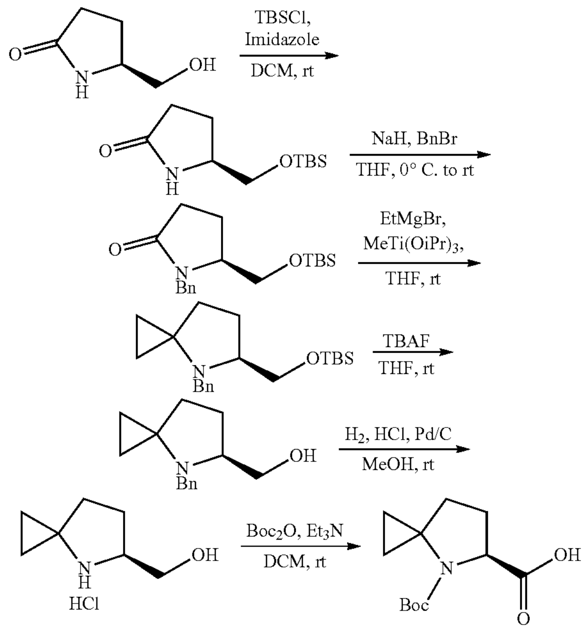

Step 1: Preparation of (5S)-5-[[(tert-butyldimethyl-silyl)oxy]methyl]pyrrolidin-2-one

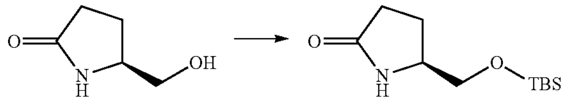

TBS-Cl (7.826 g, 51.92 mmol, 1.20 equiv) was added in several batches into a mixture of (5S)-5-(hydroxymethyl) pyrrolidin-2-one (5 g, 43.43 mmol, 1.00 equiv) and imidazole (5.913 g, 86.86 mmol, 2.00 equiv) in dichloromethane (100 mL) at room temperature. After being stirred at room temperature for 2 h the resulting solution was diluted with brine, extracted with ethyl acetate, washed with brine, dried over anhydrous sodium sulfate, and concentrated under vacuum. The residue was purified by a silica gel column eluting with ethyl acetate/petroleum ether (1:10) to afford the title compound (8.4 g, 84%) as colorless oil. LCMS [M+H$^+$] 230.

Step 2: Preparation of (5S)-1-benzyl-5-[[(tert-butyldimethylsilyl)oxy]methyl]pyrrolidin-2-one

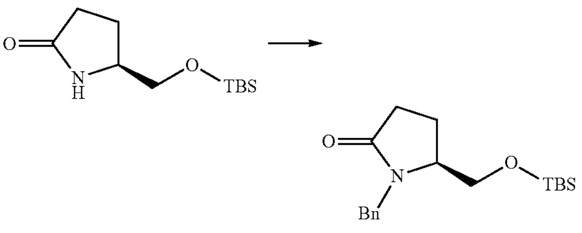

Sodium hydride (3.535 g, 147.31 mmol, 4.17 equiv) was added in several batches into a solution of (5S)-5-[[(tert-butyldimethylsilyl)oxy]methyl]pyrrolidin-2-one (8.096 g, 35.29 mmol, 1.00 equiv) in tetrahydrofuran (100 mL) at 0° C. under nitrogen. The reaction was stirred for 30 min at 0° C. and then benzyl bromide (9.051 g, 52.92 mmol, 1.50 equiv) was added dropwise with stirring at 0° C. After being stirred for 12 h at room temperature the resulting solution was diluted with saturated $NH_4Cl$, extracted with ethyl acetate, washed with brine, dried over anhydrous sodium sulfate, and concentrated under vacuum. The residue was purified by a silica gel column eluting with ethyl acetate/hexane (1/4) to afford the title compound (6 g, 53%) as yellow oil. LCMS [M+H$^+$] 320.

Step 3: Preparation of (5S)-4-benzyl-5-[[(tert-butyldimethylsilyl)oxy]methyl]-4-azaspiro[2.4]heptane

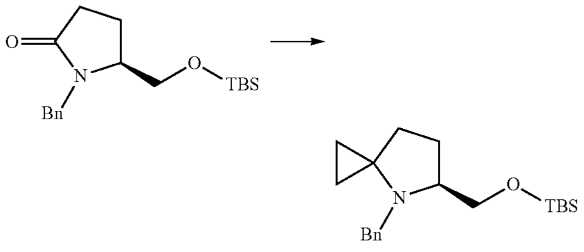

Ethylmagnesium bromide (28.1 mL, 1M in THF, 3.00 equiv) followed by methyltris(propan-2-yloxy)titanium (23.4 mL, 1M in THF, 2.50 equiv) were added dropwise into a mixture of (5S)-1-benzyl-5-[[(tert-butyldimethylsilyl)oxy]methyl]pyrrolidin-2-one (3 g, 9.39 mmol, 1.00 equiv) in tetrahydrofuran (50 mL) at room temperature under nitrogen. After being stirred for 12 h the resulting solution was quenched by water and diluted with diethyl ether. The solid was filtered out and the liquid was dried over anhydrous sodium sulfate. The mixture was concentrated under vacuum. The residue was purified by a silica gel column eluting with ethyl acetate/petroleum ether (1/20) to afford the title compound (1.4 g, 45%) as colorless oil. LCMS [M+H$^+$] 332.

Step 4: Preparation of [(5S)-4-benzyl-4-azaspiro[2.4]heptan-5-yl]methanol

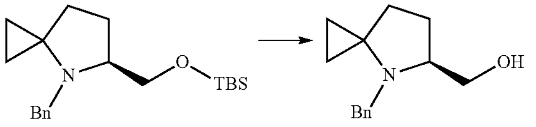

A mixture of (5S)-4-benzyl-5-[[(tert-butyldimethylsilyl)oxy]methyl]-4-azaspiro[2.4]heptane (1.4 g, 4.22 mmol, 1.00 equiv) and TBAF (4.2 mL, 1M in THF, 1.00 equiv) in tetrahydrofuran (20 mL) was stirred for 12 h at room temperature. The resulting solution was diluted with water, extracted with ethyl acetate, washed with brine, dried over anhydrous sodium sulfate, and concentrated under vacuum. The residue was purified by a silica gel column eluting with ethyl acetate/petroleum ether (1/10) to afford the title compound (340 mg, 37%) as colorless oil. LCMS [M+H$^+$] 218.

Step 5: Preparation of (5S)-4-azaspiro[2.4]heptan-5-ylmethanol hydrochloride

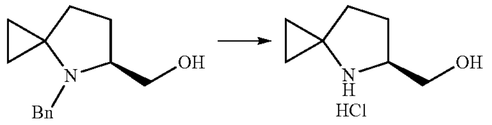 [SMILES: OC[C@@H]1CCC2(CC2)N1Cc1ccccc1 ; OC[C@@H]1CCC2(CC2)N1 ; Cl]

A mixture of [(5S)-4-benzyl-4-azaspiro[2.4]heptan-5-yl]methanol (540 mg, 2.49 mmol, 1.00 equiv) and palladium on carbon (100 mg), and concentrated hydrogen chloride (1 mL) in methanol (100 mL) was stirred for 5 h at room temperature under hydrogen. The solid was filtered out and the liquid was concentrated under vacuum. This resulted in the title compound (1.0 g) as brown oil. LCMS [M+H$^+$] 128.

Step 6: Preparation of tert-butyl (5S)-5-(hydroxymethyl)-4-azaspiro[2.4]heptane-4-carboxylate

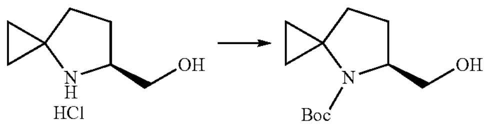 [SMILES: OC[C@@H]1CCC2(CC2)N1 ; Cl ; CC(C)(C)OC(=O)N1[C@H](CO)CCC12CC2]

A mixture of (5S)-4-azaspiro[2.4]heptan-5-ylmethanol hydrochloride (1.0 g, 6.11 mmol, 1.00 equiv), TEA (739 mg, 7.30 mmol, 1.20 equiv), and $Boc_2O$ (1.6 g, 7.33 mmol, 1.20 equiv) in dichloromethane (20 mL) was stirred for 12 h at room temperature. The resulting solution was diluted with dichloromethane, washed with saturated $NH_4Cl$ and brine, dried over anhydrous sodium sulfate, and concentrated under vacuum. The residue was purified by a silica gel column eluting with ethyl acetate/petroleum ether (1/10) to afford the title compound (350 mg, 25%) as colorless oil. LCMS [M+H$^+$] 228.

Step 7: Preparation of (5S)-4-[(tert-butoxy)carbonyl]-4-azaspiro[2.4]heptane-5-carboxylic acid

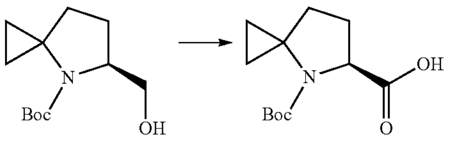 [SMILES: CC(C)(C)OC(=O)N1[C@H](CO)CCC12CC2 ; CC(C)(C)OC(=O)N1[C@H](C(=O)O)CCC12CC2]

A solution of $NaIO_4$ (848 mg, 3.96 mmol, 3.00 equiv) in water (9 mL) was added into a solution of tert-butyl (5S)-5-(hydroxymethyl)-4-azaspiro[2.4]heptane-4-carboxylate (300 mg, 1.32 mmol, 1.00 equiv) in $CH_3CN$ (6 mL)/$CCl_4$ (6 mL) at room temperature. $RuCl_3.H_2O$ (6 mg, 0.03 mmol, 0.02 equiv) was then immediately added into the above reaction mixture. The reaction was stirred for 12 h at room temperature. The resulting mixture was diluted with water, extracted with dichloromethane, dried over anhydrous sodium sulfate, and concentrated under vacuum. This resulted in the title compound (290 mg, crude) as light yellow oil. LCMS [M+H$^+$] 242.

Preparation 3: 5-(4,4,5,5-tetramethyl-1,3,2-dioxaborolan-2-yl)-2-(trifluoromethyl)pyrimidine

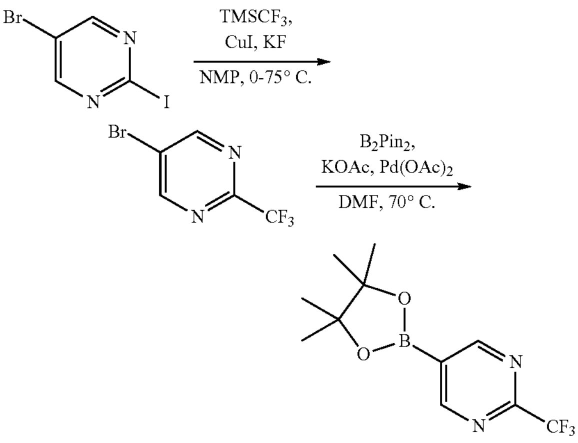

Step 1: Preparation of 5-bromo-2-(trifluoromethyl)pyrimidine

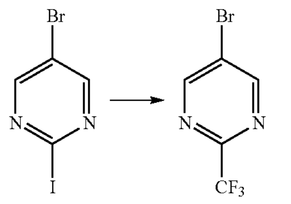 [SMILES: Brc1cnc(I)nc1 ; FC(F)(F)c1ncc(Br)cn1]

Trimethyl(trifluoromethyl)silane (400 g, 2.81 mol, 4.01 equiv) was added dropwise with stirring into a mixture of CuI (260 g, 1.37 mol, 1.95 equiv) in NMP (1500 mL), KF (82 g, 1.41 mol, 2.01 equiv), and 5-bromo-2-iodopyrimidine (200 g, 702.048 mmol, 1.0 equiv) at 0° C. under nitrogen. The mixture was then stirred for 1 h at 40° C. and then for 12 h at 75° C. The reaction was cooled and then quenched by the addition of 3 L of water. The mixture was extracted with petroleum ether (3×1 L), washed with brine (4×2 L), dried over anhydrous sodium sulfate, and concentrated under vacuum at 10° C. The crude oil was purified by a silica gel column eluting with petroleum ether to afford the title compound (50 g, 31%) (90% purity in petroleum ether) as a light yellow solid.

Step 2: Preparation of 5-(4,4,5,5-tetramethyl-1,3,2-dioxaborolan-2-yl)-2-(trifluoromethyl)pyrimidine

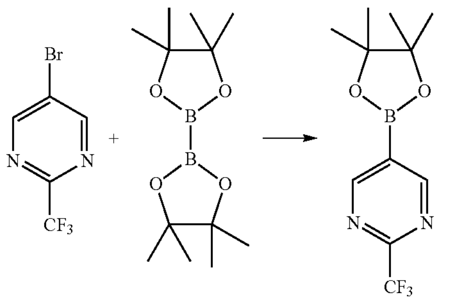

Into a 500-mL 3-necked round-bottom flask purged and maintained with an inert atmosphere of nitrogen, was placed 5-bromo-2-(trifluoromethyl)pyrimidine (16.5 g, 73.0 mmol, 1.0 equiv), N,N-dimethylformamide (150 mL), 4,4,5,5-tetramethyl-2-(tetramethyl-1,3,2-dioxaborolan-2-yl)-1,3,2-dioxaborolane (18.6 g, 73.3 mmol, 1.0 equiv), KOAc (21.5 g, 219.7 mmol, 3.0 equiv), stirred over 30 min, then followed by $Pd(OAc)_2$ (525 mg, 2.33 mmol, 0.03 equiv). The resulting solution was stirred for 12 h at 70° C. in an oil bath. The solids were filtered out. The resulting solution was diluted with 500 mL of brine. The resulting solution was extracted with 3×200 mL of ethyl acetate and the organic layers combined. The resulting mixture was washed with 3×500 mL of brine. The mixture was dried over anhydrous sodium sulfate and concentrated under vacuum. This resulted in 26 g (crude) of 5-(tetramethyl-1,3,2-dioxaborolan-2-yl)-2-(trifluoromethyl)pyrimidine as brown oil.

Preparation 4: (5-fluoro-2-(2-(trifluoromethyl)pyrimidin-5-yl)pyridin-4-yl)methanamine

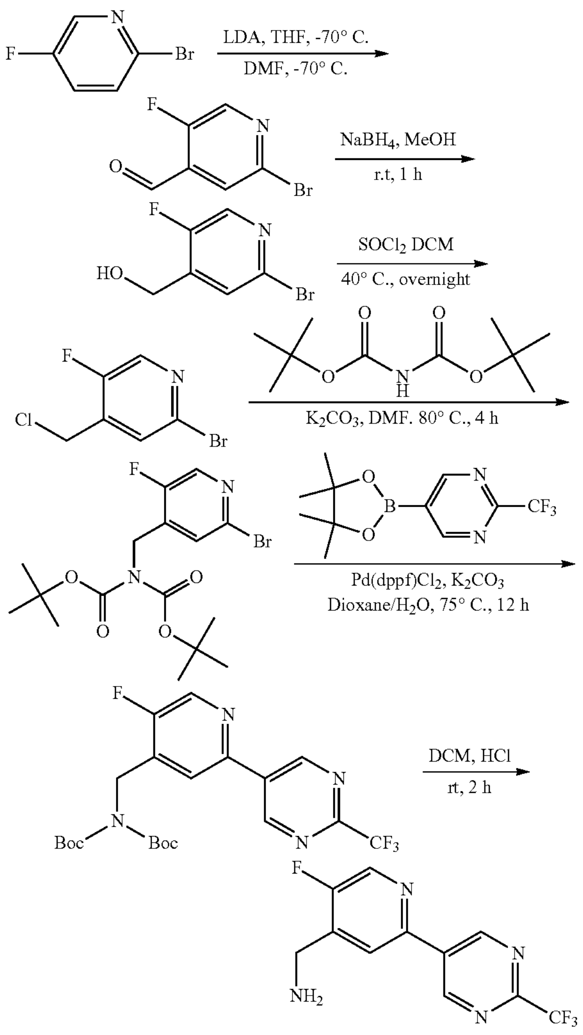

Step 1: Preparation of 2-bromo-5-fluoroisonicotinaldehyde

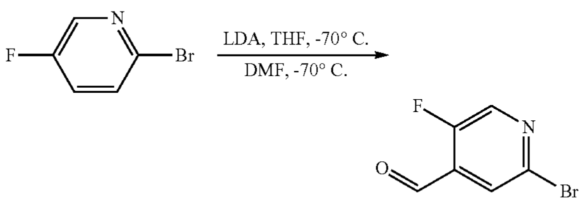

To a 3000-mL 4-necked round-bottom flask purged and maintained with an inert atmosphere of nitrogen was placed a solution of diisopropylamine (86.57 g, 1.50 equiv) in tetrahydrofuran (1500 mL) followed by the addition of n-BuLi (2.4 mol/L) (310 mL, 1.30 equiv) dropwise with stirring at −35° C. The resulting solution was stirred at −30° C. for 30 min. To this mixture was added a solution of 2-bromo-5-fluoropyridine (100 g, 568.23 mmol, 1.00 equiv) in tetrahydrofuran (200 mL) dropwise with stirring at −75° C. The resulting solution was stirred at −75° C. for an additional 2 h. To the mixture was added N,N-dimethylformamide (83.4 g, 2.00 equiv) dropwise with stirring at −70° C. The resulting solution was stirred for an additional 2 h at −70° C. and quenched by the addition of 4 N HCl. The pH value of the solution was adjusted to 6 with 4N HCl solution. The resulting solution was extracted with 3×1000 mL of ethyl acetate. The combined organic layers were washed with 1×500 mL of brine, dried over anhydrous sodium sulfate and concentrated under vacuum to afford 125 g (crude) of 2-bromo-5-fluoropyridine-4-carbaldehyde as yellow oil.

Step 2: Preparation of (2-bromo-5-fluoropyridin-4-yl)methanol

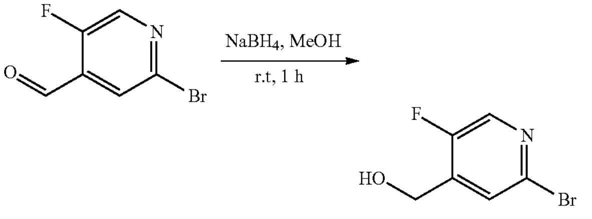

To a 2000-mL 4-necked round-bottom flask purged and maintained with an inert atmosphere of nitrogen was placed a solution of 2-bromo-5-fluoropyridine-4-carbaldehyde (125 g, 612.75 mmol, 1.00 equiv) in methanol (1000 mL) followed by the addition of $NaBH_4$ (23.4 g, 635.44 mmol, 1.00 equiv) dropwise with stirring at 0° C. The resulting solution was stirred at room temperature for 1 h, concentrated under vacuum, diluted with 500 mL of $H_2O$, and extracted with 3×800 mL of ethyl acetate. The combined organic layers were washed with 1×500 mL of brine, dried over anhydrous sodium sulfate and concentrated under vacuum. The residue was applied onto a silica gel column eluted with ethyl acetate/petroleum ether (1:4) to afford 80 g (63%) of (2-bromo-5-fluoropyridin-4-yl)methanol as a white solid.

Step 3: Preparation of 2-bromo-4-(chloromethyl)-5-fluoropyridine

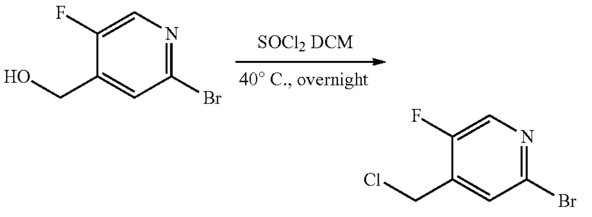

To a 2000-mL 4-necked round-bottom flask purged and maintained with an inert atmosphere of nitrogen was placed a solution of (2-bromo-5-fluoropyridin-4-yl)methanol (80 g, 388.33 mmol, 1.00 equiv) in dichloromethane (800 mL) followed by the addition of thionyl chloride (240 mL) dropwise with stirring at 0° C. The resulting solution was stirred at 40° C. overnight and concentrated under vacuum to afford 90 g (crude) of 2-bromo-4-(chloromethyl)-5-fluoropyridine as yellow oil.

Step 4: Preparation of bis-tert-butyl (2-bromo-5-fluoropyridin-4-yl)methylcarbamate

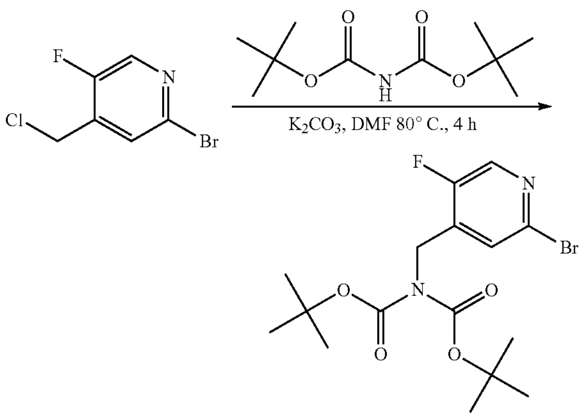

To a 2000-mL 4-necked round-bottom flask purged and maintained with an inert atmosphere of nitrogen was placed a solution of 2-bromo-4-(chloromethyl)-5-fluoropyridine (90 g, 400.97 mmol, 1.00 equiv) in N,N-dimethylformamide (900 mL), $K_2CO_3$ (167 g, 1.20 mol, 2.99 equiv) and tert-butyl N-[(tert-butoxy)carbonyl]carbamate (103.7 g, 477.30 mmol, 1.19 equiv). The resulting solution was stirred at 80° C. for 4 h, quenched by the addition of 2000 mL of water/ice, and extracted with 3×800 mL of ethyl acetate. The combined organic layers were washed with 1×600 mL of brine, dried over anhydrous sodium sulfate and concentrated under vacuum. The residue was applied onto a silica gel column eluted with ethyl acetate/petroleum ether (1:10) to afford 110 g (68%) of tert-butyl N-[(2-bromo-5-fluoropyridin-4-yl)methyl]-N-[(tert-butoxy)carbonyl]carbamate as a white solid.

Step 5: Preparation of bis-tert-butyl (5-fluoro-2-(2-(trifluoromethyl)pyrimidin-5-yl)pyridin-4-yl)methylcarbamate

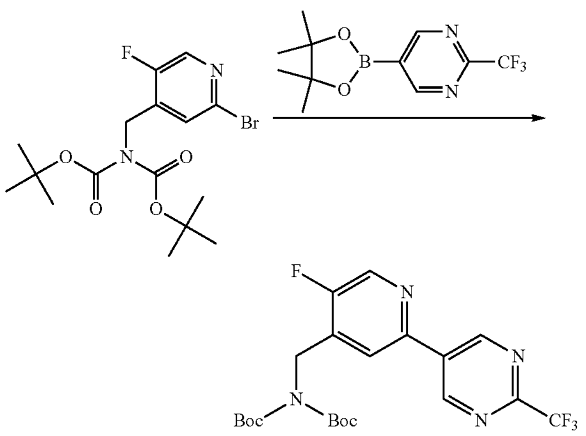

To a 2000-mL 4-necked round-bottom flask purged and maintained with an inert atmosphere of nitrogen was placed a solution of tert-butyl N-[(2-bromo-5-fluoropyridin-4-yl)methyl]-N-[(tert-butoxy)carbonyl]carbamate (105 g, 259.09 mmol, 1.00 equiv) in dioxane (1500 mL), 5-(tetramethyl-1,3,2-dioxaborolan-2-yl)-2-(trifluoromethyl)pyrimidine (142 g, 518.16 mmol, 2.00 equiv), $K_2CO_3$ (107.5 g, 772.20 mmol, 2.98 equiv) and water (150 mL), Pd(dppf)$Cl_2$ (20 g, 27.33 mmol, 0.11 equiv). The resulting solution was stirred at 75° C. for 12 h, cooled to room temperature, diluted with 2000 mL of ethyl acetate, and filtered. The filtrate was washed with 2×500 mL of water, dried over anhydrous sodium sulfate and concentrated under vacuum. The residue was applied onto a silica gel column eluted with ethyl acetate/petroleum ether (1:8) to afford 60 g (49%) of tert-butyl N-[(tert-butoxy)carbonyl]-N-([5-fluoro-2-[2-(trifluoromethyl)pyrimidin-5-yl]pyridin-4-yl]methyl)carbamate as a white solid.

Step 6: Preparation of (5-fluoro-2-(2-(trifluoromethyl)pyrimidin-5-yl)pyridin-4-yl)methanamine

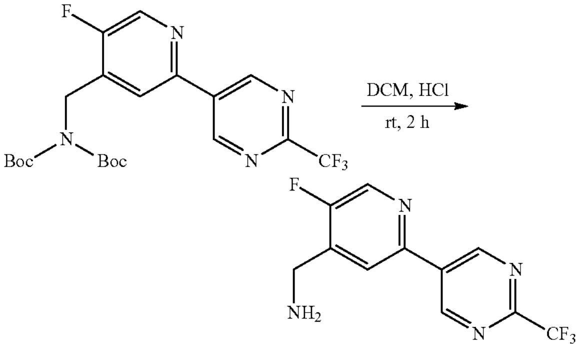

To a 1000-mL 4-necked round-bottom flask was placed a solution of tert-butyl N-[(tert-butoxy)carbonyl]-N-([5-fluoro-2-[2-(trifluoromethyl)pyrimidin-5-yl]pyridin-4-yl]methyl)carbamate (60 g, 127.00 mmol, 1.00 equiv) in dichloromethane (600 mL) followed by the introduction of hydrogen chloride (enough, gas). The resulting solution was stirred at room temperature for 2 h, concentrated under vacuum, and diluted with water. The pH value of the solution was adjusted to 9 with aqueous sodium carbonate (2 mol/L) solution. The resulting solution was extracted with 3×1000 mL of ethyl acetate. The combined organic layers were dried over anhydrous sodium sulfate and concentrated under vacuum. The residue was applied onto a silica gel column eluted with ethyl acetate/petroleum ether (9:1). The crude product was re-crystallized from EA:PE in the ratio of 1:10 to afford 20 g (58%) of [5-fluoro-2-[2-(trifluoromethyl)pyrimidin-5-yl]pyridin-4-yl]methanamine as a yellow solid. LCMS $[M+H]^+$ 273; $^1H$-NMR (300 MHz, DMSO-d6) δ9.65 (s, 2H), 8.67 (d, J=1.5 Hz, 1H), 8.43 (d, J=6.0 Hz, 1H), 3.88 (s, 2H), 2.17 (s, 2H).

Preparation 5: (2-fluoro-5-(2-(trifluoromethyl)pyrimidin-5-yl)phenyl)methanamine

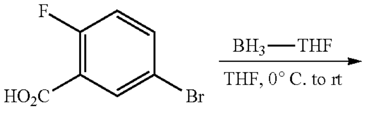

-continued

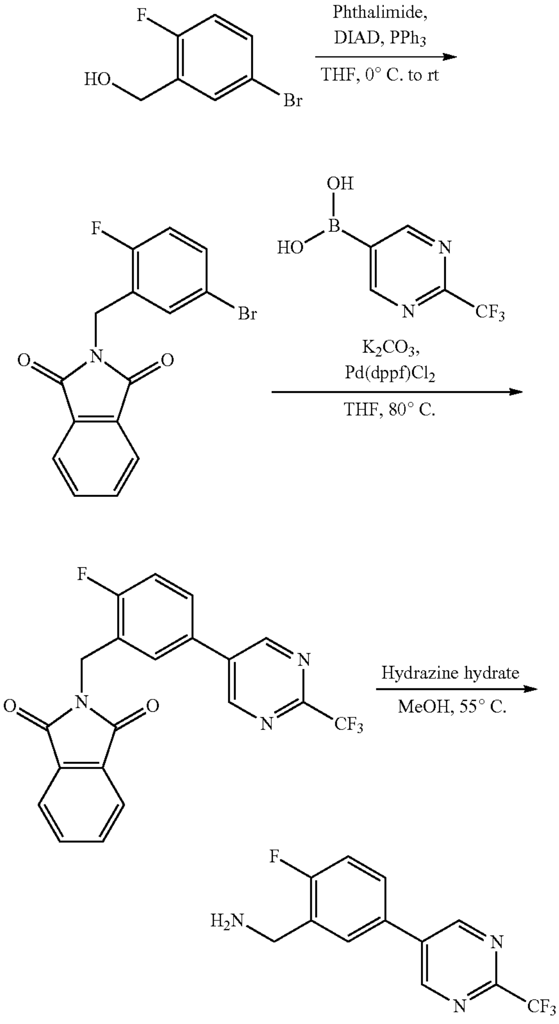

Step 1: Preparation of (5-bromo-2-fluorophenyl)methanol

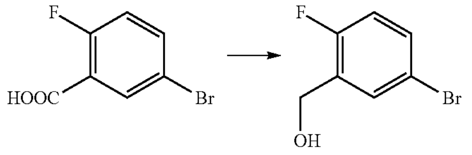 [SMILES: O=C(O)c1cc(Br)ccc1F ; OCc1cc(Br)ccc1F]

$BH_3$-THF (229 mL, 1 M in THF, 5.00 equiv) was added dropwise into a solution of 5-bromo-2-fluorobenzoic acid (10 g, 45.66 mmol, 1.00 equiv) in tetrahydrofuran (150 mL) at 0° C. under nitrogen. The resulting solution was stirred overnight at room temperature, quenched by water, extracted with ethyl acetate, washed with brine, dried over anhydrous sodium sulfate, and concentrated under vacuum. The residue was purified by a silica gel column eluting with ethyl acetate/petroleum ether (1:5) to afford the title compound (9.5 g) as light yellow oil. GCMS m/z=204, 206.

Step 2: Preparation of 2-[(5-bromo-2-fluorophenyl) methyl]-2,3-dihydro-1H-isoindole-1,3-dione

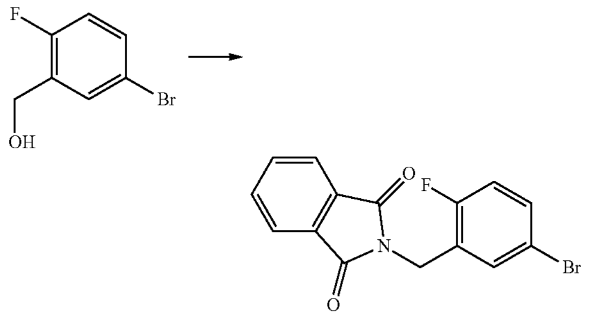

DIAD (18.8 g, 92.97 mmol, 2.01 equiv) was added dropwise into a stirred mixture of (5-bromo-2-fluorophenyl) methanol (9.5 g, 46.34 mmol, 1.00 equiv), 2,3-dihydro-1H-isoindole-1,3-dion (13.6 g, 92.44 mmol, 2.00 equiv), and $PPh_3$ (24.4 g, 93.03 mmol, 2.01 equiv) in tetrahydrofuran (300 mL) at 0° C. under nitrogen. The resulting solution was stirred overnight at room temperature and concentrated under vacuum. The residue was purified by a silica gel column eluting with ethyl acetate/petroleum ether (1:10) to afford the title compound (9.5 g, 61%) as a white solid. LCMS [M+H$^+$] 334; $^1$H NMR (300 MHz, $CDCl_3$) δ 7.89-7.83 (m, 2H), 7.78-7.70 (m, 2H), 7.66-7.63 (m, 1H), 7.40-7.35 (m, 1H), 7.09-7.03 (m, 1H), 4.78 (s, 2H).

Step 3: Preparation of 2-([2-fluoro-5-[2-(trifluoromethyl)pyrimidin-5-yl]phenyl]methyl)-2,3-dihydro-1H-isoindole-1,3-dione

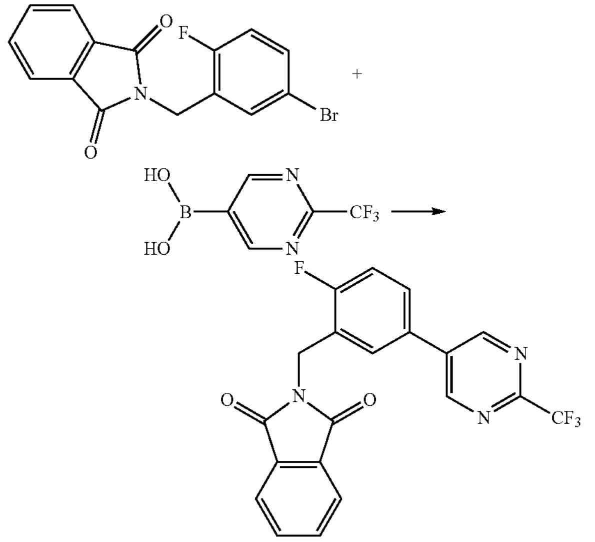

A mixture of 2-[(5-bromo-2-fluorophenyl)methyl]-2,3-dihydro-1H-isoindole-1,3-dione (2 g, 5.99 mmol, 1.00 equiv), 5-(tetramethyl-1,3,2-dioxaborolan-2-yl)-2-(trifluoromethyl)pyrimidine (2.1 g, 7.66 mmol, 1.28 equiv), Pd(dppf)$Cl_2$ (438 mg, 0.60 mmol, 0.10 equiv), and potassium carbonate (1.65 g, 11.94 mmol, 2.00 equiv) in tetrahydrofuran (25 mL) was stirred overnight at 80° C. The resulting mixture was concentrated under vacuum and the residue was purified by a silica gel column eluting with ethyl acetate/petroleum ether (1:100-1:10). This resulted in the title compound (1.7 g, 71%) as a light yellow solid.

LCMS [M+H$^+$] 402.

Step 4: Preparation of [2-fluoro-5-[2-(trifluoromethyl)pyrimidin-5-yl]phenyl]methanamine

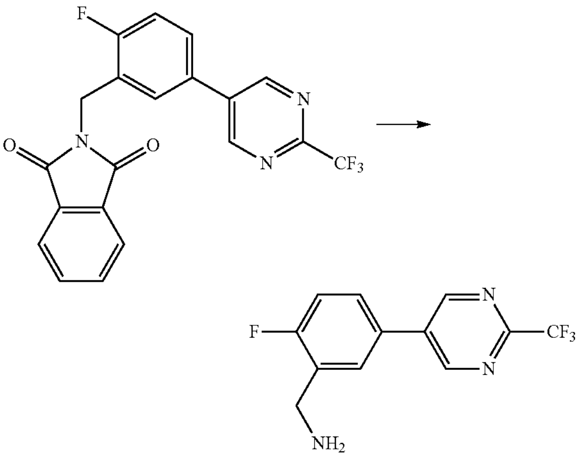

A mixture of 2-([2-fluoro-5-[2-(trifluoromethyl)pyrimidin-5-yl]phenyl]methyl)-2,3-dihydro-1H-isoindole-1,3-dione (500 mg, 1.25 mmol, 1.00 equiv) and hydrazine hydrate (623 mg, 12.45 mmol, 10.00 equiv) in methanol (10 mL) was stirred overnight at 55° C. The resulting mixture was concentrated under vacuum. The residue was dissolved in ethyl acetate. The solid was filtered out and the liquid was concentrated under vacuum. This resulted in the title compound (300 mg, crude) as light yellow oil. LCMS [M+H$^+$] 272

Preparation 6: [3-methoxy-1-[2-(trifluoromethyl) pyrimidin-5-yl]-1H-pyrazol-4-yl]methanamine

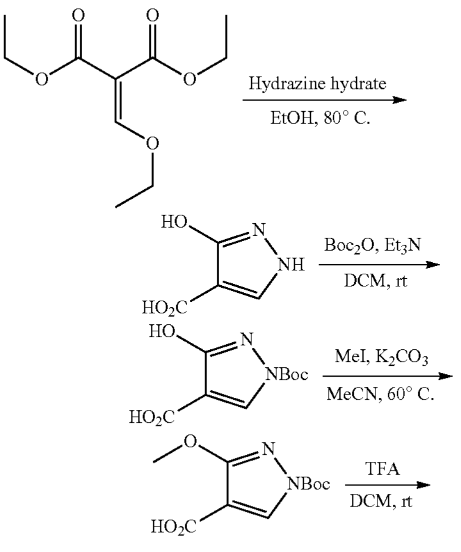

-continued

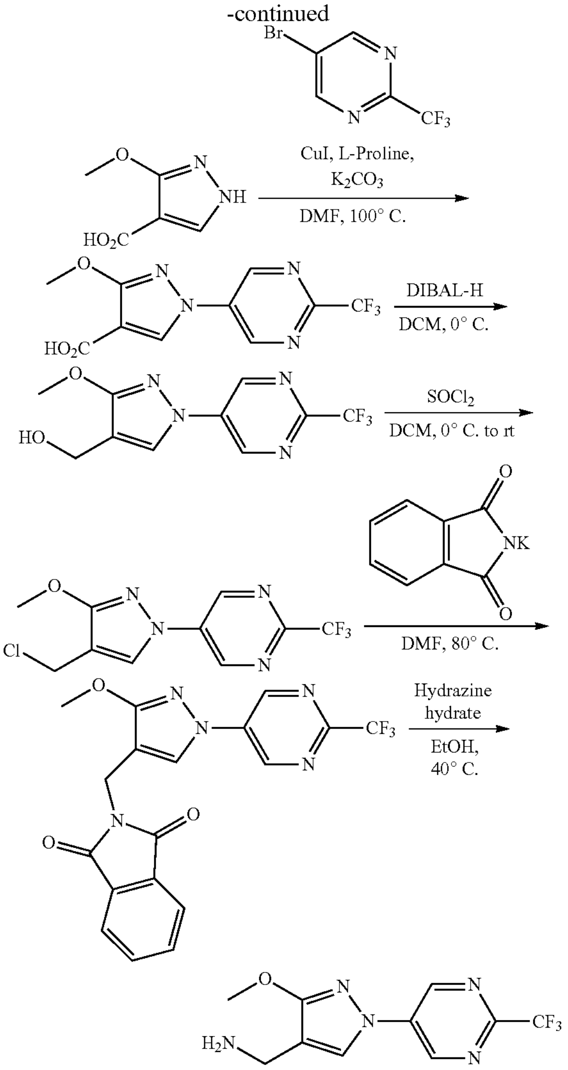

Step 1: Preparation of ethyl 3-hydroxy-1H-pyrazole-4-carboxylate

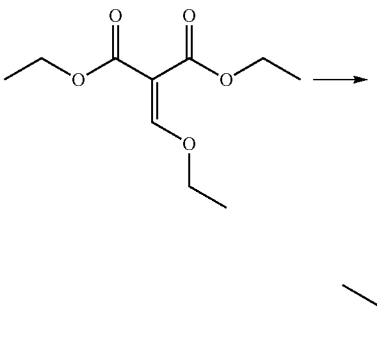

Hydrazine hydrate (18.52 g, 0.37 mol) was added dropwise into a stirred solution of 1,3-diethyl 2-(ethoxymethylidene)propanedioate (40.00 g, 0.18 mol) in ethanol (400 mL) at 0° C. The resulting mixture was stirred overnight at 80° C. The mixture was cooled to room temperature. The solid was collected by filtration to afford the title compound (18 g, 62%) as a light yellow solid. LCMS [M+H$^+$] 157.

Step 2: Preparation of 1-tert-butyl 4-ethyl 3-hydroxy-1H-pyrazole-1,4-dicarboxylate

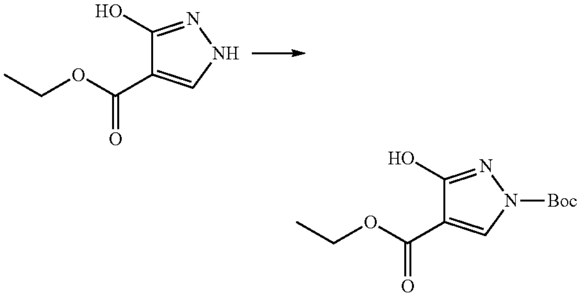

A mixture of ethyl 3-hydroxy-1H-pyrazole-4-carboxylate (10 g, 64.05 mmol), triethylamine (13 g, 128.47 mmol) and $Boc_2O$ (14 g, 64.15 mmol) in dichloromethane (200 mL) was stirred overnight at room temperature. The mixture was concentrated under vacuum and the residue was washed with ethyl acetate to afford the title compound (6 g, 37%) as a white solid. LCMS [M+H$^+$] 257.

Step 3: Preparation of 1-tert-butyl 4-ethyl 3-methoxy-1H-pyrazole-1,4-dicarboxylate

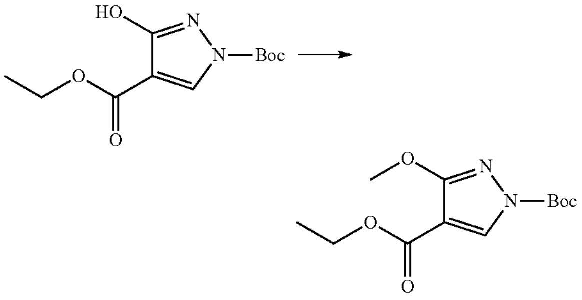

A mixture of 1-tert-butyl 4-ethyl 3-hydroxy-1H-pyrazole-1,4-dicarboxylate (500 mg, 1.95 mmol, 1.00 equiv) in $CH_3CN$ (10 mL), potassium carbonate (540 mg, 3.91 mmol, 2.00 equiv), and $CH_3I$ (830 mg, 5.85 mmol, 3.00 equiv) was stirred overnight at 60° C. The solid was filtered out and the liquid was concentrated under vacuum to afford the title compound (450 mg, 85%) as light yellow oil. LCMS [M+H$^+$] 271.

Step 4: Preparation of ethyl 3-methoxy-1H-pyrazole-4-carboxylate

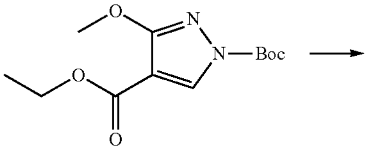

-continued

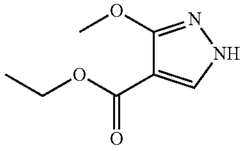

A mixture of 1-tert-butyl 4-ethyl 3-methoxy-1H-pyrazole-1,4-dicarboxylate (450 mg, 1.67 mmol) in dichloromethane (10 mL) and trifluoroacetic acid (3 mL) was stirred for 3 h at room temperature. The reaction mixture was concentrated under vacuum and diluted with water. The pH value of the mixture was adjusted to 8 with saturated aqueous sodium bicarbonate. The resulting mixture was extracted with dichloromethane, washed with brine, dried over anhydrous sodium sulfate, and concentrated under vacuum. The residue was purified by a silica gel column eluting with ethyl acetate/petroleum ether (1:5) to afford the title compound (200 mg, 71%) as light yellow oil. LCMS [M+H$^+$] 171.

Step 5: Preparation of ethyl 3-methoxy-1-[2-(trifluoromethyl)pyrimidin-5-yl]-1H-pyrazole-4-carboxylate

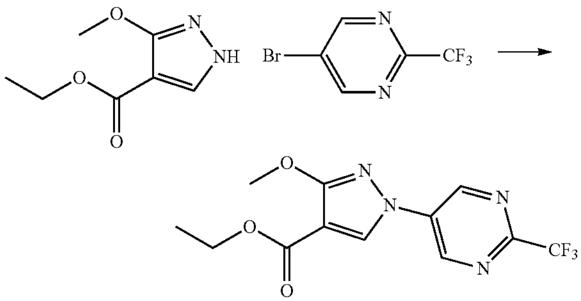

A mixture of ethyl 3-methoxy-1H-pyrazole-4-carboxylate (200 mg, 1.18 mmol), CuI (23 mg, 0.12 mmol), L-proline (28 mg, 0.24 mmol), 5-bromo-2-(trifluoromethyl)pyrimidine (320 mg, 1.41 mmol), and potassium carbonate (407 mg, 2.95 mmol) in N,N-dimethylformamide (6 mL) was stirred overnight at 100° C. under nitrogen. The solid was filtered out and the liquid was concentrated. The residue was purified by a silica gel column eluting with dichloromethane to afford the title compound (210 mg, 57%) as a light yellow solid. LCMS [M+H]$^+$ 317; $^1$H NMR (300 MHz, $CDCl_3$) δ 9.21 (s, 2H), 8.40 (s, 1H), 4.39-4.32 (m, 2H), 4.12 (s, 3H), 1.38 (t, J=7.2 Hz, 3H).

Step 6: Preparation of [3-methoxy-1-[2-(trifluoromethyl)pyrimidin-5-yl]-1H-pyrazol-4-yl]methanol

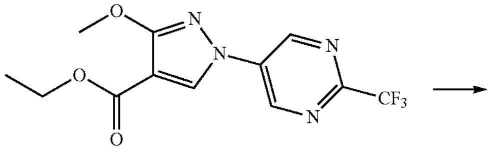

-continued

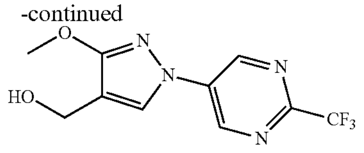

DIBAL-H (1.3 mL, 1.30 mmol, 1 mol/L in hexane) was added dropwise into a stirred solution of ethyl 3-methoxy-1-[2-(trifluoromethyl)pyrimidin-5-yl]-1H-pyrazole-4-carboxylate (200 mg, 0.63 mmol) in dichloromethane (10 mL) at 0° C. under nitrogen. After being stirred for 3 h at 0° C. the reaction was quenched with saturated aqueous ammonium chloride and extracted with dichloromethane. The combined organic layers were dried over anhydrous sodium sulfate and concentration. The residue was purified by a silica gel column eluting with dichloromethane/methanol (40:1) to afford the title compound (100 mg, 58%) as a light yellow solid. LCMS [M+H]$^+$ 275; $^1$H NMR (300 MHz, $CDCl_3$) δ 9.11 (s, 2H), 7.87 (s, 1H), 4.60 (s, 2H), 4.06 (s, 3H).

Step 7: Preparation of 5-[4-(chloromethyl)-3-methoxy-1H-pyrazol-1-yl]-2-(trifluoromethyl)pyrimidine

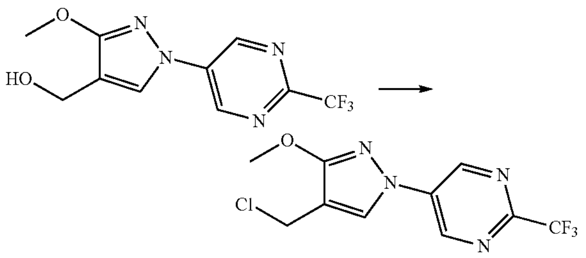

Thionyl chloride (174 mg, 1.47 mmol) was added dropwise into a stirred solution of [3-methoxy-1-[2-(trifluoromethyl)pyrimidin-5-yl]-1H-pyrazol-4-yl]methanol (100 mg, 0.37 mmol) in dichloromethane (10 mL) at 0° C. The resulting solution was stirred for 30 min at room temperature. The reaction was then quenched by saturated aqueous sodium bicarbonate, extracted with dichloromethane, washed with brine, dried over anhydrous sodium sulfate, and concentrated under vacuum. The residue was purified by a silica gel column eluting with ethyl acetate/petroleum ether (1:5) to afford the title compound (70 mg, 66%) as a light yellow solid.

Step 8: Preparation of 2-([3-methoxy-1-[2-(trifluoromethyl)pyrimidin-5-yl]-1H-pyrazol-4-yl]methyl)-2,3-dihydro-1H-isoindole-1,3-dione

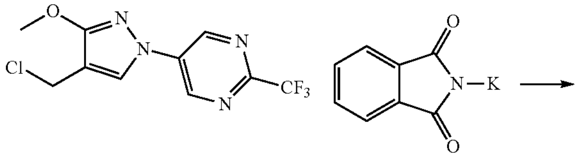

-continued

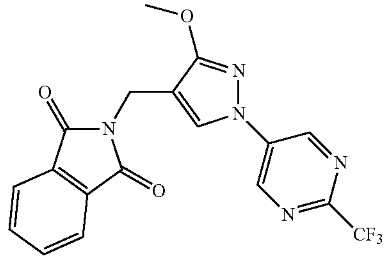

A mixture of 5-[4-(chloromethyl)-3-methoxy-1H-pyrazol-1-yl]-2-(trifluoromethyl)pyrimidine (60 mg, 0.21 mmol) in N,N-dimethylformamide (3 mL) and 2-potassio-2,3-dihydro-1H-isoindole-1,3-dione (60 mg, 0.33 mmol) was stirred for 1 h at 80° C. The resulting mixture was concentrated under vacuum. The residue was dissolved in dichloromethane. The solid was filtered out and the filtrate was concentrated to afford the title compound (80 mg, 97%) as an off-white solid. LCMS $[M+H]^+$ 404.

Step 9: Preparation of [3-methoxy-1-[2-(trifluoromethyl)pyrimidin-5-yl]-1H-pyrazol-4-yl]methanamine

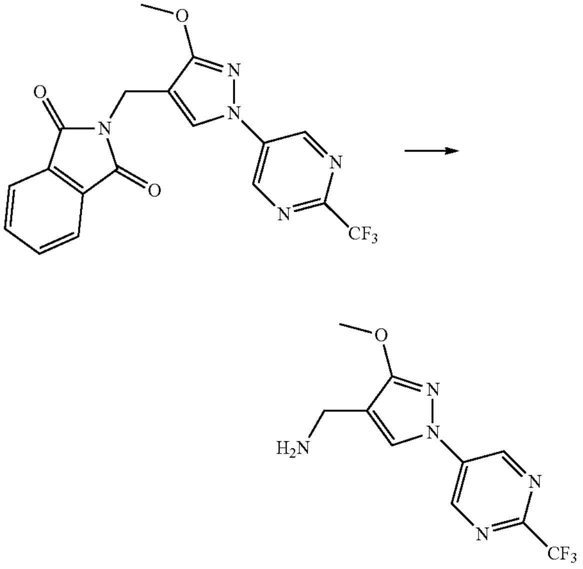

A mixture of 2-([3-methoxy-1-[2-(trifluoromethyl)pyrimidin-5-yl]-1H-pyrazol-4-yl]methyl)-2,3-dihydro-1H-isoindole-1,3-dione (150 mg, 0.38 mmol) in ethanol (10 mL) and hydrazine hydrate (190 mg, 3.80 mmol) was stirred overnight at 40° C. The reaction mixture was concentrated under vacuum and the residue was dissolved in dichloromethane. The solid was filtered out and the filtrate was concentrated under vacuum. This resulted in the title compound (70 mg, 69%) as an off-white solid. LCMS $[M+H]^+$ 274.

Preparation 7: (5-(trifluoromethyl)-2,4'-bipyrimidin-6'-yl)methanamine

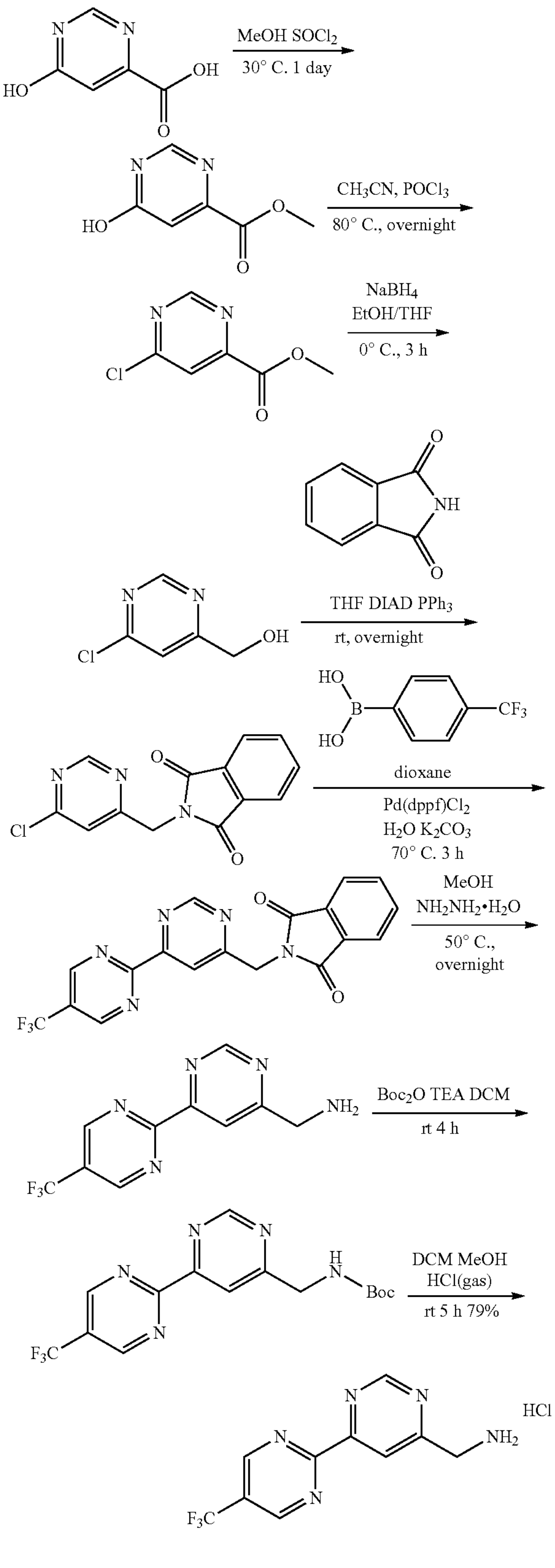

Step 1: Preparation of methyl 6-hydroxypyrimidine-4-carboxylate

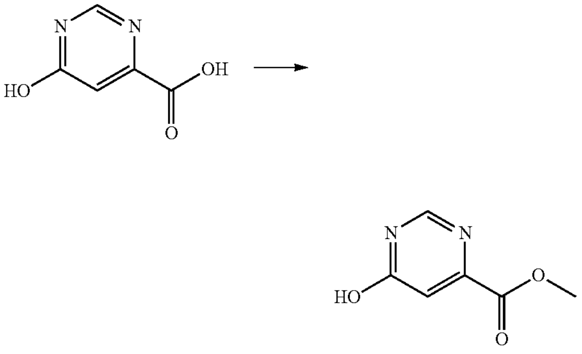

Into a 5-L 4-necked round-bottom flask purged and maintained with an inert atmosphere of nitrogen was placed 6-hydroxypyrimidine-4-carboxylic acid (100 g, 713.79 mmol, 1.00 equiv) and methanol (2000 mL) followed by the addition of thionyl chloride (210 g, 2.50 equiv) dropwise with stirring at 0° C. The resulting solution was stirred at 30° C. for 1 day and concentrated under vacuum to afford 115 g (crude) of methyl 6-hydroxypyrimidine-4-carboxylate as a off-white solid. LCMS $[M+H]^+$ 155.

Step 2: Preparation of methyl 6-chloropyrimidine-4-carboxylate

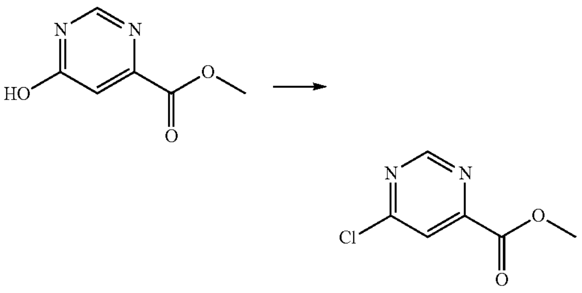

Into a 2000-mL 4-necked round-bottom flask was placed methyl 6-hydroxypyrimidine-4-carboxylate (115 g, 746.16 mmol, 1.00 equiv), $CH_3CN$ (1200 mL), and $POCl_3$ (340 g, 2.22 mol, 3.00 equiv). The resulting solution was stirred at 80° C. overnight, cooled to room temperature, concentrated under vacuum, diluted with 1000 mL of EA, and quenched with 1000 mL of water/ice. The resulting solution was extracted with 3×500 mL of ethyl acetate. The combined organic layers were washed with 1×1000 mL of water and 1×1000 mL of brine, dried over anhydrous sodium sulfate, and concentrated under vacuum. The residue was applied onto a silica gel column eluted with ethyl acetate/petroleum ether (1:4) to afford 76 g (59%) of methyl 6-chloropyrimidine-4-carboxylate as a white solid. LCMS $[M+H]^+$ 173.

Step 3: Preparation of (6-chloropyrimidin-4-yl)methanol

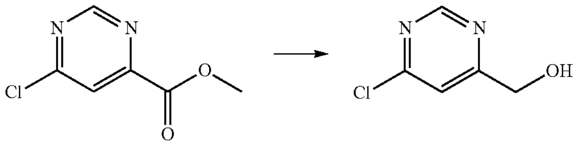

Into a 3000-mL 4-necked round-bottom flask was placed methyl 6-chloropyrimidine-4-carboxylate (80 g, 463.58 mmol, 1.00 equiv), tetrahydrofuran (1600 mL), and ethanol (160 mL) followed by the addition of $NaBH_4$ (48 g, 1.27 mol, 3.00 equiv) in several batches at 0° C. The resulting solution was stirred at 0° C. for 3 h, quenched by the addition of 1500 mL of water/ice, and extracted with 3×800 mL of ethyl acetate. The combined organic layers were washed with 1×800 mL of brine, dried over anhydrous sodium sulfate, and concentrated under vacuum. The residue was applied onto a silica gel column eluted with ethyl acetate/petroleum ether (1:2) to afford 40 g (60%) of (6-chloropyrimidin-4-yl)methanol as a yellow solid. LCMS $[M+H]^+$ 145.

Step 4: Preparation of 2-((6-chloropyrimidin-4-yl)methyl)isoindoline-1,3-dione

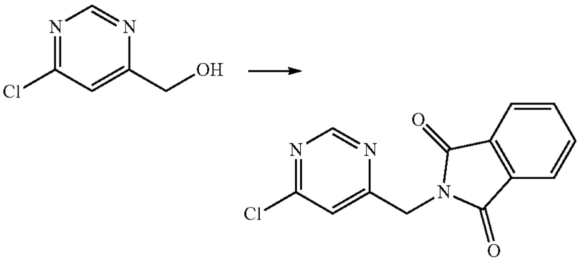

Into a 3000-mL 4-necked round-bottom flask was placed (6-chloropyrimidin-4-yl)methanol (50 g, 345.88 mmol, 1.00 equiv), tetrahydrofuran (1500 mL), 2,3-dihydro-1H-isoindole-1,3-dione (76.4 g, 519.27 mmol, 1.50 equiv), and $PPh_3$ (136 g, 518.51 mmol, 1.50 equiv) followed by the addition of DIAD (105 g, 519.26 mmol, 1.50 equiv) dropwise with stirring at 0° C. The resulting solution was stirred at room temperature overnight, concentrated under vacuum, diluted with 1000 mL of EA, stirred for additional 30 min, and filtered. The filter cake was washed with 1×300 mL of EA to afford 65 g (69%) of 2-[(6-chloropyrimidin-4-yl)methyl]-2,3-dihydro-1H-isoindole-1,3-dione as a off-white solid. LCMS $[M+H]^+$ 274.

Step 5: Preparation of 2-((5-(trifluoromethyl)-2,4'-bipyrimidin-6'-yl)methyl)isoindoline-1,3-dione

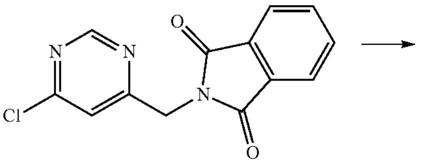

-continued

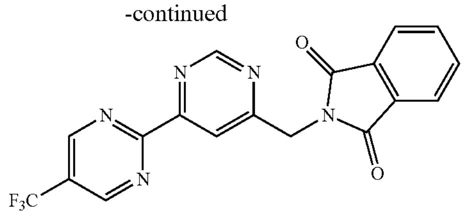

Into a 3000-mL 4-necked round-bottom flask purged and maintained with an inert atmosphere of nitrogen was placed 2-[(6-chloropyrimidin-4-yl)methyl]-2,3-dihydro-1H-isoindole-1,3-dione (50 g, 182.70 mmol, 1.00 equiv), 1,4-dioxane (1500 mL), water (70 mL), potassium carbonate (50 g, 361.77 mmol, 2.00 equiv), [2-(trifluoromethyl)pyrimidin-5-yl]boronic acid (91 g, 474.20 mmol, 2.50 equiv), and Pd(dppf)$Cl_2$ (4 g, 5.47 mmol, 0.02 equiv). The resulting solution was stirred at 70° C. for 3 h, cooled to room temperature, quenched by the addition of 3 L of water, and extracted with 3×1 L of ethyl acetate. The combined organic layers were dried over anhydrous sodium sulfate and concentrated under vacuum. The residue was applied onto a silica gel column eluted with ethyl acetate/petroleum ether (1:10) to afford 55 g (78%) of 2-([6-[2-(trifluoromethyl) pyrimidin-5-yl]pyrimidin-4-yl]methyl)-2,3-dihydro-1H-isoindole-1,3-dione as a white solid. LCMS $[M+H]^+$ 386.

Step 6: Preparation of (5-(trifluoromethyl)-2,4'-bipyrimidin-6'-yl)methanamine

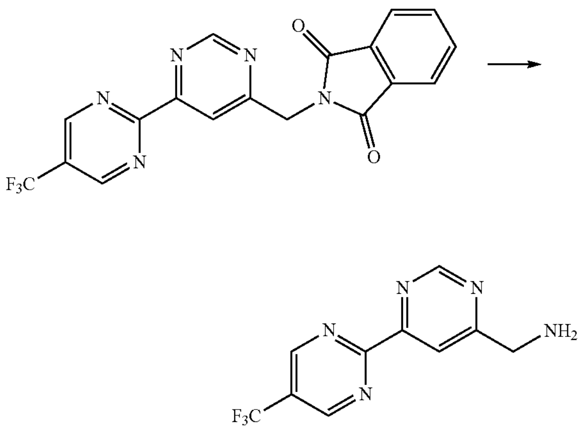

Into a 3000-mL 4-necked round-bottom flask was placed 2-([6-[2-(trifluoromethyl)pyrimidin-5-yl]pyrimidin-4-yl] methyl)-2,3-dihydro-1H-isoindole-1,3-dione (55 g, 142.75 mmol, 1.00 equiv), methanol (1500 mL), and $NH_2NH_2.H_2O$ (110 g, 15.00 equiv). The resulting solution was at 50° C. stirred overnight, cooled to room temperature, and filtered. The filtrate diluted with 1 L of $H_2O$ and extracted with 3×500 mL of ethyl acetate, The combined organic layers were dried over anhydrous sodium sulfate and concentrated under vacuum to afford 35 g (crude) of [6-[2-(trifluoromethyl)pyrimidin-5-yl]pyrimidin-4-yl]methanamine as a brown solid.

Step 7: Preparation of tert-butyl (5-(trifluoromethyl)-2,4'-bipyrimidin-6'-yl)methylcarbamate

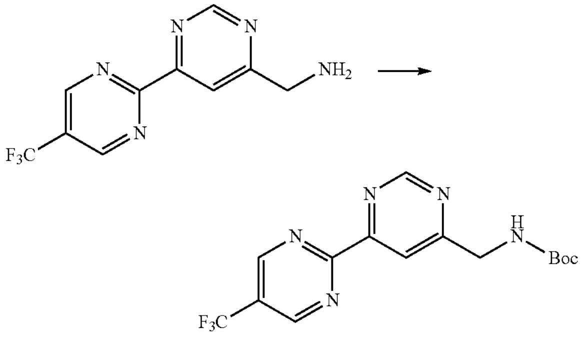

Into a 2000-mL 4-necked round-bottom flask was placed [6-[2-(trifluoromethyl)pyrimidin-5-yl]pyrimidin-4-yl]methanamine (35 g, 137.15 mmol, 1.00 equiv), dichloromethane (700 mL), TEA (20 g, 197.65 mmol, 1.50 equiv), and $(Boc)_2O$ (44 g, 201.60 mmol, 1.50 equiv). The resulting solution was stirred at room temperature for 4 h, diluted with 2 L of $H_2O$, and extracted with 3×800 mL of dichloromethane. The combined organic layers were dried over anhydrous sodium sulfate and concentrated under vacuum. The residue was applied onto a silica gel column eluted with ethyl acetate/petroleum ether (1:5). This resulted in 40 g (82%) of tert-butyl N-([6-[2-(trifluoromethyl)pyrimidin-5-yl]pyrimidin-4-yl]methyl)carbamate as a yellow solid. LCMS $[M+H]^+$ 356.

Step 8: Preparation of (5-(trifluoromethyl)-2,4'-bipyrimidin-6'-yl)methanamine hydrochloride

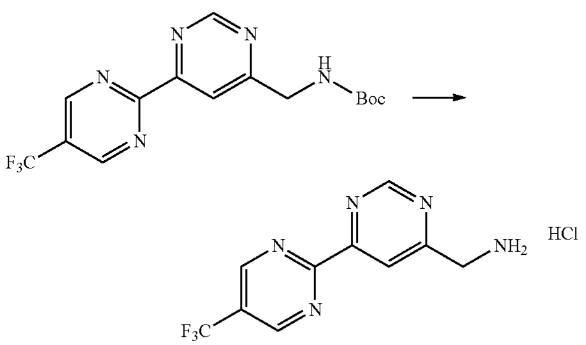

Into a 2000-mL 4-necked round-bottom flask was placed tert-butyl N-([6-[2-(trifluoromethyl)pyrimidin-5-yl]pyrimidin-4-yl]methyl)carbamate (40 g, 112.58 mmol, 1.00 equiv), dichloromethane (800 mL), and methanol (400 mL). To the above hydrogen chloride (enough, gas) was introduced in. The resulting solution was stirred at room temperature for 5 h, concentrated under vacuum, diluted with 200 mL of hexane, and filtered to afford 26 g (79%) of [6-[2-(trifluoromethyl)pyrimidin-5-yl]pyrimidin-4-yl]methanamine hydrochloride as a light yellow solid. LCMS $[M+H]^+$ 256; $^1$H-NMR (300 MHz, DMSO) δ 9.78 (2H, s), 9.45 (1H, s), 8.67-8.76 (3H, ds), 8.62 (1H, s), 4.33-4.37 (2H, t).

Preparation 8: (5-fluoro-4-((5-(trifluoromethyl)pyridin-3-yl)methoxy)pyridin-2-yl)methanamine

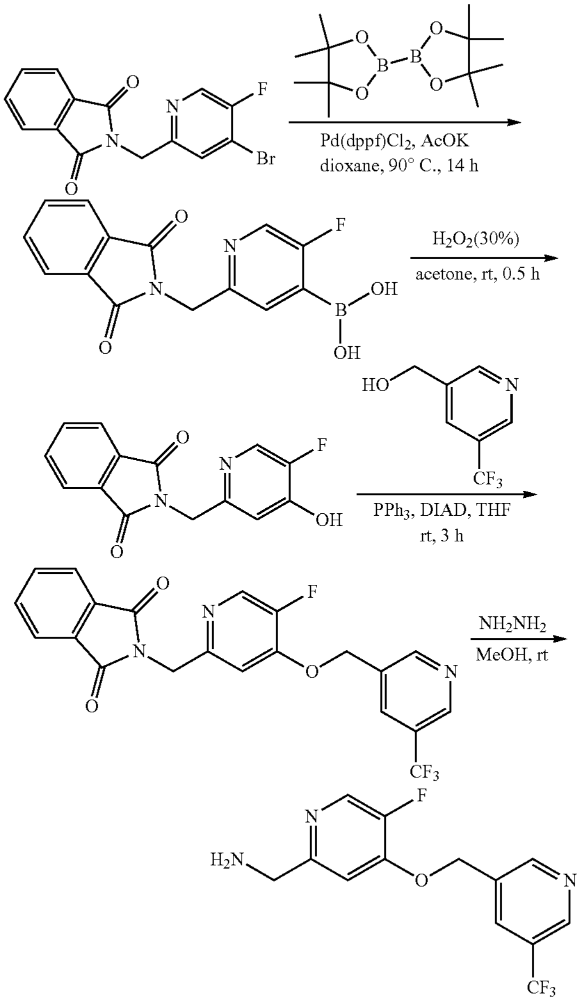

Step 1: Preparation of 2-((1,3-dioxoisoindolin-2-yl)methyl)-5-fluoropyridin-4-ylboronic Acid

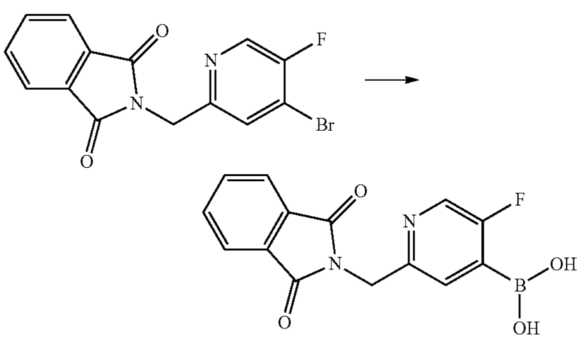

A mixture of 4,4,5,5-tetramethyl-2-(4,4,5,5-tetramethyl-1,3-dioxolan-2-yl)-1,3,2-dioxaborolane (3.5 g, 13.664 mmol, 1.500 equiv), 2-[(4-bromo-5-fluoropyridin-2-yl)

methyl]-2,3-dihydro-1H-isoindole-1,3-dione (3 g, 8.952 mmol, 1.000 equiv), KOAc (1.8 g, 18.341 mmol, 2.000 equiv), Pd(dppf)$Cl_2$ (660 mg, 0.902 mmol, 0.100 equiv), and dioxane (60 mL) was stirred overnight at 95° C. under nitrogen. The resulting solution was cooled was room temperature, diluted with EtOAc, washed with $H_2O$, dried over anhydrous sodium sulfate, and concentrated under vacuum. The residue was suspended in 100 mL of hexane. The solids were collected by filtration to afford 3 g (crude) of the title compound as a brown solid. LCMS [M+H+] 301.

Step 2: Preparation of 2-((5-fluoro-4-hydroxypyridin-2-yl)methyl)isoindoline-1,3-dione

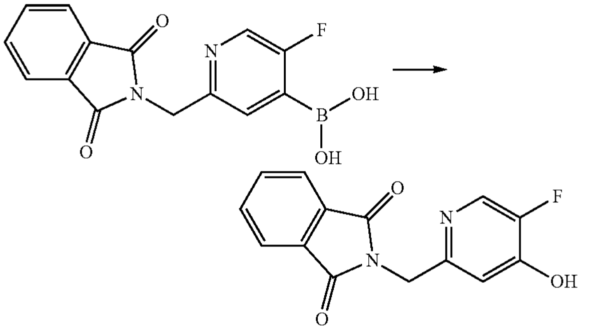

$H_2O_2$ (30%) (20 mL) was added dropwise into a solution of [2-[(1,3-dioxo-2,3-dihydro-1H-isoindol-2-yl)methyl]-5-fluoropyridin-4-yl]boronic acid (3 g, 9.998 mmol, 1.000 equiv) in acetone (60 mL) with stirring at room temperature. The resulting solution was stirred for 20 min at room temperature and concentrated under vacuum. The solids were collected by filtration. This resulted in 1.6 g (59%) of the title compound as a brown solid. LCMS [M+H+] 273

Step 3: Preparation of 2-((5-fluoro-4-((5-(trifluoromethyl)pyridin-3-yl)methoxy)pyridin-2-yl)methyl) isoindoline-1,3-dione

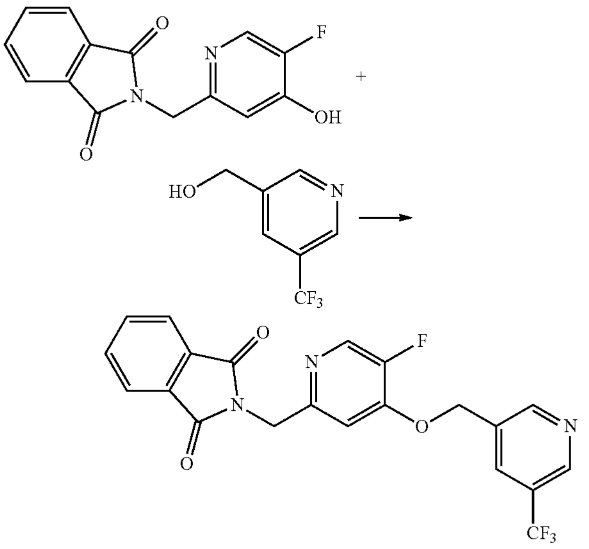

DIAD (570 mg, 2.819 mmol, 2.000 equiv) was added dropwise into a solution of 2-[(5-fluoro-4-hydroxypyridin-2-yl)methyl]-2,3-dihydro-1H-isoindole-1,3-dione (384 mg, 1.411 mmol, 1.000 equiv), (5-(trifluoromethyl)pyridin-3-yl) methanol (224 mg, 1.265 mmol, 0.900 equiv), $PPh_3$ (740 mg, 2.821 mmol, 2.000 equiv) in tetrahydrofuran (20 mL) with stirring at 0° C. under nitrogen. The resulting solution was stirred for 3 h at room temperature and concentrated under vacuum. The residue was purified by a silica gel column eluting with ethyl acetate/petroleum ether (2:1) to afford the title compound (520 mg, 85%) as a white solid. LCMS [M+H+] 432.

Step 4: Preparation of (5-fluoro-4-((5-(trifluoromethyl)pyridin-3-yl)methoxy)pyridin-2-yl)methanamine

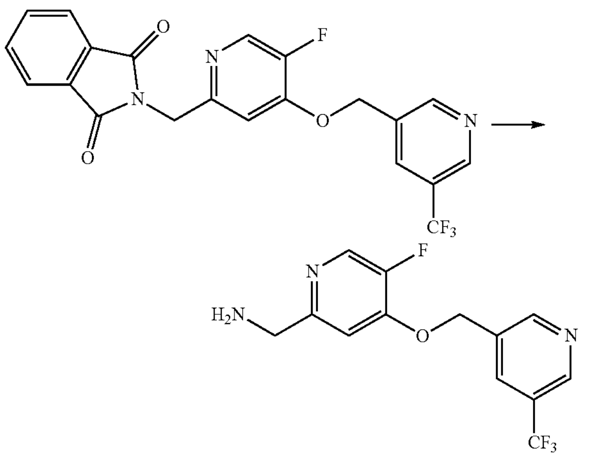

A solution of 2-((5-fluoro-4-((5-(trifluoromethyl)pyridin-3-yl)methoxy)pyridin-2-yl)methyl)isoindoline-1,3-dione (520 mg, 1.206 mmol, 1.00 equiv), hydrazine hydrate (1 mL, 80%) in methanol (10 mL) was stirred overnight at 30° C. The resulting mixture was concentrated under vacuum. The residue was dissolved in 50 mL of EtOAc. The solids were filtered out and the filtrate was concentrated under vacuum. This resulted in 350 mg (crude) of the title compound as a white solid. LCMS [M+H+] 302.

Preparation 9: [6-[3-(trifluoromethoxy)azetidin-1-yl] pyrimidin-4-yl]methanamine

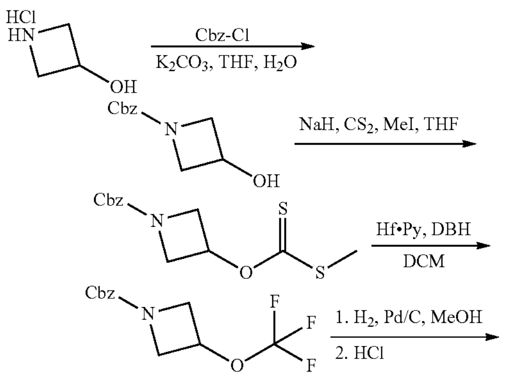

-continued

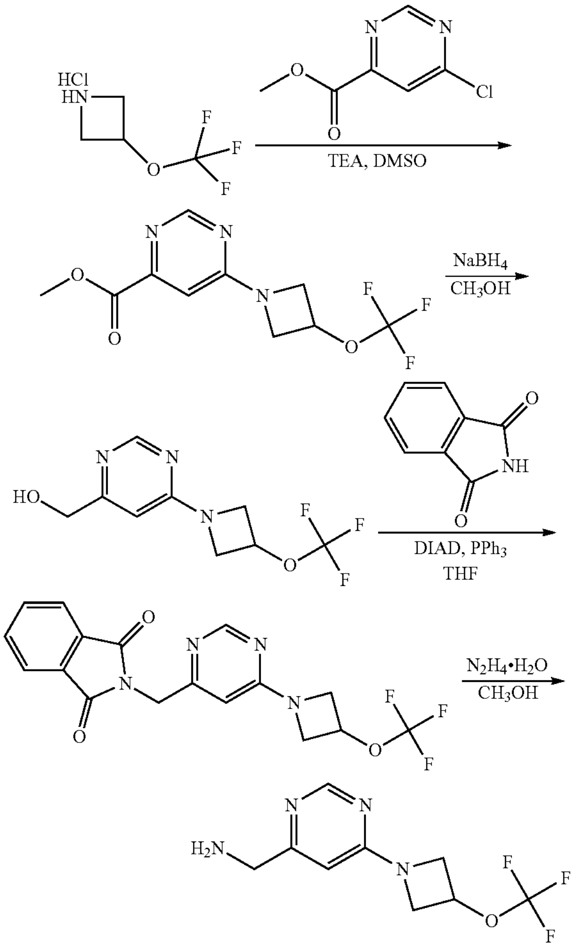

Step 1: Preparation of benzyl 3-hydroxyazetidine-1-carboxylate

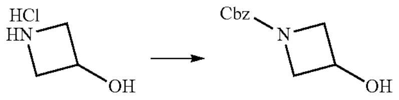 [SMILES: Cl ; OC1CNC1 ; O=C(OCc1ccccc1)N1CC(O)C1]

A mixture of azetidin-3-ol hydrochloride (12 g, 109.53 mmol, 1.00 equiv), tetrahydrofuran (150 mL), water (70 mL), and potassium carbonate (30 g, 217.07 mmol, 2.00 equiv) was stirred for 30 min at room temperature. This was followed by the addition of benzyl chloroformate (22 g, 128.96 mmol, 1.20 equiv) dropwise with stirring at 0° C. in 30 min. The resulting solution was stirred overnight at room temperature. The solids were filtered out and the solution was extracted with ethyl acetate, washed with brine, dried over anhydrous sodium sulfate, and concentrated under vacuum. The residue was purified by a silica gel column eluting with ethyl acetate/petroleum ether (1:2) to afford the title compound (20 g, 87%) as light yellow oil. LCMS $[M+H^+]$ 208; $^1$HNMR (400 MHz, DMSO-$d_6$) δ 7.39-7.30 (m, 5H), 5.70-5.69 (d, J=5.2 Hz, 1H), 5.03 (s, 2H), 4.44-4.42 (m, 1H), 4.10 (m, 2H), 3.69 (m, 2H).

Step 2: Preparation of benzyl 3-[[(methylsulfanyl) methanethioyl]oxy]azetidine-1-carboxylate

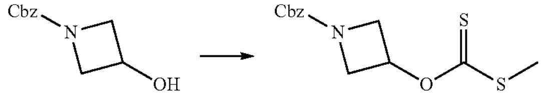 [SMILES: O=C(OCc1ccccc1)N1CC(O)C1 ; CSC(=S)OC1CN(C(=O)OCc2ccccc2)C1]

A solution of benzyl 3-hydroxyazetidine-1-carboxylate (11.5 g, 55.0 mmol, 1.00 equiv) in tetrahydrofuran (30 mL) was added dropwise into a suspension of sodium hydride (5.32 g, 221.89 mmol, 4.00 equiv) in tetrahydrofuran (80 mL) at 0° C. under nitrogen. The resulting solution was stirred for 30 min at room temperature. This was followed by the addition of a solution of carbon disulfide (12.65 g, 116.13 mmol, 3.00 equiv) in tetrahydrofuran (40 mL) dropwise with stirring at 0° C. The resulting solution was stirred for 1.5 h at 0° C. To this was added $CH_3I$ (12.33 g, 86.86 mmol, 6.00 equiv) dropwise with stirring at 0° C. The resulting solution was allowed to react, with stirring, for an additional 3 h at room temperature. The reaction was then quenched by $NH_4Cl$ (aq.), extracted with ethyl acetate, washed with brine, dried over anhydrous sodium sulfate, and concentrated under vacuum. The residue was purified by a silica gel column eluting with ethyl acetate/petroleum ether (1:5) to afford the title compound (13 g, 78%) as yellow oil. LCMS [M+H$^+$] 298; $^1$HNMR (400 MHz, $CDCl_3$) δ 7.34-7.26 (m, 5H), 5.61-5.60 (d, J=3.6 Hz, 1H), 5.10 (s, 2H), 4.39-4.35 (m, 2H), 4.12-4.10 (m, 2H), 2.56 (s, 3H).

Step 3: Preparation of benzyl 3-(trifluoromethoxy)azetidine-1-carboxylate

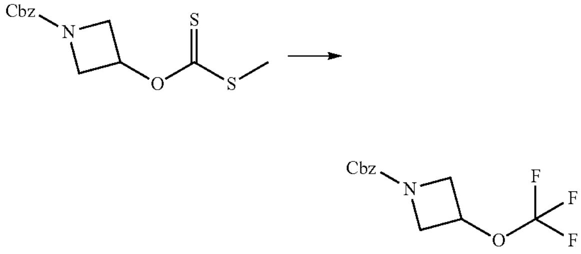

HF-Pyridine (42 g, W=70%, 22.00 equiv) was added dropwise into a mixture of 1,3-dibromo-5,5-dimethylimidazolidine-2,4-dione (11.56 g, 40.43 mmol, 3.00 equiv) and dichloromethane (100 mL) with stirring at −78° C. under nitrogen. To this was added a solution of benzyl 3-[[(methylsulfanyl)methanethioyl]oxy]azetidine-1-carboxylate (4 g, 13.45 mmol, 1.00 equiv) in dichloromethane (20 mL) at −78° C. The resulting solution was stirred overnight at room temperature. The reaction was then quenched by $NaHCO_3$ (aq.), extracted with dichloromethane, washed with brine, dried over anhydrous sodium sulfate, and concentrated under vacuum. The residue was purified by a silica gel column eluting with ethyl acetate/petroleum ether (1:5) to afford the title compound (3.5 g, 95%) as yellow oil. LCMS [M+H$^+$] 276.

Step 4: Preparation of 3-(trifluoromethoxy)azetidine

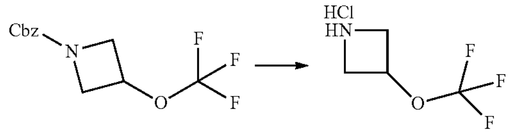 [SMILES: Cl ; O=C(OCc1ccccc1)N1CC(OC(F)(F)F)C1 ; FC(F)(F)OC1CNC1]

A mixture of benzyl 3-(trifluoromethoxy)azetidine-1-carboxylate (1 g, 3.63 mmol, 1.00 equiv), methanol (20 mL), palladium on carbon (200 mg) and concentrated hydrogen chloride (0.5 mL) was stirred for 2 h at room temperature under hydrogen. The solids were filtered out and the solution was concentrated under vacuum. This resulted in the title compound (560 mg, crude) as a light brown solid which was used for the next step without further purification. LCMS [M+H$^+$] 142.

Step 5: Preparation of methyl 6-[3-(trifluoromethoxy)azetidin-1-yl]pyrimidine-4-carboxylate

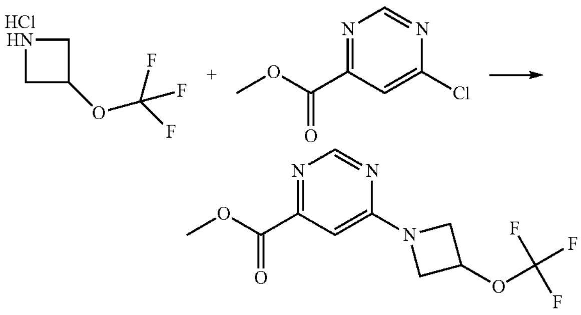

A mixture of methyl 6-chloropyrimidine-4-carboxylate (200 mg, 1.16 mmol, 1.00 equiv), 3-(trifluoromethoxy) azetidine hydrochloride (300 mg, 1.69 mmol, 1.50 equiv), DMSO (6 mL), and TEA (350 mg, 3.46 mmol, 3.00 equiv) was stirred for 5 h at room temperature. The resulting solution was diluted with ethyl acetate, washed with brine, dried over anhydrous sodium sulfate, and concentrated under vacuum. This resulted in the title compound (300 mg, 95%) as a brown solid. LCMS [M+H$^+$] 278.

Step 6: Preparation of [6-[3-(trifluoromethoxy)azetidin-1-yl]pyrimidin-4-yl]methanol

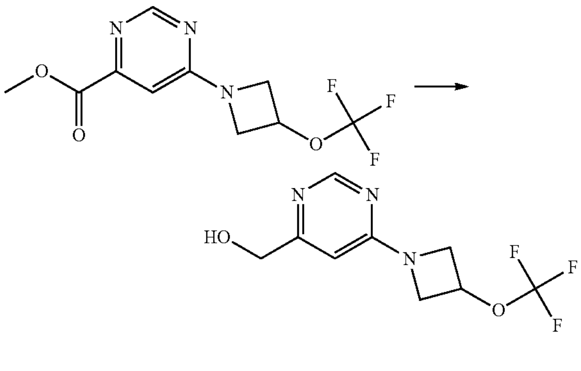

$NaBH_4$ (410 mg, 10.8 mmol, 10.00 equiv) was added in portions into a mixture of methyl 6-[3-(trifluoromethoxy) azetidin-1-yl]pyrimidine-4-carboxylate (300 mg, 1.08 mmol, 1.00 equiv) and methanol (15 mL). The resulting solution was stirred overnight at room temperature. The reaction was then quenched by water, extracted with ethyl acetate, washed with brine, dried over anhydrous sodium sulfate, and concentrated under vacuum. The residue was purified by a silica gel column eluting with dichloromethane/methanol (10:1) to afford the title compound (200 mg, 74%) as a white solid. LCMS [M+H$^+$] 250.

Step 7: Preparation of 2-([6-[3-(trifluoromethoxy) azetidin-1-yl]pyrimidin-4-yl]methyl)-2,3-dihydro-1H-isoindole-1,3-dione

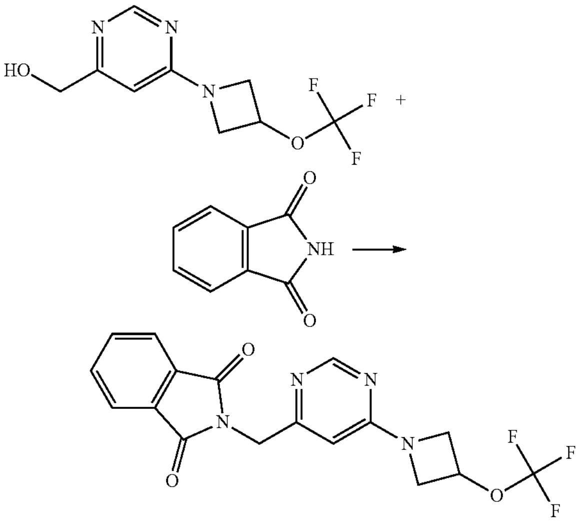

DIAD (324 mg, 1.602 mmol, 2.000 equiv) was added dropwise into a mixture of 2,3-dihydro-1H-isoindole-1,3-dione (236 mg, 1.60 mmol, 2.00 equiv), [6-[3-(trifluoromethoxy)azetidin-1-yl]pyrimidin-4-yl]methanol (200 mg, 0.80 mmol, 1.00 equiv), $PPh_3$ (420 mg, 1.60 mmol, 2.00 equiv), and tetrahydrofuran (20 mL) with stirring at 0° C. under nitrogen. The resulting solution was stirred overnight at room temperature and concentrated under vacuum. The residue was purified by a silica gel column eluting with dichloromethane/methanol (10:1). This resulted in the title compound (290 mg, 95%) as a light yellow solid. LCMS [M+H$^+$] 379.

Step 8: Preparation of [6-[3-(trifluoromethoxy)azetidin-1-yl]pyrimidin-4-yl]methanamine

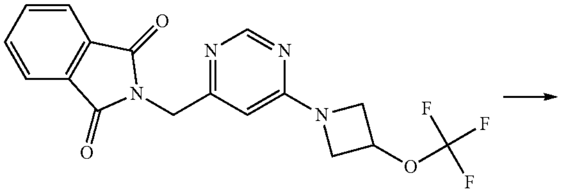

-continued

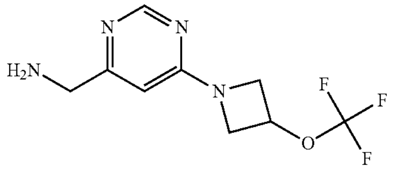

A mixture of 2-([6-[3-(trifluoromethoxy)azetidin-1-yl]pyrimidin-4-yl]methyl)-2,3-dihydro-1H-isoindole-1,3-dione (290 mg, 0.77 mmol, 1.00 equiv), methanol (15 mL), and hydrazine hydrate (80%) (1 mL) was stirred for 3 h at 40° C. The resulting mixture was concentrated under vacuum. The residue was dissolved with ethyl acetate. The solids were filtered out and the liquid was concentrated under vacuum. This resulted in the title compound (160 mg, 84%) as yellow oil. LCMS [M+H$^+$] 249.

Preparation 10: [2-cyclopropyl-6-[2-(trifluoromethyl)pyrimidin-5-yl]pyrimidin-4-yl]methanamine

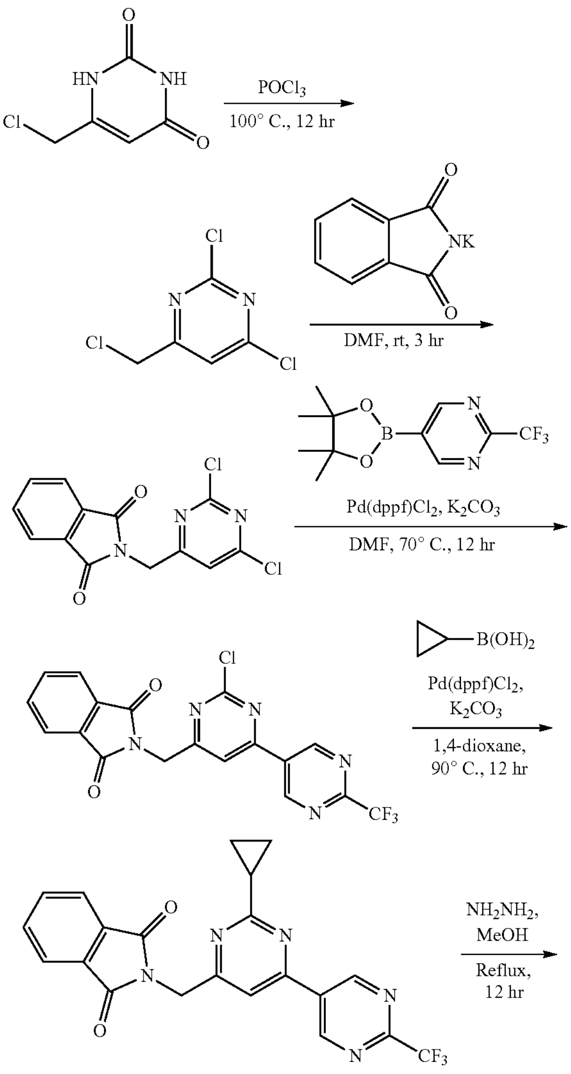

-continued

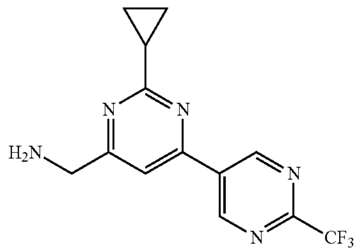

Step 1: Preparation of 2,4-dichloro-6-(chloromethyl)pyrimidine

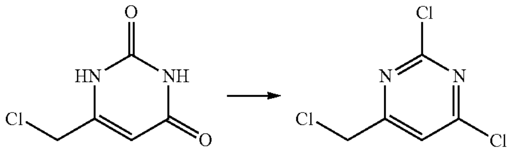 [SMILES: O=c1cc(CCl)[nH]c(=O)[nH]1 ; ClCc1cc(Cl)nc(Cl)n1]

A mixture of 6-(chloromethyl)-1,2,3,4-tetrahydropyrimidine-2,4-dione (9.2 g, 57.30 mmol, 1.00 equiv) and $POCl_3$ (50 mL) was stirred for 12 hours at 100° C. in an oil bath. The reaction was then poured into water/ice, extracted with ethyl acetate, washed with brine, dried over anhydrous sodium sulfate, and concentrated under vacuum. The residue was purified by a silica gel column eluting with petroleum ether to afford the title compound (9.5 g, 84%) as a light yellow solid. LCMS [M+H$^+$] 197.

Step 2: Preparation of 2-[(2,6-dichloropyrimidin-4-yl)methyl]-2,3-dihydro-1H-isoindole-1,3-dione

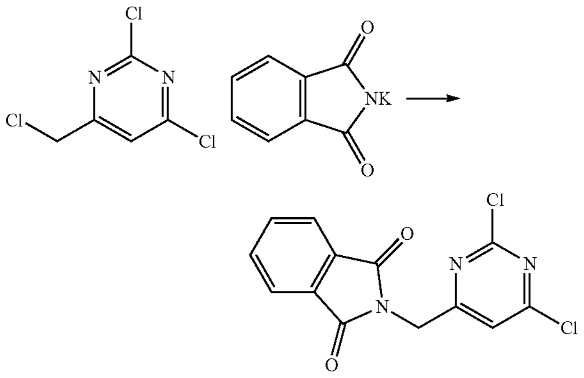

A mixture of 2-potassio-2,3-dihydro-1H-isoindole-1,3-dione (13 g, 70.19 mmol, 1.51 equiv), 2,4-dichloro-6-(chloromethyl)pyrimidine (9.2 g, 46.59 mmol, 1.00 equiv), and N,N-dimethylformamide (100 mL) was stirred for 3 hours at room temperature. The resulting solution was diluted with water. The solids were collected by filtration and dried under vacuum to afford the title compound (11.5 g, 80%) as a yellow solid. LCMS [M+H$^+$] 308.

Step 3: Preparation of 2-([2-chloro-6-[2-(trifluoromethyl)pyrimidin-5-yl]pyrimidin-4-yl]methyl)-2,3-dihydro-1H-isoindole-1,3-dione

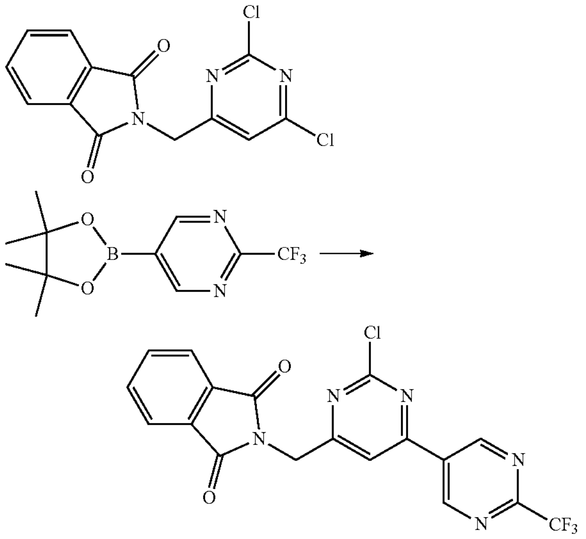

A mixture of 2-[(2,6-dichloropyrimidin-4-yl)methyl]-2,3-dihydro-1H-isoindole-1,3-dione (3.98 g, 12.91 mmol, 1.00 equiv), 5-(tetramethyl-1,3,2-dioxaborolan-2-yl)-2-(trifluoromethyl)pyrimidine (2.81 g, 10.27 mmol, 0.80 equiv), Pd(dppf)$Cl_2$ (945 mg, 1.29 mmol, 0.10 equiv), potassium carbonate (5.477 g, 39.63 mmol, 3.07 equiv), and N,N-dimethylformamide (150 mL) was stirred for 12 h at 70° C. under nitrogen. The solids were then filtered off. The resulting solution was diluted with brine, extracted with ethyl acetate, washed with brine, dried over anhydrous sodium sulfate, and concentrated under vacuum. The residue was purified by a silica gel column eluting with dichloromethane/ethyl acetate (50/1) to afford the title compound (1.75 g, 32%) as a yellow solid. LCMS [M+H$^+$] 420.

Step 4: Preparation of 2-([2-cyclopropyl-6-[2-(trifluoromethyl)pyrimidin-5-yl]pyrimidin-4-yl]methyl)-2,3-dihydro-1H-isoindole-1,3-dione

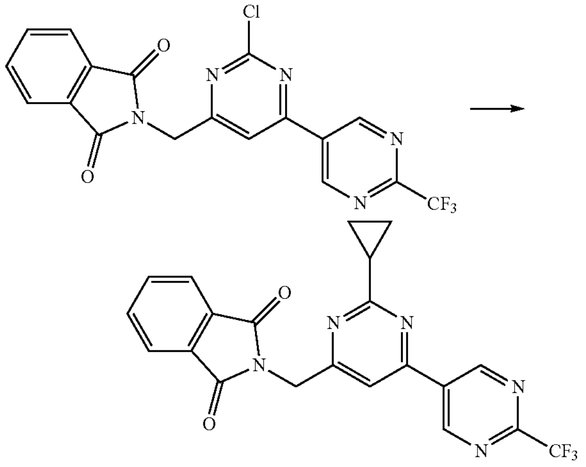

A mixture of 2-([2-chloro-6-[2-(trifluoromethyl)pyrimidin-5-yl]pyrimidin-4-yl]methyl)-2,3-dihydro-1H-isoindole-1,3-dione (190 mg, 0.45 mmol, 1.00 equiv), cyclopropylboronic acid (195 mg, 2.27 mmol, 5.02 equiv), $Pd(dppf)Cl_2$ (33 mg, 0.045 mmol, 0.10 equiv) and potassium carbonate (188 mg, 1.36 mmol, 3.01 equiv), 1,4-dioxane (10 mL) was stirred for 12 hours at 90° C. under nitrogen. The solids were filtered off. The resulting solution was diluted with brine, extracted with ethyl acetate, washed with brine, dried over anhydrous sodium sulfate, and concentrated under vacuum. The residue was purified by a silica gel column eluting with dichloromethane/ethyl acetate (50/1) to afford the title compound (175 mg, 91%) as yellow solid. LCMS [M+H$^+$] 426.

Step 5: Preparation of [2-cyclopropyl-6-[2-(trifluoromethyl)pyrimidin-5-yl]pyrimidin-4-yl]methanamine

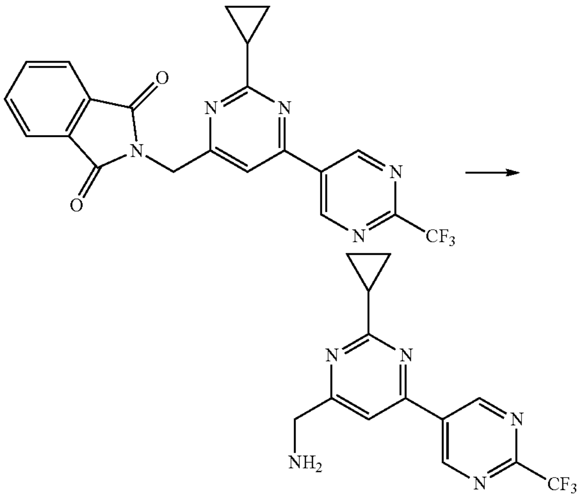

A mixture of 2-([2-cyclopropyl-6-[2-(trifluoromethyl)pyrimidin-5-yl]pyrimidin-4-yl]methyl)-2,3-dihydro-1H-isoindole-1,3-dione (175 mg, 0.41 mmol, 1.00 equiv), methanol (20 mL), $NH_2NH_2.H_2O$ (206 mg, 41.1 mmol, 10.00 equiv) was heated to reflux for 12 hours in an oil bath. The resulting mixture was concentrated under vacuum and dissolved in ethyl acetate. The precipitated solids were filtered off. The resulting solution was concentrated under vacuum to afford the title compound (121 mg) as a yellow oil. LCMS [M+H$^+$] 296.

Preparation: 11: [5-fluoro-4-[4-(trifluoromethyl)cyclohex-1-en-1-yl]pyridin-2-yl]methanamine

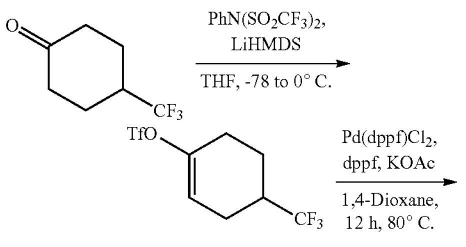

-continued

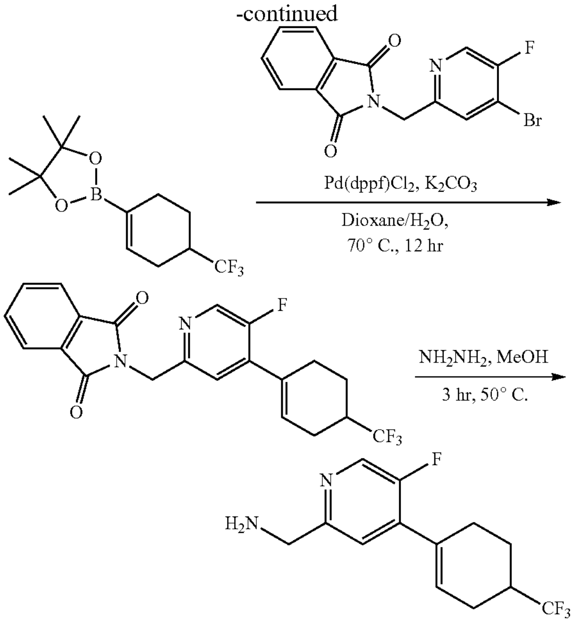

Step 1: Preparation of 4-(trifluoromethyl)cyclohex-1-enyl trifluoromethanesulfonate

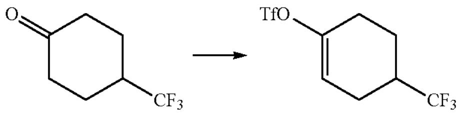 [SMILES: O=C1CCC(C(F)(F)F)CC1 ; O=S(=O)(OC1=CCC(C(F)(F)F)CC1)C(F)(F)F]

A mixture of 4-(trifluoromethyl)cyclohexan-1-one (2.17 g, 13.06 mmol, 1.00 equiv), tetrahydrofuran (80 mL), LiHMDS (15.7 mL, 1M in THF, 1.20 equiv), and 1,1,1-trifluoro-N-phenyl-N-(trifluoromethane)sulfonylmethanesulfonamide (4.67 g, 13.07 mmol, 1.00 equiv) was stirred for 9 h at −78° C. to 0° C. The mixture was quenched by aqueous $NH_4Cl$. The resulting solution was extracted with ethyl acetate, washed with brine, dried over anhydrous sodium sulfate, and concentrated under vacuum. The residue was dissolved in hexane, washed with ethylene glycol and concentrated under vacuum to afford the title compound (2.5 g, 64%) as yellow oil.

Step 2: Preparation of 4,4,5,5-tetramethyl-2-(4-(trifluoromethyl)cyclohex-1-enyl)-1,3,2-dioxaborolane

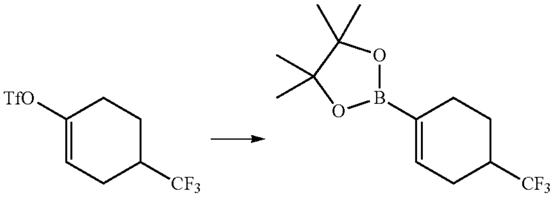

A mixture of 4-(trifluoromethyl)cyclohex-1-en-1-yltrifluoromethanesulfonate (2.24 g, 7.50 mmol, 1.00 equiv), 4,4,5,5-tetramethyl-2-(tetramethyl-1,3,2-dioxaborolan-2-yl)-1,3,2-dioxaborolane (2.86 g, 11.26 mmol, 1.50 equiv), $Pd(dppf)Cl_2$ (160 mg, 0.22 mmol, 0.03 equiv), dppf (125 mg, 0.23 mmol, 0.03 equiv), and KOAc (2.2 g, 22.42 mmol, 2.99 equiv) in dioxane (50 mL) was stirred for 12 h at 80° C. under nitrogen. The resulting mixture was concentrated under vacuum. The residue was purified by a silica gel column eluting with ethyl acetate/petroleum ether (1/20) to afford the title compound (1 g, 48%) as a white solid. LCMS $[M+H^+]$ 277. $^1$HNMR (300 MHz, $CDCl_3$) δ 6.53 (s, 1H), 2.37-1.98 (m, 7H), 1.26 (m, 12H).

Step 3: Preparation of 2-([5-fluoro-4-[4-(trifluoromethyl)cyclohex-1-en-1-yl]pyridin-2-yl]methyl)-2,3-dihydro-1H-isoindole-1,3-dione

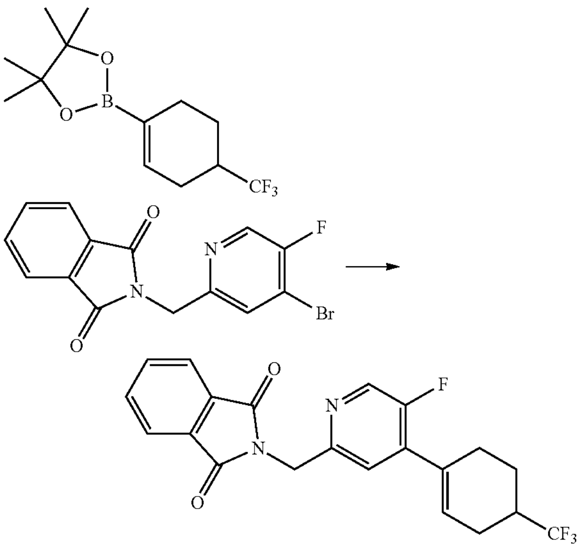

A mixture of 4,4,5,5-tetramethyl-2-[4-(trifluoromethyl)cyclohex-1-en-1-yl]-1,3,2-dioxaborolane (500 mg, 1.81 mmol, 1.00 equiv), 2-[(4-bromo-5-fluoropyridin-2-yl)methyl]-2,3-dihydro-1H-isoindole-1,3-dione (668 mg, 1.99 mmol, 1.10 equiv), $Pd(dppf)Cl_2$ (132 mg, 0.18 mmol, 0.10 equiv), and potassium carbonate (750 mg, 5.43 mmol, 3.00 equiv) in dioxane (20 mL)/water (2 mL) was stirred for 12 h at 70° C. under nitrogen. The resulting solution was diluted with ethyl acetate, washed with brine, dried over anhydrous sodium sulfate, and concentrated under vacuum. The residue was purified by a silica gel column eluting with ethyl acetate/petroleum ether (1/10) to afford the title compound (750 mg) as a white solid. LCMS $[M+H^+]$ 405.

Step 4: Preparation of [5-fluoro-4-[4-(trifluoromethyl)cyclohex-1-en-1-yl]pyridin-2-yl]methanamine

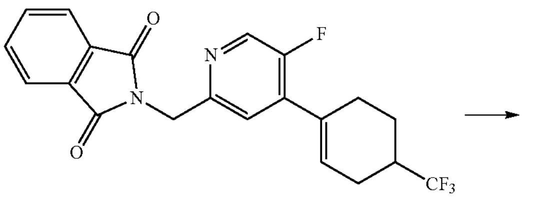

-continued

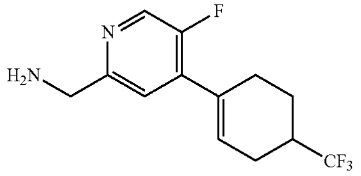

A mixture of 2-([5-fluoro-4-[4-(trifluoromethyl)cyclohex-1-en-1-yl]pyridin-2-yl]methyl)-2,3-dihydro-1H-isoindole-1,3-dione (735 mg, 1.82 mmol, 1.00 equiv), methanol (20 mL), and $NH_2NH_2.H_2O$ (909 mg, 18.16 mmol, 9.99 equiv) was stirred for 3 h at 50° C. The resulting mixture was concentrated under vacuum. The residue was dissolved in ethyl acetate. The organic layers were collected by filtration and concentrated under vacuum. This resulted in the title compound (470 mg, 94%) as yellow oil. LCMS $[M+H^+]$ 275.

Preparation 12: [3-(trifluoromethyl)-1-[4-(trifluoromethyl)cyclohexyl]-1H-pyrazol-4-yl]methanamine

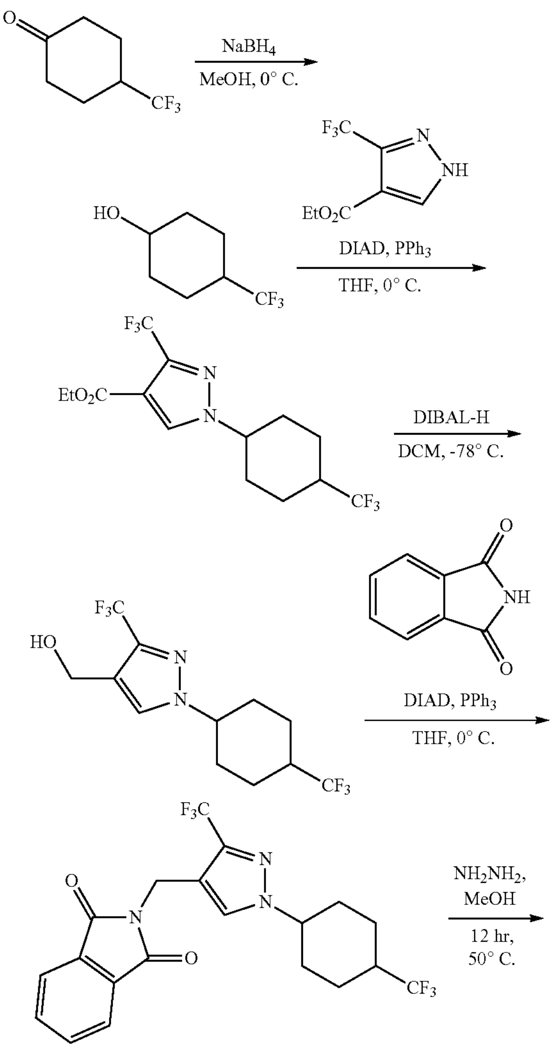

-continued

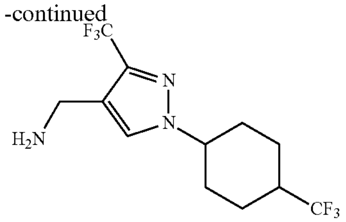

Step 1: Preparation of 4-(trifluoromethyl)cyclohexan-1-ol

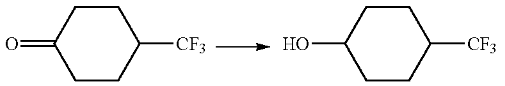

$NaBH_4$ (243 mg, 6.42 mmol, 1.00 equiv) was added in portions into a solution of 4-(trifluoromethyl)cyclohexan-1-one (1.06 g, 6.38 mmol, 1.00 equiv) in methanol (10 mL) at 0° C. under nitrogen. The resulting solution was stirred for 30 min at 0° C. The reaction was then quenched by the addition of water, extracted with ethyl acetate, washed with brine, dried over anhydrous sodium sulfate, and concentrated under vacuum. The residue was purified by a silica gel column eluting with dichloromethane/ethyl acetate (4/1) to afford the title compound (300 mg, 28%) as a light yellow solid.

Step 2: Preparation of ethyl 3-(trifluoromethyl)-1-[4-(trifluoromethyl)cyclohexyl]-1H-pyrazole-4-carboxylate

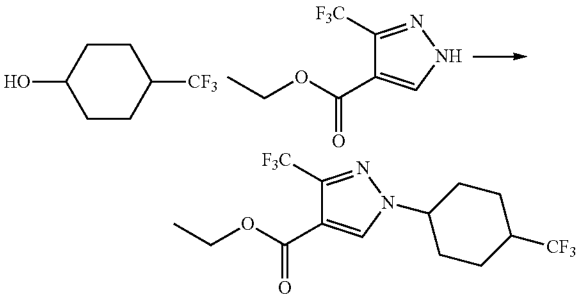

DIAD (721 mg, 3.57 mmol, 2.00 equiv) was added dropwise into a mixture of 4-(trifluoromethyl)cyclohexan-1-ol (300 mg, 1.78 mmol, 1.00 equiv), tetrahydrofuran (20 mL), ethyl 3-(trifluoromethyl)-1H-pyrazole-4-carboxylate (371 mg, 1.78 mmol, 1.00 equiv), and $PPh_3$ (936 mg, 3.57 mmol, 2.00 equiv) at 0° C. under nitrogen. The resulting solution was stirred for 12 h at room temperature. The resulting mixture was concentrated under vacuum. The residue was purified by a silica gel column eluting with ethyl acetate/petroleum ether (1/5) to afford the title compound (500 mg, 78%) as a light yellow solid. LCMS $[M+H^+]$ 359.

$^1$HNMR (400 MHz, $CDCl_3$) δ 8.10-8.05 (s, 1H), 4.42-4.32 (m, 3H), 2.41-2.24 (m, 3H), 2.06-1.98 (m, 2H), 1.88-1.83 (m, 4H), 1.39-1.23 (m, 3H).

Step 3: Preparation of [3-(trifluoromethyl)-1-[4-(trifluoromethyl)cyclohexyl]-1H-pyrazol-4-yl]methanol

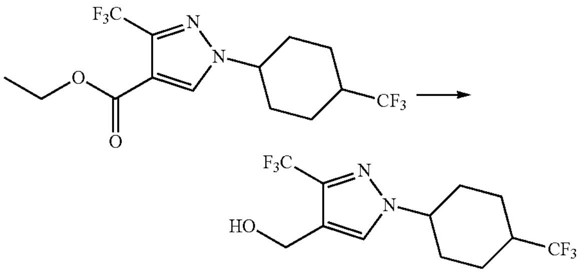

DIBAL-H (4.2 mL, 29.53 mmol, 3.01 equiv) was added dropwise into a solution of ethyl 3-(trifluoromethyl)-1-[4-(trifluoromethyl)cyclohexyl]-1H-pyrazole-4-carboxylate (500 mg, 1.34 mmol, 1.00 equiv) in dichloromethane (10 mL) at −78° C. under nitrogen. The resulting solution was stirred for 2 h at −78° C. The reaction was quenched by the addition of methanol. The resulting mixture was concentrated under vacuum. The residue was purified by a silica gel column eluting with ethyl acetate/petroleum ether (1/1) to afford the title compound (294 mg, 67%) as yellow oil. LCMS $[M+H^+]$ 317.

Step 4: Preparation of 2-[[3-(trifluoromethyl)-1-[4-(trifluoromethyl)cyclohexyl]-1H-pyrazol-4-yl]methyl]-2,3-dihydro-1H-isoindole-1,3-dione

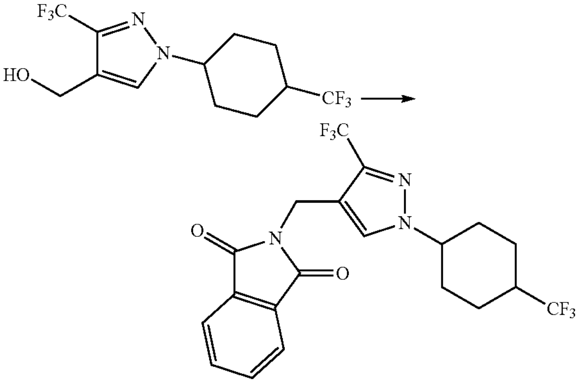

DIAD (376 mg, 1.86 mmol, 2.00 equiv) was added dropwise into a mixture of [3-(trifluoromethyl)-1-[4-(trifluoromethyl)cyclohexyl]-1H-pyrazol-4-yl]methanol (294 mg, 0.93 mmol, 1.00 equiv), tetrahydrofuran (20 mL), 2,3-dihydro-1H-isoindole-1,3-dione (274 mg, 1.86 mmol, 2.00 equiv), and $PPh_3$ (488 mg, 1.86 mmol, 2.00 equiv) at 0° C. under nitrogen. The resulting solution was stirred for 12 h at room temperature and concentrated under vacuum. The residue was purified by a silica gel column eluting with dichloromethane/petroleum ether (1/10) to afford the title compound (280 mg, 68%) as a white solid. LCMS $[M+H^+]$ 446.

$^1$HNMR (400 MHz, $CDCl_3$) δ 7.83-7.80 (m, 2H), 7.73-7.69 (m, 2H), 7.64 (s, 1H), 4.83 (s, 2H), 4.31-4.26 (m, 1H), 2.33-2.19 (m, 3H), 1.96-1.74 (m, 6H).

Step 5: Preparation of [3-(trifluoromethyl)-1-[4-(trifluoromethyl)cyclohexyl]-1H-pyrazol-4-yl]methanamine

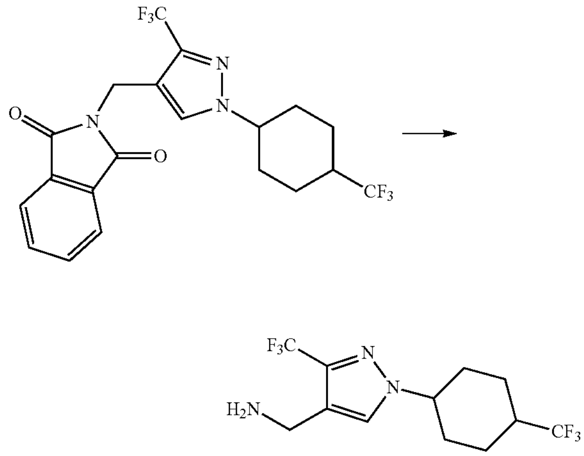

A mixture of 2-[[3-(trifluoromethyl)-1-[4-(trifluoromethyl)cyclohexyl]-1H-pyrazol-4-yl]methyl]-2,3-dihydro-1H-isoindole-1,3-dione (260 mg, 0.58 mmol, 1.00 equiv), methanol (10 mL), and $NH_2NH_2.H_2O$ (292 mg, 5.83 mmol, 9.99 equiv) was stirred for 12 h at 50° C. The resulting mixture was concentrated under vacuum. The residue was dissolved in ethyl acetate. The organic layers were collected by filtration and concentrated under vacuum. This resulted in the title compound (110 mg, 60%) as yellow oil. LCMS [M+H$^+$] 316.

Preparation 13: (6-(2-(trifluoromethyl)thiazol-5-yl)pyrimidin-4-yl)methanamine

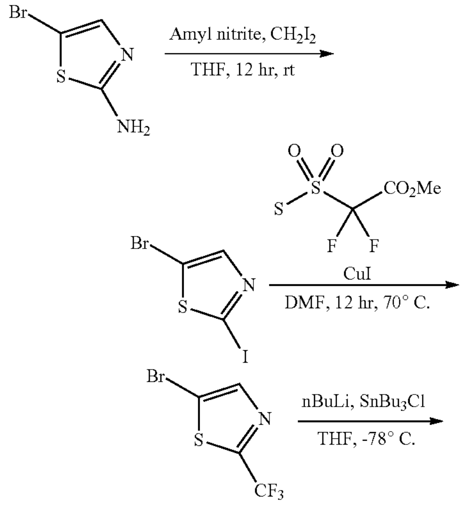

-continued

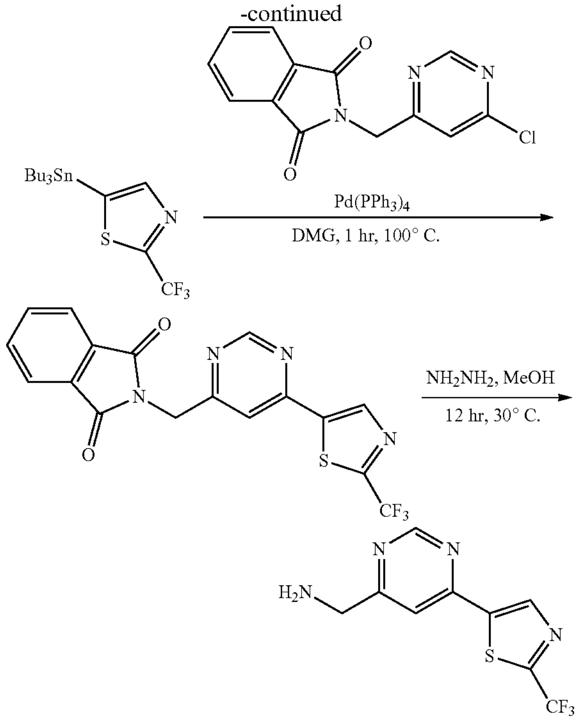

Step 1: Preparation of 5-bromo-2-iodothiazole

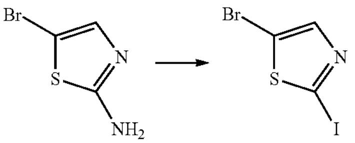 [SMILES: Nc1ncc(Br)s1 ; Brc1cnc(I)s1]

A mixture of 3-methylbutyl nitrite (8.79 g, 75.03 mmol, 1.50 equiv), diiodomethane (16.07 g, 60.00 mmol, 1.20 equiv), and 5-bromo-1,3-thiazol-2-amine hydrobromide (13.00 g, 50.01 mmol, 1.00 equiv) in THF (100 mL) was stirred for 12 h at room temperature. The resulting mixture was concentrated under vacuum. The residue was purified by a silica gel column eluting with ethyl acetate/petroleum ether (1/100) to afford the title compound (12.6 g, 87%) as yellow oil.

Step 2: Preparation of 5-bromo-2-(trifluoromethyl)thiazole

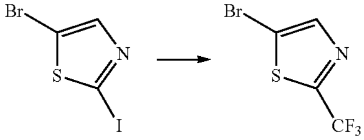 [SMILES: Brc1cnc(I)s1 ; FC(F)(F)c1ncc(Br)s1]

A mixture of 5-bromo-2-iodo-1,3-thiazole (12.6 g, 43.46 mmol, 1.00 equiv), CuI (12.4 g, 65.11 mmol, 1.5 equiv), methyl 2,2-difluoro-2-(fluorosulfonyl)acetate (12.6 g, 65.59 mmol, 1.51 equiv) in DMF (50 mL) was stirred for 12 h at 70° C. in an oil bath. The resulting solution was diluted with 100 mL of hexane, washed with brine, and dried over anhydrous sodium sulfate. This resulted in the title compound in ~100 mL of hexane.

Step 3: Preparation of 5-(tributylstannyl)-2-(trifluoromethyl)thiazole

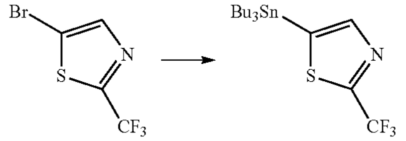

n-BuLi (8.6 mL, 2.5M in hexanes, 1.50 equiv) was added dropwise into a solution of tributyl(chloro)stannane (10.5 g, 32.3 mmol, 1.50 equiv), 5-bromo-2-(trifluoromethyl)-1,3-thiazole (50 ml in hexane, from Step 2) in THF (100 mL) at −78° C. under nitrogen. The reaction was stirred for 1 h at −78° C. and then for an additional 12 h at room temperature. The reaction was then quenched by the addition of water. The resulting solution was extracted with ethyl acetate, washed with brine, dried over anhydrous sodium sulfate, and concentrated under vacuum. The residue was purified by a silica gel column eluting with ethyl acetate/petroleum ether (1:100) to afford the title compound (2 g, 21%) as yellow oil. LCMS [M+H$^+$] 444.

Step 4: Preparation of 2-((6-(2-(trifluoromethyl)thiazol-5-yl)pyrimidin-4-yl)methyl)-isoindoline-1,3-dione

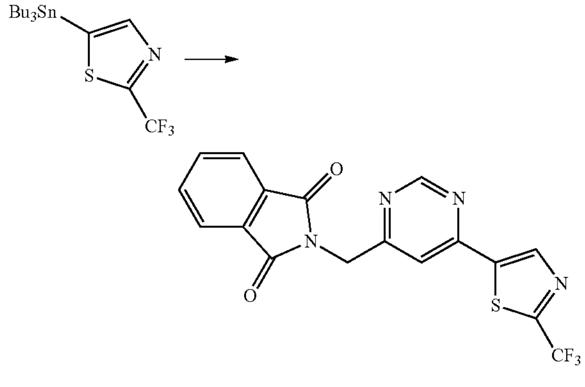

A mixture of 5-(tributylstannyl)-2-(trifluoromethyl)-1,3-thiazole (500 mg, 1.13 mmol, 1.00 equiv), 2-[(6-chloropyrimidin-4-yl)methyl]-2,3-dihydro-1H-isoindole-1,3-dione (1.00 g, 3.65 mmol, 3.23 equiv), and $Pd(PPh_3)_4$ (400 mg, 0.35 mmol, 0.31 equiv.) in DMF (10 mL) was irradiated with microwave radiation for 1 h at 100° C. under nitrogen. The resulting solution was diluted with ethyl acetate, washed with brine, dried over anhydrous sodium sulfate, and concentrated under vacuum. The residue was purified by a silica gel column eluting with ethyl acetate/petroleum ether (1/3) to afford the title compound (400 mg, 91%) as white solid. LCMS [M+H$^+$] 391.

Step 5: Preparation of (6-(2-(trifluoromethyl)thiazol-5-yl)pyrimidin-4-yl)methanamine

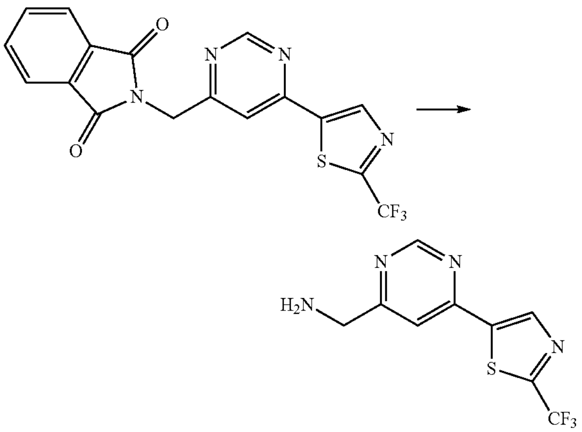

A mixture of 2-([6-[2-(trifluoromethyl)-1,3-thiazol-5-yl]pyrimidin-4-yl]methyl)-2,3-dihydro-1H-isoindole-1,3-dione (400 mg, 1.03 mmol, 1.00 equiv) and $NH_2NH_2.H_2O$ (1 g, 19.98 mmol, 19.49 equiv) in $CH_3OH$ (20 mL) was stirred for 12 h at 30° C. in an oil bath. The resulting mixture was concentrated under vacuum. The residue was dissolved in ethyl acetate. The solids were filtered out and washed with ethyl acetate. The resulting mixture was concentrated under vacuum. This resulted in the title compound (200 mg, 75%) as yellow oil. LCMS [M+H$^+$] 261.

Preparation 14: (2-isopropoxy-2'-(trifluoromethyl)-4,5'-bipyrimidin-6-yl)methanamine

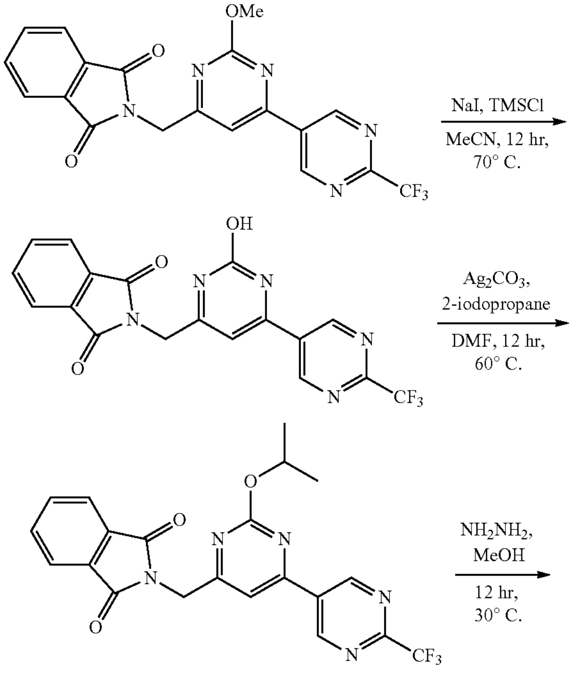

-continued

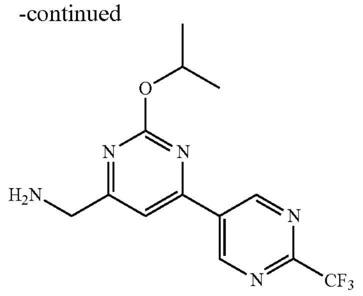

Step 1: Preparation of 2-((2-methoxy-2'-(trifluoromethyl)-4,5'-bipyrimidin-6-yl)methyl)-isoindoline-1,3-dione

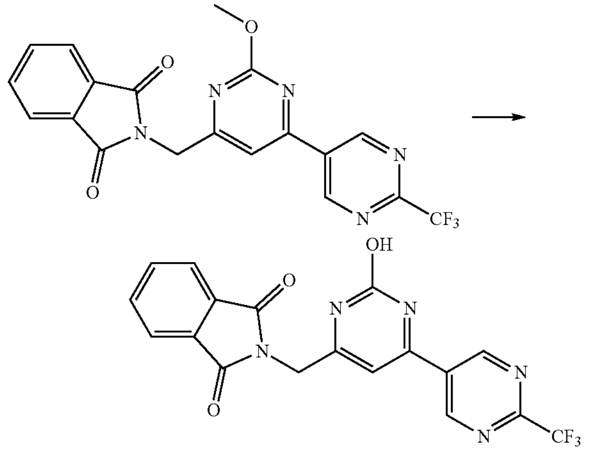

A mixture of 2-([2-methoxy-6-[2-(trifluoromethyl)pyrimidin-5-yl]pyrimidin-4-yl]methyl)-2,3-dihydro-1H-isoindole-1,3-dione (350 mg, 0.84 mmol, 1.00 equiv), NaI (315.79 mg, 2.11 mmol, 2.50 equiv), and chlorotrimethylsilane (228.88 mg, 2.11 mmol, 2.50 equiv) in $CH_3CN$ (20 mL) was stirred for 12 h at 70° C. in an oil bath under nitrogen. The reaction was then quenched by water, extracted with ethyl acetate, washed with saturated aqueous $Na_2SO_3$ and brine, dried over anhydrous sodium sulfate, and concentrated under vacuum. The residue was purified by a silica gel column eluting with dichloromethane/methanol (10:1) to afford the title compound (200 mg, 59%) as a light yellow solid. LCMS [M+H$^+$] 402.

Step 2: Preparation of 2-((2-hydroxy-2'-(trifluoromethyl)-4,5'-bipyrimidin-6-yl)methyl)isoindoline-1,3-dione

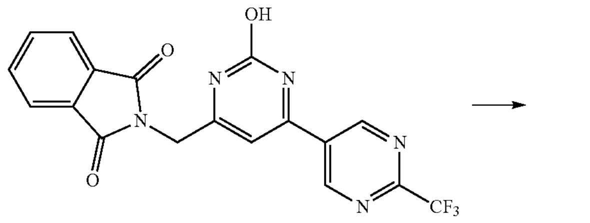

-continued

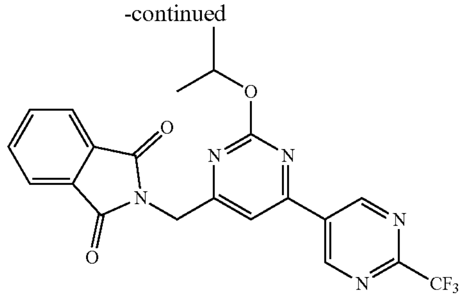

A mixture of 2-([2-hydroxy-6-[2-(trifluoromethyl)pyrimidin-5-yl]pyrimidin-4-yl]methyl)-2,3-dihydro-1H-isoindole-1,3-dione (200 mg, 0.50 mmol, 1.00 equiv), $Ag_2CO_3$ (412.28 mg, 1.50 mmol, 3.00 equiv), and 2-iodopropane (169.44 mg, 1.00 mmol, 2.00 equiv) in DMF (10 mL) was stirred for 12 h at 60° C. in an oil bath. The solids were filtered out. The resulting solution was diluted with ethyl acetate, washed with brine, dried over anhydrous sodium sulfate, and concentrated under vacuum. The residue was purified by a silica gel column eluting with ethyl acetate/petroleum ether (1:1) to afford the title compound (200 mg, 91%) as a white solid. LCMS [M+H$^+$] 444.

Step 3: Preparation of (2-isopropoxy-2'-(trifluoromethyl)-4,5'-bipyrimidin-6-yl)methanamine

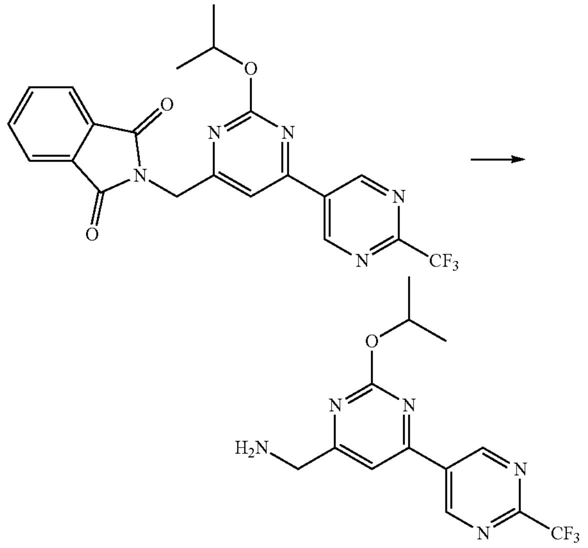

A mixture of 2-[[2-(propan-2-yloxy)-6-[2-(trifluoromethyl)pyrimidin-5-yl]pyrimidin-4-yl]methyl]-2,3-dihydro-1H-isoindole-1,3-dione (250 mg, 0.56 mmol, 1.00 equiv) and $NH_2NH_2.H_2O$ (564.53 mg, 11.28 mmol, 20.00 equiv.) in methanol (20 mL) was stirred for 12 h at 30° C. in an oil bath. The resulting mixture was concentrated under vacuum and the residue was dissolved in ethyl acetate. The solids were filtered out and the resulting solution was concentrated under vacuum. This resulted in the title compound (150 mg, 85%) as a white solid. LCMS [M+H$^+$] 314.

Preparation 15: (2S,6S)-1-(tert-butoxycarbonyl)-6-methylpiperidine-2-carboxylic Acid

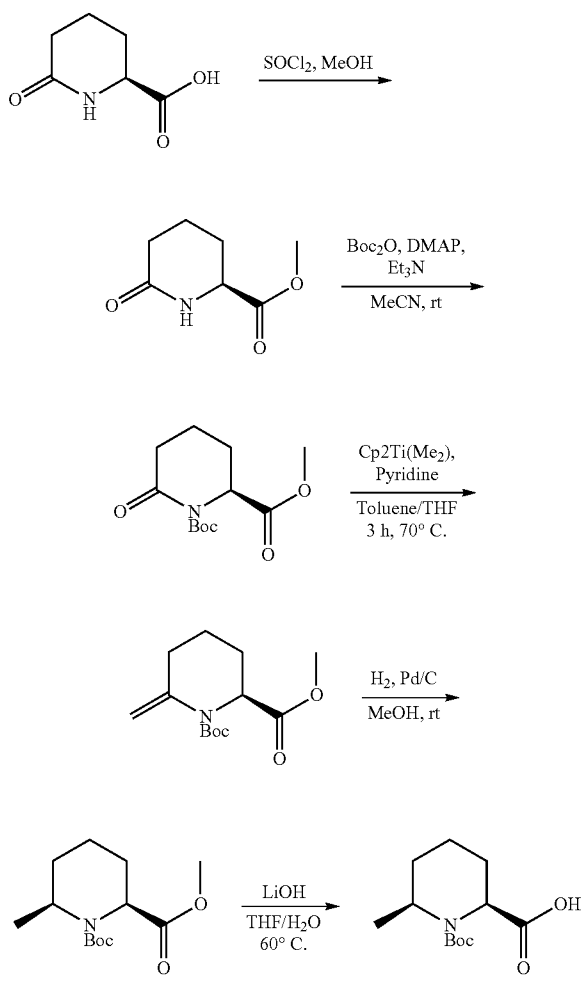

Step 1: Preparation of (S)-methyl 6-oxopiperidine-2-carboxylate

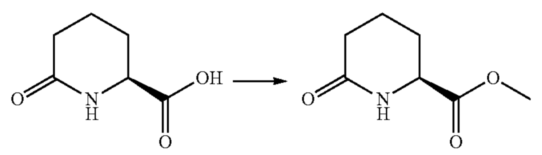

Thionyl chloride (8.3 g, 69.77 mmol, 10.00 equiv) was added to a solution of (2S)-6-oxopiperidine-2-carboxylic acid (1 g, 6.986 mmol, 1.000 equiv) in methanol (20 mL) dropwise at 0° C. The resulting solution was stirred overnight at room temperature and concentrated under vacuum. The pH value of the solution was adjusted to 8 with saturated sodium bicarbonate. The mixture was extracted with 3×50 mL of ethyl acetate, dried over anhydrous sodium sulfate, and concentrated under vacuum. This resulted in the title compound (0.5 g, 46%) as colorless oil. LCMS [M+H$^+$] 158.

Step 2: Preparation of (S)-1-tert-butyl 2-methyl 6-oxopiperidine-1,2-dicarboxylate

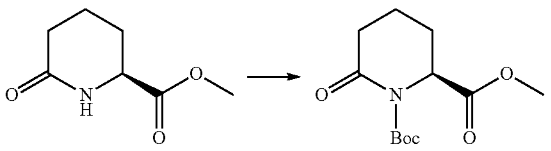 [SMILES: COC(=O)[C@@H]1CCCC(=O)N1 ; COC(=O)[C@@H]1CCCC(=O)N1C(=O)OC(C)(C)C]

A solution of methyl (2S)-6-oxopiperidine-2-carboxylate (500 mg, 3.181 mmol, 1.00 equiv), $Boc_2O$ (833 mg, 3.817 mmol, 1.20 equiv), 4-dimethylaminopyridine (78 mg, 0.638 mmol, 0.20 equiv), and TEA (478 mg, 4.72 mmol, 1.50 equiv) in $CH_3CN$ (10 mL) was stirred overnight at room temperature. The resulting mixture was concentrated under vacuum. The residue was purified by a silica gel column eluting with ethyl acetate/petroleum ether (1:20) to afford the title compound (580 mg, 71%) as light yellow oil. LCMS [M+H$^+$] 258.

Step 3: Preparation of (S)-1-tert-butyl 2-methyl6-methylenepiperidine-1,2-dicarboxylate

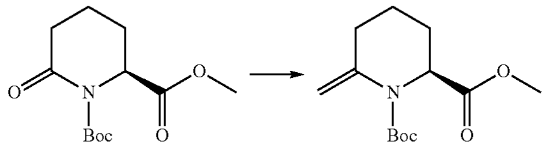

A solution of 1-tert-butyl 2-methyl (2S)-6-oxopiperidine-1,2-dicarboxylate (550 mg, 2.138 mmol, 1.00 equiv), bis (cyclopenta-1,3-dien-1-yl)dimethyltitanium (22 mL, 105.707 mmol, 5.00 equiv), and pyridine (684 mg, 8.647 mmol, 4.00 equiv) in toluene (10 ml)/THF (4 mL) was stirred for 3 h at 70° C. under nitrogen. The resulting solution was diluted with 100 ml of petroleum ether. The solids were filtered out. The filtrate was concentrated under vacuum. The residue was purified by a silica gel column eluting with ethyl acetate/petroleum ether (1:20) to afford the title compound (156 mg, 29%) as light yellow oil. LCMS [M+H$^+$] 256.

Step 4: Preparation of (2S,6S)-1-tert-butyl 2-methyl 6-methylpiperidine-1,2-dicarboxylate

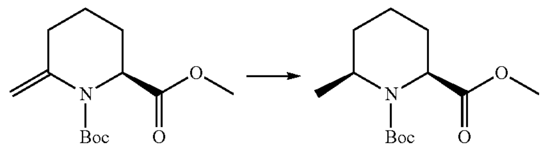

Hydrogen gas was introduced in a mixture of 1-tert-butyl 2-methyl (2S)-6-methylidenepiperidine-1,2-dicarboxylate (156 mg, 0.611 mmol, 1.00 equiv.), and palladium on carbon (20 mg) in 10 mL of methanol. The reaction mixture was stirred overnight at room temperature. The solids were filtered out. The resulting mixture was concentrated under vacuum. This resulted in 150 mg (95%) of the title compound a light yellow solid. LCMS [M+H$^+$] 258.

Step 5: Preparation of (2S,6S)-1-(tert-butoxycarbonyl)-6-methylpiperidine-2-carboxylic Acid

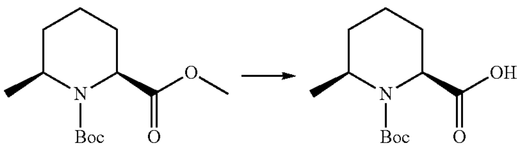

A mixture of 1-tert-butyl 2-methyl (2S,6S)-6-methylpiperidine-1,2-dicarboxylate (150 mg, 0.583 mmol, 1.00 equiv) and LiOH (42 mg, 1.754 mmol, 3.00 equiv) in tetrahydrofuran (5 mL)/water (5 mL) was stirred overnight at 60° C. The pH value of the solution was adjusted to 2 with diluted HCl. The mixture was extracted with ethyl acetate, dried over anhydrous sodium sulfate, and concentrated under vacuum. This resulted in 110 mg (78%) of the title compound as a white solid. LCMS [M+H$^+$] 244.

Preparation 16: (2S,4R)-1-(tert-butoxycarbonyl)-4-fluoro-4-methylpyrrolidine-2-carboxylic Acid

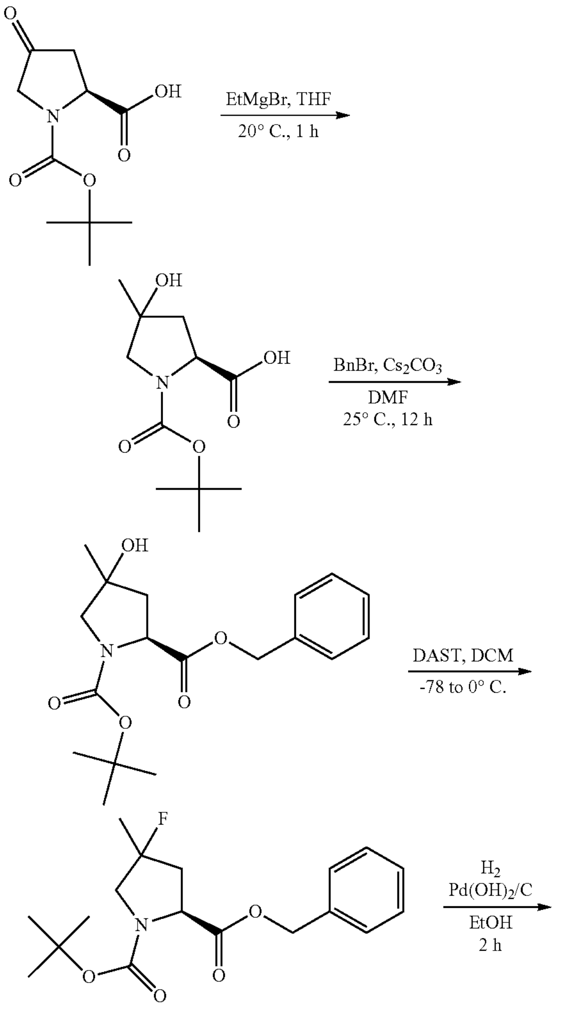

-continued

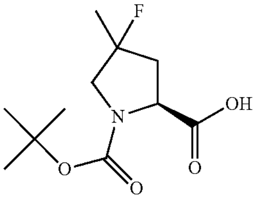

Step 1: Preparation of (2S)-1-[(tert-butoxy)carbonyl]-4-hydroxy-4-methylpyrrolidine-2-carboxylic Acid

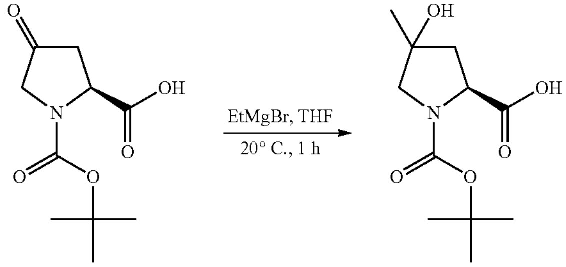 [SMILES: CC(C)(C)OC(=O)N1CC(=O)C[C@H]1C(=O)O ; CC1(O)C[C@@H](C(=O)O)N(C(=O)OC(C)(C)C)C1]

Into a 5000-mL 4-necked round-bottom flask purged and maintained with an inert atmosphere of nitrogen was placed (2S)-1-[(tert-butoxy)carbonyl]-4-oxopyrrolidine-2-carboxylic acid (219.8 g, 958.86 mmol, 1.00 equiv) and tetrahydrofuran (2000 mL) followed by the addition of bromo (methyl)magnesium (800 mL, 2.50 equiv, 3 M) dropwise with stirring at −20° C. over 30 min. The resulting solution was stirred at 20° C. for 1 h, cooled to 0° C. with an ice/salt bath, and quenched by the addition of 2000 mL of saturated aqueous $NH_4Cl$. The pH value of the solution was adjusted to 2 with hydrogen chloride (2 mol/L). The resulting solution was extracted with 3×1500 mL of ethyl acetate. The combined organic layers were then washed with 2×1000 mL of brine, dried over anhydrous sodium sulfate and concentrated under vacuum to afford of the title compound (202 g, 86%) as an off-white foam.

Step 2: Preparation of (25)-2-benzyl 1-tert-butyl 4-hydroxy-4-methylpyrrolidine-1,2-dicarboxylate

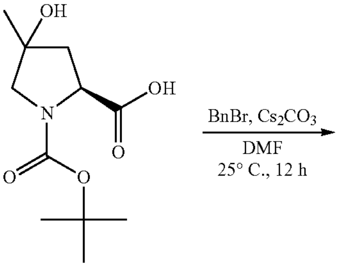

-continued

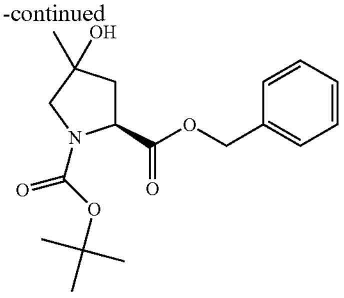

Into a 5000-mL 4-necked round-bottom flask purged and maintained with an inert atmosphere of nitrogen was placed (2S)-1-[(tert-butoxy)carbonyl]-4-hydroxy-4-methylpyrrolidine-2-carboxylic acid (202 g, 823.57 mmol, 1.00 equiv), N,N-dimethylformamide (3000 mL), and $Cs_2CO_3$ (644.6 g, 1.98 mol, 2.40 equiv) followed by the addition of (bromomethyl)benzene (169.1 g, 988.69 mmol, 1.20 equiv) dropwise with stirring. The resulting solution was stirred at 25° C. for 12 h and filtered. The filtrate was diluted with 4000 mL of $H_2O$. The resulting solution was extracted with 3×3000 mL of ethyl acetate. The combined organic layers were then washed with 5×2000 mL of $H_2O$, washed with 2×2000 mL of brine, dried over anhydrous sodium sulfate, and concentrated under vacuum. The residue was applied onto a silica gel column eluted with ethyl acetate/petroleum ether (1:9). The crude product (200 g) was purified by Flash-Prep-HPLC to afford of the title compound (103 g, 37%) as yellow oil.

Step 3: Preparation of 2-benzyl 1-tert-butyl (2S, 4R)-4-fluoro-4-methylpyrrolidine-1,2-dicarboxylate

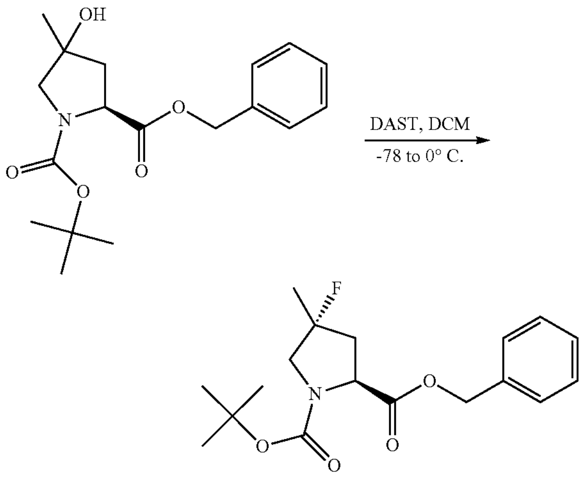

Into a 2000-mL 4-necked round-bottom flask purged and maintained with an inert atmosphere of nitrogen was placed (2S)-2-benzyl 1-tert-butyl 4-hydroxy-4-methylpyrrolidine-1,2-dicarboxylate (103 g, 307.10 mmol, 1.00 equiv) and dichloromethane (1200 mL) followed by the addition of DAST (74.2 g, 460.33 mmol, 1.50 equiv) dropwise with stirring at −78° C. The temperature of the resulting solution was increased to 0° C. gradually. The reaction was quenched by the addition of 1000 mL of saturated aqueous sodium bicarbonate and then extracted with 3×500 mL of dichloromethane. The combined organic layers were washed with 1×300 mL of $H_2O$, dried over anhydrous sodium sulfate and concentrated under vacuum. The residue was applied to a silica gel column and eluted with ethyl acetate/petroleum ether (1:40) to afford the title compound (21 g, 20%) as light yellow oil.

$^1H$ NMR: (300 MHz, $CDCl_3$): δ 7.35 (d, J=3.0 Hz, 5H), 5.20 (m, 2H), 4.49 (m, 1H), 3.84 (m, 1H), 3.43 (dd, 1H), 2.57 (m, 1H), 1.98 (m, 1H), 1.55 (m, 3H), 1.400 (m, 9H).

Step 4: Preparation of (2S,4R)-1-(tert-butoxycarbonyl)-4-fluoro-4-methylpyrrolidine-2-carboxylic Acid

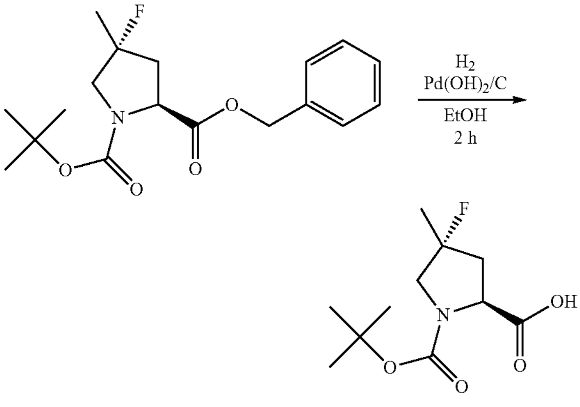

To a round-bottomed flask was added 2-benzyl 1-tert-butyl (2S)-4-fluoro-4-methylpyrrolidine-1,2-dicarboxylate (2.03 g, 6.02 mmol) and the flask was evacuated and backfilled with nitrogen (3×). Ethanol (60 mL) was added followed by palladium hydroxide on carbon (845 mg, 1.20 mmol) and nitrogen was bubbled through the solution for 5 mins. A hydrogen balloon was then added and hydrogen was bubbled through the solution for 5 mins. The reaction mixture was stirred under an atmosphere of hydrogen for 2 h. The reaction mixture was diluted with DCM and filtered through celite eluting with DCM. The filtrate was concentrated in vacuo to give the title compound (1.49 g, 100%) as a clear oil which was used directly without further purification.

$^1H$ NMR (400 MHz, DMSO) δ 12.69 (s, 1H), 4.22-4.12 (m, 1H), 3.63 (dd, J=20.9, 5.1 Hz, 1H), 3.17 (s, 2H), 2.10-1.88 (m, 1H), 1.54-1.42 (m, 3H), 1.42-1.33 (m, 9H).

Example 1: (2S,4R,5S)-4-fluoro-N-([5-fluoro-2-[2-(trifluoromethyl)pyrimidin-5-yl]pyridin-4-yl]methyl)-1-[(4-fluorobenzene)sulfonyl]-5-methylpyrrolidine-2-carboxamide

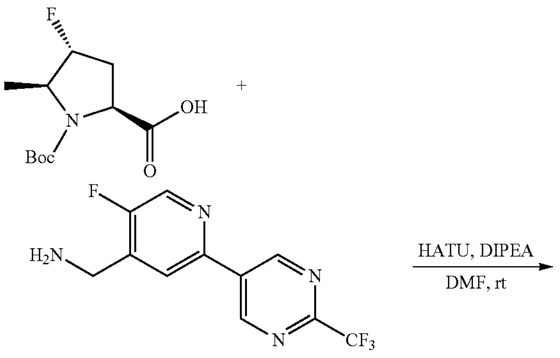

-continued

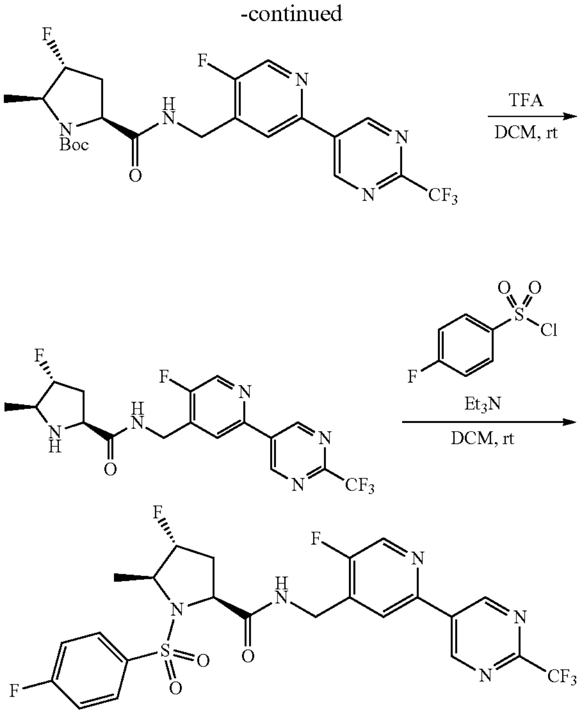

Step 1: Preparation of tert-butyl (2S,3R,5S)-3-fluoro-5-[([5-fluoro-2-[2-(trifluoromethyl)pyrimidin-5-yl]pyridin-4-yl]methyl)carbamoyl]-2-methylpyrrolidine-1-carboxylate

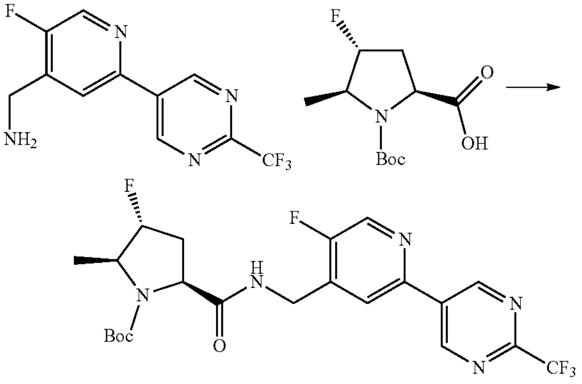

A mixture of (2S,4R,5S)-1-[(tert-butoxy)carbonyl]-4-fluoro-5-methylpyrrolidine-2-carboxylic acid (1.6 g, 6.47 mmol, 1.00 equiv), DIEA (2.39 g, 18.49 mmol, 2.86 equiv), HATU (2.82 g, 7.42 mmol, 1.15 equiv), and [5-fluoro-2-[2-(trifluoromethyl)pyrimidin-5-yl]pyridin-4-yl]methanamine (1.68 g, 6.17 mmol, 0.95 equiv) in N,N-dimethylformamide (60 mL) was stirred for 30 min at room temperature. The reaction was diluted with water, extracted with ethyl acetate, washed with brine, dried over anhydrous sodium sulfate, and concentrated under vacuum. The residue was purified by a silica gel column eluting with ethyl acetate/petroleum ether (1/5) to afford the title compound (1.95 g, 60%) as yellow oil. LCMS [M+H$^+$] 502.

Step 2: Preparation of (2S,4R,5S)-4-fluoro-N-([5-fluoro-2-[2-(trifluoromethyl)pyrimidin-5-yl]pyridin-4-yl]methyl)-5-methylpyrrolidine-2-carboxamide

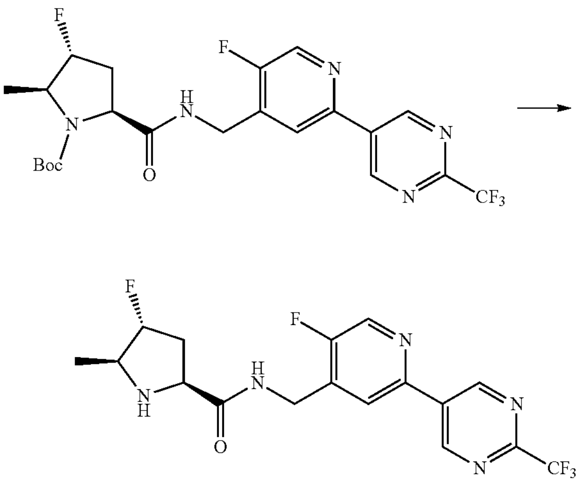

A mixture of tert-butyl (2S,3R,5S)-3-fluoro-5-[([5-fluoro-2-[2-(trifluoromethyl)pyrimidin-5-yl]pyridin-4-yl]methyl)carbamoyl]-2-methylpyrrolidine-1-carboxylate (1.95 g, 3.89 mmol, 1.00 equiv) in dichloromethane (80 mL)/trifluoroacetic acid (20 mL) was stirred for 12 h at room temperature. The resulting mixture was concentrated under vacuum. The residue was diluted with water. The pH value of the solution was adjusted to 8 with saturated solution of sodium bicarbonate. The resulting mixture was extracted with ethyl acetate, washed with brine, dried over anhydrous sodium sulfate, and concentrated under vacuum. This resulted in the title compound (900 mg) as yellow oil which was used for the next step without further purification. LCMS [M+H$^+$] 402.

Step 3: Preparation of (2S,4R,5S)-4-fluoro-N-([5-fluoro-2-[2-(trifluoromethyl)pyrimidin-5-yl]pyridin-4-yl]methyl)-1-[(4-fluorobenzene)sulfonyl]-5-methylpyrrolidine-2-carboxamide

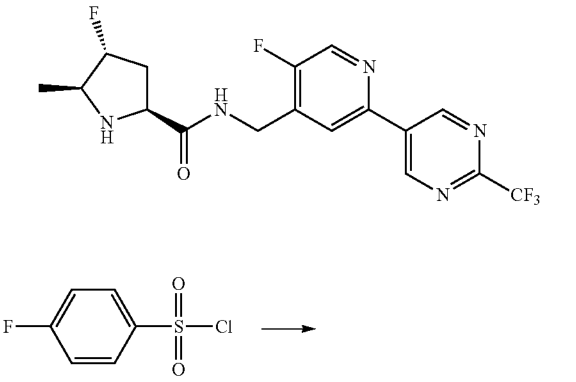

-continued

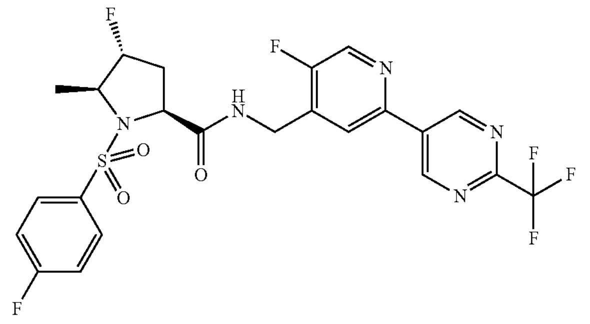

A mixture of (2S,4R,5S)-4-fluoro-N-([5-fluoro-2-[2-(trifluoromethyl)pyrimidin-5-yl]pyridin-4-yl]methyl)-5-methylpyrrolidine-2-carboxamide (900 mg, 2.24 mmol, 1.00 equiv), TEA (680 mg, 6.72 mmol, 3.00 equiv), and 4-fluorobenzene-1-sulfonyl chloride (656 mg, 3.37 mmol, 1.50 equiv) in dichloromethane (50 mL) was stirred for 12 h at room temperature. The mixture was diluted with water, extracted with ethyl acetate, washed with brine, dried over anhydrous sodium sulfate, and concentrated under vacuum. The residue was purified by a silica gel column eluting with dichloromethane/ethyl acetate (1/5). The collected fractions were combined and concentrated under vacuum. The crude product (800 mg) was purified by chiral-Prep-HPLC to afford the title compound (650 mg, 52%) as a white solid; LCMS [M+H$^+$] 560; $^1$H NMR (300 MHz, $CDCl_3$) δ 9.59 (s, 2H), 8.58-8.53 (s, 1H), 8.32-8.30 (m, 1H), 8.03-7.96 (m, 2H), 7.34-7.27 (m, 2H), 4.88-4.63 (m, 3H), 4.28-4.22 (m, 1H), 4.08-3.98 (m, 1H), 3.29-3.27 (s, 1H), 2.44-2.17 (m, 2H), 1.34-1.32 (m, 3H).

Example 2: (2S,4R,5S)-4-cyano-N-([2-fluoro-5-[2-(trifluoromethyl)pyrimidin-5-yl]phenyl]methyl)-1-[(4-fluorobenzene)sulfonyl]-5-methylpyrrolidine-2-carboxamide

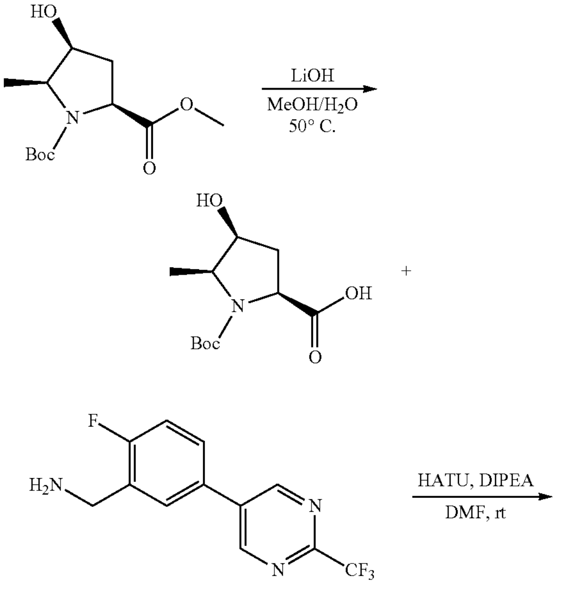

-continued

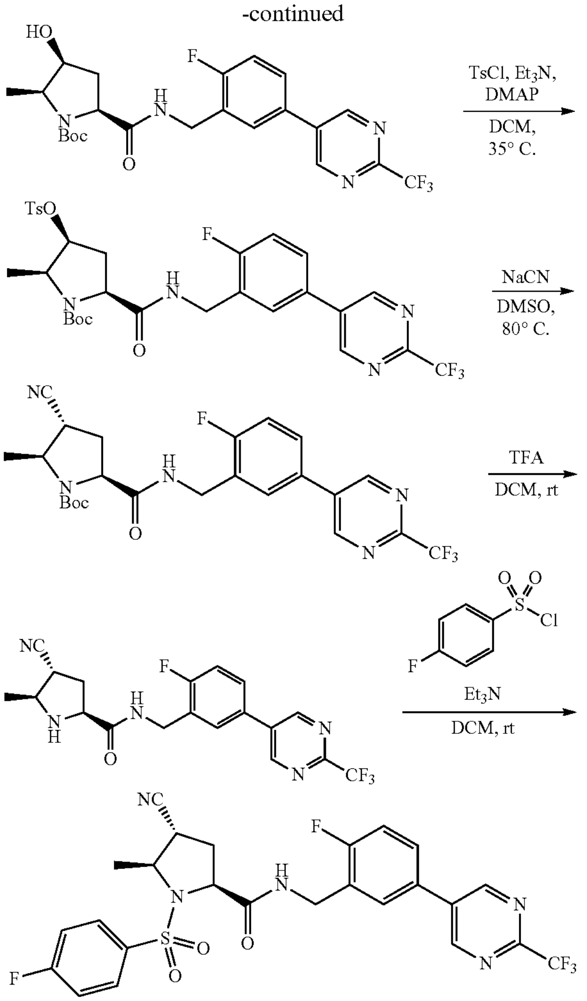

Step 1: Preparation of (2S,4S,5S)-1-[(tert-butoxy)carbonyl]-4-hydroxy-5-methylpyrrolidine-2-carboxylic Acid

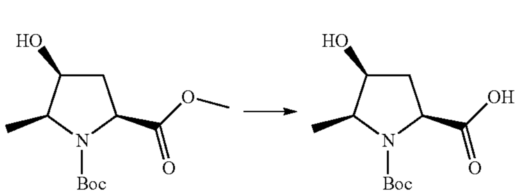

A mixture of 1-tert-butyl 2-methyl (2S,4S,5S)-4-hydroxy-5-methylpyrrolidine-1,2-dicarboxylate (8.4 g, 32.40 mmol, 1.00 equiv) and LiOH (3.1 g, 129.45 mmol, 4.00 equiv) in methanol (100 mL)/water (25 mL) was stirred for 12 h at 50° C. The resulting mixture was concentrated under vacuum. The residue was dissolved in water. The pH value of the solution was adjusted to 3 with hydrogen chloride (1N). The resulting solution was extracted with ethyl acetate, dried over anhydrous sodium sulfate, and concentrated under vacuum. This resulted in the title compound (6.1 g, 77%) as a white solid which was used for the next step without further purification. LCMS [M+H$^+$] 246.

Step 2: Preparation of tert-butyl (2S,3S,5S)-5-[([2-fluoro-5-[2-(trifluoromethyl)pyrimidin-5-yl]phenyl]methyl)carbamoyl]-3-hydroxy-2-methylpyrrolidine-1-carboxylate

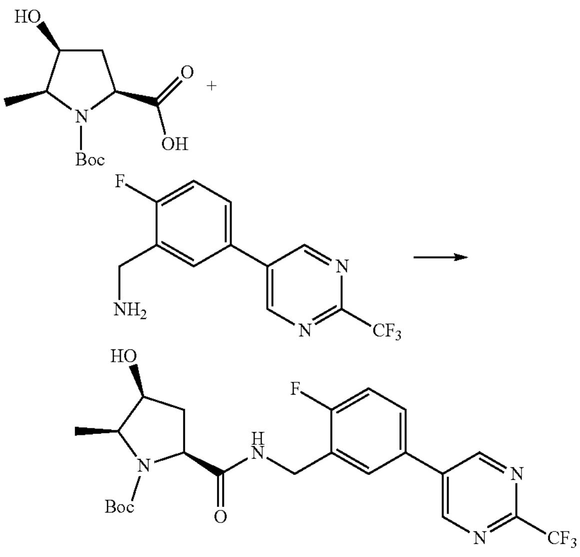

A mixture of (2S,4S,5S)-1-[(tert-butoxy)carbonyl]-4-hydroxy-5-methylpyrrolidine-2-carboxylic acid (629 mg, 2.56 mmol, 1.00 equiv), 2-fluoro-5-[2-(trifluoromethyl)pyrimidin-5-yl]phenylmethanamine (695 mg, 2.56 mmol, 1.00 equiv), HATU (1.459 g, 3.84 mmol, 1.50 equiv), and DIEA (660 mg, 5.11 mmol, 1.99 equiv) in N,N-dimethylformamide (5 mL) was stirred overnight at room temperature. The resulting solution was diluted with water, extracted with ethyl acetate, washed with brine, dried over anhydrous sodium sulfate, and concentrated under vacuum. The residue was purified by a silica gel column eluting with ethyl acetate/petroleum ether (1:1) to afford the title compound (800 mg, 63%) as light yellow oil. LCMS [M+H$^+$] 499.

Step 3: Preparation of tert-butyl (2S,3S,5S)-5-[([2-fluoro-5-[2-(trifluoromethyl)pyrimidin-5-yl]phenyl]methyl)carbamoyl]-2-methyl-3-[[(4-methylbenzene)sulfonyl]oxy]pyrrolidine-1-carboxylate

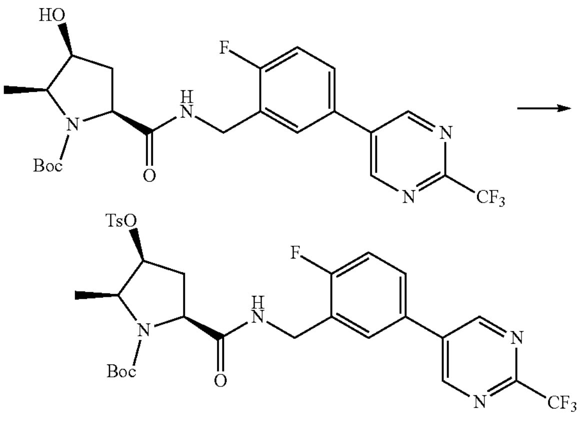

A mixture of tert-butyl (2S,3S,5S)-5-[([2-fluoro-5-[2-(trifluoromethyl)pyrimidin-5-yl]phenyl]methyl)carbamoyl]-3-hydroxy-2-methylpyrrolidine-1-carboxylate (450 mg, 0.90 mmol, 1.00 equiv), 4-toluene sulfonyl chloride (342 mg, 1.79 mmol, 1.99 equiv), and 4-dimethylaminopyridine (109 mg, 0.89 mmol, 0.99 equiv) in dichloromethane (5 mL)/TEA (181 mg, 1.79 mmol, 1.98 equiv) was stirred overnight at 35° C. The resulting mixture was diluted with dichloromethane, washed with brine, dried over anhydrous sodium sulfate, and concentrated under vacuum. The residue was purified by a silica gel column eluting with ethyl acetate/petroleum ether (1:5) to afford the title compound (200 mg, 34%) as light yellow oil. LCMS [M+H$^+$] 653.

Step 4: Preparation of tert-butyl (2S,3R,5S)-3-cyano-5-[([2-fluoro-5-[2-(trifluoromethyl)pyrimidin-5-yl]phenyl]methyl)carbamoyl]-2-methylpyrrolidine-1-carboxylate

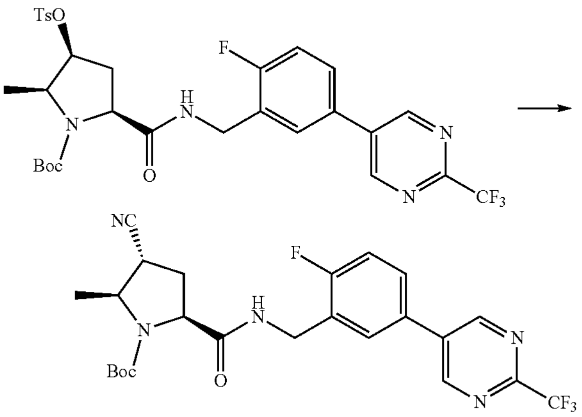

A mixture of tert-butyl (2S,3S,5S)-5-[([2-fluoro-5-[2-(trifluoromethyl)pyrimidin-5-yl]phenyl]methyl)carbamoyl]-2-methyl-3-[[(4-methylbenzene)sulfonyl]oxy]pyrrolidine-1-carboxylate (200 mg, 0.31 mmol, 1.00 equiv) and NaCN (75 mg, 1.53 mmol, 4.99 equiv) in DMSO (5 mL), was stirred overnight at 80° C. The resulting solution was diluted with water, extracted with ethyl acetate, washed with brine, dried over anhydrous sodium sulfate, and concentrated under vacuum. The residue was purified by a silica gel column eluting with ethyl acetate/petroleum ether (1:1) to afford the title compound (100 mg, crude) as light yellow oil. LCMS [M+H$^+$] 508.

Step 5: Preparation of (2S,4R,5S)-4-cyano-N-([2-fluoro-5-[2-(trifluoromethyl)pyrimidin-5-yl]phenyl]methyl)-5-methylpyrrolidine-2-carboxamide

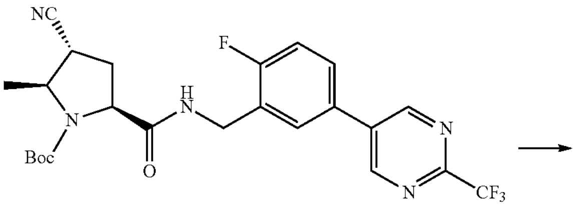

-continued

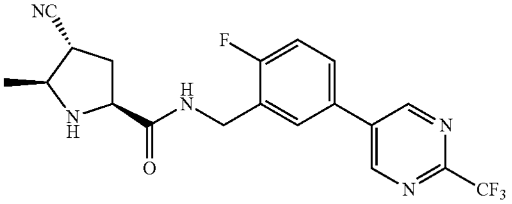

A solution of tert-butyl (2S,3R,5S)-3-cyano-5-[([2-fluoro-5-[2-(trifluoromethyl)pyrimidin-5-yl]phenyl]methyl)carbamoyl]-2-methylpyrrolidine-1-carboxylate (90 mg, 0.18 mmol, 1.00 equiv) in dichloromethane (10 mL)/trifluoroacetic acid (2 mL) was stirred overnight at room temperature. The resulting solution was concentrated under vacuum and the residue was diluted with water. The pH value of the solution was adjusted to 8 with saturated solution of sodium bicarbonate. The resulting mixture was extracted with ethyl acetate, washed with brine, dried over anhydrous sodium sulfate, and concentrated under vacuum. This resulted in the title compound (40 mg, 55%) as light yellow oil. LCMS [M+H$^+$] 408.

Step 6: Preparation of (2S,4R,5S)-4-cyano-N-([2-fluoro-5-[2-(trifluoromethyl)pyrimidin-5-yl]phenyl]methyl)-1-[(4-fluorobenzene)sulfonyl]-5-methylpyrrolidine-2-carboxamide

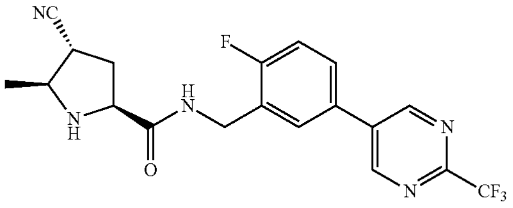

+

-continued

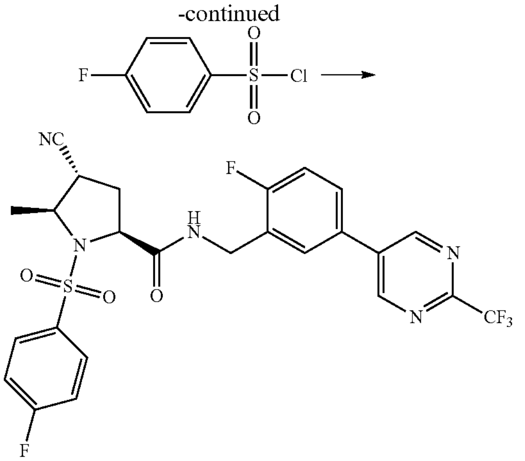

A mixture of (2S,4R,5S)-4-cyano-N-([2-fluoro-5-[2-(trifluoromethyl)pyrimidin-5-yl]phenyl]methyl)-5-methylpyrrolidine-2-carboxamide (90 mg, 0.22 mmol, 1.00 equiv) and 4-fluorobenzene-1-sulfonyl chloride (85.7 mg, 0.44 mmol, 1.99 equiv) in dichloromethane (5 mL)/TEA (44.6 mg, 0.44 mmol, 1.99 equiv) was stirred overnight at room temperature. The resulting solution was diluted with water, extracted with ethyl acetate, washed with brine, dried over anhydrous sodium sulfate, and concentrated under vacuum. The residue was purified by a silica gel column eluting with ethyl acetate/petroleum ether (1:1) followed by Prep-HPLC to afford the title compound (3.3 mg, 3%) as an off-white solid. LCMS [M+H$^+$] 566; $^1$H NMR (400 MHz, $CDCl_3$) δ 9.12 (s, 2H), 7.94-7.90 (m, 2H), 7.72-7.70 (m, 1H), 7.59-7.55 (m, 1H), 7.36-7.30 (m, 4H), 4.79-4.74 (m, 1H), 4.64-4.58 (m, 1H), 4.32-4.29 (m, 1H), 3.80 (t, J=8.6 Hz, 1H), 2.81-2.63 (m, 2H), 1.84-1.76 (m, 1H), 1.58 (s, 3H).

Example 3: (2S,5S)—N-([2-chloro-6-[2-(trifluoromethyl)pyrimidin-5-yl]pyridin-4-yl]methyl)-1-[(4-fluorobenzene)sulfonyl]-5-methylpyrrolidine-2-carboxamide

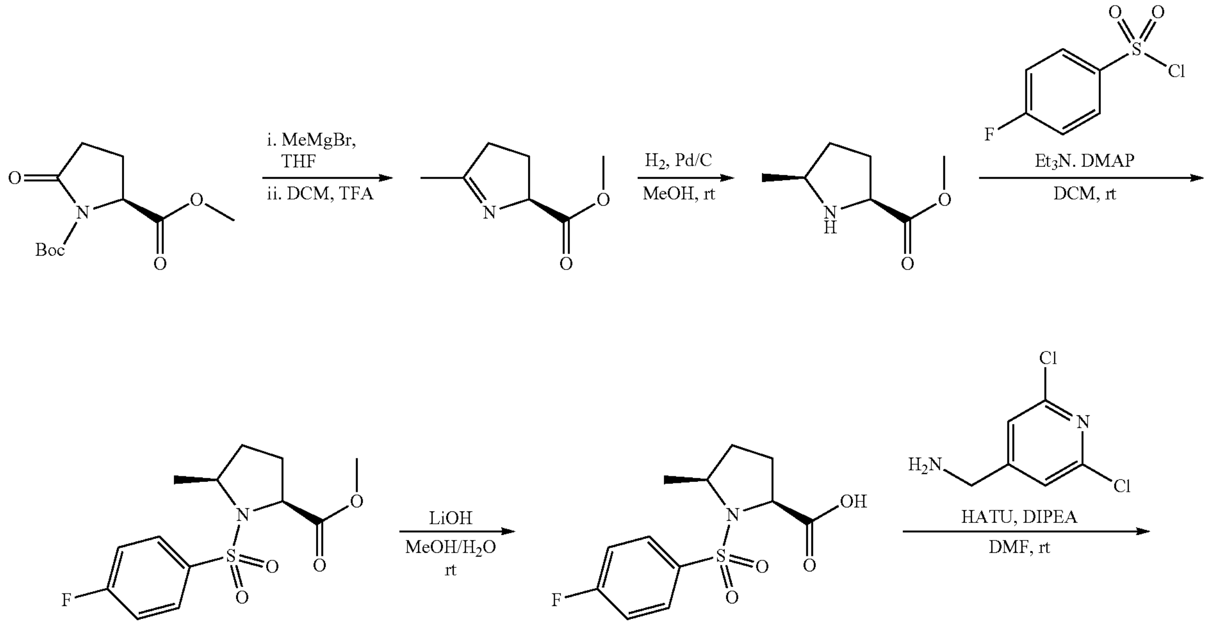

-continued

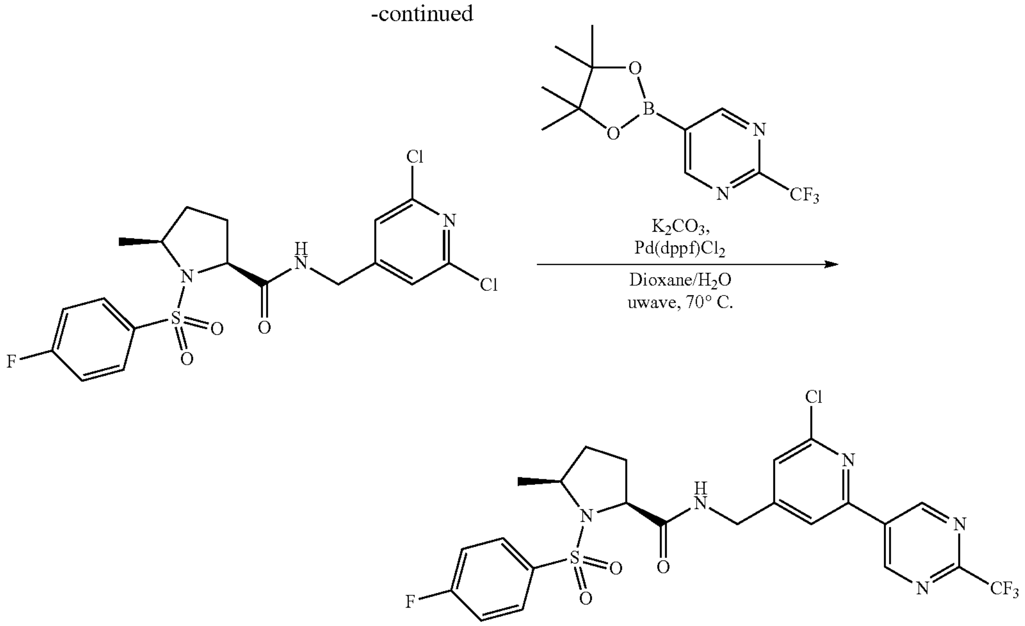

Step 1: Preparation of methyl (2S)-5-methyl-3,4-dihydro-2H-pyrrole-2-carboxylate

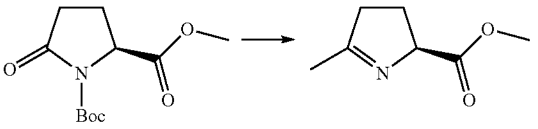

MeMgBr (34.3 mL, 3M in diethyl ether, 1.20 equiv) was added dropwise into a stirred solution of 1-tert-butyl 2-methyl (2S)-5-oxopyrrolidine-1,2-dicarboxylate (25 g, 102.77 mmol, 1.00 equiv) in tetrahydrofuran (120 mL) at −40° C. under nitrogen. The reaction was stirred for 2 h at −40° C. and overnight at room temperature. The mixture was quenched by aqueous $NH_4Cl$, extracted with ethyl acetate, washed with brine, dried over anhydrous sodium sulfate, and concentrated under vacuum. The residue was redissolved in dichloromethane (100 mL) and trifluoroacetic acid (25 mL). The resulting solution was stirred overnight at room temperature and concentrated under vacuum. This resulted in the title compound (20 g, crude) as light yellow oil. MS [M+H$^+$] 142.

Step 2: Preparation of methyl (2S,5S)-5-methylpyrrolidine-2-carboxylate

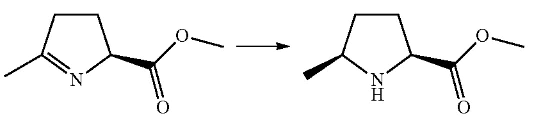

A mixture of methyl (2S)-5-methyl-3,4-dihydro-2H-pyrrole-2-carboxylate (41 g, 290.44 mmol, 1.00 equiv) and palladium on carbon (1 g) in methanol (120 mL) was stirred overnight at room temperature under hydrogen. The solid was filtered out and the liquid was concentrated under vacuum. This resulted in the title compound (40 g, crude) as a white solid. LCMS [M+H$^+$] 144.

Step 3: Preparation of methyl (2S,5S)-1-[(4-fluorobenzene)sulfonyl]-5-methylpyrrolidine-2-carboxylate

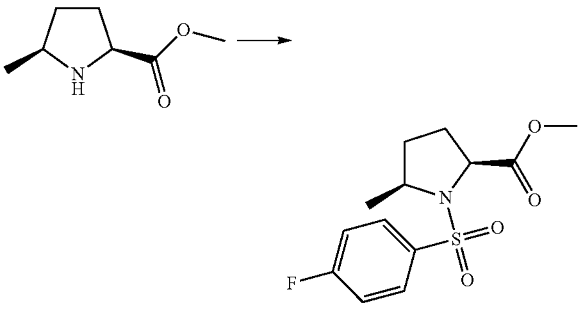

A mixture of methyl (2S,5S)-5-methylpyrrolidine-2-carboxylate (35 g, 244.44 mmol, 1.50 equiv), TEA (66.5 g, 657.18 mmol, 4.000 equiv), 4-dimethylaminopyridine (2 g, 16.37 mmol, 0.10 equiv), and 4-fluorobenzene-1-sulfonyl chloride (31.5 g, 161.86 mmol, 1.00 equiv) in dichloromethane (400 mL) was stirred for 1 h at room temperature. The resulting solution was diluted with dichloromethane, washed with brine, dried over anhydrous sodium sulfate, and concentrated under vacuum. The residue was purified by a silica gel column eluting with ethyl acetate/petroleum ether (1:4) to afford the title compound (18.8 g, 26%) as a light yellow solid. LCMS [M+H$^+$] 302.

Step 4: Preparation of (2S,5S)-1-[(4-fluorobenzene) sulfonyl]-5-methylpyrrolidine-2-carboxylic acid

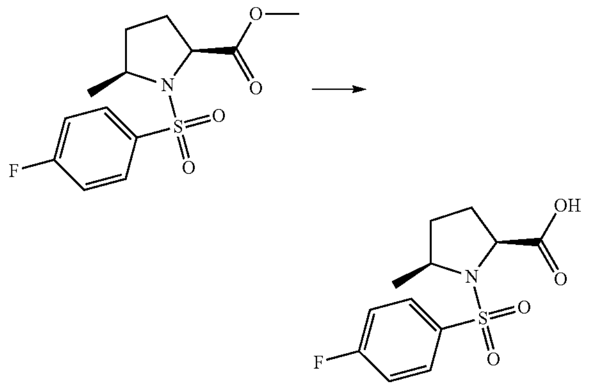

A mixture of methyl (2S,5S)-1-[(4-fluorobenzene)sulfonyl]-5-methylpyrrolidine-2-carboxylate (18.8 g, 62.39 mmol, 1.00 equiv) and LiOH (3 g, 125.27 mmol, 2.00 equiv) in methanol (60 mL)/water (40 mL) was stirred for 12 h at room temperature. The mixture was concentrated under vacuum. The residue was dissolved in water. The PH value of the solution was adjusted to 3 with diluted HCl. The mixture was extracted with dichloromethane, dried over anhydrous sodium sulfate, and concentrated under vacuum. This resulted in the title compound (1.9 g) as a white solid. LCMS [M+H$^+$] 288.

Step 5: Preparation of (2S,5S)—N-[(2,6-dichloropyridin-4-yl)methyl]-1-[(4-fluorobenzene)sulfonyl]-5-methylpyrrolidine-2-carboxamide

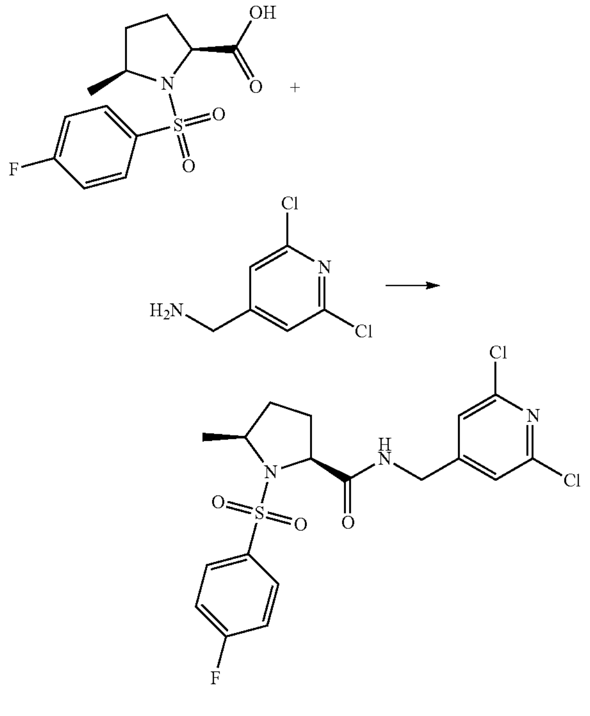

A mixture of (2S,5S)-1-[(4-fluorobenzene)sulfonyl]-5-methylpyrrolidine-2-carboxylic acid (3 g, 10.44 mmol, 1.00 equiv), HATU (4.7 g, 12.36 mmol, 1.20 equiv), DIEA (2.6 g, 20.12 mmol, 2.00 equiv), and (2,6-dichloropyridin-4-yl)methanamine (2 g, 11.30 mmol, 1.10 equiv) in N,N-dimethylformamide (100 mL) was stirred for 1 h at room temperature. The resulting solution was diluted with ethyl acetate, washed with brine, dried over anhydrous sodium sulfate, and concentrated under vacuum. The residue was purified by a silica gel column eluting with ethyl acetate/petroleum ether (1:1) to afford the title compound (3.6 g, 77%) as yellow oil. LCMS [M+H$^+$] 446.

Step 6: Preparation of (2S,5S)—N-([2-chloro-6-[2-(trifluoromethyl)pyrimidin-5-yl]pyridin-4-yl]methyl)-1-[(4-fluorobenzene)sulfonyl]-5-methylpyrrolidine-2-carboxamide

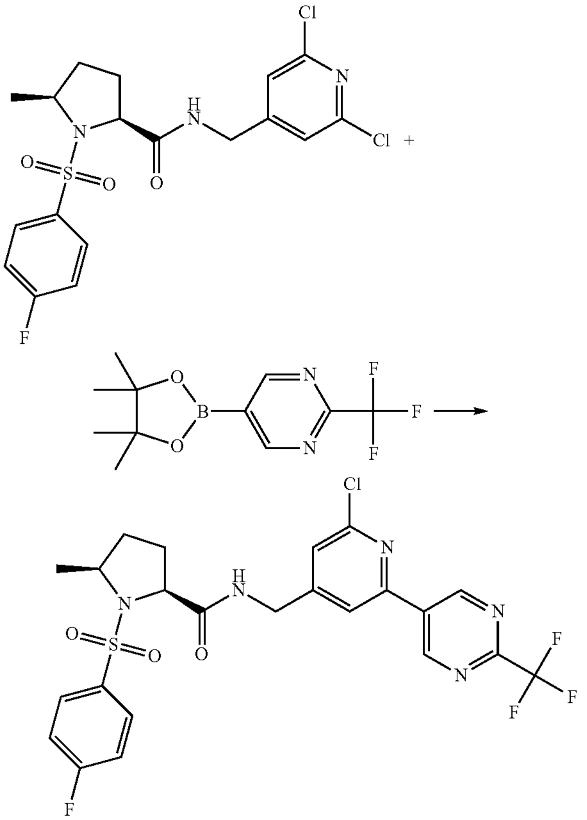

A mixture of (2S,5S)—N-[(2,6-dichloropyridin-4-yl)methyl]-1-[(4-fluorobenzene)sulfonyl]-5-methylpyrrolidine-2-carboxamide (3.5 g, 1.00 equiv), 5-(tetramethyl-1,3,2-dioxaborolan-2-yl)-2-(trifluoromethyl)pyrimidine (1.5 g, 0.70 equiv), Pd(dppf)$Cl_2$ (574 mg, 0.10 equiv), and potassium carbonate (3.2 g, 3.00 equiv) in 1,4-dioxane (20 mL)/water (2 mL) was irradiated with microwave radiation for 30 min at 70° C. under nitrogen. The resulting mixture was concentrated under vacuum. The resulting solution was diluted with ethyl acetate, washed with brine, dried over anhydrous sodium sulfate, and concentrated under vacuum. The residue was purified by a silica gel column eluting with ethyl acetate/petroleum ether (2:3) to afford the title compound (520.5 mg) as a white solid. LCMS [M+H]$^+$ 558.2; $^1$H NMR (400 MHz, $CDCl_3$) δ 9.56 (s, 2H), 7.94-7.91 (m, 3H), 7.54 (s, 1H), 7.40 (s, 1H), 7.33-7.28 (m, 2H), 4.94-4.90 (m, 1H), 4.44-4.40 (s, 1H), 4.19-4.16 (s, 1H), 3.75-3.70 (s, 1H), 2.21-2.18 (m, 1H), 1.77-1.68 (s, 2H), 1.56-1.49 (m, 4H).

Example 4: (5S)-4-[(4-fluorobenzene)sulfonyl]-N-([6-[2-(trifluoromethyl)pyrimidin-5-yl]pyrimidin-4-yl]methyl)-4-azaspiro[2.4]heptane-5-carboxamide

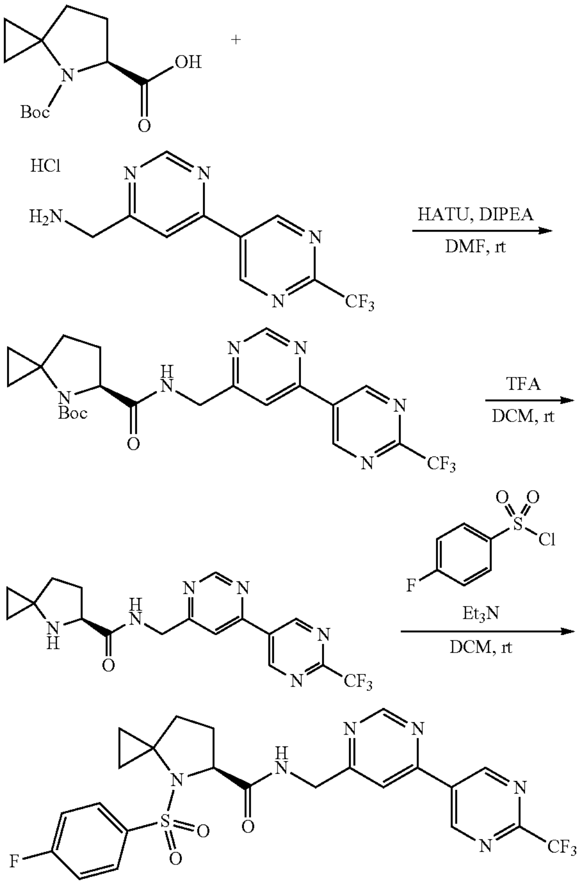

Step 8: Preparation of tert-butyl (5S)-5-[([6-[2-(trifluoromethyl)pyrimidin-5-yl]pyrimidin-4-yl]methyl)carbamoyl]-4-azaspiro[2.4]heptane-4-carboxylate

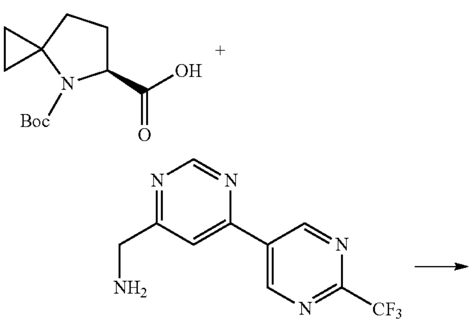

-continued

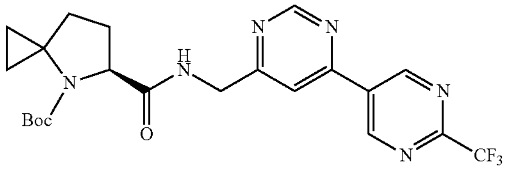

A mixture of (5S)-4-[(tert-butoxy)carbonyl]-4-azaspiro[2.4]heptane-5-carboxylic acid (290 mg, 1.20 mmol, 1.00 equiv), DIEA (466 mg, 3.61 mmol, 3.00 equiv), HATU (686 mg, 1.80 mmol, 1.50 equiv), and [6-[2-(trifluoromethyl)pyrimidin-5-yl]pyrimidin-4-yl]methanamine (153 mg, 0.60 mmol, 0.45 equiv) in N,N-dimethylformamide (10 mL) was stirred for 30 min at room temperature. The resulting solution was diluted with ethyl acetate, washed with brine, dried over anhydrous sodium sulfate, and concentrated under vacuum. The residue was purified by a silica gel column eluting with ethyl acetate/petroleum ether (1/4) to afford the title compound (395 mg, 69%) as a light yellow solid. LCMS [M+H$^+$] 479.

Step 9: Preparation of N-([6-[2-(trifluoromethyl)pyrimidin-5-yl]pyrimidin-4-yl]methyl)-4-azaspiro[2.4]heptane-5-carboxamide

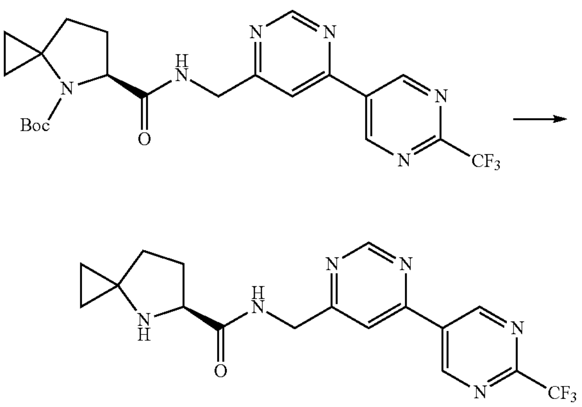 [SMILES: CC(C)(C)OC(=O)N1[C@H](C(=O)NCc2cc(-c3cnc(C(F)(F)F)nc3)ncn2)CCC12CC2 ; O=C(NCc1cc(-c2cnc(C(F)(F)F)nc2)ncn1)[C@@H]1CCC2(CC2)N1]

Trifluoroacetic acid (5 mL) was added dropwise into a solution of tert-butyl 5-[([6-[2-(trifluoromethyl)pyrimidin-5-yl]pyrimidin-4-yl]methyl)carbamoyl]-4-azaspiro[2.4]heptane-4-carboxylate (390 mg, 0.82 mmol, 1.00 equiv) in dichloromethane (25 mL) at room temperature. After being stirred for 30 min at room temperature the resulting mixture was concentrated under vacuum, diluted with saturated sodium bicarbonate, extracted with ethyl acetate, and washed with brine. The organic was dried over anhydrous sodium sulfate and concentrated under vacuum. This resulted in the title compound (140 mg, crude) as brown oil. LCMS [M+H$^+$] 379.

Step 10: Preparation of (5S)-4-[(4-fluorobenzene) sulfonyl]-N-([6-[2-(trifluoromethyl)pyrimidin-5-yl] pyrimidin-4-yl]methyl)-4-azaspiro[2.4]heptane-5-carboxamide

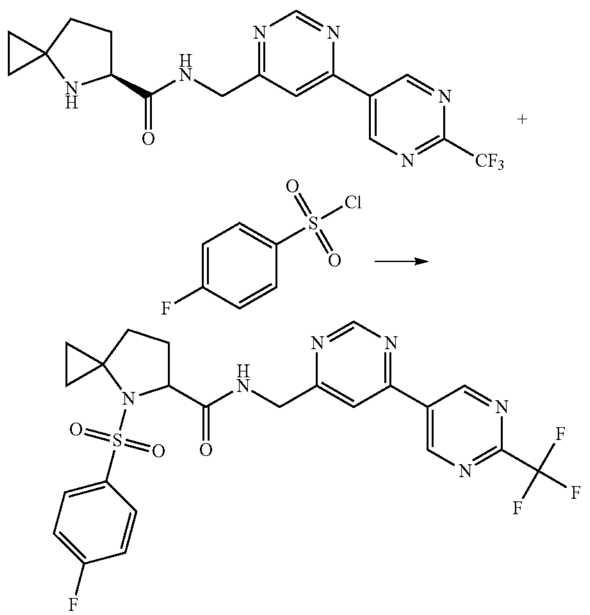

A solution of 4-fluorobenzene-1-sulfonyl chloride (88 mg, 0.452 mmol, 1.222 equiv) in tetrahydrofuran (1 mL) was added dropwise into a mixture of (5S)—N-([6-[2-(trifluoromethyl)pyrimidin-5-yl]pyrimidin-4-yl]methyl)-4-azaspiro[2.4]heptane-5-carboxamide (140 mg, 0.370 mmol, 1.000 equiv), tetrahydrofuran (7 mL), and a solution of sodium bicarbonate (90 mg, 1.07 mmol, 2.9 equiv) in water (8 mL). After being stirred for 40 min at room temperature the resulting mixture was diluted with brine, extracted with ethyl acetate, washed with brine, dried over anhydrous sodium sulfate, and concentrated under vacuum. The crude product was purified by Prep-HPLC to afford the title compound (22.2 mg, 11%) as a white solid. LCMS [M+H+] 549; $^{1}$H NMR (400 MHz, CD3OD) δ 9.69 (s, 2H), 9.32 (s, 1H), 8.15 (s, 1H), 8.02-7.98 (m, 2H), 7.53-7.52 (m, 1H), 7.33 (t, J=8.4 Hz, 2H), 5.13-5.07 (m, 1H), 4.54-4.48 (m, 2H), 2.40-2.29 (m, 2H), 2.15-2.10 (m, 1H), 1.28-1.17 (m, 2H), 0.97-0.88 (m, 2H), 0.62-0.57 (m, 1H).

Example 59: (2S,4R)-4-fluoro-N-[[5-fluoro-2-[4-(pentafluoro-sulfanyl)phenyl]-4-pyridyl]methyl]-1-(4-fluorophenyl)sulfonyl-pyrrolidine-2-carboxamide

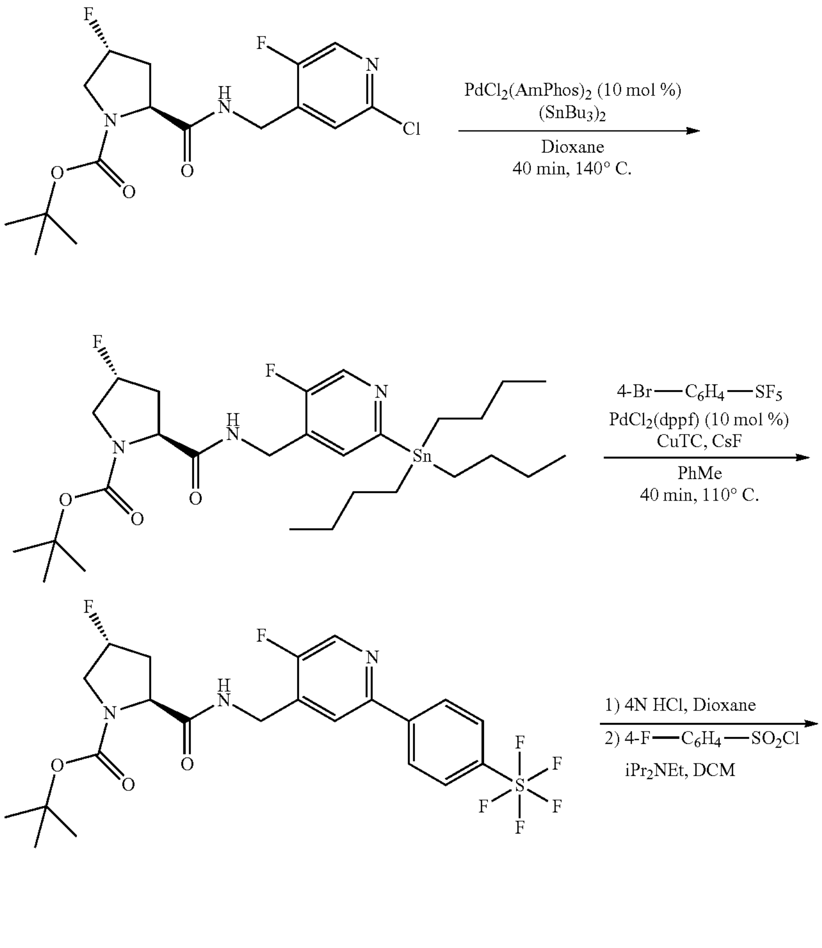

-continued

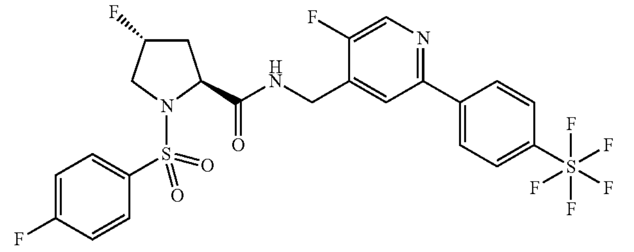

Step 1: Preparation of tert-butyl (2S,4R)-4-fluoro-2-[(5-fluoro-2-tributylstannyl-4-pyridyl)methylcarbamoyl]pyrrolidine-1-carboxylate Step 2: Preparation of tert-butyl (2S,4R)-4-fluoro-2-[[5-fluoro-2-[4-(pentafluoro-sulfanyl)phenyl]-4-pyridyl]methylcarbamoyl]pyrrolidine-1-carboxylate

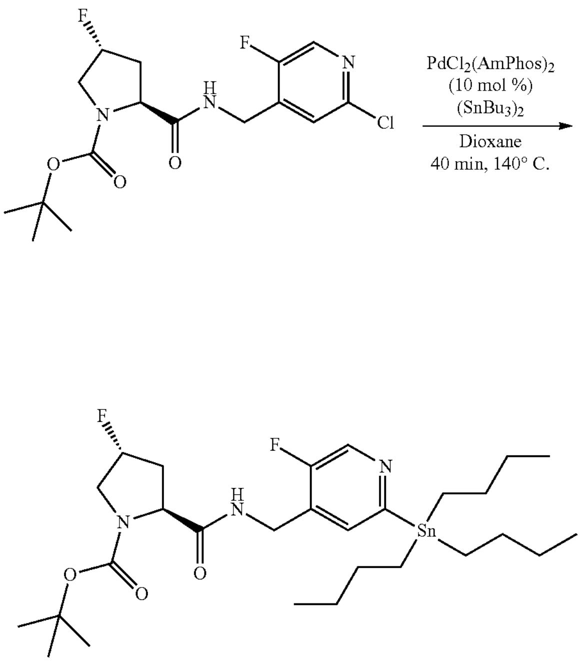

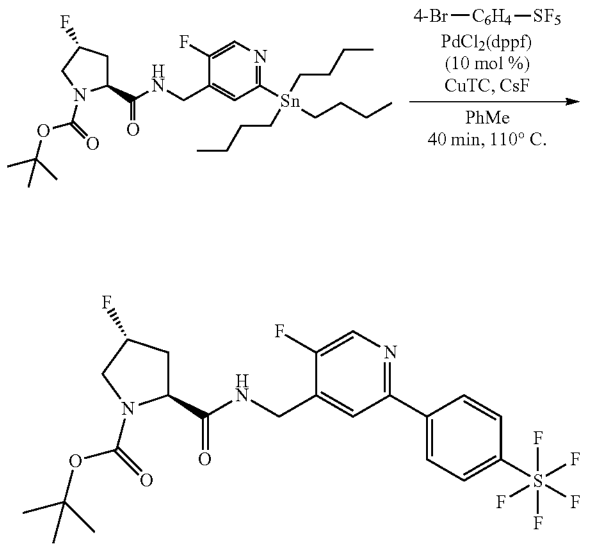

To a vial was added tert-butyl (2S,4R)-2-[(2-chloro-5-fluoro-4-pyridyl)methylcarbamoyl]-4-fluoro-pyrrolidine-1-carboxylate (269 mg, 0.716 mmol) and bis(di-tert-butyl(4-dimethylaminophenyl)phosphine)dichloropalladium(II) (53 mg, 0.072 mmol). 1,4-Dioxane (3.6 mL) was added followed by bis(tributyltin) (0.80 mL, 1.56 mmol). The reaction mixture was heated to 140° C. under microwave irradiation for 30 minutes then diluted with dichloromethane, filtered through celite, eluting with dichloromethane and the filtrate was concentrated in vacuo. The residue was adsorbed onto silica and purified by flash column chromatography with 0-50% EtOAc in heptane to afford the title compound (152 mg, 34%) as a yellow oil that solidified on standing.

To a vial containing tert-butyl (2S,4R)-4-fluoro-2-[(5-fluoro-2-tributylstannyl-4-pyridyl)methylcarbamoyl]pyrrolidine-1-carboxylate (71.9 mg, 0.114 mmol) was added toluene (2.0 mL), (4-bromophenyl)-pentafluorosulfane (38.7 mg, 0.137 mmol), 1,1'-bis(diphenylphosphino)ferrocene-palladium(II)dichloride dichloromethane complex (9.5 mg, 0.0114 mmol), copper(I) thiophene-2-carboxylate (34.0 mg, 0.171 mmol) and cesium fluoride (34.7 mg, 0.228 mmol). The vial was capped and nitrogen was bubbled through for 5 min and the reaction mixture was then heated in the microwave at 110° C. for 40 min. The reaction mixture was filtered through celite, eluting with DCM. The filtrate was washed with sat. aq. ammonium bicarbonate and the aqueous layer was extracted with DCM (2×). The combined organic layers were dried over sodium sulfate, filtered and concentrated in vacuo. The residue was adsorbed onto silica and purified by flash column chromatography with 0-100% EtOAc in heptane to afford the title compound (27.4 mg, 44%) as a yellow solid.

Step 3: Preparation of (2S,4R)-4-fluoro-N-[[5-fluoro-2-[4-(pentafluoro-sulfanyl)phenyl]-4-pyridyl]methyl]-1-(4-fluorophenyl)sulfonyl-pyrrolidine-2-carboxamide

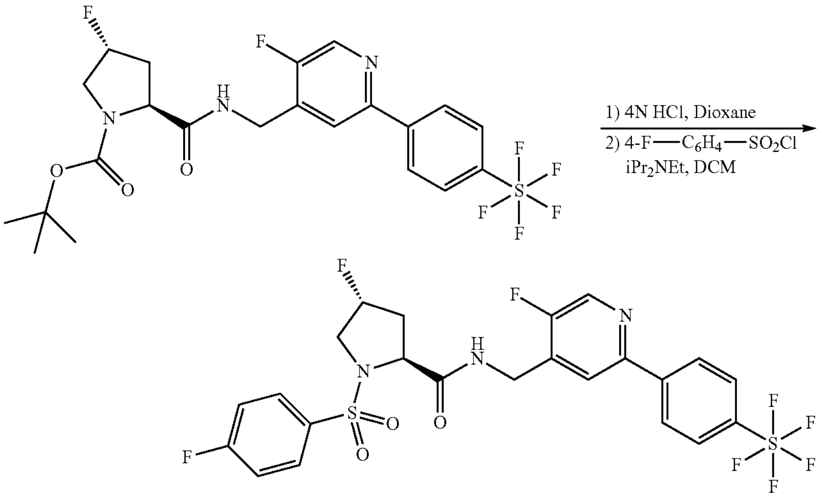

To a solution of tert-butyl (2S,4R)-4-fluoro-2-[[5-fluoro-2-[4-(pentafluoro-sulfanyl)phenyl]-4-pyridyl]methylcarbamoyl]pyrrolidine-1-carboxylate (27.4 mg, 0.0504 mmol) in dichloromethane (1 mL) was added hydrochloric acid (4 mol/L) in 1,4-dioxane (0.3 mL). The reaction mixture was stirred at room temp for 2 h. The reaction mixture was concentrated in vacuo and diluted with dichloromethane (1.5 mL). 4-Fluorobenzenesulfonyl chloride (10.8 mg, 0.0555 mmol) and triethylamine (0.021 mL, 0.151 mmol) were added and the reaction mixture was stirred at room temperature for 2 h. The reaction mixture was diluted with DCM and water, and the layers were separated and the aqueous layer was extracted with DCM (2×). The combined organic layers were dried over sodium sulfate, filtered and concentrated in vacuo. The residue was purified by RP-HPLC to yield the title compound (23.3 mg, 77%) as a white solid.

$^1$H NMR (400 MHz, DMSO) δ 9.03 (t, J=5.9 Hz, 1H), 8.68 (d, J=1.2 Hz, 1H), 8.25 (d, J=8.6 Hz, 2H), 8.11 (d, J=5.8 Hz, 1H), 8.05-7.91 (m, 4H), 7.54-7.41 (m, 2H), 5.30-5.11 (m, 1H), 4.51 (d, J=5.8 Hz, 2H), 4.23 (dd, J=10.0, 7.1 Hz, 1H), 3.79-3.55 (m, 2H), 2.44-2.36 (m, 1H), 2.21-1.98 (m, 1H).

Example 68: (1S,2S,5R)—N-((5-fluoro-2-(2-(trifluoromethyl)pyrimidin-5-yl)pyridin-4-yl)methyl)-3-(4-fluorophenylsulfonyl)-3-azabicyclo[3.1.0]hexane-2-carboxamide

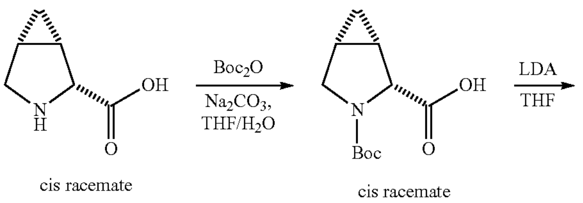

-continued

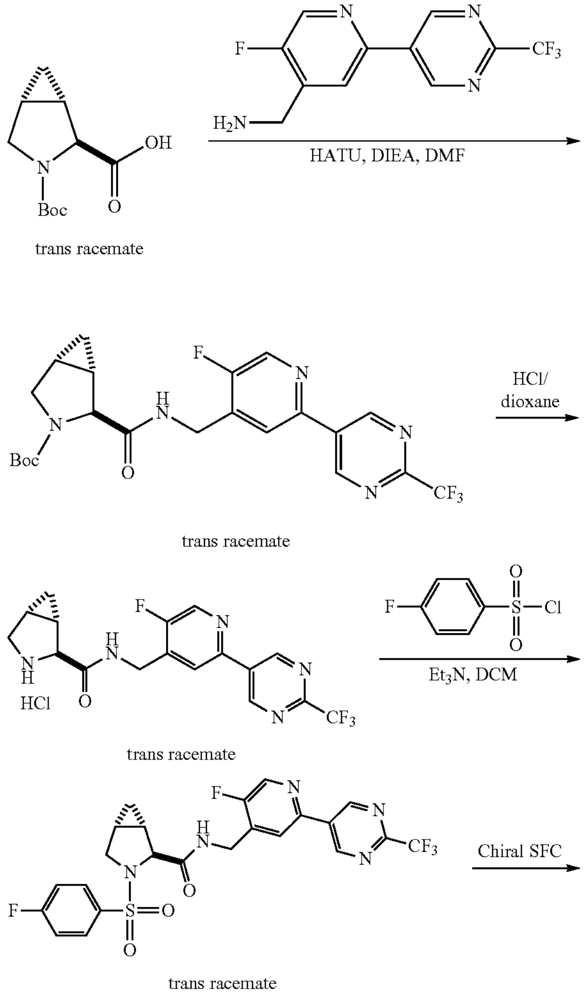

-continued

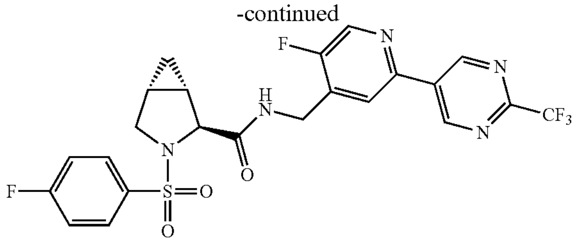

trans single enantiomer

Step 1: Preparation of 3-(tert-butoxycarbonyl)-3-aza-bicyclo[3.1.0]hexane-2-carboxylic Acid

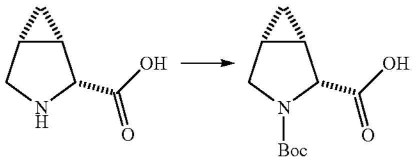

cis racemate cis racemate $Boc_2O$ (10 g, 45.820 mmol, 1.15 equiv) was added to a solution of 3-azabicyclo[3.1.0]hexane-2-carboxylic acid (5 g, 39.326 mmol, 1.00 equiv), water (100 mL) and sodium carbonate (11 g, 103.785 mmol, 2.50 equiv) in tetrahydrofuran (100 mL) at 0° C. The resulting solution was stirred overnight at room temperature. The reaction was quenched with water and washed with ethyl acetate. The aqueous layer was acidified to pH 2 with 1M HCl and the resulting mixture was extracted with ethyl acetate. The organic layers were dried with sodium sulfate, filtered, and concentrated to give the title compound as a white solid 7 g (78%). LCMS [M+H$^+$] 228.

Step 2: Preparation of 3-(tert-butoxycarbonyl)-3-aza-bicyclo[3.1.0]hexane-2-carboxylic Acid(Trans)

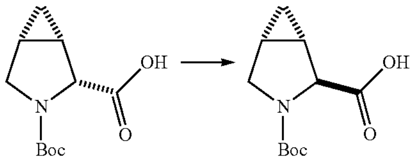

cis racemate trans racemate n-BuLi (2.5M) (9 mL, 95.54 mmol, 1.50 equiv) was added to a solution of bis(propan-2-yl)amine (2.2 g, 21.74 mmol, 1.50 equiv) in tetrahydrofuran (80 mL) dropwise with stirring at −78° C. under nitrogen. The resulting solution was stirred for 30 min at −50 to −60° C. A solution of 3-[(tert-butoxy)carbonyl]-3-azabicyclo[3.1.0]hexane-2-carboxylic acid (3.2 g, 14.081 mmol, 1.00 equiv) in tetrahydrofuran (20 mL) was then added dropwise at −60° C. and the resulting mixture was stirred for 4 hours at 0° C. The reaction was quenched with water. The aqueous layer was washed with ethyl acetate and acidified to pH 2 with 1M HCl. The resulting mixture was extracted with ethyl acetate. The organic layers were dried with sodium sulfate, filtered, and concentrated. This resulted in the title compound (2.5 g) as a yellow solid. LCMS [M+H$^+$] 228.

Step 3: Preparation of tert-butyl 2-((5-fluoro-2-(2-(trifluoromethyl)pyrimidin-5-yl)pyridin-4-yl)methylcarbamoyl)-3-aza-bicyclo[3.1.0]hexane-3-carboxylate(trans)

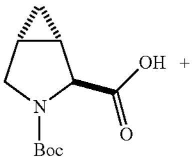

trans racemate

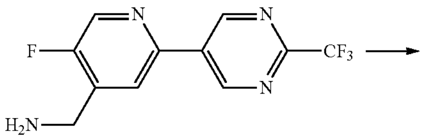

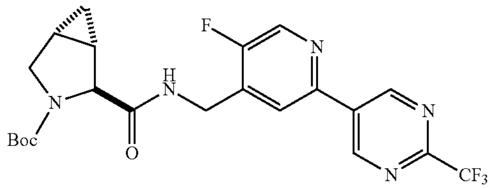

trans racemate

HATU (40 g, 105.20 mmol, 1.20 equiv) was added batchwise to a stirred solution of 3-[(tert-butoxy)carbonyl]-3-azabicyclo[3.1.0]hexane-2-carboxylic acid (20 g, 88.00 mmol, 1.00 equiv), [5-fluoro-2-[2-(trifluoromethyl)pyrimidin-5-yl]pyridin-4-yl]methanamine (24 g, 88.17 mmol, 1.00 equiv) and DIEA (34 g, 263.07 mmol, 3.00 equiv) in N,N-dimethylformamide (150 mL) at room temperature for 2 h. The reaction was diluted with water and extracted with ethyl acetate. The organic layers was dried with sodium sulfate, filtered, and concentrated. The residue was purified by a silica gel column eluting with ethyl acetate/petroleum ether (1:1) to afford the title compound (40 g) as a white solid (94%). LCMS [M+H$^+$] 482.

Step 4: Preparation of N-((5-fluoro-2-(2-(trifluoromethyl)pyrimidin-5-yl)pyridin-4-yl)methyl)-3-aza-bicyclo[3.1.0]hexane-2-carboxamide hydrochloride (trans)

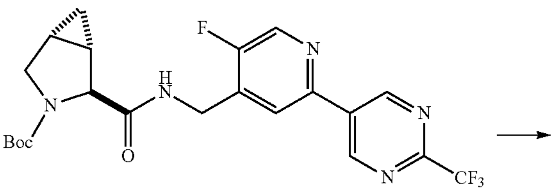

trans racemate

-continued

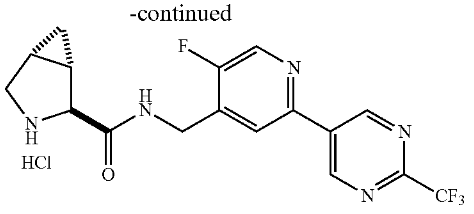

trans racemate

A solution of tert-butyl (1S,5R)-2-[([5-fluoro-2-[2-(trifluoromethyl)pyrimidin-5-yl]pyridin-4-yl]methyl)carbamoyl]-3-azabicyclo[3.1.0]hexane-3-carboxylate (40 g, 83.084 mmol, 1.00 equiv) in hydrogen chloride saturated dioxane (500 mL) was stirred overnight at room temperature. The resulting mixture was concentrated under vacuum. This resulted in 36 g of the title compound as a yellow crude solid. LCMS [M+H$^+$] 382.

Step 5: Preparation of N-((5-fluoro-2-(2-(trifluoromethyl)pyrimidin-5-yl)pyridin-4-yl)methyl)-3-(4-fluorophenylsulfonyl)-3-aza-bicyclo[3.1.0]hexane-2-carboxamide(trans)

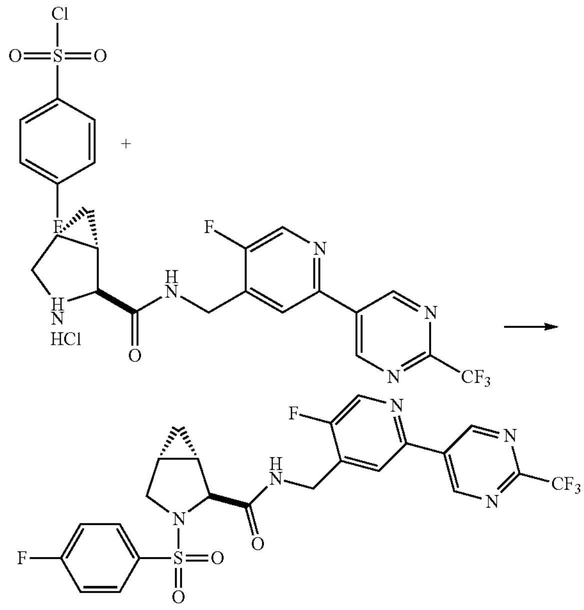

4-Fluorobenzene-1-sulfonyl chloride (19 g, 97.631 mmol, 1.20 equiv) in dichloromethane (300 mL) was added to a solution of N-([5-fluoro-2-[2-(trifluoromethyl)pyrimidin-5-yl]pyridin-4-yl]methyl)-3-azabicyclo[3.1.0]hexane-2-carboxamide hydrochloride (35 g, 83.78 mmol, 1.00 equiv) and TEA (42 g, 415.06 mmol, 5.00 equiv) in 300 mL of dichloromethane. The mixture was stirred for 3 h at room temperature, washed with 500 mL of $H_2O$, dried over sodium sulfate, and concentrated under vacuum. A solid was precipitated by the addition of ethyl acetate. The solid was collected by filtration. This resulted in 24.9 g (55%) of the title compound as a white solid. LCMS [M+H$^+$] 540.

$^1$H NMR (400 MHz, DMSO-d6) δ 9.62 (s, 2H), 8.93 (t, J=5.9 Hz, 1H), 8.79 (d, J=1.3 Hz, 1H), 8.15 (d, J=5.7 Hz, 1H), 7.95-7.91 (m, 2H), 7.47 (m, 2H), 4.57 (dd, J=16.6, 6.2 Hz, 1H), 4.45 (dd, J=16.7, 5.7 Hz, 1H), 4.24 (s, 1H), 3.78-3.75 (m, 1H), 3.50-3.33 (m, 1H), 1.58 (dt, J=7.7, 3.8 Hz, 2H), 0.57-0.52 (m, 1H), −0.86 (q, J=4.5 Hz, 1H).

Step 6: Preparation of (1S,2S,5R)—N-((5-fluoro-2-(2-(trifluoromethyl)pyrimidin-5-yl)pyridin-4-yl)methyl)-3-(4-fluorophenylsulfonyl)-3-azabicyclo[3.1.0]hexane-2-carboxamide

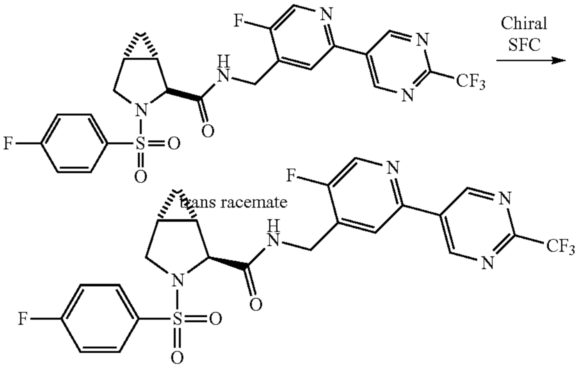

trans single enantiomer

The chiral purification of N-((5-fluoro-2-(2-(trifluoromethyl)pyrimidin-5-yl)pyridin-4-yl)methyl)-3-(4-fluorophenylsulfonyl)-3-aza-bicyclo[3.1.0]hexane-2-carboxamide (trans) was performed using a Waters-Thar 350 SFC instrument. The chiral column used was the Phenomenex Cellulose-4 packed using 5 micron particles. The purification was run under isocratic conditions with 70% Carbon Dioxide and 30% Methanol modified with 0.1% ammonia hydroxide. The total flow rate was 200 grams per minute with the back pressure regulator set at 100 bar. The active enantiomer was found to be the 3rd peak that eluted. 30 g of racemate provided the title single enantiomer as a white solid (13.17 g).

Example 71: (1S,2S,5R)-6,6-difluoro-N-((5-fluoro-2-(2-(trifluoromethyl)pyrimidin-5-yl)pyridin-4-yl)methyl)-3-((4-fluorophenyl)sulfonyl)-3-azabicyclo[3.1.0]hexane-2-carboxamide

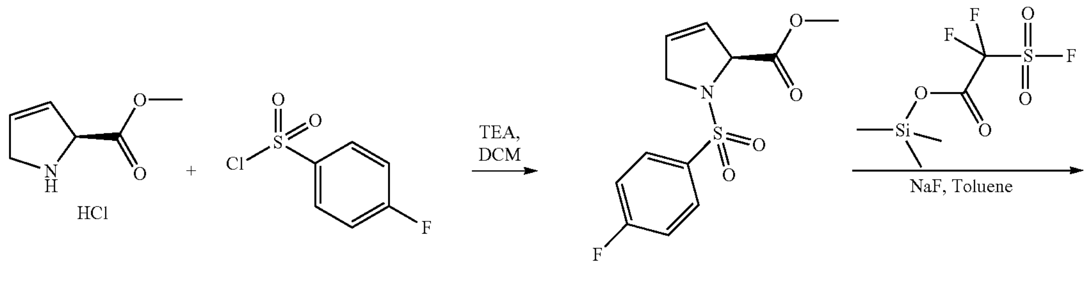

-continued

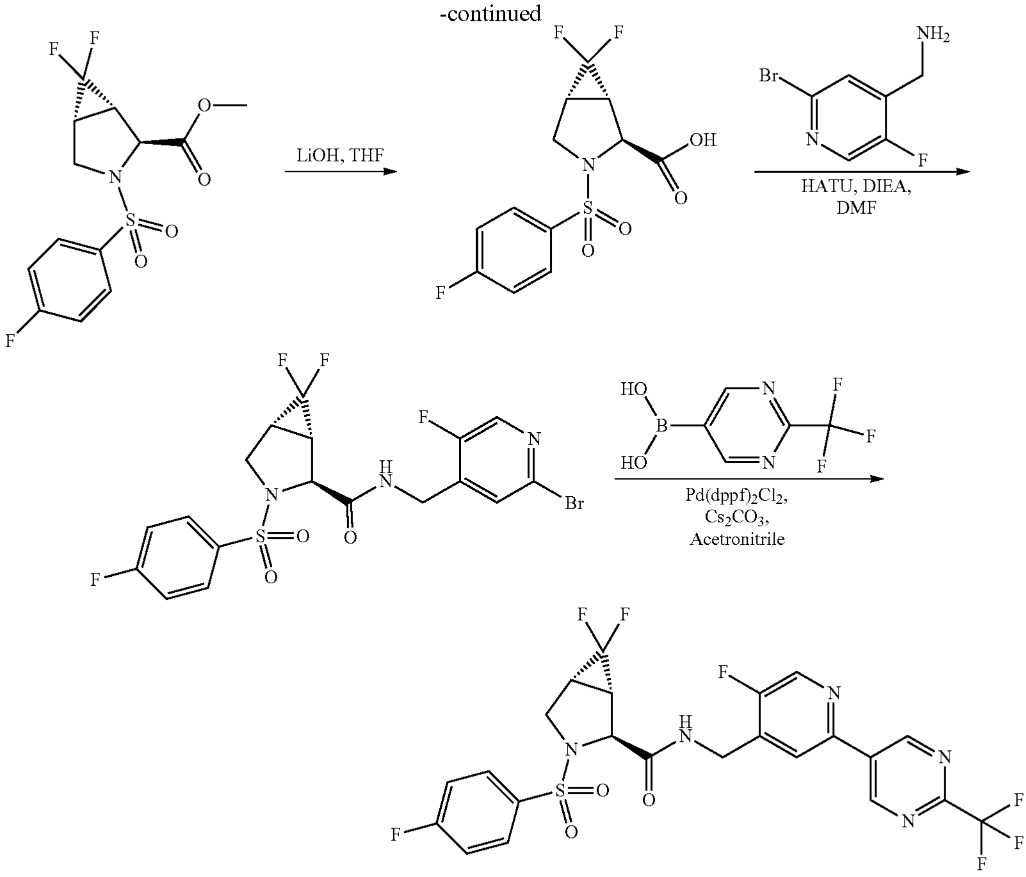

Step 1: Preparation of (S)-methyl 1-((4-fluorophenyl)sulfonyl)-2,5-dihydro-1H-pyrrole-2-carboxylate

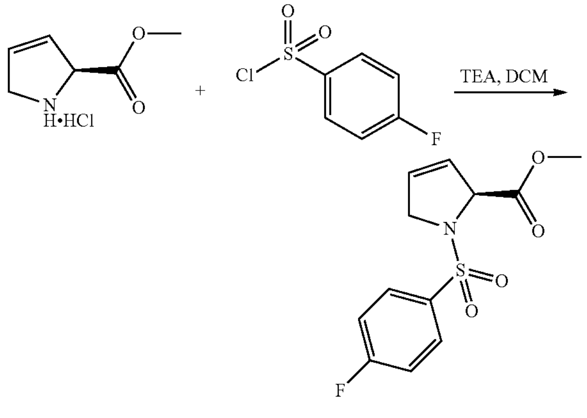

To a solution of methyl (2S)-2,5-dihydro-1H-pyrrole-2-carboxylate hydrochloride (250 mg, 1.53 mmol) in dichloromethane (3.00 mL) at 0° C. was added triethylamine (1.06 mL, 7.64 mmol) and 4-fluorobenzenesulfonyl chloride (607 mg, 3.05 mmol) dropwise. The reaction mixture was stirred at r.t. for 1 h. The reaction was then quenched with water and extracted with ethyl acetate. The crude product was purified by flash chromatography (EtOAc/Heptane eluted at 40% EtOAc) to give the title compound (292 mg, 67% yield).

MS-ESI: $[M+H]^+$ 285.9

Step 2: Preparation of (1S,2S,5R)-methyl 6,6-difluoro-3-((4-fluorophenyl)sulfonyl)-3-azabicyclo[3.1.0]hexane-2-carboxylate

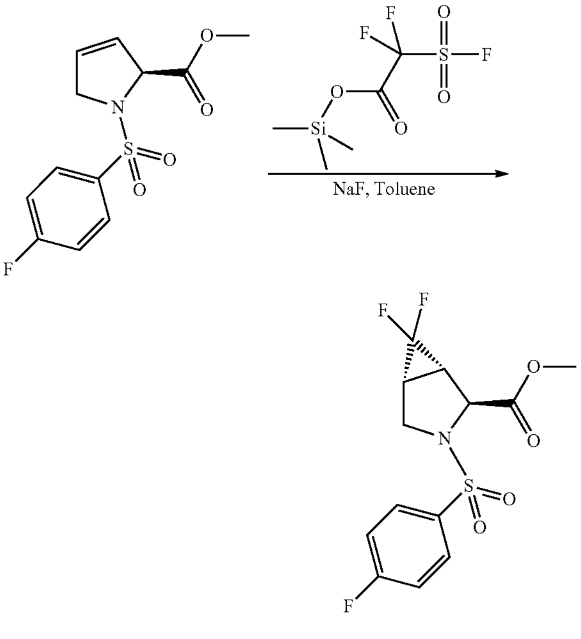

A solution of methyl (2S)-1-(4-fluorophenyl)sulfonyl-2,5-dihydropyrrole-2-carboxylate (765 mg, 2.681 mmol) in toluene (0.54 mL, 5.02 mmol) was added sodium fluoride (34 mg, 0.81 mmol). The reaction was heated at 120° C. 30 min then trimethylsilyl 2,2-difluoro-2-(fluorosulfonyl)acetate (1.12 mL, 5.36 mmol) was added over 2 h then stirred an additional 2 h at 120° C. The reaction was quenched with saturated sodium carbonate and extracted with ethyl acetate. The organic layers were dried with sodium sulfate, filtered, and concentrated via rotovap. The crude product was purified by flash chromatography (EtOAc/Heptane_eluted at 50% EtOAc) to give the title compound (140 mg, 11.7% yield).

MS-ESI: [M+H]+ 335.9

Step 3: Preparation of (1S,2S,5R)-6,6-difluoro-3-((4-fluorophenyl)sulfonyl)-3-azabicyclo[3.1.0]hexane-2-carboxylic Acid

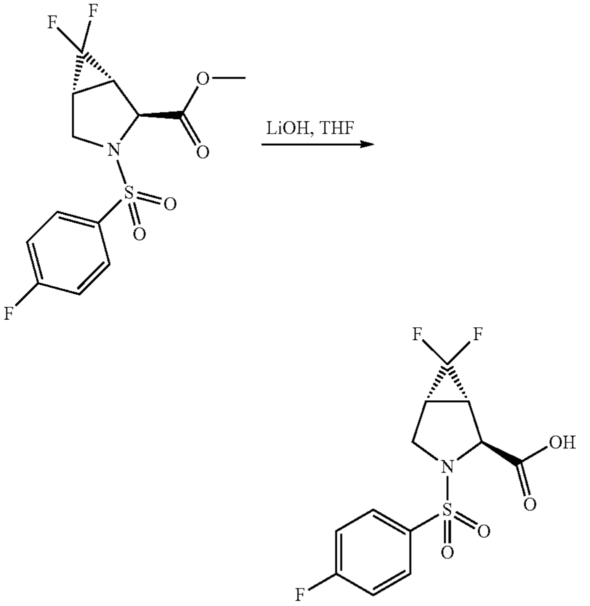

To a solution of methyl (1R,4S,5S)-6,6-difluoro-3-(4-fluorophenyl)sulfonyl-3-azabicyclo[3.1.0]hexane-4-carboxylate (140 mg, 0.42 mmol) in tetrahydrofuran (2.8 mL) and water (2.8 mL) was added lithium hydroxide hydrate (21.0 mg, 0.501 mmol). The reaction mixture was stirred at room temperature for 18 h. LCMS showed complete conversion to product. The reaction was quenched by the addition of saturated ammonium chloride, extracted with ethyl acetate, and the organic layer was concentrated to give the title compound (134 mg, 100% yield) without further purification. MS-ESI: [M+H]+ 321.9

Step 4: Preparation of (1S,2S,5R)—N-((2-bromo-5-fluoropyridin-4-yl)methyl)-6,6-difluoro-3-((4-fluorophenyl)sulfonyl)-3-azabicyclo[3.1.0]hexane-2-carboxamide

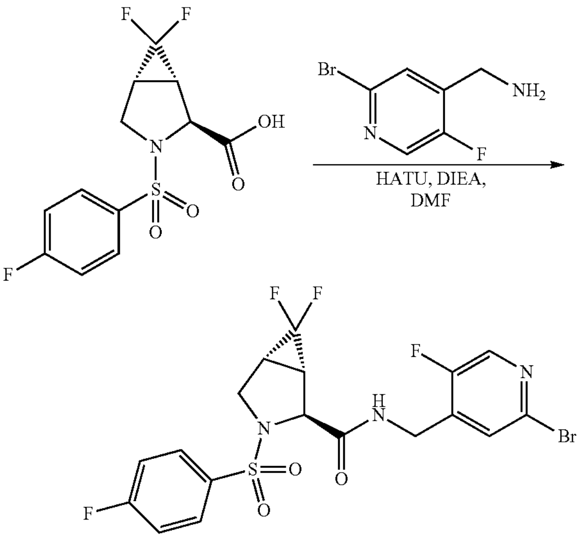

To a solution of (1R,4S,5S)-6,6-difluoro-3-(4-fluorophenyl)sulfonyl-3-azabicyclo[3.1.0]hexane-4-carboxylic acid (81 mg, 0.252 mmol) and 2-bromo-5-fluoropyridin-4-yl) methanamine (58.6 mg, 0.278 mmol) in N,N-dimethylformamide (1.00 mL) was added N,N-diisopropylethylamine (0.088 mL, 0.504 mmol) and HATU (117 mg, 0.303 mmol). The reaction mixture was then stirred at room temperature for 2 h. The reaction was quenched with water and extracted with ethyl acetate. The organic layers was dried with sodium sulfate, filtered, and concentrated via rotovap to give the title compound (128 mg, 100% yield) without further purification. MS-ESI: [M+H]+ 507.9

Step 5: Preparation of (1S,2S,5R)-6,6-difluoro-N-((5-fluoro-2-(2-(trifluoromethyl)pyrimidin-5-yl)pyridin-4-yl)methyl)-3-((4-fluorophenyl)sulfonyl)-3-azabicyclo[3.1.0]hexane-2-carboxamide

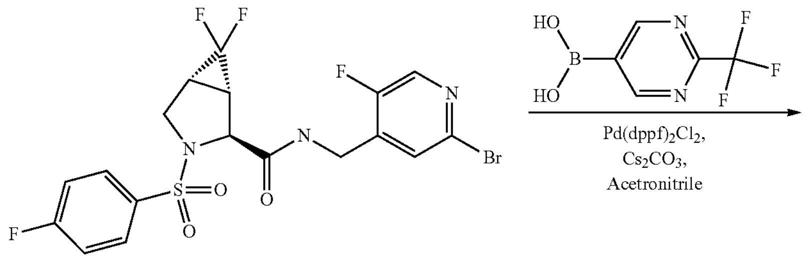

-continued

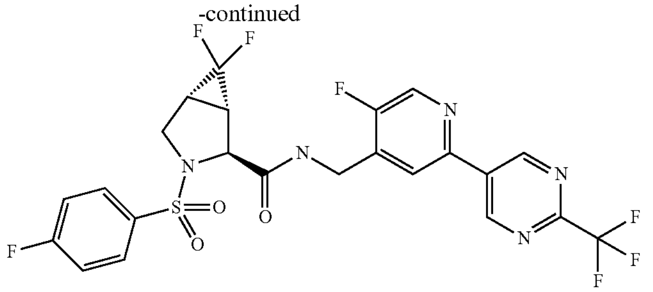

A solution of 2-(trifluoromethyl)pyrimidin-5-ylboronic acid (92 mg, 0.45 mmol), (1R,4S,5S)—N-[(2-bromo-5-fluoro-4-pyridyl)methyl]-6,6-difluoro-3-(4-fluorophenyl)sulfonyl-3-azabicyclo[3.1.0]hexane-4-carboxamide (192 mg, 0.378 mmol), cesium carbonate (246 mg, 0.756 mmol) and [1,1'-bis(diphenylphosphino)ferrocene]dichloropalladium(II) dichloromethane adduct (31.5 mg 0.0378 mmol) in acetonitrile (3.0 mL) and water (1.5 mL) was degassed. The reaction mixture was then heated at 95° C. for 2 h. The reaction was filtered thru celite, concentrated and purified by flash chromatography (MeOH/DCM eluted at 8% MeOH). Purification by reversed phase HPLC provided the title compound (62.7 mg, 27.7% yield). MS-ESI: $[M+H]^+$ 576.2

1H NMR (400 MHz, DMSO) δ 9.61-9.57 (s, 2H), 9.13-9.05 (m, 1H), 8.81-8.77 (d, J=1.3 Hz, 1H), 8.22-8.16 (d, J=5.7 Hz, 1H), 7.98-7.91 (m, 2H), 7.50-7.42 (m, 2H), 4.62-4.49 (m, 2H), 4.48-4.45 (m, 1H), 3.99-3.89 (m, 1H), 3.69-3.63 (m, 1H), 2.75-2.64 (m, 2H).

Example 78: (1S,4S,5R)-3-(4-fluorophenyl)sulfonyl-N-[[4-fluoro-3-[2-(trifluoromethyl)pyrimidin-5-yl]phenyl]methyl]-6,6-dimethyl-3-azabicyclo[3.1.0]hexane-4-carboxamide

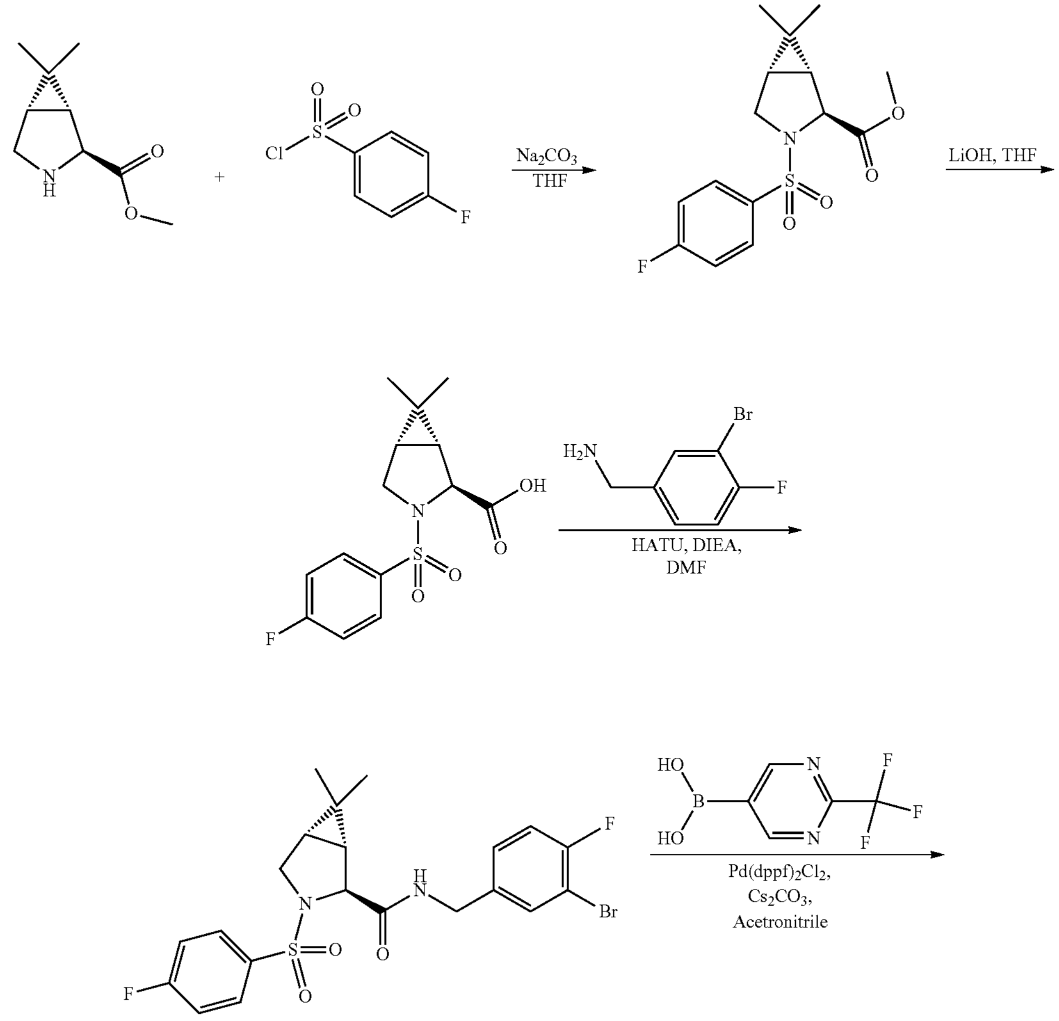

-continued

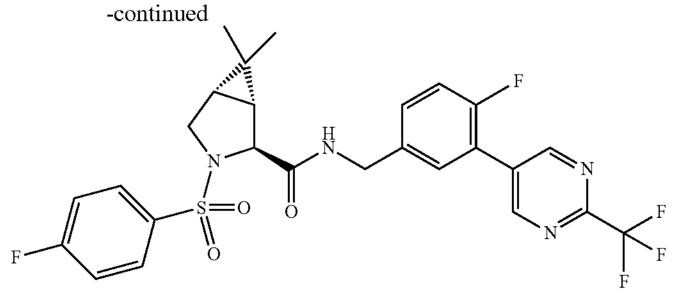

Step 1: Preparation of (1R,2S,5S)-methyl 3-(4-fluorophenylsulfonyl)-6,6-dimethyl-3-azabicyclo[3.1.0]hexane-2-carboxylate

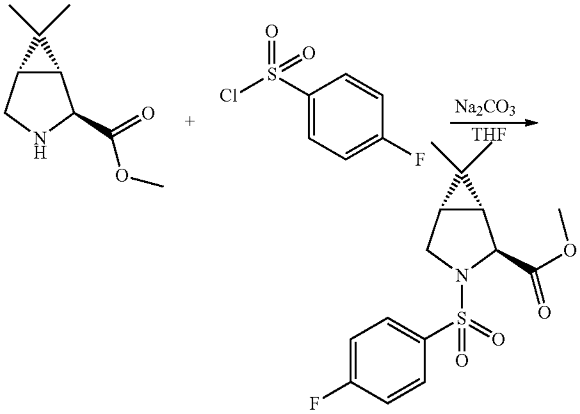

To a vial containing methyl (1S,4S,5R)-6,6-dimethyl-3-azabicyclo[3.1.0]hexane-4-carboxylate hydrochloride (390 mg, 1.90 mmol) in tetrahydrofuran (3.8 mL), and 1.0 M sodium carbonate in water (4.74 mL, 4.74 mmol) at 0° C. was added 4-fluorobenzenesulfonyl chloride (442.8 mg, 2.28 mmol). The reaction mixture was then stirred at 0° C. for 1 h. The reaction was quenched with water then extracted with ethyl acetate. The organic layers were then dried with sodium sulfate, filtered, and concentrated via rotovap. The crude product was purified by flash chromatography (EtOAc/Heptane) to give the title compound (580 mg, 93.4% yield). MS-ESI: $[M+H]^+$ 328.0

Step 2: Preparation of (1R,2S,5S)-3-((4-fluorophenyl)sulfonyl)-6,6-dimethyl-3-azabicyclo[3.1.0]hexane-2-carboxylic Acid

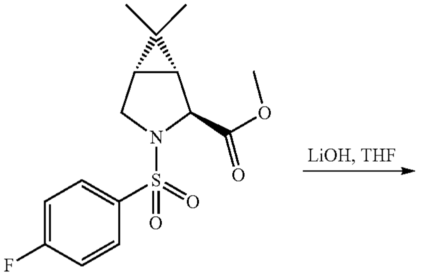

-continued

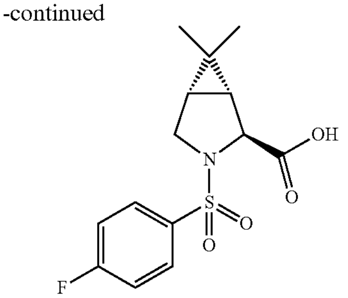

To a solution of methyl (1S,4S,5R)-3-(4-fluorophenyl)sulfonyl-6,6-dimethyl-3-azabicyclo[3.1.0]hexane-4-carboxylate (580 mg, 1.77 mmol) in tetrahydrofuran (12.0 mL) and water (12.0 mL) was added lithium hydroxide hydrate (89.20 mg, 2.13 mmol). The reaction mixture was stirred at room temperature for 18 h. LCMS showed complete conversion to product. The reaction was concentrated to give the title compound (555 mg, 100% yield) without further purification.

MS-ESI: $[M+H]^+$ 313.9

Step 3: (1R,2S,5S)—N-(3-bromo-4-fluorobenzyl)-3-((4-fluorophenyl)sulfonyl)-6,6-dimethyl-3-azabicyclo[3.1.0]hexane-2-carboxamide

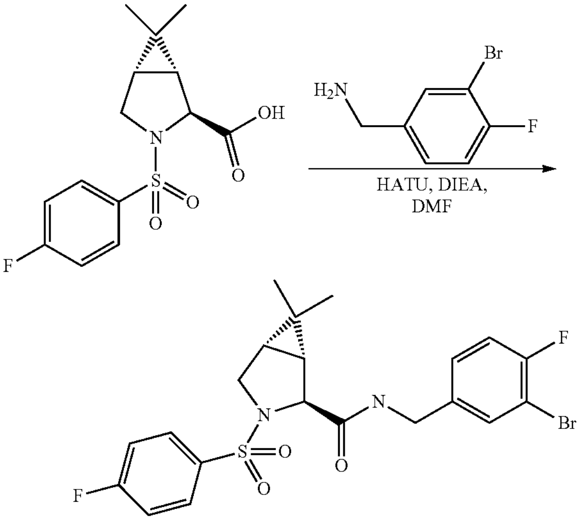

To a solution of (1S,4S,5R)-3-(4-fluorophenyl)sulfonyl-6,6-dimethyl-3-azabicyclo[3.1.0]hexane-4-carboxylic acid (97 mg, 0.31 mmol) and 3-bromo-4-fluorobenzylamine hydrochloride (83.6 mg, 0.341 mmol) in N,N-dimethylformamide (1.3 mL) was added N,N-diisopropylethylamine (0.0810 mL, 0.464 mmol) and HATU (144 mg, 0.37 mmol). The reaction mixture was stirred at room temperature for 2 h. The reaction was then quenched with water and extracted with ethyl acetate. The organic layers was dried with sodium sulfate, filtered, and concentrated via rotovap to give the title compound (155 mg, 100% yield) without further purification.

MS-ESI: $[M+H]^+$ 499.0

Step 4: (1R,2S,5S)—N-(4-fluoro-3-(2-(trifluoromethyl)pyrimidin-5-yl)benzyl)-3-((4-fluorophenyl)sulfonyl)-6,6-dimethyl-3-azabicyclo[3.1.0]hexane-2-carboxamide

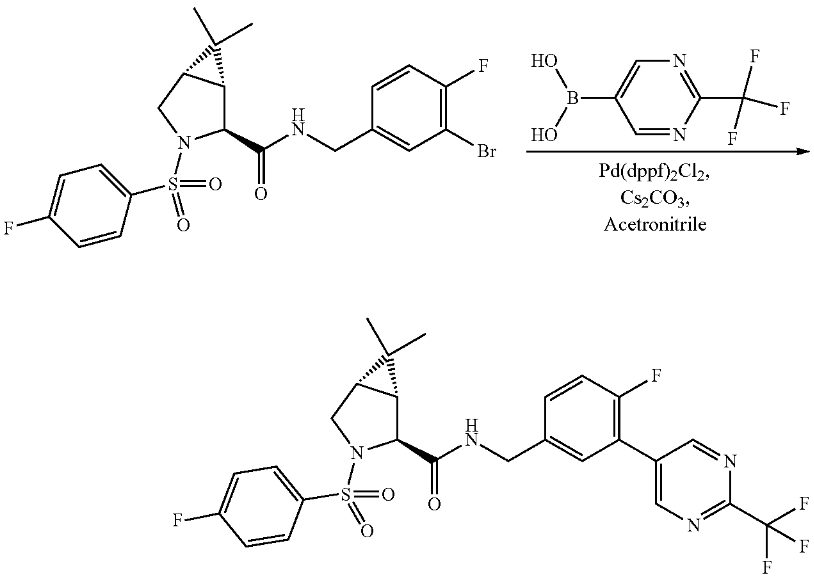

A solution of 2-(trifluoromethyl)pyrimidin-5-ylboronic acid (75 mg, 0.370 mmol), (1S,4S,5R)—N-[(3-bromo-4-fluoro-phenyl)methyl]-3-(4-fluorophenyl)sulfonyl-6,6-dimethyl-3-azabicyclo[3.1.0]hexane-4-carboxamide (154 mg, 0.3084 mmol), cesium carbonate (201.0 mg, 0.617 mmol) and [1,1'-bis(diphenylphosphino)ferrocene]dichloropalladium(II) dichloromethane adduct (26 mg, 0.031 mmol) in acetonitrile (3.0 mL) and water (1.5 mL) was degassed. The reaction mixture was then heated at 95° C. for 2 h. The reaction was filtered through celite and the crude product was purified by flash chromatography (MeOH/DCM). The final product was then purified by reversed phase chromatography to give the title compound (28 mg, 17% yield). MS-ESI: $[M+H]^+$ 567.2

1H NMR (400 MHz, DMSO) δ 9.29-9.24 (d, J=1.3 Hz, 2H), 8.80-8.74 (m, 1H), 7.87-7.81 (m, 2H), 7.72-7.67 (m, 1H), 7.55-7.48 (m, 1H), 7.47-7.37 (m, 3H), 4.45-4.30 (m, 2H), 4.10-4.03 (s, 1H), 3.70-3.62 (m, 1H), 3.23-3.17 (m, 1H), 1.54-1.46 (m, 1H), 1.38-1.30 (d, J=7.6 Hz, 1H), 0.96-0.90 (s, 3H), 0.58-0.50 (s, 3H).

The synthetic procedures disclosed below for Preparations 17-50 and Examples 93, 94, 100, 102, 103, 104, 112, 114, 115, 122, 126, 129, 142, 157, 158 are applicable to the Examples 89-158 listed in Table 2.

Preparation 17: [5-fluoro-2-[1-methyl-3-(trifluoromethyl)-1H-pyrazol-5-yl]pyridin-4-yl]methanamine

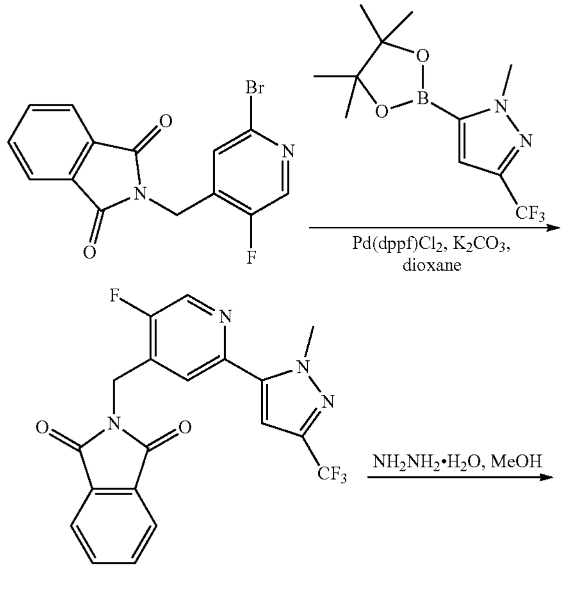

-continued

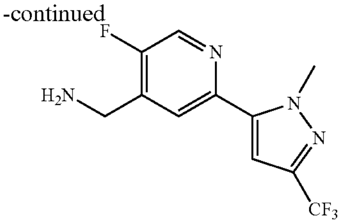

Step 1: Preparation of 2-([5-fluoro-2-[1-methyl-3-(trifluoromethyl)-1H-pyrazol-5-yl]pyridin-4-yl] methyl)-2,3-dihydro-1H-isoindole-1,3-dione

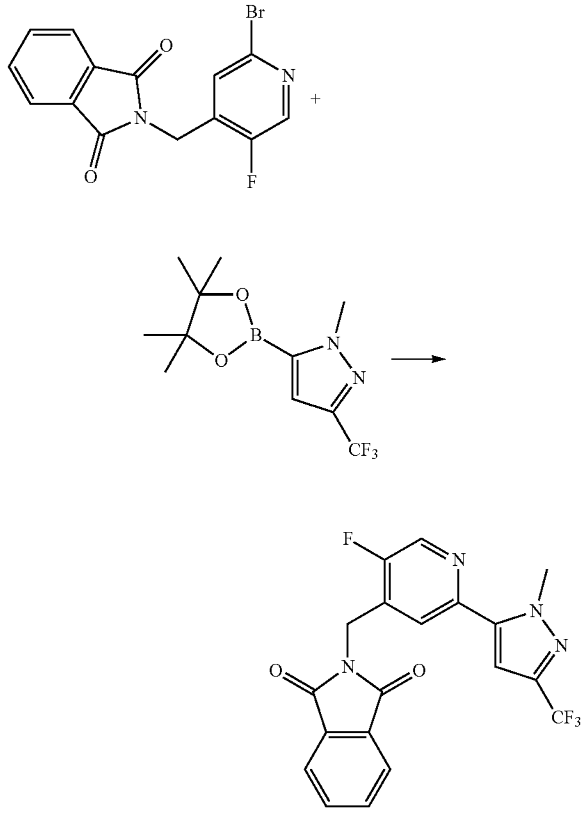

A mixture of 2-[(2-bromo-5-fluoropyridin-4-yl)methyl]-2,3-dihydro-1H-isoindole-1,3-dione (178 mg, 0.531 mmol, 0.67 equiv), 1-methyl-5-(tetramethyl-1,3,2-dioxaborolan-2-yl)-3-(trifluoromethyl)-1H-pyrazole (220 mg, 0.79 mmol, 1.00 equiv), Pd(dppf)$Cl_2$ (39 mg, 0.05 mmol, 0.06 equiv), potassium carbonate (220 mg, 1.59 mmol, 1.99 equiv), and dioxane (10 mL) was stirred for 12 h at 70° C. under nitrogen. The resulting mixture was concentrated under vacuum. The residue was diluted with ethyl acetate, washed with brine, dried over anhydrous sodium sulfate, and concentrated under vacuum. The residue was purified by a silica gel column eluting with ethyl acetate/petroleum ether (1/4) to afford the title compound (90 mg, 28%) as a white solid. LCMS [M+H$^+$]=405.

Step 2: Preparation of [5-fluoro-2-[1-methyl-3-(trifluoromethyl)-1H-pyrazol-5-yl]pyridin-4-yl]methanamine

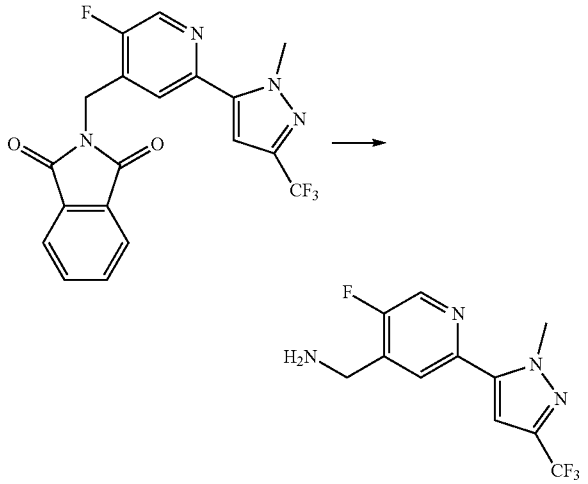

A mixture of 2-([5-fluoro-2-[1-methyl-3-(trifluoromethyl)-1H-pyrazol-5-yl]pyridin-4-yl]methyl)-2,3-dihydro-1H-isoindole-1,3-dione (90 mg, 0.22 mmol, 1.00 equiv), methanol (10 mL), and hydrazine hydrate (111 mg, 80%) was stirred for 12 h at 50° C. The resulting mixture was concentrated under vacuum. The residue was dissolved in ethyl acetate. The solid was filtered off. The filtrate was concentrated under vacuum to afford the title compound (60 mg, 98%) as a light yellow solid. LCMS [M+H$^+$]=275.

Preparation 18: [5-(fluoromethyl)-2-[2-(trifluoromethyl)pyrimidin-5-yl]pyridin-4-yl]methanamine hydrochloride

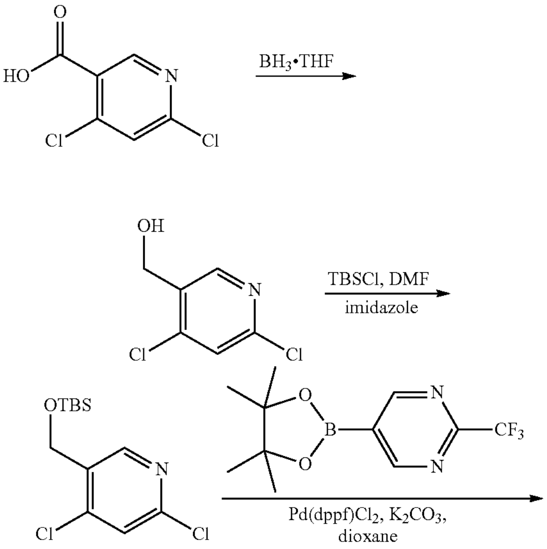

-continued

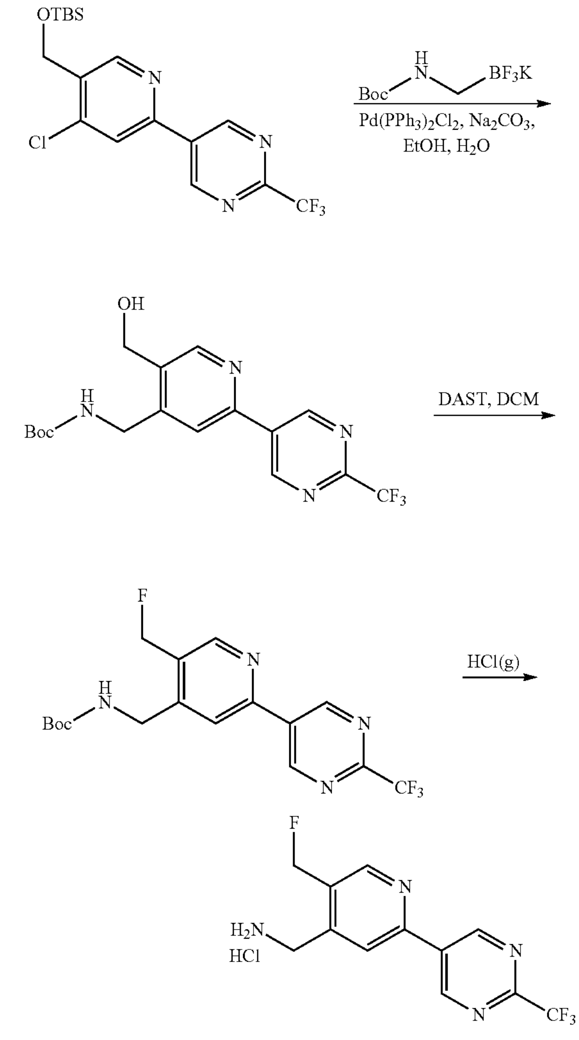

Step 1: Preparation of (4,6-dichloropyridin-3-yl)methanol

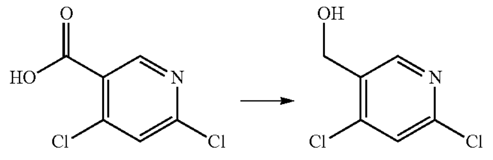 [SMILES: O=C(O)c1cnc(Cl)cc1Cl ; OCc1cnc(Cl)cc1Cl]

$BH_3$.THF (603 mL, 6.30 mol, 31.34 equiv) was added dropwise into a mixture of 4,6-dichloropyridine-3-carboxylic acid (38.6 g, 201.04 mmol, 1.00 equiv) and tetrahydrofuran (500 mL) at 0° C. under nitrogen. The reaction was stirred for 12 h at room temperature. The reaction was then quenched by 1 M of sodium bicarbonate, extracted with dichloromethane, washed with brine, dried over anhydrous sodium sulfate, and concentrated under vacuum. The residue was purified by a silica gel column eluting with ethyl acetate/petroleum ether (1/4) to afford the title compound (24.7 g, 69%) as a white solid. LCMS [$M+H^+$] 178.

Step 2: Preparation of 5-[[(tert-butyldimethylsilyl)oxy]methyl]-2,4-dichloropyridine

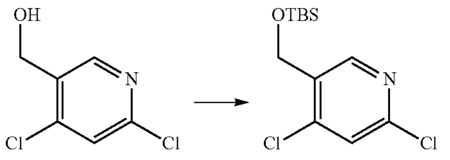 [SMILES: OCc1cnc(Cl)cc1Cl ; CC(C)(C)[Si](C)(C)OCc1cnc(Cl)cc1Cl]

A mixture of (4,6-dichloropyridin-3-yl)methanol (5 g, 28.08 mmol, 1.00 equiv), N,N-dimethylformamide (25 mL), and 1H-imidazole (5.73 g, 84.16 mmol, 2.99 equiv), tert-butyl(chloro)dimethylsilane (6.36 g, 42.19 mmol, 1.50 equiv) was stirred for 12 h at room temperature. The resulting solution was diluted with water, extracted with ethyl acetate, washed with brine, dried over anhydrous sodium sulfate, and concentrated under vacuum. The residue was purified by a silica gel column eluting with ethyl acetate/petroleum ether (1/10) to afford the title compound (8.2 g, 98.8%) as light yellow oil. LCMS [$M+H^+$] 292.

Step 3: Preparation of 5-(5-[[(tert-butyldimethylsilyl)oxy]methyl]-4-chloropyridin-2-yl)-2-(trifluoromethyl)pyrimidine

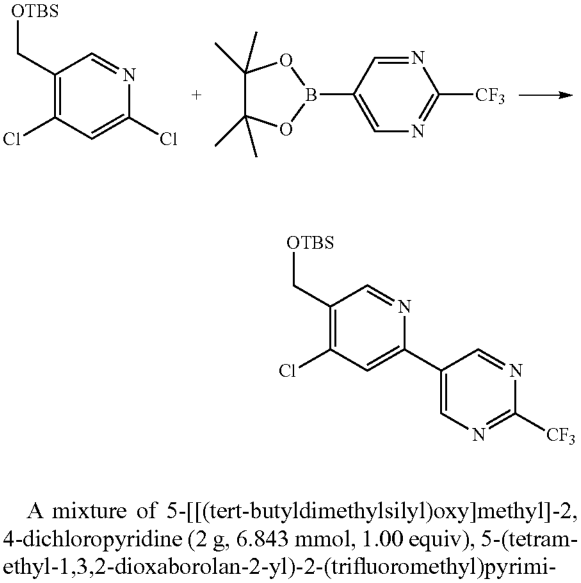

A mixture of 5-[[(tert-butyldimethylsilyl)oxy]methyl]-2,4-dichloropyridine (2 g, 6.843 mmol, 1.00 equiv), 5-(tetramethyl-1,3,2-dioxaborolan-2-yl)-2-(trifluoromethyl)pyrimidine (2.25 g, 8.21 mmol, 1.20 equiv), Pd(dppf)$Cl_2$ (500 mg, 0.68 mmol, 0.10 equiv), potassium carbonate (2.84 g, 20.549 mmol, 3.00 equiv), dioxane (80 mL), and water (8 mL) was stirred for 3 h at 80° C. under nitrogen. The resulting mixture was concentrated under vacuum, diluted with ethyl acetate, washed with brine, dried over anhydrous sodium sulfate, and concentrated under vacuum. The residue was purified by a silica gel column eluting with dichloromethane/petroleum ether (1/2) to afford the title compound (1.3 g, 47%) as a white solid. LCMS [$M+H^+$] 404.

Step 4: Preparation of tert-butyl N-[[5-(hydroxymethyl)-2-[2-(trifluoromethyl)pyrimidin-5-yl]pyridin-4-yl]methyl]carbamate

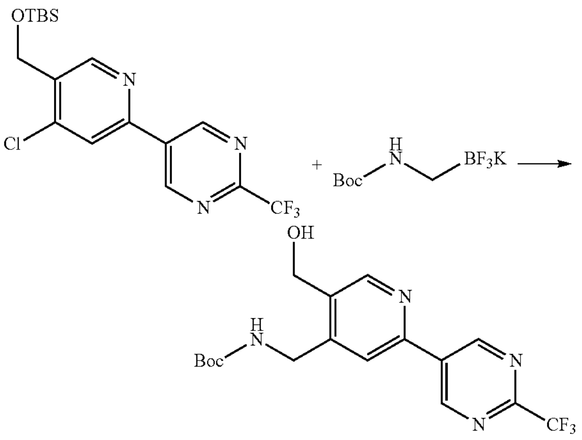

A mixture of 5-(5-[[(tert-butyldimethylsilyl)oxy]methyl]-4-chloropyridin-2-yl)-2-(trifluoromethyl)pyrimidine (500 mg, 1.23 mmol, 1.00 equiv), potassium tert-butyl N-[(trifluoro-lambda4-boranyl)methyl]carbamate (441 mg, 1.86 mmol, 1.50 equiv), $Pd(OAc)_2$ (84 mg, 0.37 mmol, 0.30 equiv), Sphos (305 mg, 0.74 mmol, 0.60 equiv), sodium carbonate (395 mg, 3.72 mmol, 3.01 equiv), ethanol (15 mL), and water (3 mL) was stirred for 12 h at 80° C. under nitrogen. The reaction mixture was filtered and the filtrate was concentrated under vacuum. The residue was dissolved in ethyl acetate, washed with brine, dried over anhydrous sodium sulfate, and concentrated under vacuum. The residue was purified by a silica gel column eluting with ethyl acetate/petroleum ether (1/1) to afford the title compound (313 mg, 66%) as a white solid. LCMS [M+H$^+$] 385.

Step 5: Preparation of tert-butyl N-[[5-(fluoromethyl)-2-[2-(trifluoromethyl)pyrimidin-5-yl]pyridin-4-yl]methyl]carbamate

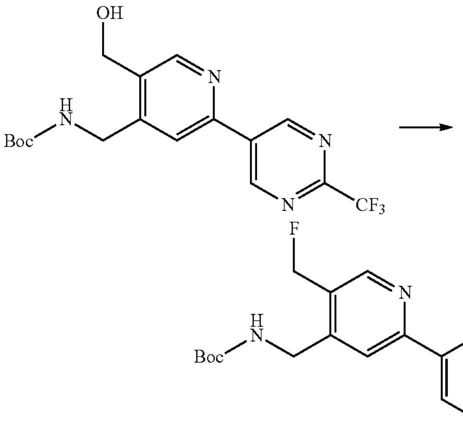

DAST (84 mg, 0.52 mmol, 2.00 equiv) was added dropwise into a mixture of tert-butyl N-[[5-(hydroxymethyl)-2-[2-(trifluoromethyl)pyrimidin-5-yl]pyridin-4-yl]methyl]carbamate (100 mg, 0.26 mmol, 1.00 equiv) and dichloromethane (5 mL) at −78° C. under nitrogen. The reaction was stirred for 2 h at room temperature. The reaction was then quenched by 1 M of sodium bicarbonate, extracted with ethyl acetate, washed with brine, dried over anhydrous sodium sulfate, and concentrated under vacuum. The residue was purified by a silica gel column eluting with ethyl acetate/petroleum ether (1/1) to afford the title compound (73 mg, 73%) as a white solid. LCMS [M+H$^+$] 387.

Step 6: Preparation of [5-(fluoromethyl)-2-[2-(trifluoromethyl)pyrimidin-5-yl]pyridin-4-yl]methanamine hydrochloride

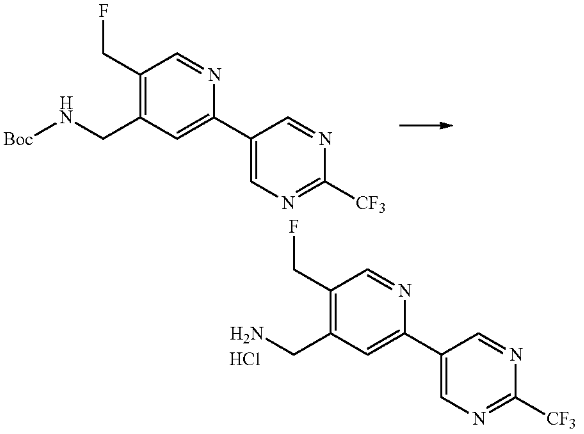

A mixture of tert-butyl N-[[5-(fluoromethyl)-2-[2-(trifluoromethyl)pyrimidin-5-yl]pyridin-4-yl]methyl]carbamate (73 mg, 0.18 mmol, 1.00 equiv), and 4N of HCl (g) in dioxane (20 mL) was stirred for 3 h at room temperature. The resulting mixture was concentrated under vacuum. This resulted in the title compound (50 mg, 92%) as a light yellow solid. LCMS [M+H$^+$] 287.

Preparation 19: [6-(trifluoromethyl)-5-[2-(trifluoromethyl)pyrimidin-5-yl]pyridin-3-yl]methanamine hydrochloride

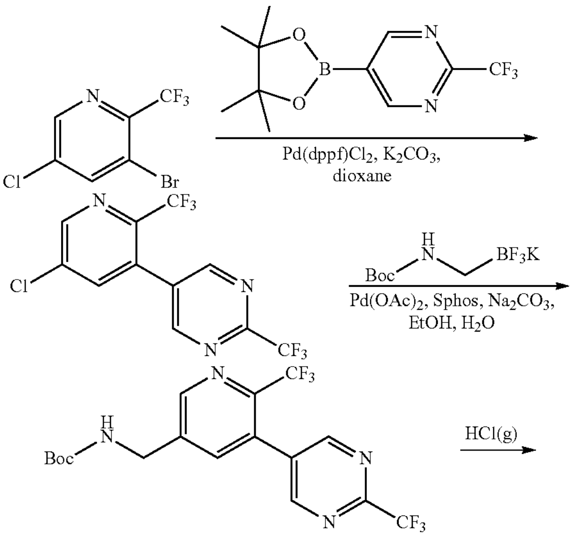

-continued

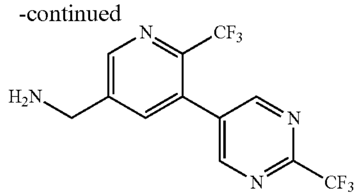

Step 1: Preparation of 5-[5-chloro-2-(trifluoromethyl)pyridin-3-yl]-2-(trifluoromethyl)pyrimidine

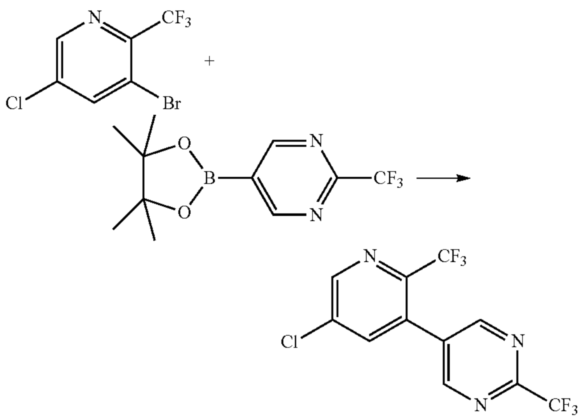

A mixture of 3-bromo-5-chloro-2-(trifluoromethyl)pyridine (300 mg, 1.15 mmol, 1.00 equiv), 5-(tetramethyl-1,3,2-dioxaborolan-2-yl)-2-(trifluoromethyl)pyrimidine (348 mg, 1.27 mmol, 1.10 equiv), $Pd(dppf)Cl_2$ (84 mg, 0.11 mmol, 0.10 equiv), potassium carbonate (478 mg, 3.45 mmol, 3.00 equiv), and dioxane (8 mL) was stirred for 3 h at 70° C. under nitrogen. The residue was dissolved in ethyl acetate, washed with brine, dried over anhydrous sodium sulfate, and concentrated under vacuum. The residue was purified by a silica gel column eluting with ethyl acetate/petroleum ether (1/10) to afford the title compound (285 mg, 76%) as a white solid. LCMS $[M+H^+]$ 328.

Step 2: Preparation of tert-butyl N-[[6-(trifluoromethyl)-5-[2-(trifluoromethyl)pyrimidin-5-yl]pyridin-3-yl]methyl]carbamate

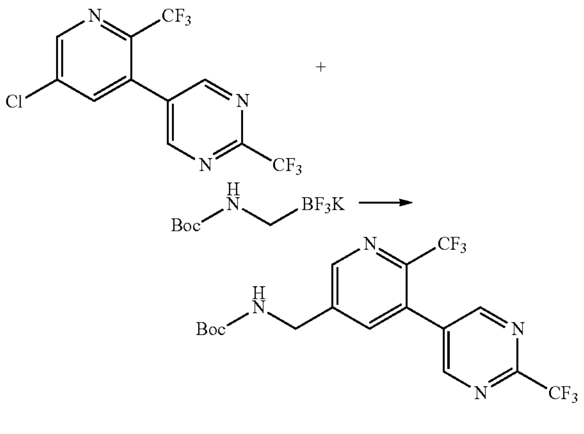

A mixture of 5-[5-chloro-2-(trifluoromethyl)pyridin-3-yl]-2-(trifluoromethyl)pyrimidine (260 mg, 0.79 mmol, 1.00 equiv), potassium tert-butyl N-[(trifluoro-lambda4-boranyl)methyl]carbamate (375 mg, 1.58 mmol, 1.99 equiv), $Pd(OAc)_2$ (18 mg, 0.08 mmol, 0.10 equiv), SPhos (162 mg, 0.39 mmol, 0.49 equiv), sodium carbonate (252 mg, 2.37 mmol, 2.99 equiv), ethanol (10 mL), and water (1 mL) was stirred for 12 h at 80° C. under nitrogen. The resulting mixture was concentrated under vacuum. The residue was dissolved in ethyl acetate, washed with brine, dried over anhydrous sodium sulfate, and concentrated under vacuum. The residue was purified by a silica gel column eluting with ethyl acetate/petroleum ether (1/10) to afford the title compound (130 mg, 39%) as a light yellow solid. LCMS $[M+H^+]$ 423.

Step 3: Preparation of [6-(trifluoromethyl)-5-[2-(trifluoromethyl)pyrimidin-5-yl]pyridin-3-yl]methanamine hydrochloride

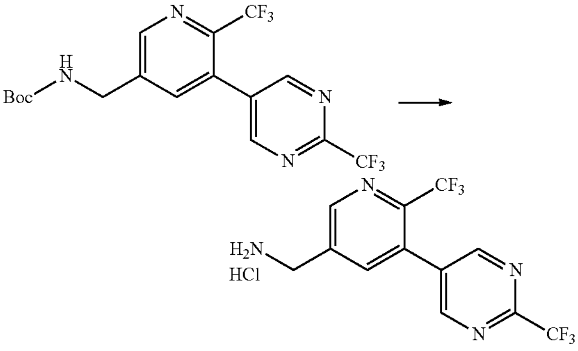

A mixture of tert-butyl N-[[6-(trifluoromethyl)-5-[2-(trifluoromethyl)pyrimidin-5-yl]pyridin-3-yl]methyl]carbamate (130 mg, 0.30 mmol, 1.00 equiv), 4N of HCl (g) in 1,4-dioxane (10 mL) was stirred for 1 h at room temperature. The resulting mixture was concentrated under vacuum. This resulted in the title compound (90 mg, 91%) as a light yellow solid. LCMS $[M+H^+]$ 323.

Preparation 20: tert-butyl (2S,3R,5S)-5-[([6-cyclopropyl-5-fluoro-4-[2-(trifluoromethyl)pyrimidin-5-yl]pyridin-2-yl]methyl)carbamoyl]-3-fluoro-2-methylpyrrolidine-1-carboxylate

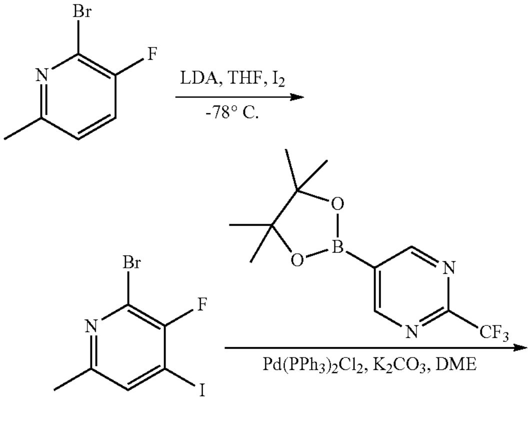

-continued

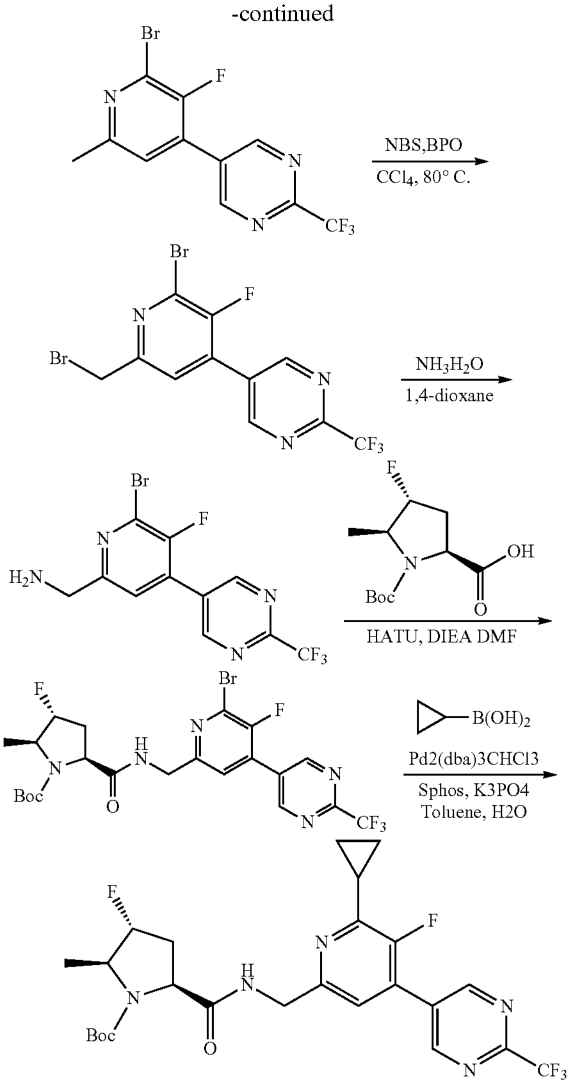

Step 1: Preparation of 2-bromo-3-fluoro-4-iodo-6-methylpyridine

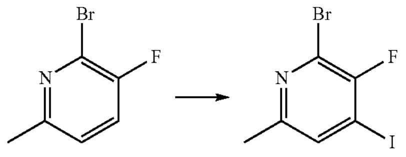

n-BuLi (50.5 mL, 1M in hexane, 1.20 equiv) was added dropwise into a stirred solution of i-$Pr_2NH$ (6.37 g, 62.95 mmol, 1.50 equiv) in tetrahydrofuran (100 mL) at −78° C. under nitrogen. The resulting solution was stirred for 30 min at −78° C. To this was added a solution of 2-bromo-3-fluoro-6-methylpyridine (8 g, 42.10 mmol, 1.00 equiv) in tetrahydrofuran (30 mL) dropwise at −78° C. The resulting solution was allowed to react for an additional 1 h at −78° C. To the mixture was added a solution of $I_2$ (16 g, 63.04 mmol, 1.50 equiv) in tetrahydrofuran (30 mL) dropwise at −78° C. The resulting solution was allowed to react for an additional 30 min at −78° C. The reaction was then quenched by saturated solution of $Na_2S_2O_3$, extracted with ethyl acetate, washed with bine, dried over anhydrous sodium sulfate, and concentrated under vacuum. The residue was purified by a silica gel column eluting with ethyl acetate/petroleum ether (1/2) to afford the title compound (12 g, 90%) as a light yellow solid. LCMS [M+H$^+$] 316.

Step 2: Preparation of 5-(2-bromo-3-fluoro-6-methylpyridin-4-yl)-2-(trifluoromethyl)pyrimidine

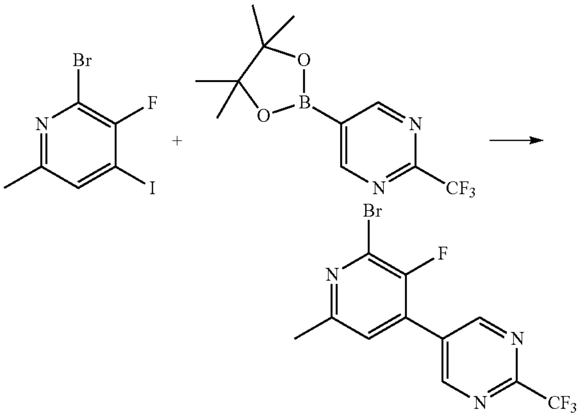

A mixture of 2-bromo-3-fluoro-4-iodo-6-methylpyridine (3 g, 9.49 mmol, 1.00 equiv), 5-(tetramethyl-1,3,2-dioxaborolan-2-yl)-2-(trifluoromethyl)pyrimidine (2.87 g, 10.47 mmol, 1.10 equiv), $Pd(PPh_3)_2Cl_2$ (668 mg, 0.95 mmol, 0.10 equiv), potassium carbonate (2.63 g, 19.03 mmol, 2.00 equiv), ethylene glycol dimethyl ether (100 mL), and water (5 mL) was stirred for overnight at 50° C. The resulting solution was diluted with ethyl acetate, washed with brine, dried over anhydrous sodium sulfate, and concentrated under vacuum. The residue was purified by a silica gel column eluting with ethyl acetate/petroleum ether (1/10) to afford the title compound (1 g, 31%) as a yellow solid. LCMS [M+H$^+$] 336.

Step 3: Preparation of 5-[2-bromo-6-(bromomethyl)-3-fluoropyridin-4-yl]-2-(trifluoromethyl)pyrimidine

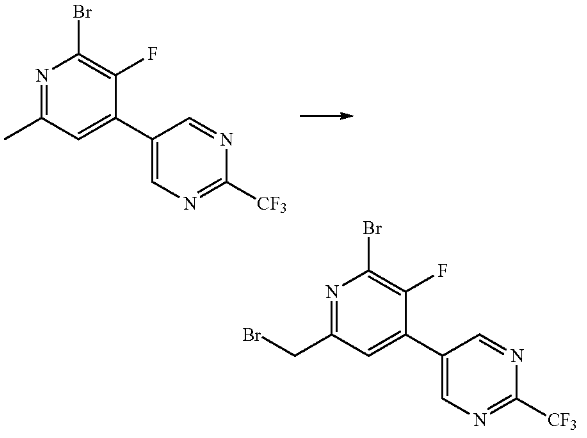

A mixture of 5-(2-bromo-3-fluoro-6-methylpyridin-4-yl)-2-(trifluoromethyl)pyrimidine (800 mg, 2.38 mmol, 1.00 equiv), $CCl_4$ (30 mL), BPO (57 mg, 0.22 mmol, 0.10 equiv), and NBS (425 mg, 2.38 mmol, 1.00 equiv) was stirred for 24 h at 80° C. under nitrogen. The resulting solution was diluted with ethyl acetate, washed with brine, dried over anhydrous sodium sulfate, and concentrated under vacuum. This resulted in the title compound (500 mg, 51%) as a yellow solid. LCMS [M+H$^+$] 416.

Step 4: Preparation of [6-bromo-5-fluoro-4-[2-(trifluoromethyl)pyrimidin-5-yl]pyridin-2-yl]methanamine

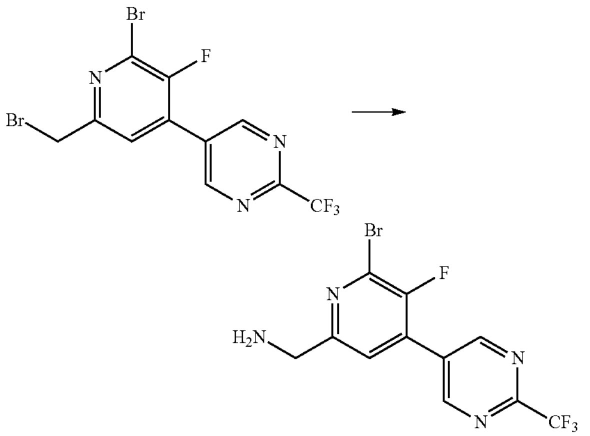

A mixture of 5-[2-bromo-6-(bromomethyl)-3-fluoropyridin-4-yl]-2-(trifluoromethyl)pyrimidine (500 mg, 1.20 mmol, 1.00 equiv), 1,4-dioxane (10 mL), and ammonia (3 mL, 40%) was stirred for 2 h at room temperature. The resulting mixture was concentrated under vacuum. This resulted in the title compound (280 mg, 66%) as a brown solid. LCMS [M+H$^+$] 351.

Step 5: Preparation of tert-butyl (2S,3R,5S)-5-[([6-bromo-5-fluoro-4-[2-(trifluoromethyl)pyrimidin-5-yl]pyridin-2-yl]methyl)carbamoyl]-3-fluoro-2-methylpyrrolidine-1-carboxylate

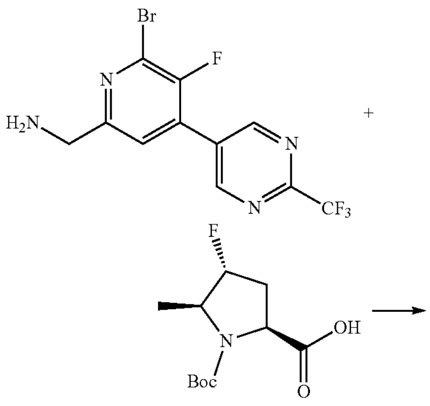

-continued

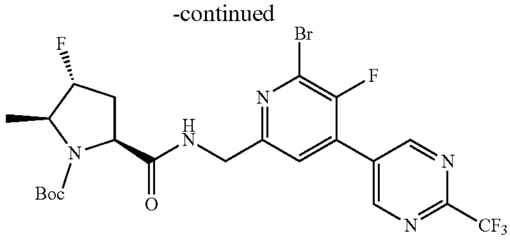

A mixture of (2S,4R,5S)-1-[(tert-butoxy)carbonyl]-4-fluoro-5-methylpyrrolidine-2-carboxylic acid (182 mg, 0.73 mmol, 1.00 equiv), HATU (338 mg, 0.88 mmol, 1.20 equiv), N,N-dimethylformamide (10 mL), DIEA (286 mg, 2.21 mmol, 3.00 equiv), and [6-bromo-5-fluoro-4-[2-(trifluoromethyl)pyrimidin-5-yl]pyridin-2-yl]methanamine (240 mg, 0.68 mmol, 1.00 equiv) was stirred for 1 h at room temperature. The resulting solution was diluted ethyl acetate, washed with brine, dried over anhydrous sodium sulfate, and concentrated under vacuum. The residue was purified by a silica gel column eluting with ethyl acetate/petroleum ether (1/3) to afford the title compound (300 mg, 70%) as light yellow oil. LCMS [M+H$^+$] 512.

Step 6: Preparation of tert-butyl (2S,3R,5S)-5-[([6-cyclopropyl-5-fluoro-4-[2-(trifluoromethyl)pyrimidin-5-yl]pyridin-2-yl]methyl)carbamoyl]-3-fluoro-2-methylpyrrolidine-1-carboxylate

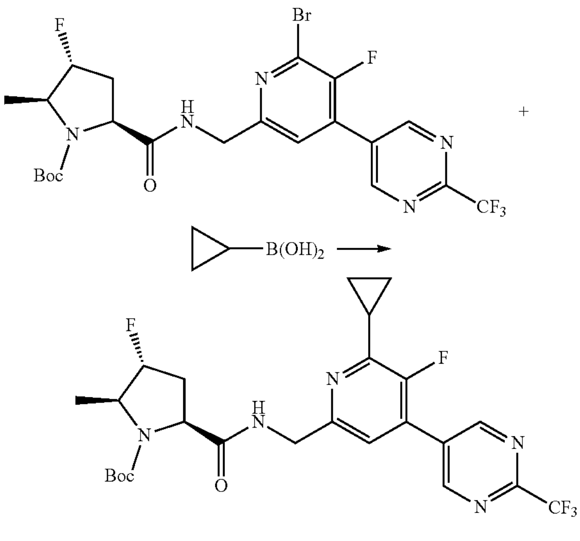

A mixture of tert-butyl (2S,3R,5S)-5-[([6-bromo-5-fluoro-4-[2-(trifluoromethyl)pyrimidin-5-yl]pyridin-2-yl]methyl)carbamoyl]-3-fluoro-2-methylpyrrolidine-1-carboxylate (200 mg, 0.34 mmol, 1.00 equiv), cyclopropylboronic acid (290 mg, 3.37 mmol, 10.00 equiv), $Pd_2(dba)_3CHCl_3$ (70 mg, 0.06 mmol, 0.20 equiv), SPhos (70 mg, 0.17 mmol, 0.50 equiv), $K_3PO_4$ (220 mg, 1.03 mmol, 3.00 equiv), toluene (5 mL), and water (0.5 mL) was stirred for overnight at 70° C. under nitrogen. The resulting solution was diluted with ethyl acetate, washed with brine, dried over anhydrous sodium sulfate, and concentrated under vacuum. The residue was purified by a silica gel column eluting with ethyl acetate/petroleum ether (1/3) to afford the title compound (140 mg, 75%) as a light yellow solid. LCMS [M+H+] 542.

Preparation 21: [5-fluoro-4-[5-fluoro-6-(trifluoromethyl)pyridin-3-yl]pyridin-2-yl]methanamine

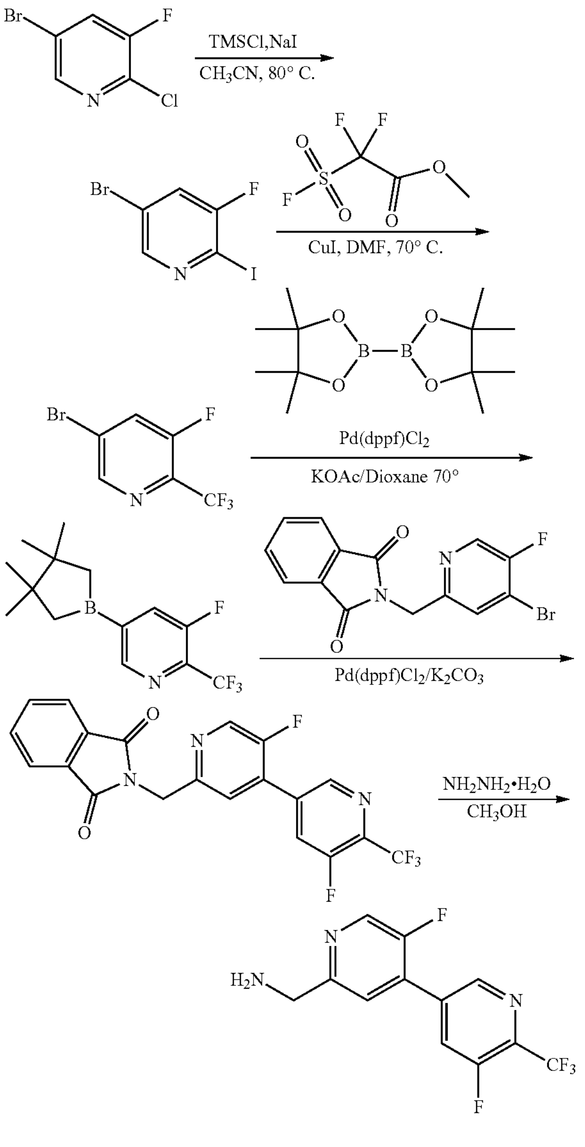

Step 1: Preparation of 5-bromo-3-fluoro-2-iodopyridine

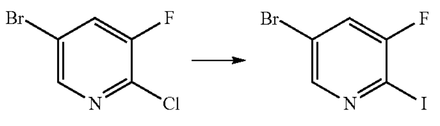 [SMILES: Fc1cc(Br)cnc1Cl ; Fc1cc(Br)cnc1I]

A mixture of 5-bromo-2-chloro-3-fluoropyridine (10 g, 47.52 mmol, 1.00 equiv), NaI (21.5 g, 143.43 mmol, 3.00 equiv), $CH_3CN$ (100 mL), and chlorotrimethylsilane (5 g, 46.02 mmol, 1.00 equiv) was stirred for 2 h at 80° C. under nitrogen. The resulting solution was diluted with ethyl acetate, washed with saturated solution of $Na_2SO_3$ and brine, dried over anhydrous sodium sulfate, and concentrated under vacuum. The residue was purified by a silica gel column eluting with petroleum ether to afford the title compound (1.5 g, 10%) as light yellow oil. LCMS [M+H+] 302.

Step 2: Preparation of 5-bromo-3-fluoro-2-(trifluoromethyl)pyridine

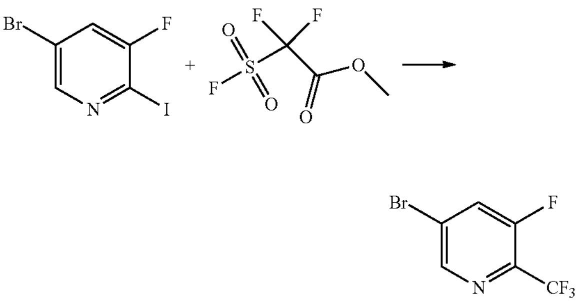

A mixture of 5-bromo-3-fluoro-2-iodopyridine (1.5 g, 4.96 mmol, 1.00 equiv), methyl 2,2-difluoro-2-(fluorosulfonyl)acetate (6.6 g, 34.35 mmol, 7.00 equiv), CuI (6.6 g, 34.65 mmol, 7.00 equiv), and N,N-dimethylformamide (100 mL) was stirred for overnight at 70° C. under nitrogen. The resulting solution was diluted with ethyl acetate, washed with brine, dried over anhydrous sodium sulfate, and concentrated under vacuum. This resulted in the title compound (1 g, 82%) as a brown solid. LCMS [M+H+] 244.

Step 3: Preparation of 3-fluoro-5-(tetramethyl-1,3,2-dioxaborolan-2-yl)-2-(trifluoromethyl)pyridine

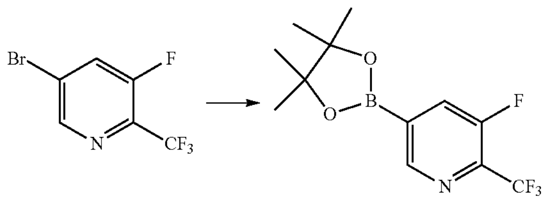 [SMILES: Fc1cc(Br)cnc1C(F)(F)F ; CC1(C)OB(c2cnc(C(F)(F)F)c(F)c2)OC1(C)C]

A mixture of 5-bromo-3-fluoro-2-(trifluoromethyl)pyridine (2 g, 8.19 mmol, 1.00 equiv), 4,4,5,5-tetramethyl-2-(tetramethyl-1,3,2-dioxaborolan-2-yl)-1,3,2-dioxaborolane (2.1 g, 8.27 mmol, 1.00 equiv), Pd(dppf)$Cl_2$ (600 mg, 0.82 mmol, 0.10 equiv), KOAc (2.41 g, 24.55 mmol, 3.00 equiv), and dioxane (120 mL) was stirred for overnight at 70° C. under nitrogen. The resulting solution was diluted with ethyl acetate, washed with brine, dried over anhydrous sodium sulfate, and concentrated under vacuum. This resulted in the title compound (2.1 g, 88%) as a brown solid. LCMS [M+H+] 292.

Step 4: Preparation of 2-([5-fluoro-4-[5-fluoro-6-(trifluoromethyl)pyridin-3-yl]pyridin-2-yl]methyl)-2,3-dihydro-1H-isoindole-1,3-dione

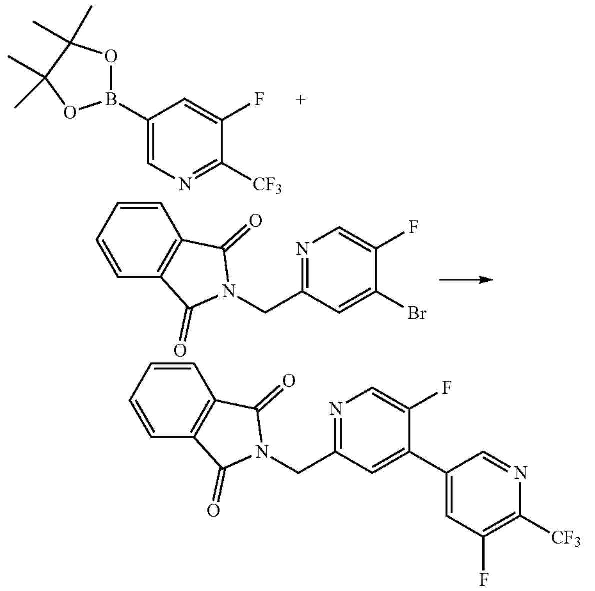

A mixture of 3-fluoro-5-(tetramethyl-1,3,2-dioxaborolan-2-yl)-2-(trifluoromethyl)pyridine (1.8 g, 6.18 mmol, 3.00 equiv), $Pd(dppf)Cl_2$ (301 mg, 0.41 mmol, 0.20 equiv), 2-[(4-bromo-5-fluoropyridin-2-yl)methyl]-2,3-dihydro-1H-isoindole-1,3-dione (688 mg, 2.05 mmol, 1.00 equiv), potassium carbonate (852 mg, 6.16 mmol, 3.00 equiv), and dioxane (50 mL) was stirred for overnight at 70° C. under nitrogen. The resulting solution was diluted with ethyl acetate, washed with brine, dried over anhydrous sodium sulfate, and concentrated under vacuum. The residue was purified by a silica gel column eluting with ethyl acetate/petroleum ether (1:2) to afford the title compound (350 mg, 41%) as a yellow solid. LCMS [M+H$^+$] 420.

Step 5: Preparation of [5-fluoro-4-[5-fluoro-6-(trifluoromethyl)pyridin-3-yl]pyridin-2-yl]methanamine

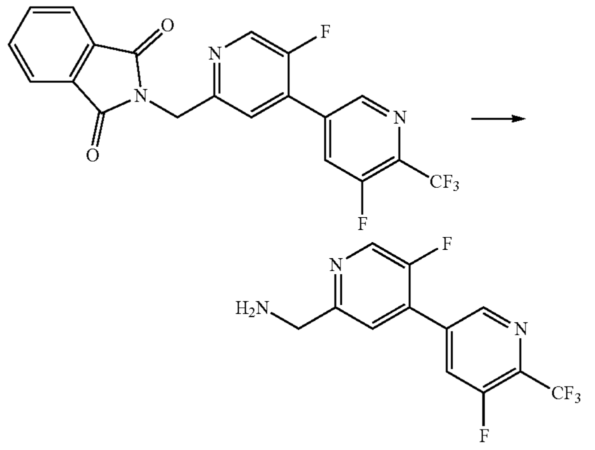

A mixture of 2-([5-fluoro-4-[5-fluoro-6-(trifluoromethyl)pyridin-3-yl]pyridin-2-yl]methyl)-2,3-dihydro-1H-isoindole-1,3-dione (350 mg, 0.83 mmol, 1.00 equiv), methanol (5 mL), and hydrazine hydrate (80%) (1 mL) was stirred for 3 h at room temperature. The resulting mixture was concentrated under vacuum. The residue was dissolved with water. The pH value of the solution was adjusted to 2 with concentrate hydrogen chloride. The resulting solution was extracted with dichloromethane. The pH value of the aqueous solution was adjusted to 8 with saturated solution of sodium bicarbonate. The resulting solution was extracted with dichloromethane, dried over anhydrous sodium sulfate, and concentrated under vacuum. This resulted in the title compound (210 mg, 87%) as a yellow solid. LCMS [M+H$^+$] 290.

Preparation 22: [2-cyclopropyl-3-(trifluoromethyl)-6-[2-(trifluoromethyl)pyrimidin-5-yl]pyridin-4-yl]methanamine

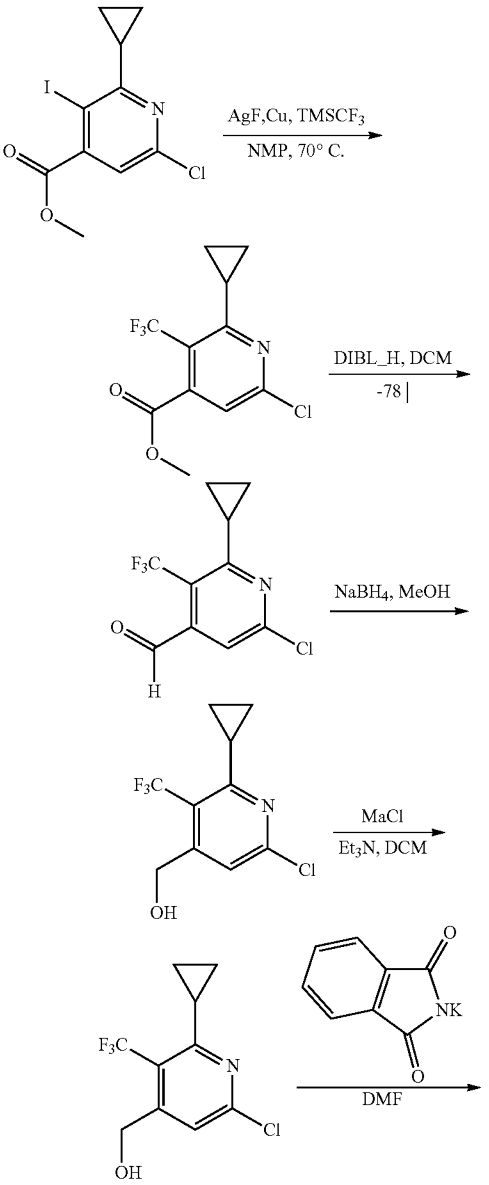

-continued

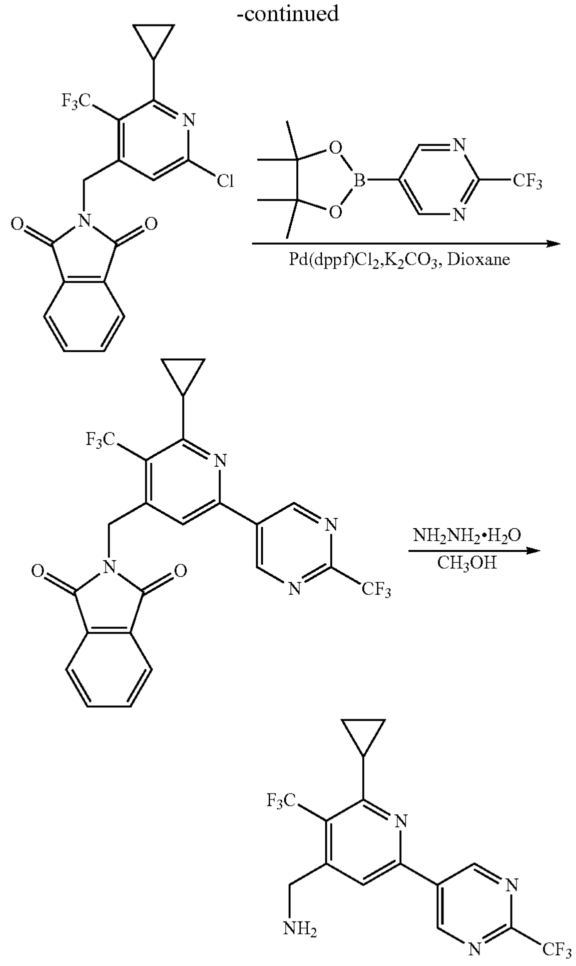

Step 1: Preparation of methyl 6-chloro-2-cyclopropyl-3-(trifluoromethyl)pyridine-4-carboxylate

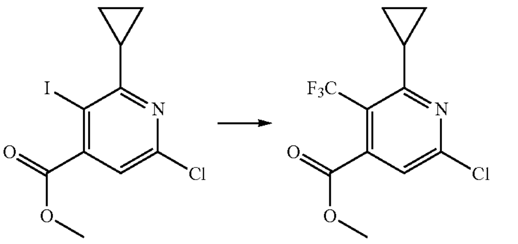 [SMILES: COC(=O)c1cc(Cl)nc(C2CC2)c1I ; COC(=O)c1cc(Cl)nc(C2CC2)c1C(F)(F)F]

A mixture of AgF (673 mg, 5.30 mmol, 1.99 equiv), NMP (15 mL), trimethyl(trifluoromethyl)silane (758 mg, 5.33 mmol, 1.99 equiv), Cu (171 mg, 2.69 mmol, 1.00 equiv), and methyl 6-chloro-2-cyclopropyl-3-iodopyridine-4-carboxylate (900 mg, 2.66 mmol, 1.00 equiv) was stirred for 12 h at room temperature and 4 h at 70° C. The reaction was quenched by water, extracted with ethyl acetate, washed with brine, dried over anhydrous sodium sulfate, and concentrated under vacuum. The residue was purified by a silica gel column eluting with ethyl acetate/petroleum ether (1/8) to afford the title compound (702 mg, 94%) as yellow oil. LCMS [M+H$^+$] 280.

Step 2: Preparation of 6-chloro-2-cyclopropyl-3-(trifluoromethyl)pyridine-4-carbaldehyde

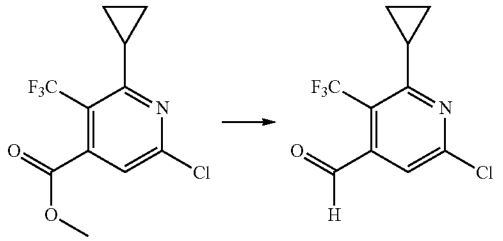 [SMILES: COC(=O)c1cc(Cl)nc(C2CC2)c1C(F)(F)F ; O=Cc1cc(Cl)nc(C2CC2)c1C(F)(F)F]

DIBAl-H (5 mL, 1M in hexanes, 4.66 equiv) was added dropwise into a solution of methyl 6-chloro-2-cyclopropyl-3-(trifluoromethyl)pyridine-4-carboxylate (300 mg, 1.07 mmol, 1.00 equiv) in dichloromethane (35 mL) at −78° C. under nitrogen. The resulting solution was stirred for 2 hours at −78° C., quenched by methanol and water, extracted with ethyl acetate, dried over anhydrous sodium sulfate, and concentrated under vacuum. This resulted in the title compound (280 mg, crude) as yellow oil. LCMS [M+H$^+$] 250.

Step 3: Preparation of [6-chloro-2-cyclopropyl-3-(trifluoromethyl)pyridin-4-yl]methanol

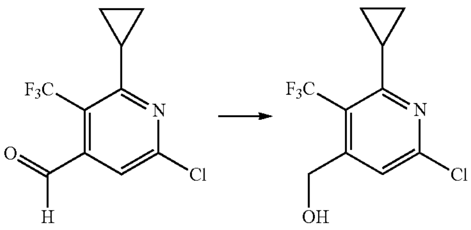 [SMILES: O=Cc1cc(Cl)nc(C2CC2)c1C(F)(F)F ; OCc1cc(Cl)nc(C2CC2)c1C(F)(F)F]

$NaBH_4$ (50 mg, 1.32 mmol, 0.50 equiv) was added in portions into a solution of 6-chloro-2-cyclopropyl-3-(trifluoromethyl)pyridine-4-carbaldehyde (650 mg, 2.60 mmol, 1.00 equiv) in methanol (30 mL) at 0° C. After being stirred for 1 h at 0° C. the reaction was quenched by water, extracted by ethyl acetate, washed with brine, dried over anhydrous sodium sulfate, and concentrated under vacuum. The residue was purified by a silica gel column eluting with ethyl acetate/petroleum ether (1/10) to afford the title compound (340 mg, 52%) as a light yellow solid. LCMS [M+H$^+$] 252.

Step 4: Preparation of [6-chloro-2-cyclopropyl-3-(trifluoromethyl)pyridin-4-yl]methyl methanesulfonate

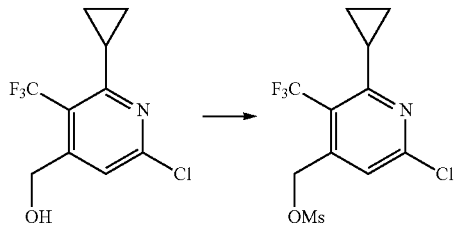 [SMILES: OCc1cc(Cl)nc(C2CC2)c1C(F)(F)F ; CS(=O)(=O)OCc1cc(Cl)nc(C2CC2)c1C(F)(F)F]

Methanesulfonyl chloride (185 mg, 1.61 mmol, 1.19 equiv) was added dropwise into a solution of [6-chloro-2-cyclopropyl-3-(trifluoromethyl)pyridin-4-yl]methanol (340 mg, 1.35 mmol, 1.00 equiv), dichloromethane (15 mL), and triethylamine (410 mg, 4.05 mmol, 2.99 equiv) at 0° C. under nitrogen. The resulting solution was stirred for 30 min at 0° C. The reaction was then quenched by water, extracted with ethyl acetate, washed with saturated solution of $NH_4Cl$ and brine, dried over anhydrous sodium sulfate, and concentrated under vacuum. This resulted in the title compound (320 mg, 72%) as a light yellow solid. LCMS [M+H$^+$] 330.

Step 5: Preparation of 2-[[6-chloro-2-cyclopropyl-3-(trifluoromethyl)pyridin-4-yl]methyl]-2,3-dihydro-1H-isoindole-1,3-dione

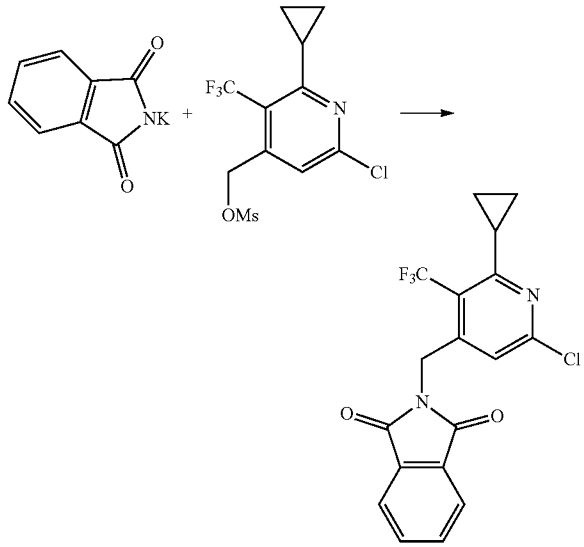

A mixture of [6-chloro-2-cyclopropyl-3-(trifluoromethyl) pyridin-4-yl]methyl methanesulfonate (400 mg, 1.21 mmol, 1.00 equiv) and potassium 1,3-dioxoisoindolin-2-ide (337 mg, 1.81 mmol, 1.49 equiv) in DMF (15 mL) was stirred for 4 h at room temperature. The reaction was quenched by water, extracted with ethyl acetate, washed with brine, dried over anhydrous sodium sulfate, and concentrated under vacuum. This resulted in the title compound (515 mg, crude) as a yellow solid. LCMS [M+H$^+$] 381.

Step 6: Preparation of 2-[[2-cyclopropyl-3-(trifluoromethyl)-6-[2-(trifluoromethyl)pyrimidin-5-yl]pyridin-4-yl]methyl]-2,3-dihydro-1H-isoindole-1,3-dione

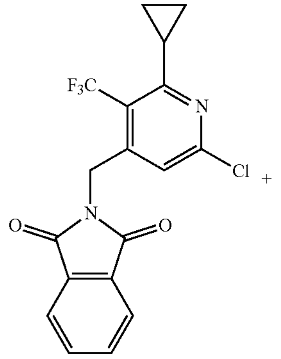

-continued

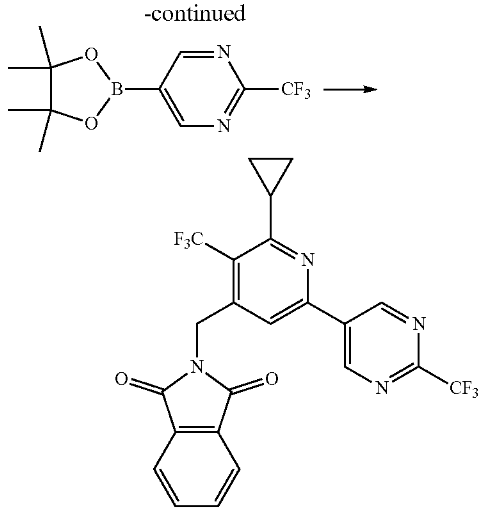

A mixture of 2-[[6-chloro-2-cyclopropyl-3-(trifluoromethyl)pyridin-4-yl]methyl]-2,3-dihydro-1H-isoindole-1,3-dione (490 mg, 1.28 mmol, 1.00 equiv), 5-(tetramethyl-1,3,2-dioxaborolan-2-yl)-2-(trifluoromethyl)pyrimidine (530 mg, 1.93 mmol, 1.50 equiv), Pd(dppf)$Cl_2$ (105 mg, 0.14 mmol, 0.11 equiv), potassium carbonate (534 mg, 3.86 mmol, 3.00 equiv), and 1,4-dioxane (10 mL) was stirred for 2 hours at 100° C. under nitrogen. The resulting mixture was concentrated under vacuum. The residue was purified by a silica gel column eluting with ethyl acetate/petroleum ether (2/3) to afford the title compound (632 mg) as a yellow solid. LCMS [M+H$^+$] 493.

Step 7: Preparation of [2-cyclopropyl-3-(trifluoromethyl)-6-[2-(trifluoromethyl)pyrimidin-5-yl]pyridin-4-yl]methanamine

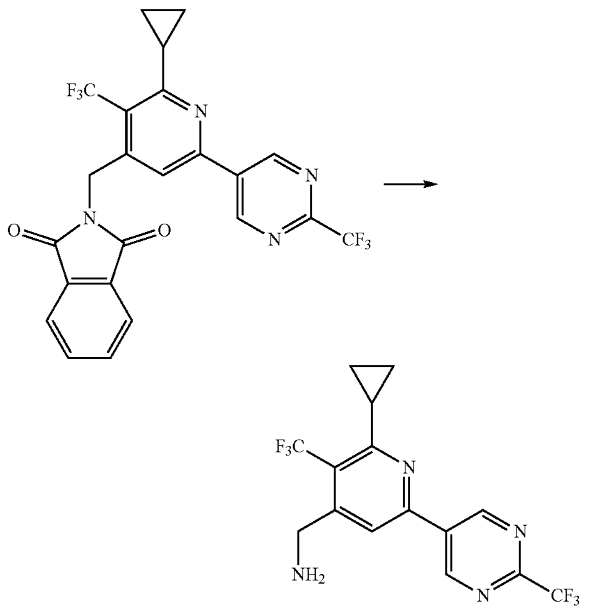

A mixture of 2-[[2-cyclopropyl-3-(trifluoromethyl)-6-[2-(trifluoromethyl)pyrimidin-5-yl]pyridin-4-yl]methyl]-2,3-dihydro-1H-isoindole-1,3-dione (293 mg, 0.59 mmol, 1.00 equiv), hydrazine hydrate (4 mL, 80%), and methanol (20 mL) was stirred for 4 h at 50° C. The resulting mixture was concentrated under vacuum. The residue was dissolved in ethyl acetate. The solid was filtered out. The filtrate was concentrated under vacuum to afford the title compound (186 mg, 86%) as a yellow solid. LCMS [M+H+] 363.

Preparation 23: (2-cyclopropyl-6-[2-[1-(trifluoromethyl)cyclopropyl]ethoxy]pyrimidin-4-yl)methanamine

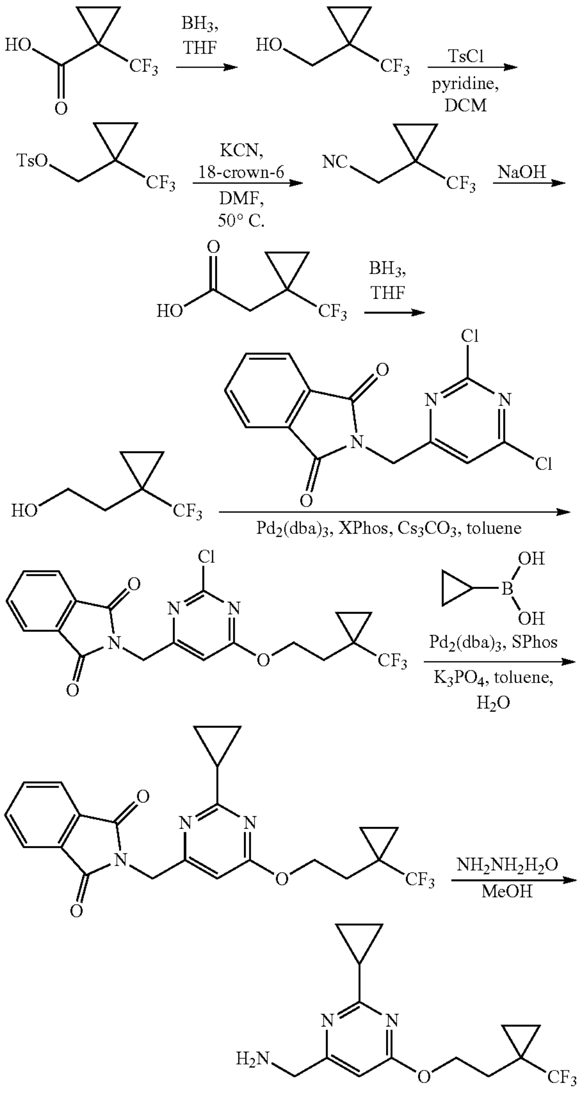

Step 1: Preparation of [1-(trifluoromethyl)cyclopropyl]methanol

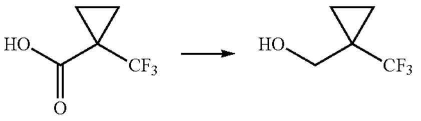 [SMILES: O=C(O)C1(C(F)(F)F)CC1 ; OCC1(C(F)(F)F)CC1]

A mixture of 1-(trifluoromethyl)cyclopropane-1-carboxylic acid (3.0 g, 19.47 mmol, 1.00 equiv), tetrahydrofuran (30 mL), $BH_3$.THF (31.2 mL, 1M in THF, 1.60 equiv) was stirred for 12 h at 40° C. under nitrogen. The reaction was quenched by saturated $NH_4Cl$ and the solid was filtered out. The liquid was extracted with ethyl acetate, washed with saturated solution of sodium bicarbonate and brine, dried over anhydrous sodium sulfate, and concentrated under vacuum. This resulted in the title compound (2.6 g, 95%) as colorless oil. GCMS [m/z] 140.

Step 2: Preparation of [1-(trifluoromethyl)cyclopropyl]methyl4-methylbenzene-1-sulfonate

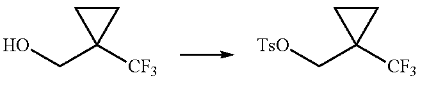

A mixture of [1-(trifluoromethyl)cyclopropyl]methanol (2.6 g, 18.56 mmol, 1.00 equiv), dichloromethane (30 mL), TEA (5.63 g, 55.64 mmol, 3.00 equiv), 4-dimethylaminopyridine (227 mg, 1.86 mmol, 0.10 equiv), and 4-methylbenzene-1-sulfonyl chloride (4.26 g, 22.36 mmol, 1.20 equiv) was stirred for 12 h at room temperature. The resulting solution was diluted with ethyl acetate, washed with brine, dried over anhydrous sodium sulfate, and concentrated under vacuum. The residue was purified by a silica gel column eluting with ethyl acetate/petroleum ether to afford the title compound (3.8 g, 70%) as colorless oil. GCMS [m/z] 294.

Step 3: Preparation of 3-[1-(trifluoromethyl)cyclopropyl]propanenitrile

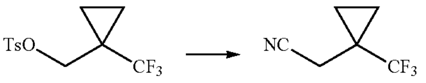

A mixture of [1-(trifluoromethyl)cyclopropyl]methyl 4-methylbenzene-1-sulfonate (3.8 g, 12.91 mmol, 1.00 equiv), N,N-dimethylformamide (50 mL), 18-crown-6 (5.12 g, 19.37 mmol, 1.50 equiv), and KCN (1.26 g, 19.35 mmol, 1.50 equiv) was stirred for 48 h at 55° C. in an oil bath. The resulting solution was diluted with ethyl acetate, washed with brine, dried over anhydrous sodium sulfate, and concentrated under vacuum. This resulted in the title compound (2.0 g, 95%) as light yellow oil. GCMS [m/z] 149.

Step 4: Preparation of 2-[1-(trifluoromethyl)cyclopropyl]acetic Acid

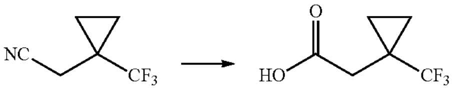

A mixture of 2-[1-(trifluoromethyl)cyclopropyl]acetonitrile (2.0 g, 13.41 mmol, 1.00 equiv), ethanol (100 mL), water (10 mL), and sodium hydroxide (11.0 g, 275.02 mmol, 20.51 equiv) was stirred for 12 h at 80° C. The resulting mixture was concentrated under vacuum and dissolved in water. The pH value was adjusted to 4 with hydrogen chloride (1N). The mixture was extracted with ethyl acetate, dried over anhydrous sodium sulfate, and concentrated under vacuum. This resulted in the title compound (1.1 g, 49%) as light yellow oil. LCMS [M−H$^+$] 167.

Step 5: Preparation of 2-[1-(trifluoromethyl)cyclopropyl]ethan-1-ol

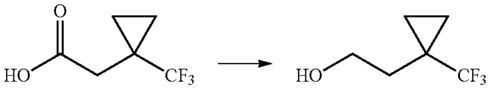

$BH_3$.THF (13 mL, 1M in THF, 2.00 equiv) was added dropwise into a mixture of 2-[1-(trifluoromethyl)cyclopropyl]acetic acid (1.1 g, 6.54 mmol, 1.00 equiv) and tetrahydrofuran (15 mL) at 0° C. under nitrogen. After being stirred for 12 h at 40° C. in an oil bath the reaction was quenched by saturated $NH_4Cl$. The solid was filtered out. The resulting solution was extracted with ethyl acetate, washed with saturated sodium bicarbonate, dried over anhydrous sodium sulfate, and concentrated under vacuum. This resulted in the title compound (1.1 g, crude) as colorless oil.

Step 6: Preparation of 2-[(2-chloro-6-[2-[1-(trifluoromethyl)cyclopropyl]ethoxy]pyrimidin-4-yl)methyl]-2,3-dihydro-1H-isoindole-1,3-dione

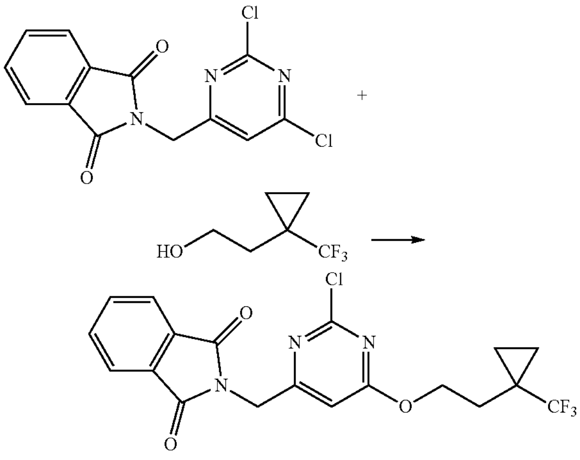

A mixture of 2-[1-(trifluoromethyl)cyclopropyl]ethan-1-ol (890 mg, 5.77 mmol, 1.00 equiv), 2-[(2,6-dichloropyrimidin-4-yl)methyl]-2,3-dihydro-1H-isoindole-1,3-dione (1.78 g, 5.78 mmol, 1.00 equiv), $Pd_2(dba)_3CHCl_3$ (598 mg, 0.58 mmol, 0.10 equiv), XantPhos (1.003 g, 1.73 mmol, 0.30 equiv), $Cs_2CO_3$ (5.652 g, 17.38 mmol, 3.00 equiv), and toluene (50 mL) was stirred for 12 h at 50° C. under nitrogen. The solid was filtered out and the solution was diluted with brine, extracted with ethyl acetate, dried over anhydrous sodium sulfate, and concentrated under vacuum. This resulted in the title compound (900 mg, 37%) as a white solid. LCMS [M+H$^+$] 426.

Step 7: Preparation of 2-[(2-cyclopropyl-6-[2-[1-(trifluoromethyl)cyclopropyl]ethoxy]pyrimidin-4-yl)methyl]-2,3-dihydro-1H-isoindole-1,3-dione

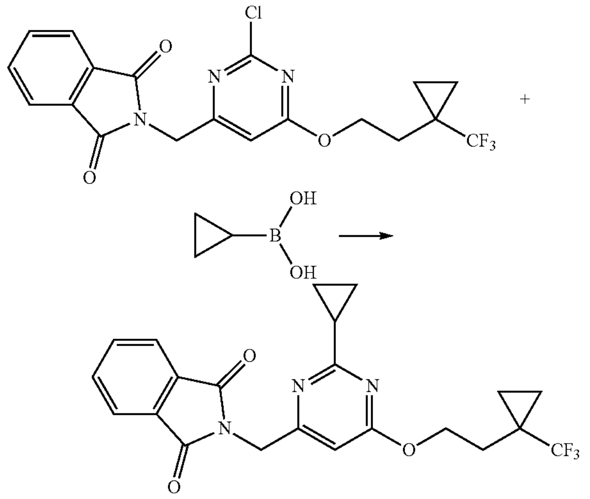

A mixture of 2-[(2-chloro-6-[2-[1-(trifluoromethyl)cyclopropyl]ethoxy]pyrimidin-4-yl)methyl]-2,3-dihydro-1H-isoindole-1,3-dione (850 mg, 2.00 mmol, 1.00 equiv), cyclopropylboronic acid (1.715 g, 19.97 mmol, 10.00 equiv), $Pd_2(dba)_3.CHCl_3$ (319 mg, 0.31 mmol, 0.15 equiv), SPhos (316 mg, 0.77 mmol, 0.39 quiv), $K_3PO_4$ (981 mg, 4.62 mmol, 2.32 quiv), toluene (20 mL), and water (2 mL) was stirred for 12 h at 100° C. under nitrogen. The solid was filtered out, dissolved in ethyl acetate, washed with brine, dried over anhydrous sodium sulfate, and concentrated under vacuum. The residue was purified by a silica gel column eluting with ethyl acetate/petroleum ether to afford the title compound (700 mg, 81%) as a yellow solid. LCMS [M+H$^+$] 432.

Step 8: Preparation of (2-cyclopropyl-6-[2-[1-(trifluoromethyl)cyclopropyl]ethoxy]pyrimidin-4-yl)methanamine

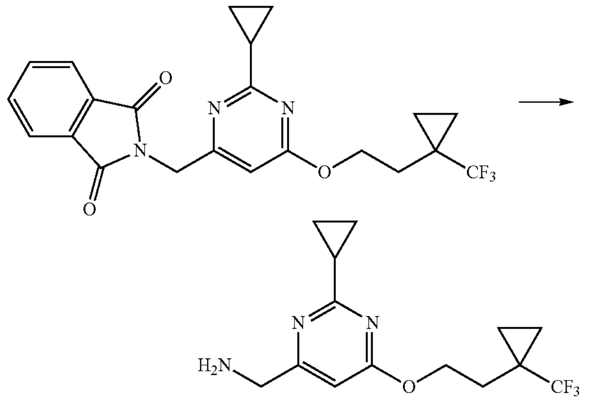

A mixture of 2[(2-cyclopropyl-6-[2-[1-(trifluoromethyl)cyclopropyl]ethoxy]pyrimidin-4-yl)methyl]-2,3-dihydro-1H-isoindole-1,3-dione (700 mg, 1.62 mmol, 1.00 equiv), methanol (20 mL), hydrazine hydrate (1.22 g, 80%) was stirred for 12 h at room temperature. The resulting mixture was concentrated under vacuum. The residue was dissolved in ethyl acetate. The solid was filtered out and the filtrate was concentrated under vacuum. This resulted in the title compound (550 mg, crude) as yellow oil. LCMS [M+H$^+$] 302.

Preparation 24: [2-[3,3-difluoro-4-(trifluoromethoxy)piperidin-1-yl]-5-fluoropyridin-4-yl]methanamine

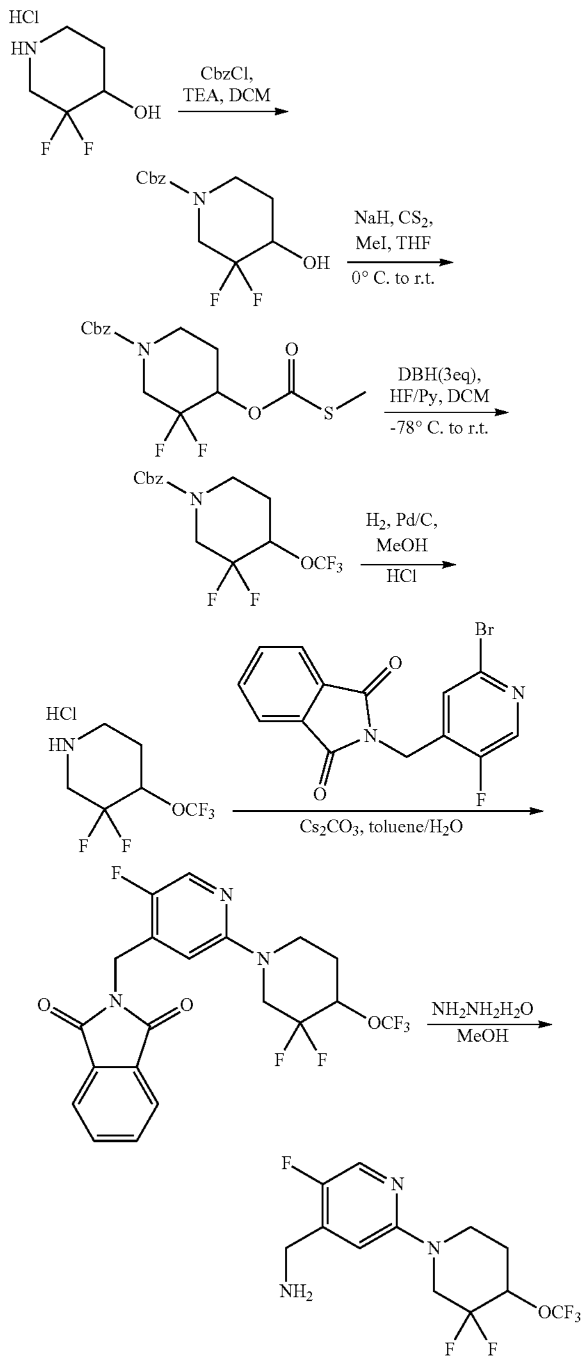

Step 1: Preparation of benzyl 3,3-difluoro-4-hydroxypiperidine-1-carboxylate

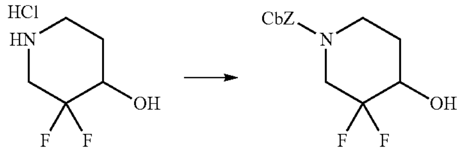

Cbz-Cl (1.087 g, 6.37 mmol, 1.11 equiv) was added dropwise into a mixture of 3,3-difluoropiperidin-4-ol hydrochloride (1 g, 5.76 mmol, 1.00 equiv) in dichloromethane (100 mL) and TEA (2.358 g, 23.30 mmol, 4.05 equiv) at 0° C. The resulting solution was stirred for 12 h at room temperature and concentrated under vacuum. The residue was diluted with saturated sodium bicarbonate, extracted with ethyl acetate, washed with brine, dried over anhydrous sodium sulfate, and concentrated under vacuum. The residue was purified by a silica gel column eluting with dichloromethane/ethyl acetate (5/1) to afford the title compound (1.55 g, 99%) as colorless oil. LCMS [M+H$^+$] 272.

Step 2: Preparation of 3,3-difluoro-4-[[(methylsulfanyl)methanethioyl]oxy]piperidine-1-carboxylate

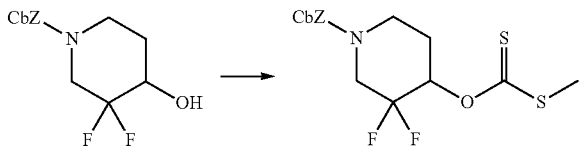

Sodium hydride (458 mg, 60% in mineral oil, 3.34 equiv) was added in several batches into a solution of benzyl 3,3-difluoro-4-hydroxypiperidine-1-carboxylate (1.55 g, 5.71 mmol, 1.00 equiv) in tetrahydrofuran (50 mL) at 0° C. under nitrogen. After 30 min carbon disulfide (1.4 mL, 23.19 mmol, 4.05 equiv) was added dropwise at 0° C. and the reaction mixture was stirred over 30 min. MeI (1.625 g, 11.45 mmol, 2.00 equiv) was then added dropwise at 0° C. The resulting solution was stirred for 12 h at room temperature, diluted with brine, extracted with ethyl acetate, dried over anhydrous sodium sulfate, and concentrated under vacuum. The residue was purified by a silica gel column eluting with dichloromethane to afford the title compound (2 g, 97%) as yellow oil. LCMS [M+H$^+$] 362.

Step 3: Preparation of benzyl 3,3-difluoro-4-(trifluoromethoxy)piperidine-1-carboxylate

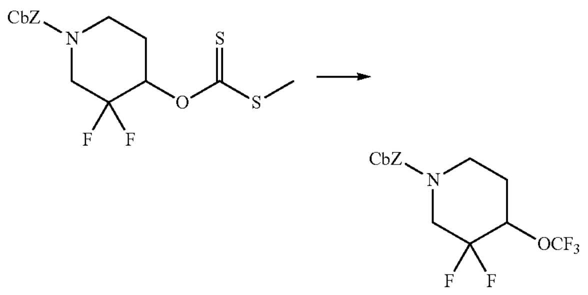

HF-pyridine (21 mL, 70%) was added dropwise into a mixture of 1,3-dibromo-5,5-dimethylimidazolidine-2,4-dione (7.915 g, 27.68 mmol, 4.00 equiv) in dichloromethane (100 mL) at −78° C. under nitrogen. A solution of benzyl 3,3-difluoro-4-[[(methylsulfanyl)methanethioyl]oxy]piperidine-1-carboxylate (2.5 g, 6.92 mmol, 1.00 equiv) in dichloromethane (4 mL) was added dropwise at −78° C. After being stirred for 12 h at room temperature the reaction was quenched by saturated sodium bicarbonate. The solid was filtered out and the solution was extracted with dichloromethane, washed with brine, dried over anhydrous sodium sulfate, and concentrated under vacuum. The residue was purified by a silica gel column eluting with dichloromethane/petroleum ether (1/1) to afford the title compound (1.3 g, 55%) as colorless oil. LCMS [M+H$^+$] 340.

Step 4: Preparation of 3,3-difluoro-4-(trifluoromethoxy)piperidine hydrochloride

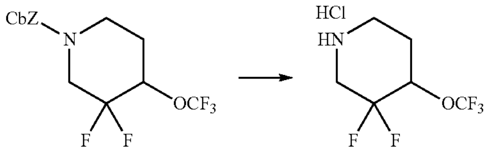

A mixture of benzyl 3,3-difluoro-4-(trifluoromethoxy) piperidine-1-carboxylate (1.3 g, 3.83 mmol, 1.00 equiv), methanol (50 mL), palladium on carbon (50 mg, 10%) was stirred for 12 h at room temperature under hydrogen. The solid was filtered out and the solution was poured into 4N HCl in dioxane and concentrated under vacuum. The residue was wash with petroleum ether/ethyl acetate (50/1) and dried under vacuum. This resulted in the title compound (970 mg, crude) as a gray solid. LCMS [M+H$^+$] 206.

Step 5: Preparation of 2-([2-[3,3-difluoro-4-(trifluoromethoxy)piperidin-1-yl]-5-fluoropyridin-4-yl] methyl)-2,3-dihydro-1H-isoindole-1,3-dione

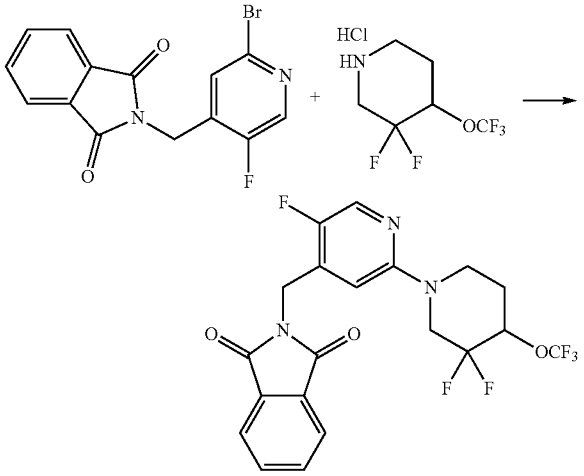

A mixture of 2-[(2-bromo-5-fluoropyridin-4-yl)methyl]-2,3-dihydro-1H-isoindole-1,3-dione (1.038 g, 3.10 mmol, 1.50 equiv), 3,3-difluoro-4-(trifluoromethoxy)piperidine hydrochloride (500 mg, 2.07 mmol, 1.00 equiv), $Pd_2(dba)_3.CHCl_3$ (214 mg, 0.21 mmol, 0.10 equiv), SPhos (170 mg, 0.41 mmol, 0.20 equiv), and $Cs_2CO_3$ (2.02 g, 6.20 mmol, 3.00 equiv) in toluene (10 mL)/water (1 mL) was stirred for 12 h at 95° C. under nitrogen. The solid was filtered out and the solution was diluted with brine, extracted with ethyl acetate, washed with brine, dried over anhydrous sodium sulfate, and concentrated under vacuum. The residue was purified by a silica gel column eluting with dichloromethane/petroleum ether (2/1) to afford the title compound (420 mg, 44%) as a white solid. LCMS [M+H$^+$] 460.

Step 6: Preparation of [2-[3,3-difluoro-4-(trifluoromethoxy)piperidin-1-yl]-5-fluoropyridin-4-yl] methanamine

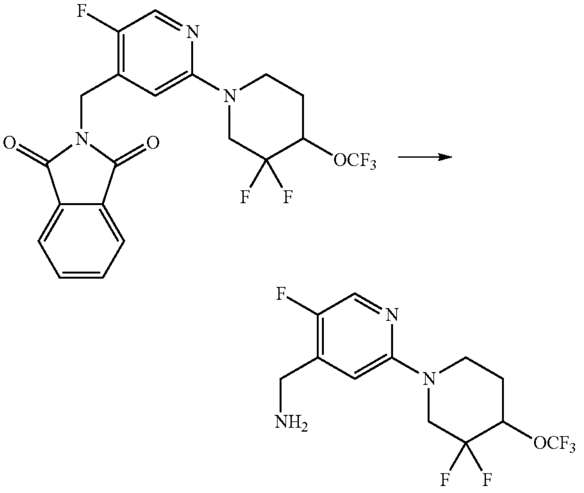

A mixture of 2-([2-[3,3-difluoro-4-(trifluoromethoxy)piperidin-1-yl]-5-fluoropyridin-4-yl]methyl)-2,3-dihydro-1H-isoindole-1,3-dione (420 mg, 0.91 mmol, 1.00 equiv) and hydrazine hydrate (457 mg, 80%) in MeOH (50 mL) was stirred at 50° C. for 12 h. The resulting mixture was concentrated under vacuum. The residue was dissolved in ethyl acetate. The solid was filtered out and the liquid was concentrated under vacuum. This resulted in the title compound (330 mg, crude) as yellow oil. LCMS [M+H$^+$] 330.

Preparation 25: [5-fluoro-2-[3-(trifluoromethoxy) cyclobutyl]pyridin-4-yl]methanamine

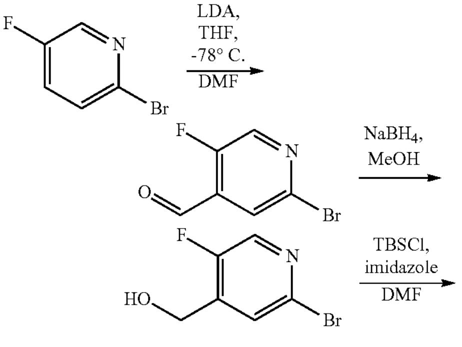

-continued

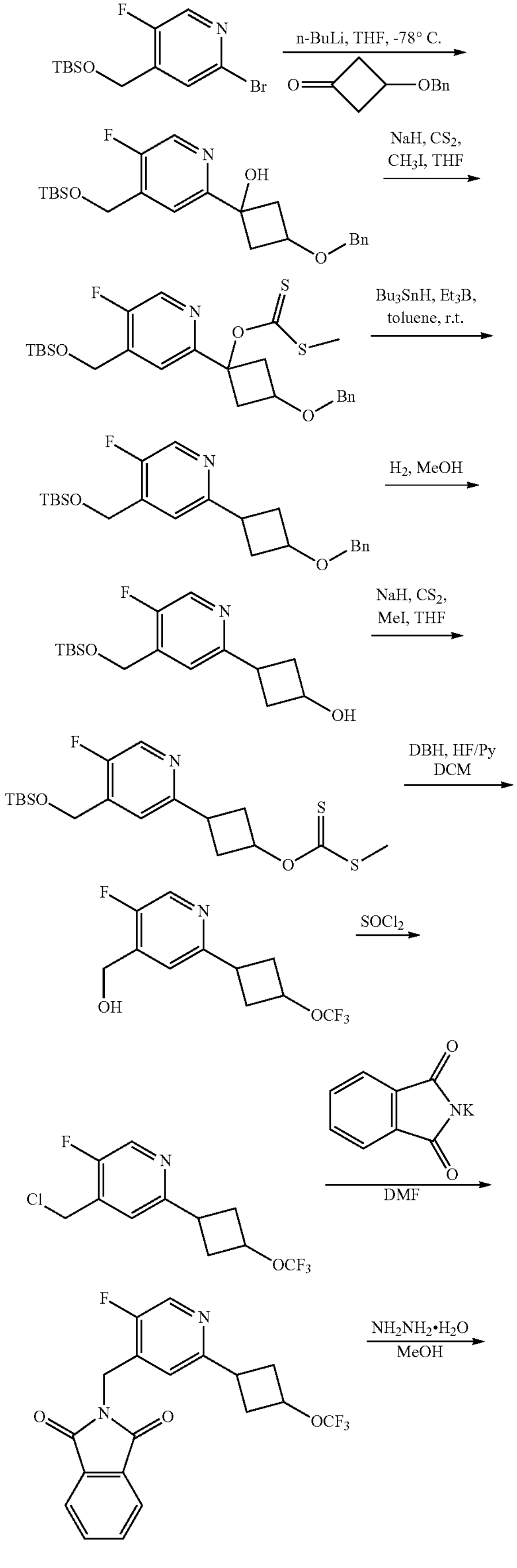

-continued

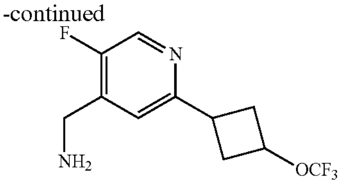

Step 1: Preparation of 2-bromo-5-fluoropyridine-4-carbaldehyde

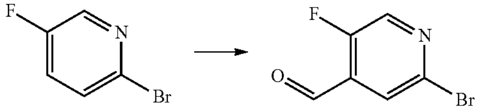 [SMILES: Fc1ccc(Br)nc1 ; O=Cc1cc(Br)ncc1F]

n-BuLi (7.4 mL, 2.5M in hexane, 1.30 equiv) was added dropwise into a solution of i-$Pr_2NH$ (2.15 g, 21.25 mmol, 1.50 equiv) in tetrahydrofuran (35 mL) at −30° C. under nitrogen. After 20 min at −30° C. the reaction mixture was cooled to −78° C. A solution of 2-bromo-5-fluoropyridine (2.5 g, 14.21 mmol, 1.00 equiv) in THF (4 mL) was added dropwise at −78° C. The resulting solution was stirred for an additional 2 hours at −78° C. To the mixture was added N,N-dimethylformamide (2.1 g, 28.73 mmol, 2.02 equiv) dropwise at −78° C. The resulting solution was stirred for 2 hours at −78° C. and 12 hours at room temperature. The reaction was quenched by saturated $NH_4Cl$ solutions, extracted with ethyl acetate, washed with saturated $NH_4Cl$ solutions and brine, dried over anhydrous sodium sulfate, and concentrated under vacuum. This resulted in the title compound (2.6 g, 90%) as light yellow oil. LCMS $[M+H^+]$ 204.

Step 2: Preparation of (2-bromo-5-fluoropyridin-4-yl)methanol

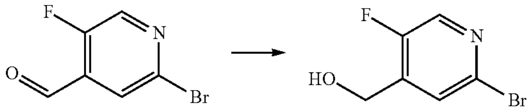 [SMILES: O=Cc1cc(Br)ncc1F ; OCc1cc(Br)ncc1F]

$NaBH_4$ (726 mg, 19.19 mmol, 1.51 equiv) was added in portions into a solution of 2-bromo-5-fluoropyridine-4-carbaldehyde (2.6 g, 12.75 mmol, 1.00 equiv) in methanol (50 mL) at 0° C. The resulting solution was stirred for 1 h at 0° C. The reaction was then quenched by saturated sodium bicarbonate solution, extracted with ethyl acetate, washed with brine, dried over anhydrous sodium sulfate, and concentrated under vacuum. This resulted in the title compound (2.5 g, 95%) as light yellow oil. LCMS $[M+H^+]$ 206.

Step 3: Preparation of 2-bromo-4-[[(tert-butyldimethylsilyl)oxy]methyl]-5-fluoropyridine

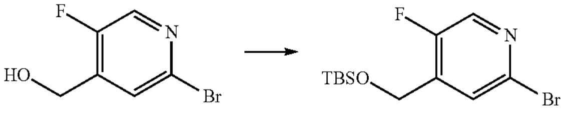 [SMILES: OCc1cc(Br)ncc1F ; CC(C)(C)[Si](C)(C)OCc1cc(Br)ncc1F]

A mixture of (2-bromo-5-fluoropyridin-4-yl)methanol (5 g, 24.27 mmol, 1.00 equiv), N,N-dimethylformamide (40 mL), imidazole (4.95 g, 72.71 mmol, 3.00 equiv), and TBSCl (5.5 g, 36.49 mmol, 1.50 equiv) was stirred for 2 h at room temperature under nitrogen. The resulting solution was diluted with water, extracted with ethyl acetate, washed with brine, dried over anhydrous sodium sulfate, and concentrated under vacuum. The residue was purified by a silica gel column eluting with ethyl acetate/petroleum ether (1/10) to afford the title compound (7.3 g, 94%) as a light yellow solid. LCMS [M+H+] 322.

Step 4: Preparation of 3-[(benzyloxy)methyl]-1-(4-[[(tert-butyldimethylsilyl)oxy]methyl]-5-fluoropyridin-2-yl)cyclobutan-1-ol

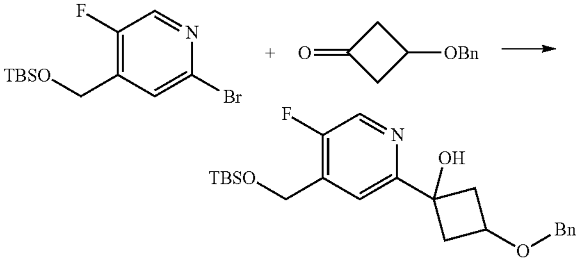

n-BuLi (3.25 mL, 34.50 mmol, 1.50 equiv) was added dropwise into a solution of 2-bromo-4-[[(tert-butyldimethylsilyl)oxy]methyl]-5-fluoropyridine (2 g, 6.25 mmol, 1.00 equiv) in tetrahydrofuran (100 mL) at −78° C. under nitrogen. The resulting solution was stirred for 1 hour at −78° C. To this mixture was added 3-(benzyloxy)cyclobutan-1-one (1.65 g, 9.36 mmol, 1.50 equiv) dropwise at −78° C. The resulting solution was then warmed to room temperature slowly and allowed to react for an additional 12 h at room temperature. The resulting solution was quenched by saturated $NH_4Cl$ saturated solution, extracted with ethyl acetate, washed with brine, dried over anhydrous sodium sulfate, and concentrated under vacuum. The residue was purified by a silica gel column eluting with ethyl acetate/petroleum ether (1/20) to afford the title compound (1.5 g, 56%) as colorless oil. LCMS [M+H+] 418.

Step 5: Preparation of [3-(benzyloxy)-1-(4-[[(tert-butyldimethylsilyl)oxy]methyl]-5-fluoropyridin-2-yl)cyclobutoxy](methylsulfanyl)methanethione

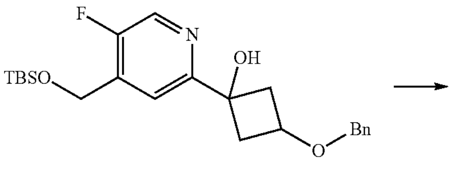

-continued

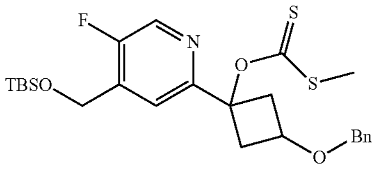

Sodium hydride (187 mg, 60% in mineral oil, 1.50 equiv) was added in portions into a solution of 3-(benzyloxy)-1-(4-[[(tert-butyldimethylsilyl)oxy]methyl]-5-fluoropyridin-2-yl)cyclobutan-1-ol (1.3 g, 3.11 mmol, 1.00 equiv) in tetrahydrofuran (80 mL) at 0° C. under nitrogen. The resulting solution was stirred for 30 min at 0° C. To this was added carbon disulfide (1.18 g, 15.50 mmol, 4.98 equiv) dropwise at 0° C. The resulting solution was stirred for 30 min at 0° C. To the mixture was added $CH_3I$ (2.2 g, 15.50 mmol, 4.98 equiv) dropwise at 0° C. The resulting solution was stirred for 12 h at room temperature, quenched by saturated $NH_4Cl$ solution, extracted with ethyl acetate, washed with brine, dried over anhydrous sodium sulfate, and concentrated under vacuum. The residue was purified by a silica gel column eluting with ethyl acetate/petroleum ether (1/10) to afford the title compound (1.1 g, 70%) as light yellow oil. LCMS [M+H+] 508.

Step 6: Preparation of 2-[3-(benzyloxy)cyclobutyl]-4-[[(tert-butyldimethylsilyl)oxy]methyl]-5-fluoropyridine

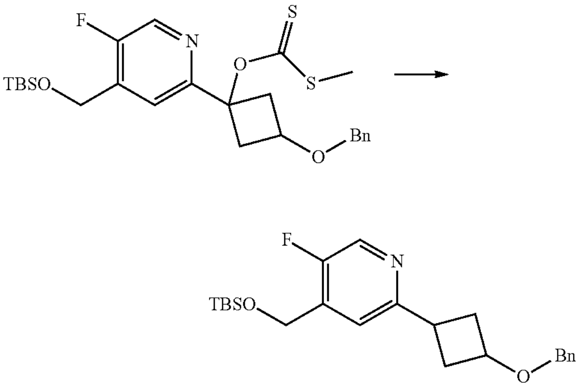

A mixture of [3-(benzyloxy)-1-(4-[[(tert-butyldimethylsilyl)oxy]methyl]-5-fluoropyridin-2-yl)cyclobutoxyl](methylsulfanyl)methanethione (4.95 g, 9.75 mmol, 1.00 equiv), toluene (50 mL), n-$Bu_3SnH$ (4.25 g, 14.60 mmol, 1.50 equiv), and triethylborane (14.6 mL, 148.99 mmol, 1.50 equiv) was stirred for 12 h at room temperature under nitrogen. The resulting mixture was concentrated under vacuum, diluted with water, extracted with ethyl acetate, washed with brine, dried over anhydrous sodium sulfate, and concentrated under vacuum. The residue was purified by a silica gel column eluting with dichloromethane/petroleum ether (1/1) to afford the title compound (3.1 g, 79%) as light yellow oil. LCMS [M+H+] 402.

Step 7: Preparation of 3-(4-[[(tert-butyldimethylsilyl)oxy]methyl]-5-fluoropyridin-2-yl)cyclobutan-1-ol

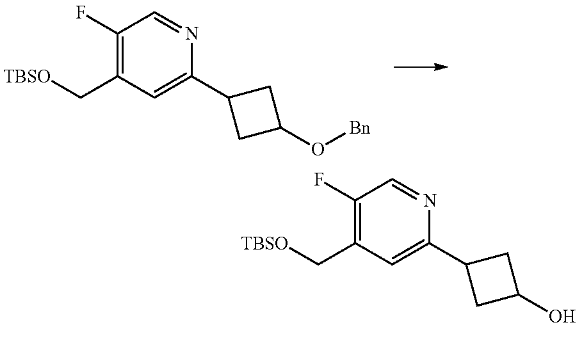

A mixture of 2-[3-(benzyloxy)cyclobutyl]-4-[[(tert-butyldimethylsilyl)oxy]methyl]-5-fluoropyridine (3 g, 7.47 mmol, 1.00 equiv), methanol (50 mL), and Raney Ni (300 mg, 3.50 mmol, 0.47 equiv) was stirred for 12 h at room temperature under hydrogen. The solid was filtered out and the liquid was concentrated under vacuum. This resulted in the title compound (1.9 g, 82%) as colorless oil. LCMS [M+H$^+$] 312.

Step 8: Preparation of [3-(4-[[(tert-butyldimethylsilyl)oxy]methyl]-5-fluoropyridin-2-yl)cyclobutoxy](methylsulfanyl)methanethione

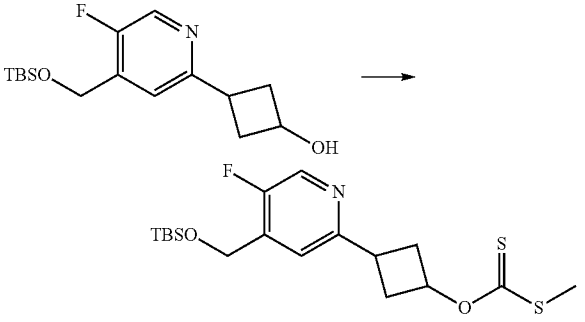

Sodium hydride (489 mg, 60% in mineral oil, 3.341 equiv) was added in several batches into a solution of 3-(4-[[(tert-butyldimethylsilyl)oxy]methyl]-5-fluoropyridin-2-yl)cyclobutan-1-ol (1.9 g, 6.10 mmol, 1.00 equiv) in tetrahydrofuran (150 mL) at 0° C. under nitrogen. The resulting solution was stirred for 30 min at 0° C. To this was added carbon disulfide (1.8 mL, 29.79 mmol, 4.88 equiv) dropwise at 0° C. The resulting solution was stirred for 30 min at 0° C. To the mixture was added MeI (1.735 g, 12.22 mmol, 2.00 equiv) dropwise at 0° C. After being stirred for 12 h at room temperature the reaction mixture was quenched with water, extracted with ethyl acetate, washed with brine, and concentrated under vacuum. The residue was purified by a silica gel column eluting with ethyl acetate/hexane (1/10) to afford the title compound (2.5 g, crude) as yellow oil. LCMS [M+H$^+$] 402.

Step 9: Preparation of [5-fluoro-2-[3-(trifluoromethoxy)cyclobutyl]pyridin-4-yl]methanol

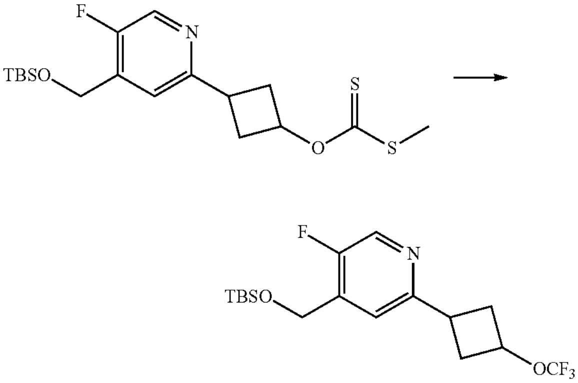

HF-pyridine (21 mL, 70%) was added dropwise into a solution of 1,3-dibromo-5,5-dimethylimidazolidine-2,4-dione (5.34 g, 18.68 mmol, 3.00 equiv) in dichloromethane (150 mL) at −78° C. under nitrogen. To this was added a solution of [3-(4-[[(tert-butyldimethylsilyl)oxy]methyl]-5-fluoropyridin-2-yl)cyclobutoxy](methylsulfanyl)methanethione (2.5 g, 6.23 mmol, 1.00 equiv) in dichloromethane (3 mL) dropwise at −78° C. After being stirred for 12 h at room temperature the reaction was quenched by saturated sodium carbonate at 0° C. The solid was filtered out and the liquid was extracted with ethyl acetate, dried over anhydrous sodium sulfate, and concentrated under vacuum. The residue was purified by a silica gel column eluting with ethyl acetate/hexane (1/5) to afford the title compound (780 mg, 47%) as colorless oil. LCMS [M+H$^+$] 266.

Step 10: Preparation of 4-(chloromethyl)-5-fluoro-2-[3-(trifluoromethoxy)cyclobutyl]pyridine

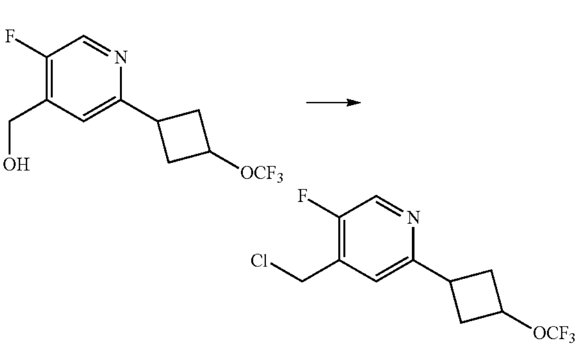

A solution of [5-fluoro-2-[3-(trifluoromethoxy)cyclobutyl]pyridin-4-yl]methanol (760 mg, 2.87 mmol, 1.00 equiv) and thionyl chloride (683 mg, 5.74 mmol, 2.00 equiv) in dichloromethane (20 mL) was stirred for 12 h at room temperature. The reaction mixture was concentrated under vacuum to afford the title compound (810 mg, crude) as green oil. LCMS [M+H$^+$] 284.

Step 11: Preparation of 2-([5-fluoro-2-[3-(trifluoromethoxy)cyclobutyl]pyridin-4-yl]methyl)-2,3-dihydro-1H-isoindole-1,3-dione

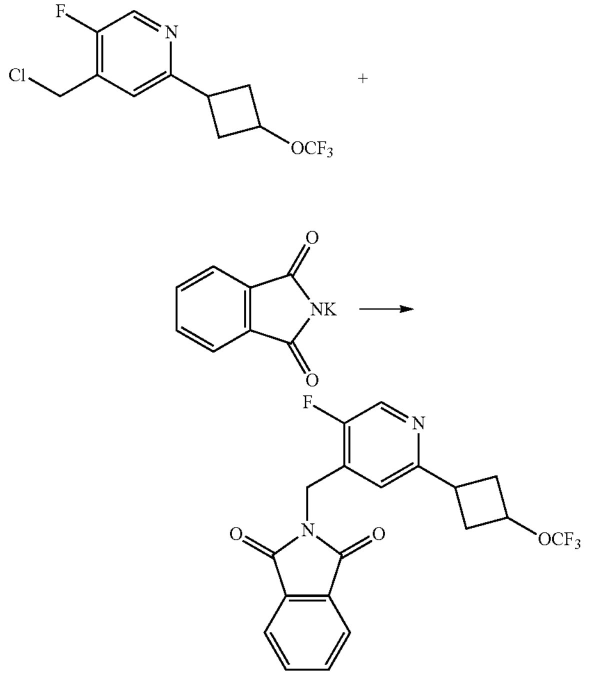

A mixture of 4-(chloromethyl)-5-fluoro-2-[3-(trifluoromethoxy)cyclobutyl]pyridine (810 mg, 2.86 mmol, 1.00 equiv), potassium 1,3-dioxoisoindolin-2-ide (1.582 g, 10.75 mmol, 3.77 equiv) and N,N-dimethylformamide (15 mL) was stirred for 3 h at room temperature. The resulting solution was diluted with brine. The solid was collected by filtration and dried over vacuum to afford the title compound (1.1 g, 98%) as a brown solid. LCMS [M+H+] 395.

Step 12: Preparation of [5-fluoro-2-[3-(trifluoromethoxy)cyclobutyl]pyridin-4-yl]methanamine

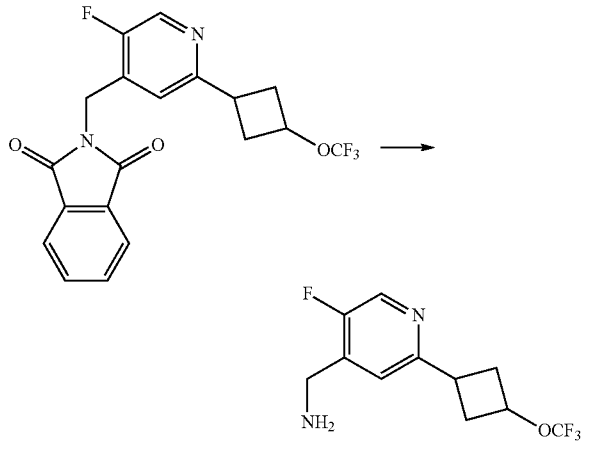

A mixture of 2-([5-fluoro-2-[3-(trifluoromethoxy)cyclobutyl]pyridin-4-yl]methyl)-2,3-dihydro-1H-isoindole-1,3-dione (1.1 g, 2.79 mmol, 1.00 equiv), and hydrazine hydrate (2.8 g, 80%) in MeOH (30 mL) was stirred for 3 h at 40° C. The resulting mixture was concentrated under vacuum. The residue was dissolved in ethyl acetate. The solid was filtered out and the liquid was concentrated under vacuum. This resulted in the title compound (735 mg, crude) of as yellow oil. LCMS [M+H+] 265.

Preparation 26: [5-(trifluoromethoxy)-2-[2-(trifluoromethyl)pyrimidin-5-yl]pyridin-4-yl]methanamine hydrochloride

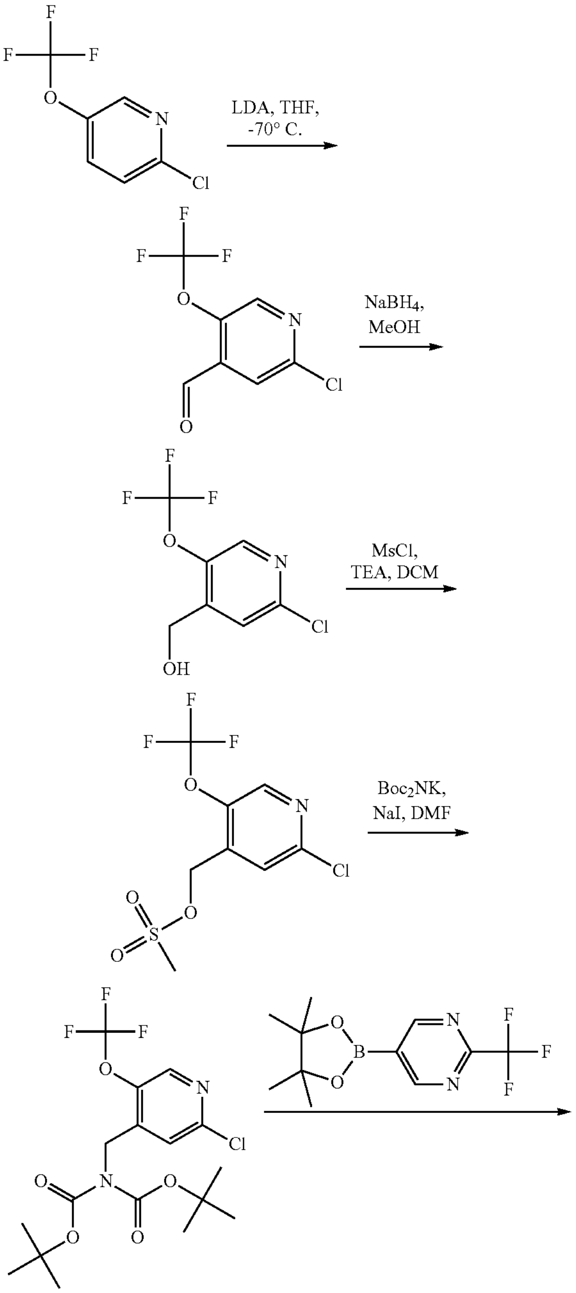

-continued

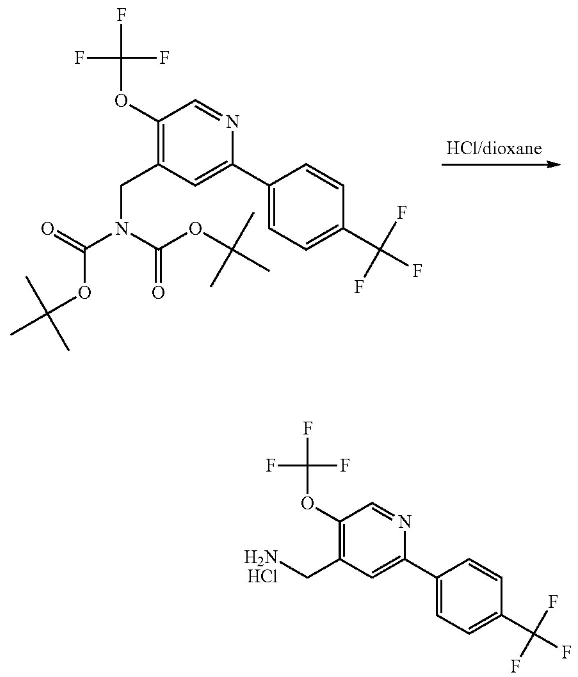

Step 1: Preparation of 2-chloro-5-(trifluoromethoxy)pyridine-4-carbaldehyde

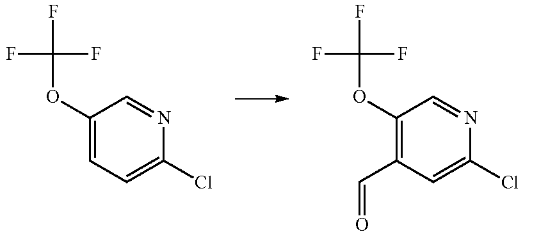 [SMILES: FC(F)(F)Oc1ccc(Cl)nc1 ; O=Cc1cc(Cl)ncc1OC(F)(F)F]

n-BuLi (20.2 mL, 2.5M in hexanes, 2.00 equiv) was added dropwise into a solution of i-$Pr_2NH$ (6.38 g, 63.05 mmol, 2.49 equiv) in tetrahydrofuran (100 mL) at 0° C. under nitrogen. The resulting solution was stirred for 15 min at 0° C. To this was added 2-chloro-5-(trifluoromethoxy) pyridine (5 g, 25.311 mmol, 1.00 equiv) dropwise at −70° C. The resulting solution was allowed to react for an additional 1 h while the temperature was maintained at −70° C. To the mixture was added N,N-dimethylformamide (9.22 g, 126.14 mmol, 4.98 equiv) dropwise at −70° C. The resulting solution was allowed to react for an additional 30 min while the temperature was maintained at −70° C. The reaction was then quenched by saturated $NH_4Cl$ solution, extracted with ethyl acetate, washed with hydrogen chloride (1M) and brine, dried over anhydrous sodium sulfate, and concentrated under vacuum. This resulted in the title compound (4.5 g, 79%) as light yellow oil. LCMS [M+H$^+$] 226.

Step 2: Preparation of [2-chloro-5-(trifluoromethoxy)pyridin-4-yl]methanol

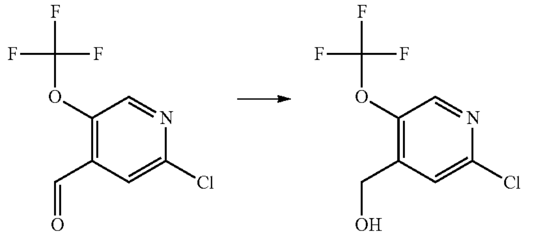 [SMILES: O=Cc1cc(Cl)ncc1OC(F)(F)F ; OCc1cc(Cl)ncc1OC(F)(F)F]

$NaBH_4$ (757 mg, 20.01 mmol, 1.00 equiv) was added in portions into a solution of 2-chloro-5-(trifluoromethoxy) pyridine-4-carbaldehyde (4.5 g, 19.95 mmol, 1.00 equiv) in methanol (100 mL) at 0° C. under nitrogen. After being stirred for 10 min at 0° C. the reaction was quenched by saturated sodium bicarbonate solution, extracted with ethyl acetate, washed with brine, dried over anhydrous sodium sulfate, and concentrated under vacuum. This resulted in the title compound (4.6 g, crude) as light yellow oil. LCMS [M+H$^+$] 228.

Step 3: Preparation of 2-chloro-5-(trifluoromethoxy)pyridin-4-yl]methyl methanesulfonate

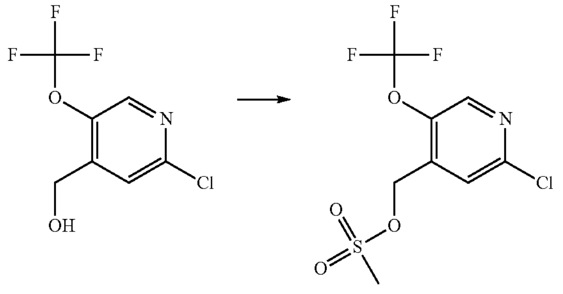 [SMILES: OCc1cc(Cl)ncc1OC(F)(F)F ; CS(=O)(=O)OCc1cc(Cl)ncc1OC(F)(F)F]

MsCl (2.8 g, 24.44 mmol, 1.21 equiv) was added dropwise into a solution of [2-chloro-5-(trifluoromethoxy)pyridin-4-yl]methanol (4.6 g, 20.21 mmol, 1.00 equiv) and TEA (6.1 g, 60.28 mmol, 2.98 equiv) in dichloromethane (100 mL). After being stirred for 15 min at 0° C. the reaction was quenched by water, extracted with ethyl acetate, washed with saturated $NH_4Cl$ solution and brine, dried over anhydrous sodium sulfate, and concentrated under vacuum. This resulted in the title compound (7.2 g, crude) as light yellow oil. LCMS [M+H$^+$] 306.

Step 4: Preparation of tert-butyl N-[(tert-butoxy) carbonyl]-N-[[2-chloro-5-(trifluoromethoxy)pyridin-4-yl]methyl]carbamate

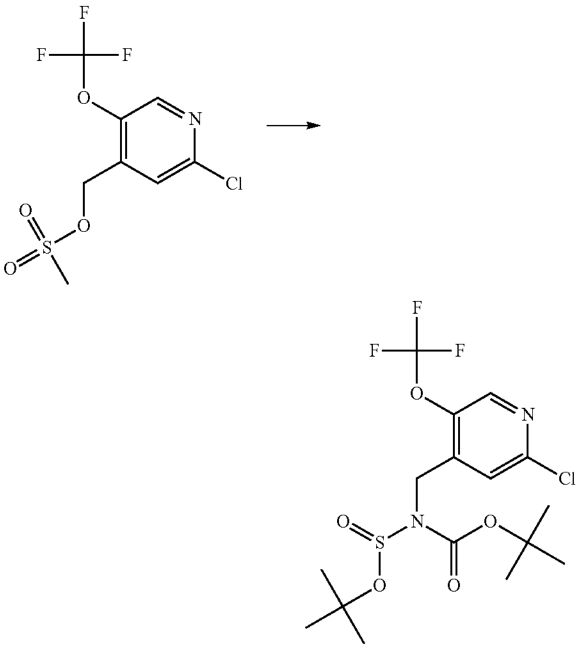 [SMILES: CS(=O)(=O)OCc1cc(Cl)ncc1OC(F)(F)F ; CC(C)(C)OC(=O)N(Cc1cc(Cl)ncc1OC(F)(F)F)S(=O)OC(C)(C)C]

A mixture of [2-chloro-5-(trifluoromethoxy)pyridin-4-yl] methyl methanesulfonate (7.2 g, 23.56 mmol, 1.00 equiv), N,N-dimethylformamide (100 mL), NaI (3.5 g, 23.35 mmol, 0.99 equiv), and tert-butyl N-[(tert-butoxy)carbonyl]-N-potassiocarbamate (9 g, 35.25 mmol, 1.50 equiv) was stirred for 1 h at room temperature. The resulting solution was diluted with water, extracted with ethyl acetate, washed with brine, dried over anhydrous sodium sulfate, and concentrated under vacuum. The residue was purified by a silica gel column eluting with ethyl acetate/petroleum ether (1/20) to afford the title compound (7.1 g, 71%) as light yellow oil. LCMS [M+H$^+$] 427.

Step 5: Preparation of tert-butyl N-[(tert-butoxy) carbonyl]-N-[[5-(trifluoromethoxy)-2-[2-(trifluoromethyl)pyrimidin-5-yl]pyridin-4-yl]methyl]carbamate

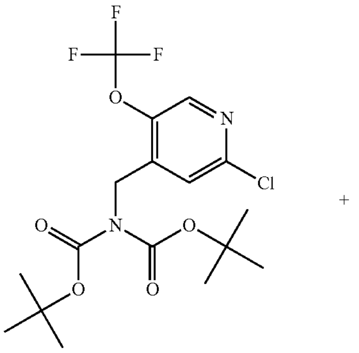

-continued

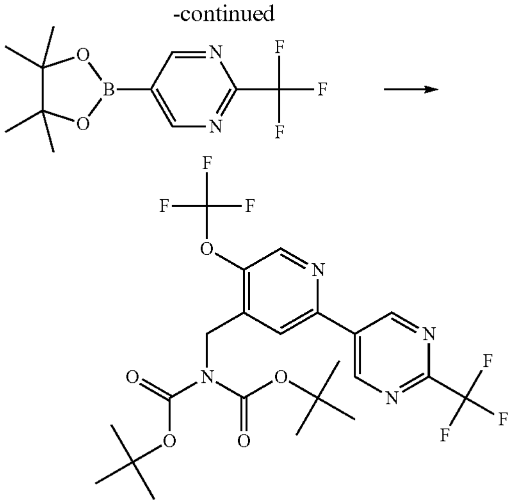

A mixture of tert-butyl N-[(tert-butoxy)carbonyl]-N-[[2-chloro-5-(trifluoromethoxy)pyridin-4-yl]methyl]carbamate (5 g, 11.72 mmol, 1.00 equiv), 5-(tetramethyl-1,3,2-dioxaborolan-2-yl)-2-(trifluoromethyl)pyrimidine (4.2 g, 15.33 mmol, 1.31 equiv), Pd(dppf)$Cl_2$ (856 mg, 1.17 mmol, 0.10 equiv), and potassium carbonate (4.8 g, 34.73 mmol, 2.96 equiv) in dioxane (100 mL) was stirred for 12 h at 85° C. under nitrogen. The resulting mixture was concentrated under vacuum. The residue was purified by a silica gel column eluting with ethyl acetate/petroleum ether (1/10) to afford the title compound (3.6 g, 57%) as a yellow solid. LCMS [M+H$^+$] 539.

Step 6: Preparation of [5-(trifluoromethoxy)-2-[2-(trifluoromethyl)pyrimidin-5-yl]pyridin-4-yl]methanamine hydrochloride

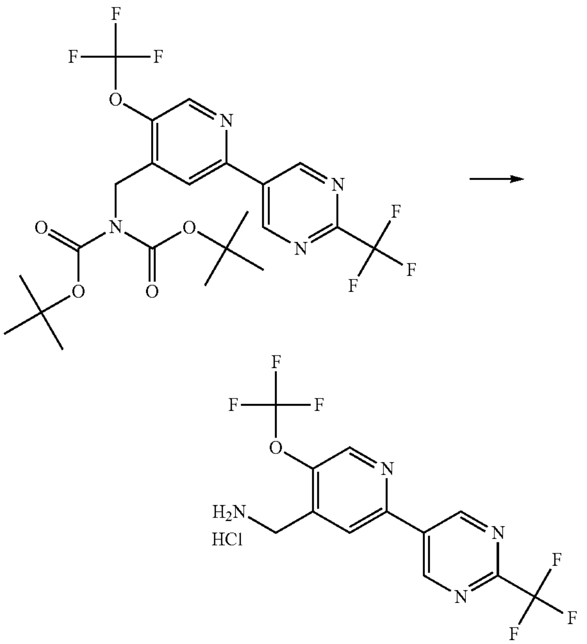

A mixture of tert-butyl N-[(tert-butoxy)carbonyl]-N-[[5-(trifluoromethoxy)-2-[2-(trifluoromethyl)pyrimidin-5-yl]

pyridin-4-yl]methyl]carbamate (3.6 g, 6.69 mmol, 1.00 equiv) and 4 N of hydrogen chloride in dioxane (30 mL) was stirred for 1 h at room temperature. The solid was collected by filtration, and dried under reduced pressure. This resulted in the title compound (2.3 g, 92%) as a light yellow solid. LCMS [M+H$^+$] 339.

Preparation 27: [2-cyclopropyl-3-fluoro-6-(trifluoromethyl)pyridin-4-yl]methanamine

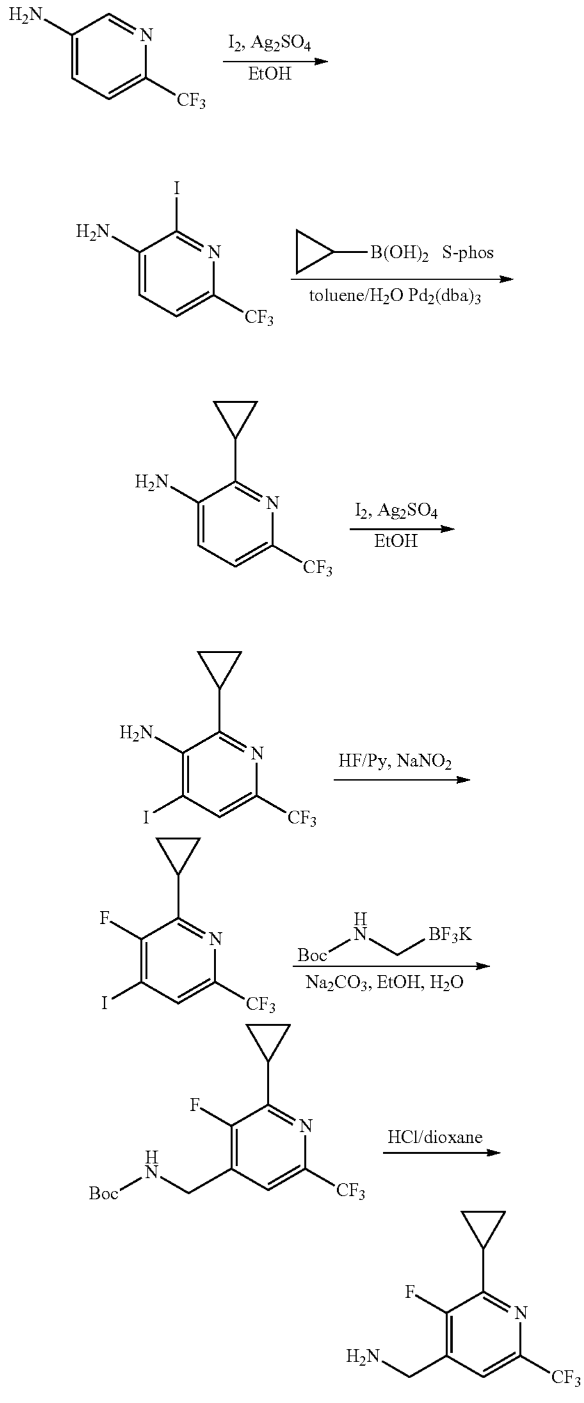

Step 1: Preparation of 2-iodo-6-(trifluoromethyl)pyridin-3-amine

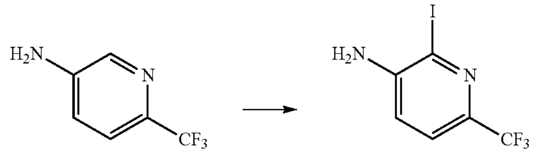 [SMILES: Nc1ccc(C(F)(F)F)nc1 ; Nc1ccc(C(F)(F)F)nc1I]

A mixture of 6-(trifluoromethyl)pyridin-3-amine (1 g, 6.17 mmol, 1.00 equiv), silver sulfate (1.9 g, 6.09 mmol, 1.00 equiv), and $I_2$ (1.57 g, 6.18 mmol, 1.00 equiv) in ethanol (30 mL) was stirred for 1 h at room temperature. The solid was filtered out and the liquid was concentrated under vacuum. The residue was purified by a silica gel column eluting with dichloromethane/petroleum ether (1/2) to afford the title compound (2 g, crude) as a white solid. LCMS [M+H$^+$] 289.

Step 2: Preparation of 2-cyclopropyl-6-(trifluoromethyl)pyridin-3-amine

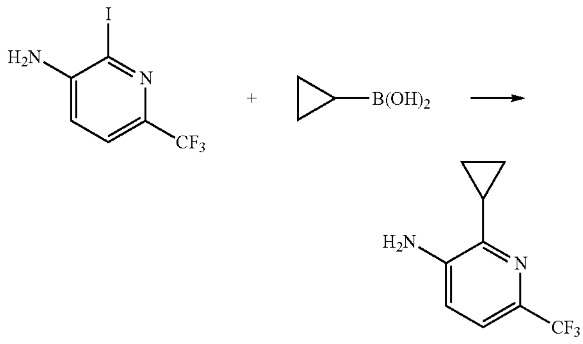

A mixture of 2-iodo-6-(trifluoromethyl)pyridin-3-amine (2 g, 6.94 mmol, 1.00 equiv), cyclopropylboronic acid (2.4 g, 27.94 mmol, 4.02 equiv), $Pd_2(dba)_3.CHCl_3$ (180 mg, 0.17 mmol, 0.03 equiv), SPhos (145 mg, 0.35 mmol, 0.05 equiv), and $K_3PO_4$ (4.4 g, 20.73 mmol, 2.99 equiv) in toluene (30 mL)/water (10 mL) was stirred for 12 h at 70° C. under nitrogen. The solid was filtered out and the solution was diluted with brine, extracted with ethyl acetate, washed with brine, dried over anhydrous sodium sulfate, and concentrated under vacuum. The residue was purified by a silica gel column eluting with dichloromethane/petroleum ether (1/10) to afford the title compound (1.2 g, 85%) as brown oil. LCMS [M+H$^+$] 203.

Step 3: Preparation of 2-cyclopropyl-4-iodo-6-(trifluoromethyl)pyridin-3-amine

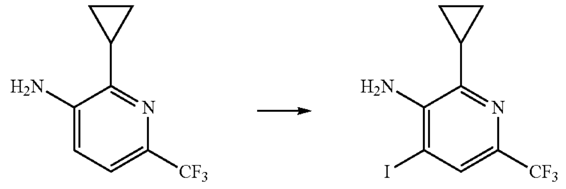 [SMILES: Nc1ccc(C(F)(F)F)nc1C1CC1 ; Nc1c(I)cc(C(F)(F)F)nc1C1CC1]

A mixture of 2-cyclopropyl-6-(trifluoromethyl)pyridin-3-amine (1 g, 4.95 mmol, 1.00 equiv), silver sulfate (1.54 g, 4.94 mmol, 1.00 equiv), and $I_2$ (1.26 g, 4.96 mmol, 1.00 equiv) in ethanol (20 mL) was stirred for 12 h at room temperature. The solid was filtered out. The resulting mixture was concentrated under vacuum. The residue was purified by a silica gel column eluting with ethyl acetate/petroleum ether (1/1) to afford the title compound (1 g, 62%) as red oil. LCMS [$M+H^+$] 329.

Step 4: Preparation of 2-cyclopropyl-3-fluoro-4-iodo-6-(trifluoromethyl)pyridine

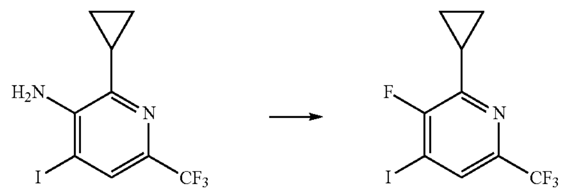 [SMILES: Nc1c(I)cc(C(F)(F)F)nc1C1CC1 ; Fc1c(I)cc(C(F)(F)F)nc1C1CC1]

$NaNO_2$ (316 mg, 4.58 mmol, 1.50 equiv) was added in several batches into a mixture of 2-cyclopropyl-4-iodo-6-(trifluoromethyl)pyridin-3-amine (1 g, 3.04 mmol, 1.00 equiv) and HF-pyridine (15 mL, 70%) at −10° C. The resulting solution was stirred for 40 min at −10° C., 30 min at room temperature, and 2 h at 80° C. The reaction was then quenched by the addition of saturated solution of sodium carbonate, extracted with ethyl acetate, washed with brine, dried over anhydrous sodium sulfate, and concentrated under vacuum. The residue was purified by a silica gel column eluting with petroleum ether to afford the title compound (350 mg, 35%) as colorless oil. LCMS [$M+H^+$] 332.

Step 5: Preparation of tert-butyl N-[[2-cyclopropyl-3-fluoro-6-(trifluoromethyl)pyridin-4-yl]methyl]carbamate

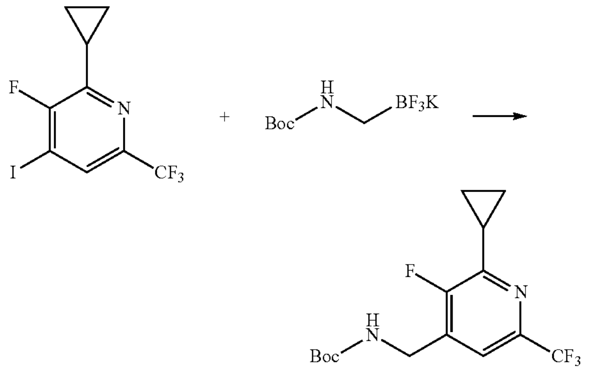

A mixture of 2-cyclopropyl-3-fluoro-4-iodo-6-(trifluoromethyl)pyridine (350 mg, 1.06 mmol, 1.00 equiv), potassium tert-butyl N-[(trifluoroboranuidyl)methyl]carbamate (300 mg, 1.27 mmol, 1.20 equiv), $Pd(OAc)_2$ (48 mg, 0.21 mmol, 0.20 equiv), SPhos (174 mg, 0.42 mmol, 0.40 equiv), and sodium carbonate (335 mg, 3.16 mmol, 2.99 equiv) in ethanol (5 mL)/water (1 mL) was stirred for 12 h at 80° C. under nitrogen. The solid was filtered out and the resulting solution was diluted with brine, extracted with ethyl acetate, washed with brine, dried over anhydrous sodium sulfate, and concentrated under vacuum. The residue was purified by a silica gel column eluting with dichloromethane/petroleum ether (1/1) to afford the title compound (200 mg, 57%) as a yellow solid. LCMS [$M+H^+$] 335.

Step 6: Preparation of [2-cyclopropyl-3-fluoro-6-(trifluoromethyl)pyridin-4-yl]methanamine hydrochloride

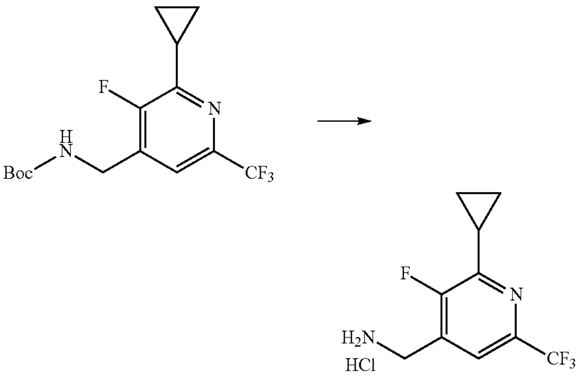

A mixture of tert-butyl N-[[2-cyclopropyl-3-fluoro-6-(trifluoromethyl)pyridin-4-yl]methyl]carbamate (200 mg, 0.60 mmol, 1.00 equiv) and 4 N of HCl in dioxane (10 mL) was stirred for 12 h at room temperature. The resulting mixture was concentrated under vacuum. The residue was precipitated with PE/EtOAc=10/1. The solid was collected by filtration to afford the title compound (80 mg, 57%) as a white solid. LCMS [$M+H^+$] 235.

Preparation 28: [2-cyclopropyl-6-[2-(trifluoromethyl)pyrimidin-5-yl]pyridin-4-yl]methanamine

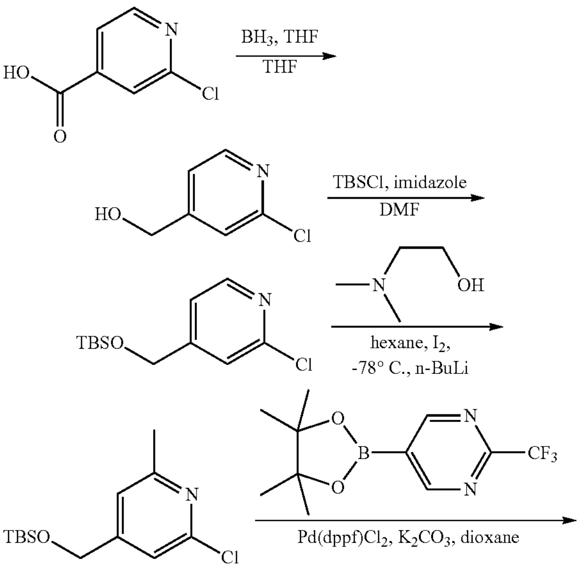

-continued

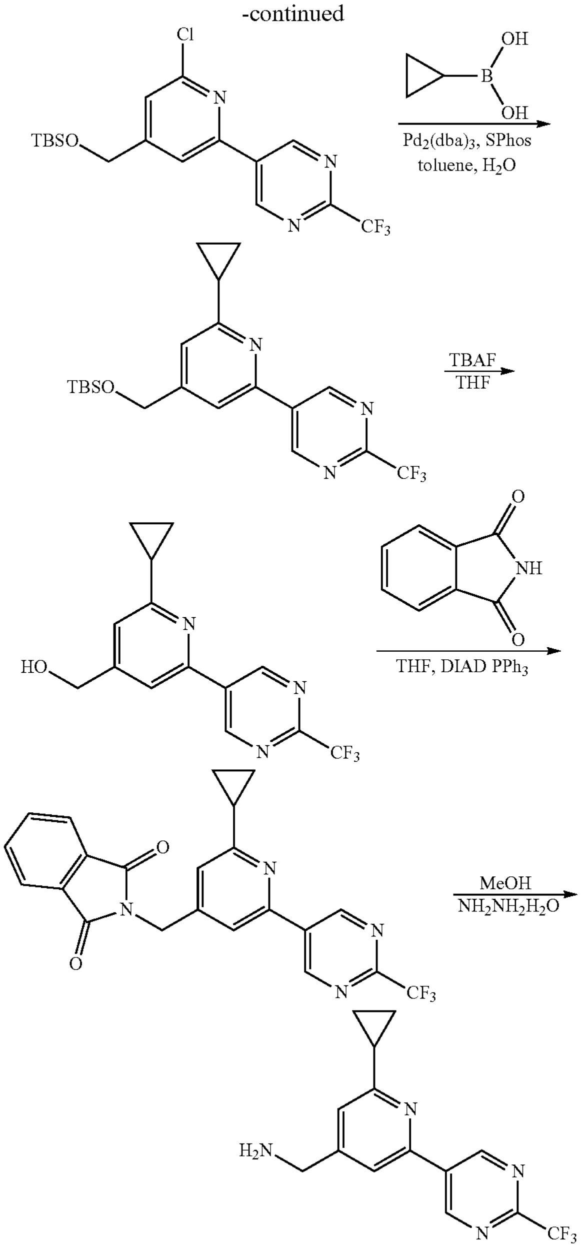

Step 1: Preparation of (2-chloropyridin-4-yl)methanol

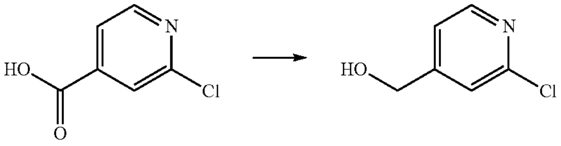 [SMILES: O=C(O)c1ccnc(Cl)c1 ; OCc1ccnc(Cl)c1]

$BH_3$.THF (190 mL, 2.21 mol, 2.99 equiv) was added dropwise into a solution of 2-chloropyridine-4-carboxylic acid (10 g, 63.47 mmol, 1.00 equiv) in tetrahydrofuran (200 mL) at 0° C. After being stirred for 12 h at room temperature the reaction was quenched by methanol and concentrated under vacuum. The residue was purified by a silica gel column eluting with dichloromethane/ethyl acetate (50/1) to afford the title compound (11.9 g, crude) as brown oil. LCMS [M+$H^+$] 144.

Step 2: Preparation of 4-[[(tert-butyldimethylsilyl)oxy]methyl]-2-chloropyridine

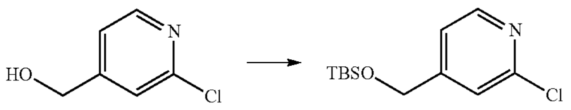 [SMILES: OCc1ccnc(Cl)c1 ; CC(C)(C)[Si](C)(C)OCc1ccnc(Cl)c1]

TBSCl (14.9 g, 98.85 mmol, 1.19 equiv) was added in several batches into a mixture of (2-chloropyridin-4-yl)methanol (11.9 g, 82.89 mmol, 1.00 equiv), N,N-dimethylformamide (100 mL) and imidazole (11.2 g, 164.52 mmol, 1.99 equiv) under nitrogen. The resulting solution was stirred for 1 h at room temperature and then diluted with brine, extracted with ethyl acetate, washed with brine, and dried over anhydrous sodium sulfate. The residue was purified by a silica gel column eluting with dichloromethane/petroleum ether (2/1). This resulted in the title compound (18 g, 84%) as a light yellow solid. LCMS [M+$H^+$] 258.

Step 3: Preparation of 4-[[(tert-butyldimethylsilyl)oxy]methyl]-2-chloro-6-iodopyridine

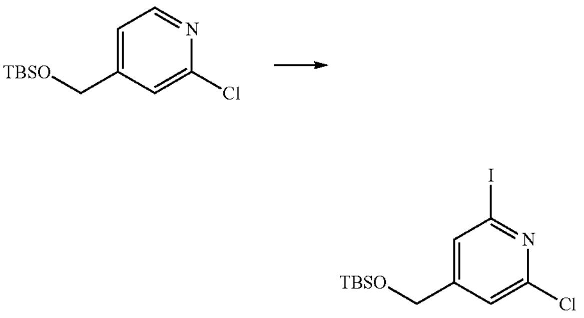

n-BuLi (46.5 mL, 2.5M in hexanes, 5.99 equiv) was added dropwise into a solution of 2-(dimethylamino)ethan-1-ol (5.1 g, 57.22 mmol, 2.95 equiv) in hexane (50 mL) at 0° C. in 1 hour under nitrogen. The resulting solution was stirred for 40 min at 0° C. To this was added a solution of 4-[[(tert-butyldimethylsilyl)oxy]methyl]-2-chloropyridine (5 g, 19.39 mmol, 1.00 equiv) in hexane (50 mL) dropwise at −70° C. in 1 hour. The resulting solution was stirred for 1.5 h while the temperature was maintained at −70° C. To the mixture was added a solution of $I_2$ (19.7 g, 77.62 mmol, 4.00 equiv) in tetrahydrofuran (200 mL) dropwise at −70° C. over 1.5 hours. After being stirred for 30 min at −70° C. the reaction was quenched by 5% of $Na_2S_2O_3$, extracted with ethyl acetate, washed with brine, dried over anhydrous sodium sulfate, and concentrated under vacuum. The residue was purified by a silica gel column eluting with dichloromethane/petroleum ether (1/2) to afford the title compound (3.5 g, 47%) as yellow oil. LCMS [M+$H^+$] 384.

Step 4: Preparation of 5-(4-[[(tert-butyldimethylsilyl)oxy]methyl]-6-chloropyridin-2-yl)-2-(trifluoromethyl)pyrimidine

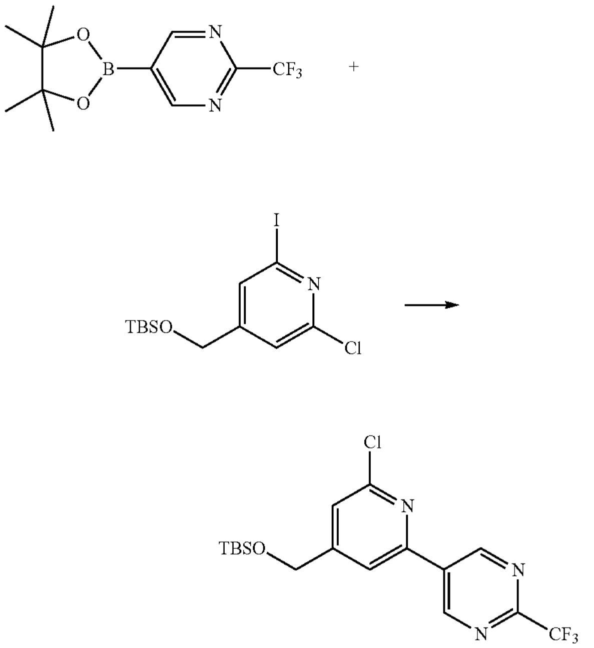

A mixture of 4-[[(tert-butyldimethylsilyl)oxy]methyl]-2-chloro-6-iodopyridine (1 g, 2.61 mmol, 1.00 equiv), 5-(tetramethyl-1,3,2-dioxaborolan-2-yl)-2-(trifluoromethyl)pyrimidine (642 mg, 2.34 mmol, 0.90 equiv), Pd(dppf)$Cl_2$ (95 mg, 0.13 mmol, 0.05 equiv), and potassium carbonate (1.08 g, 7.81 mmol, 3.00 equiv) in dioxane (10 mL)/water (1 mL) was stirred for 4 h at 60° C. under nitrogen. The solid was filtered out and the resulting solution was diluted with brine, extracted with ethyl acetate, washed with brine, dried over anhydrous sodium sulfate, and concentrated under vacuum. The residue was purified by a silica gel column eluting with ethyl acetate/petroleum ether (1/50) to afford the title compound (870 mg, 83%) as a yellow solid. LCMS [M+H$^+$] 404.

Step 5: Preparation of 5-(4-[[(tert-butyldimethylsilyl)oxy]methyl]-6-cyclopropylpyridin-2-yl)-2-(trifluoromethyl)pyrimidine

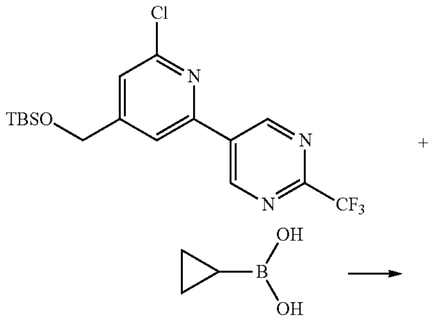

-continued

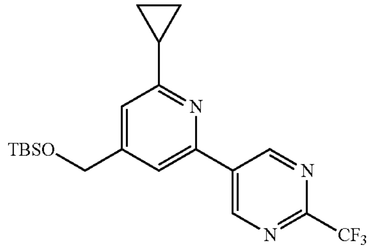

A mixture of 5-(4-[[(tert-butyldimethylsilyl)oxy]methyl]-6-chloropyridin-2-yl)-2-(trifluoromethyl)pyrimidine (870 mg, 2.15 mmol, 1.00 equiv), $Pd_2(dba)_3$ (111 mg, 0.12 mmol, 0.06 equiv), SPhos (88 mg, 0.21 mmol, 0.10 equiv), $K_3PO_4$ (1.37 g, 6.45 mmol, 3.00 equiv), and cyclopropylboronic acid (1.37 g, 15.95 mmol, 7.41 equiv) in toluene (20 mL)/water (2 mL) was stirred for 3 h at 100° C. under nitrogen. The solid was filtered out and the resulting solution was diluted with brine, extracted with ethyl acetate, dried over anhydrous sodium sulfate, and concentrated under vacuum. The residue was purified by a silica gel column eluting with ethyl acetate/petroleum ether (1/50) to afford the title compound (830 mg, 94%) as a white solid. LCMS [M+H$^+$] 410.

Step 6: Preparation of [2-cyclopropyl-6-[2-(trifluoromethyl)pyrimidin-5-yl]pyridin-4-yl]methanol

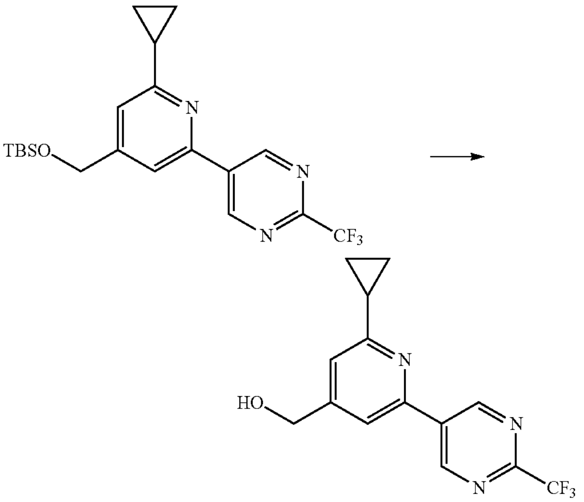

TBAF (2.43 mL, 9.29 mmol, 1.20 equiv) was added dropwise into a solution of 5-(4-[[(tert-butyldimethylsilyl)oxy]methyl]-6-cyclopropylpyridin-2-yl)-2-(trifluoromethyl)pyrimidine (830 mg, 2.03 mmol, 1.00 equiv) in tetrahydrofuran (20 mL). The resulting solution was stirred for 1 h at room temperature. The reaction was diluted with saturated solution of $NH_4Cl$, extracted with ethyl acetate, washed with brine, dried over anhydrous sodium sulfate, and concentrated under vacuum. The residue was purified by a silica gel column eluting with ethyl acetate/petroleum ether (1/5) to afford the title compound (580 mg, 97%) as a yellow solid. LCMS [M+H$^+$] 296.

Step 7: Preparation of 2-([2-cyclopropyl-6-[2-(trifluoromethyl)pyrimidin-5-yl]pyridin-4-yl]methyl)-2,3-dihydro-1H-isoindole-1,3-dione

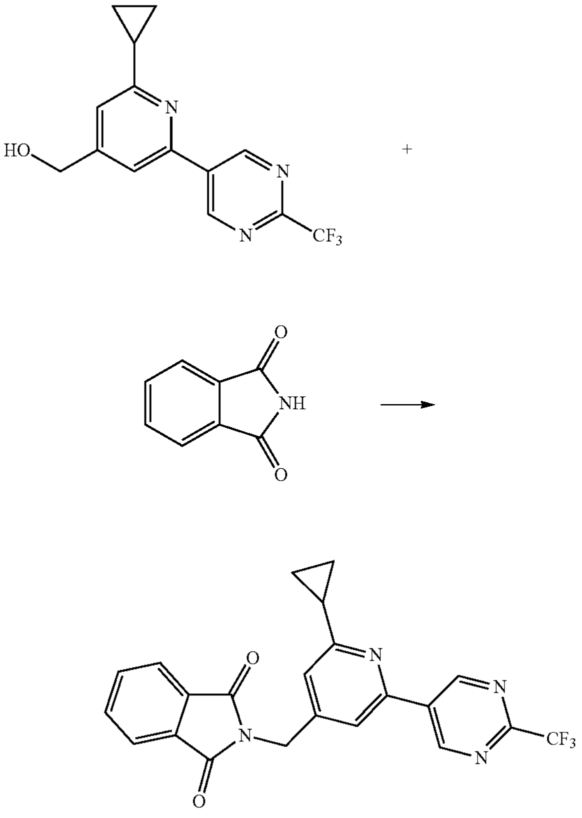

DIAD (794 mg, 3.92 mmol, 1.99 equiv) was added dropwise into a solution of [2-cyclopropyl-6-[2-(trifluoromethyl)pyrimidin-5-yl]pyridin-4-yl]methanol (580 mg, 1.96 mmol, 1.00 equiv), 2,3-dihydro-1H-isoindole-1,3-dione (578 mg, 3.93 mmol, 2.00 equiv), and $PPh_3$ (1.03 g, 3.93 mmol, 2.00 equiv) in tetrahydrofuran (50 mL) at 0° C. under nitrogen. After being stirred for 12 h at room temperature the reaction was concentrated under vacuum. The residue was purified by a silica gel column eluting with dichloromethane/petroleum ether (10/1) to afford the title compound (600 mg, 72%) as a light yellow solid. LCMS [M+H$^+$] 425.

Step 8: Preparation of [2-cyclopropyl-6-[2-(trifluoromethyl)pyrimidin-5-yl]pyridin-4-yl]methanamine

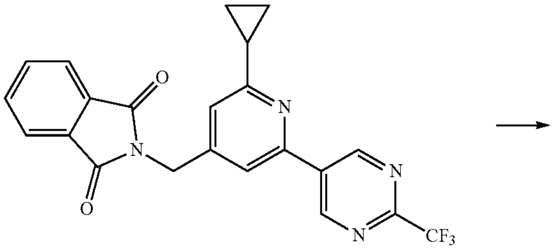

-continued

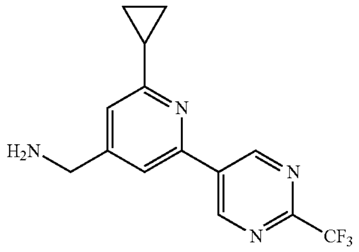

A solution of 2-([2-cyclopropyl-6-[2-(trifluoromethyl)pyrimidin-5-yl]pyridin-4-yl]methyl)-2,3-dihydro-1H-isoindole-1,3-dione (120 mg, 0.28 mmol, 1.00 equiv) and hydrazine hydrate (142 mg, 80%) in methanol (20 mL) was stirred for 3 h at 50° C. The resulting mixture was concentrated under vacuum. The residue was dissolved in ethyl acetate. The solid was filtered out and the filtrate was concentrated under vacuum. This resulted in the title compound (80 mg, 96%) as a yellow solid. LCMS [M+H$^+$] 295.

Preparation 29: [2-(trifluoromethyl)-6-[2-(trifluoromethyl)pyrimidin-5-yl]pyridin-4-yl]methanamine hydrochloride

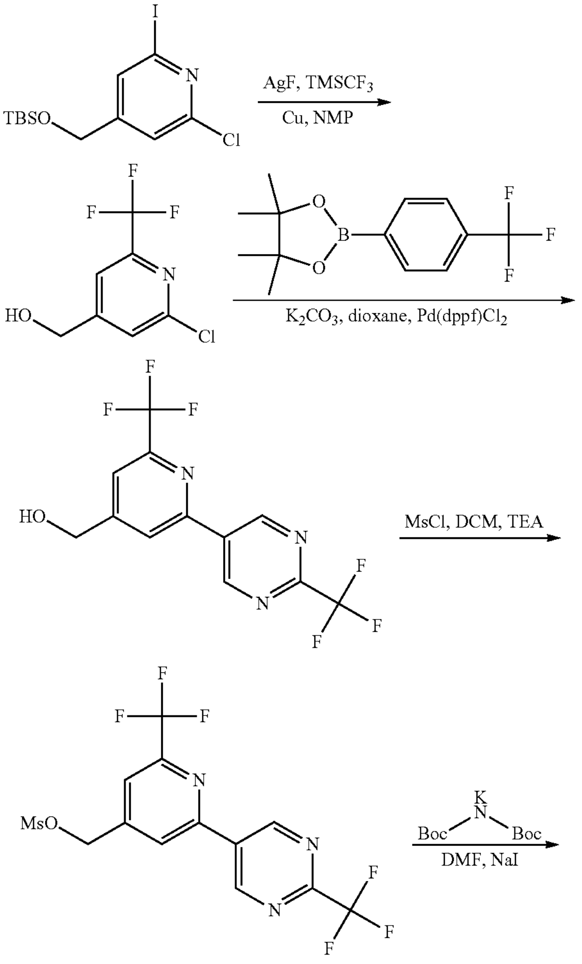

-continued

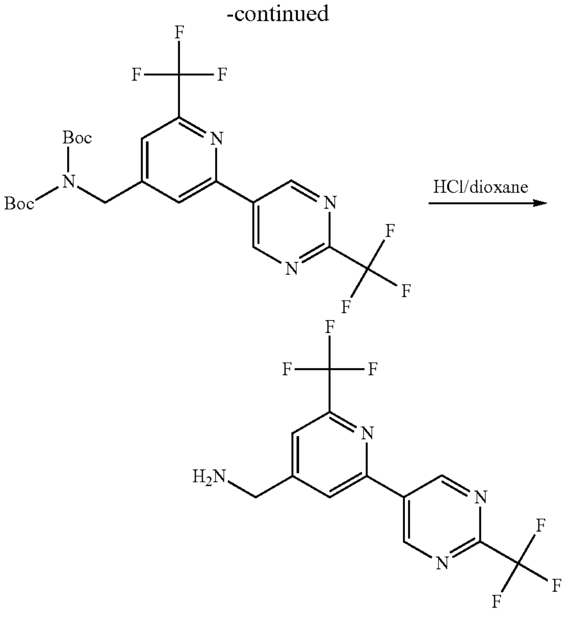

Step 1: Preparation of (2-chloro-6-(trifluoromethyl)pyridin-4-yl)methanol

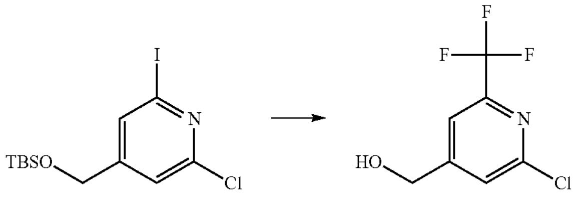 [SMILES: CC(C)(C)[Si](C)(C)OCc1cc(Cl)nc(I)c1 ; OCc1cc(Cl)nc(C(F)(F)F)c1]

A mixture of AgF (364 mg, 2.87 mmol, 2.20 equiv), trimethyl(trifluoromethyl)silane (407 mg, 2.86 mmol, 2.20 equiv), and Cu (166 mg, 2.61 mmol, 2.01 equiv) in NMP (14 mL) was stirred for 6 h at room temperature. 4-[[(tert-butyldimethylsilyl)oxy]methyl]-2-chloro-6-iodopyridine (500 mg, 1.30 mmol, 1.00 equiv) was added and the resulting solution was allowed to react for 12 h at 40° C. The solid was filtered out. The resulting solution was diluted with brine, extracted with ethyl acetate, washed with brine, dried over anhydrous sodium sulfate, and concentrated under vacuum. The residue was purified by a silica gel column eluting with ethyl acetate/petroleum ether (1/5) to afford the title compound (430 mg, crude) as yellow oil. LCMS [M+H$^+$] 212.

Step 2: Preparation of [2-(trifluoromethyl)-6-[2-(trifluoromethyl)pyrimidin-5-yl]pyridin-4-yl]methanol

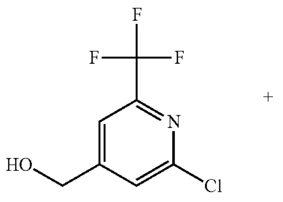

-continued

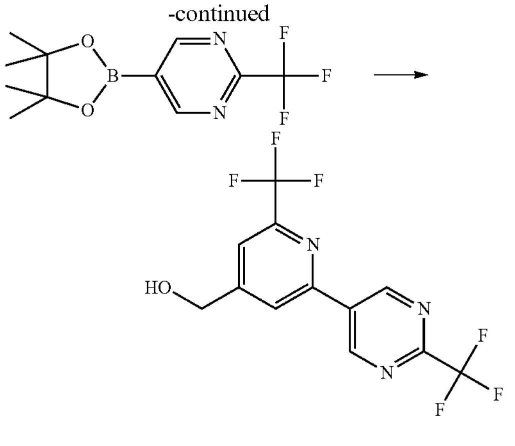

A mixture of [2-chloro-6-(trifluoromethyl)pyridin-4-yl]methanol (212 mg, 1.00 mmol, 1.00 equiv), 5-(tetramethyl-1,3,2-dioxaborolan-2-yl)-2-(trifluoromethyl)pyrimidine (274 mg, 1.00 mmol, 1.00 equiv), Pd(dppf)$Cl_2$ (14 mg, 0.02 mmol, 0.02 equiv), and potassium carbonate (414 mg, 3.00 mmol, 2.99 equiv) in dioxane (10 mL) was stirred for 12 h at 90° C. under nitrogen. The solid was filtered out. The resulting mixture was concentrated under vacuum, diluted with brine, extracted with ethyl acetate, dried over anhydrous sodium sulfate, and concentrated under vacuum. The residue was purified by a silica gel column eluting with ethyl acetate/petroleum ether (1/2) to afford the title compound (172 mg, 53%) as a white solid. LCMS [M+H$^+$] 324.

Step 3: Preparation of [2-(trifluoromethyl)-6-[2-(trifluoromethyl)pyrimidin-5-yl]pyridin-4-yl]methyl methanesulfonate

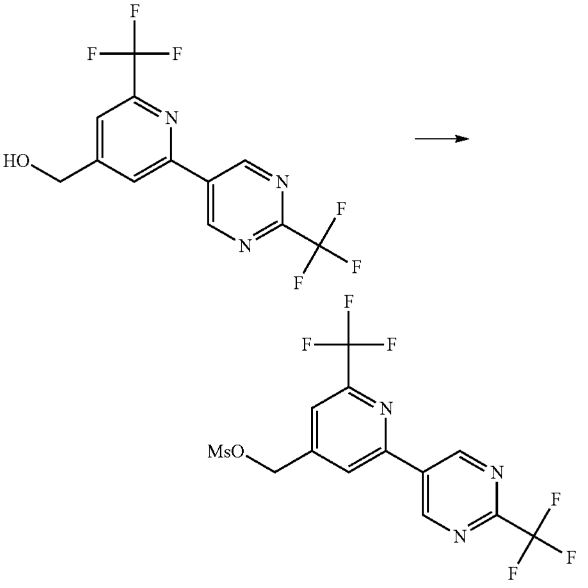

MsCl (67 mg, 0.59 mmol, 1.20 equiv) in dichloromethane (1 mL) was added dropwise into a solution of [2-(trifluoromethyl)-6-[2-(trifluoromethyl)pyrimidin-5-yl]pyridin-4-yl]methanol (157 mg, 0.49 mmol, 1.00 equiv) and TEA (147 mg, 1.45 mmol, 2.99 equiv) in dichloromethane (20 mL) at 0° C. under nitrogen. The resulting solution was stirred for 5 min at 0° C. The reaction was then quenched by saturated solution of $NH_4Cl$, extracted with ethyl acetate, washed with brine, dried over anhydrous sodium sulfate, and concentrated under vacuum. This resulted in the title compound (160 mg, 82%) as a white solid. LCMS [M+H$^+$] 402.

Step 4: Preparation of tert-butyl N-[(tert-butoxy)carbonyl]-N-[[2-(trifluoromethyl)-6-[2-(trifluoromethyl)pyrimidin-5-yl]pyridin-4-yl]methyl]carbamate

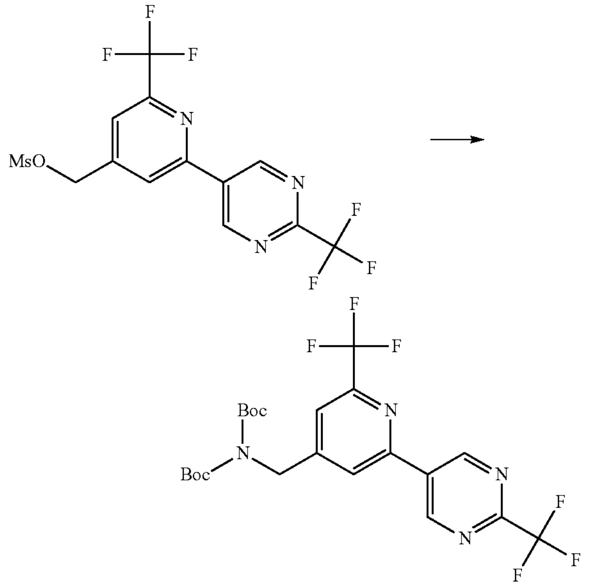

A mixture of [2-(trifluoromethyl)-6-[2-(trifluoromethyl)pyrimidin-5-yl]pyridin-4-yl]methyl methanesulfonate (140 mg, 0.35 mmol, 1.00 equiv), NaI (79 mg, 0.53 mmol, 1.51 equiv), N,N-dimethylformamide (3 mL), and potassium bis[(tert-butoxy)carbonyl]azanide (116 mg, 0.45 mmol, 1.30 equiv) was stirred for 12 h at room temperature. The resulting solution was diluted with brine, extracted with of ethyl acetate, washed with brine, dried over anhydrous sodium sulfate, and concentrated under vacuum. The residue was purified by a silica gel column eluting with ethyl acetate/petroleum ether (1/10) to afford the title compound (200 mg, crude) as colorless oil. LCMS [M+H$^+$] 523.

Step 5: Preparation of [2-(trifluoromethyl)-6-[2-(trifluoromethyl)pyrimidin-5-yl]pyridin-4-yl]methanamine hydrochloride

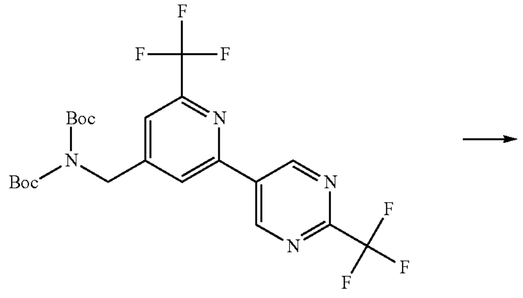

-continued

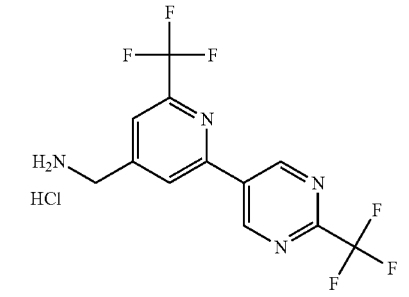

A mixture of tert-butyl N-[(tert-butoxy)carbonyl]-N-[[2-(trifluoromethyl)-6-[2-(trifluoromethyl)pyrimidin-5-yl]pyridin-4-yl]methyl]carbamate (200 mg, 0.38 mmol, 1.00 equiv) and 4 N of HCl in dioxane (15 mL) was stirred for 4 h at room temperature. The resulting mixture was concentrated under vacuum to afford the title compound (120 mg, 97%) as a white solid. LCMS [M+H$^+$] 323.

Preparation 30: [2-cyclopropyl-6-[2-(trifluoromethyl)pyrimidin-5-yl]pyrimidin-4-yl]methanamine

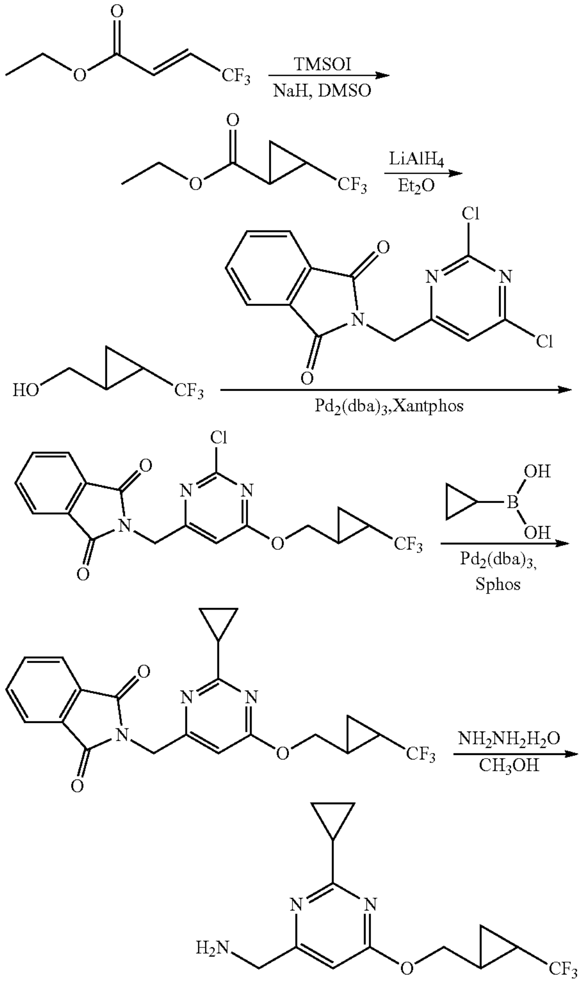

Step 1: Preparation of ethyl 2-(trifluoromethyl)cyclopropanecarboxylate

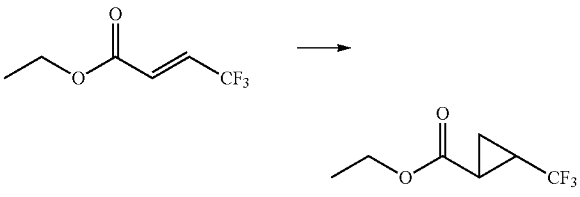

Sodium hydride (3.6 g, 90.00 mmol, 1.51 equiv, 60%) was washed with hexane (150 mL) and the solvent was removed via springe under $N_2$. To the NaH was added DMSO (100 mL) followed by trimethylsilyl hypoiodite (20 g, 92.55 mmol, 1.55 equiv). After being stirred for 2 h at room temperature ethyl (2E)-4,4,4-trifluorobut-2-enoate (10 g, 59.48 mmol, 1.00 equiv) was added to the solution. The resulting solution was stirred for 60 h at room temperature, quenched by water, extracted with ethyl ether, washed with brine, dried over anhydrous sodium sulfate, and concentrated under vacuum. This resulted in 4 g (37%) of the title compound as yellow oil. GCMS [m/z] 197.

Step 2: Preparation of (2-(trifluoromethyl)cyclopropyl)methanol

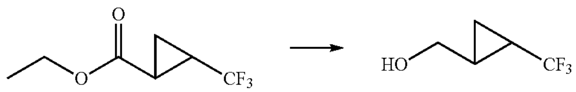

$LiAlH_4$ (1.67 g, 44.00 mmol, 2.00 equiv) was added in portions into a solution of ethyl 2-(trifluoromethyl)cyclopropane-1-carboxylate (4.00 g, 21.96 mmol, 1.00 equiv) in diethyl ether (100 mL) at 0° C. After being stirred for 4 h at room temperature the reaction was quenched by water. The solid was filtered out. The solution was dried over anhydrous sodium sulfate and concentrated under vacuum. This resulted in the title compound (2.4 g, 78%) as yellow oil. GCMS [m/z] 140.

Step 3: Preparation of 2-((2-chloro-6-((2-(trifluoromethyl)cyclopropyl)methoxy)pyrimidin-4-yl)methyl)isoindoline-1,3-dione

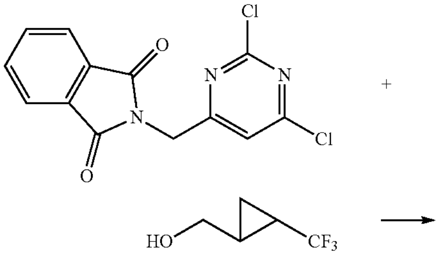

-continued

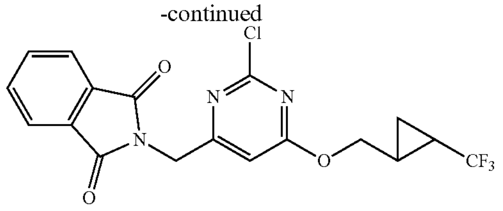

A mixture of 2-[(2,6-dichloropyrimidin-4-yl)methyl]-2,3-dihydro-1H-isoindole-1,3-dione (1.00 g, 3.24 mmol, 1.00 equiv), [2-(trifluoromethyl)cyclopropyl]methanol (1.00 g, 3.56 mmol, 1.00 equiv, 50%), $Pd_2(dba)_3.CHCl_3$ (342.66 mg, 0.33 mmol, 0.10 equiv), XantPhos (563.37 mg, 0.97 mmol, 0.30 equiv), and $Cs_2CO_3$ (3.17 g, 9.72 mmol, 2.99 equiv) in toluene (15 mL) was stirred for 4 h at 45° C. under $N_2$. The resulting mixture was concentrated under vacuum. The residue was purified by a silica gel column eluting with petroleum ether (1/5) to afford the title compound (500 mg, 37%) as a white solid. LCMS [M+H+] 412.

Step 4: Preparation of 2-((2-cyclopropyl-6-((2-(trifluoromethyl)cyclopropyl)methoxy)pyrimidin-4-yl)methyl)isoindoline-1,3-dione

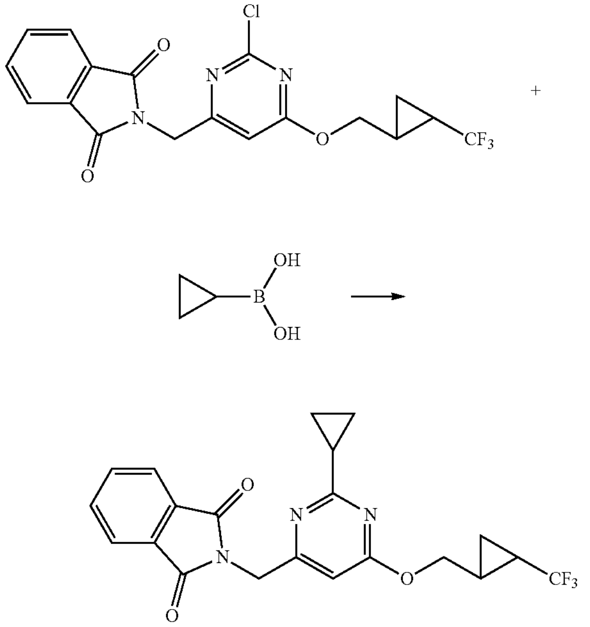 [SMILES: O=C1c2ccccc2C(=O)N1Cc1cc(OCC2CC2C(F)(F)F)nc(Cl)n1 ; "+" ; OB(O)C1CC1 ; O=C1c2ccccc2C(=O)N1Cc1cc(OCC2CC2C(F)(F)F)nc(C2CC2)n1]

A mixture of 2-[(2-chloro-6-[[2-(trifluoromethyl)cyclopropyl]methoxy]pyrimidin-4-yl)methyl]-2,3-dihydro-1H-isoindole-1,3-dione (500.00 mg, 1.20 mmol, 1.00 equiv), cyclopropylboronic acid (1.04 g, 12.00 mmol, 10.00 equiv), $Pd_2(dba)_3$ (222 mg, 0.24 mmol, 0.20 equiv), Sphos (249 mg, 0.60 mmol, 0.50 equiv), and $K_3PO_4$ (515 mg, 2.40 mmol, 2.00 equiv) in toluene (50 mL)/water (5 mL) was stirred for 4 h at 100° C. under $N_2$. The solid was filtered out and the solution was concentrated under vacuum. The residue was purified by a silica gel column eluting with petroleum ether (1/5) to afford the title compound (400 mg, 79%) as a white solid. LCMS [M+H+] 418.

Step 4: Preparation of (2-cyclopropyl-6-((2-(trifluoromethyl)cyclopropyl)methoxy)pyrimidin-4-yl) methanamine

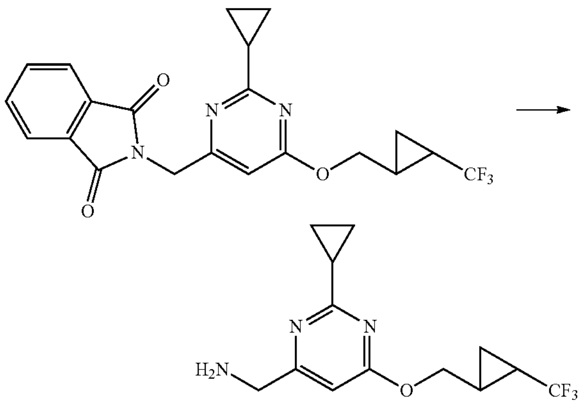

A mixture of 2-[(2-cyclopropyl-6-[[2-(trifluoromethyl) cyclopropyl]methoxy]pyrimidin-4-yl)methyl]-2,3-dihydro-1H-isoindole-1,3-dione (400 mg, 0.95 mmol, 1.00 equiv) and hydrazine (1.2 g, 19.00 mmol, 20.00 equiv, 80%) in methanol (50 mL) was stirred for 2 h at room temperature. The resulting mixture was concentrated under vacuum and dissolved in ethyl acetate. The precipitated solid was filtered off. The filtrate was concentrated under vacuum to afford the title compound (250 mg, 91%) as yellow oil. LCMS [M+H$^+$] 288.

Preparation 31: 2-((6-cyclopropyl-4-(2-(trifluoromethyl)pyrimidin-5-yl)pyridin-2-yl)methyl)isoindoline-1,3-dione

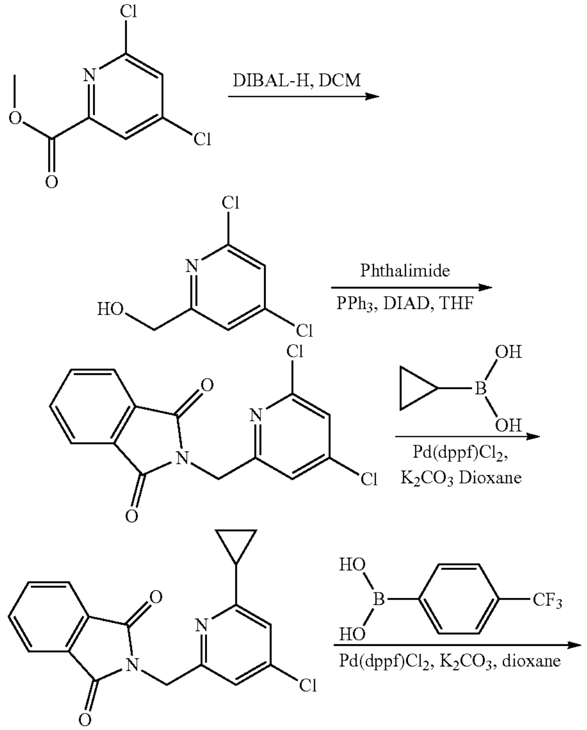

-continued

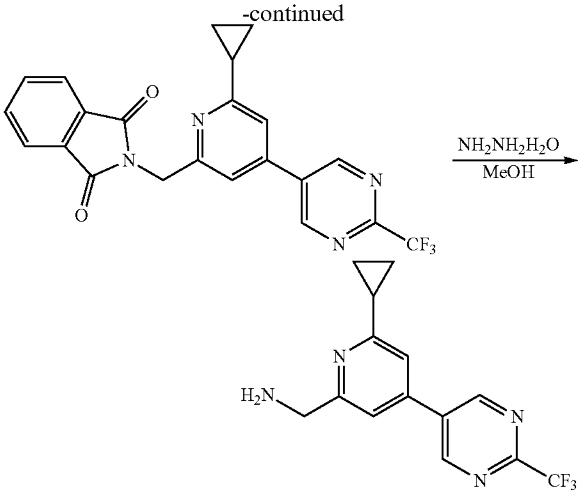

Step 1: Preparation of 4,6-dichloropyridin-2-yl)methanol

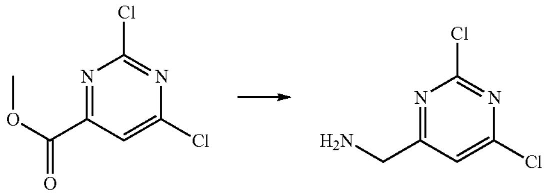

DIBAL-H (73 mL, 1M in hexane, 3.00 equiv) was added dropwise into a solution of methyl 4,6-dichloropyridine-2-carboxylate (5 g, 24.26 mmol, 1.00 equiv) in dichloromethane (100 mL) at −78° C. under $N_2$. The resulting solution was stirred for overnight at room temperature. The reaction was quenched by methanol and concentrated under vacuum. The residue was purified by a silica gel column eluting with ethyl acetate/petroleum ether (1/20) to afford the title compound (9.5 g, 84%) as a light yellow solid. LCMS [M+H$^+$] 178.

Step 2: Preparation of 2-((4,6-dichloropyridin-2-yl) methyl)isoindoline-1,3-dione

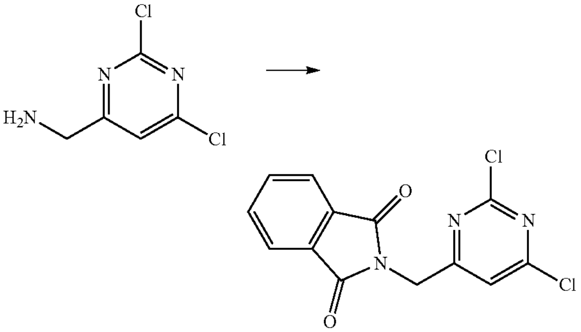

DIAD (6.87 g, 33.97 mmol, 2.00 equiv) was added dropwise into a solution of 2,3-dihydro-1H-isoindole-1,3- dione (2.50 g, 16.99 mmol, 1.00 equiv), (4,6-dichloropyridin-2-yl)methanol (4.54 g, 25.50 mmol, 1.50 equiv), and $PPh_3$ (8.91 g, 33.97 mmol, 2.00 equiv) in dry tetrahydrofuran (50 mL) under $N_2$. The resulting solution was stirred for 2 h at 0° C., concentrated under vacuum, and dissolved in ethyl acetate. The solid was collected by filtration and the filtrate was concentrated under vacuum. This resulted in the title compound (2.8 g, 54%) as a white solid. LCMS [M+H$^+$] 307.

Step 3: Preparation of 2-((4-chloro-6-cyclopropylpyridin-2-yl)methyl)isoindoline-1,3-dione

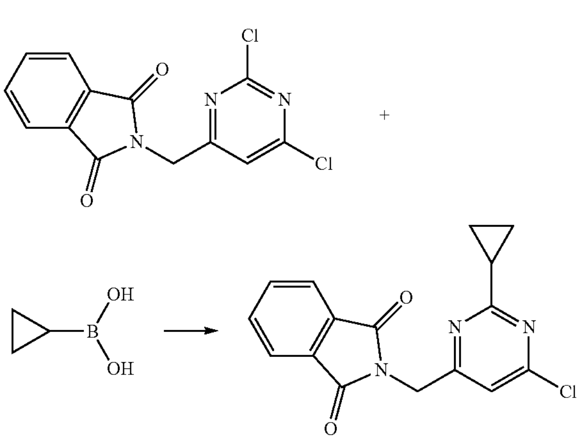

A mixture of 2-[(4,6-dichloropyridin-2-yl)methyl]-2,3-dihydro-1H-isoindole-1,3-dione (1 g, 3.25 mmol, 1.000 equiv), cyclopropylboronic acid (2.8 g, 32.59 mmol, 10.00 equiv), $Pd(dppf)Cl_2.CH_2Cl_2$ (270 mg, 0.33 mmol, 0.10 equiv), and potassium carbonate (1.4 g, 10.13 mmol, 3.11 equiv) in dioxane (50 mL) was stirred for 12 h at 70° C. under $N_2$. The solid was filtered out and the filtrate was concentrated under vacuum. The residue was purified by a silica gel column eluting with ethyl acetate/petroleum ether (1/5) to afford the title compound (700 mg, 69%) as a white solid. LCMS [M+H$^+$] 313.

Step 4: Preparation of 2-((6-cyclopropyl-4-(2-(trifluoromethyl)pyrimidin-5-yl)pyridin-2-yl)methyl) isoindoline-1,3-dione

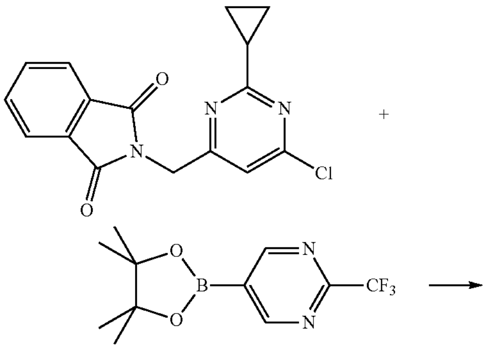

-continued

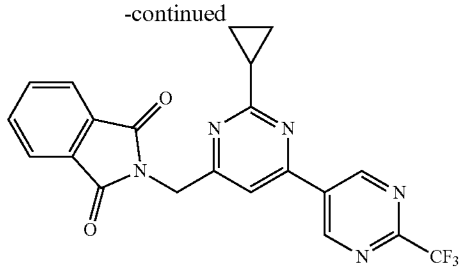

A mixture of 2-[(4-chloro-6-cyclopropylpyridin-2-yl)methyl]-2,3-dihydro-1H-isoindole-1,3-dione (700 mg, 2.23 mmol, 1.00 equiv), 5-(tetramethyl-1,3,2-dioxaborolan-2-yl)-2-(trifluoromethyl)pyrimidine (615 mg, 2.24 mmol, 1.00 equiv), $Pd(dppf)Cl_2$ (183 mg, 0.25 mmol, 0.11 equiv), and potassium carbonate (930 mg, 6.72 mmol, 3.00 equiv) in dioxane (30 mL) was stirred for 12 h at 100° C. under $N_2$. The solid was filtered out and the filtrate was concentrated under vacuum. The residue was purified by a silica gel column eluting with ethyl acetate/petroleum ether (1/4) to afford the title compound (600 mg, 63%) as a white solid. LCMS [M+H$^+$] 425.

Step 5: Preparation of 2-((6-cyclopropyl-4-(2-(trifluoromethyl)pyrimidin-5-yl)pyridin-2-yl)methyl) isoindoline-1,3-dione

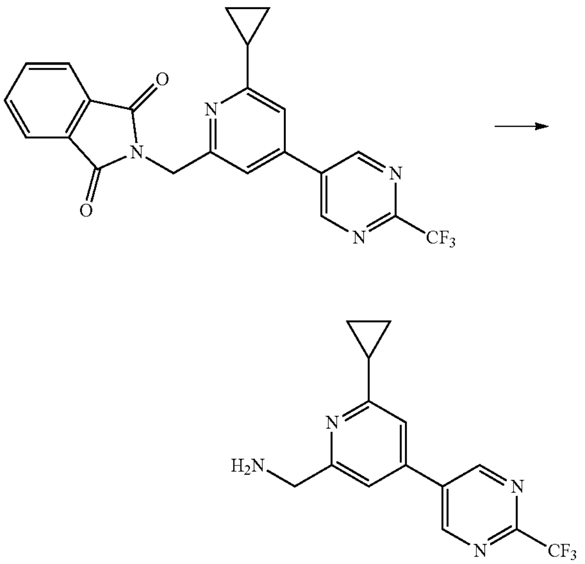

A solution of 2-([6-cyclopropyl-4-[2-(trifluoromethyl)pyrimidin-5-yl]pyridin-2-yl]methyl)-2,3-dihydro-1H-isoindole-1,3-dione (600 mg, 1.41 mmol, 1.00 equiv) and hydrazine hydrate (881 mg, 80%) in methanol (50 mL) was stirred for 2 h at 50° C. The resulting mixture was concentrated under vacuum and dissolved in ethyl acetate. The precipitated solid was filtered off. The filtrate was concentrated under vacuum to afford the title compound (400 mg, 96%) as yellow oil. [M+H$^+$] 295.

Preparation 32: (2S,3R,55)-tert-butyl 5-(((5'-cyano-5-fluoro-6'-(trifluoromethyl)-[2,3'-bipyridin]-4-yl)methyl)carbamoyl)-3-fluoro-2-methylpyrrolidine-1-carboxylate

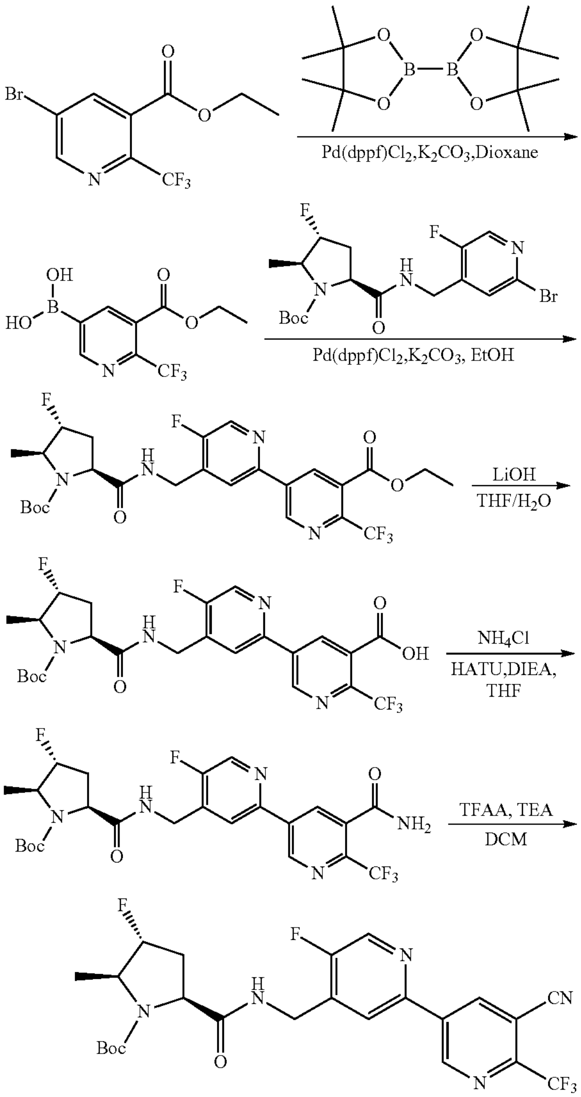

Step 1: Preparation of 5-(ethoxycarbonyl)-6-(trifluoromethyl)pyridin-3-ylboronic Acid

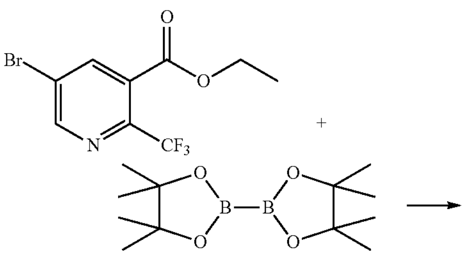

-continued

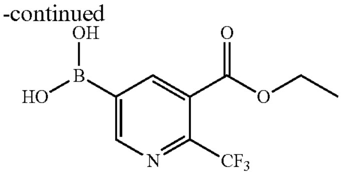

A mixture of ethyl 5-bromo-2-(trifluoromethyl)pyridine-3-carboxylate (300 mg, 1.00 mmol, 1.00 equiv), 4,4,5,5-tetramethyl-2-(tetramethyl-1,3,2-dioxaborolan-2-yl)-1,3,2-dioxaborolane (500 mg, 1.97 mmol, 1.95 equiv), Pd(dppf)$Cl_2$ dichloromethane (100 mg, 0.12 mmol, 0.12 equiv), and KOAc (300 mg, 3.06 mmol, 3.03 equiv) in dioxane (15 mL) was stirred for 2 h at 80° C. under $N_2$. The resulting solution was diluted with ethyl acetate, washed with brine, dried over anhydrous sodium sulfate, and concentrated under vacuum. This resulted in the title compound 400 mg (crude) as a black solid. LCMS [M+H$^+$] 264.

Step 2: Preparation of ethyl 4-(((2S,4R,5S)-1-(tert-butoxycarbonyl)-4-fluoro-5-methylpyrrolidine-2-carboxamido)methyl)-5-fluoro-6'-(trifluoromethyl)-2,3'-bipyridine-5'-carboxylate

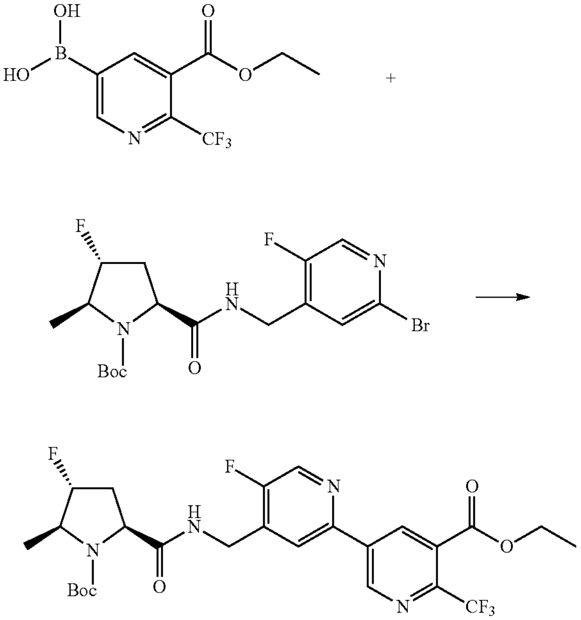

A mixture of tert-butyl (2S,3R,5S)-5-[[(2-bromo-5-fluoropyridin-4-yl)methyl]carbamoyl]-3-fluoro-2-methylpyrrolidine-1-carboxylate (120 mg, 0.27 mmol, 1.00 equiv), [5-(ethoxycarbonyl)-6-(trifluoromethyl)pyridin-3-yl]boronic acid (200 mg, 0.76 mmol, 2.75 equiv), Pd(dppf)$Cl_2$ (30 mg, 0.04 mmol, 0.15 equiv), and potassium carbonate (150 mg, 1.09 mmol, 3.92 equiv) in ethanol (15 mL)/water (3 ml) was irradiated with microwave radiation for 2 h at 100° C. under $N_2$. The resulting mixture was concentrated under vacuum. The residue was purified by a silica gel column eluting with ethyl acetate/petroleum ether (1/1) to afford the title compound (120 mg, 76%) as a white solid. LCMS [M+H$^+$] 573.

Step 3: Preparation of 4-(((2S,4R,5S)-1-(tert-butoxycarbonyl)-4-fluoro-5-methylpyrrolidine-2-carboxamido)methyl)-5-fluoro-6'-(trifluoromethyl)-2,3'-bipyridine-5'-carboxylic Acid

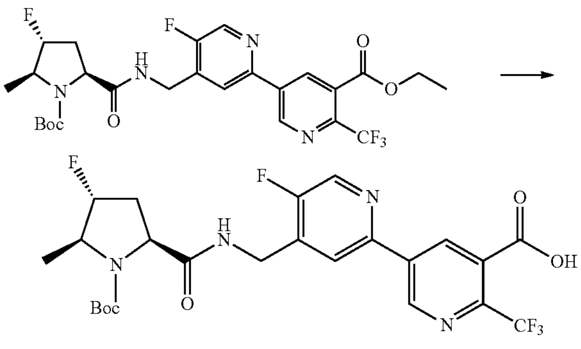

A mixture of ethyl 5-[4-([[(2S,4R,5S)-1-[(tert-butoxy)carbonyl]-4-fluoro-5-methylpyrrolidin-2-yl]formamido]methyl)-5-fluoropyridin-2-yl]-2-(trifluoromethyl)pyridine-3-carboxylate (120 mg, 0.21 mmol, 1.00 equiv) and LiOH (20 mg, 0.83 mmol, 4.00 equiv) in THF (10 mL)/water (2 mL) was stirred for 12 h at 40° C. The pH value of the solution was adjusted to 3-5 with hydrogen chloride (4 mol/L). The resulting mixture was extracted with ethyl acetate, dried over anhydrous sodium sulfate, and concentrated under vacuum. This resulted in the title compound (100 mg, 88%) as a white solid. LCMS [M+H$^+$] 545.

Step 4: Preparation of (2S,3R,5S)-tert-butyl 5-((5'-carbamoyl-5-fluoro-6'-(trifluoromethyl)-2,3'-bipyridin-4-yl)methylcarbamoyl)-3-fluoro-2-methylpyrrolidine-1-carboxylate

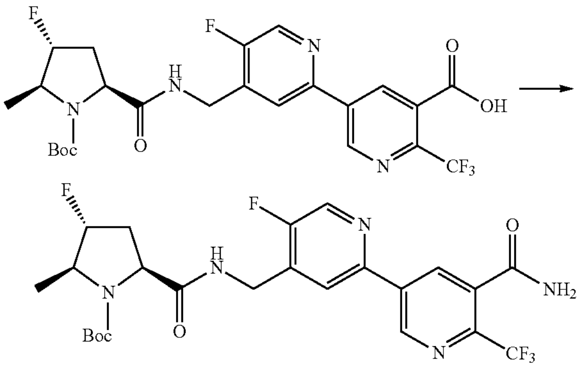

A mixture of 5-[4-([[(2S,4R,5S)-1-[(tert-butoxy)carbonyl]-4-fluoro-5-methylpyrrolidin-2-yl]formamido]methyl)-5-fluoropyridin-2-yl]-2-(trifluoromethyl)pyridine-3-carboxylic acid (100 mg, 0.18 mmol, 1.00 equiv), $NH_4Cl$ (130 mg, 2.43 mmol, 13.23 equiv), HATU (114 mg, 0.30 mmol, 1.60 equiv), and DIEA (260 mg, 2.00 mmol, 11.00 equiv) in DMF (10 mL) was stirred for 2 h at room temperature. The resulting mixture was concentrated under vacuum. The residue was purified by a silica gel column eluting with ethyl acetate/petroleum ether (1/1) to afford the title compound (90 mg, 90%) as a white solid. LCMS [M+H$^+$] 544.

Step 5: Preparation of (2S,3R,5S)-tert-butyl 5-((5'-cyano-5-fluoro-6'-(trifluoromethyl)-2,3'-bipyridin-4-yl)methylcarbamoyl)-3-fluoro-2-methylpyrrolidine-1-carboxylate

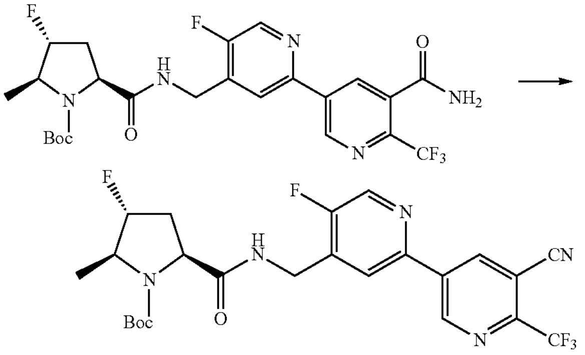

TFAA (51 mg, 0.24 mmol, 2.00 equiv) was added dropwise into a solution of tert-butyl (2S,3R,5S)-5-[([2-[5-carbamoyl-6-(trifluoromethyl)pyridin-3-yl]-5-fluoropyridin-4-yl]methyl)carbamoyl]-3-fluoro-2-methylpyrrolidine-1-carboxylate (66 mg, 0.12 mmol, 1.00 equiv), triethylamine (13 mg, 0.13 mmol, 1.06 equiv) in dichloromethane (10 mL) at 0° C. under nitrogen. After being stirred for 30 min at room temperature the reaction was quenched by water, extracted with dichloromethane, washed with brine, dried over anhydrous sodium sulfate, and concentrated under vacuum. This resulted in the title compound (80 mg, crude) as a white solid. LCMS [M+H$^+$] 526.

Preparation 33: (2-cyclopropyl-5-(2-(trifluoromethyl)pyrimidin-5-yl)pyridin-3-yl)methanamine hydrochloride

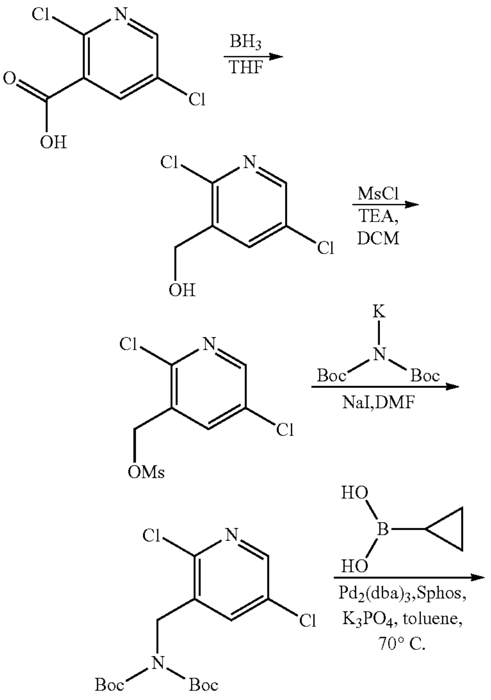

-continued

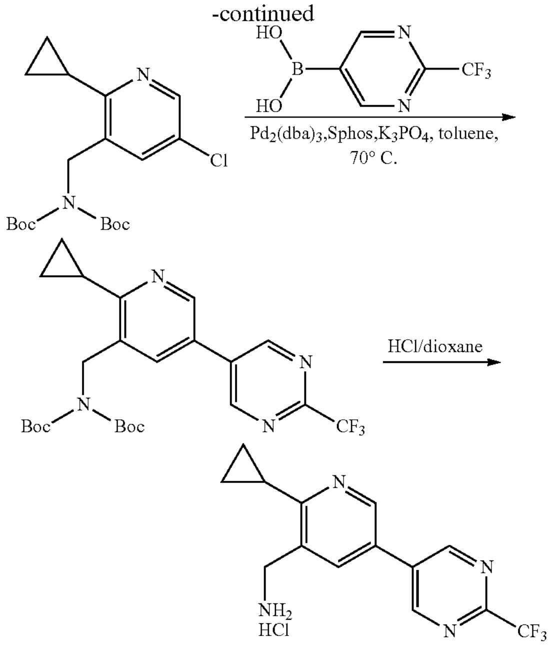

Step 1: Preparation of (2,5-dichloropyridin-3-yl)methanol

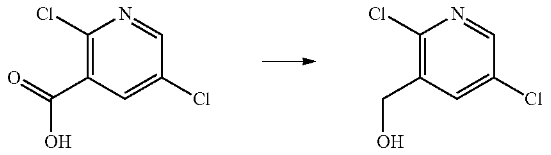 [SMILES: O=C(O)c1cc(Cl)cnc1Cl ; OCc1cc(Cl)cnc1Cl]

$BH_3$.THF (100 mL, 96 mmol, 3.00 equiv) was added dropwise into a solution of 2,5-dichloropyridine-3-carboxylic acid (6.2 g, 32.29 mmol, 1.00 equiv) in THF (150 mL) at 0° C. under $N_2$. After being stirred for 4 h at 0° C. the reaction was quenched by water, extracted with ethyl acetate, dried over anhydrous sodium sulfate, and concentrated under vacuum. This resulted in the title compound (3.5 g, 64%) as a white solid which was used for the next step without further purification. LCMS [M+H$^+$] 178.

Step 2: Preparation of (2,5-dichloropyridin-3-yl)methyl methanesulfonate

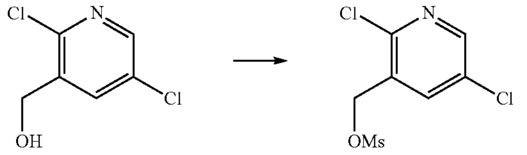 [SMILES: OCc1cc(Cl)cnc1Cl ; CS(=O)(=O)OCc1cc(Cl)cnc1Cl]

Methanesulfonyl chloride (2.4 g, 20.95 mmol, 1.24 equiv) was added dropwise into a solution of (2,5-dichloropyridin-3-yl)methanol (3 g, 16.85 mmol, 1.00 equiv) and TEA (5.2 g, 51.38 mmol, 3.04 equiv) in dichloromethane (50 mL) at 0° C. After being stirred for 30 min at 0° C. the resulting mixture was quenched with water, extracted with dichloromethane, washed with brine, dried over anhydrous sodium sulfate, and concentrated under vacuum. This resulted in the title compound (3.5 g, 64%) as a white solid which was used for the next step without further purification. LCMS [M+H$^+$] 256.

Step 3: Preparation of tert-butyl N-[(tert-butoxy)carbonyl]-N-[(2,5-dichloropyridin-3-yl)methyl]carbamate

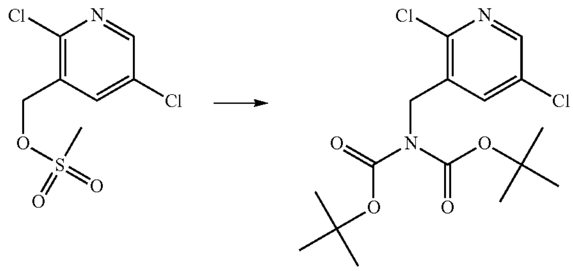 [SMILES: CS(=O)(=O)OCc1cc(Cl)cnc1Cl ; CC(C)(C)OC(=O)N(Cc1cc(Cl)cnc1Cl)C(=O)OC(C)(C)C]

A mixture of (2,5-dichloropyridin-3-yl)methyl methanesulfonate (3.4 g, 13.27 mmol, 1.00 equiv), NaI (2 g, 13.34 mmol, 1.00 equiv), and tert-butyl N-[(tert-butoxy)carbonyl]-N-potassiocarbamate (6.8 g, 26.63 mmol, 2.00 equiv) in N,N-dimethylformamide (100 mL) was stirred for 1.5 h at room temperature. The resulting solution was diluted with ethyl acetate, washed with brine, dried over anhydrous sodium sulfate, and concentrated under vacuum. The residue was purified by a silica gel column eluting with ethyl acetate/petroleum ether (1/5) to afford the title compound (4 g, 80%) as a white solid. LCMS [M+H$^+$] 377.

Step 4: Preparation of tert-butyl N-[(tert-butoxy)carbonyl]-N-[(5-chloro-2-cyclopropylpyridin-3-yl)methyl]carbamate

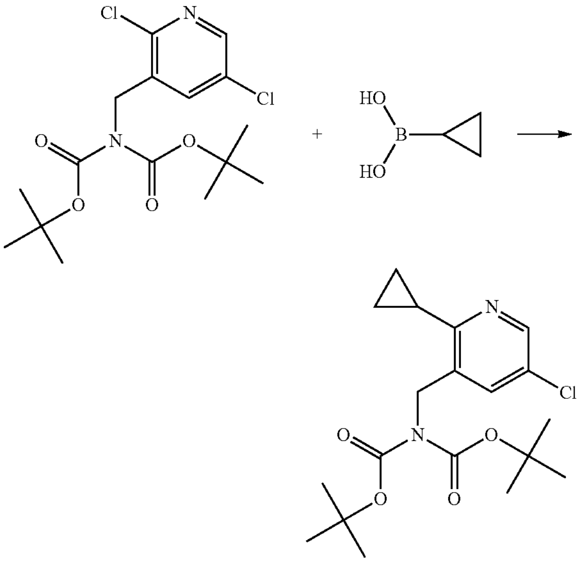

A mixture of tert-butyl N-[(tert-butoxy)carbonyl]-N-[(2,5-dichloropyridin-3-yl)methyl]carbamate (2 g, 5.30 mmol, 1.00 equiv), Pd$_2$(dba)$_3$ (550 mg, 0.60 mmol, 0.11 equiv), SPhos (436 mg, 1.06 mmol, 0.20 equiv), $K_3PO_4$ (3.4 g, 16.01 mmol, 3.02 equiv), and cyclopropylboronic acid (1.4 g, 16.29 mmol, 3.07 equiv) in water (2 mL)/toluene (20 mL) was stirred for 4 h at 70° C. under $N_2$. The reaction mixture was concentrated under vacuum. The residue was purified by a silica gel column eluting with ethyl acetate/petroleum ether (1/3) to afford the title compound (1.2 g, 59%) as a white solid. LCMS [M+H$^+$] 383.

Step 5: Preparation of tert-butyl N-[(tert-butoxy) carbonyl]-N-([2-cyclopropyl-5-[2-(trifluoromethyl) pyrimidin-5-yl]pyridin-3-yl]methyl)carbamate

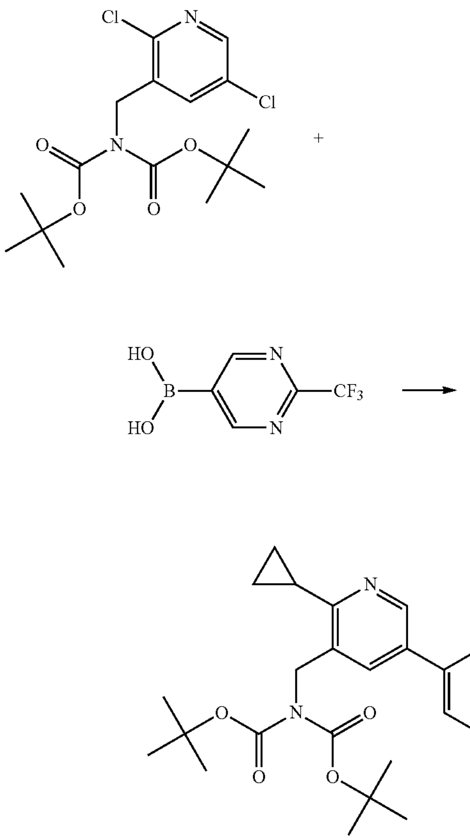

A mixture of tert-butyl N-[(tert-butoxy)carbonyl]-N-[(5-chloro-2-cyclopropylpyridin-3-yl)methyl]carbamate (600 mg, 1.56 mmol, 1.00 equiv), [2-(trifluoromethyl)pyrimidin-5-yl]boronic acid (515 mg, 2.68 mmol, 1.71 equiv), $Pd_2(dba)_3.CHCl_3$ (163 mg, 0.15 mmol, 0.10 equiv), SPhos (129 mg, 0.31 mmol, 0.20 equiv), and $K_3PO_4$ (1 g, 4.71 mmol, 3.00 equiv) in toluene (15 mL) was stirred for overnight at 100° C. under $N_2$. The solid was filtered out and the filtrate was concentrated under vacuum. The residue was purified by a silica gel column eluting with ethyl acetate/petroleum ether (1/4) to afford the title compound (250 mg, 32%) as yellow oil. LCMS [M+H$^+$] 495.

Step 6: Preparation of (2-cyclopropyl-5-(2-(trifluoromethyl)pyrimidin-5-yl)pyridin-3-yl)methanamine hydrochloride

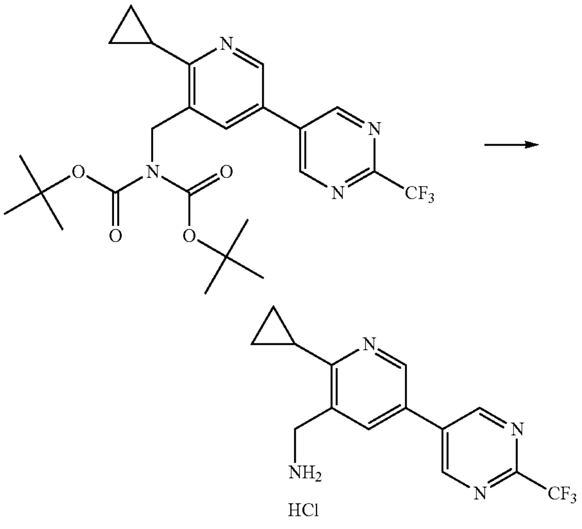

A mixture of tert-butyl N-[(tert-butoxy)carbonyl]-N-([2-cyclopropyl-5-[2-(trifluoromethyl)pyrimidin-5-yl]pyridin-3-yl]methyl)carbamate (240 mg, 0.48 mmol, 1.00 equiv) and 4 N of hydrogen chloride in 1,4-dioxane (10 mL) was stirred for 1 h at room temperature. The reaction mixture was concentrated under vacuum to afford the title compound (120 mg, 75%) as a white solid. LCMS [M+H$^+$] 295.

Preparation 34: [5-(difluoromethyl)-4-[2-(trifluoromethyl)pyrimidin-5-yl]pyridin-2-yl]methanamine

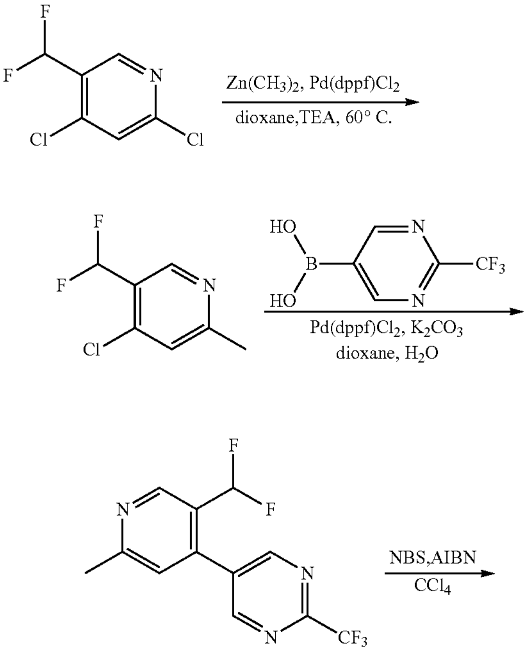

-continued

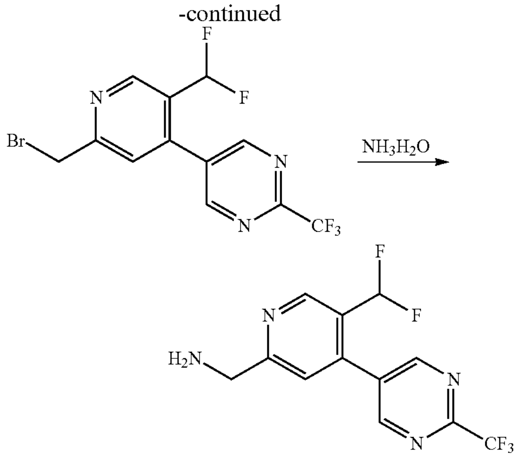

Step 1: Preparation of 4-chloro-5-(difluoromethyl)-2-methylpyridine

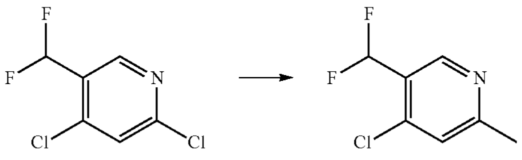

A mixture of 2,4-dichloro-5-(difluoromethyl)pyridine (2 g, 10.10 mmol, 1.00 equiv), $Pd(dppf)Cl_2$ (700 mg, 0.95 mmol, 0.09 equiv), and $Zn(CH_3)_2$ (19 ml, 1M in toluene, 1.97 equiv) in dioxane (20 mL) was stirred for 12 h at 60° C. under nitrogen. The solid was filtered off and the filtrate was diluted with water, extracted with ethyl acetate, washed with brine, dried over anhydrous sodium sulfate, and concentrated under vacuum. The residue was purified by a silica gel column eluting with petroleum ether/ethyl acetate (20/1) to afford the title compound (600 mg, 33%) as a yellow solid. LCMS [M+H$^+$] 178.

Step 2: Preparation of 5-[5-(difluoromethyl)-2-methylpyridin-4-yl]-2-(trifluoromethyl)pyrimidine

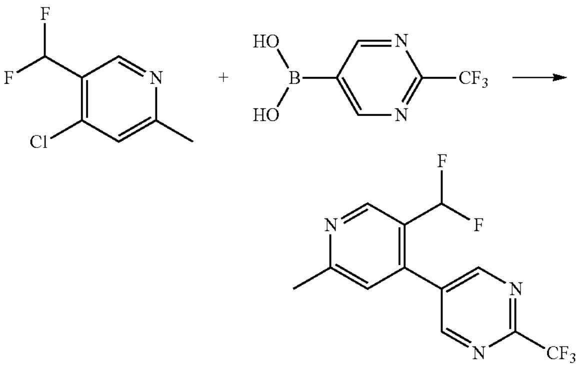

A mixture of 4-chloro-5-(difluoromethyl)-2-methylpyridine (600 mg, 3.37 mmol, 1.00 equiv), [2-(trifluoromethyl)pyrimidin-5-yl]boronic acid (716 mg, 3.73 mmol, 1.10 equiv), $Pd(dppf)Cl_2$ (248 mg, 0.33 mmol, 0.10 equiv), potassium carbonate (1.4 g, 10.13 mmol, 2.99 equiv), and dioxane (20 mL) was stirred for 12 h at 80° C. under nitrogen. The solid was filtered off and the filtrate was diluted with water, extracted with ethyl acetate, washed with brine, dried over anhydrous sodium sulfate, and concentrated under vacuum. The residue was purified by a silica gel column eluting with petroleum ether/ethyl acetate (10/1) to afford the title compound (610 mg, 62%) as a brown solid. LCMS [M+H$^+$] 290.

Step 3: Preparation of 5-[2-(bromomethyl)-5-(difluoromethyl)pyridin-4-yl]-2-(trifluoromethyl)pyrimidine

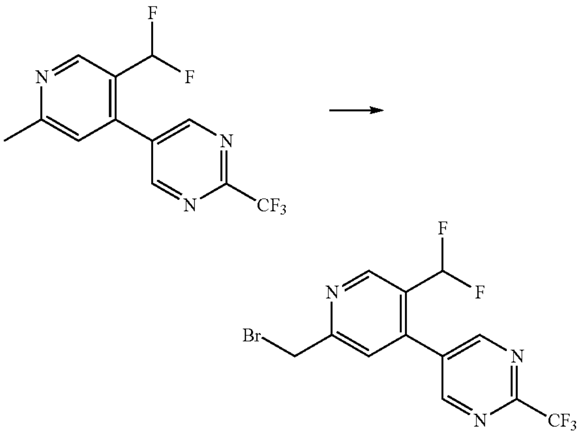

A mixture of 5-[5-(difluoromethyl)-2-methylpyridin-4-yl]-2-(trifluoromethyl)pyrimidine (500 mg, 1.72 mmol, 1.00 equiv), NBS (616 mg, 3.46 mmol, 2.00 equiv), and AIBN (85 mg, 0.51 mmol, 0.29 equiv) in dioxane (10 mL) was stirred for 12 h at 75° C. under nitrogen. The resulting solution was diluted with ethyl acetate, washed with water, dried over anhydrous sodium sulfate, and concentrated under vacuum. This resulted in the title compound (600 mg) as a white solid. LCMS [M+H$^+$] 368.

Step 4: Preparation of [5-(difluoromethyl)-4-[2-(trifluoromethyl)pyrimidin-5-yl]pyridin-2-yl]methanamine

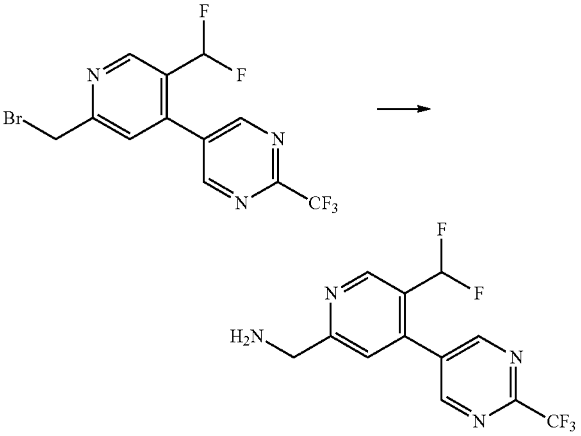

A solution of 5-[2-(bromomethyl)-5-(difluoromethyl) pyridin-4-yl]-2-(trifluoromethyl)pyrimidine (600 mg, 1.63 mmol, 1.00 equiv) in dioxane (5 mL)/ammonia (25%, 5 mL) was stirred for 1 h at room temperature. The resulting solution was diluted with brine, extracted with dichloromethane, washed with brine, dried over anhydrous sodium sulfate, and concentrated under vacuum. The residue was purified by a silica gel column eluting with dichloromethane/methanol (20/1) to afford the title compound (150 mg, 30%) as a colorless solid. LCMS [M+H$^+$] 305.

Preparation 35

(2-(trifluoromethyl)-5-(2-(trifluoromethyl)pyrimidin-5-yl)phenyl)methanamine

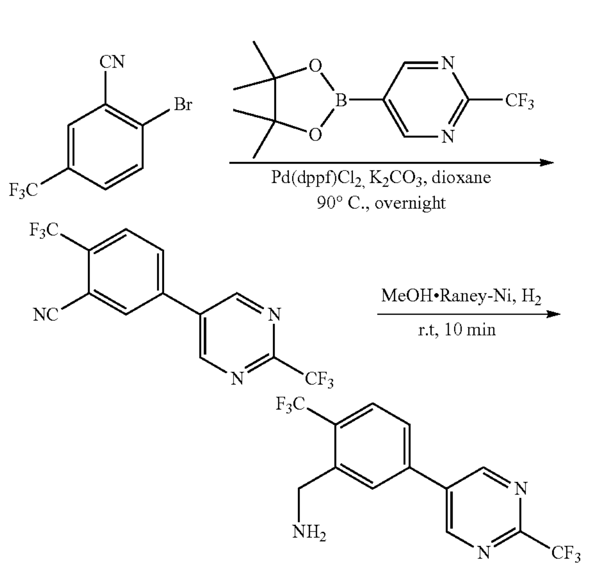

Step 1: Preparation of 2-(trifluoromethyl)-5-(2-(trifluoromethyl)pyrimidin-5-yl)benzonitrile

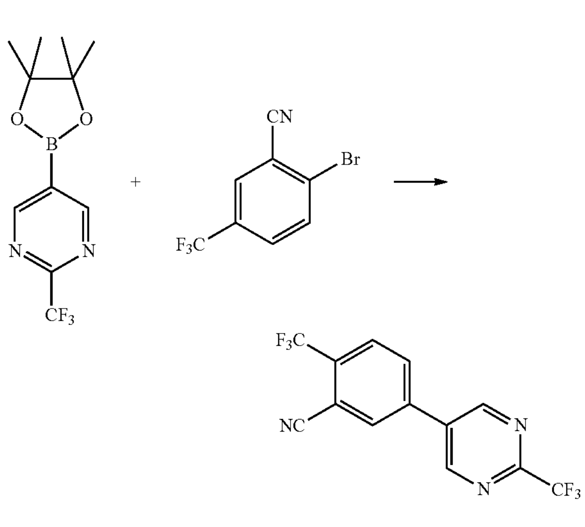

A mixture of 2-bromo-5-(trifluoromethyl)benzonitrile (476 mg, 1.90 mmol, 1.00 equiv), 5-(tetramethyl-1,3,2- dioxaborolan-2-yl)-2-(trifluoromethyl)pyrimidine (524 mg, 1.91 mmol, 1.00 equiv), potassium carbonate (528 mg, 3.82 mmol, 1.00 equiv), and Pd(dppf)$Cl_2$ (140 mg, 0.19 mmol, 1.00 equiv) in dioxane (10 mL) was stirred overnight at 90° C. under nitrogen. The resulting mixture was diluted with ethyl acetate, washed with water, dried over anhydrous sodium sulfate, and concentrated under vacuum. The residue was purified by a silica gel column eluting with ethyl acetate/petroleum ether (1/5) to afford the title compound (500 mg, 83%) as a light yellow solid. LCMS [M+H$^+$] 318.

Step 2: Preparation of (2-(trifluoromethyl)-5-(2-(trifluoromethyl)pyrimidin-5-yl)phenyl)methanamine

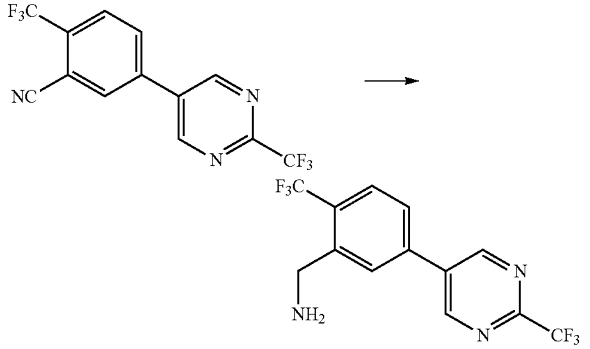

A mixture of 2-(trifluoromethyl)-5-[2-(trifluoromethyl) pyrimidin-5-yl]benzonitrile (470 mg, 1.48 mmol, 1.00 equiv), Raney-Ni (100 mg), $NH_3$ in methanol (5%, 13 mL) was stirred for 10 min at room temperature under hydrogen. The solid was filtered out and the filtrate was concentrated under vacuum. This resulted in the title compound (310 mg, 65%) as a light yellow solid. LCMS [M+H$^+$] 322.

Preparation 36: (2-bromo-5-fluoropyridin-4-yl)methanamine

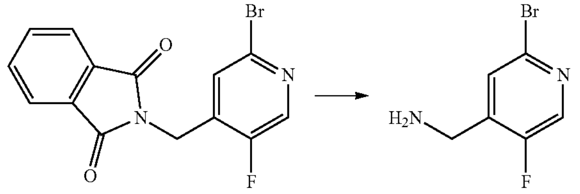 [SMILES: O=C1c2ccccc2C(=O)N1Cc1cc(Br)ncc1F ; NCc1cc(Br)ncc1F]

Step 1: Preparation of 2,4-dichloro-6-(chloromethyl)pyrimidine

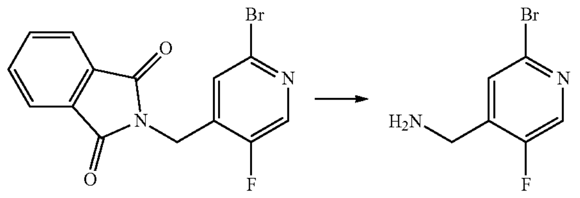 [SMILES: O=C1c2ccccc2C(=O)N1Cc1cc(Br)ncc1F ; NCc1cc(Br)ncc1F]

A mixture of 2-[(2-bromo-5-fluoropyridin-4-yl)methyl]-2,3-dihydro-1H-isoindole-1,3-dione (4 g, 11.93 mmol, 1.00 equiv) and hydrazine hydrate (8.3 mL, 80%) in methanol (50 mL) was stirred for 12 h at room temperature. The solid was filtered off and the liquid was diluted with water, extracted with ethyl acetate, washed with brine, dried over anhydrous sodium sulfate, and concentrated under vacuum. The residue was purified by a silica gel column eluting with dichloromethane/ethyl acetate (1/1) to afford the title compound (1.2 g, 49%) as a yellow solid. LCMS [M+H$^+$] 205.

Preparation 37: [2-(trifluoromethyl)-6-[2-(trifluoromethyl)pyrimidin-5-yl]pyrimidin-4-yl]methanamine hydrochloride

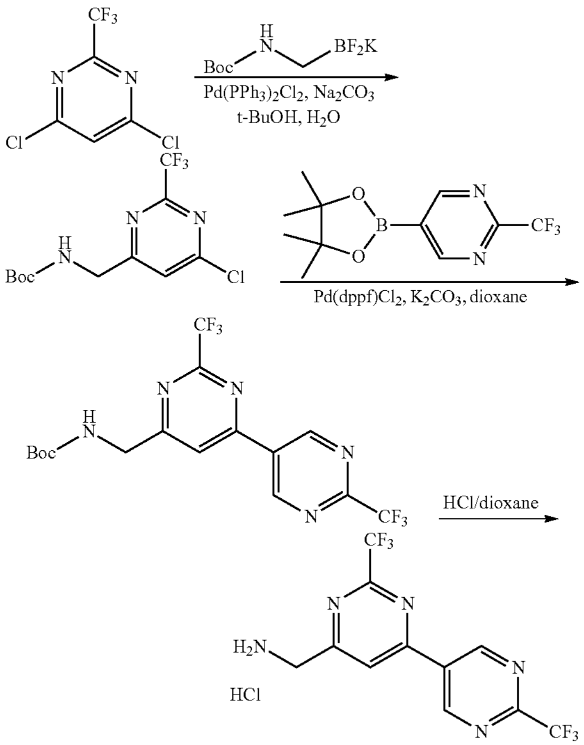

Step 1: Preparation of tert-butyl N-[[6-chloro-2-(trifluoromethyl)pyrimidin-4-yl]methyl]carbamate

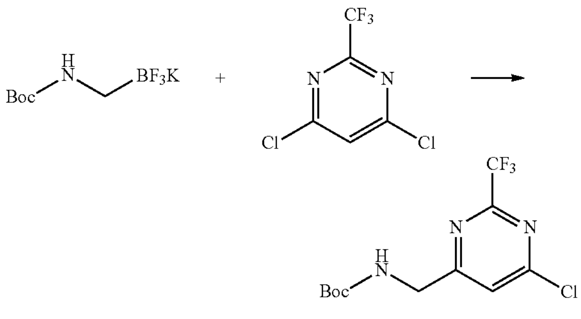

A mixture of 4,6-dichloro-2-(trifluoromethyl)pyrimidine (500 mg, 2.30 mmol, 1.00 equiv), potassium tert-butyl N-[(trifluoroboranuidyl)methyl]carbamate (546 mg, 2.30 mmol, 0.99 equiv), $Pd(PPh_3)_2Cl_2$ (162 mg, 0.23 mmol, 0.10 equiv), and sodium carbonate (488 mg, 4.60 mmol, 1.99 equiv) in t-butanol (10 mL)/water (2 mL) was stirred for 2 h at 70° C. under nitrogen. The solid was filtered off and the filtrate was diluted with water, extracted with ethyl acetate, washed with brine, dried over anhydrous sodium sulfate, and concentrated under vacuum. The residue was purified by a silica gel column eluting with ethyl acetate/petroleum ether (1/5) to afford the title compound (450 mg, 63%) as a white solid. LCMS [M+H$^+$] 312.

Step 2: Preparation of tert-butyl N-[[2-(trifluoromethyl)-6-[2-(trifluoromethyl)pyrimidin-5-yl]pyrimidin-4-yl]methyl]carbamate

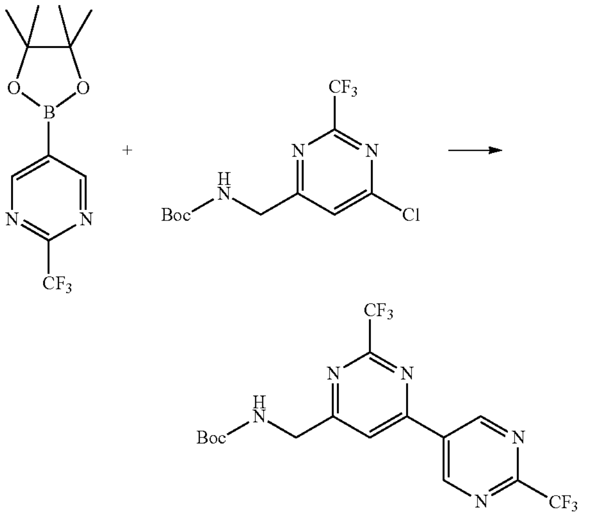

A mixture of 5-(tetramethyl-1,3,2-dioxaborolan-2-yl)-2-(trifluoromethyl)pyrimidine (450 mg, 1.64 mmol, 1.00 equiv), tert-butyl N-[[6-chloro-2-(trifluoromethyl)pyrimidin-4-yl]methyl]carbamate (396 mg, 1.27 mmol, 0.77 equiv), $Pd(dppf)Cl_2$ (106 mg, 0.14 mmol, 0.08 equiv), and potassium carbonate (400 mg, 2.89 mmol, 1.76 equiv) in dioxane (15 mL) was stirred for 3 h at 80° C. under nitrogen. The solid was filtered off. The filtrate was diluted with water, extracted with ethyl acetate, washed with brine, dried over anhydrous sodium sulfate, and concentrated under vacuum. The residue was purified by a silica gel column eluting with ethyl acetate/petroleum ether (1/5) to afford the title compound (400 mg, 58%) as a white solid. LCMS [M+H$^+$] 424.

Step 3: Preparation of [2-(trifluoromethyl)-6-[2-(trifluoromethyl)pyrimidin-5-yl]pyrimidin-4-yl]methanamine hydrochloride

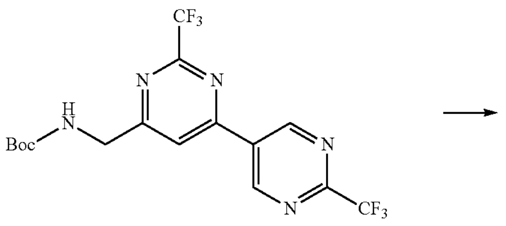

-continued

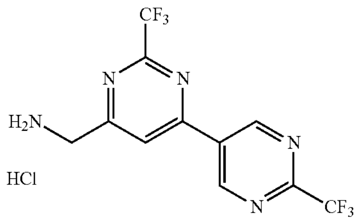

A mixture of tert-butyl N-[[2-(trifluoromethyl)-6-[2-(trifluoromethyl)pyrimidin-5-yl]pyrimidin-4-yl]methyl]carbamate (400 mg, 0.94 mmol, 1.00 equiv) and 4N HCl in 1,4-dioxane (10 mL) was stirred for 2 h at room temperature. The resulting mixture was concentrated under vacuum to afford the title compound (220 mg) as yellow oil. LCMS [M+H+] 324.

Preparation 38: [5-(2,2,2-trifluoroethyl)-2-[2-(trifluoromethyl)pyrimidin-5-yl]pyridin-4-yl]methanamine hydrochloride

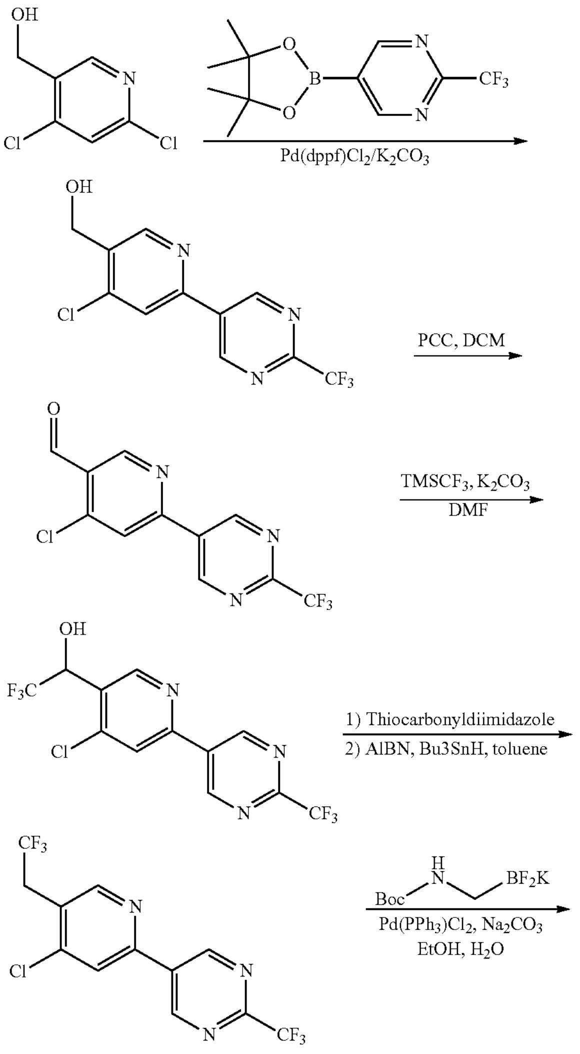

-continued

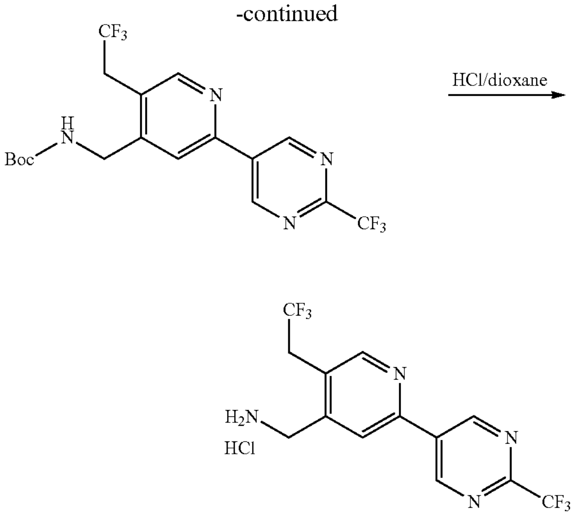

Step 1: Preparation of [4-chloro-6-[2-(trifluoromethyl)pyrimidin-5-yl]pyridin-3-yl]methanol

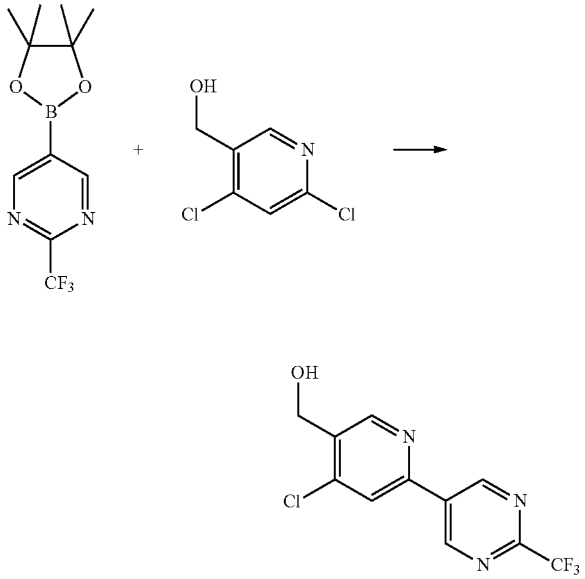

A mixture of (4,6-dichloropyridin-3-yl)methanol (200 mg, 1.123 mmol, 1.000 equiv), 5-(tetramethyl-1,3,2-dioxaborolan-2-yl)-2-(trifluoromethyl)pyrimidine (308 mg, 1.12 mmol, 1.00 equiv), potassium carbonate (310 mg, 2.23 mmol, 2.00 equiv), and $Pd(dppf)Cl_2$ (82 mg, 0.11 mmol, 0.10 equiv) in dioxane (7 mL) was stirred for 2 h at 80° C. under nitrogen. The solid was filtered off. The filtrate was diluted with water, extracted with ethyl acetate, washed with brine, dried over anhydrous sodium sulfate, and concentrated under vacuum. The residue was purified by a silica gel column eluting with ethyl acetate/petroleum ether (3/2) to afford the title compound (210 mg, 65%) as a white solid. LCMS [M+H+] 290.

Step 2: Preparation of 4-chloro-6-[2-(trifluoromethyl)pyrimidin-5-yl]pyridine-3-carbaldehyde

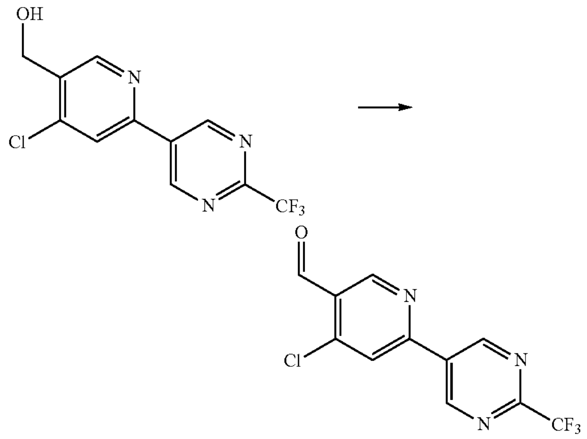

A mixture of [4-chloro-6-[2-(trifluoromethyl)pyrimidin-5-yl]pyridin-3-yl]methanol (600 mg, 2.07 mmol, 1.00 equiv), PCC (894 mg, 4.14 mmol, 2.00 equiv), silica gel (3 g), and dichloromethane (30 mL) was stirred for 4 h at room temperature. The resulting mixture was concentrated under vacuum. The residue was purified by a silica gel column eluting with ethyl acetate/petroleum ether (1/1) to afford the title compound (340 mg, 57%) as a white solid. LCMS [M+H$^+$] 288.

Step 3: Preparation of 1-[4-chloro-6-[2-(trifluoromethyl)pyrimidin-5-yl]pyridin-3-yl]-2,2,2-trifluoroethan-1-ol

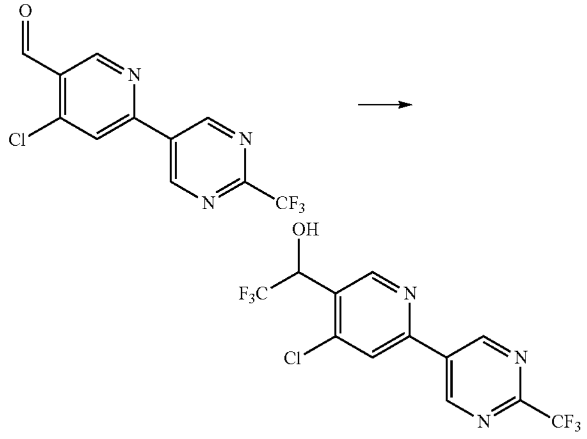

A mixture of 4-chloro-6-[2-(trifluoromethyl)pyrimidin-5-yl]pyridine-3-carbaldehyde (340 mg, 1.18 mmol, 1.00 equiv), trimethyl(trifluoromethyl)silane (338 mg, 2.37 mmol, 2.01 equiv), and potassium carbonate (181 mg, 1.31 mmol, 1.10 equiv) in N,N-dimethylformamide (10 mL) was stirred for 1 h at room temperature under nitrogen. The resulting solution was diluted with ethyl acetate, washed with brine, dried over anhydrous sodium sulfate, and concentrated under vacuum. The residue was purified by a silica gel column eluting with ethyl acetate/petroleum ether to afford the title compound (180 mg, 43%) as a white solid. LCMS [M+H$^+$] 358.

Step 4: Preparation of 5-[4-chloro-5-(2,2,2-trifluoroethyl)pyridin-2-yl]-2-(trifluoromethyl)pyrimidine

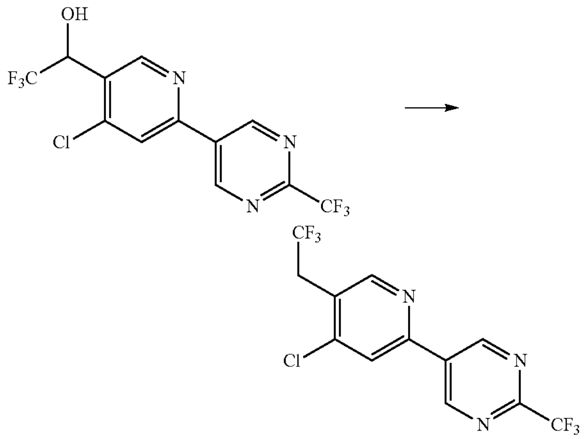

A mixture of 1-[4-chloro-6-[2-(trifluoromethyl)pyrimidin-5-yl]pyridin-3-yl]-2,2,2-trifluoroethan-1-ol (310 mg, 0.867 mmol, 1.000 equiv) and 1-[(1H-imidazol-1-yl)carbothioyl]-1H-imidazole (231 mg, 1.29 mmol, 1.50 equiv) in tetrahydrofuran (5 mL) was heated to reflux for 3 h under nitrogen. The resulting mixture was concentrated under vacuum and then dissolved with toluene (7 mL). To this was added AIBN (28 mg, 0.17 mmol, 0.20 equiv) and tri-n-butyltin hydride (378 mg, 1.30 mmol, 1.50 equiv). After being stirred for 2 h at 85° C. the resulting mixture was concentrated under vacuum. The residue was purified by a silica gel column eluting with ethyl acetate/petroleum ether (1/2) to afford the title compound (190 mg, 64%) as a white solid. LCMS [M+H$^+$] 342.

Step 5: Preparation of tert-butyl N-[[5-(2,2,2-trifluoroethyl)-2-[2-(trifluoromethyl)pyrimidin-5-yl]pyridin-4-yl]methyl]carbamate

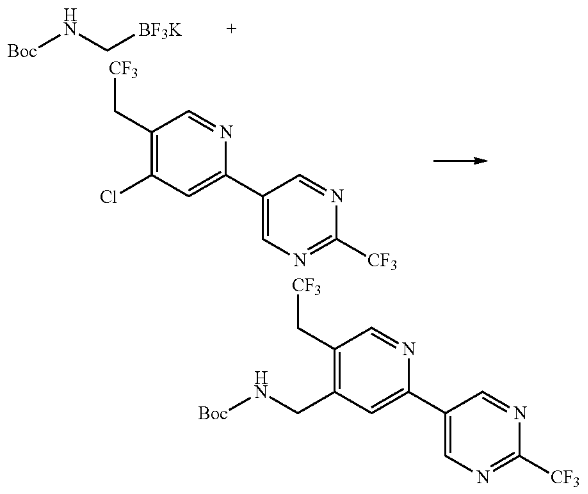

A mixture of 5-[4-chloro-5-(2,2,2-trifluoroethyl)pyridin-2-yl]-2-(trifluoromethyl)pyrimidine (16 mg, 0.04 mmol, 1.00 equiv), potassium ((tert-butoxycarbonylamino)methyl) trifluoroborate (13 mg, 0.05 mmol, 1.20 equiv), $Pd(PPh_3)_2Cl_2$ (3.3 mg, 0.01 mmol, 0.10 equiv), and sodium carbonate (10 mg, 0.09 mmol, 2.00 equiv) in ethanol (1 mL)/water (0.3 mL) was stirred for 2 h at 90° C. under nitrogen. The resulting solution was diluted with ethyl acetate, washed with water, dried over anhydrous sodium sulfate, and concentrated under vacuum. The residue was purified by a silica gel column eluting with ethyl acetate/petroleum ether (1/2) to afford the title compound (12 mg, 60%) as a white solid. LCMS [M+H$^+$] 437.

Step 6: Preparation of [5-(2,2,2-trifluoroethyl)-2-[2-(trifluoromethyl)pyrimidin-5-yl]pyridin-4-yl]methanamine hydrochloride

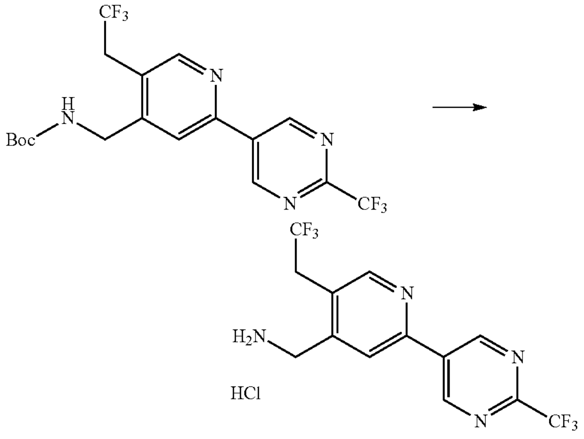

A mixture of tert-butyl N-[[5-(2,2,2-trifluoroethyl)-2-[2-(trifluoromethyl)pyrimidin-5-yl]pyridin-4-yl]methyl]carbamate (150 mg, 0.34 mmol, 1.00 equiv) and 4N HCl in 1,4-dioxane (5 mL) was stirred for 2 h at room temperature. The resulting mixture was concentrated under vacuum to afford the title compound (160 mg, crude) as a white solid. LCMS [M+H$^+$] 337.

Preparation 39: (2-(trifluoromethyl)-5-(2-(trifluoromethyl)pyrimidin-5-yl)phenyl)methanamine

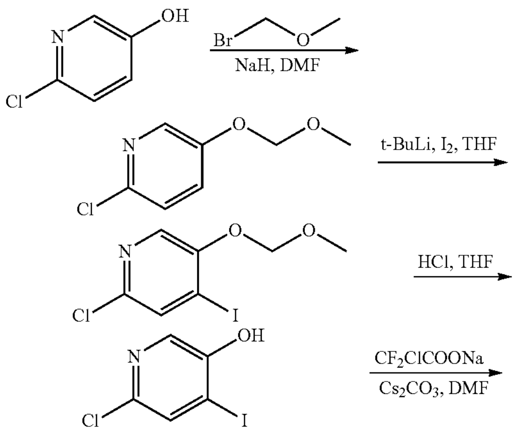

-continued

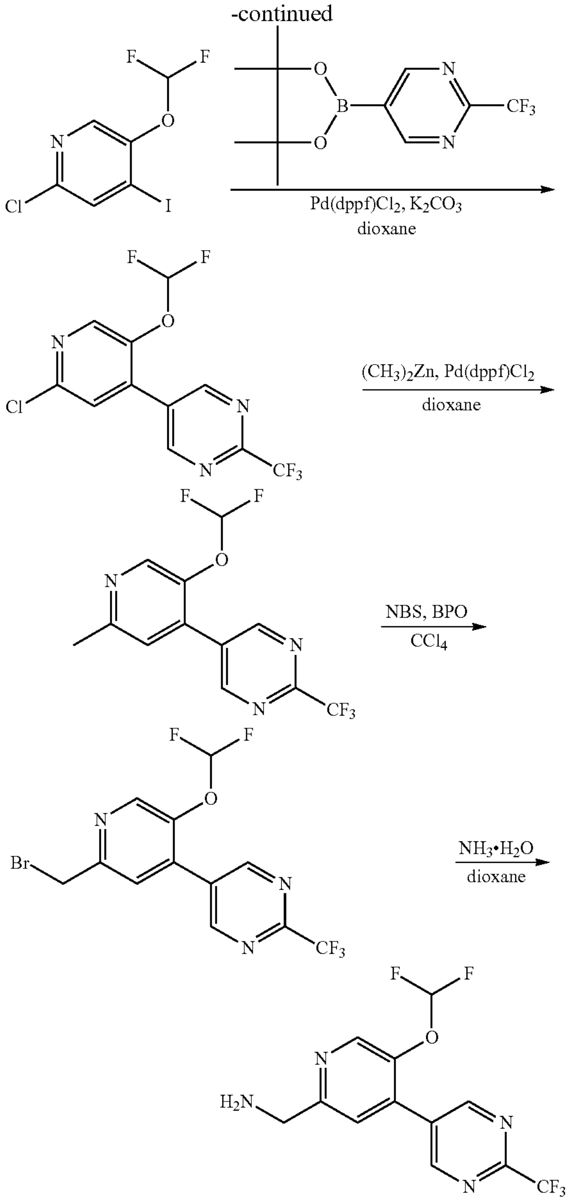

Step 1: Preparation of 2-chloro-5-(methoxymethoxy)pyridine

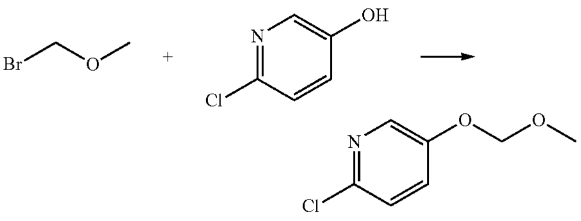

Sodium hydride (2.8 g, 60% in mineral oil, 1.26 equiv) was added in portions into a solution of 6-chloropyridin-3-ol (12 g, 92.63 mmol, 1.00 equiv) in N,N-dimethylformamide (200 mL) at 0° C. under nitrogen. The mixture was stirred for 10 minutes at room temperature. To the above was added bromo(methoxy)methane (15 g, 120.03 mmol, 1.29 equiv) dropwise and the reaction mixture was stirred for 2 h at room temperature. The reaction was quenched by water, extracted with ethyl acetate, washed with brine, dried over anhydrous sodium sulfate, and concentrated under vacuum. The residue was purified by a silica gel column eluting with petroleum ether/ethyl acetate (10/1) to afford the title compound (14 g, 87%) as colorless oil. LCMS [M+H$^+$] 174.

Step 2: Preparation of 2-chloro-4-iodo-5-(methoxymethoxy)pyridine

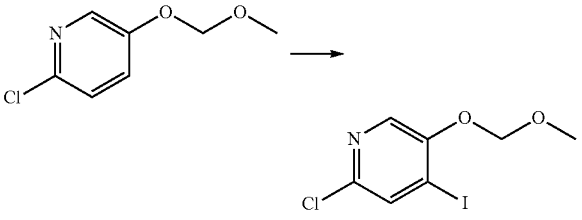

n-BuLi (25.3 mL, 2.5M in hexane) was added dropwise into a solution of 2-chloro-5-(methoxymethoxy)pyridine (10 g, 57.61 mmol, 1.00 equiv) in tetrahydrofuran (200 mL) at −78° C. and the mixture was stirred for 30 minutes under nitrogen. A solution of $I_2$ (19 g, 74.86 mmol, 1.30 equiv) in THF was added dropwise into the above solution at −78° C. After being stirred for 2 hours at −78° C. the reaction was quenched by 5% of $Na_2SO_3$ solution, extracted with ethyl acetate, washed with brine, dried over anhydrous sodium sulfate, and concentrated under vacuum. This resulted in the title compound (16 g, 93%) as a yellow solid. LCMS [M+H$^+$] 300.

Step 3: Preparation of 6-chloro-4-iodopyridin-3-ol

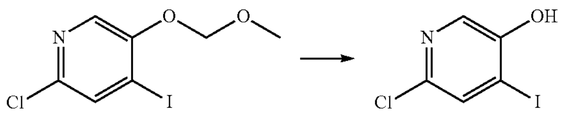

A solution of 2-chloro-4-iodo-5-(methoxymethoxy)pyridine (5 g, 16.69 mmol, 1.00 equiv) and 6N of hydrogen chloride (10 ml) in tetrahydrofuran (50 mL) was stirred for 2 hours at 60° C. The resulting solution was concentrated under vacuum, diluted with saturated sodium bicarbonate, extracted with ethyl acetate, washed with brine, dried over anhydrous sodium sulfate, and concentrated under vacuum. This resulted in the title compound (4.2 g, 98%) of as a yellow solid. LCMS [M+H$^+$] 256.

Step 4: Preparation of 2-chloro-5-(difluoromethoxy)-4-iodopyridine

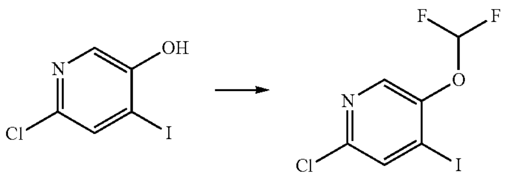 [SMILES: Oc1cnc(Cl)cc1I ; FC(F)Oc1cnc(Cl)cc1I]

A mixture of 6-chloro-4-iodopyridin-3-ol (2 g, 7.83 mmol, 1.00 equiv), $Cs_2CO_3$ (3.3 g, 10.13 mmol, 1.29 equiv), N,N-dimethylformamide (50 mL), and sodium 2-chloro-2,2-difluoroacetate (2.4 g, 15.74 mmol, 2.01 equiv) was stirred for 3 hours at 80° C. The resulting solution was diluted with ethyl acetate, washed with water and brine, dried over anhydrous sodium sulfate, and concentrated under vacuum. The residue was purified by a silica gel column eluting with ethyl acetate/petroleum ether (1/10) to afford the title compound (2.2 g, 92%) as a yellow solid. LCMS [M+H$^+$] 306.

Step 5: Preparation of 5-[2-chloro-5-(difluoromethoxy)pyridin-4-yl]-2-(trifluoromethyl)pyrimidine

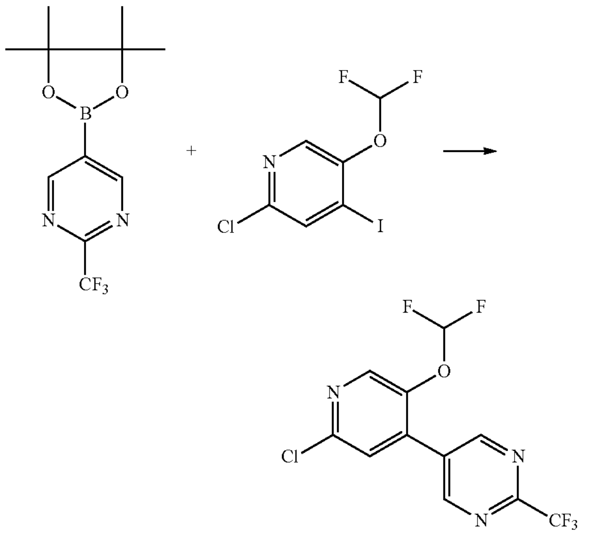

A mixture of 2-chloro-5-(difluoromethoxy)-4-iodopyridine (2 g, 6.55 mmol, 1.00 equiv), 5-(tetramethyl-1,3,2-dioxaborolan-2-yl)-2-(trifluoromethyl)pyrimidine (2.68 g, 9.78 mmol, 1.49 equiv), Pd(dppf)$Cl_2$ (480 mg, 0.66 mmol, 0.10 equiv), and potassium carbonate (2.7 g, 19.54 mmol, 2.98 equiv) in 1,4-dioxane (100 mL) was stirred for 3 h at 60° C. under nitrogen. The solid was filtered off. The filtrate was concentrated under vacuum. The residue was purified by a silica gel column eluting with ethyl acetate/petroleum ether (1/10) to afford the title compound (1.6 g, 75%) as a light yellow solid. LCMS [M+H$^+$] 326.

Step 6: Preparation of 5-[5-(difluoromethoxy)-2-methylpyridin-4-yl]-2-(trifluoromethyl)pyrimidine

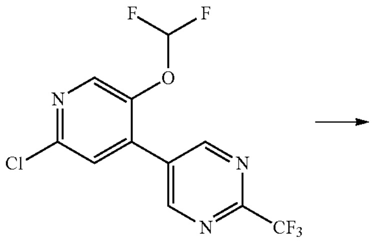

-continued

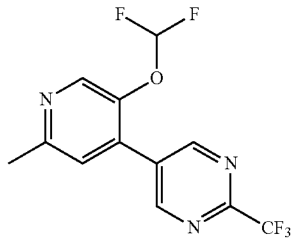

A mixture of 5-[2-chloro-5-(difluoromethoxy)pyridin-4-yl]-2-(trifluoromethyl)pyrimidine (800 mg, 2.45 mmol, 1.00 equiv), Pd(dppf)$Cl_2$ (179 mg, 0.24 mmol, 0.10 equiv), and $Zn(CH_3)_2$ (5 mL, 1M in toluene, 2.04 equiv) in dioxane (10 mL) was stirred overnight at 60° C. under nitrogen. The resulting mixture was concentrated under vacuum. The residue was purified by a silica gel column eluting with ethyl acetate/petroleum ether (1/3) to afford the title compound (600 mg, 80%) as a greenish solid. LCMS [M+H$^+$] 306.

Step 7: Preparation of 5-[2-(bromomethyl)-5-(difluoromethoxy)pyridin-4-yl]-2-(trifluoromethyl)pyrimidine

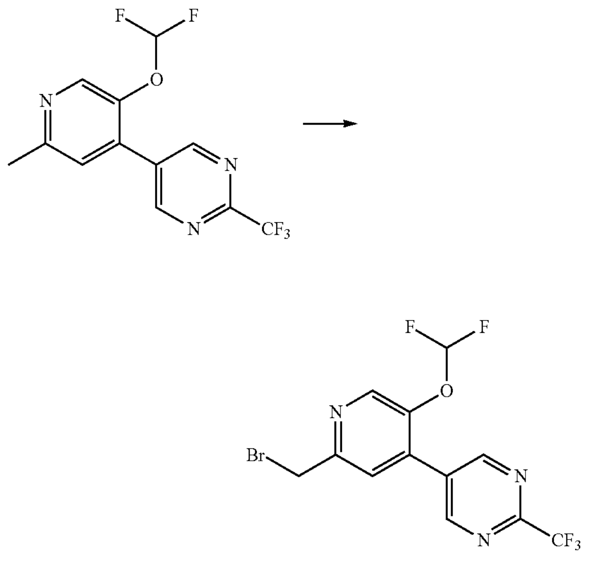

A mixture of 5-[5-(difluoromethoxy)-2-methylpyridin-4-yl]-2-(trifluoromethyl)pyrimidine (600 mg, 1.96 mmol, 1.00 equiv), BPO (150 mg, 0.58 mmol, 0.29 equiv), and NBS (420 mg, 2.36 mmol, 1.20 equiv) in $CCl_4$ (40 mL) was stirred overnight at room temperature. The resulting mixture was concentrated under vacuum. The residue was purified by a silica gel column eluting with ethyl acetate/petroleum ether (1/3) to afford the title compound (600 mg, 79%) as a greenish solid. LCMS [M+H$^+$] 384.

Step 8: Preparation of [5-(difluoromethoxy)-4-[2-(trifluoromethyl)pyrimidin-5-yl]pyridin-2-yl]methanamine

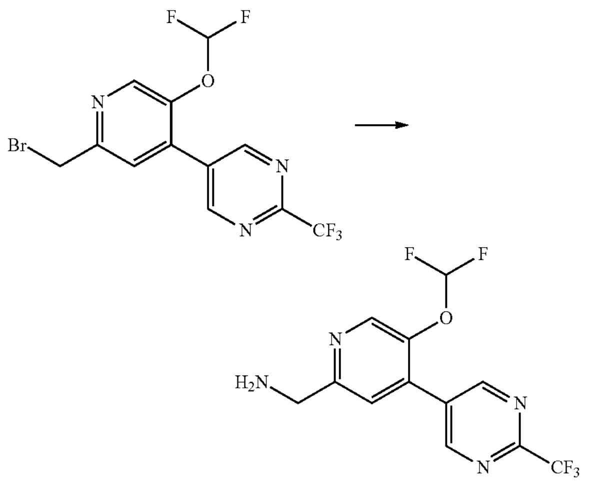

A mixture of 5-[2-(bromomethyl)-5-(difluoromethoxy)pyridin-4-yl]-2-(trifluoro methyl)pyrimidine (550 mg, 1.43 mmol, 1.00 equiv) and ammonia (25%, 2 mL) in dioxane (10 mL) was stirred for 2 h at room temperature. The resulting mixture was concentrated under vacuum. The residue was purified by a silica gel column eluting with dichloromethane/methanol (10/1) to afford the title compound (100 mg, 22%) as a greenish solid. LCMS [M+H$^+$] 321.

Preparation 40: [2-cyclopropyl-6-(trifluoromethyl)pyrimidin-4-yl]methanamine hydrochloride

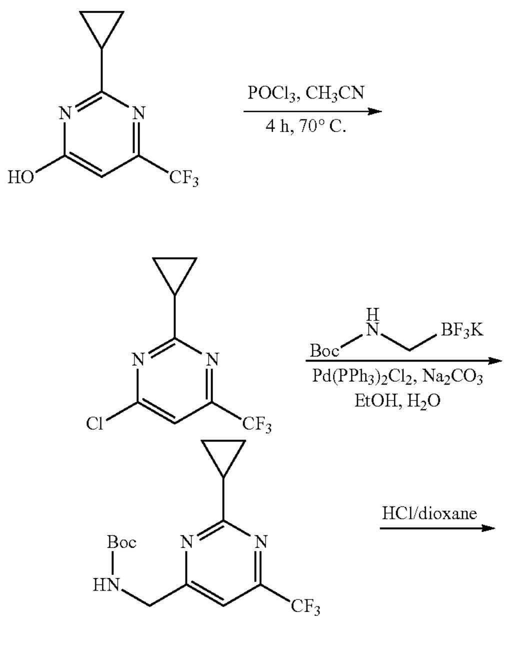

-continued

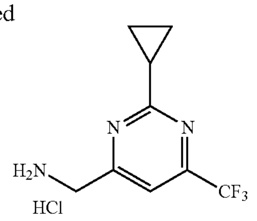

Step 1: Preparation of 4-chloro-2-cyclopropyl-6-(trifluoromethyl)pyrimidine

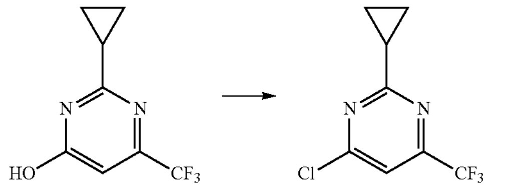 [SMILES: Oc1cc(C(F)(F)F)nc(C2CC2)n1 ; FC(F)(F)c1cc(Cl)nc(C2CC2)n1]

A solution of 2-cyclopropyl-6-(trifluoromethyl)pyrimidin-4-ol (1 g, 4.89 mmol, 1.00 equiv) and $POCl_3$ (2.2 g, 14.35 mmol, 2.93 equiv) in $CH_3CN$ (20 mL) was stirred for 4 h at 70° C. The resulting solution was diluted with water, extracted with ethyl acetate, washed with brine, dried over anhydrous sodium sulfate, and concentrated under vacuum. This resulted in the title compound (1 g, 92%) as colorless oil. LCMS [$M+H^+$] 223.

Step 2 Preparation of tert-butyl N-[[2-cyclopropyl-6-(trifluoromethyl)pyrimidin-4-yl]methyl]carbamate

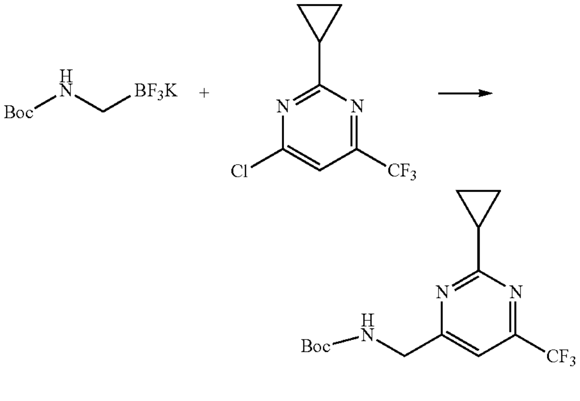

A mixture of 4-chloro-2-cyclopropyl-6-(trifluoromethyl) pyrimidine (500 mg, 2.25 mmol, 1.00 equiv), potassium tert-butyl N-[(trifluoroboranuidyl)methyl]carbamate (600 mg, 2.53 mmol, 1.13 equiv), $Pd(PPh_3)_2Cl_2$ (150 mg, 0.21 mmol, 0.01 equiv), and sodium carbonate (750 mg, 7.07 mmol, 3.15 equiv) in ethanol (20 mL)/water (2 mL) was stirred for 3 hours at 80° C. under nitrogen. The resulting mixture was concentrated under vacuum. The residue was purified by a silica gel column eluting with ethyl acetate/petroleum ether (1/4) to afford the title compound (250 mg, 35%) as greenish oil. LCMS [$M+H^+$] 318.

Step 3: Preparation of [2-cyclopropyl-6-(trifluoromethyl)pyrimidin-4-yl]methanamine hydrochloride

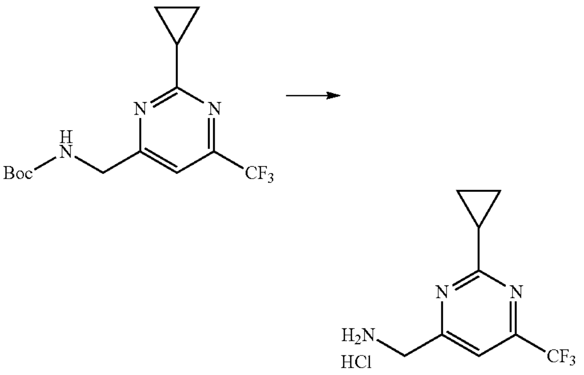

A mixture of tert-butyl N-[[2-cyclopropyl-6-(trifluoromethyl)pyrimidin-4-yl]methyl]carbamate (250.00 mg, 0.80 mmol, 1.00 equiv) in 4 N HCl in dioxane (5 mL) was stirred for 1 h at room temperature. The resulting mixture was concentrated under vacuum to afford the title compound (150 mg, 75%) as a greenish solid. LCMS [$M+H^+$] 218.

Preparation 41: (5-(trifluoromethoxy)-4-(2-(trifluoromethyl)pyrimidin-5-yl)pyridin-2-yl)methanamine hydrochloride

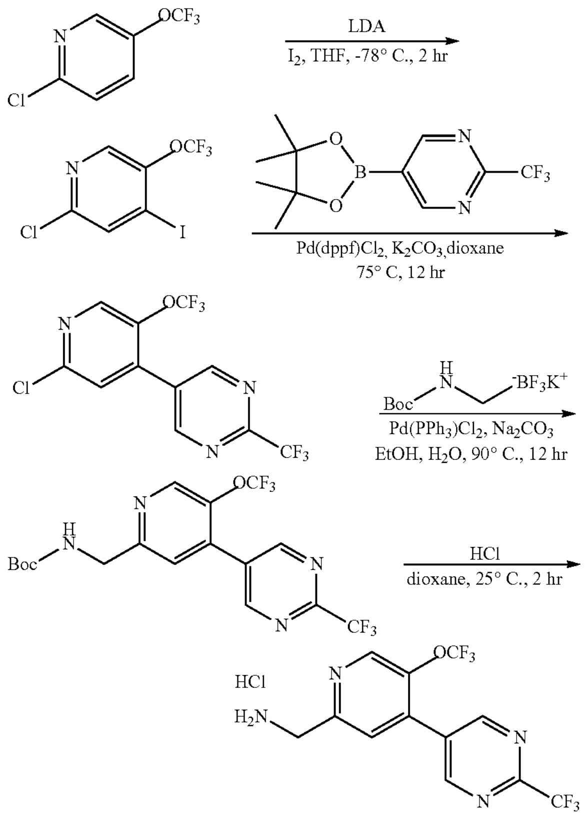

Step 1: Preparation of 2-chloro-4-iodo-5-(trifluoromethoxy)pyridine

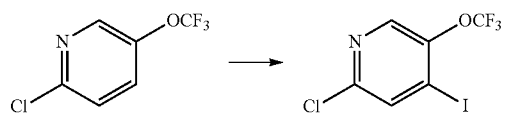 [SMILES: FC(F)(F)Oc1ccc(Cl)nc1 ; FC(F)(F)Oc1cnc(Cl)cc1I]

LDA (7.6 mL, 2M in THF, 1.20 equiv) was added dropwise into a solution of 2-chloro-5-(trifluoromethoxy) pyridine (2.5 g, 12.65 mmol, 1.00 equiv) in tetrahydrofuran (20 mL) at −78° C. and the reaction mixture was stirred for 2 hours at −78° C. under nitrogen. To the above mixture was added a solution of $I_2$ (3.5 g, 13.79 mmol, 1.09 equiv) in tetrahydrofuran (20 mL) dropwise at −78° C. After being stirred for 2 hours at room temperature the resulting mixture was then poured into water/ice, extracted with ethyl acetate, washed with brine, dried over anhydrous sodium sulfate, and concentrated under vacuum. The residue was purified by a silica gel column eluting with dichloromethane/ethyl acetate (50/1) to afford the title compound (1.75 g, 32%) as a yellow solid. LCMS [M+H$^+$] 324.

Step 2: Preparation of 5-(2-chloro-5-(trifluoromethoxy)pyridin-4-yl)-2-(trifluoromethyl)pyrimidine

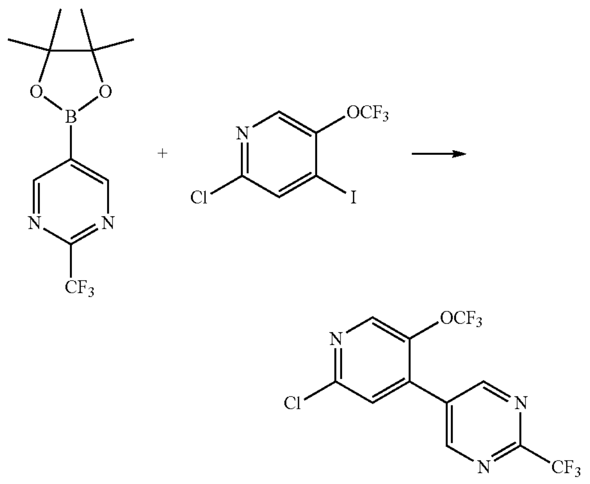

A mixture of 2-chloro-4-iodo-5-(trifluoromethoxy)pyridine (1.5 g, 4.63 mmol, 1.00 equiv), 4,4,5,5-tetramethyl-2-[4-(trifluoromethyl)phenyl]-1,3,2-dioxaborolane (1.65 g, 6.06 mmol, 1.30 equiv), Pd(dppf)$Cl_2$ (0.339 mg, 0.46 mmol, 0.01 equiv), and potassium carbonate (1.28 g, 9.26 mmol, 1.99 equiv) in dioxane (20 mL) was stirred for 12 hours at 75° C. under nitrogen. The solid was filtered off. The filtrate was diluted with water, extracted with ethyl acetate, washed with brine, dried over anhydrous sodium sulfate, and concentrated under vacuum. The residue was purified by a silica gel column eluting with ethyl acetate/petroleum ether (1/2) to afford the title compound (1.0 g, 63%) as a light yellow solid. LCMS [M+H$^+$] 344.

Step 3: Preparation of tert-butyl (5-(trifluoromethoxy)-4-(2-(trifluoromethyl)pyrimidin-5-yl) pyridin-2-yl)methylcarbamate

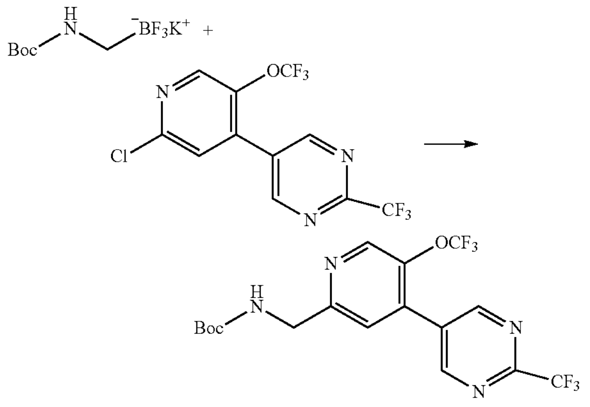

A mixture of 5-[2-chloro-5-(trifluoromethoxy)pyridin-4-yl]-2-(trifluoromethyl)pyrimidine (390 mg, 1.13 mmol, 1.00 equiv), potassium tert-butyl N-[(trifluoroboranuidyl) methyl]carbamate (350 mg, 1.47 mmol, 1.30 equiv), sodium carbonate (359 mg, 3.38 mmol, 2.98 equiv), and $Pd(PPh_3)_2Cl_2$ (79 mg, 0.11 mmol, 0.09 equiv) in ethanol (5 mL)/water (0.5 mL) was stirred for 12 hours at 90° C. under nitrogen. The solid was filtered off. The filtrate was diluted with water, extracted with ethyl acetate, washed with brine, dried over anhydrous sodium sulfate, and concentrated under vacuum. The residue was purified by a silica gel column eluting with ethyl acetate/petroleum ether (2/1) to afford the title compound (200 mg, 40%) as a light yellow solid. LCMS [M+H$^+$] 439.

Step 4: Preparation of (5-(trifluoromethoxy)-4-(2-(trifluoromethyl)pyrimidin-5-yl)pyridin-2-yl)methanamine hydrochloride

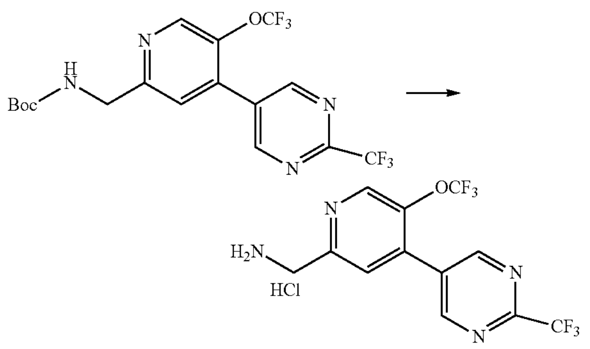

A mixture of tert-butyl N-[[5-(trifluoromethoxy)-4-[2-(trifluoromethyl)pyrimidin-5-yl]pyridin-2-yl]methyl]carbamate (180 mg, 0.41 mmol, 1.00 equiv) and 4 N HCl in dioxane (8 mL) was stirred for 5 hours at room temperature. The mixture was concentrated under vacuum to afford the title compound (130 mg, 86%) as a light yellow solid. LCMS [M+H$^+$] 339.

Preparation 42: (5-(trifluoromethyl)-4-(2-(trifluoromethyl)pyrimidin-5-yl)pyri din-2-yl)methanamine hydrochloride

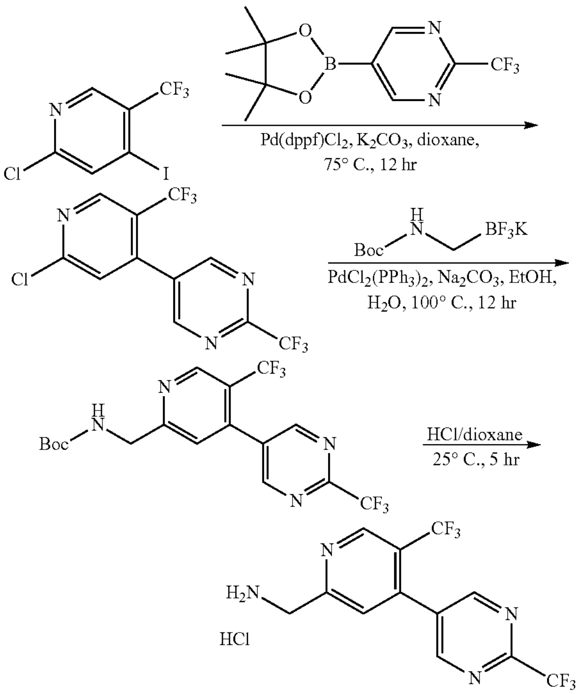

Step 1: Preparation of 5-(2-chloro-5-(trifluoromethyl)pyridin-4-yl)-2-(trifluoromethyl)pyrimidine

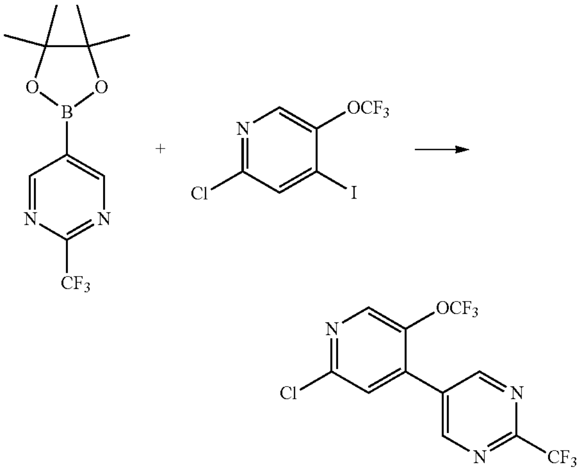

A mixture of 2-chloro-4-iodo-5-(trifluoromethyl)pyridine (1.79 g, 5.82 mmol, 1.00 equiv), 5-(tetramethyl-1,3,2-dioxaborolan-2-yl)-2-(trifluoromethyl)pyrimidine (3.2 g, 11.67 mmol, 2.00 equiv), potassium carbonate (1.6 g, 11.57 mmol, 1.98 equiv), and $Pd(PPh_3)_2Cl_2$ (813 mg, 1.15 mmol, 0.19 equiv) in dioxane (3 mL)/water (0.3 mL) was stirred for 12 hours at 75° C. under nitrogen. The resulting solution was diluted with water, extracted with ethyl acetate, washed with brine, dried over anhydrous sodium sulfate, and concentrated under vacuum. The residue was purified by a silica gel column eluting with ethyl acetate/petroleum ether (1/1) to afford the title compound (1.5 g, 79%) as a light yellow solid. LCMS [M+H$^+$] 328.

Step 2: Preparation of tert-butyl (5-(trifluoromethyl)-4-(2-(trifluoromethyl)pyrimidin-5-yl)pyridin-2-yl)methylcarbamate

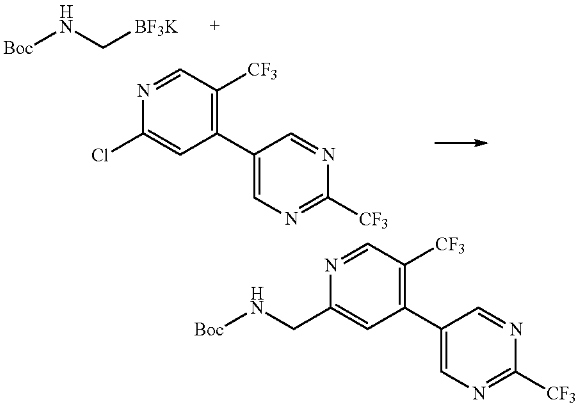

A mixture of 5-[2-chloro-5-(trifluoromethyl)pyridin-4-yl]-2-(trifluoromethyl)pyrimidine (1.1 g, 3.35 mmol, 1.00 equiv), potassium tert-butyl N-[(trifluoro-lambda4-boranyl)methyl]carbamate (1.194 g, 5.03 mmol, 1.50 equiv), $Pd(PPh_3)_2Cl_2$ (471 mg, 0.67 mmol, 0.20 equiv), and sodium carbonate (712 mg, 6.71 mmol, 2.00 equiv) in ethanol (30 mL)/water (3 mL) was stirred for 12 hours at 100° C. under nitrogen. The solid was filtered off. The filtrate was diluted with water, extracted with ethyl acetate, washed with brine, dried over anhydrous sodium sulfate, and concentrated under vacuum. The residue was purified by a silica gel column eluting with ethyl acetate/petroleum ether (1/1) to afford the title compound (1.0 g, 77%) as a light yellow solid. LCMS [M+H$^+$] 423.

Step 3: Preparation of (5-(trifluoromethyl)-4-(2-(trifluoromethyl)pyrimidin-5-yl)pyridin-2-yl)methanamine hydrochloride

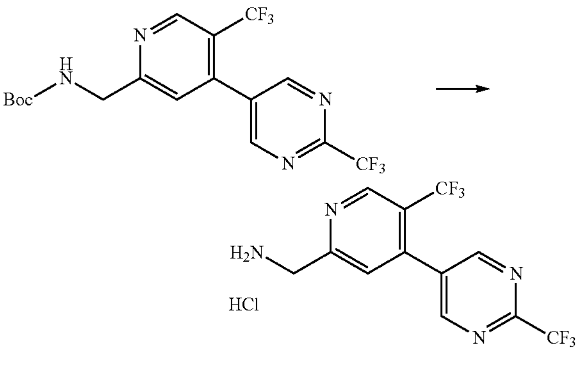

A mixture of tert-butyl N-[[5-(trifluoromethyl)-4-[2-(trifluoromethyl)pyrimidin-5-yl]pyridin-2-yl]methyl]carbamate (1.8 g, 4.26 mmol, 1.00 equiv) and 4 N HCl in 1,4- dioxane (30 mL) was stirred for 5 hours at room temperature. The mixture was concentrated under vacuum to afford the title compound (1.3 g, 85%) as light yellow oil. LCMS [M+H$^+$] 323.

Preparation 43: (2-(2,2,2-trifluoroethoxy)-2'-(trifluoromethyl)-4,5'-bipyrimidin-6-yl)methanamine hydrochloride

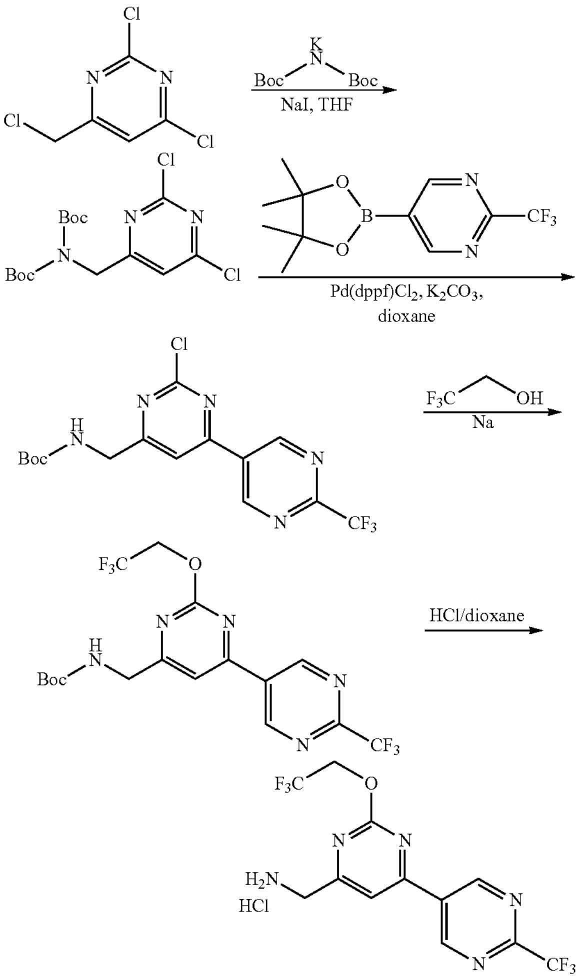

Step 1: Preparation of tert-butyl N-[(tert-butoxy) carbonyl]-N-[(3,5-dichlorophenyl)methyl]carbamate

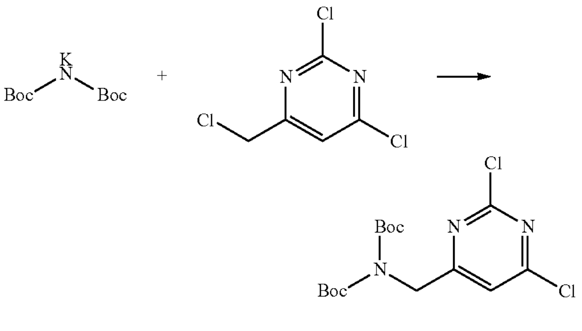

A mixture of 2,4-dichloro-6-(chloromethyl)pyrimidine (4 g, 20.25 mmol, 1.00 equiv), NaI (6.4 g, 42.69 mmol, 2.10 equiv), and tert-butyl N-[(tert-butoxy)carbonyl]-N-potassiocarbamate (8.4 g, 32.89 mmol, 1.62 equiv) in tetrahydrofuran (80 mL) was stirred for 14 h at room temperature. The reaction solution was diluted with water, extracted with ethyl acetate, washed with brine, dried over anhydrous sodium sulfate, and concentrated under vacuum. The residue was purified by a silica gel column eluting with ethyl acetate/petroleum ether (1/2) to afford the title compound (3.2 g, 42%) as an off-white solid. LCMS [M+H$^+$] 378.

Step 2: Preparation of tert-butyl (2-chloro-2'-(trifluoromethyl)-4,5'-bipyrimidin-6-yl)methylcarbamate

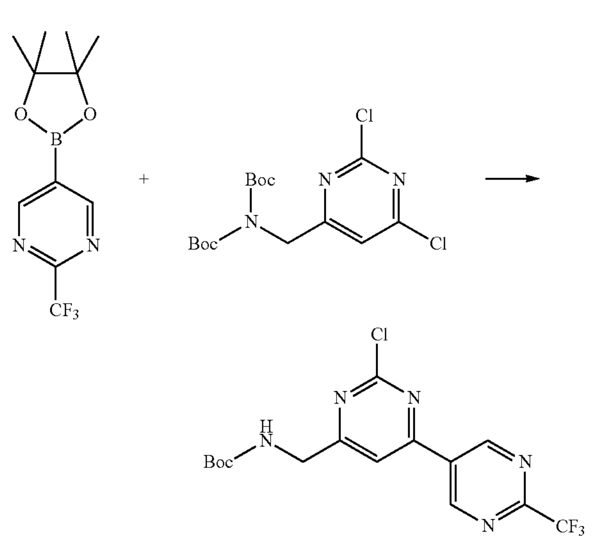

A mixture of tert-butyl N-[(tert-butoxy)carbonyl]-N-[(2,6-dichloropyrimidin-4-yl)methyl]carbamate (3.0 g, 7.93 mmol, 1.00 equiv), Pd(dppf)$Cl_2$ (562 mg, 0.76 mmol, 0.0 equiv), potassium carbonate (3.3 g, 23.96 mmol, 3.02 equiv), and 5-(tetramethyl-1,3,2-dioxaborolan-2-yl)-2-(trifluoromethyl)pyrimidine (2.19 g, 7.99 mmol, 1.00 equiv) in dioxane (100 mL)/water (10 mL) was stirred for 14 h at 80° C. under nitrogen. The resulting mixture was concentrated under vacuum. The residue was purified by a silica gel column eluting with ethyl acetate/petroleum ether (2/3) to afford the title compound (1.1 g, 36%) as a yellow solid. LCMS [M+H$^+$] 390.

Step 3: Preparation of tert-butyl (2-(2,2,2-trifluoroethoxy)-2'-(trifluoromethyl)-4,5'-bipyrimidin-6-yl) methylcarbamate

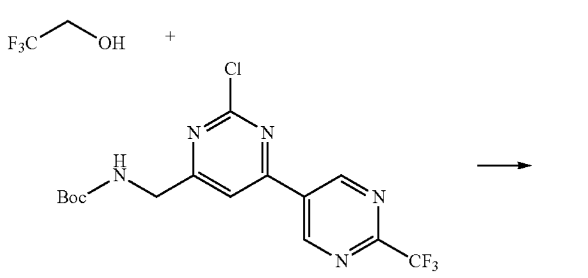

-continued

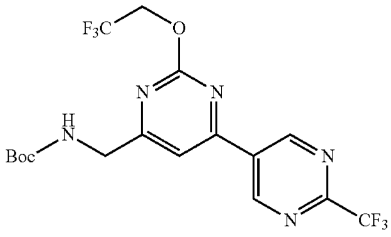

A mixture of 2,2,2-trifluoroethan-1-ol (8 g, 79.96 mmol, 62.33 equiv) and Na (50 mg, 2.17 mmol, 1.69 equiv) was stirred for 2 h at room temperature. To the above solution was added tert-butyl N-([2-chloro-6-[2-(trifluoromethyl)pyrimidin-5-yl]pyrimidin-4-yl]methyl)carbamate (500 mg, 1.28 mmol, 1.00 equiv) and the reaction mixture was stirred for 15 min at 0° C. The reaction was quenched by water, extracted with ethyl acetate, washed with brine, dried over anhydrous sodium sulfate, and concentrated under vacuum. The residue was purified by a silica gel column eluting with ethyl acetate/petroleum ether (1/2) to afford the title compound (420 mg, 72%) as an off-white solid. LCMS [M+H$^+$] 454.

Step 4: Preparation of (2-(2,2,2-trifluoroethoxy)-2'-(trifluoromethyl)-4,5'-bipyrimidin-6-yl)methanamine hydrochloride

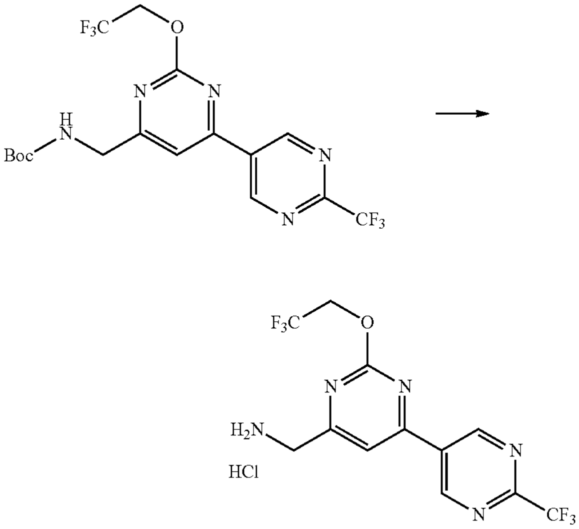 [SMILES: CC(C)(C)OC(=O)NCc1cc(-c2cnc(C(F)(F)F)nc2)nc(OCC(F)(F)F)n1 ; Cl ; NCc1cc(-c2cnc(C(F)(F)F)nc2)nc(OCC(F)(F)F)n1]

A mixture of tert-butyl N-[[2-(2,2,2-trifluoroethoxy)-6-[2-(trifluoromethyl)pyrimidin-5-yl]pyrimidin-4-yl]methyl]carbamate (400 mg, 0.88 mmol, 1.00 equiv) and saturated 4 N HCl in dioxane (15 mL) was stirred for 4 h at room temperature. The resulting mixture was concentrated under vacuum to afford the title compound (320 mg, 93%) as an off-white solid. LCMS [M+H$^+$] 354.

Preparation 44: (2S,4R,5S)—N-[[5-cyclopropyl-2-[2-(trifluoromethyl)pyrimidin-5-yl]-4-pyridyl]methyl]-4-fluoro-1-(4-fluorophenyl)sulfonyl-5-methyl-pyrrolidine-2-carboxamide

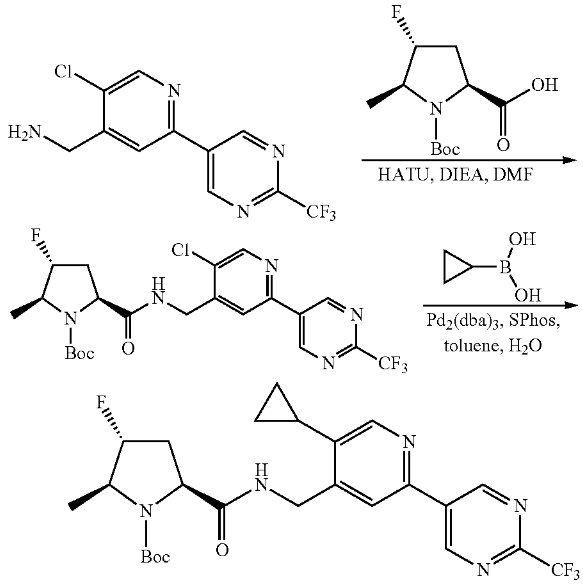

Step 1: Preparation of tert-butyl (2S,3R,5S)-5-[([5-chloro-2-[2-(trifluoromethyl)pyrimidin-5-yl]pyridin-4-yl]methyl)carbamoyl]-3-fluoro-2-methylpyrrolidine-1-carboxylate

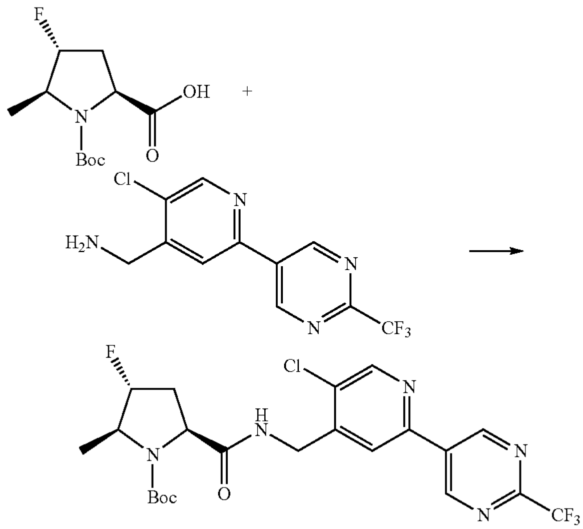

A mixture of (2S,4R,5S)-1-[(tert-butoxy)carbonyl]-4-fluoro-5-methylpyrrolidine-2-carboxylic acid (152 mg, 0.61 mmol, 0.88 equiv), [5-chloro-2-[2-(trifluoromethyl)pyrimidin-5-yl]pyridin-4-yl]methanamine (200 mg, 0.69 mmol, 1.00 equiv), DIEA (398 mg, 3.07 mmol, 4.44 equiv), and HATU (352 mg, 0.92 mmol, 1.33 equiv) in N,N-dimethylformamide (20 mL) was stirred for 1 h at room temperature.

The reaction solution was diluted with ethyl acetate, washed with water, dried over anhydrous sodium sulfate, and concentrated under vacuum. The residue was purified by a silica gel column eluting with ethyl acetate/petroleum ether (4/1) to afford the title compound (300 mg, 84%) as a white solid. LCMS [M+H$^+$] 518.

Step 2: Preparation of tert-butyl (2S,3R,5S)-5-[([5-cyclopropyl-2-[2-(trifluoromethyl)pyrimidin-5-yl]pyridin-4-yl]methyl)carbamoyl]-3-fluoro-2-methylpyrrolidine-1-carboxylate

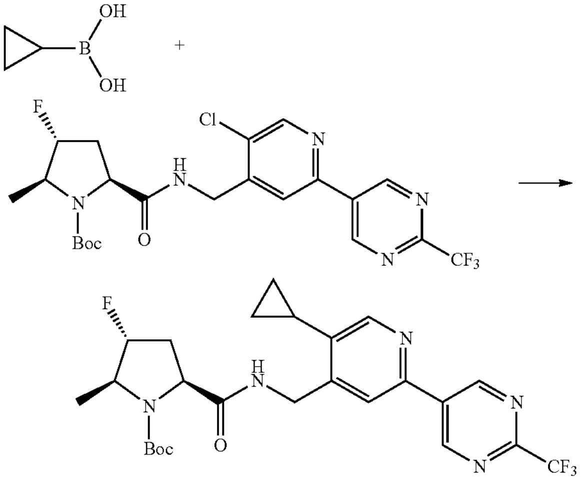

A mixture of tert-butyl (2S,3R,5S)-5-[([5-chloro-2-[2-(trifluoromethyl)pyrimidin-5-yl]pyridin-4-yl]methyl)carbamoyl]-3-fluoro-2-methylpyrrolidine-1-carboxylate (480 mg, 0.92 mmol, 1.00 equiv), $Pd_2(dba)_3$ (96 mg, 0.10 mmol, 0.11 equiv), SPhos (76 mg, 0.18 mmol, 0.20 equiv), potassium carbonate (265 mg, 1.91 mmol, 2.06 equiv), and cyclopropylboronic acid (398 mg, 4.63 mmol, 4.99 equiv) in toluene (25 mL)/water (2.5 mL) was stirred for 3 h at 100° C. under nitrogen. The reaction solution was diluted with ethyl acetate, washed with water, dried over anhydrous sodium sulfate, and concentrated under vacuum. The residue was purified by a silica gel column eluting with ethyl acetate/petroleum ether (1/1) to afford the title compound (300 mg, 62%) as a white solid. LCMS [M+H$^+$] 524.

Preparation 45: (5-(trifluoromethoxy)-2-(4-(trifluoromethyl)phenyl)pyridin-4-yl)methanamine hydrochloride

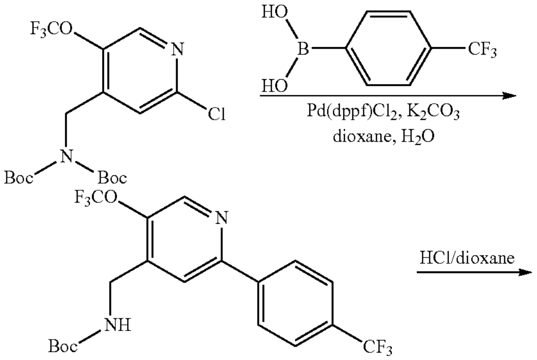

-continued

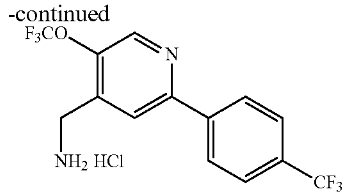

Step 1: Preparation of tert-butyl N-[(tert-butoxy)carbonyl]-N-[[5-(trifluoromethoxy)-2-[4-(trifluoromethyl)phenyl]pyridin-4-yl]methyl]carbamate

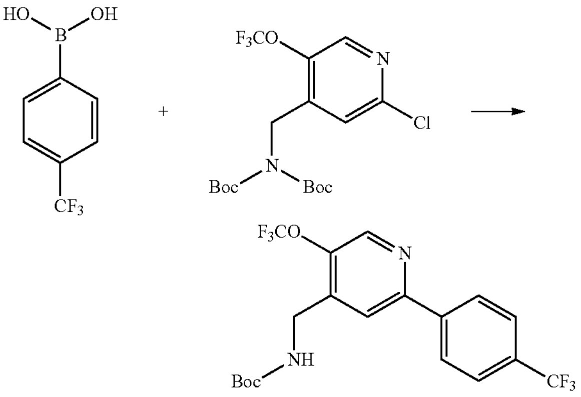

A mixture of tert-butyl N-[(tert-butoxy)carbonyl]-N-[[2-chloro-5-(trifluoromethoxy)pyridin-4-yl]methyl]carbamate (500 mg, 1.17 mmol, 1.00 equiv), $Pd(dppf)Cl_2$ (86 mg, 0.11 mmol, 0.10 equiv), [4-(trifluoromethyl)phenyl]boronic acid (335 mg, 1.76 mmol, 1.50 equiv), and potassium carbonate (323 mg, 2.33 mmol, 1.99 equiv) in water (1 mL)/dioxane (10 mL) was stirred overnight at 100° C. The resulting solution was diluted with ethyl acetate, washed with water, dried over anhydrous sodium sulfate, and concentrated under vacuum. The residue was purified by a silica gel column eluting with ethyl acetate/petroleum ether (1/1) to afford the title compound (454 mg, 89%) as a white solid. LCMS [M+H$^+$] 437.

Step 2: (5-(trifluoromethoxy)-2-(4-(trifluoromethyl)phenyl)pyridin-4-yl)methanamine hydrochloride

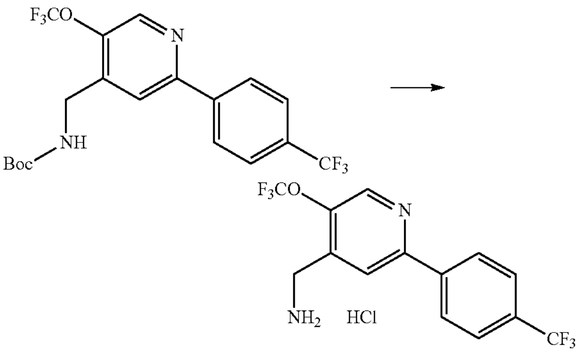

A mixture of tert-butyl N-[[5-(trifluoromethoxy)-2-[4-(trifluoromethyl)phenyl]pyridin-4-yl]methyl]carbamate (560 mg, 1.28 mmol, 1.00 equiv) in 4 N HCl in dioxane (20 mL) was stirred for 1 hour at room temperature. The resulting solution was concentrated under vacuum to afford the title compound (400 mg, 93%) as a white solid. LCMS [M+H$^+$] 337.

Preparation 46: (2',5-bis(trifluoromethyl)-2,5'-bipyrimidin-4-yl)methanamine hydrochloride

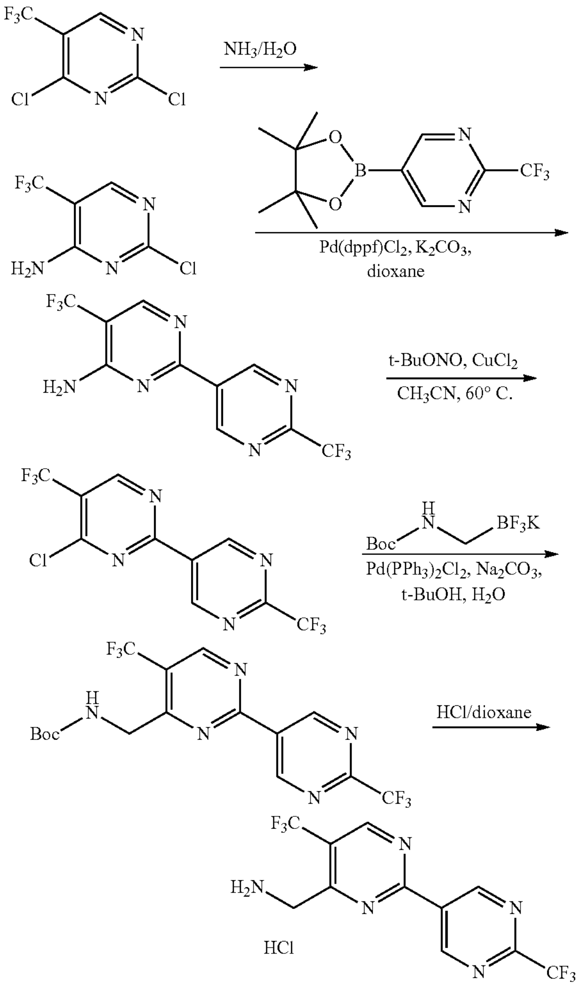

Step 1: 2-chloro-5-(trifluoromethyl)pyrimidin-4-amine

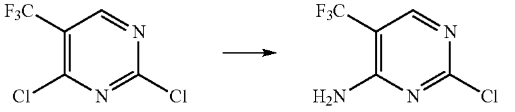

A solution of 2, 4-dichloro-5-(trifluoromethyl)pyrimidine (4.7 g, 21.66 mmol, 1.00 equiv) and ammonia (25% in methanol, 3 mL) in tetrahydrofuran (50 mL) was stirred for 4 hours at −5° C. The reaction solution was diluted with water, extracted with ethyl acetate, dried over anhydrous sodium sulfate, and concentrated under vacuum. This resulted in the title compound (2 g, 47%) as a white solid. LCMS [M+H$^+$] 198.

Step 2: Preparation of 2',5-bis(trifluoromethyl)-2,5'-bipyrimidin-4-amine

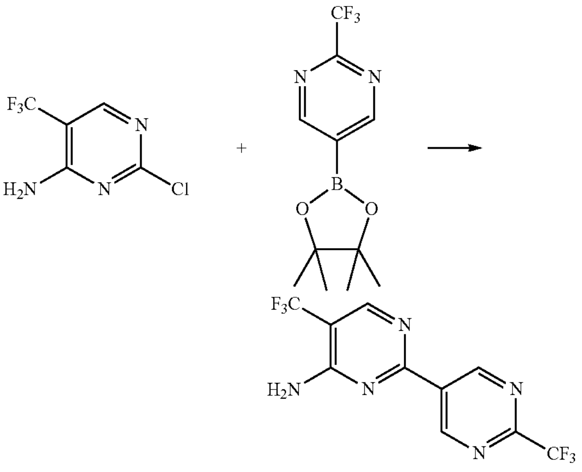

A mixture of 5-(tetramethyl-1,3,2-dioxaborolan-2-yl)-2-(trifluoromethyl)pyrimidine (2 g, 7.30 mmol, 1.00 equiv), 2-chloro-5-(trifluoromethyl)pyrimidin-4-amine (2.78 g, 14.08 mmol, 1.92 equiv), Pd(dppf)$Cl_2$ (0.74 g, 1.02 mmol, 0.13 equiv), and potassium carbonate (4.20 g, 30.41 mmol, 4.16 equiv) in dioxane (15 mL)/water (1.5 mL) was stirred for 4 hours at 90° C. under nitrogen. The reaction mixture was diluted with ethyl acetate, washed with water, dried over anhydrous sodium sulfate, and concentrated under vacuum. The residue was purified by a silica gel column eluting with ethyl acetate/petroleum ether (1/3) to afford the title compound (2.3 g, 51%) as a white solid. LCMS [M+H$^+$] 310.

Step 3: Preparation of 4-chloro-2',5-bis(trifluoromethyl)-2,5'-bipyrimidine

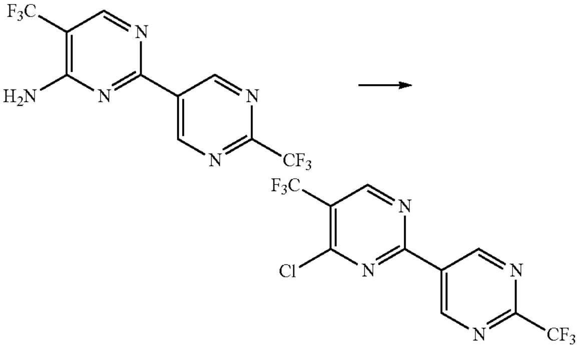

A mixture of 2',5-bis(trifluoromethyl)-2,5'-bipyrimidin-4-amine (2.3 g, 7.43 mmol, 1.00 equiv), $CuCl_2$ (1.49 g, 11.12 mmol, 1.49 equiv), and tert-butyl nitrite (1.2 g, 11.15 mmol, 1.49 equiv) in $CH_3CN$ (15 mL) was stirred overnight at 60° C. under nitrogen. The resulting solution was diluted with brine, extracted with ethyl acetate, washed with brine, dried over anhydrous sodium sulfate, and concentrated under vacuum. The residue was purified by a silica gel column eluting with ethyl acetate/petroleum ether (1/10) to afford the title compound (1.5 g, 59%) as a yellow solid. LCMS [M+H$^+$] 329.

Step 4: Preparation of tert-butyl N-[[5-(trifluoromethyl)-2-[2-(trifluoromethyl)pyrimidin-5-yl]pyrimidin-4-yl]methyl]carbamate

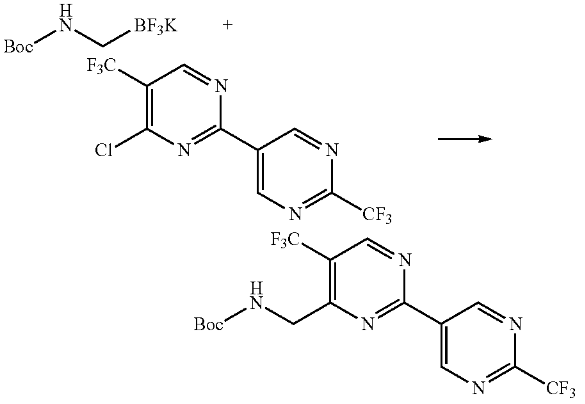

A mixture of 4-chloro-5-(trifluoromethyl)-2-[2-(trifluoromethyl)pyrimidin-5-yl]pyrimidine (300 mg, 0.91 mmol, 1.00 equiv), $Pd(PPh_3)_2Cl_2$ (128 mg, 0.18 mmol, 0.20 equiv), sodium carbonate (193 mg, 1.82 mmol, 1.99 equiv), and potassium tert-butyl N-[(trifluoro-lambda4-boranyl)methyl] carbamate (216 mg, 0.91 mmol, 0.99 equiv) in t-butanol (10 mL)/water (1 mL) was stirred for 2 hours at 80° C. under nitrogen. The resulting solution was diluted with brine, extracted with ethyl acetate, washed with brine, dried over anhydrous sodium sulfate, and concentrated under vacuum. The residue was purified by a silica gel column eluting with ethyl acetate/petroleum ether (1/8) to afford the title compound (230 mg, 60%) as white solid. LCMS [M+H$^+$] 424.

Step 5: (2',5-bis(trifluoromethyl)-2,5'-bipyrimidin-4-yl)methanamine hydrochloride

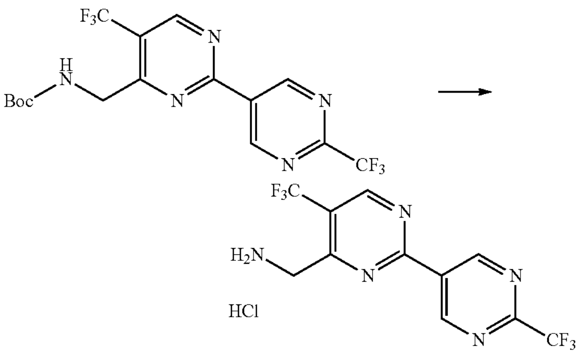

A mixture of tert-butyl N-[[5-(trifluoromethyl)-2-[2-(trifluoromethyl)pyrimidin-5-yl]pyrimidin-4-yl]methyl]carbamate (230 mg, 0.54 mmol, 1.00 equiv) in 4 N HCl in dioxane (10 mL) was stirred for 1 hour at room temperature. The resulting mixture was concentrated under vacuum to afford the title compound (230 mg, crude) as a white solid. LCMS [M+H$^+$] 324.

Preparation 47: (2-(trifluoromethyl)-5-(2-(trifluoromethyl)pyrimidin-5-yl)pyri din-3-yl)methanamine hydrochloride

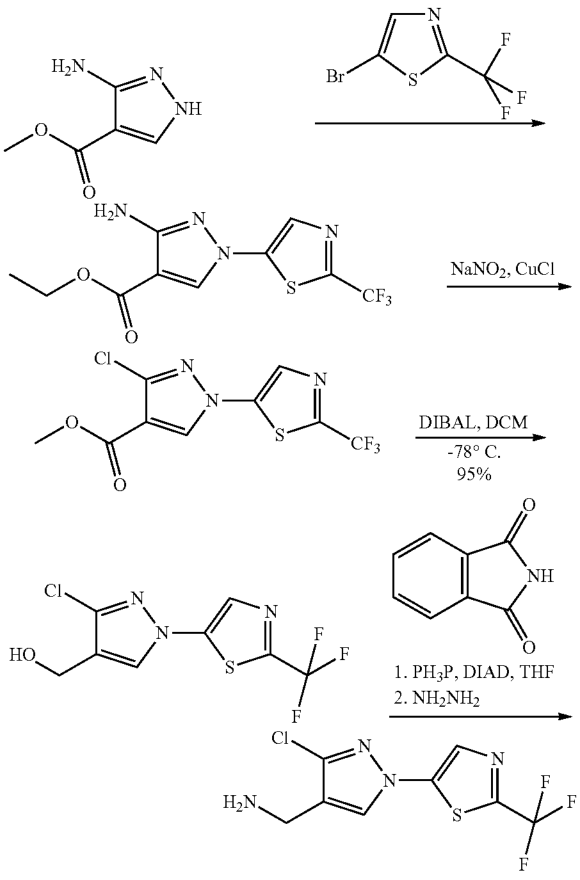

Step 1: Preparation of ethyl 3-amino-1-(2-(trifluoromethyl)thiazol-5-yl)-1H-pyrazole-4-carboxylate

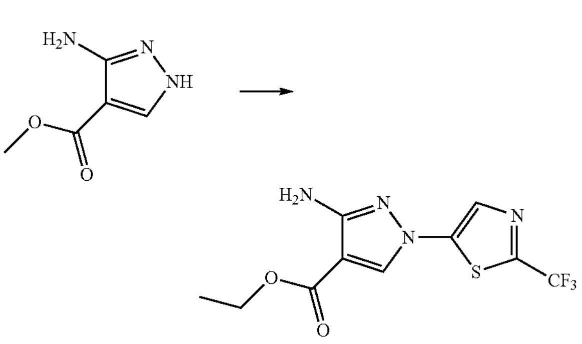

Into a pressure flask purged and maintained with an inert atmosphere of nitrogen, was placed ethyl 3-amino-1H-pyrazole-4-carboxylate (350 mg, 2.2559 mmol), 5-bromo-2-(trifluoromethyl)thiazole (523 mg, 2.2559 mmol), CuI (43 mg, 0.22559 mmol), L-proline (52 mg, 0.45118 mmol), $K_2CO_3$ (623 mg, 4.5118 mmol), DMSO (1 mL). The resulting solution was stirred for 1 overnight at 100 degrees Celsius. The solid was filtered out, and the filtrate was washed with water followed by brine. The crude was purified with isco using 50% iPrOAc/heptane gave 250 mg white solid (yield 82%).

Step 2: Preparation methyl 3-chloro-1-(2-(trifluoromethyl)thiazol-5-yl)-1H-pyrazole-4-carboxylate

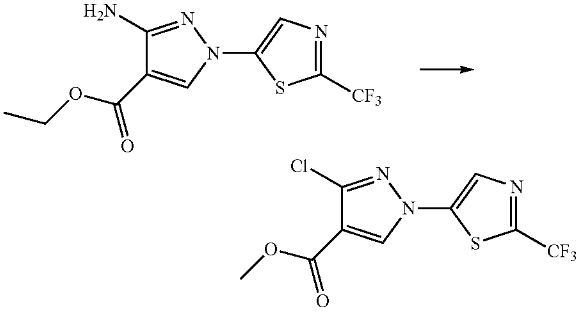

A solution of ethyl 3-amino-1-[2-(trifluoromethyl)thiazol-5-yl]pyrazole-4-carboxylate (250 mg, 0.81630 mmol) in HCl (2 mL, 24.36 mmol) was treated by the addition of $NaNO_2$ (85 mg, 1.2244 mmol) in WATER (0.5 mL) in several batches at 0 degrees Celsius. To this was added copper(I) chloride (97 mg, 0.97956 mmol) in HCl (37 mass %) in $H_2O$ (1.25 mL, 15 mmol) at 0 degrees Celsius. The resulting solution was stirred for 1 h at 0 degrees Celsius. The resulting solution was allowed to react, with stirring for overnight at room temperature. The reaction mixture was extracted with EtOAc, washed with sat. brine, dried and concentrated. The crude was purified with 50% iPrOAc/heptane to give 150 mg product (regioisomers) as white solid (yield 46%).

Step 3: Preparation (3-chloro-1-(2-(trifluoromethyl)thiazol-5-yl)-1H-pyrazol-4-yl)methanol

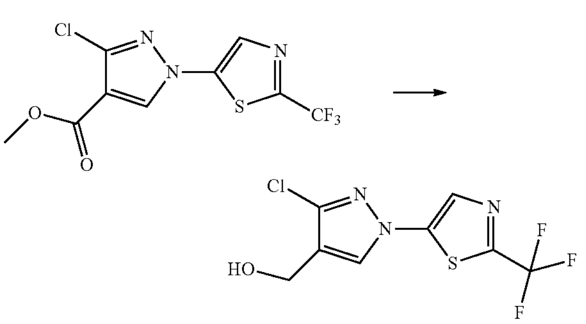

Into a 100-mL 3-necked round-bottom flask purged and maintained with an inert atmosphere of nitrogen, was placed To a screw-cap vial, add ethyl 3-chloro-1-[2-(trifluoromethyl)thiazol-5-yl]pyrazole-4-carboxylate (165 mg, 0.50660 mmol), DCM (10 mL). This was followed by the addition of DIBAl-H 1.0 M in DCM (1 mL, 1 mmol) at −78 degrees Celsius. The resulting solution was stirred for 1 h at −78 degrees Celsius in a liquid nitrogen bath. The reaction was then quenched by the addition of 3 mL of methanol. The resulting mixture was concentrated under vacuum. The residue was washed with iPrOAc to give yellow solid as 140 mg pure product (yield 97%).

Step 4: Preparation (3-chloro-1-(2-(trifluoromethyl)thiazol-5-yl)-1H-pyrazol-4-yl)methanamine

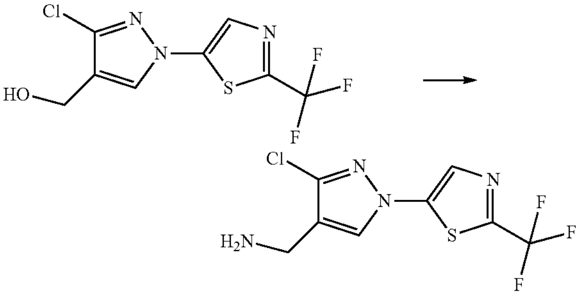

Into a round-bottom flask purged and maintained with an inert atmosphere of nitrogen, was placed [3-chloro-1-[2-(trifluoromethyl)thiazol-5-yl]pyrazol-4-yl]methanol (100 mg, 0.35253 mmol), 2,3-dihydro-1H-isoindole-1,3-dione (78 mg, 0.52880 mmol), $PPh_3$ (139 mg, 0.52880 mmol), oxolane (1 mL). This was followed by the addition of DIAD (0.1 mL, 0.52880 mmol) dropwise with stirring at 0 degrees Celsius. The resulting solution was stirred for 12 h at room temperature. The resulting solution was diluted with 80 mL of brine. The resulting solution was extracted with 3×60 mL of ethyl acetate and the organic layers combined. The resulting mixture was washed with 3×100 mL of brine. The mixture was dried over anhydrous sodium sulfate and concentrated under vacuum. The residue was applied onto a silica gel column with isopropyl acetate/heptane. The collected fractions were combined and concentrated under vacuum to give white solid 140 mg.

Into a 100-mL round-bottom flask, was placed 2-[[3-chloro-1-[2-(trifluoromethyl)thiazol-5-yl]pyrazol-4-yl]methyl]isoindoline-1,3-dione (140 mg, 0.3634 mmol), MeOH (5 mL, 123.49 mmol), NH2NH2.H2O (3.634 mmol). The resulting solution was stirred for 12 h at 50 degrees Celsius in an oil bath. The resulting mixture was concentrated under vacuum, and diluted with EtOAc. The solid was filtered out and filtrate was concentrated. This resulted in 60 mg product (yield 58%).

Preparation 48: (2-(trifluoromethyl)-5-(2-(trifluoromethyl)pyrimidin-5-yl)pyri din-3-yl)methanamine hydrochloride

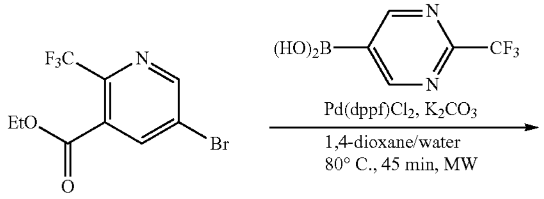

-continued

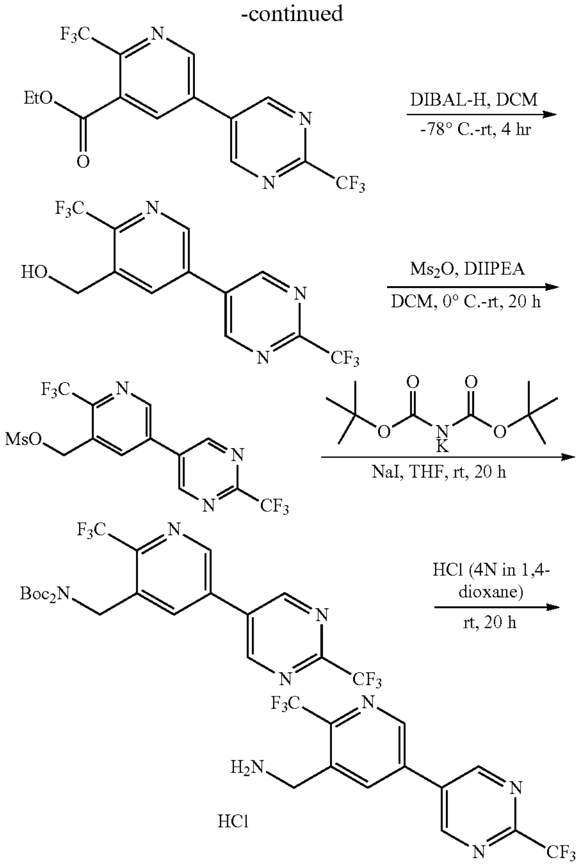

Step 1: Preparation of ethyl 2-(trifluoromethyl)-5-(2-(trifluoromethyl)pyrimidin-5-yl)nicotinate

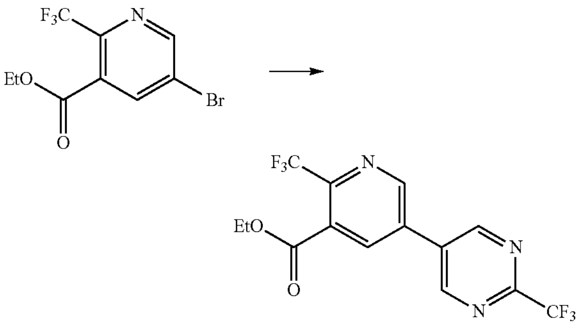

Ethyl 5-bromo-2-(trifluoromethyl)pyridine-3-carboxylate (1.00 g, 3.35 mmol, 1.0 equiv.), [2-(trifluoromethyl)pyrimidin-5-yl]boronic acid (772 mg, 4.03 mmol, 1.2 equiv.), $Pd(dppf)Cl_2$ (248 mg, 0.34 mmol, 0.1 equiv.) and $K_2CO_3$ (937 mg, 6.71 mmol, 2 equiv.) were charged in a microwave vial and purged under nitrogen. Degassed 1,4-dioxane (17 mL) and water (1.7 mL) was added and the mixture was stirred for 45 min at 80° C. in the microwave. Reaction mixture was filtered through diatomaceous earth and washed with iPrOAc. The filtrate was partitioned with water and extracted with iPrOAc (3×). The combined organic extracts were washed with brine, dried over $MgSO_4$, filtered and concentrated. The crude mixture was purified by a silica gel column eluting with iPrOAc/heptane (0-40%) to afford the title compound (1.20 g, 98%) as a white solid. LCMS [M+H+] 366.

Step 2: Preparation of (2-(trifluoromethyl)-5-(2-(trifluoromethyl)pyrimidin-5-yl)pyridin-3-yl)methanol

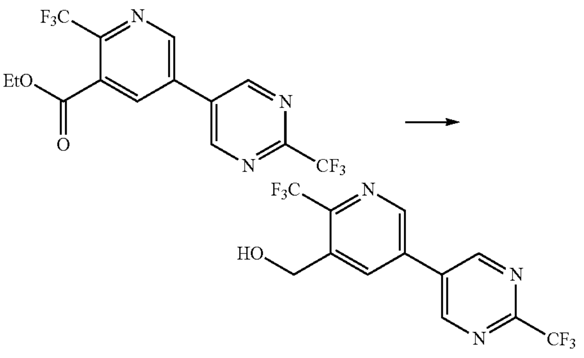

Diisobutylaluminium hydride (1.0 M in toluene) (8.20 mL, 8.20 mmol, 2.5 equiv.) was added to a solution of ethyl 2-(trifluoromethyl)-5-[2-(trifluoromethyl)pyrimidin-5-yl]pyridine-3-carboxylate (1.20 g, 3.30 mmol, 1.0 equiv.) in DCM (16 mL) at −78° C. The mixture was allowed to warm-up to rt over 4 hr. The reaction was quenched with iPrOAc at 0° C. A saturated solution of Rochelle's salt was added and the mixture was stirred at rt for 1 hr. Water was added and the aqueous layer was extracted with iPrOAc (3×). The combined organic extracts were washed with brine, dried over $MgSO_4$, filtered and concentrated. The crude mixture was purified by a silica gel column eluting with iPrOAc/heptane (0-40%) to afford the title compound (673 mg, 63%) as a dark orange residue. LCMS [M+H+] 324.

Step 3: Preparation of (2-(trifluoromethyl)-5-(2-(trifluoromethyl)pyrimidin-5-yl)pyridin-3-yl)methyl methanesulfonate

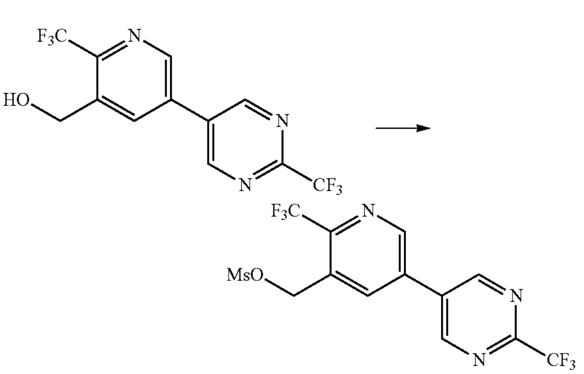

Methane sulfonic anhydride (561 mg, 3.12 mmol, 1.5 equiv.) was added to a solution of [2-(trifluoromethyl)-5-[2-(trifluoromethyl)pyrimidin-5-yl]-3-pyridyl]methanol (673 mg, 2.08 mmol, 1 equiv.) and DIPEA (1.09 mL, 6.25 mmol, 3 equiv.) in DCM (7 mL) at 0° C. The mixture was stirred at rt overnight. The reaction was quenched with saturated $NaHCO_3$ and extracted with DCM (3×). The combined organic extracts were washed with water and brine and they were dried over $MgSO_4$, filtered and concentrated to afford the title compound (907 mg, 109%) as a crude orange gummy oil. The crude product was used as-is. LCMS [M+H+] 402.

Step 4: Tert-butyl N-tert-butoxycarbonyl-N-[[2-(trifluoromethyl)-5-[2-(trifluoromethyl)pyrimidin-5-yl]-3-pyridyl]methyl]carbamate

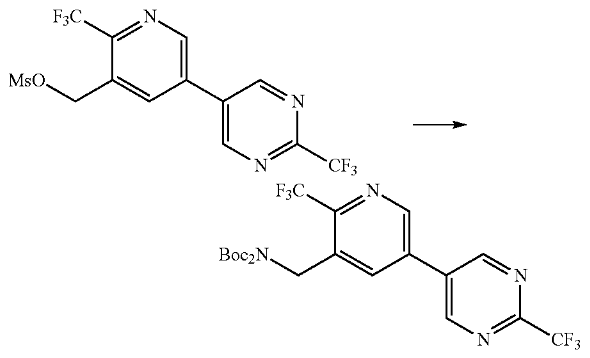

Potassium bis(Boc)amide (865 mg, 3.39 mmol, 1.5 equiv.) was added to a mixture of [2-(trifluoromethyl)-5-[2-(trifluoromethyl)pyrimidin-5-yl]-3-pyridyl]methyl methanesulfonate (907 mg, 2.26 mmol, 1.0 equiv.) and sodium iodide (359 mg, 2.37 mmol, 1.05 equiv.) in THF (15 mL). The reaction was stirred at rt overnight. The reaction mixture was partitioned in water/iPrOAc and extracted with iPrOAc (3×). The combined organic extracts were washed with water and brine and they were dried over $MgSO_4$, filtered and concentrated. The residue was purified by a silica gel column eluting with iPrOAc/heptane (0-40%) to afford the title compound (838 mg, 71%) as a white foam. LCMS [M+H+] 522.

Step 5: Preparation of (2-(trifluoromethyl)-5-(2-(trifluoromethyl)pyrimidin-5-yl)pyridin-3-yl)methanamine hydrochloride

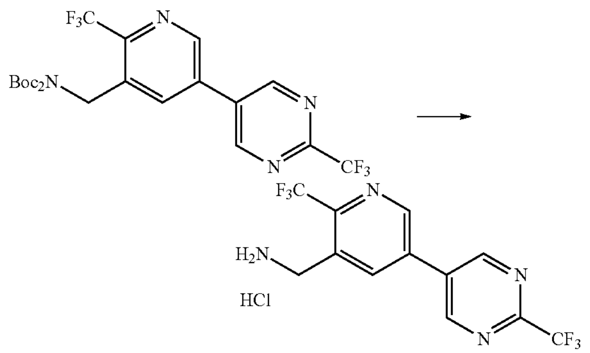

Tert-butyl N-tert-butoxycarbonyl-N-[[2-(trifluoromethyl)-5-[2-(trifluoromethyl)pyrimidin-5-yl]-3-pyridyl]methyl]carbamate (838 mg, 1.60 mmol, 1.0 equiv.) was stirred in HCl (4 N in 1,4-dioxane) (8.02 mL, 32.08 mmol, 20 equiv.) at rt overnight. The reaction mixture was concentrated under vacuum to afford the title compound (575 mg, 100%) as a crude white foam. The crude product was used as-is. LCMS [M+H+] 323.

Preparation 49: (2S,3R,55)-tert-butyl 3-fluoro-5-(((5-fluoro-4-(5-(trifluoromethyl)thiazol-2-yl)pyridin-2-yl)methyl)carbamoyl)-2-methylpyrrolidine-1-carboxylate

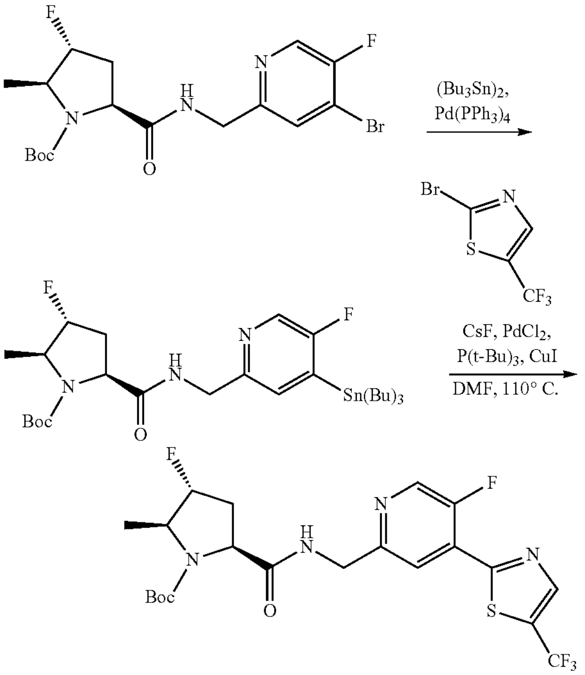

Step 1: Preparation of (2S,3R,5S)-tert-butyl 3-fluoro-5-(((5-fluoro-4-(tributylstannyl)pyridin-2-yl)methyl)carbamoyl)-2-methylpyrrolidine-1-carboxylate

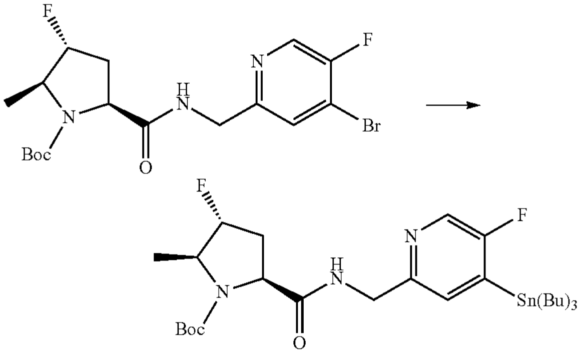

(2S,3R,5S)-tert-butyl 5-(((4-bromo-5-fluoropyridin-2-yl)methyl)carbamoyl)-3-fluoro-2-methylpyrrolidine-1-carboxylate (1 g, 2.3 mmol, 1 eq), bis(tributyltin) (3.5 mL, 6.9 mmol, 3 eq) and $Pd(PPh_3)_2Cl_2$ (162 mg, 0.23 mmol, 0.1 eq) were dissolved in toluene (12 mL) and allowed to stir at 100° C. After 3 h, another 0.1 eq of $Pd(PPh_3)_2Cl_2$ was added.

After another 5 h, the material was purified by flash chromatography (0→100% iPrOAc/heptanes) to give the product (1.5 g, 73%).

Step 2: Preparation of (2S,3R,55)-tert-butyl 3-fluoro-5-(((5-fluoro-4-(5-(trifluoromethyl)thiazol-2-yl)pyridin-2-yl)methyl)carbamoyl)-2-methylpyrrolidine-1-carboxylate

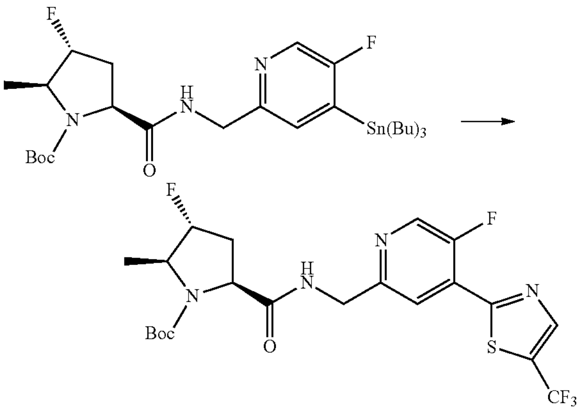

(2S,3R,5S)-tert-butyl 3-fluoro-5-(((5-fluoro-4-(tributylstannyl)pyridin-2-yl)methyl)carbamoyl)-2-methylpyrrolidine-1-carboxylate (200 mg, 0.3 mmol, 1 eq) and 2-bromo-5-(trifluoromethyl)thiazole (72 mg, 0.3 mmol, 1 eq) were dissolved in DMF (0.5 mL). CsF (94 mg, 0.6 mmol, 2 eq), then $PdCl_2$ (5.6 mg, 0.03 mmol, 0.1 eq), then tri-tertbutylphosphine (0.06 mL, 1M, 0.2 eq), and CuI (12 mg, 0.06 mmol, 0.2 eq) were added. The reaction was heated to 110° C. for 30 min. The reaction was diluted with water and DCM and extracted 2× with DCM and then concentrated. The residue was purified via flash chromatography (0→100% iPrOAc/heptanes) to give the product (82 mg, 52%).

Preparation 50: (5-fluoro-2-(2-(trifluoromethyl)pyrimidin-5-yl)pyridin-4-yl)methyl methanesulfonate

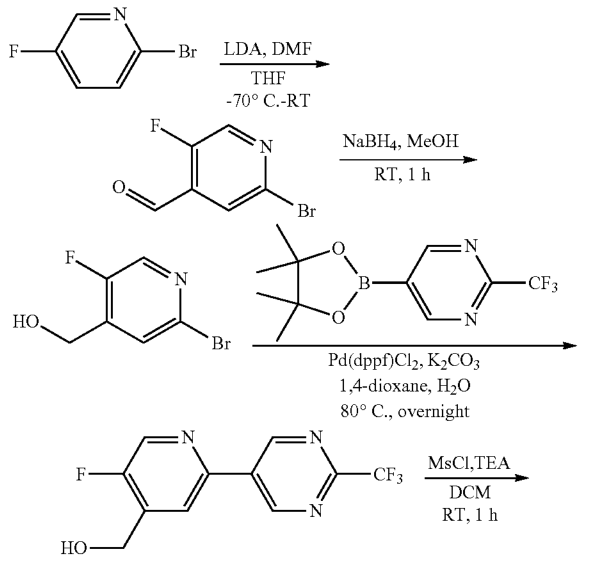

-continued

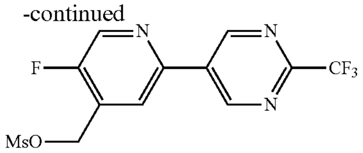

Step 1: Preparation of 2-bromo-5-fluoroisonicotinaldehyde

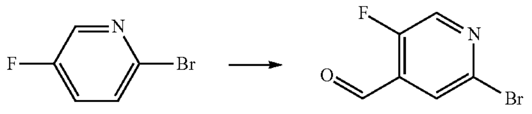 [SMILES: Fc1ccc(Br)nc1 ; O=Cc1cc(Br)ncc1F]

Into a 2-L 4-necked round-bottom flask purged and maintained with an inert atmosphere of nitrogen was placed 2-bromo-5-fluoropyridine (95 g, 539.82 mmol, 1.00 equiv) and tetrahydrofuran (950 mL) followed by the addition of LDA (2 M in tetrahydrofuran) (326 mL) dropwise with stirring at −70° C. The resulting solution was stirred at −70° C. for 1 h. To this mixture was added N,N-dimethylformamide (81 g, 1.11 mol, 2.00 equiv) at −70° C. The reaction was warmed to room temperature, quenched by the addition of 950 mL of water, and extracted with 3×700 mL of ethyl acetate. The combined organic layers were washed with 3×700 mL of brine, dried over anhydrous sodium sulfate, and concentrated under vacuum. The precipitates were collected by filtration and dried to afford 80 g (73%) of 2-bromo-5-fluoropyridine-4-carbaldehyde as a white solid.

Step 2: Preparation of (2-bromo-5-fluoropyridin-4-yl)methanol

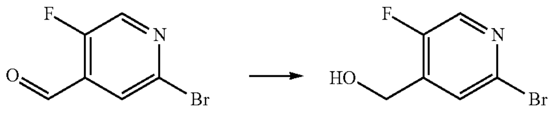 [SMILES: O=Cc1cc(Br)ncc1F ; OCc1cc(Br)ncc1F]

Into a 2-L 4-necked round-bottom flask, was placed 2-bromo-5-fluoropyridine-4-carbaldehyde (80 g, 392.16 mmol, 1.00 equiv) and methanol (800 mL) followed by the addition of $NaBH_4$ (18 g, 475.81 mmol, 1.20 equiv) in portions at 0° C. The resulting solution was stirred at room temperature for 1 h, quenched by the addition of 800 mL of water, concentrated under vacuum, and filtered. The filter cake was dried in an oven under reduced pressure to afford 61 g (76%) of (2-bromo-5-fluoropyridin-4-yl)methanol as a white solid.

Step 3: Preparation of (5-fluoro-2-(2-(trifluoromethyl)pyrimidin-5-yl)pyridin-4-yl)methanol

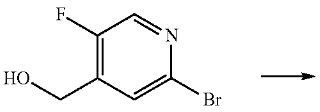

-continued

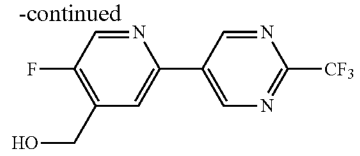

Into a 2-L 4-necked round-bottom flask purged and maintained with an inert atmosphere of nitrogen was placed (2-bromo-5-fluoropyridin-4-yl)methanol (60 g, 291.25 mmol, 1.00 equiv), 1,4-dioxane (900 mL), water (90 mL), $K_2CO_3$ (120.6 g, 866.30 mmol, 3.00 equiv), 5-(tetramethyl-1,3,2-dioxaborolan-2-yl)-2-(trifluoromethyl)pyrimidine (96 g, 350.30 mmol, 1.20 equiv), and Pd(dppf)$Cl_2$ (21.3 g, 29.11 mmol, 0.10 equiv). The resulting solution was stirred at 80° C. overnight and concentrated under vacuum. The residue was applied onto a silica gel column eluted with ethyl acetate/petroleum ether (0:1-2:3). The crude product was washed with 1×300 mL of hexane and dried to afford 79 g (crude) of [5-fluoro-2-[2-(trifluoromethyl)pyrimidin-5-yl]pyridin-4-yl]methanol as a white solid.

Step 4: Preparation of (5-fluoro-2-(2-(trifluoromethyl)pyrimidin-5-yl)pyridin-4-yl)methyl methanesulfonate

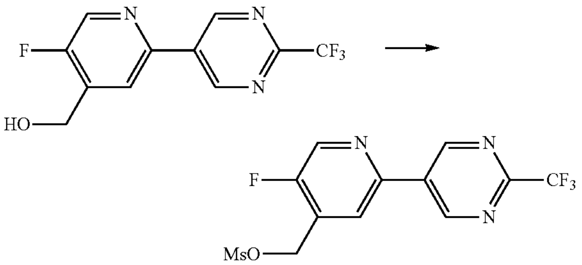

Into a 2-L 4-necked round-bottom flask, was placed [5-fluoro-2-[2-(trifluoromethyl)pyrimidin-5-yl]pyridin-4-yl]methanol (75 g, 274.54 mmol, 1.00 equiv), dichloromethane (750 mL), and TEA (83.2 g, 822.22 mmol, 3.00 equiv) followed by the addition of methanesulfonyl chloride (47.1 g, 411.17 mmol, 1.50 equiv) dropwise with stirring at 0° C. The resulting solution was stirred at room temperature for 1 h, quenched by the addition of 750 mL of water, and extracted with 3×250 mL of dichloromethane. The combined organic layers were washed with 3×500 mL of brine, dried over anhydrous sodium sulfate. and concentrated under vacuum. The residue was washed with 1×240 mL of methanol and collected by filtration. The filter cake was dried to afford 36 g (37%) of [5-fluoro-2-[2-(trifluoromethyl)pyrimidin-5-yl]pyridin-4-yl]methyl methanesulfonate as a white solid.

Preparation 51: [2-(difluoromethyl)-5-[2-(trifluoromethyl)pyrimidin-5-yl]pyridin-3-yl]methanamine

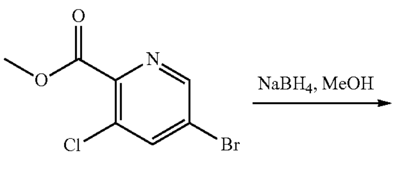

-continued

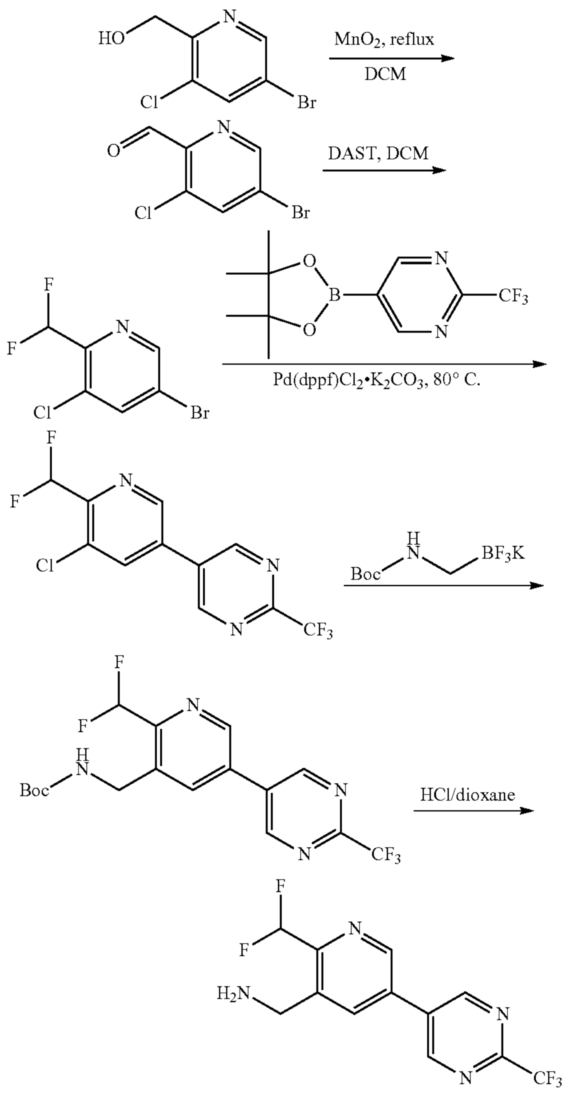

Step 1: Preparation of (5-bromo-3-chloropyridin-2-yl)methanol

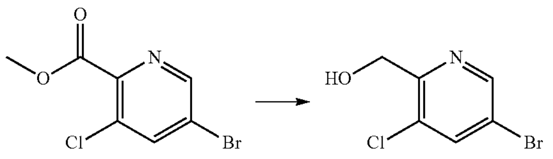

$NaBH_4$ (6 g, 158.52 mmol, 3.97 equiv) was added to a solution of methyl 5-bromo-3-chloropyridine-2-carboxylate (10 g, 39.92 mmol, 1.00 equiv) in methanol (150 mL) at 0° C. The reaction was stirred for 3 h at 0° C. The reaction was then quenched by water, diluted with ethyl acetate, washed with saturated sodium bicarbonate and brine, dried over anhydrous sodium sulfate, and concentrated under vacuum. This resulted in the title compound (8.9 g, crude) as a light yellow solid. LCMS [M+H$^+$] 224.

Step 2: Preparation of 5-bromo-3-chloropyridine-2-carbaldehyde

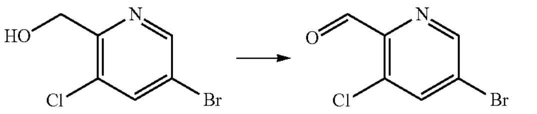 [SMILES: OCc1ncc(Br)cc1Cl ; O=Cc1ncc(Br)cc1Cl]

A mixture of (5-bromo-3-chloropyridin-2-yl)methanol (2 g, 8.99 mmol, 1.00 equiv), $MnO_2$ (7.77 g, 89.34 mmol, 9.94 equiv), and dichloromethane (150 mL) was stirred for overnight at 40° C. The solids were filtrated out and the filtrate was concentrated. The residue was purified by a silica gel column eluting with ethyl acetate/petroleum ether (1/20) to afford the title compound (1.1 g, 56%) as a light yellow solid. LCMS [M+H$^+$] 222.

Step 3: Preparation of 5-bromo-3-chloro-2-(difluoromethyl)pyridine

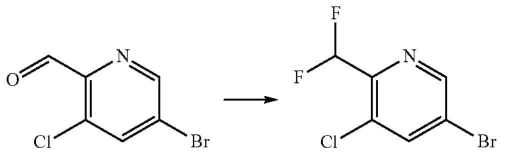 [SMILES: O=Cc1ncc(Br)cc1Cl ; FC(F)c1ncc(Br)cc1Cl]

DAST (2.39 g, 14.85 mmol, 2.98 equiv) was added dropwise into a solution of 5-bromo-3-chloropyridine-2-carbaldehyde (1.1 g, 4.99 mmol, 1.00 equiv) in dichloromethane (100 mL) under nitrogen at 0° C. The resulting solution was stirred for 1 h at room temperature. The reaction was then quenched by saturated sodium bicarbonate, extracted with ethyl acetate, dried over anhydrous sodium sulfate, and concentrated under vacuum. The residue was purified by a silica gel column eluting with ethyl acetate/petroleum ether (1/20). This resulted in the title compound (900 mg, 74%) as colorless oil. LCMS [M+H$^+$] 244.

Step 4: Preparation of 5-[5-chloro-6-(difluoromethyl)pyridin-3-yl]-2-(trifluoromethyl)pyrimidine

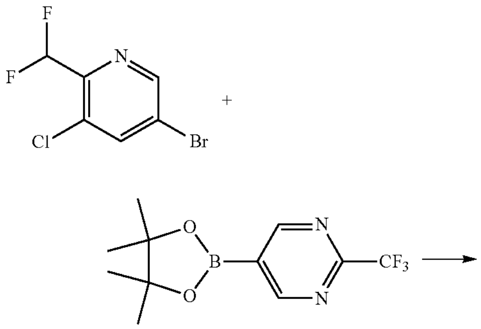

-continued

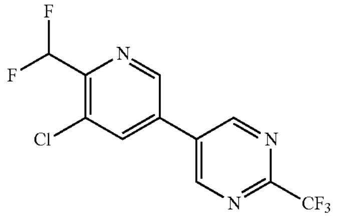

A mixture of 5-bromo-3-chloro-2-(difluoromethyl)pyridine (1 g, 4.13 mmol, 1.00 equiv), Pd(dppf)$Cl_2$ (60 mg, 0.08 mmol, 0.02 equiv), potassium carbonate (1.7 g, 12.30 mmol, 2.98 equiv), 5-(tetramethyl-1,3,2-dioxaborolan-2-yl)-2-(trifluoromethyl)pyrimidine (1.345 g, 4.91 mmol, 1.19 equiv), and dioxane (50 mL) was stirred for 2 h at 80° C. under nitrogen. The resulting mixture was concentrated under vacuum. The residue was purified by a silica gel column eluting with ethyl acetate/petroleum ether (1/10). This resulted in the title compound (850 mg, 67%) as a white solid. LCMS [M+H$^+$] 310.

Step 5: Preparation of tert-butyl N-[[2-(difluoromethyl)-5-[2-(trifluoromethyl)pyrimidin-5-yl]pyridin-3-yl]methyl]carbamate

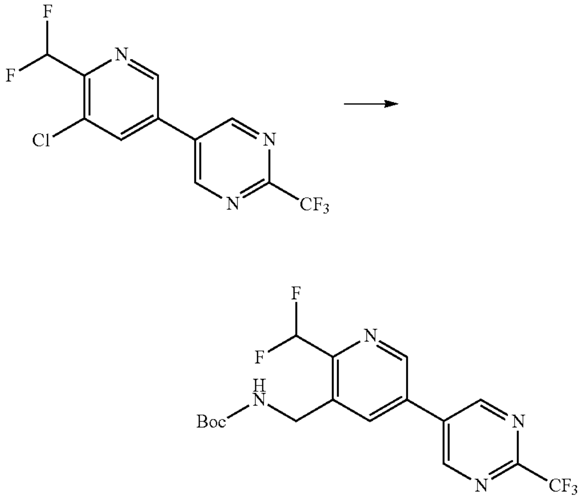

A mixture of 5-[5-chloro-6-(difluoromethyl)pyridin-3-yl]-2-(trifluoromethyl)pyrimidine (680 mg, 2.20 mmol, 1.00 equiv), potassium tert-butyl N-[(trifluoroboranuidyl)methyl]carbamate (2.599 g, 10.96 mmol, 4.99 equiv), 3$^{rd}$ generation SPhos precatalyst (342 mg, 0.44 mmol, 0.20 equiv), SPhos (180 mg, 0.44 mmol, 0.20 equiv), and $Cs_2CO_3$ (1.430 g, 4.39 mmol, 2.00 equiv) in ethanol/water (10 mL/5 mL) was stirred for overnight at 90° C. under nitrogen. The resulting mixture was concentrated under vacuum. The residue was purified by a silica gel column eluting with ethyl acetate/petroleum ether (1/2) to afford the title compound (80 mg, 9%) as yellow oil. LCMS [M+H$^+$] 405.

Step 6: Preparation of [2-(difluoromethyl)-5-[2-(trifluoromethyl)pyrimidin-5-yl]pyridin-3-yl]methanamine

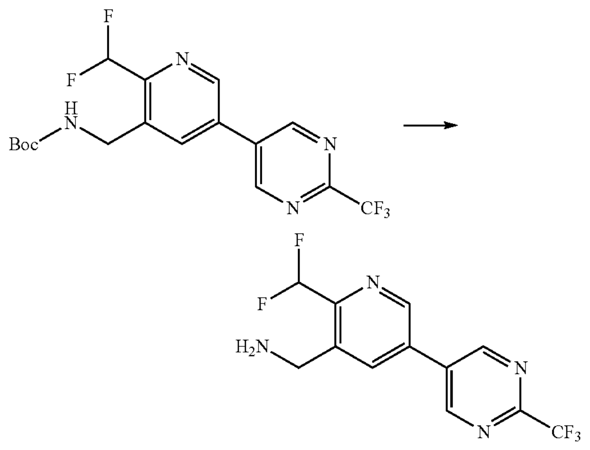

A mixture of tert-butyl N-[[2-(difluoromethyl)-5-[2-(trifluoromethyl)pyrimidin-5-yl]pyridin-3-yl]methyl]carbamate (80 mg, 0.20 mmol, 1.00 equiv), 4N HCl (g) in 1,4-dioxane (15 mL) was stirred for 12 h at room temperature. The resulting mixture was concentrated under vacuum to afford the title compound (60 mg, crude) as a brown solid. LCMS [M+H$^+$] 305.

Example 93: (2S,4R,5 S)-4-fluoro-1-(4-fluorophenyl)sulfonyl-N-[[5-fluoro-2-[2-(trifluoromethyl)thiazol-5-yl]-4-pyridyl]methyl]-5-methyl-pyrrolidine-2-carboxamide

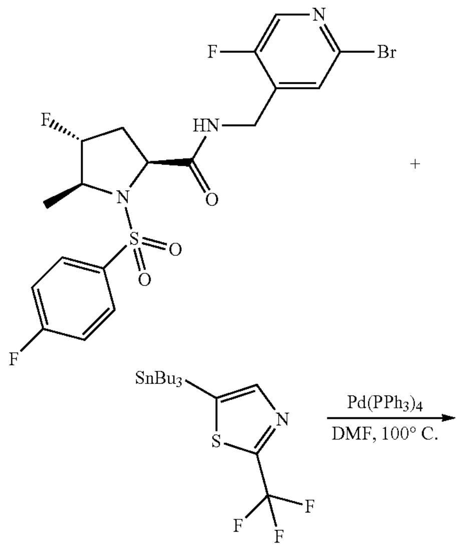

-continued

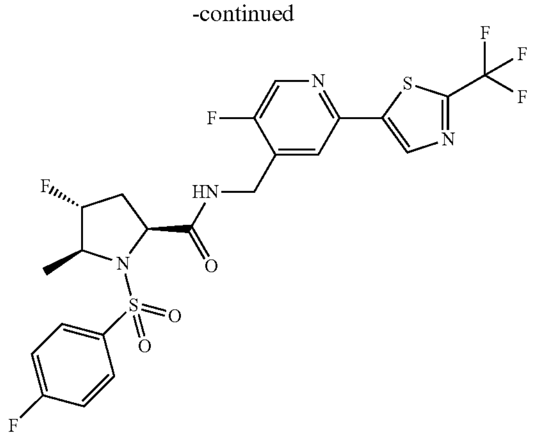

Step 1: Preparation of (2S,4R,5S)-4-fluoro-1-(4-fluorophenyl)sulfonyl-N-[[5-fluoro-2-[2-(trifluoromethyl)thiazol-5-yl]-4-pyridyl]methyl]-5-methyl-pyrrolidine-2-carboxamide

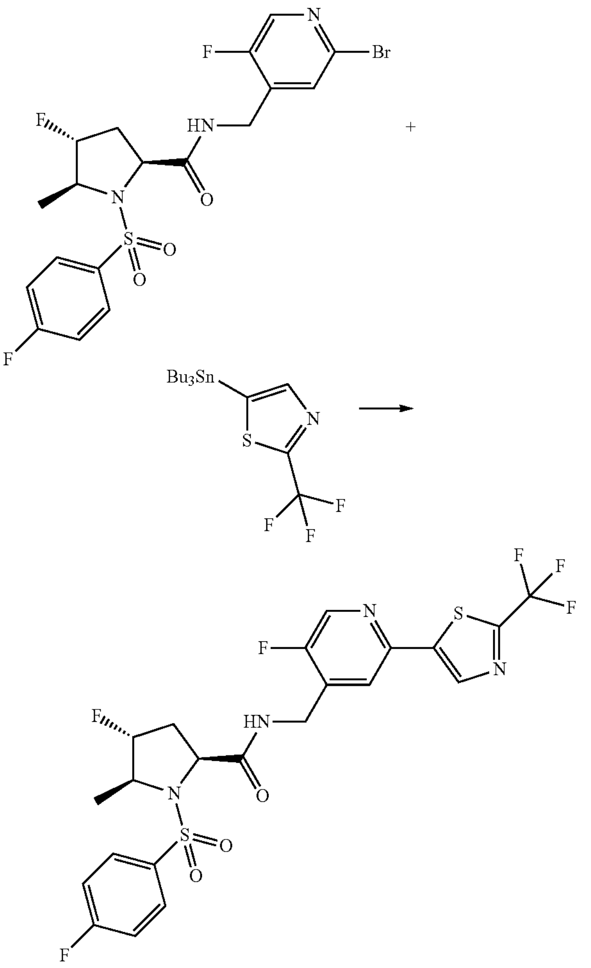

5-(tributylstannyl)-2-(trifluoromethyl)thiazole (135 mg, 0.3 mmol, 1.5 eq), (2S,4R,5S)—N-((2-bromo-5-fluoropyridin-4-yl)methyl)-4-fluoro-1-fluorophenyl)sulfonyl)-5-methylpyrrolidine-2-carboxamide (100 mg, 0.2 mmol, 1 eq)

and palladium tetrakis(triphenylphosphine) (70 mg, 0.06 mmol, 0.3 eq) were dissolved in DMF (2 mL) in a microwave vial and heated in a microwave to 100° C. for 60 min. The solution was filtered over celite and purified by HPLC to give the final product (115 mg, 41%). LCMS [M+H$^+$] 565.1. $^1$H NMR (400 MHz, DMSO-$d_6$) δ 9.04 (t, J=6.0 Hz, 1H), 8.71-8.51 (m, 2H), 8.17 (d, J=5.8 Hz, 1H), 8.13-8.01 (m, 2H), 7.62-7.38 (m, 2H), 5.02-4.79 (m, 1H), 4.69-4.34 (m, 2H), 4.25 (dd, J=10.1, 7.1 Hz, 1H), 4.06-3.85 (m, 1H), 2.45-2.02 (m, 2H), 1.22 (d, J=6.9 Hz, 3H).

Example 94: (2S,4R,5S)-4-fluoro-N-[[5-fluoro-2-[1-(2,2,3,3,3-pentafluoropropyl)-4-piperidyl]-4-pyridyl]methyl]-1-(4-fluorophenyl)sulfonyl-5-methyl-pyrrolidine-2-carboxamide

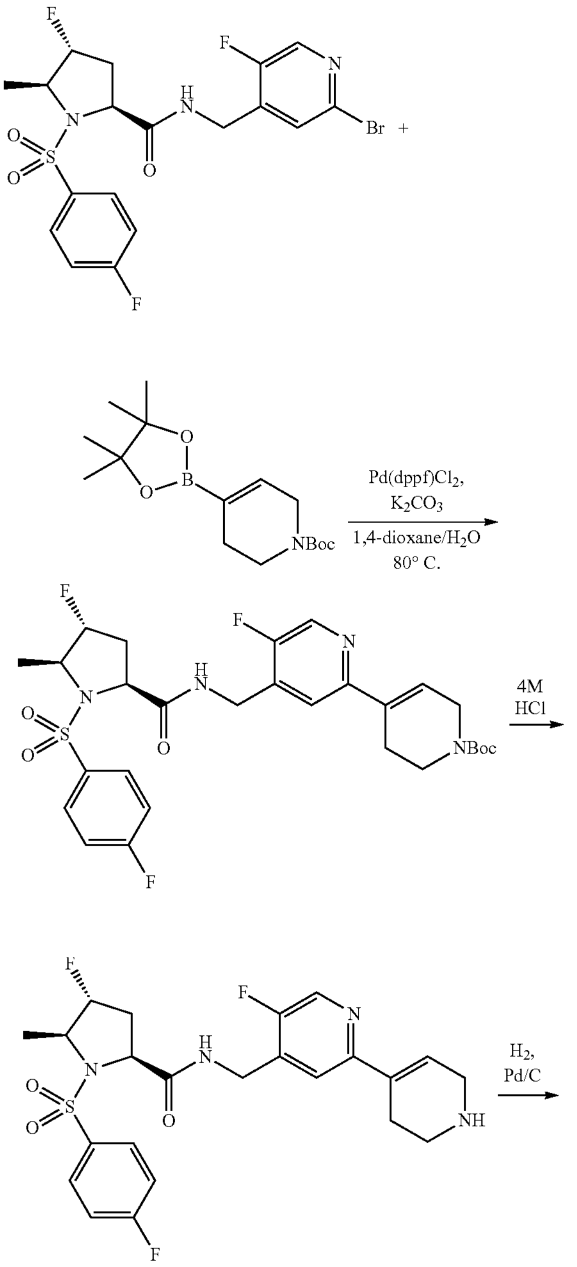

-continued

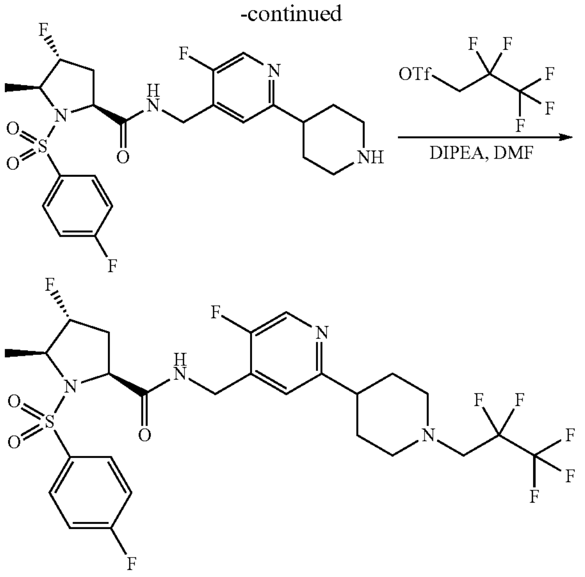

Step 1: Preparation of tert-butyl 5-fluoro-4-(((2S,4R,5S)-4-fluoro-1-((4-fluorophenyl)sulfonyl)-5-methylpyrrolidine-2-carboxamido)methyl)-5',6'-dihydro-[2,4'-bipyridine]-1'(2'H)-carboxylate

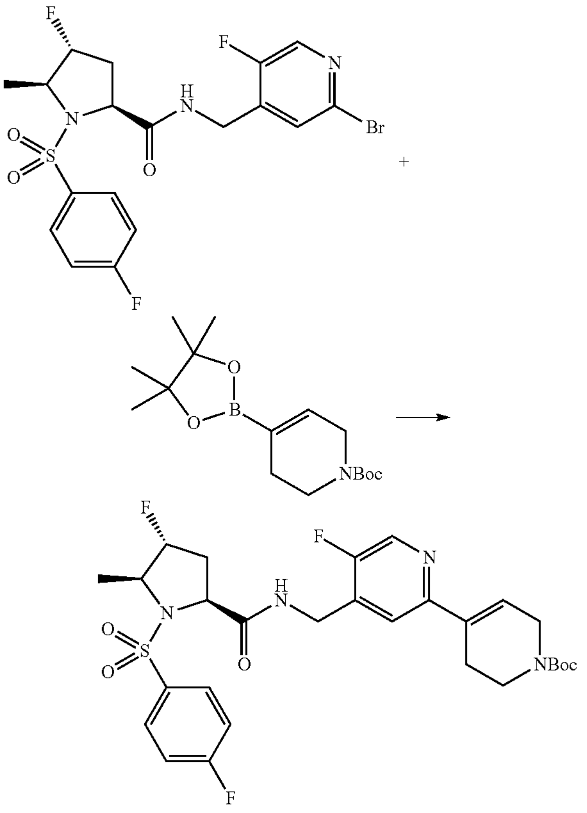

(2S,4R,5 S)—N-((2-bromo-5-fluoropyridin-4-yl)methyl)-4-fluoro-1-fluorophenyl)sulfonyl)-5-methylpyrrolidine-2-carboxamide (390 mg, 0.8 mmol, 1 eq), tert-butyl 4-(4,4,5,5-tetramethyl-1,3,2-dioxaborolan-2-yl)-5,6-dihydropyridine-1(2H)-carboxylate (270 mg, 0.9 mmol, 1.1 eq), Pd(dppf)$Cl_2$, (67 mg, 0.08 mmol, 0.1 eq) and $K_2CO_3$ (330 mg, 2.4 mmol, 3 eq) were weighed into a microwave vial and dioxane (4 mL) and water (2 mL) added. The reaction was heated in the microwave at 80° C. for 30 min. Water was added to the reaction and the solution was extracted 2× with iPrOAc, dried over $Na_2SO_4$, filtered and concentrated. The residue was purified by flash chromatography (0→10% MeOH/DCM) to give the product (344 mg, 72%).

Step 2: Preparation of (2S,4R,5S)-4-fluoro-N-((5-fluoro-1',2',3',6'-tetrahydro-[2,4'-bipyridin]-4-yl) methyl)-1-((4-fluorophenyl)sulfonyl)-5-methylpyrrolidine-2-carboxamide

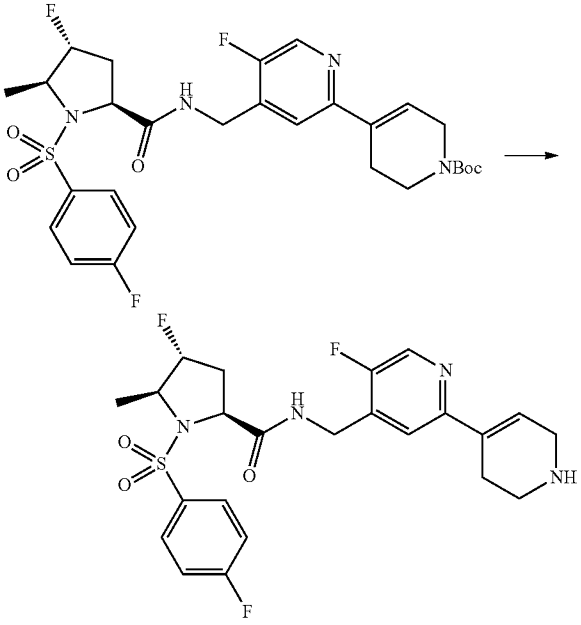

tert-butyl 5-fluoro-4-(((2S,4R,5 S)-4-fluoro-1-((4-fluorophenyl)sulfonyl)-5-methylpyrrolidine-2-carboxamido) methyl)-5',6'-dihydro-[2,4'-bipyridine]-1'(2'H)-carboxylate (344 mg, 0.58 mmol, 1 eq) was dissolved in dioxane (3 mL) and HCl (1.5 mL, 4 M in dioxane) was added dropwise. After 2 h, the reaction was complete and a precipitate had formed. The reaction was concentrated and carried on to the next step crude.

Step 3: Preparation of (2S,4R,5S)-4-fluoro-N-((5-fluoro-2-(piperidin-4-yl)pyridin-4-yl)methyl)-1-((4-fluorophenyl)sulfonyl)-5-methylpyrrolidine-2-carboxamide

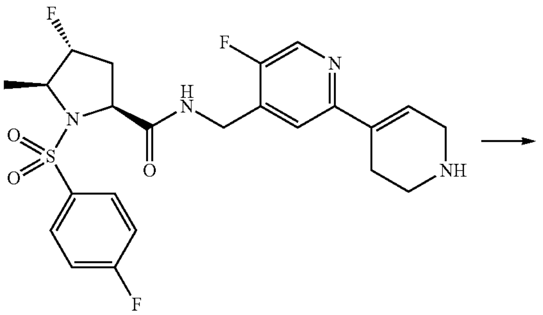

-continued

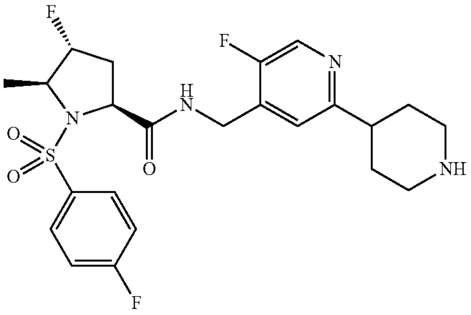

(2S,4R,5S)-4-fluoro-N-((5-fluoro-1',2',3',6'-tetrahydro-[2,4'-bipyridin]-4-yl)methyl)-1-((4-fluorophenyl)sulfonyl)-5-methylpyrrolidine-2-carboxamide (230 mg, 0.47 mmol) was dissolved in MeOH (3.5 mL). Pd/C (approx. 50 mg) was added followed by 4 M HCl in dioxane (0.06 mL) and the reaction was affixed with a balloon of hydrogen and allowed to stir for 48 h. The solution was filtered over celite and carried on crude.

Step 4: Preparation of (2S,4R,5S)-4-fluoro-N-((5-fluoro-2-(1-(2,2,3,3,3-pentafluoropropyl)piperidin-4-yl)pyridin-4-yl)methyl)-1-((4-fluorophenyl)sulfonyl)-5-methylpyrrolidine-2-carboxamide

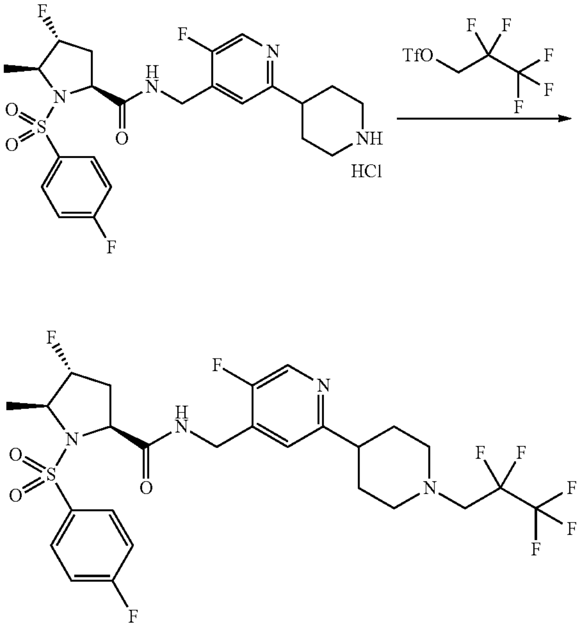 [SMILES: C[C@H]1[C@H](F)C[C@@H](C(=O)NCc2cc(C3CCNCC3)ncc2F)N1S(=O)(=O)c1ccc(F)cc1 ; Cl ; O=S(=O)(OCC(F)(F)C(F)(F)F)C(F)(F)F ; C[C@H]1[C@H](F)C[C@@H](C(=O)NCc2cc(C3CCN(CC(F)(F)C(F)(F)F)CC3)ncc2F)N1S(=O)(=O)c1ccc(F)cc1]

(2S,4R,5S)-4-fluoro-N-((5-fluoro-2-(piperidin-4-yl)pyridin-4-yl)methyl)-1-((4-fluorophenyl)sulfonyl)-5-methylpyrrolidine-2-carboxamide (35 mg, 0.065 mmol, 1 eq) was dissolved in DMF (0.3 mL). 2,2,3,3,3-pentafluoropropyl trifluoromethanesulfonate (38 mg, 0.13 mmol, 2 eq) was added, followed by diisopropylethylamine (42 mg, 0.33 mmol, 5 eq) and the reaction was allowed to stir for 24 h. The solution was purified by HPLC to give the final product (7.2 mg, 18%). LCMS [M+$H^+$] 629.2.

Example 100: (2S,4R,5 S)-4-fluoro-1-fluorophenyl) sulfonyl)-5-methyl-N-((5-methyl-2-(2-(trifluoromethyl)pyrimidin-5-yl)pyridin-4-yl)methyl)pyrrolidine-2-carboxamide

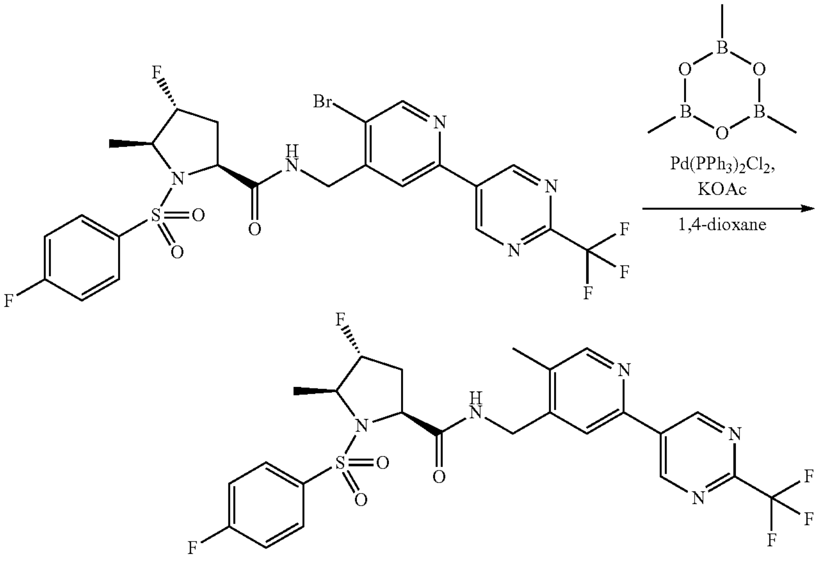

Step 1: Preparation of (2S,4R,5S)-4-fluoro-1-((4-fluorophenyl)sulfonyl)-5-methyl-N-((5-methyl-2-(2-(trifluoromethyl)pyrimidin-5-yl)pyridin-4-yl)methyl) pyrrolidine-2-carboxamide

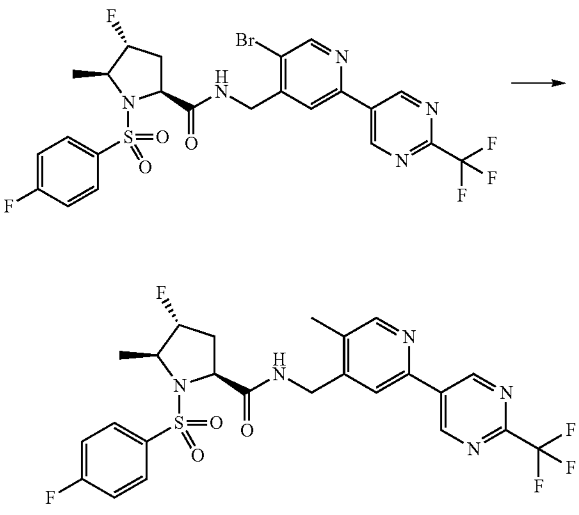

(2S,4R,5S)—N-((5-bromo-2-(2-(trifluoromethyl)pyrimidin-5-yl)pyridin-4-yl)methyl)-4-fluoro-1-((4-fluorophenyl) sulfonyl)-5-methylpyrrolidine-2-carboxamide (30 mg, 0.05 mmol, 1 eq), trimethylboroxine (9 mg, 0.07 mmol, 1.5 eq), $Pd(PPh_3)_2Cl_2$ (4 mg, 0.005 mmol, 0.1 eq) and KOAc (14 mg, 0.15 mmol, 3 eq) were dissolved in dioxane (1.2 mL) and water (0.3 mL), then heated at 100° C. for 20 h. The solution was purified by HPLC to give the final product (4.6 mg, 17%). LCMS [M+H$^+$] 556.2. NMR (400 MHz, DMSO-$d_6$) δ 9.63 (s, 2H), 8.95 (t, J=5.9 Hz, 1H), 8.66-8.52 (m, 1H), 8.13 (s, 1H), 8.10-7.97 (m, 2H), 7.57-7.37 (m, 2H), 4.90 (dd, J=51.4, 2.9 Hz, 1H), 4.45 (ddd, J=66.2, 16.9, 5.8 Hz, 2H), 4.27 (dd, J=10.1, 7.1 Hz, 1H), 4.05-3.85 (m, 1H), 2.37 (s, 5H), 1.21 (d, J=6.9 Hz, 3H).

Example 102: (2S,4R,5S)-4-fluoro-1-(4-fluorophenylsulfonyl)-5-methyl-N-((5-(trifluoromethyl)-2-(2-(trifluoromethyl)pyrimidin-5-yl)pyridin-4-yl)methyl) pyrrolidine-2-carboxamide

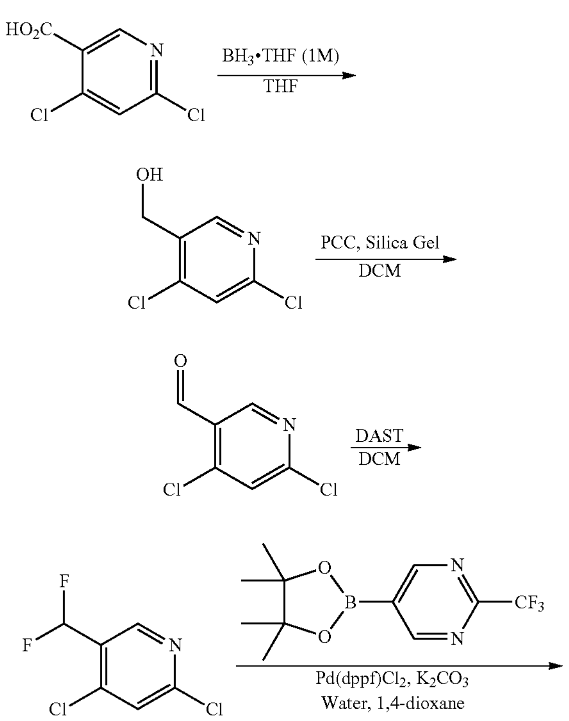

-continued

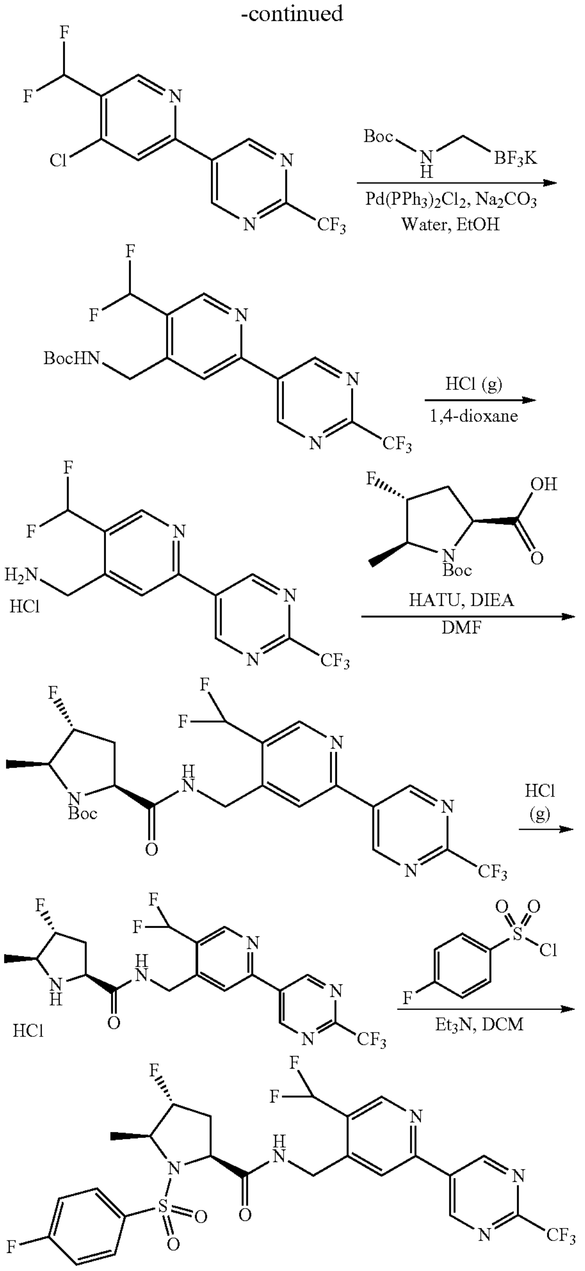

Step 1: Preparation of (4,6-dichloropyridin-3-yl)methanol

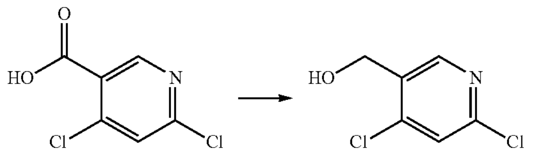 [SMILES: O=C(O)c1cnc(Cl)cc1Cl ; OCc1cnc(Cl)cc1Cl]

To a 5000-mL 4-necked round-bottom flask purged and maintained with an inert atmosphere of nitrogen was placed 4,6-dichloropyridine-3-carboxylic acid (95 g, 494.79 mmol, 1.00 equiv) and tetrahydrofuran (1000 mL) followed by the addition of $BH_3$.THF (1 M) (2111 mL, 4.20 equiv) dropwise with stirring at 0° C. The reaction mixture was stirred at 0° C. for 30 min and at room temperature overnight, quenched by the addition of 1000 mL of water/ice, and extracted with 3×1000 mL of ethyl acetate. The combined organic layers were dried over anhydrous sodium sulfate and concentrated under vacuum to afford 78.4 g (89%) of (4,6-dichloropyridin-3-yl)methanol as a white solid.

Step 2: Preparation of 4,6-dichloropyridine-3-carbaldehyde

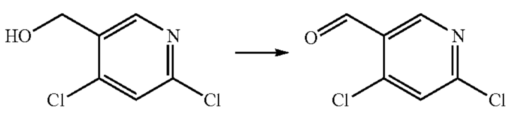 [SMILES: OCc1cnc(Cl)cc1Cl ; O=Cc1cnc(Cl)cc1Cl]

To a 2000-mL 4-necked round-bottom flask purged and maintained with an inert atmosphere of nitrogen was placed (4,6-dichloropyridin-3-yl)methanol (78.4 g, 440.41 mmol, 1.00 equiv), dichloromethane (1000 mL), PCC (284.83 g, 1.32 mol, 3.00 equiv) and Silica gel (235 g). The resulting mixture was stirred at room temperature for 4 h and concentrated under vacuum. The residue was applied onto a silica gel column eluted with ethyl acetate/petroleum ether (0:1-1:6) to afford 62 g (80%) of 4,6-dichloropyridine-3-carbaldehyde as a white solid.

Step 3: Preparation of 2,4-dichloro-5-(difluoromethyl)pyridine

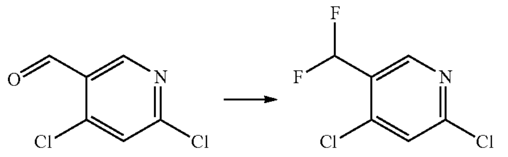 [SMILES: O=Cc1cnc(Cl)cc1Cl ; FC(F)c1cnc(Cl)cc1Cl]

To a 2000-mL 4-necked round-bottom flask purged and maintained with an inert atmosphere of nitrogen was placed 4,6-dichloropyridine-3-carbaldehyde (62 g, 352.27 mmol, 1.00 equiv) and dichloromethane (1000 mL) followed by the addition of DAST (113.7 g, 705.38 mmol, 2.00 equiv) dropwise with stirring at −20° C. The resulting solution was stirred at −20° C. for 30 min and at room temperature for additional 3 h, quenched by the addition of 500 mL of water dropwise with stirring, and extracted with 3×500 mL of dichloromethane. The combined organic layers were dried over anhydrous sodium sulfate and concentrated under vacuum. The residue was applied onto a silica gel column eluted with ethyl acetate/petroleum ether (0:1-1:0) to afford 36 g (52%) of 2,4-dichloro-5-(difluoromethyl)pyridine as a light yellow solid.

Step 4: Preparation of 5-[4-chloro-5-(difluoromethyl)pyridin-2-yl]-2-(trifluoromethyl)pyrimidine

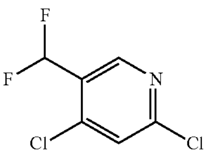

+

-continued

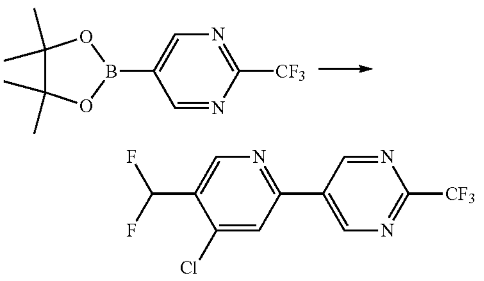

To a 3000-mL 4-necked round-bottom flask purged and maintained with an inert atmosphere of nitrogen was placed 2,4-dichloro-5-(difluoromethyl)pyridine (36 g, 181.82 mmol, 1.00 equiv), 1,4-dioxane (1800 mL), water (180 mL), 5-(tetramethyl-1,3,2-dioxaborolan-2-yl)-2-(trifluoromethyl) pyrimidine (60 g, 218.94 mmol, 1.20 equiv), potassium carbonate (78 g, 564.36 mmol, 3.00 equiv) and Pd(dppf) $Cl_2.CH_2Cl_2$ (15 g, 18 mmol, 0.10 equiv). The resulting solution was stirred at 80° C. overnight and filtered. The filtrate was concentrated under vacuum. The residue was applied onto a silica gel column eluted with ethyl acetate/petroleum ether (0:1-5:95) to afford 28 g (50%) of 5-[4-chloro-5-(difluoromethyl)pyridin-2-yl]-2-(trifluoromethyl) pyrimidine as a white solid.

Step 5: Preparation of tert-butyl N-[[5-(difluoromethyl)-2-[2-(trifluoromethyl)pyrimidin-5-yl]pyridin-4-yl]methyl]carbamate

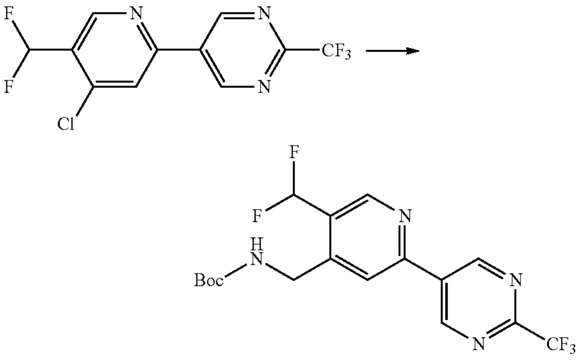

To a 3000-mL 4-necked round-bottom flask purged and maintained with an inert atmosphere of nitrogen was placed 5-[4-chloro-5-(difluoromethyl)pyridin-2-yl]-2-(trifluoromethyl)pyrimidine (20 g, 64.59 mmol, 1.00 equiv), ethanol (2000 mL), water (400 mL), potassium tert-butyl N-[(trifluoro-^4-boranyl)methyl]carbamate (20 g, 84.36 mmol, 1.30 equiv), sodium carbonate (22 g, 207.57 mmol, 3.20 equiv) and $Pd(PPh_3)_2Cl_2$ (5 g, 7.12 mmol, 0.11 equiv). The reaction mixture was first stirred at room temperature for 30 min and at 80° C. overnight and filtered. The filtrate was concentrated under vacuum. The residue was applied onto a silica gel column eluted with ethyl acetate/petroleum ether (0:1-1:6) to afford 14 g (54%) of tert-butyl N-[[5-(difluoromethyl)-2-[2-(trifluoromethyl)pyrimidin-5-yl]pyridin-4-yl]methyl] carbamate as a light yellow solid.

Step 6: Preparation of [5-(difluoromethyl)-2-[2-(trifluoromethyl)pyrimidin-5-yl]pyridin-4-yl]methanamine hydrochloride

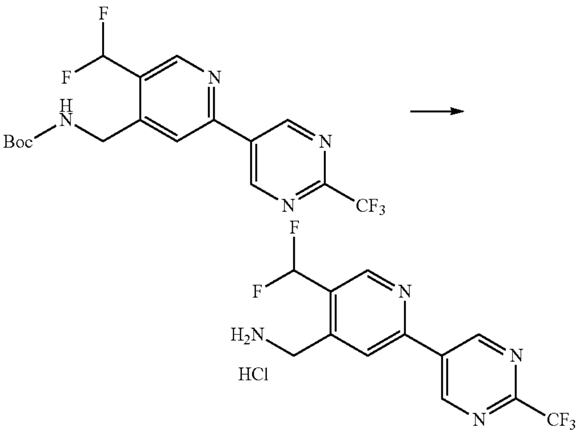

To a 1000-mL 3-necked round-bottom flask purged and maintained with an inert atmosphere of nitrogen was placed tert-butyl N-[[5-(difluoromethyl)-2-[2-(trifluoromethyl)pyrimidin-5-yl]pyridin-4-yl]methyl]carbamate (30 g, 74.20 mmol, 1.00 equiv) and 1,4-dioxane (500 mL). Into the above reaction mixture was introduced HCl (gas). The resulting solution was stirred at room temperature for 3 h, concentrated under vacuum, and filtered. The filter cake were washed with 1x300 mL of EA and dried to afford 20.37 g (81%) of [5-(difluoromethyl)-2-[2-(trifluoromethyl)pyrimidin-5-yl]pyridin-4-yl]methanamine hydrochloride as a yellow solid. LCMS [M+HCl+$H^+$] 305.

Step 7: Preparation of (2S,3R,5S)-tert-butyl 5-((5-(difluoromethyl)-2-(2-(trifluoromethyl)pyrimidin-5-yl)pyridin-4-yl)methylcarbamoyl)-3-fluoro-2-methylpyrrolidine-1-carboxylate

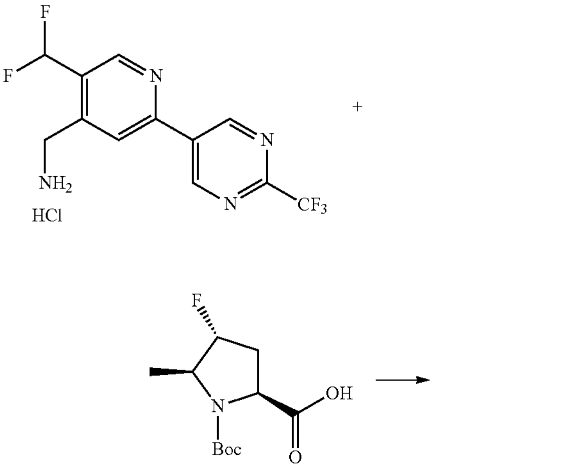

-continued

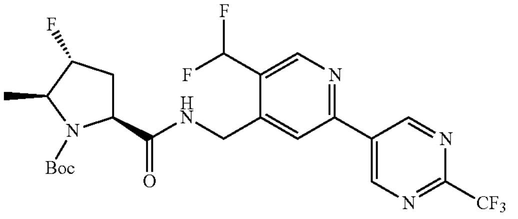

A mixture of (2S,4R,5S)-1-[(tert-butoxy)carbonyl]-4-fluoro-5-methylpyrrolidine-2-carboxylic acid (13.60 g, 55.00 mmol, 1.00 equiv), HATU (31.37 g, 82.50 mmol, 1.50 equiv), DIEA (21.33 g, 165.03 mmol, 3.00 equiv), and [5-(difluoromethyl)-2-[2-(trifluoromethyl)pyrimidin-5-yl]pyridin-4-yl]methanamine hydrochloride (18.74 g, 55.00 mmol, 1.00 equiv) in DMF (150 mL) was stirred for 2 h at room temperature. The resulting solution was diluted with ethyl acetate, washed with brine, dried over anhydrous sodium sulfate, and concentrated under vacuum. The residue was purified by a silica gel column eluting with ethyl acetate/petroleum ether (1/1) to afford the title compound (25 g, 85%) as a white solid. LCMS [M+H$^+$] 534.

Step 8: Preparation of (2S,4R,5S)—N-((5-(difluoromethyl)-2-(2-(trifluoromethyl)pyrimidin-5-yl)pyridin-4-yl)methyl)-4-fluoro-5-methylpyrrolidine-2-carboxamide hydrochloride

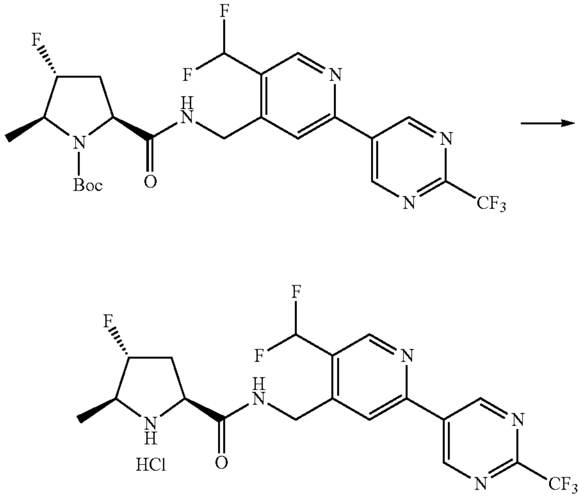

A mixture of tert-butyl N-[[5-(difluoromethyl)-2-[2-(trifluoromethyl)pyrimidin-5-yl]pyridin-4-yl]methyl]carbamate (25 g, 61.83 mmol, 1.00 equiv) and saturated HCl (g) in 1,4-dioxane (500 mL) was stirred for 12 h at room temperature. The resulting mixture was concentrated under vacuum to afford the title compound (20 g, 95%) as a white solid. LCMS [M+H$^+$] 434.

Step 9: Preparation of (2S,4R,5S)—N-((5-(difluoromethyl)-2-(2-(trifluoromethyl)pyrimidin-5-yl)pyridin-4-yl)methyl)-4-fluoro-1-(4-fluorophenylsulfonyl)-5-methylpyrrolidine-2-carboxamide

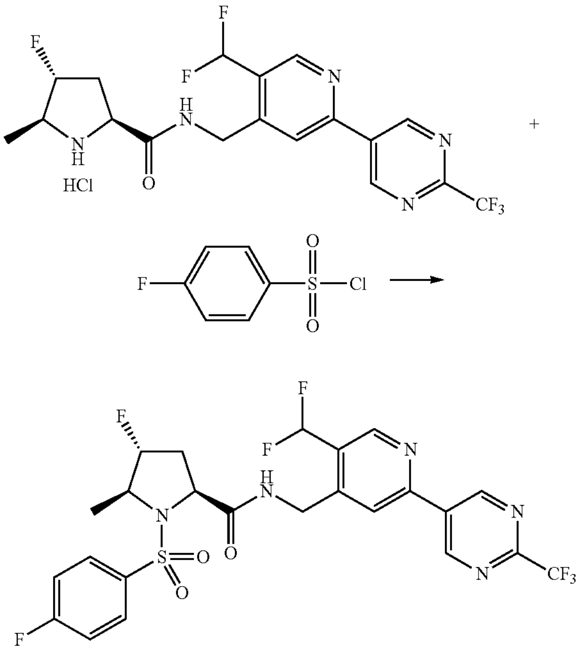

A mixture of (2S,4R,5S)—N-[[5-(difluoromethyl)-2-[2-(trifluoromethyl)pyrimidin-5-yl]pyridin-4-yl]methyl]-4-fluoro-5-methylpyrrolidine-2-carboxamide (22 g, 50.77 mmol, 1.00 equiv), triethylamine (15.5 g, 153.18 mmol, 3.00 equiv), and 4-fluorobenzene-1-sulfonyl chloride (20 g, 102.76 mmol, 2.00 equiv). in dichloromethane (500 mL) was stirred for 2 h at room temperature. The resulting mixture was washed with brine, dried over anhydrous sodium sulfate, and concentrated under vacuum. The residue was purified by a silica gel column eluting with ethyl acetate/petroleum ether (1/1) to afford the title compound (25 g, 82%) as a white solid. LCMS [M+H$^+$] 592. $^1$H NMR (400 MHz, $CDCl_3$) δ 9.70 (s, 2H), 9.01 (s, 1H), 8.38 (s, 1H), 7.94-7.91 (m, 2H), 7.40-7.38 (m, 1H), 7.30-7.26 (m, 1H), 5.24-5.18 (m, 1H), 4.75 (d, J=51.2 Hz, 1H), 4.59-4.54 (m, 1H), 4.35-4.31 (m, 1H), 4.16-4.06 (m, 1H), 2.68-2.58 (m, 1H), 1.41-1.40 (d, J=7.2 Hz, 3H).

Example 103: (2S,4R,5S)-4-fluoro-1-(4-fluorophenylsulfonyl)-5-methyl-N-((5-(trifluoromethyl)-2-(2-(trifluoromethyl)pyrimidin-5-yl)pyridin-4-yl)methyl)pyrrolidine-2-carboxamide

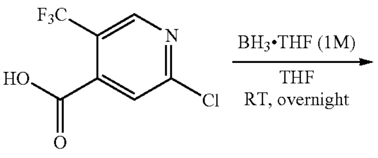

-continued

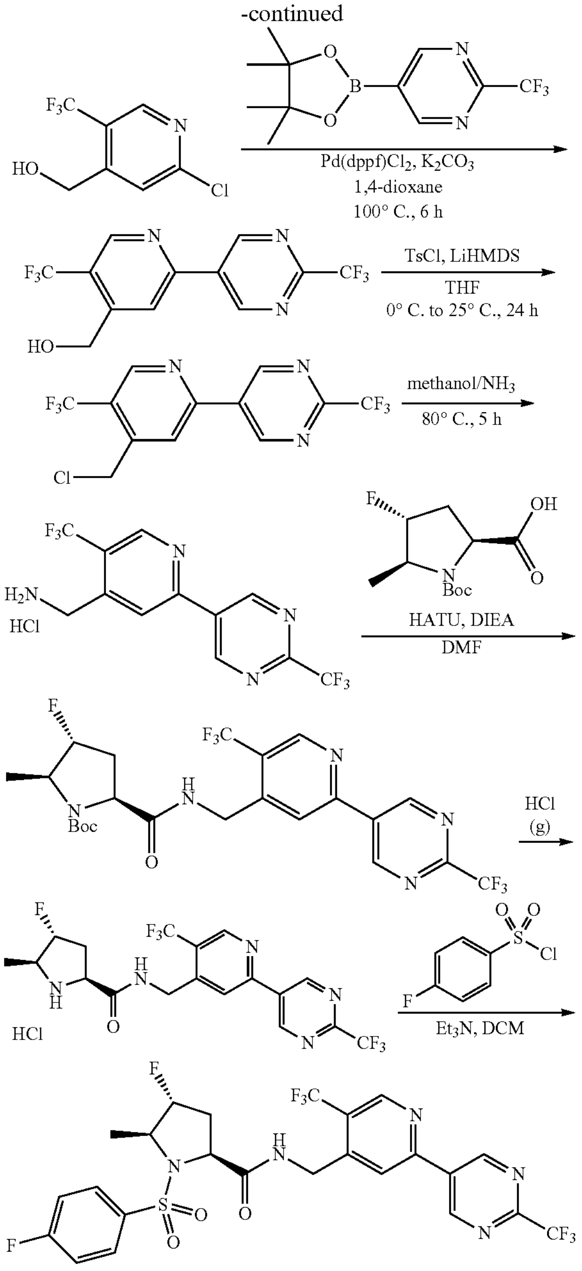

Step 1: Preparation of (2-chloro-5-(trifluoromethyl)pyridin-4-yl)methanol

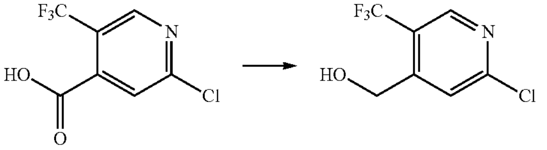 [SMILES: O=C(O)c1cc(Cl)ncc1C(F)(F)F ; OCc1cc(Cl)ncc1C(F)(F)F]

Into a 250-mL 3-necked round-bottom flask purged and maintained with an inert atmosphere of nitrogen was placed a solution of 2-chloro-5-(trifluoromethyl)pyridine-4-carboxylic acid (4.5 g, 19.95 mmol, 1.00 equiv) in tetrahydrofuran (40 mL) followed by the addition of $BH_3$.THF (1 M) (40 mL, 2.00 equiv) dropwise with stirring at 0° C. over 10 min. The resulting solution was stirred at room temperature overnight, quenched by the addition of 10 mL of methanol at 0° C., concentrated under vacuum, and extracted with ethyl acetate. The combined organic layers were washed with brine, dried over sodium sulfate, and concentrated under vacuum. The residue was purified by a silica gel column eluted with ethyl acetate/petroleum ether (1:10) to afford 3 g (crude) of [2-chloro-5-(trifluoromethyl)pyridin-4-yl]methanol as a white solid.

Step 2: Preparation of (5-(trifluoromethyl)-2-(2-(trifluoromethyl)pyrimidin-5-yl)pyridin-4-yl)methanol

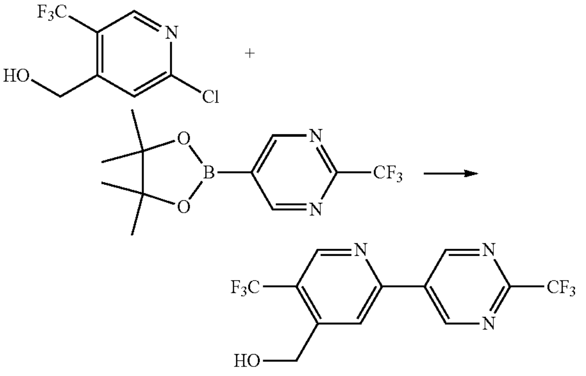

Into a 3-L 3-necked round-bottom flask purged and maintained with an inert atmosphere of nitrogen was placed [2-chloro-5-(trifluoromethyl)pyridin-4-yl]methanol (75.6 g, 357.33 mmol, 1.00 equiv), 1,4-dioxane (1.5 L), 5-(tetramethyl-1,3,2-dioxaborolan-2-yl)-2-(trifluoromethyl)pyrimidine (110 g, 401.39 mmol, 1.20 equiv), $K_2CO_3$ (148 g, 1.06 mol, 3.00 equiv), and Pd(dppf)$Cl_2$ (13 g, 17.77 mmol, 0.05 equiv). The resulting solution was stirred at 100° C. for 6 h under a nitrogen atmosphere, cooled to room temperature, and filtered. The filter cake was washed with 2×300 mL of EA. The filtrate was concentrated under vacuum. The residue was applied onto a silica gel column eluted with ethyl acetate/petroleum ether (1/5-1/2) to afford 90 g (78%) of [5-(trifluoromethyl)-2-[2-(trifluoromethyl)pyrimidin-5-yl]pyridin-4-yl]methanol as a white solid.

Step 3: Preparation of 5-[4-(chloromethyl)-5-(trifluoromethyl)pyridin-2-yl]-2-(trifluoromethyl)pyrimidine

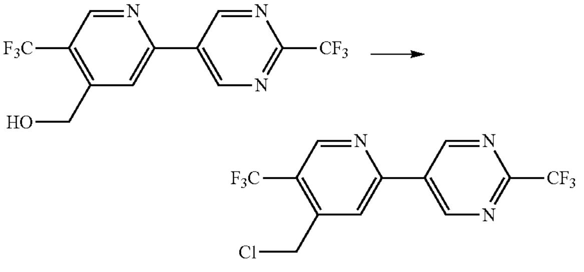

Into a 2-L 3-necked round-bottom flask purged and maintained with an inert atmosphere of nitrogen was placed a solution of [5-(trifluoromethyl)-2-[2-(trifluoromethyl)pyrimidin-5-yl]pyridin-4-yl]methanol (80 g, 247.53 mmol, 1.00 equiv) in tetrahydrofuran (800 mL) followed by the addition of LiHMDS (1 mol/L) (322 mL, 1.30 equiv) dropwise with stirring at 0° C. The mixture was stirred at 0° C. for 1 h. To this mixture was added 4-methylbenzene-1-sulfonyl chloride (61.2 g, 321.01 mmol, 1.30 equiv) in portions at 0° C. under a nitrogen atmosphere. The resulting solution was stirred from 0° C. to 25° C. for 24 h, cooled to 0° C., quenched by the addition of 100 mL of water, and extracted with 3x500 mL of ethyl acetate. The combined organic layers were dried over anhydrous sodium sulfate and concentrated under reduced pressure. The residue was purified by silica gel column chromatography eluted with ethyl acetate/petroleum ether (1/10) to afford 30 g (35%) of 5-[4-(chloromethyl)-5-(trifluoromethyl)pyridin-2-yl]-2-(trifluoromethyl)pyrimidine as a light yellow solid.

Step 4: Preparation of [5-(trifluoromethyl)-2-[2-(trifluoromethyl)pyrimidin-5-yl]pyridin-4-yl]methanamine hydrochloride

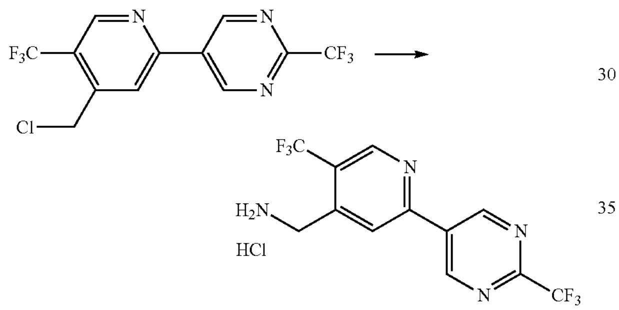

Into a 200-mL sealed tube was placed a solution of 5-[4-(chloromethyl)-5-(trifluoromethyl)pyridin-2-yl]-2-(trifluoromethyl)pyrimidine (20 g, 58.54 mmol, 1.00 equiv) in methanol/$NH_3$ (140 mL). The resulting solution was stirred at 80° C. in an oil bath for 5 h. This reaction was repeated for 2 times. The reaction mixture was cooled to room temperature and concentrated under vacuum. The pH value of the aqueous solution was adjusted to 8 with saturated aqueous sodium bicarbonate. The resulting solution was extracted with 3x300 mL of dichloromethane. The combined organic layers were dried over anhydrous sodium sulfate and concentrated under vacuum. The residue was applied onto a silica gel column eluted with 10% to 30% ethyl acetate in petroleum ether to afford 5-(trifluoromethyl)-2-[2-(trifluoromethyl)pyrimidin-5-yl]pyridin-4-yl] methanamine 33 g as a light yellow solid. The residue was dissolved in 800 mL of ethyl acetate. The product was precipitated by the addition of ethyl acetate/HCl (g). The resulting mixture was concentrated under vacuum. The solids were collected by filtration. The filter cake was washed with 3x2500 mL of ether and dried to afford 31 g (49.5%) of [5-(trifluoromethyl)-2-[2-(trifluoromethyl)pyrimidin-5-yl]pyridin-4-yl]methanamine hydrochloride as a white solid. LCMS [M+H$^+$] 323.

Step 5: Preparation of (2S,3R,5S)-tert-butyl 3-fluoro-2-methyl-5-((5-(trifluoromethyl)-2-(2-(trifluoromethyl)pyrimidin-5-yl)pyridin-4-yl)methylcarbamoyl)pyrrolidine-1-carboxylate

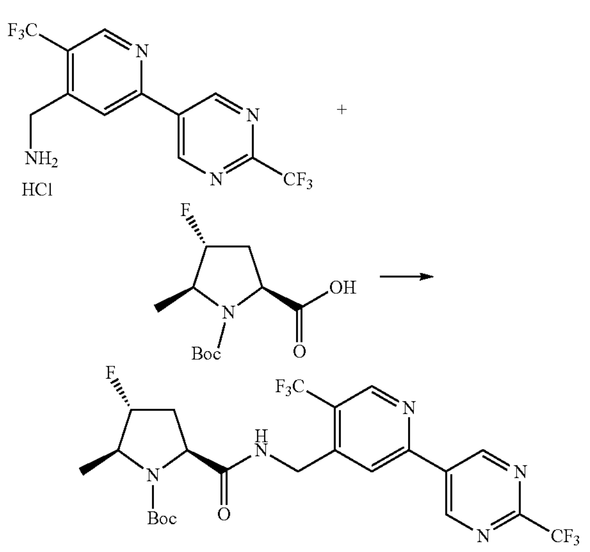

A mixture of (2S,4R,5S)-1-[(tert-butoxy)carbonyl]-4-fluoro-5-methylpyrrolidine-2-carboxylic acid (14 g, 56.62 mmol, 1.00 equiv), HATU (32 g, 84.16 mmol, 1.51 equiv), DIEA (22 g, 170.22 mmol, 3.05 equiv), and [5-(trifluoromethyl)-2-[2-(trifluoromethyl)pyrimidin-5-yl]pyridin-4-yl] methanamine hydrochloride (20 g, 55.76 mmol, 1.00 equiv) in DMF (150 mL) was stirred for 2 h at room temperature. The resulting solution was diluted with ethyl acetate, washed with brine, dried over anhydrous sodium sulfate, and concentrated under vacuum. The residue was purified by a silica gel column eluting with ethyl acetate/petroleum ether (1/1) to afford the title compound (28 g, 91%) as a white solid. LCMS [M+H$^+$] 552.

Step 6: Preparation of (2S,4R,5S)-4-fluoro-5-methyl-N-((5-(trifluoromethyl)-2-(2-(trifluoromethyl)pyrimidin-5-yl)pyridin-4-yl)methyl)pyrrolidine-2-carboxamide hydrochloride

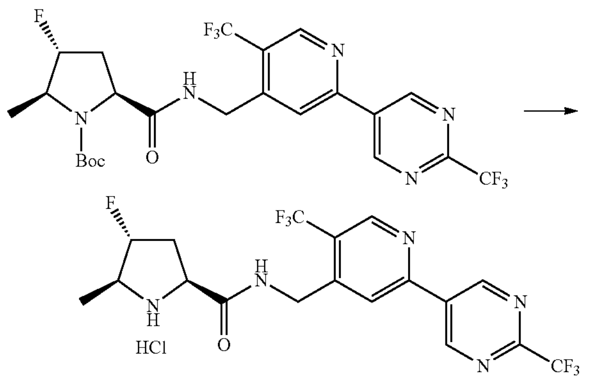

A mixture of tert-butyl (2S,3R,5S)-3-fluoro-2-methyl-5-([[5-(trifluoromethyl)-2-[2-(trifluoromethyl)pyrimidin-5-yl]

pyridin-4-yl]methyl]carbamoyl)pyrrolidine-1-carboxylate (28 g, 50.77 mmol, 1.00 equiv) and saturated HCl (g) in 1,4-dioxane (200 mL) was stirred for 12 h at room temperature. The resulting mixture was concentrated under vacuum to afford the title compound (22 g, 89%) as a white solid. LCMS [M+H$^+$] 452.

Step 7: Preparation of (2S,4R,5S)-4-fluoro-1-(4-fluorophenylsulfonyl)-5-methyl-N-((5-(trifluoromethyl)-2-(2-(trifluoromethyl)pyrimidin-5-yl)pyridin-4-yl)methyl)pyrrolidine-2-carboxamide

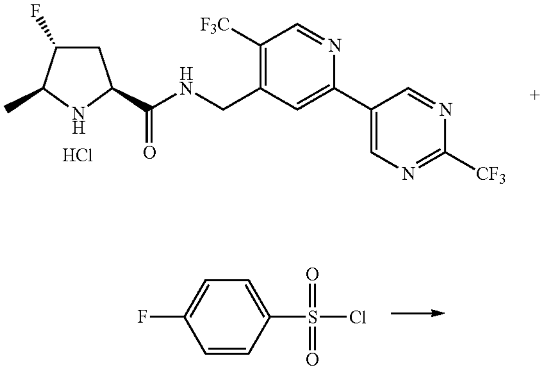

-continued

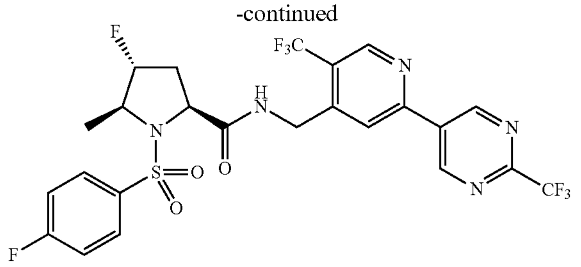

A mixture of (2S,4R,5S)-4-fluoro-5-methyl-N-[[5-(trifluoromethyl)-2-[2-(trifluoromethyl)pyrimidin-5-yl]pyridin-4-yl]methyl]pyrrolidine-2-carboxamide hydrochloride (24.5 g, 50.22 mmol, 1.00 equiv), 4-fluorobenzene-1-sulfonyl chloride (20 g, 102.76 mmol, 2.00 equiv), and TEA (15 g, 148.23 mmol, 3.00 equiv) in dichloromethane (500 mL) was stirred for 2 h at room temperature. The resulting mixture was washed with brine, dried over anhydrous sodium sulfate, and concentrated under vacuum. The residue was purified by a silica gel column eluting with ethyl acetate/petroleum ether (1/1) to afford the title compound (25 g, 82%) as a white solid. LCMS [M+H$^+$] 610. $^1$H NMR (400 MHz, $CDCl_3$) δ 9.70 (s, 2H), 9.01 (s, 1H), 8.38 (s, 1H), 7.94-7.91 (m, 2H), 7.40-7.38 (m, 1H), 7.30-7.26 (m, 1H), 5.24-5.18 (m, 1H), 4.81-4.68 (d, J=51.2 Hz, 1H), 4.59-4.54 (m, 1H), 4.35-4.31 (m, 1H), 4.16-4.06 (m, 1H), 2.68-2.58 (m, 1H), 1.41 (d, J=7.2 Hz, 3H).

Example 104: (2S,4R,5S)—N-((3-cyano-2-cyclopropyl-6-(2-(trifluoromethyl)pyrimidin-5-yl)pyridin-4-yl)methyl)-4-fluoro-1-(4-fluorophenylsulfonyl)-5-methylpyrrolidine-2-carboxamide

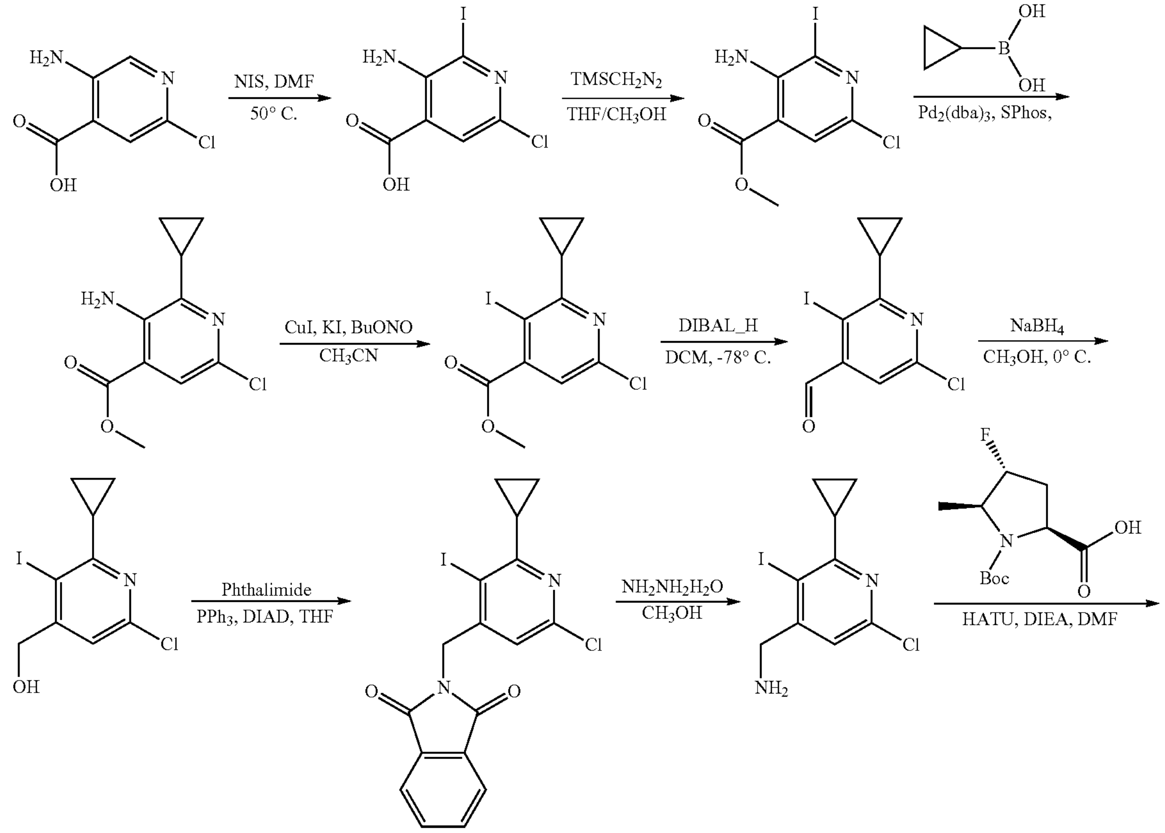

-continued

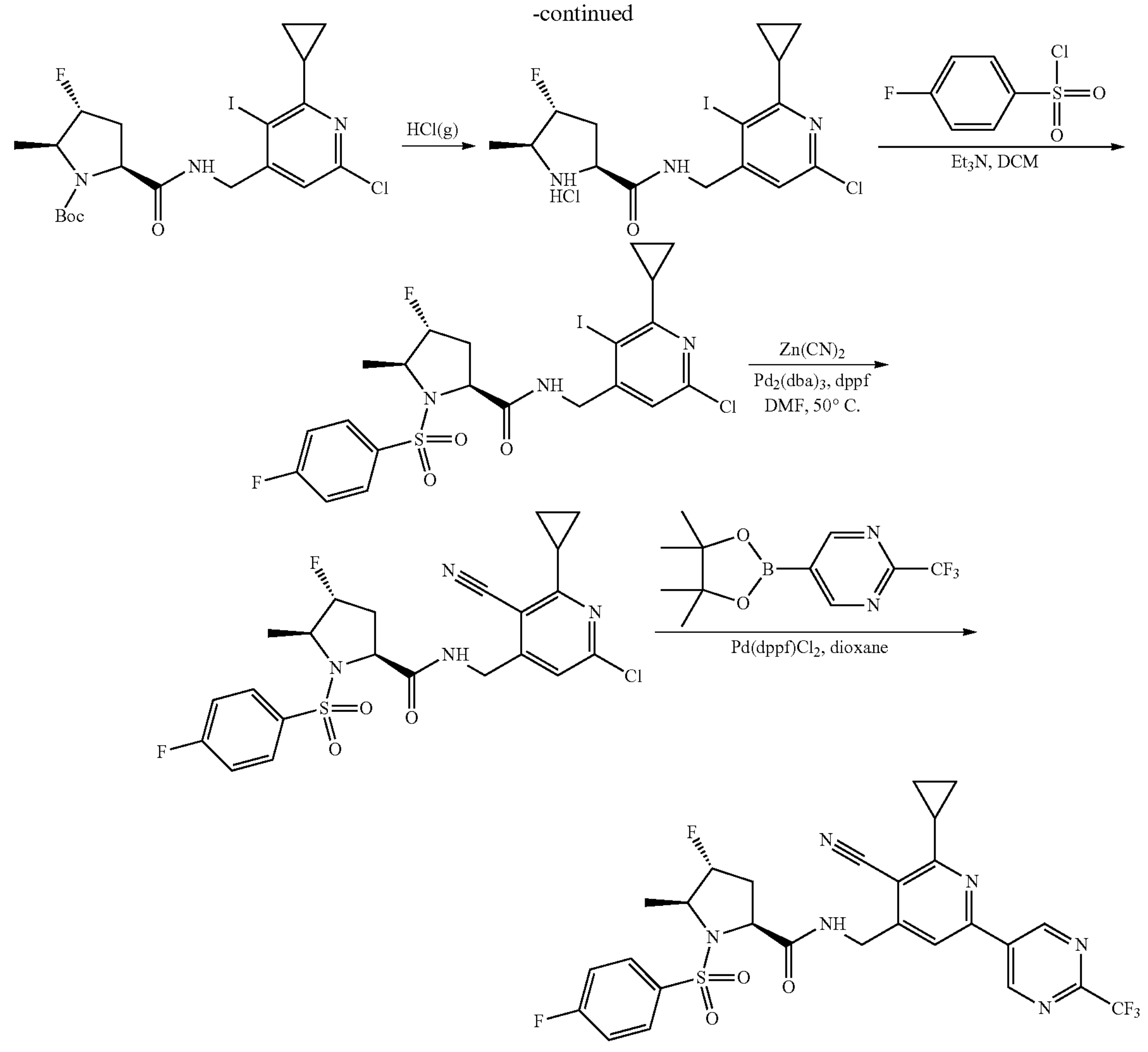

Step 1: Preparation of 3-amino-6-chloro-2-iodoisonicotinic acid

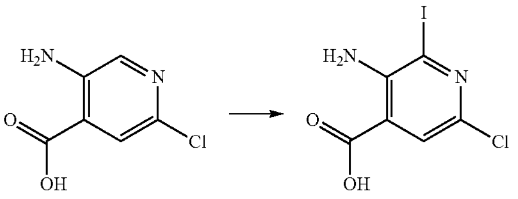 [SMILES: Nc1cnc(Cl)cc1C(=O)O ; Nc1c(C(=O)O)cc(Cl)nc1I]

A mixture of 5-amino-2-chloropyridine-4-carboxylic acid (11 g, 63.74 mmol, 1.00 equiv) and NIS (28.68 g, 127.47 mmol, 2.00 equiv) in N,N-dimethylformamide (80 mL) was stirred for 10 min at 0° C. The resulting solution was stirred for 14 h at 80° C. The reaction was quenched by iced water, extracted with ethyl acetate, washed with $Na_2S_2O_3$ (aq) and brine, dried over anhydrous sodium sulfate, and concentrated under vacuum. This resulted in the title compound (15.6 g, 82%) as a red solid. LCMS [M+H$^+$] 299.

Step 2: Preparation of methyl 3-amino-6-chloro-2-iodoisonicotinate

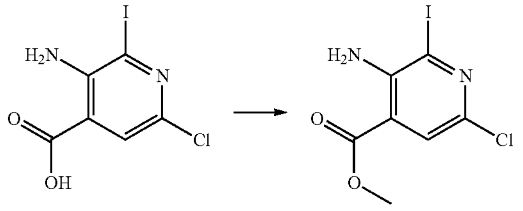

$TMSCHN_2$ (1 moL/L in THF, 100 mL, 100.00 mmol, 2.00 equiv,) was added dropwise into a solution of 3-amino-6-chloro-2-iodopyridine-4-carboxylic acid (14.5 g, 50 mmol, 1.00 equiv) in THF (60 mL)/methanol (20 mL) at 0° C. under $N_2$. The resulting solution was stirred for 14 h at room temperature and concentrated under vacuum. The residue was purified by a silica gel column eluting with ethyl acetate/petroleum ether (1/10) to afford the title compound (12.5 g, 82%) as a red solid. LCMS [M+H$^+$] 312.

Step 3: Preparation of methyl 3-amino-6-chloro-2-cyclopropylisonicotinate

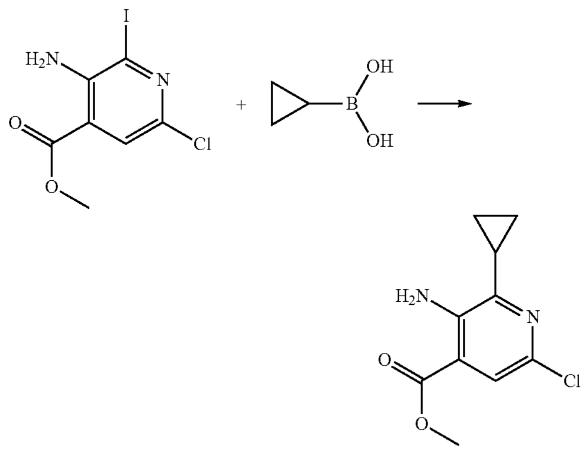

A mixture of methyl 3-amino-6-chloro-2-iodopyridine-4-carboxylate (12 g, 38.00 mmol, 1.00 equiv), cyclopropylboronic acid (19 g, 224.00 mmol, 6.00 equiv), $Pd_2(dba)_3$ (1.7 g, 1.86 mmol, 0.05 equiv), SPhos (1.4 g, 3.41 mmol, 0.10 equiv), and potassium carbonate (25 g, 180.00 mmol, 4.71 equiv) in dioxane (400 mL)/water (100 mL) was stirred for 14 h at 50° C. under $N_2$. The reaction was quenched by water, extracted with ethyl acetate, dried over anhydrous sodium sulfate, and concentrated under vacuum. The residue was purified by a silica gel column eluting with ethyl acetate/petroleum ether (1/8) to afford the title compound (8.6 g, 99%) as a yellow solid. LCMS [M+H$^+$] 227.

Step 4: Preparation of methyl 6-chloro-2-cyclopropyl-3-iodoisonicotinate

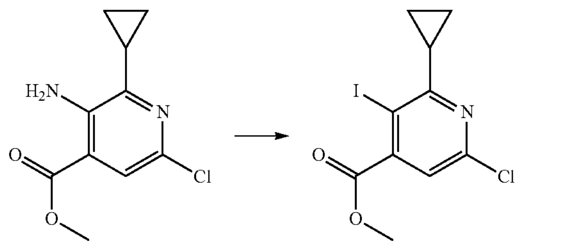

A mixture of methyl 3-amino-6-chloro-2-cyclopropylpyridine-4-carboxylate (4 g, 17.60 mmol, 1.000 equiv), KI (15 g, 90.30 mmol, 5.00 equiv), CuI (4 g, 21.00 mmol, 1.20 equiv), and t-BuONO (9 g, 87.00 mmol, 5.00 equiv) in $CH_3CN$ (100 ml) was stirred for 12 h at 80° C. under $N_2$. The reaction was quenched by water, concentrated under vacuum, extracted with ethyl acetate, dried over anhydrous sodium sulfate, and concentrated under vacuum. The residue was purified by a silica gel column eluting with ethyl acetate/petroleum ether (1/8) to afford the title compound (2 g, 34%) as yellow oil. LCMS [M+H$^+$] 338.

Step 5: Preparation of 6-chloro-2-cyclopropyl-3-iodoisonicotinaldehyde

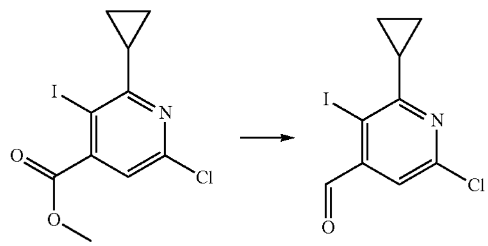

DIBAL-H (1M in THF, 13.5 mL, 13.50 mmol, 3.00 equiv,) was added dropwise to a solution of methyl 6-chloro-2-cyclopropyl-3-iodopyridine-4-carboxylate (1.5 g, 4.50 mmol, 1.00 equiv) in dichloromethane (100 mL) at −78° C. under $N_2$. After being stirred for 2 h the resulting solution was quenched by 1N of sodium hydroxide, extracted with dichloromethane, washed with brine, dried over anhydrous sodium sulfate, and concentrated under vacuum. The residue was purified by a silica gel column eluting with ethyl acetate/petroleum ether (1/5) to afford the title compound (1.3 g, 95%) as yellow oil. LCMS [M+H$^+$] 308.

Step 6: Preparation of (6-chloro-2-cyclopropyl-3-iodopyridin-4-yl)methanol

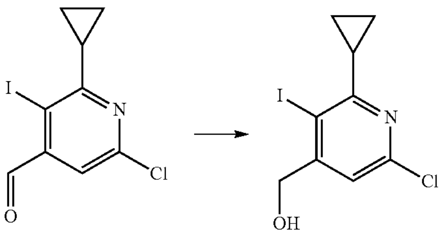 [SMILES: O=Cc1cc(Cl)nc(C2CC2)c1I ; OCc1cc(Cl)nc(C2CC2)c1I]

$NaBH_4$ (310 mg, 8.50 mmol, 2.00 equiv) was added in portions into a solution of 6-chloro-2-cyclopropyl-3-iodopyridine-4-carbaldehyde (1.3 g, 4.25 mmol, 1.00 equiv) in methanol (10 mL) at 0° C. After 30 minutes the reaction was quenched by water, extracted with ethyl acetate, dried over anhydrous sodium sulfate, and concentrated under vacuum. The residue was purified by a silica gel column eluting with ethyl acetate/petroleum ether (1/4) to afford the title compound (1.2 g, 92%) as a white solid. LCMS [M+H$^+$] 310.

Step 7: Preparation of 2-((6-chloro-2-cyclopropyl-3-iodopyridin-4-yl)methyl)isoindoline-1,3-dione

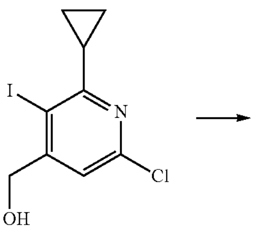

-continued

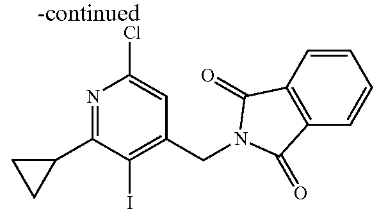

DIAD (3 g, 14.84 mmol, 3.00 equiv) was added dropwise into a solution of (6-chloro-2-cyclopropyl-3-iodopyridin-4-yl)methanol (1.2 g, 3.88 mmol, 1.00 equiv), 2,3-dihydro-1H-isoindole-1,3-dione (1.5 g, 10.20 mmol, 2.00 equiv), and $PPh_3$ (4 g, 15.25 mmol, 3.00 equiv) in tetrahydrofuran (50 mL) at 0° C. After being stirred for 12 h the resulting mixture was concentrated under vacuum. The residue was purified by a silica gel column eluting with ethyl acetate/petroleum ether (1/4) to afford the title compound (1 g, 59%) as a white solid. LCMS [M+H$^+$] 439.

Step 8: Preparation of (6-chloro-2-cyclopropyl-3-iodopyridin-4-yl)methanamine

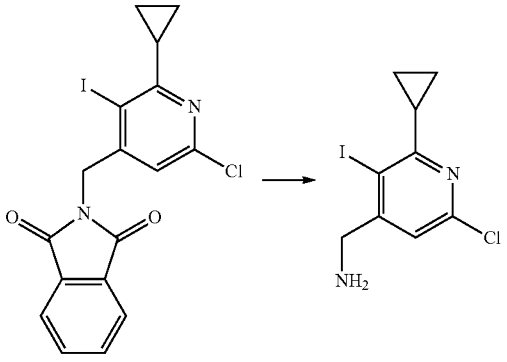 [SMILES: O=C1c2ccccc2C(=O)N1Cc1cc(Cl)nc(C2CC2)c1I ; NCc1cc(Cl)nc(C2CC2)c1I]

A solution of 2-[(6-chloro-2-cyclopropyl-3-iodopyridin-4-yl)methyl]-2,3-dihydro-1H-isoindole-1,3-dione (1 g, 2.28 mmol, 1.00 equiv) and hydrazine hydrate (1.42 g, 80%) in methanol (50 mL) was stirred for 12 h at room temperature. The resulting mixture was concentrated under vacuum and dissolved in ethyl acetate. The precipitated solid was filtered off and the filtrate was concentrated under vacuum. This resulted in the title compound (400 mg, 57%) as yellow oil. LCMS [M+H$^+$] 309.

Step 9: Preparation of (2S,3R,5S)-tert-butyl 5-((6-chloro-2-cyclopropyl-3-iodopyridin-4-yl)methylcarbamoyl)-3-fluoro-2-methylpyrrolidine-1-carboxylate

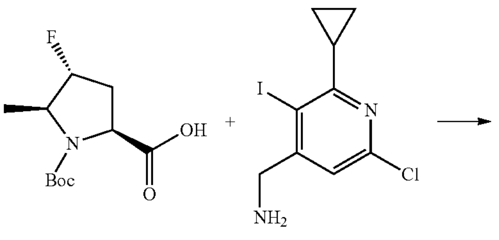

-continued

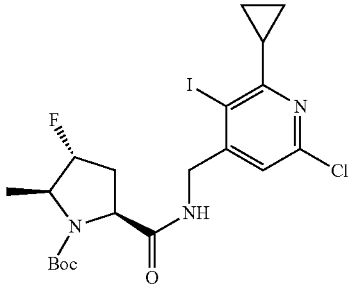

A mixture of (2S,4R,5S)-1-[(tert-butoxy)carbonyl]-4-fluoro-5-methylpyrrolidine-2-carboxylic acid (400 mg, 1.6 mmol, 1.00 equiv), HATU (922 mg, 2.42 mmol, 1.50 equiv), DIEA (627 mg, 4.85 mmol, 3.00 equiv), and (6-chloro-2-cyclopropyl-3-iodopyridin-4-yl)methanamine (499.14 mg, 1.60 mmol, 1.000 equiv) in N,N-dimethylformamide (20 mL) was stirred for 2 h at room temperature. The resulting solution was diluted with ethyl acetate, washed with brine, dried over anhydrous sodium sulfate, and concentrated under vacuum. The residue was purified by a silica gel column eluting with ethyl acetate/petroleum ether (1/1) to afford the title compound (300 mg, 34%) as a white solid. LCMS [M+H$^+$] 538.

Step 10: Preparation of (2S,4R,5S)—N-((6-chloro-2-cyclopropyl-3-iodopyridin-4-yl)methyl)-4-fluoro-5-methylpyrrolidine-2-carboxamide hydrochloride

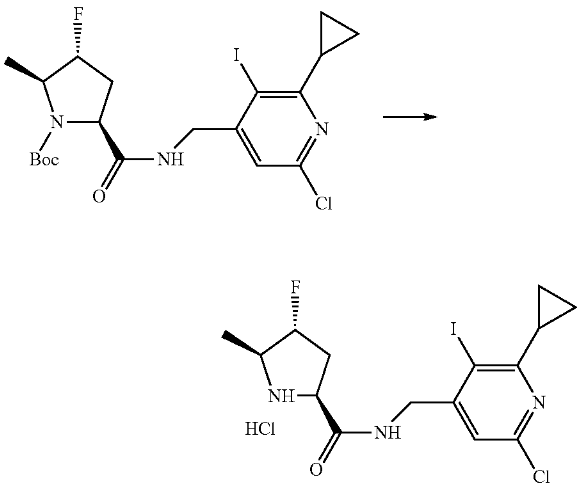 [SMILES: C[C@H]1[C@H](F)C[C@@H](C(=O)NCc2cc(Cl)nc(C3CC3)c2I)N1C(=O)OC(C)(C)C ; C[C@@H]1N[C@H](C(=O)NCc2cc(Cl)nc(C3CC3)c2I)C[C@H]1F ; Cl]

A mixture of tert-butyl (2S,3R,5S)-5-[[(6-chloro-2-cyclopropyl-3-iodopyridin-4-yl)methyl]carbamoyl]-3-fluoro-2-methylpyrrolidine-1-carboxylate (300 mg, 0.56 mmol, 1.00 equiv) and HCl (g) (saturated solution in 50 mL of 1,4-dioxane) was stirred for 1 h at room temperature. The resulting mixture was concentrated under vacuum. This resulted in the title compound (220 mg, 83%) as a white solid. LCMS [M+H$^+$] 438.

Step 11: Preparation of (2S,4R,5S)—N-((6-chloro-2-cyclopropyl-3-iodopyridin-4-yl)methyl)-4-fluoro-1-(4-fluorophenylsulfonyl)-5-methylpyrrolidine-2-carboxamide

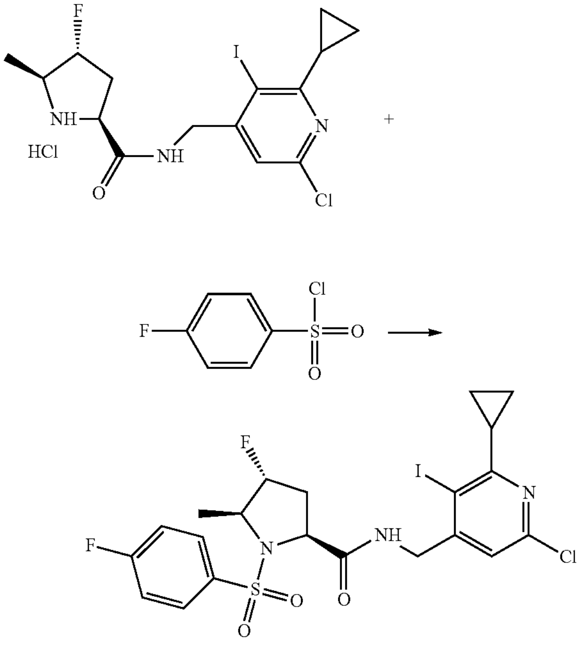

A mixture of (2S,4R,5S)—N-((6-chloro-2-cyclopropyl-3-iodopyridin-4-yl)methyl)-4-fluoro-5-methylpyrrolidine-2-carboxamide hydrochloride (150 mg, 0.31 mmol, 1.00 equiv), triethylamine (100 mg, 0.99 mmol, 3.00 equiv), and 4-fluorobenzene-1-sulfonyl chloride (124 mg, 0.64 mmol, 2.00 equiv) in dichloromethane (10 mL) was stirred for 2 h at room temperature. The resulting mixture was concentrated under vacuum. The residue was purified by a silica gel column eluting with ethyl acetate/petroleum ether (1/1) to afford the title compound (180 mg, 95%) as a white solid. LCMS [M+H$^+$] 596.

Step 12: Preparation of (2S,4R,5S)—N-((6-chloro-3-cyano-2-cyclopropylpyridin-4-yl)methyl)-4-fluoro-1-(4-fluorophenylsulfonyl)-5-methylpyrrolidine-2-carboxamide

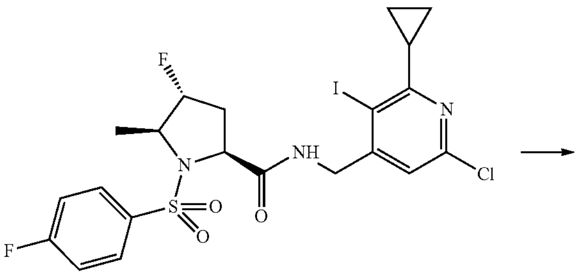

-continued

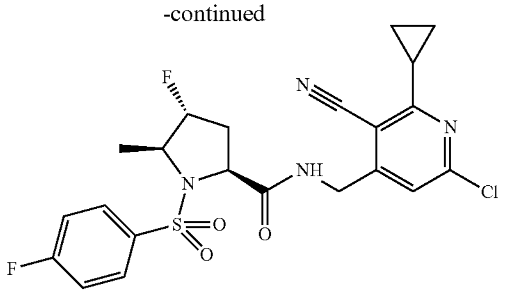

A mixture of (2S,4R,5S)—N-[(6-chloro-2-cyclopropyl-3-iodopyridin-4-yl)methyl]-4-fluoro-1-[(4-fluorobenzene)sulfonyl]-5-methylpyrrolidine-2-carboxamide (450 mg, 0.76 mmol, 1.00 equiv), $Zn(CN)_2$ (80 mg, 0.68 mmol, 0.90 equiv), $Pd2(dba)_3.CHCl_3$ (80 mg, 0.08 mmol, 0.10 equiv), and dppf (130 mg, 0.23 mmol, 0.31 equiv) in N,N-dimethylformamide (5 mL) was irradiated with microwave radiation for 1 h at 50° C. under $N_2$. The resulting solution was diluted with ethyl acetate, washed with brine, dried over anhydrous sodium sulfate, and concentrated under vacuum. The residue was purified by a silica gel column eluting with ethyl acetate/petroleum ether (1/1) to afford the title compound (200 mg, 54%) as a white solid. LCMS [M+H$^+$] 495.

Step 13: Preparation of (2S,4R,5S)—N-((3-cyano-2-cyclopropyl-6-(2-(trifluoromethyl)pyrimidin-5-yl)pyridin-4-yl)methyl)-4-fluoro-1-(4-fluorophenylsulfonyl)-5-methylpyrrolidine-2-carboxamide

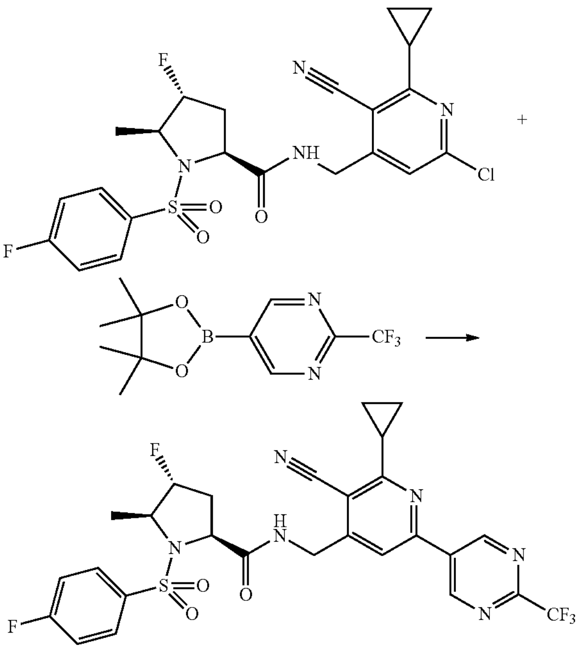

A mixture of (2S,4R,5S)—N-[(6-chloro-3-cyano-2-cyclopropylpyridin-4-yl)methyl]-4-fluoro-1-[(4-fluorobenzene)sulfonyl]-5-methylpyrrolidine-2-carboxamide (170 mg, 0.34 mmol, 1.00 equiv), 5-(tetramethyl-1,3,2-dioxaborolan-2-yl)-2-(trifluoromethyl)pyrimidine (141 mg, 0.51 mmol, 1.50 equiv), $Pd(dppf)Cl_2$ (25 mg, 0.03 mmol, 0.10 equiv), and potassium carbonate (141 mg, 1.00 mmol, 3.00 equiv)

in 1,4-dioxane (5 mL) was stirred for 2 h at 100° C. under $N_2$. The resulting mixture was concentrated under vacuum. The residue was applied onto a silica gel column eluting with ethyl acetate/petroleum ether (1/1). This resulted in the title compound (84.7 mg, 41%) as a white solid. LCMS [M+H$^+$] 607. NMR (400 MHz, $CDCl_3$) δ 9.60 (s, 2H), 8.06 (s, 1H), 7.92-7.87 (m, 2H), 7.42-7.38 (m, 1H), 7.29-7.23 (m, 2H), 5.18-5.09 (m, 1H), 4.73 (d, J=51 Hz, 1H), 4.56-4.49 (m, 1H), 4.31-4.25 (m, 1H), 4.12-4.03 (m, 1H), 2.62-2.54 (m, 2H), 2.37-2.12 (m, 1H), 1.41-1.30 (m, 3H), 1.29-1.21 (m, 4H).

Example 112: (2S,4R,5 S)-4-fluoro-1-(4-fluorophenylsulfonyl)-5-methyl-N-((5-(trifluoromethyl)-2-(5-(trifluoromethyl)pyrazin-2-yl)pyridin-4-yl)methyl) pyrrolidine-2-carboxamide

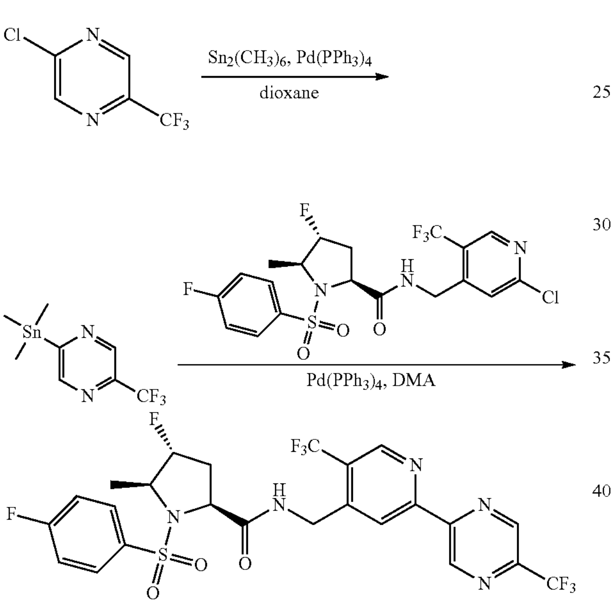

Step 1: Preparation of 2-(trifluoromethyl)-5-(trimethylstannyl)pyrazine

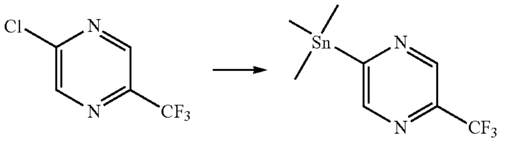

A mixture of 2-chloro-5-(trifluoromethyl)pyrazine (150 mg, 0.82 mmol, 1.00 equiv), $Pd(PPh_3)_4$ (236 mg, 0.20 mmol, 0.24 equiv), and hexamethyldistannane (403 mg, 1.23 mmol, 1.49 equiv) in dioxane (5 mL) was stirred for 1 h at 100° C. under $N_2$. The solid was filtered out and the resulting solution was concentrated under vacuum. This resulted in the title compound (150 mg, 59%) as a black solid which was used for the next step without further purification. LCMS [M+H$^+$] 313.

Step 2: Preparation of (2S,4R,5S)-4-fluoro-1-(4-fluorophenylsulfonyl)-5-methyl-N-((5-(trifluoromethyl)-2-(5-(trifluoromethyl)pyrazin-2-yl)pyridin-4-yl)methyl)pyrrolidine-2-carboxamide

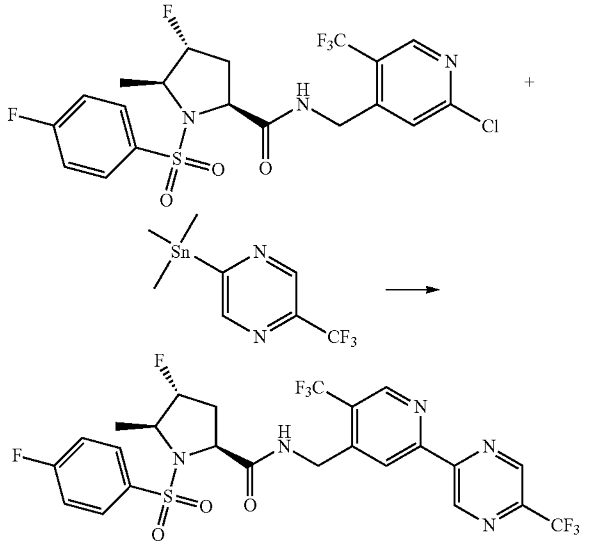

A mixture of (2S,4R,5S)—N-[[2-chloro-5-(trifluoromethyl)pyridin-4-yl]methyl]-4-fluoro-1-[(4-fluorobenzene) sulfonyl]-5-methylpyrrolidine-2-carboxamide (180 mg, 0.36 mmol, 1.00 equiv), 2-(trifluoromethyl)-5-(trimethylstannyl)pyrazine (120 mg, 0.38 mmol, 1.06 equiv), $Pd(PPh_3)_4$ (70 mg, 0.06 mmol, 0.16 equiv) in dimethylacetamide (5 mL) was irradiated with microwave radiation for 1 h under nitrogen at 150° C. The reaction was then quenched by water, extracted with ethyl acetate, washed with brine, dried over anhydrous sodium sulfate, and concentrated under vacuum. The residue was purified by Prep-HPLC to afford the title compound (41.7 mg, 19%) as a white solid. LCMS [M+H$^+$] 610. $^1$H NMR (300 MHz, $CDCl_3$) δ 9.81 (s, 1H), 8.99 (d, J=14.4 Hz, 2H), 8.70 (s, 1H), 7.95-7.92 (m, 2H), 7.60 (t, J=6.5 Hz, 1H), 7.28-7.24 (m, 2H), 4.92-4.69 (m, 3H), 4.31-4.15 (m, 2H), 2.59-2.37 (m, 2H), 1.40 (d, J=7.0 Hz, 3H).

Example 114: (2S,4R,5S)—N-([2-[6-(difluoromethoxy)pyridin-3-yl]-5-(trifluoromethyl)pyridin-4-yl]methyl)-4-fluoro-1-[(4-fluorobenzene)sulfonyl]-5-methylpyrrolidine-2-carboxamide

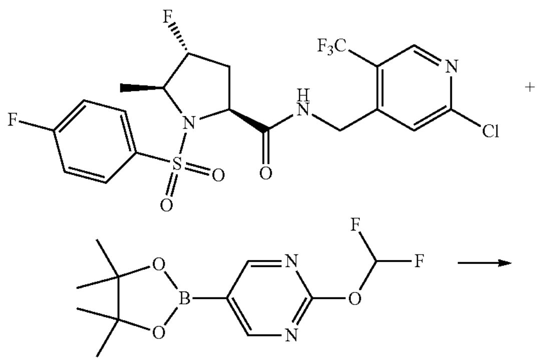

-continued

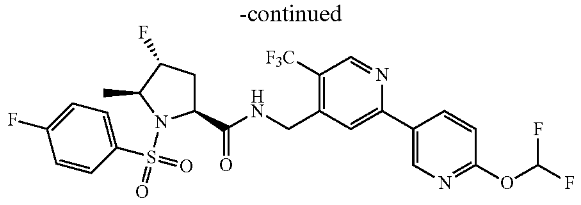

A mixture of [4-([[(2S,4R,5S)-4-fluoro-1-[(4-fluorobenzene)sulfonyl]-5-methylpyrrolidin-2-yl]formamido]methyl)-5-(trifluoromethyl)pyridin-2-yl]chloranium (94 mg, 0.18 mmol, 1.00 equiv), 2-(difluoromethoxy)-5-(tetramethyl-1,3,2-dioxaborolan-2-yl)pyridine (65 mg, 0.24 mmol, 1.27 equiv), Pd(dppf)$Cl_2$ (15 mg, 0.02 mmol, 0.10 equiv), potassium carbonate (83 mg, 0.60 mmol, 3.18 equiv), 1,4-dioxane (10 mL), and water (1 mL) was stirred for 1 h at 90° C. under nitrogen. The resulting mixture was concentrated under vacuum. The residue was purified by a silica gel column eluting with ethyl acetate/petroleum ether (1/1). The crude product (80 mg) was purified by Prep-HPLC with the following conditions (2#-AnalyseHPLC-SHIMADZU (HPLC-10)): Column, XBridge Shield RP18 OBD Column, 5 um, 19*150 mm; mobile phase, Waters (0.05% $NH_3H_2O$) and ACN (45.0% ACN up to 70.0% in 7 min); Detector, UV 220 nm. This resulted in the title compound (39.9 mg, 35%) as a white solid. LCMS [M+H$^+$] 607. $^1$H NMR (400 MHz, $CDCl_3$) δ 9.02 (s, 1H), 8.93 (s, 1H), 8.62-8.55 (m, 1H), 8.17 (s, 1H), 7.94 (dd, J=8.3, 4.8 Hz, 2H), 7.76-7.51 (m, 1H), 7.49-7.35 (m, 1H), 7.34-7.30 (m, 1H), 7.00 (d, J=8.0 Hz, 1H), 5.09 (d, J=14.8 Hz, 1H), 4.84-4.66 (m, 1H), 4.61 (d, J=16.7 Hz, 1H), 4.32 (t, J=8.8 Hz, 1H), 4.15 (dq, J=21.4, 7.1 Hz, 1H), 2.60 (td, J=17.5, 16.7, 7.4 Hz, 1H), 2.44-2.21 (m, 1H), 1.39 (d, J=6.9 Hz, 3H).

Example 115: (2S,4R,5S)-4-fluoro-1-(4-fluorophenyl)sulfonyl-5-methyl-N-[[5-(trifluoromethyl)-2-[6-(trifluoromethyl)-3-pyridyl]-4-pyridyl]methyl]pyrrolidine-2-carboxamide

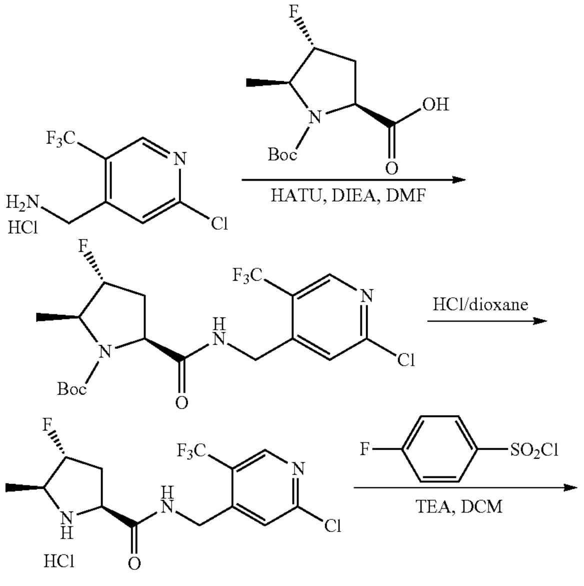

-continued

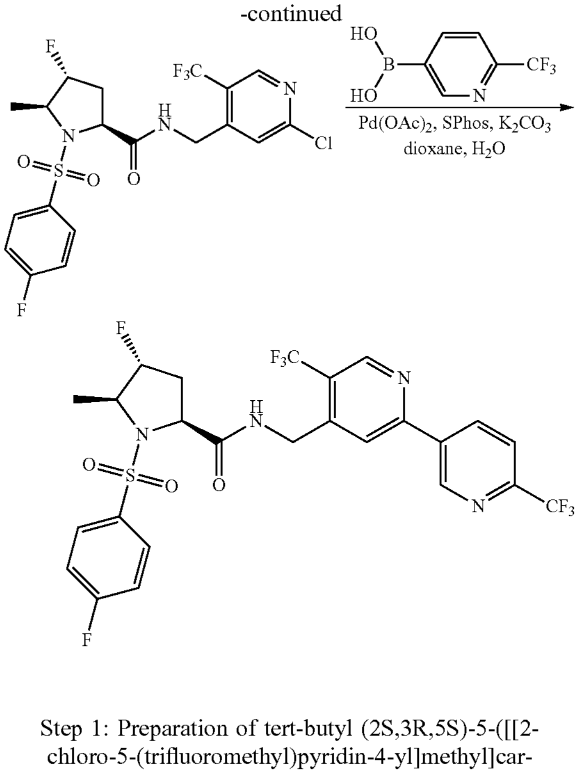

Step 1: Preparation of tert-butyl (2S,3R,5S)-5-([[2-chloro-5-(trifluoromethyl)pyridin-4-yl]methyl]carbamoyl)-3-fluoro-2-methylpyrrolidine-1-carboxylate

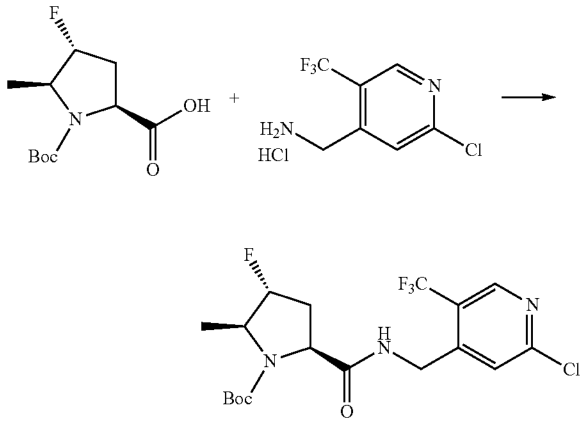 [SMILES: C[C@H]1[C@H](F)C[C@@H](C(=O)O)N1C(=O)OC(C)(C)C ; Cl ; NCc1cc(Cl)ncc1C(F)(F)F ; C[C@H]1[C@H](F)C[C@@H](C(=O)NCc2cc(Cl)ncc2C(F)(F)F)N1C(=O)OC(C)(C)C]

A mixture of (2S,4R,5S)-1-[(tert-butoxy)carbonyl]-4-fluoro-5-methylpyrrolidine-2-carboxylic acid (0.50 g, 2.02 mmol, 1.00 equiv), N,N-dimethylformamide (6 mL), DIEA (1.306 g, 10.10 mmol, 1.00 equiv), HATU (1.154 g, 3.03 mmol, 1.00 equiv), and [2-chloro-5-(trifluoromethyl)pyridin-4-yl]methanamine hydrochloride (0.55 g, 2.22 mmol, 1.00 equiv) was stirred for 30 min at room temperature. The reaction was diluted with water, extracted with ethyl acetate, washed with saturated solution of $NH_4Cl$ and brine, dried over anhydrous sodium sulfate, and concentrated under vacuum. The residue was purified by a silica gel column eluting with ethyl acetate/petroleum ether (1/6) to afford the title compound (760 mg, 78%) as light yellow oil. LCMS [M+H+] 440.

Step 2: Preparation of (2S,4R,5S)—N-[[2-chloro-5-(trifluoromethyl)pyridin-4-yl]methyl]-4-fluoro-5-methylpyrrolidine-2-carboxamide hydrochloride

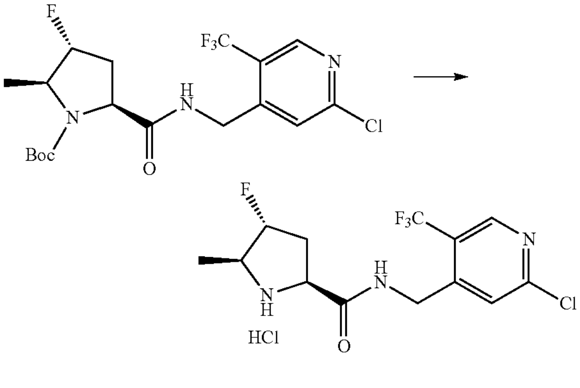

A mixture of tert-butyl (2S,3R,5S)-5-([[2-chloro-5-(trifluoromethyl)pyridin-4-yl]methyl]carbamoyl)-3-fluoro-2-methylpyrrolidine-1-carboxylate (550 mg, 1.25 mmol, 1.00 equiv) and 4 N of HCl in dioxane (10 mL) was stirred overnight at room temperature. The reaction was concentrated under vacuum to afford the title compound (450 mg, 96%) as a yellow solid. LCMS [M+H+] 340.

Step 3: Preparation of (2S,4R,5S)—N-[[2-chloro-5-(trifluoromethyl)pyridin-4-yl]methyl]-4-fluoro-1-[(4-fluorobenzene)sulfonyl]-5-methylpyrrolidine-2-carboxamide

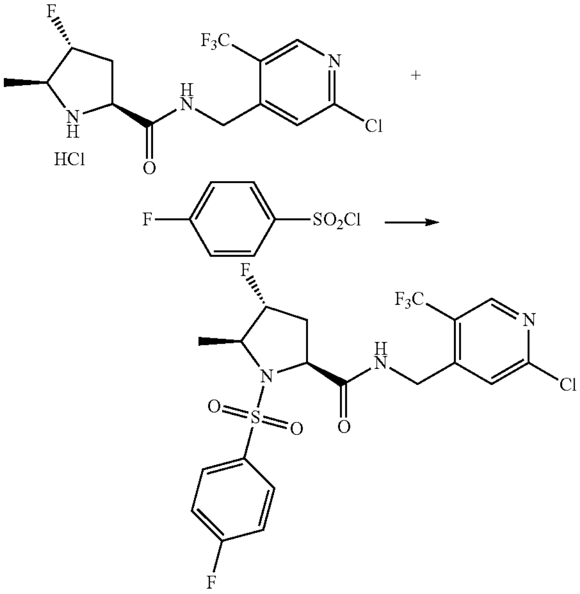

A mixture of (2S,4R,5S)—N-[[2-chloro-5-(trifluoromethyl)pyridin-4-yl]methyl]-4-fluoro-5-methylpyrrolidine-2-carboxamide hydrochloride (450 mg, 1.19 mmol, 1.00 equiv), dichloromethane (10 mL), TEA (363.1 mg, 3.58 mmol, 3.00 equiv) and 4-fluorobenzene-1-sulfonyl chloride (350.5 mg, 1.80 mmol, 1.50 equiv) was stirred for overnight at room temperature. The reaction was diluted with water, extracted with ethyl acetate, washed with saturated solution of $NH_4Cl$ and brine, dried over anhydrous sodium sulfate, and concentrated under vacuum. The residue was purified by a silica gel column eluting with ethyl acetate/petroleum ether (3/5) to afford the title compound (500 mg, 84%) as a white solid. LCMS [M+H+] 498.

Step 4: Preparation of (2S,4R,5S)-4-fluoro-1-(4-fluorophenyl)sulfonyl-5-methyl-N-[[5-(trifluoromethyl)-2-[6-(trifluoromethyl)-3-pyridyl]-4-pyridyl]methyl]pyrrolidine-2-carboxamide

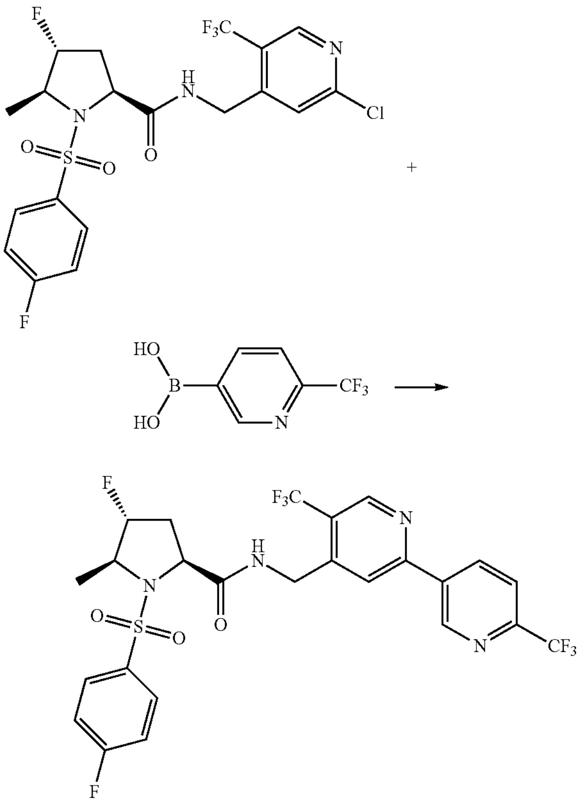

A mixture of (2S,4R,5S)—N-[[2-chloro-5-(trifluoromethyl)pyridin-4-yl]methyl]-4-fluoro-1-[(4-fluorobenzene)sulfonyl]-5-methylpyrrolidine-2-carboxamide (100 mg, 0.20 mmol, 1.00 equiv), dioxane (5 mL), water (0.5 mL), potassium carbonate (83 mg, 0.60 mmol, 2.99 equiv), [6-(trifluoromethyl)pyridin-3-yl]boronic acid (78.5 mg, 0.41 mmol, 2.04 equiv), $Pd(OAc)_2$ (4.5 mg, 0.02 mmol, 0.10 equiv), and SPhos (16.5 mg, 0.04 mmol, 0.20 equiv) was stirred overnight at 100° C. under nitrogen. The reaction was concentrated under vacuum. The residue was purified by a silica gel column eluting with ethyl acetate/petroleum ether (1/4) to afford the title compound (62.9 mg, 51%) as a white solid. LCMS [M+H+] 609. NMR (300 MHz, $CDCl_3$) δ 9.52 (s, 1H), 8.99 (s, 1H), 8.73-8.71 (m, 1H), 8.30 (s, 1H), 7.92 (dd, J=4.4, 2.5 Hz, 2H), 7.79 (d, J=8.1 Hz, 1H), 7.46-7.41 (m, 1H), 7.30-7.25 (m, 2H), 5.18-5.12 (m, 1H), 4.74 (d, J=53.7 Hz, 1H), 4.62-4.58 (m, 1H), 4.31 (t, J=8.9 Hz, 1H), 4.17-4.08 (m, 1H), 2.67-2.53 (m, 1H), 2.41-2.19 (m, 1H), 1.38 (d, J=6.9 Hz, 3H).

Example 122: (2S,4R,5S)-4-fluoro-1-(4-fluorophenylsulfonyl)-5-methyl-N-((5-(2,2,2-trifluoroethoxy)-2-(2-(trifluoromethyl)pyrimidin-5-yl)pyridin-4-yl)methyl)pyrrolidine-2-carboxamide
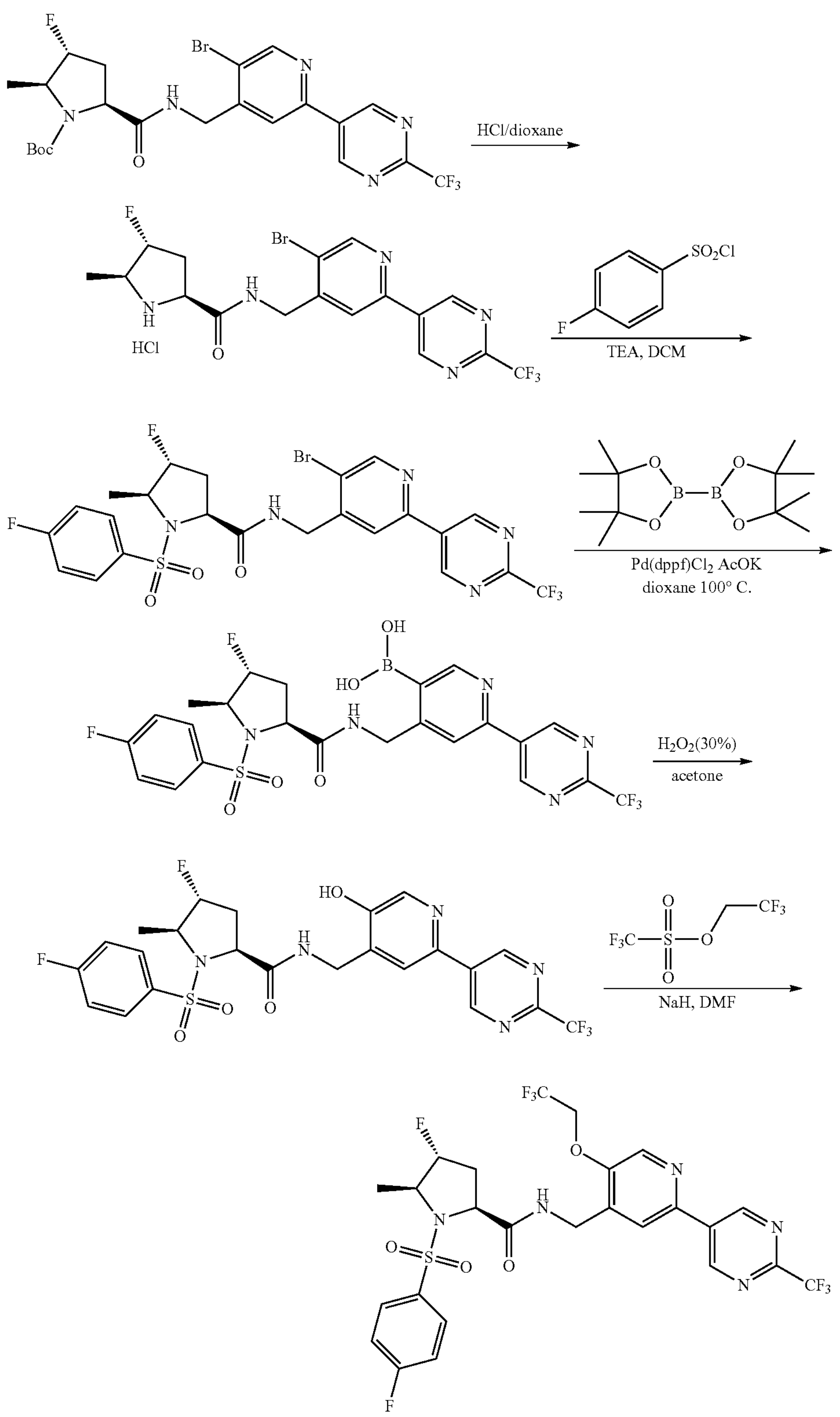

Step 1: Preparation of (2S,4R,5S)—N-((5-bromo-2-(2-(trifluoromethyl)pyrimidin-5-yl)pyridin-4-yl)methyl)-4-fluoro-5-methylpyrrolidine-2-carboxamide hydrochloride

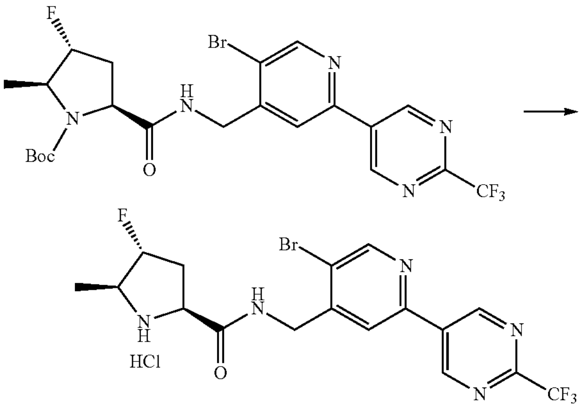

A mixture of tert-butyl (2S,3R,5S)-5-[([5-bromo-2-[2-(trifluoromethyl)pyrimidin-5-yl]pyridin-4-yl]methyl)carbamoyl]-3-fluoro-2-methylpyrrolidine-1-carboxylate (960 mg, 1.70 mmol, 1.00 equiv) and 4 N HCl in dioxane (20 mL) was stirred for 2 h at room temperature. The resulting mixture was concentrated under vacuum to afford the title compound (0.78 g, 92%) as yellow oil. LCMS $[M+H^+]$ 462.

Step 2: Preparation of (2S,4R,5S)—N-((5-bromo-2-(2-(trifluoromethyl)pyrimidin-5-yl)pyridin-4-yl)methyl)-4-fluoro-1-(4-fluorophenylsulfonyl)-5-methylpyrrolidine-2-carboxamide

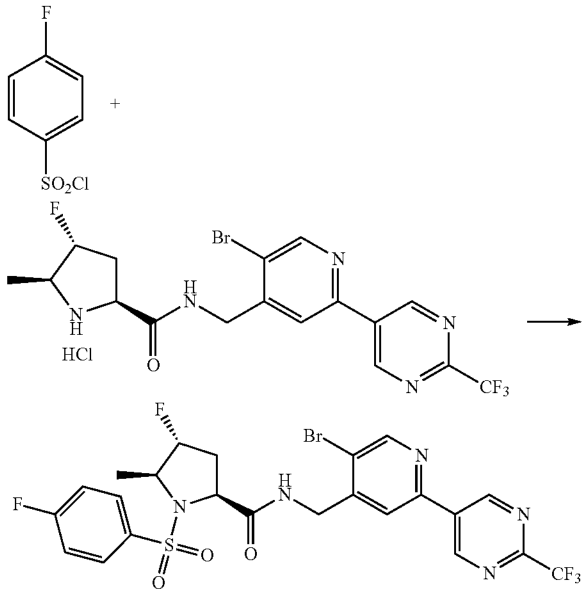

A mixture of (2S,4R,5S)—N-([5-bromo-2-[2-(trifluoromethyl)pyrimidin-5-yl]pyridin-4-yl]methyl)-4-fluoro-5-methylpyrrolidine-2-carboxamide hydrochloride (780 mg, 1.56 mmol, 1.00 equiv), TEA (480 mg, 4.74 mmol, 3.03 equiv), and 4-fluorobenzene-1-sulfonyl chloride (370 mg, 1.901 mmol, 1.216 equiv) in dichloromethane (30 mL) was stirred for 30 min at room temperature. The resulting mixture was washed with brine, dried over anhydrous sodium sulfate, and concentrated under vacuum. The residue was purified by a silica gel column eluting with ethyl acetate/petroleum ether (3/2) to afford the title compound (550 mg, 57%) as a white solid. LCMS $[M+H^+]$ 620.

Step 3: Preparation 40: 4-(((2S,4R,55)-4-fluoro-1-(4-fluorophenylsulfonyl)-5-methylpyrrolidine-2-carboxamido)methyl)-6-(2-(trifluoromethyl)pyrimidin-5-yl)pyridin-3-ylboronic Acid

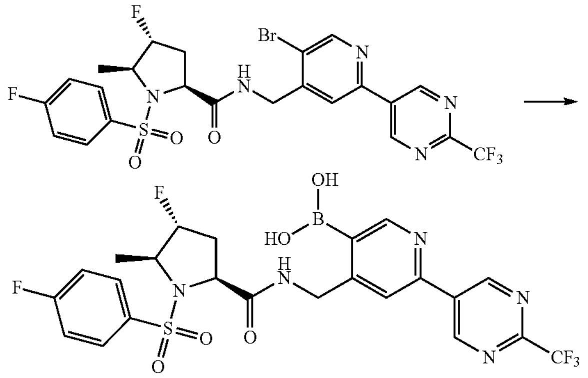

A mixture of (2S,4R,5S)—N-([5-bromo-2-[2-(trifluoromethyl)pyrimidin-5-yl]pyridin-4-yl]methyl)-4-fluoro-1-[(4-fluorobenzene)sulfonyl]-5-methylpyrrolidine-2-carboxamide (380 mg, 0.61 mmol, 1.00 equiv), 4,4,5,5-tetramethyl-2-(tetramethyl-1,3,2-dioxaborolan-2-yl)-1,3,2-dioxaborolane (312 mg, 1.22 mmol, 2.00 equiv), Pd(dppf)$Cl_2$ (50 mg, 0.06 mmol, 0.11 equiv), and potassium acetate (121 mg, 1.23 mmol, 2.01 equiv) in dioxane (8 mL) was stirred for 14 h at 100° C. under nitrogen. The reaction solution was diluted with water, extracted with ethyl acetate, washed with brine, dried over anhydrous sodium sulfate, and concentrated under vacuum. This resulted in the title compound (200 mg, 56%) as brown oil. LCMS $[M+H^+]$ 586.

Step 4: Preparation of (2S,4R,5S)-4-fluoro-1-(4-fluorophenylsulfonyl)-N-((5-hydroxy-2-(2-(trifluoromethyl)pyrimidin-5-yl)pyridin-4-yl)methyl)-5-methylpyrrolidine-2-carboxamide

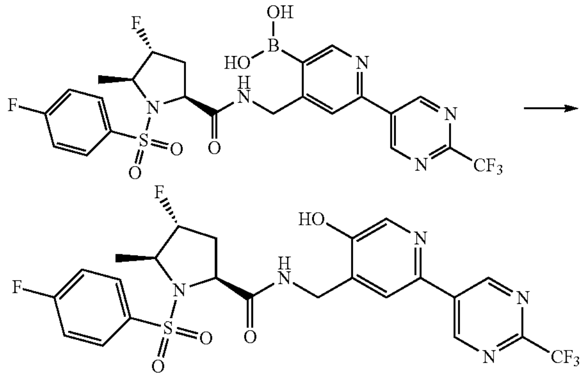

A solution of [4-([[(2S,4R)-4-fluoro-1-[(4-fluorobenzene)sulfonyl]pyrrolidin-2-yl]formamido]methyl)-6-[2-(trifluoromethyl)pyrimidin-5-yl]pyridin-3-yl]boronic acid (200 mg, 0.35 mmol, 1.00 equiv) and $H_2O_2$ (30%) (4 mL) in acetone (12 mL) was stirred for 0.5 h at room temperature. The resulting mixture was concentrated under vacuum. The residue was purified by a silica gel column eluting with ethyl acetate/petroleum ether (1/1) to afford the title compound (160 mg) as a brown solid. LCMS [M+H$^+$] 558.

Step 5: Preparation of (2S,4R,5S)-4-fluoro-1-(4-fluorophenylsulfonyl)-5-methyl-N-((5-(2,2,2-trifluoroethoxy)-2-(2-(trifluoromethyl)pyrimidin-5-yl)pyridin-4-yl)methyl)pyrrolidine-2-carboxamide

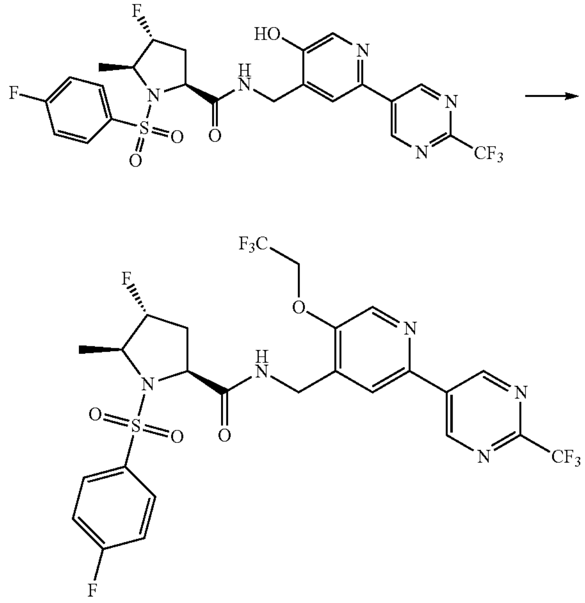

Sodium hydride (20 mg, 60% in mineral oil, 2.90 equiv) was added in portions into a solution of (2S,4R,5S)-4-fluoro-1-[(4-fluorobenzene)sulfonyl]-N-([5-hydroxy-2-[2-(trifluoromethyl)pyrimidin-5-yl]pyridin-4-yl]methyl)-5-methylpyrrolidine-2-carboxamide (160 mg, 0.28 mmol, 1.00 equiv) in N,N-dimethylformamide (8 mL) at 0° C. under nitrogen. The reaction was stirred for 5 min at 0° C. under nitrogen. To the above was added 2,2,2-trifluoroethyl trifluoromethanesulfonate (110 mg, 0.47 mmol, 1.65 equiv) and the reaction mixture was stirred for an additional 3 h at room temperature. The reaction was quenched by water, extracted with ethyl acetate, washed with brine, dried over anhydrous sodium sulfate, and concentrated under vacuum. The residue was purified by a silica gel column eluting with ethyl acetate/petroleum ether (3/2) to afford the title compound (30 mg, 16%) as a white solid. LCMS [M+H$^+$] 640.

Example 126: (2S,4R,5S)-4-fluoro-1-(4-fluorophenyl)sulfonyl-N-[[2-methoxy-6-[2-(trifluoromethyl)pyrimidin-5-yl]pyrimidin-4-yl]methyl]-5-methylpyrrolidine-2-carboxamide

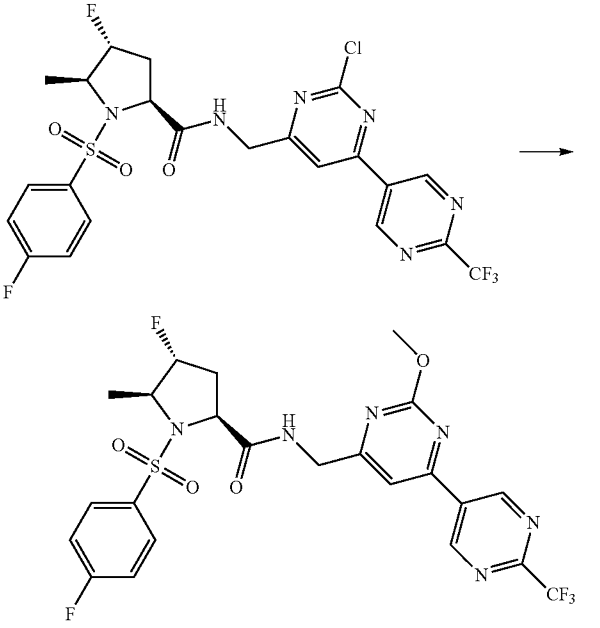

A mixture of (2S,4R,5S)—N-([2-chloro-6-[2-(trifluoromethyl)pyrimidin-5-yl]pyrimidin-4-yl]methyl)-4-fluoro-1-[(4-fluorobenzene)sulfonyl]-5-methylpyrrolidine-2-carboxamide (40 mg, 0.06 mmol, 1.00 equiv) and sodium methylate (5.3 mg, 0.09 mmol, 1.41 equiv) in methanol (10 mL) was stirred for 1 h at room temperature. The reaction was quenched by water, extracted with ethyl acetate, washed with brine, dried over anhydrous sodium sulfate, and concentrated under vacuum. The residue was purified by a silica gel column eluting with ethyl acetate/petroleum ether (2/3) to afford the title compound (25 g, 63%) as a light yellow solid. LCMS [M+H$^+$] 573.

Example 129: (2S,4R,5S)—N-((5-cyano-2-(2-(trifluoromethyl)thiazol-5-yl)pyridin-4-yl)methyl)-4-fluoro-1-((4-fluorophenyl)sulfonyl)-5-methylpyrrolidine-2-carboxamide

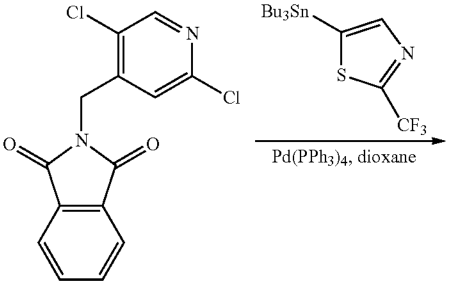

-continued

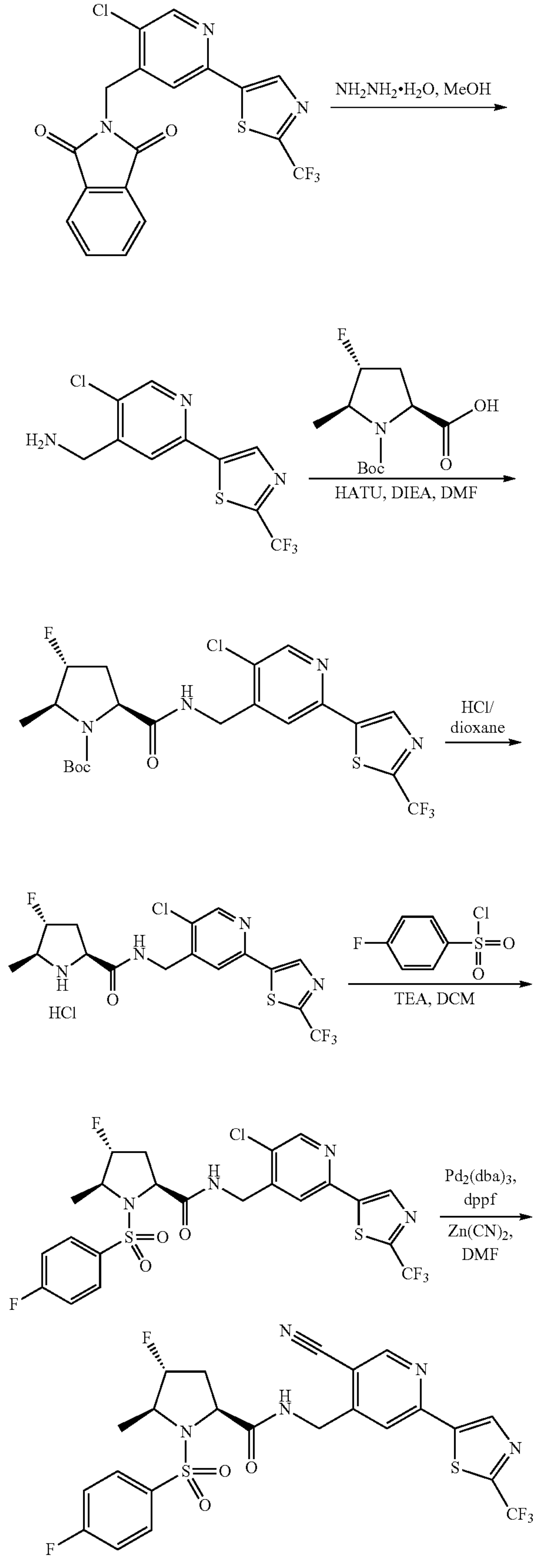

Step 1: Preparation of 2-((5-chloro-2-(2-(trifluoromethyl)thiazol-5-yl)pyridin-4-yl)methyl)isoindoline-1,3-dione

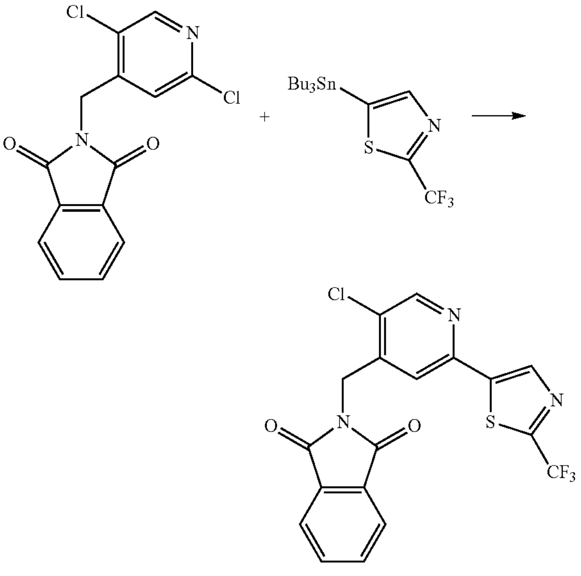

A mixture of 2-[(2,5-dichloropyridin-4-yl)methyl]-2,3-dihydro-1H-isoindole-1,3-dione (500.00 mg, 1.62 mmol, 1.00 equiv), 5-(tributylstannyl)-2-(trifluoromethyl)-1,3-thiazole (1.07 g, 2.44 mmol, 1.50 equiv), and $Pd(PPh_3)_4$ (190.00 mg, 0.16 mmol, 0.10 equiv) in N,N-dimethylformamide (10 mL) was irradiated with microwave radiation for 1 h at 100° C. under $N_2$. The resulting solution was diluted with ethyl acetate, washed with brine, dried over anhydrous sodium sulfate, and concentrated under vacuum. The residue was purified by a silica gel column eluting with dichloromethane/ethyl acetate (1/1) to afford the title compound (600 mg, 87%) as a white solid. LCMS $[M+H^+]$ 424.

Step 2: Preparation of (5-chloro-2-(2-(trifluoromethyl)thiazol-5-yl)pyridin-4-yl)methanamine

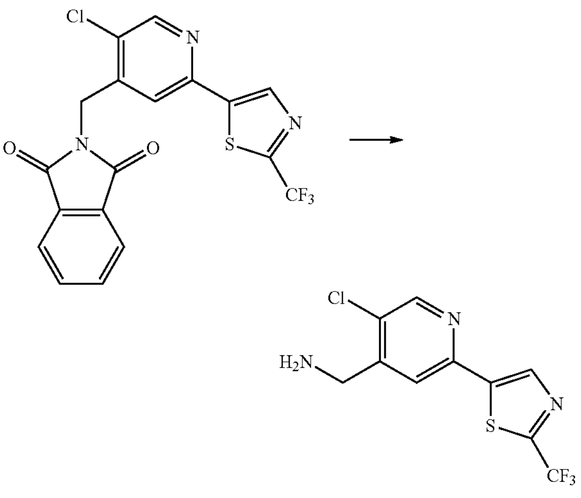

A solution of 2-([5-chloro-2-[2-(trifluoromethyl)-1,3-thiazol-5-yl]pyridin-4-yl]methyl)-2,3-dihydro-1H-isoindole-1,3-dione (300 mg, 0.70 mmol, 1.00 equiv) and hydrazine hydrate (885 mg, 80%) in methanol (30 mL) was stirred for 2 h at 50° C. in an oil bath. The resulting mixture was concentrated under vacuum and dissolved in ethyl acetate. The precipitated solid was filtered off and the filtrate was concentrated under vacuum. This resulted in the title compound (150 mg, 72%) as yellow oil. LCMS [M+H$^+$] 294.

Step 3: Preparation of (2S,3R,5S)-tert-butyl 5-(((5-chloro-2-(2-(trifluoromethyl)thiazol-5-yl)pyridin-4-yl)methyl)carbamoyl)-3-fluoro-2-methylpyrrolidine-1-carboxylate

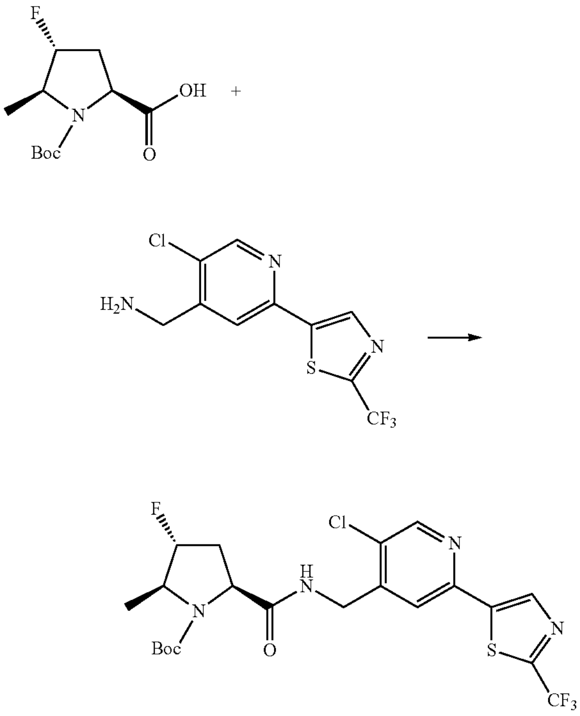

A mixture of (2S,4R,5S)-1-[(tert-butoxy)carbonyl]-4-fluoro-5-methylpyrrolidine-2-carboxylic acid (130.00 mg, 0.52 mmol, 1.00 equiv), EDCI (201.58 mg, 1.05 mmol, 2.00 equiv), HOBT (142.08 mg, 1.05 mmol, 2.00 equiv), triethylamine (159.60 mg, 1.57 mmol, 3.00 equiv), and [5-chloro-2-[2-(trifluoromethyl)-1,3-thiazol-5-yl]pyridin-4-yl]methanamine (154.41 mg, 0.52 mmol, 1.00 equiv) in N,N-dimethylformamide (5 mL) was stirred for 2 h at room temperature. The resulting solution was diluted with ethyl acetate, washed with brine, dried over anhydrous sodium sulfate, and concentrated under vacuum. The residue was purified by a silica gel column eluting with ethyl acetate/petroleum ether (1/1). This resulted in the title compound (120 mg, 44%) as a white solid. LCMS [M+H$^+$] 523.

Step 4: Preparation of (2S,4R,5S)—N-((5-chloro-2-(2-(trifluoromethyl)thiazol-5-yl)pyridin-4-yl)methyl)-4-fluoro-5-methylpyrrolidine-2-carboxamide hydrochloride

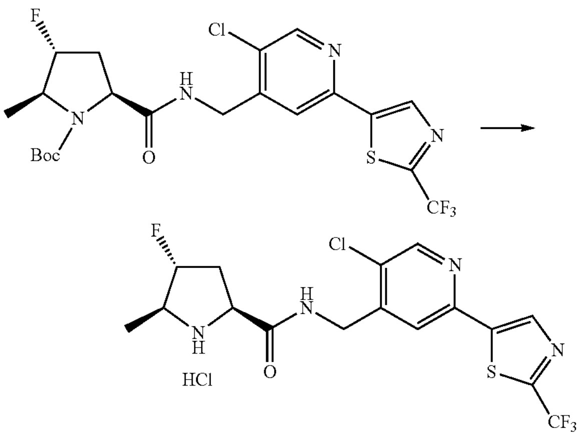

A solution of tert-butyl (2S,3R,5S)-5-[([5-chloro-2-[2-(trifluoromethyl)-1,3-thiazol-5-yl]pyridin-4-yl]methyl)carbamoyl]-3-fluoro-2-methylpyrrolidine-1-carboxylate (120 mg, 0.23 mmol, 1.00 equiv) and saturated HCl (g) in 1,4-dioxane (5 mL) was stirred for 1 h at room temperature. The resulting mixture was concentrated under vacuum to afford the title compound (100 mg, crude) as a white solid. LCMS [M+H$^+$] 423.

Step 5: Preparation of (2S,4R,5S)—N-((5-chloro-2-(2-(trifluoromethyl)thiazol-5-yl)pyridin-4-yl)methyl)-4-fluoro-1-((4-fluorophenyl)sulfonyl)-5-methylpyrrolidine-2-carboxamide

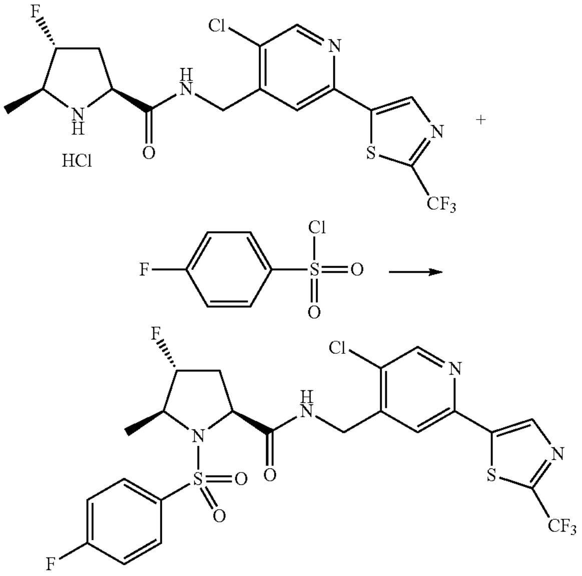

A mixture of 4-fluorobenzene-1-sulfonyl chloride (101.69 mg, 0.523 mmol, 2.000 equiv), (2S,4R,5S)—N-([5-chloro-2-[2-(trifluoromethyl)-1,3-thiazol-5-yl]pyridin-4-yl]

methyl)-4-fluoro-5-methylpyrrolidine-2-carboxamide hydrochloride (120.00 mg, 0.26 mmol, 1.00 equiv), and TEA (79.31 mg, 0.78 mmol, 3.00 equiv) in dichloromethane (20 mL) was stirred for 2 h at room temperature. The resulting mixture was concentrated under vacuum. The residue was purified by a silica gel column eluting with ethyl acetate/petroleum ether (1/1) to afford the title compound (100 mg, 66%) as a white solid. LCMS [M+H+] 581.

Step 6: Preparation of (2S,4R,5S)—N-((5-cyano-2-(2-(trifluoromethyl)thiazol-5-yl)pyridin-4-yl)methyl)-4-fluoro-1-((4-fluorophenyl)sulfonyl)-5-methylpyrrolidine-2-carboxamide

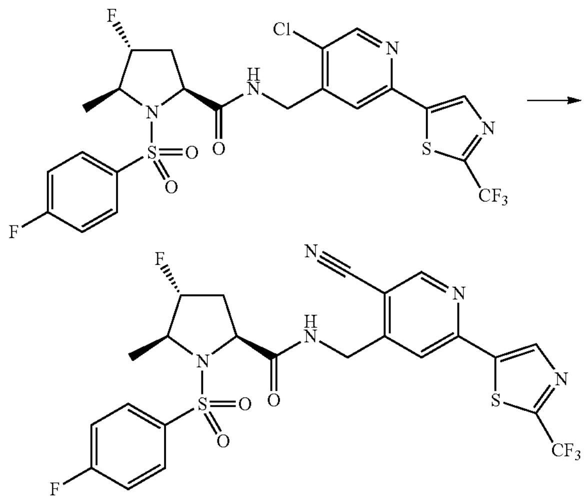

A mixture of (2S,4R,5S)—N-([5-chloro-2-[2-(trifluoromethyl)-1,3-thiazol-5-yl]pyridin-4-yl]methyl)-4-fluoro-1-[(4-fluorobenzene)sulfonyl]-5-methylpyrrolidine-2-carboxamide (80.00 mg, 0.14 mmol, 1.00 equiv), $Zn(CN)_2$ (24.26 mg, 0.21 mmol, 1.50 equiv), dppf (22.82 mg, 0.04 mmol, 0.30 equiv), and $Pd_2(dba)_3.CHCl_3$ (14.25 mg, 0.01 mmol, 0.10 equiv) in N,N-dimethylformamide (10 mL) was irradiated with microwave radiation for 1 h at 150° C. under $N_2$. The resulting solution was diluted with ethyl acetate, washed with brine, dried over anhydrous sodium sulfate, and concentrated under vacuum. The residue was purified by a silica gel column eluting with ethyl acetate/petroleum ether (1/1) to afford the title compound (25.1 mg, 32%) as a white solid. [M+H+] 572. $^1$H NMR (400 MHz, $CDCl_3$) δ 8.80 (s, 1H), 8.72 (s, 1H), 8.30 (s, 1H), 7.95-7.92 (m, 2H), 7.38-7.30 (m, 1H), 7.29-7.27 (m, 2H), 5.20-5.14 (m, 1H), 4.82-4.69 (d, J=51.2 Hz, 1H), 4.56-4.51 (m, 1H), 4.35-4.30 (m, 1H), 4.14-4.07 (m, 1H), 2.64-2.58 (m, 1H), 2.36-2.23 (m, 1H), 1.42 (d, J=6.8 Hz, 3H).

Example 142: [5-bromo-6-cyclopropyl-4-[2-(trifluoromethyl)pyrimidin-5-yl]pyridin-2-yl]methanamine

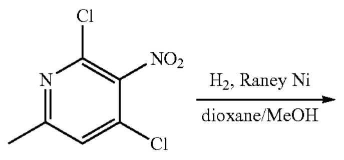

-continued

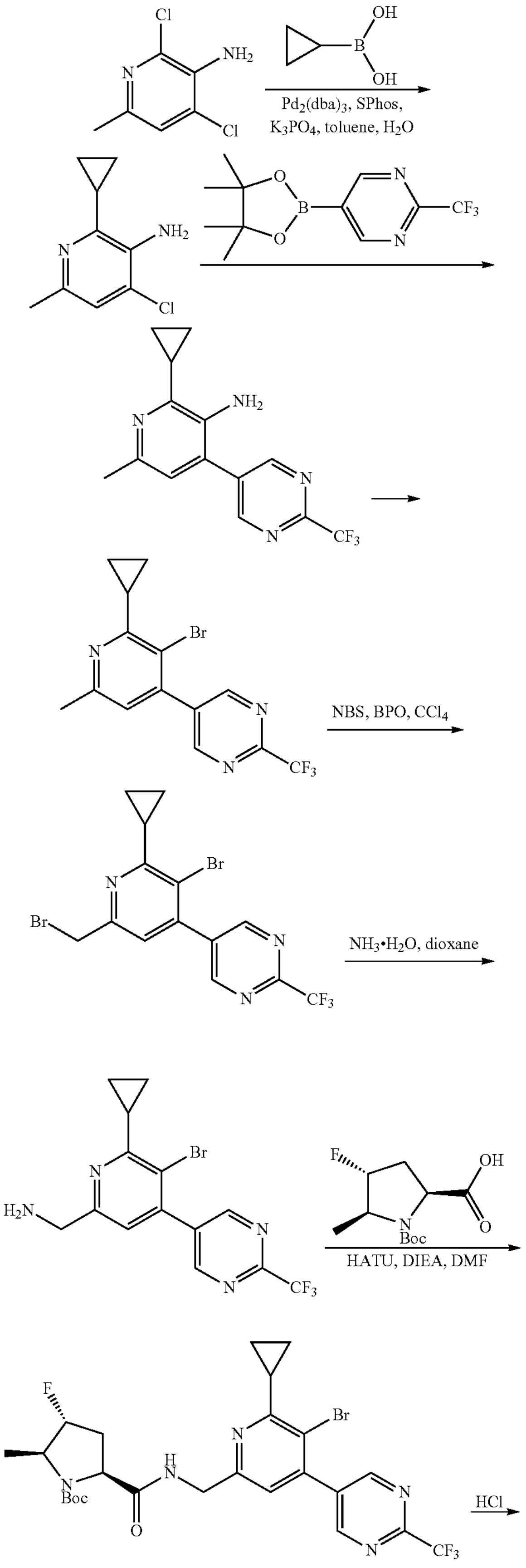

-continued

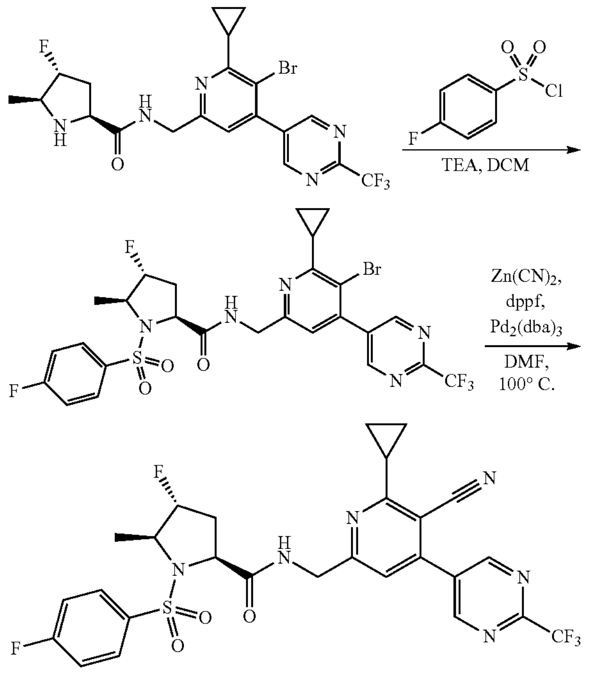

Step 1: Preparation of 2,4-dichloro-6-methylpyridin-3-amine

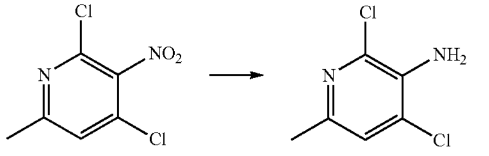

A mixture of 2,4-dichloro-6-methyl-3-nitropyridine (2.0 g, 9.66 mmol, 1.00 equiv), methanol (40 mL), 1,4-dioxane (40 mL), and Raney Ni (500 mg, 5.84 mmol, 0.60 equiv) was stirred for 6 h at room temperature under nitrogen. The solid was filtered out and the liquid was concentrated under vacuum. The residue was purified by a silica gel column with ethyl acetate/petroleum ether (1/10). This resulted in the title compound 1.6 g (94%) as colorless oil. LCMS $[M+H^+]$ 177.

Step 2: Preparation of 4-chloro-2-cyclopropyl-6-methylpyridin-3-amine

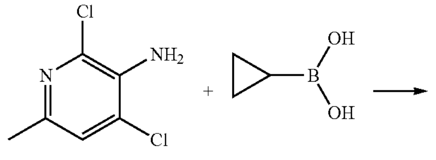

-continued

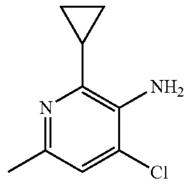

A mixture of 2,4-dichloro-6-methylpyridin-3-amine (1.8 g, 10.17 mmol, 1.00 equiv), cyclopropylboronic acid (4.4 g, 51.22 mmol, 5.04 equiv), $Pd_2(dba)_3$ (1.05 g, 1.15 mmol, 0.11 equiv), SPhos (833 mg, 2.03 mmol, 0.20 equiv), $K_3PO_4$ (6.5 g, 30.62 mmol, 3.01 equiv), toluene (80 mL), and water (8 mL) was stirred for 12 h at 60° C. under nitrogen. The resulting solution was diluted with ethyl acetate, washed with brine, dried over anhydrous sodium sulfate, and concentrated under vacuum. The residue was purified by a silica gel column eluting with ethyl acetate/petroleum ether (1/50) to afford the title compound (800 mg, 43%) as light yellow oil. LCMS $[M+H^+]$ 183.

Step 3: Preparation of 2-cyclopropyl-6-methyl-4-[2-(trifluoromethyl)pyrimidin-5-yl]pyridin-3-amine

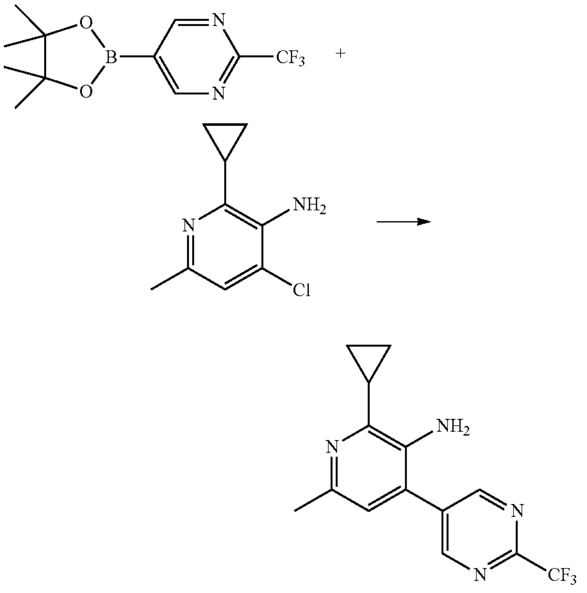

A mixture of 4-chloro-2-cyclopropyl-6-methylpyridin-3-amine (530 mg, 2.90 mmol, 1.00 equiv), 5-(tetramethyl-1,3,2-dioxaborolan-2-yl)-2-(trifluoromethyl)pyrimidine (1.19 g, 4.34 mmol, 1.50 equiv), $Pd(OAc)_2$ (65 mg, 0.29 mmol, 0.10 equiv), SPhos (238 mg, 0.58 mmol, 0.20 equiv), potassium carbonate (1.21 g, 8.76 mmol, 3.02 equiv), dioxane (80 mL), and water (8 mL) was stirred for 12 h at 90° C. under nitrogen. The resulting solution was diluted with ethyl acetate, washed with brine, dried over anhydrous sodium sulfate, and concentrated under vacuum. The residue was purified by a silica gel column eluting with ethyl acetate/petroleum ether (1/10) to afford the title compound (700 mg, 82%) as a light yellow solid. LCMS $[M+H^+]$ 295.

Step 4: Preparation of 5-(3-bromo-2-cyclopropyl-6-methylpyridin-4-yl)-2-(trifluoromethyl)pyrimidine

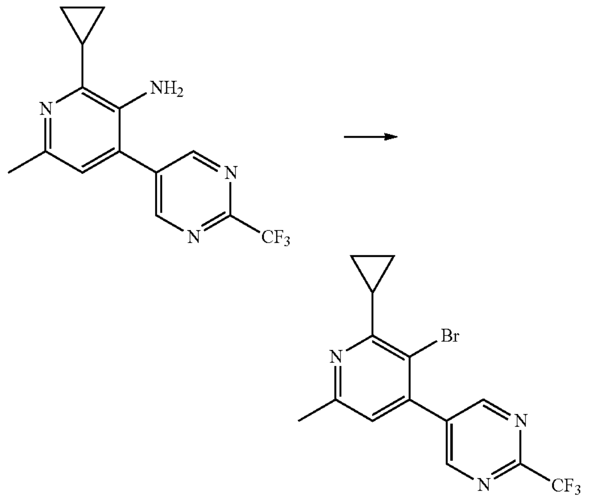

A mixture of 2-cyclopropyl-6-methyl-4-[2-(trifluoromethyl)pyrimidin-5-yl]pyridin-3-amine (900 mg, 3.06 mmol, 1.00 equiv), $CH_3CN$ (50 mL), $CuBr_2$ (1.365 g, 6.11 mmol, 2.00 equiv), and t-$BuNO_2$ (473 mg, 4.59 mmol, 1.50 equiv) was stirred for 12 h at 80° C. The resulting mixture was concentrated under vacuum, diluted with brine, extracted with ethyl acetate, washed with brine, dried over anhydrous sodium sulfate, and concentrated under vacuum. The residue was purified by a silica gel column eluting with dichloromethane/petroleum ether (1/2) to afford the title compound (600 mg, 55%) as a red solid. LCMS [M+H$^+$] 358.

Step 5: Preparation of 5-[3-bromo-6-(bromomethyl)-2-cyclopropylpyridin-4-yl]-2-(trifluoromethyl)pyrimidine

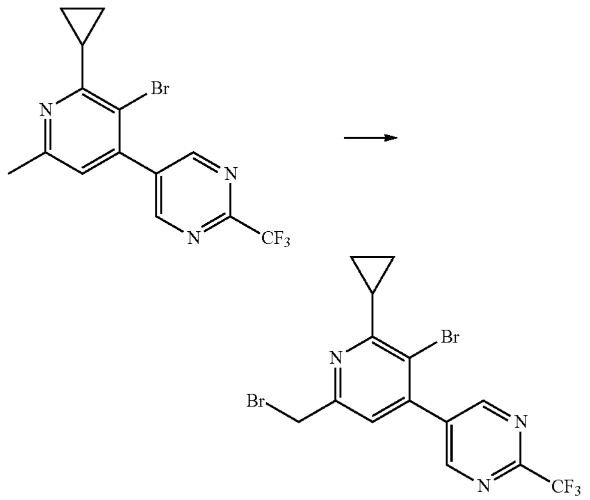

A mixture of 5-(3-bromo-2-cyclopropyl-6-methylpyridin-4-yl)-2-(trifluoromethyl)pyrimidine (550 mg, 1.54 mmol, 1.00 equiv), NBS (656 mg, 3.68 mmol, 2.40 equiv), $CCl_4$ (20 mL), and BPO (148 mg, 0.58 mmol, 0.38 equiv) was stirred for 48 h at 80° C. under nitrogen. The resulting mixture was concentrated under vacuum, diluted with brine, extracted with ethyl acetate, washed with brine, dried over anhydrous sodium sulfate, and concentrated under vacuum. The residue was purified by a silica gel column eluting with dichloromethane/petroleum ether (1/2) to afford the title compound (140 mg, 21%) as brown oil. LCMS [M+H$^+$] 438.

Step 6: Preparation of [5-bromo-6-cyclopropyl-4-[2-(trifluoromethyl)pyrimidin-5-yl]pyridin-2-yl]methanamine

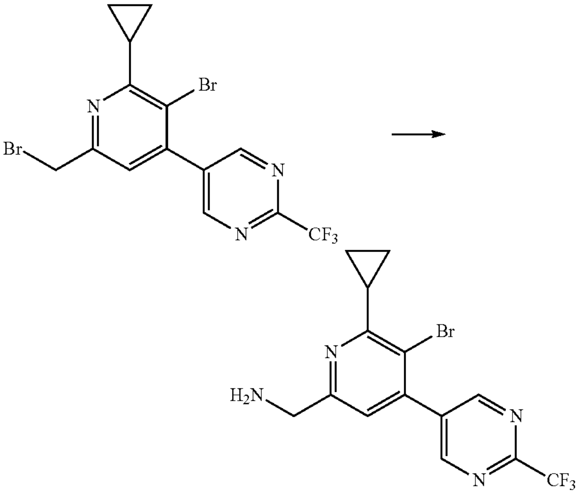

A mixture of 5-[3-bromo-6-(bromomethyl)-2-cyclopropylpyridin-4-yl]-2-(trifluoromethyl)pyrimidine (140 mg, 0.32 mmol, 1.00 equiv), dioxane (20 mL), ammonia (5 mL, 40%) was stirred for 12 h at room temperature. The resulting mixture was concentrated under vacuum to afford the title compound (120 mg, crude) as brown oil. LCMS [M+H$^+$] 373.

Step 7: Preparation of tert-butyl (2S,3R,5S)-5-[([5-bromo-6-cyclopropyl-4-[2-(trifluoromethyl)pyrimidin-5-yl]pyridin-2-yl]methyl)carbamoyl]-3-fluoro-2-methylpyrrolidine-1-carboxylate

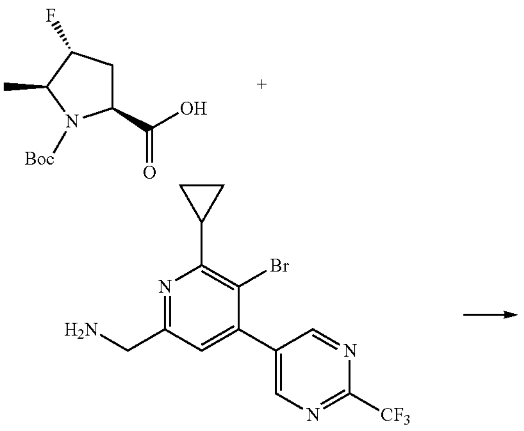

-continued

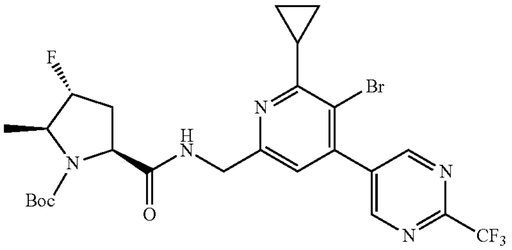

A mixture of (2S,4R,5S)-1-[(tert-butoxy)carbonyl]-4-fluoro-5-methylpyrrolidine-2-carboxylic acid (80 mg, 0.32 mmol, 1.01 equiv), HOBT (65 mg, 0.48 mmol, 1.50 equiv), EDC (93 mg, 0.60 mmol, 1.86 equiv), N,N-dimethylformamide (3 mL), DIEA (62 mg, 0.48 mmol, 1.49 equiv), [5-bromo-6-cyclopropyl-4-[2-(trifluoromethyl)pyrimidin-5-yl]pyridin-2-yl]methanamine (120 mg, 0.32 mmol, 1.00 equiv) was stirred for 12 h at room temperature. The resulting solution was diluted with brine, extracted with ethyl acetate, washed with of brine, dried over anhydrous sodium sulfate, and concentrated under vacuum. The residue was purified by a silica gel column eluting with ethyl acetate/hexane (1/2) to afford the title compound (60 mg, 31%) as yellow oil. LCMS [M+H$^+$] 602.

Step 8: Preparation of (2S,4R,5S)—N-([5-bromo-6-cyclopropyl-4-[2-(trifluoromethyl)pyrimidin-5-yl]pyridin-2-yl]methyl)-4-fluoro-5-methylpyrrolidine-2-carboxamide

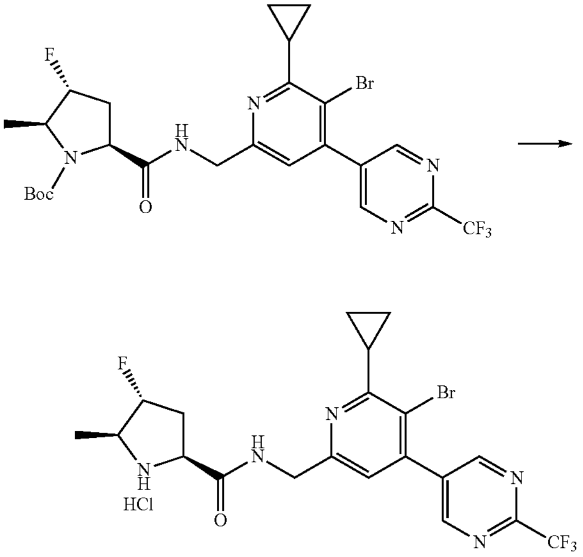 [SMILES: C[C@H]1[C@H](F)C[C@@H](C(=O)NCc2cc(-c3cnc(C(F)(F)F)nc3)c(Br)c(C3CC3)n2)N1C(=O)OC(C)(C)C ; C[C@@H]1N[C@H](C(=O)NCc2cc(-c3cnc(C(F)(F)F)nc3)c(Br)c(C3CC3)n2)C[C@H]1F ; Cl]

A mixture of tert-butyl (2S,3R,5S)-5-[([5-bromo-6-cyclopropyl-4-[2-(trifluoromethyl)pyrimidin-5-yl]pyridin-2-yl]methyl)carbamoyl]-3-fluoro-2-methylpyrrolidine-1-carboxylate (60 mg, 0.10 mmol, 1.00 equiv) and 4N of HCl in 1,4-dioxane (20 mL) was stirred for 1 h at room temperature. The resulting solution was concentrated under vacuum to afford the title compound (50 mg, crude) as yellow oil. LCMS [M+H$^+$] 502.

Step 9: Preparation of (2S,4R,5S)—N-([5-bromo-6-cyclopropyl-4-[2-(trifluoromethyl)pyrimidin-5-yl]pyridin-2-yl]methyl)-4-fluoro-1-[(4-fluorobenzene)sulfonyl]-5-methylpyrrolidine-2-carboxamide

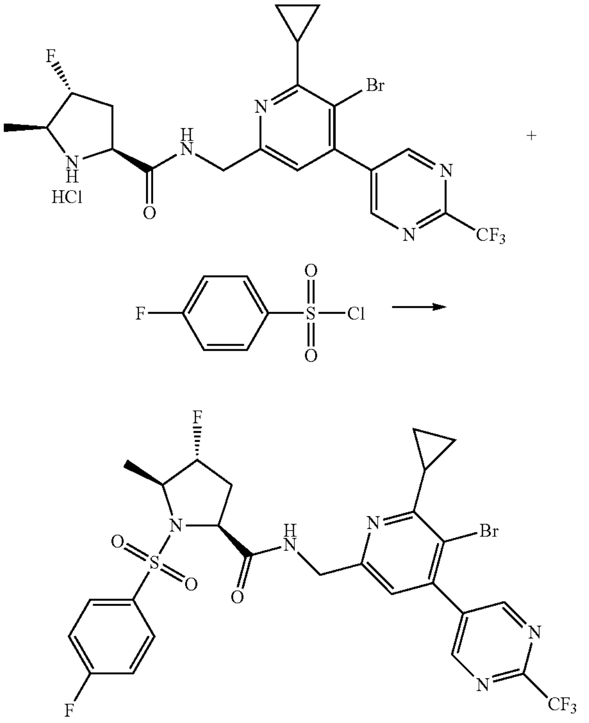

A mixture of (2S,4R,5S)—N-([5-bromo-6-cyclopropyl-4-[2-(trifluoromethyl)pyrimidin-5-yl]pyridin-2-yl]methyl)-4-fluoro-5-methylpyrrolidine-2-carboxamide (50 mg, 0.10 mmol, 1.00 equiv), 4-fluorobenzene-1-sulfonyl chloride (39 mg, 0.20 mmol, 2.01 equiv), dichloromethane (3 mL), TEA (30 mg, 0.30 mmol, 2.98 equiv) was stirred for 2 h at room temperature. The resulting mixture was concentrated under vacuum. The residue was applied onto a Prep-TLC with ethyl acetate/hexane (1/2) to afford the title compound 30 mg (46%) as yellow oil. LCMS [M+H$^+$] 662.

Step 10: Preparation of (2S,4R,5S)—N-([5-cyano-6-cyclopropyl-4-[2-(trifluoromethyl)pyrimidin-5-yl]pyridin-2-yl]methyl)-4-fluoro-1-[(4-fluorobenzene)sulfonyl]-5-methylpyrrolidine-2-carboxamide

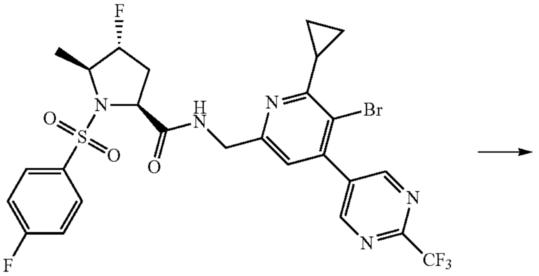

-continued

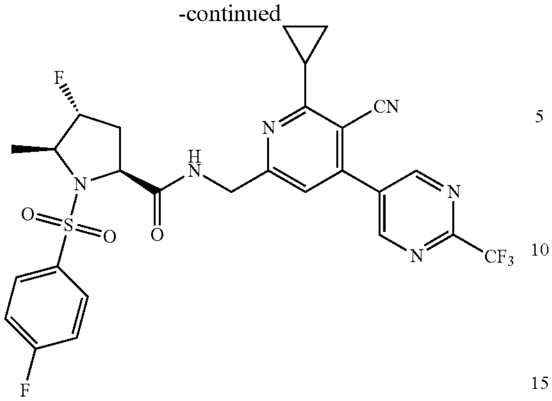

A mixture of (2S,4R,5S)—N-([5-bromo-6-cyclopropyl-4-[2-(trifluoromethyl)pyrimidin-5-yl]pyridin-2-yl]methyl)-4-fluoro-1-[(4-fluorobenzene)sulfonyl]-5-methylpyrrolidine-2-carboxamide (30 mg, 0.05 mmol, 1.00 equiv), $Zn(CN)_2$ (11 mg, 0.09 mmol, 2.06 equiv), $Pd_2(dba)_3CHCl_3$ (9 mg, 0.01 mmol, 0.19 equiv), dppf (10 mg, 0.02 mmol, 0.40 equiv), N,N-dimethylformamide (1 mL) was irradiated with microwave radiation for 2 h at 100° C. under nitrogen. The resulting solution was diluted with brine, extracted with ethyl acetate, washed with brine, and concentrated under vacuum. The residue was applied onto a silica gel column with ethyl acetate/petroleum ether (1/2) and Prep-HPLC to afford the title compound (3.6 mg, 13%) as a white solid. LCMS [M+H$^+$] 607. $^1$H NMR (400 MHz, $CDCl_3$) δ 9.20 (s, 2H), 7.90-7.86 (m, 2H), 7.68 (t, J=5.5 Hz, 1H), 7.40 (s, 1H), 7.29-7.24 (m, 2H), 4.95-4.89 (m, 1H), 4.74 (d, J=52.3 Hz, 1H), 4.55-4.49 (m, 1H), 4.27-4.08 (m, 2H), 2.68-2.25 (m, 3H), 1.46-1.28 (m, 7H).

Example 157: Sodium ((2S,4R,5S)-4-fluoro-N-((5-fluoro-2-(2-(trifluoromethyl)pyrimidin-5-yl)pyridin-4-yl)methyl)-1-((4-fluorophenyl)sulfonyl)-5-methyl-pyrrolidine-2-carboxamido)methyl phosphate

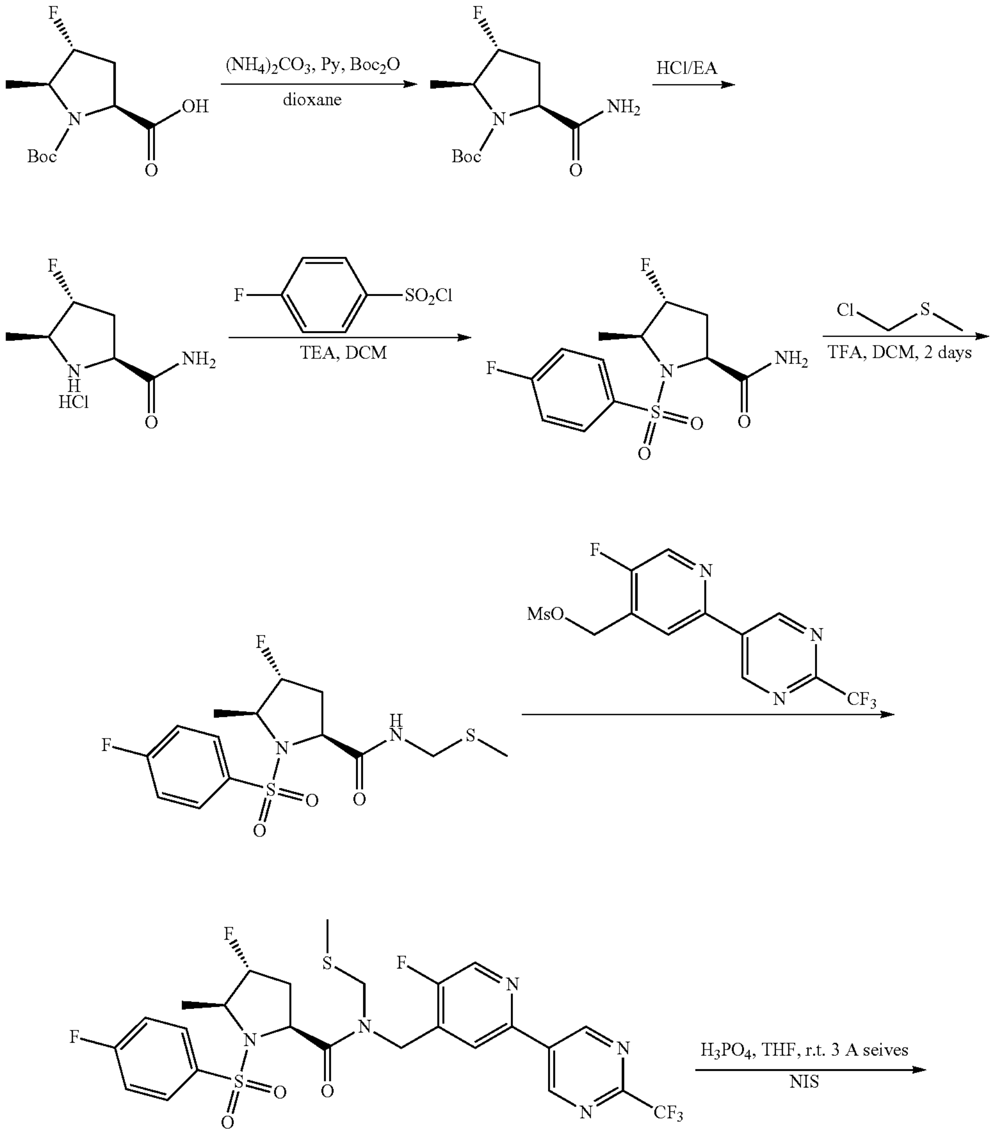

-continued

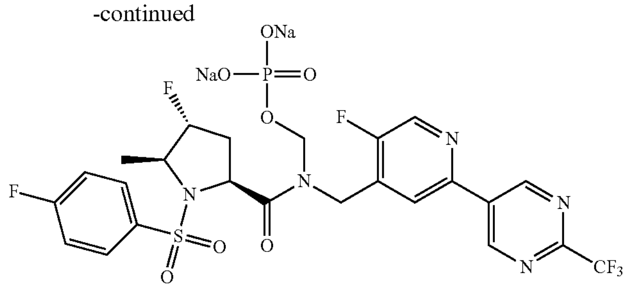

Step 1: Preparation of tert-butyl (2S,3R,5S)-5-carbamoyl-3-fluoro-2-methylpyrrolidine-1-carboxylate

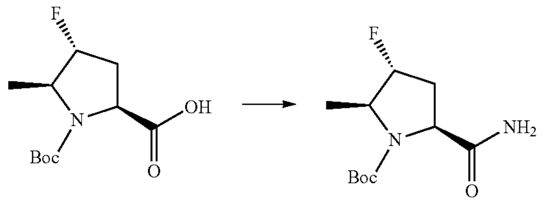 [SMILES: C[C@H]1[C@H](F)C[C@@H](C(=O)O)N1C(=O)OC(C)(C)C ; C[C@H]1[C@H](F)C[C@@H](C(N)=O)N1C(=O)OC(C)(C)C]

$(NH_4)_2CO3$ (6.1 g, 63.48 mmol, 1.30 equiv) was added in portions into a mixture of (2S,4R,5S)-1-[(tert-butoxy)carbonyl]-4-fluoro-5-methylpyrrolidine-2-carboxylic acid (12 g, 48.53 mmol, 1.00 equiv), dioxane (240 mL), pyridine (2.4 mL), and $Boc_2O$ (13.8 g, 63.23 mmol, 1.30 equiv) at 0° C. under nitrogen. The resulting solution was stirred for 12 h at room temperature. The resulting mixture was concentrated under vacuum, diluted with ethyl acetate, washed with citric acid (20% aqueous) and brine, dried over anhydrous sodium sulfate, and concentrated under vacuum. This resulted in the title compound (13 g, crude) as a light yellow solid. LCMS $[M+H^+]$ 247.

Step 2: Preparation of (2S,4R,5S)-4-fluoro-5-methylpyrrolidine-2-carboxamide hydrochloride

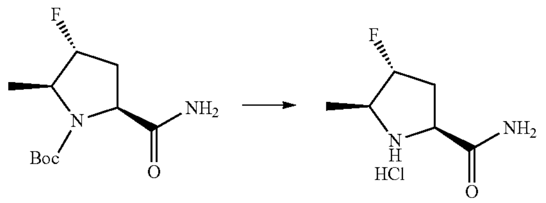

A mixture of tert-butyl (2S,3R,5S)-5-carbamoyl-3-fluoro-2-methylpyrrolidine-1-carboxylate (13 g, 52.78 mmol, 1.00 equiv) and hydrogen chloride (100 mL, 1.9 M in ethyl acetate) was stirred for 12 h at room temperature. The resulting mixture was concentrated under vacuum to afford the title compound (10 g, crude) as a light yellow solid. LCMS $[M+H^+]$ 147.

Step 3: Preparation of (2S,4R,5S)-4-fluoro-1-[(4-fluorobenzene)sulfonyl]-5-methylpyrrolidine-2-carboxamide

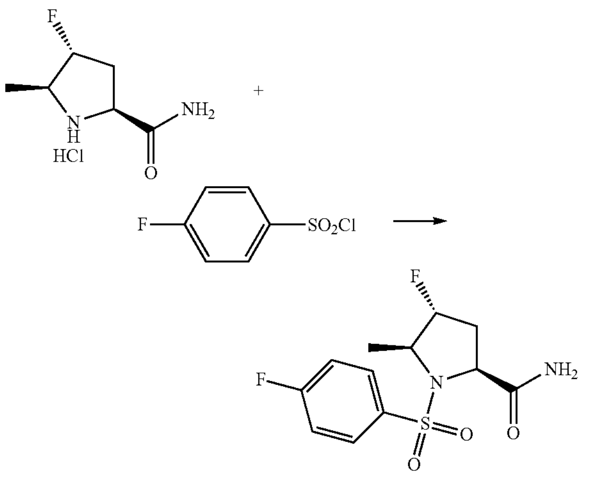

A mixture of (2S,4R,5S)-4-fluoro-5-methylpyrrolidine-2-carboxamide hydrochloride (10.1 g, 55.30 mmol, 1.00 equiv), dichloromethane (100 mL), TEA (16.7 g, 165.03 mmol, 2.98 equiv), and 4-fluorobenzene-1-sulfonyl chloride (16.1 g, 82.72 mmol, 1.49 equiv) was stirred for 12 h at room temperature. The resulting solution was diluted with water, extracted with ethyl acetate, washed with saturated solution of $NH_4Cl$ and brine, dried over sodium sulfate, and concentrated under vacuum. The residue was purified by a silica gel column eluting with ethyl acetate/petroleum ether (99/1) to afford the title compound (10 g, 59%) as a white solid. LCMS $[M+H^+]$ 305.

Step 4: Preparation of (2S,4R,5S)-4-fluoro-1-[(4-fluorobenzene)sulfonyl]-5-methyl-N-[(methylsulfanyl)methyl]pyrrolidine-2-carboxamide

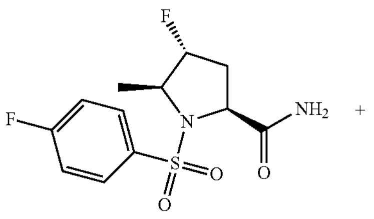

-continued

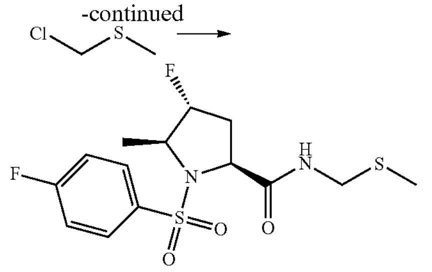

A mixture of (2S,4R,5S)-4-fluoro-1-[(4-fluorobenzene) sulfonyl]-5-methylpyrrolidine-2-carboxamide (10 g, 32.86 mmol, 1.00 equiv), dichloromethane (10 mL), trifluoroacetic acid (10 mL), and chloro(methylsulfanyl)methane (10 mL, 119.38 mmol, 3.63 equiv) was stirred for 2 days at room temperature. The resulting solution was diluted with water, extracted with ethyl acetate, dried over anhydrous sodium sulfate, and concentrated under vacuum. The residue was purified by a silica gel column eluting with ethyl acetate/petroleum ether (1/2) to afford the title compound (5.6 g, 47%) as light yellow oil. LCMS [M+H$^+$] 365.

Step 5: Preparation of (2S,4R,5S)-4-fluoro-N-([5-fluoro-2-[2-(trifluoromethyl)pyrimidin-5-yl]pyridin-4-yl]methyl)-1-[(4-fluorobenzene)sulfonyl]-5-methyl-N-[(methylsulfanyl)methyl]pyrrolidine-2-carboxamide

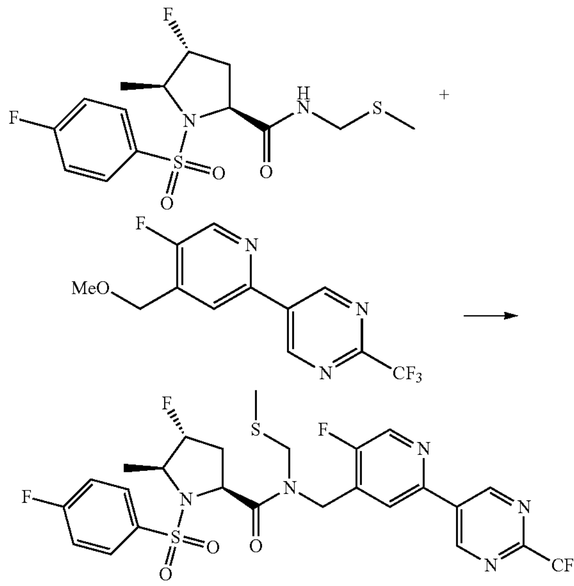

Sodium hydride (1.02 g, 60% in mineral oil, 3.00 equiv) was added in portions into a mixture of (2S,4R,55)-4-fluoro-1-[(4-fluorobenzene)sulfonyl]-5-methyl-N-[(methylsulfanyl)methyl]pyrrolidine-2-carboxamide (3.1 g, 8.50 mmol, 1.00 equiv) and tetrahydrofuran (600 mL) at −5° C. under nitrogen. The resulting mixture was stirred for 1 hour at −5° C. NaI (1.7 g, 11.34 mmol, 1.33 equiv) was added in portions at −5° C. and then [5-fluoro-2-[2-(trifluoromethyl) pyrimidin-5-yl]pyridin-4-yl]methyl methanesulfonate (3.9 g, 11.10 mmol, 1.30 equiv) in 100 mL of THF was added dropwise with stirring at −5° C. over 90 min. The resulting solution was allowed to react, with stirring, for an additional 12 h at room temperature. The reaction was quenched by water, extracted with ethyl acetate, washed with brine, dried over anhydrous sodium sulfate, and concentrated under vacuum. The residue was purified by a silica gel column eluting with ethyl acetate/petroleum ether (1/4). The collected fractions were concentrated under vacuum and re-purified by Flash-Prep-HPLC with the following conditions: Column, C18 silica gel; mobile phase, $CH_3CN$/water=5% increasing to $CH_3CN$/water=95% within 30 min; Detector, UV 254 nm. This resulted in the title compound (300 mg, 6%) as a white solid. LCMS [M+H$^+$] 620.

Step 6: Preparation of sodium ((2S,4R,5S)-4-fluoro-N-((5-fluoro-2-(2-(trifluoromethyl)pyrimidin-5-yl) pyridin-4-yl)methyl)-1-((4-fluorophenyl)sulfonyl)-5-methylpyrrolidine-2-carboxamido)methyl phosphate

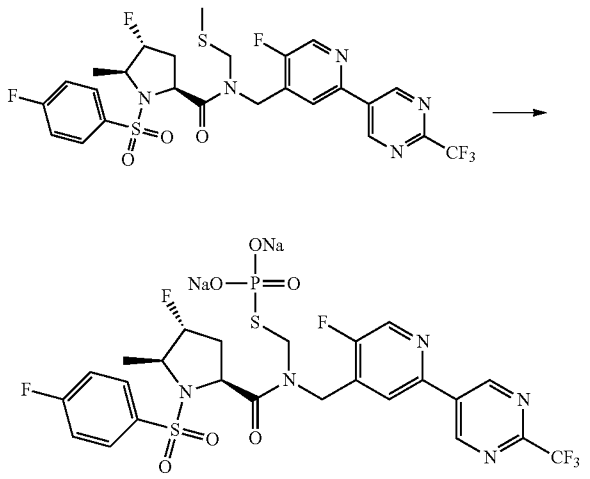

A mixture of (2S,4R,5S)-4-fluoro-N-([5-fluoro-2-[2-(trifluoromethyl)pyrimidin-5-yl]pyridin-4-yl]methyl)-1-[(4-fluorobenzene)sulfonyl]-5-methyl-N-[(methylsulfanyl) methyl]pyrrolidine-2-carboxamide (330 mg, 0.53 mmol, 1.00 equiv), tetrahydrofuran (20 mL), $H_3PO_4$ (1.60 g, 16.32 mmol, 30.65 equiv) and 3A seives was stirred for 15 min at room temperature. NIS (240 mg, 1.06 mmol, 2.00 equiv) was added in one portion at 0° C. The resulting solution was stirred for 1 h at room temperature and diluted with 20 mL of methanol. The solid was filtered out and the filtrate was quenched by 1N of $Na_2S_2O_3$. The pH value of the solution was adjusted to 10 with solid sodium carbonate. The solid was filtered out and the liquid was concentrated under vacuum. The residue was purified by Flash-Prep-HPLC with the following conditions: Column, C18 silica gel; mobile phase, methanol/$H_2O$=0 increasing to methanol/$H_2O$=100 within 30 min; Detector, UV 254 nm. The fractions were concentrated and lyophilized to dryness to provide the sodium salt (300 mg, 84%) as an off-white solid. LCMS [M+H$^+$] 670. $^1$H NMR (300 MHz, $CD_3OD$) δ 9.63 (s, 2H), 8.62 (s, 1H), 8.20 (d, J=6 Hz, 1H), 8.11 (dd, J=8.9, 5.0 Hz, 2H), 7.37 (t, J=8.7 Hz, 2H), 5.77 (dd, J=10.7, 8.1 Hz, 1 Hz), 5.29-5.15 (m, 3H), 5.19-4.78 (m, 2H), 4.05-3.95 (m, 1H), 2.90-2.79 (m, 1H), 2.41-2.23 (m, 1H), 1.32 (d, J=6.9 Hz, 3H).

Example 158: sodium ((2S,4R,5S)-4-fluoro-1-((4-fluorophenyl)sulfonyl)-5-methyl-N-((5-(trifluoromethyl)-2-(2-(trifluoromethyl)pyrimidin-5-yl)pyridin-4-yl)methyl)pyrrolidine-2-carboxamido)methyl phosphate

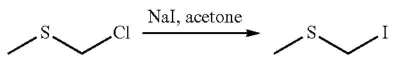

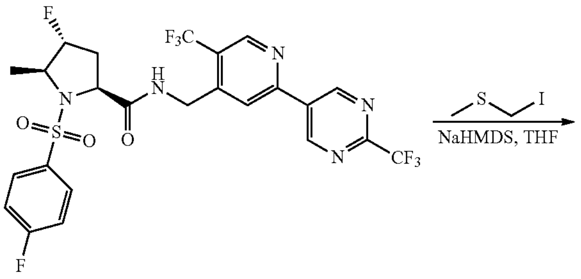

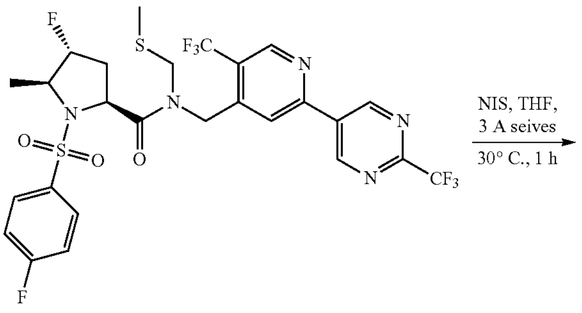

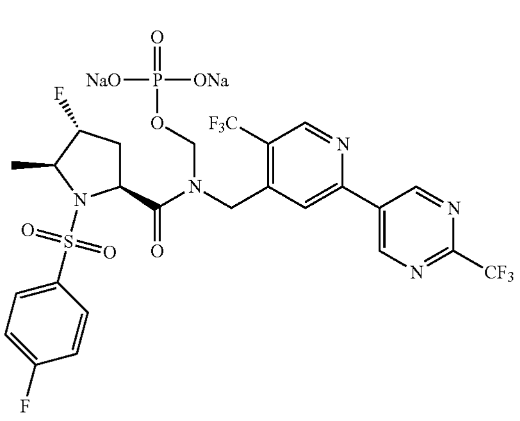

Step 1: Preparation of iodo(methylsulfanyl)methane

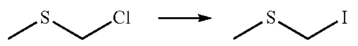

A mixture of chloro(methylsulfanyl)methane (1.5 g, 15.53 mmol, 1.00 equiv) and NaI (2.6 g, 17.35 mmol, 1.12 equiv) in acetone (20 mL) was stirred for 12 h at room temperature in a dark room. The resulting mixture was diluted with water, extracted with diethyl ether, washed with 5% aqueous of $Na_2S_2O_3$ and brine, dried over anhydrous sodium sulfate and concentrated under vacuum below 20° C. This resulted in the title compound (2.5 g, crude) as yellow oil, which was used for the next step as fresh as possible.

Step 2: Preparation of (2S,4R,5S)-4-fluoro-1-[(4-fluorobenzene)sulfonyl]-5-methyl-N-[(methyl sulfanyl)methyl]-N-[[5-(trifluoromethyl)-2-[2-(trifluoromethyl)pyrimidin-5-yl]pyridin-4-yl]methyl]pyrrolidine-2-carboxamide

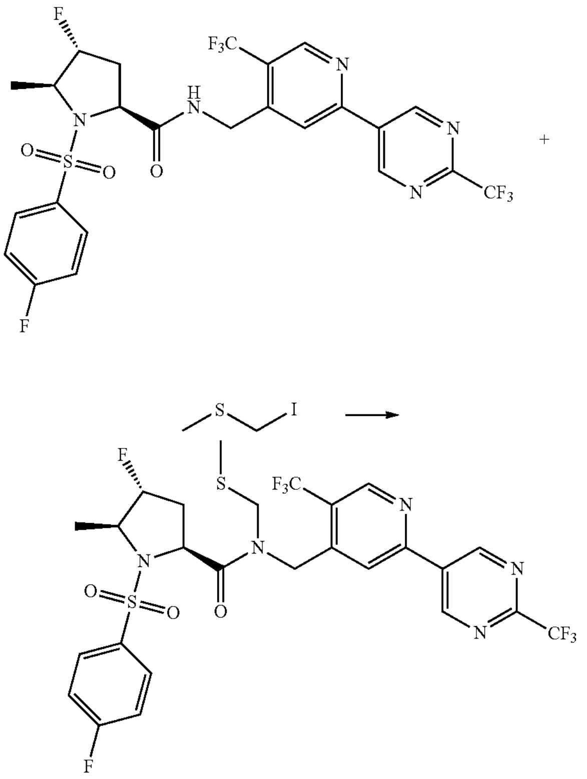

NaHMDS (2.46 mL, 2M in THF, 3.00 equiv) was added dropwise into a solution of (2S,4R,55)-4-fluoro-1-[(4-fluorobenzene)sulfonyl]-5-methyl-N-[[5-(trifluoromethyl)-2-[2-(trifluoromethyl)pyrimidin-5-yl]pyridin-4-yl]methyl]pyrrolidine-2-carboxamide (1.0 g, 1.64 mmol, 1.00 equiv) in tetrahydrofuran (150 mL) at −78° C. under nitrogen. The resulting solution was stirred for 30 min at −78° C. To this was added iodo(methylsulfanyl)methane (2.5 g, 13.30 mmol, 8.10 equiv) dropwise at −78° C. The resulting solution was stirred for 12 h at room temperature. The reaction was then quenched by water, extracted with ethyl acetate, washed with brine, dried over anhydrous sodium sulfate, and concentrated under vacuum. The residue was first purified by a silica gel column eluting with ethyl acetate/petroleum ether (1/4). The resulting product was then repurified by Flash-Prep-HPLC with the following conditions: Column, C18 silica gel; mobile phase, $CH_3CN/H_2O$ (10 mmol/L of $NH_4HCO_3$)=5% increasing to $CH_3CN/H_2O$ (10 mmol/L of $NH_4HCO_3$)=95% within 30 min; Detector, UV 254 nm. This resulted in the title compound (500 mg, 46%) as a white solid. LCMS [M+H$^+$] 670.

Step 3: Preparation sodium ((2S,4R,5S)-4-fluoro-1-((4-fluorophenyl)sulfonyl)-5-methyl-N-((5-(trifluoromethyl)-2-(2-(trifluoromethyl)pyrimidin-5-yl)pyridin-4-yl)methyl)pyrrolidine-2-carboxamido)methyl phosphate

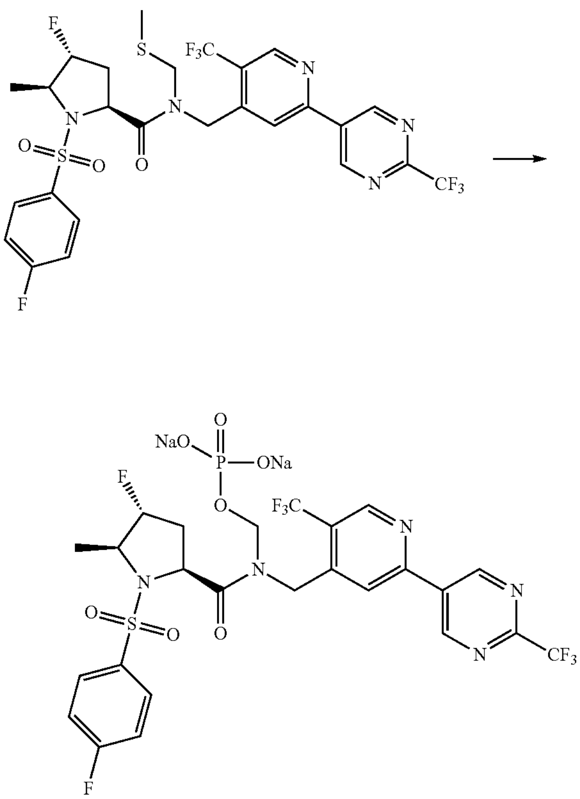

A mixture of (2S,4R,5S)-4-fluoro-1-[(4-fluorobenzene)sulfonyl]-5-methyl-N-[(methylsulfanyl)methyl]-N-[[5-(trifluoromethyl)-2-[2-(trifluoromethyl)pyrimidin-5-yl]pyridin-4-yl]methyl]pyrrolidine-2-carboxamide (420 mg, 0.63 mmol, 1.00 equiv), $H_3PO_4$ (1.88 g, 19.19 mmol, 30.59 equiv), and 3A seives in tetrahydrofuran (35 mL) was stirred for 15 min at room temperature. NIS (282 mg, 1.25 mmol, 2.00 equiv) was added in one portion at room temperature. The resulting solution was stirred for 1 h at 30° C. The resulting solution was diluted with 35 mL of methanol. The solid was filtered out. The reaction was then quenched by 5% of $Na_2S_2O_3$. The pH value of the solution was adjusted to 10 with solid sodium carbonate. The solid was filtered out. The resulting filtrate was concentrated under vacuum. The crude product was purified by Flash-Prep-HPLC with the following conditions: Column, C18 silica gel; mobile phase, methanol/$H_2O$=0% increasing to methanol/$H_2O$=100 within 30 min; Detector, UV 254 nm. The collected fractions at 15% was concentrated under vacuum and then lyophilized to dryness to provide the sodium salt (229 mg, 51%) as a white solid. LCMS [M+H$^+$] 720. $^1$H NMR (300 MHz, $CD_3OD$) δ 9.73 (s, 2H), 9.00 (s, 1H), 8.31 (s, 1H), 8.16-8.04 (m, 2H), 7.41-7.28 (m, 2H), 5.82 (dd, J=11.1, 6.6 Hz, 1H), 5.36 (d, J=17.9 Hz, 1H), 5.29-5.16 (m, 2H), 4.98-4.75 (m, 2H), 3.99-3.90 (m, 1H), 2.91-2.78 (m, 1H), 2.38-2.15 (m, 1H), 1.26 (d, J=6.9 Hz, 3H).

IC50 Determinations of Exemplified Compounds.

IC50s (effective concentration) of compounds on the human and rat TRPA1 channels were determined using a FLIPR Tetra instrument. CHO cells expressing TRPA1 were plated into 384-well plates, incubated overnight at 37 C, and loaded with BD calcium indicator dye for 1 hr at 37° C. followed by 15 minutes at room temperature. The assay buffer was Hank's Balanced Salt Solution (HBSS) containing 20 mM HEPES (pH readjusted to 7.4) along with 0.02% BSA.

Following dye load and plate cool down, compounds were added to the cells using FLIPR Tetra. Plates were then incubated with compounds for 20 minutes at room temperature prior to adding agonist. Following this incubation, ~EC80 concentration of cinnamaldehyde (75 uM for human TRPA1 and 45 uM for rat TRPA1) was added to active the channels and block of cinnamaldehyde induced calcium influx was measured.

IC50s were fit with a standard Hill function, keeping the Hill coefficient (n) fixed to 1.5. Fixing the Hill coefficient will generally reduce variability of the IC50 determination. The IC50s were individually examined to make sure the MIN and MAX points were set correctly prior to validation of the results.

The above compounds of Examples 1-4, 59, 68, 71, 78, 93, 94, 100, 102, 103, 104, 112, 114, 115, 122, 126, 129, 142, 157, 158 together with additional compounds made using the above procedures or purchased via commercial sources, are shown in Table 2 below, together with hTRPA1 $IC_{50}$ (micromolar) and proton NMR data for selected compounds.

TABLE 2

| Example | Structure | Name | hTRPA1 CHO Ca2+ AUC EVO (IC50) | $^1$H NMR | LCMS |
|---|---|---|---|---|---|
| 1. | 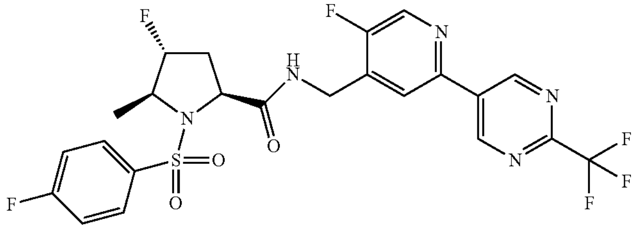 [SMILES: C[C@H]1[C@H](F)C[C@@H](C(=O)NCc2cc(-c3cnc(C(F)(F)F)nc3)ncc2F)N1S(=O)(=O)c1ccc(F)cc1] | (2S,4R,5S)-4-fluoro-1-(4-fluorophenyl) sulfonyl-N-[[5-fluoro-2-[2-(trifluorometh-yl)pyrimidin-5-yl]-4-pyridyl]meth-yl]-5-methyl-pyrrolidine-2-carboxamide | 0.00191 | $^1$HNMR(300 MHz, $CDCl_3$) δ9.59 (s, 2H), 8.58-8.53 (s, 1H), 8.32-8.30 (m, 1H), 8.03-7.96 (m, 2H), 7.34-7.27 (m, 2H), 4.88-4.63 (m, 3H), 4.28-4.22 (m, 1H), 4.08-3.98 (m, 1H), 3.29-3.27 (s, 1H), 2.44-2.17 (m, 2H), 1.34-1.32 (m, 3H). | 560 |
| 2. | 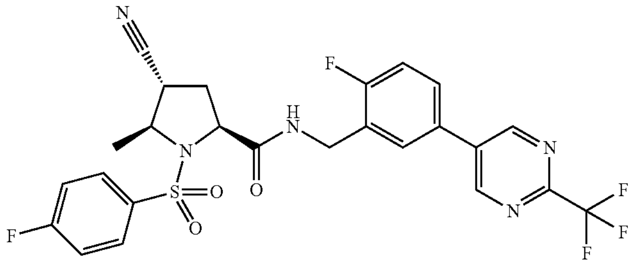 [SMILES: C[C@H]1[C@H](C#N)C[C@@H](C(=O)NCc2cc(-c3cnc(C(F)(F)F)nc3)ccc2F)N1S(=O)(=O)c1ccc(F)cc1] | (2S,4R,5S)-4-cyano-1-(4-fluorophenyl) sulfonyl-N-[[2-fluoro-5-[2-(trifluorometh-yl)pyrimidin-5-yl]phenyl] methyl]-5-methyl-pyrrolidine-2-carboxamide | 0.00746 | H NMR (400 MHz, $CDCl_3$) δ 9.12 (s, 2H), 7.94-7.90 (m, 2H), 7.72-7.70 (m, 1H), 7.59-7.55 (m, 1H), 7.36-7.30 (m, 4H), 4.79-4.74 (m, 1H), 4.64-4.58 (m, 1H), 4.32-4.29 (m, 1H), 3.82-3.79 (t, J = 8.6 Hz, 1H), 2.81-2.63 (m, 2H), 1.84-1.76 (m, 1H), 1.58 (s, 3H). | 566 |
| 3. | 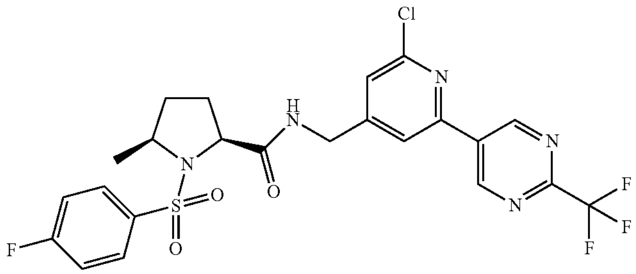 [SMILES: C[C@H]1CC[C@@H](C(=O)NCc2cc(Cl)nc(-c3cnc(C(F)(F)F)nc3)c2)N1S(=O)(=O)c1ccc(F)cc1] | (2S,5S)-N-[[2-chloro-6-[2-(trifluorometh-yl)pyrimidin-5-yl]-4-pyridyl]meth-yl]-1-(4-fluorophenyl) sulfonyl-5-methyl-pyrrolidine-2-carboxamide | 0.00112 | $^1$HNMR (400 MHz, $CDCl_3$) δ9.56 (s, 2H), 7.94-7.91 (m, 3H), 7.54 (s, 1H), 7.40 (s, 1H), 7.33-7.28 (m, 2H), 4.94-4.90 (m, 1H), 4.44-4.40 (s, 1H), 4.19-4.16 (s, 1H), 3.75-3.70 (s, 1H), 2.21-2.18 (m, 1H), 1.77-1.68 (s, 2H), 1.56-1.49 (m, 4H) | 558.2 |
| 4. | 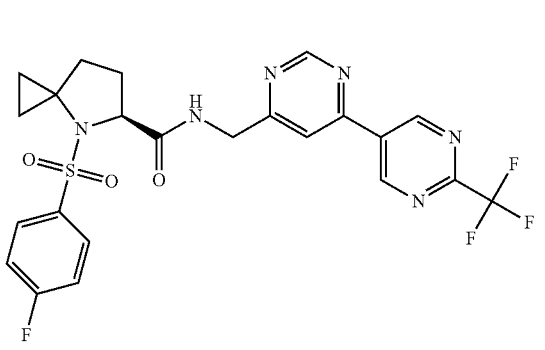 [SMILES: O=C(NCc1cc(-c2cnc(C(F)(F)F)nc2)ncn1)[C@@H]1CCC2(CC2)N1S(=O)(=O)c1ccc(F)cc1] | (5S)-4-(4-fluorophenyl) sulfonyl-N-[[6-[2-(trifluorometh-yl)pyrimidin-5-yl]pyrimidin-4-yl]methyl]-4-azaspiro[2.4] heptane-5-carboxamide | 0.0712 | $^1$HNMR(400 MHz, MeOD) δ 9.69 (s, 2H), 9.32 (s, 1H), 8.15 (s, 1H), 8.02-7.98 (m, 2H), 7.53-7.52 (m, 1H), 7.35-7.30 (t, J = 8.4 Hz, 2H), 5.13-5.07 (m, 1H), 4.54-4.48 (m, 2H), 2.40-2.29 (m, 2H), 2.15-2.10 (m, 1H), 1.28-1.17 (m, 2H), 0.97-0.88 (m, 2H), 0.62-0.57 (m, 1H) | 549 |

TABLE 2-continued

| Example | Structure | Name | hTRPA1 CHO Ca2+ AUC EVO (IC50) | $^{1}$H NMR | LCMS |
|---|---|---|---|---|---|
| 5. | 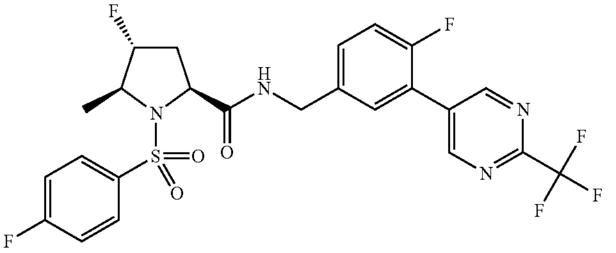 | (2S,4R,5S)-4-fluoro-1-(4-fluorophenyl)sulfonyl-N-[[4-fluoro-3-[2-(trifluoromethyl)pyrimidin-5-yl]phenyl]methyl]-5-methyl-pyrrolidine-2-carboxamide | 0.00377 | $^{1}$H NMR (400 MHz, $CDCl_3$) δ 9.16 (s, 2H), 7.86-7.79 (m, 2H), 7.59-7.56 (m, 1H), 7.49-7.46 (m, 1H), 7.30-7.28 (m, 1H), 7.25-7.22 (m, 3H), 4.84-4.46 (m, 2H), 4.45-4.39 (m, 1H), 4.26-4.22 (m, 1H), 4.16-4.09 (m, 1H), 2.51-2.25 (m, 2H), 1.32 (s, 3H). | 559 |
| 6. | 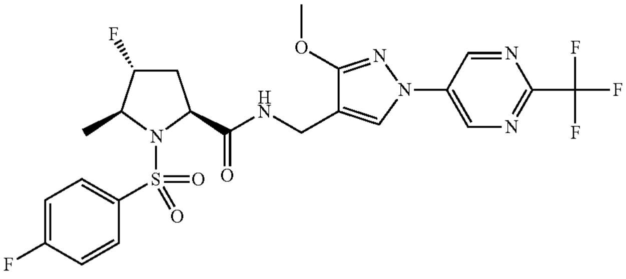 [SMILES: COc1nn(-c2cnc(C(F)(F)F)nc2)cc1CNC(=O)[C@@H]1C[C@@H](F)[C@H](C)N1S(=O)(=O)c1ccc(F)cc1] | (2S,4R,5S)-4-fluoro-1-(4-fluorophenyl)sulfonyl-N-[[3-methoxy-1-[2-(trifluoromethyl)pyrimidin-5-yl]pyrazol-4-yl]methyl]-5-methyl-pyrrolidine-2-carboxamide | 0.00962 | $^{1}$HNMR (300 MHz, $CDCl_3$) δ 9.10 (s, 2H), 8.10 (s, 1H), 7.89-7.84 (m, 2H), 7.23-7.20 (m, 3H), 4.78-4.51 (m, 2H), 4.25-4.03 (m, 6H), 2.59-2.16 (m, 2H), 1.33 (d, J = 6.9 Hz, 3H). | 561.2 |
| 7. | 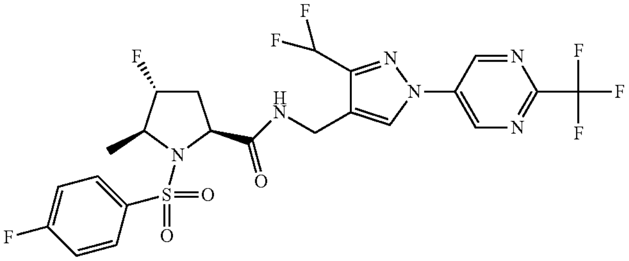 [SMILES: C[C@H]1[C@H](F)C[C@@H](C(=O)NCc2cn(-c3cnc(C(F)(F)F)nc3)nc2C(F)F)N1S(=O)(=O)c1ccc(F)cc1] | (2S,4R,5S)-N-[[3-(difluoromethyl)-1-[2-(trifluoromethyl)pyrimidin-5-yl]pyrazol-4-yl]methyl]-4-fluoro-1-(4-fluorophenyl)sulfonyl-5-methyl-pyrrolidine-2-carboxamide | 0.0262 | $^{1}$HNMR(300 MHz, $CDCl_3$) δ9.31 (s, 2H), 8.50 (s, 1H), 7.91-7.86 (m, 2H), 7.29-7.14 (m, 3H), 7.01- 6.65 (t, J = 54 Hz, 1H), 4.93-4.84 (dd, $J_1$ = 9 Hz, $J_2$ = 9 Hz, 1H), 4.79-4.61 (dd, $J_1$ = 3 Hz, $J_2$ = 3 Hz, 1H), 4.46-4.39 (dd, $J_1$ = 3 Hz, $J_2$ = 6 Hz, 1H), 4.24-4.18 (m, 1H), 4.10-4.01 (m, 1H), 2.58-2.52 (m, 1H), 2.35-2.17 (m, 1H), 1.38-1.36 (d, J = 6 Hz, 3H). | 581.2 |
| 8. | 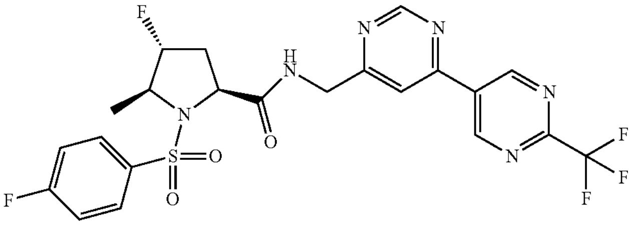 [SMILES: C[C@H]1[C@H](F)C[C@@H](C(=O)NCc2cc(-c3cnc(C(F)(F)F)nc3)ncn2)N1S(=O)(=O)c1ccc(F)cc1] | (2S,4R,5S)-4-fluoro-1-(4-fluorophenyl)sulfonyl-5-methyl-N-[[6-[2-(trifluoromethyl)pyrimidin-5-yl]pyrimidin-4-yl]methyl]pyrrolidine-2-carboxamide | 0.0173 | $^{1}$H NMR (400 MHz, $CDCl_3$) δ9.70 (s, 2H), 9.32 (m, 1H), 8.26 (s, 1H), 7.95-7.92 (s, 2H), 7.47 (s, 1H), 7.30-7.28 (m, 2H), 5.07 (s, 1H), 4.82-4.69 (d, J = 52 Hz, 1H), 4.55-4.40 (m, 1H), 4.31 (s, 1H), 4.14-4.07 (m, 1H), 2.63-2.62 (m, 1H), 2.40-2.15 (m, 1H), 1.44-1.43 (m, 3H) | 543.2 |

TABLE 2-continued

| Example | Structure | Name | hTRPA1 CHO Ca2+ AUC EVO (IC50) | $^1$H NMR | LCMS |
|---|---|---|---|---|---|
| 9. | 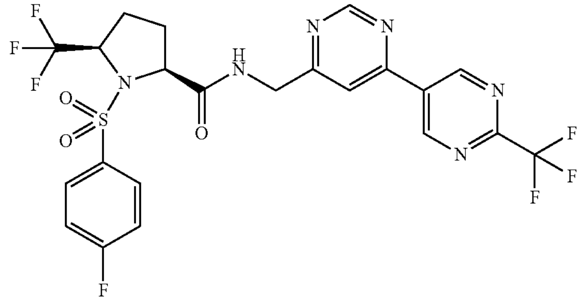 [SMILES: O=C(NCc1cc(-c2cnc(C(F)(F)F)nc2)ncn1)[C@@H]1CC[C@H](C(F)(F)F)N1S(=O)(=O)c1ccc(F)cc1] | (2S,5R)-1-(4-fluorophenyl) sulfonyl-5-(trifluorometh-yl)-N-[[6-[2-(trifluorometh-yl)pyrimidin-5-yl]pyrimidin-4-yl]methyl] pyrrolidine-2-carboxamide | 0.0422 | $^1$H NMR (400 MHz, DMSO-$d_6$) δ 9.67 (s, 2H), 9.34 (d, J = 1.3 Hz, 1H), 8.82 (t, J = 5.9 Hz, 1H), 8.20 (d, J = 1.3 Hz, 1H), 8.19-8.10 (m, 2H), 7.56-7.41 (m, 2H), 4.68 (t, J = 8.1 Hz, 1H), 4.63-4.42 (m, 2H), 4.25 (t, J = 8.0 Hz, 1H), 2.14 (s, 1H), 2.08-1.91 (m, 2H), 1.65 (d, J = 7.7 Hz, 1H). | 579.2 |
| 10. | 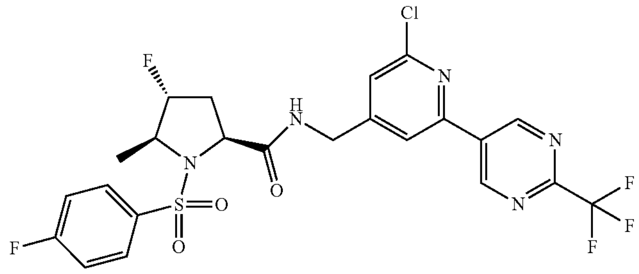 [SMILES: C[C@H]1[C@H](F)C[C@@H](C(=O)NCc2cc(Cl)nc(-c3cnc(C(F)(F)F)nc3)c2)N1S(=O)(=O)c1ccc(F)cc1] | (2S,4R,5S)-N-[[2-chloro-6-[2-(trifluorometh-yl)pyrimidin-5-yl]-4-pyridyl]meth-yl]-4-fluoro-1-(4-fluorophenyl) sulfonyl-5-methyl-pyrrolidine-2-carboxamide | 0.00226 | $^1$HNMR (300 MHz, $CDCl_3$)δ9.57 (s, 2H), 7.96 (s, 1H), 7.92-7.87 (m, 2H), 7.44-7.39 (m, 2H), 7.28-7.22 (m, 2H), 4.95-4.87 (m, 1H), 4.81-4.80 (d, J = 3 Hz, 1H), 4.64-4.63 (d, J = 3 Hz, 1H), 4.42-4.24 (m, 1H), 4.15-4.05 (m, 1H), 2.59-2.50 (m, 1H), 2.42-2.22 (m, 1H), 1.37-1.35 (d, J = 6 Hz, 3H) | |
| 11. | 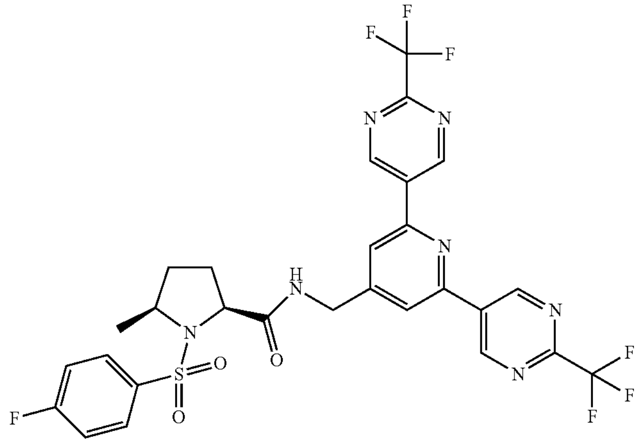 [SMILES: C[C@H]1CC[C@@H](C(=O)NCc2cc(-c3cnc(C(F)(F)F)nc3)nc(-c3cnc(C(F)(F)F)nc3)c2)N1S(=O)(=O)c1ccc(F)cc1] | (2S,5S)-N-[[2,6-bis[2-(trifluorometh-yl)pyrimidin-5-yl]-4-pyridyl]meth-yl]-1-(4-fluorophenyl) sulfonyl-5-methyl-pyrrolidine-2-carboxamide | 0.00317 | $^1$HNMR (400 MHz, $CDCl_3$) δ9.65 (s, 4H), 8.03 (s, 2H), 7.96- 7.92 (m, 2H), 7.63 (s,1H), 7.34-7.28 (m, 2H), 5.17-5.11 (m, 1H), 4.50-4.46 (m, 1H), 4.22-4.19 (m, 1H), 3.76-3.72 (m, 1H), 2.24-2.16 (m, 1H), 1.87-1.80 (m, 1H), 1.78-1.70 (m, 1H), 1.69-1.62 (m, 1H), 1.58-1.51 (m, 3H) | 670.2 |
| 12. | 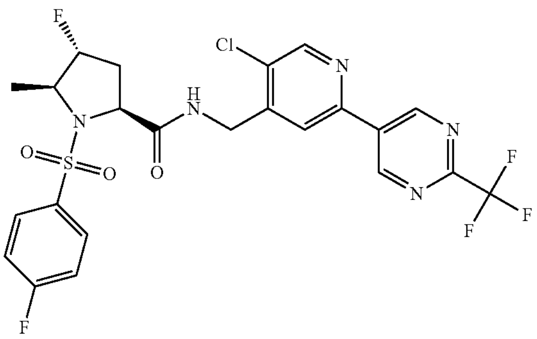 [SMILES: C[C@H]1[C@H](F)C[C@@H](C(=O)NCc2cc(-c3cnc(C(F)(F)F)nc3)ncc2Cl)N1S(=O)(=O)c1ccc(F)cc1] | (2S,4R,5S)-N-[[5-chloro-2-[2-(trifluorometh-yl)pyrimidin-5-yl]-4-pyridyl]meth-yl]-4-fluoro-1-(4-fluorophenyl) sulfonyl-5-methyl-pyrrolidine-2-carboxamide | 0.00294 | $^1$HNMR (400 MHz, $CDCl_3$) δ 9.62 (s, 2H), 8.71 (s, 1H), 8.21(s, 1H), 7.91-7.94 (m, 2H), 7.38 (s, 1H), 7.30-7.26 (m, 2H), 5.06-5.00 (m, 1H), 4.75 (d, J = 52.8 Hz, 1H), 4.49-4.43 (m, 1H), 4.32 (t, J = 8.8 Hz, 1H), 4.17-4.07(m, 1H), 2.67-2.57(m, 1H), 2.37-2.20(m, 1H), 1.27(s, 3H). | 576.1 |

TABLE 2-continued

| Example | Structure | Name | hTRPA1 CHO Ca2+ AUC EVO (IC50) | $^1$H NMR | LCMS |
|---|---|---|---|---|---|
| 13. | 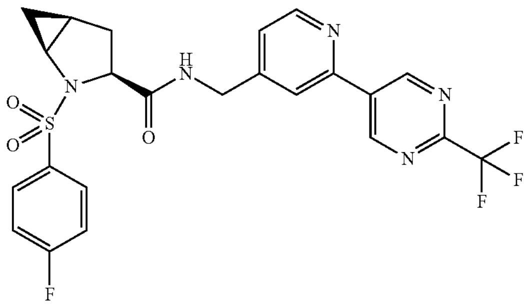 | (1S,3S,5S)-2-(4-fluorophenyl) sulfonyl-N-[[2-[2-(trifluorometh-yl)pyrimidin-5-yl]-4-pyridyl]meth-yl]-2-azabicyclo [3.1.0]hexane-3-carboxamide | 0.023 | $^1$H NMR (400 MHz, DMSO-$d_6$) δ 9.65 (d, J = 0.5 Hz, 2H), 8.74 (dd, J = 5.1, 0.7 Hz, 1H), 8.69 (t, J = 6.1 Hz, 1H), 8.11 (dd, J = 1.6, 0.8 Hz, 1H), 8.09-7.97 (m, 2H), 7.58-7.45 (m, 2H), 7.45-7.35 (m, 1H), 4.55 (dd, J = 10.9, 2.4 Hz, 1H), 4.44 (dd, J = 9.7, 6.1 Hz, 2H), 3.68 (ddd, J = 7.1, 5.8, 2.6 Hz, 1H), 1.97 (dd, J = 13.2, 2.4 Hz, 1H), 1.69-1.52 (m, 1H), 1.34 (dq, J = 8.7, 5.4 Hz, 1H), 0.71 (dt, J = 9.2, 6.8 Hz, 1H), 0.55 (ddd, J = 6.2, 4.8, 2.6 Hz, 1H). | 522.2 |
| 14. | 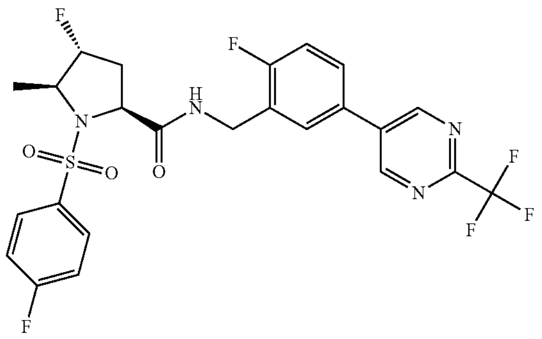 [SMILES: C[C@H]1[C@H](F)C[C@@H](C(=O)NCc2cc(-c3cnc(C(F)(F)F)nc3)ccc2F)N1S(=O)(=O)c1ccc(F)cc1] | (2S,4R,5S)-4-fluoro-1-(4-fluorophenyl) sulfonyl-N-[[2-fluoro-5-[2-(trifluorometh-yl)pyrimidin-5-yl]phenyl] methyl]-5-methyl-pyrrolidine-2-carboxamide | 0.00214 | $^1$H NMR (400 MHz, $CDCl_3$) δ 9.15 (s, 2H), 7.90-7.83 (m, 3H), 7.57-7.54 (m, 1H), 7.30-7.28 (m, 1H), 7.25-7.02 (m, 2H), 4.90-4.79 (m, 1H), 4.78-4.53 (m, 2H), 4.28-4.24 (t, J = 8.6 Hz, 1H), 4.18-4.09 (m, 1H), 2.61-2.51 (m, 1H), 2.40-2.28 (m, 1H), 1.34 (s, 3H) | 549 |
| 15. | 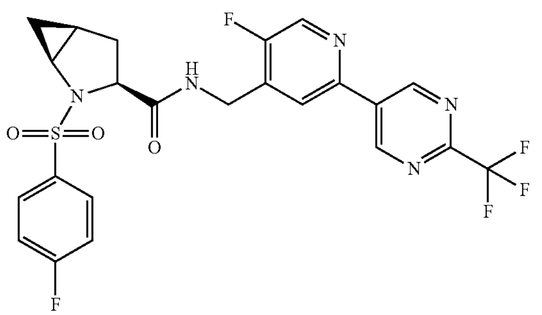 [SMILES: O=C(NCc1cc(-c2cnc(C(F)(F)F)nc2)ncc1F)[C@@H]1C[C@@H]2C[C@@H]2N1S(=O)(=O)c1ccc(F)cc1] | (1S,3S,5S)-2-(4-fluorophenyl) sulfonyl-N-[[5-fluoro-2-[2-(trifluorometh-yl)pyrimidin-5-yl]-4-pyridyl]meth-yl]-2-azabicyclo [3.1.0]hexane-3-carboxamide | 0.00060 | $^1$H NMR (400 MHz, DMSO-$d_6$) δ 9.60 (s, 2H), 8.77 (d, J = 1.3 Hz, 1H), 8.70 (t, J = 6.0 Hz, 1H), 8.13 (d, J = 5.7 Hz, 1H), 8.10-7.98 (m, 2H), 7.55-7.40 (m, 2H), 4.65-4.36 (m, 3H), 3.68 (ddd, J = 6.9, 5.7, 2.6 Hz, 1H), 1.95 (dd, J = 13.2, 2.6 Hz, 1H), 1.72-1.53 (m, 1H), 1.35 (dq, J = 10.5, 5.5 Hz, 1H), 0.71 (q, J = 7.2 Hz, 1H), 0.62-0.50 (m, 1H). | 540.2 |

TABLE 2-continued

| Example | Structure | Name | hTRPA1 CHO Ca2+ AUC EVO (IC50) | $^1$H NMR | LCMS |
|---|---|---|---|---|---|
| 16. | 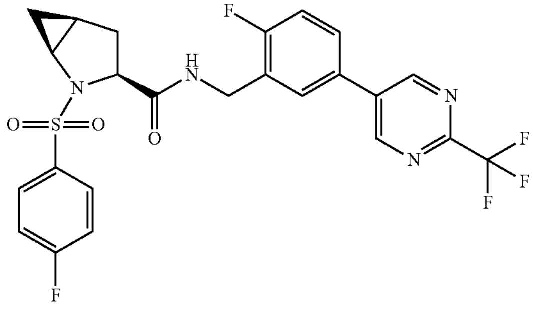 [SMILES: O=C(NCc1cc(-c2cnc(C(F)(F)F)nc2)ccc1F)[C@@H]1C[C@@H]2C[C@@H]2N1S(=O)(=O)c1ccc(F)cc1] | (1S,3S,5S)-2-(4-fluorophenyl)sulfonyl-N-[[2-fluoro-5-[2-(trifluoromethyl)pyrimidin-5-yl]phenyl]methyl]-2-azabicyclo[3.1.0]hexane-3-carboxamide | 0.00212 | $^1$H NMR (400 MHz, DMSO-$d_6$) δ 9.36 (s, 2H), 8.53 (t, J = 6.0 Hz, 1H), 8.09-7.96 (m, 2H), 7.96-7.80 (m, 2H), 7.54-7.34 (m, 3H), 4.52 (dd, J = 10.9, 2.4 Hz, 1H), 4.43 (dd, J = 10.0, 6.0 Hz, 2H), 3.65 (ddd, J = 7.0, 5.8, 2.6 Hz, 1H), 1.94 (dd, J = 13.1, 2.4 Hz, 1H), 1.67-1.54 (m, 1H), 1.41-1.23 (m, 1H), 0.73-0.60 (m, 1H), 0.57 (ddd, J = 6.1, 4.8, 2.6 Hz, 1H). | 539.2 |
| 17. | 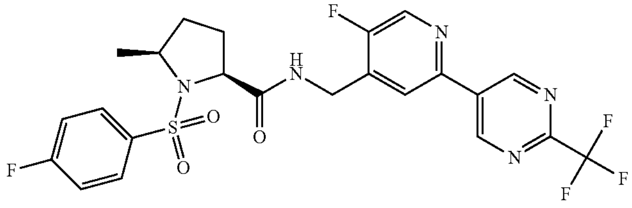 [SMILES: C[C@H]1CC[C@@H](C(=O)NCc2cc(-c3cnc(C(F)(F)F)nc3)ncc2F)N1S(=O)(=O)c1ccc(F)cc1] | (2S,5S)-1-(4-fluorophenyl)sulfonyl-N-[[5-fluoro-2-[2-(trifluoromethyl)pyrimidin-5-yl]-4-pyridyl]methyl]-5-methyl-pyrrolidine-2-carboxamide | 0.00137 | $^1$HNMR(400 MHz, $CDCl_3$): δ 9.58 (s, 2H), 8.59 (s, 1H), 8.13-8.12 (m, 1H), 7.95-7.91 (m, 2H), 7.54 (s, 1H), 7.33-7.28 (m, 2H), 5.06-5.00 (s, 1H), 4.50-4.46 (m, 1H), 4.21-4.17 (m, 1H), 3.75-3.70 (m, 1H), 2.22-2.14 (m, 1H), 1.82-1.70 (m, 2H), 1.68-1.58 (m, 1H), 1.51-1.50 (m, 3H) | 543.2 |
| 18. | 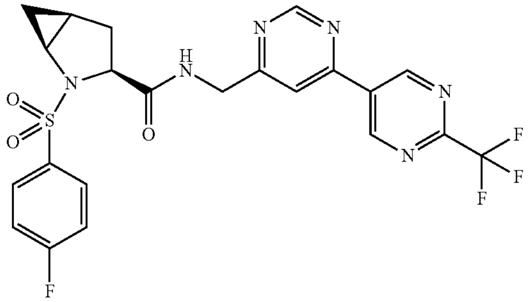 [SMILES: O=C(NCc1cc(-c2cnc(C(F)(F)F)nc2)ncn1)[C@@H]1C[C@@H]2C[C@@H]2N1S(=O)(=O)c1ccc(F)cc1] | (1S,3S,5S)-2-(4-fluorophenyl)sulfonyl-N-[[6-[2-(trifluoromethyl)pyrimidin-5-yl]pyrimidin-4-yl]methyl]-2-azabicyclo[3.1.0]hexane-3-carboxamide | 0.0298 | $^1$H NMR (400 MHz, DMSO-$d_6$) δ 9.72 (d, J = 0.5 Hz, 2H), 9.33 (d, J = 1.3 Hz, 1H), 8.69 (t, J = 6.0 Hz, 1H), 8.24-8.13 (m, 1H), 8.14-7.99 (m, 2H), 7.58-7.45 (m, 2H), 4.60 (dd, J = 10.8, 2.4 Hz, 1H), 4.56-4.44 (m, 2H), 3.69 (td, J = 6.0, 3.7 Hz, 1H), 2.00 (dd, J = 13.2, 2.4 Hz, 1H), 1.59 (td, J = 12.4, 11.9, 5.6 Hz, 1H), 1.35 (dd, J = 7.7, 5.3 Hz, 1H), 0.72 (dd, J = 8.6, 5.4 Hz, 2H). | 523.2 |
| 19. | 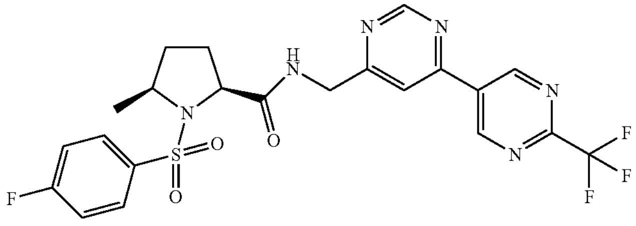 [SMILES: C[C@H]1CC[C@@H](C(=O)NCc2cc(-c3cnc(C(F)(F)F)nc3)ncn2)N1S(=O)(=O)c1ccc(F)cc1] | (2S,5S)-1-(4-fluorophenyl)sulfonyl-5-methyl-N-[[6-[2-(trifluoromethyl)pyrimidin-5-yl]pyrimidin-4-yl]methyl]pyrrolidine-2-carboxamide | 0.00522 | $^1$HNMR (300 MHz, $CDCl_3$) δ9.63 (s, 2H), 9.30 (s, 1H), 8.16 (s, 1H), 7.95-7.90 (m, 2H), 7.65-7.60 (m, 1H), 7.32-7.26 (m, 2H), 5.11-5.02 (m, 1H), 4.54-4.47 (m, 1H), 4.21-4.17 (m, 1H), 3.75-3.68 (m, 1H), 2.19-2.13 (m, 1H), 1.83-1.71 (m, 3H), 1.61-1.51 (m, 3H) | 525.2 |

TABLE 2-continued

| Example | Structure | Name | hTRPA1 CHO Ca2+ AUC EVO (IC50) | $^1$H NMR | LCMS |
|---|---|---|---|---|---|
| 20. | 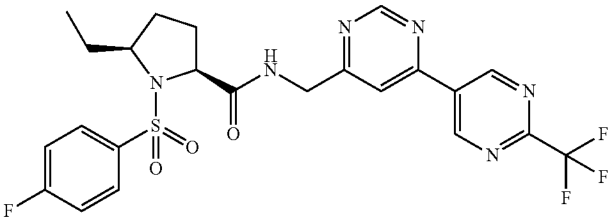 [SMILES: CC[C@H]1CC[C@@H](C(=O)NCc2cc(-c3cnc(C(F)(F)F)nc3)ncn2)N1S(=O)(=O)c1ccc(F)cc1] | (2S,5S)-5-ethyl-1-(4-fluorophenyl)sulfonyl-N-[[6-[2-(trifluoromethyl)pyrimidin-5-yl]pyrimidin-4-yl]methyl]pyrrolidine-2-carboxamide | 0.0109 | $^1$H NMR (400 MHz, DMSO) δ 9.71 (s, 2H), 9.34 (d, J = 1.3 Hz, 1H), 8.77 (t, J = 6.0 Hz, 1H), 8.24 (d, J = 1.4 Hz, 1H), 8.11-8.01 (m, 2H), 7.56-7.45 (m, 2H), 4.64-4.47 (m, 2H), 4.24-4.15 (m, 1H), 3.62-3.50 (m, 1H), 1.99-1.71 (m, 3H), 1.65-1.47 (m, 2H), 1.46-1.32 (m, 1H), 0.88 (t, J = 7.4 Hz, 3H). | 539.2 |
| 21. | 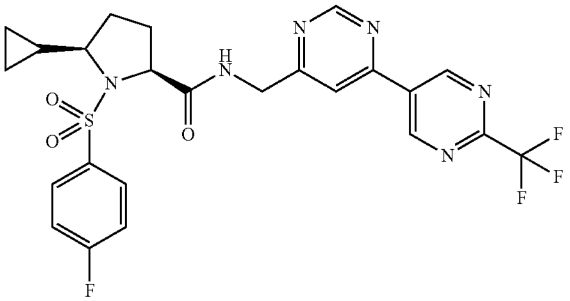 [SMILES: O=C(NCc1cc(-c2cnc(C(F)(F)F)nc2)ncn1)[C@@H]1CC[C@H](C2CC2)N1S(=O)(=O)c1ccc(F)cc1] | (2S,5R)-5-cyclopropyl-1-(4-fluorophenyl)sulfonyl-N-[[6-[2-(trifluoromethyl)pyrimidin-5-yl]pyrimidin-4-yl]methyl]pyrrolidine-2-carboxamide | 0.0713 | $^1$H NMR (400 MHz, DMSO-$d_6$) δ 9.78-9.58 (m, 2H), 9.34 (d, J = 1.3 Hz, 1H), 8.85 (t, J = 6.0 Hz, 1H), 8.32-8.20 (m, 1H), 8.14-7.96 (m, 2H), 7.58-7.33 (m, 2H), 4.70-4.41 (m, 2H), 4.23 (t, J = 7.5 Hz, 1H), 3.20-3.04 (m, 1H), 2.07-1.84 (m, 2H), 1.79-1.62 (m, 1H), 1.43 (ddt, J = 12.3, 9.6, 7.2 Hz, 1H), 1.11 (tdd, J = 8.3, 5.0, 3.4 Hz, 1H), 0.56-0.44 (m, 1H), 0.39 (ddt, J = 8.2, 1.9, 1.3 Hz, 2H), 0.25 (dtd, J = 9.4, 3.2, 1.5 Hz, 1H). | 551.2 |
| 22. | 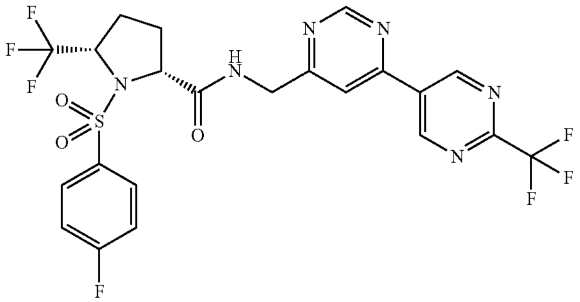 [SMILES: O=C(NCc1cc(-c2cnc(C(F)(F)F)nc2)ncn1)[C@H]1CC[C@@H](C(F)(F)F)N1S(=O)(=O)c1ccc(F)cc1] | (2R,5S)-1-(4-fluorophenyl)sulfonyl-5-(trifluoromethyl)-N-[[6-[2-(trifluoromethyl)pyrimidin-5-yl]pyrimidin-4-yl]methyl]pyrrolidine-2-carboxamide | 3.61 | $^1$H NMR (400 MHz, DMSO-$d_6$) δ 9.67 (s, 2H), 9.34 (d, J = 1.3 Hz, 1H), 8.82 (t, J = 5.9 Hz, 1H), 8.20 (d, J = 1.3 Hz, 1H), 8.19-8.05 (m, 2H), 7.63-7.40 (m, 2H), 4.68 (t, J = 8.1 Hz, 1H), 4.63-4.41 (m, 2H), 4.25 (t, J = 8.0 Hz, 1H), 2.14 (s, 1H), 2.00 (d, J = 9.5 Hz, 2H), 1.65 (d, J = 8.3 Hz, 1H). | 579.2 |
| 23. | 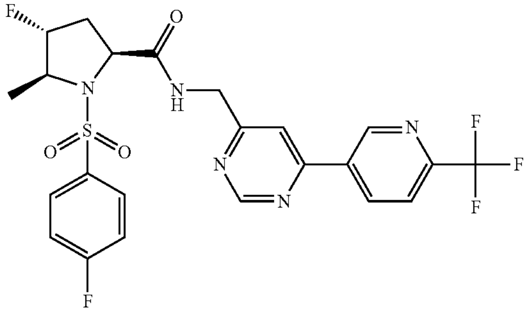 [SMILES: C[C@H]1[C@H](F)C[C@@H](C(=O)NCc2cc(-c3ccc(C(F)(F)F)nc3)ncn2)N1S(=O)(=O)c1ccc(F)cc1] | (2S,4R,5S)-4-fluoro-1-(4-fluorophenyl)sulfonyl-5-methyl-N-[[6-[6-(trifluoromethyl)-3-pyridyl]pyrimidin-4-yl]methyl]pyrrolidine-2-carboxamide | 0.0856 | $^1$HNMR (400 MHz, $CDCl_3$) δ9.55 (s, 1H), 9.31 (m, 1H), 8.75-8.73 (s, 1H), 8.20-8.16 (s, 1H), 7.94-7.89 (m, 2H), 7.84-7.83 (m, 1H), 7.61-7.51 (m, 1H), 7.28-7.18 (m, 2H), 5.05-4.90 (m, 1H), 4.82-4.69 (m, 1H), 4.70-4.58 (m, 1H), 4.31-4.22 (m, 1H), 4.15-4.10 (m, 1H), 2.60-2.57 (m, 1H), 2.57-2.27 (m, 1H), 1.44-1.35 (m, 3H). | 542.2 |

TABLE 2-continued

| Example | Structure | Name | hTRPA1 CHO Ca2+ AUC EVO (IC50) | $^1$H NMR | LCMS |
|---|---|---|---|---|---|
| 24. | 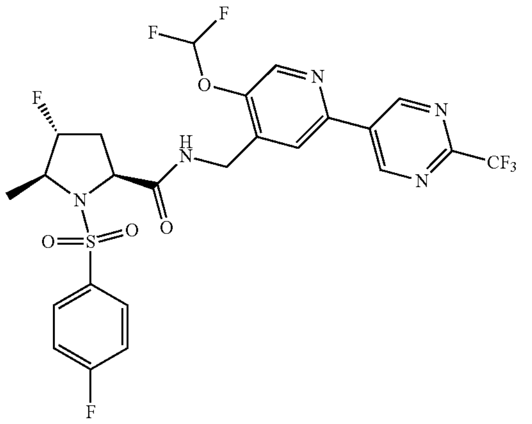 [SMILES: C[C@H]1[C@H](F)C[C@@H](C(=O)NCc2cc(-c3cnc(C(F)(F)F)nc3)ncc2OC(F)F)N1S(=O)(=O)c1ccc(F)cc1] | (2S,4R,5S)-N-((5-(difluoromethoxy)-2-(2-(trifluoromethyl)pyrimidin-5-yl)pyridin-4-yl)methyl)-4-fluoro-1-(4-fluorophenylsulfonyl)-5-methylpyrrolidine-2-carboxamide | 0.0193 | $^1$H NMR (400 MHz, $CDCl_3$) δ 9.59 (s, 2H), 8.63 (s, 1H), 8.28 (s, 1H), 7.91 (s, 2H), 7.46-7.42 (m, 1H), 7.28 (s, 2H), 6.94-6.58 (t, J = 72.0 Hz, 1H), 5.01-4.90 (m, 1H), 4.81-4.67 (d, J = 56.0 Hz, 1H), 4.48-4.41 (m, 1H), 4.31-4.24 (m, 1H), 4.15-4.08 (m, 1H), 2.62-2.56 (m, 1H), 2.36-2.07 (m, 1H), 1.40-1.38 (d, J = 8.0 Hz, 3H). | 608 |
| 25. | 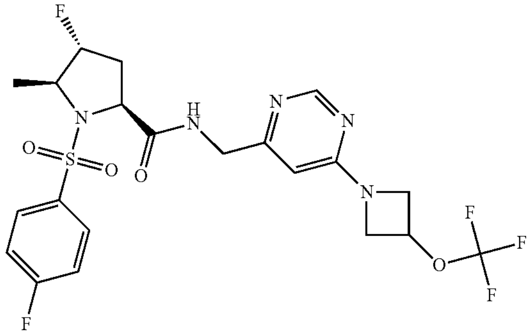 [SMILES: C[C@H]1[C@H](F)C[C@@H](C(=O)NCc2cc(N3CC(OC(F)(F)F)C3)ncn2)N1S(=O)(=O)c1ccc(F)cc1] | (2S,4R,5S)-4-fluoro-1-(4-fluorophenylsulfonyl)-5-methyl-N-((6-(3-(trifluoromethoxy)azetidin-1-yl)pyrimidin-4-yl)methyl) pyrrolidine-2-carboxamide | 2.4 | $^1$H NMR (400 MHz, $CDCl_3$) δ 8.69 (s, 1H), 7.95-7.92 (m, 2H), 7.69-7.48 (m, 1H), 7.28-7.22 (m, 2H), 6.64 (m, 1H), 5.12 (s, 1H), 4.80-4.62 (m, 2H), 4.53-4.49 (m, 2H), 4.48-4.38 (m, 1H), 4.29-4.22 (m, 3H), 4.18-4.04 (m, 1H), 2.59-2.44 (m, 1H), 2.42-2.22 (m, 1H), 1.42-1.40 (d, J = 8.0 Hz, 3H). | 536 |
| 26. | 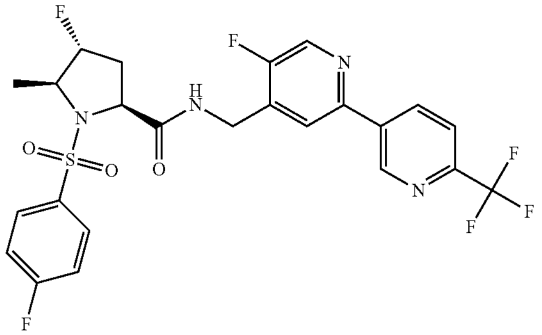 [SMILES: C[C@H]1[C@H](F)C[C@@H](C(=O)NCc2cc(-c3ccc(C(F)(F)F)nc3)ncc2F)N1S(=O)(=O)c1ccc(F)cc1] | (2S,4R,5S)-4-fluoro-N-((5-fluoro-6'-(trifluoromethyl)-2,3'-bipyridin-4-yl)methyl)-1-(4-fluorophenylsulfonyl)-5-methylpyrrolidine-2-carboxamide | 0.0412 | $^1$HNMR(300 MHz, $CDCl_3$) δ9.40 (s, 1H), 8.60-8.57 (m, 2H), 8.11-8.08 (d, J = 5.7 Hz, 1H), 7.93-7.88 (m, 2H), 7.77-7.62 (m, 1H), 7.37-7.23 (m, 3H), 4.99-4.90 (m, 1H), 4.82-3.81 (m, 1H), 4.65-4.49 (m, 1H), 4.31-4.25 (m, 1H), 4.19-4.08 (m, 1H), 2.64-2.20 (m, 2H), 1.38-1.36 (d, J = 6.9 Hz, 3H). | 559 |
| 27. | 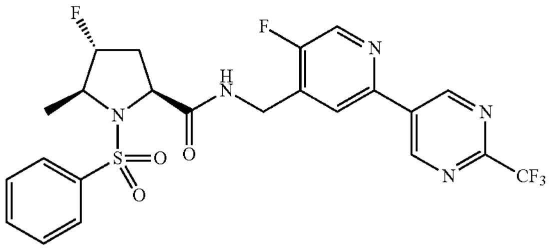 [SMILES: C[C@H]1[C@H](F)C[C@@H](C(=O)NCc2cc(-c3cnc(C(F)(F)F)nc3)ncc2F)N1S(=O)(=O)c1ccccc1] | (2S,4R,5S)-4-fluoro-N-((5-fluoro-2-(2-(trifluoromethyl)pyrimidin-5-yl)pyridin-4-yl)methyl)-5-methyl-1-(phenylsulfonyl)pyrrolidine-2-carboxamide | 0.0464 | $^1$HNMR(300 MHz, $CDCl_3$) δ9.58 (s, 2H), 8.58 (s, 1H), 8.23- 8.21 (d, J = 5.7 Hz, 1H), 7.90-7.87 (m, 2H), 7.72-7.70 (m, 1H), 7.61-7.56 (m, 2H), 7.39-7.27 (m, 1H), 5.06-4.98 (m, 1H), 4.80-4.62 (m, 1H), 4.51-4.44 (m, 1H), 4.37-4.31 (m, 1H), 4.17-4.08(m, 1H), 2.64-2.15 (m, 2H), 1.40-1.37 (d, J = 6.9 Hz, 3H). | 542 |

TABLE 2-continued

| Example | Structure | Name | hTRPA1 CHO Ca2+ AUC EVO (IC50) | $^1$H NMR | LCMS |
|---|---|---|---|---|---|
| 28. | 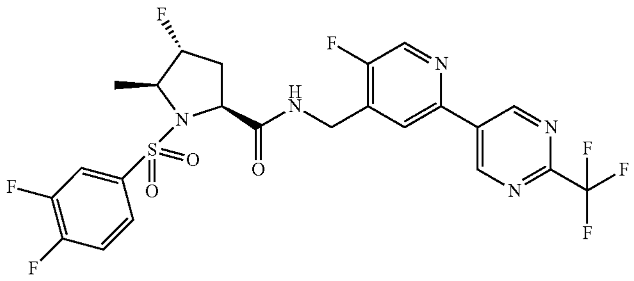 [SMILES: C[C@H]1[C@H](F)C[C@@H](C(=O)NCc2cc(-c3cnc(C(F)(F)F)nc3)ncc2F)N1S(=O)(=O)c1ccc(F)c(F)c1] | (2S,4R,5S)-1-(3,4-difluorophenylsulfonyl)-4-fluoro-N-((5-fluoro-2-(2-(trifluoromethyl)pyrimidin-5-yl)pyridin-4-yl)methyl)-5-methylpyrrolidine-2-carboxamide | 0.00696 | $^1$HNMR(300 MHz, $CDCl_3$) δ9.6-9.5 (s, 2H), 8.58-8.58 (s, 1H), 8.15-8.13 (d, J = 5.7 Hz, 1H), 7.76-7.61 (m, 2H), 7.42-7.26 (m, 1H), 5.04-4.96 (m, 1H), 4.84-4.83 (m, 1H), 4.67-4.66 (m, 1H), 4.52-4.44 (m, 1H), 4.32-4.04 (m, 1H), 3.69-3.66 (m, 1H), 2.63-2.60 (m, 2H), 1.39- 1.36 (d, J = 6.9 Hz, 3H). | 578 |
| 29. | 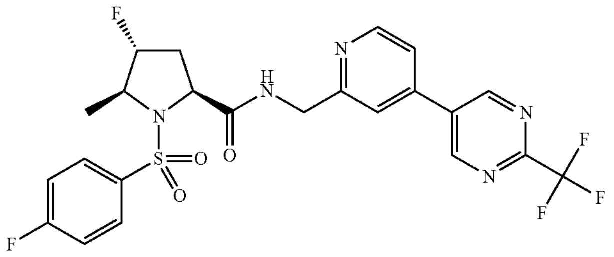 [SMILES: C[C@H]1[C@H](F)C[C@@H](C(=O)NCc2cc(-c3cnc(C(F)(F)F)nc3)ccn2)N1S(=O)(=O)c1ccc(F)cc1] | (2S,4R,5S)-4-fluoro-1-(4-fluorophenylsulfonyl)-5-methyl-N-((4-(2-(trifluoromethyl)pyrimidin-5-yl)pyridin-2-yl)methyl) pyrrolidine-2-carboxamide | 0.113 | $^1$HNMR(300 MHz, $CDCl_3$) δ 9.22 (s, 2H), 8.76(d, J = 4.8 Hz, 1H), 7.92-7.86 (m, 3H), 7.51 (d, J = 3.9 Hz, 1H), 7.65 (br, 1H), 7.26-7.20 (m, 2H), 5.06-4.98 (m, 1H), 4.81-4.62 (m, 2H), 4.29-4.23 (m, 1H), 4.13-4.03 (m, 1H), 2.62-2.33 (m, 1H), 2.28-2.08 (m, 1H), 1.40-1.34 (m, 3H). | 542 |
| 30. | 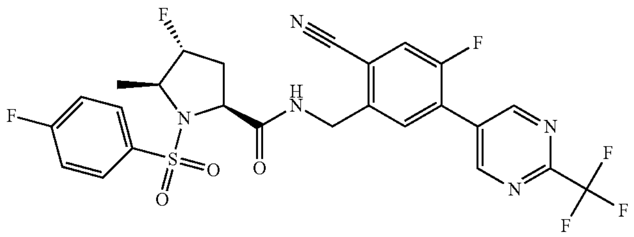 [SMILES: C[C@H]1[C@H](F)C[C@@H](C(=O)NCc2cc(-c3cnc(C(F)(F)F)nc3)c(F)cc2C#N)N1S(=O)(=O)c1ccc(F)cc1] | (2S,4R,5S)-N-(2-cyano-4-fluoro-5-(2-(trifluoromethyl)pyrimidin-5-yl)benzyl)-4-fluoro-1-(4-fluorophenylsulfonyl)-5-methylpyrrolidine-2-carboxamide | 0.00865 | $^1$HNMR(400 MHz, $CDCl_3$) δ 9.20 (s, 2H), 7.92-7.85(m, 3H), 7.60 (d, J = 9.6 Hz, 1H), 7.43-7.40 (m, 1H), 7.28-7.23 (m, 2H), 5.10-5.04 (m, 1H), 4.74 (d, J = 50.8 Hz, 1H), 4.62-4.57 (m, 1H), 4.26-4.21 (m, 1H), 4.13-4.06 (m, 1H), 2.63-2.53 (m, 1H), 2.38-2.20 (m, 1H), 1.39 (d, J = 7.2 Hz, 3H). | 584 |
| 31. | 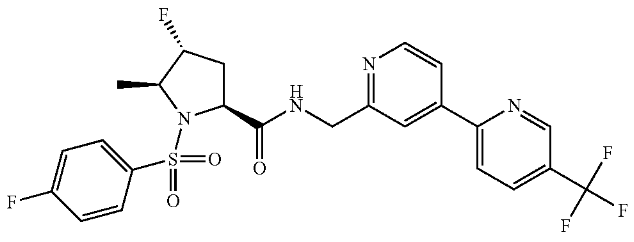 [SMILES: C[C@H]1[C@H](F)C[C@@H](C(=O)NCc2cc(-c3ccc(C(F)(F)F)cn3)ccn2)N1S(=O)(=O)c1ccc(F)cc1] | (2S,4R,5S)-4-fluoro-1-(4-fluorophenylsulfonyl)-5-methyl-N-((5-(trifluoromethyl)-2,4'-bipyridin-2'-yl)methyl) pyrrolidine-2-carboxamide | 0.0587 | $^1$HNMR(400 MHz, $CDCl_3$) δ 8.98 (s, 1H), 8.72(d, J = 5.1 Hz, 1H), 8.08-8.01 (m, 3H), 7.94-7.89 (m, 3H), 7.73 (m, 1H), 7.25-7.19 (m, 2H), 4.88-4.63 (m, 3H), 4.30-4.24 (m, 1H), 4.17-4.07 (m, 1H), 2.54-2.28 (m, 2H), 1.39 (d, J = 7.2 Hz, 3H). | 541.1 |

TABLE 2-continued

| Example | Structure | Name | hTRPA1 CHO Ca2+ AUC EVO (IC50) | $^1$H NMR | LCMS |
|---|---|---|---|---|---|
| 32. | 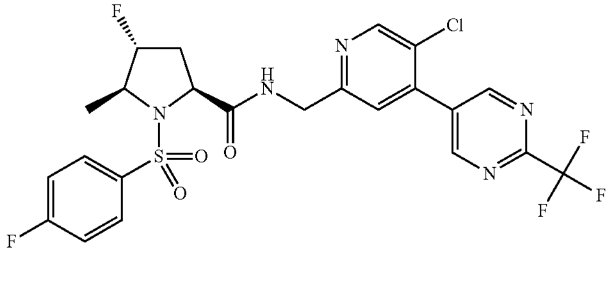 [SMILES: C[C@H]1[C@H](F)C[C@@H](C(=O)NCc2cc(-c3cnc(C(F)(F)F)nc3)c(Cl)cn2)N1S(=O)(=O)c1ccc(F)cc1] | (2S,4R,5S)-N-((5-chloro-4-(2-(trifluoromethyl)pyrimidin-5-yl)pyridin-2-yl)methyl)-4-fluoro-1-(4-fluorophenylsulfonyl)-5-methylpyrrolidine-2-carboxamide | 0.0104 | $^1$HNMR(400 MHz, $CDCl_3$) δ 9.15 (s, 2H), 8.75(s, 1H), 7.89-7.86 (m, 2H), 7.59 (m, 2H), 7.28-7.22 (m, 2H), 4.98-4.92 (m, 1H), 4.80-4.58 (m, 2H), 4.26-4.21 (m, 1H), 4.13-4.06 (m, 1H), 2.61-2.50 (m, 1H), 2.40-2.23 (m, 1H), 1.39 (d, J = 7.2 Hz, 3H). | 576 |
| 33. | 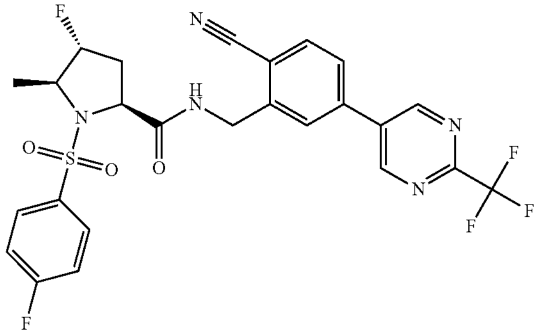 [SMILES: C[C@H]1[C@H](F)C[C@@H](C(=O)NCc2cc(-c3cnc(C(F)(F)F)nc3)ccc2C#N)N1S(=O)(=O)c1ccc(F)cc1] | (2S,4R,5S)-N-([2-cyano-5-[2-(trifluoromethyl)pyrimidin-5-yl]phenyl] methyl)-4-fluoro-1-[(4-fluorobenzene) sulfonyl]-5-methylpyrrolidine-2-carboxamide | 0.00358 | $^1$H NMR (300 MHz, $CD_3OD$) δ 9.26 (s, 2H), 8.08 (s, 1H), 7.92-7.78 (m, 4H), 7.25-7.19 (m, 2H), 4.79-4.60 (m, 3H), 4.18-4.12 (m, 1H), 4.01-3.90 (m, 1H), 2.39-2.14 (m, 2H), 1.34-1.32 (d, J = 7.2 Hz, 3H). | 566 |
| 34. | 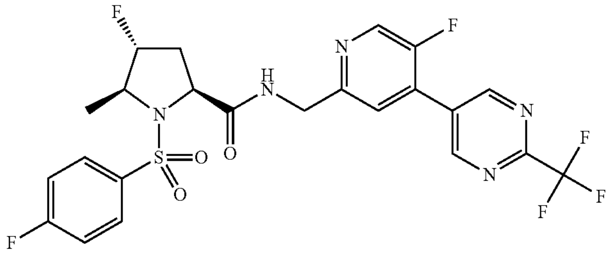 [SMILES: C[C@H]1[C@H](F)C[C@@H](C(=O)NCc2cc(-c3cnc(C(F)(F)F)nc3)c(F)cn2)N1S(=O)(=O)c1ccc(F)cc1] | (2S,4R,5S)-4-fluoro-N-([5-fluoro-4-[2-(trifluoromethyl)pyrimidin-5-yl]pyridin-2-yl]methyl)-1-[(4-fluorobenzene) sulfonyl]-5-methylpyrrolidine-2-carboxamide | 0.0388 | $^1$H NMR (300 MHz, $CDCl_3$) δ 9.24 (s, 2H), 8.62 (s, 1H), 7.91-7.86 (m, 2H), 7.76-7.74 (d, J = 5.7 Hz, 1H), 7.55 (m, 1H), 7.24-7.21 (m, 2H), 5.01-4.95 (m, 1H), 4.80-4.56 (m, 2H), 4.27-4.21 (t, J = 9.6 Hz, 1H), 4.14-4.00 (m, 1H), 2.62-2.18 (m, 2H), 1.39-1.37 (d, J = 7.2 Hz, 3H). | 560 |
| 35. | 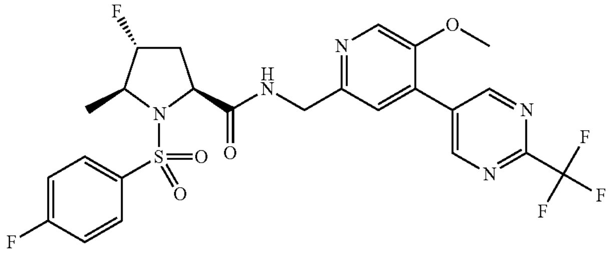 [SMILES: COc1cnc(CNC(=O)[C@@H]2C[C@@H](F)[C@H](C)N2S(=O)(=O)c2ccc(F)cc2)cc1-c1cnc(C(F)(F)F)nc1] | (2S,4R,5S)-4-fluoro-1-[(4-fluorobenzene) sulfonyl]-N-([5-methoxy-4-[2-(trifluoromethyl)pyrimidin-5-yl]pyridin-2-yl]methyl)-5-methylpyrrolidine-2-carboxamide | 0.0531 | $^1$H NMR (400 MHz, $CDCl_3$) δ 9.17(s, 2H), 8.40(s, 1H), 7.91-7.88(m, 2H), 7.67(m, 1H), 7.56 (s, 1H), 7.25-7.21 (m, 2H), 4.92-4.87(m, 1H), 4.78-4.58(m, 2H), 4.24-4.19(t, J = 9.2 Hz, 1H), 4.13-4.00(m, 4H), 2.57-2.50(m, 2H), 1.39-1.37 (d, J = 7.2 Hz, 3H). | 572 |

TABLE 2-continued

| Example | Structure | Name | hTRPA1 CHO Ca2+ AUC EVO (IC50) | $^1$H NMR | LCMS |
|---|---|---|---|---|---|
| 36. | 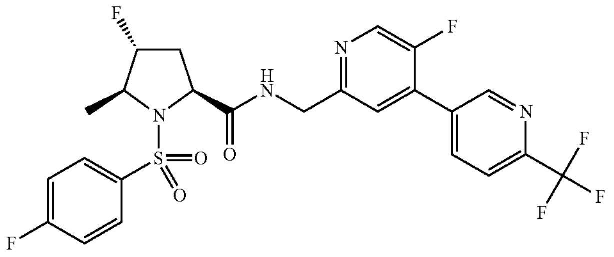 | (2S,4R,5S)-4-fluoro-N-([5-fluoro-4-[6-(trifluoromethyl)pyridin-3-yl]pyridin-2-yl]methyl)-1-[(4-fluorobenzene)sulfonyl]-5-methylpyrrolidine-2-carboxamide | 0.026 | $^1$H NMR (400 MHz, $CDCl_3$) δ 9.05 (s, 1H), 8.61 (s, 1H), 8.24-8.22 (d, J = 8 Hz, 1H), 7.93-7.90 (m, 2H), 7.85-7.83 (d, J = 8 Hz, 1H), 7.71-7.66 (m, 2H), 7.26-7.24 (m, 2H), 4.96-4.90 (m, 1H), 4.80-4.64 (m, 2H), 4.27-4.23 (t, J = 8.8 Hz, 1H), 4.17-4.06 (m, 1H), 2.61-2.50 (m, 1H), 2.42-2.25 (m, 1H), 1.41-1.39 (d, J = 6.8 Hz, 3H). | 559 |
| 37. | 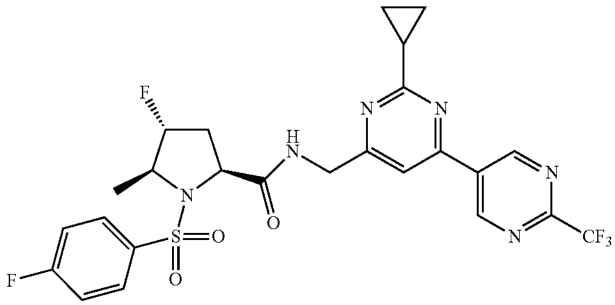 [SMILES: C[C@H]1[C@H](F)C[C@@H](C(=O)NCc2cc(-c3cnc(C(F)(F)F)nc3)nc(C3CC3)n2)N1S(=O)(=O)c1ccc(F)cc1] | (2S,4R,5S)-N-([2-cyclopropyl-6-[2-(trifluoromethyl)pyrimidin-5-yl]pyrimidin-4-yl]methyl)-4-fluoro-1-[(4-fluorobenzene)sulfonyl]-5-methylpyrrolidine-2-carboxamide | 0.0054 | $^1$H NMR (300 MHz, $CD_3OD$) δ 9.69 (s, 2H), 8.11 (s, 1H), 8.05-8.00 (m, 2H), 7.36-7.31 (t, J = 8.7 Hz, 2H), 4.91-4.73 (m, 1H), 4.65-4.49 (m, 2H), 4.30-4.25 (m, 1H), 4.11-4.04 (m, 1H), 2.47-2.32 (m, 3H), 1.37-1.35 (d, J = 6.9 Hz, 3H), 1.27-1.12 (m, 4H). | 583 |
| 38. | 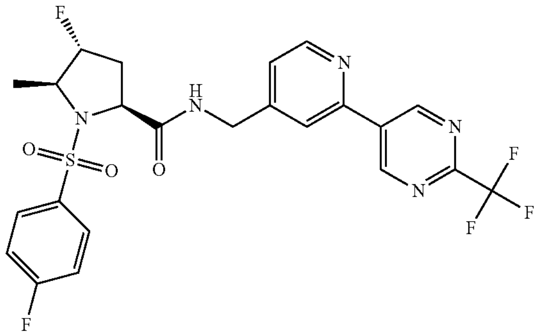 [SMILES: C[C@H]1[C@H](F)C[C@@H](C(=O)NCc2ccnc(-c3cnc(C(F)(F)F)nc3)c2)N1S(=O)(=O)c1ccc(F)cc1] | (4R,5S)-4-fluoro-1-[(4-fluorobenzene)sulfonyl]-5-methyl-N-([2-[2-(trifluoromethyl)pyrimidin-5-yl]pyridin-4-yl]methyl)pyrrolidine-2-carboxamide | 0.0694 | $^1$H NMR (400 MHz, $CD_3OD$) δ 9.63 (s, 2H), 8.70-8.69 (d, J = 5.2 Hz, 1H), 8.21 (s, 1H), 8.03-8.01 (m, 2H), 7.52-7.51 (d, J = 4 Hz, 1H), 7.36-7.31 (m, 2H), 4.86-4.74 (d, J = 46.4 Hz, 1H), 4.70-4.54 (m, 2H), 4.27-4.23 (m, 1H), 4.09-4.02 (m, 1H), 2.45-2.21 (m, 2H), 1.36-1.35 (d, J = 7.2 Hz, 3H). | 542 |
| 39. | 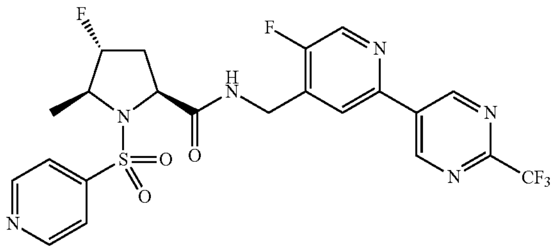 [SMILES: C[C@H]1[C@H](F)C[C@@H](C(=O)NCc2cc(-c3cnc(C(F)(F)F)nc3)ncc2F)N1S(=O)(=O)c1ccncc1] | (2S,4R,5S)-4-fluoro-N-((5-fluoro-2-(2-(trifluoromethyl)pyrimidin-5-yl)pyridin-4-yl)methyl)-5-methyl-1-(pyridin-4-ylsulfonyl)pyrrolidine-2-carboxamide | 0.63 | $^1$HNMR(300 MHz, $CDCl_3$) δ9.563 (s, 2H), 8.95-8.94 (s, 2H), 8.58-8.58 (s, 1H), 8.15-8.13 (d, J = 5.7 Hz, 1H), 7.90 (s, 2H), 7.61-7.26 (m, 1H), 4.97-4.85 (m, 2H), 4.69-4.53 (m, 1H), 4.41-4.35 (m, 1H), 4.18-4.09 (m, 1H), 2.64-2.25 (m, 2H), 1.40-1.25 (d, J = 6.9 Hz, 3H). | 543 |

TABLE 2-continued

| Example | Structure | Name | hTRPA1 CHO Ca2+ AUC EVO (IC50) | $^1$H NMR | LCMS |
|---|---|---|---|---|---|
| 40. | 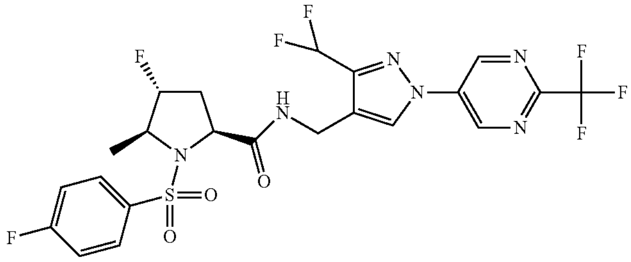 [SMILES: C[C@H]1[C@H](F)C[C@@H](C(=O)NCc2cn(-c3cnc(C(F)(F)F)nc3)nc2C(F)F)N1S(=O)(=O)c1ccc(F)cc1] | (2S,4R,5S)-N-[[3-(difluoromethyl)-1-[2-(trifluoromethyl)pyrimidin-5-yl]-1H-pyrazol-4-yl]methyl]-4-fluoro-1-[(4-fluorobenzene)sulfonyl]-5-methylpyrrolidine-2-carboxamide | 0.0431 | 1H NMR (300 MHz, CDCl3) δ 9.31 (s, 2H), 8.50 (s, 1H), 7.91-7.86 (m, 2H), 7.29-7.14 (m, 3H), 7.01-6.65 (t, 1H), 4.93-4.84 (dd, $J_1$ = 16.5 Hz, $J_2$ = 8.1 Hz, 1H), 4.79-4.61 (dd, $J_1$ = 51.0 Hz, $J_2$ = 27.0 Hz, 1H), 4.46-4.39 (dd, $J_1$ = 15.9 Hz, $J_2$ = 3.9 Hz, 1H), 4.24-4.18 (m, 1H), 4.10-4.01 (m, 1H), 2.58-2.52 (m, 1H), 2.35-2.17 (m, 1H), 1.38-1.36 (d, J = 6.9 Hz, 3H). | 581 |
| 41. | 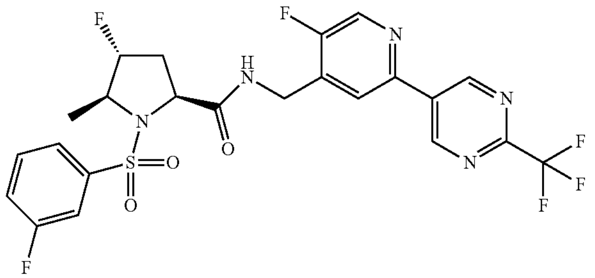 [SMILES: C[C@H]1[C@H](F)C[C@@H](C(=O)NCc2cc(-c3cnc(C(F)(F)F)nc3)ncc2F)N1S(=O)(=O)c1cccc(F)c1] | (2S,4R,5S)-4-fluoro-N-((5-fluoro-2-(2-(trifluoromethyl)pyrimidin-5-yl)pyridin-4-yl)methyl)-1-(3-fluorophenylsulfonyl)-5-methylpyrrolidine-2-carboxamide | 0.0405 | 1H NMR (400 MHz, CDCl3) δ 9.55 (s, 2H), 8.60 (s, 1H), 8.19 (d, J = 6.0 Hz, 1H), 7.73-7.69 (m, 1H), 7.62-7.57 (m, 2H), 7.44-7.39 (m, 1H), 7.33-7.28 (m, 1H), 5.05-4.99 (m, 1H), 4.82-4.81 (m, 1H), 4.53-4.47 (t, J = 8.6 Hz, 1H), 4.37-4.32 (m, 1H), 4.17-4.12 (m, 1H), 2.62-2.56 (m, 1H), 2.39-2.26 (m, 1H), 1.40-1.39 (d, J = 6.9 Hz, 3H). | 560 |
| 42. | 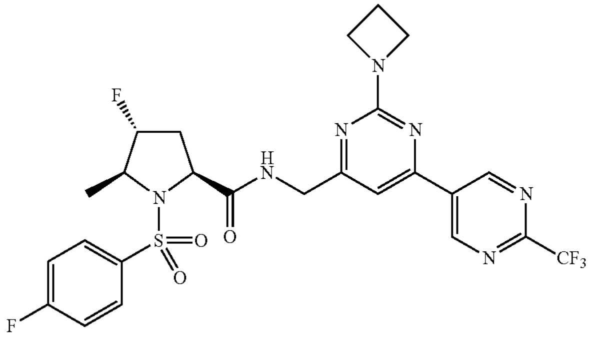 [SMILES: C[C@H]1[C@H](F)C[C@@H](C(=O)NCc2cc(-c3cnc(C(F)(F)F)nc3)nc(N3CCC3)n2)N1S(=O)(=O)c1ccc(F)cc1] | (2S,4R,5S)-N-((2-(azetidin-1-yl)-2'-(trifluoromethyl)-4,5'-bipyrimidin-6-yl)methyl)-4-fluoro-1-(4-fluorophenylsulfonyl)-5-methylpyrrolidine-2-carboxamide | 0.0219 | $^1$H NMR (300 MHz, DMSO) δ 9.60 (s, 2H), 8.95 (t, J = 7.8 Hz, 1H), 8.07-8.02 (m, 2H), 7.51-7.45 (m, 3H), 4.98-4.80 (d, J = 55.5 Hz, 1H), 4.49-4.41 (m, 1H), 4.30-4.10 (m, 6H), 4.05-3.91 (m, 1H), 2.49-2.34 (m, 4H), 1.23-1.21 (d, J = 6.9 Hz, 3H). | 598 |
| 43. | 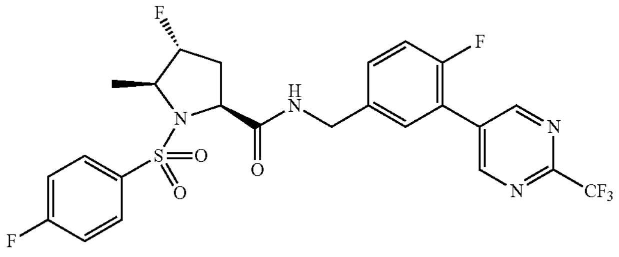 [SMILES: C[C@H]1[C@H](F)C[C@@H](C(=O)NCc2ccc(F)c(-c3cnc(C(F)(F)F)nc3)c2)N1S(=O)(=O)c1ccc(F)cc1] | (2S,4R,5S)-4-fluoro-N-(4-fluoro-3-(2-(trifluoromethyl)pyrimidin-5-yl)benzyl)-1-(4-fluorophenylsulfonyl)-5-methylpyrrolidine-2-carboxamide | 0.00939 | $^1$H NMR (MHz, $CDCl_3$) δ 9.16 (s, 2H), 7.86-7.79 (m, 2H), 7.59-7.56 (m, 1H), 7.49-7.46 (m, 1H), 7.30-7.28 (m, 1H), 7.25-7.22(m, 3H), 4.84-4.46 (m, 2H), 4.45-4.39 (m, 1H), 4.22-4.26 (m, 1H), 4.16-4.09 (m, 1H), 2.51-2.25 (m, 2H), 1.33-1.32 (d, J = 6.8 Hz, 3H). | 559 |

TABLE 2-continued

| Example | Structure | Name | hTRPA1 CHO Ca2+ AUC EVO (IC50) | $^1$H NMR | LCMS |
|---|---|---|---|---|---|
| 44. | 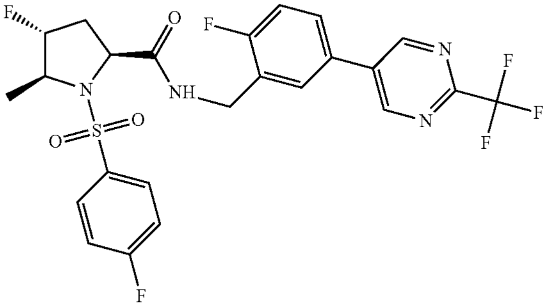 [SMILES: C[C@H]1[C@H](F)C[C@@H](C(=O)NCc2cc(-c3cnc(C(F)(F)F)nc3)ccc2F)N1S(=O)(=O)c1ccc(F)cc1] | (2S,4R,5S)-4-fluoro-N-(2-fluoro-5-(2-(trifluoromethyl)pyrimidin-5-yl)benzyl)-1-(4-fluorophenylsulfonyl)-5-methylpyrrolidine-2-carboxamide | 0.00734 | $^1$H NMR (400 MHz, $CDCl_3$) δ 9.15 (s, 2H), 7.90-7.83 (m, 3H), 7.57-7.54 (m, 1H), 7.30-7.28 (m, 1H), 7.25-7.02 (m, 2H), 4.90-4.79 (m, 1H), 4.78-4.53 (m, 2H), 4.28-4.24 (t, J = 8.6 Hz, 1H), 4.18-4.09 (m, 1H), 2.61-2.51 (m, 1H), 2.40-2.28 (m, 1H), 1.34 (d, J = 6.8 Hz, 3H). | 549 |
| 45. | 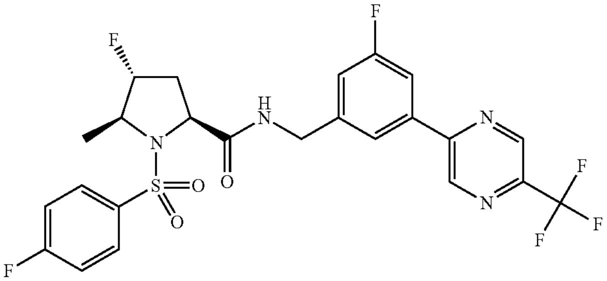 [SMILES: C[C@H]1[C@H](F)C[C@@H](C(=O)NCc2cc(F)cc(-c3cnc(C(F)(F)F)cn3)c2)N1S(=O)(=O)c1ccc(F)cc1] | (2S,4R,5S)-4-fluoro-N-(3-fluoro-5-(5-(trifluoromethyl)pyrazin-2-yl)benzyl)-1-(4-fluorophenylsulfonyl)-5-methylpyrrolidine-2-carboxamide | 0.00805 | $^1$H NMR(300 MHz, DMSO) δ 9.50 (s, 1H), 9.26 (s, 1H), 8.94-8.90 (t, J = 5.7 Hz, 1H), 8.06-7.94 (m, 4H), 7.50-7.40 (m, 3H), 4.98-4.81(dd, $J_1$ = 51.0 Hz, $J_2$ = 2.4 Hz, 1H), 4.62-4.39 (m, 2H), 4.21-4.16 (m, 1H), 3.99-3.92 (m, 1H), 2.36-2.11(m, 2H), 1.24-1.21(d, J = 6.8 Hz, 3H). | 559 |
| 46. | 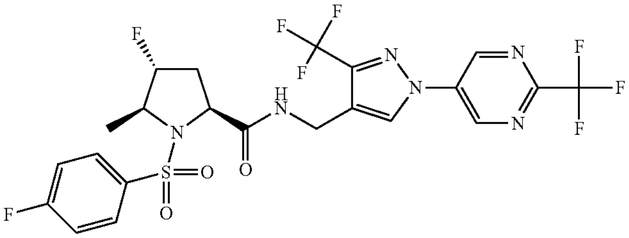 [SMILES: C[C@H]1[C@H](F)C[C@@H](C(=O)NCc2cn(-c3cnc(C(F)(F)F)nc3)nc2C(F)(F)F)N1S(=O)(=O)c1ccc(F)cc1] | (2S,4R,5S)-4-fluoro-1-(4-fluorophenylsulfonyl)-5-methyl-N-((3-(trifluoromethyl)-1-(2-(trifluoromethyl)pyrimidin-5-yl)-1H-pyrazol-4-yl)methyl) pyrrolidine-2-carboxamide | 0.0262 | $^1$H NMR (300 MHz, $CDCl_3$) δ9.31 (s, 1H), 8.60 (s, 1H), 7.91-7.86 (m, 2H), 7.29-7.23 (m, 2H), 7.18-7.14 (m, 2H), 4.93-4.79 (m, 2H), 4.39-4.22 (m, 2H), 4.10-4.01 (m, 1H), 2.65-2.51 (m, 1H), 2.35-2.31 (m, 1H), 1.39-1.36 (d, J = 7.2 Hz, 3H). | 599 |
| 47. | 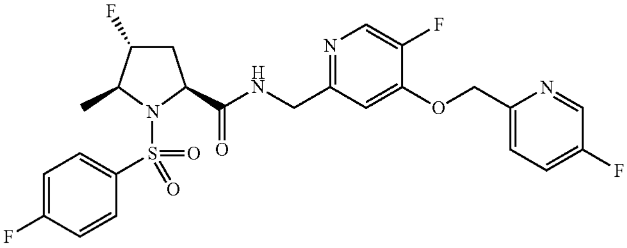 [SMILES: C[C@H]1[C@H](F)C[C@@H](C(=O)NCc2cc(OCc3ccc(F)cn3)c(F)cn2)N1S(=O)(=O)c1ccc(F)cc1] | (2S,4R,5S)-4-fluoro-N-((5-fluoro-4-((5-fluoropyridin-2-yl)methoxy) pyridin-2-yl)methyl)-1-(4-fluorophenylsulfonyl)-5-methylpyrrolidine-2-carboxamide | 1.9 | $^1$H NMR (400 MHz, DMSO) δ8.89 (t, J = 6.0 Hz, 1H), 8.57 (d, J = 2.8 Hz, 1H), 8.41 (d, J = 3.2 Hz, 1H), 8.03-7.99 (m, 2H), 7.81-7.76 (m, 1H), 7.62-7.59 (m, 1H), 7.49-7.44 (m, 2H), 7.35(d, J = 7.2 Hz, 1H), 5.31 (s, 2H), 4.95-4.82 (dd, $J_1$ = 51.6 Hz, $J_2$ = 2.4 Hz, 1H), 4.50-4.44 (m, 1H), 4.33-4.27 (m, 1H), 4.19-4.15 (m, 1H), 4.01-3.87 (m, 1H), 2.51-2.06 (m, 2H), 1.23 (d, J = 7.2 Hz, 3H). | 539 |

TABLE 2-continued

| Example | Structure | Name | hTRPA1 CHO Ca2+ AUC EVO (IC50) | $^1$H NMR | LCMS |
|---|---|---|---|---|---|
| 48. | 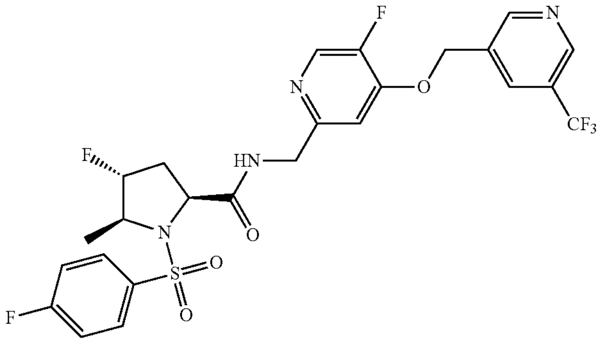 [SMILES: C[C@H]1[C@H](F)C[C@@H](C(=O)NCc2cc(OCc3cncc(C(F)(F)F)c3)c(F)cn2)N1S(=O)(=O)c1ccc(F)cc1] | (2S,4R,5S)-4-fluoro-N-((5-fluoro-4-((5-(trifluoromethyl)pyridin-3-yl)methoxy)pyridin-2-yl)methyl)-1-(4-fluorophenylsulfonyl)-5-methylpyrrolidine-2-carboxamide | 0.105 | $^1$H NMR (400 MHz, DMSO) δ8.99-8.94 (m, 3H), 8.43 (d, J = 3.2 Hz, 1H), 8.27 (s, 1H), 8.04-8.01 (m, 2H), 7.48-7.44 (t, J = 8.8 Hz, 1H), 7.41 (d, J = 6.8 Hz, 1H), 5.41 (s, 2H), 4.95-4.82 (dd, $J_1$ = 51.2 Hz, $J_2$ = 2.4 Hz, 1H), 4.53-4.47 (m, 1H), 4.35-4.29 (m, 1H), 4.23-4.19 (m, 1H), 3.97-3.90 (m, 2H), 2.50-2.10 (m, 2H), 1.23 (d, J = 7.2 Hz, 3H). | 589 |
| 49. | 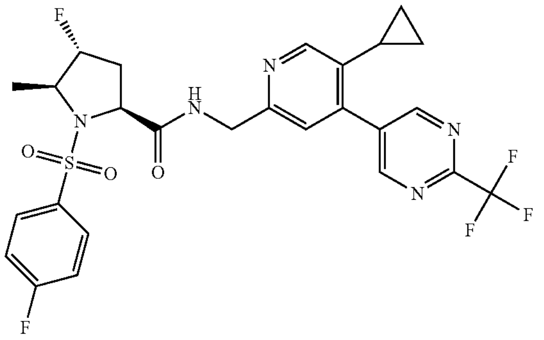 [SMILES: C[C@H]1[C@H](F)C[C@@H](C(=O)NCc2cc(-c3cnc(C(F)(F)F)nc3)c(C3CC3)cn2)N1S(=O)(=O)c1ccc(F)cc1] | (2S,4R,5S)-N-[[5-cyclopropyl-4-[2-(trifluoromethyl)pyrimidin-5-yl]-2-pyridyl]methyl]-4-fluoro-1-(4-fluorophenyl)sulfonyl-5-methyl-pyrrolidine-2-carboxamide | 0.0367 | $^1$H NMR (400 MHz, $CDCl_3$) δ 9.15 (s, 2H), 8.41 (s, 1H), 7.92-7.89 (m, 2H), 7.72 (s, 1H), 7.43 (s, 1H), 7.29-7.22 (m, 2H), 4.93-4.62 (m, 3H), 4.25-4.26 (m, 2H), 2.55-2.29 (m, 2H), 1.83-1.77 (m, 1H), 1.40-1.38 (d, J = 7.2 Hz, 3H), 1.07- 1.03 (t, J = 7.6 Hz, 2H), 0.83-0.82 (d, J = 5.6 Hz, 2H). | 582 |
| 50. | 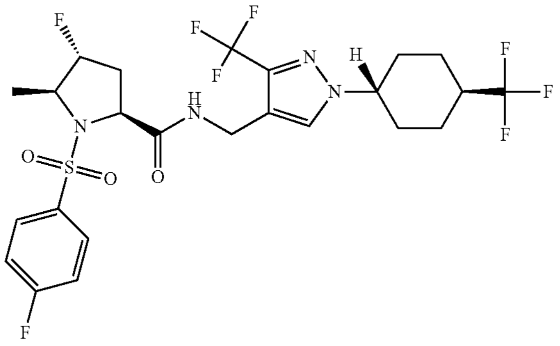 [SMILES: C[C@H]1[C@H](F)C[C@@H](C(=O)NCc2cn([C@H]3CC[C@H](C(F)(F)F)CC3)nc2C(F)(F)F)N1S(=O)(=O)c1ccc(F)cc1] | (2S,4R,5S)-4-fluoro-1-(4-fluorophenyl)sulfonyl-5-methyl-N-[[3-(trifluoromethyl)-1-[4-(trifluoromethyl)cyclohexyl]pyrazol-4-yl]methyl]pyrrolidine-2-carboxamide | 0.0505 | $^1$H NMR (400 MHz, $CDCl_3$) δ 7.89-7.87 (m, 2H), 7.77 (s, 1H), 7.29-7.23 (m, 2H), 7.07 (m, 1H), 4.76-4.60 (m, 2H), 4.45-4.34 (m, 2H), 4.19-4.06 (m, 2H), 2.43-2.40 (m, 3H), 2.24-2.21 (m, 2H), 1.98-1.91 (m, 2H), 1.84-1.80 (m, 4H), 1.33-1.31 (d, J = 6.8 Hz, 3H). | 603.2 |
| 51. | 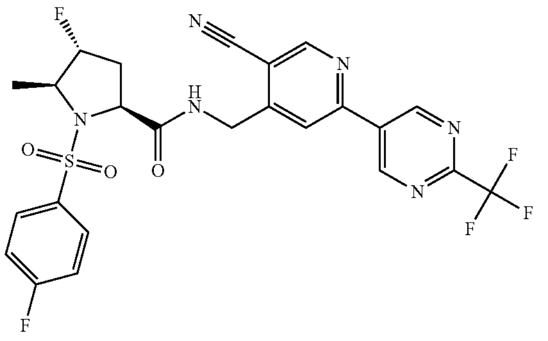 [SMILES: C[C@H]1[C@H](F)C[C@@H](C(=O)NCc2cc(-c3cnc(C(F)(F)F)nc3)ncc2C#N)N1S(=O)(=O)c1ccc(F)cc1] | (2S,4R,5S)-N-[[5-cyano-2-[2-(trifluoromethyl)pyrimidin-5-yl]-4-pyridyl]methyl]-4-fluoro-1-(4-fluorophenyl)sulfonyl-5-methyl-pyrrolidine-2-carboxamide | 0.0155 | $^1$H NMR (400 MHz, DMSO) δ 9.70 (s, 2H), 9.23-9.17 (m, 2H), 8.35 (s, 1H), 8.08-8.04 (m, 2H), 7.49 (t, J = 8.8 Hz, 2H), 4.96 (d, J = 51.6 Hz, 1H), 4.72-4.59 (m, 2H), 4.25-4.21 (m, 1H), 4.01-3.92 (m, 1H), 2.43-2.08 (m, 2H), 1.21 (d, J = 6.8 Hz, 3H). | 567.1 |

TABLE 2-continued

| Example | Structure | Name | hTRPA1 CHO Ca2+ AUC EVO (IC50) | $^1$H NMR | LCMS |
|---|---|---|---|---|---|
| 52. | 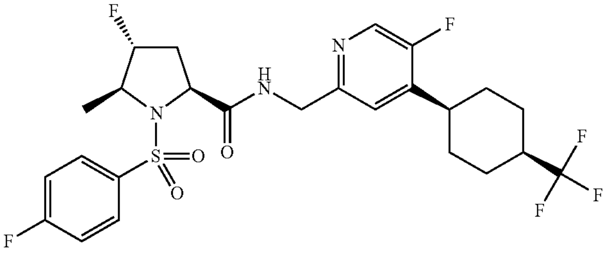 [SMILES: C[C@H]1[C@H](F)C[C@@H](C(=O)NCc2cc([C@H]3CC[C@@H](C(F)(F)F)CC3)c(F)cn2)N1S(=O)(=O)c1ccc(F)cc1] | (2S,4R,5S)-4-fluoro-1-(4-fluorophenyl)sulfonyl-N-[[5-fluoro-4-[4-(trifluoromethyl)cyclohexyl]-2-pyridyl]methyl]-5-methyl-pyrrolidine-2-carboxamide | 0.0089 | $^1$H NMR (300 MHz, $CDCl_3$) δ 8.32-8.31 (m, 1H), 7.92-7.88 (m, 2H), 7.59 (s, 1H), 7.30-7.20 (m, 3H), 4.80-4.53 (m, 3H), 4.27-4.06 (m, 2H), 2.92-2.85 (s, 1H), 2.53-2.40 (m, 2H), 2.31-1.98 (m, 5H), 1.63-1.47 (m, 4H), 1.38-1.35 (d, J = 6.9 Hz, 3H). | 564.2 |
| 53. | 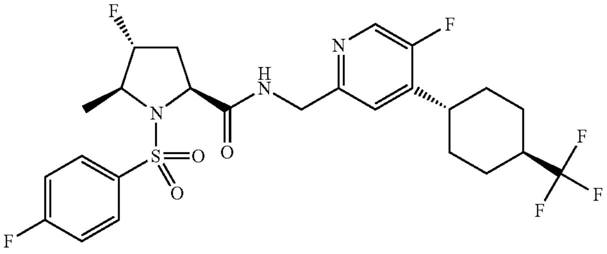 [SMILES: C[C@H]1[C@H](F)C[C@@H](C(=O)NCc2cc([C@H]3CC[C@H](C(F)(F)F)CC3)c(F)cn2)N1S(=O)(=O)c1ccc(F)cc1] | (2S,4R,5S)-4-fluoro-1-(4-fluorophenyl)sulfonyl-N-[[5-fluoro-4-[4-(trifluoromethyl)cyclohexyl]-2-pyridyl]methyl]-5-methyl-pyrrolidine-2-carboxamide | 0.0646 | $^1$H NMR (300 MHz, $CDCl_3$) 8.32-8.31 (m, 1H), 7.92-7.87 (m, 2H), 7.65 (s, 1H), 7.27-7.19 (m, 3H), 4.80-4.57 (m, 3H), 4.25-4.09 (m, 2H), 3.02-2.96 (s, 1H), 2.53-2.25 (m, 3H), 2.09-2.02 (m, 2H), 1.92-1.75 (m, 6H), 1.38-1.35 (d, J = 6.9 Hz, 3H). | 564.2 |
| 54. | 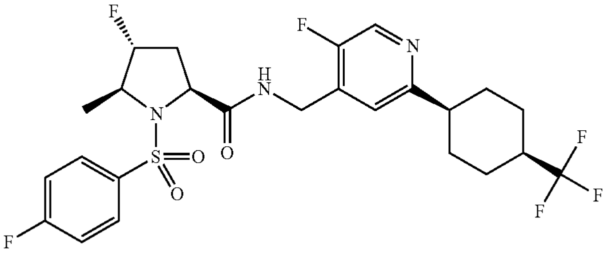 [SMILES: C[C@H]1[C@H](F)C[C@@H](C(=O)NCc2cc([C@H]3CC[C@@H](C(F)(F)F)CC3)ncc2F)N1S(=O)(=O)c1ccc(F)cc1] | (2S,4R,5S)-4-fluoro-1-(4-fluorophenyl)sulfonyl-N-[[5-fluoro-2-[4-(trifluoromethyl)cyclohexyl]-4-pyridyl]methyl]-5-methyl-pyrrolidine-2-carboxamide | 0.00638 | $^1$H NMR (300 MHz, $CDCl_3$) δ 8.36 (s, 1H), 7.89-7.86 (m, 2H), 7.38-7.20 (m, 4H), 4.79-4.50 (m, 3H), 4.25-4.06 (m, 2H), 2.99 (s, 1H), 2.59-2.10 (m, 5H), 1.83-1.70 (m, 6H), 1.33-1.31 (d, J = 6.9 Hz, 3H). | 564.2 |
| 55. | 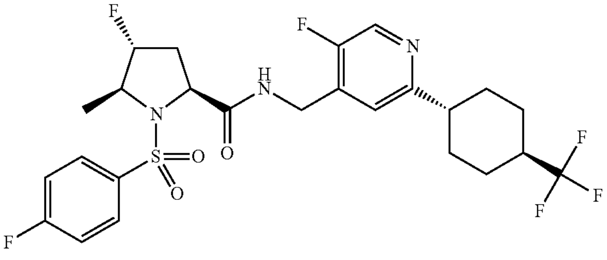 [SMILES: C[C@H]1[C@H](F)C[C@@H](C(=O)NCc2cc([C@H]3CC[C@H](C(F)(F)F)CC3)ncc2F)N1S(=O)(=O)c1ccc(F)cc1] | (2S,4R,5S)-4-fluoro-1-(4-fluorophenyl)sulfonyl-N-[[5-fluoro-2-[4-(trifluoromethyl)cyclohexyl]-4-pyridyl]methyl]-5-methyl-pyrrolidine-2-carboxamide | 0.00589 | $^1$H NMR (300 MHz, $CDCl_3$) δ 8.36 (s, 1H), 7.91-7.86 (m, 2H), 7.61 (s, 1H), 7.27-7.22 (m, 3H), 4.80-4.49 (m, 3H), 4.28-4.03 (m, 2H), 2.81 (s, 1H), 2.59-2.21 (m, 2H), 2.09-2.05 (m, 5H), 1.70-1.41 (m, 4H), 1.34-1.32 (d, J = 7.2 Hz, 3H). | 564.2 |

TABLE 2-continued

| Example | Structure | Name | hTRPA1 CHO Ca2+ AUC EVO (IC50) | $^1$H NMR | LCMS |
|---|---|---|---|---|---|
| 56. | 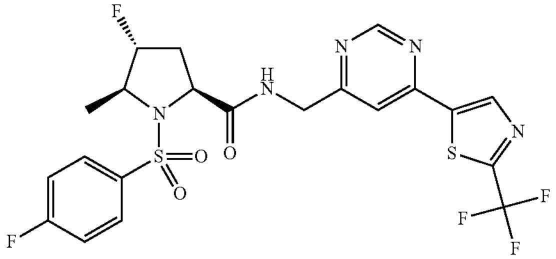 [SMILES: C[C@H]1[C@H](F)C[C@@H](C(=O)NCc2cc(-c3cnc(C(F)(F)F)s3)ncn2)N1S(=O)(=O)c1ccc(F)cc1] | (2S,4R,5S)-4-fluoro-1-(4-fluorophenyl)sulfonyl-5-methyl-N-[[6-[2-(trifluoromethyl)thiazol-5-yl]pyrimidin-4-yl]methyl]pyrrolidine-2-carboxamide | 0.0669 | $^1$H NMR (400 MHz, $CDCl_3$) δ 9.15 (s, 1H), 8.73 (s, 1H), 8.17 (s, 1H), 7.96-7.92 (m, 2H), 7.47-7.44 (m, 1H), 7.30-7.26 (m, 2H), 5.07-5.00 (m, 1H), 4.75 (d, J = 51.2 Hz, 1H), 4.54-4.48 (m, 1H), 4.34-4.30 (m, 1H), 4.15-4.06 (m, 1H), 2.67-2.57 (m, 1H), 2.39-2.21 (m, 1H), 1.43 (d, J = 6.8 Hz, 3H). | 548.1 |
| 57. | 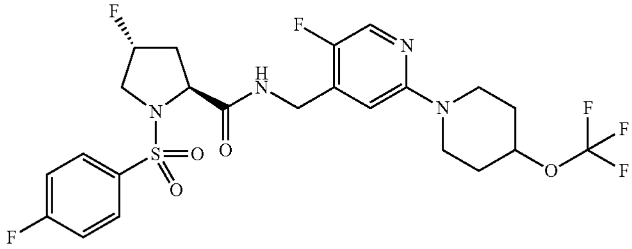 [SMILES: O=C(NCc1cc(N2CCC(OC(F)(F)F)CC2)ncc1F)[C@@H]1C[C@@H](F)CN1S(=O)(=O)c1ccc(F)cc1] | (2S,4R)-4-fluoro-1-(4-fluorophenyl)sulfonyl-N-[[5-fluoro-2-[4-(trifluoromethoxy)-1-piperidyl]-4-pyridyl]methyl]pyrrolidine-2-carboxamide | 0.0494 | $^1$H NMR (400 MHz, $CDCl_3$) δ 8.01 (s, 1H), 7.91-7.88 (m, 2H), 7.28-7.24 (m, 3H), 6.90(br, 1H), 5.07 (d, J = 51.6 Hz, 1H), 4.78-4.72 (m, 1H), 4.49-4.37 (m, 2H), 4.32-4.28 (m, 1H), 3.93-3.85 (m, 3H), 3.74-3.61 (m, 1H), 3.41-3.38 (m, 2H), 2.61-2.52 (m, 1H), 2.32-2.17 (m, 1H), 2.04-2.00 (m, 2H), 1.87-1.84 (m, 2H). | 567.1 |
| 58. | 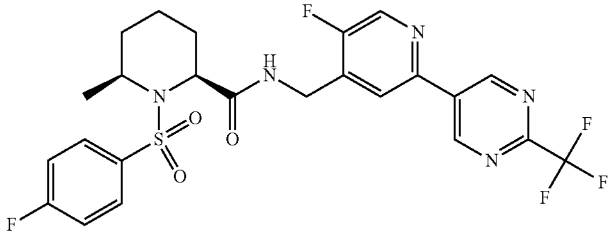 [SMILES: C[C@H]1CCC[C@@H](C(=O)NCc2cc(-c3cnc(C(F)(F)F)nc3)ncc2F)N1S(=O)(=O)c1ccc(F)cc1] | (2S,6S)-1-(4-fluorophenyl)sulfonyl-N-[[5-fluoro-2-[2-(trifluoromethyl)pyrimidin-5-yl]-4-pyridyl]methyl]-6-methyl-piperidine-2-carboxamide | 0.0739 | $^1$H NMR (400 MHz, $CDCl_3$) δ 9.53 (s, 2H), 8.61 (s, 1H), 7.96 (d, J = 5.6 Hz, 1H), 7.91-7.88 (m, 2H), 7.42 (t, J = 6.0 Hz, 1H), 7.29-7.25 (m, 2H), 4.88-4.77 (m, 1H), 4.63-4.58 (m, 1H), 4.48 (d, J = 5.6 Hz, 1H), 4.32-4.29 (m, 1H), 2.37-2.33 (m, 1H), 1.75-1.68 (m, 1H), 1.46-1.35 (m, 2H), 1.29-1.23 (m, 4H), 1.08-1.03 (m, 1H). | 540.1 |
| 59. | 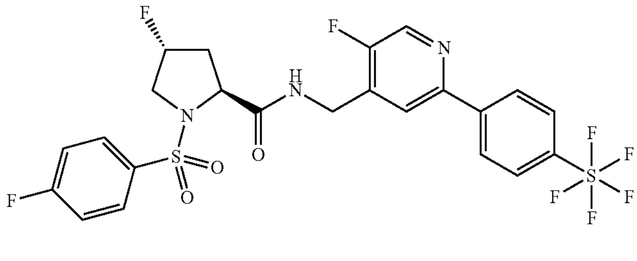 [SMILES: O=C(NCc1cc(-c2ccc(S(F)(F)(F)(F)F)cc2)ncc1F)[C@@H]1C[C@@H](F)CN1S(=O)(=O)c1ccc(F)cc1] | (2S,4R)-4-fluoro-N-[[5-fluoro-2-[4-(pentafluorosulfanyl)phenyl]-4-pyridyl]methyl]-1-(4-fluorophenyl)sulfonyl-pyrrolidine-2-carboxamide | 0.161 | $^1$H NMR (400 MHz, DMSO) δ 9.03 (t, J = 5.9 Hz, 1H), 8.68 (d, J = 1.2 Hz, 1H), 8.25 (d, J = 8.6 Hz, 2H), 8.11 (d, J = 5.8 Hz, 1H), 8.05-7.91 (m, 4H), 7.54-7.41 (m 2H), 5.30-5.11 (m, 1H), 4.51 (d, J = 5.8 Hz, 2H), 4.23 (dd, J = 10.0, 7.1 Hz, 1H), 3.79-3.55 (m, 2H), 2.44-2.36 (m, 1H), 2.21-1.98 (m, 1H). | RT = 578 min [M + H] m/z = 602.3 |

TABLE 2-continued

| Example | Structure | Name | hTRPA1 CHO Ca2+ AUC EVO (IC50) | $^1$H NMR | LCMS |
|---|---|---|---|---|---|
| 60. | 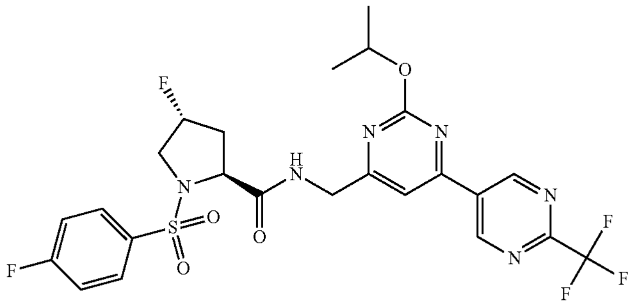 [SMILES: CC(C)Oc1nc(CNC(=O)[C@@H]2C[C@@H](F)CN2S(=O)(=O)c2ccc(F)cc2)cc(-c2cnc(C(F)(F)F)nc2)n1] | (2S,4R)-4-fluoro-1-(4-fluorophenyl)sulfonyl-N-[[2-isopropoxy-6-[2-(trifluoromethyl)pyrimidin-5-yl]pyrimidin-4-yl]methyl]pyrrolidine-2-carboxamide | 0.0831 | $^1$H NMR (400 MHz, $CD_3OD$) δ 9.70 (s, 2H), 8.04-8.00 (m, 3H), 7.37-7.32 (m, 2H), 5.52-5.46 (m, 1H), 5.14 (d, J = 52 Hz, 1H), 4.60-4.47 (m, 2H), 4.29-4.27 (m, 1H), 3.85-3.70 (m, 2H), 2.53-2.50 (m, 1H), 2.28-2.14 (m, 1H), 1.46-1.45 (d, J = 6 Hz, 6H). | 587.1 |
| 61. | 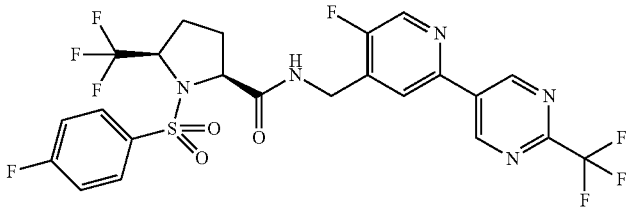 [SMILES: O=C(NCc1cc(-c2cnc(C(F)(F)F)nc2)ncc1F)[C@@H]1CC[C@H](C(F)(F)F)N1S(=O)(=O)c1ccc(F)cc1] | (2S,5R)-1-(4-fluorophenyl)sulfonyl-N-[[5-fluoro-2-[2-(trifluoromethyl)pyrimidin-5-yl]-4-pyridyl]methyl]-5-(trifluoromethyl)pyrrolidine-2-carboxamide | 0.0216 | $^1$H NMR (400 MHz, DMSO-$d_6$) δ 9.56 (s, 2H), 8.82-8.68 (m, 2H), 8.17 (d, J = 5.8 Hz, 1H), 8.16-8.09 (m, 2H), 7.54-7.41 (m, 2H), 4.65 (q, J = 8.2 Hz, 1H), 4.61-4.43 (m, 2H), 4.23 (t, J = 7.9 Hz, 1H), 2.17-2.06 (m, 1H), 1.99 (q, J = 7.2 Hz, 2H), 1.70-1.54 (m, 1H). | 596.1 |
| 62. | 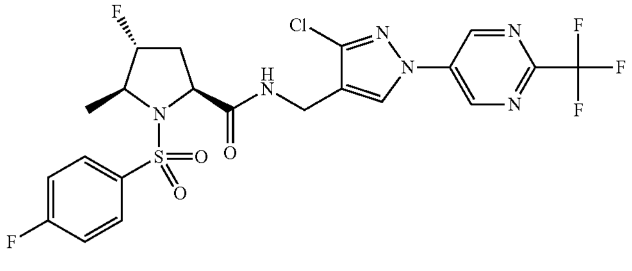 [SMILES: C[C@H]1[C@H](F)C[C@@H](C(=O)NCc2cn(-c3cnc(C(F)(F)F)nc3)nc2Cl)N1S(=O)(=O)c1ccc(F)cc1] | (2S,4R,5S)-N-[[3-chloro-1-[2-(trifluoromethyl)pyrimidin-5-yl]pyrazol-4-yl]methyl]-4-fluoro-1-(4-fluorophenyl)sulfonyl-5-methyl-pyrrolidine-2-carboxamide | 0.0582 | $^1$H NMR (400 MHz, $CDCl_3$) δ 9.25 (s, 2H), 8.42 (s, 1H), 7.92-7.88 (m, 2H), 7.29-7.25 (m, 2H), 7.19-7.16 (m, 1H), 4.80-4.66 (m, 2H), 4.30-4.05 (m, 3H), 2.63-2.53 (m, 1H), 2.37-2.20 (m, 1H), 1.39-1.37 (d, J = 7.2 Hz, 3H). | 565.1 |
| 63. | 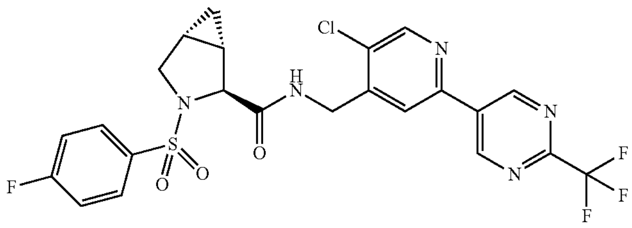 [SMILES: O=C(NCc1cc(-c2cnc(C(F)(F)F)nc2)ncc1Cl)[C@@H]1[C@H]2C[C@H]2CN1S(=O)(=O)c1ccc(F)cc1] | (1S,2S,5R)-N-[[5-chloro-2-[2-(trifluoromethyl)pyrimidin-5-yl]-4-pyridyl]methyl]-3-(4-fluorophenyl)sulfonyl-3-azabicyclo[3.1.0]hexane-2-carboxamide | 0.00616 | 1H NMR (400 MHz, DMSO-d6) δ 9.62 (s, 2H), 8.96 (t, J = 6.0 Hz, 1H), 8.85 (d, J = 0.5 Hz, 1H), 8.13 (d, J = 0.8 Hz, 1H), 8.05-7.83 (m, 2H), 7.63-7.27 (m, 2H), 4.72-4.35 (m, 2H), 4.27 (s, 1H), 3.92-3.66 (m, 1H), 3.49 (d, J = 10.6 Hz, 1H), 1.61 (dtd, J = 8.6, 7.6, 7.1, 3.9 Hz, 2H), 0.71-0.42 (m, 1H), −0.89 (q, J = 4.5 Hz, 1H). | 556.1 |

TABLE 2-continued

| Example | Structure | Name | hTRPA1 CHO Ca2+ AUC EVO (IC50) | $^1$H NMR | LCMS |
|---|---|---|---|---|---|
| 64. | 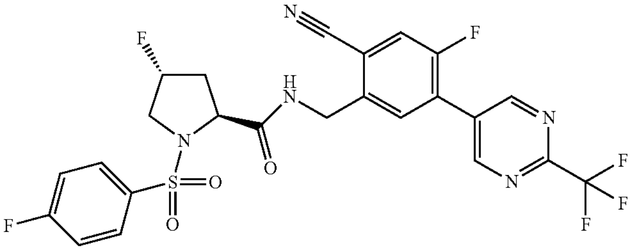 [SMILES: N#Cc1cc(F)c(-c2cnc(C(F)(F)F)nc2)cc1CNC(=O)[C@@H]1C[C@@H](F)CN1S(=O)(=O)c1ccc(F)cc1] | (2S,4R)-N-[[2-cyano-4-fluoro-5-[2-(trifluoromethyl)pyrimidin-5-yl]phenyl]methyl]-4-fluoro-1-(4-fluorophenyl)sulfonyl-pyrrolidine-2-carboxamide | 0.0445 | $^1$H NMR (400 MHz, $CDCl_3$) δ 9.31 (s, 2H), 9.08 (t, J = 5.2 Hz, 1H), 8.16 (d, J = 10 Hz, 1H), 7.97-7.93 (m, 3H), 7.47-7.42 (m, 2H), 5.18 (d, J = 52.8 Hz, 1H), 4.56 (d, J = 5.2 Hz, 2H), 4.16 (t, J = 8.4 Hz, 1H), 3.73-3.56 (m, 2H), 2.44-2.34 (m, 1H), 2.17-1.99 (m, 1H). | 570.1 |
| 65. | 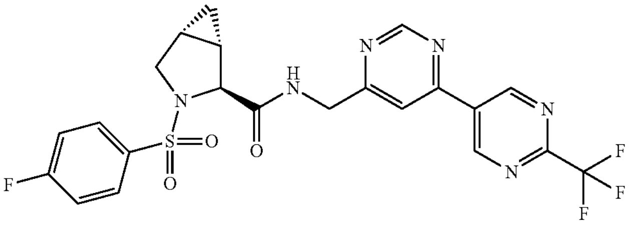 [SMILES: O=C(NCc1cc(-c2cnc(C(F)(F)F)nc2)ncn1)[C@@H]1[C@H]2C[C@H]2CN1S(=O)(=O)c1ccc(F)cc1] | (1S,2S,5R)-3-(4-fluorophenyl)sulfonyl-N-[[6-[2-(trifluoromethyl)pyrimidin-5-yl]pyrimidin-4-yl]methyl]-3-azabicyclo[3.1.0]hexane-2-carboxamide | 0.0648 | 1H NMR (400 MHz, DMSO-d6) δ 9.70 (d, J = 0.9 Hz, 2H), 9.35 (d, J = 1.3 Hz, 1H), 8.98 (t, J = 6.0 Hz, 1H), 8.18 (d, J = 1.3 Hz, 1H), 8.06-7.78 (m, 2H), 7.64-7.27 (m, 2H), 4.69-4.37 (m, 2H), 4.28 (s, 1H), 3.76 (dd, J = 10.5, 3.9 Hz, 1H), 3.49 (d, J = 10.5 Hz, 1H), 1.84-1.40 (m, 2H), 0.56 (td, J = 7.9, 5.4 Hz, 1H), −0.83 (q, J = 4.5 Hz, 1H). | 523.2 |
| 66. | 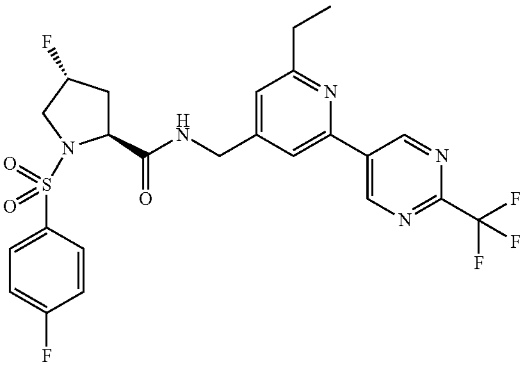 [SMILES: CCc1cc(CNC(=O)[C@@H]2C[C@@H](F)CN2S(=O)(=O)c2ccc(F)cc2)cc(-c2cnc(C(F)(F)F)nc2)n1] | (2S,4R)-N-[[2-ethyl-6-[2-(trifluoromethyl)pyrimidin-5-yl]-4-pyridyl]methyl]-4-fluoro-1-(4-fluorophenyl)sulfonyl-pyrrolidine-2-carboxamide | 0.0769 | $^1$H NMR (400 MHz, DMSO-$d_6$) δ 9.64 (s, 2H), 8.99 (t, J = 6.0 Hz, 1H), 8.07-7.89 (m, 3H), 7.50-7.44 (m, 2H), 7.41 (d, J = 1.3 Hz 1H), 5.20 (d, J = 52.3 Hz, 1H), 4.57-4.38 (m, 2H), 4.20 (dd, J = 10.0, 7.1 Hz, 1H), 3.76-3.57 (m, 2H), 2.85 (q, J = 7.6 Hz, 2H), 2.45 (dd, J = 3.8, 1.9 Hz, 1H), 2.22-1.96 (m, 1H), 1.31 (t, J = 7.6 Hz, 3H). | 556.2 |
| 67. | 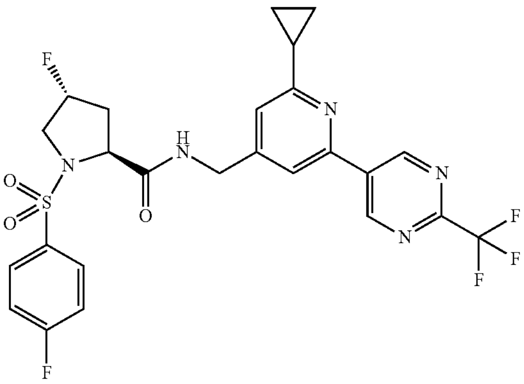 [SMILES: O=C(NCc1cc(-c2cnc(C(F)(F)F)nc2)nc(C2CC2)c1)[C@@H]1C[C@@H](F)CN1S(=O)(=O)c1ccc(F)cc1] | (2S,4R)-N-[[2-cyclopropyl-6-[2-(trifluoromethyl)pyrimidin-5-yl]-4-pyridyl]methyl]-4-fluoro-1-(4-fluorophenyl)sulfonyl-pyrrolidine-2-carboxamide | 0.0651 | $^1$H NMR (400 MHz, DMSO-$d_6$) δ 9.60 (s, 2H), 8.97 (t, J = 6.0 Hz, 1H), 8.08-7.95 (m, 2H), 7.91 (d, J = 1.3 Hz, 1H), 7.57-7.42 (m, 2H), 7.40 (d, J = 1.3 Hz, 1H), 5.20 (d, J = 52.3 Hz, 1H), 4.53-4.34 (m, 2H), 4.20 (dd, J = 10.0, 7.1 Hz, 1H), 3.73 (s, 1H), 3.71-3.57 (m, 1H), 2.45 (dd, J = 3.7, 1.8 Hz, 1H), 2.16 (ddd, J = 13.1, 8.3, 4.9 Hz, 2H), 1.14-0.95 (m, 4H). | 568.2 |

TABLE 2-continued

| Example | Structure | Name | hTRPA1 CHO Ca2+ AUC EVO (IC50) | $^1$H NMR | LCMS |
|---|---|---|---|---|---|
| 68. | 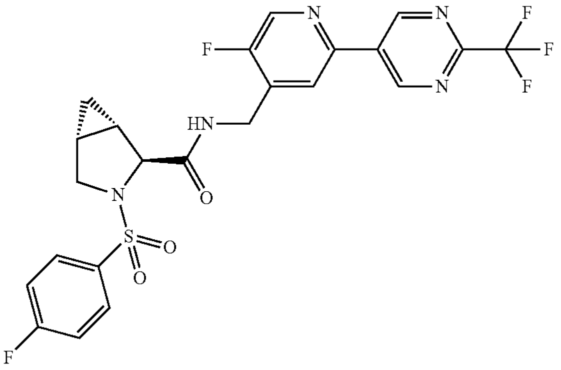 [SMILES: O=C(NCc1cc(-c2cnc(C(F)(F)F)nc2)ncc1F)[C@@H]1[C@H]2C[C@H]2CN1S(=O)(=O)c1ccc(F)cc1] | (1S,4R,5R)-3-(4-fluorophenyl)sulfonyl-N-[[5-fluoro-2-[2-(trifluoromethyl)pyrimidin-5-yl]-4-pyridyl]methyl]-3-azabicyclo[3.1.0]hexane-4-carboxamide | 0.0146 | 1H NMR (400 MHz, DMSO-d6) δ 9.60 (s, 2H), 8.92 (t, J = 5.9 Hz, 1H), 8.79 (d, J = 1.3 Hz, 1H), 8.15 (d, J = 5.7 Hz, 1H), 8.04-7.78 (m, 2H), 7.69-7.13 (m, 2H), 4.69-4.37 (m, 2H), 4.24 (s, 1H), 3.97-3.60 (m, 1H), 3.58-3.42 (m, 1H), 1.58 (dt, J = 7.7, 3.8 Hz, 2H), 0.72-0.36 (m, 1H), −0.86 (q, J = 4.5 Hz, 1H). | 540.1 |
| 69. | 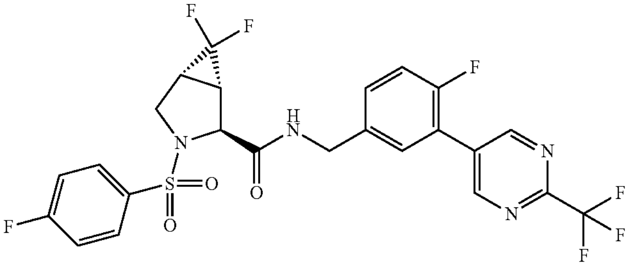 [SMILES: O=C(NCc1ccc(F)c(-c2cnc(C(F)(F)F)nc2)c1)[C@@H]1[C@@H]2[C@H](CN1S(=O)(=O)c1ccc(F)cc1)C2(F)F] | (1R,4S,5S)-6,6-difluoro-3-(4-fluorophenyl)sulfonyl-N-[[4-fluoro-3-[2-(trifluoromethyl)pyrimidin-5-yl]phenyl]methyl]-3-azabicyclo[3.1.0]hexane-4-carboxamide | 0.0457 | 1H NMR (400 MHz, DMSO) δ 9.32-9.27 (d, J = 1.3 Hz, 2H), 8.93-8.88 (m, 1H), 7.92-7.85 (m, 2H), 7.73-7.68 (m, 1H), 7.56-7.50 (m, 1H), 7.48-7.40 (m, 3H), 4.44-4.39 (m, 3H), 3.94-3.87 (m, 1H), 3.69-3.62 (m, 1H), 2.73-2.60 (m, 2H). | 575.2 |
| 70. | 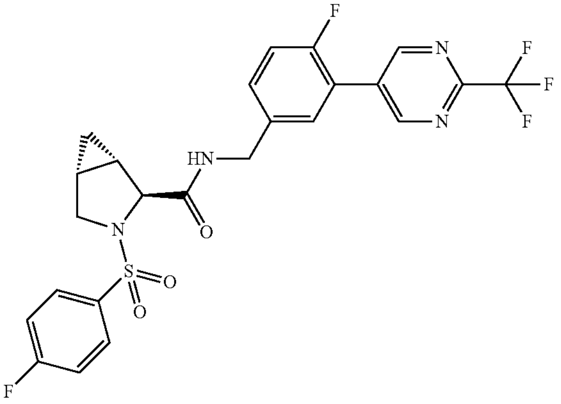 [SMILES: O=C(NCc1ccc(F)c(-c2cnc(C(F)(F)F)nc2)c1)[C@@H]1[C@H]2C[C@H]2CN1S(=O)(=O)c1ccc(F)cc1] | (1S,4R,5R)-3-(4-fluorophenyl)sulfonyl-N-[[4-fluoro-3-[2-(trifluoromethyl)pyrimidin-5-yl]phenyl]methyl]-3-azabicyclo[3.1.0]hexane-4-carboxamide | 0.0113 | 1H NMR (400 MHz, DMSO) δ 9.33-9.25 (d, J = 1.3 Hz, 2H), 8.78-8.72 (m, 1H), 7.91-7.84 (m, 2H), 7.71-7.66 (dd, J = 7.5, 2.2 Hz, 1H), 7.52-7.40 (m, 4H), 4.47-4.30 (m, 2H), 4.22-4.13 (s, 1H), 3.76-3.69 (m, 1H), 3.51-3.45 (d, J = 10.5 Hz, 1H), 1.62-1.50 (m, 2H), 0.58-0.48 (m, 1H), −0.75-−0.83 (m, 1H). | 539.2 |
| 71. | 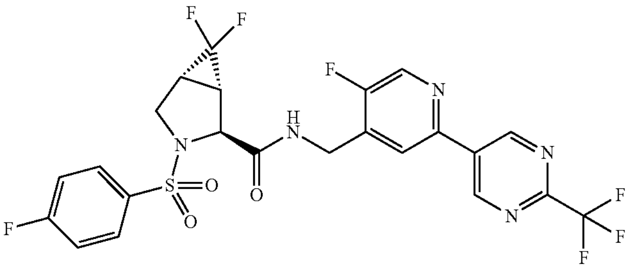 [SMILES: O=C(NCc1cc(-c2cnc(C(F)(F)F)nc2)ncc1F)[C@@H]1[C@@H]2[C@H](CN1S(=O)(=O)c1ccc(F)cc1)C2(F)F] | (1R,4S,5S)-6,6-difluoro-3-(4-fluorophenyl)sulfonyl-N-[[5-fluoro-2-[2-(trifluoromethyl)pyrimidin-5-yl]-4-pyridyl]methyl]-3-azabicyclo[3.1.0]hexane-4-carboxamide | 0.0462 | 1H NMR (400 MHz, DMSO) δ 9.61-9.57 (s, 2H), 9.13-9.05 (m, 1H), 8.81-8.77 (d, J = 1.3 Hz, 1H), 8.22-8.16 (d, J = 5.7 Hz, 1H), 7.98-7.91 (m, 2H), 7.50-7.42 (m, 2H), 4.62-4.49 (m, 2H), 4.48-4.45 (m, 1H), 3.99-3.89 (m, 1H), 3.69-3.63 (m, 1H), 2.75-2.64 (m, 2H). | 576.2 |

TABLE 2-continued

| Example | Structure | Name | hTRPA1 CHO Ca2+ AUC EVO (IC50) | $^1$H NMR | LCMS |
|---|---|---|---|---|---|
| 72. | 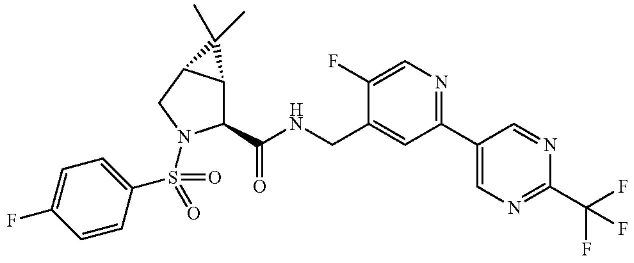 [SMILES: CC1(C)[C@@H]2[C@@H](C(=O)NCc3cc(-c4cnc(C(F)(F)F)nc4)ncc3F)N(S(=O)(=O)c3ccc(F)cc3)C[C@@H]21] | (1S,4S,5R)-3-(4-fluorophenyl) sulfonyl-N-[[5-fluoro-2-[2-(trifluoromethyl)pyrimidin-5-yl]-4-pyridyl]methyl]-6,6-dimethyl-3-azabicyclo [3.1.0]hexane-4-carboxamide | 0.0147 | 1H NMR (400 MHz, DMSO) δ 9.60-9.52 (s, 2H), 8.98-8.92 (m, 1H), 8.81-8.76 (d, J = 1.3 Hz, 1H), 8.24-8.19 (d, J = 5.6 Hz, 1H), 7.94-7.86 (m, 2H), 7.45-7.37 (m, 2H), 4.56-4.46 (m, 2H), 4.13-4.05 (m, 1H), 3.77-3.66 (m, 1H), 3.21-3.15 (m, 1H), 1.58-1.50 (m, 1H), 1.45-1.36 (m, 1H), 0.96-0.89 (s, 3H), 0.49-0.42 (s, 3H). | 568.2 |
| 73. | 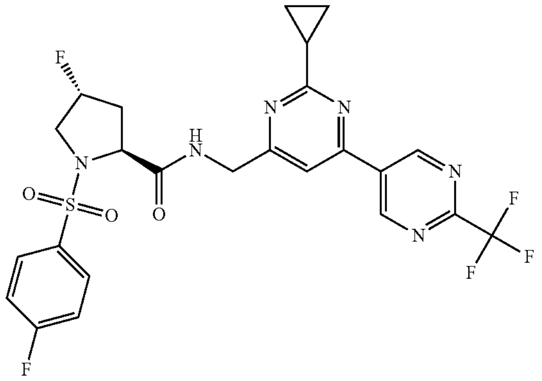 [SMILES: O=C(NCc1cc(-c2cnc(C(F)(F)F)nc2)nc(C2CC2)n1)[C@@H]1C[C@@H](F)CN1S(=O)(=O)c1ccc(F)cc1] | (2S,4R)-N-[[2-cyclopropyl-6-[2-(trifluoromethyl)pyrimidin-5-yl]pyrimidin-4-yl]methyl]-4-fluoro-1-(4-fluorophenyl) sulfonyl-pyrrolidine-2-carboxamide | 0.0567 | $^1$H NMR (400 MHz, $CDCl_3$) δ 9.62 (s, 2H), 7.93-7.87 (m, 3H), 7.59 (s, 1H), 7.27-7.23 (m, 2H), 5.07 (d, J = 51.6 Hz, 1H), 4.95-4.89 (m, 1H), 4.45-4.31 (m, 1H), 3.89-3.66 (m, 2H), 2.62-2.34 (m, 2H), 2.33-2.11 (m, 2H), 1.27-1.15 (m, 4H). | 569.1 |
| 74. | 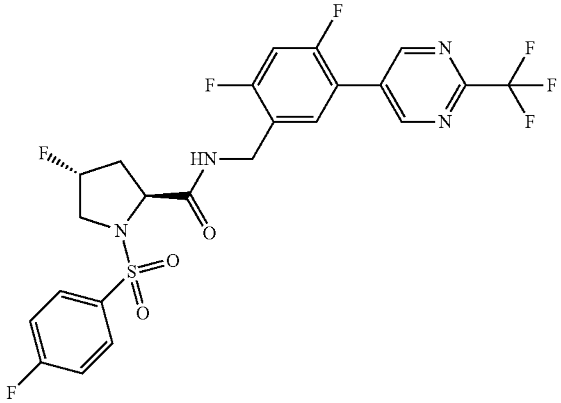 [SMILES: O=C(NCc1cc(-c2cnc(C(F)(F)F)nc2)c(F)cc1F)[C@@H]1C[C@@H](F)CN1S(=O)(=O)c1ccc(F)cc1] | (2S,4R)-N-[[2,4-difluoro-5-[2-(trifluoromethyl)pyrimidin-5-yl]phenyl] methyl]-4-fluoro-1-(4-fluorophenyl) sulfonyl-pyrrolidine-2-carboxamide | 0.0651 | 1H NMR (400 MHz, DMSO-d6) δ 9.24 (d, J = 1.4 Hz, 2H), 8.88 (t, J = 5.9 Hz, 1H), 8.04-7.87 (m, 2H), 7.82 (t, J = 8.5 Hz, 1H), 7.57 (t, J = 10.4 Hz, 1H), 7.51-7.29 (m, 2H), 5.18 (d, J = 52.5 Hz, 1H), 4.42 (d, J = 5.8 Hz, 2H), 4.17 (dd, J = 10.0, 7.1 Hz, 1H), 3.77-3.65 (m, 1H), 3.66-3.48 (m, 1H), 2.39 (dq, J = 17.0, 9.7, 8.4 Hz, 1H), 2.07 (dddd, J = 42.5, 13.8, 10.0, 3.4 Hz, 1H). | 563.2 |
| 75. | 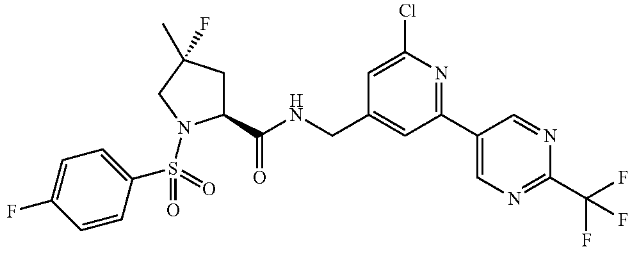 [SMILES: C[C@@]1(F)C[C@@H](C(=O)NCc2cc(Cl)nc(-c3cnc(C(F)(F)F)nc3)c2)N(S(=O)(=O)c2ccc(F)cc2)C1] | (2S,4R)-N-[[2-chloro-6-[2-(trifluoromethyl)pyrimidin-5-yl]-4-pyridyl]methyl]-4-fluoro-1-(4-fluorophenyl) sulfonyl-4-methyl-pyrrolidine-2-carboxamide | 0.0666 | 1H NMR (400 MHz, DMSO) δ 9.60 (s, 2H), 9.04 (t, J = 6.0 Hz, 1H), 8.22-8.17 (m, 1H), 8.05-7.94 (m, 2H), 7.69-7.64 (m, 1H), 7.56-7.42 (m, 2H), 4.60-4.42 (m, 2H), 4.25-4.15 (m, 1H), 3.72-3.48 (m, 2H), 2.45-2.34 (m, 1H), 2.16-1.95 (m, 1H), 1.39 (d, J = 20.8 Hz, 3H). | RT = 6.27 min [M + H] m/z = 576.2 |

TABLE 2-continued

| Example | Structure | Name | hTRPA1 CHO Ca2+ AUC EVO (IC50) | $^1$H NMR | LCMS |
|---|---|---|---|---|---|
| 76. | 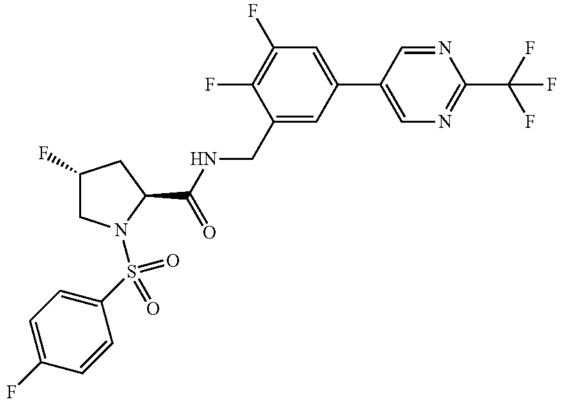 [SMILES: O=C(NCc1cc(-c2cnc(C(F)(F)F)nc2)cc(F)c1F)[C@@H]1C[C@@H](F)CN1S(=O)(=O)c1ccc(F)cc1] | (2S,4R)-N-[[2,3-difluoro-5-[2-(trifluoromethyl)pyrimidin-5-yl]phenyl]methyl]-4-fluoro-1-(4-fluorophenyl)sulfonyl-pyrrolidine-2-carboxamide | 0.0393 | 1H NMR (400 MHz, DMSO-d6) δ 9.24 (d, J = 1.4 Hz, 2H), 8.88 (t, J = 5.9 Hz, 1H), 8.04-7.87 (m, 2H), 7.82 (t, J = 8.5 Hz, 1H), 7.57 (t, J = 10.4 Hz, 1H), 7.51-7.29 (m, 2H), 5.18 (d, J = 52.5 Hz, 1H), 4.42 (d, J = 5.8 Hz, 2H), 4.17 (dd, J = 10.0, 7.1 Hz, 1H), 3.77-3.65 (m, 1H), 3.66-3.48 (m, 1H), 2.39 (dq, J = 17.0, 9.7, 8.4 Hz, 1H), 2.07 (dddd, J = 42.5, 13.8, 10.0, 3.4 Hz, 1H). | 563.2 |
| 77. | 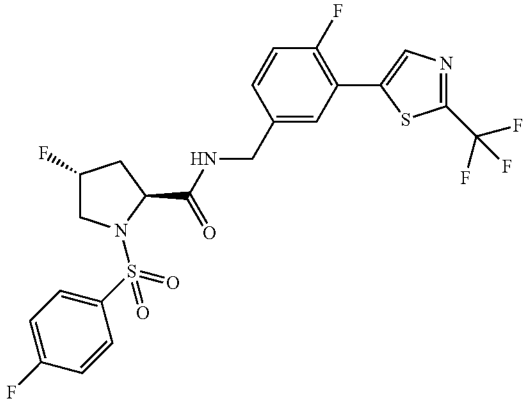 [SMILES: O=C(NCc1ccc(F)c(-c2cnc(C(F)(F)F)s2)c1)[C@@H]1C[C@@H](F)CN1S(=O)(=O)c1ccc(F)cc1] | (2S,4R)-4-fluoro-1-(4-fluorophenyl)sulfonyl-N-[[4-fluoro-3-[2-(trifluoromethyl)thiazol-5-yl]phenyl]methyl]pyrrolidine-2-carboxamide | 0.0733 | 1H NMR (400 MHz, DMSO) δ 8.92-8.85 (m, 1H), 8.61-8.56 (m, 1H), 8.02-7.95 (m, 2H), 7.94-7.88 (m, 1H), 7.53-7.42 (m, 4H), 5.28-5.10 (d, J = 52.4 Hz, 1H), 4.50-4.34 (m, 2H), 4.21-4.14 (m, 1H), 3.74-3.60 (m, 2H), 2.42-2.30 (d, J = 12.0 Hz, 1H), 2.19-1.98 (m, 1H). | 550.2 |
| 78. | 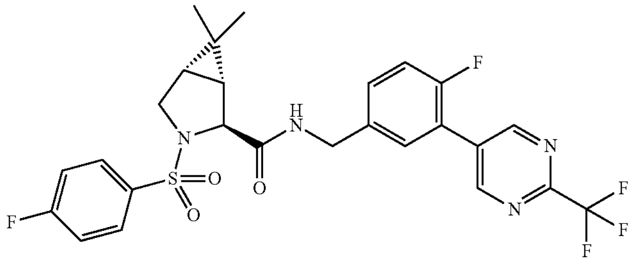 [SMILES: CC1(C)[C@@H]2[C@@H](C(=O)NCc3ccc(F)c(-c4cnc(C(F)(F)F)nc4)c3)N(S(=O)(=O)c3ccc(F)cc3)C[C@@H]21] | (1S,4S,5R)-3-(4-fluorophenyl)sulfonyl-N-[[4-fluoro-3-[2-(trifluoromethyl)pyrimidin-5-yl]phenyl]methyl]-6,6-dimethyl-3-azabicyclo[3.1.0]hexane-4-carboxamide | 0.0234 | 1H NMR (400 MHz, DMSO) δ 9.29-9.24 (d, J = 1.3 Hz, 2H), 8.80-8.74 (m, 1H), 7.87-7.81 (m, 2H), 7.72-7.67 (m, 1H), 7.55-7.48 (m, 1H), 7.47-7.37 (m, 3H), 4.45-4.30 (m, 2H), 4.10-4.03 (s, 1H), 3.70-3.62 (m, 1H), 3.23-3.17 (m, 1H), 1.54-1.46 (m, 1H), 1.38-1.30 (d, J = 7.6 Hz, 1H), 0.96-0.90 (s, 3H), 0.58-0.50 (s, 3H). | 567.2 |

TABLE 2-continued

| Example | Structure | Name | hTRPA1 CHO Ca2+ AUC EVO (IC50) | $^1$H NMR | LCMS |
|---|---|---|---|---|---|
| 79. | 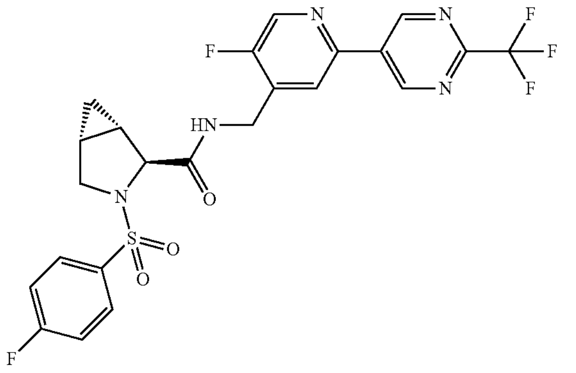 [SMILES: O=C(NCc1cc(-c2cnc(C(F)(F)F)nc2)ncc1F)[C@@H]1[C@H]2C[C@H]2CN1S(=O)(=O)c1ccc(F)cc1] | (1S,4R,5R)-3-(4-fluorophenyl)sulfonyl-N-[[5-fluoro-2-[2-(trifluoromethyl)pyrimidin-5-yl]-4-pyridyl]methyl]-3-azabicyclo[3.1.0]hexane-4-carboxamide | 0.0146 | 1H NMR (400 MHz, DMSO-d6) δ 9.60 (s, 2H), 8.92 (t, J = 5.9 Hz, 1H), 8.79 (d, J = 1.3 Hz, 1H), 8.15 (d, J = 5.7 Hz, 1H), 8.04-7.78 (m, 2H), 7.69-7.13 (m, 2H), 4.69-4.37 (m, 2H), 4.24 (s, 1H), 3.97-3.60 (m, 1H), 3.58-3.42 (m, 1H), 1.58 (dt, J = 7.7, 3.8 Hz, 2H), 0.72-0.36 (m, 1H), −0.86 (q, J = 4.5 Hz, 1H). | 540.1 |
| 80. | 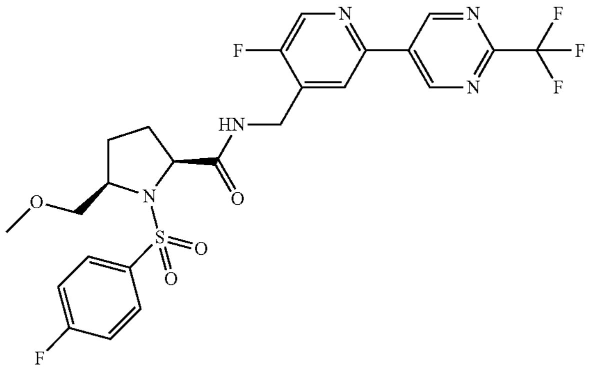 [SMILES: COC[C@H]1CC[C@@H](C(=O)NCc2cc(-c3cnc(C(F)(F)F)nc3)ncc2F)N1S(=O)(=O)c1ccc(F)cc1] | (2S,5R)-N-((5-fluoro-2-(2-(trifluoromethyl)pyrimidin-5-yl)pyridin-4-yl)methyl)-1-((4-fluorophenyl)sulfonyl)-5-(methoxymethyl)pyrrolidine-2-carboxamide | 0.0982 | $^1$H NMR (400 MHz, DMSO-$d_6$) δ 9.59 (s, 2H), 8.78 (d, J = 1.4 Hz, 1H), 8.69 (t, J = 5.9 Hz, 1H), 8.19 (d, J = 5.7 Hz, 1H), 8.12-7.97 (m, 2H), 7.57-7.42 (m, 2H), 4.55 (d, J = 5.9 Hz, 2H), 4.16 (dd, J = 7.7, 6.4 Hz, 1H), 3.83-3.70 (m, 1H), 3.57-3.43 (m, 2H), 3.24 (s, 3H), 1.96-1.71 (m, 3H), 1.54-1.41 (m, 1H). | 572.1 |
| 81. | 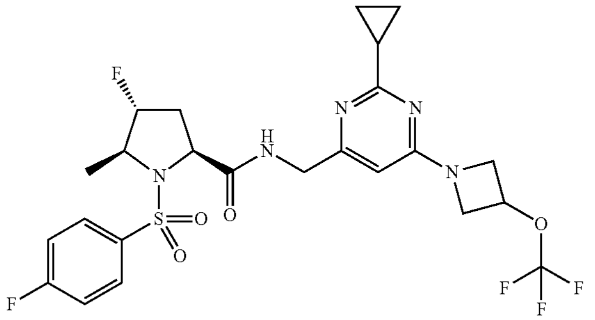 [SMILES: C[C@H]1[C@H](F)C[C@@H](C(=O)NCc2cc(N3CC(OC(F)(F)F)C3)nc(C3CC3)n2)N1S(=O)(=O)c1ccc(F)cc1] | (2S,4R,5S)-N-[[2-cyclopropyl-6-[3-(trifluoromethoxy)azetidin-1-yl]pyrimidin-4-yl]methyl]-4-fluoro-1-(4-fluorophenyl)sulfonyl-5-methyl-pyrrolidine-2-carboxamide | 0.0553 | $^1$H NMR (400 MHz, $CDCl_3$) δ 7.92-7.90 (m, 2H), 7.75-7.65 (m, 1H), 7.28-7.22 (m, 2H), 6.20 (s, 1H), 5.09-5.07 (m, 1H), 4.79-4.65 (m, 1H), 4.60-4.54 (m, 1H), 4.44-4.25 (m, 3H), 4.23-4.07 (m, 4H), 2.54-2.48 (m, 1H), 2.36-2.20 (m, 1H), 2.15-2.01 (m, 1H), 1.41-1.39 (m, 3H), 1.17-1.09 (m, 2H), 1.09-0.99 (m, 2H). | 576 |
| 82. | 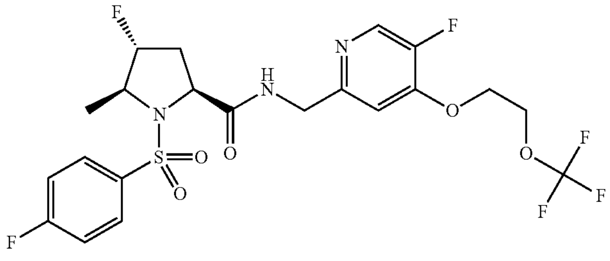 [SMILES: C[C@H]1[C@H](F)C[C@@H](C(=O)NCc2cc(OCCOC(F)(F)F)c(F)cn2)N1S(=O)(=O)c1ccc(F)cc1] | (2S,4R,5S)-4-fluoro-1-(4-fluorophenyl)sulfonyl-N-[[5-fluoro-4-[2-(trifluoromethoxy)ethoxy]-2-pyridyl]methyl]-5-methyl-pyrrolidine-2-carboxamide | 0.166 | $^1$H NMR (400 MHz, $CDCl_3$) δ 8.33 (s, 1H), 7.94-7.91 (m, 2H), 7.57-7.40 (m, 1H), 7.29-7.24 (m, 3H), 4.90-4.86 (m, 1H), 4.80-4.67 (d, J = 54.6 Hz, 1H), 4.59-4.55 (m, 1H), 4.46 (s, 2H), 4.35 (s, 2H), 4.28-4.24 (m, 1H), 4.15-4.03 (m, 1H), 2.60-2.50 (m, 1H), 2.39-2.23 (m, 1H), 1.41-1.40 (d, J = 6.8 Hz, 3H). | 542 |

TABLE 2-continued

| Example | Structure | Name | hTRPA1 CHO Ca2+ AUC EVO (IC50) | $^1$H NMR | LCMS |
|---|---|---|---|---|---|
| 83. | 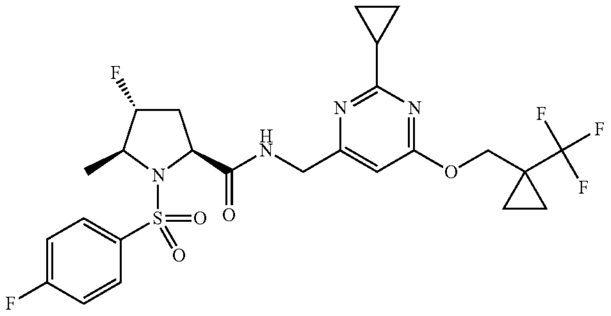 [SMILES: C[C@H]1[C@H](F)C[C@@H](C(=O)NCc2cc(OCC3(C(F)(F)F)CC3)nc(C3CC3)n2)N1S(=O)(=O)c1ccc(F)cc1] | (2S,4R,5S)-N-[[2-cyclopropyl-6-[[1-(trifluoromethyl)cyclopropyl]methoxy]pyrimidin-4-yl]methyl]-4-fluoro-1-(4-fluorophenyl)sulfonyl-5-methyl-pyrrolidine-2-carboxamide | 0.147 | $^1$H NMR (300 MHz, $CDCl_3$) δ 7.54 (m, 3H), 7.28-7.21 (m, 2H), 6.57 (m, 1H), 4.79-4.66 (d, J = 51 Hz, 1H), 4.53-4.45 (m, 4H), 4.24-4.10 (m, 2H), 2.55-2.27 (m, 2H), 2.28-2.19 (m, 1H), 1.42-1.40 (d, J = 5.1 Hz, 3H), 1.27-1.09 (m, 6H), 0.98-0.91 (m, 2H). | 575.2 |
| 84. | 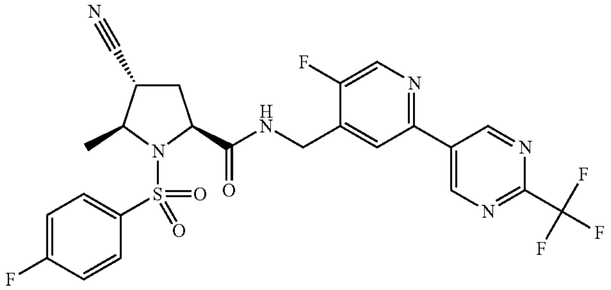 [SMILES: C[C@H]1[C@H](C#N)C[C@@H](C(=O)NCc2cc(-c3cnc(C(F)(F)F)nc3)ncc2F)N1S(=O)(=O)c1ccc(F)cc1] | (2S,4R,5S)-4-cyano-1-(4-fluorophenyl)sulfonyl-N-[[5-fluoro-2-[2-(trifluoromethyl)pyrimidin-5-yl]-4-pyridyl]methyl]-5-methyl-pyrrolidine-2-carboxamide | 0.0653 | $^1$H NMR (300 MHz, $CDCl_3$) δ 9.53 (s, 2H), 8.59 (s, 1H), 8.04-8.02 (m, 1H), 7.96-7.93 (m, 2H), 7.39-7.28 (m, 3H), 4.94-4.86 (dd, J = 17.4 Hz, J = 7.2 Hz, 1H), 4.58-4.50 (dd, J = 16.8 Hz, J = 5.1 Hz, 1H), 4.36-4.32 (m, 1H), 3.84-3.80 (m, 1H), 2.80-2.75 (m, 1H), 2.64-2.56 (m, 1H), 2.02-1.93 (m, 1H), 1.60-1.58 (d, J = 6.3 Hz, 3H). | 567.1 |
| 85. | 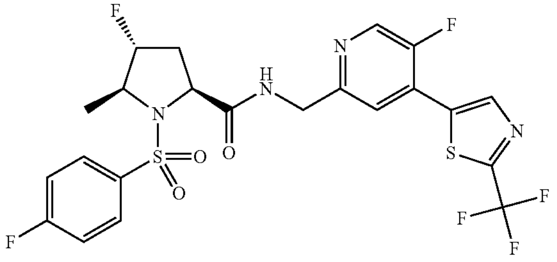 [SMILES: C[C@H]1[C@H](F)C[C@@H](C(=O)NCc2cc(-c3cnc(C(F)(F)F)s3)c(F)cn2)N1S(=O)(=O)c1ccc(F)cc1] | (2S,4R,5S)-4-fluoro-1-(4-fluorophenyl)sulfonyl-N-[[5-fluoro-4-[2-(trifluoromethyl)thiazol-5-yl]-2-pyridyl]methyl]-5-methyl-pyrrolidine-2-carboxamide | 0.0337 | $^1$H NMR (400 MHz, $CDCl_3$) δ 8.61-8.58 (m, 2H), 7.94-7.87 (m, 3H), 7.56-7.53 (m, 1H), 7.28-7.24 (m, 2H), 4.98-4.80 (m, 1H), 4.80-4.67 (d, J = 51.3, 1H), 4.67-4.53 (m, 1H), 4.30-4.26 (m, 1H), 4.15-4.08 (m, 1H), 2.59-2.55 (m, 1H), 2.37-2.26 (m, 1H), 1.42-1.40 (d, J = 7.2 Hz, 3H). | 565.1 |
| 86. | 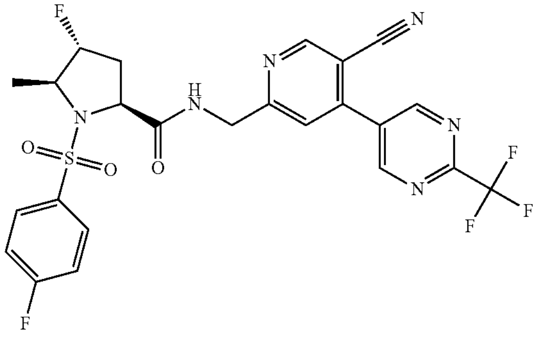 [SMILES: C[C@H]1[C@H](F)C[C@@H](C(=O)NCc2cc(-c3cnc(C(F)(F)F)nc3)c(C#N)cn2)N1S(=O)(=O)c1ccc(F)cc1] | (2S,4R,5S)-N-[[5-cyano-4-[2-(trifluoromethyl)pyrimidin-5-yl]-2-pyridyl]methyl]-4-fluoro-1-(4-fluorophenyl)sulfonyl-5-methyl-pyrrolidine-2-carboxamide | 0.124 | $^1$HNMR (400 MHz, $CDCl_3$) δ 9.29 (s, 2H), 9.05 (s, 1H), 7.90-7.86 (m, 3H), 7.54-7.53 (m, 1H), 7.29-7.24 (m, 2H), 5.13-5.07 (m, 1H), 4.81-4.61 (m, 2H), 4.29-4.25 (m, 1H), 4.12-4.05 (m, 1H), 2.64-2.54 (m, 1H), 2.39-2.22 (m, 1H), 1.41-1.40 (d, J = 7.2 Hz, 3H). | 567 |

TABLE 2-continued

| Example | Structure | Name | hTRPA1 CHO Ca2+ AUC EVO (IC50) | $^1$H NMR | LCMS |
|---|---|---|---|---|---|
| 87. | 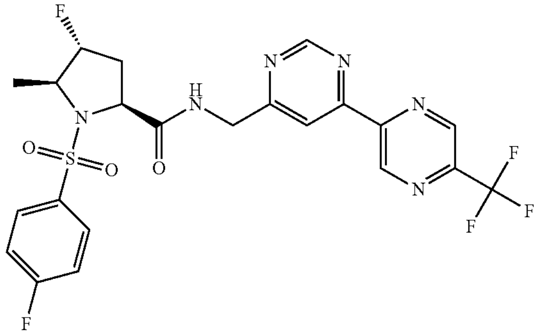 [SMILES: C[C@H]1[C@H](F)C[C@@H](C(=O)NCc2cc(-c3cnc(C(F)(F)F)cn3)ncn2)N1S(=O)(=O)c1ccc(F)cc1] | (2S,4R,5S)-4-fluoro-1-(4-fluorophenyl) sulfonyl-5-methyl-N-[[6-[5-(trifluoromethyl)pyrazin-2-yl]pyrimidin-4-yl]methyl] pyrrolidine-2-carboxamide | 0.184 | $^1$H NMR (400 MHz, $CDCl_3$) δ 9.85 (s, 1H), 9.36 (s, 1H), 9.05 (s, 1H), 8.52 (s, 1H), 7.97-7.91 (m, 2H), 7.28-7.24 (m, 3H), 4.88-4.68 (m, 3H), 4.29-4.11 (m, 2H), 2.58-2.34 (m, 2H), 1.44-1.43 (m, 3H). | 543 |
| 88. | 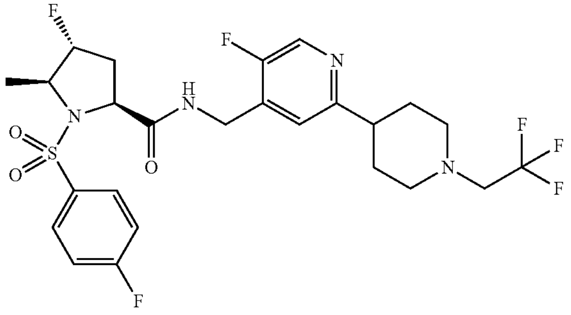 [SMILES: C[C@H]1[C@H](F)C[C@@H](C(=O)NCc2cc(C3CCN(CC(F)(F)F)CC3)ncc2F)N1S(=O)(=O)c1ccc(F)cc1] | (2S,4R,5S)-4-fluoro-1-(4-fluorophenyl) sulfonyl-N-[[5-fluoro-2-[1-(2,2,2-trifluoroethyl)-4-piperidyl]-4-pyridyl]methyl]-5-methyl-pyrrolidine-2-carboxamide | 0.0423 | 1H NMR (400 MHz, DMSO-d6) δ 8.83 (t, J = 6.0 Hz, 1H), 8.40 (d, J = 1.4 Hz, 1H), 8.09-7.91 (m, 2H), 7.53-7.42 (m, 2H), 7.39 (d, J = 6.1 Hz, 1H), 4.88 (dd, J = 51.4, 2.9 Hz, 1H), 4.54-4.27 (m, 2H), 4.19 (dd, J = 10.1, 7.1 Hz, 1H), 4.03-3.84 (m, 1H), 3.14 (q, J = 10.3 Hz, 2H), 3.02-2.89 (m, 2H), 2.72-2.53 (m, 1H), 2.47-2.03 (m, 4H), 1.85-1.61 (m, 4H), 1.20 (d, J = 6.9 Hz, 3H). | 579.2 |
| 89. | 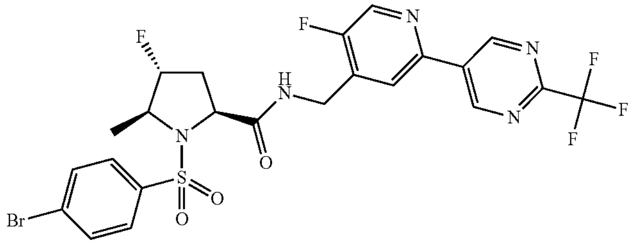 [SMILES: C[C@H]1[C@H](F)C[C@@H](C(=O)NCc2cc(-c3cnc(C(F)(F)F)nc3)ncc2F)N1S(=O)(=O)c1ccc(Br)cc1] | (2S,4R,5S)-1-(4-bromophenyl) sulfonyl-4-fluoro-N-[[5-fluoro-2-[2-(trifluoromethyl)pyrimidin-5-yl]-4-pyridyl]methyl]-5-methyl-pyrrolidine-2-carboxamide | 0.00708 | 1H NMR (400 MHz, DMSO-d6) δ 9.59 (s, 2H), 9.05 (t, J = 5.9 Hz, 1H), 8.78 (d, J = 1.3 Hz, 1H), 8.24 (d, J = 5.8 Hz, 1H), 7.97-7.80 (m, 4H), 4.90 (dd, J = 51.5, 2.8 Hz, 1H), 4.66-4.42 (m, 2H), 4.23 (dd, J = 10.1, 7.0 Hz, 1H), 4.05-3.89 (m, 1H), 2.44-2.12 (m, 2H), 1.21 (d, J = 6.9 Hz, 3H). | 622.0 |
| 90. | 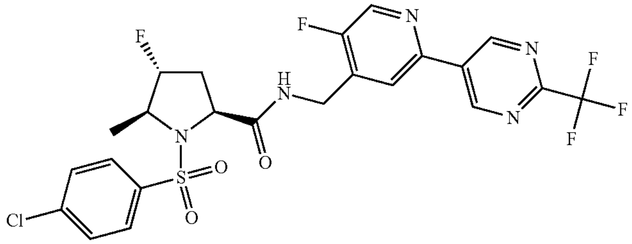 [SMILES: C[C@H]1[C@H](F)C[C@@H](C(=O)NCc2cc(-c3cnc(C(F)(F)F)nc3)ncc2F)N1S(=O)(=O)c1ccc(Cl)cc1] | (2S,4R,5S)-1-(4-chlorophenyl) sulfonyl-4-fluoro-N-[[5-fluoro-2-[2-(trifluoromethyl)pyrimidin-5-yl]-4-pyridyl[methyl]-5-methyl-pyrrolidine-2-carboxamide | 0.00250 | 1H NMR (400 MHz, DMSO-d6) δ 9.60 (s, 2H), 9.05 (t, J = 5.9 Hz, 1H), 8.78 (d, J = 1.3 Hz, 1H), 8.24 (d, J = 5.8 Hz, 1H), 8.03-7.91 (m, 2H), 7.79-7.66 (m, 2H), 4.90 (dd, J = 51.3, 2.8 Hz, 1H), 4.68-4.43 (m, 2H), 4.24 (dd, J = 10.1, 7.1 Hz, 1H), 4.03-3.88 (m, 1H), 2.47-2.09 (m, 2H), 1.21 (d, J = 6.9 Hz, 3H). | 576.1 |

TABLE 2-continued

| Example | Structure | Name | hTRPA1 CHO Ca2+ AUC EVO (IC50) | $^1$H NMR | LCMS |
|---|---|---|---|---|---|
| 91. | 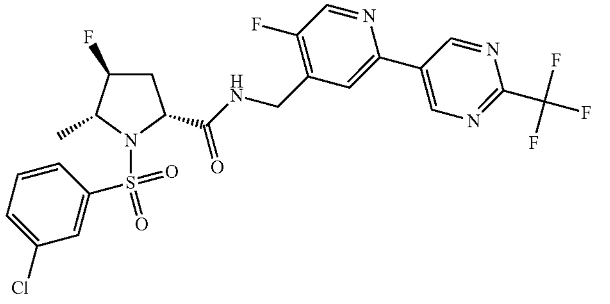 [SMILES: C[C@@H]1[C@@H](F)C[C@H](C(=O)NCc2cc(-c3cnc(C(F)(F)F)nc3)ncc2F)N1S(=O)(=O)c1cccc(Cl)c1] | (2S,4R,5S)-1-(3-chlorophenyl)sulfonyl-4-fluoro-N-[[5-fluoro-2-[2-(trifluoromethyl)pyrimidin-5-yl]-4-pyridyl]methyl]-5-methyl-pyrrolidine-2-carboxamide | 0.02002 | 1H NMR (400 MHz, DMSO-d6) δ 9.60 (s, 2H), 9.10 (t, J = 5.9 Hz, 1H), 8.78 (d, J = 1.3 Hz, 1H), 8.24 (d, J = 5.7 Hz, 1H), 8.03 (t, J = 1.9 Hz, 1H), 7.93 (ddd, J = 7.9, 1.8, 1.0 Hz, 1H), 7.80 (ddd, J = 8.1, 2.1, 1.0 Hz, 1H), 7.66 (t, J = 8.0 Hz, 1H), 4.91 (dd, J = 51.4, 2.8 Hz, 1H), 4.71-4.44 (m, 2H), 4.29 (dd, J = 10.1, 7.1 Hz, 1H), 4.08-3.94 (m, 1H), 2.45-2.10 (m, 2H), 1.21 (d, J = 6.9 Hz, 3H). | 576.1 |
| 92. | 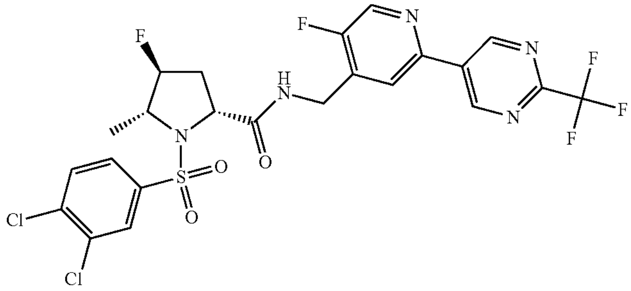 [SMILES: C[C@@H]1[C@@H](F)C[C@H](C(=O)NCc2cc(-c3cnc(C(F)(F)F)nc3)ncc2F)N1S(=O)(=O)c1ccc(Cl)c(Cl)c1] | (2S,4R,5S)-1-(3,4-dichlorophenyl)sulfonyl-4-fluoro-N-[[5-fluoro-2-[2-(trifluoromethyl)pyrimidin-5-yl]-4-pyridyl]methyl]-5-methyl-pyrrolidine-2-carboxamide | 0.00869 | 1H NMR (400 MHz, DMSO-d6) δ 9.59 (s, 2H), 9.11 (t, J = 5.9 Hz, 1H), 8.78 (d, J = 1.3 Hz, 1H), 8.27-8.18 (m, 2H), 8.00-7.86 (m, 2H), 4.93 (dd, J = 51.3, 2.8 Hz, 1H), 4.55 (ddd, J = 55.8, 16.9, 5.8 Hz, 2H), 4.30 (dd, J = 10.0, 7.1 Hz, 1H), 4.11-3.97 (m, 1H), 2.48-2.10 (m, 2H), 1.20 (d, J = 6.9 Hz, 3H). | 610.0 |
| 93. | 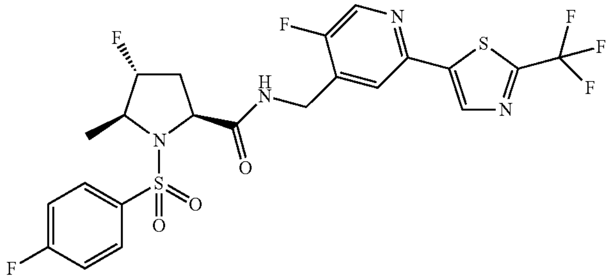 [SMILES: C[C@H]1[C@H](F)C[C@@H](C(=O)NCc2cc(-c3cnc(C(F)(F)F)s3)ncc2F)N1S(=O)(=O)c1ccc(F)cc1] | (2S,4R,5S)-4-fluoro-1-(4-fluorophenyl)sulfonyl-N-[[5-fluoro-2-[2-(trifluoromethyl)thiazol-5-yl]-4-pyridyl]methyl]-5-methyl-pyrrolidine-2-carboxamide | 0.00538 | 1H NMR (400 MHz, DMSO-d6) δ 9.04 (t, J = 6.0 Hz, 1H), 8.71-8.51 (m, 2H), 8.17 (d, J = 5.8 Hz, 1H), 8.13-8.01 (m, 2H), 7.62-7.38 (m, 2H), 5.02-4.79 (m, 1H), 4.69-4.34 (m, 2H), 4.25 (dd, J = 10.1, 7.1 Hz, 1H), 4.06-3.85 (m, 1H), 2.45-2.02 (m, 2H), 1.22 (d, J = 6.9 Hz, 3H). | 565.1 |
| 94. | 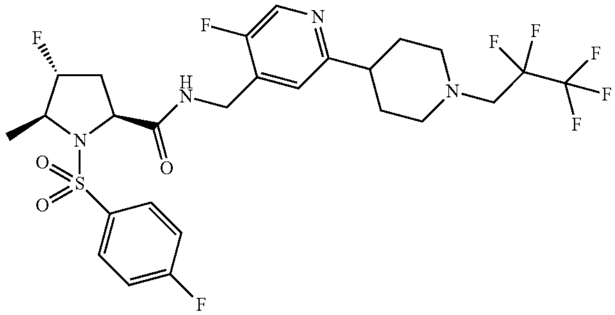 [SMILES: C[C@H]1[C@H](F)C[C@@H](C(=O)NCc2cc(C3CCN(CC(F)(F)C(F)(F)F)CC3)ncc2F)N1S(=O)(=O)c1ccc(F)cc1] | (2S,4R,5S)-4-fluoro-N-[[5-fluoro-2-[1-(2,2,3,3,3-pentafluoropropyl)-4-piperidyl]-4-pyridyl]methyl]-1-(4-fluorophenyl)sulfonyl-5-methyl-pyrrolidine-2-carboxamide | 0.00552 | | 629.2 |

TABLE 2-continued

| Example | Structure | Name | hTRPA1 CHO Ca2+ AUC EVO (IC50) | $^1$H NMR | LCMS |
|---|---|---|---|---|---|
| 95. | 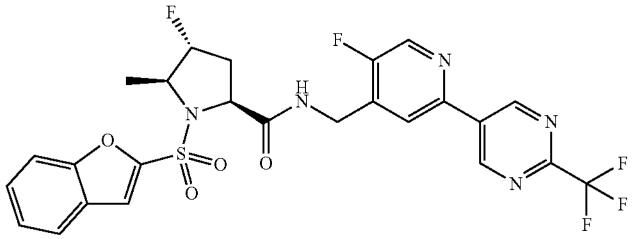 [SMILES: C[C@H]1[C@H](F)C[C@@H](C(=O)NCc2cc(-c3cnc(C(F)(F)F)nc3)ncc2F)N1S(=O)(=O)c1cc2ccccc2o1] | (2S,4R,5S)-1-(benzofuran-2-ylsulfonyl)-4-fluoro-N-[[5-fluoro-2-[2-(trifluorometh-yl)pyrimidin-5-yl]-4-pyridyl]meth-yl]-5-methyl-pyrrolidine-2-carboxamide | 0.00149 | 1H NMR (400 MHz, DMSO-d6) δ 9.60 (s, 2H), 9.04 (t, J = 5.9 Hz, 1H), 8.79 (d, J = 1.3 Hz, 1H), 8.19 (d, J = 5.7 Hz, 1H), 7.86-7.82 (m, 1H), 7.81 (d, J = 0.9 Hz, 1H), 7.71 (dd, J = 8.4, 1.0 Hz, 1H), 7.55 (ddd, J = 8.6, 7.2, 1.3 Hz, 1H), 7.41 (td, J = 7.5, 0.9 Hz, 1H), 5.09-4.78 (m, 1H), 4.64-4.39 (m, 3H), 4.10 (dt, J = 21.2, 6.9 Hz, H), 2.47-2.10 (m, 2H), 1.28 (d, J = 7.0 Hz, 3H). | 582.1 |
| 96. | 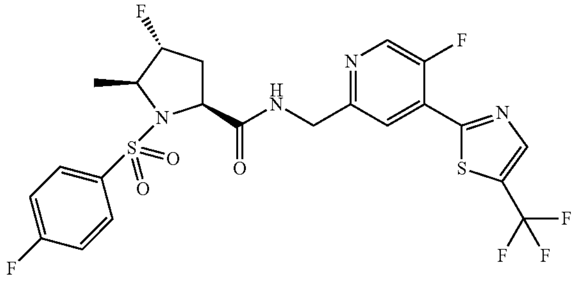 [SMILES: C[C@H]1[C@H](F)C[C@@H](C(=O)NCc2cc(-c3ncc(C(F)(F)F)s3)c(F)cn2)N1S(=O)(=O)c1ccc(F)cc1] | (2S,4R,5S)-4-fluoro-1-(4-fluorophenyl) sulfonyl-N-[[5-fluoro-4-[5-(trifluorometh-yl)thiazol-2-yl]-2-pyridyl]meth-yl]-5-methyl-pyrrolidine-2-carboxamide | 0.02250 | 1H NMR (400 MHz, DMSO-d6) δ 8.94 (t, J = 6.0 Hz, 1H), 8.83 (d, J = 2.2 Hz, 1H), 8.77 (dq, J = 2.3, 1.2 Hz, 1H), 8.17 (d, J = 5.8 Hz, 1H), 8.06-7.92 (m, 2H), 7.53-7.38 (m, 2H), 5.00-4.75 (m, 1H), 4.60-4.44 (m, 2H), 4.20 (dd, J = 10.0, 7.2 Hz, 1H), 3.96 (dtd, J = 23.1, 7.5, 6.0 Hz, 1H), 2.40-2.02 (m, 2H). | 565.1 |
| 97. | 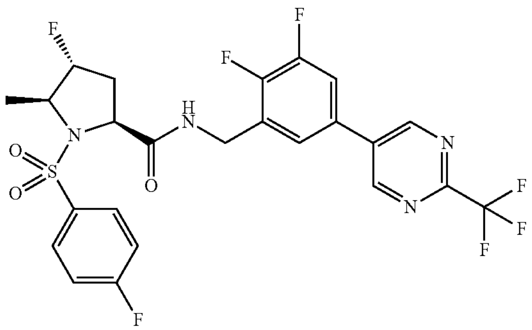 [SMILES: C[C@H]1[C@H](F)C[C@@H](C(=O)NCc2cc(-c3cnc(C(F)(F)F)nc3)cc(F)c2F)N1S(=O)(=O)c1ccc(F)cc1] | (2S,4R,5S)-N-[[2-1,3-difluoro-5-[2-(trifluorometh-yl)pyrimidin-5-yl]phenyl] methyl]-4-fluoro-1-(4-fluorophenyl) sulfonyl-5-methyl-pyrrolidine-2-carboxamide | 0.00606 | 1H NMR (400 MHz, DMSO-d6) δ 9.38 (s, 2H), 8.94 (t, J = 5.9 Hz, 1H), 8.11-7.92 (m, 3H), 7.78 (d, J = 5.5 Hz, 1H), 7.51-7.37 (m, 2H), 5.00-4.73 (m, 1H), 4.68 4.37 (m, 2H), 419 (dd, J = 10.1, 7.1 Hz, 1H), 3.92 (ddd, J = 21.6, 8.0, 6.5 Hz, 1H), 2.45-2.00 (m, 2H), 1.20 (d, J = 6.9 Hz, 3H). | 577.1 |

TABLE 2-continued

| Example | Structure | Name | hTRPA1 CHO Ca2+ AUC EVO (IC50) | $^1$H NMR | LCMS |
|---|---|---|---|---|---|
| 98. | 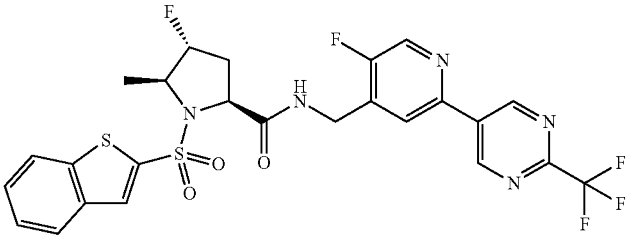 [SMILES: C[C@H]1[C@H](F)C[C@@H](C(=O)NCc2cc(-c3cnc(C(F)(F)F)nc3)ncc2F)N1S(=O)(=O)c1cc2ccccc2s1] | (2S,4R,5S)-1-(benzothiophen-2-ylsulfonyl)-4-fluoro-N-[[5-fluoro-2-[2-(trifluoromethyl)pyrimidin-5-yl]-4-pyridyl]methyl]-5-methyl-pyrrolidine-2-carboxamide | 0.00561 | 1H NMR (400 MHz, DMSO-d6) δ 9.60 (s, 2H), 9.04 (t, J = 5.9 Hz, 1H), 8.79 (d, J = 1.3 Hz, 1H), 8.25 (d, J = 0.7 Hz, 1H), 8.22 (d, J = 5.7 Hz, 1H), 8.13 (dq, J = 8.1, 0.9 Hz, 1H), 8.05 (dt, J = 7.7, 0.9 Hz, 1H), 7.68-7.44 (m, 2H), 4.93 (d, J = 53.5 Hz, 1H), 4.56 (qd, J = 16.9, 5.9 Hz, 2H), 4.39 (dd, J = 10.2, 7.1 Hz, 1H), 4.18-3.98 (m, 1H), 2.48-2.14 (m, 2H), 1.29 (d, J = 6.9 Hz, 3H). | 598.1 |
| 99. | 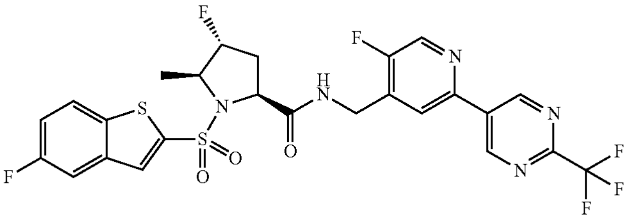 [SMILES: C[C@H]1[C@H](F)C[C@@H](C(=O)NCc2cc(-c3cnc(C(F)(F)F)nc3)ncc2F)N1S(=O)(=O)c1cc2cc(F)ccc2s1] | (2S,4R,5S)-4-fluoro-1-(5-fluorobenzothiophen-2-yl)sulfonyl-N-[[5-fluoro-2-[2-(trifluoromethyl)pyrimidin-5-yl]-4-pyridyl]methyl]-5-methyl-pyrrolidine-2-carboxamide | 0.00967 | 1H NMR (400 MHz, DMSO-d6) δ 9.60 (s, 2H), 9.04 (t, J = 5.9 Hz, 1H), 8.79 (d, J = 1.3 Hz, 1H), 8.29-8.10 (m, 3H), 7.86 (dd, J = 9.4, 2.6 Hz, 1H), 7.49 (td, J = 9.0, 2.6 Hz, 1H), 4.94 (d, J = 51.2 Hz, 1H), 4.55 (qd, J = 16.8, 5.8 Hz, 2H), 4.39 (dd, J = 10.2, 7.1 Hz, 1H), 4.16-3.99 (m, 1H), 2.48-2.12 (m, 2H), 1.29 (d, J = 6.9 Hz, 3H). | 616.1 |
| 100. | 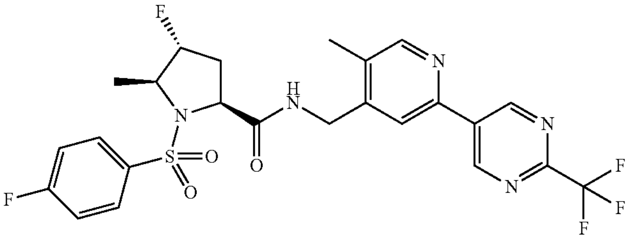 [SMILES: Cc1cnc(-c2cnc(C(F)(F)F)nc2)cc1CNC(=O)[C@@H]1C[C@@H](F)[C@H](C)N1S(=O)(=O)c1ccc(F)cc1] | (2S,4R,5S)-4-fluoro-1-(4-fluorophenyl)sulfonyl-5-methyl-N-[[5-methyl-2-[2-(trifluoromethyl)pyrimidin-5-yl]-4-pyridyl]methyl]pyrrolidine-2-carboxamide | 0.01270 | 1H NMR (400 MHz, DMSO-d6) δ 9.63 (s, 2H), 8.95 (t, J = 5.9 Hz, 1H), 8.66-8.52 (m, 1H), 8.13 (s, 1H), 8.10-7.97 (m, 2H), 7.57-7.37 (m, 2H), 4.90 (dd, J = 51.4, 2.9 Hz, 1H), 4.45 (ddd, J = 66.2, 16.9, 5.8 Hz, 2H), 4.27 (dd, J = 10.1, 7.1 Hz, 1H), 4.05-3.85 (m, 1H), 2.37 (s, 5H), 1.21 (d, J = 6.9 Hz, 3H). | 556.2 |
| 101. | 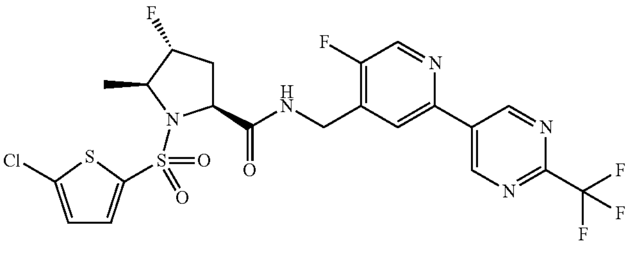 [SMILES: C[C@H]1[C@H](F)C[C@@H](C(=O)NCc2cc(-c3cnc(C(F)(F)F)nc3)ncc2F)N1S(=O)(=O)c1ccc(Cl)s1] | (2S,4R,5S)-1-[(5-chloro-2-thienyl)sulfonyl]-4-fluoro-N-[[5-fluoro-2-[2-(trifluoromethyl)pyrimidin-5-yl]-4-pyridyl]methyl]-5-methyl-pyrrolidine-2-carboxamide | 5.45E-04 | 1H NMR (400 MHz, DMSO-d6) δ 9.58 (s, 2H), 9.01 (t, J = 5.9 Hz, 1H), 8.78 (d, J = 1.3 Hz, 1H), 8.17 (d, J = 5.7 Hz, 1H), 7.79 (d, J = 4.1 Hz, 1H), 7.40 (d, J = 4.1 Hz, 1H), 4.96 (dd, J = 51.2, 2.9 Hz, 1H), 4.66-4.39 (m, 2H), 4.27 (dd, J = 10.2, 7.0 Hz, 1H), 4.11-3.87 (m, 1H), 2.50-2.12 (m, 2H). | 582.0 |

TABLE 2-continued

| Ex-am-ple | Structure | Name | hTRPA1 CHO Ca2+ AUC EVO (IC50) | $^1$H NMR | LCMS |
|---|---|---|---|---|---|
| 102. | 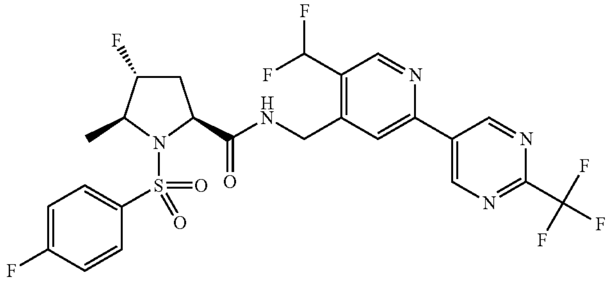 [SMILES: C[C@H]1[C@H](F)C[C@@H](C(=O)NCc2cc(-c3cnc(C(F)(F)F)nc3)ncc2C(F)F)N1S(=O)(=O)c1ccc(F)cc1] | (2S,4R,5S)-N-[[5-(difluorometh-yl)-2-[2-(trifluorometh-yl)pyrimidin-5-yl]-4-pyridyl]meth-yl]-4-fluoro-1-(4-fluorophenyl) sulfonyl-5-methyl-pyrrolidine-2-carboxamide | 0.00407 | 1H NMR (400 MHz, CDCl3) δ 9.70 (s, 2H), 8.84 (s, 1H), 8.29 (s, 1H), 7.93-7.90 (m, 2H), 7.44-7.41 (m, 1H), 7.29-7.25 (m, 2H), 6.93 (t, J = 54 Hz, 1H), 5.15-5.09 (m, 1H), 4.81-4.67 (d, J = 52 Hz, 1H), 4.58-4.57 (m, 1H), 4.33-4.28 (m, 1H), 4.15-4.08 (m, 1H), 2.64-2.56 (m, 1H), 2.37-2.22 (m, 1H), 1.39 (d, J = 7.2 Hz, 3H). | 592.1 |
| 103. | 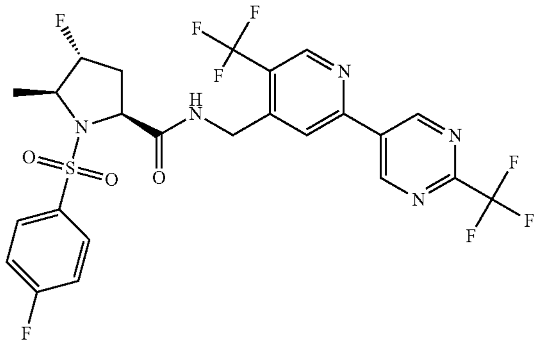 [SMILES: C[C@H]1[C@H](F)C[C@@H](C(=O)NCc2cc(-c3cnc(C(F)(F)F)nc3)ncc2C(F)(F)F)N1S(=O)(=O)c1ccc(F)cc1] | (2S,4R,5S)-4-fluoro-1-(4-fluorophenyl) sulfonyl-5-methyl-N-[[5-(trifluorometh-yl)-2-[2-(trifluorometh-yl)pyrimidin-5-yl]-4-pyridyl]meth-yl]pyrrolidine-2-carboxamide | 7.77E-04 | 1H NMR (400 MHz, CDCl3) δ 9.70 (s, 2H), 9.01 (s, 1H), 8.38 (s, 1H), 7.94-7.91 (m, 2H), 7.40-7.38 (m, 1H), 7.30-7.26 (m, 1H), 5.24-5.18 (m, 1H), 4.75 (d, J = 51.2 Hz, 1H), 4.59-4.54 (m, 1H), 4.35-4.31 (m, 1H), 4.16-4.06 (m, 1H), 2.68-2.58 (m, 1H), 1.41 (d, J = 7.2 Hz 3H). | 610 |
| 104. | 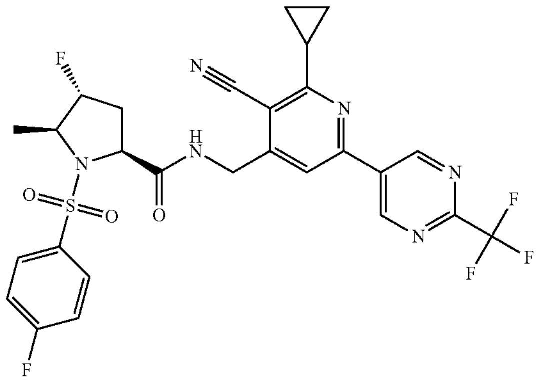 [SMILES: C[C@H]1[C@H](F)C[C@@H](C(=O)NCc2cc(-c3cnc(C(F)(F)F)nc3)nc(C3CC3)c2C#N)N1S(=O)(=O)c1ccc(F)cc1] | (2S,4R,5S)-N-[[3-cyano-2-cyclopropyl-6-[2-(trifluorometh-yl)pyrimidin-5-yl]-4-pyridyl]meth-yl]-4-fluoro-1-(4-fluorophenyl) sulfonyl-5-methyl-pyrrolidine-2-carboxamide | 6.82E-04 | 1H NMR (400 MHz, CDCl3) δ 9.60 (s, 2H), 8.06 (s, 1H), 7.92-7.87 (m, 2H), 7.42-7.38 (m, 1H), 7.29-7.23 (m, 2H), 5.18-5.09 (m, 1H), 4.73 (d, J = 51 Hz, 1H), 4.56-4.49 (m, 1H), 4.31-4.25 (m, 1H), 4.12-4.03 (m, 1H), 2.62-2.54 (m, 2H), 2.37-2.12 (m, 1H), 1.41-1.30 (m, 3H), 1.29-1.21 (m, 4H). | 607 |
| 105. | 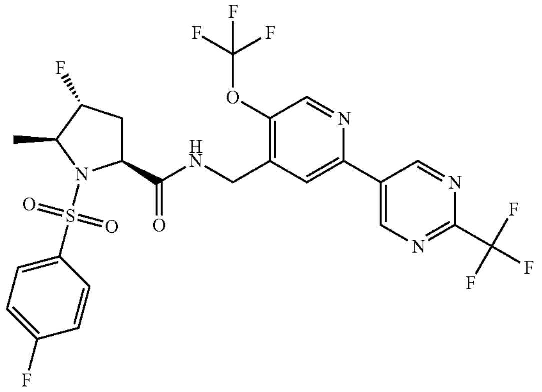 [SMILES: C[C@H]1[C@H](F)C[C@@H](C(=O)NCc2cc(-c3cnc(C(F)(F)F)nc3)ncc2OC(F)(F)F)N1S(=O)(=O)c1ccc(F)cc1] | (2S,4R,5S)-4-fluoro-1-(4-fluorophenyl) sulfonyl-5-methyl-N-[[5-(trifluorometh-oxy)-2-[2-(trifluorometh-yl)pyrimidin-5-yl]-4-pyridyl]meth-yl]pyrrolidine-2-carboxamide | 8.75E-04 | 1H NMR (400 MHz, DMSO-d6) δ 9.64 (s, 2H), 9.10 (t, J = 5.9 Hz, 1H), 8.89 (q, J = 1.4 Hz, 1H), 8.31 (s, 1H), 8.09-8.05 (m, 2H), 7.52-7.47 (m, 2H), 4.91 (d, J = 53.6 Hz, 1H), 4.61-4.52 (m, 2H), 4.26-4.22 (m, 2H), 2.45-2.10 (m, 2H), 1.22 (d, J = 6.9 Hz, 3H). | 626 |

TABLE 2-continued

| Example | Structure | Name | hTRPA1 CHO Ca2+ AUC EVO (IC50) | $^1$H NMR | LCMS |
|---|---|---|---|---|---|
| 106. | 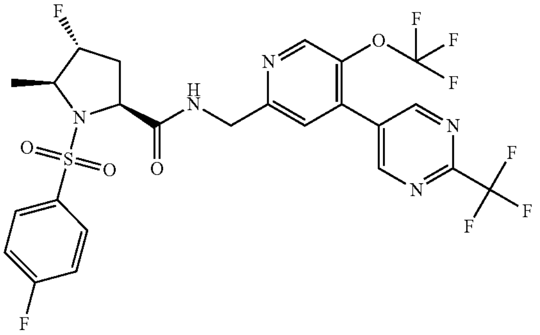 [SMILES: C[C@H]1[C@H](F)C[C@@H](C(=O)NCc2cc(-c3cnc(C(F)(F)F)nc3)c(OC(F)(F)F)cn2)N1S(=O)(=O)c1ccc(F)cc1] | (2S,4R,5S)-4-fluoro-1-(4-fluorophenyl)sulfonyl-5-methyl-N-[[5-(trifluoromethoxy)-4-[2-(trifluoromethyl)pyrimidin-5-yl]-2-pyridyl]methyl]pyrrolidine-2-carboxamide | 0.00220 | 1H NMR (400 MHz, CDCl3) δ 9.20 (s, 2H), 8.73 (s, 1H), 7.90-7.88 (m, 2H), 7.70 (s, 1H), 7.56 (s, 1H), 7.28-7.23 (m, 2H), 5.02 (dd, J = 24, 7.2 Hz, 1H), 4.80-4.58 (m, 2H), 4.26 (t, J = 8.1 Hz, 1H), 4.16-4.05 (m, 1H), 2.60-2.52 (m, 1H), 2.40-2.22 (m, 1H), 1.23 (d, J = 6.8 Hz, 3H). | 626.1 |
| 107. | 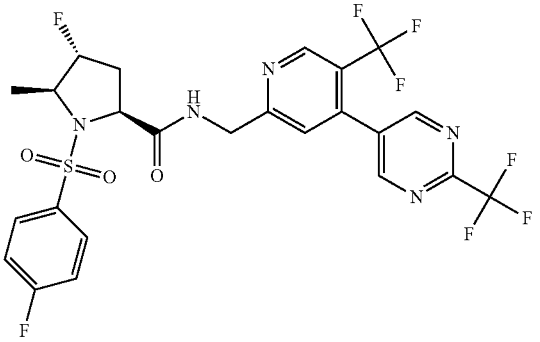 [SMILES: C[C@H]1[C@H](F)C[C@@H](C(=O)NCc2cc(-c3cnc(C(F)(F)F)nc3)c(C(F)(F)F)cn2)N1S(=O)(=O)c1ccc(F)cc1] | (2S,4R,5S)-4-fluoro-1-(4-fluorophenyl)sulfonyl-5-methyl-N-[[5-(trifluoromethyl)-4-[2-(trifluoromethyl)pyrimidin-5-yl]-2-pyridyl]methyl]pyrrolidine-2-carboxamide | 0.00974 | 1HNMR (400 MHz, DMSO-d6) δ 9.17 (s, 2H), 9.10 (s, 1H), 9.06-9.03 (s, 1H), 7.95-7.92 (m, 2H), 7.71 (s, 1H), 7.44 (t, J = 8.8 Hz, 2H), 4.94-4.80 (m, 1H), 4.69-4.54 (m, 2H), 4.19-4.15 (m, 1H), 3.94-3.87 (m, 1H), 2.51-2.11 (m, 1H), 1.17 (d, J = 3.2 Hz, 3H). | 610 |
| 108. | 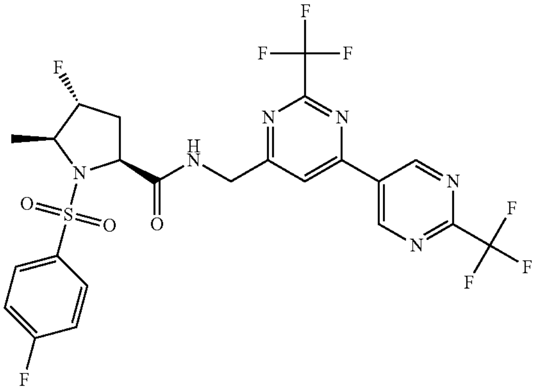 [SMILES: C[C@H]1[C@H](F)C[C@@H](C(=O)NCc2cc(-c3cnc(C(F)(F)F)nc3)nc(C(F)(F)F)n2)N1S(=O)(=O)c1ccc(F)cc1] | (2S,4R,5S)-4-fluoro-1-(4-fluorophenyl)sulfonyl-5-methyl-N-[[2-(trifluoromethyl)-6-[2-(trifluoromethyl)pyrimidin-5-yl]pyrimidin-4-yl]methyl]pyrrolidine-2-carboxamide | 0.00200 | 1HNMR (300 MHz, DMSO-d6) δ 9.71 (s, 1H), 9.26-9.22 (m, 1H), 8.50 (s, 1H), 8.09-8.04 (m, 2H), 7.52-7.46 (m, 2H), 4.86 (d, J = 54 Hz, 1H), 4.76-4.68 (m, 2H), 4.29-4.23 (m, 1H), 4.01-3.91 (m, 1H), 2.49-2.17 (m, 2H), 1.24 (d, J = 6 Hz, 3H). | 611.2 |
| 109. | 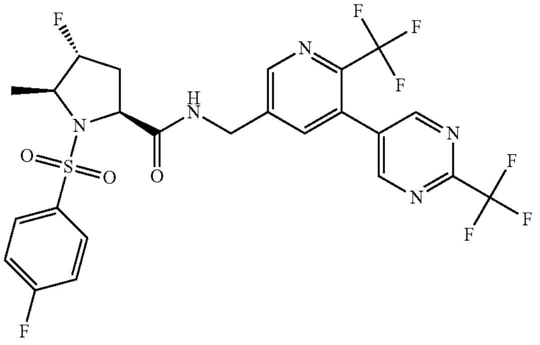 [SMILES: C[C@H]1[C@H](F)C[C@@H](C(=O)NCc2cnc(C(F)(F)F)c(-c3cnc(C(F)(F)F)nc3)c2)N1S(=O)(=O)c1ccc(F)cc1] | (2S,4R,5S)-4-fluoro-1-(4-fluorophenyl)sulfonyl-5-methyl-N-[[6-(trifluoromethyl)-5-[2-(trifluoromethyl)pyrimidin-5-yl]-3-pyridyl]methyl]pyrrolidine-2-carboxamide | 0.01688 | 1H NMR (400 MHz, CDCl3) δ 8.96 (s, 4H), 8.83 (d, J = 1.9 Hz, 2H), 7.92-7.79 (m, 6H), 7.43 (s, 3H), 7.25 (t, J = 8.4 Hz, 4H), 4.96 (dd, J = 16.1, 7.5 Hz, 2H), 4.79 (d, J = 3.2 Hz, 1H), 4.66 (s, 1H), 4.51 (dd, J = 16.1, 4.7 Hz, 2H), 4.21 (dd, J = 9.6, 8.1 Hz, 2H), 4.16-4.04 (m, 2H), 2.63-2.47 (m, 2H), 2.43-2.35 (m, 1H), 2.27 (s, 1H), 1.34 (d, J = 7.0 Hz, 6H). | 610 |

TABLE 2-continued

| Example | Structure | Name | hTRPA1 CHO Ca2+ AUC EVO (IC50) | $^1$H NMR | LCMS |
|---|---|---|---|---|---|
| 110. | 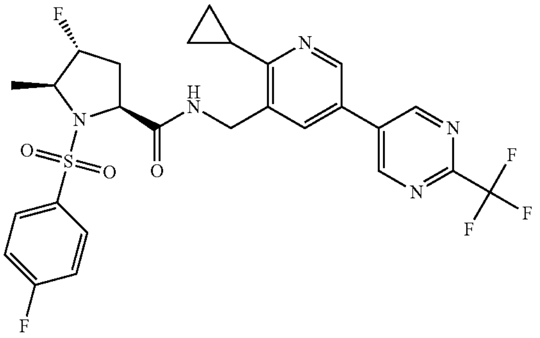 [SMILES: C[C@H]1[C@H](F)C[C@@H](C(=O)NCc2cc(-c3cnc(C(F)(F)F)nc3)cnc2C2CC2)N1S(=O)(=O)c1ccc(F)cc1] | (2S,4R,5S)-N-[[2-cyclopropyl-5-[2-(trifluorometh-yl)pyrimidin-5-yl]-3-pyridyl]meth-yl]-4-fluoro-1-(4-fluorophenyl) sulfonyl-5-methyl-pyrrolidine-2-carboxamide | 0.01056 | 1H NMR (300 MHz, CDCl3) δ 9.19 (s, 1H), 8.68 (s, 1H), 8.10 (s, 1H), 7.89-7.84(m, 2H), 7.39-7.35 (m, 1H), 7.26-7.20 (m, 2H), 5.05-4.97 (m, 1H), 4.68-4.62 (m, 2H), 4.30-4.24 (m, 1H), 4.15-4.06 (m, 1H), 2.58-2.49 (m, 1H), 2.42-2.24 (m, 1H), 2.15-2.00 (m, 1H), 1.34-1.29 (m, 5H), 1.26-1.10 (m, 2H). | 582 |
| 111. | 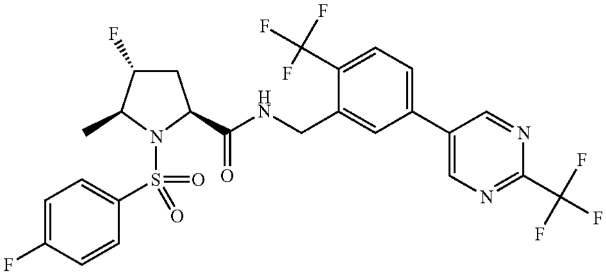 [SMILES: C[C@H]1[C@H](F)C[C@@H](C(=O)NCc2cc(-c3cnc(C(F)(F)F)nc3)ccc2C(F)(F)F)N1S(=O)(=O)c1ccc(F)cc1] | (2S,4R,5S)-4-fluoro-1-(4-fluorophenyl) sulfonyl-5-methyl-N-[[2-(trifluorometh-yl)-5-[2-(trifluorometh-yl)pyrimidin-5-yl]phenyl] methyl] pyrrolidine-2-carboxamide | 0.00175 | 1H NMR (300 MHz, DMSO-d6) δ 9.44 (s, 2H), 9.01 (t, J = 7.5 Hz, 1H), 8.12 (s, 1H), 8.03-7.94 (m, 4H), 7.46 (t, J = 8.9 Hz, 2H), 4.97-4.81 (m, 1H), 4.80-4.67 (m, 1H), 4.56-4.48 (m, 1H), 4.26-4.20 (m, 1H), 3.98-3.89 (m, 1H), 2.49-2.26 (m, 1H), 2.17-2.07 (m, 1H), 1.23 (d, J = 6.3 Hz, 3H). | 609.2 |
| 112. | 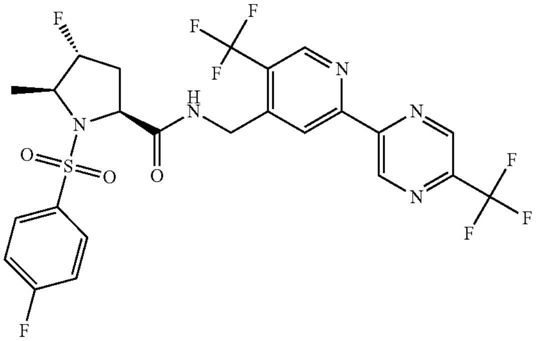 [SMILES: C[C@H]1[C@H](F)C[C@@H](C(=O)NCc2cc(-c3cnc(C(F)(F)F)cn3)ncc2C(F)(F)F)N1S(=O)(=O)c1ccc(F)cc1] | (2S,4R,5S)-4-fluoro-1-(4-fluorophenyl) sulfonyl-5-methyl-N-[[5-(trifluorometh-yl)-2-[5-(trifluorometh-yl)pyrazin-2-yl]-4-pyridyl]meth-yl]pyrrolidine-2-carboxamide | 0.00194 | 1H NMR (300 MHz, CDCl3) δ 9.81 (s, 1H), 8.99 (d, J = 14.4 Hz, 2H), 8.70 (s, 1H), 7.95-7.92 (m, 2H), 7.60 (t, J = 6.5 Hz, 1H), 7.28-7.24 (m, 2H), 4.92-4.69 (m, 3H), 4.31-4.15 (m, 2H), 2.59-2.37 (m, 2H), 1.40 (d, J = 7.0 Hz, 3H). | 610 |
| 113. | 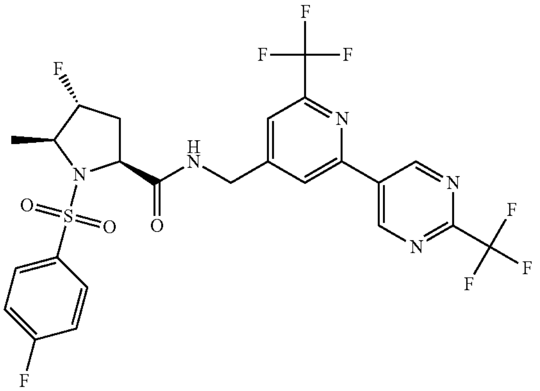 [SMILES: C[C@H]1[C@H](F)C[C@@H](C(=O)NCc2cc(-c3cnc(C(F)(F)F)nc3)nc(C(F)(F)F)c2)N1S(=O)(=O)c1ccc(F)cc1] | (2S,4R,5S)-4-fluoro-1-(4-fluorophenyl) sulfonyl-5-methyl-N-[[2-(trifluorometh-yl)-6-[2-(trifluorometh-yl)pyrimidin-5-yl]-4-pyridyl]meth-yl]pyrrolidine-2-carboxamide | 0.00447 | 1H NMR (300 MHz, CDCl3) δ 9.63 (s, 2H), 8.26 (s, 1H), 7.92-7.88 (m, 2H), 7.72 (s, 1H), 7.48 (s, 1H), 7.29-7.23 (m, 1H), 5.07-4.99 (m, 1H), 4.73 (d, J = 53.7 Hz, 1H), 4.49 (d, J = 16.8 Hz, 1H), 4.30 (t, J = 8.8 Hz, 1H), 4.11-4.04 (m, 1H), 2.66-2.52 (m, 1H), 2.41-2.18 (m, 1H), 1.40 (d, J = 7.0 Hz, 3H). | 610 |

TABLE 2-continued

| Example | Structure | Name | hTRPA1 CHO Ca2+ AUC EVO (IC50) | $^1$H NMR | LCMS |
|---|---|---|---|---|---|
| 114. | 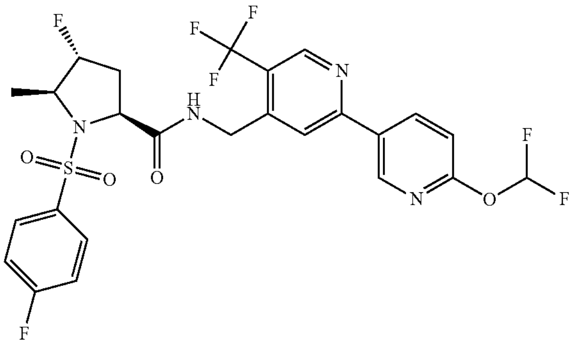 [SMILES: C[C@H]1[C@H](F)C[C@@H](C(=O)NCc2cc(-c3ccc(OC(F)F)nc3)ncc2C(F)(F)F)N1S(=O)(=O)c1ccc(F)cc1] | (2S,4R,5S)-N-[[2-[6-(difluoromethoxy)-3-pyridyl]-5-(trifluoromethyl)-4-pyridyl]methyl]-4-fluoro-1-(4-fluorophenyl)sulfonyl-5-methyl-pyrrolidine-2-carboxamide | 0.00357 | 1H NMR (400 MHz, CDCl3) δ 9.02 (s, 1H), 8.93 (s, 1H), 8.62-8.55 (m, 1H), 8.17 (s, 1H), 7.94 (dd, J = 8.3, 4.8 Hz, 2H), 7.76-7.51 (m, 1H), 7.49-7.35 (m, 1H), 7.34-7.30 (m, 1H), 7.00 (d, J = 8.0 Hz, 1H), 5.09 (d, J = 14.8 Hz, 1H), 4.84-4.66 (m, 1H), 4.61 (d, J = 16.7 Hz, 1H), 4.32 (t, J = 8.8 Hz, 1H), 4.15 (dq, J = 21.4, 7.1 Hz, 1H), 2.60 (td, J = 17.5, 16.7, 7.4 Hz, 1H), 2.44-2.21 (m, 1H), 1.39 (d, J = 6.9 Hz, 3H). | 607 |
| 115. | 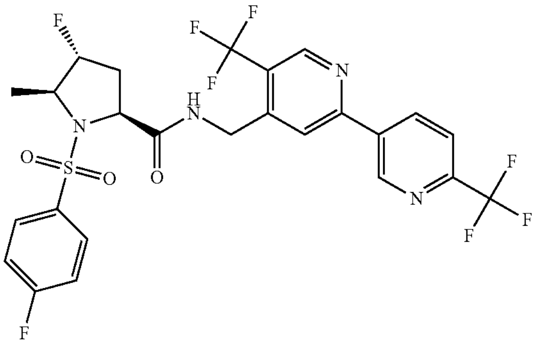 [SMILES: C[C@H]1[C@H](F)C[C@@H](C(=O)NCc2cc(-c3ccc(C(F)(F)F)nc3)ncc2C(F)(F)F)N1S(=O)(=O)c1ccc(F)cc1] | (2S,4R,5S)-4-fluoro-1-(4-fluorophenyl)sulfonyl-5-methyl-N-[[5-(trifluoromethyl)-2-[6-(trifluoromethyl)-3-pyridyl]-4-pyridyl]methyl]pyrrolidine-2-carboxamide | 0.00134 | 1H NMR (300 MHz, CDCl3) δ 9.52 (s, 1H), 8.99 (s, 1H), 8.73-8.71 (m, 1H), 8.30 (s, 1H), 7.92 (dd, J = 4.4, 2.5 Hz, 2H), 7.79 (d, J = 8.1 Hz, 1H), 7.46-7.41 (m, 1H), 7.30-7.25 (m, 2H), 5.18-5.12 (m, 1H), 4.74 (d, J = 53.7 Hz, 1H), 4.62-4.58 (m, 1H), 4.31 (t, J = 8.9 Hz, 1H), 4.17-4.08 (m, 1H), 2.67-2.53 (m, 1H), 2.41-2.19 (m, 1H), 1.38 (d, J = 6.9 Hz, 3H). | 609 |
| 116. | 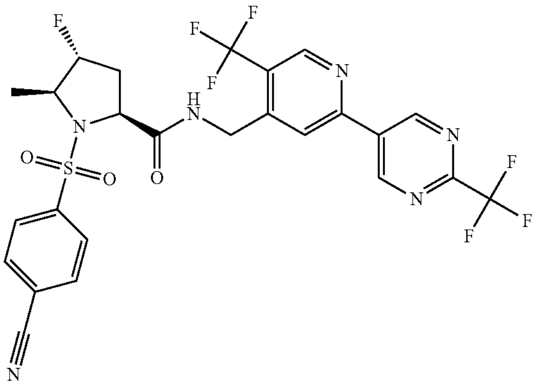 [SMILES: C[C@H]1[C@H](F)C[C@@H](C(=O)NCc2cc(-c3cnc(C(F)(F)F)nc3)ncc2C(F)(F)F)N1S(=O)(=O)c1ccc(C#N)cc1] | (2S,4R,5S)-1-(4-cyanophenyl)sulfonyl-4-fluoro-5-methyl-N-[[5-(trifluoromethyl)-2-[2-(trifluoromethyl)pyrimidin-5-yl]-4-pyridyl]methyl]pyrrolidine-2-carboxamide | 0.00575 | 1H NMR (400 MHz, CDCl3) δ 9.69 (s, 2H), 9.03 (s, 1H), 8.33 (s, 1H), 8.04 (d, J = 8.2 Hz, 2H), 7.91 (d, J = 8.2 Hz, 2H), 5.22-5.16 (m, 1H), 4.76 (d, J = 50.8 Hz, 2H), 4.63-4.58 (m, 1H), 4.36-4.31 (m, 1H), 4.17-4.07 (m, 1H), 2.69-2.59 (m, 1H), 2.40-2.22 (m, 1H), 1.41 (d, J = 6.8 Hz, 3H). | 617 |

TABLE 2-continued

| Example | Structure | Name | hTRPA1 CHO Ca2+ AUC EVO (IC50) | $^1$H NMR | LCMS |
|---|---|---|---|---|---|
| 117. | 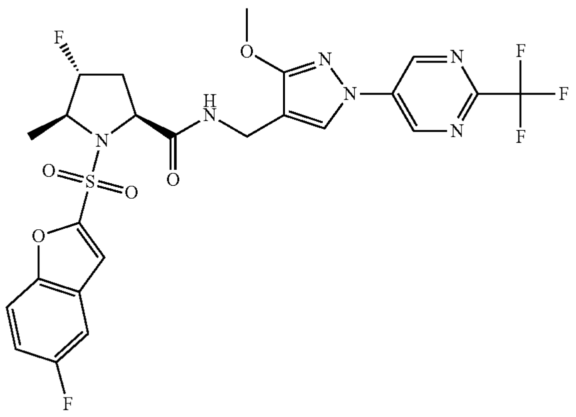 [SMILES: COc1nn(-c2cnc(C(F)(F)F)nc2)cc1CNC(=O)[C@@H]1C[C@@H](F)[C@H](C)N1S(=O)(=O)c1cc2cc(F)ccc2o1] | (2S,4R,5S)-4-fluoro-1-(5-fluorobenzo-furan-2-yl)sulfonyl-N-[[3-methoxy-1-[2-(trifluorometh-yl)pyrimidin-5-yl]pyrazol-4-yl]methyl]-5-methyl-pyrrolidine-carboxamide | 0.00109 | 1H NMR (400 MHz, CDCl3) δ 9.13 (s, 2H), 8.04 (s, 1H), 7.54-7.49 (m, 1H), 7.43 (s, 1H), 7.37-7.34 (m, 1H), 7.26-7.19 (m, 1H), 7.12-7.08 (m, 1H), 4.82-4.47 (m, 3H), 4.30-4.23 (m, 2H), 4.06 (s, 3H), 2.66-2.26 (m, 2H), 1.37 (d, J = 7.1 Hz, 3H). | 601.1 |
| 118. | 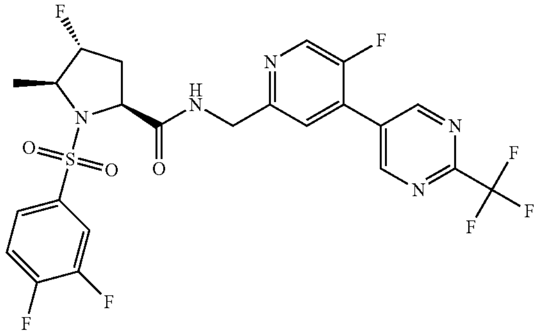 [SMILES: C[C@H]1[C@H](F)C[C@@H](C(=O)NCc2cc(-c3cnc(C(F)(F)F)nc3)c(F)cn2)N1S(=O)(=O)c1ccc(F)c(F)c1] | (2S,4R,5S)-1-(3,4-difluorophen-yl)sulfonyl-4-fluoro-N-[[5-fluoro-4-[2-(trifluorometh-yl)pyrimidin-5-yl]-2-pyridyl]meth-yl]-5-methyl-pyrrolidine-2-carboxamide | 0.00229 | 1H NMR (400 MHz, CDCl3) δ 9.25 (s, 2H), 8.61 (s, 1H), 7.74-7.63 (m, 3H), 7.49-7.40 (m, 1H), 7.37-7.31 (m, 1H), 4.96 (dd, J = 15, 5 Hz, 18), 4.83-4.65 (m, 1H), 4.61-4.54 (m, 1H), 4.27-4.22 (m, 1H), 4.13-4.02 (m, 1H), 2.60-2.51 (m, 1H), 2.43-2.24 (m, 1H), 1.37 (d, J = 7.2 Hz, 3H). | 578.2 |
| 119. | 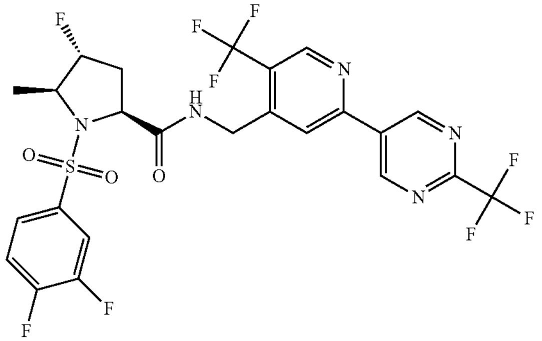 [SMILES: C[C@H]1[C@H](F)C[C@@H](C(=O)NCc2cc(-c3cnc(C(F)(F)F)nc3)ncc2C(F)(F)F)N1S(=O)(=O)c1ccc(F)c(F)c1] | (2S,4R,5S)-1-(3,4-difluorophen-yl)sulfonyl-4-fluoro-5-methyl-N-[[5-(trifluorometh-yl)-2-[2-(trifluorometh-yl)pyrimidin-5-yl]-4-pyridyl]meth-yl]pyrrolidine-2-carboxamide | 8.36E-04 | 1H NMR (300 MHz, CDCl3) δ 9.68 (s, 2H), 9.01 (s, 1H), 8.33 (s, 1H), 7.81-7.63 (m, 2H), 748-7.28 (m, 2H), 5.19 (dd, J = 17.8, 7.9 Hz, 1H), 4.84-4.61 (m, 1H), 4.64-4.52 (m, 1H), 4.34-4.28 (m, 1H), 4.18-4.02 (m, 1H), 2.68-2.57 (m, 1H), 2.39-2.21 (m, 1H), 1.40 (d, J = 7.2 Hz, 3H). | 628.1 |
| 120. | 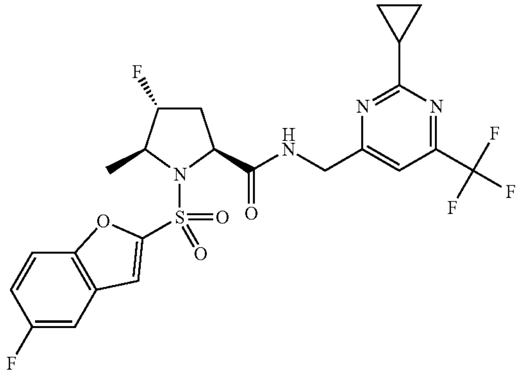 [SMILES: C[C@H]1[C@H](F)C[C@@H](C(=O)NCc2cc(C(F)(F)F)nc(C3CC3)n2)N1S(=O)(=O)c1cc2cc(F)ccc2o1] | (2S,4R,5S)-N-[[2-cyclopropyl-6-(trifluorometh-yl)pyrimidin-4-yl]methyl]-4-fluoro-1-(5-fluorobenzo-furan-2-yl)sulfonyl-5-methyl-pyrrolidine-2-carboxamide | 0.00152 | 1H NMR (400 MHz, CDCl3) δ 7.78 (t, J = 5.4 Hz, 1H), 7.56-7.48 (m, 1H), 7.47-7.17 (m, 4H), 4.73-4.56 (m, 3H), 4.39-4.24 (m, 1H), 2.68-2.30 (m, 3H), 1.39 (d, J = 7.0 Hz, 3H), 1.38-1.12 (m, 4H). | 543.1 |

TABLE 2-continued

| Example | Structure | Name | hTRPA1 CHO Ca2+ AUC EVO (IC50) | $^1$H NMR | LCMS |
|---|---|---|---|---|---|
| 121. | 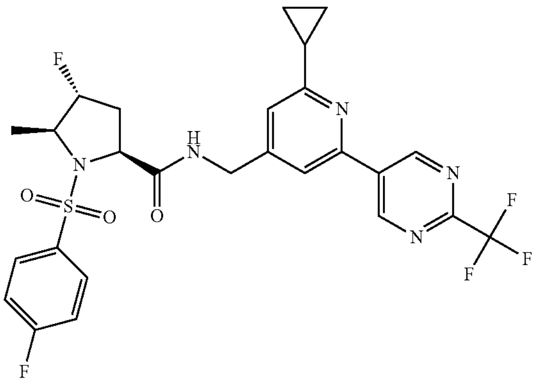 [SMILES: C[C@H]1[C@H](F)C[C@@H](C(=O)NCc2cc(-c3cnc(C(F)(F)F)nc3)nc(C3CC3)c2)N1S(=O)(=O)c1ccc(F)cc1] | (2S,4R,5S) N-[[2-cyclopropyl-6-[2-(trifluorometh-yl)pyrimidin-5-yl]-4-pyridyl]meth-yl]-4-fluoro-1-(4-fluorophenyl) sulfonyl-5-methyl-pyrrolidine-2-carboxamide | 0.00145 | 1H NMR (400 MHz, CDCl3) δ 9.54 (s, 2H), 7.93-7.90 (m, 2H), 7.74 (s, 1H), 7.41 (s, 1H), 7.28-7.25 (m, 3H), 4.91-4.86 (m, 1H), 4.73 (d, J = 54.4 Hz, 1H), 4.42-4.37 (m, 1H), 4.31-4.27 (m, 1H), 4.16-4.09 (m, 1H), 2.62-2.53 (m 1H), 2.42-2.23 (m, 2H), 1.37 (d, J = 7.0 Hz, 3H), 1.19-1.10 (m, 4H). | 582 |
| 122. | 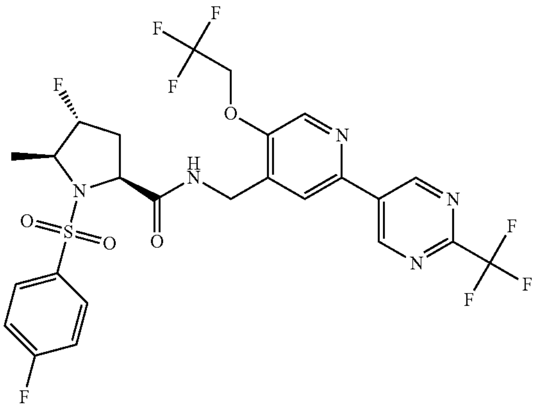 [SMILES: C[C@H]1[C@H](F)C[C@@H](C(=O)NCc2cc(-c3cnc(C(F)(F)F)nc3)ncc2OCC(F)(F)F)N1S(=O)(=O)c1ccc(F)cc1] | (2S,4R,5S)-4-fluoro-1-(4-fluorophenyl) sulfonyl-5-methyl-N-[[5-(2,2,2-trifluoroeth-oxy)-2-[2-(trifluorometh-yl)pyrimidin-5-yl]-4-pyridyl]meth-yl]pyrrolidine-2-carboxamide | 0.00551 | 1HNMR (400 MHz, DMSO-d6) δ 9.59 (s, 2H), 8.98-9.00 (m, 1H), 8.66 (s, 1H), 8.16 (s, 1H), 8.05-8.08 (m, 2H), 7.46-7.51 (m, 2H), 5.09-5.15 (m, 2H), 4.90 (d, J = 51.6 Hz, 1H), 4.48-4.54 (m, 1H), 4.31-4.37 (m, 1H), 4.22-4.26 (m, 1H), 3.92-3.99 (m, 1H), 2.15-2.38 (m, 2H), 1.21 (d, J = 7.2 Hz, 3H). | 640.1 |
| 123. | 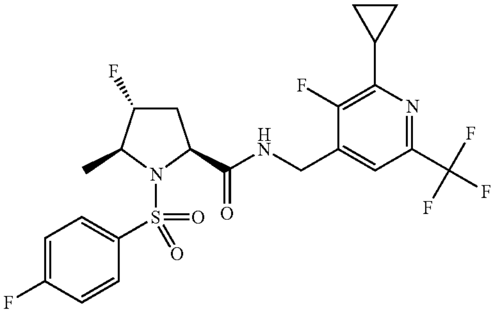 [SMILES: C[C@H]1[C@H](F)C[C@@H](C(=O)NCc2cc(C(F)(F)F)nc(C3CC3)c2F)N1S(=O)(=O)c1ccc(F)cc1] | (2S,4R,5S)-N-[[2-cyclopropyl-3-fluoro-6-(trifluorometh-yl)-4-pyridyl]meth-yl]-4-fluoro-1-(4-fluorophenyl) sulfonyl-5-methyl-pyrrolidine-2-carboxamide | 0.01078 | 1H NMR (400 MHz, CDCl3) δ 7.91-7.88 (m, 2H), 7.52-7.46 (m, 2H), 7.26-7.23 (m, 2H), 4.80-4.58 (m, 3H), 4.26-4.14 (m, 2H), 2.57-2.30 (m, 2H), 1.34 (d, J = 7.1 Hz, 3H), 1.27-1.08 (m, 4H) | 522 |

TABLE 2-continued

| Example | Structure | Name | hTRPA1 CHO Ca2+ AUC EVO (IC50) | 1H NMR | LCMS |
|---|---|---|---|---|---|
| 124. | 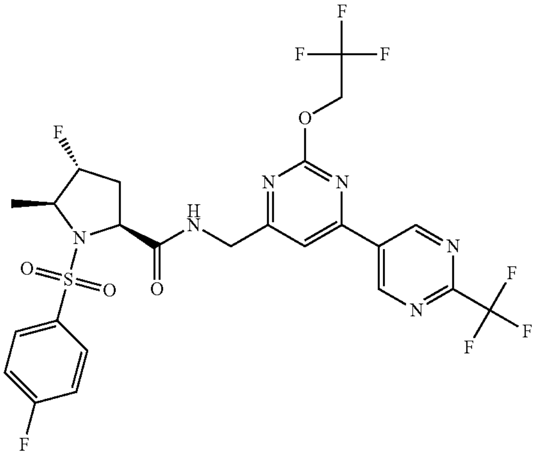 [SMILES: C[C@H]1[C@H](F)C[C@@H](C(=O)NCc2cc(-c3cnc(C(F)(F)F)nc3)nc(OCC(F)(F)F)n2)N1S(=O)(=O)c1ccc(F)cc1] | (2S,4R,5S)-4-fluoro-1-(4-fluorophenyl)sulfonyl-5-methyl-N-[[2-(2,2,2-trifluoroethoxy)-6-[2-(trifluoromethyl)pyrimidin-5-yl]pyrimidin-4-yl]methyl]pyrrolidine-2-carboxamide | 0.00230 | 1H NMR (400 MHz, CDCl3) δ 9.66 (s, 2H), 8.01 (s, 1H), 7.91-7.94 (m, 2H), 7.47-7.48 (m, 1H), 7.26-7.30 (m, 2H), 4.93-5.06 (m, 3H), 4.75 (d, J = 51.2 Hz, 1H), 4.42-4.47 (m, 1H), 4.29-4.34 (m, 1H), 4.06-4.13 (m, 1H), 2.57-2.67 (m, 1H), 2.24-2.38 (m, 1H), 1.42 (d, J = 7.2 Hz, 3H). | 641.2 |
| 125. | 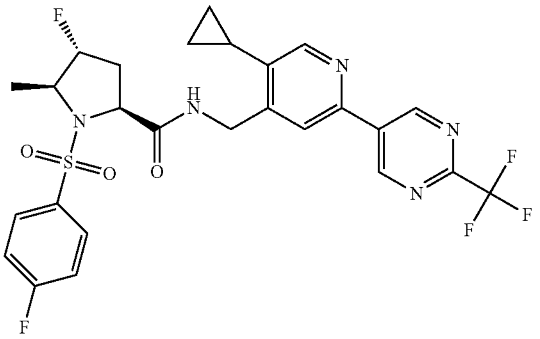 [SMILES: C[C@H]1[C@H](F)C[C@@H](C(=O)NCc2cc(-c3cnc(C(F)(F)F)nc3)ncc2C2CC2)N1S(=O)(=O)c1ccc(F)cc1] | (2S,4R,5S)-N-[[5-cyclopropyl-2-[2-(trifluoromethyl)pyrimidin-5-yl]-4-pyridyl]methyl]-4-fluoro-1-(4-fluorophenyl)sulfonyl-5-methyl-pyrrolidine-2-carboxamide | 0.0049 | 1H NMR (300 MHz, DMSO-d6) δ 9.62 (s, 2H), 9.02-8.98 (m, 1H), 8.46 (s, 1H), 8.12-8.04 (m, 3H), 7.52-7.46 (m, 2H), 4.99-4.68 (m, 2H), 4.59-4.52 (m, 1H), 4.30-4.24 (m, 1H), 4.01-3.91 (m, 1H), 2.51-1.97 (m, 3H), 1.23 (d, J = 6.9 Hz, 3H), 1.08 (m, 2H), 0.87 (m, 2H). | 582.1 |
| 126. | 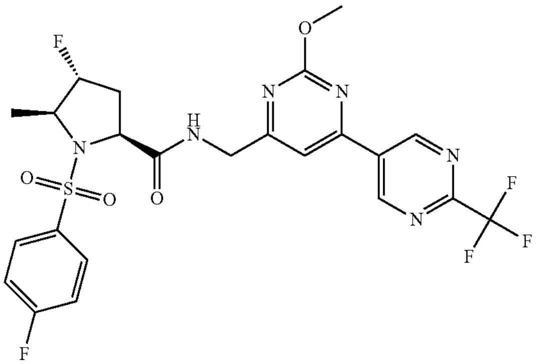 [SMILES: COc1nc(CNC(=O)[C@@H]2C[C@@H](F)[C@H](C)N2S(=O)(=O)c2ccc(F)cc2)cc(-c2cnc(C(F)(F)F)nc2)n1] | (2S,4R,5S)-4-fluoro-1-(4-fluorophenyl)sulfonyl-N-[[2-methoxy-6-[2-(trifluoromethyl)pyrimidin-5-yl]pyrimidin-4-yl]methyl]-5-methyl-pyrrolidine-2-carboxamide | 0.01279 | 1H NMR (300 MHz, CDCl3): δ 9.67 (s, 2H), 7.91-7.95 (m, 2H), 7.87 (s, 1H), 7.45-7.54 (m, 1H), 7.26-7.30 (m, 1H), 4.96-5.02 (m, 1H), 4.68-4.82 (m, 1H), 4.29-4.34 (m, 1H), 4.42-4.47 (m, 1H), 4.16 (s, 3H), 4.06-4.14 (m, 1H), 2.57-2.67 (m, 1H), 2.21-2.39 (m, 1H), 1.42 (d, J = 7.2 Hz, 3H). | 573.1 |

TABLE 2-continued

| Example | Structure | Name | hTRPA1 CHO Ca2+ AUC EVO (IC50) | $^1$H NMR | LCMS |
|---|---|---|---|---|---|
| 127. | 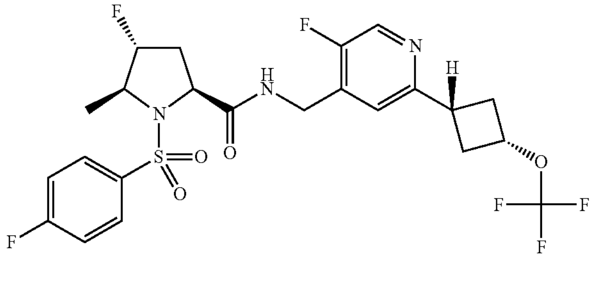 [SMILES: C[C@H]1[C@H](F)C[C@@H](C(=O)NCc2cc([C@H]3C[C@@H](OC(F)(F)F)C3)ncc2F)N1S(=O)(=O)c1ccc(F)cc1] | (2S,4R,5S)-4-fluoro-1-(4-fluorophenyl)sulfonyl-N-[[5-fluoro-2-[3-(trifluoromethoxy)cyclobutyl]-4-pyridyl]methyl]-5-methyl-pyrrolidine-2-carboxamide | 0.00427 | 1H NMR (400 MHz, DMSO-d6) δ 8.90 (t, J = 6.2 Hz, 1H), 8.49 (d, J = 1.4 Hz, 1H), 8.04-8.00 (m, 2H), 7.50-7.43 (m, 3H), 4.95-4.85 (m, 2H), 4.49 (dd, J = 16.8, 6.3 Hz, 1H), 4.35 (dd, J = 16.8, 5.5 Hz, 1H), 4.20-4.16 (m, 1H), 3.97-3.90 (m, 1H), 3.22-3.18 (m, 1H), 2.73-2.71 (m, 2H), 2.51-2.33 (m, 4H), 1.21 (d, J = 6.9 Hz, 3H). | 552 |
| 128. | 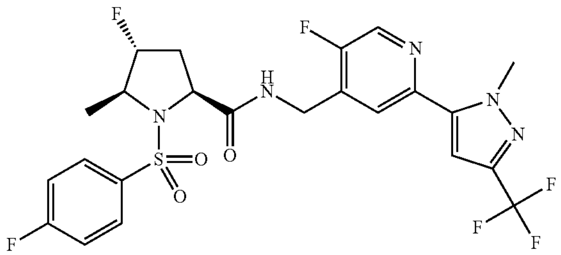 [SMILES: C[C@H]1[C@H](F)C[C@@H](C(=O)NCc2cc(-c3cc(C(F)(F)F)nn3C)ncc2F)N1S(=O)(=O)c1ccc(F)cc1] | (2S,4R,5S)-4-fluoro-N-[[5-fluoro-2-[2-methyl-5-(trifluoromethyl)pyrazol-3-yl]-4-pyridyl]methyl]-1-(4-fluorophenyl)sulfonyl-5-methyl-pyrrolidine-2-carboxamide | 0.01824 | 1H NMR (400 MHz, CDCl3) δ 8.50 (s, 1H), 7.92-7.90 (m, 2H), 7.89-7.84 (m, 1H), 7.40-7.37 (m, 1H), 7.28-7.24 (m, 2H), 7.03 (s, 1H), 4.91-4.85 (m, 1H), 4.81-4.80 (m, 1H), 4.68 (m, 1H), 4.54-4.48 (m, 1H), 4.29-4.15 (m, 1H), 2.59-2.54 (m, 1H), 2.43-2.29 (m, 1H), 1.37 (s, 3H). | 562 |
| 129. | 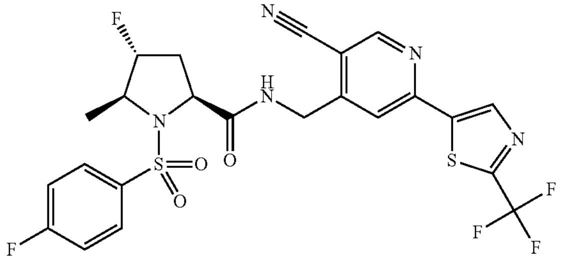 [SMILES: C[C@H]1[C@H](F)C[C@@H](C(=O)NCc2cc(-c3cnc(C(F)(F)F)s3)ncc2C#N)N1S(=O)(=O)c1ccc(F)cc1] | (2S,4R,5S)-N-[[5-cyano-2-[2-(trifluoromethyl)thiazol-5-yl]-4-pyridyl]methyl]-4-fluoro-1-(4-fluorophenyl)sulfonyl-5-methyl-pyrrolidine-2-carboxamide | 0.00414 | 1H NMR (400 MHz, CDCl3) δ 8.80 (s, 1H), 8.72 (s, 1H), 8.30 (s, 1H), 7.95-7.92 (m, 2H), 7.38-7.30 (m, 1H), 7.29-7.27 (m, 2H), 5.20-5.14 (m, 1H), 4.82-4.69 (d, J = 51.2 Hz, 1H), 4.56-4.51 (m, 1H), 4.35-4.30 (m, 1H), 4.14-4.07 (m, 1H), 2.64-2.58 (m, 1H), 2.36-2.23 (m, 1H), 1.42 (d, J = 6.8 Hz, 3H). | 572 |
| 130. | 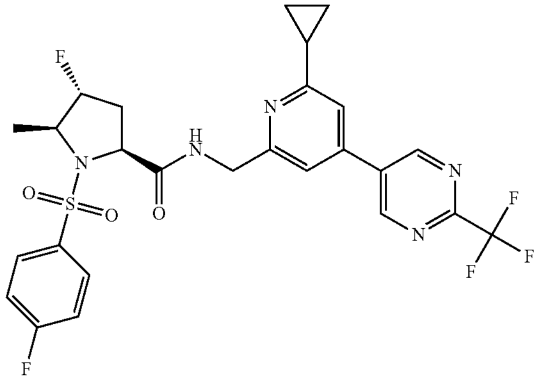 [SMILES: C[C@H]1[C@H](F)C[C@@H](C(=O)NCc2cc(-c3cnc(C(F)(F)F)nc3)cc(C3CC3)n2)N1S(=O)(=O)c1ccc(F)cc1] | (2S,4R,5S)-N-[[6-cyclopropyl-4-[2-(trifluoromethyl)pyrimidin-5-yl]-2-pyridyl]methyl]-4-fluoro-1-(4-fluorophenyl)sulfonyl-5-methyl-pyrrolidine-2-carboxamide | 0.00382 | 1 H NMR (400 MHz, CDCl3) δ 9.18 (m, 2H), 7.94-7.90 (m, 3H), 7.43 (s, 2H), 7.31-7.23 (m, 3H), 4.88-4.57 (m, 3H), 4.27-4.22 (m, 1H), 4.16-4.09 (m, 1H), 4.88-4.57 (m, 3H), 2.57-2.51 (m, 1H), 2.41-2.24 (m, 2H), 1.42-1.41 (m, 3H), 1.32-1.28 (m, 2H), 1.22-1.15 (m, 2H). | 582 |

TABLE 2-continued

| Example | Structure | Name | hTRPA1 CHO Ca2+ AUC EVO (IC50) | $^1$H NMR | LCMS |
|---|---|---|---|---|---|
| 131. | 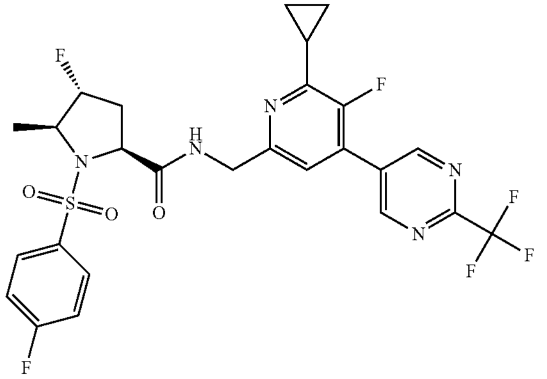 [SMILES: C[C@H]1[C@H](F)C[C@@H](C(=O)NCc2cc(-c3cnc(C(F)(F)F)nc3)c(F)c(C3CC3)n2)N1S(=O)(=O)c1ccc(F)cc1] | (2S,4R,5S)-N-[[6-cyclopropyl-5-fluoro-4-[2-(trifluorometh-yl)pyrimidin-5-yl]-2-pyridyl]meth-yl]-4-fluoro-1-(4-fluorophenyl) sulfonyl-5-methyl-pyrrolidine-2-carboxamide | 0.00404 | $^1$H NMR (400 MHz, $CDCl_3$) δ 9.21 (s, 2H), 8.03 (s, 1H), 7.97-7.93 (m, 2H), 7.47-7.45 (m, 1H), 7.28-7.24 (m, 2H), 4.90-4.64 (m, 3H), 4.17-4.02 (m, 2H), 2.56-2.48 (m, 2H), 2.46-2.25 (m, 1H), 1.61-1.60 (m, 1H), 1.59-1.56 (m, 1H), 1.42-1.40 (m, 3H), 1.30-1.28 (m, 2H). | 600 |
| 132. | 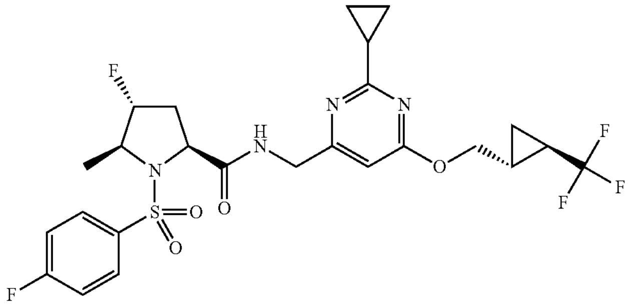 [SMILES: C[C@H]1[C@H](F)C[C@@H](C(=O)NCc2cc(OC[C@@H]3C[C@H]3C(F)(F)F)nc(C3CC3)n2)N1S(=O)(=O)c1ccc(F)cc1] | (2S,4R,5S)-N-[[2-cyclopropyl-6-[[(1R,2R)-2-(trifluorometh-yl)cycloprop-yl]methoxy] pyrimidin-4-yl]methyl]-4-fluoro-1-(4-fluorophenyl) sulfonyl-5-methyl-pyrrolidine-2-carboxamide | 0.01523 | 1H NMR (400 MHz, CDCl3) δ 7.93-7.91 (m, 3H), 7.28-7.21 (m, 2H), 6.52 (s, 1H), 4.79-4.65 (d, J = 51.6 Hz, 1H), 4.50-4.49 (d, J = 5.2 Hz, 2H), 4.31-4.16 (m, 4H), 2.50-2.20 (m, 2H), 2.20-2.08 (m, 1H), 1.73-1.60 (m, 1H), 1.59-1.50 (m, 1H), 1.41-1.40 (d, J = 7.2 Hz, 3H), 1.20-1.07 (m, 5H), 0.92-0.88 (m, 1H). | 575 |
| 133. | 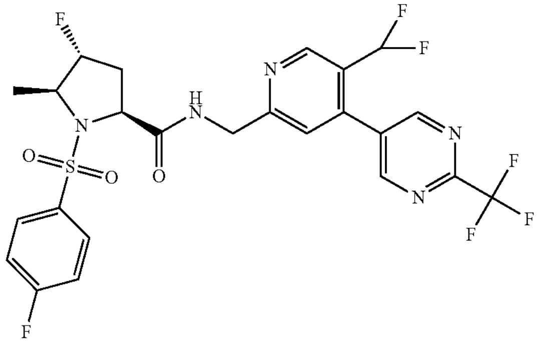 [SMILES: C[C@H]1[C@H](F)C[C@@H](C(=O)NCc2cc(-c3cnc(C(F)(F)F)nc3)c(C(F)F)cn2)N1S(=O)(=O)c1ccc(F)cc1] | (2S,4R,5S)-N-[[5-(difluorometh-yl)-4-[2-(trifluorometh-yl)pyrimidin-5-yl]-2-pyridyl]meth-yl]-4-fluoro-1-(4-fluorophenyl) sulfonyl-5-methyl-pyrrolidine-2-carboxamide | 0.03054 | 1H NMR (300 MHz, DMSO-d6): δ 9.15 (s, 2H), 9.03-9.00 (m, 1H), 8.95-8.93 (m, 1H), 7.96-7.95 (m, 2H), 7.66 (s, 1H), 7.44-7.33 (m, 2H), 7.20-7.06 (m, 1H), 4.95-4.82 (m, 1H), 4.68-4.50 (m, 2H), 4.22-4.18 (m, 1H), 3.96-3.90 (m, 1H), 2.33-2.16 (m, 2H), 1.19-1.17 (m, 3H). | 592.1 |
| 134. | 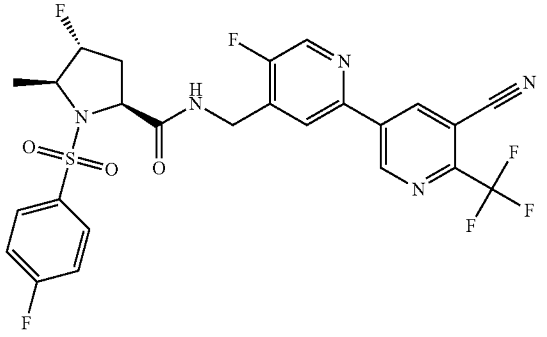 [SMILES: C[C@H]1[C@H](F)C[C@@H](C(=O)NCc2cc(-c3cnc(C(F)(F)F)c(C#N)c3)ncc2F)N1S(=O)(=O)c1ccc(F)cc1] | (2S,4R,5S)-N-[[2-[5-cyano-6-(trifluorometh-yl)-3-pyridyl]-5-fluoro-4-pyridyl]meth-yl]-4-fluoro-1-(4-fluorophenyl) sulfonyl-5-methyl-pyrrolidine-2-carboxamide | 0.03256 | 1H NMR (400 MHz, CDCl3) δ 9.60 (s, 1H), 8.97 (d, J = 1.6 Hz, 1H), 8.58 (s, 1H), 8.22 (d, J = 5.6 Hz, 1H), 7.96-7.93 (m, 2H), 7.34-7.26 (m, 2H), 5.06-5.00 (m, 1H), 4.76 (dd, J = 17.4, 4.5 Hz, 1H), 4.52-4.46 (m, 1H), 4.36-4.31 (m, 1H), 4.16-4.09 (m, 1H), 2.68-2.57 (m, 1H), 2.39-2.22 (m, 1H), 1.41 (d, J = 7.2 Hz, 3H). | 584.2 |

TABLE 2-continued

| Example | Structure | Name | hTRPA1 CHO Ca2+ AUC EVO (IC50) | $^1$H NMR | LCMS |
|---|---|---|---|---|---|
| 135. | 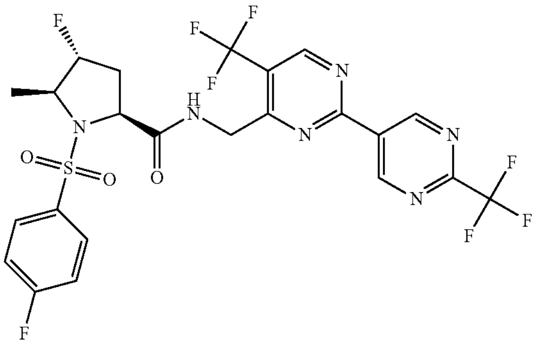 [SMILES: C[C@H]1[C@H](F)C[C@@H](C(=O)NCc2nc(-c3cnc(C(F)(F)F)nc3)ncc2C(F)(F)F)N1S(=O)(=O)c1ccc(F)cc1] | (2S,4R,5S)-4-fluoro-1-(4-fluorophenyl) sulfonyl-5-methyl-N-[[5-(trifluoromethyl)-2-[2-(trifluoromethyl)pyrimidin-5-yl]pyrimidin-4-yl]methyl] pyrrolidine-2-carboxamide | 0.01933 | 1H NMR (400 MHz, CDCl3) δ 10.02 (s, 2H), 9.11 (s, 1H), 8.34-8.32(m, 1H), 7.96-7.89 (m, 2H), 7.28-7.21 (m, 2H), 5.11-5.02(m, 1H), 4.88-4.64 (m, 2H), 4.36-4.31 (m, 1H), 4.23-4.13 (m, 1H), 2.55-2.34 (m, 2H), 1.35 (d, J = 7.0 Hz, 3H). | 611.2 |
| 136. | 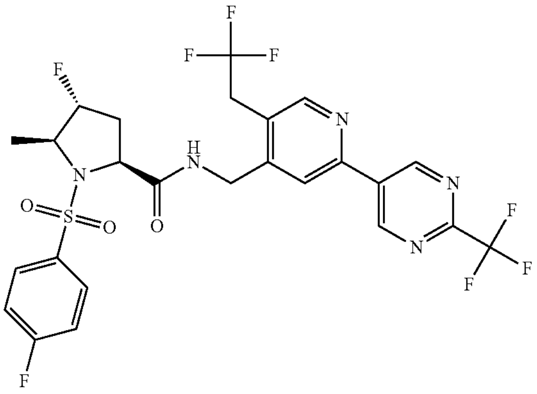 [SMILES: C[C@H]1[C@H](F)C[C@@H](C(=O)NCc2cc(-c3cnc(C(F)(F)F)nc3)ncc2CC(F)(F)F)N1S(=O)(=O)c1ccc(F)cc1] | (2S,4R,5S)-4-fluoro-1-(4-fluorophenyl) sulfonyl-5-methyl-N-[[5-(2,2,2-trifluoroethyl)-2-[2-(trifluoromethyl)pyrimidin-5-yl]-4-pyridyl]methyl]pyrrolidine-2-carboxamide | 0.00811 | 1HNMR (300 MHz, DMSO-d6) δ 9.65 (s, 1H), 9.05-9.02 (m, 1H), 8.74 (s, 1H), 8.21 (s, 1H), 8.07-8.03 (m, 2H), 7.51-7.45 (m, 2H), 4.85 (d, J = 51.0 Hz, 1H), 4.72-4.51 (m, 2H), 4.26-4.20 (m, 1H), 4.05-3.90 (m, 3H), 2.50-2.08 (m, 2H), 1.22 (d, J = 6.0 Hz, 3H). | 624.0 |
| 137. | 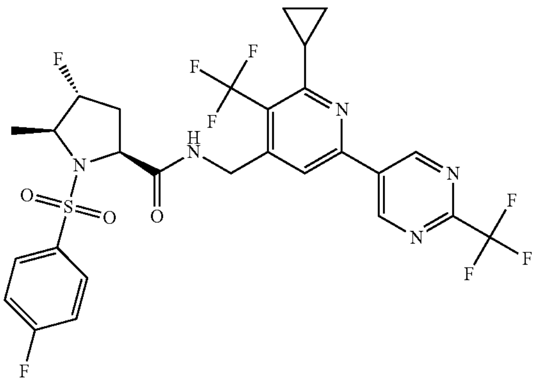 [SMILES: C[C@H]1[C@H](F)C[C@@H](C(=O)NCc2cc(-c3cnc(C(F)(F)F)nc3)nc(C3CC3)c2C(F)(F)F)N1S(=O)(=O)c1ccc(F)cc1] | (2S,4R,5S)-N-[[2-cyclopropyl-3-(trifluoromethyl)-6-[2-(trifluoromethyl)pyrimidin-5-yl]-4-pyridyl]methyl]-4-fluoro-1-(4-fluorophenyl) sulfonyl-5-methyl-pyrrolidine-2-carboxamide | 7.00E-04 | 1H NMR (400 MHz, CDCl3) δ 9.62 (s, 2H), 8.06 (s, 1H), 7.97-7.87 (m, 2H), 7.42-7.34 (m, 1H), 7.32-7.23 (m, 2H), 5.14 (dd, J = 18.2, 7.6 Hz, 1H), 4.84-4.65 (m, 1H), 4.63-4.53 (m, 1H), 4.36-4.27 (m, 1H), 4.19-4.07 (m, 1H), 2.69-2.54 (m, 1H), 2.53-2.46 (m, 1H), 2.39-2.16 (m, 1H), 1.43-1.25 (m, 5H), 1.16 (dt, J = 8.0, 3.3 Hz, 2H). | 650 |
| 138. | 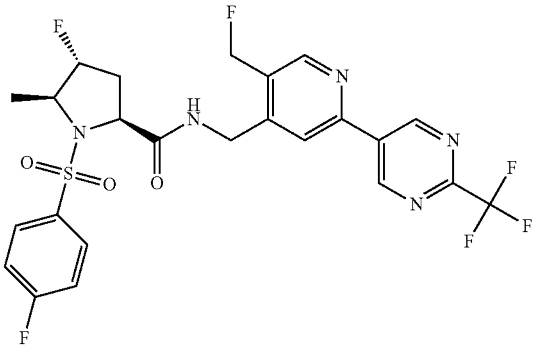 [SMILES: C[C@H]1[C@H](F)C[C@@H](C(=O)NCc2cc(-c3cnc(C(F)(F)F)nc3)ncc2CF)N1S(=O)(=O)c1ccc(F)cc1] | (2S,4R,5S-4-fluoro-N-[[5-(fluoro-methyl)-2-[2-(trifluoromethyl)pyrimidin-5-yl]-4-pyridyl]methyl]-1-(4-fluorophenyl) sulfonyl-5-methyl-pyrrolidine-2-carboxamide | 0.01165 | 1H NMR (400 MHz, CDCl3) δ 9.69-9.61 (m, 2H), 8.73-8.72 (m, 1H), 7.94-7.89 (m, 2H), 7.45-7.43 (m, 1H), 7.30-7.24 (m, 2H), 5.74-5.52 (m, 2H), 5.08-5.02 (m, 1H), 4.81-4.80 (m, 1H), 4.68-4.67 (m, 1H), 4.56-4.50 (m, 1H), 4.32-4.27 (m, 1H), 4.16-4.09 (m, 1H), 2.63-2.61 (m, 1H), 2.34 (m, 1H), 1.40-1.38 (s, 3H). | 574 |

TABLE 2-continued

| Example | Structure | Name | hTRPA1 CHO Ca2+ AUC EVO (IC50) | $^1$H NMR | LCMS |
|---|---|---|---|---|---|
| 139. | 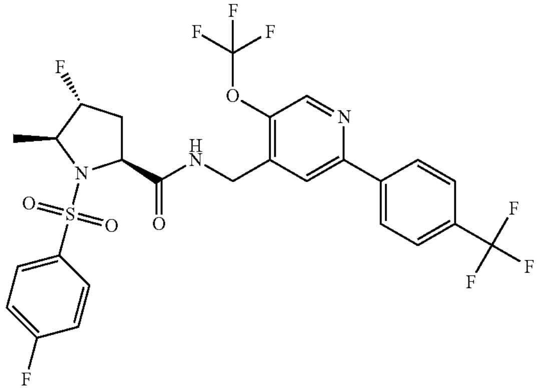 [SMILES: C[C@H]1[C@H](F)C[C@@H](C(=O)NCc2cc(-c3ccc(C(F)(F)F)cc3)ncc2OC(F)(F)F)N1S(=O)(=O)c1ccc(F)cc1] | (2S,4R,5S)-4-fluoro-1-(4-fluorophenyl) sulfonyl-5-methyl-N-[[5-(trifluorometh-oxy)-2-[4-(trifluorometh-yl)phenyl]-4-pyridyl]meth-yl]pyrrolidine-2-carboxamide | 0.00277 | 1H NMR (400 MHz, CD3OD) δ 8.65 (m, 1H), 8.37-8.31 (m, 3H), 8.07-8.03 (m, 2H), 7.73-7.71 (m, 2H), 7.38-7.33 (m, 2H), 4.78-4.66 (m, 2H), 4.36-4.29 (m, 1H), 4.13-4.05 (m, 1H), 2.47-2.25 (m, 2H), 1.37 (d, J = 7.0 Hz, 3H). | 624.1 |
| 140. | 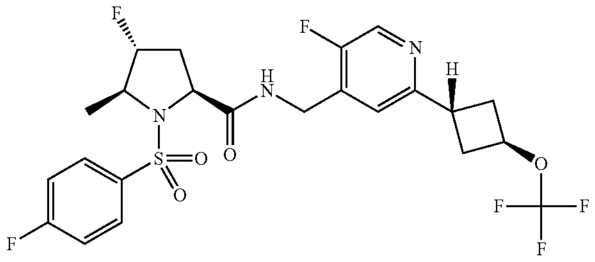 [SMILES: C[C@H]1[C@H](F)C[C@@H](C(=O)NCc2cc([C@H]3C[C@H](OC(F)(F)F)C3)ncc2F)N1S(=O)(=O)c1ccc(F)cc1] | (2S,4R,5S)-4-fluoro-1-(4-fluorophenyl) sulfonyl-N-[[5-fluoro-2-[3-(trifluorometh-oxy)cyclo-butyl]-4-pyridyl]meth-yl]-5-methyl-pyrrolidine-2-carboxamide | 0.00356 | 1H NMR (400 MHz, DMSO-d6) δ 8.89 (t, J = 6.0 Hz, 1H), 8.51 (d, J = 1.5 Hz, 1H), 8.02-8.00 (m, 2H), 7.50-7.40(m, 3H), 5.15-5.12 (m, 1H), 4.95-4.82 (d, J = 54 Hz, 1H)4.48 (dd, J = 16.8, 6.2 Hz, 1H), 4.36(dd, J = 16.7, 5.6 Hz, 1H), 4.19-4.16 (m, 1H), 3.97-3.90 (m, 1H), 3.66-3.61 (m, 1H), 2.66-2.33 (m, 6H), 1.21 (d, J = 6.9 Hz, 3H). | 552 |
| 141. | 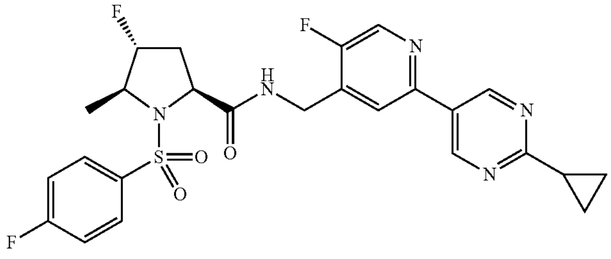 [SMILES: C[C@H]1[C@H](F)C[C@@H](C(=O)NCc2cc(-c3cnc(C4CC4)nc3)ncc2F)N1S(=O)(=O)c1ccc(F)cc1] | (2S,4R,5S)-N-[[2-(2-cyclopropyl-pyrimidin-5-yl)-5-fluoro-4-pyridyl]meth-yl]-4-fluoro-1-(4-fluorophenyl) sulfonyl-5-methyl-pyrrolidine-2-carboxamide | 0.02042 | 1HNMR (300 MHz, DMSO-d6) δ 9.21 (s, 2H), 9.03-9.02 (m, 1H), 8.69 (s, 1H), 8.07-8.01 (m, 2H), 7.51-7.49 (m, 2H), 4.89 (d, J = 54 Hz, 1H), 4.56-4.40 (m, 2H), 4.24-4.20 (m, 1H), 3.99-3.89 (m, 1H), 2.50-2.11 (m, 3H), 1.22-1.19 (m, 3H), 1.09-1.01 (m, 4H). | 532 |
| 142. | 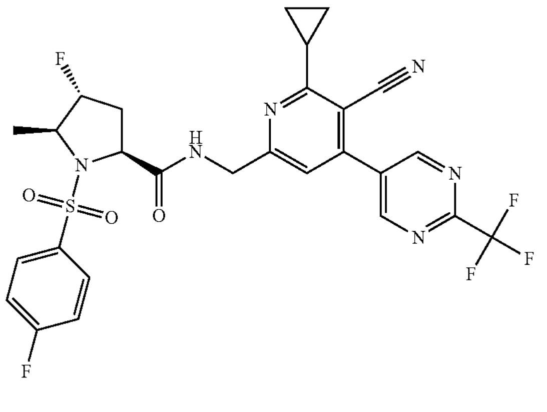 [SMILES: C[C@H]1[C@H](F)C[C@@H](C(=O)NCc2cc(-c3cnc(C(F)(F)F)nc3)c(C#N)c(C3CC3)n2)N1S(=O)(=O)c1ccc(F)cc1] | (2S,4R,5S)-N-[[5-cyano-6-cyclopropyl-4-[2-(trifluorometh-yl)pyrimidin-5-yl]-2-pyridyl]meth-yl]-4-fluoro-1-(4-fluorophenyl) sulfonyl-5-methyl-pyrrolidine-2-carboxamide | 0.01203 | 1H NMR (400 MHz, CDCl3) δ 9.20 (s, 2H), 7.90-7.86(m, 2H), 7.68 (t, J = 5.5 Hz, 1H), 7.40 (s, 1H), 7.29-7.24 (m, 2H), 4.95-4.89 (m, 1H), 4.74 (d, J = 52.3 Hz, 1H), 4.55-4.49 (m, 1H), 4.27-4.08 (m, 2H), 2.68-2.25 (m, 3H), 1.46-1.28 (m, 7H). | 607 |

TABLE 2-continued

| Example | Structure | Name | hTRPA1 CHO Ca2+ AUC EVO (IC50) | $^1$H NMR | LCMS |
|---|---|---|---|---|---|
| 143. | 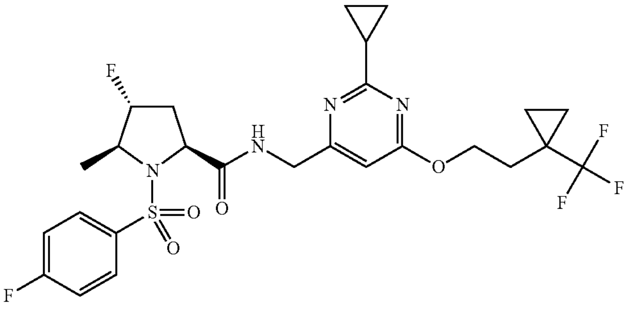 [SMILES: C[C@H]1[C@H](F)C[C@@H](C(=O)NCc2cc(OCCC3(C(F)(F)F)CC3)nc(C3CC3)n2)N1S(=O)(=O)c1ccc(F)cc1] | (2S,4R,5S)-N-[[2-cyclopropyl-6-[2-[1-(trifluoromethyl)cyclopropyl]ethoxy]pyrimidin-4-yl]methyl]-4-fluoro-1-(4-fluorophenyl)sulfonyl-5-methyl-pyrrolidine-2-carboxamide | 0.02240 | 1H NMR(300 MHz, CDCl3) δ 7.93 (s, 3H), 7.25-7.19 (m, 2H), 6.54 (s, 1H), 4.70 (d, J = 54 Hz, 1H), 4.51-4.46 (m, 4H), 4.18-4.07 (m, 2H), 2.44-2.40 (m, 3H), 2.02 (t, J = 7.3 Hz, 2H), 1.39 (d, J = 7.0 Hz, 3H), 1.83-1.00 (m, 6H), 0.70 (s, 2H). | 589 |
| 144. | 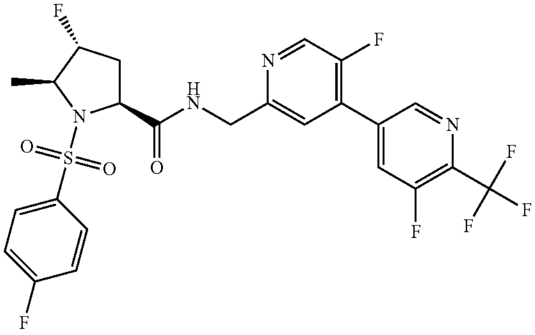 [SMILES: C[C@H]1[C@H](F)C[C@@H](C(=O)NCc2cc(-c3cnc(C(F)(F)F)c(F)c3)c(F)cn2)N1S(=O)(=O)c1ccc(F)cc1] | (2S,4R,5S)-4-fluoro-N-[[5-fluoro-4-[5-fluoro-6-(trifluoromethyl)-3-pyridyl]-2-pyridyl]methyl]-1-(4-fluorophenyl)sulfonyl-5-methyl-pyrrolidine-2-carboxamide | 0.01702 | 1H NMR (400 MHz, CDCl3) δ 8.89 (s, 1H), 8.64 (s, 1H), 8.03 (d, J = 10 Hz, 1H), 7.95-7.91 (m, 2H), 7.82-7.81 (m, 1H), 7.74-7.68 (m, 1H), 7.28-7.24 (m, 2H), 5.04-4.98 (m, 1H), 4.81-4.68 (m, 2H), 4.25-4.20 (m, 1H), 4.12-4.05 (m, 1H), 2.60-2.52 (m, 1H), 2.50-2.3 (m, 1H), 1.41 (d, J = 7.2 Hz, 3H). | 577 |
| 145. | 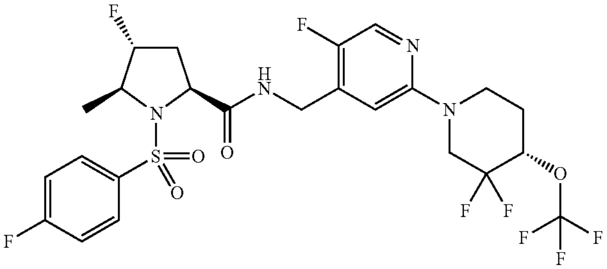 [SMILES: C[C@H]1[C@H](F)C[C@@H](C(=O)NCc2cc(N3CC[C@H](OC(F)(F)F)C(F)(F)C3)ncc2F)N1S(=O)(=O)c1ccc(F)cc1] | (2S,4R,5S)-N-[[2-[(4S)-3,3-difluoro-4-(trifluoromethoxy)-1-piperidyl]-5-fluoro-4-pyridyl]methyl]-4-fluoro-1-(4-fluorophenyl)sulfonyl-5-methyl-pyrrolidine-2-carboxamide | 0.00836 | 1H NMR (400 MHz, CDCl3) δ 8.04 (s, 1H), 7.92-7.89 (m, 2H), 7.29-7.23 (m, 3H), 7.08 (s, 1H), 4.90-4.67 (m, 2H), 4.51-4.40 (m, 2H), 4.29-4.24 (m, 2H), 4.16-3.83 (m, 3H), 3.69-3.64 (m, 1H), 2.60-2.53 (m, 1H), 2.35-2.17 (m, 3H), 1.39 (d, J = 7.0 Hz, 3H). | 617 |
| 146. | 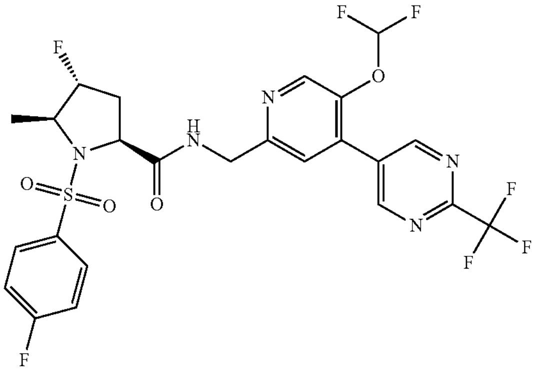 [SMILES: C[C@H]1[C@H](F)C[C@@H](C(=O)NCc2cc(-c3cnc(C(F)(F)F)nc3)c(OC(F)F)cn2)N1S(=O)(=O)c1ccc(F)cc1] | (2S,4R,5S)-N-[[5-(difluoromethoxy)-4-[2-(trifluoromethyl)pyrimidin-5-yl]-2-pyridyl]methyl]-4-fluoro-1-(4-fluorophenyl)sulfonyl-5-methyl-pyrrolidine-2-carboxamide | 0.03495 | 1H NMR (300 MHz, CDCl3) δ 9.16 (s, 4H), 8.67 (s, 2H), 7.95-7.84 (m, 4H), 7.72 (s, 2H), 7.64 (s, 2H), 7.28-7.18 (m, 3H), 6.57 (s, 1H), 5.00 (dd, J = 16.6, 7.0 Hz, 2H), 4.81 (d, J = 3.2 Hz, 1H), 4.73-4.61 (m, 3H), 4.23 (dd, J = 9.7, 7.9 Hz, 2H), 4.16-4.00 (m, 2H), 2.65-2.21 (m, 4H), 1.39 (d, J = 7.0 Hz, 6H). | 608.1 |

TABLE 2-continued

| Example | Structure | Name | hTRPA1 CHO Ca2+ AUC EVO (IC50) | $^{1}$H NMR | LCMS |
|---|---|---|---|---|---|
| 147. | 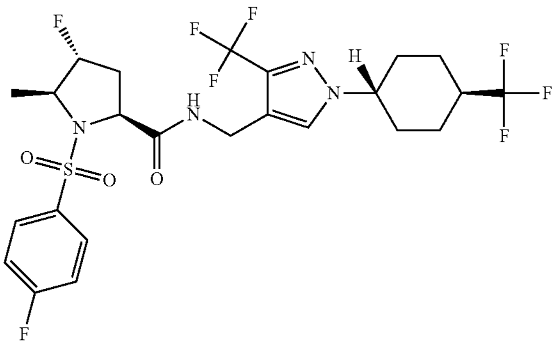 [SMILES: C[C@H]1[C@H](F)C[C@@H](C(=O)NCc2cn([C@H]3CC[C@H](C(F)(F)F)CC3)nc2C(F)(F)F)N1S(=O)(=O)c1ccc(F)cc1] | (2S,4R,5S)-4-fluoro-1-(4-fluorophenyl)sulfonyl-5-methyl-N-[[3-(trifluoromethyl)-1-[4-(trifluoromethyl)cyclohexyl]pyrazol-4-yl]methyl]pyrrolidine-2-carboxamide | 0.02453 | 1H NMR (400 MHz, CDCl3) δ 7.89-7.87 (m, 2H), 7.77 (s, 1H), 7.29-7.23 (m, 2H), 7.07 (m, 1H), 4.76-4.60 (m, 2H), 4.45-4.34 (m, 2H), 4.19-4.06 (m, 2H), 2.43-2.40 (m, 3H), 2.24-2.21 (m, 2H), 1.98-1.91 (m, 2H), 1.84-1.80 (m, 4H), 1.32 (d, J = 6.8 Hz, 3H). | 603.2 |
| 148. | 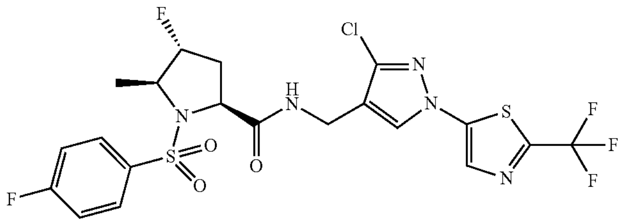 [SMILES: C[C@H]1[C@H](F)C[C@@H](C(=O)NCc2cn(-c3cnc(C(F)(F)F)s3)nc2Cl)N1S(=O)(=O)c1ccc(F)cc1] | (4R,5S)-N-[[3-chloro-1-[2-(trifluoromethyl)thiazol-5-yl]pyrazol-4-yl]methyl]-4-fluoro-1-(4-fluorophenyl)sulfonyl-5-methyl-pyrrolidine-2-carboxamide | 0.00764 | 1H NMR (400 MHz, DMSO-d6) δ 8.72 (t, J = 5.6 Hz, 1H), 8.57 (d, J = 0.7 Hz, 1H), 8.41 (q, J = 0.9 Hz, 1H), 8.10-7.88 (m, 2H), 7.55-7.34 (m, 2H), 4.87 (dd, J = 51.5, 2.8 Hz, 1H), 4.34-4.17 (m, 2H), 4.18-4.06 (m, 1H), 3.99-3.78 (m, 1H), 2.39-2.03 (m, 2H), 1.21 (d, J = 6.9 Hz, 3H). | 570 |
| 149. | 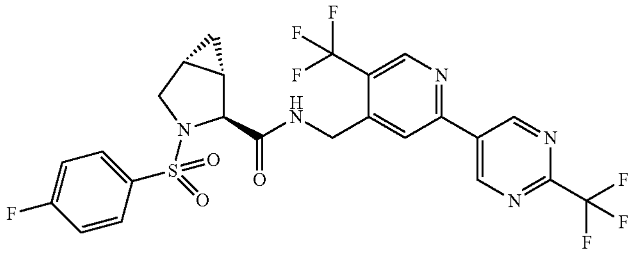 [SMILES: O=C(NCc1cc(-c2cnc(C(F)(F)F)nc2)ncc1C(F)(F)F)[C@@H]1[C@H]2C[C@H]2CN1S(=O)(=O)c1ccc(F)cc1] | (1S,2S,5R)-3-(4-fluorophenyl)sulfonyl-N-[[5-(trifluoromethyl)-2-[2-(trifluoromethyl)pyrimidin-5-yl]-4-pyridyl]methyl]-3-azabicyclo[3.1.0]hexane-2-carboxamide | 0.000756 | 1H NMR (400 MHz, DMSO-d6) δ 9.68 (s, 2H), 9.24-9.09 (m, 1H), 9.04 (t, J = 5.9 Hz, 1H), 8.27 (s, 1H), 8.07-7.75 (m, 2H), 7.62-7.21 (m, 2H), 4.81-4.42 (m, 2H), 4.27 (s, 1H), 3.90-3.69 (m, 1H), 3.58-3.43 (m, 1H), 1.76-1.42 (m, 2H), 0.70-0.43 (m, 1H), −0.91 (q, J = 4.5 Hz, 1H). | 590.1 |
| 150. | 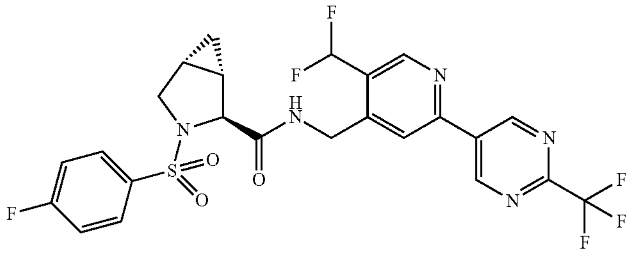 [SMILES: O=C(NCc1cc(-c2cnc(C(F)(F)F)nc2)ncc1C(F)F)[C@@H]1[C@H]2C[C@H]2CN1S(=O)(=O)c1ccc(F)cc1] | (1R,4S,5S)-N-[[5-(difluoromethyl)-2-[2-(trifluoromethyl)pyrimidin-5-yl]-4-pyridyl]methyl]-3-(4-fluorophenyl)sulfonyl-3-azabicyclo[3.1.0]hexane-4-carboxamide | 0.00572 | 1H NMR (400 MHz, DMSO-d6) δ 9.67 (s, 2H), 8.95 (d, J = 6.1 Hz, 2H), 8.19 (s, 1H), 8.06-7.83 (m, 2H), 7.59-7.38 (m, 3H), 4.81-4.47 (m, 2H), 4.25 (s, 1H), 3.78 (dd, J = 10.5, 3.9 Hz, 1H), 3.60-3.42 (m, 1H), 1.76-1.32 (m, 2H), 0.69-0.33 (m, 1H), −0.90 (q, J = 4.4 Hz, 1H). | 572.1 |

TABLE 2-continued

| Example | Structure | Name | hTRPA1 CHO Ca2+ AUC EVO (IC50) | $^1$H NMR | LCMS |
|---|---|---|---|---|---|
| 151. | 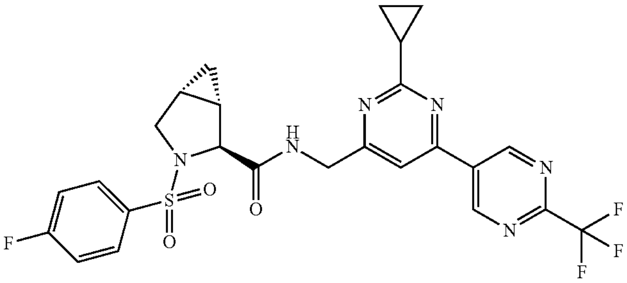 [SMILES: O=C(NCc1cc(-c2cnc(C(F)(F)F)nc2)nc(C2CC2)n1)[C@@H]1[C@H]2C[C@H]2CN1S(=O)(=O)c1ccc(F)cc1] | (1S,2S,5R)-N-[[2-cyclopropyl-6-[2-(trifluorometh-yl)pyrimidin-5-yl]pyrimidin-4-yl]-methyl]-3-(4-fluorophenyl) sulfonyl-3-azabicyclo [3.1.0]hexane-2-carboxamide | 0.0010 | 1H NMR (400 MHz, DMSO-d6) δ 966 (s, 2H), 8.90 (t, J = 6.0 Hz, 1H), 8.10-7.64 (m, 3H), 7.73-7.25 (m, 2H), 4.66-4.33 (m, 2H), 4.26 (s, 1H), 3.90-3.59 (m, 1H), 3.65-3.37 (m, 1H), 2.32 (tt, J = 7.9, 4.8 Hz, 1H), 1.78-1.32 (m, 2H), 1.32-0.95 (m, 4H), 0.80-0.34 (m, 1H), −0.85 (q, J = 4.4 Hz, 1H). | 563.1 |
| 152. | 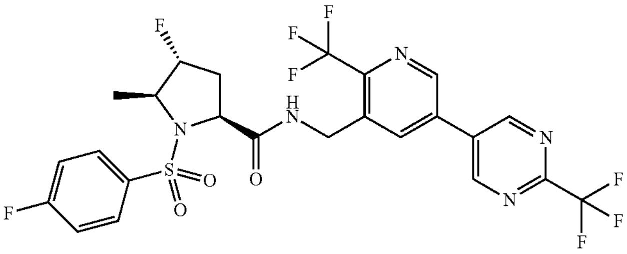 [SMILES: C[C@H]1[C@H](F)C[C@@H](C(=O)NCc2cc(-c3cnc(C(F)(F)F)nc3)cnc2C(F)(F)F)N1S(=O)(=O)c1ccc(F)cc1] | (2S,4R,5S)-4-fluoro-1-(4-fluorophenyl) sulfonyl-5-methyl-N-[[2-(trifluorometh-yl)-5-[2-(trifluorometh-yl)pyrimidin-5-yl]-3-pyridyl]meth-yl]pyrrolidine-2-carboxamide | 0.00303 | 1H NMR (400 MHz, DMSO-d6) δ 9.50 (s, 2H), 9.17 (d, J = 2.0 Hz, 1H), 9.07 (t, J = 5.9 Hz, 1H), 8.53 (d, J = 2.0 Hz, 1H), 8.06-7.98 (m, 2H), 7.47 (t, J = 8.8 Hz, 2H), 4.89 (dd, J = 51.4, 2.7 Hz, 1H), 4.72 (dd, J = 16.7, 6.0 Hz, 1H), 4.57 (dd, J = 16.5, 5.4 Hz, 1H), 4.22 (dd, J = 10.2, 7.1 Hz, 1H), 3.94 (dq, J = 21.4, 6.8 Hz, 1H), 2.43-2.33 (m, 1H), 2.34-2.09 (m, 1H), 1.20 (d, J = 6.9 Hz, 3H). | 610.1 |
| 153. | 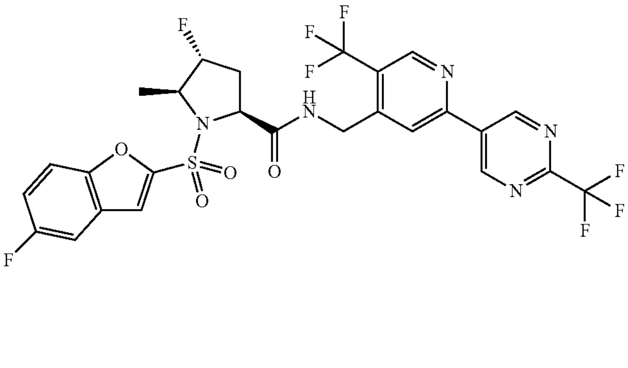 [SMILES: C[C@H]1[C@H](F)C[C@@H](C(=O)NCc2cc(-c3cnc(C(F)(F)F)nc3)ncc2C(F)(F)F)N1S(=O)(=O)c1cc2cc(F)ccc2o1] | (2S,4R,5S)-4-fluoro-1-(5-fluorobenzo-furan-2-yl)sulfonyl-5-methyl-N-[[5-(trifluorometh-yl)-2-[2-(trifluorometh-yl)pyrimidin-5-yl]-4-pyridyl]meth-yl]pyrrolidine-2-carboxamide | 2.29E-04 | 1H NMR (400 MHz, DMSO-d6) δ 9.68 (s, 2H), 9.19-9.11 (m, 2H), 8.31 (s, 1H), 7.82 (d, J = 0.9 Hz, 1H), 7.78 (dd, J = 9.1, 4.1 Hz, 1H), 7.67 (dd, J = 8.4, 2.7 Hz, 1H), 7.42 (td, J = 9.2, 2.7 Hz, 1H), 5.09-4.84 (m, 1H), 4.64 (qd, J = 17.4, 5.7 Hz, 2H), 4.50 (dd, J = 10.2, 7.2 Hz, 1H), 4.13 (dq, J = 21.3, 6.9 Hz, 1H), 2.47-2.17 (m, 2H), 1.28 (d, J = 6.9 Hz, 3H). | 650.1 |

TABLE 2-continued

| Ex-am-ple | Structure | Name | hTRPA1 CHO Ca2+ AUC EVO (IC50) | $^1$H NMR | LCMS |
|---|---|---|---|---|---|
| 154. | 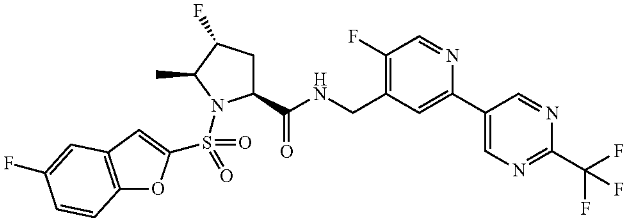 [SMILES: C[C@H]1[C@H](F)C[C@@H](C(=O)NCc2cc(-c3cnc(C(F)(F)F)nc3)ncc2F)N1S(=O)(=O)c1cc2cc(F)ccc2o1] | (2S,4R,5S)-4-fluoro-1-(5-fluorobenzo-furan-2-yl)sulfonyl-N-[[5-fluoro-2-[2-(trifluorometh-yl)pyrimidin-5-yl]-4-pyridyl]meth-yl]-5-methyl-pyrrolidine-2-carboxamide | 8.90E-04 | 1H NMR (400 MHz, DMSO-d6) δ 9.59 (s, 2H), 9.05 (t, J = 5.9 Hz, 1H), 8.78 (d, J = 1.3 Hz, 1H), 8.18 (d, J = 5.8 Hz, 1H), 7.78 (s, 1H), 7.78-7.73 (m, 1H), 7.66 (dd, J = 8.5, 2.7 Hz, 1H), 7.41 (td, J = 9.2, 2.8 Hz, 1H), 4.95 (dd, J = 51.4, 2.7 Hz, 1H), 4.63-4.41 (m, 3H), 4.19- 4.04 (m, 1H), 2.47-2.14 (m, 2H), 1.28 (d, J = 7.0 Hz, 3H). | 600.1 |
| 155. | 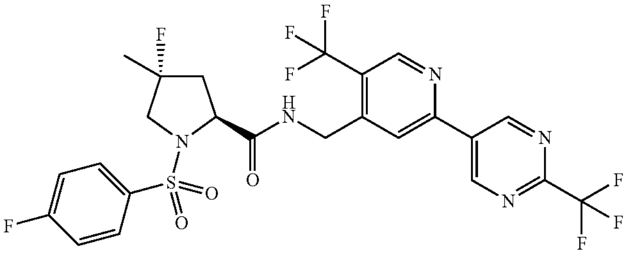 [SMILES: C[C@@]1(F)C[C@@H](C(=O)NCc2cc(-c3cnc(C(F)(F)F)nc3)ncc2C(F)(F)F)N(S(=O)(=O)c2ccc(F)cc2)C1] | (2S,4R)-4-fluoro-1-(4-fluorophenyl) sulfonyl-4-methyl-N-[[5-(trifluorometh-yl)-2-[2-(trifluorometh-yl)pyrimidin-5-yl]-4-pyridyl]meth-yl]pyrrolidine-2-carboxamide | 0.00424 | 1H NMR (400 MHz, DMSO-d6) δ 9.69 (s, 2H), 9.16 (t, J = 6.0 Hz, 1H), 9.13 (s, 1H), 8.39 (s, 1H), 8.06-7.98 (m, 2H), 7.53-7.43 (m, 2H), 4.63 (d, J = 5.8 Hz, 2H), 4.27 (dd, J = 10.2, 7.0 Hz, 1H), 3.76-3.48 (m, 2H), 2.48-2.35 (m, 1H), 2.19- 1.98 (m, 1H), 1.38 (d, J = 20.6 Hz, 3H). | 610.1 |
| 156. | 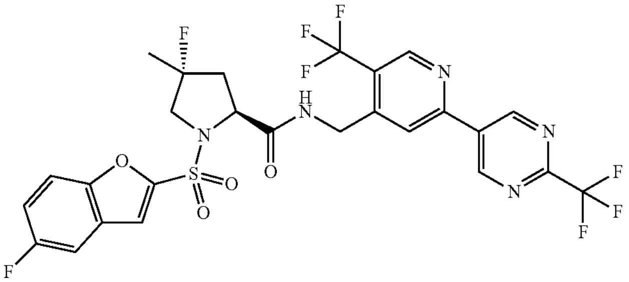 [SMILES: C[C@@]1(F)C[C@@H](C(=O)NCc2cc(-c3cnc(C(F)(F)F)nc3)ncc2C(F)(F)F)N(S(=O)(=O)c2cc3cc(F)ccc3o2)C1] | (2S,4R)-4-fluoro-1-(5-fluorobenzo-furan-2-yl)sulfonyl-4-methyl-N-[[5-(trifluorometh-yl)-2-[2-(trifluorometh-yl)pyrimidin-5-yl]-4-pyridyl]meth-yl]pyrrolidine-2-carboxamide | 0.00193 | 1H NMR (400 MHz, DMSO-d6) δ 9.68 (s, 2H), 9.19 (t, J = 5.9 Hz, 1H), 9.13 (s, 1H), 8.32 (s, 1H), 7.81-7.75 (m, 2H), 7.66 (dd, J = 8.5, 2.7 Hz, 1H), 7.47-7.37 (m, 1H), 4.73-4.48 (m, 3H), 3.85-3.63 (m, 2H), 2.59-2.51 (m, 1H), 2.23-2.04 (m, 1H), 1.40 (d, J = 20.9 Hz, 3H). | 650.1 |
| 157. | 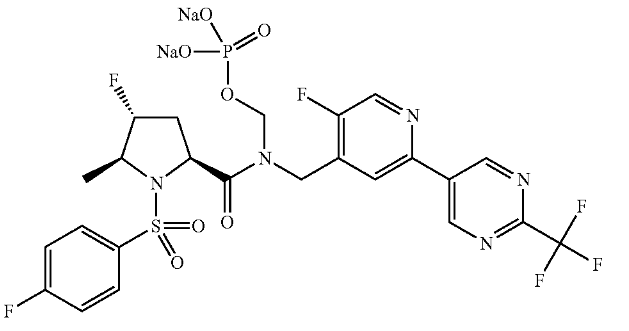 | sodium ((2S,4R,5S)-4-fluoro-N-((5-fluoro-2-(2-(trifluorometh-yl)pyrimidin-5-yl)pyridin-4-yl)methyl)-1-((4-fluorophenyl) sulfonyl)-5-methylpyrrol-idine-2-carboxamido) methyl-phosphate | 1.2 | 1H NMR (300 MHz, CD3OD) δ 9.63 (s, 2H), 8.62 (s, 1H), 8.20 (d, J = 6 Hz, 1H), 8.11 (dd, J = 8.9, 5.0 Hz, 2H), 7.37 (t, J = 8.7 Hz, 2H), 5.77 (dd, J = 10.7, 8.1 Hz, 1 Hz), 5.29-5.15 (m, 3H), 5.19-4.78 (m, 2H), 4.05-3.95 (m, 1H), 2.90-2.79 (m, 1H), 2.41-2.23 (m, 1H), 1.32 (d, J = 6.9 Hz, 3H). | 670 |

TABLE 2-continued

| Example | Structure | Name | hTRPA1 CHO Ca2+ AUC EVO (IC50) | $^1$H NMR | LCMS |
|---|---|---|---|---|---|
| 158. | 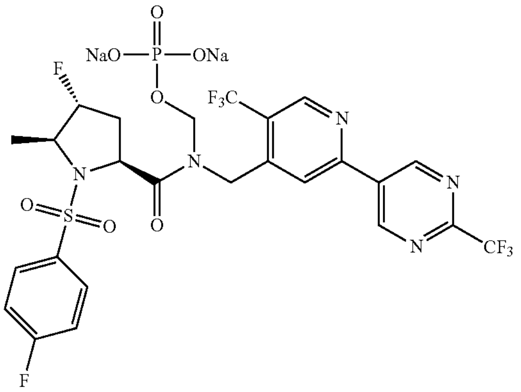 | sodium ((2S,4R,5S)-4-fluoro-1-((4-fluorophenyl) sulfonyl)-5-methyl-N-((5-(trifluorometh-yl)-2-(2-(trifluorometh-yl)pyrimidin-5-yl)pyridin-4-yl)methyl) pyrrolidine-2-carboxamido) methyl-phosphate | 14000 | 1H NMR (300 MHz, CD3OD) δ 9.73 (s, 2H), 9.00 (s, 1H), 8.31 (s, 1H), 8.16-8.04 (m, 2H), 7.41-7.28 (m, 2H), 5.82 (dd, J = 11.1, 6.6 Hz, 1H), 5.36 (d, J = 17.9 Hz, 1H), 5.29-5.16 (m, 2H), 4.98-4.75 (m, 2H), 3.99-3.90 (m, 1H), 2.91-2.78 (m, 1H), 2.38-2.15 (m, 1H), 1.26 (d, J = 6.9 Hz, 3H). | 720 |
| 159. | 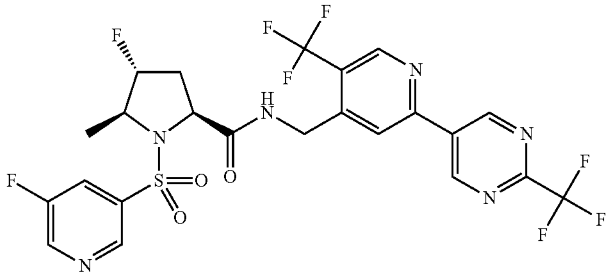 [SMILES: C[C@H]1[C@H](F)C[C@@H](C(=O)NCc2cc(-c3cnc(C(F)(F)F)nc3)ncc2C(F)(F)F)N1S(=O)(=O)c1cncc(F)c1] | (2S,4R,5S)-4-fluoro-1-[(5-fluoro-3-pyridyl)sulfon-yl]-5-methyl-N-[[5-(trifluorometh-yl)-2-[2-(trifluorometh-yl)pyrimidin-5-yl]-4-pyridyl]meth-yl]pyrrolidine-2-carboxamide | 0.00231 | $^1$H NMR (400 MHz, $CDCl_3$) δ 9.68 (s, 2H), 9.04 (s, 1H), 8.96 (s, 1H), 8.80 (s, 1H), 8.31 (s, 1H), 7.92-7.89 (m, 1H), 7.31-7.29 (m, 1H), 5.18-5.12 (m, 1H), 4.87-4.73 (d, J = 50.8 Hz, 1H), 4.66-4.61 (m, 1H), 4.38-4.34 (m, 1H), 4.17-4.11 (m, 1H), 2.71-2.61 (m, 1H), 2.44-2.27 (m, 1H), 1.42 (d, J = 7.2 Hz, 3H). | 611 |
| 160. | 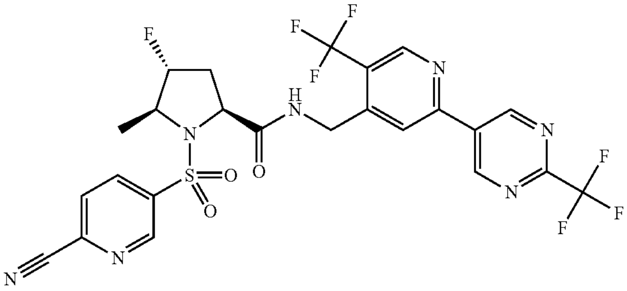 [SMILES: C[C@H]1[C@H](F)C[C@@H](C(=O)NCc2cc(-c3cnc(C(F)(F)F)nc3)ncc2C(F)(F)F)N1S(=O)(=O)c1ccc(C#N)nc1] | (2S,4R,5S)-1-[(6-cyano-3-pyridyl)sulfon-yl]-4-fluoro-5-methyl-N-[[5-(trifluorometh-yl)-2-[2-(trifluorometh-yl)pyrimidin-5-yl]-4-pyridyl]meth-yl]pyrrolidine-2-carboxamide | 0.00727 | $^1$H NMR (400 MHz, $CDCl_3$) δ 9.67 (s, 2H), 9.18 (s, 1H), 9.04 (s, 1H), 8.34-8.32(m, 1H), 8.27 (s, 1H), 7.93 (d, J = 8.0 Hz, 1H), 7.26-7.23 (m, 1H), 5.18-5.12 (m, 1H), 4.88-4.75 (d, J = 50.8 Hz, 1H), 4.68-4.62 (m, 1H), 4.34-4.30 (m, 1H), 4.17-4.10 (m, 1H), 2.73-2.60 (m, 1H), 2.47-2.31 (m, 1H), 1.42 (d, J = 7.0 Hz, 3H). | 618 |

TABLE 2-continued

| Example | Structure | Name | hTRPA1 CHO Ca2+ AUC EVO (IC50) | $^1$H NMR | LCMS |
|---|---|---|---|---|---|
| 161. | 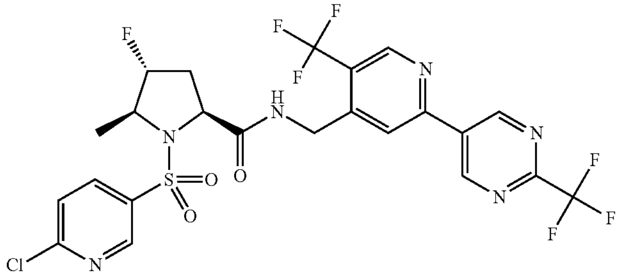 [SMILES: C[C@H]1[C@H](F)C[C@@H](C(=O)NCc2cc(-c3cnc(C(F)(F)F)nc3)ncc2C(F)(F)F)N1S(=O)(=O)c1ccc(Cl)nc1] | (2S,4R,5S)-1-[(6-chloro-3-pyridyl)sulfonyl]-4-fluoro-5-methyl-N-[[5-(trifluoromethyl)-2-[2-(trifluoromethyl)pyrimidin-5-yl]-4-pyridyl]methyl]pyrrolidine-2-carboxamide | 0.00196 | $^1$H NMR (400 MHz, $CDCl_3$) δ 9.68 (s, 2H), 9.03 (s, 1H), 8.90 (d, J = 2.5 Hz, 1H), 8.30 (s, 1H), 8.12-8.10 (m, 1H), 7.57 (d, J = 8.4 Hz, 1H), 7.34-7.30 (m, 1H), 5.18-5.14 (m, 1H), 4.87-4.74 (d, J = 50.8 Hz, 1H), 4.65-4.59 (m, 1H), 4.34-4.29 (m, 1H), 4.16-4.09 (m, 1H), 2.72-2.61 (m, 1H), 2.43-2.26 (m, 1H), 1.41 (d, J = 7.2 Hz, 3H). | 627 |
| 162. | 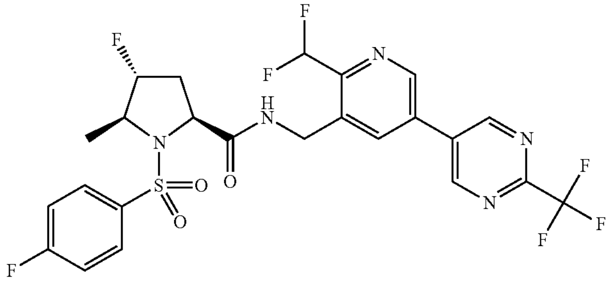 [SMILES: C[C@H]1[C@H](F)C[C@@H](C(=O)NCc2cc(-c3cnc(C(F)(F)F)nc3)cnc2C(F)F)N1S(=O)(=O)c1ccc(F)cc1] | (2S,4R,5S)-N-[[2-(difluoromethyl)-5-[2-(trifluoromethyl)pyrimidin-5-yl]-3-pyridyl]methyl]-4-fluoro-1-(4-fluorophenyl)sulfonyl-5-methyl-pyrrolidine-2-carboxamide | 0.00234 | $^1$H NMR (300 MHz, $CDCl_3$) δ 9.25 (s, 2H), 8.78 (s, 1H), 8.40 (s, 1H), 7.89-7.84 (m, 2H), 7.31-7.21(m, 3H), 6.82 (t, J = 54.3 Hz, 1H), 5.22-5.14 (m, 1H), 4.80-4.62 (m, 2H), 4.27-4.11 (m, 1H), 4.09-4.02 (m, 1H), 2.64-2.50 (m, 1H), 2.37-2.13 (m, 1H), 1.38 (d, J = 7.0 Hz, 3H). | 592 |

It is to be understood that the invention is not limited to the particular embodiments of the invention described above, as variations of the particular embodiments may be made and still fall within the scope of the appended claims. All documents cited to or relied upon herein are expressly incorporated by reference.

We claim:

1. A compound selected from:

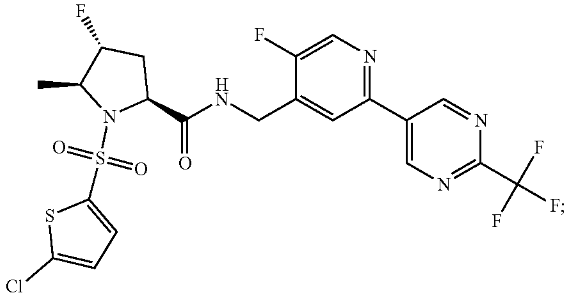

-continued

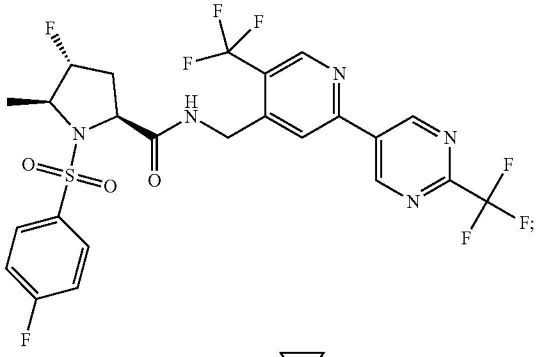

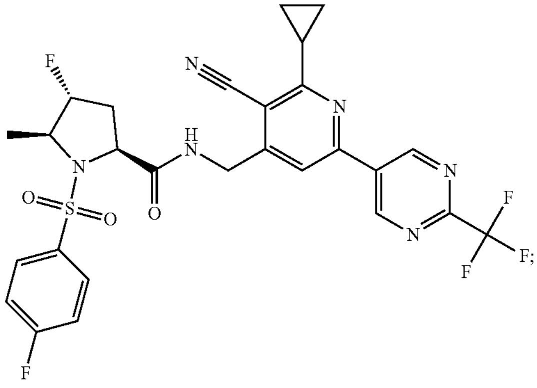

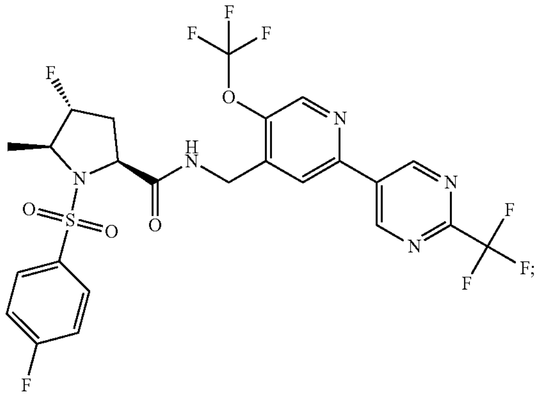
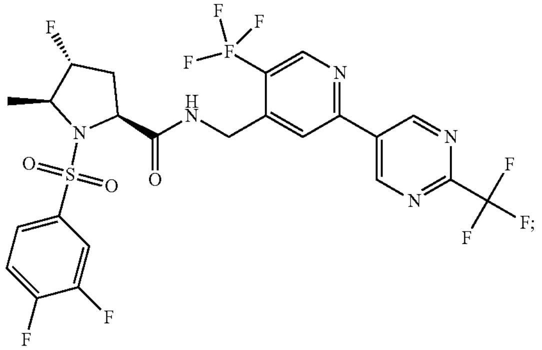
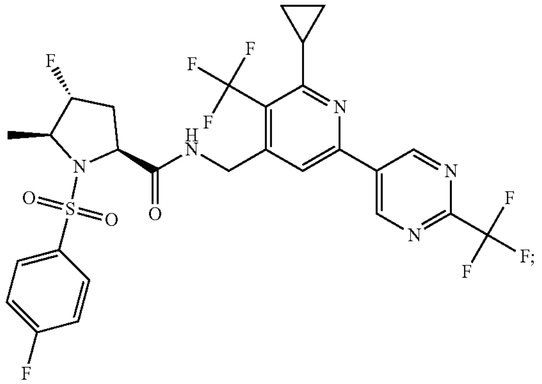
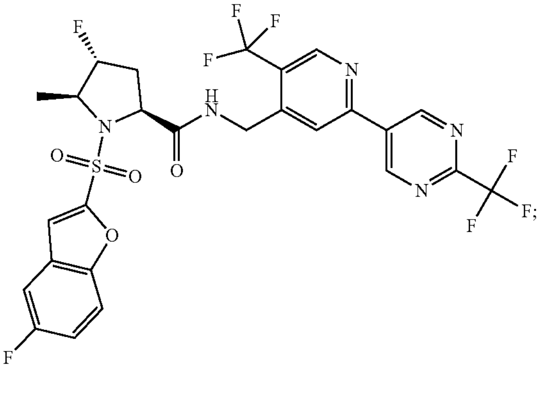
and
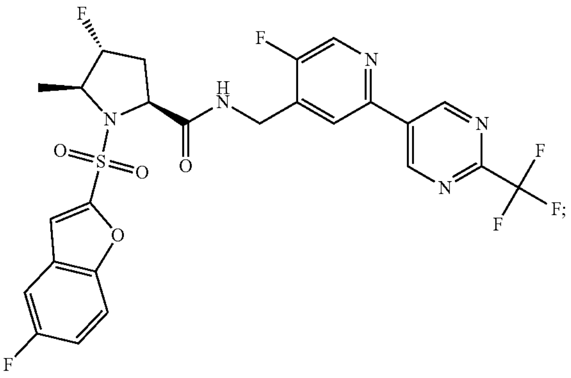
or a pharmaceutically acceptable salt thereof.
2. The compound:
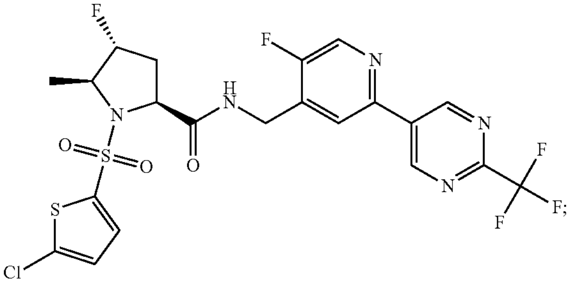 [SMILES: C[C@H]1[C@H](F)C[C@@H](C(=O)NCc2cc(-c3cnc(C(F)(F)F)nc3)ncc2F)N1S(=O)(=O)c1ccc(Cl)s1]
or a pharmaceutically acceptable salt thereof.
3. The compound:
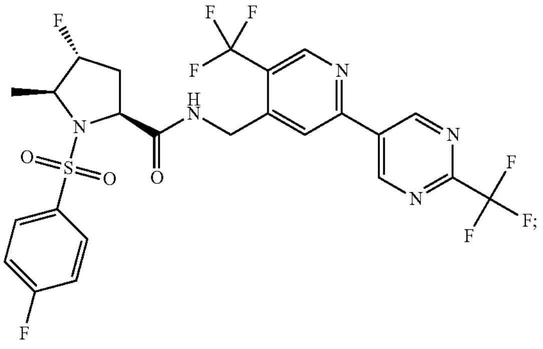 [SMILES: C[C@H]1[C@H](F)C[C@@H](C(=O)NCc2cc(-c3cnc(C(F)(F)F)nc3)ncc2C(F)(F)F)N1S(=O)(=O)c1ccc(F)cc1]
or a pharmaceutically acceptable salt thereof.

4. The compound:

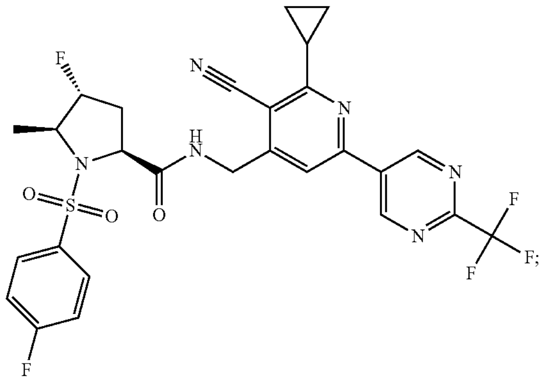 [SMILES: C[C@H]1[C@H](F)C[C@@H](C(=O)NCc2cc(-c3cnc(C(F)(F)F)nc3)nc(C3CC3)c2C#N)N1S(=O)(=O)c1ccc(F)cc1]

or a pharmaceutically acceptable salt thereof.

5. The compound:

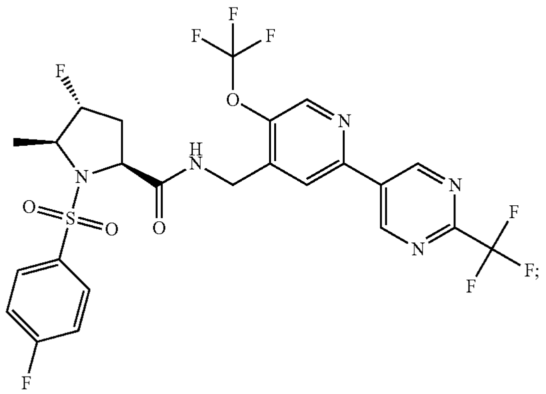 [SMILES: C[C@H]1[C@H](F)C[C@@H](C(=O)NCc2cc(-c3cnc(C(F)(F)F)nc3)ncc2OC(F)(F)F)N1S(=O)(=O)c1ccc(F)cc1]

or a pharmaceutically acceptable salt thereof.

6. The compound:

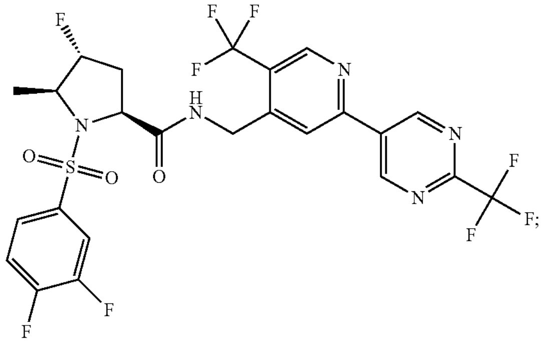 [SMILES: C[C@H]1[C@H](F)C[C@@H](C(=O)NCc2cc(-c3cnc(C(F)(F)F)nc3)ncc2C(F)(F)F)N1S(=O)(=O)c1ccc(F)c(F)c1]

or a pharmaceutically acceptable salt thereof.

7. The compound:

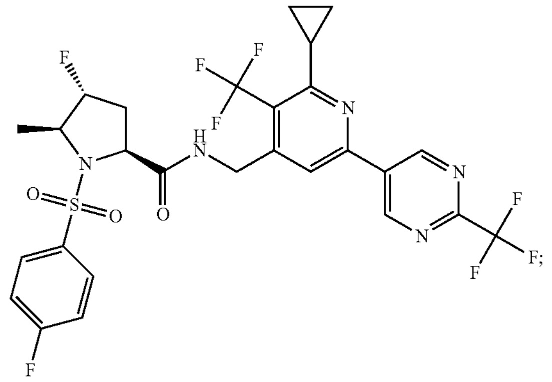 [SMILES: C[C@H]1[C@H](F)C[C@@H](C(=O)NCc2cc(-c3cnc(C(F)(F)F)nc3)nc(C3CC3)c2C(F)(F)F)N1S(=O)(=O)c1ccc(F)cc1]

or a pharmaceutically acceptable salt thereof.

8. The compound:

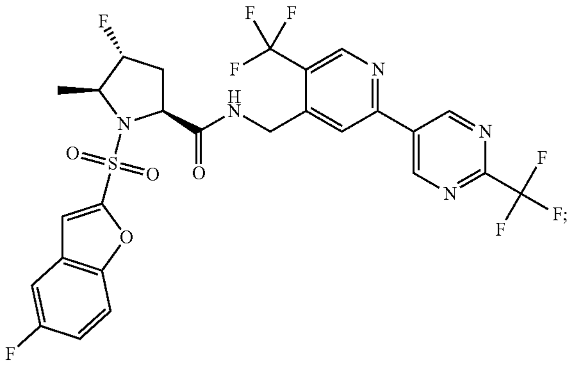 [SMILES: C[C@H]1[C@H](F)C[C@@H](C(=O)NCc2cc(-c3cnc(C(F)(F)F)nc3)ncc2C(F)(F)F)N1S(=O)(=O)c1cc2cc(F)ccc2o1]

or a pharmaceutically acceptable salt thereof.

9. The compound:

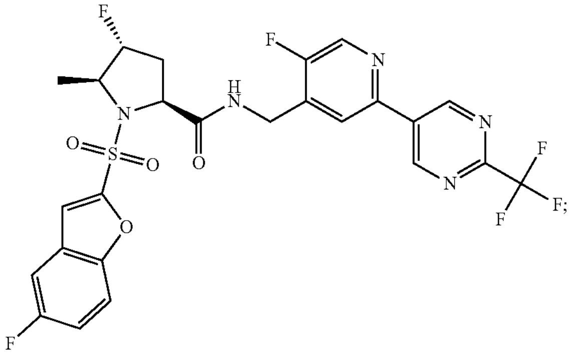 [SMILES: C[C@H]1[C@H](F)C[C@@H](C(=O)NCc2cc(-c3cnc(C(F)(F)F)nc3)ncc2F)N1S(=O)(=O)c1cc2cc(F)ccc2o1]

or a pharmaceutically acceptable salt thereof.

10. A pharmaceutical composition, comprising a compound as described in claim 1 or a pharmaceutically acceptable salt thereof, and a pharmaceutically acceptable carrier, diluent or excipient.

* * * * *